US009988369B2

(12) United States Patent
Chen et al.

(10) Patent No.: US 9,988,369 B2
(45) Date of Patent: Jun. 5, 2018

(54) HETEROCYCLIC TRIAZOLE COMPOUNDS AS AGONISTS OF THE APJ RECEPTOR

(71) Applicant: AMGEN INC., Thousand Oaks, CA (US)

(72) Inventors: Xiaoqi Chen, Palo Alto, CA (US); Yinhong Chen, Hayward, CA (US); Alan C. Cheng, San Francisco, CA (US); Richard V. Connors, Mesa, AZ (US); Mikkel V. Debenedetto, Waltham, MA (US); Paul John Dransfield, Arlington, MA (US); Zice Fu, Foster City, CA (US); James S. Harvey, Brookline, MA (US); Julie Anne Heath, Chico, CA (US); Simon J. Hedley, Thousand Oaks, CA (US); Jonathan Houze, Cambridge, MA (US); Ted C. Judd, Granada Hills, CA (US); Aarif Yusuf Khakoo, Woodside, CA (US); David John Kopecky, Studio City, CA (US); Su-Jen Lai, Boston, MA (US); Zhihua Ma, Lexington, MA (US); Nobuko Nishimura, West Hills, CA (US); Steven H. Olson, Millbrae, CA (US); Vatee Pattaropong, Bedford, MA (US); Gayathri Swaminath, Brisbane, CA (US); Xiaodong Wang, Johns Creek, GA (US); Wen-Chen Yeh, Belmont, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days. days.

(21) Appl. No.: 15/584,109

(22) Filed: May 2, 2017

(65) Prior Publication Data
US 2017/0320860 A1 Nov. 9, 2017

Related U.S. Application Data

(60) Provisional application No. 62/422,763, filed on Nov. 16, 2016, provisional application No. 62/330,923, filed on May 3, 2016.

(51) Int. Cl.
| | | |
|---|---|---|
| C07D 405/14 | (2006.01) |
| A61K 31/437 | (2006.01) |
| A61K 31/4439 | (2006.01) |
| A61K 31/497 | (2006.01) |
| A61K 31/506 | (2006.01) |
| A61K 31/5383 | (2006.01) |
| A61K 45/06 | (2006.01) |
| C07D 405/04 | (2006.01) |
| C07D 471/04 | (2006.01) |
| C07D 498/04 | (2006.01) |
| C07D 401/14 | (2006.01) |
| C07D 403/04 | (2006.01) |

(Continued)

(52) U.S. Cl.
CPC .......... *C07D 405/14* (2013.01); *A61K 31/437* (2013.01); *A61K 31/4439* (2013.01); *A61K 31/497* (2013.01); *A61K 31/506* (2013.01); *A61K 31/5383* (2013.01); *A61K 45/06* (2013.01); *C07D 401/14* (2013.01); *C07D 403/04* (2013.01); *C07D 403/14* (2013.01); *C07D 405/04* (2013.01); *C07D 409/14* (2013.01); *C07D 471/04* (2013.01); *C07D 498/04* (2013.01)

(58) Field of Classification Search
CPC .................................................... C07D 405/14
See application file for complete search history.

(56) References Cited

U.S. PATENT DOCUMENTS

| | | |
|---|---|---|
| 4,941,912 A | 7/1990 | Kirsten et al. |
| 5,302,718 A | 4/1994 | Agback et al. |

(Continued)

FOREIGN PATENT DOCUMENTS

| | | |
|---|---|---|
| AU | 199886243 B2 | 4/1999 |
| AU | 2012200157 A1 | 9/2012 |

(Continued)

OTHER PUBLICATIONS

International Search Report and Written Opinion for analogous PCT Application No. PCT/US2017/030501, dated Jul. 31, 2017.

(Continued)

*Primary Examiner* — Shawquia Jackson
(74) *Attorney, Agent, or Firm* — Bernard P. Friedrichsen

(57) ABSTRACT

Compounds of Formula I and Formula II, pharmaceutically acceptable salts thereof, stereoisomers of any of the foregoing, or mixtures thereof are agonists of the APJ Receptor and may have use in treating cardiovascular and other conditions. Compounds of Formula I and Formula II have the following structures:

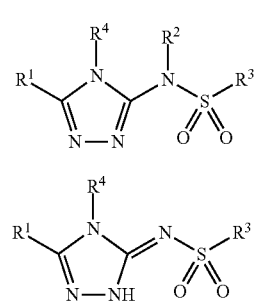

where the definitions of the variables are provided herein.

67 Claims, 7 Drawing Sheets

(51) Int. Cl.
*C07D 403/14* (2006.01)
*C07D 409/14* (2006.01)

(56) References Cited

U.S. PATENT DOCUMENTS

| | | | |
|---|---|---|---|
| 5,328,803 A | 7/1994 | Fujikura et al. |
| 5,411,839 A | 5/1995 | Harder et al. |
| 5,451,588 A | 9/1995 | Baker et al. |
| 5,510,362 A | 4/1996 | Matassa et al. |
| 5,563,026 A | 10/1996 | Singer |
| 5,910,504 A | 6/1999 | Hutchinson |
| 6,069,141 A | 5/2000 | Barbachyn et al. |
| 6,194,090 B1 | 2/2001 | Okada |
| 6,555,693 B2 | 4/2003 | Ge et al. |
| 6,586,423 B2 | 7/2003 | Bilodeau et al. |
| 6,727,364 B2 | 4/2004 | Tullis et al. |
| 6,787,555 B2 | 9/2004 | Tullis et al. |
| 6,790,846 B2 | 9/2004 | Clark et al. |
| 7,084,145 B2 | 8/2006 | Armour et al. |
| 7,084,164 B2 | 8/2006 | Tobe et al. |
| 7,169,797 B2 | 1/2007 | Xin et al. |
| 7,297,168 B2 | 11/2007 | Murphy et al. |
| 7,361,669 B2 | 4/2008 | Scarborough et al. |
| 7,371,757 B2 | 5/2008 | Morningstar et al. |
| 7,615,569 B2 | 11/2009 | Fulp et al. |
| 7,635,751 B2 | 12/2009 | Kitada et al. |
| 7,638,541 B2 | 12/2009 | Chen et al. |
| 7,718,683 B2 | 5/2010 | Charvat et al. |
| 7,776,897 B2 | 8/2010 | Murakami et al. |
| 7,820,665 B2 | 10/2010 | Booker et al. |
| 8,034,834 B2 | 10/2011 | Du et al. |
| 8,053,456 B2 | 11/2011 | Sun et al. |
| 8,063,083 B2 | 11/2011 | Foley |
| 8,076,486 B2 | 12/2011 | Goutopoulos et al. |
| 8,101,618 B2 | 1/2012 | Kawamoto et al. |
| 8,252,822 B2 | 8/2012 | An et al. |
| 8,299,107 B2 | 10/2012 | Chimmanamada et al. |
| 8,318,790 B2 | 11/2012 | Ying et al. |
| 8,399,464 B2 | 3/2013 | Kuramochi et al. |
| 8,415,377 B2 | 4/2013 | Sun et al. |
| 8,426,602 B2 | 4/2013 | Meibom et al. |
| 8,431,604 B2 | 4/2013 | Netz et al. |
| 8,445,518 B2 | 5/2013 | Charvat et al. |
| 8,466,170 B2 | 6/2013 | Klein |
| 8,492,427 B2 | 7/2013 | Gancia et al. |
| 8,563,741 B2 | 10/2013 | Qian et al. |
| 8,648,104 B2 | 2/2014 | Du et al. |
| 8,673,848 B2 | 3/2014 | Zecri et al. |
| 8,742,133 B2 | 6/2014 | Ying et al. |
| 8,778,977 B2 | 7/2014 | Lind et al. |
| 8,835,464 B2 | 9/2014 | Sun et al. |
| 8,883,827 B2 | 11/2014 | Holsworth et al. |
| 9,156,796 B2 | 10/2015 | Hachtel et al. |
| 9,573,936 B2 | 2/2017 | Chen et al. |
| 2002/0107245 A1 | 8/2002 | Wagle et al. |
| 2004/0167188 A1 | 8/2004 | Xin et al. |
| 2005/0075275 A1 | 4/2005 | Albrecht et al. |
| 2005/0165015 A1 | 7/2005 | Ncube |
| 2005/0170431 A1 | 8/2005 | Ibrahim et al. |
| 2005/0288347 A1 | 12/2005 | Hodge et al. |
| 2006/0156480 A1 | 7/2006 | Lim |
| 2006/0281749 A1 | 12/2006 | Wagle et al. |
| 2008/0153869 A1 | 6/2008 | Bressi et al. |
| 2008/0249131 A1 | 10/2008 | Girardet et al. |
| 2009/0318438 A1 | 12/2009 | Chen et al. |
| 2010/0130472 A1 | 5/2010 | Young et al. |
| 2010/0249185 A1 | 9/2010 | Du et al. |
| 2010/0280032 A1 | 11/2010 | Zhou et al. |
| 2011/0046125 A1 | 2/2011 | Ying |
| 2011/0158825 A1 | 6/2011 | Byrd et al. |
| 2011/0190257 A1 | 8/2011 | Heald et al. |
| 2011/0207788 A1 | 8/2011 | Amberg et al. |
| 2011/0265691 A1 | 11/2011 | Orth et al. |
| 2012/0094837 A1 | 4/2012 | Muhlthau et al. |
| 2012/0208828 A1 | 8/2012 | Holsworth et al. |
| 2012/0238576 A1 | 9/2012 | Tao et al. |
| 2013/0034536 A1 | 2/2013 | Gedulin |
| 2013/0040950 A1 | 2/2013 | Short et al. |
| 2013/0059807 A1 | 3/2013 | Gedulin et al. |
| 2013/0059845 A1 | 3/2013 | Song et al. |
| 2013/0108573 A1 | 5/2013 | Gedulin et al. |
| 2013/0109671 A1 | 5/2013 | Gedulin et al. |
| 2013/0150385 A1 | 6/2013 | Blackman et al. |
| 2013/0156755 A1 | 6/2013 | Blackman et al. |
| 2013/0266636 A1 | 10/2013 | Cheresh et al. |
| 2013/0303505 A1 | 11/2013 | Bollu et al. |
| 2014/0005181 A1 | 1/2014 | Smith et al. |
| 2016/0058705 A1 | 3/2016 | Rajadas et al. |
| 2016/0060349 A1 | 3/2016 | Van Schravendijk et al. |
| 2016/0340336 A1 | 11/2016 | Chen et al. |
| 2016/0355507 A1 | 12/2016 | Johnson et al. |
| 2017/0035744 A1 | 2/2017 | Chen et al. |
| 2017/0037026 A1 | 2/2017 | Chen et al. |
| 2017/0042871 A1 | 2/2017 | Chen et al. |
| 2017/0042872 A1 | 2/2017 | Chen et al. |
| 2017/0042897 A1 | 2/2017 | Chen et al. |
| 2017/0044131 A1 | 2/2017 | Chen et al. |
| 2017/0281625 A1 | 10/2017 | Chen et al. |
| 2017/0355734 A1 | 12/2017 | Llorens-Cortez et al. |

FOREIGN PATENT DOCUMENTS

| | | |
|---|---|---|
| DE | 3928605 A1 | 3/1991 |
| DE | 4035141 A1 | 5/1992 |
| EP | 0330959 A2 | 2/1989 |
| EP | 0409332 A2 | 1/1991 |
| EP | 0484750 A1 | 10/1991 |
| JP | 2003-5356 A | 8/2003 |
| JP | 2003-321456 A | 11/2003 |
| JP | 2005-170939 A | 6/2005 |
| WO | 91/11909 A1 | 8/1991 |
| WO | 99/43671 A1 | 9/1999 |
| WO | 01/87855 A1 | 11/2001 |
| WO | 2005/039569 A1 | 5/2005 |
| WO | 2006/026488 A1 | 3/2006 |
| WO | 2006/055760 A1 | 5/2006 |
| WO | 2006/080533 A1 | 8/2006 |
| WO | 2006/095783 A1 | 9/2006 |
| WO | 2006/100588 A1 | 9/2006 |
| WO | 2006/109817 A1 | 10/2006 |
| WO | 2007/007688 A1 | 1/2007 |
| WO | 2007/139952 A2 | 12/2007 |
| WO | 2007/139967 A2 | 12/2007 |
| WO | 2008/008375 A2 | 1/2008 |
| WO | 2008/021364 A2 | 2/2008 |
| WO | 2008/103352 A1 | 8/2008 |
| WO | 2009/075890 A2 | 6/2009 |
| WO | 2009/115503 A1 | 9/2009 |
| WO | 2010/017545 A2 | 2/2010 |
| WO | 2011/146801 A1 | 11/2011 |
| WO | 2012/076898 A1 | 6/2012 |
| WO | 2012/116247 A1 | 8/2012 |
| WO | 2013/067162 A1 | 5/2013 |
| WO | 2013/067165 A1 | 5/2013 |
| WO | 2013/074594 A1 | 5/2013 |
| WO | 2013/106437 A1 | 7/2013 |
| WO | 2013/106614 A1 | 7/2013 |
| WO | 2013/111110 A2 | 8/2013 |
| WO | 2013/148857 A1 | 10/2013 |
| WO | 2013/184755 A1 | 12/2013 |
| WO | 2014/044738 A1 | 3/2014 |
| WO | 2014/099984 A1 | 6/2014 |
| WO | 2014/150326 A1 | 9/2014 |
| WO | 2014/194270 A1 | 12/2014 |
| WO | 2015/140296 A2 | 9/2015 |
| WO | 2015/163818 A1 | 10/2015 |
| WO | 2015/184011 A2 | 12/2015 |
| WO | 2015/188073 A1 | 12/2015 |
| WO | 2017/066402 A1 | 4/2017 |
| WO | 2017/091513 A1 | 6/2017 |
| WO | 2017/096130 A1 | 6/2017 |
| WO | 2017/100558 A1 | 6/2017 |
| WO | 2017/106396 A1 | 6/2017 |
| WO | 2017/165640 A1 | 9/2017 |

(56) References Cited

FOREIGN PATENT DOCUMENTS

| | | |
|---|---|---|
| WO | 2017/174758 A1 | 10/2017 |
| WO | 2017/218617 A1 | 12/2017 |
| WO | 2017/218633 A1 | 12/2017 |

OTHER PUBLICATIONS

SciFinder Structure Search with Substances Performed May 20, 2016.

SciFinder Structure Search with References Performed May 20, 2016.

SciFinder Structure Search Sulfonamide Tail with Substance Performed May 12, 2016.

Berry, M. F. et al., "Apelin Has In Vivo Inotropic Effects on Normal and Failing Hearts," Circulation 110, pp. II187-II193, (2004).

Cheng, D. et al., "Discovery of Pyridinyl Acetamide Derivatives as Potent, Selective, and Orally Bioavailable Porcupine Inhibitors," ACS Med Chem Letters issn:19485875; doi:10.1021/acsmedchemlett.6b00038; Iccn:2009200243; oclcnum:455500725; serissn:1948-5875; itc:84452717; itcp:10547084 (2016).

Chun, H. et al., "Apelin Signaling Antagonizes ANG II Effects in Mouse Models of Atherosclerosis," J. Clin. Invest. 118(10), pp. 3343-3354 (2008).

Japp, A. G. et al., "Acute Cardiovascular Effects of Apelin in Humans," Circulation 121, pp. 1818-1827 (2010).

Modzelewska-Banachiewicz et al., "Synthesis and Biological Action of 3-4-Disubstituted 5- Arylsulphonylamino-1,2,4-triazoles," Pharmazie 54, pp. 588-589 (1999).

Pauli, A. et al., "Toddler: An Embryonic Signal That Promotes Cell Movement via Apelin Receptors," Science 343, pp. 1248636-0-1248636-8 (2014).

Siddiquee, K. et al., "The Apelin receptor Inhibits the Angiotensin II Type 1 Receptor Via Allosteric Trans-Inhibition," Br. J. Pharmacol. 168, pp. 1104-1117 (2013).

Siddiquee, K. et al., "Apelin Protects Against Angiotensin II-Induced Cardiovascular Fibrosis and Decreases Plasminogen Activator Inhibitor Type-1 Production," J. Hypertension 29, pp. 724-731 (2011).

Tatemoto, K. et al., "Isolation and Characterization of a Novel Endogenous Peptide Ligand for the Human APJ Receptor," Bioch. Biophys. Res. Comm., 251, pp. 471-476 (1998).

Hosoya, M. et al., "Molecular and Functional Characteristics of APJ. Tissue Distribution of mRNA and Interaction with the Endogenous Ligand Apelin," J. Biol. Chem. 275(28), pp. 21061-21067 (2000).

Maguire, J. J. et al., "[Pyr$^1$]Apelin-13 Identified as the Predominant Apelin Isoform in the Human Heart: Vasocactive Mechanism and Inotropic Action in Disease," Hypertension 54(3), pp. 598-604, (2009).

Barnes, G. et al., "Translational Promise of the Apelin-APJ System," Heart 96(13), pp. 1011-1016 (2010).

Kawamata, Y. et al., "Molecular Properties of Apelin: Tissue Distribution and Receptor Binding," Biochemica et Biophysica Acta 1538(2-3), pp. 162-171 (2001).

Nishizawa, N. et al., "High Potency Analog of Apelin, A Ligand of Orphan GPCT APJ," T Shiori (ed.) Petptide Science 2000: Proceedings of the 37th Japanese Peptide Symposium, pp. 151-154 (2000).

Medhurst, A. D. et al., "Pharmacological and Immunohistochemical Characteization of the APJ Receptor and its Endogenous Ligand Apelin," J. Neurochem. 84(5), pp. 1162-1172 (2003).

Hamada, J. et al., "Evaluation of Novel Cyclic Analogoues of Apelin," Int. J. Mol. Med. 22, pp. 547-552 (2008).

Murza, A. et al., "Elucidation of the Structure-Activity Relationships of Apelin: Influence of Unnatural Amino Acids on Binding, Signaling, and Plasma Stability," ChemMedChem 7(2), pp. 318-325 (2012).

Thomas, J. B. et al., "Identification of 1-({[1-(4-Fluorophenyl)-5-(2-methoxyphenyl)-1H-pyrazol-3-yl]carbonyl}amino)cyclohexane Carboxylic Acid as a Selective Nonpeptide Neurotensin Receptor Type 2 Compound," J. Med. Chem. 57, pp. 5318-5332 (2014).

Thomas, J.B. et al., "Identification of N-[5-{[(4-Methylphenyl)sulfonyl]amino}-3- (trifluoroacetyl)-1H-indol-1-yl)acetyl]-L-leucine (NTRC-824), a Neurotensin-like Nonpeptide Compound Selective for the Neurotensin Receptor Type 2," J. Med. Chem. 57, pp. 7472-7477 (2014).

Thomas, J. B. et al., "The Amide Linker in Nonpeptide Neurotensin Receptor Ligands Plays a Key Role in Calcium Signaling at the Neurotensin Receptor Type 2," Bioorg. Med. Chem. Lett. 25, pp. 2060-2064 (2015).

Thompson, M. E. "α,N-Alkanesulfonamide Dianions: Formation and Chemoselective C-Alkylation," J. Org. Chem. 49, pp. 1700-1703 (1984).

Wang, Y-G. et al., "Selenium-Based Safety-Catch Linker: Solid-Phase Synthesis of Vinyl-Substituted Oxadiazoles and Triazoles," J. Comb. Chem. 9, pp. 513-519 (2007).

Singh, O. M. et al., "A Facile One-Pot Synthetic Method for 1,2,4-Triazoles and 1,3-Disubstituted Thioureas," J. Chem. Res. pp. 483-485 (2006).

Carlsen, P.J.J. et al., "Synthesis of Unsymmetrically Substituted 4H-1,2,4-Triazoles," J. Heterocyclic Chem. 31, pp. 805-807 (1994).

Navidpour, L. et al., "Synthetic Approaches Towards the Sulfonamide Substituted-4,5-diaryl-4H-1,2,4-triazole-3-thiones," J. Heterocyclic Chem. 44, pp. 1323-1331 (2007).

Hassan, A. A. et al., "Thiosemicarbazides in Heterocyclization," J. Heterocyclic Chem. 48, pp. 495-516 (2011).

Sugane, T. et al., "Synthesis and Biological Evaluation of 3-Biphenyl-4-yl-4-phenyl-4H-1,2,4-triazoles as Novel Glycine Transporter 1 Inhibitors," J. Med. Chem. 54, pp. 387-391 (2011).

Ivanova, N. V. et al., "A Convenient Synthesis of 4,5-Disubstituted 1,2,4-Triazoles Functionalized in Position 3," Synthesis 1, pp. 156-160 (2005).

Modzelewska-Banaschiewicz, B et al., "Antiviral Activity of the Products of Cyclization of Dimethyl 2[1-arylamino-1-arylmethylideine)hydrazono]succinate," Eur. J. Med. Chem. 36, pp. 93-99 (2001).

SciFinder Structure Search with Substances Performed Sep. 1, 2016.

SciFinder Structure Search with References Performed Sep. 1, 2016.

Sitarz, M. et al., "2. Studies on Pyrazine Derivatives, Part 39. Synthesis, Reactions and Tuberculostatic Activity of 3-Pyrazinyl-1,2,4-triazolo[4.3-a]-1,3-diazacycloalkanes," Chemistry of Heterocyclic Compounds, 41(2), pp. 200-207 (2005).

Johnson, M. G. et al., "Convenient Route to Secondary Sulfinates: Application to the Stereospecific Synthesis of α-C-Chiral Sulfonamides," Organic Letters 16(23), pp. 6248-6251 (2014).

Enders, D. et al., "Asymmetric Synthesis of α-Substituted N-Methylsulfonamides," Helvetica Chimica Acta, 85, pp. 3657-3677 (2002).

Zhou, T. et al., "Enantioselective Synthesis of Chiral Sulfones by Ir-Catalyzed Asymmetric Hydrogenation: A Facile Approach to the Preparation of Chiral Allylic and Homoallylic Compounds," J. Am. Chem Soc., 134, pp. 13592-13595 (2012).

Koch, F. M. et al., "Lewis Acid/Base Catalyzed [2+2]-Cycloaddition of Sulfenes and Aldehydes: A Versatile Entry to Chiral Sulfonyl and Sulfinyl Derivatives," Chem. Eur. J., 17, pp. 3679-03692 (2011).

Choi, J. et al., "Stereoconvergent Arylations and Alkenylations of Unactivated Alkyl Electrophiles: Catalytic Enantioselective Synthesis of Secondary Sulfonamides and Sulfones," J. Am. Chem. Soc., pp. 12161-12165 (2014).

HETEROCYCLIC TRIAZOLE COMPOUNDS AS AGONISTS OF THE APJ RECEPTOR

CROSS REFERENCES TO RELATED APPLICATIONS

This application claims the benefit of U.S. Provisional Application No. 62/330,923, filed on May 3, 2016, and U.S. Provisional Application No. 62/422,763, filed on Nov. 16, 2016, both of which are hereby incorporated by reference in their entireties and for all purposes as if fully set forth herein.

FIELD OF THE INVENTION

The present invention relates to compounds capable of acting as agonists of the APJ Receptor, and compositions that include compounds that are agonists of the APJ Receptor. The compounds and compositions may be used to activate the APJ Receptor and to treat various disease conditions. An example of one area where such compounds may be used is in the treatment of cardiovascular conditions. In particular, the compounds may be used to improve contractility and ejection fraction in subjects with chronic heart failure and may be used to treat patients with heart failure with reduced ejection fraction and patients with heart failure with preserved ejection fraction.

BACKGROUND OF THE INVENTION

Apelin is the endogenous ligand for APJ (APLNR, angiotensin receptor like-1). The APJ receptor is a member of the rhodopsin-like G protein-coupled receptor (GPCR) family. The apelin/APJ system has been observed in many tissues such as heart, kidney, pancreas, lung and the central nervous system. This suggests diverse roles of the system in the physiology and pathology of mammals.

Apelin peptides are processed from a 77 residue pre-pro form into smaller bioactive fragments, mainly a 36 residue form (Apelin 42-77—also referred to as Apelin-36) and a smaller 13 residue polypeptide (Apelin 65-77—also referred to as Apelin-13) Hosoya et al., J. Biol. Chem. 275:21061-21067, 2000. Apelin peptides were previously determined to be endogenous ligands for the orphan APJ receptor, a member of the seven transmembrane G-protein-coupled receptor superfamily. Tatemoto et al., Biochem. Biophysi. Res. Commun. 251:471-476, 1998. One of the shorter more active isoforms identified, pyroglutamated apelin-13 ([PE65]Apelin-13 (65-77), has been reported to be the most potent and abundant form of apelin in cardiac tissue. Maguire et al., Hypertension 54:598-604, 2009. In vitro and preclinical models have suggested that the apelin/APJ system has a role in cardiovascular homeostasis as well as metabolism. Barnes et al., Heart 96:1011-1016, 2010. Circulating apelin levels are transient and Apelin-13 has a brief plasma half-life of <5 min leading to short-lived cardiovascular effects.

In vitro, exogenous apelin increases contractility at subnanomolar concentrations in atrial strips and whole rat hearts, and increases sarcomere shortening by up to 140% in isolated cardiomyocytes. Barnes et al., Heart 96:1011-1016, 2010. Apelin also has a potent inotropic effect in an ex vivo isolated heart assay. In vivo, acute apelin infusion restores ejection fraction, increases cardiac output and reduces left ventricular end-diastolic pressure in rats with chronic heart failure. Berry et al., Circulation 110:187-193, 2004. Exogenous apelin potently enhances myocardial contractility without inducing left ventricular hypertrophy concomitant with reduction in ventricular preload and afterload. Barnes et al., Heart 96:1011-1016, 2010.

Studies from Kawamata et al and Hosoya et al have shown that that shorter peptide apelin-13 had approximately a 3.5-fold higher in vitro affinity to the APJ receptor than apelin-36. Kawamata et al., BBA 1538: 162-171, 2001, Hosoya et al., JBC 275: 21061-21067. Apelin-13 analogues were reported having a single substitution with either canonical or non-canonical amino acids. The authors also reported double and triple substitutions in apelin 66-77 and apelin 63-77, but not in apelin-13. The emphasis was on peptides reported to have higher in vitro affinity and potency than apelin-13. Nishizawa et al., in: T. Shioiri (ed.), Peptide Science 2000: Proceedings of the 37$^{th}$ Japanese Peptide Symposium, pp. 151-154. Several if not all of these modified peptides are reported in later studies. U.S. Pat. No. 7,635,751.

In a 2003 study (Medhurst et al., J. Neurochemistry 84:1162-1172, 2003) in vitro activity of apelin-36, apelin-17 and apelin-13 was compared. It was concluded that all three peptides were approximately equipotent. C-terminal amidation resulted in about a 14-fold decrease in affinity. A more recent study (Hamada et al., J. Mol. Med. 22:547-552, 2008) reported cyclic analogues of apelin-13. When tested for in vitro activity all three analogues maintained function activity, although with reduced potency relative to apelin-13.

A shortened 12 amino acid-apelin peptide having ligand activity on APJ was reported in a 2009 patent (U.S. Pat. No. 7,635,751). The peptide could have a substitution of one non-canonical amino acid. In another application, WO 2013/111110 A2 and U.S. Pat. No. 8,673,848, cyclic mimetics of apelin have also been reported.

Another study reported synthesizing analogs of apelin-13 with amino acid substitutions with non-canonical amino acids at the C-terminal end of the molecule, but no pegylation at the N- or C-terminus or another site specific location. The use of internal PEG spacers (short PEG (n=4 or 6), however, was also reported in lower activity peptide analogs with deletions in the middle of the sequence that contained fewer amino acid residues than apelin-13. Murza et al. ChemMedChem 7:318-325, 2012. Additionally, PCT/US2013/075773 describes a group of modifications, including substitution of non-canonical amino acids and changes at the N- and C-terminal of the apelin molecule that can affect, inter alia, the potency of the molecule. The increased potency can be a result of increased half-life or decreased degradation relative to wild-type apelin.

Despite the advancements that have been made with respect to peptides, a need exists for small molecule agonists of the APJ receptor. However, some progress has been made in this area. For example, WO 2014/044738 discloses various benzimidazole-carboxylic acid amide derivatives as modulators of the APJ Receptor. Other small molecule agonists of the APJ receptor are disclosed in U.S. Pat. Appl. Pub. No. US 2016/0340336 and WO 2016/187308. Still other small molecule agonists of the APJ receptor are disclosed in WO 2015/184011 and in WO 2015/188073.

A need continues to exist for agonists of the APJ receptor that may be used to treat various cardiovascular and other conditions. The present application discloses such agonists of the APJ receptor s that may be suitable for use as therapeutic agents in treating a variety of conditions. These compounds may find particular benefit in treating cardiovascular conditions. For example, such compounds may be beneficial in treating conditions such as chronic systolic heart failure and chronic diastolic heart failure.

SUMMARY OF THE INVENTION

In one aspect, the invention provides a compound of Formula I or Formula II:

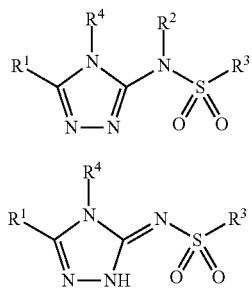

or a pharmaceutically acceptable salt thereof, a tautomer thereof, a pharmaceutically acceptable salt of the tautomer, a stereoisomer of any of the foregoing, or a mixture thereof, wherein:

$R^1$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1a}$ may also be oxo unless $R^1$ is a 6-membered heterocyclic group that includes one N atom and includes at least one double bond, and further wherein two $R^{1a}$ substituents on adjacent carbon atoms or on an adjacent carbon atom and an adjacent N atom of a 5- or 6-membered heterocyclic $R^1$ group may join to form a 6 membered ring that may be saturated, partially saturated, or aromatic and may include 0, 1, or 2 N atoms and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O) ($C_1$-$C_6$ alkyl), —C(=O)—($C_1$-$C_6$ alkyl), —C(=O) OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, or a monocyclic 3-6 membered cycloalkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents; and $R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent.

In one aspect, the invention provides a compound of Formula I or Formula II:

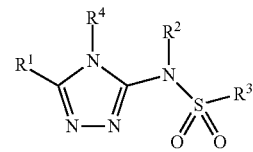

I

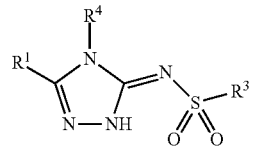

II or a pharmaceutically acceptable salt thereof, a tautomer thereof, a pharmaceutically acceptable salt of the tautomer, a stereoisomer of any of the foregoing, or a mixture thereof, wherein:

$R^1$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1a}$ may also be oxo unless $R^1$ is a 6-membered heterocyclic group that includes one N atom and includes at least one double bond, and further wherein two $R^{1a}$ substituents on adjacent carbon atoms or on an adjacent carbon atom and an adjacent N atom of a 5- or 6-membered heterocyclic $R^1$ group may join to form a 6 membered ring that may be saturated, partially saturated, or aromatic and may include 0, 1, or 2 N atoms and may further optionally be substituted with 1 or 2 $R^{1a'}$ substituent and may include an oxo substituent if the ring is not an aromatic ring and further wherein two substituents on adjacent carbon atoms or on an adjacent carbon atom and an adjacent N atom of a 5- or 6-membered heterocyclic $R^1$ group may join to form a 5 membered ring that may be saturated, partially saturated, or aromatic and may include 0, 1, or 2 heteroatoms selected from N, O, or S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —(CR$^{3b}$R$^{3c}$)-Q, a group of formula —(CR$^{3d}$R$^{3e}$)–(CR$^{3f}$R$^{3g}$)-Q, a group of formula —(CR$^{3d}$R$^{3e}$)–(CR$^{3f}$R$^{3g}$)—C(=O)-Q, a group of formula —(CR$^{3d}$R$^{3e}$)–(CR$^{3f}$R$^{3g}$)—CH(OH)-Q, a group of formula —(CR$^{3d}$R$^{3e}$)–(CR$^{3f}$R$^{3g}$)–(CR$^{3f}$R$^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, $C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —CN, —$C_1$-$C_6$ alkyl, —$C_1$-$C_6$ haloalkyl, —$C_1$-$C_6$ perhaloalkyl, —OH, alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, and the heterocyclyl $R^4$ group are unsubstituted or are substituted with 1, 2, 3, or 4 $R^{4a}$ substituents, and further wherein the cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S and is unsaturated or partially unsaturated and is optionally substituted with 1 or 2 oxo substituents, and further wherein the heterocyclyl of the $R^4$ group may be further substituted with 1 oxo substituent;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, heterocyclyl, a monocyclic 3-6 membered cycloalkyl group, or a 5 or 6 membered heteroaryl ring containing 1, 2, or 3 heteroatoms selected from N, O, or S, wherein the heterocyclyl of the —($C_1$-$C_6$ alkyl)-heterocyclyl and heterocyclyl $R^{4b}$ groups is a 3-6 membered ring comprising 1 or 2 heteroatoms independently selected from N, O, or S and is unsaturated or partially unsaturated and is optionally substituted with 1 or 2 oxo substituents, and further wherein the phenyl and heteroaryl $R^{4b}$ groups are unsubstituted or are substituted with 1 or 2 $R^{4aa}$ substituents;

$R^{4c}$ in each instance is independently selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a monocyclic 3-6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a monocyclic 3-6 membered cycloalkyl $R^{4c}$ group, the 3 to 6 membered heterocyclyl $R^{4c}$ group, the phenyl $R^{4c}$ group, or the a 5 or 6 membered heteroaryl $R^{4c}$ ring are unsubstituted or are substituted with 1 or 2 $R^{4aa}$ substituents; and further wherein the 3 to 6 membered cycloalkyl $R^{4c}$ group and the 3 to 6 membered heterocyclyl $R^{4c}$ group may optionally be additionally substituted with an oxo substituent; and $R^{4aa}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), or —S(=O)$_2$—($C_1$-$C_6$ alkyl).

Numerous other embodiments of the compound of Formula I and Formula II are set forth herein.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments.

In other embodiments, the invention provides a method of treating a cardiovascular condition. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides a method of improving cardiac contractility in a subject. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments.

In still other embodiments, the invention provides a method of increasing ejection fraction in a subject suffering from a cardiovascular condition. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In such embodiments, the ejection fraction is increased in the subject after administration.

In still other embodiments, the invention provides a method of treating a condition in a subject where it is desired to activate the APJ Receptor. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the condition is obesity or diabetes whereas in other such embodiments, the condition is diabetic nephropathy or chronic kidney disease.

In other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for use in treating a cardiovascular condition. In some such embodiments, the cardiovascular condition is heart failure.

In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the cardiac contractility in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the ejection fraction in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for treating a condition in a subject where it is desired to activate the APJ Receptor. In some such embodiments, the condition is obesity or diabetes whereas in other such embodiments, the condition is diabetic nephropathy or chronic kidney disease.

Other objects, features and advantages of the invention will become apparent to those skilled in the art from the following description and claims.

DETAILED DESCRIPTION OF THE INVENTION

Figure 1A:
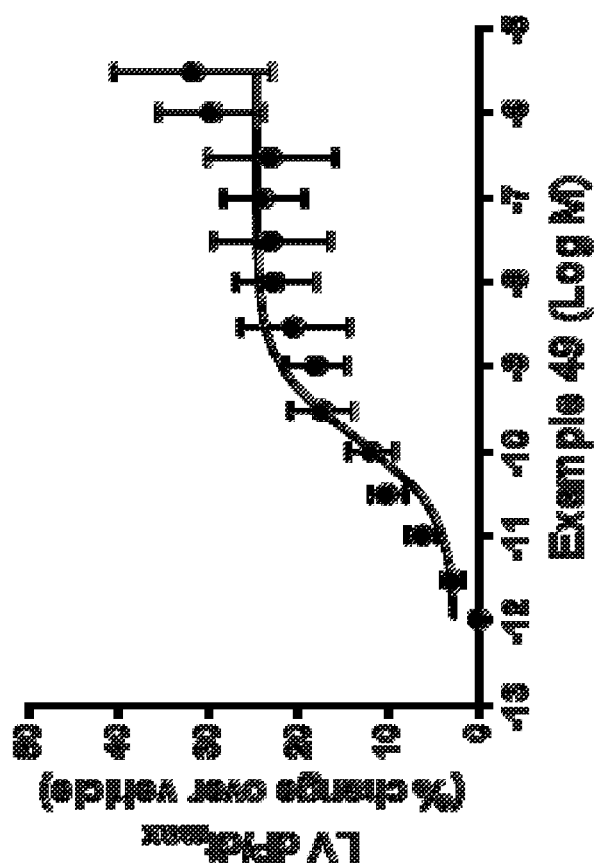
FIG. 1A is a graph of left ventricular dP/dt$_{max}$ as a function of concentration of Example 49.0 compared with vehicle in ex vivo naive Sprague Dawley rat hearts obtained using the Langendorff apparatus. This shows Example 49.0 increases load independent cardiac contractility in isolated perfused rat hearts.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

The term "comprising" is meant to be open ended, i.e., all encompassing and non-limiting. It may be used herein synonymously with "having" or "including". Comprising is intended to include each and every indicated or recited component or element(s) while not excluding any other components or elements. For example, if a composition is said to comprise A and B. This means that the composition has A and B in it, but may also include C or even C, D, E, and other additional components.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. For example, when $R^4$ is a phenyl group and is substituted with two groups bonded to the C atoms adjacent to the point of attachment to the N atom of the triazole, then rotation of the phenyl may be restricted. In some instances, the barrier of rotation is high enough that the different atropisomers may be separated and isolated.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

As described above, this invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula.

As noted above, compounds of the invention may exist in multiple tautomeric forms. This is particularly true in compounds of Formula I where $R^2$ is H. These forms are illustrated below as Tautomer A and Tautomer B:

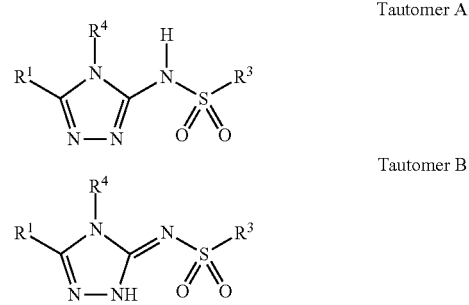

Compounds of the invention are depicted structurally and named as compounds in the "Tautomer A" form. However, it is specifically contemplated and known that the compounds exist in "Tautomer B" form and thus compounds in "Tautomer B" form are expressly considered to be part of the invention. For this reason, the claims refer to compounds of Formula I and Formula II. Depending on the compound, some compounds may exist primarily in one form more than another. Also, depending on the compound and the energy required to convert one tautomer to the other, some compounds may exist as mixtures at room temperature whereas others may be isolated in one tautomeric form or the other. Examples of other tautomers associated with compounds of the invention are those with a pyridone group (a pyridinyl) for which hydroxypyridine is a tautomer and compounds with a ketone group with the enol tautomer. Examples of these are shown below.

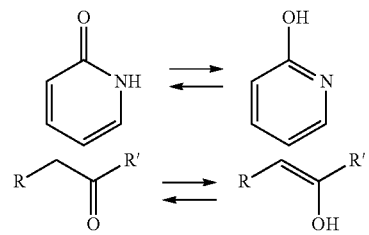

Compounds of the present disclosure include, but are not limited to, compounds of Formula I and Formula II and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as ($C_1$-$C_4$)alkyl esters. In other embodiments, the term "compound" encompasses the compound itself, pharmaceutically acceptable salts thereof, tautomers of the compound, pharmaceutically acceptable salts of the tautomers.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain naturally occurring or unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, if a variable is said or shown to be H, this means that variable may also be deuterium (D) or tritium (T).

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 10 carbon atoms or 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a $(C_1$-$C_6)$alkyl group and an alkyl group having 1 to 4 carbon atoms may be referred to as a $(C_1$-$C_4)$alkyl. This nomenclature may also be used for alkyl groups with differing numbers of carbon atoms. The term "alkyl may also be used when an alkyl group is a substituent that is further substituted in which case a bond between a second hydrogen atom and a C atom of the alkyl substituent is replaced with a bond to another atom such as, but not limited to, a halogen, or an O, N, or S atom. For example, a group —O—($C_1$-$C_6$ alkyl)-OH will be recognized as a group where an —O atom is bonded to a $C_1$-$C_6$ alkyl group and one of the H atoms bonded to a C atom of the $C_1$-$C_6$ alkyl group is replaced with a bond to the O atom of an —OH group. As another example, a group —O—($C_1$-$C_6$ alkyl)-O—($C_1$-$C_6$ alkyl) will be recognized as a group where an —O atom is bonded to a first $C_1$-$C_6$ alkyl group and one of the H atoms bonded to a C atom of the first $C_1$-$C_6$ alkyl group is replaced with a bond to a second O atom that is bonded to a second $C_1$-$C_6$ alkyl group.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl(allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a $(C_2$-$C_6)$alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —$(C_2$-$C_6)$alkynyl group.

"Alkoxy" refers to a radical —OR where R represents an alkyl group as defined herein. Representative examples include, but are not limited to, methoxy, ethoxy, propoxy, butoxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O—($C_1$-$C_6$) alkyl or as —O—($C_1$-$C_6$ alkyl) groups. In some embodiments, an alkoxy group may include 1 to 4 carbon atoms and may be designated as —O—($C_1$-$C_4$) alkyl or as —O—($C_1$-$C_4$ alkyl) groups.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is a heteroaryl group, not an aryl group, as defined herein.

"Carbonyl" refers to the radical —C(O) which may also be referred to as —C(=O) group.

"Carboxy" refers to the radical —C(O)OH which may also be referred to as —C(=O)OH.

"Cyano" refers to the radical —CN.

"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring. For example, a cycloalkyl group having 3 to 8 ring members may be referred to as a $(C_3$-$C_8)$cycloalkyl, a cycloalkyl group having 3 to 7 ring members may be referred to as a $(C_3$-$C_7)$cycloalkyl and a cycloalkyl group having 4 to 7 ring members may be referred to as a $(C_4$-$C_7)$cycloalkyl. In certain embodiments, the cycloalkyl group can be a $(C_3$-$C_{10})$cycloalkyl, a $(C_3$-$C_8)$cycloalkyl, a $(C_3$-$C_7)$cycloalkyl, a $(C_3$-$C_6)$cycloalkyl, or a $(C_4$-$C_7)$cycloalkyl group and these may be referred to as $C_3$-$C_{10}$ cycloalkyl, $C_3$-$C_8$ cycloalkyl, $C_3$-$C_7$ cycloalkyl, $C_3$-$C_6$ cycloalkyl, or $C_4$-$C_7$ cycloalkyl groups using alternative language.

"Heterocyclyl" and "heterocyclic" refer to a cyclic group that includes at least one saturated, partially unsaturated, but non-aromatic, cyclic ring. Heterocyclyl groups include at least one heteroatom as a ring member. Typical heteroatoms include, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

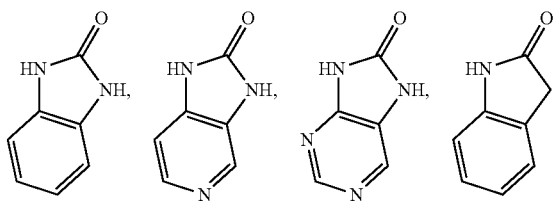 [SMILES: O=c1[nH]c2ccccc2[nH]1 ; O=c1[nH]c2ccncc2[nH]1 ; O=c1[nH]c2cncnc2[nH]1 ; O=C1Cc2ccccc2N1]

In some embodiments, a heterocyclyl group includes 5 to 10 ring members of which 1, 2, 3 or 4 or 1, 2, or 3 are heteroatoms independently selected from O, S, or N. In other embodiments, a heterocyclyl group includes 3 to 7 ring members of which 1, 2, or 3 heteroatom are independently selected from O, S, or N. In such 3-7 membered heterocyclyl groups, only 1 of the ring atoms is a heteroatom when the ring includes only 3 members and includes 1 or 2 heteroatoms when the ring includes 4 members. In some embodiments, a heterocyclyl group includes 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Heterocyclyl groups may be fully saturated, but may also include one or more double bonds. Examples of such heterocyclyl groups include, but are not limited to, 1,2,3,6-tetrahydropyridinyl, 3,6-dihydro-2H-pyranyl, 3,4-dihydro-2H-pyranyl, 2,5-dihydro-1H-pyrolyl, 2,3-dihydro-1H-pyrolyl, 1H-azirinyl, 1,2-dihydroazetenyl, and the like. Substituted heterocyclyl also includes ring systems substituted with one or more oxo (=O) or oxide (—O⁻) substituents, such as piperidinyl N-oxide, morpholinyl-N-oxide, 1-oxo-1-thiomorpholinyl, pyridinonyl, benzimidazolonyl, benzo[d]oxazol-2(3H)-only, 3,4-dihydroisoquinolin-1(2H)-only, indolin-only, 1H-imidazo[4,5-c]pyridin-2(3H)-only, 7H-purin-8(9H)-only, imidazolidin-2-only, 1H-imidazol-2(3H)-only, 1,1-dioxo-1-thiomorpholinyl, and the like. In heterocyclyl group containing a sulfur atom, the sulfur atom may be bonded to 0, 1, or 2 O atoms in addition to the adjacent ring members such that the sulfur may in various oxidation states. For example, a saturated 5-membered heterocycle containing one heteroatom which is a S may include the following heterocycles.

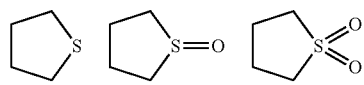

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, or N, with the remaining ring atoms being carbon. In monocyclic heteroaryl groups, the single ring is aromatic and includes at least one heteroatom. In some embodiments, a monocyclic heteroaryl group may include 5 or 6 ring members and may include 1, 2, 3, or 4 heteroatoms, 1, 2, or 3 heteroatoms, 1 or 2 heteroatoms, or 1 heteroatom where the heteroatom(s) are independently selected from O, S, or N. In bicyclic aromatic rings, both rings are aromatic. In bicyclic heteroaryl groups, at least one of the rings must include a heteroatom, but it is not necessary that both rings include a heteroatom although it is permitted for them to do so. For example, the term "heteroaryl" includes a 5- to 7-membered heteroaromatic ring fused to a carbocyclic aromatic ring or fused to another heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient" refers to a broad range of ingredients that may be combined with a compound or salt of the present invention to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. As those skilled in the art will recognize this amount is typically not limited to a single dose, but may comprise multiple dosages over a significant period of time as required to bring about a therapeutic or prophylactic response in the subject. Thus, a "therapeutically effective amount" is not limited to the amount in a single capsule or tablet, but may include more than one capsule or tablet, which is the dose prescribed by a qualified physician or medical care provider. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments

The embodiments listed below are presented in numbered form for convenience and in ease and clarity of reference in referring back to multiple embodiments.

In an first embodiment, the invention provides a compound of Formula I or Formula II:

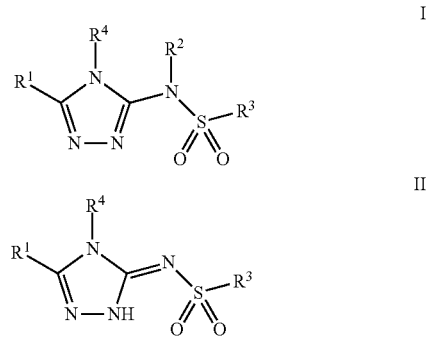

or a pharmaceutically acceptable salt thereof, a tautomer thereof, a pharmaceutically acceptable salt of the tautomer, a stereoisomer of any of the foregoing, or a mixture thereof, wherein:

$R^1$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1a}$ may also be oxo unless $R^1$ is a 6-membered heterocyclic group that includes one N atom and includes at least one double bond, and further wherein two $R^{1a}$ substituents on adjacent carbon atoms or on an adjacent carbon atom and an adjacent N atom of a 5- or 6-membered heterocyclic $R^1$ group may join to form a 6 membered ring that may be saturated, partially saturated, or aromatic and may include 0, 1, or 2 N atoms and may further optionally be substituted with 1 or 2 $R^{1a'}$ substituent and may include an oxo substituent if the ring is not an aromatic ring and further wherein two $R^{1a}$ substituents on adjacent carbon atoms or on an adjacent carbon atom and an adjacent N atom of a 5- or 6-membered heterocyclic $R^1$ group may join to form a 5 membered ring that may be saturated, partially saturated, or aromatic and may include 0, 1, or 2 heteroatoms selected from N, O, or S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —(CR$^{3b}$R$^{3c}$)-Q, a group of formula —(CR$^{3d}$R$^{3e}$)–(CR$^{3f}$R$^{3g}$)-Q, a group of formula —(CR$^{3d}$R$^{3e}$)–(CR$^{3f}$R$^{3g}$)—C(=O)-Q, a group of formula —(CR$^{3d}$R$^{3e}$)–(CR$^{3f}$R$^{3g}$)—CH(OH)-Q, a group of formula —(CR$^{3d}$R$^{3e}$)–(CR$^{3f}$R$^{3g}$)–(CR$^{3f}$R$^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), perhaloalkyl), alkyl)-OH, alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), ($C_1$-$C_6$ perhaloalkyl), —O—($C_1$-$C_6$ alkyl)-OH, alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), ($C_1$-$C_6$ perhaloalkyl), —O—($C_1$-$C_6$ alkyl)-OH, alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, and the heterocyclyl $R^4$ group are unsubstituted or are substituted with 1, 2, 3, or 4 $R^{4a}$ substituents, and further wherein the cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S and is unsaturated or partially unsaturated and is optionally substituted with 1 or 2 oxo substituents, and further wherein the heterocyclyl of the $R^4$ group may be further substituted with 1 oxo substituent;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, heterocyclyl, a monocyclic 3-6 membered cycloalkyl group, or a 5 or 6 membered heteroaryl ring containing 1, 2, or 3 heteroatoms selected from N, O, or S, wherein the heterocyclyl of the —($C_1$-$C_6$ alkyl)-heterocyclyl and heterocyclyl $R^{4b}$ groups is a 3-6 membered ring comprising 1 or 2 heteroatoms independently selected from N, O, or S and is unsaturated or partially unsaturated and is optionally substituted with 1 or 2 oxo substituents, and further wherein the phenyl and heteroaryl $R^{4b}$ groups are unsubstituted or are substituted with 1 or 2 $R^{4aa}$ substituents;

$R^{4c}$ in each instance is independently selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a monocyclic 3-6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a monocyclic 3-6 membered cycloalkyl $R^{4c}$ group, the 3 to 6 membered heterocyclyl $R^{4c}$ group, the phenyl $R^{4c}$ group, or the a 5 or 6 membered heteroaryl $R^{4c}$ ring are unsubstituted or are substituted with 1 or 2 $R^{4aa}$ substituents; and further wherein the 3 to 6 membered cycloalkyl $R^{4c}$ group and the 3 to 6 membered heterocyclyl $R^{4c}$ group may optionally be additionally substituted with an oxo substituent; and $R^{4aa}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), or —S(=O)$_2$—($C_1$-$C_6$ alkyl).

2. The compound of embodiment 1 or the pharmaceutically acceptable salt thereof, the tautomer thereof, the pharmaceutically acceptable salt of the tautomer, the stereoisomer of any of the foregoing, or the mixture thereof, wherein one of the following is true:
1) two $R^{1a}$ substituents on adjacent carbon atoms or on an adjacent carbon atom and an adjacent N atom of a 5- or 6-membered heterocyclic $R^1$ group join to form a 6 membered ring that may be saturated, partially saturated, or aromatic and may include 0, 1, or 2 N atoms and may further optionally be substituted with 1 or 2 $R^{1a'}$ substituents and may include an oxo substituent if the ring is not an aromatic ring; or
2) two $R^{1a}$ substituents on adjacent carbon atoms or on an adjacent carbon atom and an adjacent N atom of a 5- or 6-membered heterocyclic $R^1$ group join to form a 5 membered ring that may be saturated, partially saturated, or aromatic and may include 0, 1, or 2 heteroatoms selected from N, O, or S and may further optionally be substituted with 1 or 2 $R^{1a'}$ substituent and may include an oxo substituent if the ring is not an aromatic ring.

3. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from

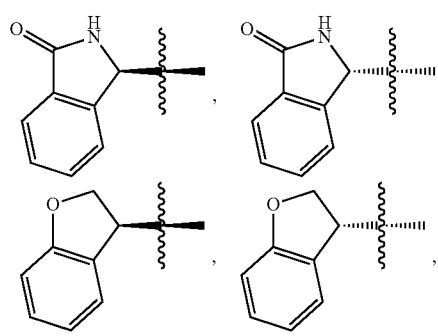

-continued

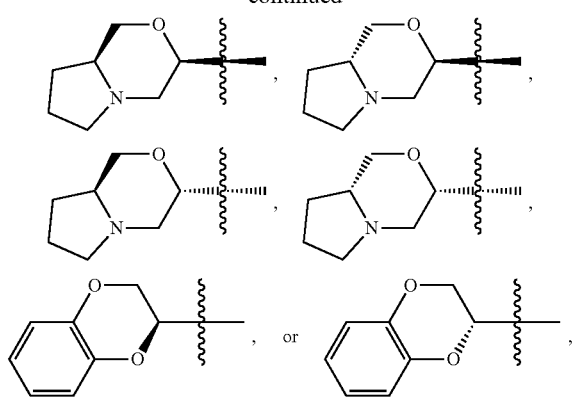

wherein the symbol ⌇, when drawn across a bond, indicates the point of attachment to the rest of the molecule.

4. The compound of embodiment 1 or the pharmaceutically acceptable salt thereof, the stereoisomer of any of the foregoing, or the mixture thereof, wherein $R^4$ is selected from a straight or branched chain $C_1$-$C_6$ alkyl group that is unsubstituted or is substituted with 1, 2, or 3 $R^{4c}$ substituents.

5. The compound of embodiment 1 or the pharmaceutically acceptable salt thereof, the stereoisomer of any of the foregoing, or the mixture thereof, wherein $R^4$ is selected from

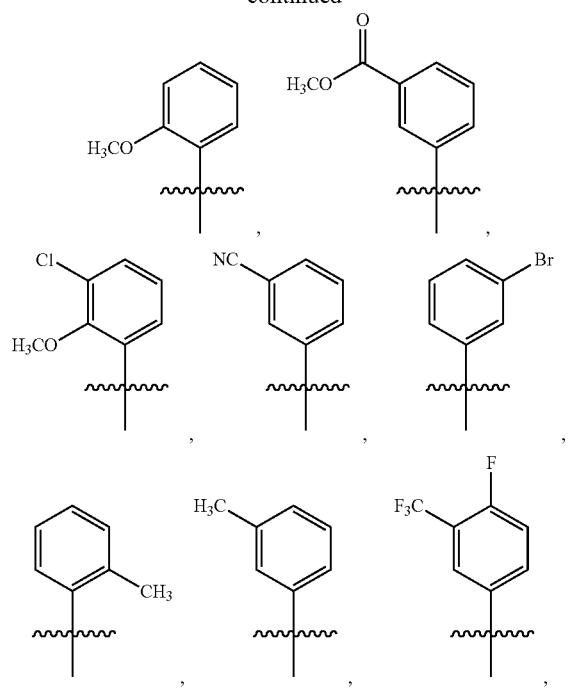

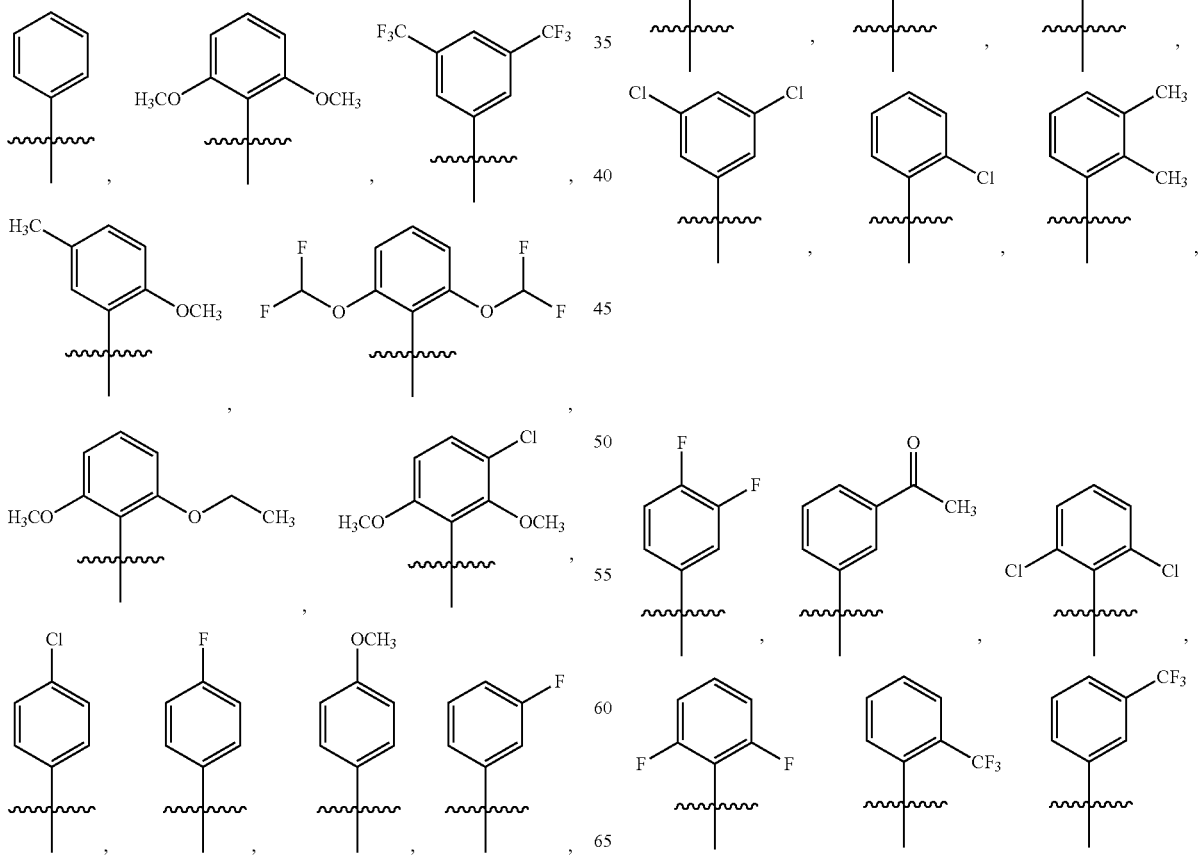

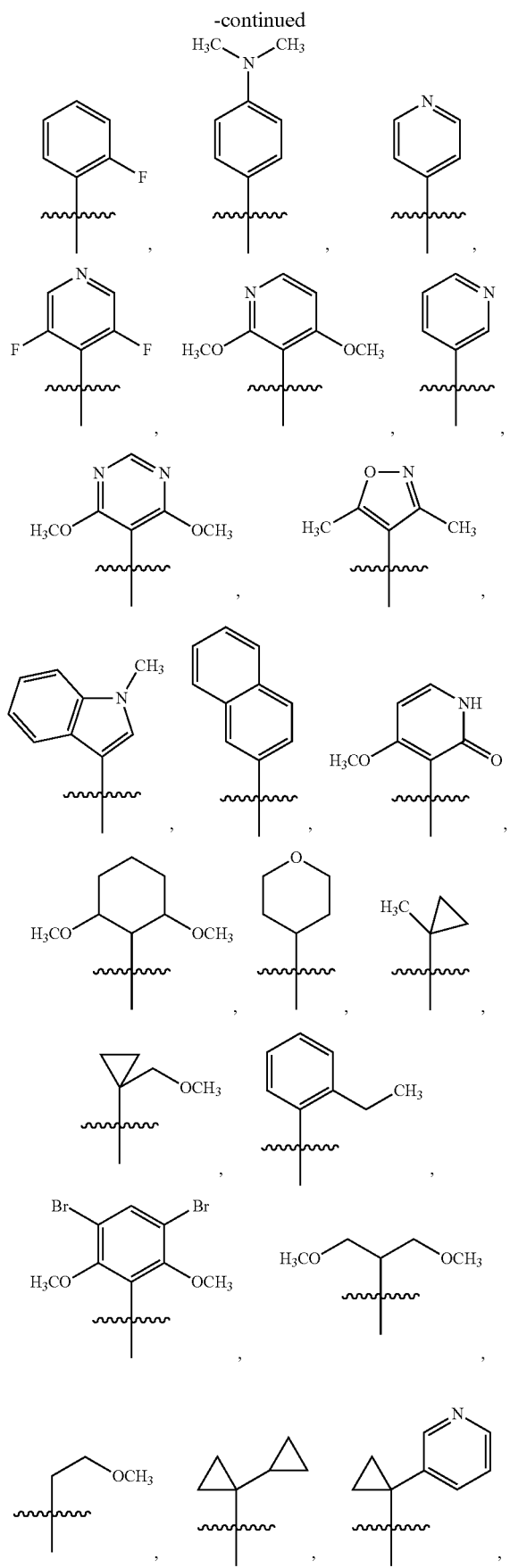

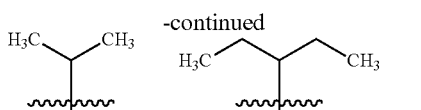

wherein the symbol ∿, when drawn across a bond, indicates the point of attachment to the rest of the molecule.

6. The compound of embodiment 1 or the pharmaceutically acceptable salt thereof, the stereoisomer of any of the foregoing, or the mixture thereof, wherein $R^4$ is selected from

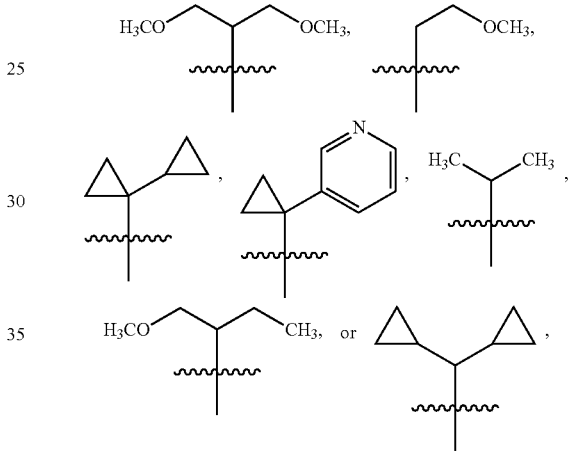

wherein the symbol ∿, when drawn across a bond, indicates the point of attachment to the rest of the molecule.

7. The compound of embodiment 1 or the pharmaceutically acceptable salt thereof, the stereoisomer of any of the foregoing, or the mixture thereof, wherein $R^4$ is selected from

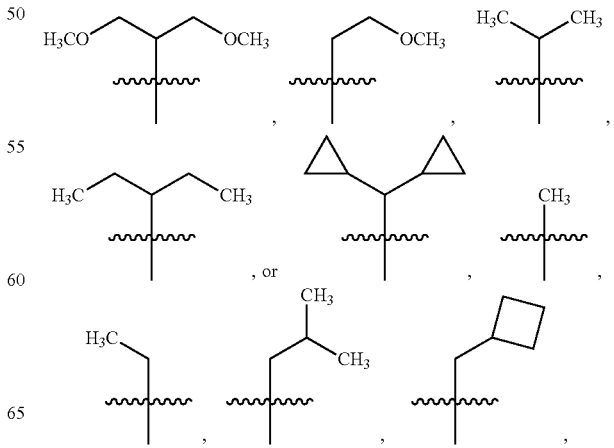

-continued

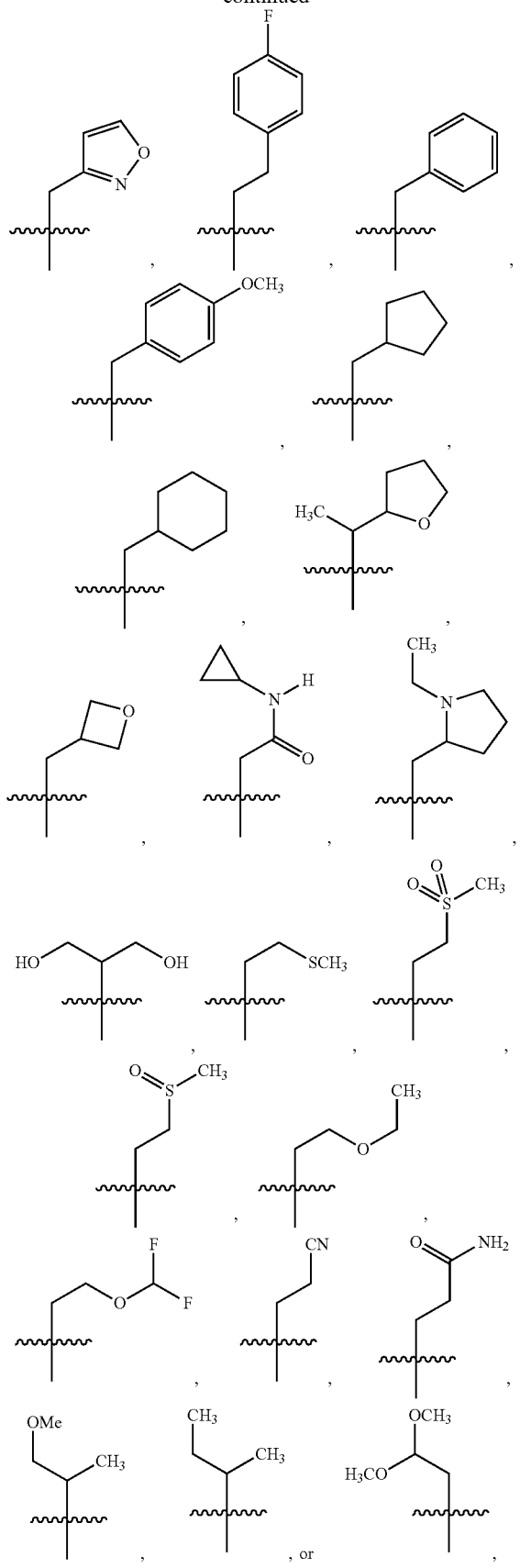

wherein the symbol ⌇, when drawn across a bond, indicates the point of attachment to the rest of the molecule.

In an eighth embodiment, the invention provides a compound of Formula I or Formula II:

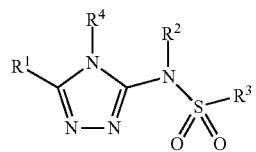

I

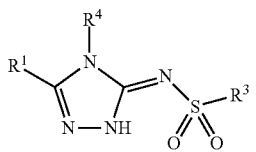

II or a pharmaceutically acceptable salt thereof, a tautomer thereof, a pharmaceutically acceptable salt of the tautomer, a stereoisomer of any of the foregoing, or a mixture thereof, wherein:

$R^1$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1a}$ may also be oxo unless $R^1$ is a 6-membered heterocyclic group that includes one N atom and includes at least one double bond, and further wherein two $R^{1a}$ substituents on adjacent carbon atoms or on an adjacent carbon atom and an adjacent N atom of a 5- or 6-membered heterocyclic $R^1$ group may join to form a 6 membered ring that may be saturated, partially saturated, or aromatic and may include 0, 1, or 2 N atoms and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH(C$_1$-C$_6$ alkyl), —C(=O)N(C$_1$-C$_6$ alkyl)$_2$ or —S(=O)$_2$—(C$_1$-C$_6$ alkyl);

R$^2$ is selected from —H, or C$_1$-C$_4$ alkyl or is absent in the compounds of Formula II;

R$^3$ is selected from an unsubstituted C$_1$-C$_{10}$ alkyl, a C$_1$-C$_{10}$ alkyl substituted with 1, 2, or 3 R$^{3a}$ substituents, a group of formula —(CR$^{3b}$R$^{3c}$)-Q, a group of formula —(CR$^{3d}$R$^{3e}$)–(CR$^{3f}$R$^{3g}$)-Q, a group of formula —(CR$^{3d}$R$^{3e}$)–(CR$^{3f}$R$^{3g}$)—C(=O)-Q, a group of formula —(CR$^{3d}$R$^{3e}$)–(CR$^{3f}$R$^{3g}$)—CH(OH)-Q, a group of formula —(CR$^{3d}$R$^{3e}$)–(CR$^{3f}$R$^{3g}$)–(CR$^{3f}$R$^{3g}$)-Q, a group of formula —(C$_3$-C$_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 R$^{3h}$ substituents, and further wherein the C$_3$-C$_8$ cycloalkyl of the —(C$_3$-C$_8$ cycloalkyl)-Q group is unsubstituted or is substituted with 1 or 2 R$^{3h}$ substituents;

R$^{3a}$ in each instance is independently selected from —F, —Cl, —CN, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —C$_2$-C$_6$ alkenyl, —C$_2$-C$_6$ alkynyl, —NH$_2$, —NH(C$_1$-C$_6$ alkyl), or —N(C$_1$-C$_6$ alkyl)$_2$;

R$^{3b}$ and R$^{3c}$ are independently selected from —H, —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3d}$ and R$^{3e}$ are independently selected from —H, —F, —Cl, —CN, —C$_1$-C$_6$ alkyl, —C$_1$-C$_6$ haloalkyl, —C$_1$-C$_6$ perhaloalkyl, —OH, —(C$_1$-C$_6$ alkyl)-OH, —(C$_1$-C$_6$ alkyl)-O—(C$_1$-C$_6$ alkyl), —(C$_1$-C$_6$ alkyl)-O—(C$_1$-C$_6$ alkyl)-phenyl, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, alkyl)-O—(C$_1$-C$_6$ alkyl), —NH$_2$, —NH(C$_1$-C$_6$ alkyl), or —N(C$_1$-C$_6$ alkyl)$_2$;

R$^{3f}$ and R$^{3g}$ are independently selected from —H, —F, —CN, —C$_1$-C$_6$ alkyl, —C$_1$-C$_6$ haloalkyl, —C$_1$-C$_6$ perhaloalkyl, —OH, —(C$_1$-C$_6$ alkyl)-OH, alkyl), —O—(C$_1$-C$_6$ alkyl), —O—(C$_1$-C$_6$ haloalkyl), —O—(C$_1$-C$_6$ perhaloalkyl), —O—(C$_2$-C$_6$ alkenyl), alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3h}$ in each instance is independently selected from —F, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, alkyl)-O—(C$_1$-C$_6$ alkyl), —NH$_2$, —NH(C$_1$-C$_6$ alkyl), —N(C$_1$-C$_6$ alkyl)$_2$, —C(=O)—(C$_1$-C$_6$ alkyl), —C(=O)—(C$_3$-C$_6$ cycloalkyl), —C(=O)—O—(C$_1$-C$_6$ alkyl), oxo, or —C(=O)-(heterocyclyl), wherein the heterocyclyl group of the R$^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic C$_6$-C$_{10}$ aryl group, a monocyclic or bicyclic heteroaryl group with 5 to 10 ring members containing 1, 2, or 3 heteroatoms independently selected from N, O, or S, a C$_3$-C$_8$ cycloalkyl group, a 3 to 10 membered heterocyclyl group containing 1, 2, or 3 heteroatoms independently selected from N, O, or S, wherein the C$_6$-C$_{10}$ aryl, the heteroaryl, the cycloalkyl, and the heterocyclyl Q groups are unsubstituted or are substituted with 1, 2, 3, or 4 R$^Q$ substituents; and further wherein the Q heterocyclyl group may additionally be substituted with 1 or 2 oxo substituents, and the Q heteroaryl group may include an N-oxide if the heteroaryl includes a N heteroatom;

R$^Q$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —C$_2$-C$_6$ alkenyl, —C$_2$-C$_6$ alkynyl, —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, —NHC(=O)(C$_1$-C$_6$ alkyl), —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, —S(=O)$_2$—(C$_1$-C$_6$ alkyl), —(C$_1$-C$_6$ alkyl)-OH, —(C$_1$-C$_6$ alkyl)-O—(C$_1$-C$_6$ alkyl), —(C$_1$-C$_6$ alkyl)-NH$_2$, —(C$_1$-C$_6$ alkyl)-NH—(C$_1$-C$_6$ alkyl), —(C$_1$-C$_6$ alkyl)-N—(C$_1$-C$_6$ alkyl)$_2$, phenyl, a heterocyclyl group, a alkyl)heterocyclyl group, or a heteroaryl group with 5 or 6 ring members and 1, 2, or 3, heteroatoms independently selected from N, O, or S, wherein the heterocyclyl groups of the R$^Q$ heterocyclyl and —(C$_1$-C$_6$ alkyl)heterocyclyl groups have 3 to 6 ring members of which 1 or 2 are heteroatoms independently selected from N, O, or S, and further wherein the heterocyclyl and the heterocyclyl of the —(C$_1$-C$_6$ alkyl)heterocyclyl R$^Q$ groups may be further substituted with one or two oxo substituents and a substituent selected from —F, —Cl, —Br, —I, —CN, —OH, —C$_1$-C$_6$ alkyl, or —C(=O)—(C$_1$-C$_6$ alkyl);

R$^4$ is selected from a monocyclic or bicyclic C$_6$-C$_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, or a monocyclic 3-6 membered cycloalkyl group, wherein the C$_6$-C$_{10}$ aryl, the heteroaryl, the heterocyclyl, and the cycloalkyl R$^4$ group are unsubstituted or are substituted with 1, 2, 3, or 4 R$^{4a}$ substituents; and R$^{4a}$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —(C$_1$-C$_6$ alkyl)-OH, —(C$_1$-C$_6$ alkyl)-O—(C$_1$-C$_6$ alkyl), —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, NH(C$_1$-C$_6$ alkyl-OH), —N(C$_1$-C$_6$ alkyl-OH)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, phenyl, —S(=O)$_2$—(C$_1$-C$_6$ alkyl), —(C$_1$-C$_6$ alkyl)-heterocyclyl, or heterocyclyl wherein the heterocyclyl of the —(C$_1$-C$_6$ alkyl)-heterocyclyl and heterocyclyl R$^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the R$^4$ group may be further substituted with 1 oxo substituent.

9. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein R$^1$ is a saturated 4-, 5-, or 6-membered heterocyclic group that includes 1 or 2 heteroatoms independently selected from N, O, or S and is unsubstituted or is substituted with 1, 2, or 3 $R^{1a}$ substituents.

10. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from tetrahydrofuranyl, tetrahydropyranyl, oxetanyl, dioxanyl, pyrrolidinyl, piperidinyl, dioxotetrahydrothiopyranyl, dioxotetrahydrothiophenyl, morpholinyl, dioxolanyl, or tetrahydrothiophenyl, any of which may unsubstituted or substituted with 1, 2, or 3 independently selected $R^{1a}$ substituents.

11. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from tetrahydrofuranyl, tetrahydropyranyl, oxetanyl, dioxanyl, or pyrrolidinyl, any of which may unsubstituted or substituted with 1, 2, or 3 independently selected $R^{1a}$ substituents.

12. The compound of embodiment 11 or the pharmaceutically acceptable salt thereof, the tautomer thereof, the pharmaceutically acceptable salt of the tautomer, the stereoisomer of any of the foregoing, or the mixture thereof, wherein $R^1$ is selected from tetrahydrofuran-2-yl, tetrahydrofuran-3-yl, tetrahydropyran-2-yl, tetrahydropyran-3-yl, tetrahydropyran-4-yl, oxetan-2-yl, oxetan-3-yl, 1,4-dioxan-2-yl, pyrrolidin-2-yl, or pyrrolidin-3-yl any of which may unsubstituted or substituted with 1, 2, or 3 independently selected $R^{1a}$ substituents.

13. The compound of any one of embodiments 10-12 or the pharmaceutically acceptable salt thereof, the tautomer thereof, the pharmaceutically acceptable salt of the tautomer, the stereoisomer of any of the foregoing, or the mixture thereof, wherein $R^1$ is unsubstituted or $R^1$ is substituted with 1, 2, or 3 $R^{1a}$ substituents independently selected from —$C_1$-$C_6$ alkyl, —C(=O)—O—($C_1$-$C_6$ alkyl), or oxo.

14. The compound of embodiment 1 or embodiment 8 the pharmaceutically acceptable salt thereof, the tautomer thereof, the pharmaceutically acceptable salt of the tautomer, the stereoisomer of any of the foregoing, or the mixture thereof, wherein $R^1$ is selected from

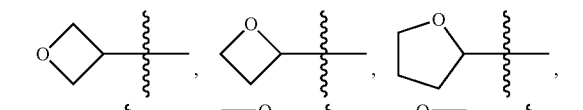

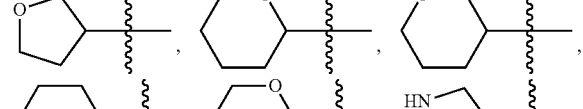

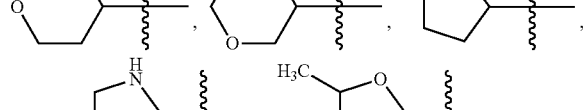

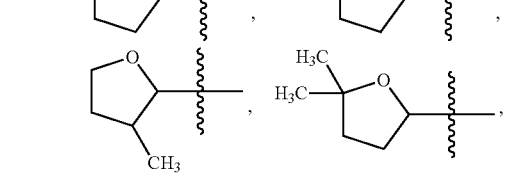

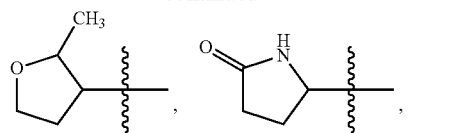

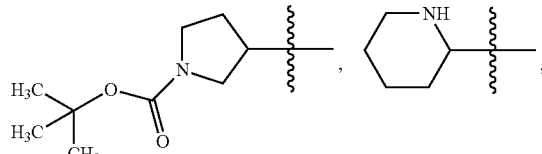

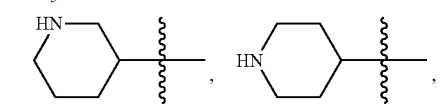

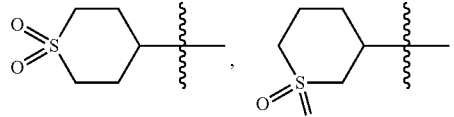

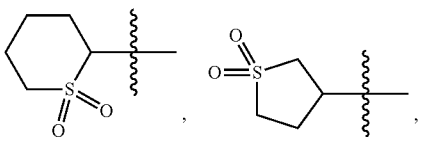

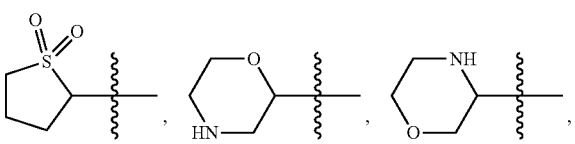

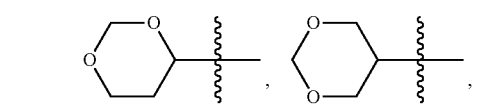

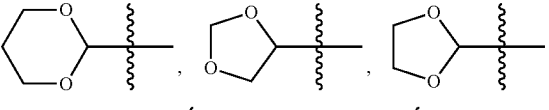

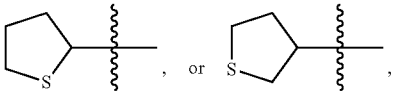

wherein the symbol ⁓, when drawn across a bond, indicates the point of attachment to the rest of the molecule.

15. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from

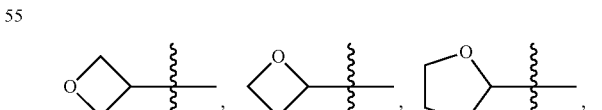

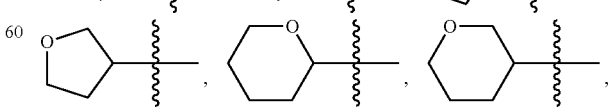

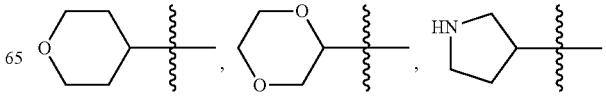

-continued

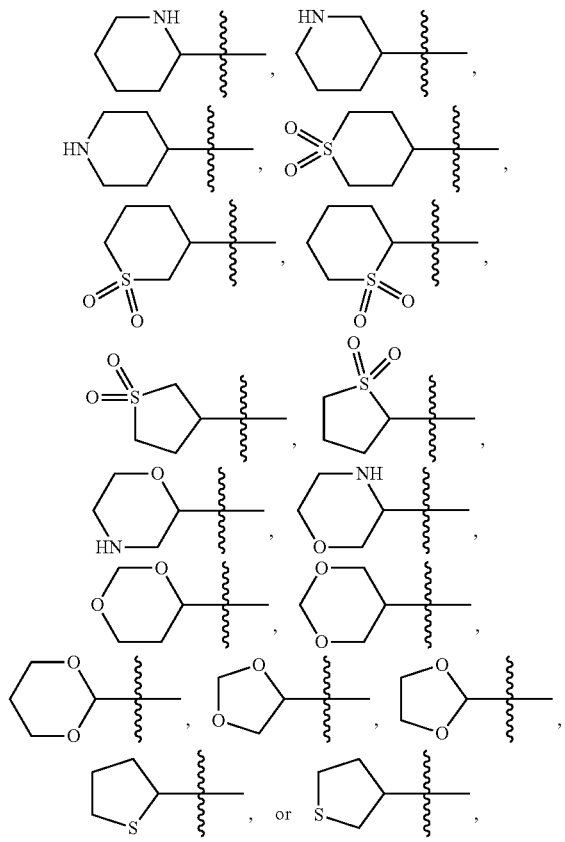

wherein the symbol ∿, when drawn across a bond, indicates the point of attachment to the rest of the molecule.

16. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from wherein the symbol ∿, when drawn across a bond, indicates the point of attachment to the rest of the molecule.

17. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from


wherein the symbol ∿, when drawn across a bond, indicates the point of attachment to the rest of the molecule.

18. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from

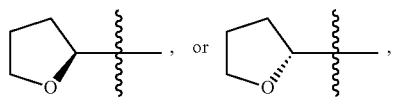 [SMILES: *[C@@H]1CCCO1 ; *[C@H]1CCCO1]

wherein the symbol ∿, when drawn across a bond, indicates the point of attachment to the rest of the molecule.

19. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from

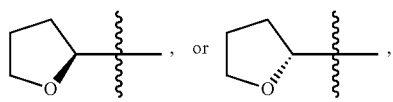

wherein the symbol ∿, when drawn across a bond, indicates the point of attachment to the rest of the molecule.

20. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from

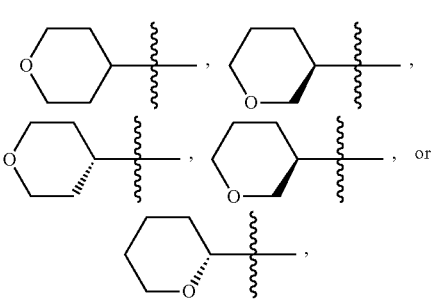

wherein the symbol ∿, when drawn across a bond, indicates the point of attachment to the rest of the molecule.

21. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from

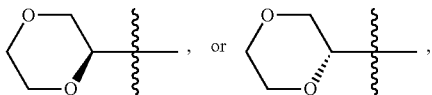 [SMILES: *[C@@H]1COCCO1 ; *[C@H]1COCCO1]

wherein the symbol ∽, when drawn across a bond, indicates the point of attachment to the rest of the molecule.

22. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from

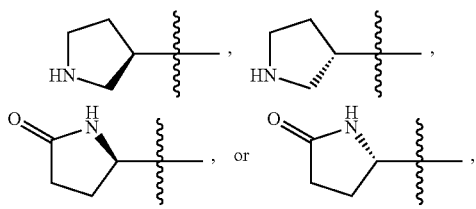

wherein the symbol ∽, when drawn across a bond, indicates the point of attachment to the rest of the molecule.

23. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from

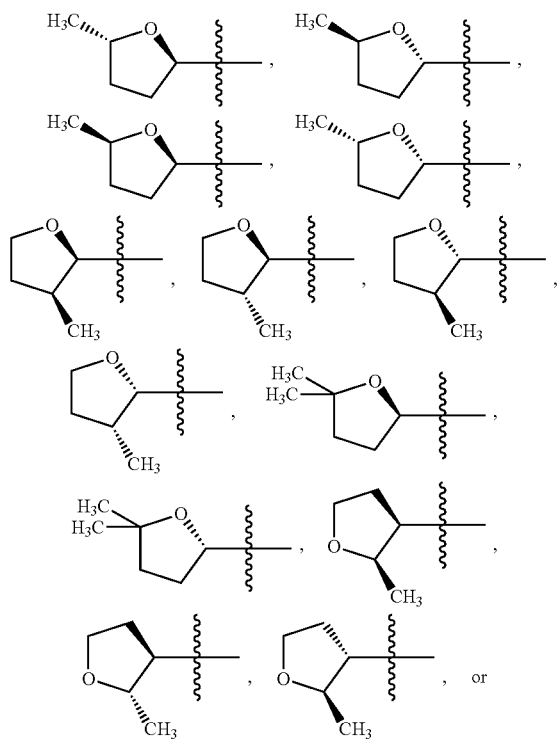

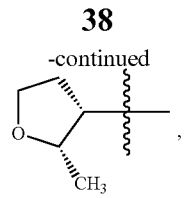

wherein the symbol ∽, when drawn across a bond, indicates the point of attachment to the rest of the molecule.

24. The compound of embodiment 1 or embodiment 8 or the pharmaceutically acceptable salt thereof, the tautomer thereof, the pharmaceutically acceptable salt of the tautomer, the stereoisomer of any of the foregoing, or the mixture thereof, wherein $R^1$ is selected from

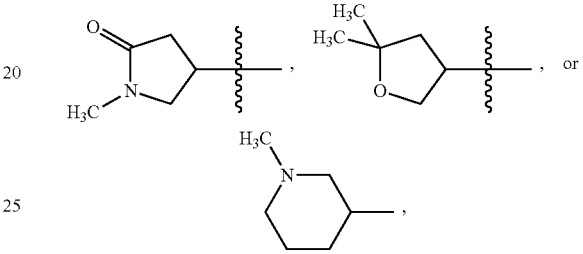

wherein the symbol ∽, when drawn across a bond, indicates the point of attachment to the rest of the molecule.

25. The compound of any one of embodiments 1-3 or 8-24 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, or pyrimidinyl, any of which may be unsubstituted or substituted with 1, 2, or 3 $R^{4a}$ substituents.

26. The compound of any one of embodiments 1-3 or 8-24 or the pharmaceutically acceptable salt thereof, the tautomer thereof, the pharmaceutically acceptable salt of the tautomer, the stereoisomer of any of the foregoing, or the mixture thereof, wherein $R^4$ is a cyclopropyl, cyclobutyl, cyclopentyl, cyclohexyl, or tetrahydropyranyl, any of which may be unsubstituted or substituted with 1, 2, or 3 $R^{4a}$ substituents.

27. The compound of any one of embodiments 1-3 or 8-26 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —OH, —O—($C_1$-$C_6$ alkyl), —O—($C_1$-$C_6$ haloalkyl), —O—($C_1$-$C_6$ perhaloalkyl), —C(=O)OH, —C(=O)—O—($C_1$-$C_6$ alkyl), —$NH_2$, —NH($C_1$-$C_6$ alkyl), —N($C_1$-$C_6$ alkyl)$_2$, NH($C_1$-$C_6$ alkyl-OH), —C(=O)$NH_2$, —C(=O)NH ($C_1$-$C_6$ alkyl), or —C(=O)N($C_1$-$C_6$ alkyl)$_2$.

28. The compound of embodiment 27 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —$CH_3$, —F, —Cl, —Br, —CN, —$CF_3$, —$OCH_3$, or —$OCHF_2$.

29. The compound of embodiment 27 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F or, —OCH$_3$.

30. The compound of any one of embodiments 1-3 or 8-24 or the pharmaceutically acceptable salt thereof, the tautomer thereof, the pharmaceutically acceptable salt of the tautomer, the stereoisomer of any of the foregoing, or the mixture thereof, wherein $R^4$ is selected from

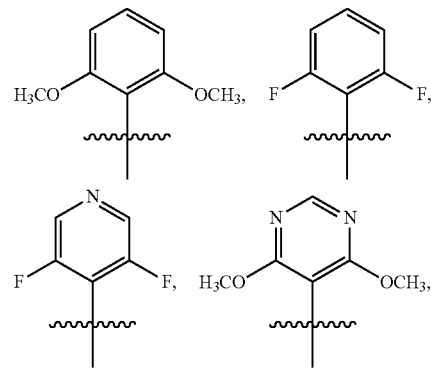

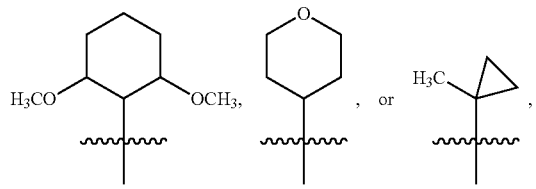

wherein the symbol ∿, when drawn across a bond, indicates the point of attachment to the rest of the molecule.

31. The compound of any one of embodiments 1-3 or 8-24 or the pharmaceutically acceptable salt thereof, the tautomer thereof, the pharmaceutically acceptable salt of the tautomer, the stereoisomer of any of the foregoing, or the mixture thereof, wherein $R^4$ is

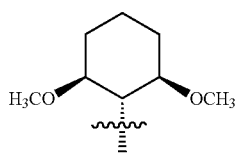

wherein the symbol ∿, when drawn across a bond, indicates the point of attachment to the rest of the molecule.

32. The compound of any one of embodiments 1-3 or 8-24 or the pharmaceutically acceptable salt thereof, the stereoisomer of any of the foregoing, or the mixture thereof, wherein $R^4$ is selected from

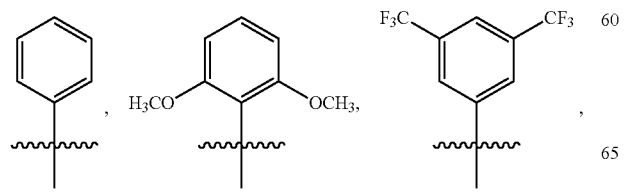

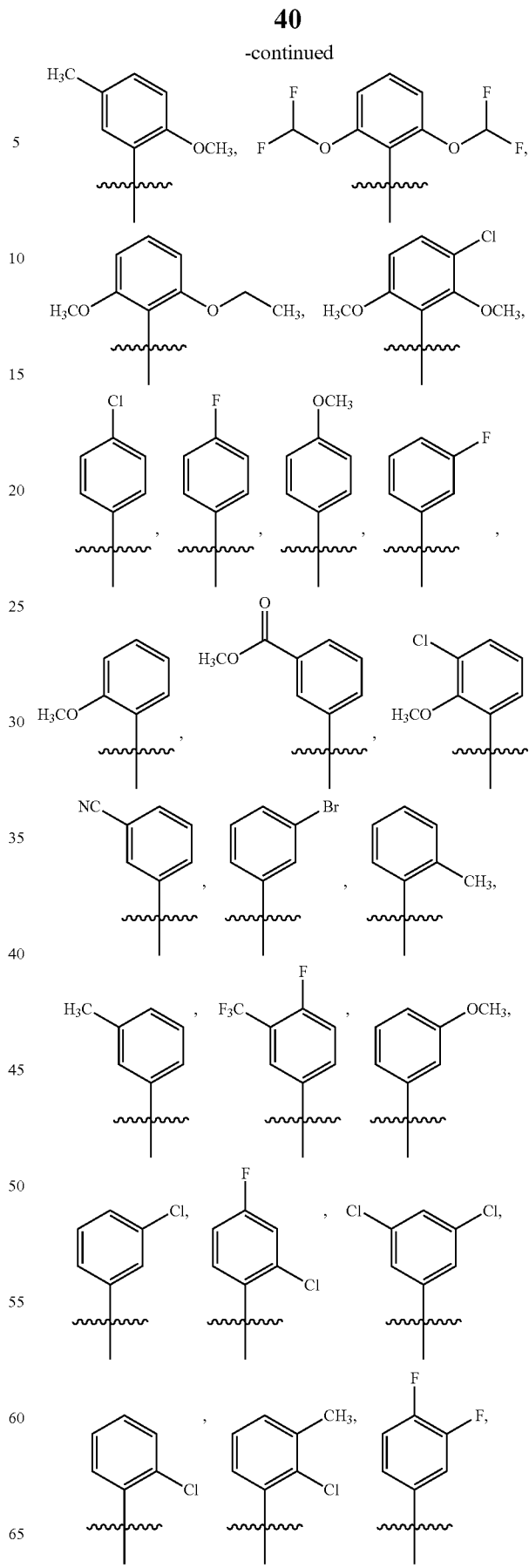

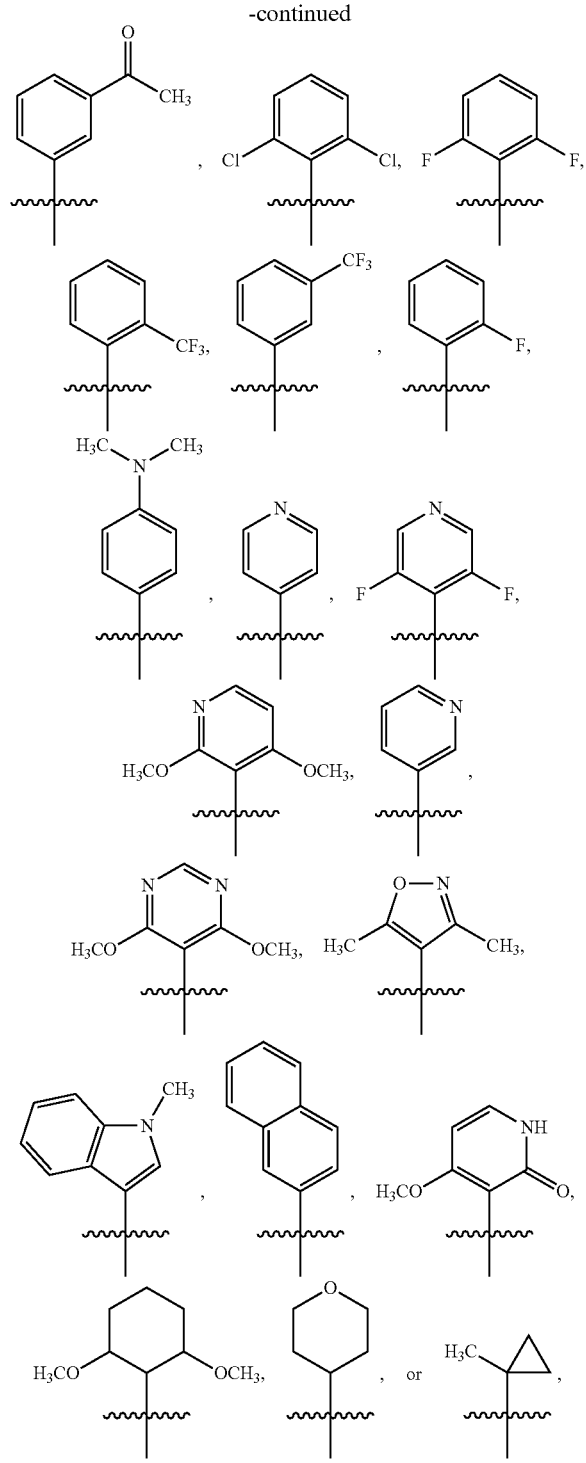

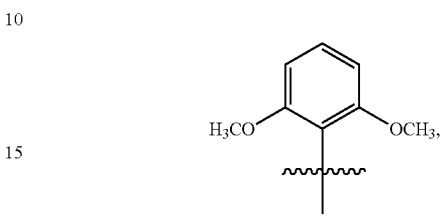

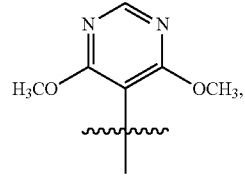 [SMILES: *c1c(OC)ncnc1OC]

wherein the symbol ⟿, when drawn across a bond, indicates the point of attachment to the rest of the molecule.

33. The compound of any one of embodiments 1-3 or 8-24 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl substituted with 1 or 2 $R^{4a}$ substituents.

34. The compound of embodiment 33 or the pharmaceutically acceptable salt thereof, the tautomer thereof, the pharmaceutically acceptable salt of the tautomer, the stereoisomer of any of the foregoing, or the mixture thereof, wherein the $R^{4a}$ substituents are —O—($C_1$-$C_2$ alkyl) groups.

35. The compound of embodiment 33 or the pharmaceutically acceptable salt thereof, the tautomer thereof, the pharmaceutically acceptable salt of the tautomer, the stereoisomer of any of the foregoing, or the mixture thereof, wherein $R^4$ is wherein the symbol ⟿, when drawn across a bond, indicates the point of attachment to the rest of the molecule.

36. The compound of any one of embodiments 1-3 or 8-24 or the pharmaceutically acceptable salt thereof, the tautomer thereof, the pharmaceutically acceptable salt of the tautomer, the stereoisomer of any of the foregoing, or the mixture thereof, wherein $R^4$ is a pyrimidinyl substituted with 1 or 2 $R^{4a}$ substituents.

37. The compound of embodiment 36 or the pharmaceutically acceptable salt thereof, the tautomer thereof, the pharmaceutically acceptable salt of the tautomer, the stereoisomer of any of the foregoing, or the mixture thereof, wherein the $R^{4a}$ substituents are —O—($C_1$-$C_2$ alkyl) groups.

38. The compound of embodiment 36 or the pharmaceutically acceptable salt thereof, the tautomer thereof, the pharmaceutically acceptable salt of the tautomer, the stereoisomer of any of the foregoing, or the mixture thereof, wherein $R^4$ is wherein the symbol ⟿, when drawn across a bond, indicates the point of attachment to the rest of the molecule.

39. The compound of any one of embodiments 1-38 or the pharmaceutically acceptable salt thereof, the tautomer thereof, the pharmaceutically acceptable salt of the tautomer, the stereoisomer of any of the foregoing, or the mixture thereof, wherein $R^2$ is —H or is absent in the compounds of Formula II.

40. The compound of any one of embodiments 1-39 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyrazine-1-oxide, pyridazinyl, pyridinyl, phenyl, oxazolyl, thiazolyl, imidazolyl, pyrazolyl, piperidinyl, piperidin-2-onyl, tetrahydropyrimidin-2(1H)-onyl, 1,3-oxazinan-2-onyl, pyrrolidin-2-onyl, pyrrolidinyl, cyclopentyl, cyclohexyl, benzimidazolyl, isoindolinonyl, 1H-imidazo[4,5-c]pyridinyl, pyrazolo[1,5-a]pyridinyl, imidazo[1,2-a]pyridinyl, imidazo[1,5-a]pyridinyl, 6,7-dihydro-5H-pyrazolo[5,1-b][1,3]oxazinyl, or 3,4-dihydro-2H-pyrano[3,2-b]pyridinyl, any of which may be unsubstituted or substituted with 1, 2, or 3 $R^Q$ substituents.

41. The compound of any one of embodiments 1-39 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyridinyl, phenyl, or tetrahydropyrimidin-2(1H)-onyl, any of which may be unsubstituted or substituted with 1, 2, or 3 $R^Q$ substituents.

42. The compound of any one of embodiments 1-39 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyridinyl, or phenyl, any of which may be unsubstituted or substituted with 1, 2, or 3 $R^Q$ substituents.

43. The compound of any one of embodiments 1-39 or the pharmaceutically acceptable salt thereof, the tautomer thereof, the pharmaceutically acceptable salt of the tautomer, the stereoisomer of any of the foregoing, or the mixture thereof, wherein Q is an unsubstituted phenyl or is a phenyl substituted with 1, 2, or 3 $R^Q$ substituents.

44. The compound of any one of embodiments 1-39 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

45. The compound of any one of embodiments 1-39 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl, pyridinyl, or pyrazinyl group and Q is unsubstituted or is substituted with 1, 2, or 3 $R^Q$ substituents.

46. The compound of any one of embodiments 1-39 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl group and Q is unsubstituted or is substituted with 1, 2, or 3 $R^Q$ substituents.

47. The compound of any one of embodiments 1-46 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), or —O—($C_1$-$C_6$ perhaloalkyl).

48. The compound of any one of embodiments 1-46 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, or —$CH_3$.

49. The compound of any one of embodiments 1-39 or the pharmaceutically acceptable salt thereof, the tautomer thereof, the pharmaceutically acceptable salt of the tautomer, the stereoisomer of any of the foregoing, or the mixture thereof, wherein Q is selected from

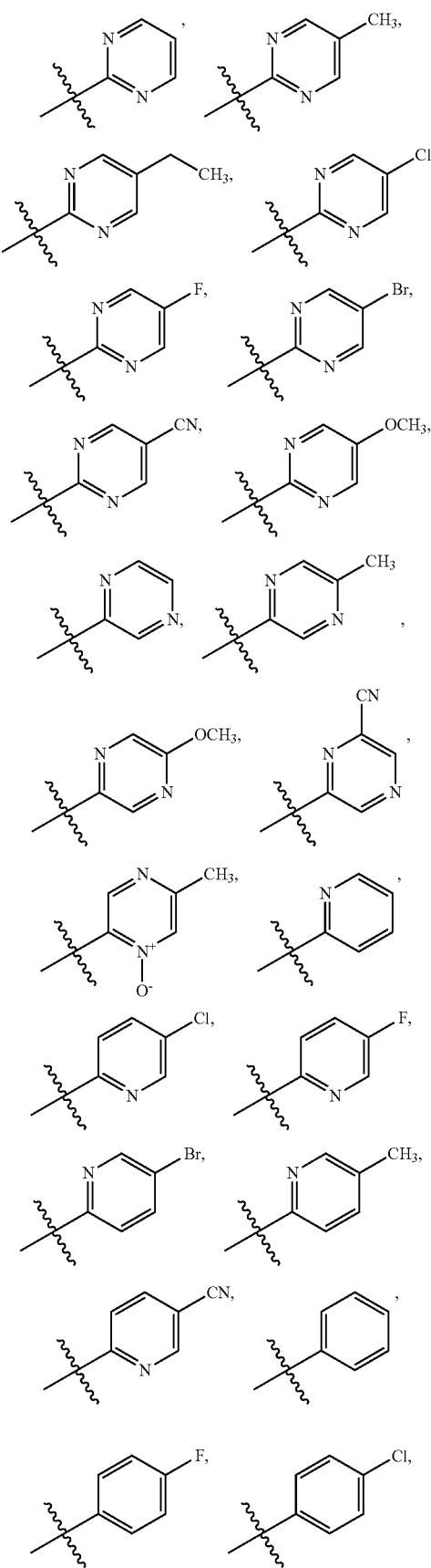

-continued

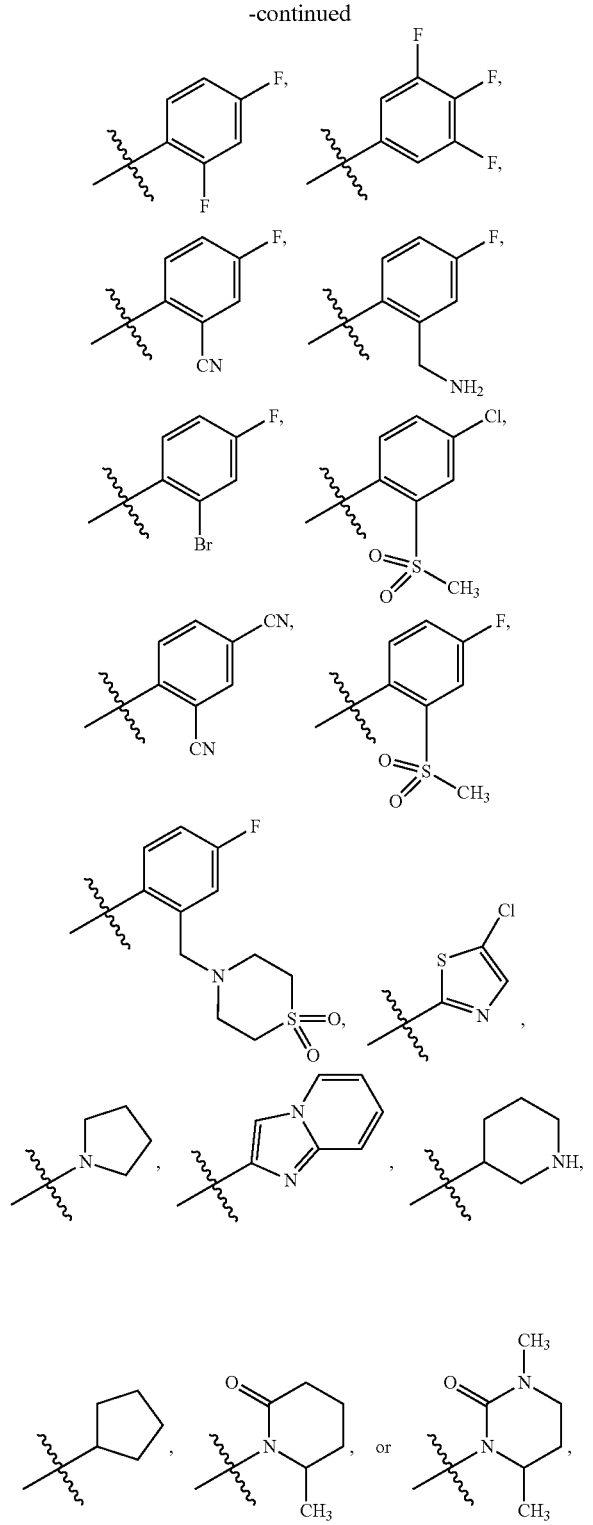

wherein the symbol ~~, when drawn across a bond, indicates the point of attachment to the rest of the molecule.

50. The compound of embodiment 49 or the pharmaceutically acceptable salt thereof, the tautomer thereof, the pharmaceutically acceptable salt of the tautomer, the stereoisomer of any of the foregoing, or the mixture thereof, wherein Q is selected from


wherein the symbol ~~, when drawn across a bond, indicates the point of attachment to the rest of the molecule.

51. The compound of embodiment 49 or the pharmaceutically acceptable salt thereof, the tautomer thereof, the pharmaceutically acceptable salt of the tautomer, the stereoisomer of any of the foregoing, or the mixture thereof, wherein Q is selected from

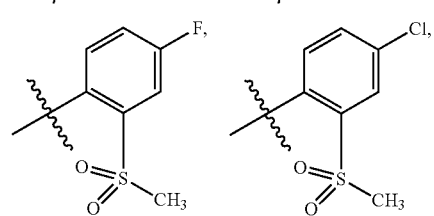

-continued

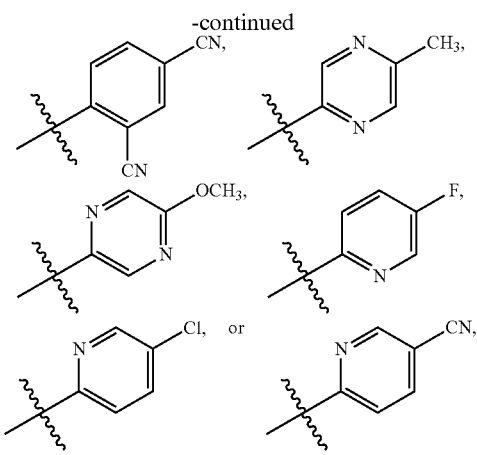

wherein the symbol ⁓, when drawn across a bond, indicates the point of attachment to the rest of the molecule.

52. The compound of embodiment 49 or the pharmaceutically acceptable salt thereof, the tautomer thereof, the pharmaceutically acceptable salt of the tautomer, the stereoisomer of any of the foregoing, or the mixture thereof, wherein Q is

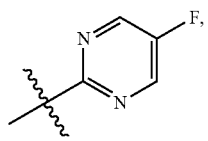 [SMILES: *c1ncc(F)cn1]

wherein the symbol ⁓, when drawn across a bond, indicates the point of attachment to the rest of the molecule.

53. The compound of embodiment 49 or the pharmaceutically acceptable salt thereof, the tautomer thereof, the pharmaceutically acceptable salt of the tautomer, the stereoisomer of any of the foregoing, or the mixture thereof, wherein Q is

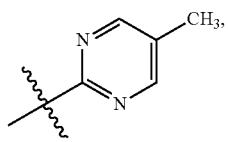 [SMILES: *c1ncc(C)cn1]

wherein the symbol ⁓, when drawn across a bond, indicates the point of attachment to the rest of the molecule.

54. The compound of embodiment 49 or the pharmaceutically acceptable salt thereof, the tautomer thereof, the pharmaceutically acceptable salt of the tautomer, the stereoisomer of any of the foregoing, or the mixture thereof, wherein Q is

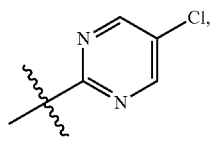 [SMILES: *c1ncc(Cl)cn1]

wherein the symbol ⁓, when drawn across a bond, indicates the point of attachment to the rest of the molecule.

55. The compound of embodiment 49 or the pharmaceutically acceptable salt thereof, the tautomer thereof, the pharmaceutically acceptable salt of the tautomer, the stereoisomer of any of the foregoing, or the mixture thereof, wherein Q is

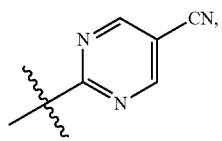 [SMILES: *c1ncc(C#N)cn1]

wherein the symbol ⁓, when drawn across a bond, indicates the point of attachment to the rest of the molecule.

56. The compound of embodiment 49 or the pharmaceutically acceptable salt thereof, the tautomer thereof, the pharmaceutically acceptable salt of the tautomer, the stereoisomer of any of the foregoing, or the mixture thereof, wherein Q is

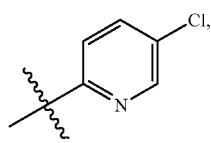 [SMILES: *c1ccc(Cl)cn1]

wherein the symbol ⁓, when drawn across a bond, indicates the point of attachment to the rest of the molecule.

57. The compound of embodiment 49 or the pharmaceutically acceptable salt thereof, the tautomer thereof, the pharmaceutically acceptable salt of the tautomer, the stereoisomer of any of the foregoing, or the mixture thereof, wherein Q is

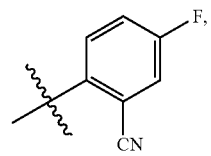

wherein the symbol ⁓, when drawn across a bond, indicates the point of attachment to the rest of the molecule.

58. The compound of embodiment 49 or the pharmaceutically acceptable salt thereof, the tautomer thereof, the pharmaceutically acceptable salt of the tautomer, the stereoisomer of any of the foregoing, or the mixture thereof, wherein Q is

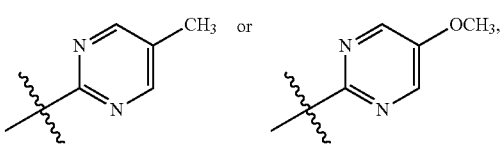

wherein the symbol ⁓, when drawn across a bond, indicates the point of attachment to the rest of the molecule.

59. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein R³ is selected from a group of formula —(CR³ᵈR³ᵉ)–(CR³ᶠR³ᵍ)-Q, or a group of formula -(heterocyclyl)-Q.

60. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein R³ is a group of formula —(CR³ᵈR³ᵉ)–(CR³ᶠR³ᵍ)-Q.

61. The compound of embodiment 60 or the pharmaceutically acceptable salt thereof, the tautomer thereof, the pharmaceutically acceptable salt of the tautomer, the stereoisomer of any of the foregoing, or the mixture thereof, wherein R³ is a group of formula —(CR³ᵈR³ᵉ)–(CR³ᶠR³ᵍ)-Q and further wherein,
- R³ᵈ and R³ᵉ are independently selected from —H, —C₁-C₆ alkyl, —(C₁-C₆ alkyl)-OH, or —(C₁-C₆ alkyl)-O—(C₁-C₆ alkyl); and
- R³ᶠ and R³ᵍ are independently selected from —H, —F, —C₁-C₆ alkyl, —C₁-C₆ haloalkyl, —C₁-C₆ perhaloalkyl, —OH, —O—(C₁-C₆ alkyl), —O—(C₁-C₆ haloalkyl), —O—(C₁-C₆ perhaloalkyl), or —O—(C₂-C₆ alkenyl).

62. The compound of embodiment 60 or the pharmaceutically acceptable salt thereof, the tautomer thereof, the pharmaceutically acceptable salt of the tautomer, the stereoisomer of any of the foregoing, or the mixture thereof, wherein R³ is a group of formula —(CR³ᵈR³ᵉ)–(CR³ᶠR³ᵍ)-Q and further wherein,
- R³ᵈ and R³ᵉ are independently selected from —H, or —C₁-C₆ alkyl; and
- R³ᶠ and R³ᵍ are independently selected from —H, —C₁-C₆ alkyl, —OH, or —O—(C₁-C₆ alkyl).

63. The compound of any one of embodiments 60-62 or the pharmaceutically acceptable salt thereof, the tautomer thereof, the pharmaceutically acceptable salt of the tautomer, the stereoisomer of any of the foregoing, or the mixture thereof, wherein at least one of R³ᵈ, R³ᵉ, R³ᶠ, or R³ᵍ is not —H.

64. The compound of any one of embodiments 60-63 or the pharmaceutically acceptable salt thereof, the tautomer thereof, the pharmaceutically acceptable salt of the tautomer, the stereoisomer of any of the foregoing, or the mixture thereof, wherein at least one of R³ᵈ, R³ᵉ, R³ᶠ, or R³ᵍ is a —C₁-C₆ alkyl.

65. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein R³ is a group of formula -(heterocyclyl)-Q.

66. The compound of embodiment 65 or the pharmaceutically acceptable salt thereof, the tautomer thereof, the pharmaceutically acceptable salt of the tautomer, the stereoisomer of any of the foregoing, or the mixture thereof, wherein the heterocyclyl of the -(heterocyclyl)-Q R³ group is a piperidinyl that is unsubstituted or is substituted with 1 or 2 R³ʰ substituent.

67. The compound of embodiment 65 or 66 or the pharmaceutically acceptable salt thereof, the tautomer thereof, the pharmaceutically acceptable salt of the tautomer, the stereoisomer of any of the foregoing, or the mixture thereof, wherein the heterocyclyl of the -(heterocyclyl)-Q R³ group is a piperidinyl that is unsubstituted or is substituted with 1 or 2 R³ʰ substituent independently selected from —OH, or —O—(C₁-C₆ alkyl).

68. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein R³ is selected from

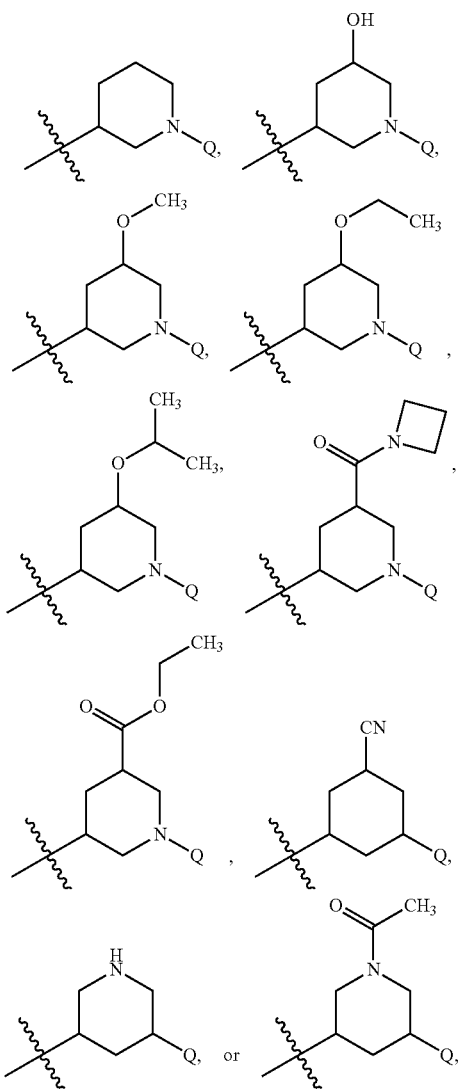

wherein the symbol , when drawn across a bond, indicates the point of attachment to the rest of the molecule.

69. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein R³ is selected from

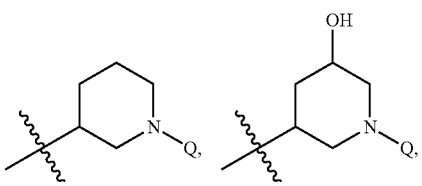

-continued

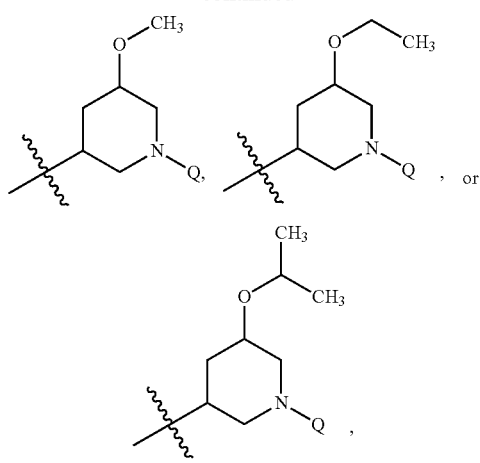

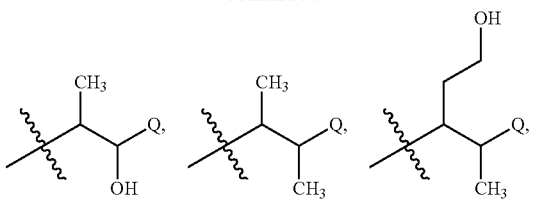

wherein the symbol ⌇, when drawn across a bond, indicates the point of attachment to the rest of the molecule.

70. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein $R^3$ is selected from

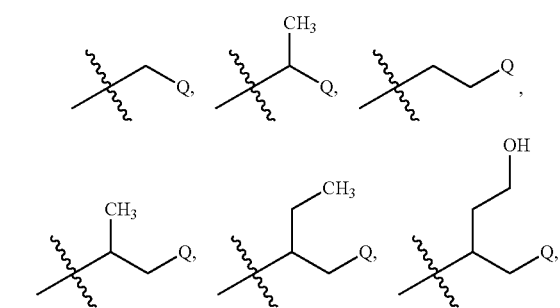

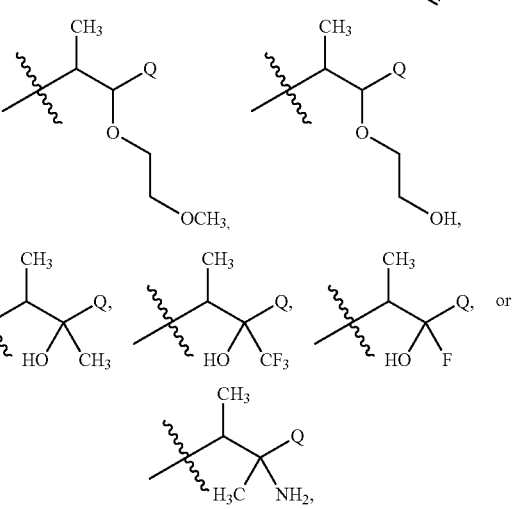

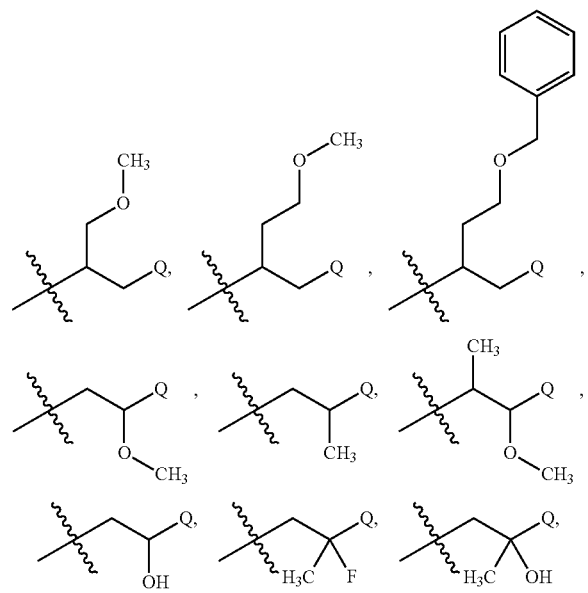

wherein the symbol ⌇, when drawn across a bond, indicates the point of attachment to the rest of the molecule.

71. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein $R^3$ is selected from

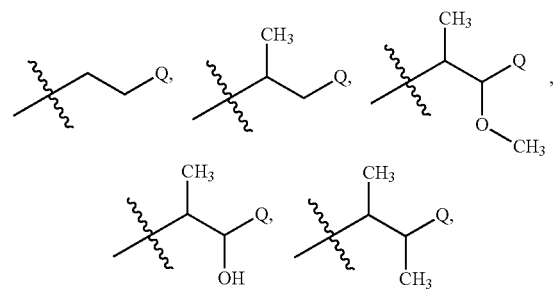

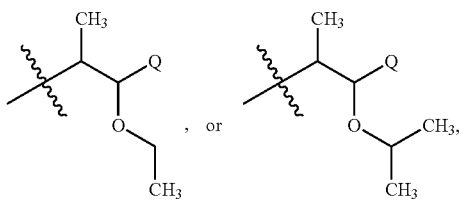

, or wherein the symbol ∿, when drawn across a bond, indicates the point of attachment to the rest of the molecule.

72. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein $R^3$ is

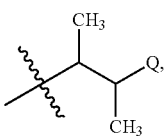

wherein the symbol ∿, when drawn across a bond, indicates the point of attachment to the rest of the molecule.

73. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein $R^3$ is

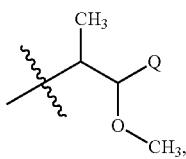

wherein the symbol ∿, when drawn across a bond, indicates the point of attachment to the rest of the molecule.

74. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein $R^3$ is selected from

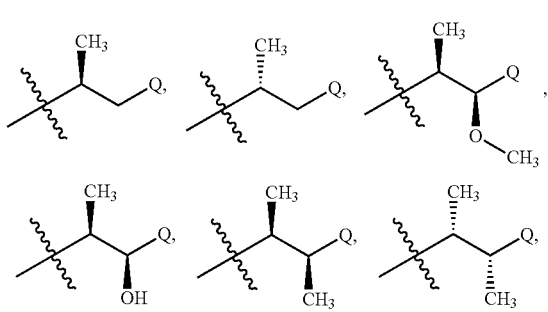

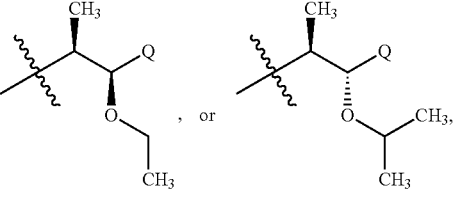

, or wherein the symbol ∿, when drawn across a bond, indicates the point of attachment to the rest of the molecule.

75. The compound of any one of embodiments 1-58 or the pharmaceutically acceptable salt thereof, the tautomer thereof, the pharmaceutically acceptable salt of the tautomer, the stereoisomer of any of the foregoing, or the mixture thereof, wherein $R^3$ is

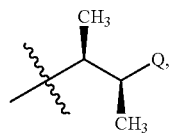

wherein the symbol ∿, when drawn across a bond, indicates the point of attachment to the rest of the molecule.

76. The compound of embodiment 8, wherein the compound is selected from
(2S,3R)—N-(4-(((1r,2R,6S)-2,6-dimethoxycyclohexyl)-5-((2S)-tetrahydro-2-furanyl)-4H-1,2,4-triazol-3-yl)-3-(5-methyl-2-pyrimidinyl)-2-butanesulfonamide;
(2S,3R)—N-(4-(((1r,2R,6S)-2,6-dimethoxycyclohexyl)-5-((2R)-tetrahydro-2-furanyl)-4H-1,2,4-triazol-3-yl)-3-(5-methyl-2-pyrimidinyl)-2-butanesulfonamide;
(2S,3R)—N-(4-(((1r,2R,6S)-2,6-dimethoxycyclohexyl)-5-((3S)-tetrahydro-3-furanyl)-4H-1,2,4-triazol-3-yl)-3-(5-methyl-2-pyrimidinyl)-2-butanesulfonamide;
(2S,3R)—N-(4-(((1r,2R,6S)-2,6-dimethoxycyclohexyl)-5-((3R)-tetrahydro-3-furanyl)-4H-1,2,4-triazol-3-yl)-3-(5-methyl-2-pyrimidinyl)-2-butanesulfonamide;
(R)—N-(4-(2,6-dimethoxyphenyl)-5-((R)-tetrahydrofuran-3-yl)-4H-1,2,4-triazol-3-yl)-1-(5-fluoropyrimidin-2-yl)propane-2-sulfonamide;
(R)—N-(4-(2,6-dimethoxyphenyl)-5-((S)-tetrahydrofuran-3-yl)-4H-1,2,4-triazol-3-yl)-1-(5-fluoropyrimidin-2-yl)propane-2-sulfonamide;
(S)—N-(4-(2,6-dimethoxyphenyl)-5-((R)-tetrahydrofuran-3-yl)-4H-1,2,4-triazol-3-yl)-1-(5-fluoropyrimidin-2-yl)propane-2-sulfonamide;
(S)—N-(4-(2,6-dimethoxyphenyl)-5-((S)-tetrahydrofuran-3-yl)-4H-1,2,4-triazol-3-yl)-1-(5-fluoropyrimidin-2-yl)propane-2-sulfonamide;
(R)-2-(4-chlorophenyl)-N-(4-(2,6-dimethoxyphenyl)-5-(tetrahydrofuran-3-yl)-4H-1,2,4-triazol-3-yl)ethanesulfonamide;
(S)-2-(4-chlorophenyl)-N-(4-(2,6-dimethoxyphenyl)-5-(tetrahydrofuran-3-yl)-4H-1,2,4-triazol-3-yl)ethanesulfonamide;
(2R)—N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide;
(2S)—N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide;

(2S,3R)—N-(4-(2,6-difluorophenyl)-5-((2S)-tetrahydro-2-furanyl)-4H-1,2,4-triazol-3-yl)-3-(5-methyl-2-pyrimidinyl)-2-butanesulfonamide;
(2S,3R)—N-(4-(2,6-difluorophenyl)-5-((2R)-tetrahydro-2-furanyl)-4H-1,2,4-triazol-3-yl)-3-(5-methyl-2-pyrimidinyl)-2-butanesulfonamide;
(2S,3R)—N-(4-(2,6-difluorophenyl)-5-((3R)-tetrahydro-3-furanyl)-4H-1,2,4-triazol-3-yl)-3-(5-methyl-2-pyrimidinyl)-2-butanesulfonamide;
(2S,3R)—N-(4-(2,6-difluorophenyl)-5-((3S)-tetrahydro-3-furanyl)-4H-1,2,4-triazol-3-yl)-3-(5-methyl-2-pyrimidinyl)-2-butanesulfonamide;
(2S,3R)—N-(4-(2,6-difluorophenyl)-5-((3S)-tetrahydro-2H-pyran-3-yl)-4H-1,2,4-triazol-3-yl)-3-(5-methyl-2-pyrimidinyl)-2-butanesulfonamide;
(2S,3R)—N-(4-(2,6-difluorophenyl)-5-((3R)-tetrahydro-2H-pyran-3-yl)-4H-1,2,4-triazol-3-yl)-3-(5-methyl-2-pyrimidinyl)-2-butanesulfonamide;
(2S,3R)-3-(5-cyano-2-pyrimidinyl)-N-(4-(2,6-dimethoxyphenyl)-5-((2S)-tetrahydro-2-furanyl)-4H-1,2,4-triazol-3-yl)-2-butanesulfonamide;
(2S,3R)-3-(5-cyano-2-pyrimidinyl)-N-(4-(2,6-dimethoxyphenyl)-5-((2R)-tetrahydro-2-furanyl)-4H-1,2,4-triazol-3-yl)-2-butanesulfonamide;
(2S,3R)—N-(4-(3,5-difluoro-4-pyridinyl)-5-((2S)-tetrahydro-2-furanyl)-4H-1,2,4-triazol-3-yl)-3-(5-methyl-2-pyrimidinyl)-2-butanesulfonamide;
(2S,3R)—N-(4-(3,5-difluoro-4-pyridinyl)-5-((2R)-tetrahydro-2-furanyl)-4H-1,2,4-triazol-3-yl)-3-(5-methyl-2-pyrimidinyl)-2-butanesulfonamide;
(2S,3R)-3-(5-chloro-2-pyrimidinyl)-N-(4-(4,6-dimethoxy-5-pyrimidinyl)-5-(3-oxetanyl)-4H-1,2,4-triazol-3-yl)-2-butanesulfonamide;
(2S,3R)-3-(5-chloro-2-pyrimidinyl)-N-(4-(2,6-dimethoxyphenyl)-5-(3-oxetanyl)-4H-1,2,4-triazol-3-yl)-2-butanesulfonamide;
(2S,3R)-3-(5-chloro-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide;
(2S,3R)-3-(5-chloro-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide;
(2S,3R)-3-(5-chloro-2-pyrimidinyl)-N-(4-(2,6-dimethoxyphenyl)-5-((2R)-1,4-dioxan-2-yl)-4H-1,2,4-triazol-3-yl)-2-butanesulfonamide;
(2S,3R)-3-(5-chloro-2-pyrimidinyl)-N-(4-(2,6-dimethoxyphenyl)-5-((2S)-1,4-dioxan-2-yl)-4H-1,2,4-triazol-3-yl)-2-butanesulfonamide;
tert-butyl(3R)-3-(5-(((((1S,2R)-2-(5-chloro-2-pyrimidinyl)-1-methylpropyl)sulfonyl)amino)-4-(2,6-dimethoxyphenyl)-4H-1,2,4-triazol-3-yl)-1-pyrrolidinecarboxylate;
tert-butyl(3S)-3-(5-(((((1S,2R)-2-(5-chloro-2-pyrimidinyl)-1-methylpropyl)sulfonyl)amino)-4-(2,6-dimethoxyphenyl)-4H-1,2,4-triazol-3-yl)-1-pyrrolidinecarboxylate;
2-(2-cyano-4-fluorophenyl)-N-(4-(2,6-dimethoxyphenyl)-5-((2R)-5-oxo-2-pyrrolidinyl)-4H-1,2,4-triazol-3-yl)ethanesulfonamide;
2-(2-cyano-4-fluorophenyl)-N-(4-(2,6-dimethoxyphenyl)-5-((2S)-5-oxo-2-pyrrolidinyl)-4H-1,2,4-triazol-3-yl)ethanesulfonamide;
(1R,2S)—N-(4-(2,6-dimethoxyphenyl)-5-((R)-pyrrolidin-3-yl)-4H-1,2,4-triazol-3-yl)-1-methoxy-1-(5-methylpyrimidin-2-yl)propane-2-sulfonamide;
(1R,2S)—N-(4-(2,6-dimethoxyphenyl)-5-((S)-pyrrolidin-3-yl)-4H-1,2,4-triazol-3-yl)-1-methoxy-1-(5-methylpyrimidin-2-yl)propane-2-sulfonamide;
(2S,3R)-3-(5-chloro-2-pyrimidinyl)-N-(4-(2,6-dimethoxyphenyl)-5-((2S)-tetrahydro-2-furanyl)-4H-1,2,4-triazol-3-yl)-2-butanesulfonamide;
(2S,3R)-3-(5-chloro-2-pyrimidinyl)-N-(4-(2,6-dimethoxyphenyl)-5-((2R)-tetrahydro-2-furanyl)-4H-1,2,4-triazol-3-yl)-2-butanesulfonamide;
(2S,3R)—N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide;
(2S,3R)—N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide;
(1R,2S)-1-(5-chloropyrimidin-2-yl)-N-(4-(2,6-dimethoxyphenyl)-5-((R)-tetrahydrofuran-2-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((S)-tetrahydrofuran-2-yl)-4H-1,2,4-triazol-3-yl)-1-methoxypropane-2-sulfonamide;
(2S,3R)—N-(4-(2,6-dimethoxyphenyl)-5-((R)-tetrahydrofuran-3-yl)-4H-1,2,4-triazol-3-yl)-3-(5-methylpyrimidin-2-yl)butane-2-sulfonamide;
(2S,3R)—N-(4-(2,6-dimethoxyphenyl)-5-((S)-tetrahydrofuran-3-yl)-4H-1,2,4-triazol-3-yl)-3-(5-methylpyrimidin-2-yl)butane-2-sulfonamide;
(1R,2S)-1-(5-chloropyrimidin-2-yl)-N-(4-(2,6-dimethoxyphenyl)-5-((R)-tetrahydrofuran-3-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((S)-tetrahydrofuran-3-yl)-4H-1,2,4-triazol-3-yl)-1-methoxypropane-2-sulfonamide;
(2S,3R)—N-(4-(2,6-dimethoxyphenyl)-5-((R)-tetrahydro-2H-pyran-3-yl)-4H-1,2,4-triazol-3-yl)-3-(5-methylpyrimidin-2-yl)butane-2-sulfonamide;
(2S,3R)—N-(4-(2,6-dimethoxyphenyl)-5-((S)-tetrahydro-2H-pyran-3-yl)-4H-1,2,4-triazol-3-yl)-3-(5-methylpyrimidin-2-yl)butane-2-sulfonamide;
(2S,3R)-3-(5-chloropyrimidin-2-yl)-N-(4-(2,6-dimethoxyphenyl)-5-((R)-tetrahydrofuran-3-yl)-4H-1,2,4-triazol-3-yl)butane-2-sulfonamide;
(2S,3R)-3-(5-chloropyrimidin-2-yl)-N-(4-(2,6-dimethoxyphenyl)-5-((S)-tetrahydrofuran-3-yl)-4H-1,2,4-triazol-3-yl)butane-2-sulfonamide;
(2S,3R)-3-(5-chloropyrimidin-2-yl)-N-(4-(2,6-dimethoxyphenyl)-5-((R)-tetrahydro-2H-pyran-3-yl)-4H-1,2,4-triazol-3-yl)butane-2-sulfonamide;
(2S,3R)-3-(5-chloropyrimidin-2-yl)-N-(4-(2,6-dimethoxyphenyl)-5-((S)-tetrahydro-2H-pyran-3-yl)-4H-1,2,4-triazol-3-yl)butane-2-sulfonamide;
(1R,2S)-1-(5-chloropyrimidin-2-yl)-N-(4-(2,6-dimethoxyphenyl)-5-((R)-tetrahydro-2H-pyran-3-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((S)-tetrahydro-2H-pyran-3-yl)-4H-1,2,4-triazol-3-yl)-1-methoxypropane-2-sulfonamide;
(1S,2S)—N-(4-(2,6-dimethoxyphenyl)-5-((S)-tetrahydrofuran-2-yl)-4H-1,2,4-triazol-3-yl)-1-isopropoxy-1-(5-methylpyrazin-2-yl)propane-2-sulfonamide;
(1S,2S)—N-(4-(2,6-dimethoxyphenyl)-5-((R)-tetrahydrofuran-2-yl)-4H-1,2,4-triazol-3-yl)-1-isopropoxy-1-(5-methylpyrazin-2-yl)propane-2-sulfonamide;
(2S,3R)-3-(5-chloropyrimidin-2-yl)-N-(4-(2,6-dimethoxyphenyl)-5-((2S,3R)-3-methyltetrahydrofuran-2-yl)-4H-1,2,4-triazol-3-yl)butane-2-sulfonamide;
(2S,3R)-3-(5-chloropyrimidin-2-yl)-N-(4-(2,6-dimethoxyphenyl)-5-((2R,3S)-3-methyltetrahydrofuran-2-yl)-4H-1,2,4-triazol-3-yl)butane-2-sulfonamide;

(2S,3R)—N-(4-(4,6-dimethoxypyrimidin-5-yl)-5-((S)-tetrahydrofuran-2-yl)-4H-1,2,4-triazol-3-yl)-3-(5-methylpyrimidin-2-yl)butane-2-sulfonamide;

(2S,3R)—N-(4-(4,6-dimethoxypyrimidin-5-yl)-5-((R)-tetrahydrofuran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((2R,3S)-3-methyltetrahydrofuran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((2S,3R)-3-methyltetrahydrofuran-2-yl)-4H-1,2,4-triazol-3-yl)-3-(5-methylpyrimidin-2-yl)butane-2-sulfonamide;

(1R,2S)-1-(5-chloropyrimidin-2-yl)-N-(4-(2,6-dimethoxyphenyl)-5-((2R,3S)-3-methyltetrahydrofuran-2-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((2S,3R)-3-methyltetrahydrofuran-2-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((2S,5S)-5-methyltetrahydrofuran-2-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((2R,5R)-5-methyltetrahydrofuran-2-yl)-4H-1,2,4-triazol-3-yl)-1-methoxypropane-2-sulfonamide;

(1R,2S)-1-(5-chloropyrimidin-2-yl)-N-(4-(4,6-dimethoxypyrimidin-5-yl)-5-((S)-tetrahydrofuran-2-yl)-4H-1,2,4-triazol-3-yl)-1-methoxypropane-2-sulfonamide;

(1R,2S)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)-1-methoxypropane-2-sulfonamide;

(2S,3R)-3-(5-chloropyrimidin-2-yl)-N-(4-(4,6-dimethoxypyrimidin-5-yl)-5-((S)-tetrahydrofuran-2-yl)-4H-1,2,4-triazol-3-yl)butane-2-sulfonamide;

(2S,3R)-3-(5-chloropyrimidin-2-yl)-N-(4-(4,6-dimethoxypyrimidin-5-yl)-5-((R)-tetrahydrofuran-2-yl)-4H-1,2,4-triazol-3-yl)butane-2-sulfonamide;

(1R,2S)-1-(5-chloropyrimidin-2-yl)-N-(4-(2,6-dimethoxyphenyl)-5-((S)-tetrahydro-2H-pyran-2-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((R)-tetrahydro-2H-pyran-2-yl)-4H-1,2,4-triazol-3-yl)-1-methoxypropane-2-sulfonamide;

(2S,3R)—N-(4-(2,6-dimethoxyphenyl)-5-((S)-tetrahydro-2H-pyran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-tetrahydro-2H-pyran-2-yl)-4H-1,2,4-triazol-3-yl)-3-(5-methylpyrimidin-2-yl)butane-2-sulfonamide;

(2S,3R)-3-(5-chloropyrimidin-2-yl)-N-(4-(2,6-dimethoxyphenyl)-5-((S)-tetrahydro-2H-pyran-2-yl)-4H-1,2,4-triazol-3-yl)butane-2-sulfonamide;

(2S,3R)—N-(4-(2,6-dimethoxyphenyl)-5-((S)-tetrahydrofuran-2-yl)-4H-1,2,4-triazol-3-yl)-3-(5-methylpyrazin-2-yl)butane-2-sulfonamide;

(2S,3R)—N-(4-(2,6-dimethoxyphenyl)-5-((R)-tetrahydrofuran-2-yl)-4H-1,2,4-triazol-3-yl)-3-(5-methylpyrazin-2-yl)butane-2-sulfonamide;

(1R,2S)-1-(5-chloropyrimidin-2-yl)-N-(4-(4,6-dimethoxypyrimidin-5-yl)-5-((S)-tetrahydro-2H-pyran-3-yl)-4H-1,2,4-triazol-3-yl)-1-methoxypropane-2-sulfonamide;

(1R,2S)-1-(5-chloropyrimidin-2-yl)-N-(4-(4,6-dimethoxypyrimidin-5-yl)-5-((R)-tetrahydro-2H-pyran-3-yl)-4H-1,2,4-triazol-3-yl)-1-methoxypropane-2-sulfonamide;

(2S,3R)-3-(5-chloropyrimidin-2-yl)-N-(4-(4,6-dimethoxypyrimidin-5-yl)-5-((R)-tetrahydrofuran-3-yl)-4H-1,2,4-triazol-3-yl)butane-2-sulfonamide;

(2S,3R)-3-(5-chloropyrimidin-2-yl)-N-(4-(4,6-dimethoxypyrimidin-5-yl)-5-((S)-tetrahydrofuran-3-yl)-4H-1,2,4-triazol-3-yl)butane-2-sulfonamide;

(1S,2S)—N-(4-(4,6-dimethoxypyrimidin-5-yl)-5-((S)-tetrahydrofuran-2-yl)-4H-1,2,4-triazol-3-yl)-1-isopropoxy-1-(5-methylpyrimidin-2-yl)propane-2-sulfonamide;

(1S,2S)—N-(4-(4,6-dimethoxypyrimidin-5-yl)-5-((R)-tetrahydrofuran-2-yl)-4H-1,2,4-triazol-3-yl)-1-isopropoxy-1-(5-methylpyrimidin-2-yl)propane-2-sulfonamide;

(1S,2S)—N-(4-(2,6-dimethoxyphenyl)-5-((S)-tetrahydrofuran-2-yl)-4H-1,2,4-triazol-3-yl)-1-isopropoxy-1-(5-methylpyrimidin-2-yl)propane-2-sulfonamide;

(1S,2S)—N-(4-(2,6-dimethoxyphenyl)-5-((R)-tetrahydrofuran-2-yl)-4H-1,2,4-triazol-3-yl)-1-isopropoxy-1-(5-methylpyrimidin-2-yl)propane-2-sulfonamide;

(1S,2S)—N-(4-(2,6-dimethoxyphenyl)-5-((S)-tetrahydrofuran-3-yl)-4H-1,2,4-triazol-3-yl)-1-isopropoxy-1-(5-methylpyrimidin-2-yl)propane-2-sulfonamide;

(1S,2S)—N-(4-(2,6-dimethoxyphenyl)-5-((S)-tetrahydrofuran-3-yl)-4H-1,2,4-triazol-3-yl)-1-isopropoxy-1-(5-methylpyrimidin-2-yl)propane-2-sulfonamide;

(2S,3R)-3-(5-chloropyrimidin-2-yl)-N-(4-(4,6-dimethoxypyrimidin-5-yl)-5-((S)-tetrahydro-2H-pyran-3-yl)-4H-1,2,4-triazol-3-yl)butane-2-sulfonamide;

(2S,3R)-3-(5-chloropyrimidin-2-yl)-N-(4-(4,6-dimethoxypyrimidin-5-yl)-5-((R)-tetrahydro-2H-pyran-3-yl)-4H-1,2,4-triazol-3-yl)butane-2-sulfonamide;

(1R,2S)-1-(5-chloropyrimidin-2-yl)-N-(4-(2,6-dimethoxyphenyl)-5-(tetrahydro-2H-pyran-4-yl)-4H-1,2,4-triazol-3-yl)-1-methoxypropane-2-sulfonamide;

(2S,3R)—N-(4-(4,6-dimethoxypyrimidin-5-yl)-5-((S)-tetrahydrofuran-2-yl)-4H-1,2,4-triazol-3-yl)-3-(5-methylpyrazin-2-yl)butane-2-sulfonamide;

(2S,3R)—N-(4-(4,6-dimethoxypyrimidin-5-yl)-5-((R)-tetrahydrofuran-2-yl)-4H-1,2,4-triazol-3-yl)-3-(5-methylpyrazin-2-yl)butane-2-sulfonamide;

(2S,3R)—N-(4-(2,6-dimethoxyphenyl)-5-((S)-tetrahydro-2H-pyran-2-yl)-4H-1,2,4-triazol-3-yl)-3-(5-methylpyrazin-2-yl)butane-2-sulfonamide;

(2S,3R)—N-(4-(2,6-dimethoxyphenyl)-5-((R)-tetrahydro-2H-pyran-2-yl)-4H-1,2,4-triazol-3-yl)-3-(5-methylpyrazin-2-yl)butane-2-sulfonamide;

(1R,2S)-1-(5-chloropyrimidin-2-yl)-N-(4-(2,6-dimethoxyphenyl)-5-((S)-5,5-dimethyltetrahydrofuran-2-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((R)-5,5-dimethyltetrahydrofuran-2-yl)-4H-1,2,4-triazol-3-yl)-1-methoxypropane-2-sulfonamide;

(1R,2S)-1-(5-chloropyrimidin-2-yl)-1-methoxy-N-(4-(1-methylcyclopropyl)-5-((S)-tetrahydrofuran-2-yl)-4H-1,2,4-triazol-3-yl)propane-2-sulfonamide;

(1R,2S)-1-(5-chloropyrimidin-2-yl)-1-methoxy-N-(4-(1-methylcyclopropyl)-5-((R)-tetrahydrofuran-2-yl)-4H-1,2,4-triazol-3-yl)propane-2-sulfonamide;

(1R,2S)-1-(5-chloropyrimidin-2-yl)-1-methoxy-N-(4-(1-methylcyclopropyl)-5-((S)-tetrahydro-2H-pyran-2-yl)-4H-1,2,4-triazol-3-yl)propane-2-sulfonamide;

(1R,2S)-1-(5-chloropyrimidin-2-yl)-1-methoxy-N-(4-(1-methylcyclopropyl)-5-((R)-tetrahydro-2H-pyran-2-yl)-4H-1,2,4-triazol-3-yl)propane-2-sulfonamide;

(1R,2S)-1-(5-chloropyrimidin-2-yl)-N-(4-(2,6-dimethoxyphenyl)-5-((2R,3R)-2-methyltetrahydrofuran-3-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((2S,3S)-2-methyltetrahydrofuran-3-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((2R,3S)-2-methyltetrahydrofuran-3-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((2S,3R)-2-methyltetrahydrofuran-3-yl)-4H-1,2,4-triazol-3-yl)-1-methoxypropane-2-sulfonamide;

(2S,3R)-3-(5-chloropyrimidin-2-yl)-N-(4-(2,6-dimethoxyphenyl)-5-((2R,3R)-2-methyltetrahydrofuran-3-yl)-4H-1,2,4-triazol-3-yl)butane-2-sulfonamide;

(2S,3R)-3-(5-chloropyrimidin-2-yl)-N-(4-(2,6-dimethoxyphenyl)-5-((2S,3S)-2-methyltetrahydrofuran-3-yl)-4H-1,2,4-triazol-3-yl)butane-2-sulfonamide;

(2S,3R)-3-(5-chloropyrimidin-2-yl)-N-(4-(2,6-dimethoxyphenyl)-5-((2R,3S)-2-methyltetrahydrofuran-3-yl)-4H-1,2,4-triazol-3-yl)butane-2-sulfonamide;

(2S,3R)-3-(5-chloropyrimidin-2-yl)-N-(4-(2,6-dimethoxyphenyl)-5-((2S,3R)-2-methyltetrahydrofuran-3-yl)-4H-1,2,4-triazol-3-yl)butane-2-sulfonamide;

(2S,3R)—N-(4-(2,6-dimethoxyphenyl)-5-((2S,3S)-2-methyltetrahydrofuran-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((2R,3R)-2-methyltetrahydrofuran-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((2R,3S)-2-methyltetrahydrofuran-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((2S,3R)-2-methyltetrahydrofuran-3-yl)-4H-1,2,4-triazol-3-yl)-3-(5-methylpyrimidin-2-yl)butane-2-sulfonamide;

(1R,2S)-1-(5-chloropyrimidin-2-yl)-1-methoxy-N-(4-(1-methylcyclopropyl)-5-((R)-tetrahydrofuran-3-yl)-4H-1,2,4-triazol-3-yl)propane-2-sulfonamide;

(1R,2S)-1-(5-chloropyrimidin-2-yl)-1-methoxy-N-(4-(1-methylcyclopropyl)-5-((S)-tetrahydrofuran-3-yl)-4H-1,2,4-triazol-3-yl)propane-2-sulfonamide;

(1R,2S)-1-(5-chloropyrimidin-2-yl)-1-methoxy-N-(4-(1-methylcyclopropyl)-5-((R)-tetrahydro-2H-pyran-3-yl)-4H-1,2,4-triazol-3-yl)propane-2-sulfonamide;

(1R,2S)-1-(5-chloropyrimidin-2-yl)-1-methoxy-N-(4-(1-methylcyclopropyl)-5-((S)-tetrahydro-2H-pyran-3-yl)-4H-1,2,4-triazol-3-yl)propane-2-sulfonamide;

(1R,2S)-1-methoxy-N-(4-(1-methylcyclopropyl)-5-((R)-tetrahydrofuran-3-yl)-4H-1,2,4-triazol-3-yl)-1-(5-methylpyrazin-2-yl)propane-2-sulfonamide;

(1R,2S)-1-methoxy-N-(4-(1-methylcyclopropyl)-5-((S)-tetrahydrofuran-3-yl)-4H-1,2,4-triazol-3-yl)-1-(5-methylpyrazin-2-yl)propane-2-sulfonamide;

(1R,2S)-1-methoxy-N-(4-(1-methylcyclopropyl)-5-((R)-tetrahydro-2H-pyran-3-yl)-4H-1,2,4-triazol-3-yl)-1-(5-methylpyrazin-2-yl)propane-2-sulfonamide;

(1R,2S)-1-methoxy-N-(4-(1-methylcyclopropyl)-5-((S)-tetrahydro-2H-pyran-3-yl)-4H-1,2,4-triazol-3-yl)-1-(5-methylpyrazin-2-yl)propane-2-sulfonamide;

(2S,3R)—N-(4-(2,6-dimethoxyphenyl)-5-((R)-tetrahydrofuran-3-yl)-4H-1,2,4-triazol-3-yl)-3-(5-methylpyrazin-2-yl)butane-2-sulfonamide;

(2S,3R)—N-(4-(2,6-dimethoxyphenyl)-5-((S)-tetrahydrofuran-3-yl)-4H-1,2,4-triazol-3-yl)-3-(5-methylpyrazin-2-yl)butane-2-sulfonamide;

(2S,3R)—N-(4-(2,6-dimethoxyphenyl)-5-((R)-tetrahydro-2H-pyran-3-yl)-4H-1,2,4-triazol-3-yl)-3-(5-methylpyrazin-2-yl)butane-2-sulfonamide;

(2S,3R)—N-(4-(2,6-dimethoxyphenyl)-5-((S)-tetrahydro-2H-pyran-3-yl)-4H-1,2,4-triazol-3-yl)-3-(5-methylpyrazin-2-yl)butane-2-sulfonamide;

(1S,2S)—N-(4-(2,6-dimethoxyphenyl)-5-((R)-tetrahydro-2H-pyran-3-yl)-4H-1,2,4-triazol-3-yl)-1-isopropoxy-1-(5-methylpyrimidin-2-yl)propane-2-sulfonamide;

(1S,2S)—N-(4-(2,6-dimethoxyphenyl)-5-((S)-tetrahydro-2H-pyran-3-yl)-4H-1,2,4-triazol-3-yl)-1-isopropoxy-1-(5-methylpyrimidin-2-yl)propane-2-sulfonamide;

(1R,2S)-1-(5-chloropyrimidin-2-yl)-N-(4-(4,6-dimethoxypyrimidin-5-yl)-5-((S)-5,5-dimethyltetrahydrofuran-2-yl)-4H-1,2,4-triazol-3-yl)-1-methoxypropane-2-sulfonamide;

(1R,2S)-1-(5-chloropyrimidin-2-yl)-N-(4-(4,6-dimethoxypyrimidin-5-yl)-5-((R)-5,5-dimethyltetrahydrofuran-2-yl)-4H-1,2,4-triazol-3-yl)-1-methoxypropane-2-sulfonamide;

(1R,2S)—N-(4-(2,6-dimethoxyphenyl)-5-((S)-tetrahydrofuran-3-yl)-4H-1,2,4-triazol-3-yl)-1-hydroxy-1-(5-methylpyrimidin-2-yl)propane-2-sulfonamide;

(1R,2S)—N-(4-(2,6-dimethoxyphenyl)-5-((R)-tetrahydrofuran-3-yl)-4H-1,2,4-triazol-3-yl)-1-hydroxy-1-(5-methylpyrimidin-2-yl)propane-2-sulfonamide;

(2S,3R)-3-(5-chloropyrimidin-2-yl)-N-(4-(2,6-dimethoxyphenyl)-5-((R)-oxetan-2-yl)-4H-1,2,4-triazol-3-yl)butane-2-sulfonamide;

(2S,3R)-3-(5-chloropyrimidin-2-yl)-N-(4-(2,6-dimethoxyphenyl)-5-((S)-oxetan-2-yl)-4H-1,2,4-triazol-3-yl)butane-2-sulfonamide;

(S)-2-(4-chlorophenyl)-N-(4-(2,6-dimethoxyphenyl)-5-(tetrahydrofuran-2-yl)-4H-1,2,4-triazol-3-yl)ethanesulfonamide;

(R)-2-(4-chlorophenyl)-N-(4-(2,6-dimethoxyphenyl)-5-(tetrahydrofuran-2-yl)-4H-1,2,4-triazol-3-yl)ethanesulfonamide;

(S)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide;

(R)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide;

(2S,3R)-3-(5-cyano-2-pyrimidinyl)-N-(4-(2,6-dimethoxyphenyl)-5-((3R)-tetrahydro-3-furanyl)-4H-1,2,4-triazol-3-yl)-2-butanesulfonamide;

(2S,3R)-3-(5-cyano-2-pyrimidinyl)-N-(4-(2,6-dimethoxyphenyl)-5-((3S)-tetrahydro-3-furanyl)-4H-1,2,4-triazol-3-yl)-2-butanesulfonamide;

(2S,3R)—N-(4-(2,6-dimethoxyphenyl)-5-((2R)-1,4-dioxan-2-yl)-4H-1,2,4-triazol-3-yl)-3-(5-methoxy-2-pyrimidinyl)-2-butanesulfonamide;

(2S,3R)—N-(4-(2,6-dimethoxyphenyl)-5-((2S)-1,4-dioxan-2-yl)-4H-1,2,4-triazol-3-yl)-3-(5-methoxy-2-pyrimidinyl)-2-butanesulfonamide;

(2S,3R)—N-(4-(4,6-dimethoxy-5-pyrimidinyl)-5-((2R)-1,4-dioxan-2-yl)-4H-1,2,4-triazol-3-yl)-3-(5-methoxy-2-pyrimidinyl)-2-butanesulfonamide;

(2S,3R)—N-(4-(4,6-dimethoxy-5-pyrimidinyl)-5-((2S)-1,4-dioxan-2-yl)-4H-1,2,4-triazol-3-yl)-3-(5-methoxy-2-pyrimidinyl)-2-butanesulfonamide;

(3R,5S)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidine sulfonamide;

(3R,5S)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidine sulfonamide;

(3S,5R)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidine sulfonamide;

(3S,5R)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidine sulfonamide;
(3R,5S)—N-(4-(2,6-dimethoxyphenyl)-5-((2R)-1,4-dioxan-2-yl)-4H-1,2,4-triazol-3-yl)-1-(5-fluoro-2-pyrimidinyl)-5-(1-methylethoxy)-3-piperidine sulfonamide;
(3R,5S)—N-(4-(2,6-dimethoxyphenyl)-5-((2S)-1,4-dioxan-2-yl)-4H-1,2,4-triazol-3-yl)-1-(5-fluoro-2-pyrimidinyl)-5-(1-methylethoxy)-3-piperidine sulfonamide;
(3S,5R)—N-(4-(2,6-dimethoxyphenyl)-5-((2R)-1,4-dioxan-2-yl)-4H-1,2,4-triazol-3-yl)-1-(5-fluoro-2-pyrimidinyl)-5-(1-methylethoxy)-3-piperidine sulfonamide;
(3S,5R)—N-(4-(2,6-dimethoxyphenyl)-5-((2S)-1,4-dioxan-2-yl)-4H-1,2,4-triazol-3-yl)-1-(5-fluoro-2-pyrimidinyl)-5-(1-methylethoxy)-3-piperidine sulfonamide;
(2S,3R)—N-(4-(2,6-dimethoxyphenyl)-5-((R)-1,1-dioxidotetrahydrothiophen-3-yl)-4H-1,2,4-triazol-3-yl)-3-(5-methylpyrimidin-2-yl)butane-2-sulfonamide;
(2S,3R)—N-(4-(2,6-dimethoxyphenyl)-5-((S)-1,1-dioxidotetrahydrothiophen-3-yl)-4H-1,2,4-triazol-3-yl)-3-(5-methylpyrimidin-2-yl)butane-2-sulfonamide;
(1R,2S)—N-(4-(4,6-dimethoxypyrimidin-5-yl)-5-((S)-tetrahydrofuran-2-yl)-4H-1,2,4-triazol-3-yl)-1-methoxy-1-(5-methylpyrazin-2-yl)propane-2-sulfonamide;
(1R,2S)—N-(4-(4,6-dimethoxypyrimidin-5-yl)-5-((R)-tetrahydrofuran-2-yl)-4H-1,2,4-triazol-3-yl)-1-methoxy-1-(5-methylpyrazin-2-yl)propane-2-sulfonamide;
(1R,2S)-1-(5-chloropyrimidin-2-yl)-N-(4-(2,6-dimethoxyphenyl)-5-((R)-1,1-dioxidotetrahydrothiophen-3-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((S)-1,1-dioxidotetrahydrothiophen-3-yl)-4H-1,2,4-triazol-3-yl)-1-methoxypropane-2-sulfonamide;
(2S,3R)-3-(5-chloropyrimidin-2-yl)-N-(4-(2,6-dimethoxyphenyl)-5-((R)-1,1-dioxidotetrahydrothiophen-3-yl)-4H-1,2,4-triazol-3-yl)butane-2-sulfonamide;
(2S,3R)-3-(5-chloropyrimidin-2-yl)-N-(4-(2,6-dimethoxyphenyl)-5-((S)-1,1-dioxidotetrahydrothiophen-3-yl)-4H-1,2,4-triazol-3-yl)butane-2-sulfonamide;
(2S,3R)-3-(5-chloropyrimidin-2-yl)-N-(4-(4,6-dimethoxypyrimidin-5-yl)-5-((S)-tetrahydro-2H-pyran-2-yl)-4H-1,2,4-triazol-3-yl)butane-2-sulfonamide;
(2S,3R)-3-(5-chloropyrimidin-2-yl)-N-(4-(4,6-dimethoxypyrimidin-5-yl)-5-((R)-tetrahydro-2H-pyran-2-yl)-4H-1,2,4-triazol-3-yl)butane-2-sulfonamide;
(1R,2S)—N-(4-(2,6-dimethoxyphenyl)-5-((S)-tetrahydro-2H-pyran-3-yl)-4H-1,2,4-triazol-3-yl)-1-hydroxy-1-(5-methylpyrimidin-2-yl)propane-2-sulfonamide;
(1R,2S)—N-(4-(2,6-dimethoxyphenyl)-5-((R)-tetrahydro-2H-pyran-3-yl)-4H-1,2,4-triazol-3-yl)-1-hydroxy-1-(5-methylpyrimidin-2-yl)propane-2-sulfonamide;
(2S,3R)-3-(5-chloropyrimidin-2-yl)-N-(4-(4,6-dimethoxypyrimidin-5-yl)-5-((R)-1,4-dioxan-2-yl)-4H-1,2,4-triazol-3-yl)butane-2-sulfonamide;
(2S,3R)-3-(5-chloropyrimidin-2-yl)-N-(4-(4,6-dimethoxypyrimidin-5-yl)-5-((S)-1,4-dioxan-2-yl)-4H-1,2,4-triazol-3-yl)butane-2-sulfonamide;
(1R,2S)-1-(5-chloropyrimidin-2-yl)-N-(4-(2,6-dimethoxyphenyl)-5-((R)-1,4-dioxan-2-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((S)-1,4-dioxan-2-yl)-4H-1,2,4-triazol-3-yl)-1-methoxypropane-2-sulfonamide;
(1R,2S)-1-(5-chloropyrimidin-2-yl)-1-methoxy-N-(4-(1-methylcyclopropyl)-5-((2S,5S)-5-methyltetrahydrofuran-2-yl)-4H-1,2,4-triazol-3-yl)propane-2-sulfonamide;
(1R,2S)-1-(5-chloropyrimidin-2-yl)-1-methoxy-N-(4-(1-methylcyclopropyl)-5-((2R,5R)-5-methyltetrahydrofuran-2-yl)-4H-1,2,4-triazol-3-yl)propane-2-sulfonamide;
(1R,2S)—N-(4-(2,6-dimethoxyphenyl)-5-((R)-1,4-dioxan-2-yl)-4H-1,2,4-triazol-3-yl)-1-methoxy-1-(5-methylpyrimidin-2-yl)propane-2-sulfonamide;
(1R,2S)—N-(4-(2,6-dimethoxyphenyl)-5-((S)-1,4-dioxan-2-yl)-4H-1,2,4-triazol-3-yl)-1-methoxy-1-(5-methylpyrimidin-2-yl)propane-2-sulfonamide;
(1R,2S)—N-(4-(2,6-dimethoxyphenyl)-5-((R)-1,4-dioxan-2-yl)-4H-1,2,4-triazol-3-yl)-1-ethoxy-1-(5-methylpyrimidin-2-yl)propane-2-sulfonamide;
(1R,2S)—N-(4-(2,6-dimethoxyphenyl)-5-((S)-1,4-dioxan-2-yl)-4H-1,2,4-triazol-3-yl)-1-ethoxy-1-(5-methylpyrimidin-2-yl)propane-2-sulfonamide;
(2S,3R)—N-(4-(2,6-dimethoxyphenyl)-5-((R)-1,4-dioxan-2-yl)-4H-1,2,4-triazol-3-yl)-3-(5-methylpyrimidin-2-yl)butane-2-sulfonamide;
(2S,3R)—N-(4-(2,6-dimethoxyphenyl)-5-((S)-1,4-dioxan-2-yl)-4H-1,2,4-triazol-3-yl)-3-(5-methylpyrimidin-2-yl)butane-2-sulfonamide;
(2S,3R)—N-(4-(2,6-dimethoxyphenyl)-5-((R)-1,4-dioxan-2-yl)-4H-1,2,4-triazol-3-yl)-3-(5-methoxypyrazin-2-yl)butane-2-sulfonamide;
(2S,3R)—N-(4-(2,6-dimethoxyphenyl)-5-((S)-1,4-dioxan-2-yl)-4H-1,2,4-triazol-3-yl)-3-(5-methoxypyrazin-2-yl)butane-2-sulfonamide;
(1S,2S)—N-(4-(2,6-dimethoxyphenyl)-5-((S)-5,5-dimethyltetrahydrofuran-2-yl)-4H-1,2,4-triazol-3-yl)-1-isopropoxy-1-(5-methylpyrimidin-2-yl)propane-2-sulfonamide;
(1S,2S)—N-(4-(2,6-dimethoxyphenyl)-5-((R)-5,5-dimethyltetrahydrofuran-2-yl)-4H-1,2,4-triazol-3-yl)-1-isopropoxy-1-(5-methylpyrimidin-2-yl)propane-2-sulfonamide;
(1S,2S)—N-(4-(2,6-dimethoxyphenyl)-5-((S)-tetrahydro-2H-pyran-2-yl)-4H-1,2,4-triazol-3-yl)-1-isopropoxy-1-(5-methylpyrazin-2-yl)propane-2-sulfonamide;
(1S,2S)—N-(4-(2,6-dimethoxyphenyl)-5-((R)-tetrahydro-2H-pyran-2-yl)-4H-1,2,4-triazol-3-yl)-1-isopropoxy-1-(5-methylpyrazin-2-yl)propane-2-sulfonamide;
(1S,2S)—N-(4-(2,6-dimethoxyphenyl)-5-((R)-tetrahydrofuran-3-yl)-4H-1,2,4-triazol-3-yl)-1-isopropoxy-1-(5-methylpyrazin-2-yl)propane-2-sulfonamide;
(1S,2S)—N-(4-(2,6-dimethoxyphenyl)-5-((S)-tetrahydrofuran-3-yl)-4H-1,2,4-triazol-3-yl)-1-isopropoxy-1-(5-methylpyrazin-2-yl)propane-2-sulfonamide;
(1S,2S)—N-(4-(2,6-dimethoxyphenyl)-5-((R)-tetrahydro-2H-pyran-3-yl)-4H-1,2,4-triazol-3-yl)-1-isopropoxy-1-(5-methylpyrazin-2-yl)propane-2-sulfonamide;
(1S,2S)—N-(4-(2,6-dimethoxyphenyl)-5-((S)-tetrahydro-2H-pyran-3-yl)-4H-1,2,4-triazol-3-yl)-1-isopropoxy-1-(5-methylpyrazin-2-yl)propane-2-sulfonamide;
(1S,2S)—N-(4-(2,6-dimethoxyphenyl)-5-((R)-1,4-dioxan-2-yl)-4H-1,2,4-triazol-3-yl)-1-isopropoxy-1-(5-methylpyrazin-2-yl)propane-2-sulfonamide;
(1S,2S)—N-(4-(2,6-dimethoxyphenyl)-5-((S)-1,4-dioxan-2-yl)-4H-1,2,4-triazol-3-yl)-1-isopropoxy-1-(5-methylpyrazin-2-yl)propane-2-sulfonamide;
(2R,3S)—N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide;
(2R,3S)—N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide;

(1R,2S)-1-(5-chloropyrimidin-2-yl)-N-(5-((S)-5,5-dimethyltetrahydrofuran-2-yl)-4-(tetrahydro-2H-pyran-4-yl)-4H-1,2,4-triazol-3-yl)-1-methoxypropane-2-sulfonamide;

(1R,2S)-1-(5-chloropyrimidin-2-yl)-N-(5-((R)-5,5-dimethyltetrahydrofuran-2-yl)-4-(tetrahydro-2H-pyran-4-yl)-4H-1,2,4-triazol-3-yl)-1-methoxypropane-2-sulfonamide;

(2S,3R)—N-(4-(2,6-dimethoxyphenyl)-5-((S)-tetrahydrothiophen-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-tetrahydrothiophen-2-yl)-4H-1,2,4-triazol-3-yl)-3-(5-methylpyrimidin-2-yl)butane-2-sulfonamide;

(1R,2S)-1-(5-chloropyrimidin-2-yl)-1-methoxy-N-(5-((2S,5S)-5-methyltetrahydrofuran-2-yl)-4-(tetrahydro-2H-pyran-4-yl)-4H-1,2,4-triazol-3-yl)propane-2-sulfonamide;

(1R,2S)-1-(5-chloropyrimidin-2-yl)-1-methoxy-N-(5-((2R,5R)-5-methyltetrahydrofuran-2-yl)-4-(tetrahydro-2H-pyran-4-yl)-4H-1,2,4-triazol-3-yl)propane-2-sulfonamide;

(2S,3R)—N-(4-(2,6-dimethoxyphenyl)-5-((2R)-4-(methylsulfonyl)-2-morpholinyl)-4H-1,2,4-triazol-3-yl)-3-(5-methyl-2-pyrimidinyl)-2-butanesulfonamide;

(2S,3R)—N-(4-(2,6-dimethoxyphenyl)-5-((2S)-4-(methylsulfonyl)-2-morpholinyl)-4H-1,2,4-triazol-3-yl)-3-(5-methyl-2-pyrimidinyl)-2-butanesulfonamide;

(1R,2S)—N-(5-((S)-2,3-dihydrobenzofuran-2-yl)-4-(4,6-dimethoxypyrimidin-5-yl)-4H-1,2,4-triazol-3-yl)-1-methoxy-1-(5-methylpyrimidin-2-yl)propane-2-sulfonamide;

or (1R,2S)—N-(5-((R)-2,3-dihydrobenzofuran-2-yl)-4-(4,6-dimethoxypyrimidin-5-yl)-4H-1,2,4-triazol-3-yl)-1-methoxy-1-(5-methylpyrimidin-2-yl)propane-2-sulfonamide; or the pharmaceutically acceptable salt thereof, the tautomer thereof, the pharmaceutically acceptable salt of the tautomer, the stereoisomer of any of the foregoing, or the mixture thereof.

77. The compound of embodiment 8, wherein the compound is selected from (2S,3R)—N-(4-(2,6-dimethoxyphenyl)-5-((S)-pyrrolidin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-pyrrolidin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-piperidin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-piperidin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-piperidin-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-piperidin-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-(piperidin-4-yl)-4H-1,2,4-triazol-3-yl)-3-(5-methylpyrimidin-2-yl)butane-2-sulfonamide;

(2S,3R)—N-(4-(2,6-dimethoxyphenyl)-5-(1,1-dioxidotetrahydro-2H-thiopyran-4-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-1,1-dioxidotetrahydro-2H-thiopyran-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-1,1-dioxidotetrahydro-2H-thiopyran-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-1,1-dioxidotetrahydro-2H-thiopyran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-1,1-dioxidotetrahydro-2H-thiopyran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-1,1-dioxidotetrahydrothiophen-2-yl)-4H-1,2,4-triazol-2-yl)-3-(5-methylpyrimidin-2-yl)butane-2-sulfonamide;

(2S,3R)—N-(4-(2,6-dimethoxyphenyl)-5-((S)-1,1-dioxidotetrahydrothiophen-2-yl)-4H-1,2,4-triazol-2-yl)-3-(5-methylpyrimidin-2-yl)butane-2-sulfonamide;

((2S,3R)—N-(4-(2,6-dimethoxyphenyl)-5-((S)-morpholin-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-morpholin-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-morpholin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-morpholin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-(1,3-dioxan-5-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-1,3-dioxolan-4-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-1,3-dioxolan-4-yl)-4H-1,2,4-triazol-3-yl)-3-(5-methylpyrimidin-2-yl)butane-2-sulfonamide;

(2S,3R)—N-(4-(2,6-dimethoxyphenyl)-5-(1,3-dioxolan-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-(1,3-dioxan-2-yl)-4H-1,2,4-triazol-3-yl)-3-(5-methylpyrimidin-2-yl)butane-2-sulfonamide;

(3R,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3R,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3S,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3S,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3R,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3R,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3S,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3S,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide;

(2S,3R)—N-(4-(2,6-dimethoxyphenyl)-5-((S)-tetrahydrothiophen-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-tetrahydrothiophen-3-yl)-4H-1,2,4-triazol-3-yl)-3-(5-methylpyrimidin-2-yl)butane-2-sulfonamide;

(S)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)piperidine-3-sulfonamide;

(R)-1-(5-chloropyrimidin-2-yl)-N-(4-(4,6-dimethoxypyrimidin-5-yl)-5-((S)-tetrahydrofuran-2-yl)-4H-1,2,4-triazol-3-yl)piperidine-3-sulfonamide;

(S)-1-(5-chloropyrimidin-2-yl)-N-(4-(4,6-dimethoxypyrimidin-5-yl)-5-((S)-tetrahydrofuran-2-yl)-4H-1,2,4-triazol-3-yl)piperidine-3-sulfonamide;

(R)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)piperidine-3-sulfonamide;

(S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)piperidine-3-sulfonamide;

(S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)piperidine-3-sulfonamide;

(R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)piperidine-3-sulfonamide;

(R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)piperidine-3-sulfonamide;

(3R,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-hydroxypiperidine-3-sulfonamide;

(3R,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-hydroxypiperidine-3-sulfonamide;

(3R,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-hydroxypiperidine-3-sulfonamide;

(3R,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-hydroxypiperidine-3-sulfonamide;

(3S,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-hydroxypiperidine-3-sulfonamide;

(3S,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-hydroxypiperidine-3-sulfonamide;

(3S,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-hydroxypiperidine-3-sulfonamide;

(3S,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-hydroxypiperidine-3-sulfonamide;

(3R,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide;

(3R,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide;

(3R,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide;

(3R,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide;

(3S,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide;

(3S,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide;

(3S,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide;

(3S,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide;

(3R,5S)—N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide;

(3R,5S)—N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide;

(3R,5R)—N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide;

(3R,5R)—N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide;

(3S,5R)—N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide;

(3S,5R)—N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide;

(3S,5S)—N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide;

(3S,5S)—N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide;

(3R,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3R,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3R,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3R,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3S,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3S,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3S,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3S,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide;

(S)—N-(4-(2,6-dimethoxyphenyl)-5-((R)-tetrahydrofuran-2-yl)-4H-1,2,4-triazol-3-yl)-1-(5-fluoropyrimidin-2-yl)piperidine-3-sulfonamide;

(S)—N-(4-(2,6-dimethoxyphenyl)-5-((S)-tetrahydrofuran-2-yl)-4H-1,2,4-triazol-3-yl)-1-(5-fluoropyrimidin-2-yl)piperidine-3-sulfonamide;
(R)—N-(4-(2,6-dimethoxyphenyl)-5-((R)-tetrahydrofuran-2-yl)-4H-1,2,4-triazol-3-yl)-1-(5-fluoropyrimidin-2-yl)piperidine-3-sulfonamide;
(R)—N-(4-(2,6-dimethoxyphenyl)-5-((S)-tetrahydrofuran-2-yl)-4H-1,2,4-triazol-3-yl)-1-(5-fluoropyrimidin-2-yl)piperidine-3-sulfonamide;
(3R,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide;
(3R,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide;
(3R,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide;
(3R,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide;
(3S,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide;
(3S,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide;
(3S,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide;
(3S,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide;
(3R,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide;
(3R,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide;
(3R,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide;
(3R,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide;
(3S,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide;
(3S,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide;
(3S,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide;
(3S,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide;
(3R,5S)—N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide;
(3R,5S)—N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide;
(3R,5R)—N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide;
(3R,5R)—N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide;
(3S,5R)—N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide;
(3S,5R)—N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide;
(3S,5S)—N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide; or
(3S,5S)—N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide; or
the pharmaceutically acceptable salt thereof, or the mixture thereof.

78. The compound of embodiment 8, wherein the compound is selected from
(2S,3R)-3-(5-chloropyrimidin-2-yl)-N-(4-(2,6-dimethoxyphenyl)-5-((R)-tetrahydrofuran-3-yl)-4H-1,2,4-triazol-3-yl)butane-2-sulfonamide;
(2S,3R)-3-(5-chloropyrimidin-2-yl)-N-(4-(2,6-dimethoxyphenyl)-5-((S)-tetrahydrofuran-3-yl)-4H-1,2,4-triazol-3-yl)butane-2-sulfonamide;
(2S,3R)—N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide;
(2S,3R)—N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide;
(2S,3R)-3-(5-chloro-2-pyrimidinyl)-N-(4-(2,6-dimethoxyphenyl)-5-((2R)-1,4-dioxan-2-yl)-4H-1,2,4-triazol-3-yl)-2-butanesulfonamide;
(2S,3R)-3-(5-chloro-2-pyrimidinyl)-N-(4-(2,6-dimethoxyphenyl)-5-((2S)-1,4-dioxan-2-yl)-4H-1,2,4-triazol-3-yl)-2-butanesulfonamide;
(2S,3R)-3-(5-chloropyrimidin-2-yl)-N-(4-(4,6-dimethoxypyrimidin-5-yl)-5-((R)-1,4-dioxan-2-yl)-4H-1,2,4-triazol-3-yl)butane-2-sulfonamide;
(2S,3R)-3-(5-chloropyrimidin-2-yl)-N-(4-(4,6-dimethoxypyrimidin-5-yl)-5-((S)-1,4-dioxan-2-yl)-4H-1,2,4-triazol-3-yl)butane-2-sulfonamide;
(1S,2S)—N-(4-(4,6-dimethoxypyrimidin-5-yl)-5-((S)-tetrahydrofuran-2-yl)-4H-1,2,4-triazol-3-yl)-1-isopropoxy-1-(5-methylpyrimidin-2-yl)propane-2-sulfonamide;
(1S,2S)—N-(4-(4,6-dimethoxypyrimidin-5-yl)-5-((R)-tetrahydrofuran-2-yl)-4H-1,2,4-triazol-3-yl)-1-isopropoxy-1-(5-methylpyrimidin-2-yl)propane-2-sulfonamide;
(1R,2S)-1-(5-chloropyrimidin-2-yl)-N-(4-(4,6-dimethoxypyrimidin-5-yl)-5-((S)-5,5-dimethyltetrahydrofuran-2-yl)-4H-1,2,4-triazol-3-yl)-1-methoxypropane-2-sulfonamide;
(1R,2S)-1-(5-chloropyrimidin-2-yl)-N-(4-(4,6-dimethoxypyrimidin-5-yl)-5-((R)-5,5-dimethyltetrahydrofuran-2-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((R)-1,4-dioxan-2-yl)-4H-1,2,4-triazol-3-yl)-1-methoxypropane-2-sulfonamidep;
(1R,2S)-1-(5-chloropyrimidin-2-yl)-N-(4-(2,6-dimethoxyphenyl)-5-((S)-1,4-dioxan-2-yl)-4H-1,2,4-triazol-3-yl)-1-methoxypropane-2-sulfonamide;
(1S,2S)—N-(4-(2,6-dimethoxyphenyl)-5-((S)-5,5-dimethyltetrahydrofuran-2-yl)-4H-1,2,4-triazol-3-yl)-1-isopropoxy-1-(5-methylpyrimidin-2-yl)propane-2-sulfonamide;

(1S,2S)—N-(4-(2,6-dimethoxyphenyl)-5-((R)-5,5-dimethyltetrahydrofuran-2-yl)-4H-1,2,4-triazol-3-yl)-1-isopropoxy-1-(5-methylpyrimidin-2-yl)propane-2-sulfonamide;

(1R,2S)-1-(5-chloropyrimidin-2-yl)-N-(4-(2,6-dimethoxyphenyl)-5-((S)-tetrahydro-2H-pyran-2-yl)-4H-1,2,4-triazol-3-yl)-1-methoxypropane-2-sulfonamide; or (1R,2S)-1-(5-chloropyrimidin-2-yl)-N-(4-(2,6-dimethoxyphenyl)-5-((R)-tetrahydro-2H-pyran-2-yl)-4H-1,2,4-triazol-3-yl)-1-methoxypropane-2-sulfonamide; or the pharmaceutically acceptable salt thereof, or the mixture thereof.

79. The compound of embodiment 1, wherein the compound is selected from (2S,3R)-3-(5-chloro-2-pyrimidinyl)-N-(4-(2,6-dimethoxyphenyl)-5-((1S)-3-oxo-2,3-dihydro-1H-isoindol-1-yl)-4H-1,2,4-triazol-3-yl)-2-butanesulfonamide;

(2S,3R)-3-(5-chloro-2-pyrimidinyl)-N-(4-(2,6-dimethoxyphenyl)-5-((1R)-3-oxo-2,3-dihydro-1H-isoindol-1-yl)-4H-1,2,4-triazol-3-yl)-2-butanesulfonamide;

(1R,2S)—N-(4-(2,6-dimethoxyphenyl)-5-((1R)-3-oxo-2,3-dihydro-1H-isoindol-1-yl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-((1S)-3-oxo-2,3-dihydro-1H-isoindol-1-yl)-4H-1,2,4-triazol-3-yl)-1-methoxy-1-(5-methyl-2-pyrimidinyl)-2-propanesulfonamide;

(1R,2S)—N-(5-((3S)-2,3-dihydro-1-benzofuran-3-yl)-4-(2,6-dimethoxyphenyl)-4H-1,2,4-triazol-3-yl)-1-methoxy-1-(5-methyl-2-pyrimidinyl)-2-propanesulfonamide;

(1R,2S)—N-(5-((3R)-2,3-dihydro-1-benzofuran-3-yl)-4-(2,6-dimethoxyphenyl)-4H-1,2,4-triazol-3-yl)-1-methoxy-1-(5-methyl-2-pyrimidinyl)-2-propanesulfonamide;

(1R,2S)-1-(5-chloro-2-pyrimidinyl)-1-methoxy-N-(4-(2-methoxyphenyl)-5-((2S)-tetrahydro-2-furanyl)-4H-1,2,4-triazol-3-yl)-2-propanesulfonamide;

(1R,2S)-1-(5-chloro-2-pyrimidinyl)-N-(4-(2-ethylphenyl)-5-((2S)-tetrahydro-2-furanyl)-4H-1,2,4-triazol-3-yl)-1-methoxy-2-propanesulfonamide;

(1R,2S)-1-(5-chloro-2-pyrimidinyl)-1-methoxy-N-(4-(2-methylphenyl)-5-((2S)-tetrahydro-2-furanyl)-4H-1,2,4-triazol-3-yl)-2-propanesulfonamide;

(1R,2S)—N-(4-(2-chlorophenyl)-5-((2S)-tetrahydro-2-furanyl)-4H-1,2,4-triazol-3-yl)-1-(5-chloro-2-pyrimidinyl)-1-methoxy-2-propanesulfonamide;

(1R,2S)-1-(5-chloro-2-pyrimidinyl)-N-(4-(2-fluorophenyl)-5-((2S)-tetrahydro-2-furanyl)-4H-1,2,4-triazol-3-yl)-1-methoxy-2-propanesulfonamide;

(2S,3R)-3-(5-chloro-2-pyrimidinyl)-N-(5-((2R)-1,4-dioxan-2-yl)-4-(tetrahydro-2H-pyran-4-yl)-4H-1,2,4-triazol-3-yl)-2-butanesulfonamide;

(2S,3R)-3-(5-chloro-2-pyrimidinyl)-N-(5-((2S)-1,4-dioxan-2-yl)-4-(tetrahydro-2H-pyran-4-yl)-4H-1,2,4-triazol-3-yl)-2-butanesulfonamide;

(1R,2S)-1-(5-chloro-2-pyrimidinyl)-N-(5-((2R)-1,4-dioxan-2-yl)-4-(tetrahydro-2H-pyran-4-yl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(tetrahydro-2H-pyran-4-yl)-4H-1,2,4-triazol-3-yl)-1-methoxy-2-propanesulfonamide;

(2S,3R)—N-(4-(2,6-dimethoxyphenyl)-5-((2R,5R)-5-methyltetrahydro-2-furanyl)-4H-1,2,4-triazol-3-yl)-3-(5-methoxy-2-pyrimidinyl)-2-butanesulfonamide;

(2S,3R)—N-(4-(2,6-dimethoxyphenyl)-5-((2S,5S)-5-methyltetrahydro-2-furanyl)-4H-1,2,4-triazol-3-yl)-3-(5-methoxy-2-pyrimidinyl)-2-butanesulfonamide;

(1R,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide;

(2S,3R)-3-(5-chloro-2-pyrimidinyl)-N-(4-(3,5-dibromo-2,6-dimethoxyphenyl)-5-((3S)-tetrahydro-3-furanyl)-4H-1,2,4-triazol-3-yl)-2-butanesulfonamide;

(1S,2S)—N-(4-(2,6-dimethoxyphenyl)-5-((2S)-1,4-dioxan-2-yl)-4H-1,2,4-triazol-3-yl)-1-(1-methylethoxy)-1-(5-methyl-2-pyrimidinyl)-2-propanesulfonamide;

(1S,2S)—N-(4-(2,6-dimethoxyphenyl)-5-((2R)-1,4-dioxan-2-yl)-4H-1,2,4-triazol-3-yl)-1-(1-methylethoxy)-1-(5-methyl-2-pyrimidinyl)-2-propanesulfonamide;

(2S,3R)—N-(4-(2,6-dimethoxyphenyl)-5-((3R,8aR)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(2S,3R)—N-(4-(2,6-dimethoxyphenyl)-5-((3R,8aS)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(2S,3R)—N-(4-(2,6-dimethoxyphenyl)-5-((3S,8aR)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(2S,3R)—N-(4-(2,6-dimethoxyphenyl)-5-((3S,8aS)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(1R,2S)-1-(5-chloro-2-pyrimidinyl)-N-(5-((2R)-2,3-dihydro-1,4-benzodioxin-2-yl)-4-(2,6-dimethoxyphenyl)-4H-1,2,4-triazol-3-yl)-1-methoxy-2-propanesulfonamide;

(1R,2S)-1-(5-chloro-2-pyrimidinyl)-N-(5-((2S)-2,3-dihydro-1,4-benzodioxin-2-yl)-4-(2,6-dimethoxyphenyl)-4H-1,2,4-triazol-3-yl)-1-methoxy-2-propanesulfonamide;

(1S,2S)-1-(1-methylethoxy)-1-(5-methyl-2-pyrazinyl)-N-(5-((2S)-tetrahydro-2-furanyl)-4-(tetrahydro-2H-pyran-4-yl)-4H-1,2,4-triazol-3-yl)-2-propanesulfonamide;

(1S,2S)-1-(1-methylethoxy)-1-(5-methyl-2-pyrazinyl)-N-(5-((2R)-tetrahydro-2-furanyl)-4-(tetrahydro-2H-pyran-4-yl)-4H-1,2,4-triazol-3-yl)-2-propanesulfonamide;

(1S,2S)-1-(1-methylethoxy)-1-(5-methyl-2-pyrazinyl)-N-(5-((2S,5S)-5-methyltetrahydro-2-furanyl)-4-(tetrahydro-2H-pyran-4-yl)-4H-1,2,4-triazol-3-yl)-2-propanesulfonamide;

(1S,2S)-1-(1-methylethoxy)-1-(5-methyl-2-pyrazinyl)-N-(5-((2R,5R)-5-methyltetrahydro-2-furanyl)-4-(tetrahydro-2H-pyran-4-yl)-4H-1,2,4-triazol-3-yl)-2-propanesulfonamide;

(1R,2S)-1-(5-chloro-2-pyridinyl)-N-(4-(2,6-dimethoxyphenyl)-5-((2R)-1,4-dioxan-2-yl)-4H-1,2,4-triazol-3-yl)-1-methoxy-2-propanesulfonamide;

(1R,2S)-1-(5-chloro-2-pyridinyl)-N-(4-(2,6-dimethoxyphenyl)-5-((2S)-1,4-dioxan-2-yl)-4H-1,2,4-triazol-3-yl)-1-methoxy-2-propanesulfonamide;

(1R,2R)—N-(4-(2,6-dimethoxyphenyl)-5-((2S)-1,4-dioxan-2-yl)-4H-1,2,4-triazol-3-yl)-1-imidazo[1,2-a]pyridin-2-yl-1-(1-methylethoxy)-2-propanesulfonamide;

(2S,3R)-3-(5-chloro-2-pyridinyl)-N-(4-(2,6-dimethoxyphenyl)-5-((2R)-1,4-dioxan-2-yl)-4H-1,2,4-triazol-3-yl)-2-butanesulfonamide;

(2S,3R)-3-(5-chloro-2-pyridinyl)-N-(4-(2,6-dimethoxyphenyl)-5-((2S)-1,4-dioxan-2-yl)-4H-1,2,4-triazol-3-yl)-2-butanesulfonamide;

(2S,3R)—N-(4-(2,6-dimethoxyphenyl)-5-((3R)-1-methyl-3-piperidinyl)-4H-1,2,4-triazol-3-yl)-3-(5-methyl-2-pyrimidinyl)-2-butanesulfonamide;

(2S,3R)—N-(4-(2,6-dimethoxyphenyl)-5-((3S)-1-methyl-3-piperidinyl)-4H-1,2,4-triazol-3-yl)-3-(5-methyl-2-pyrimidinyl)-2-butanesulfonamide;

(1R,2S)-1-(5-chloro-2-pyrimidinyl)-N-(5-((2R)-1,4-dioxan-2-yl)-4-(1-methylcyclopropyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(1-methylcyclopropyl)-4H-1,2,4-triazol-3-yl)-1-methoxy-2-propanesulfonamide;

(2S,3R)—N-(4-(2,6-dimethoxyphenyl)-5-((3R)-tetrahydro-3-furanyl)-4H-1,2,4-triazol-3-yl)-3-(5-fluoro-2-pyrimidinyl)-2-butanesulfonamide;

(2S,3R)—N-(4-(2,6-dimethoxyphenyl)-5-((3S)-tetrahydro-3-furanyl)-4H-1,2,4-triazol-3-yl)-3-(5-fluoro-2-pyrimidinyl)-2-butanesulfonamide;

(2S,3R)—N-(4-(2,6-dimethoxyphenyl)-5-((2R)-1,4-dioxan-2-yl)-4H-1,2,4-triazol-3-yl)-3-(5-fluoro-2-pyrimidinyl)-2-butanesulfonamide;

(2S,3R)—N-(4-(2,6-dimethoxyphenyl)-5-((2S)-1,4-dioxan-2-yl)-4H-1,2,4-triazol-3-yl)-3-(5-fluoro-2-pyrimidinyl)-2-butanesulfonamide;

(2S,3R)—N-(4-(4,6-dimethoxy-5-pyrimidinyl)-5-((2R)-1,4-dioxan-2-yl)-4H-1,2,4-triazol-3-yl)-3-(5-fluoro-2-pyrimidinyl)-2-butanesulfonamide;

(2S,3R)—N-(4-(4,6-dimethoxy-5-pyrimidinyl)-5-((2S)-1,4-dioxan-2-yl)-4H-1,2,4-triazol-3-yl)-3-(5-fluoro-2-pyrimidinyl)-2-butanesulfonamide;

(1S,2S)-1-(5-chloro-2-pyrimidinyl)-N-(4-(4,6-dimethoxy-5-pyrimidinyl)-5-((2S)-5,5-dimethyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(4,6-dimethoxy-5-pyrimidinyl)-5-((2R)-5,5-dimethyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((3R)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((3S)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2R)-1,4-dioxan-2-yl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2S)-1,4-dioxan-2-yl)-4H-1,2,4-triazol-3-yl)-1-(2-propanyloxy)-2-propanesulfonamide;

(1R,2S)-1-(5-chloro-2-pyrimidinyl)-1-methoxy-N-(4-(1-(methoxymethyl)cyclopropyl)-5-((2S,5S)-5-methyltetrahydro-2-furanyl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-((2R,5R)-5-methyltetrahydro-2-furanyl)-4H-1,2,4-triazol-3-yl)-2-propanesulfonamide;

(1R,2S)-1-(5-chloro-2-pyrimidinyl)-N-(5-((2S)-5,5-dimethyltetrahydro-2-furanyl)-4-(2-methoxyethyl)-4H-1,2,4-triazol-3-yl)-1-methoxy-2-propanesulfonamide;

(1R,2S)-1-(5-chloro-2-pyrimidinyl)-N-(5-((2R)-5,5-dimethyltetrahydro-2-furanyl)-4-(2-methoxyethyl)-4H-1,2,4-triazol-3-yl)-1-methoxy-2-propanesulfonamide;

(1R,2S)-1-(5-chloro-2-pyrimidinyl)-N-(5-((2S)-5,5-dimethyltetrahydro-2-furanyl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(5-((2R)-5,5-dimethyltetrahydro-2-furanyl)-4-(1-(methoxymethyl)cyclopropyl)-4H-1,2,4-triazol-3-yl)-1-methoxy-2-propanesulfonamide;

(1S,2S)-1-(5-chloro-2-pyrimidinyl)-N-(4-(4,6-dimethoxy-5-pyrimidinyl)-5-((3S)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(4,6-dimethoxy-5-pyrimidinyl)-5-((3R)-tetrahydro-3-furanyl)-4H-1,2,4-triazol-3-yl)-1-(2-propanyloxy)-2-propanesulfonamide;

(1R,2S)-1-(5-chloro-2-pyrimidinyl)-N-(4-(2,6-dimethoxyphenyl)-5-((3R)-1-methyl-5-oxo-3-pyrrolidinyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((3S)-1-methyl-5-oxo-3-pyrrolidinyl)-4H-1,2,4-triazol-3-yl)-1-methoxy-2-propanesulfonamide;

(1R,2S)-1-(5-chloro-2-pyrimidinyl)-N-(5-((2R)-1,4-dioxan-2-yl)-4-(1-(3-pyridinyl)cyclopropyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(1-(3-pyridinyl)cyclopropyl)-4H-1,2,4-triazol-3-yl)-1-methoxy-2-propanesulfonamide;

(1R,2S)-1-(5-chloro-2-pyrimidinyl)-1-methoxy-N-(4-(2-propanyl)-5-((3R)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(2-propanyl)-5-((3S)-tetrahydro-3-furanyl)-4H-1,2,4-triazol-3-yl)-2-propanesulfonamide;

(1R,2S)-1-(5-chloro-2-pyrimidinyl)-N-(5-((2S)-5,5-dimethyltetrahydro-2-furanyl)-4-(2-propanyl)-4H-1,2,4-triazol-3-yl)-1-methoxy-2-propanesulfonamide;

(1R,2S)-1-(5-chloro-2-pyrimidinyl)-N-(5-((2R)-5,5-dimethyltetrahydro-2-furanyl)-4-(2-propanyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(2-propanyl)-4H-1,2,4-triazol-3-yl)-1-methoxy-2-propanesulfonamide;

(1R,2S)-1-(5-chloro-2-pyrimidinyl)-N-(5-((2R)-1,4-dioxan-2-yl)-4-(2-propanyl)-4H-1,2,4-triazol-3-yl)-1-methoxy-2-propanesulfonamide;

(1R,2S)-1-(5-chloro-2-pyrimidinyl)-1-methoxy-N-(4-(1-(methoxymethyl)cyclopropyl)-5-((3R)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-((3S)-tetrahydro-3-furanyl)-4H-1,2,4-triazol-3-yl)-2-propanesulfonamide;

(1R,2S)-1-(5-chloro-2-pyrimidinyl)-N-(5-((2R)-1,4-dioxan-2-yl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((3S)-tetrahydro-3-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((3R)-tetrahydro-3-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2R)-5,5-dimethyltetrahydro-2-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2S)-5,5-dimethyltetrahydro-2-furanyl)-4H-1,2,4-triazol-3-yl)-1-methoxy-2-propanesulfonamide;

(1R,2S)-1-(5-chloro-2-pyrimidinyl)-1-methoxy-N-(4-(2-methoxyethyl)-5-((3S)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(2-methoxyethyl)-5-((3R)-tetrahydro-3-furanyl)-4H-1,2,4-triazol-3-yl)-2-propanesulfonamide;

(1R,2S)-1-(5-chloro-2-pyrimidinyl)-N-(5-((2S)-1,4-dioxan-2-yl)-4-(2-methoxyethyl)-4H-1,2,4-triazol-3-yl)-1-methoxy-2-propanesulfonamide;

(1R,2S)-1-(5-chloro-2-pyrimidinyl)-N-(5-((2R)-1,4-dioxan-2-yl)-4-(2-methoxyethyl)-4H-1,2,4-triazol-3-yl)-1-methoxy-2-propanesulfonamide;

(1S,2S)—N-(4-(4,6-dimethoxy-5-pyrimidinyl)-5-((3R)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1S,2S)—N-(4-(4,6-dimethoxy-5-pyrimidinyl)-5-((3S)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1R,2S)-1-(5-chloro-2-pyrimidinyl)-N-(4-(4,6-dimethoxy-5-pyrimidinyl)-5-((3R)-5,5-dimethyltetrahydro-3-furanyl)-4H-1,2,4-triazol-3-yl)-1-methoxy-2-propanesulfonamide;

(1R,2S)-1-(5-chloro-2-pyrimidinyl)-N-(4-(4,6-dimethoxy-5-pyrimidinyl)-5-((3S)-5,5-dimethyltetrahydro-3-furanyl)-4H-1,2,4-triazol-3-yl)-1-methoxy-2-propanesulfonamide;

(2S,3R)-3-(5-chloro-2-pyrimidinyl)-N-(4-(4,6-dimethoxy-5-pyrimidinyl)-5-((3R)-5,5-dimethyltetrahydro-3-furanyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-((3S)-5,5-dimethyltetrahydro-3-furanyl)-4H-1,2,4-triazol-3-yl)-2-butanesulfonamide;

(1S,2S)-1-(5-chloro-2-pyrimidinyl)-N-(4-(1-(methoxymethyl)cyclopropyl)-5-((3R)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(1-(methoxymethyl)cyclopropyl)-5-((3S)-tetrahydro-3-furanyl)-4H-1,2,4-triazol-3-yl)-1-(2-propanyloxy)-2-propanesulfonamide;

(1S,2S)—N-(4-(4,6-dimethoxy-5-pyrimidinyl)-5-((3R)-tetrahydro-3-furanyl)-4H-1,2,4-triazol-3-yl)-1-(5-fluoro-2-pyrimidinyl)-1-(2-propanyloxy)-2-propanesulfonamide;

(1S,2S)—N-(4-(4,6-dimethoxy-5-pyrimidinyl)-5-((3S)-tetrahydro-3-furanyl)-4H-1,2,4-triazol-3-yl)-1-(5-fluoro-2-pyrimidinyl)-1-(2-propanyloxy)-2-propanesulfonamide;

(1S,2S)—N-(4-(4,6-dimethoxy-5-pyrimidinyl)-5-((3R)-tetrahydro-3-furanyl)-4H-1,2,4-triazol-3-yl)-1-(5-methyl-2-pyridinyl)-1-(2-propanyloxy)-2-propanesulfonamide;

(1S,2S)—N-(4-(4,6-dimethoxy-5-pyrimidinyl)-5-((3S)-tetrahydro-3-furanyl)-4H-1,2,4-triazol-3-yl)-1-(5-methyl-2-pyridinyl)-1-(2-propanyloxy)-2-propanesulfonamide;

(1R,2S)—N-(4-([1,1'-bi(cyclopropyl)]-1-yl)-5-((2R)-1,4-dioxan-2-yl)-4H-1,2,4-triazol-3-yl)-1-(5-chloro-2-pyrimidinyl)-1-methoxy-2-propanesulfonamide;

(1R,2S)—N-(4-([1,1'-bi(cyclopropyl)]-1-yl)-5-((2S)-1,4-dioxan-2-yl)-4H-1,2,4-triazol-3-yl)-1-(5-chloro-2-pyrimidinyl)-1-methoxy-2-propanesulfonamide;

(1R,2S)—N-(4-([1,1'-bi(cyclopropyl)]-1-yl)-5-((2R)-1,4-dioxan-2-yl)-4H-1,2,4-triazol-3-yl)-1-methoxy-1-(5-methyl-2-pyrazinyl)-2-propanesulfonamide;

(1R,2S)—N-(4-([1,1'-bi(cyclopropyl)]-1-yl)-5-((2S)-1,4-dioxan-2-yl)-4H-1,2,4-triazol-3-yl)-1-methoxy-1-(5-methyl-2-pyrazinyl)-2-propanesulfonamide;

(1R,2S)-1-(5-chloro-2-pyrimidinyl)-N-(4-(1,3-dimethoxy-2-propanyl)-5-((2R)-tetrahydro-2-furanyl)-4H-1,2,4-triazol-3-yl)-1-methoxy-2-propanesulfonamide;

(2S,3R)-3-(5-chloro-2-pyrimidinyl)-N-(4-(3,5-dibromo-2,6-dimethoxyphenyl)-5-((3R)-tetrahydro-3-furanyl)-4H-1,2,4-triazol-3-yl)-2-butanesulfonamide;

(1R,2S)-1-(5-chloro-2-pyrimidinyl)-N-(4-(1,3-dimethoxy-2-propanyl)-5-((2S)-tetrahydro-2-furanyl)-4H-1,2,4-triazol-3-yl)-1-methoxy-2-propanesulfonamide;

(2S,3R)—N-(4-(2,6-dimethoxyphenyl)-5-((2R)-5,5-dimethyltetrahydro-2-furanyl)-4H-1,2,4-triazol-3-yl)-3-(5-fluoro-2-pyrimidinyl)-2-butanesulfonamide;

(2S,3R)—N-(4-(2,6-dimethoxyphenyl)-5-((2S)-5,5-dimethyltetrahydro-2-furanyl)-4H-1,2,4-triazol-3-yl)-3-(5-fluoro-2-pyrimidinyl)-2-butanesulfonamide;

(1R,2S)-1-(5-chloro-2-pyrimidinyl)-N-(5-((2R)-1,4-dioxan-2-yl)-4-(3-pentanyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(3-pentanyl)-4H-1,2,4-triazol-3-yl)-1-methoxy-2-propanesulfonamide;

(1R,2S)-1-(5-chloro-2-pyrimidinyl)-N-(4-(dicyclopropylmethyl)-5-((2R)-1,4-dioxan-2-yl)-4H-1,2,4-triazol-3-yl)-1-methoxy-2-propanesulfonamide;

(1R,2S)-1-(5-chloro-2-pyrimidinyl)-N-(4-(dicyclopropylmethyl)-5-((2S)-1,4-dioxan-2-yl)-4H-1,2,4-triazol-3-yl)-1-methoxy-2-propanesulfonamide;

(2S,3R)-3-(5-chloro-2-pyrimidinyl)-N-(4-(2,6-dimethoxyphenyl)-5-((2R)-5-oxo-2-pyrrolidinyl)-4H-1,2,4-triazol-3-yl)-2-butanesulfonamide; or (2S,3R)-3-(5-chloro-2-pyrimidinyl)-N-(4-(2,6-dimethoxyphenyl)-5-((2S)-5-oxo-2-pyrrolidinyl)-4H-1,2,4-triazol-3-yl)-2-butanesulfonamide; or the pharmaceutically acceptable salt thereof, or the mixture thereof.

80. The compound of embodiment 8, wherein the compound has the Formula IA

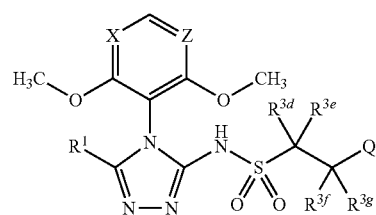

or is the pharmaceutically acceptable salt thereof, the tautomer thereof, the pharmaceutically acceptable salt of the tautomer, the stereoisomer of any of the foregoing, or the mixture thereof, wherein:

$R^1$ is as defined in embodiment 8;

X is selected from CH or N;

Z is selected from CH or N;

$R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and $R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), or —O—($C_2$-$C_6$ alkenyl).

Q is a phenyl group or a monocyclic heteroaryl group with 6 ring members containing 1 or 2 N heteroatoms, wherein the phenyl and the monocyclic heteroaryl Q groups are unsubstituted or are substituted with 1, 2, or 3 $R^Q$ substituent; and $R^Q$ is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), —($C_1$-$C_6$ alkyl)-$NH_2$ or —S(=O)$_2$—($C_1$-$C_6$ alkyl).

81. The compound of embodiment 80 or the pharmaceutically acceptable salt thereof, the tautomer thereof, the pharmaceutically acceptable salt of the tautomer, the stereoisomer of any of the foregoing, or the mixture thereof, wherein:

$R^{3d}$ and $R^{3e}$ are independently selected from —H, —$C_1$-$C_6$ alkyl, or —($C_1$-$C_6$ alkyl)-OH; and $R^{3f}$ and $R^{3g}$ are independently selected from —H, —$C_1$-$C_6$ alkyl, —OH, or —O—($C_1$-$C_6$ alkyl).

82. The compound of embodiment 80 or embodiment 81 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is not —H.

83. The compound of any one of embodiments 80-82 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is —$CH_3$.

84. The compound of any one of embodiments 80-83 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, or —$CH_3$.

85. The compound of embodiment 8, wherein the compound has the Formula IB

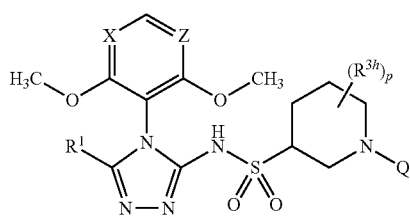

IB or is the pharmaceutically acceptable salt thereof, the tautomer thereof, the pharmaceutically acceptable salt of the tautomer, the stereoisomer of any of the foregoing, or the mixture thereof, wherein:

$R^1$ is as defined in embodiment 8;
X is selected from CH or N;
Z is selected from CH or N;
$R^{3h}$ is independently selected from —OH, or —O—($C_1$-$C_6$ alkyl);
the subscript p is selected from 0, 1, 2, or 3;
Q is a phenyl group or a monocyclic heteroaryl group with 6 ring members containing 1 or 2 N heteroatoms, wherein the phenyl and the monocyclic heteroaryl Q groups are unsubstituted or are substituted with 1, 2, or 3 $R^Q$ substituent; and $R^Q$ is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), —($C_1$-$C_6$ alkyl)-$NH_2$ or —S(=O)$_2$—($C_1$-$C_6$ alkyl).

86. The compound of embodiment 85 or the pharmaceutically acceptable salt thereof, the tautomer thereof, the pharmaceutically acceptable salt of the tautomer, the stereoisomer of any of the foregoing, or the mixture thereof, wherein p is 0 or 1 and $R^{3h}$ is selected from —OH, —$OCH_3$, —$OCH_2CH_3$, or —$OCH(CH_3)_2$.

87. The compound of any one of embodiments 80-86 or the pharmaceutically acceptable salt thereof, the tautomer thereof, the pharmaceutically acceptable salt of the tautomer, the stereoisomer of any of the foregoing, or the mixture thereof, wherein:

X is CH;
Z is CH; and
Q is a phenyl, a pyrimidinyl, a pyridinyl, or a pyrazinyl any of which are unsubstituted or are substituted with 1, 2, or 3 $R^Q$ substituent.

88. The compound of any one of embodiments 80-86 or the pharmaceutically acceptable salt thereof, the tautomer thereof, the pharmaceutically acceptable salt of the tautomer, the stereoisomer of any of the foregoing, or the mixture thereof, wherein:

X is N;
Z is N; and
Q is a phenyl, a pyrimidinyl, a pyridinyl, or a pyrazinyl any of which are unsubstituted or are substituted with 1, 2, or 3 $R^Q$ substituent.

89. The compound of any one of embodiments 80-88 or the pharmaceutically acceptable salt thereof, the tautomer thereof, the pharmaceutically acceptable salt of the tautomer, the stereoisomer of any of the foregoing, or the mixture thereof, wherein $R^1$ is selected from tetrahydrofuranyl, tetrahydropyranyl, oxetanyl, dioxanyl, pyrrolidinyl, piperidinyl, dioxotetrahydrothiopyranyl, dioxotetrahydrothiophenyl, morpholinyl, dioxolanyl, or tetrahydrothiophenyl, any of which may unsubstituted or substituted with 1, 2, or 3 independently selected $R^{1a}$ substituents.

90. The compound of any one of embodiments 80-88 or the pharmaceutically acceptable salt thereof, the tautomer thereof, the pharmaceutically acceptable salt of the tautomer, the stereoisomer of any of the foregoing, or the mixture thereof, wherein $R^1$ is selected from tetrahydrofuranyl, tetrahydropyranyl, oxetanyl, dioxanyl, or pyrrolidinyl, any of which may unsubstituted or substituted with 1, 2, or 3 independently selected $R^{1a}$ substituents.

91. The compound of embodiment 89 or 90 or the pharmaceutically acceptable salt thereof, the tautomer thereof, the pharmaceutically acceptable salt of the tautomer, the stereoisomer of any of the foregoing, or the mixture thereof, wherein $R^1$ is unsubstituted or $R^1$ is substituted with 1, 2, or 3 $R^{1a}$ substituents independently selected from —$C_1$-$C_6$ alkyl, —C(=O)—O—($C_1$-$C_6$ alkyl), or oxo.

92. The compound of embodiment 1, wherein the compound is selected from (S)-2-(2-cyano-4-fluorophenyl)-N-(4-(2,6-dimethoxyphenyl)-5-(tetrahydrofuran-3-yl)-4H-1,2,4-triazol-3-yl)ethanesulfonamide;

(1R,2S)-1-(5-chloro-2-pyrimidinyl)-N-(4-(2,6-dimethoxyphenyl)-5-((3aR,6aR)-hexahydro-3 aH-cyclopenta[b]furan-3a-yl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((3aS,6aS)-hexahydro-3aH-cyclopenta[b]furan-3a-yl)-4H-1,2,4-triazol-3-yl)-1-methoxy-2-propanesulfonamide;

(1R)—N-(4-(2,6-dimethoxyphenyl)-5-((2S)-tetrahydro-2-furanyl)-4H-1,2,4-triazol-3-yl)-1-phenylethanesulfonamide;

(1S)—N-(4-(2,6-dimethoxyphenyl)-5-((2R)-tetrahydro-2-furanyl)-4H-1,2,4-triazol-3-yl)-1-phenylethanesulfonamide;

(1S,2S)-1-(5-chloro-2-pyrimidinyl)-N-(4-cyclopropyl-5-((2S,5S)-5-methyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-cyclopropyl-5-((2R,5R)-5-methyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1-(2-propanyloxy)-2-propanesulfonamide;

(1S,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1-(2-propanyloxy)-2-propanesulfonamide;

(1S,2S)—N-(4-(1,3-dimethoxy-2-propanyl)-5-((2S,5S)-5-methyltetrahydro-2-furanyl)-4H-1,2,4-triazol-3-yl)-1-(5-methyl-2-pyrimidinyl)-1-(2-propanyloxy)-2-propanesulfonamide;

(1S,2S)—N-(4-(1,3-dimethoxy-2-propanyl)-5-((2R,5R)-5-methyltetrahydro-2-furanyl)-4H-1,2,4-triazol-3-yl)-1-(5-methyl-2-pyrimidinyl)-1-(2-propanyloxy)-2-propanesulfonamide;

(1S,2S)—N-(4-(1,3-dimethoxy-2-propanyl)-5-((2S,5S)-5-methyltetrahydro-2-furanyl)-4H-1,2,4-triazol-3-yl)-1-(5-fluoro-2-pyrimidinyl)-1-(2-propanyloxy)-2-propanesulfonamide;

(1S,2S)—N-(4-(1,3-dimethoxy-2-propanyl)-5-((2R,5R)-5-methyltetrahydro-2-furanyl)-4H-1,2,4-triazol-3-yl)-1-(5-fluoro-2-pyrimidinyl)-1-(2-propanyloxy)-2-propanesulfonamide;

(1S,2S)—N-(4-(1,3-dimethoxy-2-propanyl)-5-((2S,5S)-5-methyltetrahydro-2-furanyl)-4H-1,2,4-triazol-3-yl)-1-(5-methoxy-2-pyrimidinyl)-1-(2-propanyloxy)-2-propanesulfonamide;

(1S,2S)—N-(4-(1,3-dimethoxy-2-propanyl)-5-((2R,5R)-5-methyltetrahydro-2-furanyl)-4H-1,2,4-triazol-3-yl)-1-(5-methoxy-2-pyrimidinyl)-1-(2-propanyloxy)-2-propanesulfonamide;

(1S,2S)—N-(4-(1,3-dimethoxy-2-propanyl)-5-((2S,5S)-5-methyltetrahydro-2-furanyl)-4H-1,2,4-triazol-3-yl)-1-(5-methyl-2-pyrazinyl)-1-(2-propanyloxy)-2-propanesulfonamide;

(1S,2S)—N-(4-(1,3-dimethoxy-2-propanyl)-5-((2R,5R)-5-methyltetrahydro-2-furanyl)-4H-1,2,4-triazol-3-yl)-1-(5-methyl-2-pyrazinyl)-1-(2-propanyloxy)-2-propanesulfonamide;

(1S,2S)—N-(4-(1,3-dimethoxy-2-propanyl)-5-((2S,5S)-5-methyltetrahydro-2-furanyl)-4H-1,2,4-triazol-3-yl)-1-(5-methyl-2-pyridinyl)-1-(2-propanyloxy)-2-propanesulfonamide;

(1S,2S)—N-(4-(1,3-dimethoxy-2-propanyl)-5-((2R,5R)-5-methyltetrahydro-2-furanyl)-4H-1,2,4-triazol-3-yl)-1-(5-methyl-2-pyridinyl)-1-(2-propanyloxy)-2-propanesulfonamide;

(2S,3R)—N-(4-(1,3-dimethoxy-2-propanyl)-5-((2S,5S)-5-methyltetrahydro-2-furanyl)-4H-1,2,4-triazol-3-yl)-3-(5-fluoro-2-pyrimidinyl)-2-butanesulfonamide;

(2S,3R)—N-(4-(1,3-dimethoxy-2-propanyl)-5-((2R,5R)-5-methyltetrahydro-2-furanyl)-4H-1,2,4-triazol-3-yl)-3-(5-fluoro-2-pyrimidinyl)-2-butanesulfonamide;

(2S,3R)—N-(4-(1,3-dimethoxy-2-propanyl)-5-((2S,5S)-5-methyltetrahydro-2-furanyl)-4H-1,2,4-triazol-3-yl)-3-(5-methoxy-2-pyrimidinyl)-2-butanesulfonamide;

(2S,3R)—N-(4-(1,3-dimethoxy-2-propanyl)-5-((2R,5R)-5-methyltetrahydro-2-furanyl)-4H-1,2,4-triazol-3-yl)-3-(5-methoxy-2-pyrimidinyl)-2-butanesulfonamide;

(2S,3R)-3-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-2-butanesulfonamide;

(2S,3R)-3-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-2-butanesulfonamide;

(2S,3R)-3-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-2-butanesulfonamide;

(2S,3R)-3-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-2-butanesulfonamide;

(2S,3R)—N-(4-(1,3-dimethoxy-2-propanyl)-5-((2S,5S)-5-methyltetrahydro-2-furanyl)-4H-1,2,4-triazol-3-yl)-3-(5-methoxy-2-pyrazinyl)-2-butanesulfonamide;

(2S,3R)—N-(4-(1,3-dimethoxy-2-propanyl)-5-((2R,5R)-5-methyltetrahydro-2-furanyl)-4H-1,2,4-triazol-3-yl)-3-(5-methoxy-2-pyrazinyl)-2-butanesulfonamide;

(1R,2S)—N-(4-(1,3-dimethoxy-2-propanyl)-5-((2S,5S)-5-methyltetrahydro-2-furanyl)-4H-1,2,4-triazol-3-yl)-1-methoxy-1-(5-methoxy-2-pyrazinyl)-2-propanesulfonamide;

(1R,2S)—N-(4-(1,3-dimethoxy-2-propanyl)-5-((2R,5R)-5-methyltetrahydro-2-furanyl)-4H-1,2,4-triazol-3-yl)-1-methoxy-1-(5-methoxy-2-pyrazinyl)-2-propanesulfonamide;

(1R,2S)-1-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide;

(1R,2S)-1-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide;

(2S,3R)-3-(5-cyano-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide;

(2S,3R)-3-(5-cyano-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide;

2-(5-chloro-2-pyrimidinyl)-N-(4-(2,6-dimethoxyphenyl)-5-((3S)-tetrahydro-3-furanyl)-4H-1,2,4-triazol-3-yl)ethanesulfonamide;

2-(5-chloro-2-pyrimidinyl)-N-(4-(2,6-dimethoxyphenyl)-5-((2S)-tetrahydro-2-furanyl)-4H-1,2,4-triazol-3-yl)ethanesulfonamide;

2-(5-chloro-2-pyrimidinyl)-N-(4-(2,6-dimethoxyphenyl)-5-((2R)-tetrahydro-2-furanyl)-4H-1,2,4-triazol-3-yl)ethanesulfonamide;

2-(5-chloro-2-pyrimidinyl)-N-(4-(2,6-dimethoxyphenyl)-5-((3R)-tetrahydro-3-furanyl)-4H-1,2,4-triazol-3-yl)ethanesulfonamide;

(2S,3R)-3-(5-chloro-2-pyrimidinyl)-N-(4-(2,6-dimethoxyphenyl)-5-((3R)-5,5-dimethyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3S)-5,5-dimethyltetrahydro-3-furanyl)-4H-1,2,4-triazol-3-yl)-2-butanesulfonamide;

(2S,3R)—N-(4-(2,6-dimethoxyphenyl)-5-((3R)-5,5-dimethyltetrahydro-3-furanyl)-4H-1,2,4-triazol-3-yl)-3-(5-fluoro-2-pyrimidinyl)-2-butanesulfonamide;

(2S,3R)—N-(4-(2,6-dimethoxyphenyl)-5-((3S)-5,5-dimethyltetrahydro-3-furanyl)-4H-1,2,4-triazol-3-yl)-3-(5-fluoro-2-pyrimidinyl)-2-butanesulfonamide;

(1R,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1-methoxy-2-propanesulfonamide;

(1S,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1-(2-propanyloxy)-2-propanesulfonamide;

(1R,2S)-1-(5-chloro-2-pyrimidinyl)-1-methoxy-N-(4-(1,2-oxazol-3-ylmethyl)-5-((3R)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(1,2-oxazol-3-ylmethyl)-5-((3S)-tetrahydro-3-furanyl)-4H-1,2,4-triazol-3-yl)-2-propanesulfonamide;

(1R,2S)-1-(5-chloro-2-pyrimidinyl)-1-methoxy-N-(5-((2R,5R)-5-methyltetrahydro-2-furanyl)-4-(1,2-oxazol-3-ylmethyl)-4H-1,2,4-triazol-3-yl)-2-propanesulfonamide;

(1R,2S)-1-(5-chloro-2-pyrimidinyl)-1-methoxy-N-(5-((2S,5S)-5-methyltetrahydro-2-furanyl)-4-(1,2-oxazol-3-ylmethyl)-4H-1,2,4-triazol-3-yl)-2-propanesulfonamide;

(1R,2S)-1-(5-chloro-2-pyrimidinyl)-N-(4-(2,6-dimethoxyphenyl)-5-((2S)-1-methyl-5-oxo-2-pyrrolidinyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((2R)-1-methyl-5-oxo-2-pyrrolidinyl)-4H-1,2,4-triazol-3-yl)-1-methoxy-2-propanesulfonamide;

(1S,2S)—N-(4-(2,6-dimethoxyphenyl)-5-((3S)-tetrahydro-3-furanyl)-4H-1,2,4-triazol-3-yl)-1-(5-methyl-2-pyridinyl)-1-(2-propanyloxy)-2-propanesulfonamide;

(1S,2S)—N-(4-(2,6-dimethoxyphenyl)-5-((3R)-tetrahydro-3-furanyl)-4H-1,2,4-triazol-3-yl)-1-(5-methyl-2-pyridinyl)-1-(2-propanyloxy)-2-propanesulfonamide;

(2S,3R)-3-(5-chloro-2-pyridinyl)-N-(4-(2,6-dimethoxyphenyl)-5-((3S)-tetrahydro-3-furanyl)-4H-1,2,4-triazol-3-yl)-2-butanesulfonamide;

(2S,3R)-3-(5-chloro-2-pyridinyl)-N-(4-(2,6-dimethoxyphenyl)-5-((3R)-tetrahydro-3-furanyl)-4H-1,2,4-triazol-3-yl)-2-butanesulfonamide;

(1S,2S)—N-(4-(2,6-dimethoxyphenyl)-5-((3R)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1S,2S)—N-(4-(2,6-dimethoxyphenyl)-5-((3S)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1S,2S)-1-(5-chloro-2-pyrimidinyl)-N-(4-(2,6-dimethoxyphenyl)-5-((2S)-5,5-dimethyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2R)-5,5-dimethyltetrahydro-2-furanyl)-4H-1,2,4-triazol-3-yl)-1-(2-propanyloxy)-2-propanesulfonamide;

(2S,3R)-3-(5-chloro-2-pyrimidinyl)-N-(4-((1R)-1-(1,2-oxazol-3-yl)ethyl)-5-((3S)-tetrahydro-3-furanyl)-4H-1,2,4-triazol-3-yl)-2-butanesulfonamide;

(2S,3R)-3-(5-chloro-2-pyrimidinyl)-N-(4-((1S)-1-(1,2-oxazol-3-yl)ethyl)-5-((3S)-tetrahydro-3-furanyl)-4H-1,2,4-triazol-3-yl)-2-butanesulfonamide;

(1S,2S)—N-(4-(2,6-dimethoxyphenyl)-5-((2S)-1-methyl-5-oxo-2-pyrrolidinyl)-4H-1,2,4-triazol-3-yl)-1-(5-methyl-2-pyrimidinyl)-1-(2-propanyloxy)-2-propanesulfonamide;

(1S,2S)—N-(4-(2,6-dimethoxyphenyl)-5-((2R)-1-methyl-5-oxo-2-pyrrolidinyl)-4H-1,2,4-triazol-3-yl)-1-(5-methyl-2-pyrimidinyl)-1-(2-propanyloxy)-2-propanesulfonamide;

(2S,3R)-3-(5-chloro-2-pyrimidinyl)-N-(4-(2,6-dimethoxyphenyl)-5-((2S)-1-methyl-5-oxo-2-pyrrolidinyl)-4H-1,2,4-triazol-3-yl)-2-butanesulfonamide;

2-(5-chloro-2-pyrimidinyl)-N-(4-(2,6-dimethoxyphenyl)-5-((2R)-1,4-dioxan-2-yl)-4H-1,2,4-triazol-3-yl)ethanesulfonamide;

2-(5-chloro-2-pyrimidinyl)-N-(4-(2,6-dimethoxyphenyl)-5-((2S)-1,4-dioxan-2-yl)-4H-1,2,4-triazol-3-yl)ethanesulfonamide;

(1S)—N-(4-(2,6-dimethoxyphenyl)-5-((2S)-tetrahydro-2-furanyl)-4H-1,2,4-triazol-3-yl)-1-(3-methoxyphenyl)ethanesulfonamide;

(1R)—N-(4-(2,6-dimethoxyphenyl)-5-((2R)-tetrahydro-2-furanyl)-4H-1,2,4-triazol-3-yl)-1-(3-methoxyphenyl)ethanesulfonamide;

(1R)—N-(4-(2,6-dimethoxyphenyl)-5-((2S)-tetrahydro-2-furanyl)-4H-1,2,4-triazol-3-yl)-1-(3-methoxyphenyl)ethanesulfonamide;

(1S)—N-(4-(2,6-dimethoxyphenyl)-5-((2R)-tetrahydro-2-furanyl)-4H-1,2,4-triazol-3-yl)-1-(3-methoxyphenyl)ethanesulfonamide;

(1S)—N-(4-(2,6-dimethoxyphenyl)-5-((2S)-tetrahydro-2-furanyl)-4H-1,2,4-triazol-3-yl)-1-(2-fluorophenyl)ethanesulfonamide;

(1R)—N-(4-(2,6-dimethoxyphenyl)-5-((2R)-tetrahydro-2-furanyl)-4H-1,2,4-triazol-3-yl)-1-(2-fluorophenyl)ethanesulfonamide;

(1R)—N-(4-(2,6-dimethoxyphenyl)-5-((2S)-tetrahydro-2-furanyl)-4H-1,2,4-triazol-3-yl)-1-(2-fluorophenyl)ethanesulfonamide;

(1S)—N-(4-(2,6-dimethoxyphenyl)-5-((2R)-tetrahydro-2-furanyl)-4H-1,2,4-triazol-3-yl)-1-(2-fluorophenyl)ethanesulfonamide;

(1R)—N-(4-(2,6-dimethoxyphenyl)-5-((2R)-tetrahydro-2-furanyl)-4H-1,2,4-triazol-3-yl)-1-phenylethanesulfonamide;

(1S)-1-(3-chlorophenyl)-N-(4-(2,6-dimethoxyphenyl)-5-((2S)-tetrahydro-2-furanyl)-4H-1,2,4-triazol-3-yl)ethanesulfonamide;

(1R)-1-(3-chlorophenyl)-N-(4-(2,6-dimethoxyphenyl)-5-((2R)-tetrahydro-2-furanyl)-4H-1,2,4-triazol-3-yl)ethanesulfonamide;

(1R)-1-(3-chlorophenyl)-N-(4-(2,6-dimethoxyphenyl)-5-((2S)-tetrahydro-2-furanyl)-4H-1,2,4-triazol-3-yl)ethanesulfonamide;

(1S)-1-(3-chlorophenyl)-N-(4-(2,6-dimethoxyphenyl)-5-((2R)-tetrahydro-2-furanyl)-4H-1,2,4-triazol-3-yl)ethanesulfonamide;

(2S,3R)-3-(5-chloro-2-pyrimidinyl)-N-(4-(2,6-dimethoxyphenyl)-5-((3S,5R)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3R,5R)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3S,5S)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3R,5S)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2S)-2-oxetanyl)-4H-1,2,4-triazol-3-yl)-2-butanesulfonamide;

(2S,3R)—N-(4-(2,6-bis((trideutero)methyloxy)phenyl)-5-((3S)-tetrahydro-3-furanyl)-4H-1,2,4-triazol-3-yl)-3-(5-chloro-2-pyrimidinyl)-2-butanesulfonamide; or (2S,3R)—N-(4-(2,6-bis((trideutero)methyloxy)phenyl)-5-((3R)-tetrahydro-3-furanyl)-4H-1,2,4-triazol-3-yl)-3-(5-chloro-2-pyrimidinyl)-2-butanesulfonamide; or the pharmaceutically acceptable salt thereof, or the mixture thereof.

93. A pharmaceutical composition, comprising the compound of any one of embodiments 1-92 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

94. A pharmaceutical composition, comprising the compound of any one of embodiments 1-92 or the pharmaceutically acceptable salt thereof and at least one pharmaceutically acceptable excipient.

95. A pharmaceutical composition, comprising the compound of any one of embodiments 1-92 and at least one pharmaceutically acceptable excipient.

96. A pharmaceutical composition, comprising the pharmaceutically acceptable salt of the compound of any one of embodiments 1-92 and at least one pharmaceutically acceptable excipient.

97. The pharmaceutical composition of any one of embodiments 93-96, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

98. The pharmaceutical composition of any one of embodiments 93-96, further comprising a therapeutic agent selected from an angiotensin converting enzyme (ACE) inhibitor or an angiotensin-receptor blocker (ARB).

99. A method of treating a cardiovascular condition, the method comprising: administering to a subject an effective amount of the compound of any one of embodiments 1-92 or the pharmaceutically acceptable salt thereof, the stereoisomer of any of the foregoing, or the mixture thereof, or the pharmaceutical composition of any one of embodiments 93-96.

100. The method of embodiment 99, wherein the cardiovascular condition is heart failure.

101. The method of embodiment 99, wherein the cardiovascular condition is heart failure with reduced ejection fraction.

102. The method of embodiment 99, wherein the cardiovascular condition is heart failure with preserved ejection fraction.

103. The method of embodiment 99, wherein the cardiovascular condition is chronic systolic heart failure or chronic diastolic heart failure.

104. The method of embodiment 99, wherein the cardiovascular condition is acute heart failure.

105. The method of embodiment 99, wherein the cardiovascular condition is hypertension.

106. A method of improving cardiac contractility in a subject suffering from a cardiovascular condition, the method comprising: administering to the subject an effective amount of the compound of any one of embodiments 1-92 or the pharmaceutically acceptable salt thereof, the stereoisomer of any of the foregoing, or the mixture thereof, or the pharmaceutical composition of any one of embodiments 93-96, wherein cardiac contractility is improved in the subject after administration.

107. A method of increasing ejection fraction in a subject suffering from a cardiovascular condition, the method comprising: administering to the subject an effective amount of the compound of any one of embodiments 1-92 or the pharmaceutically acceptable salt thereof, the stereoisomer of any of the foregoing, or the mixture thereof, or the pharmaceutical composition of any one of embodiments 93-36, wherein the ejection fraction is increased in the subject after administration.

108. A method of treating a condition in a subject where it is desired to activate the APJ Receptor, the method comprising: administering to the subject an effective amount of the compound of any one of embodiments 1-92 or the pharmaceutically acceptable salt thereof, the stereoisomer of any of the foregoing, or the mixture thereof or the pharmaceutical composition of any one of embodiments 93-96.

109. The method of embodiment 108, wherein the condition is obesity or diabetes.

110. The method of embodiment 108, wherein the condition is diabetic nephropathy or chronic kidney disease.

111. The method of any one of embodiments 99-110, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

112. The method of any one of embodiments 99-110, wherein the method includes administering at least one additional therapeutic agent to the subject, wherein the additional therapeutic agent is selected from an angiotensin converting enzyme (ACE) inhibitor or an angiotensin-receptor blocker (ARB).

113. A compound of any one of embodiments 1-92 or the pharmaceutically acceptable salt thereof, the stereoisomer of any of the foregoing, or the mixture thereof, or the pharmaceutical composition of any one of embodiments 93-96 for use in treating a cardiovascular condition.

114. The compound of embodiments 113, wherein the cardiovascular condition is heart failure.

115. The compound of embodiment 113, wherein the cardiovascular condition is heart failure with reduced ejection fraction.

116. The compound of embodiment 113, wherein the cardiovascular condition is heart failure with preserved ejection fraction.

117. The compound of embodiment 113, wherein the cardiovascular condition is chronic systolic heart failure or chronic diastolic heart failure.

118. The compound of embodiment 113, wherein the cardiovascular condition is acute heart failure.

119. The compound of embodiment 113, wherein the cardiovascular condition is hypertension.

120. A compound of any one of embodiments 1-92 or the pharmaceutically acceptable salt thereof, the stereoisomer of any of the foregoing, or the mixture thereof, or the pharmaceutical composition of any one of embodiments 93-96 for use in activating the APJ Receptor or for treating a condition where it is desirable to activate the APJ Receptor.

121. The compound of embodiment 120, wherein the condition is obesity or diabetes.

122. The compound of embodiment 120, wherein the condition is diabetic nephropathy or chronic kidney disease.

123. A use of the compound of any one of embodiments 1-92 or the pharmaceutically acceptable salt thereof, the stereoisomer of any of the foregoing, or the mixture thereof in the preparation of a medicament for treating a cardiovascular condition.

124. The use of embodiment 123, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

125. The use of embodiment 123, further comprising a therapeutic agent selected from an angiotensin converting enzyme (ACE) inhibitor or an angiotensin-receptor blocker (ARB).

126. The use of the compound of any one of embodiments 123-125, wherein the cardiovascular condition is heart failure.

127. The use of the compound of any one of embodiments 123-125, wherein the cardiovascular condition is heart failure with reduced ejection fraction.

128. The use of the compound of any one of embodiments 123-125, wherein the cardiovascular condition is heart failure with preserved ejection fraction.

129. The use of the compound of any one of embodiments 123-125, wherein the cardiovascular condition is chronic systolic heart failure or chronic diastolic heart failure.

130. The use of the compound of any one of embodiments 123-125, wherein the cardiovascular condition is acute heart failure.

131. The use of the compound of any one of embodiments 123-125, wherein the cardiovascular condition is hypertension.

132. A use of the compound of any one of embodiments 1-92 or the pharmaceutically acceptable salt thereof, the stereoisomer of any of the foregoing, or the mixture thereof in the preparation of a medicament for activating the APJ Receptor or treating a condition where it is desirable to activate the APJ Receptor.

133. The use of embodiment 132, wherein the condition is obesity or diabetes.

134. The use of embodiment 132, wherein the condition is diabetic nephropathy or chronic kidney disease.

135. A treatment regimen for a cardiovascular disease, the regimen comprising: the compound of any one of embodiments 1-92 or the pharmaceutically acceptable salt thereof, the stereoisomer of any of the foregoing, or the mixture thereof 136. The treatment regimen of embodiment 135, wherein the regimen further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

137. The treatment regimen of embodiment 135, wherein the regimen further comprises a therapeutic agent selected from an angiotensin converting enzyme (ACE) inhibitor or an angiotensin-receptor blocker (ARB).

138. A kit, the kit comprising: the compound of any one of embodiments 1-91 or the pharmaceutically acceptable salt thereof, the stereoisomer of any of the foregoing, or the mixture thereof.

139. The kit of embodiment 138, wherein the kit further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

140. The kit of embodiment 138, wherein the kit further comprises a therapeutic agent selected from an angiotensin converting enzyme (ACE) inhibitor or an angiotensin-receptor blocker (ARB).

141 In another embodiment, the invention provides a compound of Formula V, a salt thereof, a tautomer thereof, or a salt of the tautomer:

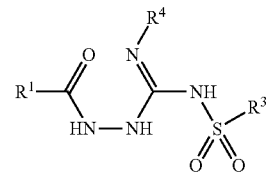

V wherein:

$R^1$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1a}$ may also be oxo unless $R^1$ is a 6-membered heterocyclic group that includes one N atom and includes at least one double bond, and further wherein two $R^{1a}$ substituents on adjacent carbon atoms or on an adjacent carbon atom and an adjacent N atom of a 5- or 6-membered heterocyclic $R^1$ group may join to form a 6 membered ring that may be saturated, partially saturated, or aromatic and may include 0, 1, or 2 N atoms and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), perhaloalkyl), alkyl)-OH, alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, alkyl)-OH, —($C_1$-$C_6$ alkyl)-O—($C_1$-$C_6$ alkyl), —($C_1$-$C_6$ alkyl)-O—($C_1$-$C_6$ alkyl), phenyl, —O—($C_1$-$C_6$ alkyl), —O—($C_1$-$C_6$ haloalkyl), —O—($C_1$-$C_6$ perhaloalkyl), alkyl)-OH, alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), alkyl)-OH, alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), alkyl)-OH, alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, or a monocyclic 3-6 membered cycloalkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents; and $R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent.

142. The compound of embodiment 141, the salt thereof, the tautomer thereof, or the salt of the tautomer, wherein the intermediate has any of the $R^1$, $R^{1a}$, $R^3$, $R^{3a}$, $R^{3b}$, $R^{3c}$, $R^{3d}$, $R^{3e}$, $R^{3f}$, $R^{3g}$, $R^{3h}$, $R^4$, $R^{4a}$, Q, or $R^Q$, values or combinations of values of any one of embodiments 9-75.

143 In another embodiment, the invention provides a compound of Formula V, a salt thereof, a tautomer thereof, or a salt of the tautomer:

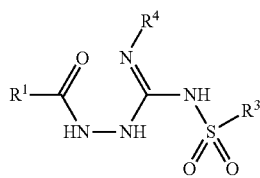

V wherein:
$R^1$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1a}$ may also be oxo unless $R^1$ is a 6-membered heterocyclic group that includes one N atom and includes at least one double bond, and further wherein two $R^{1a}$ substituents on adjacent carbon atoms or on an adjacent carbon atom and an adjacent N atom of a 5- or 6-membered heterocyclic $R^1$ group may join to form a 6 membered ring that may be saturated, partially saturated, or aromatic and may include 0, 1, or 2 N atoms and may further optionally be substituted with 1 or 2 $R^{1a'}$ substituent and may include an oxo substituent if the ring is not an aromatic ring and further wherein two $R^{1a}$ substituents on adjacent carbon atoms or on an adjacent carbon atom and an adjacent N atom of a 5- or 6-membered heterocyclic $R^1$ group may join to form a 5 membered ring that may be saturated, partially saturated, or aromatic and may include 0, 1, or 2 heteroatoms selected from N, O, or S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3d}R^{3e}$)–($CR^{3f}R^{3g}$)-Q, a group of formula —($CR^{3d}R^{3e}$)–($CR^{3f}R^{3g}$)—C(=O)-Q, a group of formula —($CR^{3d}R^{3e}$)–($CR^{3f}R^{3g}$)—CH(OH)-Q, a group of formula —($CR^{3d}R^{3e}$)–($CR^{3f}R^{3g}$)–($CR^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, and the heterocyclyl $R^4$ group are unsubstituted or are substituted with 1, 2, 3, or 4 $R^{4a}$ substituents, and further wherein the cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S and is unsaturated or partially unsaturated and is optionally substituted with 1 or 2 oxo substituents, and further wherein the heterocyclyl of the $R^4$ group may be further substituted with 1 oxo substituent;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ ($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, heterocyclyl, a monocyclic 3-6 membered cycloalkyl group, or a 5 or 6 membered heteroaryl ring containing 1, 2, or 3 heteroatoms selected from N, O, or S, wherein the heterocyclyl of the —($C_1$-$C_6$ alkyl)-heterocyclyl and heterocyclyl $R^{4b}$ groups is a 3-6 membered ring comprising 1 or 2 heteroatoms independently selected from N, O, or S and is unsaturated or partially unsaturated and is optionally substituted with 1 or 2 oxo substituents, and further wherein the phenyl and heteroaryl $R^{4b}$ groups are unsubstituted or are substituted with 1 or 2 $R^{4aa}$ substituents;

$R^{4c}$ in each instance is independently selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a monocyclic 3-6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a monocyclic 3-6 membered cycloalkyl $R^{4c}$ group, the 3 to 6 membered heterocyclyl $R^{4c}$ group, the phenyl $R^{4c}$ group, or the a 5 or 6 membered heteroaryl $R^{4c}$ ring are unsubstituted or are substituted with 1 or 2 $R^{4aa}$ substituents; and further wherein the 3 to 6 membered cycloalkyl $R^{4c}$ group and the 3 to 6 membered heterocyclyl $R^{4c}$ group may optionally be additionally substituted with an oxo substituent; and $R^{4aa}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N(C$_3$-C$_6$ cycloalkyl)$_2$, —S(=O)—(C$_1$-C$_6$ alkyl), or —S(=O)$_2$—(C$_1$-C$_6$ alkyl).

144. The compound of embodiment 143, the salt thereof, the tautomer thereof, or the salt of the tautomer, wherein the intermediate has any of the R$^1$, R$^{1a}$, R$^3$, R$^{3a}$, R$^{3b}$, R$^{3c}$, R$^{3d}$, R$^{3e}$, R$^{3f}$, R$^{3g}$, R$^{3h}$, R$^4$, R$^{4a}$, Q, or R$^Q$, values or combinations of values of any one of embodiments 2-75.

145. In another embodiment, the provides a method for preparing a compound of Formula VI, a salt thereof, a tautomer thereof, or a salt of the tautomer:

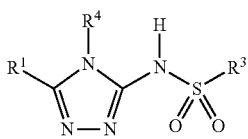

VI the method comprising:
a) cyclizing a compound of Formula V, a salt thereof, a tautomer thereof, or a salt of the tautomer in the presence of an acid or a base to form the compound of Formula VI, the salt thereof, the tautomer thereof, or the salt of the tautomer,

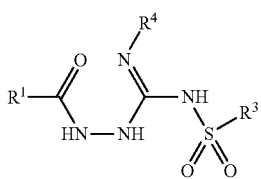

V wherein:
R$^1$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 R$^{1a}$ substituents;
R$^{1a}$ in each instance is independently selected from —F, —Cl, —Br, —I, —C$_1$-C$_6$ alkyl, —C$_1$-C$_6$ haloalkyl, —C$_1$-C$_6$ perhaloalkyl, —(C$_1$-C$_6$ alkyl)-O—(C$_1$-C$_6$ alkyl), —CN, —OH, —O—(C$_1$-C$_6$ alkyl), —O—(C$_1$-C$_6$ haloalkyl), —O—(C$_1$-C$_6$ perhaloalkyl), —C$_2$-C$_6$ alkenyl, —O—(C$_1$-C$_6$ alkyl)-OH, —O—(C$_1$-C$_6$ alkyl)-O—(C$_1$-C$_6$ alkyl), —O—(C$_1$-C$_6$ haloalkyl)-OH, —O—(C$_1$-C$_6$ haloalkyl)-O—(C$_1$-C$_6$ alkyl), —O—(C$_1$-C$_6$ perhaloalkyl)-OH, —O—(C$_1$-C$_6$ perhaloalkyl)-O—(C$_1$-C$_6$ alkyl), —NH$_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, —NHS(=O)$_2$—(C$_1$-C$_6$ alkyl), or —S(=O)$_2$—(C$_1$-C$_6$ alkyl), wherein R$^{1a}$ may also be oxo unless R$^1$ is a 6-membered heterocyclic group that includes one N atom and includes at least one double bond, and further wherein two R$^{1a}$ substituents on adjacent carbon atoms or on an adjacent carbon atom and an adjacent N atom of a 5- or 6-membered heterocyclic R$^1$ group may join to form a 6 membered ring that may be saturated, partially saturated, or aromatic and may include 0, 1, or 2 N atoms and may further optionally be substituted with 1 or 2 R$^{1a'}$ substituent and may include an oxo substituent if the ring is not an aromatic ring;
R$^{1a'}$ is in each instance independently selected from —F, —Cl, —Br, —I, —C$_1$-C$_6$ alkyl, —C$_1$-C$_6$ haloalkyl, —C$_1$-C$_6$ perhaloalkyl, C$_3$-C$_8$ cycloalkyl —(C$_1$-C$_6$ alkyl)-O—(C$_1$-C$_6$ alkyl), —CN, —OH, —O—(C$_1$-C$_6$ alkyl), —O—(C$_1$-C$_6$ haloalkyl), —O—(C$_1$-C$_6$ perhaloalkyl), —C$_2$-C$_6$ alkenyl, —O—(C$_1$-C$_6$ alkyl)-OH, —O—(C$_1$-C$_6$ alkyl)-O—(C$_1$-C$_6$ alkyl), —O—(C$_1$-C$_6$ haloalkyl)-OH, —O—(C$_1$-C$_6$ haloalkyl)-O—(C$_1$-C$_6$ alkyl), —O—(C$_1$-C$_6$ perhaloalkyl)-OH, —O—(C$_1$-C$_6$ perhaloalkyl)-O—(C$_1$-C$_6$ alkyl), —NH$_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$ or —S(=O)$_2$—(C$_1$-C$_6$ alkyl);
R$^3$ is selected from an unsubstituted C$_1$-C$_{10}$ alkyl, a C$_1$-C$_{10}$ alkyl substituted with 1, 2, or 3 R$^{3a}$ substituents, a group of formula —(CR$^{3b}$R$^{3c}$)-Q, a group of formula —(CR$^{3d}$R$^{3e}$)–(CR$^{3f}$R$^{3g}$)-Q, a group of formula —(CR$^{3d}$R$^{3e}$)–(CR$^{3f}$R$^{3g}$)—C(=O)-Q, a group of formula —(CR$^{3d}$R$^{3e}$)–(CR$^{3f}$R$^{3g}$)—CH(OH)-Q, a group of formula —(CR$^{3d}$R$^{3e}$)–(CR$^{3f}$R$^3$)–(CR$^{3f}$R$^{3g}$)-Q, a group of formula —(C$_3$-C$_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 R$^{3h}$ substituents, and further wherein the C$_3$-C$_8$ cycloalkyl of the —(C$_3$-C$_8$ cycloalkyl)-Q group is unsubstituted or is substituted with 1 or 2 R$^{3h}$ substituents;
R$^{3a}$ in each instance is independently selected from —F, —Cl, —CN, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —C$_2$-C$_6$ alkenyl, —C$_2$-C$_6$ alkynyl, —NH$_2$, —NH(C$_1$-C$_6$ alkyl), or —N(C$_1$-C$_6$ alkyl)$_2$;
R$^{3b}$ and R$^{3c}$ are independently selected from —H, —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;
R$^{3d}$ and R$^{3e}$ are independently selected from —H, —F, —Cl, —CN, —C$_1$-C$_6$ alkyl, —C$_1$-C$_6$ haloalkyl, —C$_1$-C$_6$ perhaloalkyl, —OH, —(C$_1$-C$_6$ alkyl)-OH, —(C$_1$-C$_6$ alkyl)-O—(C$_1$-C$_6$ alkyl), —(C$_1$-C$_6$ alkyl)-O—(C$_1$-C$_6$ alkyl)-phenyl, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;
R$^{3f}$ and R$^{3g}$ are independently selected from —H, —F, —Cl, —CN, —C$_1$-C$_6$ alkyl, —C$_1$-C$_6$ haloalkyl, —C$_1$-C$_6$ perhaloalkyl, —OH, —(C$_1$-C$_6$ alkyl)-OH, —(C$_1$-C$_6$ alkyl)-O—(C$_1$-C$_6$ alkyl), —O—(C$_1$-C$_6$ alkyl), —O—(C$_1$-C$_6$ haloalkyl), —O—(C$_1$-C$_6$ perhaloalkyl), —O—(C$_2$-C$_6$ alkenyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;
R$^{3h}$ in each instance is independently selected from —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), —N(C$_1$-C$_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, or a monocyclic 3-6 membered cycloalkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents; and $R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent.

146. The method of embodiment 145, wherein $R^1$, $R^{1a}$, $R^3$, $R^{1a}$, $R^{3b}$, $R^{3c}$, $R^{3d}$, $R^{3e}$, $R^{3f}$, $R^{3g}$, $R^{3h}$, $R^4$, $R^{4a}$, Q, or $R^Q$, have any of the values or combination of values of any one of embodiments 8-75.

147. The method of embodiment 145 or embodiment 146, wherein cyclizing further comprises heating the compound of Formula V, the salt thereof, the tautomer thereof, or the salt of the tautomer in the presence of the acid or the base.

148. The method of embodiment 147, wherein heating the compound of Formula V, the salt thereof, the tautomer thereof, or the salt of the tautomer comprises heating the compound to a temperature of from 50° C. to 100° C.

149. The method of embodiment 147, wherein heating the compound of Formula V, the salt thereof, the tautomer thereof, or the salt of the tautomer comprises heating the compound to a temperature of from 60° C. to 85° C.

150. The method of any one of embodiments 145-149, wherein the cyclizing of the compound of Formula V, the salt thereof, the tautomer thereof, or the salt of the tautomer is performed in the presence of the base.

151. The method of any one of embodiments 145-150, wherein the base is a metal hydroxide.

152. The method of embodiment 151, wherein the metal hydroxide is selected from NaOH or LiOH.

153. The method of any one of embodiments 150-152, wherein the cyclizing is carried out in an alcohol solvent.

154. The method of embodiment 153, wherein the alcohol is isopropanol.

155. The method of any one of embodiments 145-149, wherein cyclizing further comprises heating the compound of Formula V, the salt thereof, the tautomer thereof, or the salt of the tautomer in the presence of the acid.

156. The method of embodiment 155, wherein the acid is selected from a sulfonic acid, a carboxylic acid, polyphosphoric acid, phosphoric acid, sulfuric acid, or hydrochloric acid.

157. The method of embodiment 156, wherein the sulfonic acid is methanesulfonic acid.

158. The method of embodiment 156, wherein the acid is trifluoroacetic acid, acetic acid, or trichloroacetic acid.

159. The method of any one of embodiments 155-158, wherein the cyclizing is carried out in a cyclic ether, an acyclic ether, N,N-dimethylformamide, or acetonitrile.

160. The method of embodiment 159, wherein the cyclizing is carried out in a cyclic ether.

161. The method of embodiment 160, wherein the cyclic ether is selected from tetrahydrofuran, tetrahydropyran, or 1,4-dioxane.

162. The method of embodiment 160, wherein the cyclic ether is 1,4-dioxane.

163. In another embodiment, the provides a method for preparing a compound of Formula VI, a salt thereof, a tautomer thereof, or a salt of the tautomer:

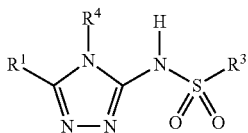

VI the method comprising:
a) cyclizing a compound of Formula V, a salt thereof, a tautomer thereof, or a salt of the tautomer in the presence of an acid or a base to form the compound of Formula VI, the salt thereof, the tautomer thereof, or the salt of the tautomer,

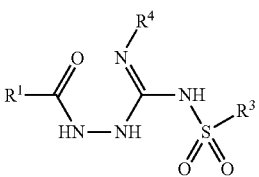

V wherein:
$R^1$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1a}$ substituents;
$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1a}$ may also be oxo unless $R^1$ is a 6-membered heterocyclic group that includes one N atom and includes at least one double bond, and further wherein two $R^{1a}$ substituents on adjacent carbon atoms or on an adjacent carbon atom and an adjacent N atom of a 5- or 6-membered heterocyclic $R^1$ group may join to form a 6 membered ring that may be saturated, partially saturated, or aromatic and may include 0, 1, or 2 N atoms and may further optionally be substituted with 1 or 2 $R^{1a'}$ substituent and may include an oxo substituent if the ring is not an aromatic ring and further wherein two $R^{1a}$ substituents on adjacent carbon atoms or on an adjacent carbon atom and an adjacent N atom of a 5- or 6-membered heterocyclic $R^1$ group may join to form a 5 membered ring that may be saturated, partially saturated, or aromatic and may include 0, 1, or 2 heteroatoms selected from N, O, or S and may further optionally be substituted with 1 or 2 $R^{1a'}$ substituent and may include an oxo substituent if the ring is not an aromatic ring;
$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);
$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3d}R^{3e}$)–($CR^{3f}R^{3g}$)-Q, a group of formula —($CR^{3d}R^{3e}$)–($CR^{3f}R^{3g}$)—C(=O)-Q, a group of formula —($CR^{3d}R^{3e}$)–($CR^{3f}R^{3g}$)—CH(OH)-Q, a group of formula —($CR^{3d}R^{3e}$)–($CR^{3f}R^3$)–($CR^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;
$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;
$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;
$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;
$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;
$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, and the heterocyclyl $R^4$ group are unsubstituted or are substituted with 1, 2, 3, or 4 $R^{4a}$ substituents, and further wherein the cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S and is unsaturated or partially unsaturated and is optionally substituted with 1 or 2 oxo substituents, and further wherein the heterocyclyl of the $R^4$ group may be further substituted with 1 oxo substituent;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, heterocyclyl, a monocyclic 3-6 membered cycloalkyl group, or a 5 or 6 membered heteroaryl ring containing 1, 2, or 3 heteroatoms selected from N, O, or S, wherein the heterocyclyl of the —($C_1$-$C_6$ alkyl)-heterocyclyl and heterocyclyl $R^{4b}$ groups is a 3-6 membered ring comprising 1 or 2 heteroatoms independently selected from N, O, or S and is unsaturated or partially unsaturated and is optionally substituted with 1 or 2 oxo substituents, and further wherein the phenyl and heteroaryl $R^{4b}$ groups are unsubstituted or are substituted with 1 or 2 $R^{4aa}$ substituents;

$R^{4c}$ in each instance is independently selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a monocyclic 3-6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a monocyclic 3-6 membered cycloalkyl $R^{4c}$ group, the 3 to 6 membered heterocyclyl $R^{4c}$ group, the phenyl $R^{4c}$ group, or the a 5 or 6 membered heteroaryl $R^{4c}$ ring are unsubstituted or are substituted with 1 or 2 $R^{4aa}$ substituents; and further wherein the 3 to 6 membered cycloalkyl $R^{4c}$ group and the 3 to 6 membered heterocyclyl $R^{4c}$ group may optionally be additionally substituted with an oxo substituent; and $R^{4aa}$ in each instance is selected from —F, —Cl, —Br, —I, —CN, —OH, —O—($C_1$-$C_6$ alkyl), —O—($C_1$-$C_6$ haloalkyl), perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N(C$_1$-C$_6$ alkyl)(C$_3$-C$_6$ cycloalkyl), —C(=O)N(C$_3$-C$_6$ cycloalkyl)$_2$, —S(=O)—(C$_1$-C$_6$ alkyl), or —S(=O)$_2$—(C$_1$-C$_6$ alkyl).

164. The method of embodiment 163, wherein R$^1$, R$^{1a}$, R$^3$, R$^{3a}$, R$^{3b}$, R$^{3c}$, R$^{3d}$, R$^{3e}$, R$^{3f}$, R$^{3g}$, R$^{3h}$, R$^4$, R$^{4a}$, Q, or R$^Q$ have any of the values or combination of values of any one of embodiments 2-75.

165. The method of embodiment 163 or embodiment 164, wherein cyclizing further comprises heating the compound of Formula V, the salt thereof, the tautomer thereof, or the salt of the tautomer in the presence of the acid or the base.

166. The method of embodiment 165, wherein heating the compound of Formula V, the salt thereof, the tautomer thereof, or the salt of the tautomer comprises heating the compound to a temperature of from 50° C. to 100° C.

167. The method of embodiment 165, wherein heating the compound of Formula V, the salt thereof, the tautomer thereof, or the salt of the tautomer comprises heating the compound to a temperature of from 60° C. to 85° C.

168. The method of any one of embodiments 163-167, wherein the cyclizing of the compound of Formula V, the salt thereof, the tautomer thereof, or the salt of the tautomer is performed in the presence of the base.

169. The method of any one of embodiments 163-168, wherein the base is a metal hydroxide.

170. The method of embodiment 169, wherein the metal hydroxide is selected from NaOH or LiOH.

171. The method of any one of embodiments 168-170, wherein the cyclizing is carried out in an alcohol solvent.

172. The method of embodiment 171, wherein the alcohol is isopropanol.

173. The method of any one of embodiments 163-167, wherein cyclizing further comprises heating the compound of Formula V, the salt thereof, the tautomer thereof, or the salt of the tautomer in the presence of the acid.

174. The method of embodiment 173, wherein the acid is selected from a sulfonic acid, a carboxylic acid, polyphosphoric acid, phosphoric acid, sulfuric acid, or hydrochloric acid.

175 The method of embodiment 174, wherein the sulfonic acid is methanesulfonic acid.

176. The method of embodiment 174, wherein the acid is trifluoroacetic acid, acetic acid, or trichloroacetic acid.

177. The method of any one of embodiments 173-176, wherein the cyclizing is carried out in a cyclic ether, an acyclic ether, N,N-dimethylformamide, or acetonitrile.

178. The method of embodiment 177, wherein the cyclizing is carried out in a cyclic ether.

179. The method of embodiment 178, wherein the cyclic ether is selected from tetrahydrofuran, tetrahydropyran, or 1,4-dioxane.

180. The method of embodiment 178, wherein the cyclic ether is 1,4-dioxane.

In some embodiments, the compound is a salt. Such salts may be anhydrous or associated with water as a hydrate. In some embodiments, the compound may be in a neutral form as a base or an acid.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the embodiments and at least one pharmaceutically acceptable excipient, carrier or diluent. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of a cardiovascular condition or other condition such as obesity or diabetes, for activating the APJ Receptor. In some embodiments, the pharmaceutical composition is formulated for oral delivery whereas in other embodiments, the pharmaceutical composition is formulated for intravenous delivery. In some embodiments, the pharmaceutical composition is formulated for oral administration once a day or QD, and in some such formulations is a tablet.

In some embodiments, the subject is a mammal. In some such embodiments, the mammal is a rodent. In other such embodiments, the mammal is a canine. In still other embodiments, the subject is a primate and, in some such embodiments, is a human.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be administered to provide systemic distribution of the compound within the patient. Therefore, in some embodiments, the compounds of the invention are administered to produce a systemic effect in the body.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

The compound of the invention, the pharmaceutically acceptable salt thereof, the tautomer thereof, the pharmaceutically acceptable salt of the tautomer, the stereoisomer of any of the foregoing, or the mixture thereof may find use in treating a number of conditions. For example, in some embodiments, the invention comprises methods or uses that include the use or administration of the compound, the pharmaceutically acceptable salt thereof, the tautomer thereof, the pharmaceutically acceptable salt of the tautomer, the stereoisomer of any of the foregoing, or the mixture thereof of the invention, in treating a subject suffering from a cardiovascular condition. In some embodiments, the cardiovascular condition includes, but is not limited to, coronary heart disease, stroke, heart failure, systolic heart failure, diastolic heart failure, diabetic heart failure, heart failure with preserved ejection fraction, heart failure with reduced ejection fraction, cardiomyopathy, myocardial infarction, myocardial remodeling after cardiac surgery, valvular heart disease, hypertension including, essential hypertension, pulmonary hypertension, portal hypertension, systolic hypertension, aortic aneurysm such as abdominal aortic aneurysm, or atrial fibrillation including improving arrhythmia. In some embodiments, the cardiovascular condition is heart failure. In some such embodiments, the heart failure is heart failure with reduced ejection fraction whereas in other embodiments it is heart failure with preserved ejection fraction. In other such embodiments the subject may have systolic heart failure or chronic diastolic heart failure and is thus useful in treating heart failure patients with systolic dysfunction and in treating heart failure patients with diastolic dysfunction. In some embodiments, the cardiovascular condition may be acute heart failure whereas in other embodiments, the cardiovascular condition is hypertension.

As noted, the compounds of the invention may be used to treat a number of diseases and disorders. Thus, in some embodiments, the invention provides a method of treating a disease or disorder selected from acute decompensated heart failure, chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes, gestational diabetes, obesity, peripheral arterial disease, cerebrovascular accidents, transient ischemic attacks, traumatic brain injuries, amyotrophic lateral sclerosis, burn injuries, sunburn, edema, and preeclampsia in a subject. Such methods include administering a compound of the invention, a pharmaceutically acceptable salt thereof, a tautomer thereof, a pharmaceutically acceptable salt of the tautomer, a stereoisomer of any of the foregoing, a mixture thereof, or a pharmaceutical composition that includes any of these to a subject in need thereof.

In some embodiments, the invention provides a method of improving cardiac contractility in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac contraction may lead to significant improvements in methods for treating heart failure patients.

In some embodiments, the invention provides a method of improving cardiac relaxation in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac relaxation may lead to significant improvements in methods for treating heart failure patients.

In some embodiments, the invention provides a method of improving ventricular arterial coupling in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in ventricular arterial coupling may lead to significant improvements in methods for treating heart failure patients.

In some embodiments, the invention provides a method of increasing ejection fraction in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

The compounds of the invention may also find potential benefit in improving cardiac relaxation and thus find utility in treating certain heart failure patients. The compounds of the invention may thus find utility in improving inotropic function in some embodiments and may also find utility in improving lusitropic function.

In some embodiments, the invention provides a method of treating condition in a subject where it is desired to activate the APJ Receptor. Such methods include administration of the compound, the pharmaceutically acceptable salt thereof, the tautomer thereof, the pharmaceutically acceptable salt of the tautomer, the stereoisomer of any of the foregoing, or the mixture thereof of the invention to the subject. In some such embodiments, the condition is obesity or diabetes whereas in other embodiments, the condition is diabetic nephropathy or chronic kidney disease. In some such embodiments, the condition is type II diabetes.

The compounds of the invention may find utility in treating a number of other conditions. For example, the compounds of the invention may find utility in treating patients with conditions related to renal perfusion, hyperglycemia, aquaresis, and diuresis. In some embodiments, the invention provides a method of treating one of these subjects that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The compounds of the invention may further find utility in arginine vasopressin (AVP) regulation and in angiotensin receptor (AT1R) regulation.

The compounds of the invention may find utility in treating a number of other conditions or producing desired outcomes or results. For example, the compounds of the invention may find utility in activating stem cells, more specifically cardiac stem cells, and even more specifically endogenous cardiac stem cells. Thus, the compounds of the invention may find utility in activating heart stem cells in a subject such as in a human patient. The compounds of the invention may yet further find utility in regrowing tissue and in assisting functional recovery after transplanting cells such as cells with bone marrow-derived mesenchymal stem cells. The compounds of the invention may also find utility in increasing cardiac stem cell proliferation and may be used to do such in patients that have suffered a myocardial infarction. As another example, the compounds of the invention may find utility in reducing infarct size, in promoting cardiac repair, and in activating stem cells and progenitors in post-myocardial infarction subjects. As still yet another example, the compounds of the invention may be used during surgery such as heart bypass surgery or heart transplant procedures as a therapeutic to reduce reperfusion injury. In some embodiments, the invention provides a method of treating one of these subjects or improving the condition in a subject that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that is used to treat subjects with chronic heart failure or hypertension.

As described above some methods of the invention comprise the administration of a compound of the invention and an additional therapeutic agent (i.e., a therapeutic agent other than a compound of the invention). In some embodiments, the invention encompasses administration of an additional therapeutic agent that is used to treat subjects with chronic heart failure or hypertension. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent such as, but not limited to, an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, a neutral endopeptidase (NEP) inhibitor, a vasodilator, an aldosterone antagonist, a natriuretic, a saluretic, a centrally acting hypertensive, an aldosterone synthase inhibitor, or an endothelin receptor antagonist. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor. In some such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an angiotensin converting enzyme (ACE) inhibitor or an angiotensin-receptor blocker (ARB). In some such embodiments, the additional therapeutic agent is thus an angiotensin converting enzyme (ACE) inhibitor whereas in others it is an angiotensin-receptor blocker (ARB). In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as a neutral endopeptidase (NEP) inhibitor. In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an inhibitor of the funny current. In some embodiments, the method of use may include two or more additional therapeutic agents. For example, in some embodiments, the invention may include a compound of the invention, the pharmaceutically acceptable salt thereof, the tautomer thereof, the pharmaceutically acceptable salt of the tautomer, the stereoisomer of any of the foregoing, or the mixture thereof and additional therapeutic agents such as an ACE inhibitor and a NEP inhibitor.

Therapeutic agents such as α-blockers may be used in conjunction with the compounds of the invention. Examples of α-blockers include, but are not limited to, doxazosin, prazosin, tamsulosin, and terazosin and their pharmaceutically acceptable salts.

Therapeutic agents such as β-blockers may be used in conjunction with the compounds of the invention. Examples of β-blockers include, but are not limited to, acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol, and their pharmaceutically acceptable salts.

Calcium channel blockers may also be used as therapeutic agents in conjunctions with the compounds of the present invention. Examples of calcium channel blockers, include, but are not limited to, dihydropyridines (DHPs) and non-DHPs. Examples of DHPs include, but are not limited to, amlodipine, felodipine, isradipine, lacidipine, nicardipine, nifedipine, nigulpidine, nilutipine, nimodiphine, nisoldipine, nitrendipine, nivaldipine, ryosidine, and their pharmaceutically acceptable salts. Examples of Non-DHPs include, but are not limited to, anipamil, diltiazem, fendiline, flunarizine, gallpamil, mibefradil, prenylamine, tiapamil, verapamil, and their pharmaceutically acceptable salts.

Diuretics may also be used in conjunction with the compounds of the present invention. Examples include, but are not limited to, thiazide derivatives such as, but not limited to, amiloride, chlorothalidon, chlorothiazide, hydrochlorthiazide, and methylchlorothiazide and pharmaceutically acceptable salts thereof Centrally acting hypertensive agents may also be used in conjunction with the compounds of the present invention. Examples, include, but are not limited to, clonidine, guanabenz, guanfacine, methyldopa, and pharmaceutically acceptable salts thereof.

ACE inhibitors may be used in conjunction with the compounds of the present invention. Examples of ACE inhibitors that may be used include, but are not limited to, alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril and their pharmaceutically acceptable salts. Examples of some dual ACE/NEP inhibitors include, but are not limited to omapatrilat, fasidotril, and fasidotrilat and their pharmaceutically acceptable salts.

ARBs may also be used as therapeutic agents in conjunction with the compounds of the present invention. Examples of ARBs include, but are not limited to, candesartan, eprosartan, irbesartan, losartan, olmesartan, tasosartan, telmisartan, and valsartan and their pharmaceutically acceptable salts. Examples of some dual ARB/NEP inhibitors include, but are not limited to combinations of valsartan and sacubitril and their pharmaceutically acceptable salts.

NEP inhibitors may also be used as therapeutic agents in conjunction with the compounds of the present invention. An example of a NEP inhibitor includes, but it not limited to, sacubitril and its pharmaceutically acceptable salts.

Aldosterone synthase inhibitors may also be used as therapeutic agents in combination with the compounds of the present invention. Examples of aldosterone synthase inhibitors include, but are not limited to, anastrozole, fadrozole, and exemestane and their pharmaceutically acceptable salts.

Endothelin antagonists are other therapeutic agents that may be used in conjunction with the compounds of the present invention. Examples include, but are not limited to, bosentan, enrasentan, atrasentan, darusentan, macitentan, sitaxentan, and tezosentan, and their pharmaceutically acceptable salts.

Inhibitors of the funny current ($I_f$) may also be used in conjunction with the compounds of the invention. An example of an inhibitor of the funny current is ivabradine and its pharmaceutically acceptable salts.

Myosin activators may also be used in conjunction with the compounds of the invention. Examples of myosin activators include cardiac myosin activators.

It will be recognized that for purposes of this application, a therapeutic agent other than one of the present invention includes compounds such as known prodrugs that are converted into the therapeutic agent after administration. For example, a compound without antineoplastic activity, but that is converted into an antineoplastic agent in the body after administration, may be administered along with a compound of the invention. As another example, sacubitril is considered a NEP inhibitor for the purposes of this application even though it is a prodrug that is converted into sacubitrilat by de-ethylation via esterases.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of cardiovascular conditions.

If formulated as a fixed dose, such combination products employ the compounds of this invention within the accepted dosage ranges. Compounds of any of the embodiments described herein may also be administered sequentially with known agents for use in treating cardiovascular conditions such as heart failure and hypertension when a combination formulation is inappropriate. The invention is not limited in the sequence of administration as compounds of the invention may be administered either prior to, simultaneous with, or after administration of a known therapeutic agent.

The invention is further described by reference to the following examples, which are intended to exemplify the claimed invention but not to limit it in any way.

EXAMPLES

Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen or argon atmosphere. Purity was measured using Agilent 1100 Series high performance liquid chromatography (HPLC) systems with UV detection at 254 nm and 215 nm (System A: Agilent Zorbax Eclipse XDB-C8 4.6× 150 mm, 5 micron, 5 to 100% ACN in $H_2O$ with 0.1% TFA for 15 min at 1.5 mL/min; System B: Zorbax SB-C8, 4.6×75 mm, 10 to 90% ACN in $H_2O$ with 0.1% formic acid for 12 min at 1.0 mL/min). Silica gel chromatography was generally performed with prepacked silica gel cartridges (Biotage or Teledyne-Isco). $^1H$ NMR spectra were recorded on a Bruker AV-400 (400 MHz) spectrometer or a Varian 400 MHz spectrometer at ambient temperature, or the NMR spectra were collected with a Bruker Avance III spectrometer operating at a proton frequency of 500.13 MHz using a 10 μL Protasis CapNMR flow probe. NMR samples were delivered to the flow probe using a Protasis One-Minute NMR™ Automation system comprised of a Discovery Tower™ Sample Manager and a Waters Liquid Handler made by CTC, Switzerland (Model 2777). All observed protons are reported as parts per million (ppm) downfield from tetramethylsilane (TMS) or another internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series LC-MS with UV detection at 254 nm and 215 nm and a low resonance electrospray mode (ESI).

A wide variety of sulfonamide tails and $R^4$ groups can be used to synthesize compounds of the invention such as those set forth in WO 2016/187308 and U.S. Pat. Appl. Pub. No. US 2016/0340336 which are hereby incorporated by reference in their entireties and for all purposes as if specifically set forth herein. Thus, compounds of the present invention may be prepared using any of the $R^3$, $R^4$, and Q groups taught in WO 2016/187308 and U.S. Pat. Appl. Pub. No. US 2016/0340336.

The following Abbreviations are used to refer to various reagents and solvents:

ACN Acetonitrile

AcOH Acetic Acid d day or days

CV Column volume

DCM Dichloromethane

DEA Diethylamine

DMF N,N-Dimethylformamide

DMA Dimethylacetamide

DMAP 4-Dimethylaminopyridine

DMSO Dimethylsulfoxide

EtOAc Ethyl Acetate

EtOH Ethanol

EtOTf Ethyl trifluoromethanesulfonate h hour or hours

HATU 1-[Bis(dimethylamino)methylene]-1H-1,2,3-triazolo[4,5-b]pyridinium 3-oxid hexafluorophosphate IPA Isopropanol LAH Lithium aluminum hydride min minute or minutes MeOH Methanol MeOTf Methyl trifluoromethanesulfonate MS Mass spectrum MSA Methane sulfonic acid RT Room temperature SFC Supercritical fluid chromatography TBAF Tetrabutylammonium fluoride TBS t-Butyldimethylsilane TBSOTf t-Butyldimethylsilyl trifluoromethanesulfonate TEA Triethylamine TFA Trifluoroacetic acid THF Tetrahydrofuran TLC Thin Layer Chromatography

Example 1.0: Preparation of (2S,3R)-3-(5-methyl-pyrimidin-2-yl)butane-2-sulfonamide

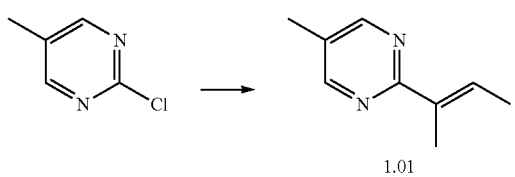

(E)-2-(But-2-en-2-yl)-5-methylpyrimidine, Example 1.01

2-Chloro-5-methyl-pyrimidine (18 mL, 151 mmol), potassium (Z)-but-2-en-2-yltrifluoroborate (Sigma Aldrich, 31 g, 191 mmol), tricyclohexylphosphine (8.5 g, 30.2 mmol), and $Pd_2(dba)_3$ (13.82 g, 15.09 mmol) were added to a flask, which was then degassed and backfilled with nitrogen. To the flask was added 1,4-dioxane (252 mL) and aqueous potassium phosphate tribasic (37.5 mL, 453 mmol). The resulting reaction was heated at 100° C. for 16 h. The reaction was then cooled to RT. The residue was filtered through a plug of silica gel and then loaded onto silica gel (0-20% EtOAc in heptanes) to afford (E)-2-(but-2-en-2-yl)-5-methylpyrimidine 1.01 (19 g, 125 mmol, 83% yield).

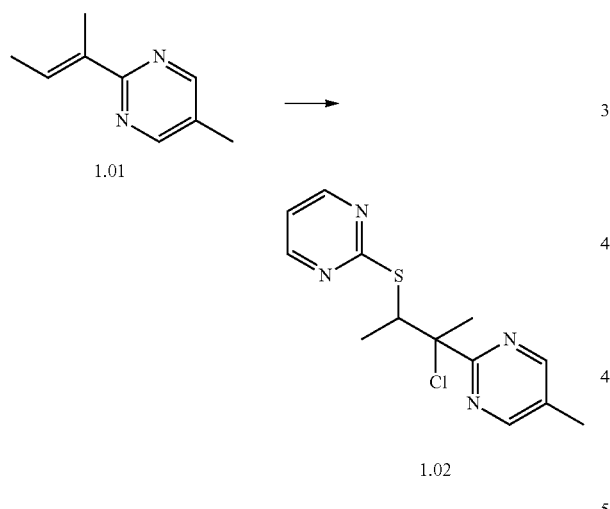

2-(2-Chloro-3-(pyrimidin-2-ylthio)butan-2-yl)-5-methylpyrimidine, Example 1.02

To a solution of pyrimidine-2-thiol (14.8 g, 132 mmol) in DCM (440 mL) was added sulfuryl chloride (10.73 mL, 132 mmol). The reaction was stirred at 0° C. for 1 h and a further 1 h at 23° C. To the cloudy reaction mixture was added (E)-2-(but-2-en-2-yl)-5-methylpyrimidine 1.01 (20 g, 132 mmol) dropwise, and the mixture was further stirred for 2 h. The reaction mixture was concentrated in vacuo. Aqueous sodium bicarbonate was added to neutralize the reaction mixture. The reaction was extracted with EtOAc and concentrated in vacuo. The residue was purified on silica gel with 0-25% EtOAc in hexanes to give the desired product 2-(2-chloro-3-(pyrimidin-2-ylthio)butan-2-yl)-5-methylpyrimidine 1.02 (30 g, 76% yield).

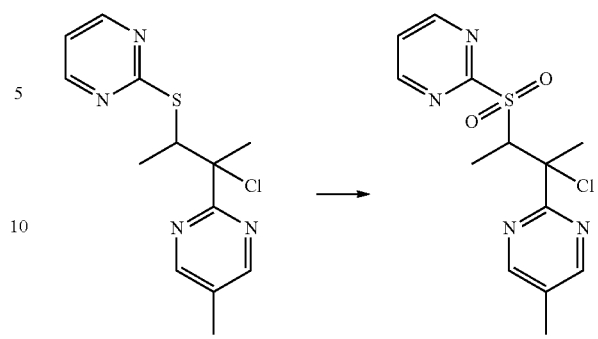

2-(2-Chloro-3-(pyrimidin-2-ylsulfonyl)butan-2-yl)-5-methylpyrimidine, Example 1.03

To a solution of 2-(2-chloro-3-(pyrimidin-2-ylthio)butan-2-yl)-5-methylpyrimidine 1.02 (30 g, 100 mmol) in DCM (201 mL) was added meta-chloroperoxybenzoic acid (45.0 g, 201 mmol). The reaction was stirred at 23° C. for 1 d. The reaction was concentrated in vacuo and aqueous sodium bicarbonate and sodium thiosulfate were added. The mixture was then extracted with EtOAc and concentrated in vacuo to give the desired product 2-(2-chloro-3-(pyrimidin-2-ylsulfonyl)butan-2-yl)-5-methylpyrimidine 1.03 (33.2 g, 100 mmol, 100% yield).

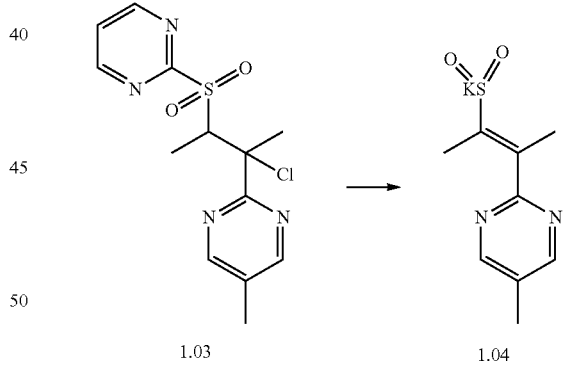

Potassium (E)-3-(5-methylpyrimidin-2-yl)but-2-ene-2-sulfinate, Example 1.04

To a solution of 2-(2-chloro-3-(pyrimidin-2-ylsulfonyl)butan-2-yl)-5-methylpyrimidine 1.03 (33 g, 100 mmol) in MeOH (249 mL) was added potassium carbonate (27.6 g, 200 mmol). The reaction was stirred at 23° C. for 16 h. The reaction was concentrated in vacuo to give the desired product potassium (E)-3-(5-methylpyrimidin-2-yl)but-2-ene-2-sulfinate 1.04 (21.57 g, 100% yield), that was used without further purification.

111

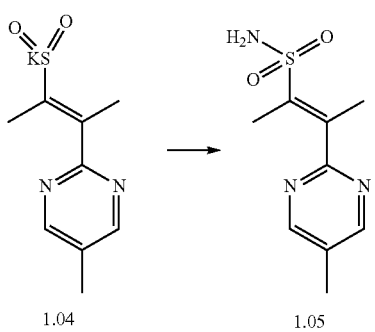

1.04 → 1.05

(E)-3-(5-Methylpyrimidin-2-yl)but-2-ene-2-sulfonamide, Example 1.05

To a solution of potassium (E)-3-(5-methylpyrimidin-2-yl)but-2-ene-2-sulfinate (Example 1.04, 21.57 g, 85 mmol) in water (424 mL, 85 mmol) was added potassium acetate (5.30 mL, 85 mmol), followed by amidoperoxymonosulfuric acid (19.18 g, 170 mmol). The reaction was stirred at 23° C. for 24 h. The reaction was then extracted with EtOAc and concentrated in vacuo. The product thus obtained was purified on silica gel eluting with 0-50% EtOAc in hexanes to give the desired product (E)-3-(5-methylpyrimidin-2-yl)but-2-ene-2-sulfonamide 1.05 (12 g, 61.2% yield).

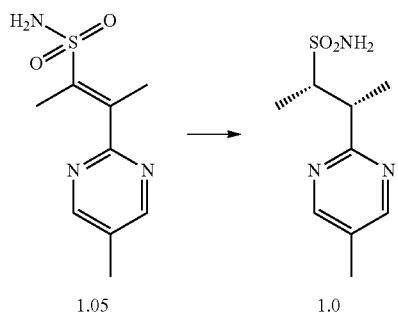

1.05 → 1.0

112

(2S,3R)-3-(5-Methylpyrimidin-2-yl)butane-2-sulfonamide, Example 1.0

A 900 mL pressure reactor was charged under nitrogen flow with (E)-3-(5-methylpyrimidin-2-yl)but-2-ene-2-sulfonamide, Example 1.05 (40.00 g, 0.1760 mol, 1 equivalent), zinc trifluoromethane sulfonate (12.79 g, 0.0352 mol, 0.2 equivalent, Aldrich), bis(1,5-cyclooctadiene)rhodium(I) tetrafluoroborate (1.43 g, 0.00352 mol, 0.02 equivalent, Strem Chemicals, Inc.), (S)-1-[(R)-2-(di-1-naphthylphosphino)ferrocenyl]-ethyl-di-tert.-butylphosphine (2.60 g, 0.00405 mol, 0.023 equivalent, Solvias) and MeOH (520 mL). The mixture was purged with nitrogen and then with hydrogen, and the media was stirred under 3-4 bars of hydrogen for 20 h. The reaction was monitored by HPLC and showed a complete conversion. The reactor was purged with nitrogen, and the resulting suspension was concentrated at 35° C. under industrial vacuum to give the material as an orange solid. The material thus obtained was mixed with EtOH (742 mL) and the resulting suspension was stirred at 20-25° C. for 40 min. The solid was filtered, washed with EtOH (2×97 mL) and dried at 40° C. under vacuum to give the title compound as a white powder (85.2% yield, 99% ee). $^1$H NMR (400 MHz, DMSO-$d_6$): δ 8.61 (s, 2H), 6.84 (s, 2H), 3.69 (tt, J=12.4, 4.5 Hz, 2H), 2.25 (s, 3H), 1.32 (d, J=6.9 Hz, 3H), 1.20 (d, J=7.0 Hz, 3H). LCMS (ESI, positive ion) m/z; 230.1 (M+H)$^+$.

The compounds in the following table were synthesized following the procedure in Example 1.0 using the known starting material as described.

TABLE 1

| Example | Reagents | Structure, Name and Data |
|---|---|---|
| 1.1 | 2-chloro-5-fluoro-pyrimidine. | (2S,3R)-3-(5-fluoropyrimidin-2-yl)butane-2-sulfonamide. LCMS ESI (pos) m/z: 234.2 (M + H)$^+$. |

TABLE 1-continued

| Example | Reagents | Structure, Name and Data |
|---|---|---|
| 1.2 | 2-bromo-5-methylpyrazine. The title compound was the first isomer to elute under the following SFC conditions: Run on Thar 200 SFC with 250 × 30 mm AD-H column with 20 mL/min MeOH (+20 mM $NH_3$) + 80 g/min $CO_2$, 20% co-solvent at 100 g/min. Temperature. = 29° C., Outlet pressure = 100 bar, Wavelength = 271 nm. Injected 1.0 mL of 550 mg of the enantiomerically enriched product dissolved in 20 mL MeOH:DCM, 15:5; c = 27.5 mg/mL and 27.5 mg per injection. Cycle time 5.0 min, run time 13 min. | 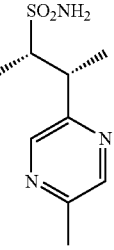<br>(2S,3R)-3-(5-methylpyrazin-2-yl)butane-2-sulfonamide. $^1$H NMR (400 MHz, DMSO-$d_6$) δ 8.46 (d, J = 6.5 Hz, 2H), 6.84 (s, 2H), 3.63 (qd, J = 7.0, 4.3 Hz, 1H), 3.44 (qd, J = 7.0, 4.3 Hz, 1H), 2.47 (s, 3H), 1.31 (d, J = 7.0 Hz, 3H), 1.23 (d, J = 7.0 Hz, 3H). LCMS (ESI, positive ion) m/z; 230.0 (M + H)$^+$. |
| 1.3 | 2-bromo-5-methylpyrazine. The title compound is the enantiomer of Example 1.2. Example 1.2 is the second isomer to elute from AD-H column on subjecting the enantiomerically enriched product to the SFC conditions described in Example 1.2. | <br>(2R,3S)-3-(5-methylpyrazin-2-yl)butane-2-sulfonamide. LCMS-ESI (pos) m/z: 230.0 (M + H)$^+$. |
| 1.4 | 2-chloro-5-chloro-pyrimidine. Recrystallization: Example 1.4 (38 g, 90% ee) was dissolved in IPA (400 mL) at 70° C. | 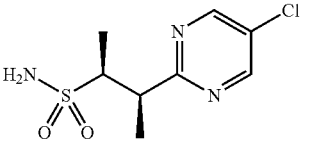<br>(2S,3R)-3-(5-chloropyrimidin-2-yl)butane-2-sulfonamide. $^1$H NMR (400 MHz, DMSO-$d_6$) δ 8.93-8.85 (m, 2H), 6.86 (d, J = 4.0 Hz, 2H), 3.73-3.59 (m, 2H), 1.31 (dt, J = 7.3, 2.4 Hz, 3H), 1.25-1.19 (m, 3H). LCMS (ESI +ve ion) m/z: 250.2 (M + H)$^+$. |
| 1.5 | 2-bromo-5-methoxypyrazine. | 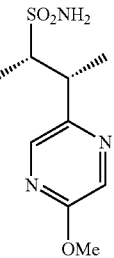<br>(2S,3R)-3-(5-methoxypyrazin-2-yl)butane-2-sulfonamide. $^1$H NMR (400 MHz, DMSO-$d_6$) δ 8.26 (d, J = 1.4 Hz, 1H), 8.12 (d, J = 1.4 Hz, 1H), 6.84 (s, 2H), 3.90 (d, J = 1.5 Hz, 3H), 3.62 (dd, J = 7.1, 4.3 Hz, 1H), 3.42-3.38 (m, 1H), 1.32 (d, J = 1.5 Hz, 3H), 1.23-1.21 (m, 3H). LCMS (ESI +ve ion) m/z: 246.2 (M + H)$^+$. |

Example 2.0: Preparation of (2S,3R)—N-(4-((1r,2R,6S)-2,6-dimethoxycyclohexyl)-5-((2S)-tetrahydro-2-furanyl)-4H-1,2,4-triazol-3-yl)-3-(5-methyl-2-pyrimidinyl)-2-butanesulfonamide or (2S,3R)—N-(4-((1r,2R,6S)-2,6-dimethoxycyclohexyl)-5-((2R)-tetrahydro-2-furanyl)-4H-1,2,4-triazol-3-yl)-3-(5-methyl-2-pyrimidinyl)-2-butanesulfonamide

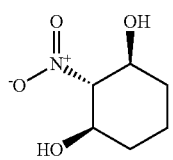

(1R,2r,3S)-2-Nitrocyclohexane-1,3-diol, Example 2.1

A 500 mL round bottom flask was charged with glutaric dialdehyde (12.5 g, 50 mL, 25% aqueous solution, 125 mmol) and diluted with nitromethane (27.6 mL, 512 mmol) and a 1:1 solution of MeOH (69.3 mL) and water (69.3 mL). The solution was cooled to 0° C. and sodium carbonate (48.4 g, 457 mmol) in 69.3 mL of water was added. The resulting mixture was warmed to RT and stirred for 4 h. Carefully, AcOH (32.3 mL, 570 mmol) was added and the solution was concentrated in vacuo to remove all organics (bath temp 30-35° C.). Next, the water solution was partitioned with ether (5×200 mL), and the ether layer was dried over sodium sulfate, filtered and concentrated to dryness. The material was then recrystallized with EtOAc to obtain the desired product (1R,2r,3S)-2-nitrocyclohexane-1,3-diol (7.5 g, 37.3%).

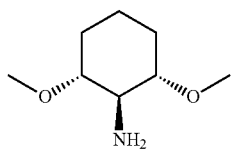

(1R,2r,6S)-2,6-Dimethoxycyclohexanamine, Example 2.2

Silver(I) oxide (6.15 mL, 192 mmol) was added to a DMF (96 mL) solution containing iodomethane (30.0 mL, 479 mmol) and (1R,2r,3S)-2-nitrocyclohexane-1,3-diol (7.72 g, 47.9 mmol). The resulting mixture was stirred overnight at 23° C. The reaction was then filtered and the filtrated was partitioned with EtOAc/water, washed with brine dried over sodium sulfate and concentrated. Next, the residue was dissolved in EtOH and Raney 2400 nickel (0.316 mL, 47.9 mmol) was added. The reaction was shaken in a Parr hydrogenator at 50 psi overnight. The reaction was then carefully filtered and concentrated in vacuo.

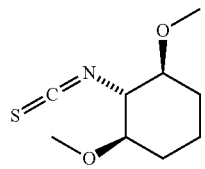

(1R,2r,3S)-2-Isothiocyanato-1,3-dimethoxycyclohexane, Example 2.3

1,1″-Thiocarbonyldi-2(1H)-pyridone (0.802 g, 3.45 mmol) was added to a DCM (15.70 mL) solution containing (1r,2R,6S)-2,6-dimethoxycyclohexanamine (0.5 g, 3.14 mmol). The resulting mixture was stirred overnight at 23° C. The reaction was concentrated and purified on silica eluting with a hexanes/EtOAc gradient (0-100%). Desired fractions were pooled and concentrated to yield the title compound (0.45 g, 71%).

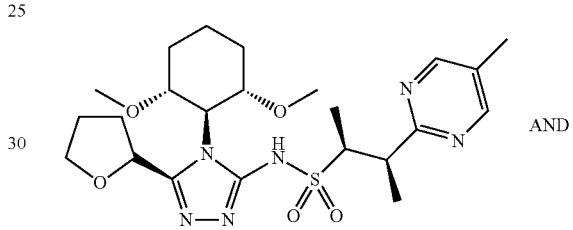

AND

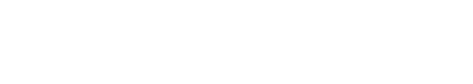

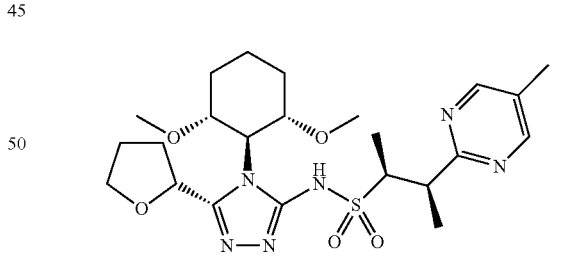

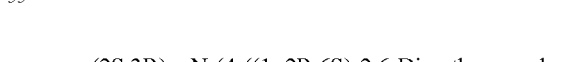

(2S,3R)—N-(4-((1r,2R,6S)-2,6-Dimethoxycyclohexyl)-5-((2S)-tetrahydro-2-furanyl)-4H-1,2,4-triazol-3-yl)-3-(5-methyl-2-pyrimidinyl)-2-butanesulfonamide and (2S,3R)—N-(4-((1r,2R,6S)-2,6-dimethoxycyclohexyl)-5-((2R)-tetrahydro-2-furanyl)-4H-1,2,4-triazol-3-yl)-3-(5-methyl-2-pyrimidinyl)-2-butanesulfonamide, Example 2.4

The title compound was synthesized following the procedure in Example 140.0 using the starting materials as described (2S,3R)-3-(5-methylpyrimidin-2-yl)butane-2-sulfonamide (Example 1.0), (S)-tetrahydrofuran-2-carbohydrazide and (R)-tetrahydrofuran-2-carbohydrazide (commercially available Enamine), and (1R,2r,3S)-2-isothiocyanato-1,3-dimethoxycyclohexane (Example 2.3).

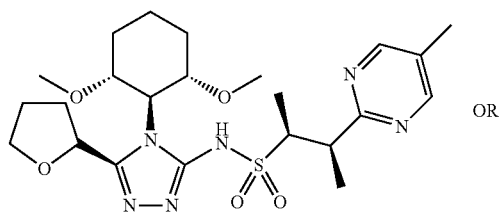

2.0

OR

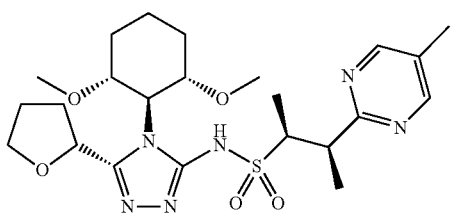

(2S,3R)—N-(4-((1r,2R,6S)-2,6-Dimethoxycyclohexyl)-5-((2S)-tetrahydro-2-furanyl)-4H-1,2,4-triazol-3-yl)-3-(5-methyl-2-pyrimidinyl)-2-butanesulfonamide or (2S,3R)—N-(4-((1r,2R,6S)-2,6-dimethoxycyclohexyl)-5-((2R)-tetrahydro-2-furanyl)-4H-1,2,4-triazol-3-yl)-3-(5-methyl-2-pyrimidinyl)-2-butanesulfonamide, Example 2.0

A chiral SFC purification of Example 2.4 was performed to separate the enantiomers. Preparative SFC methodology: Column: Chiralpak AS-H (2×25 cm)+AS-H (2×15 cm), Mobile Phase: 70:30 (A:B) A: Liquid CO₂; B: IPA, Flow-rate: 70 mL/min, 215 nm, Inlet Pressure: 141 bar and provided two peaks of >99.5% ee: The first eluting peak was assigned as Example 2.0. ¹H NMR (500 MHz, CD₃OD) δ 1.10-1.23 (m, 2H) 1.38-1.42 (m, 3H) 1.45 (d, J=6.75 Hz, 3H) 1.80-1.89 (m, 1H) 1.94-2.08 (m, 2H) 2.16-2.22 (m, 1H) 2.24-2.31 (m, 2H) 2.32 (s, 3H) 2.47-2.57 (m, 1H) 3.23 (s, 3H) 3.27 (s, 3H) 3.33-3.35 (m, 1H) 3.78-3.86 (m, 2H) 3.86-3.94 (m, 2H) 3.96-4.02 (m, 1H) 4.06-4.13 (m, 1H) 4.42 (td, J=10.57, 4.54 Hz, 1H) 5.01 (dd, J=7.53, 5.19 Hz, 1H) 8.58 (s, 2H). LCMS-ESI (pos) m/z: 509.6 (M+H)⁺.

Example 3.0. Preparation of (2S,3R)—N-(4-((1r,2R,6S)-2,6-dimethoxycyclohexyl)-5-((2S)-tetrahydro-2-furanyl)-4H-1,2,4-triazol-3-yl)-3-(5-methyl-2-pyrimidinyl)-2-butanesulfonamide or (2S,3R)—N-(4-((1r,2R,6S)-2,6-dimethoxycyclohexyl)-5-((2R)-tetrahydro-2-furanyl)-4H-1,2,4-triazol-3-yl)-3-(5-methyl-2-pyrimidinyl)-2-butanesulfonamide

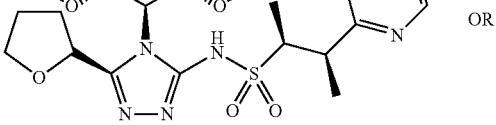

3.0

OR

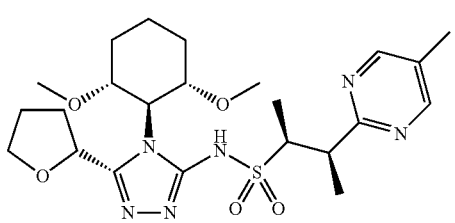

(2S,3R)—N-(4-((1r,2R,6S)-2,6-Dimethoxycyclohexyl)-5-((2S)-tetrahydro-2-furanyl)-4H-1,2,4-triazol-3-yl)-3-(5-methyl-2-pyrimidinyl)-2-butanesulfonamide or (2S,3R)—N-(4-((1r,2R,6S)-2,6-dimethoxycyclohexyl)-5-((2R)-tetrahydro-2-furanyl)-4H-1,2,4-triazol-3-yl)-3-(5-methyl-2-pyrimidinyl)-2-butanesulfonamide, Example 3.0

The second eluting peak was assigned from the purification noted in Example 2.0 was assigned as Example 3.0. ¹H NMR (500 MHz, CD₃OD) δ 1.10-1.23 (m, 2H) 1.30-1.37 (m, 1H) 1.38-1.42 (m, 3H) 1.45 (d, J=6.75 Hz, 3H) 1.80-1.89 (m, 1H) 1.94-2.08 (m, 2H) 2.16-2.22 (m, 1H) 2.24-2.31 (m, 2H) 2.32 (s, 3H) 2.47-2.57 (m, 1H) 3.23 (s, 3H) 3.27 (s, 3H) 3.33-3.35 (m, 1H) 3.78-3.86 (m, 2H) 3.86-3.94 (m, 2H) 3.96-4.02 (m, 1H) 4.06-4.13 (m, 1H) 4.42 (td, J=10.57, 4.54 Hz, 1H) 5.01 (dd, J=7.53, 5.19 Hz, 1H) 8.58 (s, 2H). LCMS-ESI (pos) m/z: 509.6 (M+H)⁺.

The compounds set forth in the following table were synthesized following the procedure in Example 2.4 using the known starting material as described.

TABLE 2

| Example | Reagents | Structure, Name and Data |
|---|---|---|
| 4.0 | (2S,3R)-3-(5-methylpyrimidin-2-yl)butane-2-sulfonamide (Example 1.0), (S)-tetrahydrofuran-3-carbohydrazide and (R)-tetrahydrofuran-3-carbohydrazide (Enamine), (1R,2r,3S)-2-isothiocyanato-1,3-dimethoxycyclohexane (Example 2.3). The mixture was separated by preparative SFC using the following methodology: Column: Chiralpak AS-H (2 × 25 cm) + AS-H (2 × 15 cm), Mobile Phase: 85:15 (A:B) A: Liquid $CO_2$; B: MeOH, Flowrate: 80 mL/min, 215 nm, Inlet Pressure: 120 bar to deliver Example 4.0 as peak 1. | 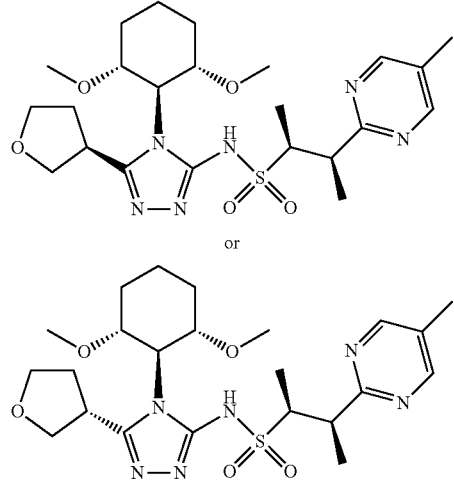 [SMILES: CO[C@H]1CCC[C@@H](OC)[C@@H]1n1c(NS(=O)(=O)[C@@H](C)[C@H](C)c2ncc(C)cn2)nnc1[C@@H]1CCOC1 ; CO[C@H]1CCC[C@@H](OC)[C@@H]1n1c(NS(=O)(=O)[C@@H](C)[C@H](C)c2ncc(C)cn2)nnc1[C@H]1CCOC1]<br>or<br>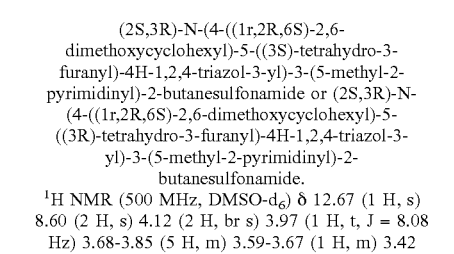<br>(2S,3R)-N-(4-((1r,2R,6S)-2,6-dimethoxycyclohexyl)-5-((3S)-tetrahydro-3-furanyl)-4H-1,2,4-triazol-3-yl)-3-(5-methyl-2-pyrimidinyl)-2-butanesulfonamide or (2S,3R)-N-(4-((1r,2R,6S)-2,6-dimethoxycyclohexyl)-5-((3R)-tetrahydro-3-furanyl)-4H-1,2,4-triazol-3-yl)-3-(5-methyl-2-pyrimidinyl)-2-butanesulfonamide.<br>$^1$H NMR (500 MHz, DMSO-$d_6$) δ 12.67 (1 H, s) 8.60 (2 H, s) 4.12 (2 H, br s) 3.97 (1 H, t, J = 8.08 Hz) 3.68-3.85 (5 H, m) 3.59-3.67 (1 H, m) 3.42 (1 H, quin, J = 7.06 Hz) 3.14 (3 H, s) 3.12 (3 H, s) 2.24 (3 H, s) 2.14-2.22 (4 H, m) 1.75 (1 H, br s) 1.37 (3 H, d, J = 7.14 Hz) 1.22 (3 H, d, J = 7.01 Hz) 1.09-1.18 (3 H, m). LCMS-ESI (pos) m/z: 509.6 (M + H)$^+$. |
| 5.0 | (2S,3R)-3-(5-methylpyrimidin-2-yl)butane-2-sulfonamide (Example 1.0), (S)-tetrahydrofuran-3-carbohydrazide and (R)-tetrahydrofuran-3-carbohydrazide (Enamine), (1R,2r,3S)-2-isothiocyanato-1,3-dimethoxycyclohexane (Example 2.4). The mixture was separated by preparative SFC using the following methodology: Column: Chiralpak AS-H (2 × 25 cm) + AS-H (2 × 15 cm), Mobile Phase: 85:15 (A:B) A: Liquid $CO_2$; B: MeOH, Flowrate: 80 mL/min, 215 nm, Inlet Pressure: 120 bar to deliver Example 5.0 as peak 2. | 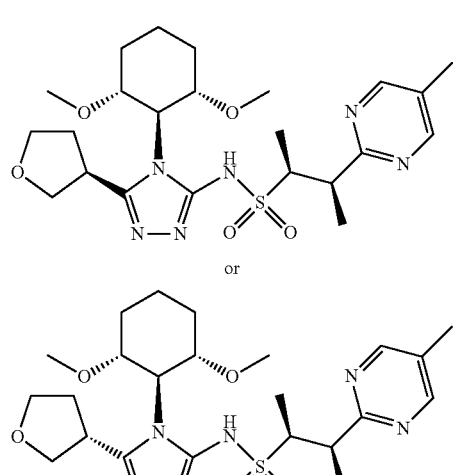<br>or<br>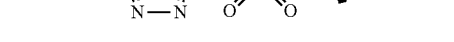<br>(2S,3R)-N-(4-((1r,2R,6S)-2,6-dimethoxycyclohexyl)-5-((3S)-tetrahydro-3-furanyl)-4H-1,2,4-triazol-3-yl)-3-(5-methyl-2-pyrimidinyl)-2-butanesulfonamide or (2S,3R)-N-(4-((1r,2R,6S)-2,6-dimethoxycyclohexyl)-5-((3R)-tetrahydro-3-furanyl)-4H-1,2,4-triazol-3-yl)-3-(5-methyl-2-pyrimidinyl)-2-butanesulfonamide.<br>$^1$H NMR (500 MHz, DMSO-$d_6$) δ 12.67 (1 H, s) 8.60 (2 H, s) 4.12 (2 H, br d, J = 7.79 Hz) 3.96 (1 H, t, J = 8.04 Hz) 3.67-3.86 (5 H, m) 3.63 (1 H, br d, J = 3.57 Hz) 3.42 (1 H, quin, J = 7.01 Hz) 3.14 (3 H, s) 3.11 (3 H, s) 2.12-2.28 (7 H, m) 1.75 (1 H, |

TABLE 2-continued

| Example | Reagents | Structure, Name and Data |
|---|---|---| br s) 1.37 (3 H, d, J = 7.07 Hz) 1.20-1.26 (3 H, m) 1.08-1.18 (3 H, m). LCMS-ESI (pos) m/z: 509.6 (M + H)⁺.

Example of 6.0. Preparation of (R)—N-(4-(2,6-dimethoxyphenyl)-5-((R-tetrahydrofuran-3-yl)-4H-1,2,4-triazol-3-yl)-1-(5-fluoropyrimidin-2-yl)propane-2-sulfonamide compound and (R)—N-(4-(2,6-dimethoxyphenyl)-5-((S)-tetrahydrofuran-3-yl)-4H-1,2,4-triazol-3-yl)-1-(5-fluoropyrimidin-2-yl) propane-2-sulfonamide and (S)—N-(4-(2,6-dimethoxyphenyl)-5-((R)-tetrahydrofuran-3-yl)-4H-1,2,4-triazol-3-yl)-1-(5-fluoropyrimidin-2-yl) propane-2-sulfonamide and (S)—N-(4-(2,6-dimethoxyphenyl)-5-((S)-tetrahydrofuran-3-yl)-4H-1,2,4-triazol-3-yl)-1-(5-fluoropyrimidin-2-yl) propane-2-sulfonamide 6.1

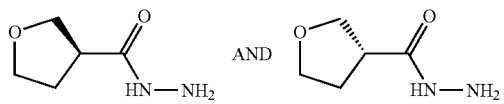

(S)-Tetrahydrofuran-3-carbohydrazide and (R)-tetrahydrofuran-3-carbohydrazide, Example 6.1

To a mixture of tetrahydro-3-furanoic acid (2.0 mL, 20.9 mmol) and TEA (5.8 mL, 42 mmol) in THF (42 mL) was added dropwise isobutyl chloroformate (2.86 mL, 23.00 mmol). The resulting mixture was stirred at 0° C. for 1 h before hydrazine (0.67 mL, 23.00 mmol) was added. The resulting mixture was allowed to stir at RT for 1 h. The mixture was then concentrated, and chloroform (200 mL) and water (20 mL) were added to dissolve the residue. The organic layer was separated, and the aqueous phase was lyophilized. EtOH (50 mL×3) was used to triturate the solid 3 times. The combined EtOH solution was concentrated and dried to give tetrahydrofuran-3-carbohydrazide (2.27 g). LCMS ESI (pos) m/z=131.1 (M+H)⁺.

6.2

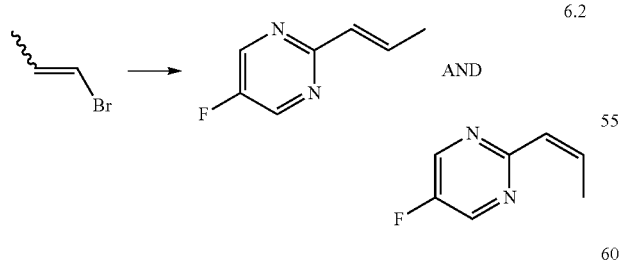

(E)-5-Fluoro-2-(prop-1-en-1-yl)pyrimidine and (Z)-5-fluoro-2-(prop-1-en-1-yl)pyrimidine, Example 6.2

To magnesium turnings (9.0 g, 371.9 mmol) was added 1-2 crystals of iodine under anhydrous conditions. The mixture was heated at 60° C. for 5 min under reduced pressure to activate the magnesium. The flask was then cooled to RT and THF (370 mL) was added. The resulting mixture was heated to 65° C., (Z/E)-1-bromo-1-propene (45 g, 371.9 mmol) was added dropwise, and the mixture was then stirred at 65° C. for 2 h under a nitrogen atmosphere. The mixture was then cooled to RT and transferred to an ice bath. Zinc chloride (1M in diethyl ether, 283 mL, 283 mmol) was then added dropwise over 10 min. The internal temperature of the reaction was kept at ~10° C.-15° C. during the addition, and the resulting organozinc reagent was stirred at RT for 45 min. In a separate round bottomed flask, a solution of 2-chloro-5-fluoropyrimidine (commercially available from Novochemy, Jupiter, Fla., USA) (25 g, 189 mmol), S-phos (7.7 g, 18.8 mmol) and palladium (II) acetate (2.1 g, 9.4 mmol) in THF (38 mL) were degassed with nitrogen gas for 5 min. The organozinc reagent was then added dropwise. The resulting mixture was heated at 60° C. for 12 h. After completion of reaction (monitored by TLC), the reaction mixture was quenched with water (50 mL) and acidified with 1N hydrochloric acid (700 mL, pH ~2). The mixture was then extracted with diethyl ether (2×500 mL). The combined organic layers were washed with brine (200 mL), dried over sodium sulphate and concentrated under reduced pressure at 20° C. to a volume of approximately 50 mL, which was used in the next step.

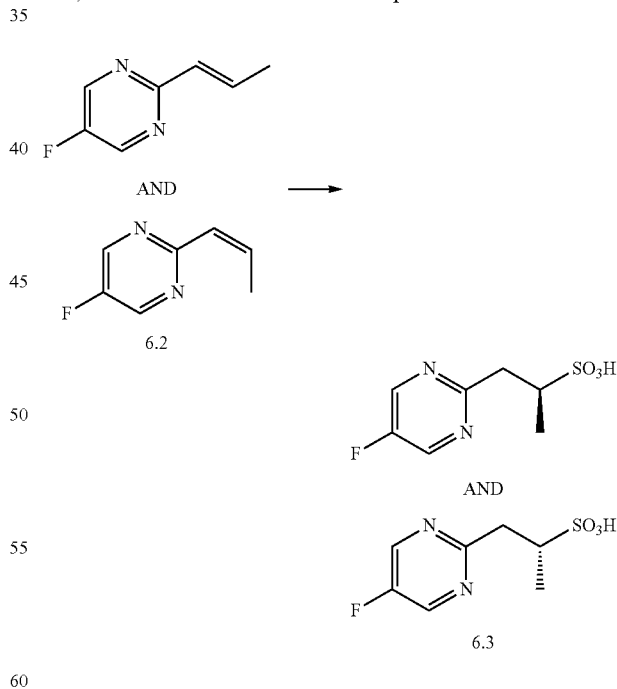

(S)-1-(5-Fluoropyrimidin-2-yl)propane-2-sulfonic acid and (R)-1-(5-fluoropyrimidin-2-yl)propane-2-sulfonic acid, Example 6.3

To a solution of 6.2 (188.6 mmol) in THF (50 mL) was added an aqueous solution of sodium bisulfite (19.6 g, 188.6 mmol in 100 mL of H₂O). The reaction mixture was stirred at ambient temperature for 20 h. Once the reaction was complete (monitored by TLC), the mixture was acidified to approximately pH 1 with concentrated HCl (10 mL). The aqueous layer was then concentrated under reduced pressure to furnish the initial product which was suspended in EtOH (250 mL). The product thus obtained was heated to reflux, filtered hot, and rinsed with hot EtOH (100 mL). The filtrate was concentrated under reduced pressure to give a brown solid, which was recrystallized from IPA (50 mL) to afford the title compound 6.3 (20 g, 48%) as a brown solid. $^1$H NMR (400 MHz, D₂O) δ 8.69 (s, 2H), 3.47 (td, J=9.8, 8.2, 4.0 Hz, 2H), 3.06 (dd, J=16.1, 10.2 Hz, 1H), 1.24 (d, J=6.5 Hz, 3H). LCMS-ESI (neg.) m/z: 118.9 (M–H)⁻.

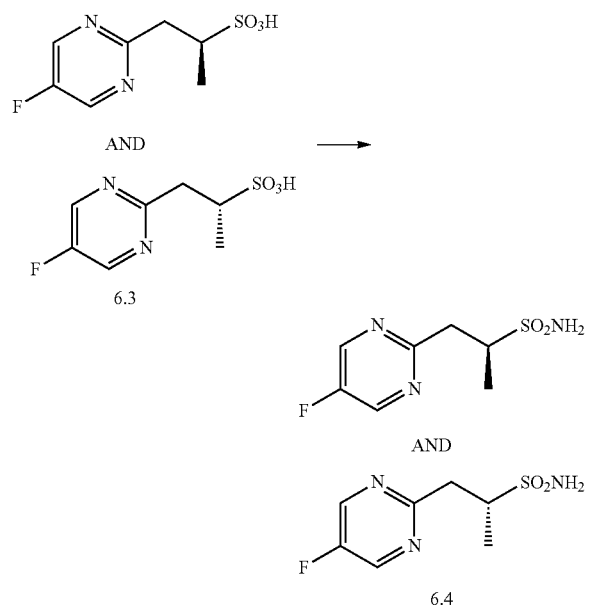

(S)-1-(5-Fluoropyrimidin-2-yl)propane-2-sulfonamide and (R)-1-(5-fluoropyrimidin-2-yl)propane-2-sulfonamide, Example 6.4

A solution of 6.3 (80 g, 360 mmol) in thionyl chloride (268 mL, 3600 mmol) was heated at 60° C. for 3 h. The reaction was concentrated under reduced pressure to afford the sulfonyl chloride compound, which was azeotroped with toluene (3×300 mL). The residue was diluted with DCM (1.0 L) and ammonia gas was bubbled through the solution for 15 min at −78° C. The mixture was then stirred at RT for 1 h. Thereafter, the reaction mixture was filtered through a Celite® brand filter agent pad and the pad was washed with DCM (100 mL) and EtOAc (100 mL). The combined filtrate was then concentrated under reduced pressure to obtain a residue which was purified by column chromatography (silica gel, elution 0-60% EtOAc in hexanes) to furnish the title compound 6.4 (43 g, 54%) as a white solid. $^1$H NMR (400 MHz, DMSO-d₆) δ 8.86 (d, J=1.1 Hz, 2H), 6.90 (s, 2H), 3.57-3.51 (m, 2H), 2.93 (dd, J=15.4, 11.1 Hz, 1H), 1.19 (d, J=6.5 Hz, 3H). LCMS-ESI (pos) m/z: 220.0 (M+H)⁺.

(S)—N-((2,6-Dimethoxyphenyl)carbamothioyl)-1-(5-fluoropyrimidin-2-yl)propane-2-sulfonamide and (R)—N-((2,6-dimethoxyphenyl)carbamothioyl)-1-(5-fluoropyrimidin-2-yl)propane-2-sulfonamide, Example 6.2

To a solution of (S)-1-(5-fluoropyrimidin-2-yl)propane-2-sulfonamide and (R)-1-(5-fluoropyrimidin-2-yl)propane-2-sulfonamide (Example 6.4, 1.8 g, 8.21 mmol) in DMF (10 mL) was added cesium carbonate (4.01 g, 12.3 mmol) in portions. The mixture was stirred at RT for 5 min before 2-isothiocyanato-1,3-dimethoxybenzene (Example 10.0, 1.68 g, 8.62 mmol) was added in portions. The resulting solution was allowed to stir at RT and was monitored by LCMS. Upon completion, 20 mL of water was added and the mixture was acidified by addition of aqueous HCl solution, 2.0 N (6.2 mL), to pH=~5. The precipitate was collected and washed with water three times. It was then dried under vacuum to give of N-((2,6-dimethoxyphenyl) carbamothioyl)-1-(5-fluoropyrimidin-2-yl)propane-2-sulfonamide (3.37 g, 99%). LCMS ESI (pos) m/z=415.1 (M+H)⁺.

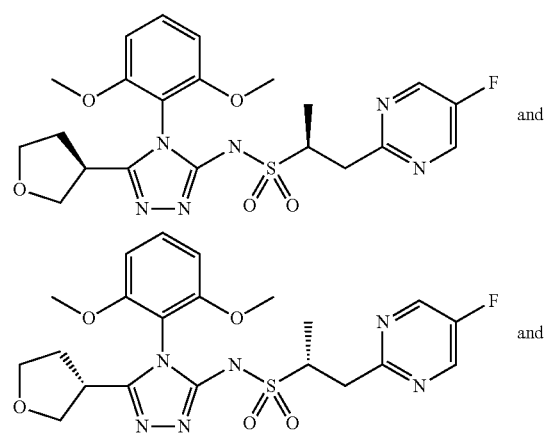

-continued

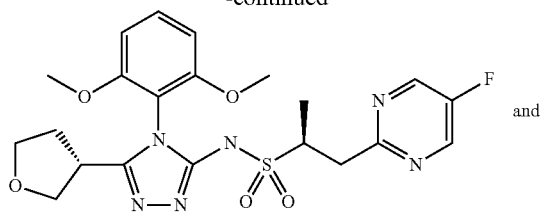
and

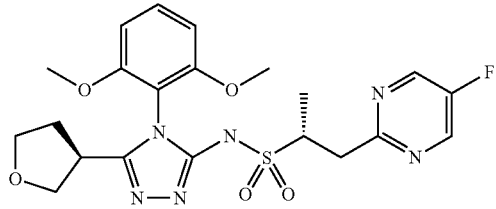

(R)—N-(4-(2,6-Dimethoxyphenyl)-5-((R)-tetrahydrofuran-3-yl)-4H-1,2,4-triazol-3-yl)-1-(5-fluoropyrimidin-2-yl)propane-2-sulfonamide and (R)—N-(4-(2,6-dimethoxyphenyl)-5-((S)-tetrahydrofuran-3-yl)-4H-1,2,4-triazol-3-yl)-1-(5-fluoropyrimidin-2-yl)propane-2-sulfonamide and (S)—N-(4-(2,6-dimethoxyphenyl)-5-((R)-tetrahydrofuran-3-yl)-4H-1,2,4-triazol-3-yl)-1-(5-fluoropyrimidin-2-yl)propane-2-sulfonamide and (S)—N-(4-(2,6-dimethoxyphenyl)-5-((S)-tetrahydrofuran-3-yl)-4H-1,2,4-triazol-3-yl)-1-(5-fluoropyrimidin-2-yl)propane-2-sulfonamide, Example 6.0

To a mixture of Example 6.5 (0.150 g, 0.36 mmol) and Example 6.1 (0.090 g, 0.69 mmol) in DMF (1.72 mL) was added anhydrous copper (II) chloride (0.046 g, 0.345 mmol) in portions at RT. The mixture was stirred at RT and was monitored by LCMS. After the starting material was completely consumed, TFA (0.053 mL, 0.69 mmol) was dropwise added and the resulting mixture was allowed to stir at 110° C. and monitored by LCMS. Upon completion, the mixture was cooled to RT and directly subjected to reverse phase-HPLC purification to give the title compound (17 mg, 10%). $^1$H NMR (400 MHz, CDCl$_3$) δ 8.53 (s, 2H), 7.43 (d, J=8.5, 8.5 Hz, 1H), 6.65 (d, J=8.6 Hz, 2H), 3.63-3.95 (m, 13H), 2.97-3.08 (m, 2H), 2.22-2.32 (m, 1H), 1.98-2.07 (m, 1H), 1.27 (d, J=6.7 Hz, 3H). LCMS ESI (pos) m/z=493.1 (M+H)$^+$.

Example 7.0. Preparation of (R)-2-(4-chlorophenyl)-N-(4-(2,6-dimethoxyphenyl)-5-(tetrahydrofuran-3-yl)-4H-1,2,4-triazol-3-yl)ethanesulfonamide (Example 2.0) and (S)-2-(4-chlorophenyl)-N-(4-(2,6-dimethoxyphenyl)-5-(tetrahydrofuran-3-yl)-4H-1,2,4-triazol-3-yl)ethanesulfonamide 7.1

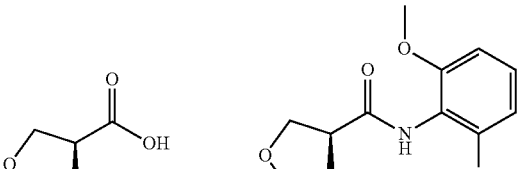
AND
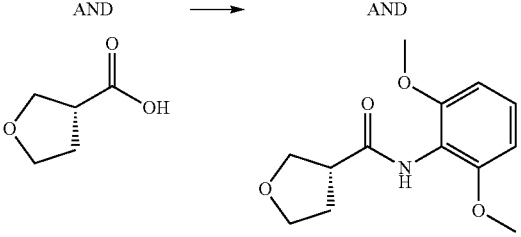

(S)—N-(2,6-Dimethoxyphenyl)tetrahydrofuran-3-carboxamide and (R)—N-(2,6-dimethoxyphenyl)tetrahydrofuran-3-carboxamide, Example 7.1

An ice-cooled solution of tetrahydro-3-furoic acid (Sigma-Aldrich, 3.0 g, 26.1 mmol) in DMF (52 mL) was treated with TEA (10.9 mL, 78 mmol) via syringe followed by HATU (10.9 g, 28.7 mmol) directly. After 5 min, 2,6-dimethoxyaniline (Amfinecom Inc., 4.0 g, 26.1 mmol) was added. The resulting orange solution was warmed to RT and stirred for 60 min. The mixture was then partitioned between brine (100 mL) and EtOAc (4×). The combined organic layers were dried over anhydrous magnesium sulfate and concentrated. The residue was purified by silica gel chromatography (eluent: 0-100% EtOAc in hexanes) to provide 7.1 (2.50 g, 38% yield) as a white solid. LCMS-ESI (pos) m/z: 252.2 (M+H)$^+$.

7.1

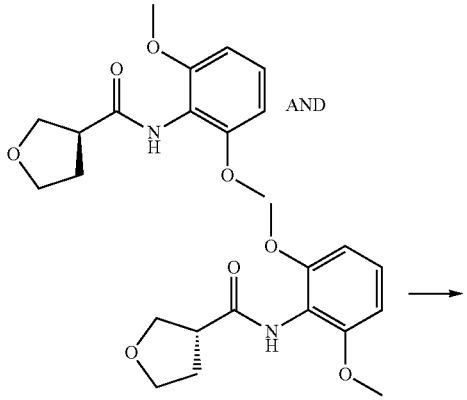

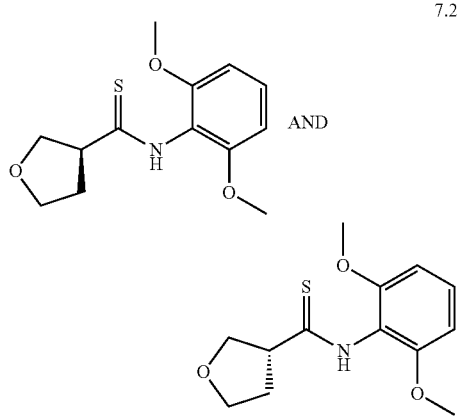

7.2

(S)—N-(2,6-Dimethoxyphenyl)tetrahydrofuran-3-carbothioamide and (R)—N-(2,6-dimethoxyphenyl)tetrahydrofuran-3-carbothioamide, Example 7.2

To a suspension of 7.1 (2.50 g, 10.0 mmol) in toluene (33 mL) was added Lawesson's reagent (2.09 g, 5.2 mmol). The resulting slurry was heated at reflux for 3 h and was then allowed to cool to RT. The reaction mixture was concentrated, and the residue was purified by silica gel chromatography (eluent: 0-100% EtOAc in hexanes) to provide 7.2 (2.34 g, 88% yield) as a yellow solid. LCMS-ESI (pos) m/z: 268.1 (M+H)+.

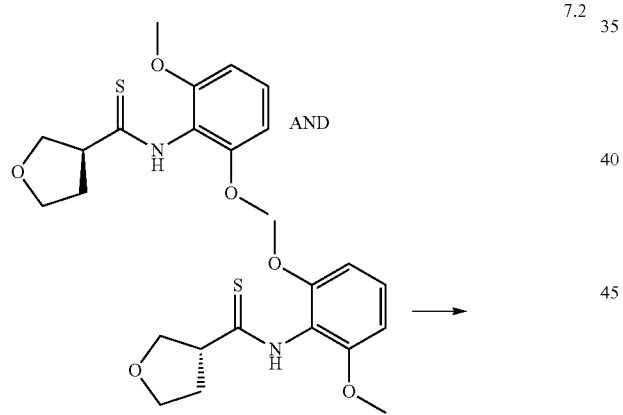

7.2

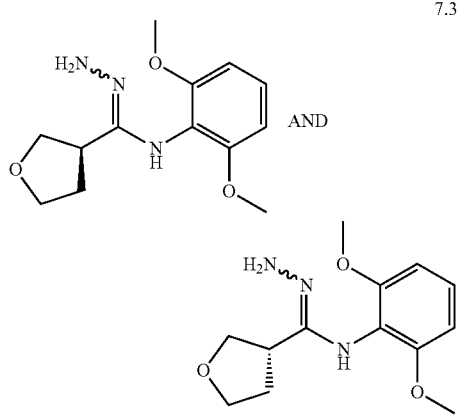

7.3

(R)—N-(2,6-Dimethoxyphenyl)tetrahydrofuran-3-carbohydrazonamide and (S)—N-(2,6-dimethoxyphenyl)tetrahydrofuran-3-carbohydrazonamide, Example 7.3

To a slurry of 7.2 (2.04 g, 7.6 mmol) in THF (38 mL) was added hydrazine hydrate (80%, 3.0 mL, 76 mmol) via syringe. The resulting slurry was heated at 60° C. for 3 h and was then allowed to cool to RT. The reaction was quenched with a small volume of brine and extracted with EtOAc containing a small volume of THF (6×). The combined organic layers were dried over anhydrous sodium sulfate and concentrated. The residue was purified by chromatography using a neutral alumina column (eluent: 0-5% MeOH in DCM) to provide 7.3 (553 mg, 27% yield) as a pink oil. LCMS-ESI (pos) m/z: 266.1 (M+H)+.

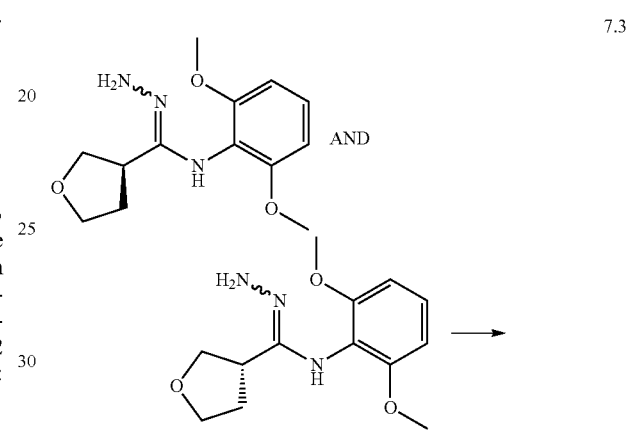

7.3


7.4

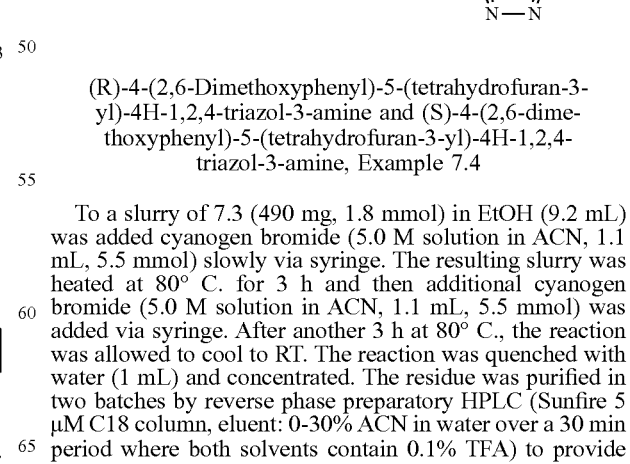

(R)-4-(2,6-Dimethoxyphenyl)-5-(tetrahydrofuran-3-yl)-4H-1,2,4-triazol-3-amine and (S)-4-(2,6-dimethoxyphenyl)-5-(tetrahydrofuran-3-yl)-4H-1,2,4-triazol-3-amine, Example 7.4

To a slurry of 7.3 (490 mg, 1.8 mmol) in EtOH (9.2 mL) was added cyanogen bromide (5.0 M solution in ACN, 1.1 mL, 5.5 mmol) slowly via syringe. The resulting slurry was heated at 80° C. for 3 h and then additional cyanogen bromide (5.0 M solution in ACN, 1.1 mL, 5.5 mmol) was added via syringe. After another 3 h at 80° C., the reaction was allowed to cool to RT. The reaction was quenched with water (1 mL) and concentrated. The residue was purified in two batches by reverse phase preparatory HPLC (Sunfire 5 µM C18 column, eluent: 0-30% ACN in water over a 30 min period where both solvents contain 0.1% TFA) to provide 7.4 (150 mg, 28% yield) as a pink solid. LCMS-ESI (pos) m/z: 291.2 (M+H)+.

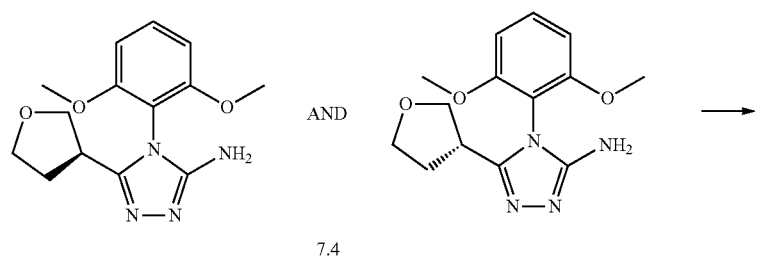

7.4

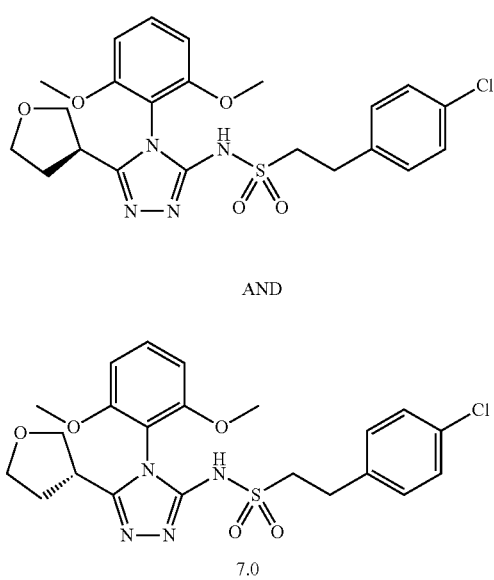

AND 7.0

(R)-2-(4-Chlorophenyl)-N-(4-(2,6-dimethoxyphenyl)-5-(tetrahydrofuran-3-yl)-4H-1,2,4-triazol-3-yl)ethanesulfonamide and (S)-2-(4-chlorophenyl)-N-(4-(2,6-dimethoxyphenyl)-5-(tetrahydrofuran-3-yl)-4H-1,2,4-triazol-3-yl)ethanesulfonamide, Example 7.0

To a solution of 7.4 (100 mg, 0.34 mmol) and TEA (240 µL, 1.7 mmol) in DCM (3.5 mL) was added 2-(4-chlorophenyl)ethanesulfonyl chloride (Synchem Inc., 107 mg, 0.45 mmol). The resulting solution was stirred at RT for 3 d and then additional 2-(4-chlorophenyl)ethanesulfonyl chloride (Synchem Inc., 25 mg, 0.10 mmol) and a catalytic amount of DMAP were added. After an additional 4 h at RT, the reaction was concentrated. The residue was purified by reverse phase preparatory HPLC (Sunfire 5 µM C18 column, eluent: 30-65% ACN in water over a 20 min period where both solvents contain 0.1% TFA) to provide Example 7.0 (21 mg, 12% yield) as a white solid.

Example 8.0. Preparation of (R)-2-(4-chlorophenyl)-N-(4-(2,6-dimethoxyphenyl)-5-(tetrahydrofuran-3-yl)-4H-1,2,4-triazol-3-yl)ethanesulfonamide or (S)-2-(4-chlorophenyl)-N-(4-(2,6-dimethoxyphenyl)-5-(tetrahydrofuran-3-yl)-4H-1,2,4-triazol-3-yl)ethanesulfonamide 8.0

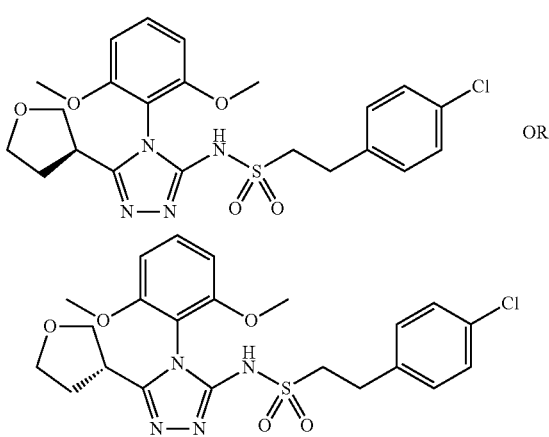

(R)-2-(4-Chlorophenyl)-N-(4-(2,6-dimethoxyphenyl)-5-(tetrahydrofuran-3-yl)-4H-1,2,4-triazol-3-yl)ethanesulfonamide or (S)-2-(4-chlorophenyl)-N-(4-(2,6-dimethoxyphenyl)-5-(tetrahydrofuran-3-yl)-4H-1,2,4-triazol-3-yl)ethanesulfonamide, Example 8.0

Example 7.0 (21 mg) was separated by preparative SFC (Column: 250×21 mm Chiralpak IA, 25 g/min EtOH containing 20 mM ammonia+25 g/min CO$_2$, 100 bar, 218 nm, Inj vol.: 0.8 mL of a 10.1 mg/mL solution of sample in MeOH). The first eluting peak (3.9 mg) was isolated as (R)-2-(4-chlorophenyl)-N-(4-(2,6-dimethoxyphenyl)-5-(tetrahydrofuran-3-yl)-4H-1,2,4-triazol-3-yl)ethanesulfonamide or (S)-2-(4-chlorophenyl)-N-(4-(2,6-dimethoxyphenyl)-5-(tetrahydrofuran-3-yl)-4H-1,2,4-triazol-3-yl)ethanesulfonamide. $^1$H NMR (400 MHz, CDCl$_3$) δ 7.45 (t, J=8.5 Hz, 1H), 7.26 (d, J=8.6 Hz, 2H), 7.09 (d, J=8.6 Hz, 2H), 6.67 (d, J=8.6 Hz, 2H), 3.88-3.97 (m, 1H), 3.74-3.84 (m, 9H), 3.20-3.26 (m, 2H), 2.95-3.08 (m, 3H), 2.21-2.32 (m, 1H), 1.98-2.08 (m, 1H). LCMS-ESI (pos) m/z: 493.1 (M+H)$^+$.

Example 9.0. Preparation of (R)-2-(4-chlorophenyl)-N-(4-(2,6-dimethoxyphenyl)-5-(tetrahydrofuran-3-yl)-4H-1,2,4-triazol-3-yl)ethanesulfonamide or (S)-2-(4-chlorophenyl)-N-(4-(2,6-dimethoxyphenyl)-5-(tetrahydrofuran-3-yl)-4H-1,2,4-triazol-3-yl)ethanesulfonamide

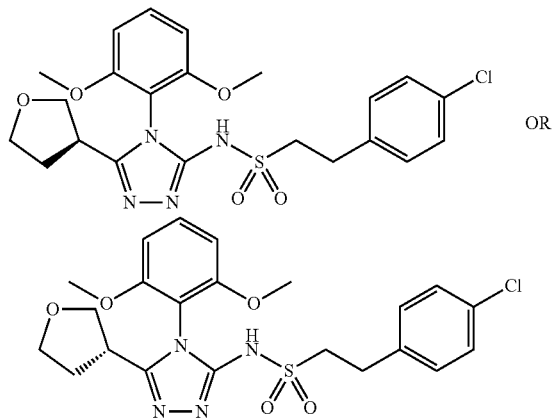

9.0

OR (R)-2-(4-Chlorophenyl)-N-(4-(2,6-dimethoxyphenyl)-5-(tetrahydrofuran-3-yl)-4H-1,2,4-triazol-3-yl)ethanesulfonamide or (S)-2-(4-chlorophenyl)-N-(4-(2,6-dimethoxyphenyl)-5-(tetrahydrofuran-3-yl)-4H-1,2,4-triazol-3-yl)ethanesulfonamide, Example 9.0

Further elution under the conditions described in Example 8.0 afforded the second eluting peak, Example 9.0 (6.3 mg); R)-2-(4-chlorophenyl)-N-(4-(2,6-dimethoxyphenyl)-5-(tetrahydrofuran-3-yl)-4H-1,2,4-triazol-3-yl)ethanesulfonamide or (S)-2-(4-chlorophenyl)-N-(4-(2,6-dimethoxyphenyl)-5-(tetrahydrofuran-3-yl)-4H-1,2,4-triazol-3-yl)ethanesulfonamide. $^1$H NMR (400 MHz, CDCl$_3$) δ 7.45 (t, J=8.5 Hz, 1H), 7.26 (d, J=8.6 Hz, 2H), 7.09 (d, J=8.6 Hz, 2H), 6.67 (d, J=8.6 Hz, 2H), 3.89-3.96 (m, 1H), 3.74-3.84 (m, 9H), 3.20-3.27 (m, 2H), 2.96-3.08 (m, 3H), 2.21-2.32 (m, 1H), 1.98-2.09 (m, 1H). LCMS-ESI (pos) m/z: 493.1 (M+H)$^+$.

Example 10.0. Preparation of 2-isothiocyanato-1,3-dimethoxybenzene

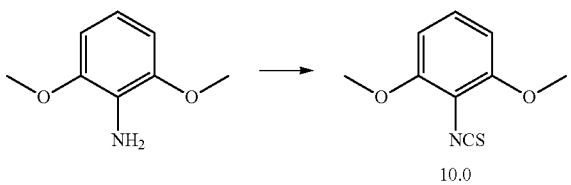

2-Isothiocyanato-1,3-dimethoxybenzene, Example 10.0

To a solution of 2,6-dimethoxyaniline (500 g, 3.25 mol, 1 eq) in DCM (5.0 L) was added 2,6-Lutidine (1.5 L, 13.0 mol, 4 eq). The reaction mixture was cooled to 0° C. (internal temperature) and CSCl$_2$ (374 mL, 4.88 mol, 1.5 eq) was added drop-wise. The reaction mixture was allowed to stir for 2 h. The solvent was then evaporated under reduced pressure and the material thus obtained was purified by SiO$_2$ column to provide Example 10.0, 2-isothiocyanato-1,3-dimethoxybenzene, as a white solid (1.06 g, 2.80 mol, 86%). LCMS (ESI pos ion) m/z: (M+H)$^+$=196. $^1$H NMR (400 MHz, CDCl$_3$) δ 7.16 (t, J=8.48 Hz, 1H), 6.55 (d, J=8.48 Hz, 2H), 3.90 (app s, 6H).

The compounds set forth in the following table were synthesized following the procedure in Example 10.0 using the known starting material as described.

TABLE 3

| Example | Reagents | Structure, Name and Data |
|---|---|---|
| 10.1 | 4,6-dimethoxypyrimidin-5-amine (D-L Chiral chemicals). | 5-isothiocyanato-4,6-dimethoxypyrimidine. LCMS-ESI (pos) m/z: 198.1 (M + H)$^+$. |
| 10.2 | 1-isothiocyanato-2-methoxybenzene (commercially available from Alfa Aesar). | 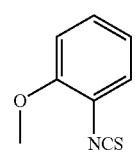 1-isothiocyanato-2-methoxybenzene. $^1$H NMR (400 MHz, DMSO-d$_6$) δ 3.89 (s, 3H), 6.96 (td, J = 7.68, 1.27 Hz, 1H), 7.16 (dd, J = 8.31, 1.27 Hz, 1H), 7.30 (dd, J = 7.92, 1.66 Hz, 1H), 7.31-7.37 (m, 1H). |

TABLE 3-continued

| Example | Reagents | Structure, Name and Data |
|---|---|---|
| 10.3 | 3,5-difluoropyridin-4-amine (commercially available from Ark Pharm Inc, Libertyville, IL). | 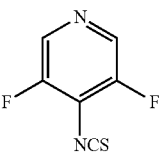 3,5-difluoro-4-isothiocyanato-pyridine. LCMS-ESI (pos) m/z: 173.0 (M + H)+. |

Example 11.0: Preparation of (1R,2S)-1-methoxy-1-(5-methylpyrimidin-2-yl)propane-2-sulfonamide, 11.0

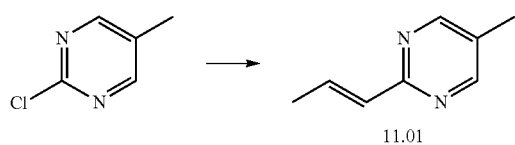

(E)-5-Methyl-2-(prop-1-en-1-yl)pyrimidine, Example 11.01

To a 500 mL round bottomed flask was added 2-chloro-5-methylpyrimidine (12 g, 93 mmol), potassium (E)-trifluoro(prop-1-en-1-yl)borate (17.27 g, 117 mmol), and potassium phosphate (59.4 g, 280 mmol). The flask was purged with $N_2$ (5×) and then 1,4-dioxane (200 mL) and water (20 mL) were added. The resulting yellow suspension was bubbled with Ar for 15 min and then 1,1-bis[(di-t-butyl-p-methylaminophenyl]palladium (II) chloride (Amphos, commercially available from Strem, 2.64 g, 3.73 mmol) was added, a reflux condenser was attached, and the reaction was warmed to 90° C. in an oil bath and stirred under $N_2$ for 16.5 h. The reaction was then cooled to RT. The reaction was diluted with water (250 mL), and extracted with EtOAc (2×250 mL). The organic layers were combined, dried ($MgSO_4$), and concentrated. The residue was purified by flash chromatography on silica gel eluting with 0-20% EtOAc/hexanes) to afford (E)-5-methyl-2-(prop-1-en-1-yl)pyrimidine 11.01 (12.96 g, 97 mmol, 100% yield) as a yellow/orange oily solid. $^1$H NMR (300 MHz, $CDCl_3$) δ=8.49 (s, 2H), 7.01-7.20 (m, 1H), 6.57 (dd, J=15.6, 1.7 Hz, 1H), 2.29 (s, 3H), 1.97 (dd, J=6.8, 1.6 Hz, 3H). LCMS (ESI pos ion) m/z: 135.2 (M+H)+.

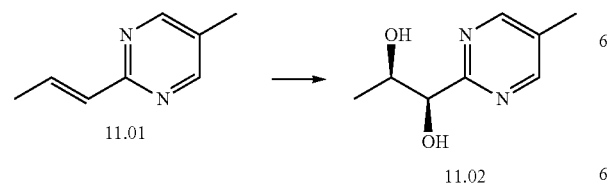

(1R,2R)-1-(5-Methylpyrimidin-2-yl)propane-1,2-diol, Example 11.02

Racemic conditions. To a solution of (E)-5-methyl-2-(prop-1-en-1-yl)pyrimidine, 11.01 (5.75 g, 42.9 mmol) and 4-methylmorpholine-4-oxide (7.53 g, 64.3 mmol) in acetone (60 mL) and water (6 mL) was added osmium tetroxide, 4 wt. %, in water (0.681 mL, 0.111 mmol). The resulting reaction mixture was stirred at RT under $N_2$ for 21.5 h. LCMS showed complete conversion to a product corresponding to the mass of the desired product (M+H)+=169. The reaction was passed through a Varian Chem-Elut cartridge to remove water and was concentrated in vacuo. Water was still present, the residue was dissolved in DCM, dried ($MgSO_4$), and concentrated. The residue was purified by flash chromatography (120 g $SiO_2$, 0-10% MeOH:DCM) to give the racemic syn-diol (1S,2S)-1-(5-methylpyrimidin-2-yl)propane-1,2-diol and (1R,2R)-1-(5-methylpyrimidin-2-yl)propane-1,2-diol (5.85 g, 34.8 mmol, 81% yield) as a light yellow solid. $^1$H NMR (300 MHz, $CDCl_3$) δ 8.59 (s, 2H), 4.67 (br. s., 1H), 4.33 (br. s., 1H), 4.09-4.25 (m, 1H), 2.86 (d, J=7.2 Hz, 1H), 2.36 (s, 3H), 1.30 (d, J=6.6 Hz, 3H). LCMS (ESI pos ion) m/z: 169.2 (M+H). Chiral conditions. A batch of AD-mix-beta was prepared from: (26 mg, 0.07 mmol) $K_2OsO_2(OH)_4$; (16.4 g, 49.9 mmol) $K_3Fe(CN)_6$; (6.89 g, 49.9 mmol) $K_2CO_3$; (125 mg, 0.16 mmol) (DHQD)$_2$PHAL. In a 50 mL round bottom flask was added t-BuOH (5 mL), water (5.00 mL), and 1.4 g of AD-mix-beta (prepared above) and methanesulfonamide (95 mg, 1.00 mmol). The mixture was stirred at RT until clear, and then cooled to 0° C. (E)-5-Methyl-2-(prop-1-en-1-yl)pyrimidine (Example 11.01 168 mg, 1 mmol) in t-BuOH (1 mL) was added, and the slurry was stirred at 0° C. for 2 h. LCMS (1.5 h) showed ~10% conversion. The reaction was allowed to warm slowly to RT as the ice bath melted, and then it was stirred for an additional 22 h. LCMS showed ~90% conversion. The reaction was quenched with saturated aqueous sodium sulfite (10 mL), and extracted with EtOAc (2×20 mL). The combined organic layers were washed with 2 N NaOH (10 mL), dried ($MgSO_4$), and concentrated. The aqueous layer was extracted with DCM (2×50 mL), EtOAc (2×50 mL), and 10% IPA in $CHCl_3$ (2×50 mL). The combined organic layers were concentrated and the residue purified by flash column chromatography (12 g $SiO_2$, 5-100% 3:1 EtOAc:EtOH/heptane) to give (1R,2R)-1-(5-methylpyrimidin-2-yl)propane-1,2-diol (Example 11.02, 88.6 mg, 0.527 mmol, 53% yield) as a clear, colorless oil. Chiral Analysis: SFC Chiral Analysis showed the % ee to be 94.8% using an AS-H (100×2.1 mm, 3 um), 10% organic modifier (IPA with 20 mM ammonia), 90% carbon dioxide. F=1.0 mL/min, column temperature=RT, BRP=105 bar.

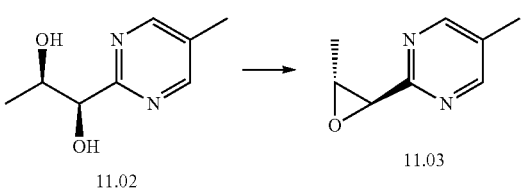

5-Methyl-2-((2R,3R)-3-methyloxiran-2-yl)pyrimidine, Example 11.03

To a solution of syn-diol (1R,2R)-1-(5-methylpyrimidin-2-yl)propane-1,2-diol 11.02 (1.46 g, 8.68 mmol) in DCM (25 mL) (cooled with a RT water bath) was added 1,1,1-trimethoxyethane (2.50 mL, 2.29 mmol). Chlorotrimethylsilane (2.50 mL, 19.7 mmol) was then added in 2 portions 5 min apart. The reaction had a small exotherm during the first added portion of chlorotrimethylsilane (23-28° C.). The reaction was stirred at RT under $N_2$ for 23 h. LCMS indicated incomplete conversion. Thus, an additional 1.25 equivalent. of 1,1,1-trimethoxyethane (1.25 mL, 9.95 mmol) and chlorotrimethylsilane (1.25 mL, 9.85 mmol) were added, and the reaction was stirred for an additional 24 h. LCMS; ((M+H)$^+$=229). The reaction was then concentrated in vacuo. The residue was dissolved in MeOH (20 mL) and potassium carbonate (1.50 g, 10.85 mmol) was added. The reaction was then stirred at RT for 4 h. LCMS (4 h) showed complete conversion to product corresponding to the desired epoxide. LCMS; ((M+H)$^+$=151). The reaction was filtered, the filter cake washed with DCM (5 mL), and the combined filtrates concentrated in vacuo. The residue was purified by flash column chromatography on silica gel eluting with 0-100% EtOAc/hexanes) to afford 5-methyl-2-((2R,3R)-3-methyloxiran-2-yl)pyrimidine 11.03 (1.00 g, 6.6 mmol, 77%) as a clear, light yellow oil. $^1$H NMR (300 MHz, CDCl$_3$) δ 8.54 (s, 2H), 3.81 (d, J=1.9 Hz, 1H), 3.32-3.53 (m, 1H), 2.31 (s, 3H), 1.50 (d, J=5.1 Hz, 3H). LCMS (ESI pos ion) m/z: 151.2 (M+H)$^+$.

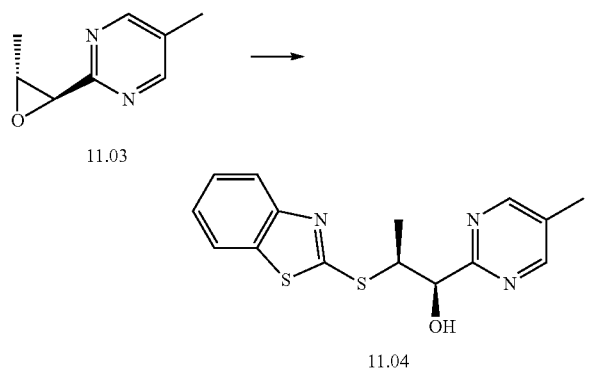

(1R,2S)-2-(Benzo[d]thiazol-2-ylthio)-1-(5-methyl-pyrimidin-2-yl)propan-1-ol, Example 11.04

To a solution of 5-methyl-2-((2R,3R)-3-methyloxiran-2-yl)pyrimidine 11.03 (250 mg, 1.33 mmol) in DCM (5 mL) was added benzo[d]thiazole-2-thiol (245 mg, 1.465 mmol), followed by tris(((trifluoromethyl)sulfonyl)oxy)ytterbium (83 mg, 0.133 mmol). The suspension was heated in a 35° C. heating block for 17 h and showed 100% conversion to the desired product. The reaction was cooled to RT, loaded on a plug of silica, and purified by flash chromatography (12 g SiO$_2$, 5-100% 3:1 EtOAc:EtOH/heptane) to afford (1R,2S)-2-(benzo[d]thiazol-2-ylthio)-1-(5-methylpyrimidin-2-yl)propan-1-ol 11.04 (428 mg, 1.35 mmol, 100% yield) as a clear colorless oil. $^1$H NMR (300 MHz, CDCl$_3$) δ 8.60 (s, 2H), 7.88 (d, J=7.6 Hz, 1H), 7.71-7.81 (m, 1H), 7.42 (td, J=7.7, 1.3 Hz, 1H), 7.27-7.35 (m, 1H), 5.31 (s, 1H), 4.70 (qd, J=7.1, 3.1 Hz, 1H), 2.32 (s, 3H), 1.33 (d, J=7.0 Hz, 3H). LCMS (ESI pos ion) m/z: 318.2 (M+H)$^+$.

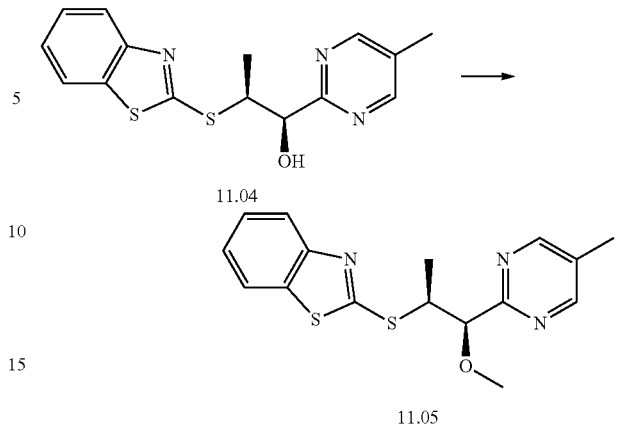

2-(((1R,2S)-1-Methoxy-1-(5-methylpyrimidin-2-yl)propan-2-yl)thio)benzo[d]thiazole, Example 11.05

To a 50 mL flask equipped with a magnetic stirrer was charged (1R,2S)-2-(benzo[d]thiazol-2-ylthio)-1-(5-methylpyrimidin-2-yl)propan-1-ol (11.04, 350 mg, 1.103 mmol) in 2-methyltetrahydrofuran (1.1 mL). The reaction mixture was cooled to −78° C. and potassium bis(trimethylsilyl)amide (1.0M solution in THF, 1.32 μL, 1.32 mmol)) was added dropwise (total addition time: 2 min., turned to yellow solution). The resulting mixture was stirred for 1 h and then MeOTf (374 μL, 3.31 mmol) was added dropwise. The reaction mixture was then stirred at −78° C. for 15 min. LCMS showed complete conversion to the product. The reaction mixture was quenched by adding saturated aqueous NH$_4$Cl solution (30 mL) at −78° C. The reaction was then allowed to warm to RT, and the aqueous layer was back extracted with EtOAc (3×75 mL). The combined organic layers were washed with brine, dried (Na$_2$SO$_4$), and concentrated. The material thus obtained was purified by chromatography through a Biotage 50 g ultra silica gel column, eluting with a gradient of 0-25% EtOAc in hexanes, to provide 2-(((1R,2S))-1-methoxy-1-(5-methylpyrimidin-2-yl)propan-2-yl)thio)benzo[d]thiazole 11.05 (0.32 g, 75% for two runs) as a light-yellow oil.

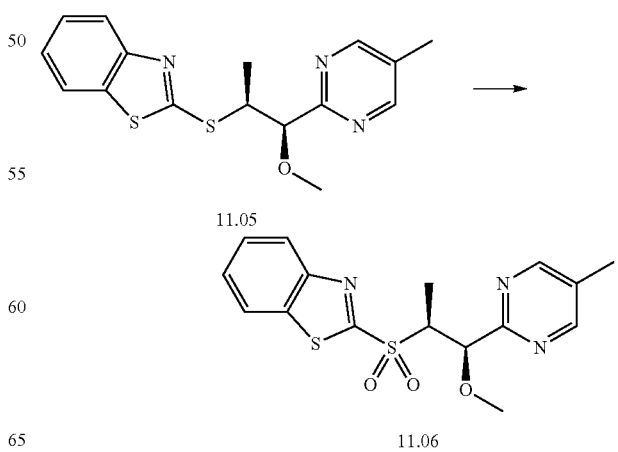

2-(((1R,2S)-1-Methoxy-1-(5-methylpyrimidin-2-yl) propan-2-yl)sulfonyl)benzo[d]thiazole, Example, Example 11.06

A solution of 2-(((1R,2S)-1-methoxy-1-(5-methylpyrimidin-2-yl)propan-2-yl)thio)benzo[d]thiazole 11.05 (313 mg, 0.94 mmol) in DCM (2.8 mL) at 0° C. was treated with 3-chloroperoxybenzoic acid (77% max., 476 mg, 2.13 mmol). The reaction was stirred at 0° C. for 1 h before the ice bath was removed. LCMS showed desired product, sulfoxide, and the presumed sulfoxide/sulfone. The mixture was allowed to warm to ambient temperature and stirred for an additional 40 h. The reaction was quenched with saturated aqueous sodium bisulfite (6 mL), saturated aqueous sodium bicarbonate (5 mL), and was then stirred for 10 min. The reaction was extracted with EtOAc (2×20 mL), and the organic layers were combined, washed with saturated aqueous $NaHCO_3$ (10 mL), brine (10 mL), dried ($MgSO_4$), and filtered. Iodide/starch strip indicator showed no peroxide present. The filtrates were concentrated to give a clear, colorless oil (360 mg). Purification of the residue by flash chromatography (40 g $SiO_2$, 0-100% 3:1 EtOAc:EtOH/heptane) gave 2-(((1R,2S)-1-methoxy-1-(5-methylpyrimidin-2-yl)propan-2-yl)sulfonyl)benzo[d]thiazole 11.06 (285 mg, 0.78 mmol, 83% yield, 77% purity) as a white foam. $^1$H NMR (300 MHz, $CDCl_3$) δ 8.57 (s, 2H), 8.18-8.28 (m, 1H) 7.97-8.05 (m, 1H), 7.54-7.67 (m, 2H), 5.25-5.34 (m, 1H), 4.23 (qd, J=7.2, 3.1 Hz, 1H), 3.41 (s, 3H), 2.31 (s, 3H), 1.49 (d, J=7.2 Hz, 3H). LCMS (ESI pos ion) m/z: 364.0 (M+H).

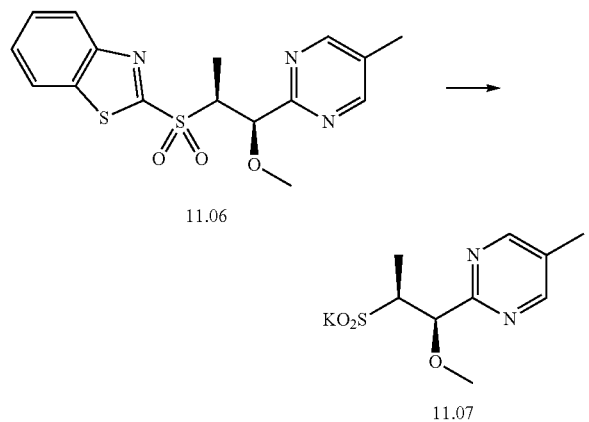

Potassium (1R,2S)-1-methoxy-1-(5-methylpyrimidin-2-yl)propane-2-sulfinate, Example 11.07

To a solution of 2-(((1R,2S)-1-methoxy-1-(5-methylpyrimidin-2-yl)propan-2-yl)sulfonyl)benzo[d]thiazole 11.06 (268 mg, 0.74 mmol) in MeOH (1843 μL) was added potassium carbonate (204 mg, 1.48 mmol). The reaction was stirred at RT for 17 h. LCMS showed desired product formation as the sulfinic acid 11.07. LCMS ((M+H)$^+$=231.1). The reaction was concentrated in vacuo (yellow solid) and used directly in the following step. Epimerization occurred in this reaction (~15%).

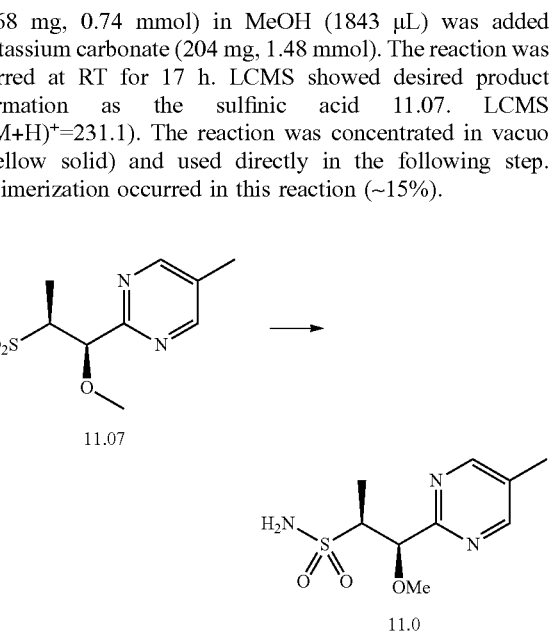

(1R,2S)-1-Methoxy-1-(5-methylpyrimidin-2-yl)propane-2-sulfonamide, Example 11.0

To a suspension of potassium (1R,2S)-1-methoxy-1-(5-methylpyrimidin-2-yl)propane-2-sulfinate (Example 11.07, 198 mg, 0.74 mmol) in water (3.7 mL) was added potassium acetate (72.4 mg, 0.74 mmol), followed by hydroxylamine-o-sulfonic acid, 97%, 167 mg, 1.48 mmol). The reaction mixture was stirred at RT for 4.5 h. LCMS showed desired product formation plus a small peak that corresponded to the stereoisomer. The reaction mixture was extracted with EtOAc (2×), and the organic layers were combined, dried ($Na_2SO_4$), and concentrated in vacuo. The residue was loaded onto a silica gel column eluting with 0-30% (3:1 EtOAc:EtOH):DCM to afford (1R,2S)-1-methoxy-1-(5-methylpyrimidin-2-yl)propane-2-sulfonamide 11.0 (114 mg, 0.465 mmol, 63.0% yield) as a white solid. (contained ~15% other diastereomer). $^1$H NMR (300 MHz, $CDCl_3$) δ 8.63 (s, 2H), 5.10 (d, J=3.3 Hz, 1H), 4.78 (br. s., 2H), 3.74 (qd, J=7.1, 3.3 Hz, 1H), 3.51 (s, 3H), 2.36 (s, 3H), 1.33 (d, J=7.1 Hz, 3H). LCMS (ESI pos ion) m/z: 246.1 (M+H)$^+$.

The compounds set forth in the following table were synthesized following the procedure in Example 11.0 using the known starting material as described.

TABLE 4

| Example | Reagents | Structure, Name and Data |
|---|---|---|
| 11.1 | 2-bromo-5-methyl pyrazine (NOWA parmaceuticals). | (1R,2S)-1-methoxy-1-(5-methylpyrazin-2-yl)propane-2-sulfonamide (Example 11.1) LCMS-ESI (pos) m/z: 246.2 (M + H)$^+$. |

TABLE 4-continued

| Example | Reagents | Structure, Name and Data |
|---|---|---|
| 11.2 | 2-chloro-5-fluoropyrimidine (Oakwood). | 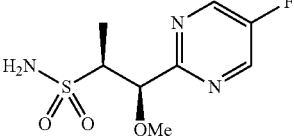<br>(1R,2S)-1-(5-fluoropyrimidin-2-yl)-1-methoxypropane-2-sulfonamide, LCMS-ESI (pos) m/z: 250.1 (M + H)+. |
| 11.3 | 2,5-dichloropyrimidine (Oakwood). | 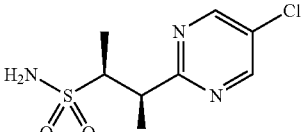<br>(1R,2S)-1-(5-chloropyrimidin-2-yl)-1-methoxypropane-2-sulfonamide (Example 11.3), LCMS-ESI (pos) m/z: 265.9 (M + H)+. |
| 11.4 | 2-chloropyrimidine (Acros Organics). | 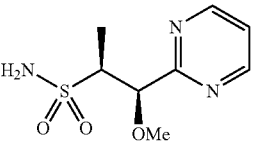<br>(1R,2S)-1-methoxy-1-(pyrimidin-2-yl)propane-2-sulfonamide, LCMS-ESI (pos) m/z: 232.0 (M + H)+. |
| 11.5 | 2-chloro-5-fluoropyrimidine (Oakwood) EtOTf used in place of MeOTf in Example 11.5. | 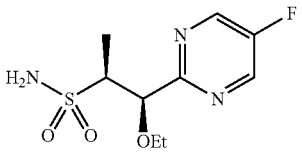 [SMILES: CCO[C@H](c1ncc(F)cn1)[C@H](C)S(N)(=O)=O]<br>(1R,2S)-1-ethoxy-1-(5-fluoropyrimidin-2-yl)propane-2-sulfonamide, LCMS-ESI (pos) m/z: 264.0 (M + H)+. |
| 11.6 | 2-chloro-5-fluoropyrimidine (Oakwood) TBSOTf used in place of MeOTf in Example 11.5. | 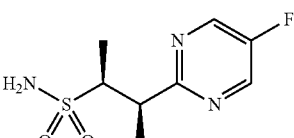<br>(1R,2S)-1-(tert-butyldimethylsilyl)oxy)-1-(5-fluoropyrimidin-2-yl)propane-2-sulfonamide, LCMS-ESI (pos) m/z: 350.1 (M + H)+. |
| 11.7 | 2,5-dichloropyrimidine (Oakwood), EtOTf used in place of MeOTf in Example 11.05. | 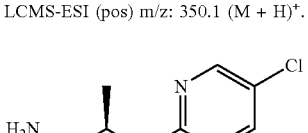<br>(1R,2S)-1-(5-chloropyrimidin-2-yl)-1-ethoxypropane-2-sulfonamide, LCMS-ESI (pos) m/z: 279.9. |

Example 11.8: Preparation of Example (1R,2S)-1-methoxy-1-(5-methoxypyrimidin-2-yl)propane-2-sulfonamide

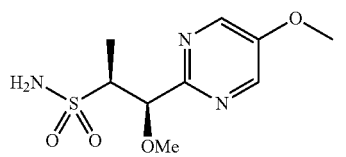

11.8

(1R,2S)-1-Methoxy-1-(5-methoxypyrimidin-2-yl)propane-2-sulfonamide, Example 11.8

The title compound was obtained as a by-product of the synthesis of (1R,2S)-1-methoxy-1-(5-fluoropyrimidin-2-yl)propane-2-sulfonamide (Example 11.2) during the analogous step to that found in Example 11.07 and isolated in the final step of the synthesis of Example 11.2 to give the title compound 11.8 (240 mg, 10.2% yield) as a white solid. $^1$H NMR (CDCl$_3$) δ: 8.46 (s, 2H), 5.11 (d, J=3.4 Hz, 1H), 4.77 (br. s, 2H), 3.97 (s, 3H), 3.67-3.77 (m, 1H), 3.50 (s, 3H), 1.35 (d, J=7.0 Hz, 3H). LCMS-ESI (pos) m/z: 284.1 (M+Na)$^+$.

Example 12.0: Preparation of N,N-bis(4-methoxybenzyl)ethanesulfonamide

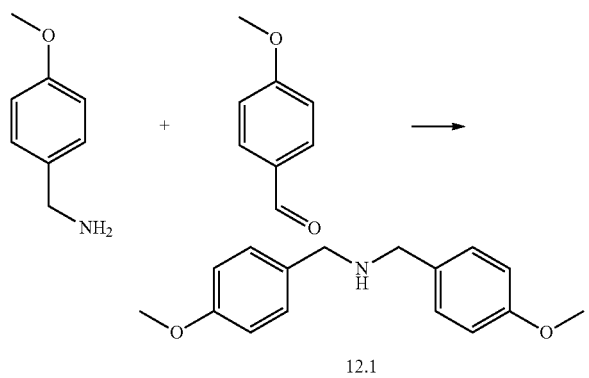

12.1

Bis(4-methoxybenzyl)amine, Example 12.1. 4-Methoxybenzylamine (neat, 600 g, 4.37 mol, 1 eq) and 4-methoxybenzaldehyde (532 mL, 4.37 mol, 1 eq) were added to a 10 L round bottomed flask at ambient temperature with stirring. The reaction spontaneously warmed and a white precipitate was observed. The mixture was stirred for 1 h. To the above mixture was added anhydrous EtOH (4.8 L) and stirring was continued at RT for 15-30 min. This was followed by the addition of sodium borohydride granules (99 g, 2.62 mol, 0.6 eq) portionwise over ~2 h. During the addition of NaBH$_4$, the internal temperature of the reaction rose up to 42° C. The resulting mixture was then stirred at ambient temperature overnight. Next, the reaction was quenched slowly with water (600 mL). The mixture was concentrated on a rotary evaporator at 50° C. The residue was partitioned between water (4 L) and DCM (4 L). The aqueous layer was extracted with more DCM (2×2 L). The combined organic layers were dried over Na$_2$SO$_4$, filtered and concentrated in vacuo to give bis(4-methoxybenzyl)amine 12.1 (1112 g, 99% yield) as a semi-solid. The material was used directly in the next step without further purification. $^1$H-NMR (400 MHz, CDCl$_3$) δ 7.28 (t, J=7.12 Hz, 4H), 6.89 (d, J=8.60 Hz, 4H), 3.83 (app s, 6H), 3.76 (s, 4H) (—NH proton not observed). LCMS (ESI pos ion) m/z: =258.4 (M+H)$^+$.

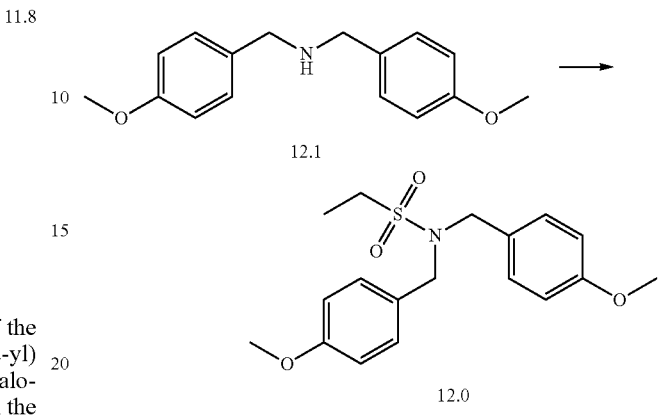

12.0

N,N-Bis(4-methoxybenzyl)ethanesulfonamide, Example 12.0

To a solution of bis(4-methoxybenzyl)amine 12.1 (900 g, 3.49 mol, 1 eq) in DCM (9 L) was added TEA (634 mL, 4.55 mol, 1.3 eq), followed by dropwise addition of ethanesulfonyl chloride (399 mL, 4.19 mol, 1.2 eq). The internal temperature was kept between 5-10° C. during the addition of the ethane sulfonyl chloride. Once the addition was complete, the cooling bath was removed. After 1.5 h, TLC showed complete loss of starting material. The reaction was quenched by the addition of water (4 L) to the reaction mixture. The layers were separated and the aqueous layer extracted with DCM (2×2 L). The combined organic layers were washed with brine (2×1 L), dried over Na$_2$SO$_4$, and concentrated in vacuo. The material thus obtained was adsorbed onto a plug of silica gel and purified by chromatography (silica gel (60-120 mesh) eluting with a gradient of 10-80% EtOAc in hexanes) to provide the title compound 12.0 (1125 g, 3.22 mol, 92%) as white solid. $^1$H-NMR (400 MHz, CDCl$_3$) δ 7.23 (dd, J=2.08, 6.62 Hz, 4H), 6.90 (dd, J=2.12, 6.60 Hz, 4H), 4.29 (s, 4H), 3.83 (app s, 6H), 2.92 (q, J=7.40 Hz, 2H), 1.33 (t, J=7.40 Hz, 3H). GC-MS (ESI pos ion) m/z: =372.2 (M+Na)$^+$.

Example 13.0: Preparation of (1S,2S)-1-isopropoxy-1-(5-methylpyrimidin-2-yl)propane-2-sulfonamide (Example 13.5)

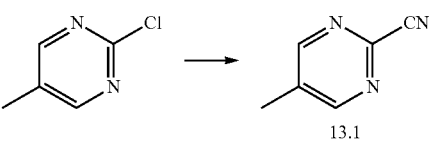

13.1

5-Methylpyrimidine-2-carbonitrile, Example 13.1

A solution of 2-chloro-5-methylpyrimidine (500 g, 3889 mmol, 1.0 equivalent) in DMF (5000 mL) was degassed with N$_2$ for 20 min and dppf (108 g, 194 mmol, 0.05 equivalent) and Pd$_2$(dba)$_3$ (178 g, 194 mmol, 0.05 equivalent) were added to the reaction mixture. Zn(CN)$_2$ (685 g, 5834 mmol, 1.5 equivalent) was added, and the reaction mixture was heated at 100° C. for 16 h. The reaction was quenched with water (5000 mL) and stirred for 10 min. The reaction mixture was then filtered through a pad of Celite® brand filter agent. The filtrate was diluted with water (4 L) and extracted with EtOAc (2×4 L). The combined organic layers were washed with brine (4 L), dried over Na$_2$SO$_4$, filtered, and concentrated under reduced pressure to give the product which was further purified by column chromatography using silica gel (60-120 mesh) and 0-10% EtOAc in hexanes to obtain Example 13.1 (330 g, 71%) as off white solid. $^1$H NMR (400 MHz, DMSO-d$_6$) δ 8.89 (s, 2H), 2.39 (s, 3H).

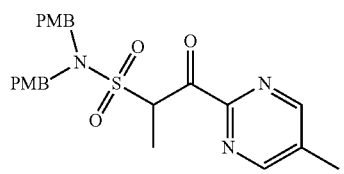

13.2

N,N-Bis(4-methoxybenzyl)-1-(5-methylpyrimidin-2-yl)-1-oxopropane-2-sulfonamide, Example 13.2. To a solution of Example 12.0 (293 g, 839 mmol, 2.0 equivalent) in THF (2000 mL) was added isopropylmagnesium chloride (420 mL, 839 mmol, 2.0 equivalent, 2.0 M in diethyl ether) at 0° C. The reaction mixture was stirred at 25° C. for 3 h. To the reaction mixture was added 5-methylpyrimidine-2-carbonitrile (50 g, 420 mmol, 1.0 equivalent) in THF (100 mL) at 0° C. The resulting mixture was then stirred at RT for 2 h. The reaction was quenched with 1.5 N HCl (500 mL), and water (2000 mL) was added. The resulting mixture was then stirred for 10 min. The mixture was extracted with EtOAc (2×1 L) and the combined organic layers were washed with brine (500 mL), dried over Na$_2$SO$_4$ and filtered. The organic layer was concentrated under reduced pressure to provide the compound which was purified by column chromatography using silica gel (100-200 mesh) and 0-50% EtOAc in hexanes as eluent to obtain Example 13.2 (60 g, 30% yield) as brown liquid. $^1$H NMR (400 MHz, DMSO-d$_6$) δ 8.90 (s, 2H), 7.15-7.09 (m, 4H), 6.85-6.80 (m, 4H), 4.34-4.18 (m, 5H), 3.71 (app s, 6H), 2.39 (s, 3H), 1.50 (d, J=6.9 Hz, 3H). LCMS (ESI +ve ion) m/z: (M+H)$^+$: 470.0.

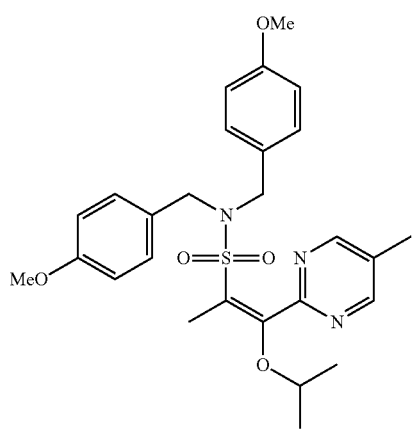

13.3

(E)-1-Isopropoxy-N,N-bis(4-methoxybenzyl)-1-(5-methylpyrimidin-2-yl)prop-1-ene-2-sulfonamide, Example 13.3

To a solution of Example 13.2 (120 g, 256 mmol, 1.0 equivalent) in DMF (1200 mL) was added 2-iodopropane (129 mL, 1278 mmol, 5.0 equivalent) and potassium carbonate (70.6 g, 511 mmol, 2.0 equivalent). The reaction mixture was then stirred at 60° C. for 14 h. The reaction was quenched with water (1000 mL), stirred for 10 min, and extracted with EtOAc (2×1 L). The combined organic layers were washed with brine (1000 mL), dried over Na$_2$SO$_4$, filtered and concentrated under reduced pressure to give the material. The product thus obtained was purified by column chromatography using silica gel (100-200 mesh) and 0-50% EtOAc in hexanes as eluent to obtain Example 13.3 (75 g, 57.4% yield) as off white solid. $^1$H NMR (400 MHz, DMSO-d$_6$) δ 8.72 (s, 2H), 7.09 (d, J=8.3 Hz, 4H), 6.86 (d, J=8.3 Hz, 4H), 4.16 (s, 4H), 3.73 (s, 3H), 3.73 (s, 3H), 3.71-3.67 (m, 1H), 2.31 (s, 3H), 1.87 (s, 3H), 1.19-1.16 (m, 6H). LCMS (ESI +ve ion) m/z: (M+H)$^+$: 512.1.

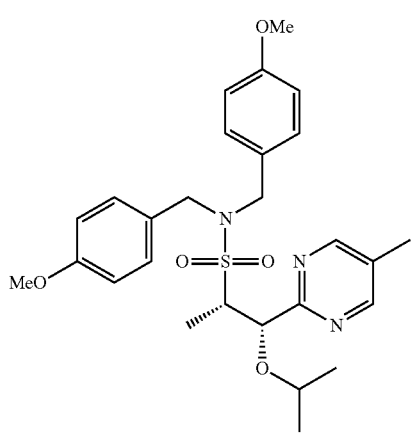

13.4

(1S,2R)-1-Isopropoxy-N,N-bis(4-methoxybenzyl)-1-(5-methylpyrimidin-2-yl)propane-2-sulfonamide, Example 13.4

To a solution of Example 13.3 (180 g, 352 mmol, 1.0 equivalent) in MeOH (1800 mL) was added zinc triflate (256 g, 704 mmol, 2.0 equivalent) and (S)—RuCl[(p-cymene (BINAP)]Cl (6.54 g, 7.04 mmol, 0.02 equivalent). The resulting mixture was then heated at 60° C. under H$_2$ pressure (60 psi) for 16 h. The reaction mixture was concentrated under reduced pressure to obtain an initial product which was further purified by column chromatography using silica gel (60-120 mesh) and 0-50% EtOAc in DCM as eluent to obtain Example 13.4 (140 g, 77%, 92% ee) as off white solid. $^1$H NMR (400 MHz, DMSO-$d_6$) δ 8.71 (s, 2H), 7.25-7.15 (m, 4H), 6.95-6.75 (m, 4H), 4.82 (dd, J=7.8, 1.8 Hz, 1H), 4.39 (d, J=15.6 Hz, 2H), 4.13 (d, J=15.7 Hz, 2H), 3.82 (qd, J=8.5, 7.9, 6.0 Hz, 1H), 3.65 (app s, 6H), 3.41-3.35 (m, 1H), 2.27 (s, 3H), 1.12 (dd, J=6.2, 1.8 Hz, 3H), 1.02 (dd, J=7.1, 2.0 Hz, 3H), 0.96 (dd, J=6.3, 1.8 Hz, 3H). LCMS (ESI +ve ion) m/z: (M+H)$^+$: 514.2.

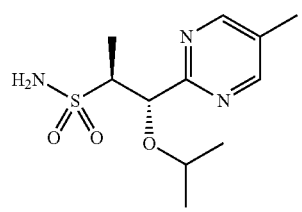

13.5

(1S,2S)-1-Isopropoxy-1-(5-methylpyrimidin-2-yl) propane-2-sulfonamide, Example 13.5

To a solution of Example 13.4 (140.0 g, 273 mmol, 1.0 equivalent) in DCM (500 mL) was added TFA (250 mL) at 0° C. The resulting reaction mixture was then stirred at RT for 16 h. Next, the reaction mixture was concentrated under reduced pressure, dissolved in DCM (1000 mL) and washed with saturated aqueous NaHCO$_3$ solution (1000 mL). The organic layer was dried over Na$_2$SO$_4$, filtered and concentrated under reduced pressure to obtain the initial material which was further purified by column chromatography using silica gel (60-120 mesh) and 0-2% MeOH in DCM to obtain Example 13.5 (72 g, 97% yield, 90% ee) as an off white solid. Example 13.5 (72 g, 90% ee) was suspended in IPA (500 mL) and heated to 70° C. until the mixture became homogeneous. Once the solution became homogeneous, the mixture was cooled to RT overnight. The white solid thus obtained was filtered, dried under vacuum to obtain Example 13.5 (30 g, >99%). The mother liquor was concentrated, and the solid obtained was recrystallized again utilizing the same procedure. $^1$H NMR (400 MHz, DMSO-$d_6$) δ 8.70 (d, J=2.3 Hz, 2H), 6.45 (d, J=2.4 Hz, 2H), 4.68 (dd, J=8.8, 2.5 Hz, 1H), 3.59-3.52 (m, 1H), 3.48 (ddd, J=9.7, 7.4, 4.9 Hz, 1H), 2.29 (d, J=2.6 Hz, 3H), 1.13 (dd, J=6.1, 2.5 Hz, 3H), 0.93 (dd, J=7.1, 2.5 Hz, 3H), 0.88 (dd, J=6.3, 2.5 Hz, 3H). LCMS (ESI +ve ion) m/z: (M+H)$^+$: 274.1.

Example 14.0. Preparation of (2S,3R)-3-(5-chloro-pyridin-2-yl)butane-2-sulfonamide (Example 14.0)

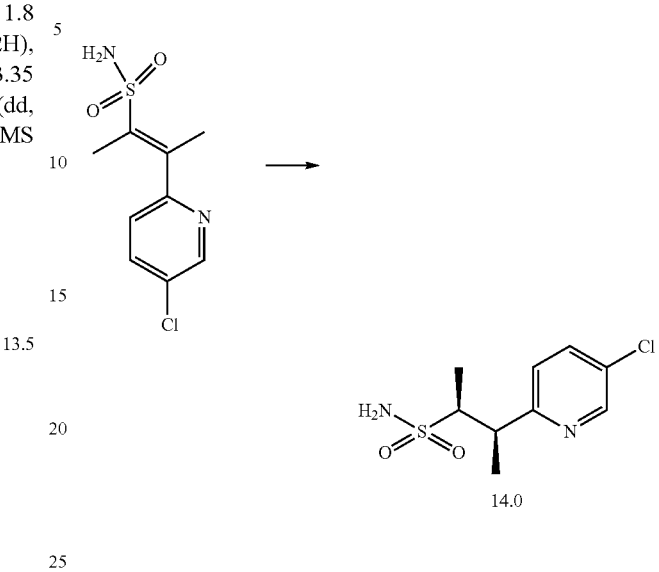

(2S,3R)-3-(5-Chloropyridin-2-yl)butane-2-sulfonamide, Example 14.0

To a solution of (E)-2-(5-chloropyridin-2-yl)ethenesulfonamide (10 g, 40.5 mmol) in MeOH (100 mL) was added zinc trifluoromethanesulfonate (2.95 g, 8.11 mmol), bis(1, 5-cyclooctadiene)rhodium(I) tetrafluroborate (0.329 g, 0.811 mmol) and (S)-1-2-(di-1-naphthylphosphino)ferrocenyl-ethyl-di-tert-butylphosphine (0.651 g, 1.013 mmol). The reaction mixture was degassed with argon and hydrogen three times and then the mixture was charged with hydrogen (50 Psi) in a 200 mL Mini-clave at RT for 16 h followed by heating at 65° C. for 16 h. The reaction was checked by TLC for completion which showed that starting material was completely absent. The reaction mass was concentrated under reduced pressure providing the product which was purified by column chromatography (silica gel 60-120 mesh) using 40-45% of EtOAc in petroleum ether as an eluent affording the desired product (2S,3R)-3-(5-chloropyridin-2-yl)butane-2-sulfonamide (Example 14.0, 9 g, 36.2 mmol, 89%) as a brownish solid in 82% ee. Recrystallization from i-PrOH yielded >97% ee material. $^1$H NMR (400 MHz, DMSO-d6) δ 1.19 (d, J=7.05 Hz, 3H) 1.29 (d, J=7.05 Hz, 3H) 3.46 (qd, J=7.08, 3.84 Hz, 1H) 3.63 (qd, J=7.08, 3.84 Hz, 1H) 6.82 (s, 2H) 7.36 (d, J=8.50 Hz, 1H) 7.88 (dd, J=8.50, 2.70 Hz, 1H) 8.56 (d, J=2.28 Hz, 1H). LCMS-ESI (pos) m/z: 249.0 (M+H)$^+$.

The compounds set forth in the following table were synthesized following the procedure in Example 6.0 using the known starting material as described.

TABLE 5

| | | |
|---|---|---|
| 15.0 | (S)-1-(5-fluoropyrimidin-2-yl)propane-2-sulfonamide and (R)-1-(5-fluoropyrimidin-2-yl)propane-2-sulfonamide (Example 6.4), tetrahydro-2H-pyran-4-carbohydrazide (commercially available from Combi-Blocks Inc., San Diego, CA, USA), 2-isothiocyanato-1,3-dimethoxybenzene (Example 10.0). | 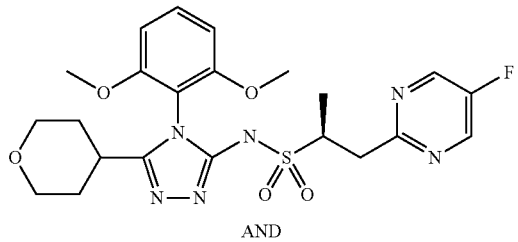<br>AND<br>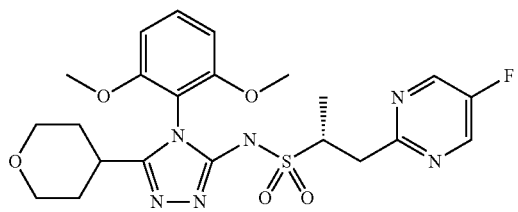<br>(2R)-N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide and (2S)-N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide.<br>LCMS-ESI (pos) mz: 506.8 (M + H)+. |
| 16.0 | The racemic compound Example 15.0 was separated by SFC (250 × 30 mm IA column with 28 g/min MeOH (20 mM Ammonia) and 72 g/min CO$_2$, 30% co-solvent at 100 g/min on Thar 200. Temperature = 22° C.; wavelength = 220 nm; injection volume = 0.5 mL of a solution of 30 mg sample dissolved in 4 mL MeOH; c = 7.5 mg/mL, 3.75 mg/injection). This was the first isomer to elute under these conditions. | 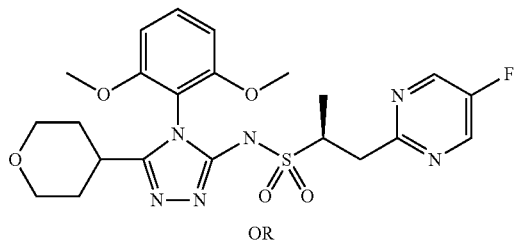<br>OR<br>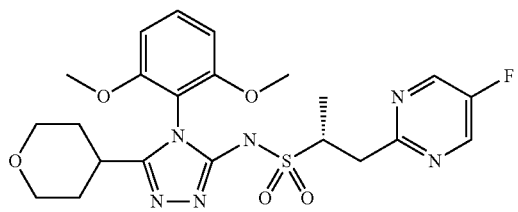<br>(2R)-N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide or (2S)-N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide.<br>$^1$H NMR (400 MHz, CDCl$_3$) δ 10.81 (br. s, 1H), 8.53 (s, 2H), 7.43 (t, J = 8.4 Hz, 1H), 6.67 (dd, J = 8.6, 2.3 Hz, 2H), 3.96 (d, J = 11.7 Hz, 2H), 3.81 (s, 3H), 3.80 (s, 3H), 3.71-3.78 (m, 1H), 3.67 (dd, J = 14.8, 3.6 Hz, 1H), 3.31 (td, J = 11.5, 2.0 Hz, 2H), 3.05 (dd, J = 14.7, 10.0 Hz, 1H), 2.36-2.56 (m, 1H), 1.73-1.97 (m, 2H), 1.64 (d, J = 13.1 Hz, 2H), 1.27 (d, J = 6.7 Hz, 3H).<br>LCMS-ESI (pos) m/z: 506.8 (M + H)+. |

TABLE 5-continued

| 17.0 | The racemic compound Example 15.0 was separated by SFC (250 × 30 mm IA column with 28 g/min MeOH (20 mM Ammonia) and 72 g/min CO₂, 30% co-solvent at 100 g/min on Thar 200. Temperature = 22° C.; wavelength = 220 nm; injection volume = 0.5 mL of a solution of 30 mg sample dissolved in 4 mL MeOH; c = 7.5 mg/mL, 3.75 mg/injection). This was the second isomer to elute under these conditions. | 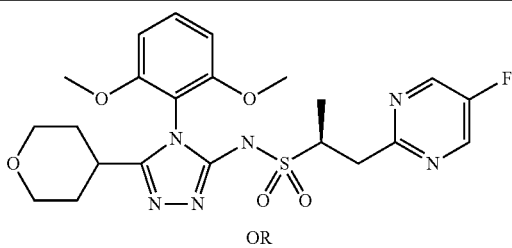<br>OR<br>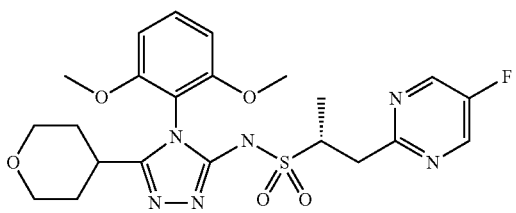<br><br>(2R)-N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide or (2S)-N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide.<br>¹H NMR (400 MHz, CDCl₃) δ 8.53 (s, 2H), 7.43 (t, J = 8.3 Hz, 1H), 6.60-6.73 (m, 2H), 3.96 (d, J = 11.9 Hz, 2H), 3.82 (s, 3H), 3.80 (s, 3H), 3.71-3.78 (m, 1H), 3.67 (dd, J = 14.8, 4.0 Hz, 1H), 3.24-3.39 (m, 2H), 3.05 (dd, J = 14.7, 10.0 Hz, 1H), 2.36-2.55 (m, 1H), 1.75-1.94 (m, 2H), 1.64 (d, J = 13.1 Hz, 2H), 1.21-1.34 (m, 3H). LCMS-ESI (pos) m/z: 506.8 (M + H)⁺. |

The compounds set forth in the following table were synthesized following the procedure in Example 140.0 using the known starting material as described.

TABLE 6

| 18.0 | (2S,3R)-3-(5-methylpyrimidin-2-yl)butane-2-sulfonamide (Example 1.0), (R)-tetrahydrofuran-2-carbohydrazide (commercially available from Enamine, Kiev, Ukraine), 1,3-difluoro-2-isothiocyanatobenzene (commercially available from Sigma-Aldrich Corp, St. Louis, MO, USA). | 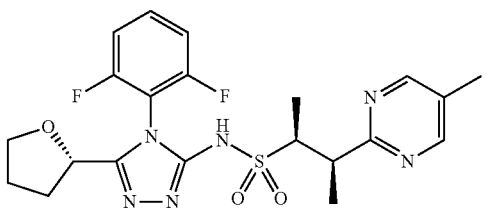 [SMILES: Cc1cnc([C@@H](C)[C@H](C)S(=O)(=O)Nc2nnc([C@@H]3CCCO3)n2-c2c(F)cccc2F)nc1]<br><br>(2S,3R)-N-(4-(2,6-difluorophenyl)-5-((2S)-tetrahydro-2-furanyl)-4H-1,2,4-triazol-3-yl)-3-(5-methyl-2-pyrimidinyl)-2-butanesulfonamide.<br>¹H NMR (400 MHz, CDCl₃) δ 11.35 (br s, 1 H) 8.51 (d, J = 0.62 Hz, 2 H) 7.49 (tt, J = 8.58, 6.19 Hz, 1 H) 7.04-7.12 (m, 2 H) 4.76 (dd, J = 7.62, 5.34 Hz, 1 H) 3.86 (quin, J = 6.82 Hz, 1 H) 3.61-3.80 (m, 3 H) 2.39-2.49 (m, 1 H) 2.28 (s, 3 H) 2.10-2.24 (m, 1 H) 1.90-2.05 (m, 2 H) 1.36 (d, J = 5.91 Hz, 3 H) 1.35 (d, J = 5.80 Hz, 3 H). LCMS-ESI (pos) m/z: 479.2 (M + H)⁺. |
| 19.0 | (2S,3R)-3-(5-methylpyrimidin-2-yl)butane-2-sulfonamide (Example 1.0), (S)-tetrahydrofuran-2-carbohydrazide (commercially available from Enamine, Kiev, Ukraine), 1,3-difluoro-2-isothiocyanatobenzene (commercially available from Sigma-Aldrich Corp, St. Louis, MO, USA). | 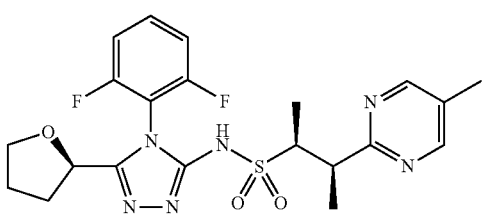 [SMILES: Cc1cnc([C@@H](C)[C@H](C)S(=O)(=O)Nc2nnc([C@H]3CCCO3)n2-c2c(F)cccc2F)nc1]<br><br>(2S,3R)-N-(4-(2,6-difluorophenyl)-5-((2R)-tetrahydro-2-furanyl)-4H-1,2,4-triazol-3-yl)-3- |

TABLE 6-continued

| | | |
|---|---|---|
| | | (5-methyl-2-pyrimidinyl)-2-butanesulfonamide. 1H NMR (400 MHz, CDCl$_3$) δ 11.27 (br s, 1 H) 8.51 (d, J = 0.62 Hz, 2 H) 7.49 (tt, J = 8.58, 6.19 Hz, 1 H) 7.03-7.12 (m, 2 H) 4.77 (dd, J = 7.67, 5.18 Hz, 1 H) 3.82-3.90 (m, 1 H) 3.68-3.80 (m, 2 H) 3.59-3.67 (m, 1 H) 2.39-2.49 (m, 1 H) 2.28 (s, 3 H) 2.10-2.20 (m, 1 H) 1.84-1.97 (m, 2 H) 1.36 (d, J = 7.15 Hz, 3 H) 1.33 (d, J = 7.05 Hz, 3 H). LCMS-ESI (pos) m/z: 479.2 (M + H)$^+$. |
| 20.0 | (2S,3R)-3-(5-methylpyrimidin-2-yl)butane-2-sulfonamide (Example 1.0), (R)-tetrahydrofuran-3-carbohydrazide and (S)-tetrahydrofuran-3-carbohydrazide (commercially available from Enamine, Kiev, Ukraine), 1,3-difluoro-2-isothiocyanatobenzene (commercially available from Sigma-Aldrich Corp, St. Louis, MO, USA). The mixture was separated by SFC Chiralpak AD-H, 20% MeOH. This was the first isomer to elute under these conditions. | 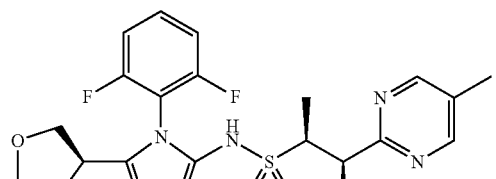<br>OR<br>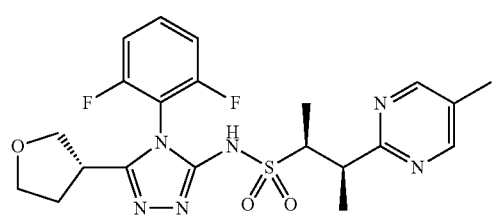<br>(2S,3R)-N-(4-(2,6-difluorophenyl)-5-((3R)-tetrahydro-3-furanyl)-4H-1,2,4-triazol-3-yl)-3-(5-methyl-2-pyrimidinyl)-2-butanesulfonamide or (2S,3R)-N-(4-(2,6-difluorophenyl)-5-((3S)-tetrahydro-3-furanyl)-4H-1,2,4-triazol-3-yl)-3-(5-methyl-2-pyrimidinyl)-2-butanesulfonamide. <sup></sup>1H NMR (400 MHz, CDCl$_3$) δ 11.26 (br s, 1 H) 8.53 (s, 2 H) 7.52-7.61 (m, 1 H) 7.14 (td, J = 8.55, 3.84 Hz, 2 H) 3.96 (td, J = 8.40, 6.01 Hz, 1 H) 3.82-3.91 (m, 4 H) 3.66-3.72 (m, 1 H) 3.07-3.16 (m, 1 H) 2.30 (s, 3 H) 2.21-2.29 (m, 1 H) 2.08-2.17 (m, 1 H) 1.38 (d, J = 4.35 Hz, 3 H) 1.36 (d, J = 4.35 Hz, 3 H). LCMS-ESI (pos) m/z: 479.2 (M + H)$^+$. |
| 21.0 | Further elution under the conditions described in Example 20.0 afforded the second eluting isomer. | 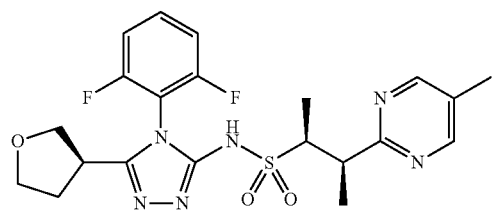<br>OR<br>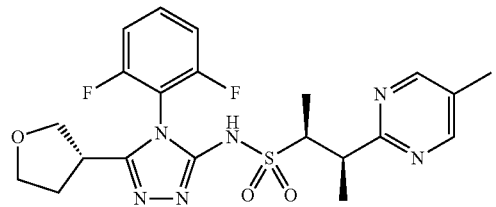<br>(2S,3R)-N-(4-(2,6-difluorophenyl)-5-((3R)-tetrahydro-3-furanyl)-4H-1,2,4-triazol-3-yl)-3-(5-methyl-2-pyrimidinyl)-2-butanesulfonamide or (2S,3R)-N-(4-(2,6-difluorophenyl)-5-((3S)-tetrahydro-3-furanyl)-4H-1,2,4-triazol-3-yl)-3-(5-methyl-2-pyrimidinyl)-2-butanesulfonamide. <sup></sup>1H NMR (400 MHz, CDCl$_3$) δ 11.23 (br s, 1 H) 8.53 (d, J = 0.62 Hz, 2 H) 7.51-7.60 (m, 1 H) 7.10-7.19 (m, 2 H) 3.96 (td, J = 8.32, 6.06 Hz, 1 H) 3.80-3.91 (m, 4 H) 3.70 (quin, J = 6.95 Hz, 1 H) 3.06-3.15 (m, 1 H) 2.30 (s, 3 H) 2.24 (ddd, J = 12.85, |

TABLE 6-continued 7.93, 6.38 Hz, 1 H) 2.06-2.15 (m, 1 H) 1.38 (d, J = 5.08 Hz, 3 H) 1.36 (d, J = 5.08 Hz, 3 H). LCMS-ESI (pos) m/z: 479.2 (M + H)+.

22.0 (2S,3R)-3-(5-methylpyrimidin-2-yl)butane-2-sulfonamide (Example 1.0), (R)-(R)-tetrahydro-2H-pyran-3-carbohydrazide and (S)-tetrahydro-2H-pyran-3-carbohydrazide and (S)-(R)-tetrahydro-2H-pyran-3-carbohydrazide and (S)-tetrahydro-2H-pyran-3-carbohydrazide (commercially available from Synthonix, Wake Forest, NC, USA), 1,3-difluoro-2-isothiocyanatobenzene (commercially available from Sigma-Aldrich Corp, St. Louis, MO, USA). The mixture was separated by SFC Chiralpak AD-H, 25% MeOH. This was the first isomer to elute under these conditions.

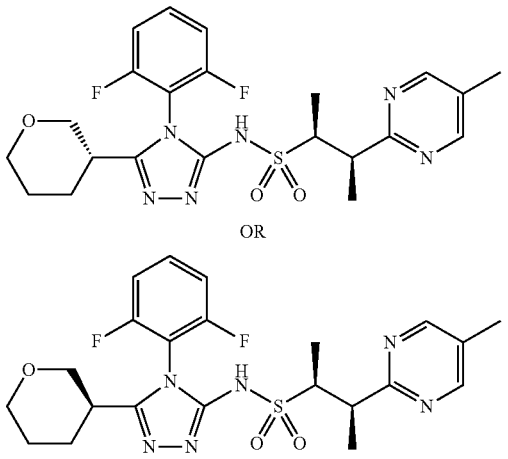 [SMILES: Cc1cnc([C@@H](C)[C@H](C)S(=O)(=O)Nc2nnc([C@@H]3CCCOC3)n2-c2c(F)cccc2F)nc1 ; Cc1cnc([C@@H](C)[C@H](C)S(=O)(=O)Nc2nnc([C@H]3CCCOC3)n2-c2c(F)cccc2F)nc1]

OR (2S,3R)-N-(4-(2,6-difluorophenyl)-5-((3S)-tetrahydro-2H-pyran-3-yl)-4H-1,2,4-triazol-3-yl)-3-(5-methyl-2-pyrimidinyl)-2-butanesulfonamide or (2S,3R)-N-(4-(2,6-difluorophenyl)-5-((3R)-tetrahydro-2H-pyran-3-yl)-4H-1,2,4-triazol-3-yl)-3-(5-methyl-2-pyrimidinyl)-2-butanesulfonamide. $^1$H NMR (400 MHz, CDCl$_3$) δ 11.27 (br s, 1 H) 8.53 (d, J = 0.62 Hz, 2 H) 7.55 (tt, J = 8.62, 6.21 Hz, 1 H) 7.05-7.21 (m, 2 H) 3.80-3.97 (m, 3 H) 3.69 (quin, J = 6.89 Hz, 1 H) 3.52 (dd, J = 11.25, 10.21 Hz, 1 H) 3.44 (td, J = 11.51, 2.90 Hz, 1 H) 2.51-2.69 (m, 1 H) 2.30 (s, 3 H) 1.96-2.04 (m, 1 H) 1.79-1.95 (m, 1 H) 1.54-1.77 (m, 2 H) 1.37 (d, J = 6.79 Hz, 3 H) 1.35 (d, J = 6.79 Hz, 3 H). LCMS-ESI (pos) m/z: 493.2 (M + H)+.

23.0 The mixture was separated by SFC Chiralpak AD-H, 25% MeOH. This was the second isomer to elute under these conditions.

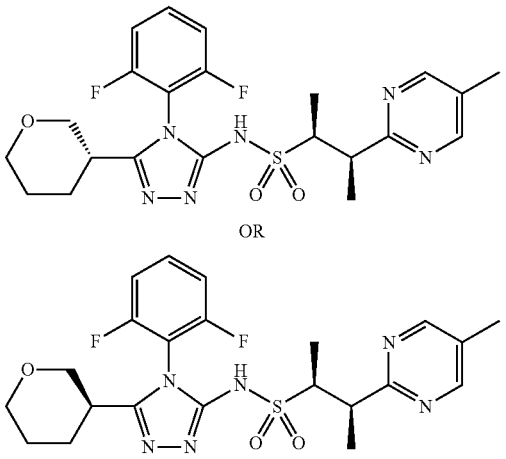 [SMILES: Cc1cnc([C@@H](C)[C@H](C)S(=O)(=O)Nc2nnc([C@@H]3CCCOC3)n2-c2c(F)cccc2F)nc1 ; Cc1cnc([C@@H](C)[C@H](C)S(=O)(=O)Nc2nnc([C@H]3CCCOC3)n2-c2c(F)cccc2F)nc1]

OR (2S,3R)-N-(4-(2,6-difluorophenyl)-5-((3S)-tetrahydro-2H-pyran-3-yl)-4H-1,2,4-triazol-3-yl)-3-(5-methyl-2-pyrimidinyl)-2-butanesulfonamide or (2S,3R)-N-(4-(2,6-difluorophenyl)-5-((3R)-tetrahydro-2H-pyran-3-yl)-4H-1,2,4-triazol-3-yl)-3-(5-methyl-2-pyrimidinyl)-2-butanesulfonamide. $^1$H NMR (400 MHz, CDCl$_3$) δ 11.23 (br s, 1 H) 8.53 (d, J = 0.62 Hz, 2 H) 7.55 (tt, J = 8.64, 6.23 Hz, 1 H) 7.13 (tt, J = 8.75, 1.41 Hz, 2 H) 3.81-3.98 (m, 3 H) 3.70 (quin, J = 6.87 Hz, 1 H) 3.52 (dd, J = 11.35, 10.21 Hz, 1 H) 3.44 (td, J = 11.56, 2.70 Hz, 1 H) 2.55-2.64 (m, 1 H) 2.30 (s, 3 H) 1.95-2.04 (m, 1 H) 1.80-1.95 (m, 1 H) 1.47-1.74 (m, 2 H) 1.37 (d, J = 7.05 Hz, 3 H) 1.35 (d, J = 7.05 Hz, 3 H). LCMS-ESI (pos) m/z: 493.2 (M + H)+.

Example 24.0. Preparation of (2S,3R)-3-(5-cyano-2-pyrimidinyl)-N-(4-(2,6-dimethoxyphenyl)-5-((2S)-tetrahydro-2-furanyl)-4H-1,2,4-triazol-3-yl)-2-butanesulfonamide or (2S,3R)-3-(5-cyano-2-pyrimidinyl)-N-(4-(2,6-dimethoxyphenyl)-5-((2R)-tetrahydro-2-furanyl)-4H-1,2,4-triazol-3-yl)-2-butanesulfonamide

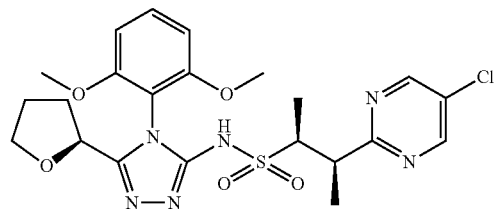

OR

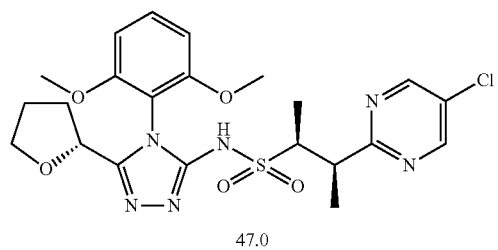

47.0

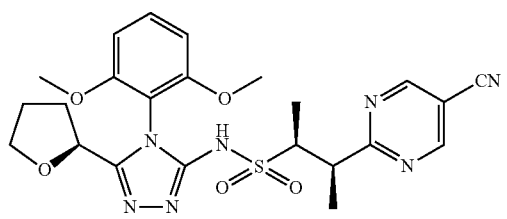

OR

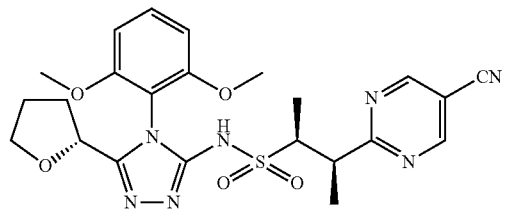

24.0

(2S,3R)-3-(5-Cyano-2-pyrimidinyl)-N-(4-(2,6-dimethoxyphenyl)-5-((2S)-tetrahydro-2-furanyl)-4H-1,2,4-triazol-3-yl)-2-butanesulfonamide or (2S,3R)-3-(5-cyano-2-pyrimidinyl)-N-(4-(2,6-dimethoxyphenyl)-5-((2R)-tetrahydro-2-furanyl)-4H-1,2,4-triazol-3-yl)-2-butanesulfonamide, Example 24.0

To a vial flask was added (2S,3R)-3-(5-chloro-2-pyrimidinyl)-N-(4-(2,6-dimethoxyphenyl)-5-((2S)-tetrahydro-2-furanyl)-4H-1,2,4-triazol-3-yl)-2-butanesulfonamide or (2S,3R)-3-(5-chloro-2-pyrimidinyl)-N-(4-(2,6-dimethoxyphenyl)-5-((2R)-tetrahydro-2-furanyl)-4H-1,2,4-triazol-3-yl)-2-butanesulfonamide (Example 47.0, 0.086 g, 0.164 mmol)), methanesulfonato(2-dicyclohexylphosphino-2',4',6'-tri-i-propyl-1,1'-biphenyl)(2'-amino-1,1'-biphenyl-2-yl)palladium(II) (0.070 g, 0.082 mmol) and zinc cyanide (10.44 μl, 0.164 mmol) in DMA (0.8 mL). The reaction mixture was heated at 80° C. for 3 h. The reaction mixture was then cooled to RT. The product was purified by chromatography through a Redi-Sep pre-packed silica gel column (12 g), eluting with a gradient of 0% to 80% (3:1 EtOAc:EtOH) in heptane to afford (2S,3R)-3-(5-cyano-2-pyrimidinyl)-N-(4-(2,6-dimethoxyphenyl)-5-((2S)-tetrahydro-2-furanyl)-4H-1,2,4-triazol-3-yl)-2-butanesulfonamide or (2S,3R)-3-(5-cyano-2-pyrimidinyl)-N-(4-(2,6-dimethoxyphenyl)-5-((2R)-tetrahydro-2-furanyl)-4H-1,2,4-triazol-3-yl)-2-butanesulfonamide, Example 24.0 (0.033 g, 0.063 mmol, 39% yield) as a white solid. $^1$H NMR (400 MHz, CDCl$_3$) δ 10.71 (s, 1H) 8.91 (s, 2H) 7.41 (t, J=8.50 Hz, 1H) 6.65 (d, J=8.50 Hz, 2H) 4.61 (dd, J=7.31, 5.44 Hz, 1H) 3.82-3.88 (m, 1H) 3.80 (s, 3H) 3.80 (s, 3H) 3.74-3.79 (m, 3H) 2.18-2.28 (m, 1H) 1.80-2.04 (m, 3H) 1.35 (m, 6H). LCMS-ESI (pos) m/z: 514.2 (M+H)$^+$.

The compounds set forth in the following table were synthesized following the procedure in Example 140.0 using the known starting material as described.

TABLE 7

| | | |
|---|---|---|
| 25.0 | (2S,3R)-3-(5-methylpyrimidin-2-yl)butane-2-sulfonamide (Example 1.0), (R)-tetrahydrofuran-2-carbohydrazide (commercially available from Enamine, Kiev, Ukraine), 3,5-difluoro-4-isothiocyanatopyridine (Example 10.3). | 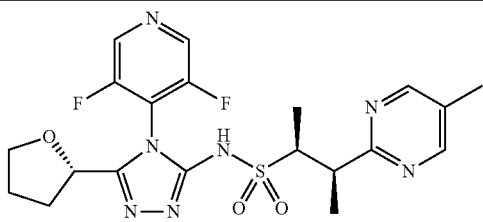 |
| | (2S,3R)-N-(4-(3,5-difluoro-4-pyridinyl)-5-((2S)-tetrahydro-2-furanyl)-4H-1,2,4-triazol-3-yl)-3-(5-methyl-2-pyrimidinyl)-2-butanesulfonamide. $^1$H NMR (400 MHz, CDCl$_3$) δ 11.46 (br s, 1 H) 8.57 (d, J = 3.21 Hz, 2 H) 8.54 (d, J = 0.73 Hz, 2 H) 4.82 (dd, J = 7.31, 5.23 Hz, 1 H) 3.83-3.95 (m, 1 H) 3.74 (td, J = 7.88, 6.12 Hz, 1 H) 3.59-3.69 (m, 2 H) 2.46-2.59 (m, 1 H) 2.30 (s, 3 H) 2.19-2.28 (m, 1 H) 1.88-2.08 (m, 2 H) 1.39 (m, 6 H). LCMS-ESI (pos) m/z: 480.2 (M + H)$^+$. | |
| 26.0 | (2S,3R)-3-(5-methylpyrimidin-2-yl)butane-2-sulfonamide (Example 1.0), (S)-tetrahydrofuran-2-carbohydrazide (commercially available from Enamine, Kiev, Ukraine), 3,5-difluoro-4-isothiocyanatopyridine (Example 10.3). | 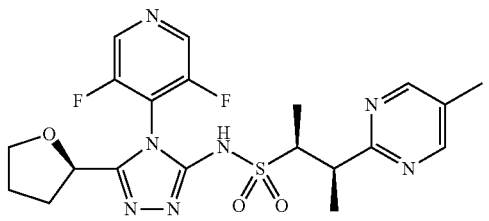 [SMILES: Cc1cnc([C@@H](C)[C@H](C)S(=O)(=O)Nc2nnc([C@H]3CCCO3)n2-c2c(F)cncc2F)nc1] |
| | (2S,3R)-N-(4-(3,5-difluoro-4-pyridinyl)-5-((2R)-tetrahydro-2-furanyl)-4H-1,2,4-triazol-3-yl)-3-(5-methyl-2-pyrimidinyl)-2-butanesulfonamide. 1H NMR (500 MHz, DMSO-d6) δ 8.87 (s., 2 H) 8.56 (s, 2 H) 4.76-4.88 (m, 1 H) 3.64 (d, J = 7.01 Hz, 2 H) 3.36-3.50 (m, 2 H) 2.54 (s, 1 H) 2.23 (s, 3 H) 2.09-2.19 (m, 1 H) 1.77-1.89 (m, 2 H) 1.22 (d, J = 6.75 Hz, 3 H) 1.09 (d, J = 6.75 Hz, 3 H). LCMS-ESI (pos) m/z: 480.2 (M + H)$^+$. | |

Example 27.0. Preparation of (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide

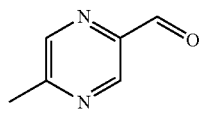

27.1

5-Methylpyrazine-2-carbaldehyde, Example 27.1

A solution of LAH (164.0 mL, 0.164 mol, 1.0M in THF, 0.5 equivalent.) was added to a suspension of methyl 5-methylpyrazine-2-carboxylate (50 g, 0.328 mol, 1.0 equivalent.) in anhydrous THF (750 mL) at −78° C. The internal temperature was kept below −72° C. during the addition of LAH. On completion of addition, the reaction mixture was left to stir at −78° C. for a further 20 min and then quenched with glacial AcOH (50.0 mL) at the same temperature. The resulting mixture was warmed to RT, and the volatiles were removed by evaporation under vacuum. The residue was dissolved in 1.5 N HCl (500 mL) and extracted with DCM (2×2 L). The organic layers were combined, washed with saturated aqueous sodium hydrogen carbonate solution (2×500 mL), dried over anhydrous Na$_2$SO$_4$, and concentrated in vacuo to yield the product as a brown oil. The material thus obtained was purified by column chromatography (silica gel 60-120 mesh) eluting with a gradient of 10% EtOAc in petroleum ether to provide the title compound as a pale yellow liquid (21.3 g, 53%). TLC Info: (9.0/1.0 Petroleum ether/EtOAc). $^1$H NMR (400 MHz, CDCl$_3$) δ 10.14 (s, 1H), 9.07 (d, J=1.5 Hz, 1H), 8.63 (d, J=1.4 Hz, 1H), and 2.70 (s, 3H). LCMS (ESI positive ion) m/z: 123 (M+H)$^+$.

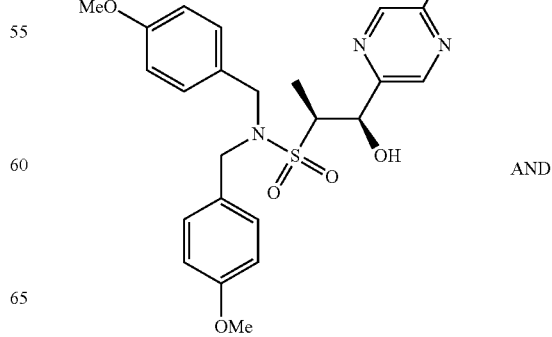

27.2

AND

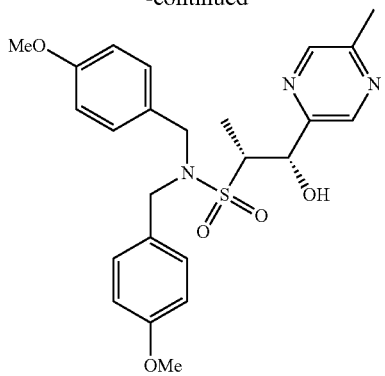

(1R,2S)-1-Hydroxy-N,N-bis(4-methoxybenzyl)-1-(5-methylpyrazin-2-yl)propane-2-sulfonamide and (1S,2R)-1-hydroxy-N,N-bis(4-methoxybenzyl)-1-(5-methylpyrazin-2-yl)propane-2-sulfonamide, Example 27.2

To a solution of N,N-bis(4-methoxybenzyl)ethanesulfonamide (Example 12.0, 73.13 g, 0.209 mol, 1.2 equivalent.) in anhydrous THF (600 mL) at −78° C. was slowly added n-butyl lithium (83.71 mL, 0.209 mol, 2.5 M solution in hexanes, 1.2 equivalent.) via additional funnel, and the resulting mixture was stirred for 10 min. Next, a solution of 5-methylpyrazine-2-carbaldehyde (Example 27.1, 21.3 g, 0.174 mol, 1.0 equivalent.) in anhydrous THF (150 mL) was added, and the mixture was stirred at the same temperature for 45 min and then allowed to warm to RT for 2 h. The reaction mixture was then quenched by addition of aqueous ammonium chloride (200 mL) and extracted with EtOAc (2×2 L). The combined organic layers were washed with brine (2×500 mL). No product was observed in the ammonium chloride or brine layers. After drying over anhydrous Na$_2$SO$_4$, the filtrate was concentrated in vacuo, to afford the product as an oil. The product thus obtained was purified by flash column chromatography (silica gel, 230-400 mesh) to afford the two isomers. The faster moving isomer (32 g) was obtained as a white solid from the column with a gradient of 10% to 30% EtOAc in petroleum ether. $^1$H NMR (400 MHz, DMSO-d$_6$) δ 8.61 (d, J=1.5 Hz, 1H), 8.51 (d, J=1.5 Hz, 1H), 7.22-7.11 (m, 4H), 6.90-6.80 (m, 4H), 6.10 (d, J=5.9 Hz, 1H), 5.29 (dd, J=5.9, 2.2 Hz, 1H), 4.36-4.16 (m, 4H), 3.73 (app s, 6H), 3.70-3.66 (m, 1H) 2.50 (merged with solvent peak, 3H) and 1.10 (d, J=7.0 Hz, 3H). LCMS (ESI positive ion) m/z: 472.4 (M+H)$^+$.

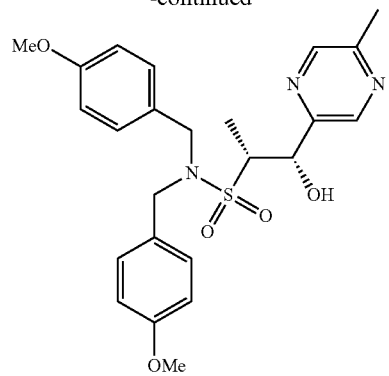

(1S,2S)-1-Hydroxy-N,N-bis(4-methoxybenzyl)-1-(5-methyl-pyrazin-2-yl)propane-2-sulfonamide and (1R,2R)-1-hydroxy-N,N-bis(4-methoxybenzyl)-1-(5-methyl-pyrazin-2-yl)propane-2-sulfonamide, Example 28.3

Further elution of the mixture in Example 27.2 with a gradient of 30% to 35% EtOAc in petroleum ether yielded Example 27.3 (16 g, pale yellow gummy liquid). $^1$H NMR (400 MHz, CDCl$_3$) δ 8.62 (d, J=1.6 Hz, 1H), 8.44 (d, J=1.5 Hz, 1H), 7.25-7.12 (m, 4H), 6.93-6.82 (m, 4H), 5.17 (d, J=7.1 Hz, 1H), 4.47 (d, J=15.2 Hz, 3H), 4.14 (d, J=15.4 Hz, 2H), 3.82 (s, 3H), 3.82 (s, 3H), 3.66-3.61 (m, 1H), 2.60 (d, J=2.0 Hz, 3H), and 1.08 (dd, J=7.2, 2.1 Hz, 3H). LCMS (ESI positive ion) m/z: 472.4 (M+H)+.

27.4

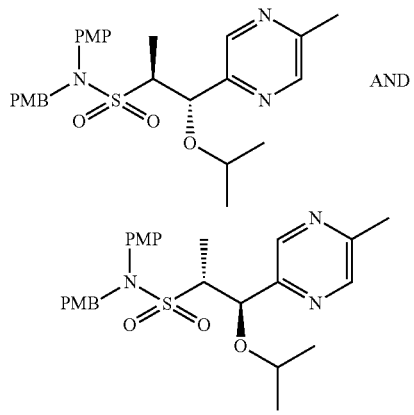

(1S,2S)-1-Isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methylpyrazin-2-yl)propane-2-sulfonamide, Example 27.4

To a flask containing (1S,2S)-1-hydroxy-N,N-bis(4-methoxybenzyl)-1-(5-methylpyrazin-2-yl)propane-2-sulfonamide and (1R,2R)-1-hydroxy-N,N-bis(4-methoxybenzyl)-1-(5-methylpyrazin-2-yl)propane-2-sulfonamide (Example 27.3, 4.16 g, 8.81 mmol) and isopropyl iodide (12.3 mL, 123 mmol) in anhydrous toluene (35 mL) was added silver(I) oxide (4.17 g, 18.0 mmol) carefully in portions. Upon complete addition of silver oxide, the reac- 27.3

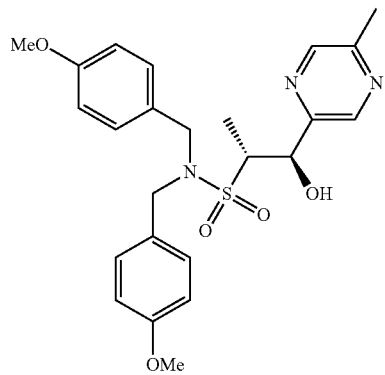

tion was protected from light and heated to an internal temperature of 72° C. After 60 h, the mixture was cooled to RT and then filtered through a Chemglass disposable filter that was rinsed with EtOAc. The filtrate was concentrated under reduced pressure. The dark brown residue was loaded onto a silica gel column (10-55% EtOAc in heptanes). Fractions containing the product were combined and then concentrated under reduced pressure to afford a dark brown oil as (1S,2S)-1-isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methyl-pyrazin-2-yl)propane-2-sulfonamide (Example 27.4, 1.52 g, 2.97 mmol, 34% yield) that was used without further purification. $^1$H NMR (400 MHz, DMSO-d$_6$) δ 8.58 (d, J=1.5 Hz, 1H), 8.54 (d, J=0.8 Hz, 1H), 7.20-7.15 (m, 4H), 6.89-6.85 (m, 4H), 4.81 (d, J=7.0 Hz, 1H), 4.35-4.29 (m, 2H), 4.20-4.13 (m, 2H), 3.76-3.71 (m, 7H), 3.39 (quin, J=6.1 Hz, 1H), 2.51 (s, 3H), 1.13 (d, J=6.0 Hz, 3H), 1.05 (d, J=7.3 Hz, 3H), 0.99 (d, J=6.2 Hz, 3H). LCMS (pos) m/z: 514.0 (M+H)+.

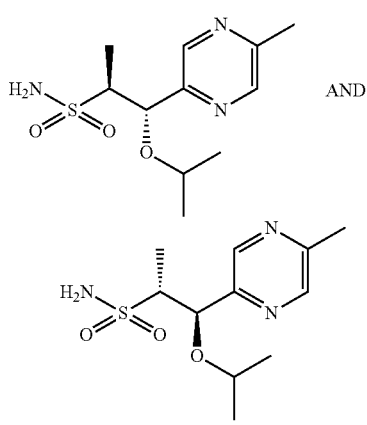

(1R,2R)-1-Isopropoxy-1-(5-methylpyrazin-2-yl)propane-2-sulfonamide and (1S,2S)-1-isopropoxy-1-(5-methylpyrazin-2-yl)propane-2-sulfonamide (Example 27.0), Example 27.5

Anisole (1.3 mL, 11.9 mmol) was added to a flask containing (1S,2S)-1-isopropoxy-N,N-bis(4-methoxyben-zyl)-1-(5-methylpyrazin-2-yl)propane-2-sulfonamide and (1R,2R)-1-isopropoxy-N,N-bis(4-methoxybenzyl)-1-(5-methylpyrazin-2-yl)propane-2-sulfonamide (Example 27.4, 1.5 g, 3 mmol) and DCM (7.5 mL). The homogeneous solution was cooled in an ice-water bath. After 15 min, TFA (7.6 mL, 99 mmol) was added dropwise to the reaction solution. Upon complete addition of TFA, the reaction was allowed to warm to 23° C. After 20 h, the brownish reaction solution was concentrated under reduced pressure. The residue was loaded onto a silica gel column (15-85% EtOAc in heptanes). Fractions containing the product were concentrated under reduced pressure to afford (1R,2R)-1-isopropoxy-1-(5-methylpyrazin-2-yl)propane-2-sulfonamide and (1S,2S)-1-isopropoxy-1-(5-methylpyrazin-2-yl)propane-2-sulfonamide or (1S,2S)-1-isopropoxy-1-(5-methyl-pyrazin-2-yl)propane-2-sulfonamide (Example 27.5, 714 mg, 2.6 mmol, 88% yield) as an off white solid. LCMS (pos) m/z: 274.0 (M+H)+.

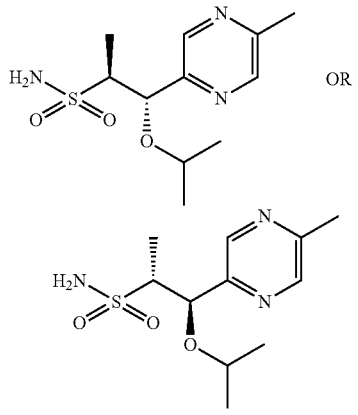

(1R,2R)-1-Isopropoxy-1-(5-methylpyrazin-2-yl)propane-2-sulfonamide or (1S,2S)-1-isopropoxy-1-(5-methylpyrazin-2-yl)propane-2-sulfonamide Example 27.6

(1R,2R)-1-Isopropoxy-1-(5-methylpyrazin-2-yl)propane-2-sulfonamide and (1S,2S)-1-isopropoxy-1-(5-methyl-pyrazin-2-yl)propane-2-sulfonamide (Example 27.5, 714 mg, 2.6 mmol) was purified by preparative SFC using the following methodology: Column: IC (2×25 cm) Mobile Phase: 70:30 (A:B) A: Liquid CO$_2$, B: IPA to afford peak 1 as (1R,2R)-1-isopropoxy-1-(5-methylpyrazin-2-yl)propane-2-sulfonamide or (1S,2S)-1-isopropoxy-1-(5-methyl-pyrazin-2-yl)propane-2-sulfonamide (Example 27.6, 293 mg, 1.07 mmol, 36% yield). $^1$H NMR (400 MHz, DMSO-d$_6$) δ 8.60 (d, J=1.5 Hz, 1H), 8.53 (d, J=0.8 Hz, 1H), 6.52 (s, 2H), 4.77 (d, J=7.0 Hz, 1H), 3.56-3.45 (m, 2H), 1.15 (d, J=6.0 Hz, 3H), 1.05 (d, J=7.0 Hz, 3H), 0.96 (d, J=6.2 Hz, 3H). (Obscured CH$_3$ in DMSO peak). LCMS (pos) m/z: 274.2 (M+H)+.

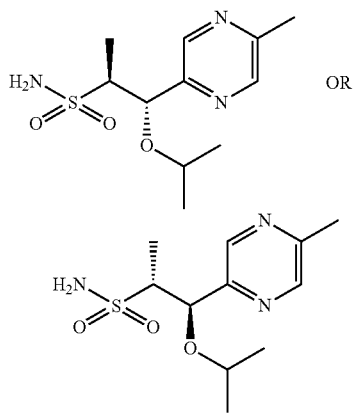

(1R,2R)-1-Isopropoxy-1-(5-methylpyrazin-2-yl)propane-2-sulfonamide or (1S,2S)-1-isopropoxy-1-(5-methylpyrazin-2-yl)propane-2-sulfonamide Example 27.0

Further elution under the conditions described in Example 27.6 afforded the second eluting peak as (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0, 303 mg, 1.11 mmol, 37% yield). ¹H NMR (400 MHz, DMSO-d₆) δ 8.60 (d, J=1.5 Hz, 1H), 8.53 (d, J=1.0 Hz, 1H), 6.52 (s, 2H), 4.77 (d, J=7.0 Hz, 1H), 3.58-3.44 (m, 2H), 1.27-1.14 (m, 3H), 1.05 (d, J=7.0 Hz, 3H), 1.00-0.91 (m, 3H). (Obscured CH₃ in DMSO peak). LCMS (pos) m/z: 274.2 (M+H)⁺.

Example 28.0: Preparation of (1R,2S)-1-((tert-butyldimethylsilyl)oxy)-N,N-bis(4-methoxybenzyl)-1-(5-methylpyrimidin-2-yl)propane-2-sulfonamide

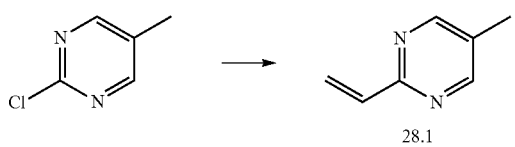

28.1

5-Methyl-2-vinylpyrimidine, Example 28.1

A 3 L 3-necked round bottomed flask was fitted with a reflux condenser, a temperature controller and a septum and was charged with 2-chloro-5-methylpyrimidine (81 mL, 778 mmol), potassium vinyltrifluoroborate (156 g, 1167 mmol), triphenylphosphine (18.02 mL, 78 mmol), cesium carbonate (156 mL, 1945 mmol) and a large stir bar. Water (1565 mL) was added, and the mixture was stirred for several min and then THF (244 mL) was added. Argon was bubbled through the mixture for 5 min and then palladium (II) chloride (1.72 g, 38.9 mmol) was added. The reaction was further sparged with argon for 5 mins. The temperature was raised to 62° C. and stirring continued to completion. The reaction was then cooled to RT and filtered through two Whatman GF/F filter cups, rinsing with ether. The mixture was transferred to a separatory funnel, and the layers were separated. The aqueous layer was further extracted with diethyl ether (4×200 mL). The organic layers were combined and dried over anhydrous MgSO₄ and then filtered. The mixture was partially concentrated on a rotary evaporator at 20° C. and 115 torr for an extended period of time to give an orange liquid. The material was further purified by Kugel Rohr distillation to isolate the title compound (65.4 g, 70%) as a light yellow oil. ¹H NMR (400 MHz, CDCl₃) δ 2.31 (s, 3H), 5.68 (d, J=10.56 Hz, 1H), 6.55 (d, J=17.22 Hz, 1H), 6.86 (dd, J=17.41, 10.56 Hz, 1H), 8.54 (s, 2H). LCMS-ESI (pos) m/z: 121.1 (M+H)⁺.

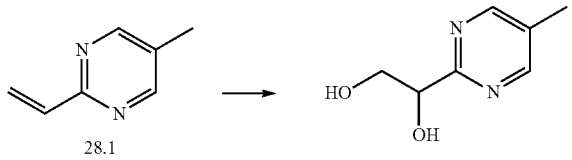

1-(5-Methylpyrimidin-2-yl)ethane-1,2-diol, Example 28.2

To a 2000 mL round-bottomed flask was added 5-methyl-2-vinylpyrimidine (64.5 g, 537 mmol), osmium tetroxide (0.204 mL, 3.93 mmol), 1,4-dioxane (537 mL, 537 mmol), 4-methylmorpholine-N-oxide (50% wt. in water, 40 mL, 341 mmol), and 4-methylmorpholine-N-oxide (94 g, 805 mmol) was added in addition to the solution based reagent. The reaction mixture was stirred over 2 d. LCMS showed that the reaction was complete, and the solvent was removed in vacuo. The compound was purified by silica gel. The gradient was 100% heptanes for 3 CV's, then 0-100% EtOAc-EtOH (3:1) in heptanes for 6 CV's, then 100% EtOAc:EtOH (3:1) for 5 CV's. The desired compound was collected and concentrated in vacuo. The material was triturated with 40% EtOAc in hexanes to give a solid which was filtered. The solid was washed with 20% EtOAc in hexanes several times and then dried to give the title compound (67.3 g). ¹H NMR (400 MHz, CDCl₃) δ 8.59 (s, 2H), 4.81-4.98 (m, 1H), 3.88-4.19 (m, 2H), 2.36 (s, 3H).

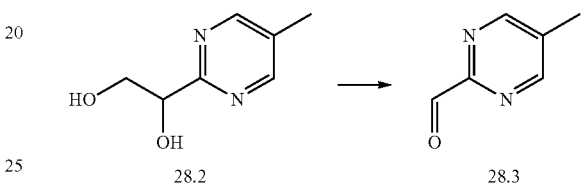

28.2　　　28.3

5-Methylpyrimidine-2-carbaldehyde, Example 28.3

A 5 L flask equipped with a mechanical stirrer was charged with 1-(5-methylpyrimidin-2-yl)ethane-1,2-diol (64.3 g, 417 mmol), 1,4-dioxane (1043 mL) and water (261 mL). The reaction was cooled in an ice-water bath. Sodium periodate (223 g, 1043 mmol) was added, and the internal temperature was monitored until it returned to RT. The reaction was further stirred at RT for 2 h and 20 min. DCM (2 L) was then added. The resulting solution was filtered through a plug of dried MgSO₄ (700 g). The plug was washed with DCM (7 L). The solvent was concentrated in vacuo, and the aldehyde was azeotroped with toluene to afford the title compound (44 g) as a white solid. LCMS-ESI (pos) m/z: 122.8 (M+H)⁺.

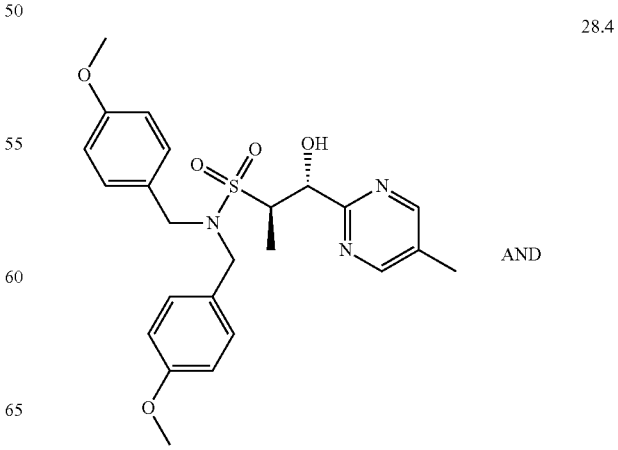

28.4

AND

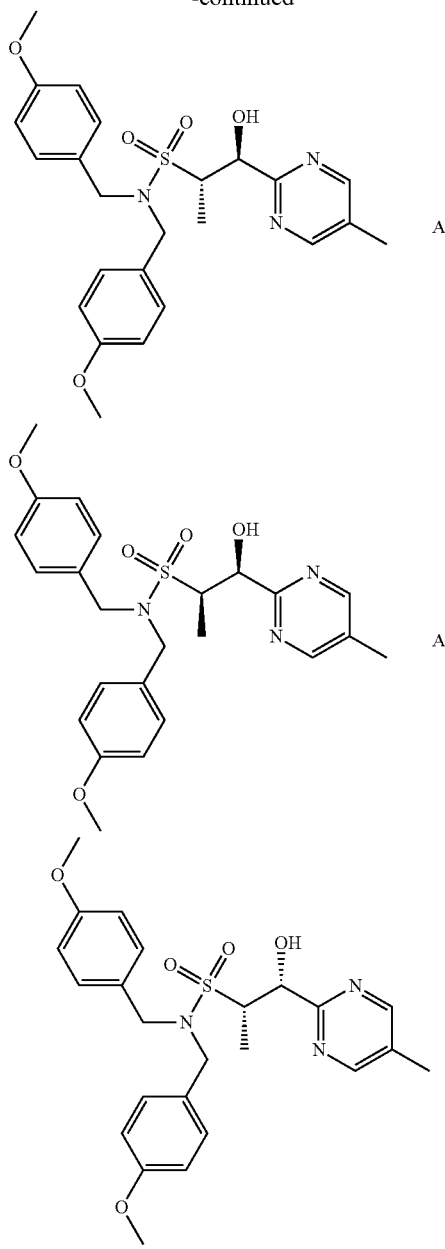

(1R,2S)-1-Hydroxy-N,N-bis(4-methoxybenzyl)-1-(5-methylpyrimidin-2-yl)propane-2-sulfonamide and (1S,2S)-1-hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide
Example 28.4

A 3 L flask was charged with N,N-bis(4-methoxybenzyl) ethanesulfonamide (Example 12.0, 151 g, 432 mmol) and anhydrous THF (1200 mL) under nitrogen and then equipped with a pre-dried addition funnel under nitrogen. The flask was cooled in a dry ice-acetone bath. n-Butyl-lithium (1.6 M, 270 mL, 432 mmol) was first cannulated into the additional funnel and was then added slowly into the reaction flask, and the mixture was stirred for 10 min. 5-Methylpyrimidine-2-carbaldehyde (28.3, 44 g, 360 mmol) in THF (300 mL) was then cannulated into the reaction. The reaction continued at −78° C. for 45 min and then was warmed to RT and stirring continued for 2 h and 10 min. A saturated solution of ammonium chloride was added to quench the reaction and the mixture was extracted with EtOAc and concentrated in vacuo to give the product.

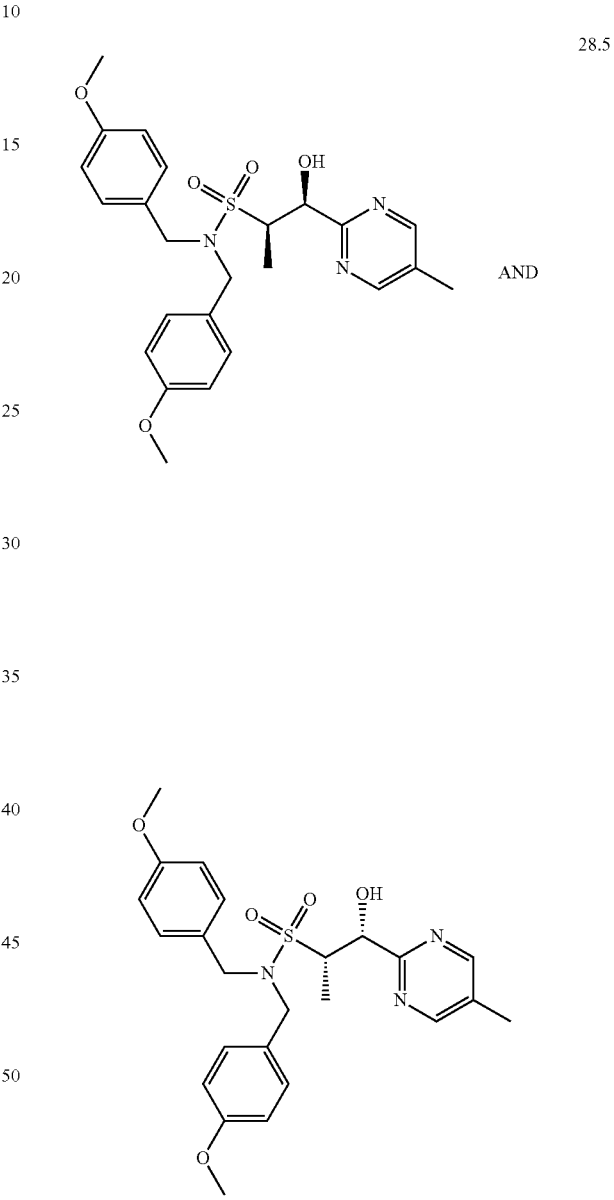

28.5

(1R,2S)-1-Hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide,
Example 28.5

The mixture of diastereomers from Example 28.4 was separated and purified on silica gel eluting with 0-50% EtOAc gradient in DCM to give the title compound (56.4 g). LCMS-ESI (pos) m/z: 472.1 (M+H)$^+$.

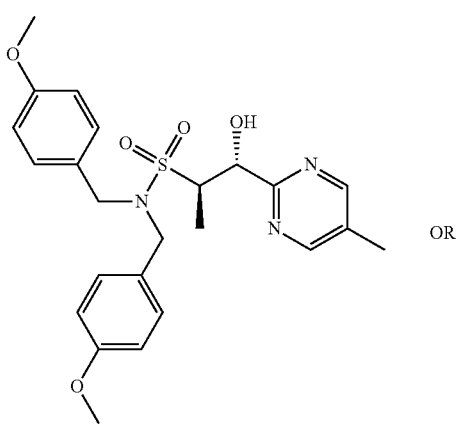

OR

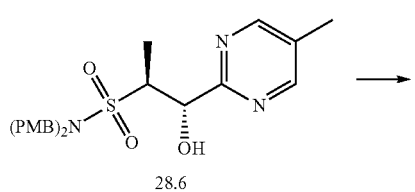

28.6

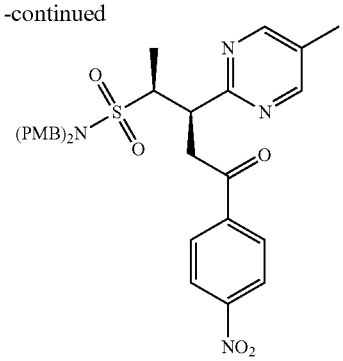

28.7

(1R,2S)-2-(N,N-Bis(4-methoxybenzyl)sulfamoyl)-1-(5-methylpyrimidin-2-yl)propyl 4-nitrobenzoate, Example 28.7

To a stirred solution of (1S,2S)-1-hydroxy-N,N-bis(4-methoxybenzyl)-1-(5-methylpyrimidin-2-yl)propane-2-sulfonamide (22.7 g, 48.1 mmol) in toluene (241 mL) was added 4-nitrobenzoic acid (12.07 g, 72.2 mmol), and triphenylphosphine (18.94 g, 72.2 mmol) followed by dropwise addition of (E)-diisopropyl diazene-1,2-dicarboxylate (14.22 mL, 72.2 mmol). The mixture was stirred at RT overnight and showed desired product formation by LCMS. The reaction was concentrated in vacuo and purified on silica gel eluting with 0-50% EtOAc/hexanes to give the desired compound (1R,2S)-2-(N,N-bis(4-methoxybenzyl)sulfamoyl)-1-(5-methylpyrimidin-2-yl)propyl 4-nitrobenzoate (29.9 g, 48.1 mmol, 100% yield). LCMS-ESI (pos) m/z: 621.3 (M+H)⁺.

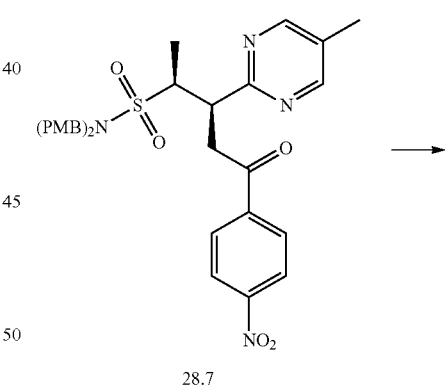

28.7

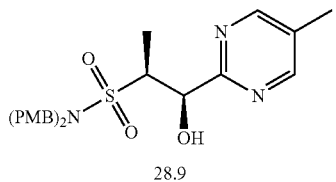

28.9

(1R,2S)-2-(N,N-Bis(4-methoxybenzyl)sulfamoyl)-1-(5-methylpyrimidin-2-yl)propyl 4-nitrobenzoate, Example 28.9

(1S,2S)-1-Hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide Example 11.05

Further elution under the conditions described in Example 28.5 afforded the title compound. LCMS-ESI (pos) m/z: 472.1 (M+H)⁺.

To a stirred solution of 28.7 (76 g, 122 mmol) in MeOH (612 mL) at 0° C. was added potassium carbonate (16.92 g, 122 mmol). The mixture was allowed to warm to RT over 1 h to show the desired product by LCMS: The reaction was then concentrated in vacuo and purified on silica gel eluting with 0-40% EtOAc in hexanes to give (1R,2S)-1-hydroxy-N,N-bis(4-methoxybenzyl)-1-(5-methylpyrimidin-2-yl)propane-2-sulfonamide LCMS-ESI (pos) m/z: 472.0 (M+H)⁺.

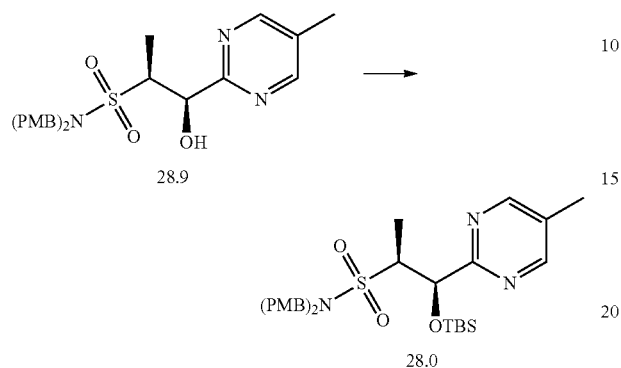

(1R,2S)-1-((tert-Butyldimethylsilyl)oxy)-N,N-bis(4-methoxybenzyl)-1-(5-methylpyrimidin-2-yl)propane-2-sulfonamide, Example 28.0

To a stirred solution of (1R,2S)-1-hydroxy-N,N-bis(4-methoxybenzyl)-1-(5-methylpyrimidin-2-yl)propane-2-sulfonamide (Example 28.9, 28 g, 59.4 mmol) in DCM (297 mL, 59.4 mmol) at 0° C. was added TBSOTf (15.00 mL, 65.3 mmol), followed by TEA (9.12 mL, 65.3 mmol). The mixture was allowed to warm to RT over 1 h and showed desired product by LCMS. The reaction was concentrated in vacuo, and purified on silica gel eluting with 0-30% EtOAc in hexanes to give the desired compound (1R,2S)-1-((tert-butyldimethylsilyl)oxy)-N,N-bis(4-methoxybenzyl)-1-(5-methylpyrimidin-2-yl)propane-2-sulfonamide (15 g, 25.6 mmol, 43.1% yield). LCMS-ESI (pos) m/z: 586.0 (M+H)⁺.

Example 29.0: Preparation of (1R,2S)-1-ethoxy-1-(5-methylpyrimidin-2-yl)propane-2-sulfonamide and (1S,2R)-1-ethoxy-1-(5-methylpyrimidin-2-yl)propane-2-sulfonamide

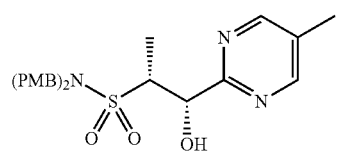

AND

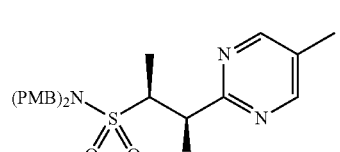

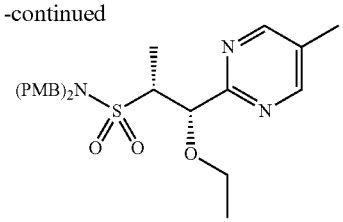

AND

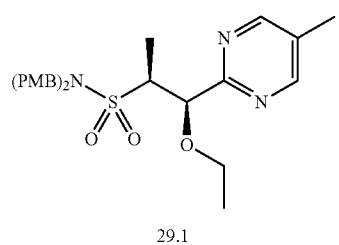

(1R,2S)-1-Ethoxy-N,N-bis(4-methoxybenzyl)-1-(5-methylpyrimidin-2-yl)propane-2-sulfonamide and (1S,2R)-1-ethoxy-N,N-bis(4-methoxybenzyl)-1-(5-methylpyrimidin-2-yl)propane-2-sulfonamide, Example 29.1

To a −78° C. solution of Example 28.2 (1.62 g, 3.4 mmol) in THF (70 mL) was added potassium bis(trimethylsilyl)amide (1.0M solution in THF, 10.6 mL, 10.6 mmol) slowly via syringe. After 1.25 h, EtOTf (1.4 mL, 10.6 mmol) was added slowly via syringe. The resulting orange solution was stirred at −78° C. for 45 min and then was quenched with a 2:1 mixture of saturated aqueous ammonium chloride and water (75 mL). The resulting mixture was extracted with EtOAc (4×). The combined organic layers were dried over anhydrous sodium sulfate and concentrated in vacuo. The residue was purified by silica gel chromatography (eluent: 10-65% EtOAc in hexanes over a 40 min period) to provide 29.1 (1.02 g, 60% yield) as a light yellow oil. LCMS-ESI (pos) m/z: 500.1 (M+H)⁺.

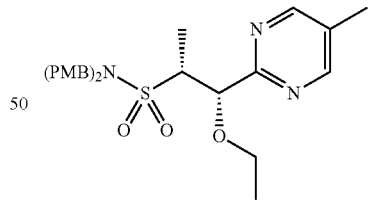

AND

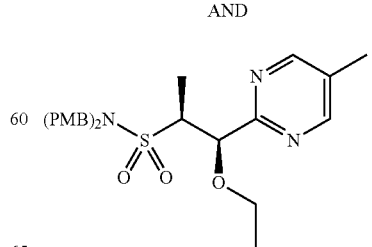

-continued

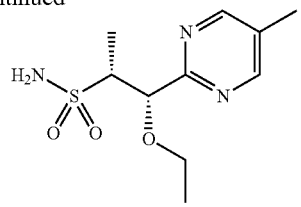

AND

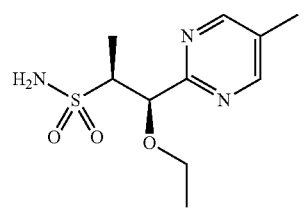

29.0

(1R,2S)-1-Ethoxy-1-(5-methylpyrimidin-2-yl)propane-2-sulfonamide and (1S,2R)-1-ethoxy-1-(5-methylpyrimidin-2-yl)propane-2-sulfonamide, Example 29.0

Example 29.1 (1.02 g, 2.0 mmol) was dissolved in TFA (14 mL). Anisole (466 µL, 4.3 mmol) was then added via syringe. The resulting orange solution was stirred at RT for 16.5 h and then concentrated in vacuo. The residue was purified by silica gel chromatography (eluent: pure DCM grading to 4.5% MeOH in DCM over a 45 min period) to provide the title compound 29.0 (495 mg, 93% yield) as a white solid. LCMS-ESI (pos) m/z: 260.0 (M+H)$^+$.

The compounds set forth in the following table were synthesized following the procedure in Example 29.0 using the known starting material as described.

TABLE 8

| Example | Reagents | Structure, Name and Data |
|---|---|---|
| 29.1 | 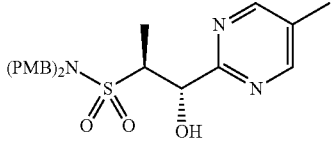<br>AND<br><br>Material prepared in an analogous manner to that of Example 28.2 employing the cis olefin. | 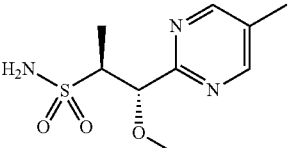<br>AND<br><br>(1R,2R)-1-ethoxy-1-(5-methylpyrimidin-2-yl)propane-2-sulfonamide and (1S,2S)-1-ethoxy-1-(5-methylpyrimidin-2-yl)propane-2-sulfonamide, LCMS-ESI (pos) m/z: 260.0 (M + H)$^+$. |

Example 30.0. Preparation of (2R,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2R,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide 30.0

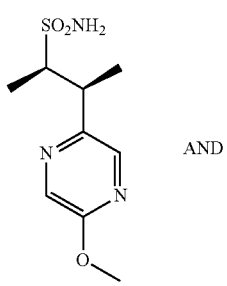 AND

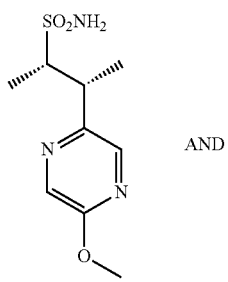 AND

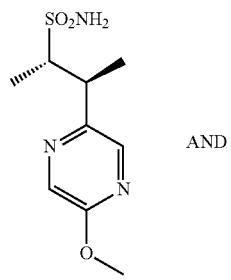 AND

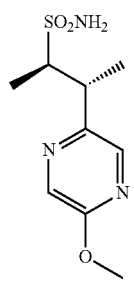

(2R,3R)-3-(5-Methoxypyrazin-2-yl)butane-2-sulfonamide and (2R,3S)-3-(5-methoxypyrazin-2-yl)butane-2-sulfonamide and (2S,3R)-3-(5-methoxypyrazin-2-yl)butane-2-sulfonamide and (2S,3S)-3-(5-methoxypyrazin-2-yl)butane-2-sulfonamide, Example 30.0

Example 30.0 was synthesized following the procedure in Example 1.0 using 2-bromo-5-methoxypyrazine (commercially available from Ark Pharm, Inc.). LCMS-ESI (pos) m/z: 246.2 (M+H)$^+$.

Following the procedure in Example 140.0 and 142.0 the following compounds may be synthesized using the intermediates and conditions as described.

TABLE 9

| Example | Reagents | Structure, Name and Data |
|---|---|---|
| 31.0 | Employing (S)-tert-butyl 3-sulfamoylpiperidine-1-carboxylate and (R)-tert-butyl 3-sulfamoylpiperidine-1-carboxylate (Example 227.0), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0) under the conditions described would deliver the desired material; tert-butyl 3-(N-(4-(4,6-dimethoxypyrimidin-5-yl)-5-tetrahydrofuran-2-yl)-4H-1,2,4-triazol-3-yl)sulfamoyl)piperidine-1-carboxylate. Following the chemistry employed in Example 167.0 using 2-chloro-5-fluoro-pyrimidine would deliver the title compound. | 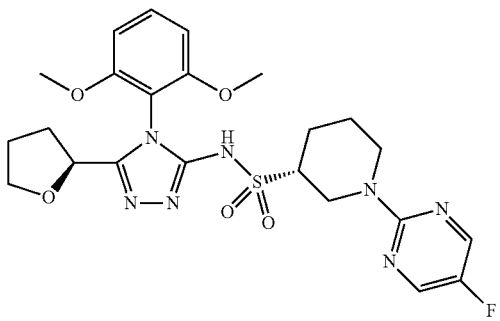<br>AND<br>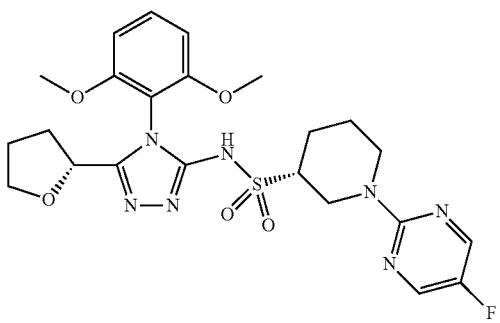<br>AND<br>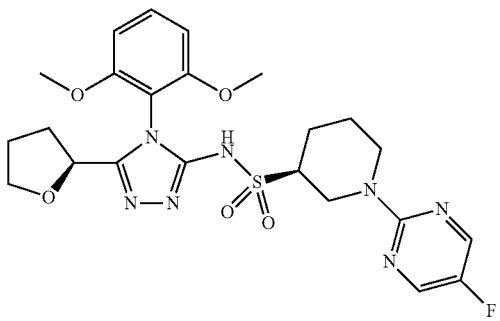<br>AND<br>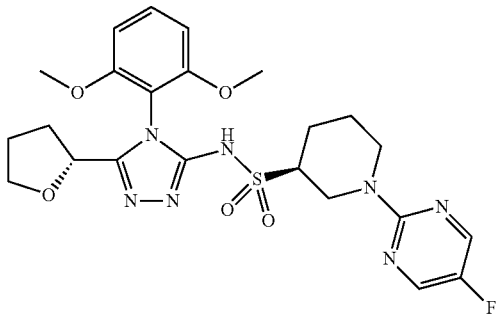 [SMILES: COc1cccc(OC)c1-n1c(NS(=O)(=O)[C@H]2CCCN(c3ncc(F)cn3)C2)nnc1[C@H]1CCCO1]<br>(S)-N-(4-(2,6-dimethoxyphenyl)-5-((R)-tetrahydrofuran-2-yl)-4H-1,2,4-triazol-3-yl)-1-(5-fluoropyrimidin-2-yl)piperidine-3-sulfonamide and (S)-N-(4-(2,6-dimethoxyphenyl)-5-((S)-tetrahydrofuran-2-yl)-4H-1,2,4-triazol-3-yl)-1-(5-fluoropyrimidin-2-yl)piperidine-3-sulfonamide and (R)-N-(4-(2,6-dimethoxyphenyl)-5-((R)-tetrahydrofuran-2-yl)-4H-1,2,4-triazol-3-yl)-1-(5-fluoropyrimidin-2-yl)piperidine-3-sulfonamide |

US 9,988,369 B2

177 178

TABLE 9-continued

| Example | Reagents | Structure, Name and Data |
|---|---|---|
| | | and (R)-N-(4-(2,6-dimethoxyphenyl)-5-((S)-tetrahydrofuran-2-yl)-4H-1,2,4-triazol-3-yl)-1-(5-fluoropyrimidin-2-yl)piperidine-3-sulfonamide. |
| 32.0 | (3S,5S)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide, Example 228.0, (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). | 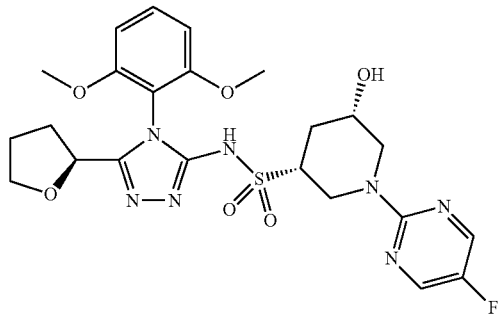<br>AND<br>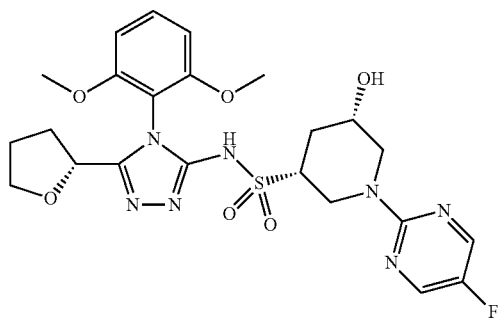<br>AND<br>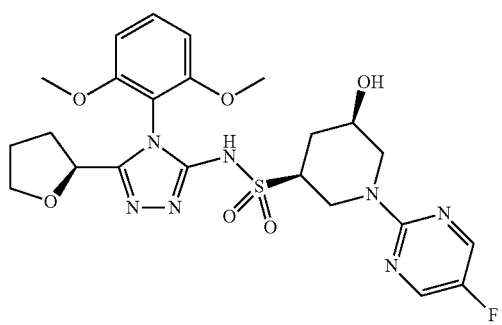<br>AND<br>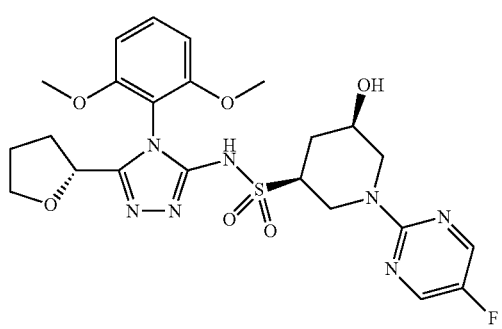<br>AND |

TABLE 9-continued
| Example | Reagents | Structure, Name and Data |
|---|---|---|
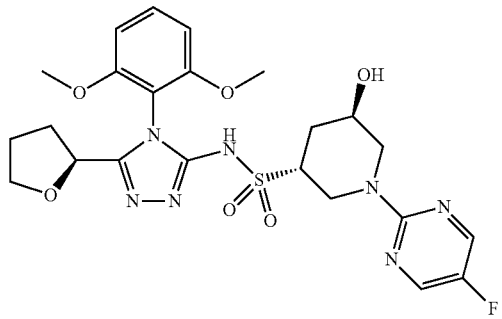
AND
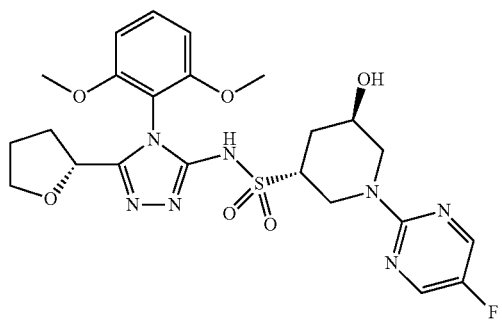
AND
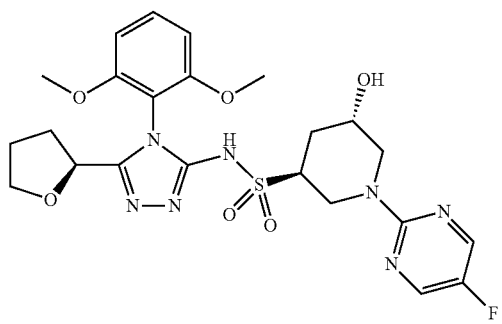
AND
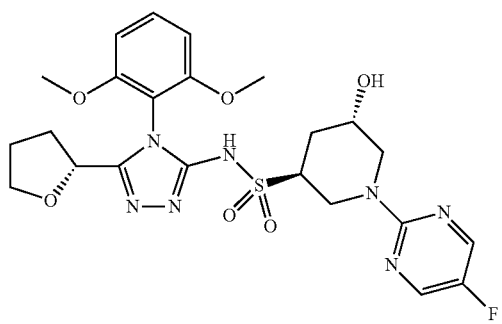 [SMILES: COc1cccc(OC)c1-n1c(NS(=O)(=O)[C@H]2C[C@H](O)CN(c3ncc(F)cn3)C2)nnc1[C@H]1CCCO1]
(3R,5S)-N-(4-(2,6-dimethoxyphenyl)-5-((S)-
tetrahydrofuran-2-yl)-4H-1,2,4-triazol-3-yl)-1-(5-
fluoropyrimidin-2-yl)-5-hydroxypiperidine-3-
sulfonamide and (3R,5S)-N-(4-(2,6-
dimethoxyphenyl)-5-((R)-tetrahydrofuran-2-yl)-
4H-1,2,4-triazol-3-yl)-1-(5-fluoropyrimidin-2-
yl)-5-hydroxypiperidine-3-sulfonamide and
(3R,5R)-N-(4-(2,6-dimethoxyphenyl)-5-((S)-
tetrahydrofuran-2-yl)-4H-1,2,4-triazol-3-yl)-1-(5-

TABLE 9-continued

| Example | Reagents | Structure, Name and Data |
|---|---|---|
| | | fluoropyrimidin-2-yl)-5-hydroxypiperidine-3-sulfonamide and (3R,5R)-N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide and (3S,5R)-N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide and (3S,5R)-N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide and (3S,5S)-N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide and (3S,5S)-N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide. |
| 33.0 | (3S,5R)-1-(5-fluoropyrimidin-2-yl)-5-methoxypiperidine-3-sulfonamide and (3R,5S)-1-(5-fluoropyrimidin-2-yl)-5-methoxypiperidine-3-sulfonamide, Example 229.3 and (3S,5S)-1-(5-fluoropyrimidin-2-yl)-5-methoxypiperidine-3-sulfonamide and (3R,5R)-1-(5-fluoropyrimidin-2-yl)-5-methoxypiperidine-3-sulfonamide, Example 229.4, (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). | 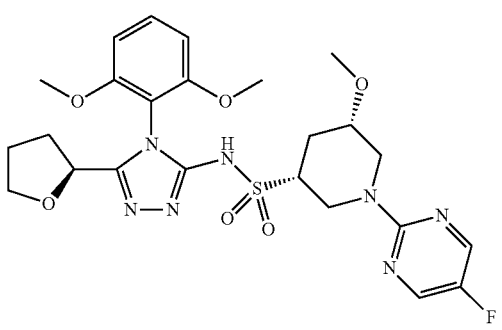

AND

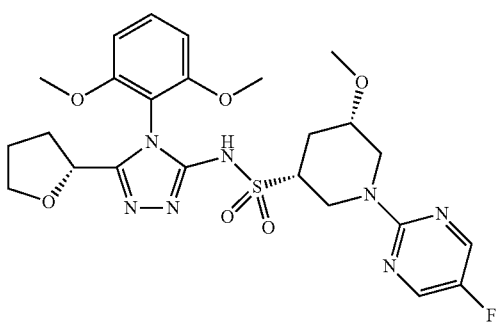

AND

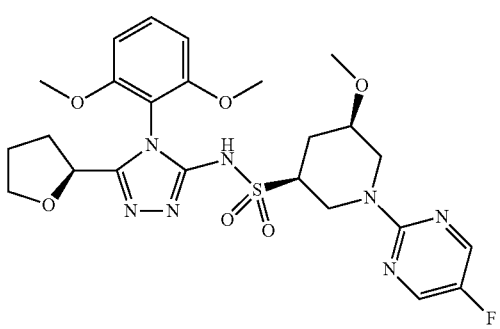

AND |

TABLE 9-continued
| Example | Reagents | Structure, Name and Data |
|---|---|---|
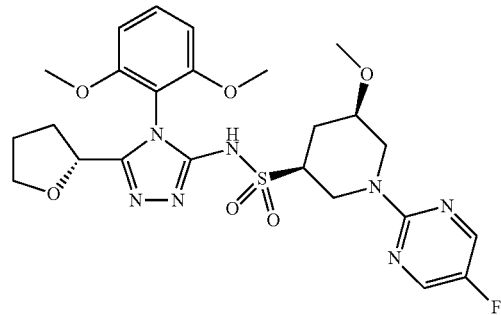
AND
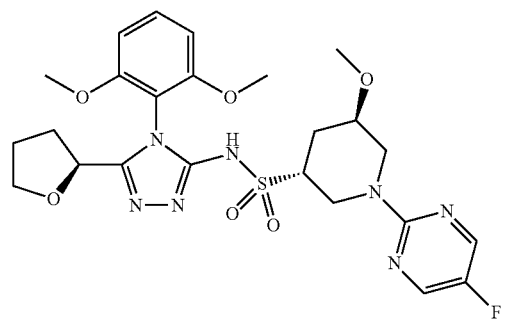
AND
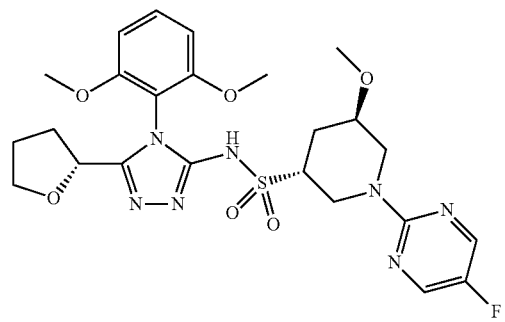
AND TABLE 9-continued

| Example | Reagents | Structure, Name and Data |
|---|---|---|

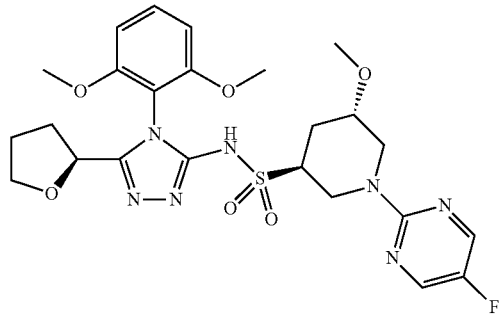

AND

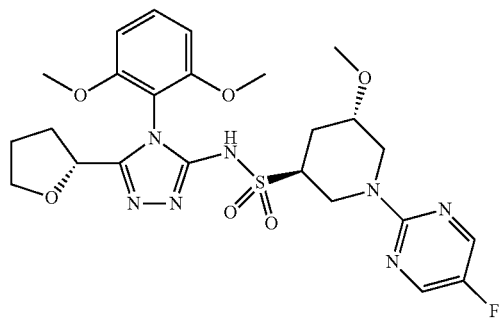 [SMILES: COc1cccc(OC)c1-n1c(NS(=O)(=O)[C@H]2C[C@H](OC)CN(c3ncc(F)cn3)C2)nnc1[C@H]1CCCO1]

(3R,5S)-N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide and (3R,5S)-N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide and (3R,5R)-N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide and (3R,5R)-N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide and (3S,5R)-N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide and (3S,5R)-N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide and (3S,5S)-N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide and (3S,5S)-N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide.

TABLE 9-continued

| Example | Reagents | Structure, Name and Data |
|---|---|---|
| 34.0 | (3S,5S)-5-ethoxy-1-(5-fluoropyrimidin-2-yl)piperidine-3-sulfonamide and (3S,5R)-5-ethoxy-1-(5-fluoropyrimidin-2-yl)piperidine-3-sulfonamide and (3R,5S)-5-ethoxy-1-(5-fluoropyrimidin-2-yl)piperidine-3-sulfonamide and (3R,5R)-5-ethoxy-1-(5-fluoropyrimidin-2-yl)piperidine-3-sulfonamide may be made in analogous manner to that described in Example 229.0 employing 5-ethoxypyridine-3-sulfonyl chloride, (R)-tetrahydrofuran-2-carbohydrazide and (S)-tetrahydrofuran-2-carbohydrazide (commercially available from Enamine), 2-isothiocyanato-1,3-dimethoxybenzene (Example 10.0) | 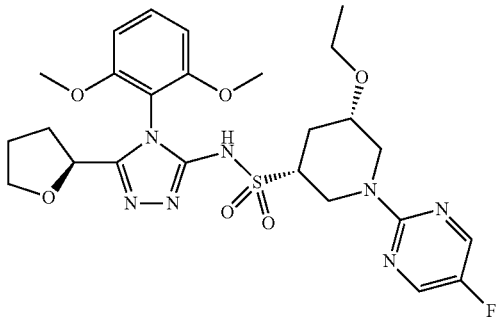<br>AND<br>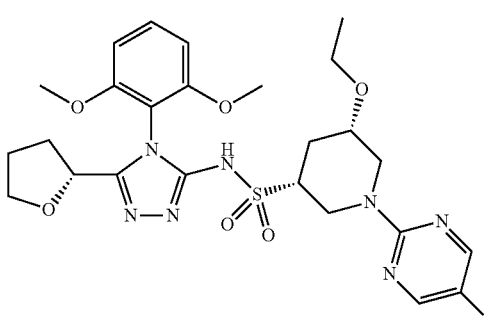<br>AND<br>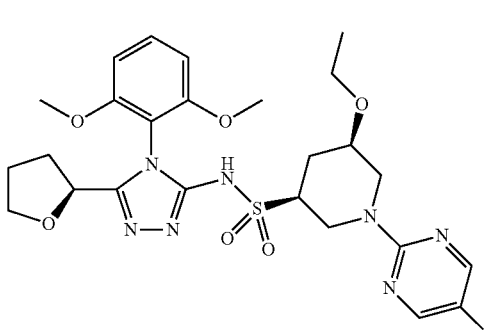<br>AND<br>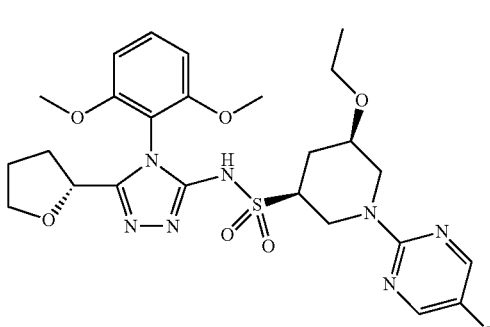<br>AND |

TABLE 9-continued
| Example | Reagents | Structure, Name and Data |
|---|---|---|
| | | 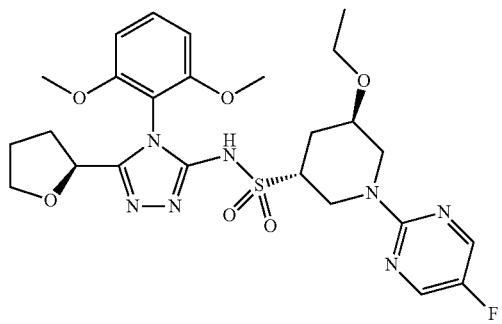
AND
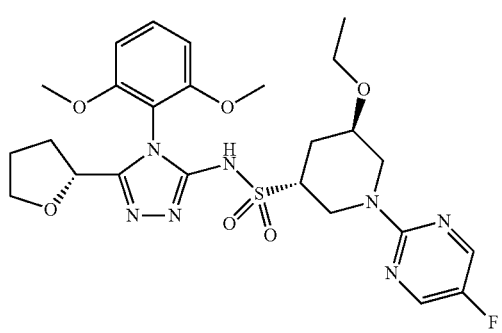
AND
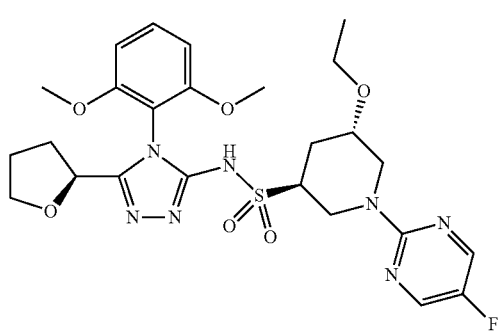
AND
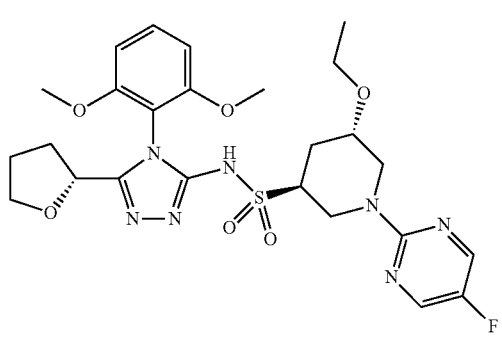 [SMILES: CCO[C@H]1C[C@H](S(=O)(=O)Nc2nnc([C@H]3CCCO3)n2-c2c(OC)cccc2OC)CN(c2ncc(F)cn2)C1]
(3R,5S)-N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide and (3R,5S)-N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide and (3R,5R)-N-(4-(2,6-dimethoxyphenyl)-5-((R)- |

TABLE 9-continued

| Example | Reagents | Structure, Name and Data |
|---|---|---|
| | | tetrahydrofuran-2-yl)-4H-1,2,4-triazol-3-yl)-5-ethoxy-1-(5-fluoropyrimidin-2-yl)piperidine-3-sulfonamide and (3R,5R)-N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide and (3S,5R)-N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide and (3S,5R)-N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide and (3S,5S)-N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide and (3S,5S)-N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide |

Example 35.0. Preparation of (2S,3R)-3-(5-chloro-2-pyrimidinyl)-N-(4-(4,6-dimethoxy-5-pyrimidinyl)-5-(3-oxetanyl)-4H-1,2,4-triazol-3-yl)-2-butanesulfonamide

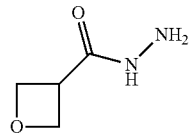

35.1

Oxetane-3-carbohydrazide, Example 35.1

To a solution of methyl oxetane-3-carboxylate (1 g, 8.61 mmol) in MeOH (17 mL) was added hydrazine (2.70 mL, 86 mmol). The reaction was stirred at 23° C. for 62 h. LCMS showed desired product oxetane-3-carbohydrazide. The solution was concentrated in vacuo. The residual white solid was triturated with EtOAc. The product was used without further purification. LCMS-ESI (pos) m/z: 117.2 (M+H)$^+$.

Following the procedure in Example 140.0, the following compounds were also synthesized using the intermediates and conditions as described.

TABLE 10

| Example | Reagents | Structure, Name and Data |
|---|---|---|
| 35.0 | (2S,3R)-3-(5-chloropyrimidin-2-yl)butane-2-sulfonamide (Example 1.4), oxetane-3-carbohydrazide, (Example 35.1), 5-isothiocyanato-4,6-dimethoxypyrimidine (Example 10.1). | (2S,3R)-3-(5-chloro-2-pyrimidinyl)-N-(4-(4,6-dimethoxy-5-pyrimidinyl)-5-(3-oxetanyl)-4H-1,2,4-triazol-3-yl)-2-butanesulfonamide. $^1$H NMR (400 MHz, CD$_2$Cl$_2$) δ 1.32 (d, J = 7.05 Hz, 3 H) 1.36 (d, J = 7.05 Hz, 3 H) 3.65-3.73 (m, 1 H) 3.73-3.83 (m, 1 H) 3.88 (11, J = 8.45, 6.69 Hz, 1 H) 4.00 (s, 3 H) 4.01 (s, 3 H) 4.74 (dd, J = 8.40, 5.91 Hz, 2 H) 4.83-4.92 (m, 2 H) 8.56 (s, 1 H) 8.67 (s, 2 H) 10.88 (br. s., 1 H). LCMS-ESI (pos) m/z: 511.2 (M + H)$^+$. |

| Example | Reagents | Structure, Name and Data |
|---|---|---|
| 36.0 | (2S,3R)-3-(5-chloropyrimidin-2-yl)butane-2-sulfonamide (Example 1.4), oxetane-3-carbohydrazide, (Example 35.1), 2-isothiocyanato-1,3-dimethoxybenzene (Example 10.0). | (2S,3R)-3-(5-chloro-2-pyrimidinyl)-N-(4-(2,6-dimethoxyphenyl)-5-(3-oxetanyl)-4H-1,2,4-triazol-3-yl)-2-butanesulfonamide. <br> $^1$H NMR (400 MHz, CDCl$_3$) δ 1.29 (d, J = 6.84 Hz, 3 H) 1.33 (d, J = 6.84 Hz, 3 H) 3.72 (s, 3 H) 3.73 (s, 3 H) 3.74-3.84 (m, 3 H) 4.62 (ddd, J = 8.40, 6.12, 2.07 Hz, 2 H) 4.86 (dt, J = 9.23, 6.48 Hz, 2 H) 6.60 (dd, J = 8.50, 3.94 Hz, 2 H) 7.36 (t, J = 8.39 Hz, 1 H) 8.59 (s, 2 H) 11.11 (br. s., 1 H). LCMS-ESI (pos) m/z: 509.2 (M + H)$^+$. |
| 37.0 | (2S,3R)-3-(5-chloropyridin-2-yl)butane-2-sulfonamide (Example 14.0), (R)-tetrahydrofuran-3-carbohydrazide and (S)-tetrahydrofuran-3-carbohydrazide(Frontier Scientific Services, Inc.), 5-isothiocyanato-4,6-dimethoxypyrimidine (Example 10.1). Example 37.0 was the first peak (earlier peak vs. its opposite THF epimer) on IC column. Peak assignment was determined by SFC: Chiralpak IC, 40% MeOH. | OR <br><br> (2S,3R)-3-(5-chloro-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide or (2S,3R)-3-(5-chloro-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide. <br> $^1$H NMR (400 MHz, CD$_3$OD) δ 1.22 (d, J = 7.05 Hz, 3 H) 1.28-1.36 (m, 3 H) 2.03-2.23 (m, 2 H) 3.09-3.22 (m, 1 H) 3.53 (qd, J = 7.01, 4.25 Hz, 1 H) 3.58-3.70 (m, 1 H) 3.72-3.96 (m, 4 H) 4.01 (s, 3 H) 4.02 (s, 3 H) 7.27 (d, J = 8.50 Hz, 1 H) 7.75 (dd, J = 8.50, 2.49 Hz, 1 H) 8.46 (d, J = 3.70 Hz, 1 H) 8.58 (s, 1 H). LCMS-ESI (pos) m/z: 524.2 (M + H)$^+$. |

TABLE 10-continued

| Example | Reagents | Structure, Name and Data |
|---|---|---|
| 38.0 | The title compound is the THF epimer of Example 37. The second peak (later peak vs. its THF epimer) on Chiralpak IC column. SFC: Chiralpak IC, 40% MeOH | 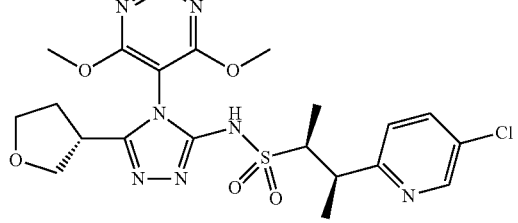<br>OR<br>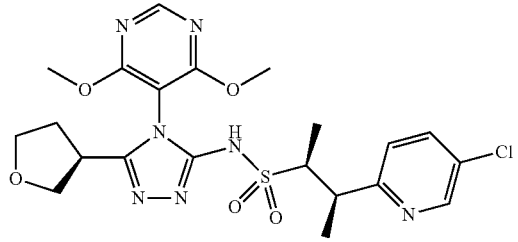<br>(2S,3R)-3-(5-chloro-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide or (2S,3R)-3-(5-chloro-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide.<br>$^1$H NMR (400 MHz, CD$_3$OD) δ 1.22 (d, J = 7.05 Hz, 3 H) 1.32 (d, J = 7.05 Hz, 3 H) 1.99-2.21 (m, 2 H) 3.11-3.24 (m, 1 H) 3.47-3.58 (m, 1 H) 3.63 (qd, J = 7.15, 4.25 Hz, 1 H) 3.73-3.96 (m, 4 H) 4.01 (s, 3 H) 4.02 (s, 3 H) 7.27 (d, J = 8.50 Hz, 1 H) 7.75 (dd, J = 8.40, 2.59 Hz, 1 H) 8.46 (d, J = 2.62 Hz, 1 H) 8.58 (s, 1 H). LCMS-ESI (pos) m/z: 524.1 (M + H)$^+$. |
| 39.0 | (2S,3R)-3-(5-chloropyridin-2-yl)butane-2-sulfonamide (Example 1.4), (R)-1,4-dioxane-2-carbohydrazide and (S)-1,4-dioxane-2-carbohydrazide (Frontier Scientific Services, Inc.), 2-isothiocyanato-1,3-dimethoxybenzene (Example 10.0). Example 39.0 was the first peak (earlier peak vs. its opposite dioxane epimer) on AD-H column. Peak assignment was determined by SFC: Chiralpak AD-H, 40% IPA. | 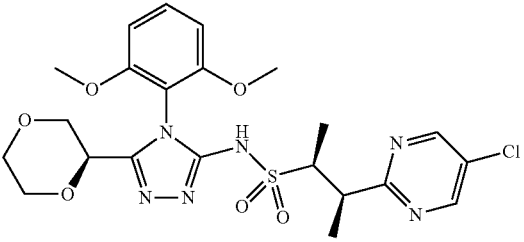<br>OR<br>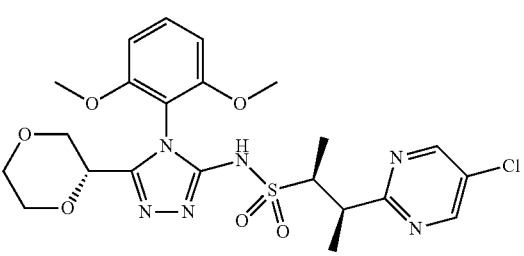<br>(2S,3R)-3-(5-chloro-2-pyrimidinyl)-N-(4-(2,6-dimethoxyphenyl)-5-((2R)-1,4-dioxan-2-yl)-4H-1,2,4-triazol-3-yl)-2-butanesulfonamide or (2S,3R)-3-(5-chloro-2-pyrimidinyl)-N-(4-(2,6-dimethoxyphenyl)-5-((2S)-1,4-dioxan-2-yl)-4H-1,2,4-triazol-3-yl)-2-butanesulfonamide.<br>$^1$H NMR (400 MHz, CDCl$_3$) δ 1.33 (d, J = 6.84 Hz, 3 H) 1.36 (d, J = 7.05 Hz, 3 H) 3.53-3.63 (m, 1 H) 3.68-3.72 (m, 2 H) 3.73-3.80 (m, 1 H) 3.80 (s, 3 H) 3.81 (s, 3 H) 3.82-3.92 (m, 4 H) |

TABLE 10-continued

| Example | Reagents | Structure, Name and Data |
|---|---|---|
| | | 4.29 (dd, J = 8.29, 3.32 Hz, 1 H) 6.64-6.69 (m, 2 H) 7.43 (t, J = 8.50 Hz, 1 H) 8.63 (s, 2 H). LCMS-ESI (pos) m/z: 539.1 (M + H)+. |
| 40.0 | The title compound is the dioxane epimer of Example 39.0. The second peak (later peak vs. its dioxane epimer) on Chiralpak IC column. Peak assignment was determined by SFC: Chiralpak AD-H, 40% IPA. | 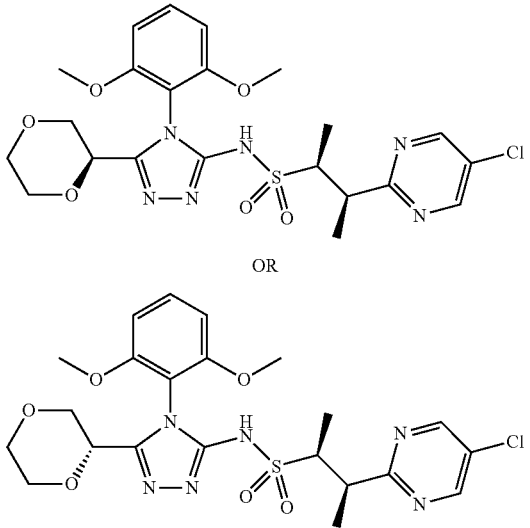 [SMILES: COc1cccc(OC)c1-n1c(NS(=O)(=O)[C@@H](C)[C@H](C)c2ncc(Cl)cn2)nnc1[C@@H]1COCCO1 ; COc1cccc(OC)c1-n1c(NS(=O)(=O)[C@@H](C)[C@H](C)c2ncc(Cl)cn2)nnc1[C@H]1COCCO1]<br>OR<br><br>(2S,3R)-3-(5-chloro-2-pyrimidinyl)-N-(4-(2,6-dimethoxyphenyl)-5-((2R)-1,4-dioxan-2-yl)-4H-1,2,4-triazol-3-yl)-2-butanesulfonamide or (2S,3R)-3-(5-chloro-2-pyrimidinyl)-N-(4-(2,6-dimethoxyphenyl)-5-((2S)-1,4-dioxan-2-yl)-4H-1,2,4-triazol-3-yl)-2-butanesulfonamide. <br>$^1$H NMR (400 MHz, CDCl$_3$) δ 1.33 (d, J = 7.05 Hz, 3 H) 1.36 (d, J = 7.05 Hz, 3 H) 3.50-3.64 (m, 1 H) 3.68-3.73 (m, 2 H) 3.73-3.78 (m, 1 H) 3.80 (s, 3H) 3.81 (s, 3H) 3.78-3.92 (m, 4 H) 4.29 (dd, J = 8.19, 3.42 Hz, 1 H) 6.66 (ddd, J = 11.71, 8.50, 0.93 Hz, 2 H) 7.43 (t, J = 8.50 Hz, 1 H) 8.63 (s, 2 H). LCMS-ESI (pos) m/z: 539.0 (M + H)+. |
| 41.0 | (2S,3R)-3-(5-chloropyridin-2-yl)butane-2-sulfonamide (Example 1.4), (R)-tert-butyl 3-(hydrazinecarbonyl)pyrrolidine-1-carboxylate and (S)-tert-butyl 3-(hydrazinecarbonyl)pyrrolidine-1-carboxylate (Frontier Scientific Services, Inc.), 2-isothiocyanato-1,3-dimethoxybenzene (Example 10.0). Example 41.0 was the first peak (earlier peak vs. its opposite pyrrolidine epimer) on AD-H column. Peak assignment was determined by SFC: Chiralpak AD-H, 35% IPA. | 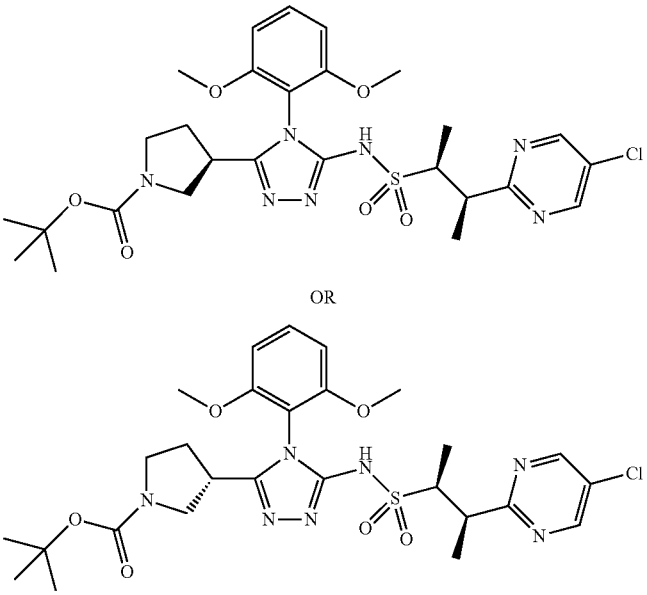 [SMILES: COc1cccc(OC)c1-n1c(NS(=O)(=O)[C@@H](C)[C@H](C)c2ncc(Cl)cn2)nnc1[C@@H]1CCN(C(=O)OC(C)(C)C)C1 ; COc1cccc(OC)c1-n1c(NS(=O)(=O)[C@@H](C)[C@H](C)c2ncc(Cl)cn2)nnc1[C@H]1CCN(C(=O)OC(C)(C)C)C1]<br>OR<br><br>tert-butyl (3R)-3-(5-(((((1S,2R)-2-(5-chloro-2-pyrimidinyl)-1-methylpropyl)sulfonyl)amino)-4-(2,6-dimethoxyphenyl)-4H-1,2,4-triazol-3-yl)-1-pyrrolidinecarboxylate or tert-butyl (3S)-345-(((((1S,2R)-2-(5-chloro-2-pyrimidinyl)-1- |

TABLE 10-continued

| Example | Reagents | Structure, Name and Data |
|---|---|---|
| | | methylpropyl)sulfonyl)amino)-4-(2,6-dimethoxyphenyl)-4H-1,2,4-triazol-3-yl)-1-pyrrolidinecarboxylate.<br>¹H NMR (400 MHz, CD₃OD) δ 1.28 (d, J = 6.84 Hz, 3 H) 1.33 (d, J = 7.05 Hz, 3 H) 1.45 (s, 9 H) 2.02-2.10 (m, 1 H) 2.10-2.21 (m, 1 H) 3.02-3.09 (m, 1 H) 3.35-3.55 (m, 4 H) 3.67-3.78 (m, 2 H) 3.84 (s, 3H) 3.85 (s, 3 H) 6.85 (d, J = 8.27 Hz, 2 H) 7.54 (t, J = 8.18 Hz, 1 H) 8.72 (s, 2 H). LCMS-ESI (pos) m/z: 621.3 (M + H)⁺. |
| 42.0 | The title compound is the pyrrolidine epimer of Example 41.0. The second peak (later peak vs. its pyrrolidine epimer) on Chiralpak IC column. Peak assignment was determined by SFC: Chiralpak AD-H, 35% IPA. | 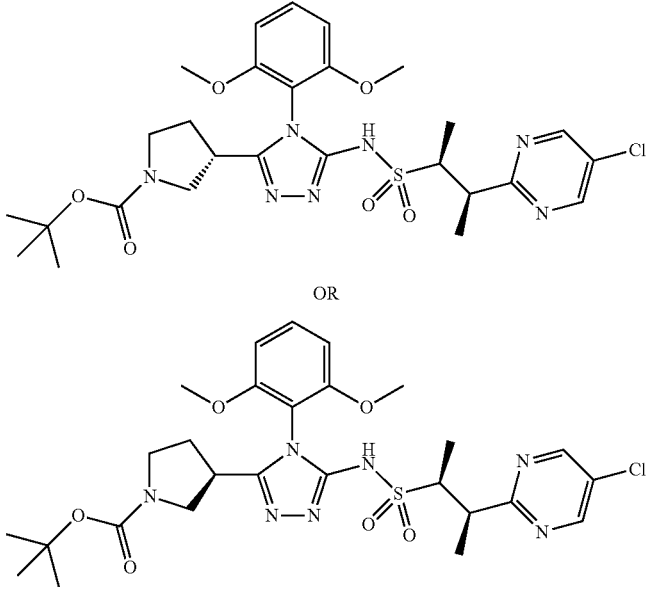 [SMILES: COc1cccc(OC)c1-n1c(NS(=O)(=O)[C@@H](C)[C@H](C)c2ncc(Cl)cn2)nnc1[C@H]1CCN(C(=O)OC(C)(C)C)C1 ; COc1cccc(OC)c1-n1c(NS(=O)(=O)[C@@H](C)[C@H](C)c2ncc(Cl)cn2)nnc1[C@@H]1CCN(C(=O)OC(C)(C)C)C1]<br>OR<br>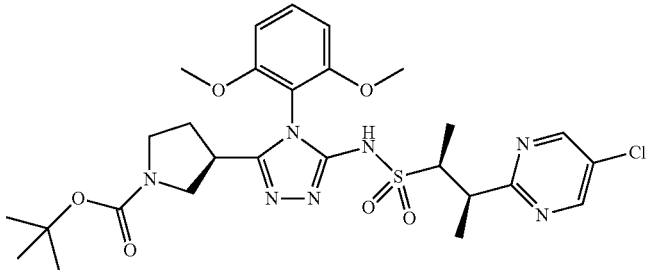<br>tert-butyl (3S)-3-(5-((((1S,2R)-2-(5-chloro-2-pyrimidinyl)-1-methylpropyl)sulfonyl)amino)-4-(2,6-dimethoxyphenyl)-4H-1,2,4-triazol-3-yl)-1-pyrrolidinecarboxylate or tert-butyl (3R)-3-(5-((((1S,2R)-2-(5-chloro-2-pyrimidinyl)-1-methylpropyl)sulfonyl)amino)-4-(2,6-dimethoxyphenyl)-4H-1,2,4-triazol-3-yl)-1-pyrrolidinecarboxylate. ¹H NMR (400 MHz, CD₃OD) δ 1.26 (d, J = 6.84 Hz, 3 H) 1.32 (d, J = 7.05 Hz, 3 H) 1.44 (s, 9 H) 1.98-2.20 (m, 2 H) 2.95-3.11 (m, 1 H) 3.34-3.53 (m, 4 H) 3.61-3.79 (m, 2 H) 3.82 (s, 3 H) 3.84 (s, 3 H) 6.84 (d, J = 8.71 Hz, 2 H) 7.53 (t, J = 8.23 Hz, 1 H) 8.71 (s, 2 H). LCMS-ESI (pos) m/z: 621.4 (M + H)⁺. |

Example 43.0. Preparation of 2-(2-cyano-4-fluorophenyl)-N-(4-(2,6-dimethoxyphenyl)-5-((2R)-5-oxo-2-pyrrolidinyl)-4H-1,2,4-triazol-3-yl)ethanesulfonamide

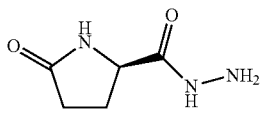

43.1

Ethyl (R)-(−)-2-pyrrolidone-5-carboxylate, Example 43.1

To a 250-mL round-bottomed flask was added ethyl (R)-(−)-2-pyrrolidone-5-carboxylate (4.62 g, 29.4 mmol, available from Aldrich) and anhydrous hydrazine (3.36 mL, 147 mmol) in MeOH (30 mL). The reaction mixture was stirred at 23° C. for 72 h. LCMS analysis indicated the reaction was complete. The solution was concentrated in vacuo to give the material as a white solid. The solid thus obtained was triturated with ether to afford the title compound, Example 43.1 (4.2 g, 29.3 mmol, 100% yield) as a white solid. LCMS-ESI (pos), m/z, 144.2 (M+H)⁺.

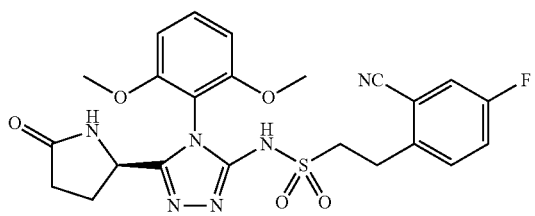

2-(2-Cyano-4-fluorophenyl)-N-(4-(2,6-dimethoxyphenyl)-5-((2R)-5-oxo-2-pyrrolidinyl)-4H-1-1,2,4-triazol-3-yl)ethanesulfonamide, Example 43.0

The title compound was prepared from Example 43.1 and Example 146.7 using the conditions described in Example 140.0. $^1$H NMR (500 MHz, CDCl$_3$) δ 7.48-7.53 (m, 1H) 7.40 (dd, J=8.56, 5.14 Hz, 1H) 7.32 (dd, J=7.83, 2.69 Hz, 1H) 7.26 (td, J=8.38, 2.81 Hz, 1H) 6.72 (t, J=8.80 Hz, 2H) 4.61 (dd, J=8.07, 5.14 Hz, 1H) 3.87 (s, 3H) 3.85 (s, 3H) 3.34-3.42 (m, 2H) 3.26-3.34 (m, 2H) 2.23-2.46 (m, 4H). LCMS-ESI (pos), m/z, 515.2 (M+H)$^+$.

Example 44.0. Preparation of 2-(2-cyano-4-fluorophenyl)-N-(4-(2,6-dimethoxyphenyl)-5-((2R)-5-oxo-2-pyrrolidinyl)-4H-1,2,4-triazol-3-yl)ethanesulfonamide

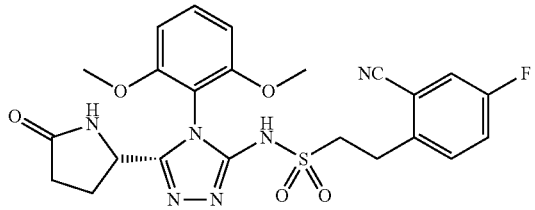

2-(2-Cyano-4-fluorophenyl)-N-(4-(2,6-dimethoxyphenyl)-5-((2S)-5-oxo-2-pyrrolidinyl)-4H-1,2,4-triazol-3-yl)ethanesulfonamide, Example 44.0

The title compound was prepared from ethyl (S)-(−)-2-pyrrolidone-5-carboxylate (available from Aldrich) using the same chemistry methodology as that described in Example 43.0. $^1$H NMR (500 MHz, CDCl$_3$) δ 7.48-7.54 (m, 1H) 7.40 (dd, J=8.56, 5.14 Hz, 1H) 7.32 (dd, J=7.83, 2.69 Hz, 1H) 7.26 (td, J=8.38, 2.81 Hz, 1H) 6.72 (t, J=8.80 Hz, 2H) 4.61 (dd, J=7.95, 5.01 Hz, 1H) 3.87 (s, 3H) 3.85 (s, 3H) 3.34-3.43 (m, 2H) 3.25-3.33 (m, 2H) 2.23-2.46 (m, 4H). LCMS-ESI (pos), m/z: 515.2 (M+H)$^+$.

Example 45.0. Preparation (1R,2S)—N-(4-(2,6-dimethoxyphenyl)-5-((R)-pyrrolidin-3-yl)-4H-1,2,4-triazol-3-yl)-1-methoxy-1-(5-methylpyrimidin-2-yl) propane-2-sulfonamide and (1R,2S)—N-(4-(2,6-dimethoxyphenyl)-5-((S)-pyrrolidin-3-yl)-4H-1,2,4-triazol-3-yl)-1-methoxy-1-(5-methylpyrimidin-2-yl) propane-2-sulfonamide

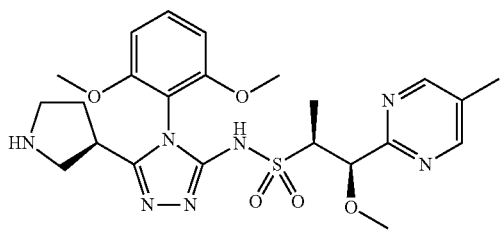

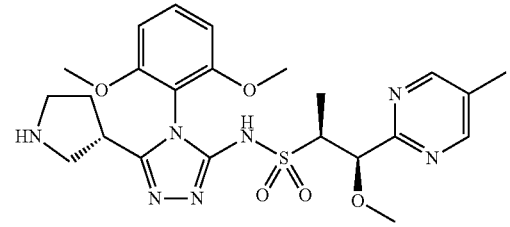

(1R,2S)—N-(4-(2,6-Dimethoxyphenyl)-5-((R)-pyrrolidin-3-yl)-4H-1,2,4-triazol-3-yl)-1-methoxy-1-(5-methylpyrimidin-2-yl)propane-2-sulfonamide and (1R,2S)—N-(4-(2,6-dimethoxyphenyl)-5-((S)-pyrrolidin-3-yl)-4H-1,2,4-triazol-3-yl)-1-methoxy-1-(5-methylpyrimidin-2-yl)propane-2-sulfonamide, Example 45.0

Following the procedure in Example 140.0 using MSA instead of sodium hydroxide afforded the title compound. $^1$H NMR (500 MHz, DMSO-d$_6$) δ 12.98 (br. s., 1H), 8.89-9.22 (m, 2H), 8.64 (s, 2H), 7.54 (t, J=8.50 Hz, 1H), 6.83-6.94 (m, 2H), 4.79 (br. s., 1H), 3.77 (m, 6H), 3.35-3.42 (m, 1H), 3.16-3.34 (m, 4H), 3.10-3.15 (m, 4H), 2.26 (s, 3H), 1.96 (q, J=7.42 Hz, 2H), 1.12 (d, J=6.94 Hz, 3H). LCMS-ESI (pos) m/z: 518.1 (M+H)$^+$.

Following the procedure in Example 140.0, the following compounds were also synthesized using the intermediates and conditions as described.

TABLE 11

| Example | Reagents | Structure, Name and Data |
|---|---|---|
| 47.0 | (2S,3R)-3-(5-chloropyrimidin-2-yl)butane-2-sulfonamide (Example 1.4), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid CO$_2$, B: IPA, Flow Rate: 60 mL/min, 220 nm, 100 bar inlet pressure to deliver peak 1. | OR<br><br>(2S,3R)-3-(5-chloro-2-pyrimidinyl)-N-(4-(2,6-dimethoxyphenyl)-5-((2S)-tetrahydro-2-furanyl)-4H-1,2,4-triazol-3-yl)-2-butanesulfonamide or (2S,3R)-3-(5-chloro-2-pyrimidinyl)-N-(4-(2,6-dimethoxyphenyl)-5-((2R)-tetrahydro-2-furanyl)-4H-1,2,4-triazol-3-yl)-2-butanesulfonamide. $^1$H NMR (400 MHz, DMSO-d$_6$) δ 12.77 (s, 1H), 8.89-8.83 (m, 2H), 7.47 (t, J = 8.5 Hz, 1H), 6.82 (dd, J = 1.5, 8.5 Hz, 2H), 4.49 (dd, J = 5.7, 7.8 Hz, 1H), 3.74 (s, 3H), 3.73 (s, 3H), 3.68-3.60 (m, 2H), 3.57-3.47 (m, 2H), 2.15-2.06 (m, 1H), 2.05-1.95 (m, 1H), 1.84-1.75 (m, 2H), 1.23 (d, J = 7.0 Hz, 3H), 1.09 (d, J = 7.0 Hz, 3H). LCMS (pos) m/z: 523.2 (M + H)$^+$. |
| 48.0 | (2S,3R)-3-(5-methylpyrimidin-2-yl)butane-2-sulfonamide (Example 1.0), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). | AND<br><br>(2S,3R)-N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide and (2S,3R)-N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide. $^1$H NMR (500 MHz, DMSO-d$_6$) 12.92 (s, 1H), 8.58 (s, 2H), 7.47 (t, J = 8.6 Hz, 1H), 6.82 (dd, J = 3.2, 8.4 Hz, 2H), 4.49 (dd, J = 5.6, 7.7 Hz, 1H), 3.73 (s, 3H), 3.71 (s, 3H), 3.68-3.61 (m, 2H), 3.59-3.53 (m, 1H), 3.53-3.47 (m, 1H), 2.23 (s, 3H), 2.13-2.06 (m, 1H), 2.03-1.95 (m, 1H), 1.84-1.74 (m, 2H), 1.22 (d, J = 7.0 Hz, 3H), 1.06 (d, J = 7.0 Hz, 3H). LCMS (pos) m/z: 503.2 (M + H)$^+$. |

TABLE 11-continued

| Example | Reagents | Structure, Name and Data |
|---|---|---|
| 49.0 | (2S,3R)-3-(5-methylpyrimidin-2-yl)butane-2-sulfonamide (Example 1.0), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid $CO_2$, B: IPA, Flow Rate: 60 mL/min, 220 nm, 100 bar inlet pressure to provide peak 1. | 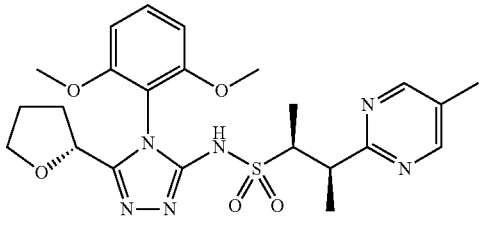<br>OR<br>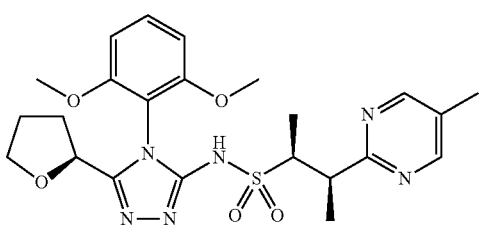<br>(2S,3R)-N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide. $^1$H NMR (400 MHz, $CD_2Cl_2$) δ 11.00 (br. s., 1H), 8.50 (d, J = 0.6 Hz, 2H), 7.50-7.43 (m, 1H), 6.71 (q, J = 1.0 Hz, 1H), 6.69 (q, J = 1.0 Hz, 1H), 4.63-4.57 (m, 1H), 3.80 (s, 3H), 3.79 (s, 3H), 3.77-3.58 (m, 4H), 2.30-2.22 (m, 4H), 2.05-1.81 (m, 3H), 1.30 (d, J = 7.0 Hz, 3H), 1.25 (d, J = 7.0 Hz, 3H). LCMS (pos) m/z: 503.2 (M + H)$^+$. |
| 50.0 | (2S,3R)-3-(5-methylpyrimidin-2-yl)butane-2-sulfonamide (Example 1.0), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid $CO_2$, B: IPA, Flow Rate: 60 mL/min, 220 nm, 100 bar inlet pressure to provide peak 2. | 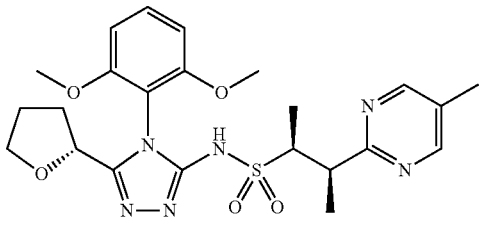<br>OR<br>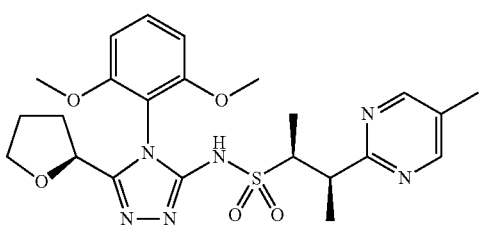<br>(2S,3R)-N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide. $^1$H NMR (400 MHz, $CD_2Cl_2$) δ 11.06 (br. s., 1H), 8.51 (d, J = 0.6 Hz, 2H), 7.49-7.43 (m, 1H), 6.73-6.67 (m, 2H), 4.62-4.56 (m, 1H), 3.83-3.80 (m, 3H), 3.79 (s, 3H), 3.77-3.68 (m, 3H), 3.64-3.57 (m, 1H), 2.30-2.20 (m, 4H), 2.07-1.82 (m, 3H), 1.30 (d, J = 7.0 Hz, 3H), 1.26 (d, J = 7.0 Hz, 3H). LCMS (pos) m/z: 503.2 (M + H)$^+$. |

TABLE 11-continued

| Example | Reagents | Structure, Name and Data |
|---|---|---|
| 51.0 | (1R,2S)-1-(5-chloropyrimidin-2-yl)-1-methoxypropane-2-sulfonamide (Example 11.3), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: AD-H (2 × 25 cm) Mobile Phase: 65:35 (A:B) A: Liquid $CO_2$, B: IPA, Flow Rate: 80 mL/min, 215 nm, 100 bar inlet pressure to deliver peak 1. | 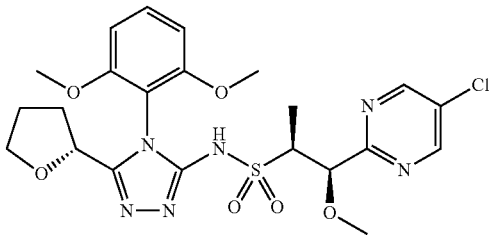<br>OR<br>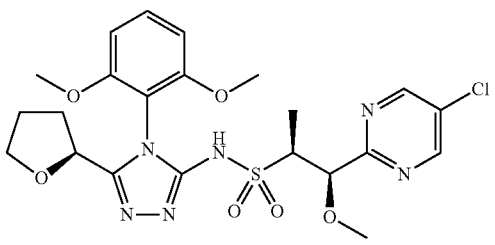<br>(1R,2S)-1-(5-chloropyrimidin-2-yl)-N-(4-(2,6-dimethoxyphenyl)-5-((R)-tetrahydrofuran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-tetrahydrofuran-2-yl)-4H-1,2,4-triazol-3-yl)-1-methoxypropane-2-sulfonamide. $^1$H NMR (400 MHz, DMSO-$d_6$) δ 12.82 (br. s., 1H), 8.96-8.88 (m, 2H), 7.48 (t, J = 8.5 Hz, 1H), 6.83 (dd, J = 1.7, 8.5 Hz, 2H), 4.77 (d, J = 4.4 Hz, 1H), 4.50 (dd, J = 5.6, 7.7 Hz, 1H), 3.76 (s, 3H), 3.74 (s, 3H), 3.67-3.60 (m, 1H), 3.58-3.35 (m, 2H), 3.14 (s, 3H), 2.14-2.05 (m, 1H), 2.04-1.94 (m, 1H), 1.84-1.75 (m, 2H), 1.13 (d, J = 6.8 Hz, 3H). LCMS (pos) m/z: 539.0 (M + H)$^+$. |
| 52.0 | (1R,2S)-1-(5-chloropyrimidin-2-yl)-1-methoxypropane-2-sulfonamide (Example 11.3), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: AD-H (2 × 25 cm) Mobile Phase: 65:35 (A:B) A: Liquid $CO_2$, B: IPA, Flow Rate: 80 mL/min, 215 nm, 100 bar inlet pressure to deliver peak 2. | 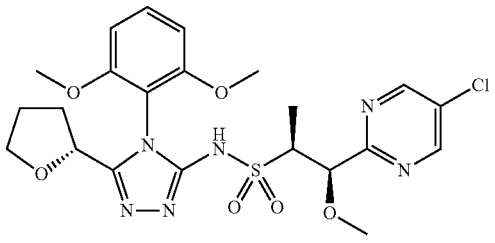<br>OR<br>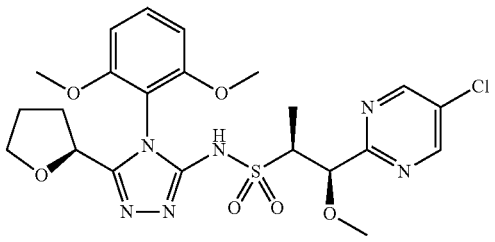<br>(1R,2S)-1-(5-chloropyrimidin-2-yl)-N-(4-(2,6-dimethoxyphenyl)-5-((R)-tetrahydrofuran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-tetrahydrofuran-2-yl)-4H-1,2,4-triazol-3-yl)-1-methoxypropane-2-sulfonamide. $^1$H NMR (400 MHz, DMSO-$d_6$) δ 12.88 (br. s., 1H), 9.00-8.83 (m, 2H), 7.48 (t, J = 8.5 Hz, 1H), 6.83 (d, J = 8.5 Hz, 2H), 4.77 (d, J = 4.4 Hz, 1H), 4.50 (dd, J = 5.6, 7.7 Hz, 1H), 3.75 (s, 3H), 3.74 (s, 3H), 3.68-3.61 (m, 1H), 3.54-3.47 (m, 1H), 3.43-3.36 (m, 1H), 3.14 (s, 3H), 2.14-2.05 (m, |

TABLE 11-continued

| Example | Reagents | Structure, Name and Data |
|---|---|---|
| | | 1H), 2.04-1.93 (m, 1H), 1.84-1.74 (m, 2H), 1.14 (d, J = 6.8 Hz, 3H). LCMS (pos) m/z: 539.0 (M + H)⁺. |
| 53.0 | (2S,3R)-3-(5-chloropyrimidin-2-yl)butane-2-sulfonamide (Example 1.4), (R)-tetrahydrofuran-2-carbohydrazide and (S)-tetrahydrofuran-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid CO$_2$, B: IPA, Flow Rate: 60 mL/min, 220 nm, 100 bar inlet pressure to deliver peak 2. | 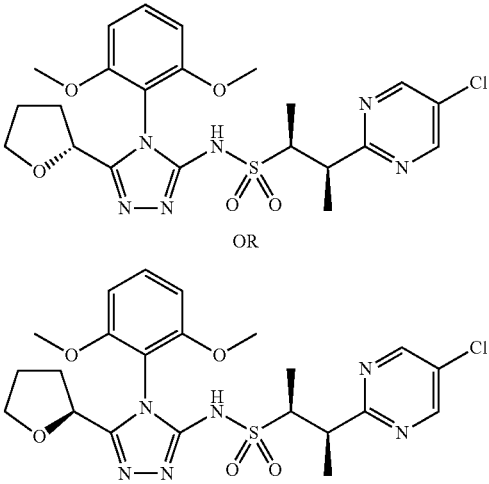 [SMILES: COc1cccc(OC)c1-n1c(NS(=O)(=O)[C@@H](C)[C@H](C)c2ncc(Cl)cn2)nnc1[C@H]1CCCO1 ; COc1cccc(OC)c1-n1c(NS(=O)(=O)[C@@H](C)[C@H](C)c2ncc(Cl)cn2)nnc1[C@@H]1CCCO1]  OR  (2S,3R)-3-(5-chloro-2-pyrimidinyl)-N-(4-(2,6-dimethoxyphenyl)-5-((2S)-tetrahydro-2-furanyl)-4H-1,2,4-triazol-3-yl)-2-butanesulfonamide or (2S,3R)-3-(5-chloro-2-pyrimidinyl)-N-(4-(2,6-dimethoxyphenyl)-5-((2R)-tetrahydro-2-furanyl)-4H-1,2,4-triazol-3-yl)-2-butanesulfonamide. ¹H NMR (400 MHz, DMSO-d$_6$) δ 12.88 (s, 1H), 8.86 (s, 2H), 7.47 (t, J = 8.5 Hz, 1H), 6.82 (dd, J = 1.3, 8.6 Hz, 2H), 4.49 (dd, J = 5.6, 7.7 Hz, 1H), 3.79-3.67 (m, 6H), 3.67-3.48 (m, 4H), 2.12-2.04 (m, 1H), 2.03-1.95 (m, 1H), 1.84-1.75 (m, 2H), 1.22 (d, J = 7.0 Hz, 3H), 1.09 (d, J = 6.8 Hz, 3H). LCMS (pos) m/z: 523.0 (M + H)⁺. |
| 54.0 | (2S,3R)-3-(5-methylpyrimidin-2-yl)butane-2-sulfonamide (Example 1.0), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: AS-H (2 × 25 cm) Mobile Phase: 73:27 (A:B) A: Liquid CO$_2$, B: MeOH, Flow Rate: 80 mL/min, 215 nm, 100 bar inlet pressure to deliver peak 1. | 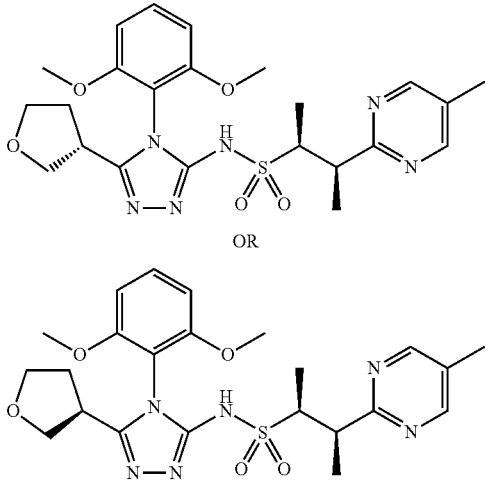 [SMILES: COc1cccc(OC)c1-n1c(NS(=O)(=O)[C@@H](C)[C@H](C)c2ncc(C)cn2)nnc1[C@H]1CCOC1 ; COc1cccc(OC)c1-n1c(NS(=O)(=O)[C@@H](C)[C@H](C)c2ncc(C)cn2)nnc1[C@@H]1CCOC1]  OR  (2S,3R)-N-(4-(2,6-dimethoxyphenyl)-5-((R)-tetrahydrofuran-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-tetrahydrofuran-3-yl)-4H-1,2,4-triazol-3-yl)-3-(5-methylpyrimidin-2-yl)butane-2-sulfonamide. ¹H NMR (400 MHz, DMSO-d$_6$) δ 12.59 (br. s., 1H), 8.58 (s, 2H), 7.51 (t, J = 8.5 Hz, 1H), 6.85 (dd, J = 4.1, 8.5 Hz, 2H), 3.80-3.72 (m, 7H), 3.69-3.60 (m, 4H), 3.60-3.54 (m, 1H), 3.01-2.91 (m, 1H), 2.23 (s, 3H), 2.11-2.01 (m, 1H), 1.99-1.90 (m, 1H), 1.22 (d, J = 7.0 Hz, 3H), 1.06 (d, J = 7.0 Hz, 3H). |

TABLE 11-continued

| Example | Reagents | Structure, Name and Data |
|---|---|---|
| | | LCMS (pos) m/z: 503.0 (M + H)⁺. |
| 55.0 | (2S,3R)-3-(5-methylpyrimidin-2-yl)butane-2-sulfonamide (Example 1.0), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: AS-H (2 × 25 cm) Mobile Phase: 73:27 (A:B) A: Liquid $CO_2$, B: MeOH, Flow Rate: 80 mL/min, 215 nm, 100 bar inlet pressure to deliver peak 2. | 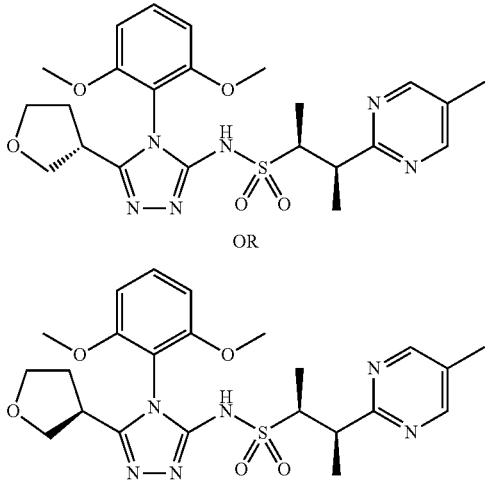 [SMILES: COc1cccc(OC)c1-n1c(NS(=O)(=O)[C@@H](C)[C@H](C)c2ncc(C)cn2)nnc1[C@H]1CCOC1 ; COc1cccc(OC)c1-n1c(NS(=O)(=O)[C@@H](C)[C@H](C)c2ncc(C)cn2)nnc1[C@@H]1CCOC1]<br>OR<br><br>(2S,3R)-N-(4-(2,6-dimethoxyphenyl)-5-((R)-tetrahydrofuran-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-tetrahydrofuran-3-yl)-4H-1,2,4-triazol-3-yl)-3-(5-methylpyrimidin-2-yl)butane-2-sulfonamide. $^1$H NMR (400 MHz, DMSO-$d_6$) δ 12.63 (br. s., 1H), 8.58 (d, J = 0.6 Hz, 2H), 7.51 (t, J = 8.5 Hz, 1H), 6.85 (d, J = 8.5 Hz, 2H), 3.81-3.72 (m, 7H), 3.69-3.60 (m, 4H), 3.55 (dq, J = 3.3, 6.9 Hz, 1H), 2.99-2.90 (m, 1H), 2.23 (s, 3H), 2.09-1.99 (m, 1H), 1.98-1.88 (m, 1H), 1.22 (d, J = 7.0 Hz, 3H), 1.06 (d, J = 7.0 Hz, 3H). LCMS (pos) m/z: 503.0 (M + H)⁺. |
| 56.0 | (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: AS-H (2 × 25 cm) Mobile Phase: 73:27 (A:B) A: Liquid $CO_2$, B: MeOH, Flow Rate: 80 mL/min, 215 nm, 100 bar inlet pressure to deliver peak 1. | 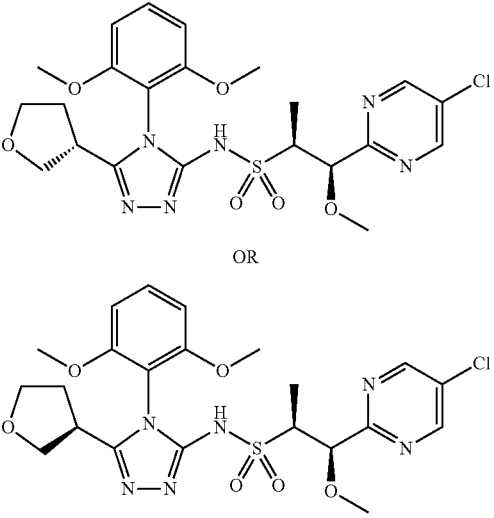 [SMILES: COc1cccc(OC)c1-n1c(NS(=O)(=O)[C@@H](C)[C@H](OC)c2ncc(Cl)cn2)nnc1[C@H]1CCOC1 ; COc1cccc(OC)c1-n1c(NS(=O)(=O)[C@@H](C)[C@H](OC)c2ncc(Cl)cn2)nnc1[C@@H]1CCOC1]<br>OR<br><br>(1R,2S)-1-(5-chloropyrimidin-2-yl)-N-(4-(2,6-dimethoxyphenyl)-5-((R)-tetrahydrofuran-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-tetrahydrofuran-3-yl)-4H-1,2,4-triazol-3-yl)-1-methoxypropane-2-sulfonamide. $^1$H NMR (400 MHz, DMSO-$d_6$) δ 12.81 (br. s., 1H), 8.95-8.90 (m, 2H), 7.52 (t, J = 8.5 Hz, 1H), 6.87 (d, J = 8.7 Hz, 2H), 4.76 (d, J = 4.4 Hz, 1H), 3.84-3.72 (m, 7H), 3.67-3.60 (m, 3H), 3.44-3.36 (m, 1H), 3.14 (s, 3H), 2.95 (qd, J = 6.8, 8.7 Hz, 1H), 2.09-2.01 (m, 1H), 2.01-1.89 (m, 1H), 1.13 (d, J = 7.0 Hz, 3H). LCMS (pos) m/z: 539.0 |

TABLE 11-continued

| Example | Reagents | Structure, Name and Data |
|---|---|---|
| 57.0 | (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: AS-H (2 × 25 cm) Mobile Phase: 73:27 (A:B) A: Liquid $CO_2$, B: MeOH, Flow Rate: 80 mL/min, 215 nm, 100 bar inlet pressure to deliver peak 2. | 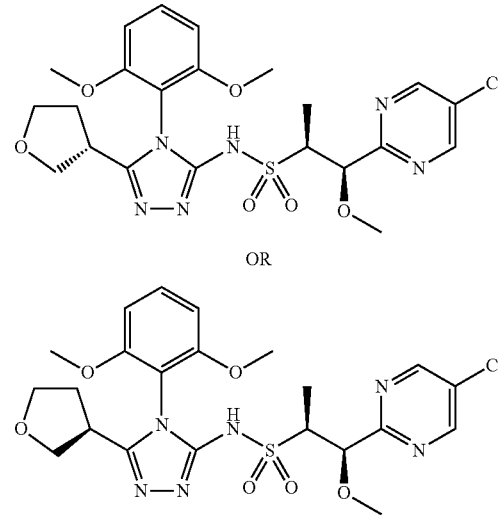<br>(1R,2S)-1-(5-chloropyrimidin-2-yl)-N-(4-(2,6-dimethoxyphenyl)-5-((R)-tetrahydrofuran-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-tetrahydrofuran-3-yl)-4H-1,2,4-triazol-3-yl)-1-methoxypropane-2-sulfonamide. $^1$H NMR (400 MHz, DMSO-$d_6$) δ 12.82 (s, 1H), 8.95-8.89 (m, 2H), 7.52 (t, J = 8.5 Hz, 1H), 6.87 (dd, J = 3.0, 8.6 Hz, 2H), 4.76 (d, J = 4.4 Hz, 1H), 3.83-3.72 (m, 7H), 3.69-3.60 (m, 3H), 3.44-3.36 (m, 1H), 3.14 (s, 3H), 2.95 (qd, J = 6.7, 8.9 Hz, 1H), 2.09-2.00 (m, 1H), 1.99-1.89 (m, 1H), 1.13 (d, J = 6.8 Hz, 3H). LCMS (pos) m/z: 539.0 (M + H)$^+$. |
| 58.0 | (2S,3R)-3-(5-methylpyrimidin-2-yl)butane-2-sulfonamide (Example 1.0), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 15 cm) Mobile Phase: 58:42 (A:B) A: Liquid $CO_2$, B: IPA, Flow Rate: 80 mL/min, 215 nm, 100 bar inlet pressure to deliver peak 1. | 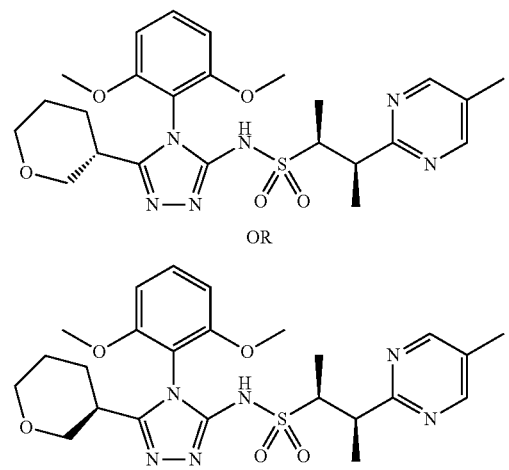 [SMILES: COc1cccc(OC)c1-n1c(NS(=O)(=O)[C@@H](C)[C@H](C)c2ncc(C)cn2)nnc1[C@H]1CCCOC1 ; COc1cccc(OC)c1-n1c(NS(=O)(=O)[C@@H](C)[C@H](C)c2ncc(C)cn2)nnc1[C@@H]1CCCOC1]<br>(2S,3R)-N-(4-(2,6-dimethoxyphenyl)-5-((R)-tetrahydro-2H-pyran-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-tetrahydro-2H-pyran-3-yl)-4H-1,2,4-triazol-3-yl)-3-(5-methylpyrimidin-2-yl)butane-2-sulfonamide. $^1$H NMR (400 MHz, DMSO-$d_6$) δ 12.86 (br. s., 1H), 8.58 (d, J = 0.8 Hz, 2H), 7.56-7.48 (m, 1H), 6.87 (d, J = 8.7 Hz, 2H), 3.78-3.70 (m, 7H), 3.69-3.61 (m, 2H), 3.53 (dq, J = 3.2, 7.0 Hz, 1H), 3.31-3.26 (m, 2H), 2.32 (tt, J = 4.0, 10.6 Hz, 1H), 2.23 (s, 3H), 1.85-1.75 (m, 1H), 1.75-1.66 (m, 1H), 1.66-1.56 (m, 1H), 1.47-1.34 (m, 1H), 1.21 (d, J = 7.3 Hz, 3H), |

TABLE 11-continued

| Example | Reagents | Structure, Name and Data |
|---|---|---|
| | | 1.05 (d, J = 7.0 Hz, 3H). LCMS (pos) m/z: 517.2 (M + H)+. |
| 59.0 | (2S,3R)-3-(5-methylpyrimidin-2-yl)butane-2-sulfonamide (Example 1.0), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 15 cm) Mobile Phase: 58:42 (A:B) A: Liquid CO$_2$, B: IPA, Flow Rate: 80 mL/min, 215 nm, 100 bar inlet pressure to deliver peak 2. | 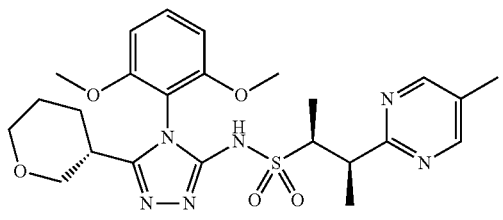<br>OR<br>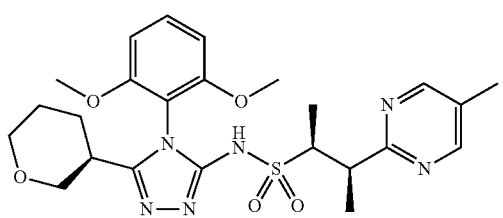<br>(2S,3R)-N-(4-(2,6-dimethoxyphenyl)-5-((R)-tetrahydro-2H-pyran-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-tetrahydro-2H-pyran-3-yl)-4H-1,2,4-triazol-3-yl)-3-(5-methylpyrimidin-2-yl)butane-2-sulfonamide. $^1$H NMR (400 MHz, DMSO-d$_6$) δ 12.86 (s, 1H), 8.58 (s, 2H), 7.52 (dt, J = 1.7, 8.5 Hz, 1H), 6.90-6.84 (m, 2H), 3.78-3.70 (m, 7H), 3.68-3.60 (m, 2H), 3.57-3.50 (m, 1H), 3.32-3.26 (m, 2H), 2.37-2.26 (m, 1H), 2.23 (s, 3H), 1.85-1.77 (m, 1H), 1.76-1.64 (m, 1H), 1.63-1.56 (m, 1H), 1.47-1.34 (m, 1H), 1.21 (d, J = 7.3 Hz, 3H), 1.05 (d, J = 6.8 Hz, 3H). LCMS (pos) m/z: 517.2 (M + H)+. |
| 60.0 | (2S,3R)-3-(5-chloropyrimidin-2-yl)butane-2-sulfonamide (Example 1.4), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0)<br>The mixture was purified by preparative SFC using the following methodology: Column: AS-H (2 × 25 cm) Mobile Phase: 65:35 (A:B) A: Liquid CO$_2$, B: MeOH, Flow Rate: 60 mL/min, 220 nm, 100 bar inlet pressure to deliver peak 1. | 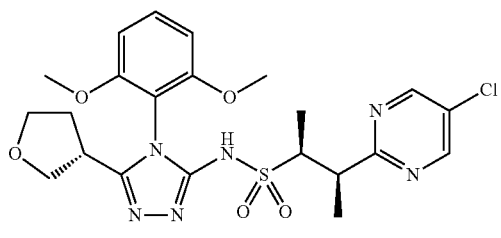<br>OR<br>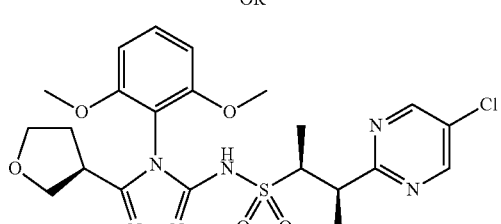<br>(2S,3R)-3-(5-chloropyrimidin-2-yl)-N-(4-(2,6-dimethoxyphenyl)-5-((R)-tetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-tetrahydrofuran-3-yl)-4H-1,2,4-triazol-3-yl)butane-2-sulfonamide. $^1$H NMR (400 MHz, CD$_2$Cl$_2$) δ 8.63 (s, 2H), 7.49 (t, J = 8.5 Hz, 1H), 6.72 (dd, J = 5.2, 8.5 Hz, 2H), 3.91-3.85 (m, 1H), 3.84-3.76 (m, 7H), 3.76-3.67 (m, 4H), 3.05-2.96 (m, 1H), 2.27-2.18 (m, 1H), 2.00 (dddd, J = 5.8, 7.4, 8.9, 12.7 Hz, 1H), 1.31 (d, J = 6.8 Hz, 3H), 1.26 (d, J = 6.8 Hz, 3H). LCMS (pos) m/z: 523.0 (M + H)+. |

| Example | Reagents | Structure, Name and Data |
|---|---|---|
| 61.0 | (2S,3R)-3-(5-chloropyrimidin-2-yl)butane-2-sulfonamide (Example 1.4), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: AS-H (2 × 25 cm) Mobile Phase: 65:35 (A:B) A: Liquid $CO_2$, B: MeOH, Flow Rate: 60 mL/min, 220 nm, 100 bar inlet pressure to deliver peak 2. | 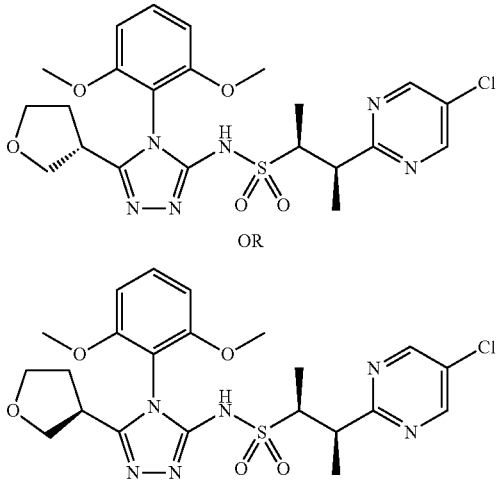 [SMILES: COc1cccc(OC)c1-n1c(NS(=O)(=O)[C@@H](C)[C@H](C)c2ncc(Cl)cn2)nnc1[C@H]1CCOC1 ; COc1cccc(OC)c1-n1c(NS(=O)(=O)[C@@H](C)[C@H](C)c2ncc(Cl)cn2)nnc1[C@@H]1CCOC1]  OR  (2S,3R)-3-(5-chloropyrimidin-2-yl)-N-(4-(2,6-dimethoxyphenyl)-5-((R)-tetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-tetrahydrofuran-3-yl)-4H-1,2,4-triazol-3-yl)butane-2-sulfonamide. $^1$H NMR (400 MHz, $CD_2Cl_2$) δ 8.67-8.58 (m, 2H), 7.53-7.45 (m, 1H), 6.72 (dd, J = 2.2, 8.6 Hz, 2H), 3.91-3.85 (m, 1H), 3.84-3.77 (m, 7H), 3.77-3.66 (m, 4H), 3.00 (qd, J = 7.0, 8.9 Hz, 1H), 2.27-2.16 (m, 1H), 2.00 (dddd, J = 5.8, 7.4, 9.0, 12.7 Hz, 1H), 1.31 (d, J = 6.8 Hz, 3H), 1.26 (d, J = 6.8 Hz, 3H). LCMS (pos) m/z: 523.0 (M + H)$^+$. |
| 62.0 | (2S,3R)-3-(5-chloropyrimidin-2-yl)butane-2-sulfonamide (Example 1.4), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 25 cm) Mobile Phase: 75:25 (A:B) A: Liquid $CO_2$, B: MeOH, Flow Rate: 65 mL/min, 220 nm, 100 bar inlet pressure to deliver peak 1. | 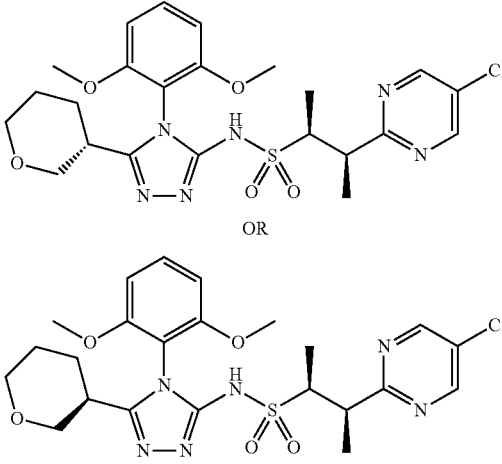  OR  (2S,3R)-3-(5-chloropyrimidin-2-yl)-N-(4-(2,6-dimethoxyphenyl)-5-((R)-tetrahydro-2H-pyran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-tetrahydro-2H-pyran-3-yl)-4H-1,2,4-triazol-3-yl)butane-2-sulfonamide. $^1$H NMR (400 MHz, $CD_2Cl_2$) δ 10.80 (s, 1H), 8.67-8.59 (m, 2H), 7.54-7.45 (m, 1H), 6.73 (dd, J = 1.3, 8.6 Hz, 2H), 3.86-3.83 (m, 1H), 3.80 (s, 3H), 3.80 (s, 3H), 3.73-3.63 (m, 2H), 3.47-3.34 (m, 2H), 2.48 (tdd, J = 4.0, 10.4, 11.3 Hz, 1H), 1.96-1.89 (m, 1H), 1.85-1.73 (m, 1H), 1.71-1.39 (m, 3H), 1.31 (d, J = 7.0 Hz, 3H), 1.25 (d, J = 6.8 Hz, 3H). LCMS (pos) m/z: 537.0 (M + H)$^+$. |

TABLE 11-continued

| Example | Reagents | Structure, Name and Data |
|---|---|---|
| 63.0 | (2S,3R)-3-(5-chloropyrimidin-2-yl)butane-2-sulfonamide (Example 1.4), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 25 cm) Mobile Phase: 75:25 (A:B) A: Liquid $CO_2$, B: MeOH, Flow Rate: 65 mL/min, 220 nm, 100 bar inlet pressure to deliver peak 2. | 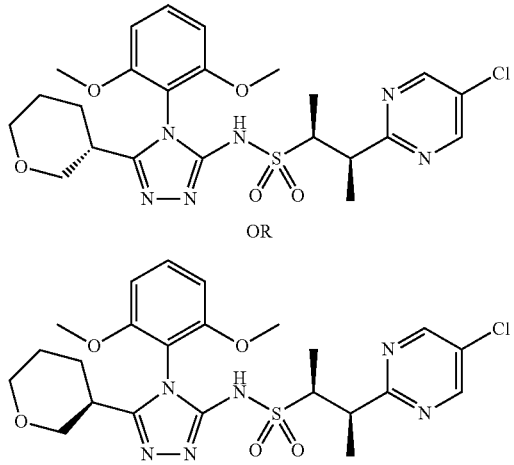 [SMILES: COc1cccc(OC)c1-n1c(NS(=O)(=O)[C@@H](C)[C@H](C)c2ncc(Cl)cn2)nnc1[C@H]1CCCOC1 ; COc1cccc(OC)c1-n1c(NS(=O)(=O)[C@@H](C)[C@H](C)c2ncc(Cl)cn2)nnc1[C@@H]1CCCOC1]<br>OR<br><br>(2S,3R)-3-(5-chloropyrimidin-2-yl)-N-(4-(2,6-dimethoxyphenyl)-5-((R)-tetrahydro-2H-pyran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-tetrahydro-2H-pyran-3-yl)-4H-1,2,4-triazol-3-yl)butane-2-sulfonamide. $^1$H NMR (400 MHz, $CD_2Cl_2$) δ 10.76 (s, 1H), 8.67-8.59 (m, 2H), 7.52-7.46 (m, 1H), 6.77-6.69 (m, 2H), 3.86-3.82 (m, 1H), 3.81 (s, 3H), 3.79 (s, 3H), 3.71-3.63 (m, 2H), 3.45-3.34 (m, 2H), 2.48 (tt, J = 4.0, 10.8 Hz, 1H), 1.97-1.89 (m, 1H), 1.85-1.75 (m, 1H), 1.71-1.43 (m, 3H), 1.30 (d, J = 6.8 Hz, 3H), 1.25 (d, J = 6.8 Hz, 3H). LCMS (pos) m/z: 537.0 (M + H)$^+$. |
| 64.0 | (1R,2S)-1-(5-chloropyrimidin-2-yl)-1-methoxypropane-2-sulfonamide (Example 11.3), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 15 cm) Mobile Phase: 65:35 (A:B) A: Liquid $CO_2$, B: IPA (0.1% DEA), Flow Rate: 65 mL/min, 220 nm, 100 bar inlet pressure to deliver peak 1. | 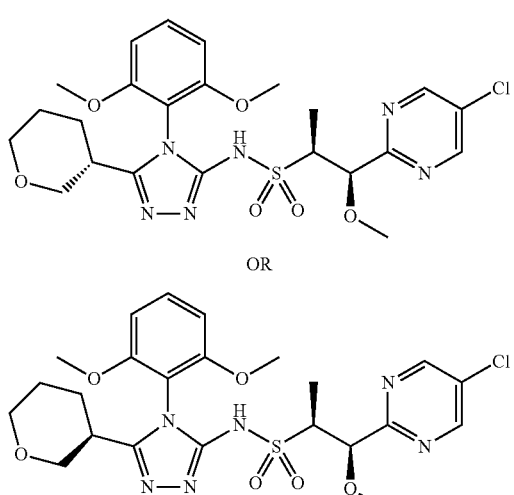<br>OR<br><br>(1R,2S)-1-(5-chloropyrimidin-2-yl)-N-(4-(2,6-dimethoxyphenyl)-5-((R)-tetrahydro-2H-pyran-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-tetrahydro-2H-pyran-3-yl)-4H-1,2,4-triazol-3-yl)-1-methoxypropane-2-sulfonamide. $^1$H NMR (400 MHz, $CD_2Cl_2$) δ 8.77-8.69 (m, 2H), 7.56-7.51 (m, 1H), 6.78-6.74 (m, 2H), 4.89 (d, J = 4.6 Hz, 1H), 3.90-3.86 (m, 1H), 3.85-3.80 (m, 7H), 3.62-3.56 (m, 1H), 3.49-3.37 (m, 2H), 3.27 (s, 3H), 2.57-2.49 (m, 1H), 1.99-1.92 (m, 1H), 1.88-1.77 (m, 1H), 1.70-1.63 (m, 1H), 1.61-1.49 (m, 1H), 1.28 (d, J = 7.0 Hz, 3H). LCMS (pos) m/z: 553.0 (M + H)$^+$. |

TABLE 11-continued

| Example | Reagents | Structure, Name and Data |
|---|---|---|
| 65.0 | (1R,2S)-1-(5-chloropyrimidin-2-yl)-1-methoxypropane-2-sulfonamide (Example 11.3), tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 15 cm) Mobile Phase: 65:35 (A:B) A: Liquid $CO_2$, B: IPA (0.1% DEA), Flow Rate: 65 mL/min, 220 nm, 100 bar inlet pressure to deliver peak 2. | 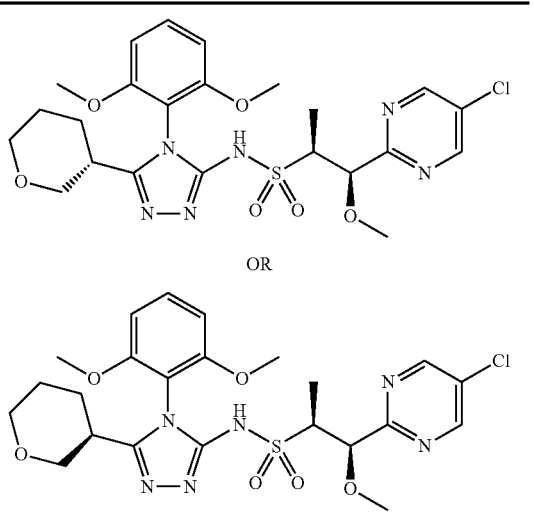<br><br>OR<br><br>(1R,2S)-1-(5-chloropyrimidin-2-yl)-N-(4-(2,6-dimethoxyphenyl)-5-((R)-tetrahydro-2H-pyran-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-tetrahydro-2H-pyran-3-yl)-4H-1,2,4-triazol-3-yl)-1-methoxypropane-2-sulfonamide. $^1$H NMR (400 MHz, $CD_2Cl_2$) δ 8.73-8.66 (m, 2H), 7.53-7.46 (m, 1H), 6.76-6.71 (m, 2H), 4.85 (d, J = 4.6 Hz, 1H), 3.86-3.79 (m, 8H), 3.55 (dq, J = 4.6, 7.0 Hz, 1H), 3.45-3.34 (m, 2H), 3.24 (s, 3H), 2.49 (tdd, J = 4.0, 10.4, 11.3 Hz, 1H), 1.96-1.90 (m, 1H), 1.85-1.74 (m, 1H), 1.68-1.60 (m, 1H), 1.57-1.47 (m, 1H), 1.24 (d, J = 7.0 Hz, 3H). LCMS (pos) m/z: 553.0 (M + H)$^+$. |
| 66.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: IC (2 × 15 cm) Mobile Phase: 55:45 (A:B) A: Liquid $CO_2$, B: MeOH, Flow Rate: 60 mL/min, 275 nm, 100 bar inlet pressure to deliver peak 1. | 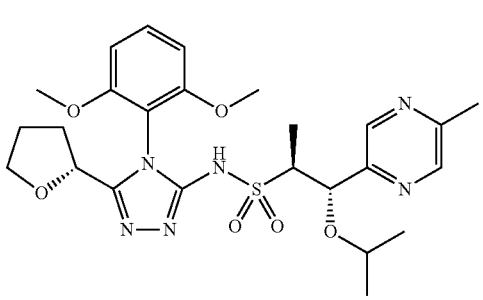<br><br>OR<br><br>or |

TABLE 11-continued

| Example | Reagents | Structure, Name and Data |
|---|---|---|

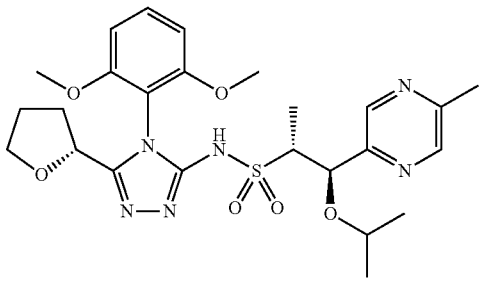

OR

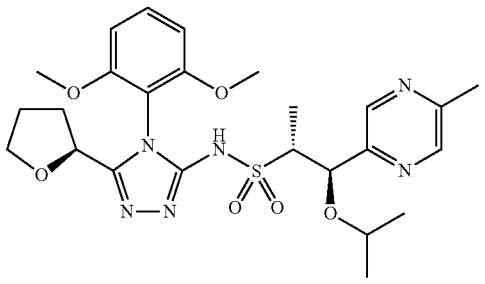 [SMILES: COc1cccc(OC)c1-n1c(NS(=O)(=O)[C@H](C)[C@H](OC(C)C)c2cnc(C)cn2)nnc1[C@@H]1CCCO1]

(1S,2S)-N-(4-(2,6-dimethoxyphenyl)-5-((S)-
tetrahydrofuran-2-yl)-4H-1,2,4-triazol-3-yl)-1-
isopropoxy-1-(5-methylpyrazin-2-yl)propane-2-
sulfonamide or (1S,2S)-N-(4-(2,6-
dimethoxyphenyl)-5-((R)-tetrahydrofuran-2-yl)-4H-
1,2,4-triazol-3-yl)-1-isopropoxy-1-(5-
methylpyrazin-2-yl)propane-2-sulfonamide or
(1R,2R)-N-(4-(2,6-dimethoxyphenyl)-5-((S)-
tetrahydrofuran-2-yl)-4H-1,2,4-triazol-3-yl)-1-
isopropoxy-1-(5-methylpyrazin-2-yl)propane-2-
sulfonamide or (1R,2R)-N-(4-(2,6-
dimethoxyphenyl)-5-((R)-tetrahydrofuran-2-yl)-4H-
1,2,4-triazol-3-yl)-1-isopropoxy-1-(5-
methylpyrazin-2-yl)propane-2-sulfonamide. $^1$H
NMR (400 MHz, DMSO-$d_6$) δ 12.87 (br. s., 1H),
8.49-8.39 (m, 2H), 7.53-7.44 (m, 1H), 6.84 (d,
J = 8.5 Hz, 2H), 4.74 (d, J = 6.2 Hz, 1H), 4.50 (dd,
J = 5.4, 7.7 Hz, 1H), 3.77 (app s, 6H), 3.67-3.61 (m,
1H), 3.54-3.47 (m, 1H), 3.43-3.36 (m, 2H), 2.47
(s, 3H), 2.15-2.05 (m, 1H), 2.03-1.93 (m, 1H),
1.84-1.75 (m, 2H), 1.01 (d, J = 6.0 Hz, 3H), 0.98 (d,
J = 7.3 Hz, 3H), 0.85 (d, J = 6.0 Hz, 3H). LCMS (pos)
m/z: 547.2 (M + H)$^+$.

TABLE 11-continued

| Example | Reagents | Structure, Name and Data |
|---|---|---|
| 67.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: IC (2 × 15 cm) Mobile Phase: 55:45 (A:B) A: Liquid $CO_2$, B: MeOH, Flow Rate: 60 mL/min, 275 nm, 100 bar inlet pressure to deliver peak 2. | 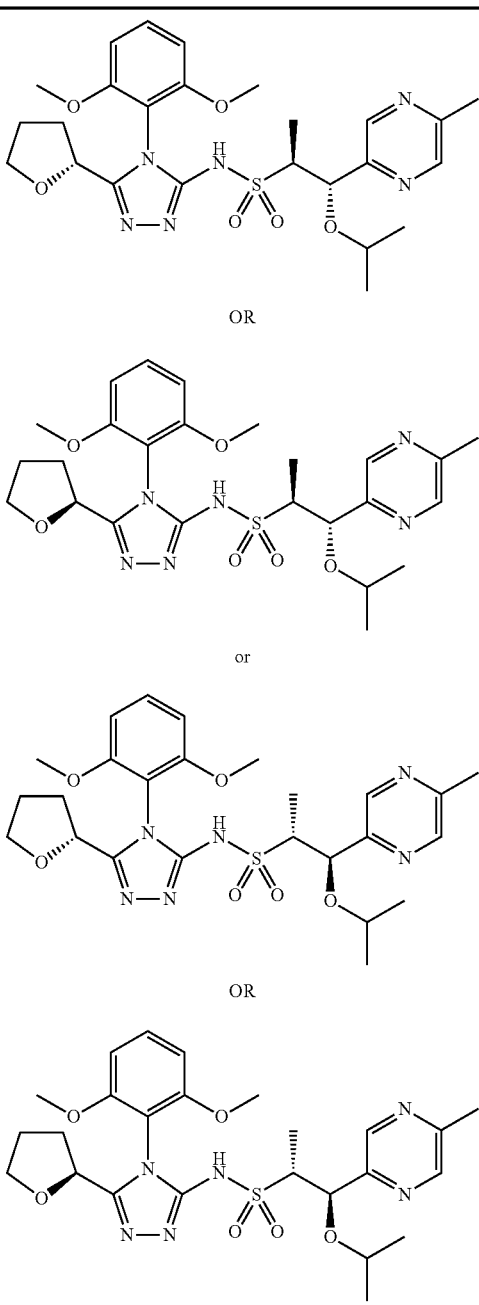<br><br>(1S,2S)-N-(4-(2,6-dimethoxyphenyl)-5-((S)-tetrahydrofuran-2-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-((R)-tetrahydrofuran-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((S)-tetrahydrofuran-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((R)-tetrahydrofuran-2-yl)-4H-1,2,4-triazol-3-yl)-1-isopropoxy-1-(5-methylpyrazin-2-yl)propane-2-sulfonamide. $^1$H NMR (400 MHz, DMSO-$d_6$) δ 12.85 (br. s., 1H), 8.45 (s, 1H), 8.41 (d, J = 1.5 Hz, 1H), 7.48 (t, J = 8.5 |

| Example | Reagents | Structure, Name and Data |
|---|---|---|
| | | Hz, 1H), 6.84 (dd, J = 2.5, 8.5 Hz, 2H), 4.75 (d, J = 6.0 Hz, 1H), 4.50 (dd, J = 5.4, 7.7 Hz, 1H), 3.77 (s, 3H), 3.77 (s, 3H), 3.67-3.61 (m, 1H), 3.54-3.47 (m, 1H), 3.44-3.36 (m, 2H), 2.47 (s, 3H), 2.14-2.05 (m, 1H), 2.03-1.93 (m, 1H), 1.83-1.75 (m, 2H), 1.02 (d, J = 6.0 Hz, 3H), 0.99 (d, J = 7.0 Hz, 3H), 0.86 (d, J = 6.2 Hz, 3H). LCMS (pos) m/z: 547.2 (M + H)+. |
| 68.0 | (2S,3R)-3-(5-chloropyrimidin-2-yl)butane-2-sulfonamide (Example 1.4), (2R,3S)-3-methyltetrahydrofuran-2-carbohydrazide and (2S,3R)-3-methyltetrahydrofuran-2-carbohydrazide (commercially available from Enamine), 2-isothiocyanato-1,3-dimethoxybenzene (Example 10.0). | 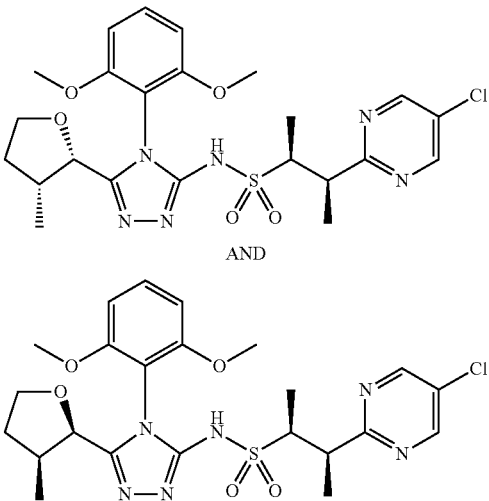 [SMILES: COc1cccc(OC)c1-n1c(NS(=O)(=O)[C@@H](C)[C@H](C)c2ncc(Cl)cn2)nnc1[C@H]1OCC[C@H]1C ; COc1cccc(OC)c1-n1c(NS(=O)(=O)[C@@H](C)[C@H](C)c2ncc(Cl)cn2)nnc1[C@@H]1OCC[C@@H]1C]<br>AND<br>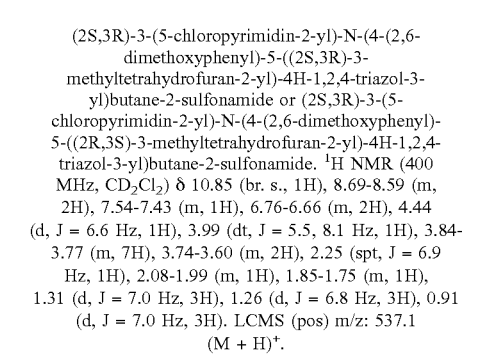<br>(2S,3R)-3-(5-chloropyrimidin-2-yl)-N-(4-(2,6-dimethoxyphenyl)-5-((2S,3R)-3-methyltetrahydrofuran-2-yl)-4H-1,2,4-triazol-3-yl)butane-2-sulfonamide or (2S,3R)-3-(5-chloropyrimidin-2-yl)-N-(4-(2,6-dimethoxyphenyl)-5-((2R,3S)-3-methyltetrahydrofuran-2-yl)-4H-1,2,4-triazol-3-yl)butane-2-sulfonamide. 1H NMR (400 MHz, CD2Cl2) δ 10.85 (br. s., 1H), 8.69-8.59 (m, 2H), 7.54-7.43 (m, 1H), 6.76-6.66 (m, 2H), 4.44 (d, J = 6.6 Hz, 1H), 3.99 (dt, J = 5.5, 8.1 Hz, 1H), 3.84-3.77 (m, 7H), 3.74-3.60 (m, 2H), 2.25 (spt, J = 6.9 Hz, 1H), 2.08-1.99 (m, 1H), 1.85-1.75 (m, 1H), 1.31 (d, J = 7.0 Hz, 3H), 1.26 (d, J = 6.8 Hz, 3H), 0.91 (d, J = 7.0 Hz, 3H). LCMS (pos) m/z: 537.1 (M + H)+. |
| 69.0 | (2S,3R)-3-(5-methylpyrimidin-2-yl)butane-2-sulfonamide (Example 1.0), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: AS-H (2 × 25 cm) Mobile Phase: 80:20 (A:B) A: Liquid CO2, B: MeOH, Flow Rate: 70 mL/min, 215 nm, 100 bar inlet pressure to deliver peak 1. | 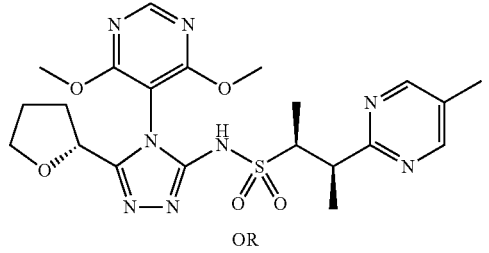<br>OR<br>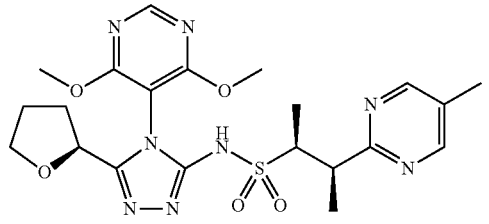<br>(2S,3R)-N-(4-(4,6-dimethoxypyrimidin-5-yl)-5-((S)-tetrahydrofuran-2-yl)-4H-1,2,4-triazol-3-yl)-3-(5-methylpyrimidin-2-yl)butane-2-sulfonamide or (2S,3R)-N-(4-(4,6-dimethoxypyrimidin-5-yl)-5- |

TABLE 11-continued

| Example | Reagents | Structure, Name and Data |
|---|---|---|
| | | ((R)-tetrahydrofuran-2-yl)-4H-1,2,4-triazol-3-yl)-3-(5-methylpyrimidin-2-yl)butane-2-sulfonamide. $^1$H NMR (400 MHz, DMSO-d$_6$) δ 13.02 (br.s., 1H), 8.66-8.62 (m, 1H), 8.58 (d, J = 0.6 Hz, 2H), 4.74-4.63 (m, 1H), 3.96-3.91 (m, 3H), 3.91 (s, 3H), 3.69-3.58 (m, 3H), 3.53-3.45 (m, 1H), 2.27-2.21 (m, 3H), 2.21-2.13 (m, 1H), 2.11-2.01 (m, 1H), 1.82 (quin, J = 7.1 Hz, 2H), 1.23 (d, J = 7.0 Hz, 3H), 1.10-1.02 (m, 3H). LCMS (pos) m/z: 505.2 (M + H)$^+$. |
| 70.0 | (2S,3R)-3-(5-methylpyrimidin-2-yl)butane-2-sulfonamide (Example 1.0), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: AS-H (2 × 25 cm) Mobile Phase: 80:20 (A:B) A: Liquid CO$_2$, B: MeOH, Flow Rate: 70 mL/min, 215 nm, 100 bar inlet pressure to deliver peak 2. | 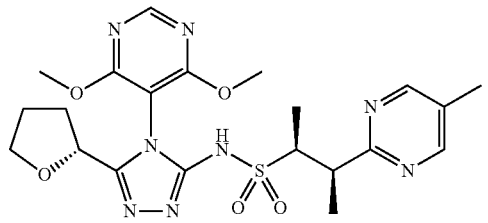<br>OR<br>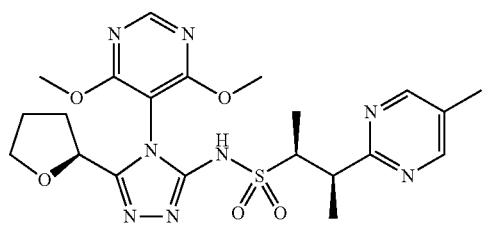<br>(2S,3R)-N-(4-(4,6-dimethoxypyrimidin-5-yl)-5-((S)-tetrahydrofuran-2-yl)-4H-1,2,4-triazol-3-yl)-3-(5-methylpyrimidin-2-yl)butane-2-sulfonamide or (2S,3R)-N-(4-(4,6-dimethoxypyrimidin-5-yl)-5-((R)-tetrahydrofuran-2-yl)-4H-1,2,4-triazol-3-yl)-3-(5-methylpyrimidin-2-yl)butane-2-sulfonamide. $^1$H NMR (400 MHz, DMSO-d$_6$) δ 13.08 (br. s., 1H), 8.65 (s, 1H), 8.58 (d, J = 0.6 Hz, 2H), 4.67 (dd, J = 5.2, 7.7 Hz, 1H), 3.99-3.92 (m, 3H), 3.91 (s, 3H), 3.73-3.62 (m, 2H), 3.59 (qd, J = 3.4, 10.3 Hz, 1H), 3.52-3.45 (m, 1H), 2.23 (s, 3H), 2.22-2.15 (m, 1H), 2.12-2.02 (m, 1H), 1.88-1.78 (m, 2H), 1.23 (d, J = 7.0 Hz, 3H), 1.08 (d, J = 6.8 Hz, 3H). LCMS (pos) m/z: 505.2 (M + H)$^+$. |
| 71.0 | (2S,3R)-3-(5-methylpyrimidin-2-yl)butane-2-sulfonamide (Example 1.0), (2R,3S)-3-methyltetrahydrofuran-2-carbohydrazide and (2S,3R)-3-methyltetrahydrofuran-2-carbohydrazide (commercially available from Enamine), 2-isothiocyanato-1,3-dimethoxybenzene (Example 10.0) The mixture was purified by preparative SFC using the following methodology: Column: AD-H (2 × 25 cm) Mobile Phase: 70:30 (A:B) A: Liquid CO$_2$, B: MeOH, Flow Rate: 80 mL/min, 258 nm, 100 bar inlet pressure to deliver peak 1. | 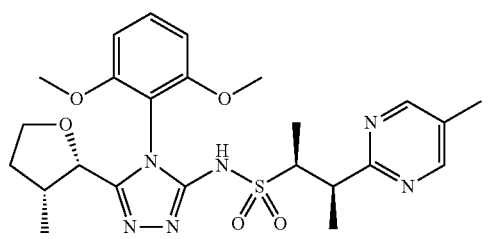<br>OR<br><br>(2S,3R)-N-(4-(2,6-dimethoxyphenyl)-5-((2R,3S)-3-methyltetrahydrofuran-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((2S,3R)-3- |

TABLE 11-continued

| Example | Reagents | Structure, Name and Data |
|---|---|---|
| | | methyltetrahydrofuran-2-yl)-4H-1,2,4-triazol-3-yl)-3-(5-methylpyrimidin-2-yl)butane-2-sulfonamide. <br> $^1$H NMR (400 MHz, CD$_2$Cl$_2$) δ 8.51 (d, J = 0.6 Hz, 2H), 7.50-7.44 (m, 1H), 6.73-6.69 (m, 2H), 4.44 (d, J = 6.6 Hz, 1H), 4.00 (dt, J = 5.4, 8.1 Hz, 1H), 3.81-3.77 (m, 7H), 3.76-3.70 (m, 1H), 3.64-3.59 (m, 1H), 2.29-2.24 (m, 4H), 2.08-2.00 (m, 1H), 1.86-1.77 (m, 1H), 1.31 (d, J = 7.0 Hz, 3H), 1.25 (d, J = 7.0 Hz, 3H), 0.91 (d, J = 7.0 Hz, 3H). LCMS (pos) m/z: 517.2 (M + H)$^+$. |
| 72.0 | (2S,3R)-3-(5-methylpyrimidin-2-yl)butane-2-sulfonamide (Example 1.0), (2R,3S)-3-methyltetrahydrofuran-2-carbohydrazide and (2S,3R)-3-methyltetrahydrofuran-2-carbohydrazide (commercially available from Enamine), 2-isothiocyanato-1,3-dimethoxybenzene (Example 10.0) The mixture was purified by preparative SFC using the following methodology: Column: AD-H (2 × 25 cm) Mobile Phase: 70:30 (A:B) A: Liquid CO$_2$, B: MeOH, Flow Rate: 80 mL/min, 258 nm, 100 bar inlet pressure to deliver peak 2. | 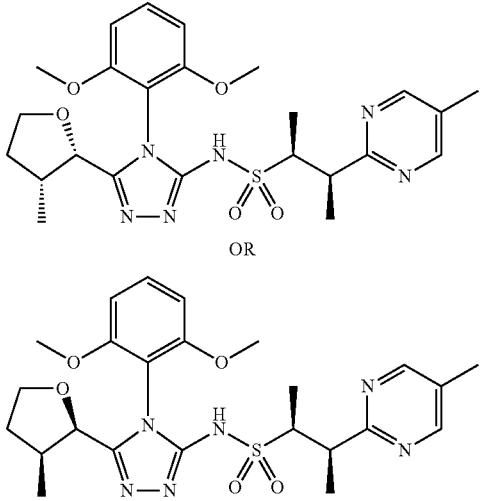 [SMILES: COc1cccc(OC)c1-n1c(NS(=O)(=O)[C@@H](C)[C@H](C)c2ncc(C)cn2)nnc1[C@H]1OCC[C@H]1C ; COc1cccc(OC)c1-n1c(NS(=O)(=O)[C@@H](C)[C@H](C)c2ncc(C)cn2)nnc1[C@@H]1OCC[C@@H]1C] <br> (2S,3R)-N-(4-(2,6-dimethoxyphenyl)-5-((2R,3S)-3-methyltetrahydrofuran-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((2S,3R)-3-methyltetrahydrofuran-2-yl)-4H-1,2,4-triazol-3-yl)-3-(5-methylpyrimidin-2-yl)butane-2-sulfonamide. <br> $^1$H NMR (400 MHz, CD$_2$Cl$_2$) δ 8.50 (d, J = 0.8 Hz, 2H), 7.50-7.43 (m, 1H), 6.75-6.68 (m, 2H), 4.45 (d, J = 6.6 Hz, 1H), 4.03-3.95 (m, 1H), 3.82-3.75 (m, 7H), 3.75-3.69 (m, 1H), 3.68-3.60 (m, 1H), 2.32-2.20 (m, 4H), 2.08-1.99 (m, 1H), 1.86-1.76 (m, 1H), 1.30 (d, J = 7.0 Hz, 3H), 1.24 (d, J = 7.0 Hz, 3H), 0.92 (d, J = 7.0 Hz, 3H). LCMS (pos) m/z: 517.2 (M + H)$^+$. |

TABLE 11-continued

| Example | Reagents | Structure, Name and Data |
|---|---|---|
| 73.0 | (1R,2S)-1-(5-chloropyrimidin-2-yl)-1-methoxypropane-2-sulfonamide (Example 11.3), (2R,3S)-3-methyltetrahydrofuran-2-carbohydrazide and (2S,3R)-3-methyltetrahydrofuran-2-carbohydrazide (commercially available from Enamine), 2-isothiocyanato-1,3-dimethoxybenzene (Example 10.0). The mixture was purified by preparative SFC using the following methodology: Column: IC (2 × 15 cm) Mobile Phase: 55:45 (A:B) A: Liquid CO$_2$, B: MeOH, Flow Rate: 80 mL/min, 273 nm, 100 bar inlet pressure to deliver peak 1. | OR<br><br>(1R,2S)-1-(5-chloropyrimidin-2-yl)-N-(4-(2,6-dimethoxyphenyl)-5-((2R,3S)-3-methyltetrahydrofuran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((2S,3R)-3-methyltetrahydrofuran-2-yl)-4H-1,2,4-triazol-3-yl)-1-methoxypropane-2-sulfonamide. $^1$H NMR (400 MHz, CD$_2$Cl$_2$) δ 10.85 (br. s., 1H), 8.76-8.63 (m, 2H), 7.54-7.42 (m, 1H), 6.76-6.68 (m, 2H), 4.86 (d, J = 4.6 Hz, 1H), 4.46 (d, J = 6.6 Hz, 1H), 3.98 (dt, J = 5.5, 8.0 Hz, 1H), 3.85-3.75 (m, 7H), 3.57 (dq, J = 4.6, 7.0 Hz, 1H), 3.25 (s, 3H), 2.26 (spt, J = 6.9 Hz, 1H), 2.08-1.98 (m, 1H), 1.86-1.74 (m, 1H), 1.25 (d, J = 7.0 Hz, 3H), 0.91 (d, J = 7.0 Hz, 3H). LCMS (pos) m/z: 553.0 (M + H)$^+$. |
| 74.0 | (1R,2S)-1-(5-chloropyrimidin-2-yl)-1-methoxypropane-2-sulfonamide (Example 11.3), (2R,3S)-3-methyltetrahydrofuran-2-carbohydrazide and (2S,3R)-3-methyltetrahydrofuran-2-carbohydrazide (commercially available from Enamine), 2-isothiocyanato-1,3-dimethoxybenzene (Example 10.0) The mixture was purified by preparative SFC using the following methodology: Column: IC (2 × 15 cm) Mobile Phase: 55:45 (A:B) A: Liquid CO$_2$, B: MeOH, Flow Rate: 80 mL/min, 273 nm, 100 bar inlet pressure to deliver peak 2. | OR<br><br>(1R,2S)-1-(5-chloropyrimidin-2-yl)-N-(4-(2,6-dimethoxyphenyl)-5-((2R,3S)-3-methyltetrahydrofuran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((2S,3R)-3-methyltetrahydrofuran-2-yl)-4H-1,2,4-triazol-3-yl)-1-methoxypropane-2-sulfonamide. $^1$H NMR (400 MHz, CD$_2$Cl$_2$) δ 10.87 (br. s., 1H), 8.75- |

TABLE 11-continued

| Example | Reagents | Structure, Name and Data |
|---|---|---|
| | | 8.67 (m, 2H), 7.53-7.44 (m, 1H), 6.75-6.68 (m, 2H), 4.86 (d, J = 4.6 Hz, 1H), 4.46 (d, J = 6.6 Hz, 1H), 4.03-3.95 (m, 1H), 3.84-3.75 (m, 7H), 3.61-3.53 (m, 1H), 3.25 (s, 3H), 2.25 (spt, J = 6.9 Hz, 1H), 2.10-1.98 (m, 1H), 1.84-1.75 (m, 1H), 1.25 (d, J = 7.0 Hz, 3H), 0.90 (d, J = 7.0 Hz, 3H). LCMS (pos) m/z: 553.0 (M + H)$^+$. |
| 75.0 | (2S,3R)-3-(5-chloropyrimidin-2-yl)butane-2-sulfonamide (Example 1.4), (2R,3S)-3-methyltetrahydrofuran-2-carbohydrazide and (2S,3R)-3-methyltetrahydrofuran-2-carbohydrazide (commercially available from Enamine), 2-isothiocyanato-1,3-dimethoxybenzene (Example 10.0) The mixture was purified by preparative SFC using the following methodology: Column: AD-H (2 × 25 cm) Mobile Phase: 70:30 (A:B) A: Liquid CO$_2$, B: MeOH, Flow Rate: 80 mL/min, 272 nm, 100 bar inlet pressure to deliver peak 1. | 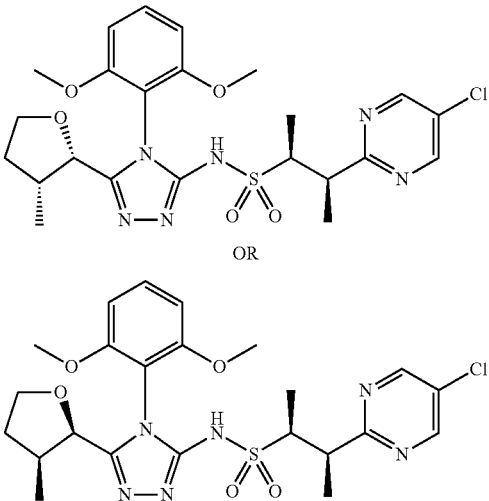 [SMILES: COc1cccc(OC)c1-n1c(NS(=O)(=O)[C@@H](C)[C@H](C)c2ncc(Cl)cn2)nnc1[C@H]1OCC[C@H]1C ; COc1cccc(OC)c1-n1c(NS(=O)(=O)[C@@H](C)[C@H](C)c2ncc(Cl)cn2)nnc1[C@@H]1OCC[C@@H]1C]OR<br><br>(2S,3R)-3-(5-chloropyrimidin-2-yl)-N-(4-(2,6-dimethoxyphenyl)-5-((2R,3S)-3-methyltetrahydrofuran-2-yl)-4H-1,2,4-triazol-3-yl)butane-2-sulfonamide or (2S,3R)-3-(5-chloropyrimidin-2-yl)-N-(4-(2,6-dimethoxyphenyl)-5-((2S,3R)-3-methyltetrahydrofuran-2-yl)-4H-1,2,4-triazol-3-yl)butane-2-sulfonamide. $^1$H NMR (400 MHz, CD$_2$Cl$_2$) δ 10.85 (br. s., 1H), 8.69-8.59 (m, 2H), 7.54-7.43 (m, 1H), 6.76-6.66 (m, 2H), 4.44 (d, J = 6.6 Hz, 1H), 3.99 (dt, J = 5.5, 8.1 Hz, 1H), 3.84-3.77 (m, 7H), 3.74-3.60 (m, 2H), 2.25 (spt, J = 6.9 Hz, 1H), 2.08-1.99 (m, 1H), 1.85-1.75 (m, 1H), 1.31 (d, J = 7.0 Hz, 3H), 1.26 (d, J = 6.8 Hz, 3H), 0.91 (d, J = 7.0 Hz, 3H). LCMS (pos) m/z: 537.2 (M + H)$^+$. |
| 76.0 | (2S,3R)-3-(5-chloropyrimidin-2-yl)butane-2-sulfonamide (Example 1.4), (2R,3S)-3-methyltetrahydrofuran-2-carbohydrazide and (2S,3R)-3-methyltetrahydrofuran-2-carbohydrazide (commercially available from Enamine), 2-isothiocyanato-1,3-dimethoxybenzene (Example 10.0) The mixture was purified by preparative SFC using the following methodology: Column: AD-H (2 × 25 cm) Mobile Phase: 70:30 (A:B) A: Liquid CO$_2$, B: MeOH, Flow Rate: 80 mL/min, 272 nm, 100 bar inlet pressure to deliver peak 2. | 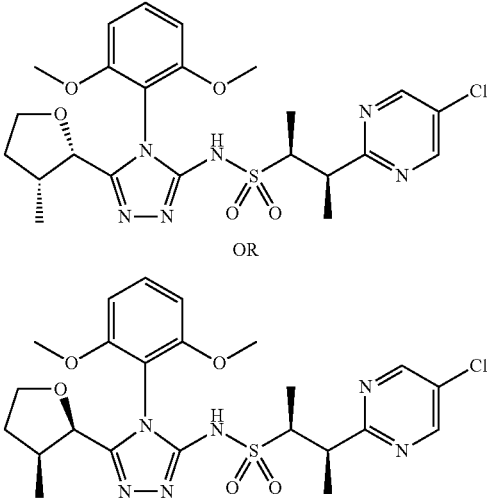 [SMILES: COc1cccc(OC)c1-n1c(NS(=O)(=O)[C@@H](C)[C@H](C)c2ncc(Cl)cn2)nnc1[C@H]1OCC[C@H]1C ; COc1cccc(OC)c1-n1c(NS(=O)(=O)[C@@H](C)[C@H](C)c2ncc(Cl)cn2)nnc1[C@@H]1OCC[C@@H]1C]OR<br><br>(2S,3R)-3-(5-chloropyrimidin-2-yl)-N-(4-(2,6-dimethoxyphenyl)-5-((2R,3S)-3-methyltetrahydrofuran-2-yl)-4H-1,2,4-triazol-3-yl)butane-2-sulfonamide or (2S,3R)-3-(5- |

TABLE 11-continued

| Example | Reagents | Structure, Name and Data |
|---|---|---|
| | | chloropyrimidin-2-yl)-N-(4-(2,6-dimethoxyphenyl)-5-((2S,3R)-3-methyltetrahydrofuran-2-yl)-4H-1,2,4-triazol-3-yl)butane-2-sulfonamide. $^1$H NMR (400 MHz, CD$_2$Cl$_2$) δ 10.80 (br. s., 1H), 8.66-8.58 (m, 2H), 7.51-7.44 (m, 1H), 6.75-6.68 (m, 2H), 4.44 (d, J = 6.6 Hz, 1H), 4.03-3.96 (m, 1H), 3.86-3.77 (m, 7H), 3.74-3.64 (m, 2H), 2.26 (spt, J = 7.0 Hz, 1H), 2.08-1.99 (m, 1H), 1.85-1.76 (m, 1H), 1.30 (d, J = 7.0 Hz, 3H), 1.25 (d, J = 6.8 Hz, 3H), 0.92 (d, J = 7.0 Hz, 3H). LCMS (pos) m/z: 537.2 (M + H)$^+$. |
| 77.0 | (1R,2S)-1-(5-chloropyrimidin-2-yl)-1-methoxypropane-2-sulfonamide (Example 11.3), (2S,5S)-5-methyltetrahydrofuran-2-carbohydrazide and (2R,5R)-5-methyltetrahydrofuran-2-carbohydrazide (commercially available from Ukrorgsyntez), 2-isothiocyanato-1,3-dimethoxybenzene (Example 10.0) The mixture was purified by preparative SFC using the following methodology: Column: AD-H (2 × 25 cm) Mobile Phase: 80:20 (A:B) A: Liquid CO$_2$, B: EtOH, Flow Rate: 70 mL/min, 220 nm, 100 bar inlet pressure to deliver peak 1. | 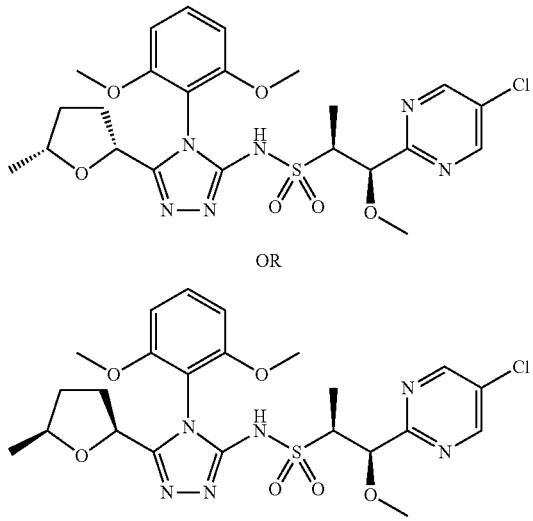 [SMILES: COc1cccc(OC)c1-n1c(NS(=O)(=O)[C@@H](C)[C@H](OC)c2ncc(Cl)cn2)nnc1[C@H]1CC[C@@H](C)O1 ; COc1cccc(OC)c1-n1c(NS(=O)(=O)[C@@H](C)[C@H](OC)c2ncc(Cl)cn2)nnc1[C@@H]1CC[C@H](C)O1]<br>(1R,2S)-1-(5-chloropyrimidin-2-yl)-N-(4-(2,6-dimethoxyphenyl)-5-((2S,5S)-5-methyltetrahydrofuran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((2R,5R)-5-methyltetrahydrofuran-2-yl)-4H-1,2,4-triazol-3-yl)-1-methoxypropane-2-sulfonamide. $^1$H NMR (400 MHz, CD$_2$Cl$_2$) δ 10.76 (br. s., 1H), 8.71 (s, 2H), 7.47 (t, J = 8.5 Hz, 1H), 6.72-6.66 (m, 2H), 4.86 (d, J = 4.6 Hz, 1H), 4.59 (dd, J = 4.9, 8.2 Hz, 1H), 4.00-3.88 (m, 1H), 3.82-3.80 (m, 3H), 3.79 (s, 3H), 3.62-3.54 (m, 1H), 3.28-3.23 (m, 3H), 2.33-2.23 (m, 1H), 2.07-2.01 (m, 1H), 2.00-1.90 (m, 1H), 1.44-1.34 (m, 1H), 1.28-1.23 (m, 3H), 1.07 (d, J = 6.0 Hz, 3H). LCMS (pos) m/z: 553.2 (M + H)$^+$. |

TABLE 11-continued

| Example | Reagents | Structure, Name and Data |
|---|---|---|
| 78.0 | (1R,2S)-1-(5-chloropyrimidin-2-yl)-1-methoxypropane-2-sulfonamide (Example 11.3), (2S,5S)-5-methyltetrahydrofuran-2-carbohydrazide and (2R,5R)-5-methyltetrahydrofuran-2-carbohydrazide (commercially available from Ukrorgsyntez), 2-isothiocyanato-1,3-dimethoxybenzene (Example 10.0). The mixture was purified by preparative SFC using the following methodology: Column: AD-H (2 × 25 cm) Mobile Phase: 80:20 (A:B) A: Liquid CO$_2$, B: EtOH, Flow Rate: 70 mL/min, 220 nm, 100 bar inlet pressure to deliver peak 2. | (1R,2S)-1-(5-chloropyrimidin-2-yl)-N-(4-(2,6-dimethoxyphenyl)-5-((2S,5S)-5-methyltetrahydrofuran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((2R,5R)-5-methyltetrahydrofuran-2-yl)-4H-1,2,4-triazol-3-yl)-1-methoxypropane-2-sulfonamide. $^1$H NMR (400 MHz, CD$_2$Cl$_2$) δ 10.84 (br. s., 1H), 8.77-8.67 (m, 2H), 7.52-7.43 (m, 1H), 6.76-6.67 (m, 2H), 4.86 (d, J = 4.6 Hz, 1H), 4.72-4.58 (m, 1H), 4.01-3.88 (m, 1H), 3.81 (s, 3H), 3.80-3.76 (m, 3H), 3.62-3.54 (m, 1H), 3.25 (s, 3H), 2.32-2.23 (m, 1H), 2.10-2.02 (m, 1H), 2.00-1.89 (m, 1H), 1.43-1.32 (m, 1H), 1.26 (d, J = 7.0 Hz, 3H), 1.13-1.05 (m, 3H). LCMS (pos) m/z: 553.2 (M + H)$^+$. |
| 79.0 | (1R,2S)-1-(5-chloropyrimidin-2-yl)-1-methoxypropane-2-sulfonamide (Example 11.3), (R)-tetrahydrofuran-2-carbohydrazide and (S)-tetrahydrofuran-2-carbohydrazide (commercially available from Enamine), 5-isothiocyanato-4,6-dimethoxypyrimidine (Example 10.1). The mixture was purified by preparative SFC using the following methodology: Column: AD-H (2 × 15 cm) Mobile Phase: 65:35 (A:B) A: Liquid CO$_2$, B: IPA, Flow Rate: 80 mL/min, 260 nm, 100 bar inlet pressure to deliver peak 1. | (1R,2S)-1-(5-chloropyrimidin-2-yl)-N-(4-(4,6-dimethoxypyrimidin-5-yl)-5-((S)-tetrahydrofuran-2-yl)-4H-1,2,4-triazol-3-yl)-1-methoxypropane-2-sulfonamide or (1R,2S)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)-1-methoxypropane-2-sulfonamide. $^1$H NMR (400 MHz, DMSO-d$_6$) δ 13.11 (s, 1H), 8.93 (s, 2H), 8.66 (s, 1H), 4.78 (d, J = 3.9 Hz, 1H), 4.69 (dd, J = 5.3, 7.8 Hz, 1H), 3.98-3.91 (m, 6H), 3.68 (td, J = 6.7, 8.1 |

TABLE 11-continued

| Example | Reagents | Structure, Name and Data |
|---|---|---|
| | | Hz, 1H), 3.52-3.45 (m, 1H), 3.40 (dq, J = 4.1, 7.0 Hz, 1H), 3.13 (s, 3H), 2.25-2.15 (m, 1H), 2.07 (qd, J = 7.5, 12.5 Hz, 1H), 1.88-1.78 (m, 2H), 1.14 (d, J = 6.8 Hz, 3H). LCMS (pos) m/z: 541.0 (M + H)+. |
| 80.0 | (1R,2S)-1-(5-chloropyrimidin-2-yl)-1-methoxypropane-2-sulfonamide (Example 11.3), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: AD-H (2 × 15 cm) Mobile Phase: 65:35 (A:B) A: Liquid CO$_2$, B: IPA, Flow Rate: 80 mL/min, 260 nm, 100 bar inlet pressure to deliver peak 2. | 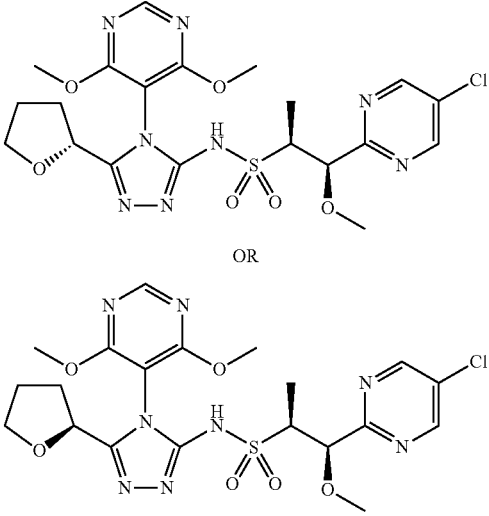<br>OR<br><br>(1R,2S)-1-(5-chloropyrimidin-2-yl)-N-(4-(4,6-dimethoxypyrimidin-5-yl)-5-((S)-tetrahydrofuran-2-yl)-4H-1,2,4-triazol-3-yl)-1-methoxypropane-2-sulfonamide or (1R,2S)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)-1-methoxypropane-2-sulfonamide. $^1$H NMR (400 MHz, DMSO-d$_6$) δ 13.11 (s, 1H), 8.93 (s, 2H), 8.66 (s, 1H), 4.77 (d, J = 4.1 Hz, 1H), 4.69 (dd, J = 5.2, 7.7 Hz, 1H), 3.96 (s, 3H), 3.94 (s, 3H), 3.71-3.64 (m, 1H), 3.52-3.45 (m, 1H), 3.44-3.37 (m, 1H), 3.15-3.11 (m, 3H), 2.26-2.15 (m, 1H), 2.13-2.03 (m, 1H), 1.89-1.78 (m, 2H), 1.13 (d, J = 7.0 Hz, 3H). LCMS (pos) m/z: 541.1 (M + H)+. |
| 81.0 | (2S,3R)-3-(5-chloropyrimidin-2-yl)butane-2-sulfonamide (Example 1.4), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: AS-H (2 × 25 cm) Mobile Phase: 75:25 (A:B) A: Liquid CO$_2$, B: MeOH, Flow Rate: 70 mL/min, 260 nm, 100 bar inlet pressure to deliver peak 1. | 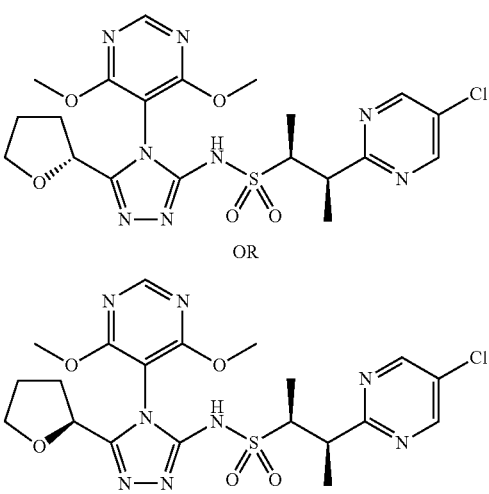 [SMILES: COc1ncnc(OC)c1-n1c(NS(=O)(=O)[C@@H](C)[C@H](C)c2ncc(Cl)cn2)nnc1[C@H]1CCCO1 ; COc1ncnc(OC)c1-n1c(NS(=O)(=O)[C@@H](C)[C@H](C)c2ncc(Cl)cn2)nnc1[C@@H]1CCCO1]<br>OR<br><br>(2S,3R)-3-(5-chloropyrimidin-2-yl)-N-(4-(4,6-dimethoxypyrimidin-5-yl)-5-((S)-tetrahydrofuran-2-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((R)-tetrahydrofuran-2-yl)-4H-1,2,4-triazol-3-yl)butane-2-sulfonamide. $^1$H NMR (400 MHz, DMSO-d$_6$) δ 13.09 (br. s., 1H), 8.90-8.81 (m, 2H), 8.68-8.63 (m, 1H), 4.67 (dd, J = 5.4, 7.7 Hz, 1H), 3.93 (s, 3H), 3.93-3.88 (m, |

TABLE 11-continued

| Example | Reagents | Structure, Name and Data |
|---|---|---|
| | | 3H), 3.71-3.61 (m, 2H), 3.60-3.54 (m, 1H), 3.52-3.47 (m, 1H), 2.24-2.14 (m, 1H), 2.12-2.03 (m, 1H), 1.82 (quin, J = 7.1 Hz, 2H), 1.23 (d, J = 7.0 Hz, 3H), 1.10 (d, J = 6.8 Hz, 3H). LCMS (pos) m/z: 525.0 (M + H)$^+$. |
| 82.0 | (2S,3R)-3-(5-chloropyrimidin-2-yl)butane-2-sulfonamide (Example 1.4), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: AS-H (2 × 25 cm) Mobile Phase: 75:25 (A:B) A: Liquid CO$_2$, B: MeOH, Flow Rate: 70 mL/min, 260 nm, 100 bar inlet pressure to deliver peak 2. | (2S,3R)-3-(5-chloropyrimidin-2-yl)-N-(4-(4,6-dimethoxypyrimidin-5-yl)-5-((S)-tetrahydrofuran-2-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((R)-tetrahydrofuran-2-yl)-4H-1,2,4-triazol-3-yl)butane-2-sulfonamide. $^1$H NMR (400 MHz, DMSO-d$_6$) δ 12.89 (br. s., 1H), 8.90-8.84 (m, 2H), 8.67-8.63 (m, 1H), 4.67 (dd, J = 5.4, 7.7 Hz, 1H), 3.98-3.93 (m, 3H), 3.93-3.90 (m, 3H), 3.70-3.56 (m, 3H), 3.51-3.45 (m, 1H), 2.27-2.15 (m, 1H), 2.13-2.02 (m, 1H), 1.87-1.78 (m, 2H), 1.27-1.22 (m, 3H), 1.15-1.08 (m, 3H). LCMS (pos) m/z: 525.0 (M + H)$^+$. |
| 83.0 | (1R,2S)-1-(5-chloropyrimidin-2-yl)-1-methoxypropane-2-sulfonamide (Example 11.3), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: OZ-H (2 × 25 cm) Mobile Phase: 65:35 (A:B) A: Liquid CO$_2$, B: EtOH, Flow Rate: 70 mL/min, 215 nm, 100 bar inlet pressure to deliver peak 1. | (1R,2S)-1-(5-chloropyrimidin-2-yl)-N-(4-(2,6-dimethoxyphenyl)-5-((S)-tetrahydro-2H-pyran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((R)-tetrahydro-2H-pyran-2-yl)-4H-1,2,4-triazol-3-yl)-1-methoxypropane-2-sulfonamide. $^1$H NMR (400 MHz, DMSO-d$_6$) δ 12.90 (br. s., 1H), 8.92 (s, 2H), 7.47 (t, J = 8.5 Hz, 1H), 6.82 (dd, J = 2.1, 8.5 Hz, 2H), 4.77 (d, J = 4.4 Hz, 1H), 4.01 (dd, J = 3.3, 8.7 Hz, 1H), |

TABLE 11-continued

| Example | Reagents | Structure, Name and Data |
|---|---|---|
| | | 3.74 (s, 3H), 3.72 (s, 3H), 3.67-3.60 (m, 1H), 3.45-3.37 (m, 1H), 3.22-3.11 (m, 4H), 1.86-1.64 (m, 3H), 1.52-1.35 (m, 3H), 1.14 (d, J = 6.8 Hz, 3H). LCMS (pos) m/z: 553.0 (M + H)⁺. |
| 84.0 | (1R,2S)-1-(5-chloropyrimidin-2-yl)-1-methoxypropane-2-sulfonamide (Example 11.3), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: OZ-H (2 × 25 cm) Mobile Phase: 65:35 (A:B) A: Liquid CO₂, B: EtOH, Flow Rate: 70 mL/min, 215 nm, 100 bar inlet pressure to deliver peak 2. | 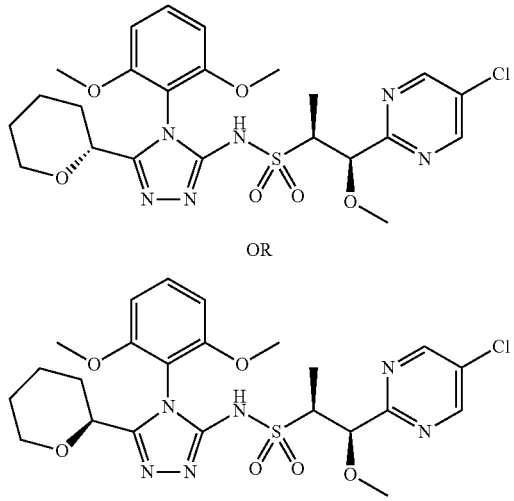 [SMILES: COc1cccc(OC)c1-n1c(NS(=O)(=O)[C@@H](C)[C@H](OC)c2ncc(Cl)cn2)nnc1[C@H]1CCCCO1 ; COc1cccc(OC)c1-n1c(NS(=O)(=O)[C@@H](C)[C@H](OC)c2ncc(Cl)cn2)nnc1[C@@H]1CCCCO1]<br><br>(1R,2S)-1-(5-chloropyrimidin-2-yl)-N-(4-(2,6-dimethoxyphenyl)-5-((S)-tetrahydro-2H-pyran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((R)-tetrahydro-2H-pyran-2-yl)-4H-1,2,4-triazol-3-yl)-1-methoxypropane-2-sulfonamide. ¹H NMR (400 MHz, DMSO-d₆) δ 12.92 (s, 1H), 8.92 (s, 2H), 7.47 (t, J = 8.5 Hz, 1H), 6.83 (d, J = 8.7 Hz, 2H), 4.77 (d, J = 4.4 Hz, 1H), 4.01 (dd, J = 3.3, 8.7 Hz, 1H), 3.75 (s, 3H), 3.71 (s, 3H), 3.66-3.59 (m, 1H), 3.46-3.37 (m, 1H), 3.23-3.10 (m, 4H), 1.86-1.65 (m, 3H), 1.50-1.35 (m, 3H), 1.13 (d, J = 7.0 Hz, 3H). LCMS (pos) m/z: 553.1 (M + H)⁺. |
| 85.0 | (2S,3R)-3-(5-methylpyrimidin-2-yl)butane-2-sulfonamide (Example 1.0), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: AD-H (2 × 25 cm) Mobile Phase: 80:20 (A:B) A: Liquid CO₂, B: MeOH, Flow Rate: 60 mL/min, 220 nm, 100 bar inlet pressure to deliver peak 1. | 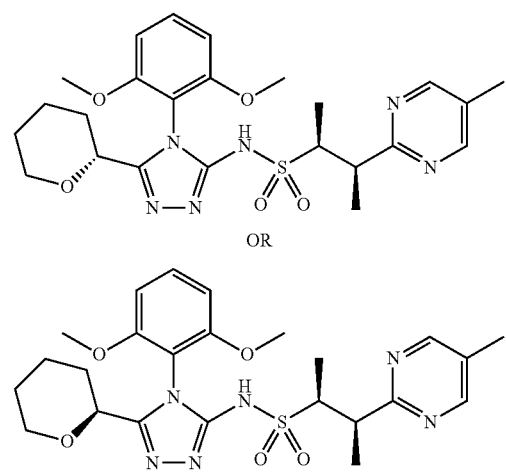 [SMILES: COc1cccc(OC)c1-n1c(NS(=O)(=O)[C@@H](C)[C@H](C)c2ncc(C)cn2)nnc1[C@H]1CCCCO1 ; COc1cccc(OC)c1-n1c(NS(=O)(=O)[C@@H](C)[C@H](C)c2ncc(C)cn2)nnc1[C@@H]1CCCCO1]<br><br>(2S,3R)-N-(4-(2,6-dimethoxyphenyl)-5-((S)-tetrahydro-2H-pyran-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((R)-tetrahydro-2H-pyran-2-yl)-4H-1,2,4-triazol-3-yl)-3-(5-methylpyrimidin-2-yl)butane-2-sulfonamide. ¹H NMR (400 MHz, DMSO-d₆) δ 12.86 (br. s., 1H), 8.58 (d, J = 0.6 Hz, 2H), 7.46 (t, J = 8.5 Hz, 1H), 6.81 (d, J = 8.5 Hz, 2H), 3.99 (dd, J = 3.4, 9.0 Hz, 1H), 3.73 (s, 3H), 3.68 (s, 3H), 3.68-3.60 (m, 2H), 3.60-3.53 (m, 1H), 3.15 (td, J = 6.1, 11.8 Hz, 1H), 2.23 (s, 3H), |

TABLE 11-continued

| Example | Reagents | Structure, Name and Data |
|---|---|---|
| | | 1.86-1.65 (m, 3H), 1.50-1.35 (m, 3H), 1.22 (d, J = 7.0 Hz, 3H), 1.07 (d, J = 7.0 Hz, 3H). LCMS (pos) m/z: 517.2 (M + H)⁺. |
| 86.0 | (2S,3R)-3-(5-methylpyrimidin-2-yl)butane-2-sulfonamide (Example 1.0), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: AD-H (2 × 25 cm) Mobile Phase: 80:20 (A:B) A: Liquid $CO_2$, B: MeOH, Flow Rate: 60 mL/min, 220 nm, 100 bar inlet pressure to deliver peak 2. | 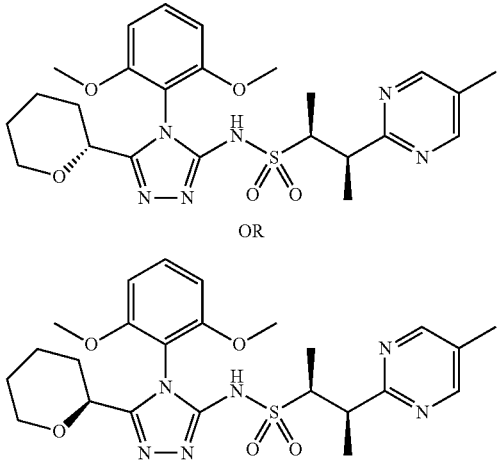 [SMILES: COc1cccc(OC)c1-n1c(NS(=O)(=O)[C@@H](C)[C@H](C)c2ncc(C)cn2)nnc1[C@H]1CCCCO1 ; COc1cccc(OC)c1-n1c(NS(=O)(=O)[C@@H](C)[C@H](C)c2ncc(C)cn2)nnc1[C@@H]1CCCCO1]<br>OR<br><br>(2S,3R)-N-(4-(2,6-dimethoxyphenyl)-5-((S)-tetrahydro-2H-pyran-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((R)-tetrahydro-2H-pyran-2-yl)-4H-1,2,4-triazol-3-yl)-3-(5-methylpyrimidin-2-yl)butane-2-sulfonamide. ¹H NMR (400 MHz, DMSO-$d_6$) δ 12.87 (br. s., 1H), 8.58 (d, J = 0.6 Hz, 2H), 7.46 (t, J = 8.5 Hz, 1H), 6.85-6.77 (m, 2H), 4.00 (dd, J = 3.4, 8.8 Hz, 1H), 3.72 (s, 3H), 3.69 (s, 3H), 3.67-3.60 (m, 2H), 3.58-3.50 (m, 1H), 3.15 (td, J = 6.1, 11.7 Hz, 1H), 2.23 (s, 3H), 1.86-1.66 (m, 3H), 1.52-1.35 (m, 3H), 1.23 (d, J = 7.0 Hz, 3H), 1.07 (d, J = 7.0 Hz, 3H). LCMS (pos) m/z: 517.2 (M + H)⁺. |
| 87.0 | (2S,3R)-3-(5-chloropyrimidin-2-yl)butane-2-sulfonamide (Example 1.4), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: AD-H (2 × 25 cm) Mobile Phase: 80:20 (A:B) A: Liquid $CO_2$, B: MeOH, Flow Rate: 60 mL/min, 220 nm, 100 bar inlet pressure to deliver peak 1. | 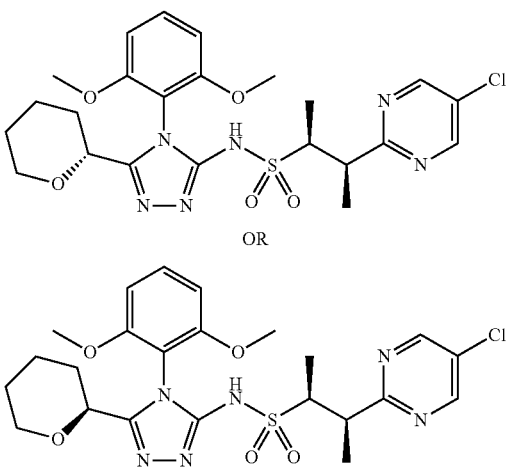 [SMILES: COc1cccc(OC)c1-n1c(NS(=O)(=O)[C@@H](C)[C@H](C)c2ncc(Cl)cn2)nnc1[C@H]1CCCCO1 ; COc1cccc(OC)c1-n1c(NS(=O)(=O)[C@@H](C)[C@H](C)c2ncc(Cl)cn2)nnc1[C@@H]1CCCCO1]<br>OR<br><br>(2S,3R)-3-(5-chloropyrimidin-2-yl)-N-(4-(2,6-dimethoxyphenyl)-5-((S)-tetrahydro-2H-pyran-2-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-tetrahydro-2H-pyran-2-yl)-4H-1,2,4-triazol-3-yl)butane-2-sulfonamide. ¹H NMR (400 MHz, DMSO-$d_6$) δ 12.89 (s, 1H), 8.86-8.80 (m, 2H), 7.49-7.42 (m, 1H), 6.85-6.78 (m, 2H), 4.00 (dd, J = 3.5, 8.9 Hz, 1H), 3.74 (s, 3H), 3.72-3.68 (m, 3H), 3.68-3.61 (m, 2H), 3.57-3.49 (m, 1H), 3.20-3.11 (m, 1H), 1.85-1.66 (m, 3H), 1.51-1.35 (m, 3H), 1.23 (d, J = 7.0 Hz, 3H), 1.10 (d, J = 6.8 Hz, 3H). LCMS (pos) m/z: 537.1 (M + H)⁺. |

TABLE 11-continued

| Example | Reagents | Structure, Name and Data |
|---|---|---|
| 88.0 | (2S,3R)-3-(5-chloropyrimidin-2-yl)butane-2-sulfonamide (Example 1.4), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: AD-H (2 × 25 cm) Mobile Phase: 80:20 (A:B) A: Liquid $CO_2$, B: MeOH, Flow Rate: 60 mL/min, 220 nm, 100 bar inlet pressure to deliver peak 2. | 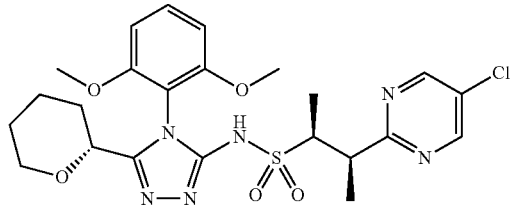<br>OR<br>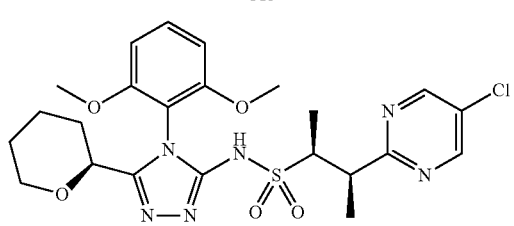<br>(2S,3R)-3-(5-chloropyrimidin-2-yl)-N-(4-(2,6-dimethoxyphenyl)-5-((S)-tetrahydro-2H-pyran-2-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-tetrahydro-2H-pyran-2-yl)-4H-1,2,4-triazol-3-yl)butane-2-sulfonamide. $^1$H NMR (400 MHz, DMSO-$d_6$) δ 12.90 (s, 1H), 8.87-8.81 (m, 2H), 7.47 (t, J = 8.5 Hz, 1H), 6.81 (dd, J = 3.9, 8.5 Hz, 2H), 4.00 (dd, J = 3.6, 8.8 Hz, 1H), 3.74 (s, 3H), 3.70 (s, 3H), 3.67-3.59 (m, 2H), 3.58-3.50 (m, 1H), 3.15 (td, J = 6.0, 11.8 Hz, 1H), 1.85-1.66 (m, 3H), 1.52-1.35 (m, 3H), 1.23 (d, J = 7.3 Hz, 3H), 1.10 (d, J = 7.0 Hz, 3H). LCMS (pos) m/z: 537.2 (M + H)$^+$. |
| 89.0 | (2S,3R)-3-(5-methylpyrazin-2-yl)butane-2-sulfonamide (Example 1.2), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: IC (2 × 15 cm) Mobile Phase: 67:33 (A:B) A: Liquid $CO_2$, B: IPA, Flow Rate: 60 mL/min, 220 nm, 100 bar inlet pressure to deliver peak 1. | 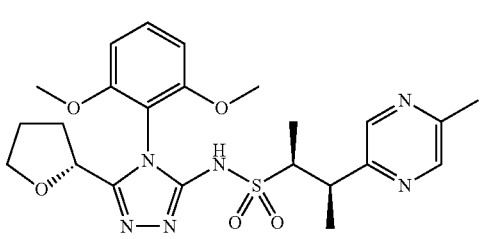<br>OR<br><br>(2S,3R)-N-(4-(2,6-dimethoxyphenyl)-5-((S)-tetrahydrofuran-2-yl)-4H-1,2,4-triazol-3-yl)-3-(5-methylpyrazin-2-yl)butane-2-sulfonamide or (2S,3R)-N-(4-(2,6-dimethoxyphenyl)-5-((R)-tetrahydrofuran-2-yl)-4H-1,2,4-triazol-3-yl)-3-(5-methylpyrazin-2-yl)butane-2-sulfonamide. $^1$H NMR (400 MHz, DMSO-$d_6$) δ 12.89 (br. s., 1H), 8.43 (s, 1H), 8.30(s, 1H), 7.48 (t, J = 8.4 Hz, 1H), 6.83 (dd, J = 1.2, 8.5 Hz, 2H), 4.50 (dd, J = 5.6, 7.7 Hz, 1H), 3.74 (s, 3H), 3.73 (s, 3H), 3.67-3.61 (m, 1H), 3.60-3.48 (m, 2H), 3.29-3.21 (m, 1H), 2.44 (s, 3H), 2.16-2.06 (m, 1H), 2.04-1.94 (m, 1H), 1.83-1.75 (m, 2H), 1.22 (d, J = 7.0 Hz, 3H), 1.10 (d, J = 7.0 Hz, 3H). LCMS (pos) m/z: 503.2 (M + H)$^+$. |

TABLE 11-continued

| Example | Reagents | Structure, Name and Data |
|---|---|---|
| 90.0 | (2S,3R)-3-(5-methylpyrazin-2-yl)butane-2-sulfonamide (Example 1.2), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: IC (2 × 15 cm) Mobile Phase: 67:33 (A:B) A: Liquid CO$_2$, B: IPA, Flow Rate: 60 mL/min, 220 nm, 100 bar inlet pressure to deliver peak 2. | 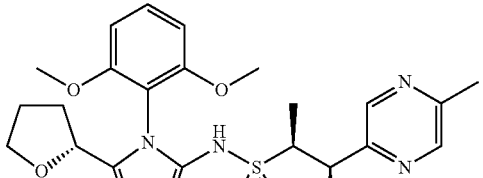<br>OR<br>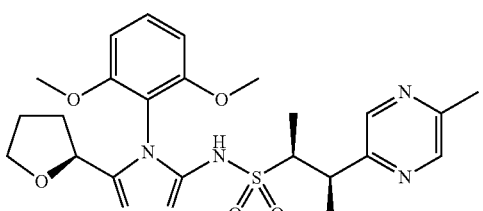<br>(2S,3R)-N-(4-(2,6-dimethoxyphenyl)-5-((S)-tetrahydrofuran-2-yl)-4H-1,2,4-triazol-3-yl)-3-(5-methylpyrazin-2-yl)butane-2-sulfonamide or (2S,3R)-N-(4-(2,6-dimethoxyphenyl)-5-((R)-tetrahydrofuran-2-yl)-4H-1,2,4-triazol-3-yl)-3-(5-methylpyrazin-2-yl)butane-2-sulfonamide. $^1$H NMR (400 MHz, DMSO-d$_6$) δ 12.88 (br. s., 1H), 8.43 (s, 1H), 8.30 (s, 1H), 7.47 (t, J = 8.5 Hz, 1H), 6.83 (dd, J = 1.9, 8.5 Hz, 2H), 4.49 (dd, J = 5.6, 7.7 Hz, 1H), 3.74 (s, 3H), 3.73 (s, 3H), 3.67-3.61 (m, 1H), 3.59-3.48 (m, 2H), 3.29-3.21 (m, 1H), 2.44 (s, 3H), 2.15-2.05 (m, 1H), 2.02-1.93 (m, 1H), 1.85-1.73 (m, 2H), 1.22 (d, J = 7.0 Hz, 3H), 1.09 (d, J = 7.0 Hz, 3H). LCMS (pos) m/z: 503.2 (M + H)$^+$. |
| 91.0 | (1R,2S)-1-(5-chloropyrimidin-2-yl)-1-methoxypropane-2-sulfonamide (Example 11.3), (R)-tetrahydro-2H-pyran-3-carbohydrazide and (S)-tetrahydro-2H-pyran-3-carbohydrazide (commercially available from Synthonix), 5-isothiocyanato-4,6-dimethoxypyrimidine (Example 10.1). The mixture was purified by preparative SFC using the following methodology: Column: AD-H (2 × 15 cm) Mobile Phase: 65:35 (A:B) A: Liquid CO$_2$, B: IPA, Flow Rate: 80 mL/min, 220 nm, 100 bar inlet pressure to deliver peak 1. | 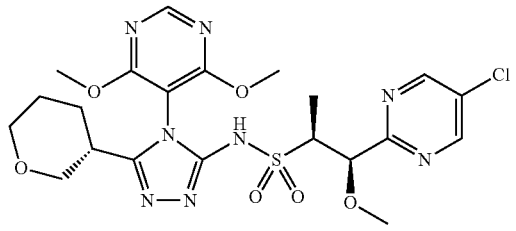<br>OR<br>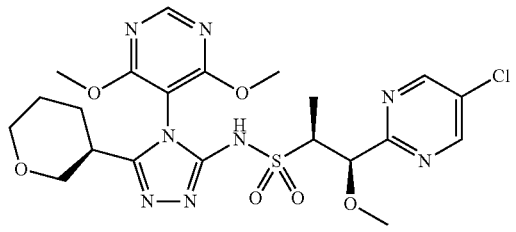<br>(1R,2S)-1-(5-chloropyrimidin-2-yl)-N-(4-(4,6-dimethoxypyrimidin-5-yl)-5-((S)-tetrahydro-2H-pyran-3-yl)-4H-1,2,4-triazol-3-yl)-1-methoxypropane-2-sulfonamide or (1R,2S)-1-(5-chloropyrimidin-2-yl)-N-(4-(4,6-dimethoxypyrimidin-5-yl)-5-((R)-tetrahydro-2H-pyran-3-yl)-4H-1,2,4-triazol-3-yl)-1-methoxypropane-2-sulfonamide. $^1$H NMR (400 MHz, DMSO-d$_6$) δ 13.06 (s, 1H), 8.93 (s, 2H), 8.71 (s, 1H), 4.77 (d, J = 3.9 Hz, 1H), 3.97 (s, 3H), 3.97-3.91 (m, 3H), 3.81-3.75 (m, 1H), 3.74 (d, J = 6.2 Hz, 1H), 3.41-3.32 (m, 3H), 3.18-3.07 (m, 3H), 2.56-2.51 (m, 1H), 1.83 (d, J = 9.1 Hz, 1H), 1.75-1.65 (m, |

TABLE 11-continued

| Example | Reagents | Structure, Name and Data |
|---|---|---|
| | | 1H), 1.65-1.57 (m, 1H), 1.56-1.44 (m, 1H), 1.11 (d, J = 7.0 Hz, 3H). LCMS (pos) m/z: 555.0 (M + H)+. |
| 92.0 | (1R,2S)-1-(5-chloropyrimidin-2-yl)-1-methoxypropane-2-sulfonamide (Example 11.3), (R)-tetrahydro-2H-pyran-3-carbohydrazide and (S)-tetrahydro-2H-pyran-3-carbohydrazide (commercially available from Synthonix), 5-isothiocyanato-4,6-dimethoxypyrimidine (Example 10.1). The mixture was purified by preparative SFC using the following methodology: Column: AD-H (2 × 15 cm) Mobile Phase: 65:35 (A:B) A: Liquid CO$_2$, B: IPA, Flow Rate: 80 mL/min, 220 nm, 100 bar inlet pressure to deliver peak 2. | 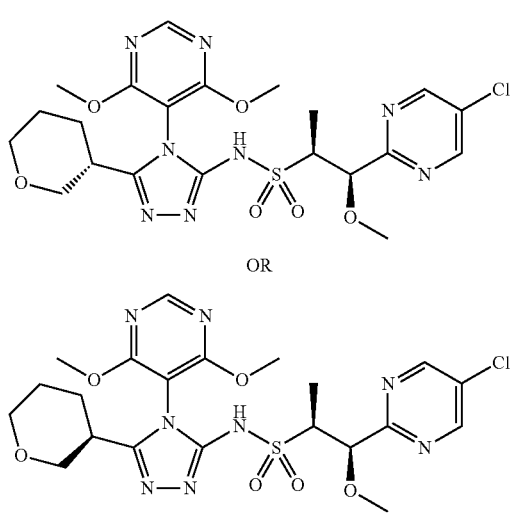 [SMILES: COc1ncnc(OC)c1-n1c(NS(=O)(=O)[C@@H](C)[C@H](OC)c2ncc(Cl)cn2)nnc1[C@H]1CCCOC1 ; COc1ncnc(OC)c1-n1c(NS(=O)(=O)[C@@H](C)[C@H](OC)c2ncc(Cl)cn2)nnc1[C@@H]1CCCOC1]<br>OR<br><br>(1R,2S)-1-(5-chloropyrimidin-2-yl)-N-(4-(4,6-dimethoxypyrimidin-5-yl)-5-((S)-tetrahydro-2H-pyran-3-yl)-4H-1,2,4-triazol-3-yl)-1-methoxypropane-2-sulfonamide or (1R,2S)-1-(5-chloropyrimidin-2-yl)-N-(4-(4,6-dimethoxypyrimidin-5-yl)-5-((R)-tetrahydro-2H-pyran-3-yl)-4H-1,2,4-triazol-3-yl)-1-methoxypropane-2-sulfonamide. $^1$H NMR (400 MHz, DMSO-d$_6$) δ 13.06 (s, 1H), 8.93 (s, 2H), 8.71 (s, 1H), 4.77 (d, J = 3.9 Hz, 1H), 3.97 (s, 3H), 3.96 (s, 3H), 3.78-3.69 (m, 2H), 3.47-3.33 (m, 3H), 3.19-3.09 (m, 3H), 2.61-2.51 (m, 1H), 1.84 (d, J = 9.7 Hz, 1H), 1.78-1.66 (m, 1H), 1.66-1.58 (m, 1H), 1.55-1.42 (m, 1H), 1.12 (d, J = 6.8 Hz, 3H). LCMS (pos) m/z: 555.2 (M + H)+. |
| 93.0 | (2S,3R)-3-(5-chloropyrimidin-2-yl)butane-2-sulfonamide (Example 1.4), (R)-tetrahydrofuran-3-carbohydrazide and (S)-tetrahydrofuran-3-carbohydrazide (commercially available from Astatech Inc.), 5-isothiocyanato-4,6-dimethoxypyrimidine (Example 10.1). The mixture was purified by preparative SFC using the following methodology: Column: IC (2 × 15 cm) Mobile Phase: 70:30 (A:B) A: Liquid CO$_2$, B: MeOH, Flow Rate: 60 mL/min, 220 nm, 100 bar inlet pressure to deliver peak 1. | 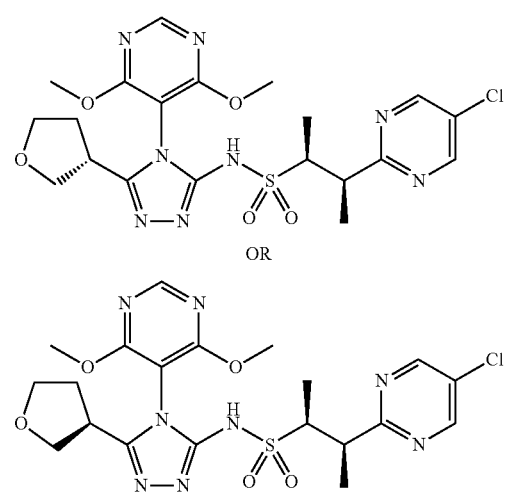<br>OR<br><br>(2S,3R)-3-(5-chloropyrimidin-2-yl)-N-(4-(4,6-dimethoxypyrimidin-5-yl)-5-((R)-tetrahydrofuran-3-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((S)-tetrahydrofuran-3-yl)-4H-1,2,4-triazol-3-yl)butane-2-sulfonamide. $^1$H NMR (400 MHz, DMSO-d$_6$) δ 13.00 (br. s., 1H), 8.86 (s, 2H), 8.74-8.66 (m, 1H), 4.01-3.93 (m, 6H), 3.81-3.75 (m, 1H), 3.75-3.71 (m, 1H), 3.69-3.60 (m, 3H), 3.59-3.53 (m, 1H), 3.20-3.12 (m, |

TABLE 11-continued

| Example | Reagents | Structure, Name and Data |
|---|---|---|
| | | 1H), 2.01 (q, J = 7.0 Hz, 2H), 1.23 (d, J = 7.0 Hz, 3H), 1.10 (d, J = 7.0 Hz, 3H). LCMS (pos) m/z: 525.0 (M + H)⁺. |
| 94.0 | (2S,3R)-3-(5-chloropyrimidin-2-yl)butane-2-sulfonamide (Example 1.4), (R)-tetrahydrofuran-3-carbohydrazide and (S)-tetrahydrofuran-3-carbohydrazide (commercially available from Astatech Inc.), 5-isothiocyanato-4,6-dimethoxypyrimidine (Example 10.1). The mixture was purified by preparative SFC using the following methodology: Column: IC (2 × 15 cm) Mobile Phase: 70:30 (A:B) A: Liquid CO$_2$, B: MeOH, Flow Rate: 60 mL/min, 220 nm, 100 bar inlet pressure to deliver peak 2. | (2S,3R)-3-(5-chloropyrimidin-2-yl)-N-(4-(4,6-dimethoxypyrimidin-5-yl)-5-((R)-tetrahydrofuran-3-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((S)-tetrahydrofuran-3-yl)-4H-1,2,4-triazol-3-yl)butane-2-sulfonamide. ¹H NMR (400 MHz, DMSO-d$_6$) δ 12.97 (br. s., 1H), 8.86 (s, 2H), 8.71-8.68 (m, 1H), 3.95 (s, 3H), 3.95 (s, 3H), 3.81-3.72 (m, 2H), 3.71-3.61 (m, 3H), 3.60-3.53 (m, 1H), 3.19-3.11 (m, 1H), 2.05-1.96 (m, 2H), 1.23 (d, J = 7.0 Hz, 3H), 1.10 (d, J = 7.0 Hz, 3H). LCMS (pos) m/z: 525.0 (M + H)⁺. |
| 95.0 | (1S,2S)-1-isopropoxy-1-(5-methylpyrimidin-2-yl)propane-2-sulfonamide (Example 13.5), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: Regis Whelk-O S, S (2 × 25 cm) Mobile Phase: 70:30 (A:B) A: Liquid CO$_2$, B: IPA, Flow Rate: 70 mL/min, 215 nm, 100 bar inlet pressure to deliver peak 1. | (1S,2S)-N-(4-(4,6-dimethoxypyrimidin-5-yl)-5-((S)-tetrahydrofuran-2-yl)-4H-1,2,4-triazol-3-yl)-1-isopropoxy-1-(5-methylpyrimidin-2-yl)propane-2-sulfonamide or (1S,2S)-N-(4-(4,6-dimethoxypyrimidin-5-yl)-5-((R)-tetrahydrofuran-2-yl)-4H-1,2,4-triazol-3-yl)-1-isopropoxy-1-(5-methylpyrimidin-2-yl)propane-2-sulfonamide. ¹H NMR (400 MHz, CD$_2$Cl$_2$) δ 12.53 (br. s., 1H), 8.62 |

| Example | Reagents | Structure, Name and Data |
|---|---|---|
| | | (d, J = 0.6 Hz, 2H), 8.51 (s, 1H), 4.79 (d, J = 4.1 Hz, 1H), 4.67 (dd, J = 5.0, 7.7 Hz, 1H), 4.04 (s, 3H), 4.01 (s, 3H), 3.79-3.72 (m, 1H), 3.72-3.65 (m, 1H), 3.65-3.58 (m, 1H), 3.52 (td, J = 6.0, 12.2 Hz, 1H), 2.34 (s, 3H), 2.33-2.25 (m, 1H), 2.12-2.03 (m, 1H), 2.01-1.85 (m, 2H), 1.35 (d, J = 7.0 Hz, 3H), 1.08 (d, J = 6.0 Hz, 3H), 0.98-0.92 (m, 3H). LCMS (pos) m/z: 549.2 (M + H)$^+$. |
| 96.0 | (1S,2S)-1-isopropoxy-1-(5-methylpyrimidin-2-yl)propane-2-sulfonamide (Example 13.5), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: Regis Whelk-O S, S (2 × 25 cm) Mobile Phase: 70:30 (A:B) A: Liquid CO$_2$, B: IPA, Flow Rate: 70 mL/min, 215 nm, 100 bar inlet pressure to deliver peak 2. | 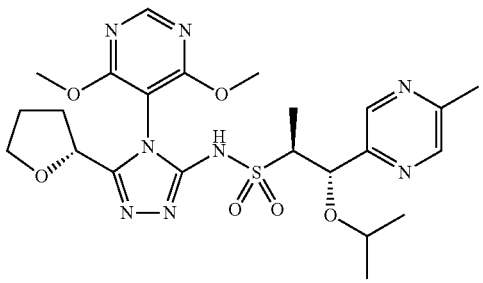<br>OR<br>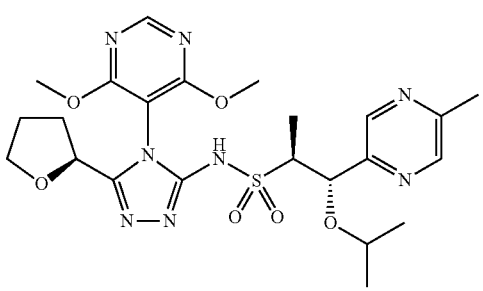<br>(1S,2S)-N-(4-(4,6-dimethoxypyrimidin-5-yl)-5-((S)-tetrahydrofuran-2-yl)-4H-1,2,4-triazol-3-yl)-1-isopropoxy-1-(5-methylpyrimidin-2-yl)propane-2-sulfonamide or (1S,2S)-N-(4-(4,6-dimethoxypyrimidin-5-yl)-5-((R)-tetrahydrofuran-2-yl)-4H-1,2,4-triazol-3-yl)-1-isopropoxy-1-(5-methylpyrimidin-2-yl)propane-2-sulfonamide. $^1$H NMR (400 MHz, CD$_2$Cl$_2$) δ 8.63 (d, J = 0.8 Hz, 2H), 8.50 (s, 1H), 4.80 (d, J = 3.7 Hz, 1H), 4.70 (dd, J = 4.7, 7.8 Hz, 1H), 4.05 (s, 3H), 3.99 (s, 3H), 3.73 (dt, J = 6.1, 7.8 Hz, 1H), 3.64-3.57 (m, 2H), 3.57-3.50 (m, 1H), 2.49-2.42 (m, 1H), 2.34 (s, 3H), 2.15-2.06 (m, 1H), 2.00-1.87 (m, 2H), 1.42 (d, J = 7.0 Hz, 3H), 1.08 (d, J = 6.0 Hz, 3H), 0.95 (d, J = 6.2 Hz, 3H). LCMS (pos) m/z: 549.2 (M + H)$^+$. |

TABLE 11-continued

| Example | Reagents | Structure, Name and Data |
|---|---|---|
| 97.0 | (1S,2S)-1-isopropoxy-1-(5-methylpyrimidin-2-yl)propane-2-sulfonamide (Example 13.5), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: OD-H (2 × 25 cm) Mobile Phase: 80:20 (A:B) A: Liquid CO$_2$, B: IPA, Flow Rate: 70 mL/min, 220 nm, 100 bar inlet pressure to deliver peak 1. | (1S,2S)-N-(4-(2,6-dimethoxyphenyl)-5-((S)-tetrahydrofuran-2-yl)-4H-1,2,4-triazol-3-yl)-1-isopropoxy-1-(5-methylpyrimidin-2-yl)propane-2-sulfonamide or (1S,2S)-N-(4-(2,6-dimethoxyphenyl)-5-((R)-tetrahydrofuran-2-yl)-4H-1,2,4-triazol-3-yl)-1-isopropoxy-1-(5-methylpyrimidin-2-yl)propane-2-sulfonamide. $^1$H NMR (400 MHz, DMSO-d$_6$) δ 12.85 (s, 1H), 8.65 (d, J = 0.8 Hz, 2H), 7.47 (t, J = 8.5 Hz, 1H), 6.88-6.81 (m, 2H), 4.69 (d, J = 7.3 Hz, 1H), 4.51 (dd, J = 5.4, 7.7 Hz, 1H), 3.79 (s, 3H), 3.77 (s, 3H), 3.67-3.61 (m, 1H), 3.54-3.49 (m, 1H), 3.43-3.35 (m, 2H), 2.27 (s, 3H), 2.14-2.06 (m, 1H), 2.01-1.93 (m, 1H), 1.83-1.75 (m, 2H), 0.98 (d, J = 6.0 Hz, 3H), 0.92 (d, J = 7.0 Hz, 3H), 0.79 (d, J = 6.2 Hz, 3H). LCMS (pos) m/z: 547.2 (M + H)$^+$. |
| 98.0 | (1S,2S)-1-isopropoxy-1-(5-methylpyrimidin-2-yl)propane-2-sulfonamide (Example 13.5), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: OD-H (2 × 25 cm) Mobile Phase: 80:20 (A:B) A: Liquid CO$_2$, B: IPA, Flow Rate: 70 mL/min, 220 nm, 100 bar inlet pressure to deliver peak 2. | (1S,2S)-N-(4-(2,6-dimethoxyphenyl)-5-((S)-tetrahydrofuran-2-yl)-4H-1,2,4-triazol-3-yl)-1- |

| Example | Reagents | Structure, Name and Data |
|---|---|---|
| | | isopropoxy-1-(5-methylpyrimidin-2-yl)propane-2-sulfonamide or (1S,2S)-N-(4-(2,6-dimethoxyphenyl)-5-((R)-tetrahydrofuran-2-yl)-4H-1,2,4-triazol-3-yl)-1-isopropoxy-1-(5-methylpyrimidin-2-yl)propane-2-sulfonamide. $^1$H NMR (400 MHz, DMSO-$d_6$) δ 12.86 (s, 1H), 8.65 (d, J = 0.6 Hz, 2H), 7.51-7.44 (m, 1H), 6.84 (dd, J = 1.6, 8.6 Hz, 2H), 4.68 (d, J = 7.7 Hz, 1H), 4.51 (dd, J = 5.4, 7.7 Hz, 1H), 3.78 (s, 3H), 3.78 (s, 3H), 3.67-3.61 (m, 1H), 3.52-3.49 (m, 1H), 3.43-3.35 (m, 2H), 2.27 (s, 3H), 2.15-2.06 (m, 1H), 2.04-1.94 (m, 1H), 1.85-1.76 (m, 2H), 0.97 (d, J = 6.2 Hz, 3H), 0.89 (d, J = 7.0 Hz, 3H), 0.81-0.76 (m, 3H). LCMS (pos) m/z: 547.2 (M + H)$^+$. |
| 99.0 | (1S,2S)-1-isopropoxy-1-(5-methylpyrimidin-2-yl)propane-2-sulfonamide (Example 13.5), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: AS-H (2 × 15 cm) Mobile Phase: 45:55 (A:B) A: Liquid $CO_2$, B: IPA, Flow Rate: 80 mL/min, 220 nm, 100 bar inlet pressure to deliver peak 1. | 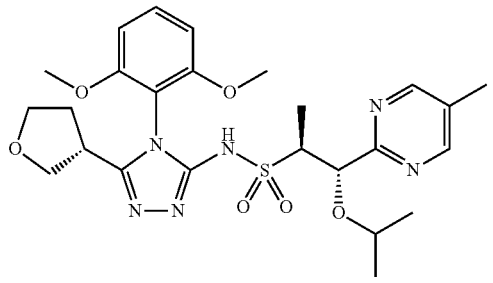<br>OR<br>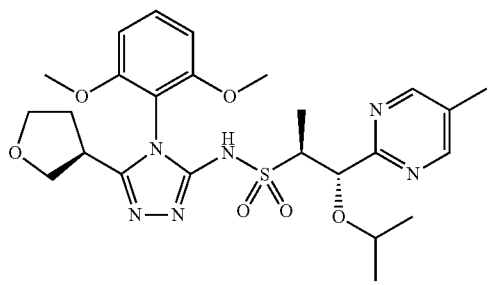<br>(1S,2S)-N-(4-(2,6-dimethoxyphenyl)-5-((R)-tetrahydrofuran-3-yl)-4H-1,2,4-triazol-3-yl)-1-isopropoxy-1-(5-methylpyrimidin-2-yl)propane-2-sulfonamide or (1S,2S)-N-(4-(2,6-dimethoxyphenyl)-5-((S)-tetrahydrofuran-3-yl)-4H-1,2,4-triazol-3-yl)-1-isopropoxy-1-(5-methylpyrimidin-2-yl)propane-2-sulfonamide. $^1$H NMR (400 MHz, DMSO-$d_6$) δ 12.79 (br. s., 1H), 8.65 (d, J = 0.6 Hz, 2H), 7.52 (t, J = 8.5 Hz, 1H), 6.90-6.84 (m, 2H), 4.68 (d, J = 7.5 Hz, 1H), 3.81 (s, 3H), 3.79 (s, 3H), 3.77-3.72 (m, 1H), 3.68-3.59 (m, 3H), 3.44-3.35 (m, 2H), 2.96 (qd, J = 6.7, 8.8 Hz, 1H), 2.27 (s, 3H), 2.09-1.90 (m, 2H), 0.97 (d, J = 6.0 Hz, 3H), 0.90 (d, J = 7.0 Hz, 3H), 0.78 (d, J = 6.0 Hz, 3H). LCMS (pos) m/z: 547.2 (M + H)$^+$. |

TABLE 11-continued

| Example | Reagents | Structure, Name and Data |
|---|---|---|
| 100.0 | (1S,2S)-1-isopropoxy-1-(5-methylpyrimidin-2-yl)propane-2-sulfonamide (Example 13.5), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: AS-H (2 × 15 cm) Mobile Phase: 45:55 (A:B) A: Liquid $CO_2$, B: IPA, Flow Rate: 80 mL/min, 220 nm, 100 bar inlet pressure to deliver peak 2. | 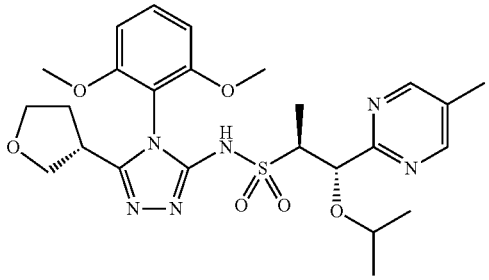<br>OR<br>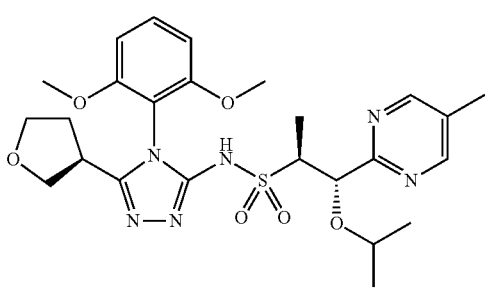<br><br>(1S,2S)-N-(4-(2,6-dimethoxyphenyl)-5-((R)-tetrahydrofuran-3-yl)-4H-1,2,4-triazol-3-yl)-1-isopropoxy-1-(5-methylpyrimidin-2-yl)propane-2-sulfonamide or (1S,2S)-N-(4-(2,6-dimethoxyphenyl)-5-((S)-tetrahydrofuran-3-yl)-4H-1,2,4-triazol-3-yl)-1-isopropoxy-1-(5-methylpyrimidin-2-yl)propane-2-sulfonamide. $^1$H NMR (400 MHz, DMSO-$d_6$) δ 12.79 (s, 1H), 8.65 (d, J = 0.6 Hz, 2H), 7.52 (t, J = 8.5 Hz, 1H), 6.87 (dd, J = 1.2, 8.7 Hz, 2H), 4.68 (d, J = 7.3 Hz, 1H), 3.81 (s, 3H), 3.80(s, 3H), 3.74 (dt, J = 6.0, 8.0 Hz, 1H), 3.67-3.61 (m, 3H), 3.42-3.35 (m, 2H), 2.95 (qd, J = 6.7, 8.9 Hz, 1H), 2.27 (s, 3H), 2.08-1.99 (m, 1H), 1.98-1.88 (m, 1H), 0.97 (d, J = 6.2 Hz, 3H), 0.90 (d, J = 7.0 Hz, 3H), 0.78 (d, J = 6.2 Hz, 3H). LCMS (pos) m/z: 547.2 (M + H)$^+$. |
| 101.0 | (2S,3R)-3-(5-chloropyrimidin-2-yl)butane-2-sulfonamide (Example 1.4), (R)-tetrahydro-2H-pyran-3-carbohydrazide and (S)-tetrahydro-2H-pyran-3-carbohydrazide (commercially available from Synthonix), 5-isothiocyanato-4,6-dimethoxypyrimidine (Example 10.1). The mixture was purified by preparative SFC using the following methodology: Column: AD-H (2 × 15 cm) Mobile Phase: 60:40 (A:B) A: Liquid $CO_2$, B: IPA, Flow Rate: 80 mL/min, 218 nm, 100 bar inlet pressure to deliver peak 1. | 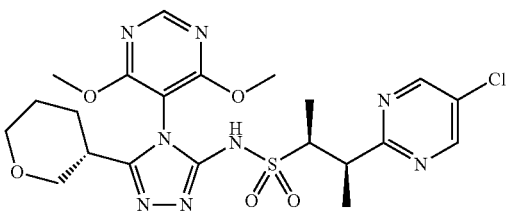<br>OR<br>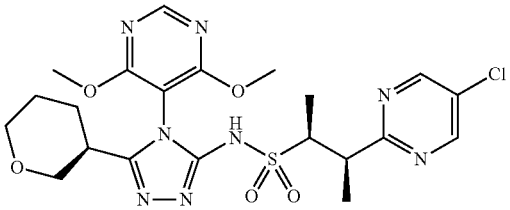<br><br>(2S,3R)-3-(5-chloropyrimidin-2-yl)-N-(4-(4,6-dimethoxypyrimidin-5-yl)-5-((S)-tetrahydro-2H-pyran-3-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((R)-tetrahydro-2H-pyran-3-yl)-4H-1,2,4-triazol-3-yl)butane-2-sulfonamide. $^1$H NMR (400 MHz, $CD_2Cl_2$) δ 10.82 (s, 1H), 8.67-8.61 (m, 2H), 8.57-8.49 (m, 1H), 4.04-3.97 (m, 6H), 3.90-3.81 (m, |

| Example | Reagents | Structure, Name and Data |
|---|---|---|
| | | 2H), 3.75-3.61 (m, 2H), 3.46 (dd, J = 10.3, 11.3 Hz, 1H), 3.40 (dt, J = 2.7, 11.4 Hz, 1H), 2.49 (tdd, J = 4.0, 10.2, 11.3 Hz, 1H), 1.99-1.90 (m, 1H), 1.87-1.75 (m, 1H), 1.71-1.58 (m, 2H), 1.31 (d, J = 7.0 Hz, 3H), 1.26 (d, J = 6.8 Hz, 3H). LCMS (pos) m/z: 539.0 (M + H)+. |
| 102.0 | (2S,3R)-3-(5-chloropyrimidin-2-yl)butane-2-sulfonamide (Example 1.4), (R)-tetrahydro-2H-pyran-3-carbohydrazide and (S)-tetrahydro-2H-pyran-3-carbohydrazide (commercially available from Synthonix), 5-isothiocyanato-4,6-dimethoxypyrimidine (Example 10.1). The mixture was purified by preparative SFC using the following methodology: Column: AD-H (2 × 15 cm) Mobile Phase: 60:40 (A:B) A: Liquid $CO_2$, B: IPA, Flow Rate: 80 mL/min, 218 nm, 100 bar inlet pressure to deliver peak 2. | 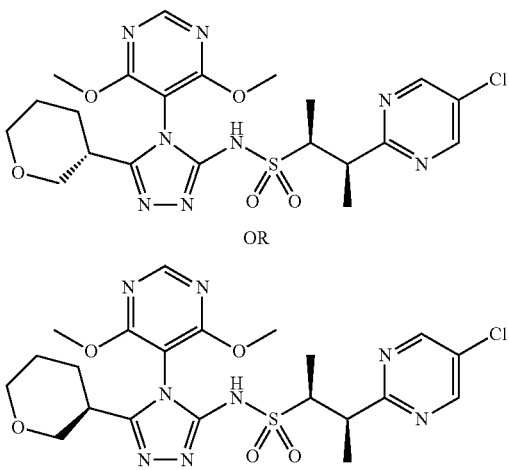 [SMILES: COc1ncnc(OC)c1-n1c(NS(=O)(=O)[C@@H](C)[C@H](C)c2ncc(Cl)cn2)nnc1[C@H]1CCCOC1 ; COc1ncnc(OC)c1-n1c(NS(=O)(=O)[C@@H](C)[C@H](C)c2ncc(Cl)cn2)nnc1[C@@H]1CCCOC1]<br>OR<br><br>(2S,3R)-3-(5-chloropyrimidin-2-yl)-N-(4-(4,6-dimethoxypyrimidin-5-yl)-5-((S)-tetrahydro-2H-pyran-3-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((R)-tetrahydro-2H-pyran-3-yl)-4H-1,2,4-triazol-3-yl)butane-2-sulfonamide. $^1$H NMR (400 MHz, $CD_2Cl_2$) δ 8.63 (s, 2H), 8.54 (s, 1H), 4.00 (s, 3H), 3.99 (s, 3H), 3.91-3.82 (m, 2H), 3.76-3.64 (m, 2H), 3.51-3.36 (m, 2H), 2.50 (ft, J = 4.0, 10.7 Hz, 1H), 1.99-1.91 (m, 1H), 1.89-1.76 (m, 1H), 1.71-1.63 (m, 1H), 1.62-1.52 (m, 1H), 1.32 (d, J = 6.8 Hz, 3H), 1.26 (d, J = 6.8 Hz, 3H). LCMS (pos) m/z: 539.0 (M + H)+. |
| 103.0 | (1R,2S)-1-(5-chloropyrimidin-2-yl)-1-methoxypropane-2-sulfonamide (Example 11.3), tetrahydro-2H-pyran-4-carbohydrazide (commercially available from ChemBridge Corporation), 2-isothiocyanato-1,3-dimethoxybenzene (Example 10.0). | 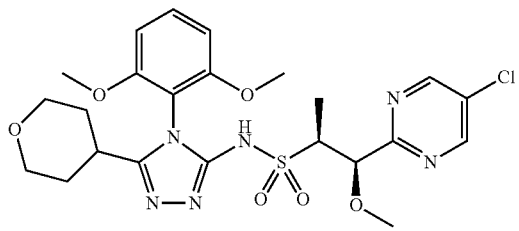 [SMILES: COc1cccc(OC)c1-n1c(NS(=O)(=O)[C@@H](C)[C@H](OC)c2ncc(Cl)cn2)nnc1C1CCOCC1]<br><br>(1R,2S)-1-(5-chloropyrimidin-2-yl)-N-(4-(2,6-dimethoxyphenyl)-5-(tetrahydro-2H-pyran-4-yl)-4H-1,2,4-triazol-3-yl)-1-methoxypropane-2-sulfonamide. $^1$H NMR (400 MHz, DMSO-$d_6$) δ 12.79 (s, 1H), 8.96-8.88 (m, 2H), 7.51 (t, J = 8.5 Hz, 1H), 6.87 (dd, J = 0.7, 8.6 Hz, 2H), 4.76 (d, J = 4.4 Hz, 1H), 3.84-3.71 (m, 8H), 3.43-3.35 (m, 1H), 3.25-3.17 (m, 2H), 3.14 (s, 3H), 2.46-2.36 (m, 1H), 1.67-1.50 (m, 4H), 1.12 (d, J = 6.8 Hz, 3H). LCMS (pos) m/z: 553.0 (M + H)+. |

TABLE 11-continued

| Example | Reagents | Structure, Name and Data |
|---|---|---|
| 104.0 | (2S,3R)-3-(5-methylpyrazin-2-yl)butane-2-sulfonamide (Example 1.2), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: AS-H (2 × 25 cm) Mobile Phase: 75:25 (A:B) A: Liquid $CO_2$, B: IPA, Flow Rate: 80 mL/min, 270 nm, 100 bar inlet pressure to deliver peak 1. | 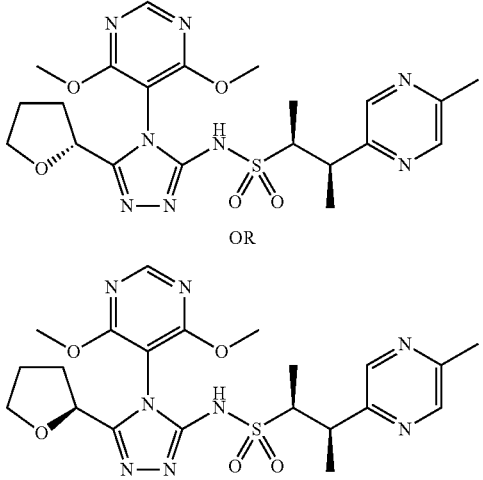 [SMILES: COc1ncnc(OC)c1-n1c(NS(=O)(=O)[C@@H](C)[C@H](C)c2cnc(C)cn2)nnc1[C@H]1CCCO1 ; COc1ncnc(OC)c1-n1c(NS(=O)(=O)[C@@H](C)[C@H](C)c2cnc(C)cn2)nnc1[C@@H]1CCCO1]<br>OR<br><br>(2S,3R)-N-(4-(4,6-dimethoxypyrimidin-5-yl)-5-((S)-tetrahydrofuran-2-yl)-4H-1,2,4-triazol-3-yl)-3-(5-methylpyrazin-2-yl)butane-2-sulfonamide or (2S,3R)-N-(4-(4,6-dimethoxypyrimidin-5-yl)-5-((R)-tetrahydrofuran-2-yl)-4H-1,2,4-triazol-3-yl)-3-(5-methylpyrazin-2-yl)butane-2-sulfonamide. $^1$H NMR (400 MHz, DMSO-$d_6$) δ 13.14 (s, 1H), 8.68-8.63 (m, 1H), 8.43 (s, 1H), 8.34 (d, J = 1.2 Hz, 1H), 4.68 (dd, J = 5.3, 7.6 Hz, 1H), 3.94 (s, 3H), 3.92 (s, 3H), 3.71-3.65 (m, 1H), 3.61-3.53 (m, 1H), 3.53-3.33 (m, 2H), 2.45 (s, 3H), 2.24-2.14 (m, 1H), 2.12-2.02 (m, 1H), 1.82 (quin, J = 7.1 Hz, 2H), 1.22 (d, J = 7.0 Hz, 3H), 1.10 (d, J = 7.0 Hz, 3H). LCMS (pos) m/z: 505.2 (M + H)$^+$. |
| 105.0 | (2S,3R)-3-(5-methylpyrazin-2-yl)butane-2-sulfonamide (Example 1.2), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: AS-H (2 × 25 cm) Mobile Phase: 75:25 (A:B) A: Liquid $CO_2$, B: IPA, Flow Rate: 80 mL/min, 270 nm, 100 bar inlet pressure to deliver peak 2. | 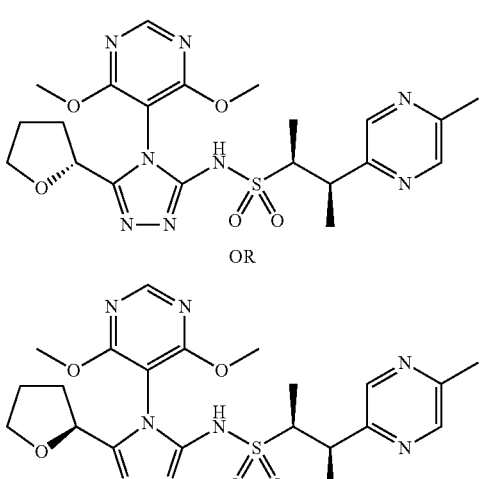<br>OR<br><br>(2S,3R)-N-(4-(4,6-dimethoxypyrimidin-5-yl)-5-((S)-tetrahydrofuran-2-yl)-4H-1,2,4-triazol-3-yl)-3-(5-methylpyrazin-2-yl)butane-2-sulfonamide or (2S,3R)-N-(4-(4,6-dimethoxypyrimidin-5-yl)-5-((R)-tetrahydrofuran-2-yl)-4H-1,2,4-triazol-3-yl)-3-(5-methylpyrazin-2-yl)butane-2-sulfonamide. NMR (400 MHz, DMSO-$d_6$) δ 13.14 (s, 1H), 8.69-8.62 (m, 1H), 8.43 (s, 1H), 8.34 (d, J = 1.5 Hz, 1H), 4.69 (dd, J = 5.3, 7.8 Hz, 1H), 3.94 (s, 3H), 3.93 (s, 3H), 3.71-3.64 (m, 1H), 3.60-3.52 (m, 1H), 3.52-3.33 (m, 2H), 2.45 (s, 3H), 2.24-2.15 (m, 1H), 2.13-2.03 (m, 1H), 1.82 (quin, J = 7.1 Hz, 2H), 1.23 (d, J = 7.3 Hz, 3H), 1.11 (d, J = 7.0 Hz, 3H). LCMS (pos) m/z: 505.2 (M + H)$^+$. |

TABLE 11-continued

| Example | Reagents | Structure, Name and Data |
|---|---|---|
| 106.0 | (2S,3R)-3-(5-methylpyrazin-2-yl)butane-2-sulfonamide (Example 1.2), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: AD-H (2 × 25 cm) Mobile Phase: 85:15 (A:B) A: Liquid $CO_2$, B: IPA, Flow Rate: 60 mL/min, 220 nm, 100 bar inlet pressure to deliver peak 1. | 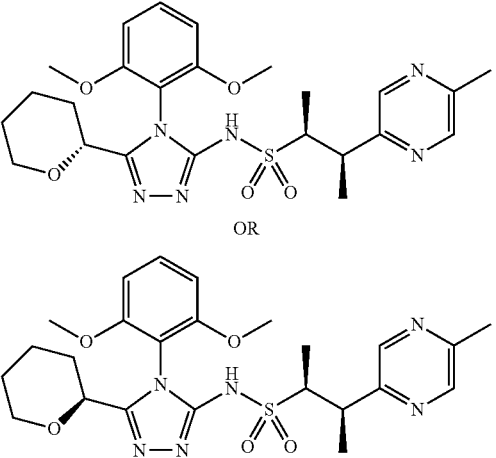 [SMILES: COc1cccc(OC)c1-n1c(NS(=O)(=O)[C@@H](C)[C@H](C)c2cnc(C)cn2)nnc1[C@H]1CCCCO1 ; COc1cccc(OC)c1-n1c(NS(=O)(=O)[C@@H](C)[C@H](C)c2cnc(C)cn2)nnc1[C@@H]1CCCCO1]<br>OR<br>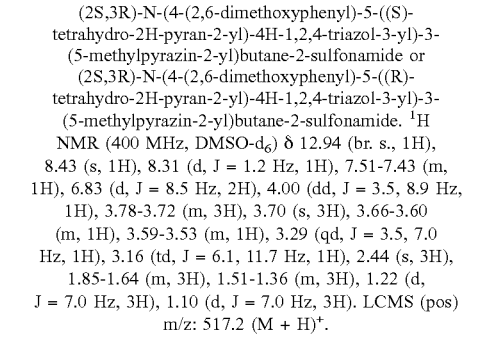<br>(2S,3R)-N-(4-(2,6-dimethoxyphenyl)-5-((S)-tetrahydro-2H-pyran-2-yl)-4H-1,2,4-triazol-3-yl)-3-(5-methylpyrazin-2-yl)butane-2-sulfonamide or (2S,3R)-N-(4-(2,6-dimethoxyphenyl)-5-((R)-tetrahydro-2H-pyran-2-yl)-4H-1,2,4-triazol-3-yl)-3-(5-methylpyrazin-2-yl)butane-2-sulfonamide. $^1$H NMR (400 MHz, DMSO-$d_6$) δ 12.94 (br. s., 1H), 8.43 (s, 1H), 8.31 (d, J = 1.2 Hz, 1H), 7.51-7.43 (m, 1H), 6.83 (d, J = 8.5 Hz, 2H), 4.00 (dd, J = 3.5, 8.9 Hz, 1H), 3.78-3.72 (m, 3H), 3.70 (s, 3H), 3.66-3.60 (m, 1H), 3.59-3.53 (m, 1H), 3.29 (qd, J = 3.5, 7.0 Hz, 1H), 3.16 (td, J = 6.1, 11.7 Hz, 1H), 2.44 (s, 3H), 1.85-1.64 (m, 3H), 1.51-1.36 (m, 3H), 1.22 (d, J = 7.0 Hz, 3H), 1.10 (d, J = 7.0 Hz, 3H). LCMS (pos) m/z: 517.2 (M + H)$^+$. |
| 107.0 | (2S,3R)-3-(5-methylpyrazin-2-yl)butane-2-sulfonamide (Example 1.2), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: AD-H (2 × 25 cm) Mobile Phase: 85:15 (A:B) A: Liquid $CO_2$, B: IPA, Flow Rate: 60 mL/min, 220 nm, 100 bar inlet pressure to deliver peak 2. | 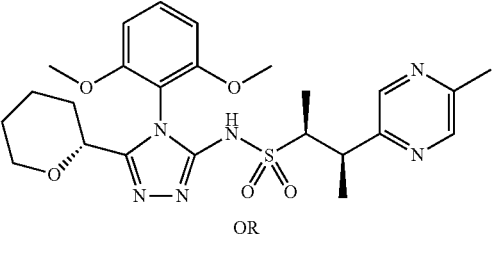<br>OR<br>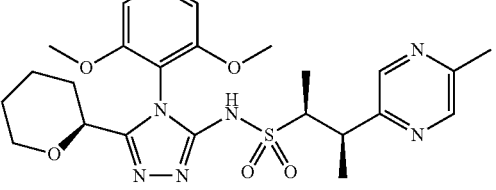<br>(2S,3R)-N-(4-(2,6-dimethoxyphenyl)-5-((S)-tetrahydro-2H-pyran-2-yl)-4H-1,2,4-triazol-3-yl)-3-(5-methylpyrazin-2-yl)butane-2-sulfonamide or (2S,3R)-N-(4-(2,6-dimethoxyphenyl)-5-((R)-tetrahydro-2H-pyran-2-yl)-4H-1,2,4-triazol-3-yl)-3-(5-methylpyrazin-2-yl)butane-2-sulfonamide. $^1$H NMR (400 MHz, DMSO-$d_6$) δ 12.94 (br. s., 1H), 8.43 (s, 1H), 8.30 (d, J = 0.8 Hz, 1H), 7.47 (t, J = 8.5 Hz, 1H), 6.82 (dd, J = 3.9, 8.5 Hz, 2H), 4.01 (dd, J = 3.4, 8.8 Hz, 1H), 3.74 (s, 3H), 3.71 (s, 3H), 3.66-3.54 (m, 2H), 3.31-3.25 (m, 1H), 3.19-3.11 (m, 1H), 2.44 (s, 3H), 1.86-1.66 (m, 3H), 1.51-1.35 (m, 3H), 1.22 (d, J = 7.3 Hz, 3H), 1.10 (d, J = 7.0 Hz, 3H). LCMS (pos) m/z: 517.2 (M + H)$^+$. |

Example 108.0: Preparation of (1R,2S)-1-(5-chloropyrimidin-2-yl)-N-(4-(2,6-dimethoxyphenyl)-5-((S)-5,5-dimethyltetrahydrofuran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((R)-5,5-dimethyltetrahydrofuran-2-yl)-4H-1,2,4-triazol-3-yl)-1-methoxypropane-2-sulfonamide

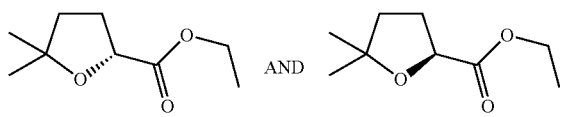

(R)-Ethyl 5,5-dimethyltetrahydrofuran-2-carboxylate and (S)-ethyl 5,5-dimethyltetrahydrofuran-2-carboxylate, Example 108.1

To a flask containing 5,5-dimethyloxolane-2-carboxylic acid (commercially available from Enamine, 891 mg, 6.2 mmol) in EtOH (25 mL) was added sulfuric acid (0.04 mL, 0.75 mmol) dropwise at 23° C. The homogeneous solution was heated to 85° C. After 6.5 h, the reaction was cooled to RT and concentrated under reduced pressure. The colorless residue was carefully diluted with water. After extracting three times with EtOAc, the organic layers were pooled and then dried over anhydrous sodium sulfate. After filtration and concentration under reduced pressure, the colorless residue was identified as Example 108.1 (674 mg, 3.9 mmol, 63% yield) and was used without further purification. LCMS (pos) m/z: 173.4 (M+H)$^+$.

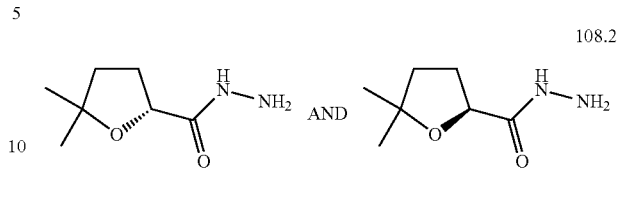

(R)-5,5-Dimethyltetrahydrofuran-2-carbohydrazide and (S)-5,5-dimethyltetrahydrofuran-2-carbohydrazide, Example 108.2

To a flask containing (R)-ethyl 5,5-dimethyltetrahydrofuran-2-carboxylate and (S)-ethyl 5,5-dimethyltetrahydrofuran-2-carboxylate (Example 108.1, 557 mg, 3.2 mmol) was added EtOH (13 mL). The solution was cooled in an ice water bath. After 20 min, hydrazine monohydrate (0.32 mL, 6.6 mmol) was added carefully and dropwise to the homogeneous solution. Upon complete addition of hydrazine monohydrate, the mixture was allowed to warm to 23° C. After 17 h, EtOAc was added to the mixture and it was then stirred for 30 min at 23° C. The mixture was then concentrated under reduced pressure to afford (R)-5,5-dimethyltetrahydrofuran-2-carbohydrazide and (S)-5,5-dimethyltetrahydrofuran-2-carbohydrazide, Example 108.2 (451 mg, 2.8 mmol, 88% yield) as a white solid which was used without further purification. LCMS (pos) m/z: 159.0 (M+H)$^+$.

Following the procedure in Example 140.0, the following compounds were also synthesized using the intermediates and conditions as described.

TABLE 12

| Example | Reagents | Structure, Name and Data |
|---|---|---|
| 108.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), 2-isothiocyanato-1,3-dimethoxybenzene (Example 10.0). The mixture was purified by preparative SFC using the following methodology: Column:AD-H (2 × 25 cm) Mobile Phase: 70:30 (A:B) A: Liquid CO$_2$, B: IPA to deliver peak 1. | 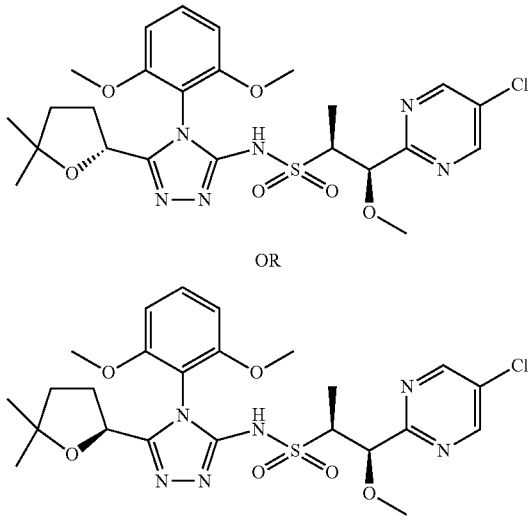 [SMILES: COc1cccc(OC)c1-n1c(NS(=O)(=O)[C@@H](C)[C@H](OC)c2ncc(Cl)cn2)nnc1[C@H]1CCC(C)(C)O1 ; COc1cccc(OC)c1-n1c(NS(=O)(=O)[C@@H](C)[C@H](OC)c2ncc(Cl)cn2)nnc1[C@@H]1CCC(C)(C)O1] (1R,2S)-1-(5-chloropyrimidin-2-yl)-N-(4-(2,6-dimethoxyphenyl)-5-((S)-5,5-dimethyltetrahydrofuran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((R)-5,5-dimethyltetrahydrofuran-2-yl)-4H-1,2,4-triazol-3-yl)-1-methoxypropane-2-sulfonamide. $^1$H NMR (500 MHz, CD$_2$Cl$_2$) δ 10.81 (br. s., 1H), 8.74-8.69 (m, 2H), 7.51-7.43 (m, 1H), 6.71 (d, J = 1.6 Hz, 1H), 6.69 (d, J = 1.6 Hz, 1H), 4.85 (d, J = 4.4 Hz, 1H), 4.67 (dd, J = 5.7, 7.8 Hz, 1H), 3.81 (s, 3H), 3.79 (s, 3H), 3.57 (dq, J = 4.8, 7.0 Hz, 1H), 3.25 (s, 3H), 2.33-2.26 (m, |

| Example | Reagents | Structure, Name and Data |
|---------|----------|--------------------------|
| | | 1H), 2.12 (qd, J = 7.8, 12.7 Hz, 1H), 1.69 (t, J = 7.4 Hz, 2H), 1.25 (d, J = 7.0 Hz, 3H), 1.11 (s, 3H), 1.10 (s, 3H). LCMS (pos) m/z: 567.0 (M + H)+. |
| 109.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid CO₂, B: IPA to deliver peak 2. | 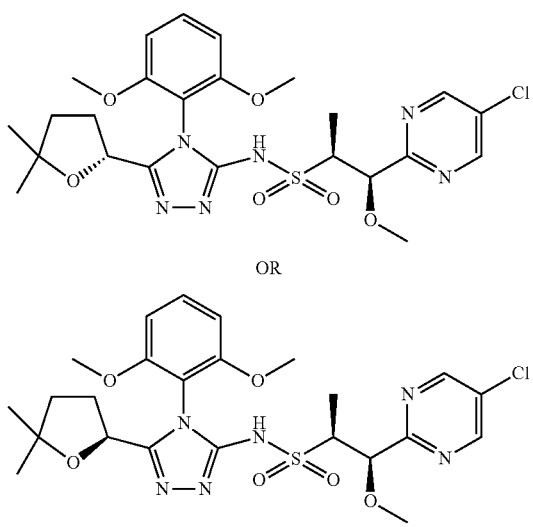 [SMILES: COc1cccc(OC)c1-n1c(NS(=O)(=O)[C@@H](C)[C@H](OC)c2ncc(Cl)cn2)nnc1[C@H]1CCC(C)(C)O1 ; COc1cccc(OC)c1-n1c(NS(=O)(=O)[C@@H](C)[C@H](OC)c2ncc(Cl)cn2)nnc1[C@@H]1CCC(C)(C)O1]<br>OR<br><br>(1R,2S)-1-(5-chloropyrimidin-2-yl)-N-(4-(2,6-dimethoxyphenyl)-5-((S)-5,5-dimethyltetrahydrofuran-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((R)-5,5-dimethyltetrahydrofuran-2-yl)-4H-1,2,4-triazol-3-yl)-1-methoxypropane-2-sulfonamide. ¹H NMR (500 MHz, CD₂Cl₂) δ 10.77 (br. s., 1H), 8.76-8.68 (m, 2H), 7.50-7.43 (m, 1H), 6.70 (dd, J = 4.7, 8.6 Hz, 2H), 4.86 (d, J = 4.7 Hz, 1H), 4.66 (dd, J = 5.4, 7.8 Hz, 1H), 3.81 (s, 3H), 3.79 (s, 3H), 3.57 (dq, J = 4.7, 7.0 Hz, 1H), 3.25 (s, 3H), 2.34-2.26 (m, 1H), 2.12 (qd, J = 7.8, 13.0 Hz, 1H), 1.70 (t, J = 7.4 Hz, 2H), 1.24 (d, J = 7.0 Hz, 3H), 1.10 (s, 3H), 1.09 (s, 3H). LCMS (pos) m/z: 567.0 (M + H)+. |
| 110.0 | (1R,2S)-1-(5-chloropyrimidin-2-yl)-1-methoxypropane-2-sulfonamide (Example 11.3), (R)-tetrahydrofuran-2-carbohydrazide and (S)-tetrahydrofuran-2-carbohydrazide (commercially available from Enamine), 1-isothiocyanato-1-methylcyclopropane (commercially available from Enamine). The mixture was purified by preparative SFC using the following methodology: Column: AD-H (2 × 25 cm) Mobile Phase: 55:45 (A:B) A: Liquid CO₂, B: MeOH, Flow Rate: 80 mL/min, 219 nm, 100 bar inlet pressure to deliver peak 1. | 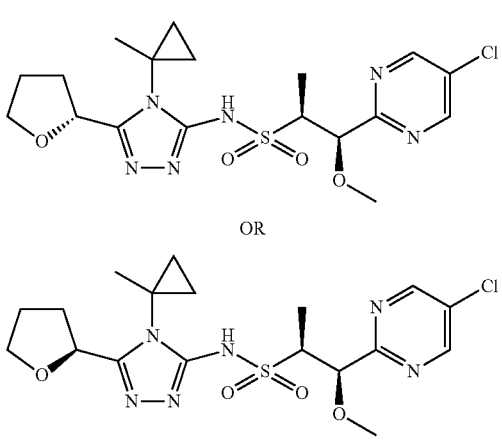 [SMILES: CO[C@H](c1ncc(Cl)cn1)[C@H](C)S(=O)(=O)Nc1nnc([C@H]2CCCO2)n1C1(C)CC1 ; CO[C@H](c1ncc(Cl)cn1)[C@H](C)S(=O)(=O)Nc1nnc([C@@H]2CCCO2)n1C1(C)CC1]<br>OR<br><br>(1R,2S)-1-(5-chloropyrimidin-2-yl)-1-methoxy-N-(4-(1-methylcyclopropyl)-5-((S)-tetrahydrofuran-2-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((R)-tetrahydrofuran-2-yl)-4H-1,2,4-triazol-3-yl)propane-2-sulfonamide. ¹H NMR (500 MHz, CD₂Cl₂) δ 10.82 (br. s., 1H), 8.78-8.70 (m, 2H), 5.11 (dd, J = 5.4, 7.5 Hz, 1H), 4.99 (d, J = 3.9 Hz, 1H), 3.95-3.88 (m, 1H), 3.87-3.80 (m, 1H), 3.59 (dq, J = 3.9, 7.1 Hz, 1H), 3.25-3.19 (m, 3H), 2.54-2.45 (m, 1H), 2.27-2.18 (m, 1H), 2.15-2.06 (m, 1H), 2.05-1.94 (m, 1H), 1.51 (s, 3H), 1.48-1.42 (m, 1H), 1.35 (d, J = 7.0 Hz, 3H), 1.16-1.09 (m, 1H), 1.05-0.97 (m, 2H). LCMS (pos) m/z: 457.2 (M + H)+. |

TABLE 12-continued

| Example | Reagents | Structure, Name and Data |
|---|---|---|
| 111.0 | (1R,2S)-1-(5-chloropyrimidin-2-yl)-1-methoxypropane-2-sulfonamide (Example 11.3), (R)-tetrahydrofuran-2-carbohydrazide and (S)-tetrahydrofuran-2-carbohydrazide (commercially available from Enamine), 1-isothiocyanato-1-methylcyclopropane (commercially available from Enamine). The mixture was purified by preparative SFC using the following methodology: Column: AD-H (2 × 25 cm) Mobile Phase: 55:45 (A:B) A: Liquid $CO_2$, B: MeOH, Flow Rate: 80 mL/min, 219 nm, 100 bar inlet pressure to deliver peak 2. | 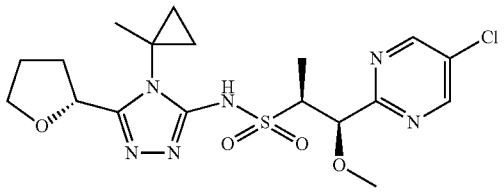<br>OR<br>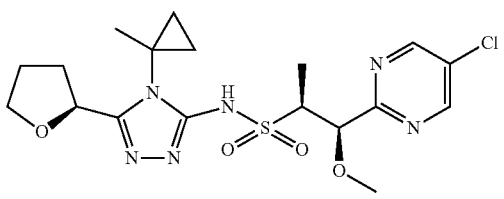<br><br>(1R,2S)-1-(5-chloropyrimidin-2-yl)-1-methoxy-N-(4-(1-methylcyclopropyl)-5-((S)-tetrahydrofuran-2-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((R)-tetrahydrofuran-2-yl)-4H-1,2,4-triazol-3-yl)propane-2-sulfonamide. $^1$H NMR (500 MHz, $CD_2Cl_2$) δ 8.79-8.68 (m, 2H), 5.12 (dd, J = 5.7, 7.5 Hz, 1H), 5.01 (d, J = 3.6 Hz, 1H), 3.90 (dt, J = 5.6, 7.8 Hz, 1H), 3.82 (q, J = 7.3 Hz, 1H), 3.56 (dq, J = 3.6, 7.0 Hz, 1H), 3.19 (s, 3H), 2.54-2.45 (m, 1H), 2.27-2.18 (m, 1H), 2.15-2.06 (m, 1H), 2.05-1.94 (m, 1H), 1.52 (s, 3H), 1.47-1.39 (m, 1H), 1.35 (d, J = 7.0 Hz, 3H), 1.24-1.16 (m, 1H), 1.05-0.95 (m, 2H). LCMS (pos) m/z: 457.2 (M + H)$^+$. |
| 112.0 | (1R,2S)-1-(5-chloropyrimidin-2-yl)-1-methoxypropane-2-sulfonamide (Example 11.3), (R)-tetrahydro-2H-pyran-2-carbohydrazide and (S)-tetrahydro-2H-pyran-2-carbohydrazide (commercially available from Ukrorgsyntez), 1-isothiocyanato-1-methylcyclopropane (commercially available from Enamine). The mixture was purified by preparative SFC using the following methodology: Column: AD-H (2 × 25 cm) Mobile Phase: 65:35 (A:B) A: Liquid $CO_2$, B: MeOH, Flow Rate: 80 mL/min, 219 nm, 100 bar inlet pressure to deliver peak 1. | 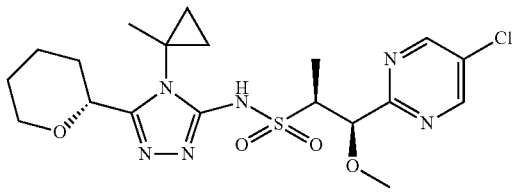<br>OR<br>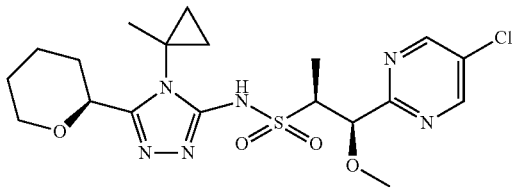<br><br>(1R,2S)-1-(5-chloropyrimidin-2-yl)-1-methoxy-N-(4-(1-methylcyclopropyl)-5-((S)-tetrahydro-2H-pyran-2-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((R)-tetrahydro-2H-pyran-2-yl)-4H-1,2,4-triazol-3-yl)propane-2-sulfonamide. $^1$H NMR (500 MHz, $CD_2Cl_2$) δ 10.82 (br. s., 1H), 8.76-8.69 (m, 2H), 4.98 (d, J = 3.9 Hz, 1H), 4.54 (dd, J = 2.5, 10.5 Hz, 1H), 4.07-4.00 (m, 1H), 3.63-3.55 (m, 2H), 3.21 (s, 3H), 2.10-1.98 (m, 2H), 1.85 (d, J = 11.9 Hz, 1H), 1.74-1.64 (m, 2H), 1.62-1.59 (m, 1H), 1.50 (s, 3H), 1.40 (d, J = 10.6 Hz, 1H), 1.35 (d, J = 7.3 Hz, 3H), 1.19-1.10 (m, 1H), 1.03-0.95 (m, 2H). LCMS (pos) m/z: 471.0 (M + H)$^+$. |

TABLE 12-continued

| Example | Reagents | Structure, Name and Data |
|---|---|---|
| 113.0 | (1R,2S)-1-(5-chloropyrimidin-2-yl)-1-methoxypropane-2-sulfonamide (Example 11.3), (R)-tetrahydro-2H-pyran-2-carbohydrazide and (S)-tetrahydro-2H-pyran-2-carbohydrazide (commercially available from Ukrorgsyntez), 1-isothiocyanato-1-methylcyclopropane (commercially available from Enamine). The mixture was purified by preparative SFC using the following methodology: Column: AD-H (2 × 25 cm) Mobile Phase: 65:35 (A:B) A: Liquid CO$_2$, B: MeOH, Flow Rate: 80 mL/min, 219 nm, 100 bar inlet pressure to deliver peak 2. | 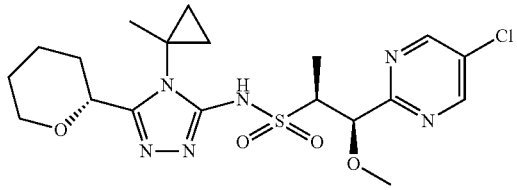 OR 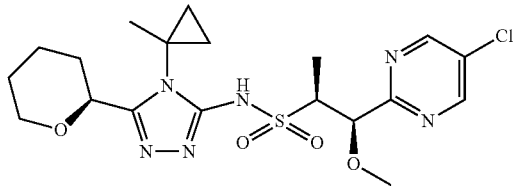<br>(1R,2S)-1-(5-chloropyrimidin-2-yl)-1-methoxy-N-(4-(1-methylcyclopropyl)-5-((S)-tetrahydro-2H-pyran-2-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((R)-tetrahydro-2H-pyran-2-yl)-4H-1,2,4-triazol-3-yl)propane-2-sulfonamide. $^1$H NMR (500 MHz, CD$_2$Cl$_2$) δ 8.76-8.69 (m, 2H), 4.99 (d, J = 3.6 Hz, 1H), 4.53 (dd, J = 2.3, 10.9 Hz, 1H), 4.07-4.00 (m, 1H), 3.62-3.53 (m, 2H), 3.19 (s, 3H), 2.09-1.97 (m, 2H), 1.85 (d, J = 12.7 Hz, 1H), 1.71-1.58 (m, 3H), 1.50 (s, 3H), 1.42-1.36 (m, 1H), 1.34 (d, J = 7.0 Hz, 3H), 1.21 (d, J = 10.9 Hz, 1H), 1.01-0.94 (m, 2H). LCMS (pos) m/z: 471.2 (M + H)$^+$. |
| 114.0 | (1R,2S)-1-(5-chloropyrimidin-2-yl)-1-methoxypropane-2-sulfonamide (Example 11.3), (2S,3R)-2-methyltetrahydrofuran-3-carbohydrazide and (2R,3S)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology #1: Column: AS-H (2 × 25 cm) Mobile Phase: 75:25 (A:B) A: Liquid CO$_2$, B: MeOH, Flow Rate: 80 mL/min, 220 nm, 100 bar inlet pressure. Then by preparative SFC using the following methodology #2: Column: AD-H (2 × 15 cm) Mobile Phase: 50:50 (A:B) A: Liquid CO$_2$, B: IPA, Flow Rate: 80 mL/min, 220 nm, 100 bar inlet. Then by preparative SFC using the following methodology #3: Column: AD-H (2 × 50 cm) Mobile Phase: 80:20 (A:B) A: Liquid CO$_2$, B: MeOH, Flow Rate: 80 mL/min, 220 nm, 100 bar inlet pressure to deliver peak 1. | 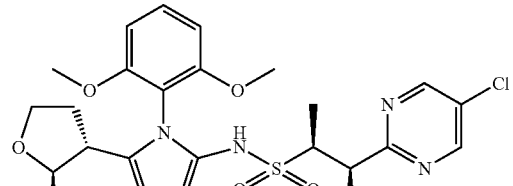 OR 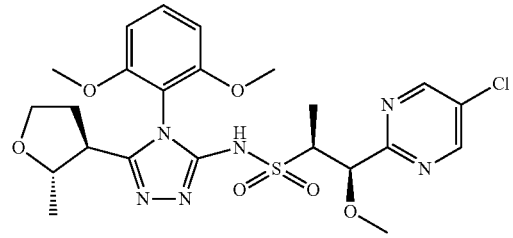<br>(1R,2S)-1-(5-chloropyrimidin-2-yl)-N-(4-(2,6-dimethoxyphenyl)-5-((2R,3R)-2-methyltetrahydrofuran-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((2S,3S)-2-methyltetrahydrofuran-3-yl)-4H-1,2,4-triazol-3-yl)-1-methoxypropane-2-sulfonamide. $^1$H NMR (500 MHz, CD$_2$Cl$_2$) δ 8.78-8.70 (m, 2H), 7.53-7.47 (m, 1H), 6.73 (d, J = 8.3 Hz, 2H), 4.86 (d, J = 4.7 Hz, 1H), 4.17-4.08 (m, 1H), 3.90-3.78 (m, 8H), 3.63-3.54 (m, 1H), 3.30-3.23 (m, 3H), 2.50-2.43 (m, 1H), 2.14-2.07 (m, 1H), 2.07-1.98 (m, 1H), 1.26 (d, J = 7.0 Hz, 3H), 1.07 (d, J = 6.0 Hz, 3H). LCMS (pos) m/z: 553.2 (M + H)$^+$. |

TABLE 12-continued

| Example | Reagents | Structure, Name and Data |
|---------|----------|--------------------------|
| 115.0 | (1R,2S)-1-(5-chloropyrimidin-2-yl)-1-methoxypropane-2-sulfonamide (Example 11.3), (2S,3R)-2-methyltetrahydrofuran-3-carbohydrazide and (2R,3S)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology #1: Column: AS-H (2 × 25 cm) Mobile Phase: 75:25 (A:B) A: Liquid $CO_2$, B: MeOH, Flow Rate: 80 mL/min, 220 nm, 100 bar inlet pressure. Then by preparative SFC using the following methodology #2: Column: AD-H (2 × 15 cm) Mobile Phase: 50:50 (A:B) A: Liquid $CO_2$, B: IPA, Flow Rate: 80 mL/min, 220 nm, 100 bar inlet pressure to deliver peak 2. | 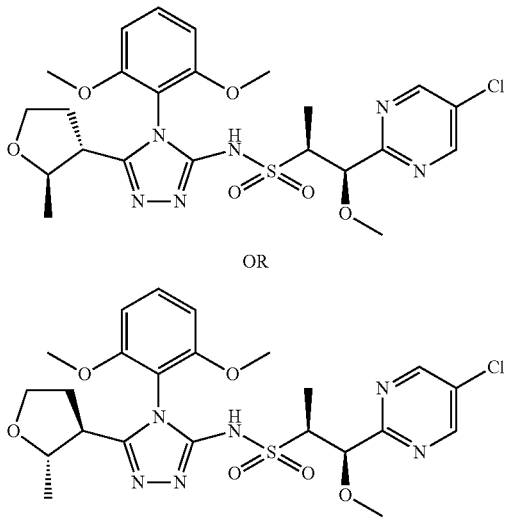 [SMILES: COc1cccc(OC)c1-n1c(NS(=O)(=O)[C@@H](C)[C@H](OC)c2ncc(Cl)cn2)nnc1[C@H]1CCO[C@@H]1C ; COc1cccc(OC)c1-n1c(NS(=O)(=O)[C@@H](C)[C@H](OC)c2ncc(Cl)cn2)nnc1[C@@H]1CCO[C@H]1C]<br>OR<br><br>(1R,2S)-1-(5-chloropyrimidin-2-yl)-N-(4-(2,6-dimethoxyphenyl)-5-((2R,3S)-2-methyltetrahydrofuran-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((2S,3R)-2-methyltetrahydrofuran-3-yl)-4H-1,2,4-triazol-3-yl)-1-methoxypropane-2-sulfonamide. $^1$H NMR (500 MHz, $CD_2Cl_2$) δ 10.80 (br. s., 1H), 8.78-8.67 (m, 2H), 7.49 (t, J = 8.6 Hz, 1H), 6.73 (dd, J = 1.8, 8.6 Hz, 2H), 4.87 (d, J = 4.7 Hz, 1H), 4.00 (dt, J = 4.0, 8.5 Hz, 1H), 3.90-3.84 (m, 1H), 3.82 (s, 3H), 3.80 (s, 3H), 3.72-3.66 (m, 1H), 3.60-3.54 (m, 1H), 3.25 (s, 3H), 3.00-2.94 (m, 1H), 2.45 (qd, J = 8.5, 12.5 Hz, 1H), 2.18 (dtd, J = 3.9, 8.0, 12.2 Hz, 1H), 1.25 (d, J = 7.0 Hz, 3H), 0.95 (d, J = 6.5 Hz, 3H). LCMS (pos) m/z: 553.2 (M + H)$^+$. |
| 116.0 | (1R,2S)-1-(5-chloropyrimidin-2-yl)-1-methoxypropane-2-sulfonamide (Example 11.3), (2S,3S)-2-methyltetrahydrofuran-3-carbohydrazide and (2R,3R)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology: Column: AS-H (2 × 25 cm) Mobile Phase: 75:25 (A:B) A: Liquid $CO_2$, B: MeOH, Flow Rate: 80 mL/min, 220 nm, 100 bar inlet pressure to deliver peak 2. | 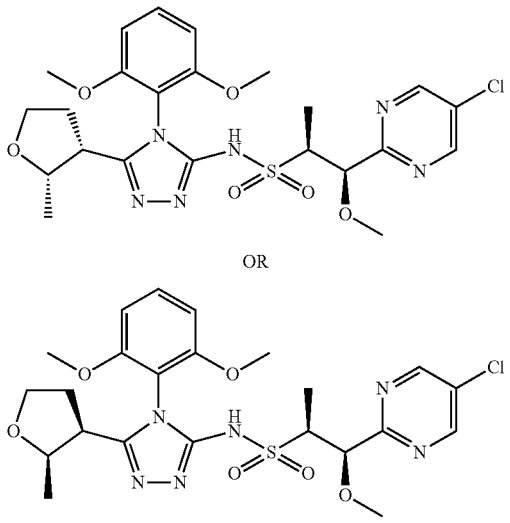 [SMILES: COc1cccc(OC)c1-n1c(NS(=O)(=O)[C@@H](C)[C@H](OC)c2ncc(Cl)cn2)nnc1[C@H]1CCO[C@H]1C ; COc1cccc(OC)c1-n1c(NS(=O)(=O)[C@@H](C)[C@H](OC)c2ncc(Cl)cn2)nnc1[C@@H]1CCO[C@@H]1C]<br>OR<br><br>(1R,2S)-1-(5-chloropyrimidin-2-yl)-N-(4-(2,6-dimethoxyphenyl)-5-((2R,3S)-2-methyltetrahydrofuran-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((2S,3R)-2-methyltetrahydrofuran-3-yl)-4H-1,2,4-triazol-3-yl)-1-methoxypropane-2-sulfonamide. $^1$H NMR (500 MHz, $CD_2Cl_2$) δ 10.79 (br. s., 1H), 8.75-8.66 (m, 2H), 7.49 (t, J = 8.6 Hz, 1H), 6.73 (d, J = 8.6 Hz, 2H), 4.86 (d, J = 4.7 Hz, 1H), 4.01 (dt, J = 4.0, 8.5 Hz, 1H), 3.87 (quin, J = 6.5 Hz, 1H), 3.81 (s, 3H), 3.80 (s, 3H), 3.73-3.65 (m, 1H), 3.60-3.55 (m, 1H), 3.25 (s, 3H), 3.02-2.95 (m, 1H), 2.45 (qd, J = 8.5, 12.6 Hz, 1H), 2.17 (dtd, J = 4.2, 8.0, 12.3 Hz, 1H), 1.26 (d, J = 7.0 Hz, 3H), 0.98 (d, J = 6.5 Hz, 3H). LCMS (pos) m/z: 553.2 (M + H)$^+$. |

TABLE 12-continued

| Example | Reagents | Structure, Name and Data |
|---|---|---|
| 117.0 | (2S,3R)-3-(5-chloropyrimidin-2-yl)butane-2-sulfonamide (Example 1.4), (2S,3R)-2-methyltetrahydrofuran-3-carbohydrazide and (2R,3S)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology #1: Column: AS-H (2 × 25 cm) Mobile Phase: 70:30 (A:B) A: Liquid CO₂, B: MeOH, Flow Rate: 80 mL/min, 215 nm, 100 bar inlet pressure. Then by preparative SFC using the following methodology #2: Column: AD-H (2 × 15 cm) Mobile Phase: 80:20 (A:B) A: Liquid CO₂, B: MeOH, Flow Rate: 80 mL/min, 220 nm, 100 bar inlet pressure to deliver peak 1. | 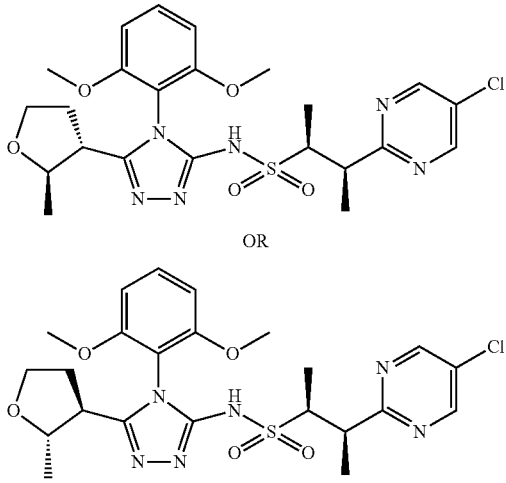 [SMILES: COc1cccc(OC)c1-n1c(NS(=O)(=O)[C@@H](C)[C@H](C)c2ncc(Cl)cn2)nnc1[C@H]1CCO[C@@H]1C ; COc1cccc(OC)c1-n1c(NS(=O)(=O)[C@@H](C)[C@H](C)c2ncc(Cl)cn2)nnc1[C@@H]1CCO[C@H]1C]<br>OR<br><br>(2S,3R)-3-(5-chloropyrimidin-2-yl)-N-(4-(2,6-dimethoxyphenyl)-5-((2R,3R)-2-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((2S,3S)-2-methyltetrahydrofuran-3-yl)-4H-1,2,4-triazol-3-yl)butane-2-sulfonamide. $^1$H NMR (500 MHz, CD$_2$Cl$_2$) δ 8.70-8.59 (m, 2H), 7.53-7.47 (m, 1H), 6.72 (dd, J = 5.2, 8.6 Hz, 2H), 4.16-4.09 (m, 1H), 3.87-3.83 (m, 1H), 3.83-3.80 (m, 7H), 3.74-3.65 (m, 2H), 2.46 (td, J = 7.4, 9.3 Hz, 1H), 2.10 (dtd, J = 5.7, 7.5, 12.8 Hz, 1H), 2.05-1.97 (m, 1H), 1.31 (d, J = 6.7 Hz, 3H), 1.26 (d, J = 6.7 Hz, 3H), 1.07 (d, J = 6.0 Hz, 3H). LCMS (pos) m/z: 537.1 (M + H)⁺. |
| 118.0 | (2S,3R)-3-(5-chloropyrimidin-2-yl)butane-2-sulfonamide (Example 1.4), (2S,3S)-2-methyltetrahydrofuran-3-carbohydrazide and (2R,3R)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology #1: Column: AS-H (2 × 25 cm) Mobile Phase: 70:30 (A:B) A: Liquid CO₂, B: MeOH, Flow Rate: 80 mL/min, 215 nm, 100 bar inlet pressure. Then by preparative SFC using the following methodology #2: Column: AD-H (2 × 15 cm) Mobile Phase: 80:20 (A:B) A: Liquid CO₂, B: MeOH, Flow Rate: 80 mL/min, 220 nm, 100 bar inlet pressure to deliver peak 2. | 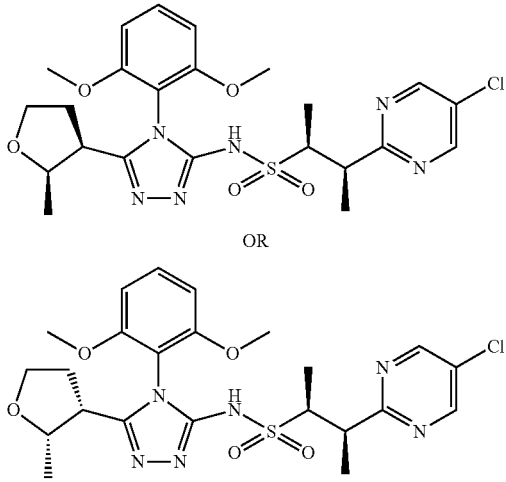 [SMILES: COc1cccc(OC)c1-n1c(NS(=O)(=O)[C@@H](C)[C@H](C)c2ncc(Cl)cn2)nnc1[C@@H]1CCO[C@@H]1C ; COc1cccc(OC)c1-n1c(NS(=O)(=O)[C@@H](C)[C@H](C)c2ncc(Cl)cn2)nnc1[C@H]1CCO[C@H]1C]<br>OR<br><br>(2S,3R)-3-(5-chloropyrimidin-2-yl)-N-(4-(2,6-dimethoxyphenyl)-5-((2R,3S)-2-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((2S,3R)-2-methyltetrahydrofuran-3-yl)-4H-1,2,4-triazol-3-yl)butane-2-sulfonamide. $^1$H NMR (500 MHz, CD$_2$Cl$_2$) δ 10.81 (br. s., 1H), 8.67-8.61 (m, 2H), 7.52-7.45 (m, 1H), 6.72 (dd, J = 4.7, 8.6 Hz, 2H), 4.04-3.98(m, 1H), 3.86 (quin, J = 6.6 Hz, 1H), 3.81 (s, 3H), 3.78 (s, 3H), 3.74-3.64 (m, 3H), 2.99-2.93 (m, 1H), 2.45 (qd, J = 8.6, 12.5 Hz, 1H), 2.17 (dtd, J = 4.2, 8.0, 12.2 Hz, 1H), 1.32 (d, J = 7.0 Hz, 3H), 1.26 (d, J = 6.7 Hz, 3H), 0.96 (d, J = 6.5 Hz, 3H). LCMS (pos) m/z: 537.2 (M + H)⁺. |

TABLE 12-continued

| Example | Reagents | Structure, Name and Data |
|---|---|---|
| 119.0 | (2S,3R)-3-(5-chloropyrimidin-2-yl)butane-2-sulfonamide (Example 1.4), (2R,3R)-2-methyltetrahydrofuran-3-carbohydrazide and (2S,3S)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology: Column: AS-H (2 × 25 cm) Mobile Phase: 70:30 (A:B) A: Liquid CO$_2$, B: MeOH, Flow Rate: 80 mL/min, 215 nm, 100 bar inlet pressure to deliver peak 2. | 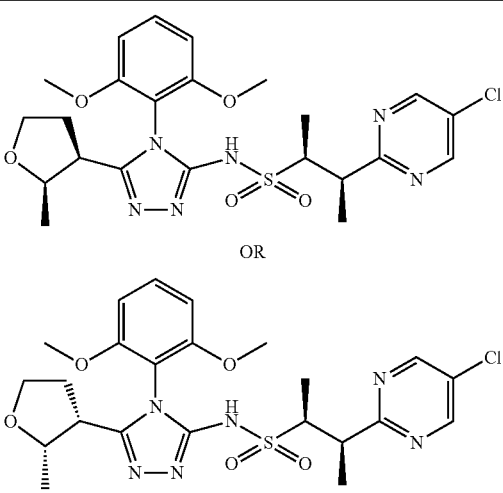<br>OR<br><br>(2S,3R)-3-(5-chloropyrimidin-2-yl)-N-(4-(2,6-dimethoxyphenyl)-5-((2R,3S)-2-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((2S,3R)-2-methyltetrahydrofuran-3-yl)-4H-1,2,4-triazol-3-yl)butane-2-sulfonamide. $^1$H NMR (500 MHz, CD$_2$Cl$_2$) δ 10.80 (br. s., 1H), 8.68-8.59 (m, 2H), 7.53-7.43 (m, 1H), 6.72 (dd, J = 5.1, 8.4 Hz, 2H), 4.01 (dt, J = 4.2, 8.6 Hz, 1H), 3.87 (quin, J = 6.5 Hz, 1H), 3.80 (s, 3H), 3.79 (s, 3H), 3.73-3.65 (m, 3H), 3.01-2.93 (m, 1H), 2.45 (qd, J = 8.6, 12.5 Hz, 1H), 2.17 (dtd, J = 4.2, 8.0, 12.2 Hz, 1H), 1.34-1.29 (m, 3H), 1.27-1.24 (m, 3H), 0.98 (d, J = 6.5 Hz, 3H). LCMS (pos) m/z: 537.2 (M + H)$^+$. |
| 120.0 | (2S,3R)-3-(5-methylpyrimidin-2-yl)butane-2-sulfonamide (Example 1.0), (2S,3R)-2-methyltetrahydrofuran-3-carbohydrazide and (2R,3S)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology #1: Column: AS-H (2 × 25 cm) Mobile Phase: 70:30 (A:B) A: Liquid CO$_2$, B: MeOH, Flow Rate: 80 mL/min, 215 nm, 100 bar inlet pressure. Then by preparative SFC using the following methodology #2: Column: AD-H (2 × 15 cm) Mobile Phase: 80:20 (A:B) A: Liquid CO$_2$, B: MeOH, Flow Rate: 80 mL/min, 220 nm, 100 bar inlet pressure to deliver peak 1. | 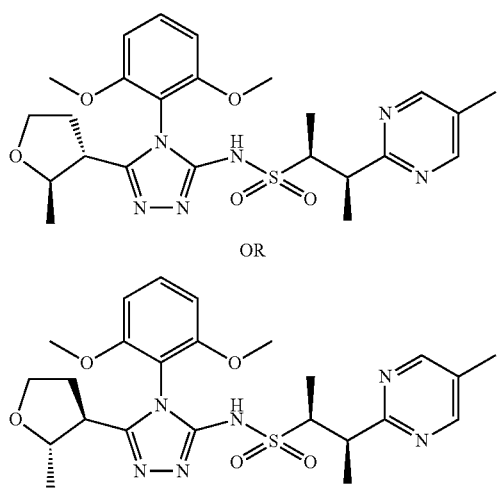 [SMILES: COc1cccc(OC)c1-n1c(NS(=O)(=O)[C@@H](C)[C@H](C)c2ncc(C)cn2)nnc1[C@H]1CCO[C@@H]1C ; COc1cccc(OC)c1-n1c(NS(=O)(=O)[C@@H](C)[C@H](C)c2ncc(C)cn2)nnc1[C@@H]1CCO[C@H]1C]<br>OR<br><br>(2S,3R)-N-(4-(2,6-dimethoxyphenyl)-5-((2S,3S)-2-methyltetrahydrofuran-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((2R,3R)-2-methyltetrahydrofuran-3-yl)-4H-1,2,4-triazol-3-yl)-3-(5-methylpyrimidin-2-yl)butane-2-sulfonamide. $^1$H NMR (500 MHz, CD$_2$Cl$_2$) δ 8.50 (s, 2H), 7.49 (t, J = 8.6 Hz, 1H), 6.72 (dd, J = 5.3, 8.4 Hz, 2H), 4.16-4.09 (m, 1H), 3.89-3.83 (m, 1H), 3.83-3.79 (m, 7H), 3.76-3.70 (m, 1H), 3.66-3.60 (m, 1H), 2.46 (td, J = 7.5, 9.3 Hz, 1H), 2.27 (s, 3H), 2.15-2.08 (m, 1H), 2.06-1.97 (m, 1H), 1.31 (d, J = 7.3 Hz, 3H), 1.26 (d, J = 7.0 Hz, 3H), 1.08 (d, J = 6.0 Hz, 3H). LCMS (pos) m/z: 517.2 (M + H)$^+$. |

TABLE 12-continued

| Example | Reagents | Structure, Name and Data |
|---|---|---|
| 121.0 | (2S,3R)-3-(5-methylpyrimidin-2-yl)butane-2-sulfonamide (Example 1.0), (2S,3S)-2-methyltetrahydrofuran-3-carbohydrazide and (2R,3R)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology #1: Column: AS-H (2 × 25 cm) Mobile Phase: 70:30 (A:B) A: Liquid $CO_2$, B: MeOH, Flow Rate: 80 mL/min, 215 nm, 100 bar inlet pressure. Then by preparative SFC using the following methodology #2: Column: AD-H (2 × 15 cm) Mobile Phase: 80:20 (A:B) A: Liquid $CO_2$, B: MeOH, Flow Rate: 80 mL/min, 220 nm, 100 bar inlet pressure to deliver peak 2. | 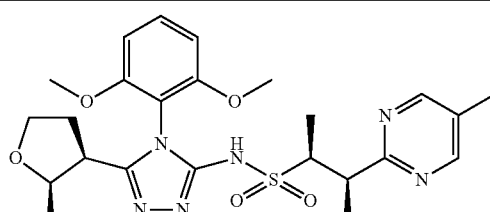<br>OR<br>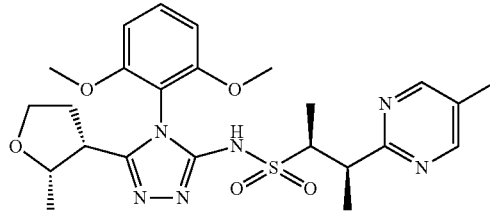<br>(2S,3R)-N-(4-(2,6-dimethoxyphenyl)-5-((2R,3S)-2-methyltetrahydrofuran-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((2S,3R)-2-methyltetrahydrofuran-3-yl)-4H-1,2,4-triazol-3-yl)-3-(5-methylpyrimidin-2-yl)butane-2-sulfonamide.<br>$^1$H NMR (500 MHz, $CD_2Cl_2$) δ 8.57-8.50 (m, 2H), 7.53-7.45 (m, 1H), 6.72 (dd, J = 4.5, 8.4 Hz, 2H), 4.01 (dt, J = 4.0, 8.5 Hz, 1H), 3.87 (quin, J = 6.6 Hz, 1H), 3.80 (s, 3H), 3.78 (s, 3H), 3.76-3.71 (m, 1H), 3.71-3.66 (m, 1H), 3.65-3.60 (m, 1H), 3.00-2.93 (m, 1H), 2.46 (qd, J = 8.6, 12.7 Hz, 1H), 2.27 (s, 3H), 2.22-2.13 (m, 1H), 1.31 (d, J = 7.0 Hz, 3H), 1.25 (d, J = 7.0 Hz, 3H), 0.97 (d, J = 6.2 Hz, 3H). LCMS (pos) m/z: 517.2 (M + H)$^+$. |
| 122.0 | (2S,3R)-3-(5-methylpyrimidin-2-yl)butane-2-sulfonamide (Example 1.0), (2S,3R)-2-methyltetrahydrofuran-3-carbohydrazide and (2R,3S)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology #1: Column: AS-H (2 × 25 cm) Mobile Phase: 70:30 (A:B) A: Liquid $CO_2$, B: MeOH, Flow Rate: 80 mL/min, 215 nm, 100 bar inlet pressure. Then by preparative SFC using the following methodology #2: Column: AD-H (2 × 15 cm) Mobile Phase: 80:20 (A:B) A: Liquid $CO_2$, B: MeOH, Flow Rate: 80 mL/min, 220 nm, 100 bar inlet pressure to deliver peak 3. | 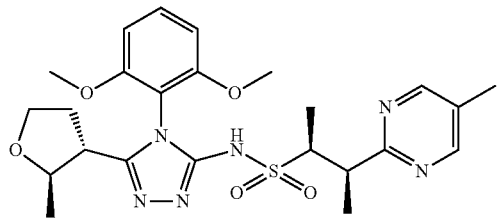<br>OR<br>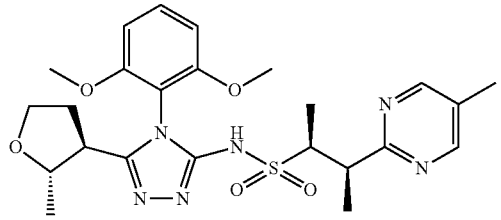<br>(2S,3R)-N-(4-(2,6-dimethoxyphenyl)-5-((2S,3S)-2-methyltetrahydrofuran-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((2R,3R)-2-methyltetrahydrofuran-3-yl)-4H-1,2,4-triazol-3-yl)-3-(5-methylpyrimidin-2-yl)butane-2-sulfonamide.<br>$^1$H NMR (500 MHz, $CD_2Cl_2$) δ 11.03 (br. s., 1H), 8.51 (s, 2H), 7.49 (t, J = 8.6 Hz, 1H), 6.72 (dd, J = 4.2, 8.6 Hz, 2H), 4.17-4.09 (m, 1H), 3.87-3.79 (m, 8H), 3.73 (quin, J = 6.6 Hz, 1H), 3.67-3.61 (m, 1H), 2.46 (td, J = 7.5, 9.2 Hz, 1H), 2.27 (s, 3H), 2.14-2.06 (m, 1H), 2.05-1.97 (m, 1H), 1.31 (d, J = 7.0 Hz, 3H), 1.27-1.25 (m, 3H), 1.08 (d, J = 6.0 Hz, 3H). LCMS (pos) m/z: 517.2 (M + H)$^+$. |

TABLE 12-continued

| Example | Reagents | Structure, Name and Data |
|---|---|---|
| 123.0 | (2S,3R)-3-(5-methylpyrimidin-2-yl)butane-2-sulfonamide (Example 1.0), (2S,3S)-2-methyltetrahydrofuran-3-carbohydrazide and (2R,3R)-2-methyltetrahydrofuran-3-carbohydrazide hydrochloride (commercially available from Ukrorgsyntez), 2-isothiocyanato-1,3-dimethoxybenzene (Example 10.0). The mixture was purified by preparative SFC using the following methodology: Column: AS-H (2 × 25 cm) Mobile Phase: 70:30 (A:B) A: Liquid $CO_2$, B: MeOH, Flow Rate: 80 mL/min, 215 nm, 100 bar inlet pressure to deliver peak 2. | 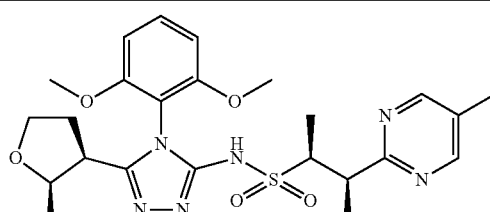<br>OR<br>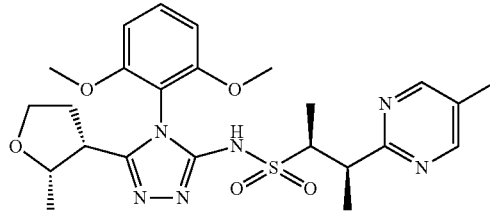<br>(2S,3R)-N-(4-(2,6-dimethoxyphenyl)-5-((2R,3S)-2-methyltetrahydrofuran-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((2S,3R)-2-methyltetrahydrofuran-3-yl)-4H-1,2,4-triazol-3-yl)-3-(5-methylpyrimidin-2-yl)butane-2-sulfonamide. $^1$H NMR (500 MHz, $CD_2Cl_2$) δ 11.02 (br. s., 1H), 8.50 (s, 2H), 7.48 (t, J = 8.6 Hz, 1H), 6.72 (dd, J = 5.2, 8.6 Hz, 2H), 4.01 (dt, J = 4.0, 8.5 Hz, 1H), 3.87 (quin, J = 6.5 Hz, 1H), 3.79 (3H), 3.79 (s, 3H), 3.75-3.71 (m, 1H), 3.71-3.61 (m, 2H), 3.01-2.92 (m, 1H), 2.45 (qd, J = 8.6, 12.5 Hz, 1H), 2.26 (s, 3H), 2.17 (dtd, J = 3.9, 8.0, 12.2 Hz, 1H), 1.30 (d, J = 7.0 Hz, 3H), 1.25 (d, J = 7.0 Hz, 3H), 0.98 (d, J = 6.5 Hz, 3H). LCMS (pos) m/z: 517.2 $(M + H)^+$. |
| 124.0 | (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.), 1-isothiocyanato-1-methylcyclopropane (commercially available from Enamine). The mixture was purified by preparative SFC using the following methodology: Column: OZ-H (2 × 15 cm) Mobile Phase: 50:50 (A:B) A: Liquid $CO_2$, B: MeOH, Flow Rate: 80 mL/min, 220 nm, 100 bar inlet pressure to deliver peak 1. | 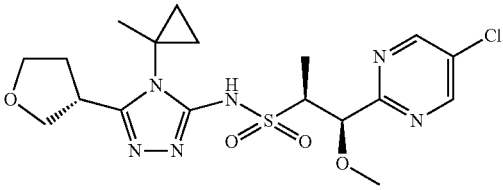<br>OR<br>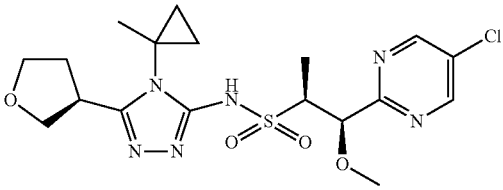<br>(1R,2S)-1-(5-chloropyrimidin-2-yl)-1-methoxy-N-(4-(1-methylcyclopropyl)-5-((R)-tetrahydrofuran-3-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((S)-tetrahydrofuran-3-yl)-4H-1,2,4-triazol-3-yl)propane-2-sulfonamide. $^1$H NMR (400 MHz, $CD_2Cl_2$) δ 10.73 (br. s., 1H), 8.76-8.68 (m, 2H), 4.99 (d, J = 3.7 Hz, 1H), 4.17 (t, J = 8.1 Hz, 1H), 4.03-3.96 (m, 1H), 3.95-3.89 (m, 1H), 3.83 (dd, J = 7.0, 8.3 Hz, 1H), 3.69-3.62 (m, 1H), 3.61-3.54 (m, 1H), 3.20 (s, 3H), 2.37 (dddd, J = 5.7, 7.2, 8.8, 12.6 Hz, 1H), 2.25-2.16 (m, 1H), 1.49 (s, 3H), 1.35 (d, J = 7.0 Hz, 3H), 1.30-1.20 (m, 1H), 1.20-1.12 (m, 1H), 1.10-1.02 (m, 2H). LCMS (pos) m/z: 457.0 $(M + H)^+$. |

TABLE 12-continued

| Example | Reagents | Structure, Name and Data |
|---|---|---|
| 125.0 | (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.), 1-isothiocyanato-1-methylcyclopropane (commercially available from Enamine). The mixture was purified by preparative SFC using the following methodology: Column: OZ-H (2 × 15 cm) Mobile Phase: 50:50 (A:B) A: Liquid $CO_2$, B: MeOH, Flow Rate: 80 mL/min, 220 nm, 100 bar inlet pressure to deliver peak 2. | 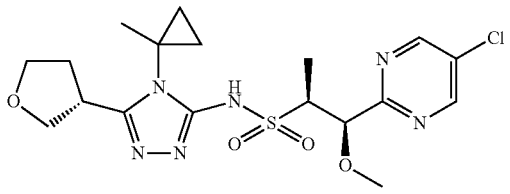<br>OR<br>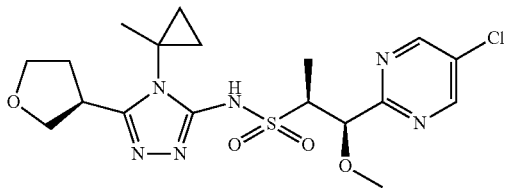<br>(1R,2S)-1-(5-chloropyrimidin-2-yl)-1-methoxy-N-(4-(1-methylcyclopropyl)-5-((R)-tetrahydrofuran-3-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((S)-tetrahydrofuran-3-yl)-4H-1,2,4-triazol-3-yl)propane-2-sulfonamide. $^1$H NMR (400 MHz, $CD_2Cl_2$) δ 10.75 (br. s., 1H), 8.75-8.69 (m, 2H), 5.00 (d, J = 3.7 Hz, 1H), 4.17 (t, J = 8.1 Hz, 1H), 4.03-3.96 (m, 1H), 3.95-3.89 (m, 1H), 3.84 (dd, J = 7.2, 8.4 Hz, 1H), 3.69-3.62 (m, 1H), 3.61-3.54 (m, 1H), 3.21 (s, 3H), 2.42-2.32 (m, 1H), 2.24-2.14 (m, 1H), 1.49 (s, 3H), 1.35 (d, J = 7.0 Hz, 3H), 1.30-1.16 (m, 2H), 1.12-1.02 (m, 2H). LCMS (pos) m/z: 457.2 (M + H)$^+$. |
| 126.0 | (1R,2S)-1-(5-chloropyrimidin-2-yl)-1-methoxypropane-2-sulfonamide (Example 11.3), (R)-tetrahydro-2H-pyran-3-carbohydrazide and (S)-tetrahydro-2H-pyran-3-carbohydrazide (commercially available from Synthonix), 1-isothiocyanato-1-methylcyclopropane (commercially available from Enamine). The mixture was purified by preparative SFC using the following methodology: Column: IC (2 × 15 cm) Mobile Phase: 40:60 (A:B) A: Liquid $CO_2$, B: MeOH, Flow Rate: 80 mL/min, 220 nm, 100 bar inlet pressure to deliver peak 1. | 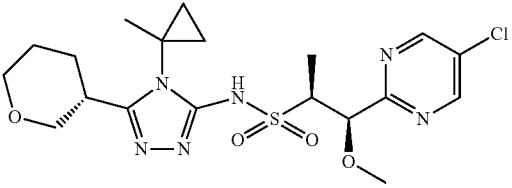<br>OR<br>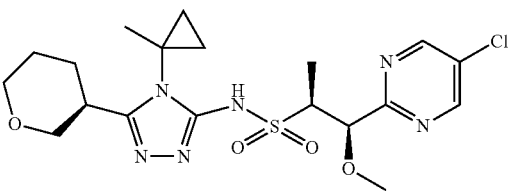<br>(1R,2S)-1-(5-chloropyrimidin-2-yl)-1-methoxy-N-(4-(1-methylcyclopropyl)-5-((R)-tetrahydro-2H-pyran-3-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((S)-tetrahydro-2H-pyran-3-yl)-4H-1,2,4-triazol-3-yl)propane-2-sulfonamide. $^1$H NMR (400 MHz, $CD_2Cl_2$) δ 10.71 (br. s., 1H), 8.75-8.68 (m, 2H), 4.99 (d, J = 3.7 Hz, 1H), 4.03-3.93 (m, 2H), 3.60-3.50 (m, 2H), 3.49-3.41 (m, 1H), 3.27-3.20 (m, 1H), 3.18 (s, 3H), 2.19-2.10 (m, 1H), 1.91-1.73 (m, 3H), 1.52-1.46 (m, 3H), 1.39-1.32 (m, 3H), 1.32-1.12 (m, 2H), 1.12-1.02 (m, 2H). LCMS (pos) m/z: 471.2 (M + H)$^+$. |

TABLE 12-continued

| Example | Reagents | Structure, Name and Data |
|---|---|---|
| 127.0 | (1R,2S)-1-(5-chloropyrimidin-2-yl)-1-methoxypropane-2-sulfonamide (Example 11.3), (R)-tetrahydro-2H-pyran-3-carbohydrazide and (S)-tetrahydro-2H-pyran-3-carbohydrazide (commercially available from Synthonix), 1-isothiocyanato-1-methylcyclopropane (commercially available from Enamine). The mixture was purified by preparative SFC using the following methodology: Column: IC (2 × 15 cm) Mobile Phase: 40:60 (A:B) A: Liquid $CO_2$, B: MeOH, Flow Rate: 80 mL/min, 220 nm, 100 bar inlet pressure to deliver peak 2. | 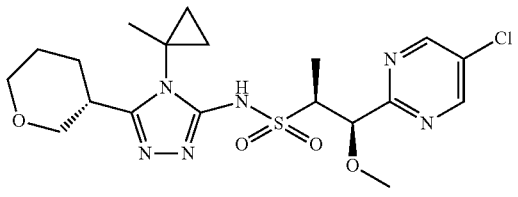<br>OR<br>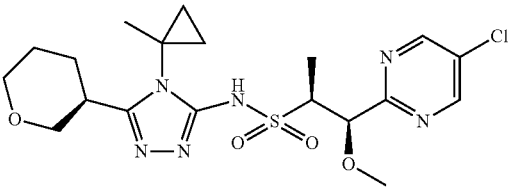<br><br>(1R,2S)-1-(5-chloropyrimidin-2-yl)-1-methoxy-N-(4-(1-methylcyclopropyl)-5-((R)-tetrahydro-2H-pyran-3-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((S)-tetrahydro-2H-pyran-3-yl)-4H-1,2,4-triazol-3-yl)propane-2-sulfonamide. $^1$H NMR (400 MHz, $CD_2Cl_2$) δ 10.72 (br. s., 1H), 8.74-8.70 (m, 2H), 4.99 (d, J = 3.7 Hz, 1H), 4.06-3.94 (m, 2H), 3.60-3.44 (m, 3H), 3.27-3.21 (m, 1H), 3.21-3.17 (m, 3H), 2.14-2.08 (m, 1H), 1.90-1.73 (m, 3H), 1.49 (s, 3H), 1.34 (d, J = 7.0 Hz, 3H), 1.31-1.11 (m, 2H), 1.11-1.03 (m, 2H). LCMS (pos) m/z: 471.0 $(M + H)^+$. |
| 128.0 | (1R,2S)-1-methoxy-1-(5-methylpyrazin-2-yl)propane-2-sulfonamide (Example 11.1), (R)-tetrahydrofuran-3-carbohydrazide and (S)-tetrahydrofuran-3-carbohydrazide (commercially available from Astatech Inc.), 1-isothiocyanato-1-methylcyclopropane (commercially available from Enamine). The mixture was purified by preparative SFC using the following methodology: Column: OZ-H (2 × 15 cm) Mobile Phase: 55:45 (A:B) A: Liquid $CO_2$, B: MeOH, Flow Rate: 80 mL/min, 216 nm, 100 bar inlet pressure to deliver peak 1. | 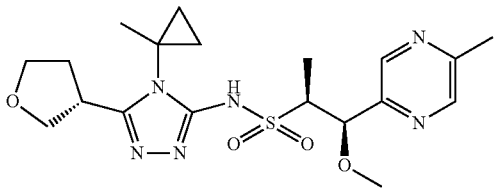<br>OR<br>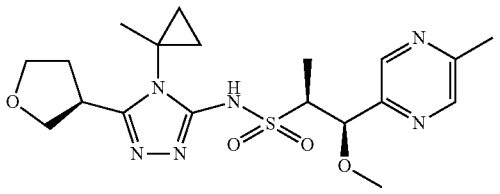<br><br>(1R,2S)-1-methoxy-N-(4-(1-methylcyclopropyl)-5-((R)-tetrahydrofuran-3-yl)-4H-1,2,4-triazol-3-yl)-1-(5-methylpyrazin-2-yl)propane-2-sulfonamide or (1R,2S)-1-methoxy-N-(4-(1-methylcyclopropyl)-5-((S)-tetrahydrofuran-3-yl)-4H-1,2,4-triazol-3-yl)-1-(5-methylpyrazin-2-yl)propane-2-sulfonamide. $^1$H NMR (400 MHz, $CD_2Cl_2$) δ 10.71 (br. s., 1H), 8.51 (d, J = 1.2 Hz, 1H), 8.41 (d, J = 1.0 Hz, 1H), 5.04 (d, J = 2.7 Hz, 1H), 4.18 (t, J = 8.1 Hz, 1H), 4.04-3.97 (m, 1H), 3.96-3.89 (m, 1H), 3.84 (dd, J = 7.3, 8.3 Hz, 1H), 3.69-3.61 (m, 1H), 3.41 (dq, J = 2.7, 7.0 Hz, 1H), 3.25 (s, 3H), 2.53 (s, 3H), 2.43-2.32 (m, 1H), 2.26-2.16 (m, 1H), 1.49 (s, 3H), 1.27 (d, J = 7.0 Hz, 4H), 1.22-1.12 (m, 1H), 1.11-1.01 (m, 2H). LCMS (pos) m/z: 437.2 $(M + H)^+$. |

TABLE 12-continued

| Example | Reagents | Structure, Name and Data |
|---|---|---|
| 129.0 | (1R,2S)-1-methoxy-1-(5-methylpyrazin-2-yl)propane-2-sulfonamide (Example 11.1), (R)-tetrahydrofuran-3-carbohydrazide and (S)-tetrahydrofuran-3-carbohydrazide (commercially available from Astatech Inc.), 1-isothiocyanato-1-methylcyclopropane (commercially available from Enamine). The mixture was purified by preparative SFC using the following methodology: Column: OZ-H (2 × 15 cm) Mobile Phase: 55:45 (A:B) A: Liquid CO$_2$, B: MeOH, Flow Rate: 80 mL/min, 216 nm, 100 bar inlet pressure to deliver peak 1. | 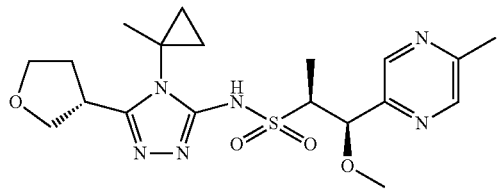<br>OR<br>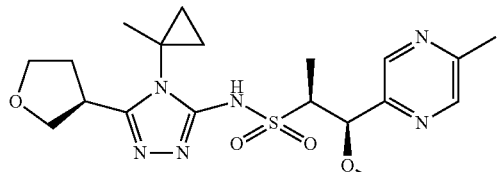<br><br>(1R,2S)-1-methoxy-N-(4-(1-methylcyclopropyl)-5-((R)-tetrahydrofuran-3-yl)-4H-1,2,4-triazol-3-yl)-1-(5-methylpyrazin-2-yl)propane-2-sulfonamide or (1R,2S)-1-methoxy-N-(4-(1-methylcyclopropyl)-5-((S)-tetrahydrofuran-3-yl)-4H-1,2,4-triazol-3-yl)-1-(5-methylpyrazin-2-yl)propane-2-sulfonamide. $^1$H NMR (400 MHz, CD$_2$Cl$_2$) δ 10.80 (br. s., 1H), 8.51 (d, J = 1.2 Hz, 1H), 8.41 (d, J = 1.0 Hz, 1H), 5.04 (d, J = 2.7 Hz, 1H), 4.18 (t, J = 8.0 Hz, 1H), 4.03-3.96 (m, 1H), 3.96-3.89 (m, 1H), 3.85 (dd, J = 7.2, 8.4 Hz, 1H), 3.65 (qd, J = 7.3, 8.9 Hz, 1H), 3.42 (dq, J = 2.6, 7.1 Hz, 1H), 3.26 (s, 3H), 2.54 (s, 3H), 2.43-2.33 (m, 1H), 2.25-2.15 (m, 1H), 1.49 (s, 3H), 1.28 (d, J = 7.0 Hz, 3H), 1.21 (br. s., 2H), 1.12-1.04 (m, 2H). LCMS (pos) m/z: 437.2 (M + H)$^+$. |
| 130.0 | (1R,2S)-1-methoxy-1-(5-methylpyrazin-2-yl)propane-2-sulfonamide (Example 11.1), (R)-tetrahydro-2H-pyran-3-carbohydrazide and (S)-tetrahydro-2H-pyran-3-carbohydrazide (commercially available from Synthonix), 1-isothiocyanato-1-methylcyclopropane (commercially available from Enamine). The mixture was purified by preparative SFC using the following methodology: Column: OZ-H (2 × 15 cm) Mobile Phase: 55:45 (A:B) A: Liquid CO$_2$, B: MeOH, Flow Rate: 80 mL/min, 218 nm, 100 bar inlet pressure to deliver peak 1. | 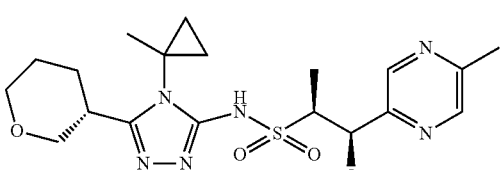<br>OR<br>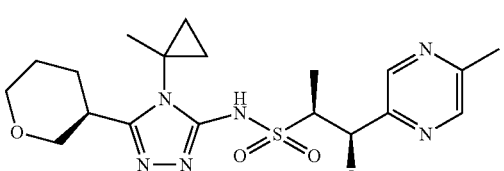<br><br>(1R,2S)-1-methoxy-N-(4-(1-methylcyclopropyl)-5-((R)-tetrahydro-2H-pyran-3-yl)-4H-1,2,4-triazol-3-yl)-1-(5-methylpyrazin-2-yl)propane-2-sulfonamide or (1R,2S)-1-methoxy-N-(4-(1-methylcyclopropyl)-5-((S)-tetrahydro-2H-pyran-3-yl)-4H-1,2,4-triazol-3-yl)-1-(5-methylpyrazin-2-yl)propane-2-sulfonamide. $^1$H NMR (400 MHz, CD$_2$Cl$_2$) δ 8.50 (d, J = 1.5 Hz, 1H), 8.40 (d, J = 1.0 Hz, 1H), 5.03 (d, J = 2.5 Hz, 1H), 4.05-3.92 (m, 2H), 3.57-3.50 (m, 1H), 3.50-3.42 (m, 1H), 3.41-3.35 (m, 1H), 3.30-3.17 (m, 4H), 2.53 (s, 3H), 2.17-2.09 (m, 1H), 1.91-1.81 (m, 1H), 1.81-1.72 (m, 2H), 1.49 (s, 3H), 1.27 (d, J = 7.0 Hz, 3H), 1.19 (br. s., 2H), 1.10-1.05 (m, 2H). LCMS (pos) m/z: 451.2 (M + H)$^+$. |

TABLE 12-continued

| Example | Reagents | Structure, Name and Data |
|---|---|---|
| 131.0 | (1R,2S)-1-methoxy-1-(5-methylpyrazin-2-yl)propane-2-sulfonamide (Example 11.1), (R)-tetrahydro-2H-pyran-3-carbohydrazide and (S)-tetrahydro-2H-pyran-3-carbohydrazide (commercially available from Synthonix), 1-isothiocyanato-1-methylcyclopropane (commercially available from Enamine). The mixture was purified by preparative SFC using the following methodology: Column: OZ-H (2 × 15 cm) Mobile Phase: 55:45 (A:B) A: Liquid CO$_2$, B: MeOH, Flow Rate: 80 mL/min, 218 nm, 100 bar inlet pressure to deliver peak 2. | 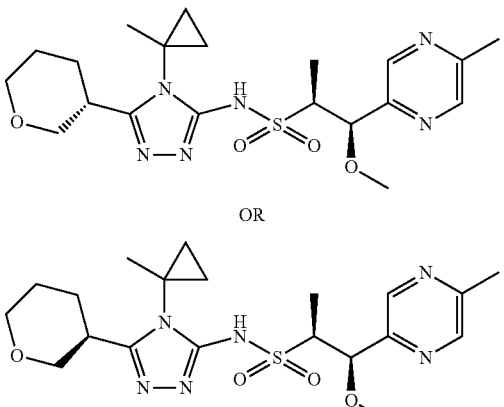<br><br>OR<br><br>(1R,2S)-1-methoxy-N-(4-(1-methylcyclopropyl)-5-((R)-tetrahydro-2H-pyran-3-yl)-4H-1,2,4-triazol-3-yl)-1-(5-methylpyrazin-2-yl)propane-2-sulfonamide or (1R,2S)-1-methoxy-N-(4-(1-methylcyclopropyl)-5-((S)-tetrahydro-2H-pyran-3-yl)-4H-1,2,4-triazol-3-yl)-1-(5-methylpyrazin-2-yl)propane-2-sulfonamide. $^1$H NMR (400 MHz, CD$_2$Cl$_2$) δ 8.53 (d, J = 1.2 Hz, 1H), 8.43 (d, J = 1.5 Hz, 1H), 5.07 (d, J = 2.7 Hz, 1H), 4.11-3.96 (m, 2H), 3.62-3.48 (m, 2H), 3.43 (dq, J = 2.6, 7.1 Hz, 1H), 3.32-3.22 (m, 4H), 2.56 (s, 3H), 2.17-2.10 (m, 1H), 1.95-1.76 (m, 3H), 1.52 (s, 3H), 1.30 (d, J = 7.0 Hz, 3H), 1.28-1.12 (m, 2H), 1.12-1.04 (m, 2H). LCMS (pos) m/z: 451.2 (M + H)$^+$. |
| 132.0 | (2S,3R)-3-(5-methylpyrazin-2-yl)butane-2-sulfonamide (Example 1.2), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: AS-H (2 × 25 cm) Mobile Phase: 75:25 (A:B) A: Liquid CO$_2$, B: MeOH, Flow Rate: 60 mL/min, 276 nm, 100 bar inlet pressure to deliver peak 1. | 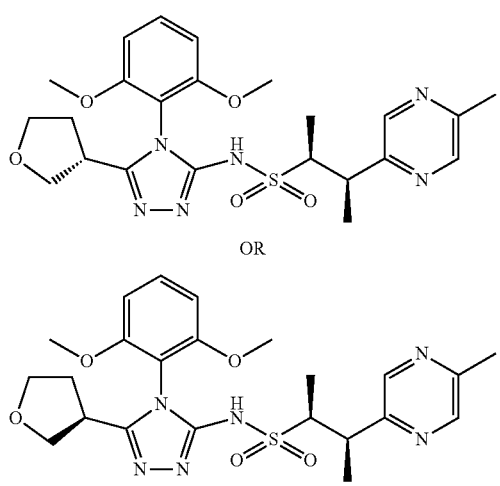 [SMILES: COc1cccc(OC)c1-n1c(NS(=O)(=O)[C@@H](C)[C@H](C)c2cnc(C)cn2)nnc1[C@H]1CCOC1 ; COc1cccc(OC)c1-n1c(NS(=O)(=O)[C@@H](C)[C@H](C)c2cnc(C)cn2)nnc1[C@@H]1CCOC1]<br><br>OR<br><br>(2S,3R)-N-(4-(2,6-dimethoxyphenyl)-5-((R)-tetrahydrofuran-3-yl)-4H-1,2,4-triazol-3-yl)-3-(5-methylpyrazin-2-yl)butane-2-sulfonamide or (2S,3R)-N-(4-(2,6-dimethoxyphenyl)-5-((S)-tetrahydrofuran-3-yl)-4H-1,2,4-triazol-3-yl)-3-(5-methylpyrazin-2-yl)butane-2-sulfonamide. $^1$H NMR (400 MHz, CD$_2$Cl$_2$) δ 10.73 (br. s., 1H), 8.33 (s, 1H), 8.28 (d, J = 1.5 Hz, 1H), 7.53-7.45 (m, 1H), 6.76-6.66 (m, 2H), 3.89-3.84 (m, 1H), 3.84-3.78 (m, 6H), 3.77-3.59 (m, 4H), 3.44 (dq, J = 4.3, 7.0 Hz, 1H), 2.99 (qd, J = 7.0, 9.0 Hz, 1H), 2.49 (s, 3H), 2.27-2.18 (m, 1H), 2.01 (dddd, J = 5.7, 7.4, 9.0, 12.7 Hz, 1H), 1.31 (d, J = 7.0 Hz, 3H), 1.24 (d, J = 7.0 Hz, 3H). LCMS (pos) m/z: 503.2 (M + H)$^+$. |

| Example | Reagents | Structure, Name and Data |
|---|---|---|
| 133.0 | (2S,3R)-3-(5-methylpyrazin-2-yl)butane-2-sulfonamide (Example 1.2), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: AS-H (2 × 25 cm) Mobile Phase: 75:25 (A:B) A: Liquid $CO_2$, B: MeOH, Flow Rate: 60 mL/min, 276 nm, 100 bar inlet pressure to deliver peak 2. | 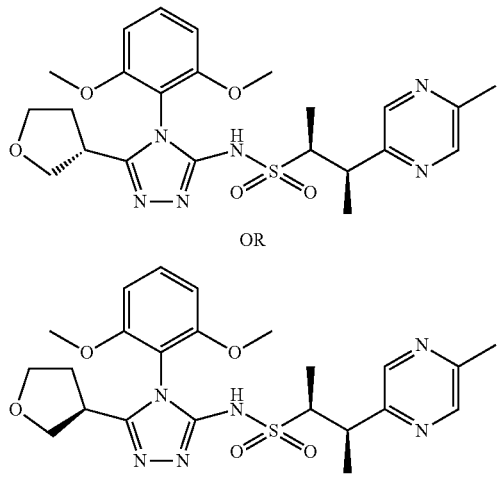 [SMILES: COc1cccc(OC)c1-n1c(NS(=O)(=O)[C@@H](C)[C@H](C)c2cnc(C)cn2)nnc1[C@H]1CCOC1 ; COc1cccc(OC)c1-n1c(NS(=O)(=O)[C@@H](C)[C@H](C)c2cnc(C)cn2)nnc1[C@@H]1CCOC1]<br>(2S,3R)-N-(4-(2,6-dimethoxyphenyl)-5-((R)-tetrahydrofuran-3-yl)-4H-1,2,4-triazol-3-yl)-3-(5-methylpyrazin-2-yl)butane-2-sulfonamide or (2S,3R)-N-(4-(2,6-dimethoxyphenyl)-5-((S)-tetrahydrofuran-3-yl)-4H-1,2,4-triazol-3-yl)-3-(5-methylpyrazin-2-yl)butane-2-sulfonamide. $^1$H NMR (400 MHz, $CD_2Cl_2$) δ 10.72 (br. s., 1H), 8.35 (s, 1H), 8.28 (d, J = 1.2 Hz, 1H), 7.52-7.45 (m, 1H), 6.76-6.69 (m, 2H), 3.89-3.84 (m, 1H), 3.83-3.78 (m, 7H), 3.77-3.71 (m, 2H), 3.67-3.60 (m, 1H), 3.45 (dq, J = 4.5, 7.0 Hz, 1H), 2.99 (qd, J = 7.1, 8.9 Hz, 1H), 2.50 (s, 3H), 2.24-2.15 (m, 1H), 2.04-1.94 (m, 1H), 1.31 (d, J = 7.0 Hz, 3H), 1.25 (d, J = 7.0 Hz, 3H). LCMS (pos) m/z: 503.2 (M + H)$^+$. |
| 134.0 | (2S,3R)-3-(5-methylpyrazin-2-yl)butane-2-sulfonamide (Example 1.2), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene. The mixture was purified by preparative SFC using the following methodology: Column: AD-H (2 × 25 cm) Mobile Phase: 60:40 (A:B) A: Liquid $CO_2$, B: IPA, Flow Rate: 80 mL/min, 276 nm, 100 bar inlet pressure to deliver peak 1. | 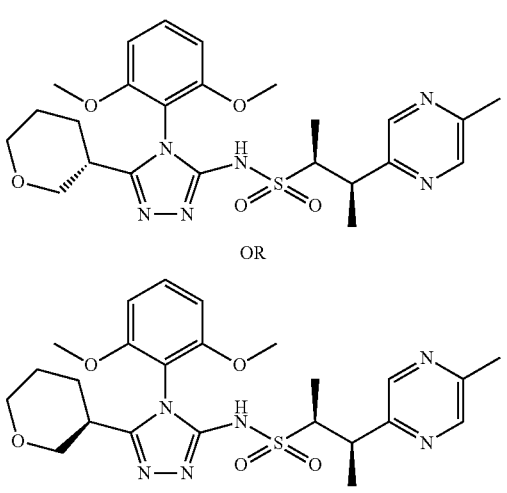 [SMILES: COc1cccc(OC)c1-n1c(NS(=O)(=O)[C@@H](C)[C@H](C)c2cnc(C)cn2)nnc1[C@H]1CCCOC1 ; COc1cccc(OC)c1-n1c(NS(=O)(=O)[C@@H](C)[C@H](C)c2cnc(C)cn2)nnc1[C@@H]1CCCOC1]<br>(2S,3R)-N-(4-(2,6-dimethoxyphenyl)-5-((R)-tetrahydro-2H-pyran-3-yl)-4H-1,2,4-triazol-3-yl)-3-(5-methylpyrazin-2-yl)butane-2-sulfonamide or (2S,3R)-N-(4-(2,6-dimethoxyphenyl)-5-((S)-tetrahydro-2H-pyran-3-yl)-4H-1,2,4-triazol-3-yl)-3-(5-methylpyrazin-2-yl)butane-2-sulfonamide. $^1$H NMR (400 MHz, $CD_2Cl_2$) δ 10.78 (br. s., 1H), 8.36-8.31 (m, 1H), 8.27 (d, J = 1.2 Hz, 1H),7.53-7.46 (m, 1H), 6.73 (qd, J = 1.1, 8.6 Hz, 2H), 3.86-3.79 (m, 8H), 3.67-3.61 (m, 1H), 3.47-3.34 (m, 3H), 2.55-2.45 (m, 4H), 1.95-1.88 (m, 1H), 1.86-1.74 (m, 1H), 1.68-1.59 (m, 1H), 1.58-1.47 (m, 1H), 1.30 (d, J = 7.3 Hz, 3H), 1.24 (d, J = 6.8 Hz, 3H). LCMS (pos) m/z: 517.2 (M + H)$^+$. |

TABLE 12-continued

| Example | Reagents | Structure, Name and Data |
|---|---|---|
| 135.0 | (2S,3R)-3-(5-methylpyrazin-2-yl)butane-2-sulfonamide (Example 1.2), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 25 cm) Mobile Phase: 60:40 (A:B) A: Liquid CO$_2$, B: IPA, Flow Rate: 80 mL/min, 276 nm, 100 bar inlet pressure to deliver peak 2. | 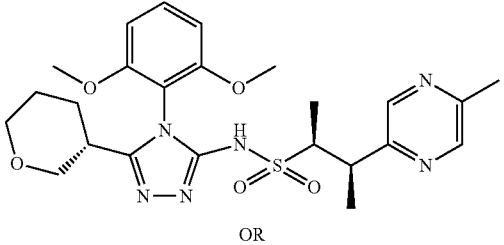<br>(2S,3R)-N-(4-(2,6-dimethoxyphenyl)-5-((R)-tetrahydro-2H-pyran-3-yl)-4H-1,2,4-triazol-3-yl)-3-(5-methylpyrazin-2-yl)butane-2-sulfonamide or (2S,3R)-N-(4-(2,6-dimethoxyphenyl)-5-((S)-tetrahydro-2H-pyran-3-yl)-4H-1,2,4-triazol-3-yl)-3-(5-methylpyrazin-2-yl)butane-2-sulfonamide. $^1$H NMR (400 MHz, CD$_2$Cl$_2$) δ 10.72 (br. s., 1H), 8.36 (s, 1H), 8.27 (d, J = 1.5 Hz, 1H), 7.55-7.46 (m, 1H), 6.79-6.70 (m, 2H), 3.86-3.76 (m, 8H), 3.66-3.59 (m, 1H), 3.48-3.34 (m, 3H), 2.55-2.45 (m, 4H), 1.97-1.90 (m, 1H), 1.86-1.76 (m, 1H), 1.67-1.61 (m, 1H), 1.59-1.47 (m, 1H), 1.31 (d, J = 7.0 Hz, 3H), 1.24 (d, J = 7.0 Hz, 3H). LCMS (pos) m/z: 517.2 (M + H)$^+$. |
| 136.0 | (1S,2S)-1-isopropoxy-1-(5-methylpyrimidin-2-yl)propane-2-sulfonamide (Example 13.5), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 25 cm) Mobile Phase: 75:25 (A:B) A: Liquid CO$_2$, B: IPA, Flow Rate: 80 mL/min, 215 nm, 100 bar inlet pressure to deliver peak 1. | 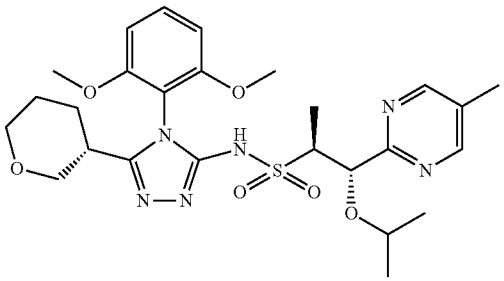<br>(1S,2S)-N-(4-(2,6-dimethoxyphenyl)-5-((R)-tetrahydro-2H-pyran-3-yl)-4H-1,2,4-triazol-3-yl)-1-isopropoxy-1-(5-methylpyrimidin-2-yl)propane-2-sulfonamide or (1S,2S)-N-(4-(2,6-dimethoxyphenyl)-5-((S)-tetrahydro-2H-pyran-3-yl)-4H-1,2,4-triazol-3-yl)-1-isopropoxy-1-(5-methylpyrimidin-2-yl)propane-2-sulfonamide. $^1$H NMR (500 MHz, CD$_2$Cl$_2$) δ 12.45 (br. s., 1H), 8.63 (s, 2H), 7.49 (t, J = 8.4 Hz, 1H), 6.74 (t, J = 7.8 Hz, 2H), 4.79 (d, J = 4.2 Hz, 1H), 3.90-3.86(m, 3H), 3.86-3.77 (m, 5H), 3.62-3.56 (m, 1H), 3.56-3.51 (m, 1H), 3.41-3.34 (m, 2H), 2.48 (ft, J = 4.0, 11.0 Hz, 1H), 2.34 (s, 3H), 2.00-1.94 (m, 1H), 1.85 (dq, J = 4.0, 12.4 Hz, 1H), 1.69-1.62 (m, 1H), 1.59-1.49 (m, 1H), 1.36 (d, J = 7.0 Hz, 3H), 1.07 (d, J = 6.0 Hz, 3H), 0.95 (d, J = 6.2 Hz, 3H). LCMS (pos) m/z: 561.2 (M + H)$^+$. |

TABLE 12-continued

| Example | Reagents | Structure, Name and Data |
|---|---|---|
| 137.0 | (1S,2S)-1-isopropoxy-1-(5-methylpyrimidin-2-yl)propane-2-sulfonamide (Example 13.5), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 25 cm) Mobile Phase: 75:25 (A:B) A: Liquid $CO_2$, B: IPA, Flow Rate: 80 mL/min, 215 nm, 100 bar inlet pressure to deliver peak 2. | 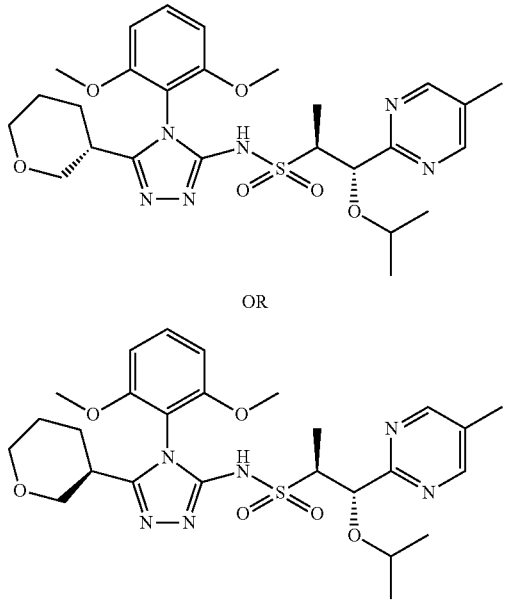 [SMILES: COc1cccc(OC)c1-n1c(NS(=O)(=O)[C@@H](C)[C@@H](OC(C)C)c2ncc(C)cn2)nnc1[C@H]1CCCOC1 ; COc1cccc(OC)c1-n1c(NS(=O)(=O)[C@@H](C)[C@@H](OC(C)C)c2ncc(C)cn2)nnc1[C@@H]1CCCOC1]<br><br>OR<br><br>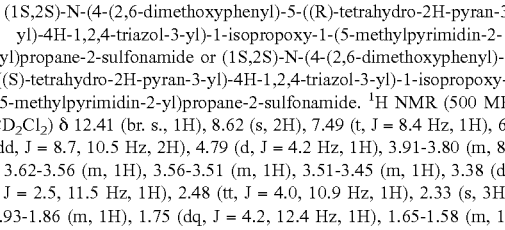<br><br>(1S,2S)-N-(4-(2,6-dimethoxyphenyl)-5-((R)-tetrahydro-2H-pyran-3-yl)-4H-1,2,4-triazol-3-yl)-1-isopropoxy-1-(5-methylpyrimidin-2-yl)propane-2-sulfonamide or (1S,2S)-N-(4-(2,6-dimethoxyphenyl)-5-((S)-tetrahydro-2H-pyran-3-yl)-4H-1,2,4-triazol-3-yl)-1-isopropoxy-1-(5-methylpyrimidin-2-yl)propane-2-sulfonamide. $^1$H NMR (500 MHz, $CD_2Cl_2$) δ 12.41 (br. s., 1H), 8.62 (s, 2H), 7.49 (t, J = 8.4 Hz, 1H), 6.74 (dd, J = 8.7, 10.5 Hz, 2H), 4.79 (d, J = 4.2 Hz, 1H), 3.91-3.80 (m, 8H), 3.62-3.56 (m, 1H), 3.56-3.51 (m, 1H), 3.51-3.45 (m, 1H), 3.38 (dt, J = 2.5, 11.5 Hz, 1H), 2.48 (tt, J = 4.0, 10.9 Hz, 1H), 2.33 (s, 3H), 1.93-1.86 (m, 1H), 1.75 (dq, J = 4.2, 12.4 Hz, 1H), 1.65-1.58 (m, 1H), 1.56-1.46 (m, 1H), 1.34 (d, J = 7.0 Hz, 3H), 1.08 (d, J = 6.0 Hz, 3H), 0.96 (d, J = 6.2 Hz, 3H). LCMS (pos) m/z: 561.2 (M + H)$^+$. |
| 138.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), 5-isothiocyanato-4,6-dimethoxypyrimidine (Example 10.1). The mixture was purified by preparative SFC using the following methodology: Column: AD-H (2 × 25 cm) Mobile Phase: 70:30 (A:B) A: Liquid $CO_2$, B: IPA, Flow Rate: 80 mL/min, 218 nm, 100 bar inlet pressure to deliver peak 1. | 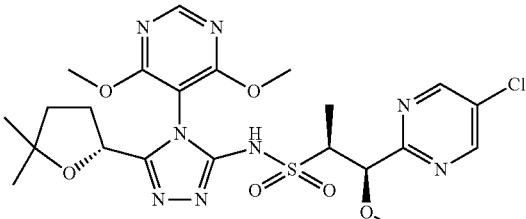<br><br>OR<br><br>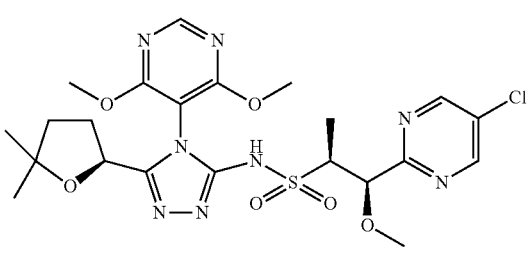<br><br>(1R,2S)-1-(5-chloropyrimidin-2-yl)-N-(4-(4,6-dimethoxypyrimidin-5-yl)-5-((S)-5,5-dimethyltetrahydrofuran-2-yl)-4H-1,2,4-triazol-3-yl)-1-methoxypropane-2-sulfonamide or (1R,2S)-1-(5-chloropyrimidin-2-yl)-N-(4-(4,6-dimethoxypyrimidin-5-yl)-5-((R)-5,5-dimethyltetrahydrofuran-2-yl)-4H-1,2,4-triazol-3-yl)-1-methoxypropane-2-sulfonamide. $^1$H NMR (500 MHz, $CD_2Cl_2$ δ 10.79 (br. s., 1H), 8.71 (s, 2H), 8.52 (s, 1H), 4.86 (d, J = 4.4 Hz, 1H), 4.73 (dd, J = 5.6, 7.7 Hz, 1H), 4.00 (s, 3H), 3.99 (s, 3H), 3.62-3.55 (m, 1H), |

TABLE 12-continued

| Example | Reagents | Structure, Name and Data |
|---|---|---|
| | | 3.25 (s, 3H), 2.43-2.35 (m, 1H), 2.28-2.19 (m, 1H), 1.78-1.65 (m, 2H), 1.25 (d, J = 7.0 Hz, 3H), 1.09 (s, 3H), 1.02 (s, 3H). LCMS (pos) m/z: 569.2 (M + H)+. |
| 139.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), 5-isothiocyanato-4,6-dimethoxypyrimidine (Example 10.1). The mixture was purified by preparative SFC using the following methodology: Column: AD-H (2 × 25 cm) Mobile Phase: 70:30 (A:B) A: Liquid CO$_2$, B: IPA, Flow Rate: 80 mL/min, 218 nm, 100 bar inlet pressure to deliver peak 2. | (1R,2S)-1-(5-chloropyrimidin-2-yl)-N-(4-(4,6-dimethoxypyrimidin-5-yl)-5-((S)-5,5-dimethyltetrahydrofuran-2-yl)-4H-1,2,4-triazol-3-yl)-1-methoxypropane-2-sulfonamide or (1R,2S)-1-(5-chloropyrimidin-2-yl)-N-(4-(4,6-dimethoxypyrimidin-5-yl)-5-((R)-5,5-dimethyltetrahydrofuran-2-yl)-4H-1,2,4-triazol-3-yl)-1-methoxypropane-2-sulfonamide. $^1$H NMR (500 MHz, CD$_2$Cl$_2$) δ 10.77 (br. s., 1H), 8.71 (s, 2H), 8.51 (s, 1H), 4.87 (d, J = 4.4 Hz, 1H), 4.73 (dd, J = 5.7, 7.8 Hz, 1H), 4.00 (s, 3H), 3.99 (s, 3H), 3.62-3.55 (m, 1H), 3.25 (s, 3H), 2.43-2.35 (m, 1H), 2.28-2.19 (m, 1H), 1.79-1.66 (m, 2H), 1.25 (d, J = 7.0 Hz, 3H), 1.10 (s, 3H), 1.04 (s, 3H). LCMS (pos) m/z: 569.2 (M + H)+. |

Example 140.0: Preparation of (1R,2S)—N-(4-(2,6-dimethoxyphenyl)-5-((R)-tetrahydrofuran-3-yl)-4H-1,2,4-triazol-3-yl)-1-hydroxy-1-(5-methylpyrimidin-2-yl)propane-2-sulfonamide or (1R,2S)—N-(4-(2,6-dimethoxyphenyl)-5-((S)-tetrahydrofuran-3-yl)-4H-1,2,4-triazol-3-yl)-1-hydroxy-1-(5-methylpyrimidin-2-yl)propane-2-sulfonamide 140.1

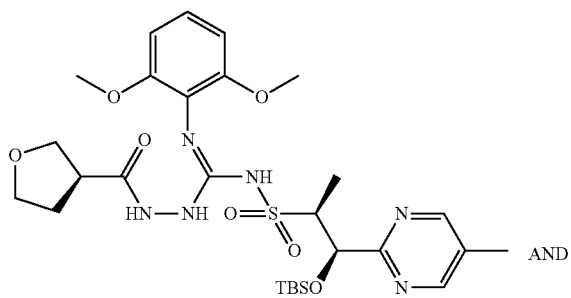

AND

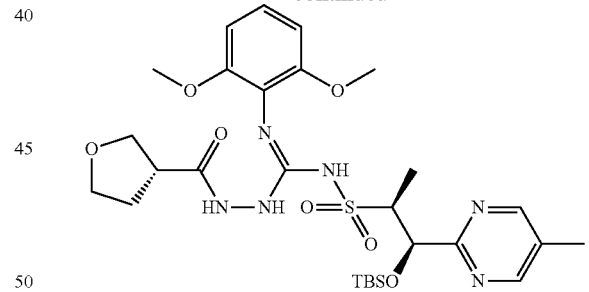

(Z)—N-(((1R,2S)-1-((tert-Butyldimethylsilyl)oxy)-1-(5-methylpyrimidin-2-yl)propan-2-yl)sulfonyl)-N'-(2,6-dimethoxyphenyl)-2-((S)-tetrahydrofuran-3-carbonyl)hydrazinecarboximidamide and (Z)—N-(1R,2S)-1-((tert-butyldimethylsilyl)oxy)-1-(5-methylpyrimidin-2-yl)propan-2-yl)sulfonyl)-N'-(2,6-dimethoxyphenyl)-2-((R)-tetrahydrofuran-3-carbonyl)hydrazinecarboximidamide, Example 140.1

To a vial containing (1R,2S)-1-((tert-butyldimethylsilyl)oxy)-1-(5-methylpyrimidin-2-yl)propane-2-sulfonamide Example 28.0 (348 mg, 1.0 mmol) was added ACN (4 mL). After 10 min, 2-isothiocyanato-1,3-dimethoxybenzene (Example 10.0, 210 mg, 1.1 mmol) was added carefully in portions. The mixture was cooled in an ice-bath and then cesium carbonate (430 mg, 1.3 mmol) was added carefully in portions to the homogeneous solution. Upon complete addition of cesium carbonate, the mixture was allowed to warm to 23° C. After 19 h, the mixture was cooled in an ice-water bath. After 20 min, (R)-tetrahydrofuran-3-carbohydrazide and (S)-tetrahydrofuran-3-carbohydrazide (commercially available from Astatech Inc., 132 mg, 1.0 mmol) and then silver nitrate (341 mg, 2.0 mmol) were carefully added in portions. The mixture was allowed to warm to 23° C. After 25 additional min, the mixture was loaded directly onto a Biotage SNAP Ultra column and purified (10-40% 3:1 EtOAc:EtOH in heptane). Fractions containing product were combined and then concentrated under reduced pressure to afford Example 140.1 (389 mg, 0.61 mmol, 61% yield) as a colorless film which was used without further purification. LCMS (pos) m/z: 637.2 (M+H)$^+$.

column (10-65% 3:1 EtOAc:EtOH in heptane.) Fractions containing product were combined and then concentrated under reduced pressure to afford Example 140.2 (247 mg, 0.40 mmol, 65% yield) as a light yellow residue which was used without further purification. LCMS (pos) m/z: 619.2 (M+H)$^+$.

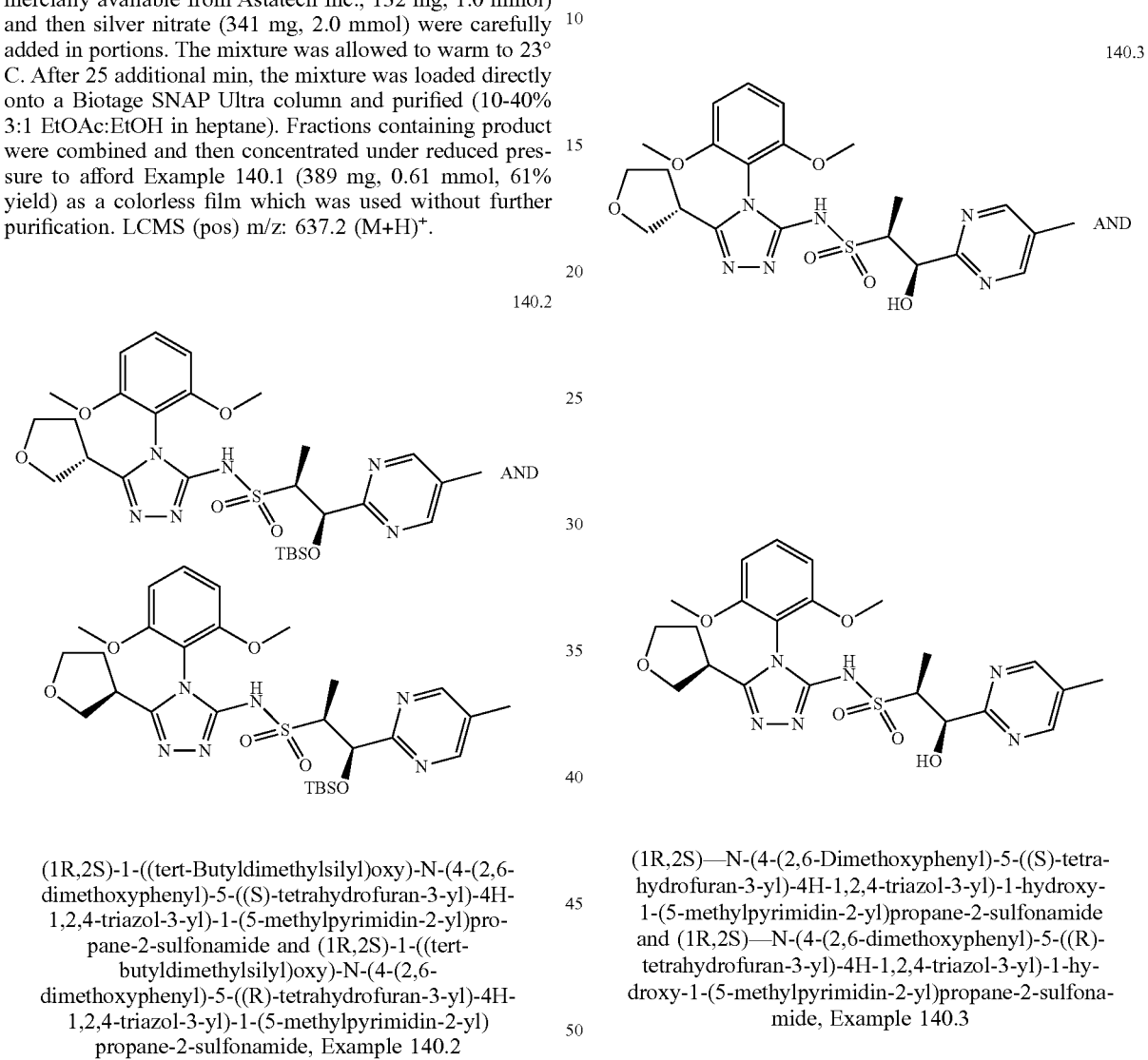

(1R,2S)-1-((tert-Butyldimethylsilyl)oxy)-N-(4-(2,6-dimethoxyphenyl)-5-((S)-tetrahydrofuran-3-yl)-4H-1,2,4-triazol-3-yl)-1-(5-methylpyrimidin-2-yl)propane-2-sulfonamide and (1R,2S)-1-((tert-butyldimethylsilyl)oxy)-N-(4-(2,6-dimethoxyphenyl)-5-((R)-tetrahydrofuran-3-yl)-4H-1,2,4-triazol-3-yl)-1-(5-methylpyrimidin-2-yl)propane-2-sulfonamide, Example 140.2

To a vial containing Example 140.1 (389 mg, 0.61 mmol) in IPA (1.6 mL) and water (0.8 mL) was added sodium hydroxide 1.0 N standard solution (0.8 mL, 0.8 mmol) carefully and dropwise. Upon complete addition of the 1 N NaOH, the mixture was heated on a preheated stir plate at 80° C. After 2 h, the reaction was cooled to RT and then it was diluted with water. The pH was carefully adjusted with dropwise addition of 1 N HCl to a pH-7. The reaction mixture was then extracted three times with DCM. The organic layers were pooled then dried over anhydrous magnesium sulfate. After filtration and concentration under reduced pressure, the residue was loaded onto a silica gel (1R,2S)—N-(4-(2,6-Dimethoxyphenyl)-5-((S)-tetrahydrofuran-3-yl)-4H-1,2,4-triazol-3-yl)-1-hydroxy-1-(5-methylpyrimidin-2-yl)propane-2-sulfonamide and (1R,2S)—N-(4-(2,6-dimethoxyphenyl)-5-((R)-tetrahydrofuran-3-yl)-4H-1,2,4-triazol-3-yl)-1-hydroxy-1-(5-methylpyrimidin-2-yl)propane-2-sulfonamide, Example 140.3

A vial containing Example 140.2 (247 mg, 0.40 mmol) in anhydrous THF (1 mL) was cooled in an ice bath to 0° C. After 20 min, TBAF (1.0 M solution in THF, 0.4 mL, 0.40 mmol)) was added carefully and dropwise. Upon complete addition of TBAF solution, the mixture was allowed to warm to 23° C. After 3 d, the mixture was carefully concentrated under reduced pressure. The residue was loaded onto a silica gel column (25-95% (3:1) EtOAc:EtOH in heptane). Fractions containing product were combined and then concentrated under reduced pressure to afford Example 140.3 as a colorless film which was submitted for chiral SFC purification. LCMS (pos) m/z: 505.2 (M+H)$^+$.

Following the procedure in Example 140.0, the following compounds were also synthesized using the intermediates and conditions as described.

TABLE 13

| Example | Reagents | Structure, Name and Data |
|---|---|---|
| 140.0 | (1R,2S)-N-(4-(2,6-dimethoxyphenyl)-5-((S)-tetrahydrofuran-3-yl)-4H-1,2,4-triazol-3-yl)-1-hydroxy-1-(5-methylpyrimidin-2-yl)propane-2-sulfonamide and (1R,2S)-N-(4-(2,6-dimethoxyphenyl)-5-((R)-tetrahydrofuran-3-yl)-4H-1,2,4-triazol-3-yl)-1-hydroxy-1-(5-methylpyrimidin-2-yl)propane-2-sulfonamide (Example 140.3). The mixture was purified by preparative SFC using the following methodology: Column: AS-H (2 × 25 cm) Mobile Phase: 75:25 (A:B) A: Liquid CO$_2$, B: MeOH, Flow Rate: 80 mL/min, 230 nm, 100 bar inlet pressure to deliver peak 1. | 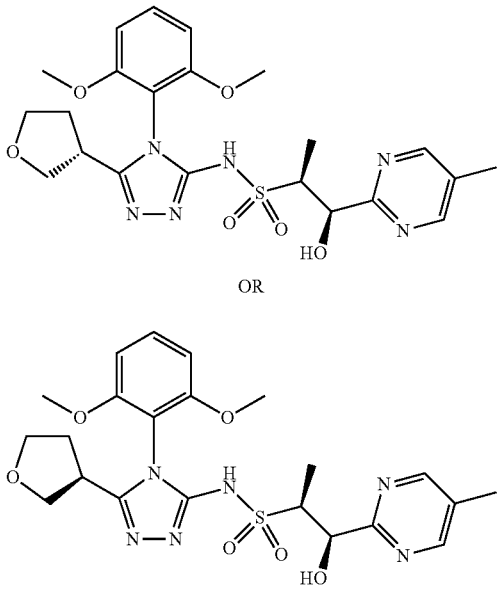<br>OR<br><br>(1R,2S)-N-(4-(2,6-dimethoxyphenyl)-5-((S)-tetrahydrofuran-3-yl)-4H-1,2,4-triazol-3-yl)-1-hydroxy-1-(5-methylpyrimidin-2-yl)propane-2-sulfonamide or (1R,2S)-N-(4-(2,6-dimethoxyphenyl)-5-((R)-tetrahydrofuran-3-yl)-4H-1,2,4-triazol-3-yl)-1-hydroxy-1-(5-methylpyrimidin-2-yl)propane-2-sulfonamide. $^1$H NMR (500 MHz, CD$_2$Cl$_2$) δ 8.56 (s, 2H), 7.49 (t, J = 8.4 Hz, 1H), 6.72 (d, J = 8.6 Hz, 2H), 5.38 (s, 1H), 3.89-3.83 (m, 1H), 3.82 (s, 3H), 3.78 (s, 3H), 3.77-3.70 (m, 3H), 3.68-3.63 (m, 1H), 3.05-2.98 (m, 1H), 2.33-2.28 (m, 3H), 2.25 (dd, J = 7.7, 12.6 Hz, 1H), 2.08-1.99 (m, 1H), 1.05 (d, J = 7.0 Hz, 3H). LCMS (pos) m/z: 505.2 (M + H)$^+$. |
| 141.0 | (1R,2S)-N-(4-(2,6-dimethoxyphenyl)-5-((S)-tetrahydrofuran-3-yl)-4H-1,2,4-triazol-3-yl)-1-hydroxy-1-(5-methylpyrimidin-2-yl)propane-2-sulfonamide and (1R,2S)-N-(4-(2,6-dimethoxyphenyl)-5-((R)-tetrahydrofuran-3-yl)-4H-1,2,4-triazol-3-yl)-1-hydroxy-1-(5-methylpyrimidin-2-yl)propane-2-sulfonamide (Example 140.3). The mixture was purified by preparative SFC using the following methodology: Column: AS-H (2 × 25 cm) Mobile Phase: 75:25 (A:B) A: Liquid CO$_2$, B: MeOH, Flow Rate: 80 mL/min, 230 nm, 100 bar inlet pressure to deliver peak 2. | 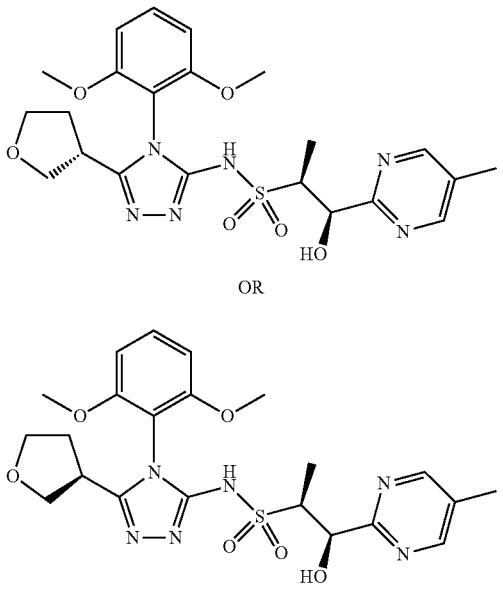<br>OR<br><br>(1R,2S)-N-(4-(2,6-dimethoxyphenyl)-5-((S)-tetrahydrofuran-3-yl)-4H-1,2,4-triazol-3-yl)-1-hydroxy-1-(5-methylpyrimidin-2-yl)propane-2-sulfonamide or (1R,2S)-N-(4-(2,6-dimethoxyphenyl)-5-((R)-tetrahydrofuran-3-yl)-4H-1,2,4-triazol-3-yl)-1-hydroxy-1-(5-methylpyrimidin-2-yl)propane-2-sulfonamide. $^1$NMR (500 MHz, |

TABLE 13-continued

| Example | Reagents | Structure, Name and Data |
|---------|----------|--------------------------|
| | | CD$_2$Cl$_2$) δ 10.82 (br. s., 1H), 8.57 (s, 2H), 7.49 (t, J = 8.6 Hz, 1H), 6.73 (t, J = 7.5 Hz, 2H), 5.38 (s, 1H), 3.89-3.83 (m, 1H), 3.83-3.78 (m, 7H), 3.78-3.63 (m, 3H), 3.06-2.97 (m, 1H), 2.31 (s, 3H), 2.23-2.15 (m, 1H), 2.04-1.95 (m, 1H), 1.05 (d, J = 6.7 Hz, 3H). LCMS (pos) m/z: 505.2 (M + H)$^+$. |

Example 142.0: Preparation of (2S,3R)-3-(5-chloropyrimidin-2-yl)-N-(4-(2,6-dimethoxyphenyl)-5-((S)-oxetan-2-yl)-4H-1,2,4-triazol-3-yl)butane-2-sulfonamide and (2S,3R)-3-(5-chloropyrimidin-2-yl)-N-(4-(2,6-dimethoxyphenyl)-5-((R)-oxetan-2-yl)-4H-1,2,4-triazol-3-yl)butane-2-sulfonamide

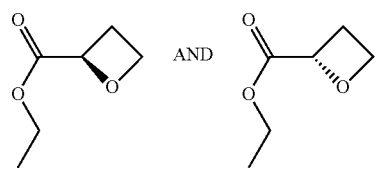

(S)-Ethyl oxetane-2-carboxylate and (R)-Ethyl oxetane-2-carboxylate, Example 142.1

To a vial containing (R)-oxetane-2-carboxylic acid and (S)-oxetane-2-carboxylic acid (commercially available from Advanced ChemBlocks Inc.) (320 mg, 3.14 mmol) was added DMF (6.2 mL). After 10 min, potassium carbonate (657 mg, 4.75 mmol) was added carefully in portions. The mixture was cooled in an ice-bath and then iodoethane (0.26 mL, 3.2 mmol) was added dropwise to the heterogeneous solution. Upon complete addition of iodoethane, the mixture was allowed to warm to 23° C. After 20 h, the reaction was diluted with water and then extracted three times with a 1:1 mixture of toluene and EtOAc. The organic layers were pooled and then dried over anhydrous sodium sulfate. After filtration and concentration under reduced pressure, the colorless residue was tentatively assigned as Example 142.1 (127 mg, 0.97 mmol, 31.1% yield) that was used without further purification. $^1$H NMR (400 MHz, CD$_2$Cl$_2$) δ 5.08 (dd, J=6.7, 9.0 Hz, 1H), 4.68-4.61 (m, 2H), 4.24-4.18 (m, 2H), 3.00-2.94 (m, 1H), 2.74-2.65 (m, 1H), 1.30-1.26 (m, 3H).

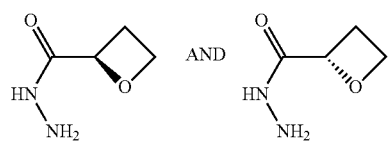

(R)-Oxetane-2-carbohydrazide and (S)-oxetane-2-carbohydrazide, Example 142.2

To a vial containing (S)-ethyl oxetane-2-carboxylate and (R)-ethyl oxetane-2-carboxylate Example 142.1 (127 mg, 0.97 mmol) was added EtOH (3.8 mL). The solution was cooled in an ice water bath. After 20 min, hydrazine, monohydrate (0.1 mL, 2.1 mmol) was added carefully and dropwise to the homogeneous solution. Upon complete addition of hydrazine monohydrate, the mixture was allowed to warm to RT. After 17 h, EtOAc was added to the mixture and the resulting mixture was then stirred for 30 min at 23° C. The mixture was concentrated under reduced pressure to afford Example 142 as a colorless film which was used without further purification. LCMS (pos) m/z: 117.4 (M+H)$^+$.

Following the procedure in Example 140.0, the following compounds were also synthesized using the intermediates and conditions as described.

TABLE 14

| Example | Reagents | Structure, Name and Data |
|---------|----------|--------------------------|
| 142.0 | (2S,3R)-3-(5-chloropyrimidin-2-yl)butane-2-sulfonamide (Example 1.4), (R)-oxetane-2-carbohydrazide and (S)-oxetane-2-carbohydrazide (Example 142.2), 2-isothiocyanato-1,3-dimethoxybenzene (Example 10.0). | AND |

TABLE 14-continued

| Example | Reagents | Structure, Name and Data |
|---|---|---|
| | | 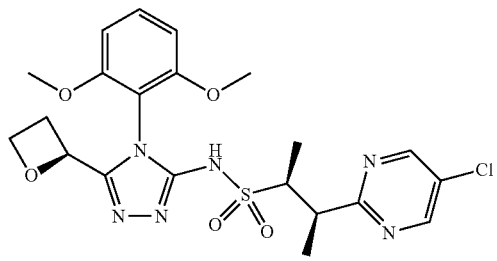 [SMILES: COc1cccc(OC)c1-n1c(NS(=O)(=O)[C@@H](C)[C@H](C)c2ncc(Cl)cn2)nnc1[C@@H]1CCO1]<br>(2S,3R)-3-(5-chloropyrimidin-2-yl)-N-(4-(2,6-dimethoxyphenyl)-5-((R)-oxetan-2-yl)-4H-1,2,4-triazol-3-yl)butane-2-sulfonamide and (2S,3R)-3-(5-chloropyrimidin-2-yl)-N-(4-(2,6-dimethoxyphenyl)-5-((S)-oxetan-2-yl)-4H-1,2,4-triazol-3-yl)butane-2-sulfonamide. $^1$H NMR (400 MHz, DMSO-d$_6$) δ 13.07 (s, 1H), 8.88-8.84 (m, 2H), 7.52-7.46 (m, 1H), 6.86-6.81 (m, 2H), 5.27 (dd, J = 6.9, 8.2 Hz, 1H), 4.45 (dt, J = 5.7, 7.8 Hz, 1H), 4.17-4.11 (m, 1H), 3.72 (s, 3H), 3.72 (s, 3H), 3.67-3.63 (m, 1H), 3.59-3.54 (m, 1H), 2.87-2.77 (m, 2H), 1.24 (d, J = 7.3 Hz, 3H), 1.11 (d, J = 6.8 Hz, 3H). LCMS (pos) m/z: 509.0 (M + H)$^+$. |

Example 143.0. Preparation of (S)-2-(4-chlorophenyl)-N-(4-(2,6-dimethoxyphenyl)-5-(tetrahydrofuran-2-yl)-4H-1,2,4-triazol-3-yl)ethanesulfonamide and (R)-2-(4-chlorophenyl)-N-(4-(2,6-dimethoxyphenyl)-5-(tetrahydrofuran-2-yl)-4H-1,2,4-triazol-3-yl)ethanesulfonamide 143.1

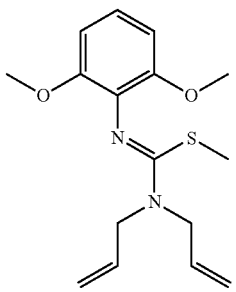

Methyl N,N-diallyl-N'-(2,6-dimethoxyphenyl)carbamimidothioate, Example 143.1

Sodium hydride (60% dispersion in mineral oil, 0.8 g, 20 mmol)) was added in one portion to a solution of diallylamine (2.5 mL, 20 mmol) in THF (20 mL) at RT under nitrogen. After 5 min, a solution of 2-isothiocyanato-1,3-dimethoxybenzene, Example 10.0 (3.9 g, 20 mmol) in DMF (20 mL) was injected dropwise into the reaction mixture. The reaction was then stirred at RT for 1 h. To the resulting mixture was injected dropwise methyl 4-methylbenzenesulfonate (3.7 g, 20 mmol), and the resulting mixture was stirred for 2 h. The reaction mixture was quenched with a saturated NH$_4$Cl solution and extracted with EtOAc. The organic layer was washed with brine, dried over Na$_2$SO$_4$, filtered and concentrated in vacuo. The material thus obtained was loaded on 220 g silica gel column, eluted with DCM to provide the title compound (4.6 g, 16 mmol, 79% yield) as a colorless oil. LCMS-ESI (pos) m/z: 307.0 (M+H)$^+$.

143.2

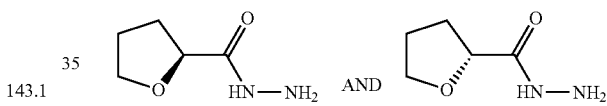

(S)-Tetrahydrofuran-2-carbohydrazide and (R)-tetrahydrofuran-2-carbohydrazide, Example 143.2

To a solution of (S)-methyl tetrahydrofuran-2-carboxylate and (R)-methyl tetrahydrofuran-2-carboxylate (20 mL, 166 mmol) in MeOH (237 mL) at 23° C., was added hydrazine (10.4 mL, 332 mmol). The mixture was heated to 80° C. for 3 d. The mixture was concentrated under reduced pressure and placed under high vacuum overnight. The cake was washed with Et$_2$O and then with hexanes. The solid was placed on high vacuum for 16 h to provide the title compound (16 g, 123 mmol, 74% yield). $^1$H NMR (400 MHz, DMSO-d$_6$) δ 8.96 (br. s., 1H), 4.25 (br. s., 2H), 4.15-4.22 (m, 1H), 3.81-3.91 (m, 1H), 3.67-3.75 (m, 1H), 2.01-2.11 (m, 1H), 1.75-1.88 (m, 3H).

143.3

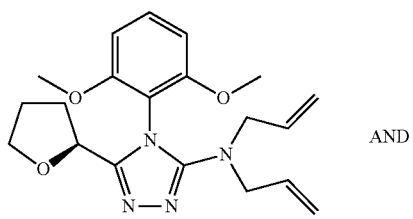

AND

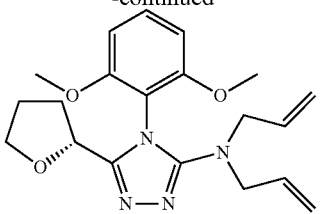

(S)—N,N-Diallyl-4-(2,6-dimethoxyphenyl)-5-(tetrahydrofuran-2-yl)-4H-1,2,4-triazol-3-amine and (R)—N,N-diallyl-4-(2,6-dimethoxyphenyl)-5-(tetrahydrofuran-2-yl)-4H-1,2,4-triazol-3-amine, Example 143.3

TFA (1.1 mL, 15.2 mmol) was added dropwise to a mixture of Example 143.1 (4.7 g, 15.2 mmol) and Example 143.2 (3.0 g, 22.8 mmol) in dioxane (100 mL). The mixture was then heated at 90° C. using an oil bath for 26 h. To the reaction mixture was injected more Example 143.2 (1.1 g, 8.1 mmol) in dioxane (3 mL) and then heating continued at 90° C. for an additional 16 h. The reaction was cooled to RT, and the solvent was removed in vacuo. The residue was loaded on a 120 g silica gel column, eluted with gradient 0%-50% (MeOH:DCM:Concentrated NH$_4$OH solution=9:90:1) in DCM to provide enriched title compound (1.8 g, 4.9 mmol, 33% yield), which was used directly in the next step without further purification. LCMS-ESI (pos) m/z: 371.1 (M+H)$^+$.

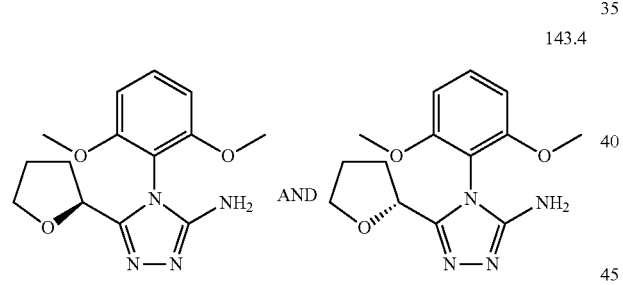

(S)-4-(2,6-Dimethoxyphenyl)-5-(tetrahydrofuran-2-yl)-4H-1,2,4-triazol-3-amine and (R)-4-(2,6-dimethoxyphenyl)-5-(tetrahydrofuran-2-yl)-4H-1,2,4-triazol-3-amine, Example 143.4

A solution of Example 143.3 (558 mg, 1.5 mmol) and 1,3-dimethylpyrimidine-2,4,6(1H,3H,5H)-trione (941 mg, 6.0 mmol) in dioxane (10 mL) in a 2-dram vial was purged with nitrogen gas for 1 min. Tetrakis(triphenylphosphine)palladium(0) (696 mg, 0.60 mmol) was added in one portion and the flask was purged again with nitrogen for another min. The reaction mixture was then heated at 85° C. for 30 h and then cooled down to RT. The reaction mixture was loaded on a 24 g silica gel column, eluted with 0%-100% EtOAc in DCM and then 0%-100% (MeOH:DCM:NH$_4$OH=9:90:1) in DCM to provide enriched title compound (92 mg, 0.32 mmol, 21% yield), which was used directly in the next step without further purification. LCMS-ESI (pos) m/z: 291.0 (M+H)$^+$.

143.0

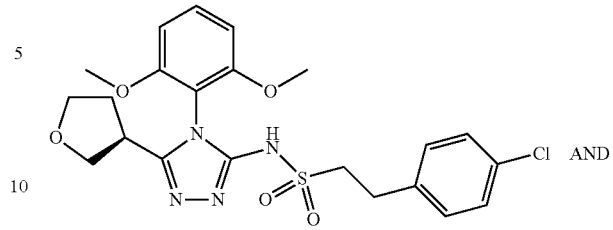

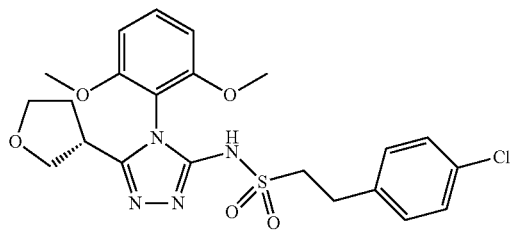

(S)-2-(4-Chlorophenyl)-N-(4-(2,6-dimethoxyphenyl)-5-(tetrahydrofuran-2-yl)-4H-1,2,4-triazol-3-yl)ethanesulfonamide and (R)-2-(4-chlorophenyl)-N-(4-(2,6-dimethoxyphenyl)-5-(tetrahydrofuran-2-yl)-4H-1,2,4-triazol-3-yl)ethanesulfonamide, Example 143.0

2-(4-Chlorophenyl)ethanesulfonyl chloride (Synchem Inc., 88 mg, 0.368 mmol) was added to a mixture of (±)-4-(2,6-dimethoxyphenyl)-5-(tetrahydrofuran-2-yl)-4H-1,2,4-triazol-3-amine, Example 143.4 (89 mg, 0.307 mmol) and TEA (0.128 mL, 0.920 mmol) in DCM (2 mL) in one portion. The reaction mixture was stirred at RT for 20 h. The mixture was then diluted with 10 mL DCM and washed with 10 mL saturated NH$_4$Cl(aq), dried over Na$_2$SO$_4$, filtered and concentrated under reduced pressure. The residue was purified on a 24 g prepacked silica gel column using a combiflash eluting with a solvent gradient 0-100% EtOAc:DCM to provide Example 143.0, 2-(4-chlorophenyl)-N-(4-(2,6-dimethoxyphenyl)-5-(tetrahydrofuran-2-yl)-4H-1,2,4-triazol-3-yl)ethanesulfonamide (26 mg, 0.053 mmol, 17% yield) as a white powder. $^1$H NMR (400 MHz, DMSO-d$_6$) δ 13.01 (s, 1H) 7.48 (t, J=8.51 Hz, 1H) 7.30-7.35 (m, 2H) 7.21 (m, J=8.41 Hz, 2H) 6.84 (d, J=8.61 Hz, 2H) 4.51 (dd, J=7.73, 5.58 Hz, 1H) 3.76 (s, 3H) 3.75 (s, 3H) 3.61-3.67 (m, 1H) 3.48-3.56 (m, 1H) 3.09-3.17 (m, 2H) 2.82-2.90 (m, 2H) 2.05-2.14 (m, 1H) 1.94-2.04 (m, 1H) 1.75-1.84 (m, 2H). LCMS-ESI (pos) m/z: 493.1 (M+H)$^+$.

Example 144.0. Preparation of (S)-2-(4-chlorophenyl)-N-(4-(2,6-dimethoxyphenyl)-5-(tetrahydrofuran-2-yl)-4H-1,2,4-triazol-3-yl)ethanesulfonamide or (R)-2-(4-chlorophenyl)-N-(4-(2,6-dimethoxyphenyl)-5-(tetrahydrofuran-2-yl)-4H-1,2,4-triazol-3-yl) ethanesulfonamide

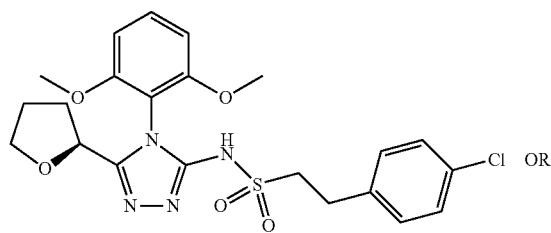

144.0

Example 145.0. Preparation of (S)-2-(4-chlorophenyl)-N-(4-(2,6-dimethoxyphenyl)-5-(tetrahydrofuran-2-yl)-4H-1,2,4-triazol-3-yl)ethanesulfonamide or (R)-2-(4-chlorophenyl)-N-(4-(2,6-dimethoxyphenyl)-5-(tetrahydrofuran-2-yl)-4H-1,2,4-triazol-3-yl) ethanesulfonamide

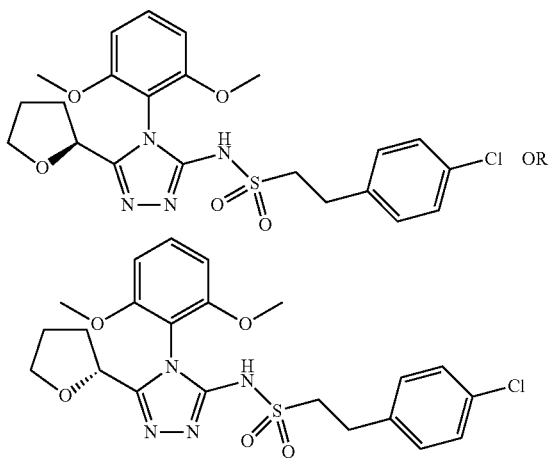

145.0

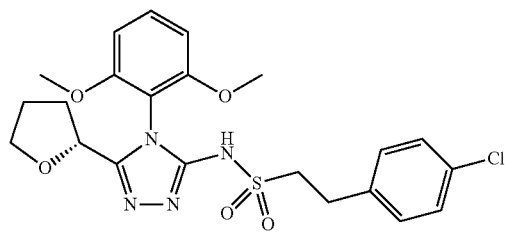

(S)-2-(4-Chlorophenyl)-N-(4-(2,6-dimethoxyphenyl)-5-(tetrahydrofuran-2-yl)-4H-1,2,4-triazol-3-yl) ethanesulfonamide or (R)-2-(4-chlorophenyl)-N-(4-(2,6-dimethoxyphenyl)-5-(tetrahydrofuran-2-yl)-4H-1,2,4-triazol-3-yl)ethanesulfonamide, Example 144.0

The title compound was the first isomer to elute under the following SFC conditions from the mixture of Example 143.0: 250×30 mm OJ column with 32 g/min MeOH (+20 mM NH$_3$)+48 g/min CO$_2$ on Thar 80 SFC. Outlet pressure=100 bar; Temp.=25° C.; Wavelength=220 nm. Used 0.8 mL per injection of 5.0 mg/mL solution of Example 143.0 in MeOH. $^1$H NMR (400 MHz, DMSO-d$_6$) δ 13.00 (br. s, 1H), 7.48 (t, J=8.5 Hz, 1H), 7.31-7.35 (m, 2H), 7.19-7.23 (m, J=8.4 Hz, 2H), 6.84 (d, J=8.6 Hz, 2H), 4.50 (dd, J=7.6, 5.5 Hz, 1H), 3.75 (s, 3H), 3.74 (s, 3H), 3.60-3.67 (m, 1H), 3.50 (q, J=7.0 Hz, 1H), 3.17-3.11 (m, 2H), 2.82-2.89 (m, 2H), 2.05-2.15 (m, 1H), 1.93-2.04 (m, 1H), 1.74-1.83 (m, 2H). LCMS-ESI (pos) m/z: 493.1 (M+H)$^+$.

(S)-2-(4-Chlorophenyl)-N-(4-(2,6-dimethoxyphenyl)-5-(tetrahydrofuran-2-yl)-4H-1,2,4-triazol-3-yl) ethanesulfonamide or (R)-2-(4-chlorophenyl)-N-(4-(2,6-dimethoxyphenyl)-5-(tetrahydrofuran-2-yl)-4H-1,2,4-triazol-3-yl)ethanesulfonamide, Example 145.0

Example 145.0 is the enantiomer of Example 144.0. Example 145.0 was the second isomer to elute on subjecting Example 143.0 to the SFC conditions described in Example 144.0. $^1$H NMR (400 MHz, DMSO-d$_6$) δ 13.00 (br s, 1H), 7.48 (t, J=8.5 Hz, 1H), 7.30-7.35 (m, 2H), 7.19-7.23 (m, J=8.4 Hz, 2H), 6.84 (d, J=8.4 Hz, 2H), 4.50 (dd, J=7.6, 5.7 Hz, 1H), 3.75 (s, 3H), 3.74 (s, 3H), 3.60-3.70 (m, 1H), 3.50 (q, J=7.2 Hz, 1H), 3.10-3.18 (m, 2H), 2.82-2.89 (m, 2H), 2.05-2.15 (m, 1H), 1.94-2.03 (m, 1H), 1.74-1.84 (m, 2H). LCMS-ESI (pos) m/z: 493.1 (M+H)$^+$.

Example 146.0. Preparation of (S)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide and (R)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide

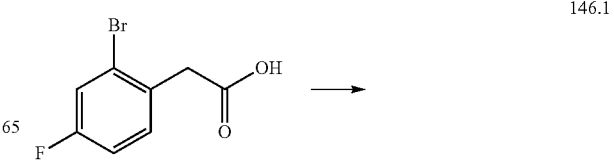

146.1

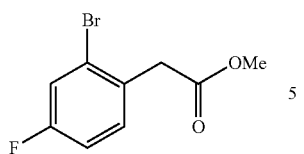

Methyl 2-(2-bromo-4-fluorophenyl) acetate, Example 146.1

To a solution of 2-bromo-4-fluorophenyl acetic acid (commercially available from Combi-Blocks Inc., San Diego, Calif., USA. 25.0 g, 0.11 mols) in MeOH (100 mL) was added thionyl chloride (23.5 mL, 0.32 mol) dropwise at 0° C. The resulting mixture was then heated to 80° C. for 16 h. The mixture was cooled to RT and the volatiles were removed under vacuum. The material thus obtained was diluted with DCM and washed with an aqueous solution of sodium bicarbonate and water. The organic layer was then dried over sodium sulfate, filtered and evaporated to afford Example 146.1 (26 g, 100%), which was used as such in the next step. $^1$H NMR (400 MHz, DMSO-d6) δ 0.59 (dd, J=8.6, 2.6 Hz, 1H), 7.47 (dd, J=8.5, 6.2 Hz, 1H), 7.25 (td, J=8.5, 2.7 Hz, 1H), 3.82 (s, 2H), 3.63 (s, 3H).

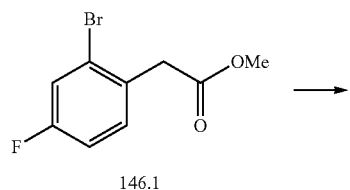

Methyl 2-(2-cyano-4-fluorophenyl) acetate, Example 146.2

To a solution of Example 146.1 (8.0 g, 0.032 mols) in DMA (60 mL) was added zinc cyanide (5.7 g, 0.049 mol). The flask was then degassed with argon and bis-(tri-tert-butylphosphine)palladium(0) (1.7 g, 0.003 mol) was added. The resulting mixture was then heated at 110° C. for 18 h in a sealed tube. Thereafter, the reaction mixture was cooled to RT, diluted with water and extracted with EtOAc. The combined organic layers were dried over sodium sulphate and evaporated in vacuo. The product thus obtained was purified by column chromatography using silica gel and 20-25% EtOAc and hexanes as eluent to obtain Example 146.2 (5.4 g, 86%) as light brown liquid. $^1$H NMR (400 MHz, DMSO-d6) δ 0.91-7.81 (m, 1H), 7.68-7.51 (m, 2H), 3.95 (s, 2H), 3.65 (s, 3H). LCMS-ESI (neg.) m/z: 192.2 (M−H)$^-$.

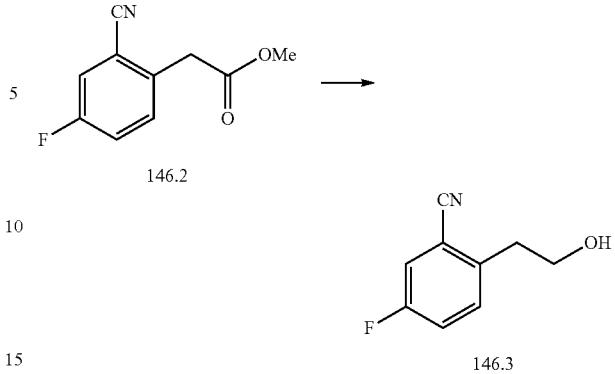

5-Fluoro-2-(2-hydroxyethyl)benzonitrile, Example 146.3

To a solution of Example 146.2 (5.3 g, 0.027 mol) in THF (60 mL) at 0° C. was added LiBH$_4$ (1.2 g, 0.055 mol) portion-wise. The resulting mixture was stirred at RT for 5 h. After completion of the reaction (monitored by TLC), the reaction mixture was cooled to 0° C. and quenched with water. The solvent was evaporated to obtain the material which was further diluted with water and extracted with EtOAc. The combined organic layers were dried over Na$_2$SO$_4$, filtered and evaporated in vacuo to obtain the material, which was purified by column chromatography using silica gel and 15-20% EtOAc in hexanes as eluent to obtain Example 146.3 (3.1 g, 67%) as light brown liquid. $^1$H NMR (400 MHz, DMSO-d6) δ 7.81-7.73 (m, 1H), 7.52 (dd, J=10.6, 8.0 Hz, 2H), 4.82 (t, J=5.2 Hz, 1H), 3.64 (dd, J=11.9, 6.5 Hz, 2H), 2.91 (t, J=6.6 Hz, 2H).

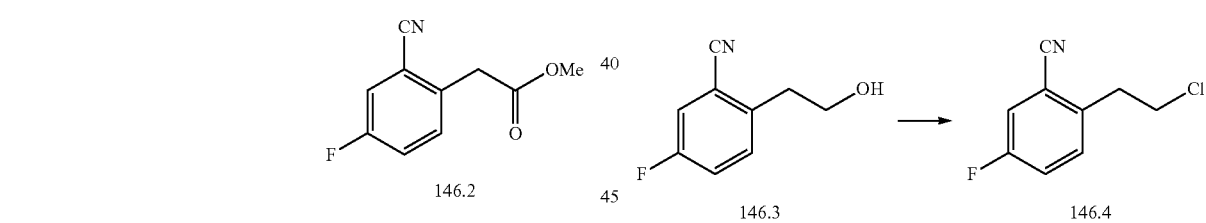

2-(2-Chloroethyl)-5-fluorobenzonitrile Example 146.4

To a solution of Example 146.3 (3.0 g, 0.018 mol) in DCM (50 mL) was added thionyl chloride (6.6 mL, 0.091 mol) dropwise followed by DMF (4 drops) at 0° C. The resulting mixture was heated at 55° C. for 7 h. After completion of the reaction (monitored by TLC), the reaction mixture was concentrated in vacuo to obtain the material, which was diluted with water and extracted with EtOAc. The combined organic layers were dried over Na$_2$SO$_4$, filtered and evaporated in vacuo to obtain the compound Example 146.4 (3.0 g, 90%) as a brown liquid which was used in the next step without further purification. $^1$H NMR (400 MHz, DMSO-d6) δ 7.81-7.84 (dd, J=2.4 Hz, 8.8 Hz, 1H), 7.56-7.66 (m, 2H), 3.90-3.94 (t, J=6.8 Hz, 13.6 Hz, 2H), 3.22-3.25 (t, J=6.8 Hz, 13.2 Hz, 2H). LCMS-ESI (neg.) m/z: 182.0 (M−H)$^-$.

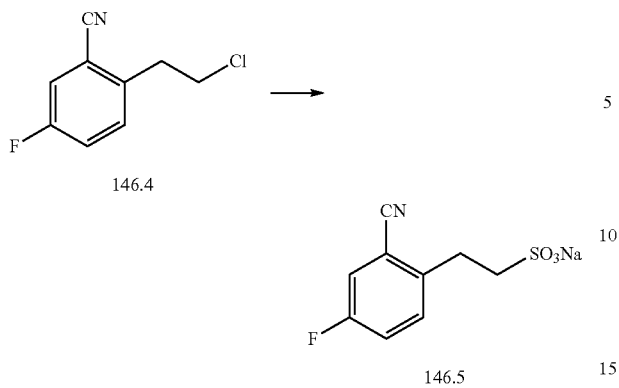
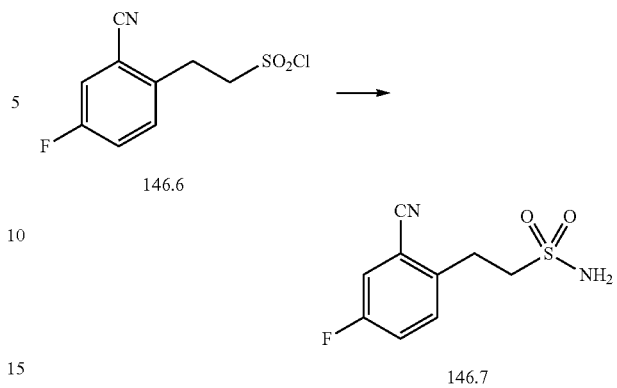

Sodium 2-(2-cyano-4-fluorophenyl)ethanesulfonate, Example 146.5

To a solution of Example 146.4 (3.0 g, 0.016 mol) in H$_2$O (50 mL) at RT was added sodium sulfite (3.1 g, 0.024 mol). The reaction mixture was heated to reflux for 18 h. After completion of the reaction (monitored by TLC), the reaction mixture was concentrated in vacuo to obtain the material, which was further stirred with EtOAc and filtered to obtain Example 146.5 (5.8 g) as an off-white solid, which was used in the next reaction without further purification. $^1$H NMR (400 MHz, DMSO-d6) δ 7.74-7.76 (dd, J=2 Hz, 8.4 Hz, 1H), 7.47-7.55 (m, 2H), 3.05-3.09 (t, J=8 Hz, 16.4 Hz, 2H), 2.69-2.74 (t, J=8.4 Hz, 16.4 Hz, 2H). LCMS-ESI (neg.) m/z: 228.0 (M−H)$^−$.

2-(2-Cyano-4-fluorophenyl)ethanesulfonamide, Example 146.7

To a mixture of aqueous ammonia (10 mL, 77 mmol) and DCM (30 mL, 468 mmol) was added Example 146.6 (1.42 g, 5.73 mmol) in portions at RT. The reaction mixture was stirred at 23° C. for 2 h. LCMS analysis indicated the reaction was complete. The mixture was neutralized by adding concentrated HCl solution, and then extracted with DCM. The extract was washed with water and saturated sodium bicarbonate solution twice, dried Na$_2$SO$_4$ and concentrated. The residue was dried to give the title compound Example 146.7 (1.1 g, 4.82 mmol, 84% yield) as a white solid. LCMS-ESI (pos), m/z: 229.1 (M+H)$^+$.

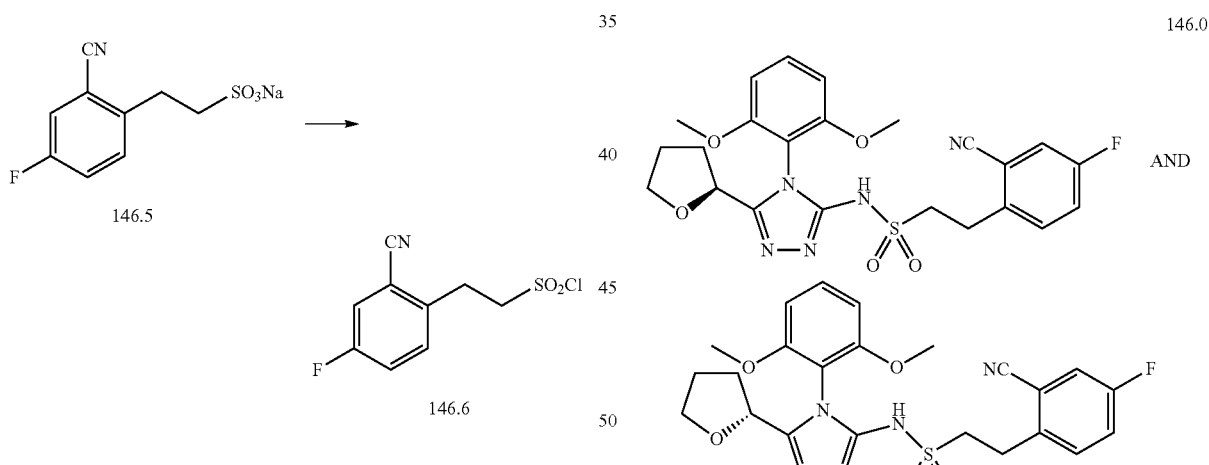

2-(2-Cyano-4-fluorophenyl)ethanesulfonyl chloride, Example 146.6

To a solution of Example 146.5 (5.8 g) in benzene (50 mL) was added thionyl chloride (2.5 mL, 0.035 mol) dropwise followed by DMF (3 drops) at 0° C. The resulting mixture was heated to reflux for 16 h. After completion of the reaction (monitored by TLC), the mixture was cooled to 25° C., poured into ice water and extracted with EtOAc. The EtOAc layer was dried over Na$_2$SO$_4$, filtered and evaporated in vacuo to obtain Example 146.6 (3.4 g, 84% over two steps) as a brown solid. $^1$H NMR (400 MHz, CDCl$_3$) δ 7.47-7.38 (m, 2H), 7.33 (td, J=8.2, 2.7 Hz, 1H), 3.98 (dd, J=8.7, 6.7 Hz, 2H), 3.56-3.53 (m, 2H). LCMS-ESI (neg.) m/z: 245.9 (M−H)$^−$.

(S)-2-(2-Cyano-4-fluorophenyl)-N-(4-(2,6-dimethoxyphenyl)-5-(tetrahydrofuran-2-yl)-4H-1,2,4-triazol-3-yl)ethanesulfonamide and (R)-2-(2-cyano-4-fluorophenyl)-N-(4-(2,6-dimethoxyphenyl)-5-(tetrahydrofuran-2-yl)-4H-1,2,4-triazol-3-yl) ethanesulfonamide, Example 146.0

The title compound was prepared from Example 143.4 (110 mg, 0.379 mmol) and Example 146.7 (141 mg, 0.568 mmol), using the procedure described in Example 143.0 providing the title compound Example 146.0 (66 mg, 0.13 mmol, 35% yield) as a white solid. $^1$H NMR (400 MHz, DMSO-d$_6$) δ 13.06 (s, 1H) 7.79 (dd, J=8.71, 2.64 Hz, 1H) 7.44-7.55 (m, 3H) 6.83 (d, J=8.41 Hz, 2H) 4.51 (dd, J=7.73, 5.38 Hz, 1H) 3.75 (d, J=2.35 Hz, 6H) 3.60-3.67 (m, 1H) 3.46-3.57 (m, 1H) 3.15-3.25 (m, 2H) 3.02-3.15 (m, 2H) 2.05-2.14 (m, 1H) 1.93-2.03 (m, 1H) 1.74-1.84 (m, 2H). LCMS-ESI (pos) m/z: 502.1 (M+H)$^+$.

Example 147.0. Preparation of (S)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide or (R)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide

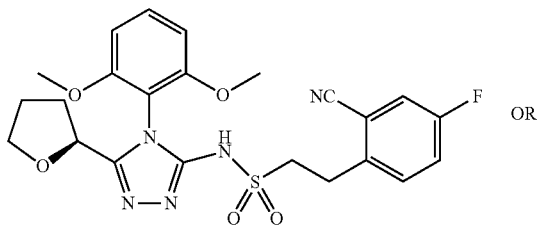

147.0

OR

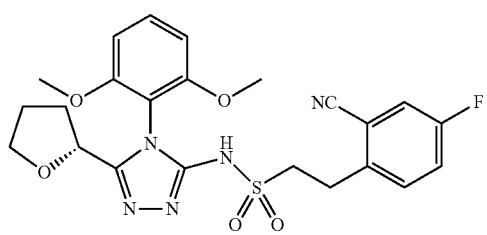

(S)-2-(2-Cyano-4-fluorophenyl)-N-(4-(2,6-dimethoxyphenyl)-5-(tetrahydrofuran-2-yl)-4H-1,2,4-triazol-3-yl)ethanesulfonamide or (R)-2-(2-cyano-4-fluorophenyl)-N-(4-(2,6-dimethoxyphenyl)-5-(tetrahydrofuran-2-yl)-4H-1,2,4-triazol-3-yl) ethanesulfonamide, Example 147.0

The title compound was the first isomer to elute under the following SFC conditions from the mixture of Example 146.0: OJ-H (2×15 cm) 20% EtOH/CO$_2$, 100 bar 70 mL/min, 220 nm. Injection vol.: 1 mL, 3.6 mg/mL of Example 146.0 in EtOH. $^1$H NMR (400 MHz, CD$_2$Cl$_2$) δ 1.84-2.10 (m, 3H) 2.22-2.37 (m, 1H) 3.24-3.34 (m, 4H) 3.66-3.83 (m, 2H) 3.85 (s, 3H) 3.86 (s, 3H) 4.65 (dd, J=7.53, 5.18 Hz, 1H) 6.72-6.80 (m, 2H) 7.25-7.33 (m, 1H) 7.35-7.42 (m, 2H) 7.52 (t, J=8.51 Hz, 1H) 10.72 (br. s., 1H). LCMS-ESI (pos), m/z: 502.1 (M+H)$^+$.

Example 148.0. Preparation of (S)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide or (R)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide 148.0

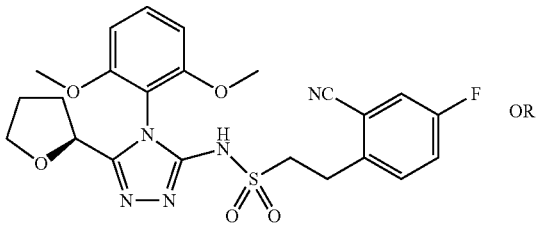

OR (S)-2-(2-Cyano-4-fluorophenyl)-N-(4-(2,6-dimethoxyphenyl)-5-(tetrahydrofuran-2-yl)-4H-1,2,4-triazol-3-yl)ethanesulfonamide or (R)-2-(2-cyano-4-fluorophenyl)-N-(4-(2,6-dimethoxyphenyl)-5-(tetrahydrofuran-2-yl)-4H-1,2,4-triazol-3-yl) ethanesulfonamide, Example 148.0

Example 148.0 is the enantiomer of Example 147.0. Example 148.0 was the second isomer to elute from the OJ-H column under the conditions described in Example 147.0. $^1$H NMR (400 MHz, CD$_2$Cl$_2$) δ 1.84-2.10 (m, 3H) 2.22-2.35 (m, 1H) 3.24-3.35 (m, 4H) 3.67-3.81 (m, 2H) 3.85 (s, 3H) 3.86 (s, 3H) 4.65 (dd, J=7.63, 5.28 Hz, 1H) 6.73-6.79 (m, 2H) 7.26-7.33 (m, 1H) 7.34-7.42 (m, 2H) 7.52 (t, J=8.51 Hz, 1H) 10.73 (br. s., 1H) LCMS-ESI (pos), m/z: 502.1 (M+H)$^+$.

Following the procedure in Example 140.0 and 142.0 the following compounds may be synthesized using the intermediates and conditions described in the following table.

TABLE 15

| Example | Reagents | Structure, Name and Data |
|---|---|---|
| 149.0 | (2S,3R)-3-(5-methylpyrimidin-2-yl)butane-2-sulfonamide (Example 1.0), (R)-tert-butyl 2-(hydrazinecarbonyl)pyrrolidine-1-carboxylate and (S)-tert-butyl 2-(hydrazinecarbonyl)pyrrolidine-1-carboxylate (commercially available from Combi-blocks), 2-isothiocyanato-1,3-dimethoxybenzene (Example 10.0). tert-Butoxycarbonyl removal will be conducted by the addition of TFA, under standard reaction conditions. | 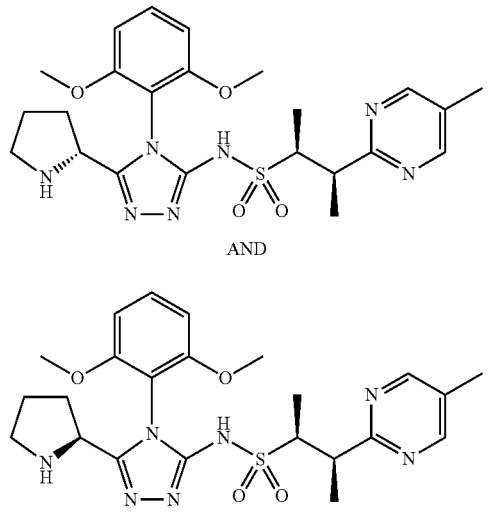<br><br>(2S,3R)-N-(4-(2,6-dimethoxyphenyl)-5-((S)-pyrrolidin-2-yl)-4H-1,2,4-triazol-3-yl)-3-(5-methylpyrimidin-2-yl)butane-2-sulfonamide and (2S,3R)-N-(4-(2,6-dimethoxyphenyl)-5-((R)-pyrrolidin-2-yl)-4H-1,2,4-triazol-3-yl)-3-(5-methylpyrimidin-2-yl)butane-2-sulfonamide. |
| 150.0 | (2S,3R)-3-(5-methylpyrimidin-2-yl)butane-2-sulfonamide (Example 1.0), (S)-methyl piperidine-2-carboxylate hydrochloride and (R)-methyl piperidine-2-carboxylate hydrochloride (commercially available from Combi-blocks), 2-isothiocyanato-1,3-dimethoxybenzene (Example 10.0). | 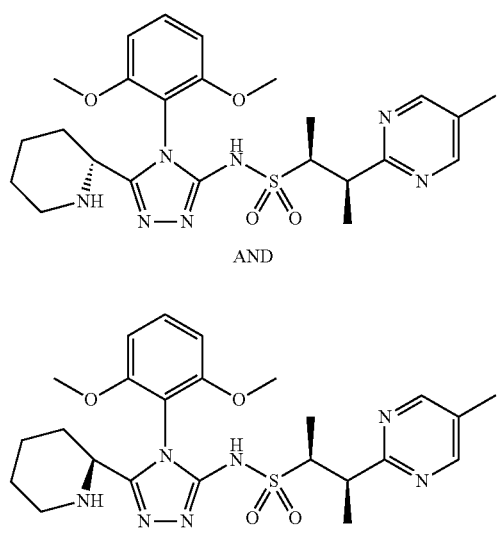<br><br>(2S,3R)-N-(4-(2,6-dimethoxyphenyl)-5-((S)-piperidin-2-yl)-4H-1,2,4-triazol-3-yl)-3-(5-methylpyrimidin-2-yl)butane-2-sulfonamide and (2S,3R)-N-(4-(2,6-dimethoxyphenyl)-5-((R)-piperidin-2-yl)-4H-1,2,4-triazol-3-yl)-3-(5-methylpyrimidin-2-yl)butane-2-sulfonamide. |

TABLE 15-continued

| Example | Reagents | Structure, Name and Data |
|---|---|---|
| 151.0 | (2S,3R)-3-(5-methylpyrimidin-2-yl)butane-2-sulfonamide (Example 1.0), (S)-1-(4-chlorobenzyl)piperidine-3-carbohydrazide and (R)-1-(4-chlorobenzyl)piperidine-3-carbohydrazide (commercially available from Matrix Scientific), 2-isothiocyanato-1,3-dimethoxybenzene (Example 10.0). para-Chlorobenzyl removal will be conducted under standard hydrogenolysis conditions with Pd/C. | 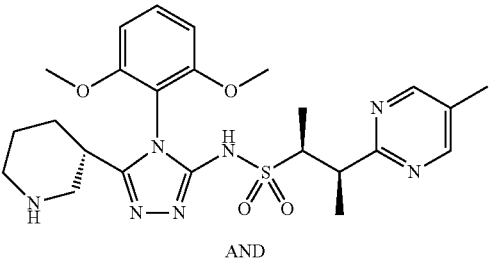 [SMILES: COc1cccc(OC)c1-n1c(NS(=O)(=O)[C@@H](C)[C@H](C)c2ncc(C)cn2)nnc1[C@H]1CCCNC1]<br>AND<br><br>(2S,3R)-N-(4-(2,6-dimethoxyphenyl)-5-((S)-piperidin-3-yl)-4H-1,2,4-triazol-3-yl)-3-(5-methylpyrimidin-2-yl)butane-2-sulfonamide and (2S,3R)-N-(4-(2,6-dimethoxyphenyl)-5-((R)-piperidin-3-yl)-4H-1,2,4-triazol-3-yl)-3-(5-methylpyrimidin-2-yl)butane-2-sulfonamide. |
| 152.0 | (2S,3R)-3-(5-methylpyrimidin-2-yl)butane-2-sulfonamide (Example 1.0), 1-pyrimidin-2-yl-piperidine-4-carboxylic acid hydrazide (commercially available from Enamine), 2-isothiocyanato-1,3-dimethoxybenzene (Example 10.0). Pyrimidine removal from the piperidine will be conducted under standard hydrolysis conditions with potassium carbonate in MeOH. | 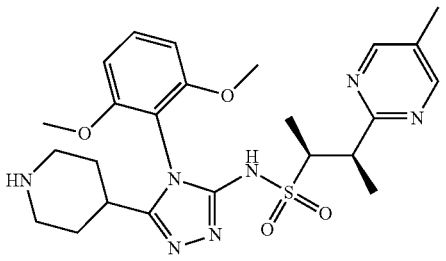 [SMILES: COc1cccc(OC)c1-n1c(NS(=O)(=O)[C@@H](C)[C@H](C)c2ncc(C)cn2)nnc1C1CCNCC1]<br><br>(2S,3R)-N-(4-(2,6-dimethoxyphenyl)-5-(piperidin-4-yl)-4H-1,2,4-triazol-3-yl)-3-(5-methylpyrimidin-2-yl)butane-2-sulfonamide. |
| 153.0 | (2S,3R)-3-(5-methylpyrimidin-2-yl)butane-2-sulfonamide (Example 1.0), tetrahydro-2H-thiopyran-4-carboxylic acid 1,1-dioxide (commercially available from Enamine), 2-isothiocyanato-1,3-dimethoxybenzene (Example 10.0). | 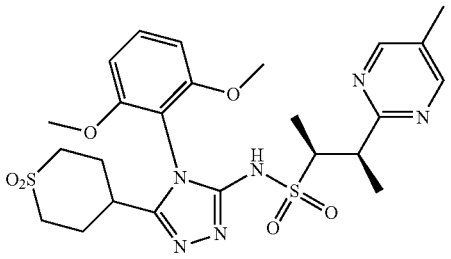 [SMILES: COc1cccc(OC)c1-n1c(NS(=O)(=O)[C@@H](C)[C@H](C)c2ncc(C)cn2)nnc1C1CCS(=O)(=O)CC1]<br><br>(2S,3R)-N-(4-(2,6-dimethoxyphenyl)-5-(1,1-dioxidotetrahydro-2H-thiopyran-4-yl)-4H-1,2,4-triazol-3-yl)-3-(5-methylpyrimidin-2-yl)butane-2-sulfonamide. |
| 154.0 | (2S,3R)-3-(5-methylpyrimidin-2-yl)butane-2-sulfonamide (Example 1.0), (R)-tetrahydro-2H-thiopyran-3-carboxylic acid 1,1-dioxide and (S)-tetrahydro-2H-thiopyran-3-carboxylic acid 1,1-dioxide (commercially available from Enamine), 2-isothiocyanato-1,3-dimethoxybenzene (Example 10.0). | 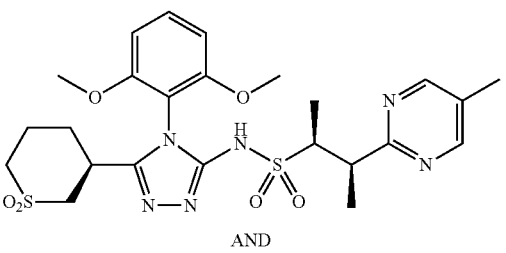 [SMILES: COc1cccc(OC)c1-n1c(NS(=O)(=O)[C@@H](C)[C@H](C)c2ncc(C)cn2)nnc1[C@@H]1CCCS(=O)(=O)C1]<br>AND |

TABLE 15-continued

| Example | Reagents | Structure, Name and Data |
|---|---|---|
| | | 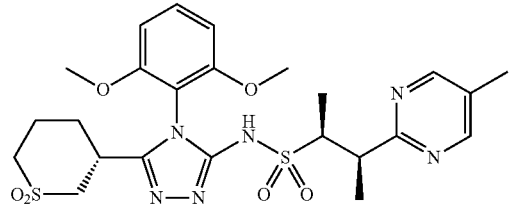 [SMILES: COc1cccc(OC)c1-n1c(NS(=O)(=O)[C@@H](C)[C@H](C)c2ncc(C)cn2)nnc1[C@H]1CCCS(=O)(=O)C1]
(2S,3R)-N-(4-(2,6-dimethoxyphenyl)-5-((R)-1,1-dioxidotetrahydro-2H-thiopyran-3-yl)-4H-1,2,4-triazol-3-yl)-3-(5-methylpyrimidin-2-yl)butane-2-sulfonamide and (2S,3R)-N-(4-(2,6-dimethoxyphenyl)-5-((S)-1,1-dioxidotetrahydro-2H-thiopyran-3-yl)-4H-1,2,4-triazol-3-yl)-3-(5-methylpyrimidin-2-yl)butane-2-sulfonamide. |
| 155.0 | (2S,3R)-3-(5-methylpyrimidin-2-yl)butane-2-sulfonamide (Example 1.0), (R)-tetrahydro-2H-thiopyran-2-carboxylic acid 1,1-dioxide and (S)-tetrahydro-2H-thiopyran-2-carboxylic acid 1,1-dioxide (commercially available from Enamine), 2-isothiocyanato-1,3-dimethoxybenzene (Example 10.0). | 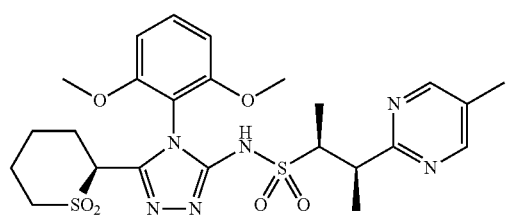
AND
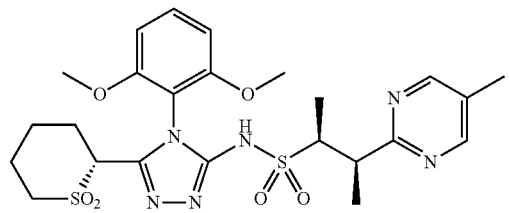
(2S,3R)-N-(4-(2,6-dimethoxyphenyl)-5-((R)-1,1-dioxidotetrahydro-2H-thiopyran-2-yl)-4H-1,2,4-triazol-3-yl)-3-(5-methylpyrimidin-2-yl)butane-2-sulfonamide and (2S,3R)-N-(4-(2,6-dimethoxyphenyl)-5-((S)-1,1-dioxidotetrahydro-2H-thiopyran-2-yl)-4H-1,2,4-triazol-3-yl)-3-(5-methylpyrimidin-2-yl)butane-2-sulfonamide. |
| 156.0 | (2S,3R)-3-(5-methylpyrimidin-2-yl)butane-2-sulfonamide (Example 1.0), (S)-tetrahydrothiophene-2-carboxylic acid 1,1-dioxide and (R)-tetrahydrothiophene-2-carboxylic acid 1,1-dioxide (commercially available from Asta Tech), 2-isothiocyanato-1,3-dimethoxybenzene (Example 10.0). | 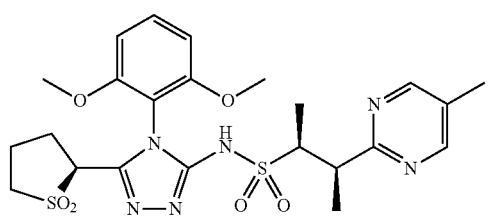
AND
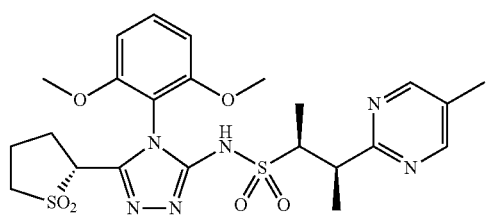
(2S,3R)-N-(4-(2,6-dimethoxyphenyl)-5-((R)-1,1-dioxidotetrahydrothiophen-2-yl)-4H-1,2,4-triazol-2-yl)-3-(5-methylpyrimidin-2-yl)butane-2- |

| Example | Reagents | Structure, Name and Data |
|---|---|---|
| | | sulfonamide and (2S,3R)-N-(4-(2,6-dimethoxyphenyl)-5-((S)-1,1-dioxidotetrahydrothiophen-2-yl)-4H-1,2,4-triazol-2-yl)-3-(5-methylpyrimidin-2-yl)butane-2-sulfonamide. |
| 158.0 | (2S,3R)-3-(5-methylpyrimidin-2-yl)butane-2-sulfonamide (Example 1.0), (S)-ethyl morpholine-3-carboxylate hydrochloride and (R)-ethyl morpholine-3-carboxylate hydrochloride (commercially available from Manchester Organics), 2-isothiocyanato-1,3-dimethoxybenzene (Example 10.0). | 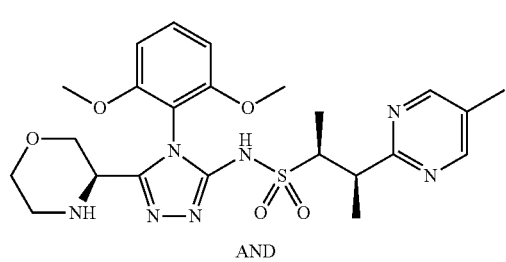 [SMILES: COc1cccc(OC)c1-n1c(NS(=O)(=O)[C@@H](C)[C@H](C)c2ncc(C)cn2)nnc1[C@@H]1COCCN1]<br>AND<br>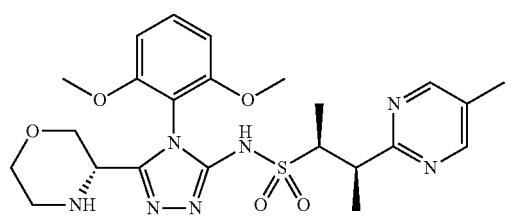 [SMILES: COc1cccc(OC)c1-n1c(NS(=O)(=O)[C@@H](C)[C@H](C)c2ncc(C)cn2)nnc1[C@H]1COCCN1]<br>((2S,3R)-N-(4-(2,6-dimethoxyphenyl)-5-((S)-morpholin-3-yl)-4H-1,2,4-triazol-3-yl)-3-(5-methylpyrimidin-2-yl)butane-2-sulfonamide and (2S,3R)-N-(4-(2,6-dimethoxyphenyl)-5-((R)-morpholin-3-yl)-4H-1,2,4-triazol-3-yl)-3-(5-methylpyrimidin-2-yl)butane-2-sulfonamide. |
| 159.0 | (2S,3R)-3-(5-methylpyrimidin-2-yl)butane-2-sulfonamide (Example 1.0), (S)-ethyl morpholine-2-carboxylate 2,2,2-trifluoroacetate and (R)-ethyl morpholine-2-carboxylate 2,2,2-trifluoroacetate (commercially available from Matrix Scientific), 2-isothiocyanato-1,3-dimethoxybenzene (Example 10.0). | 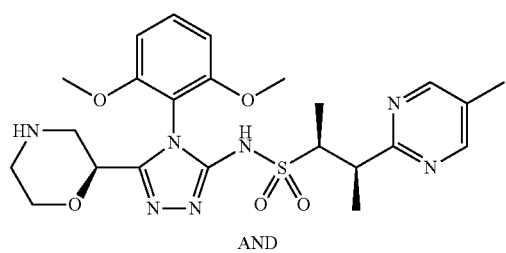 [SMILES: COc1cccc(OC)c1-n1c(NS(=O)(=O)[C@@H](C)[C@H](C)c2ncc(C)cn2)nnc1[C@@H]1CNCCO1]<br>AND<br>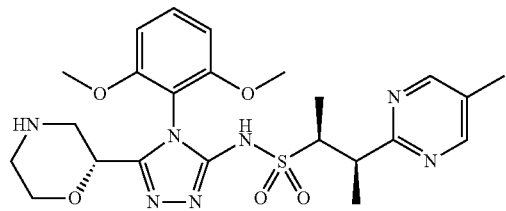 [SMILES: COc1cccc(OC)c1-n1c(NS(=O)(=O)[C@@H](C)[C@H](C)c2ncc(C)cn2)nnc1[C@H]1CNCCO1]<br>(2S,3R)-N-(4-(2,6-dimethoxyphenyl)-5-((R)-morpholin-2-yl)-4H-1,2,4-triazol-3-yl)-3-(5-methylpyrimidin-2-yl)butane-2-sulfonamide and (2S,3R)-N-(4-(2,6-dimethoxyphenyl)-5-((S)-morpholin-2-yl)-4H-1,2,4-triazol-3-yl)-3-(5-methylpyrimidin-2-yl)butane-2-sulfonamide. |

TABLE 15-continued

| Example | Reagents | Structure, Name and Data |
|---|---|---|
| 161.0 | (2S,3R)-3-(5-methylpyrimidin-2-yl)butane-2-sulfonamide (Example 1.0), 1,2-dioxane-5-carboxylic acid (commercially available from Urorsy Building Blocks library), 2-isothiocyanato-1,3-dimethoxybenzene (Example 10.0). | (2S,3R)-N-(4-(2,6-dimethoxyphenyl)-5-(1,3-dioxan-5-yl)-4H-1,2,4-triazol-3-yl)-3-(5-methylpyrimidin-2-yl)butane-2-sulfonamide. |
| 162.0 | (2S,3R)-3-(5-methylpyrimidin-2-yl)butane-2-sulfonamide (Example 1.0), (S)-1,3-dioxolane-4-carboxylic acid and (R)-1,3-dioxolane-4-carboxylic acid (commercially available from Tyger scientific), 2-isothiocyanato-1,3-dimethoxybenzene (Example 10.0). | AND<br><br>(2S,3R)-N-(4-(2,6-dimethoxyphenyl)-5-((S)-1,3-dioxolan-4-yl)-4H-1,2,4-triazol-3-yl)-3-(5-methylpyrimidin-2-yl)butane-2-sulfonamide and (2S,3R)-N-(4-(2,6-dimethoxyphenyl)-5-((R)-1,3-dioxolan-4-yl)-4H-1,2,4-triazol-3-yl)-3-(5-methylpyrimidin-2-yl)butane-2-sulfonamide. |
| 163.0 | (2S,3R)-3-(5-methylpyrimidin-2-yl)butane-2-sulfonamide (Example 1.0), 1,3-dioxolane-2-carboxylic acid (commercially available from Aurora building blocks), 2-isothiocyanato-1,3-dimethoxybenzene (Example 10.0). | (2S,3R)-N-(4-(2,6-dimethoxyphenyl)-5-(1,3-dioxolan-2-yl)-4H-1,2,4-triazol-3-yl)-3-(5-methylpyrimidin-2-yl)butane-2-sulfonamide. |
| 164.0 | (2S,3R)-3-(5-methylpyrimidin-2-yl)butane-2-sulfonamide (Example 1.0), 1,3-dioxane-2-carboxylic acid (commercially available from Enamine building blocks), 2-isothiocyanato-1,3-dimethoxybenzene (Example 10.0). | (2S,3R)-N-(4-(2,6-dimethoxyphenyl)-5-(1,3-dioxan-2-yl)-4H-1,2,4-triazol-3-yl)-3-(5-methylpyrimidin-2-yl)butane-2-sulfonamide. |

TABLE 15-continued

| Example | Reagents | Structure, Name and Data |
|---|---|---|
| 165.0 | (3S,5R)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide and (3R,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide, Example 179.4, (R)-1,4-dioxane-2-carbohydrazide and (S)-1,4-dioxane-2-carbohydrazide (Frontier Scientific Services, Inc.), 2-isothiocyanato-1,3-dimethoxybenzene (Example 10.0). | 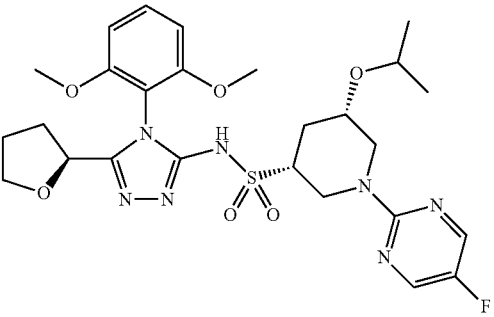<br>AND<br>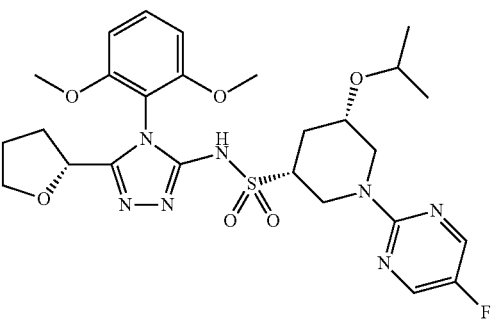<br>AND<br>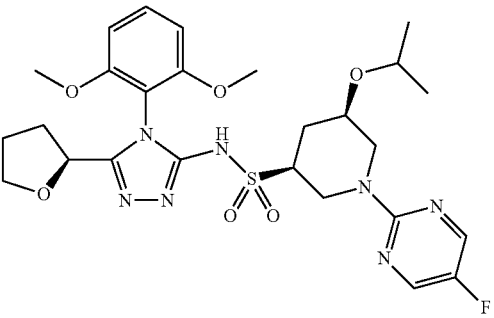<br>AND<br>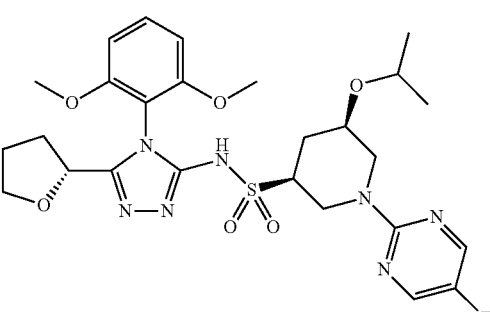<br>AND |

TABLE 15-continued
| Example | Reagents | Structure, Name and Data |
|---|---|---|
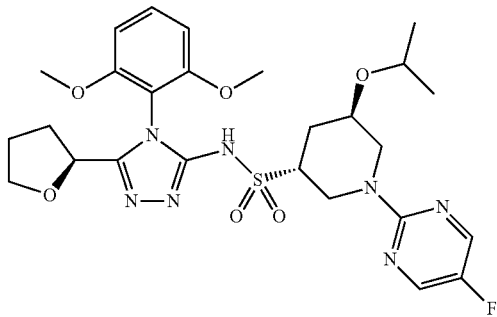
AND
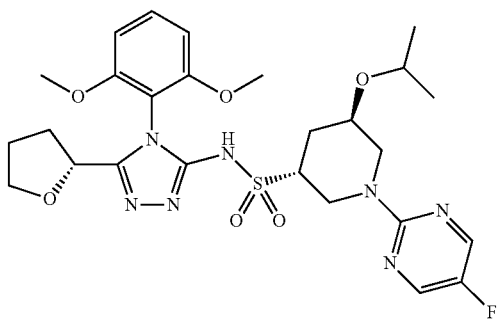
AND
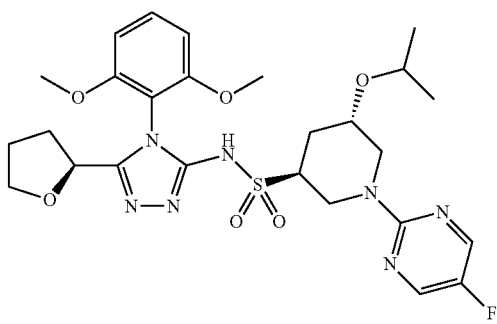
AND
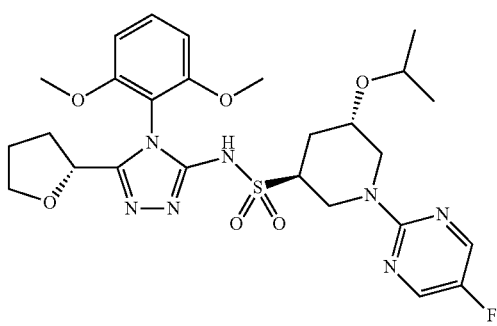 [SMILES: COc1cccc(OC)c1-n1c(NS(=O)(=O)[C@H]2C[C@H](OC(C)C)CN(c3ncc(F)cn3)C2)nnc1[C@H]1CCCO1]
(3R,5S)-N-(4-(2,6-dimethoxyphenyl)-5-((S)-
tetrahydrofuran-2-yl)-4H-1,2,4-triazol-3-yl)-1-(5-
fluoropyrimidin-2-yl)-5-isopropoxypiperidine-3-
sulfonamide and (3R,5S)-N-(4-(2,6-
dimethoxyphenyl)-5-((R)-tetrahydrofuran-2-yl)-
4H-1,2,4-triazol-3-yl)-1-(5-fluoropyrimidin-2-yl)-
5-isopropoxypiperidine-3-sulfonamide and
(3S,5R)-N-(4-(2,6-dimethoxyphenyl)-5-((S)-
tetrahydrofuran-2-yl)-4H-1,2,4-triazol-3-yl)-1-(5-

TABLE 15-continued

| Example | Reagents | Structure, Name and Data |
|---|---|---|
| | | fluoropyrimidin-2-yl)-5-isopropoxypiperidine-3-sulfonamide and (3S,5R)-N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide and (3R,5R)-N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide and (3R,5R)-N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide and (3S,5S)-N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide and (3S,5S)-N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide. |
| 166.0 | (2S,3R)-3-(5-methylpyrimidin-2-yl)butane-2-sulfonamide (Example 1.0), (S)-tetrahydrothiophene-3-carboxylic acid and (R)-tetrahydrothiophene-3-carboxylic acid (commercially available from Enamine building blocks), 2-isothiocyanato-1,3-dimethoxybenzene (Example 10.0). | 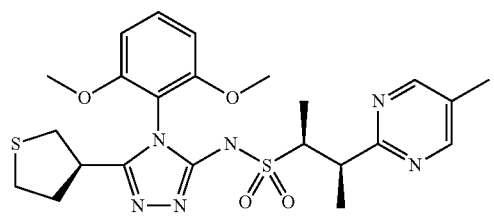<br>AND<br>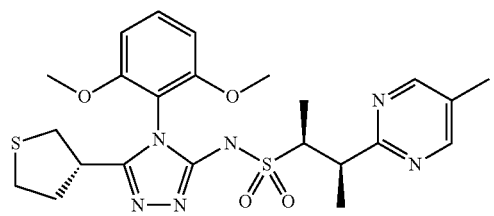 [SMILES: COc1cccc(OC)c1-n1c(NS(=O)(=O)[C@@H](C)[C@H](C)c2ncc(C)cn2)nnc1[C@@H]1CCSC1]<br>(2S,3R)-N-(4-(2,6-dimethoxyphenyl)-5-((S)-tetrahydrothiophen-3-yl)-4H-1,2,4-triazol-3-yl)-3-(5-methylpyrimidin-2-yl)butane-2-sulfonamide and (2S,3R)-N-(4-(2,6-dimethoxyphenyl)-5-((R)-tetrahydrothiophen-3-yl)-4H-1,2,4-triazol-3-yl)-3-(5-methylpyrimidin-2-yl)butane-2-sulfonamide. |

TABLE 15-continued

| Example | Reagents | Structure, Name and Data |
|---|---|---|
| 167.0 | Employing (S)-tert-butyl 3-sulfamoylpiperidine-1-carboxylate and (R)-tert-butyl 3-sulfamoylpiperidine-1-carboxylate (Example 227.0), (R)-tetrahydrofuran-2-carbohydrazide and (S)-tetrahydrofuran-2-carbohydrazide (commercially available from Enamine), 5-isothiocyanato-4,6-dimethoxypyrimidine (Example 10.1) under the conditions described would deliver the desired material; tert-butyl 3-(N-(4-(4,6-dimethoxypyrimidin-5-yl)-5-tetrahydrofuran-2-yl)-4H-1,2,4-triazol-3-yl)sulfamoyl)piperidine-1-carboxylate. Removal of the Boc would be accomplished by employing 10 equivalents of TFA in a 0.5M DCM solution at RT, until LCMS deemed the reaction was complete to deliver product. This would be placed in a sealed vial with 10 eq of hunigs base and 5 equivalents of 2,5-dichloropyrimidine in 2-methyltetrahydrofuran. The reaction would be heated at 80° C. until LCMS showed the title compound. | 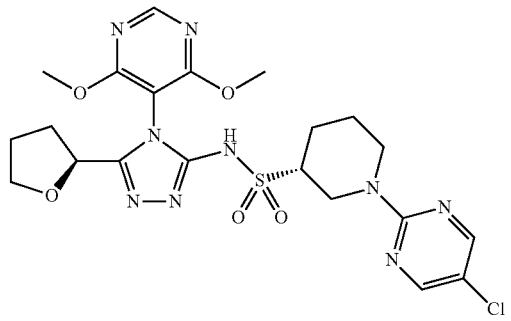<br>AND<br>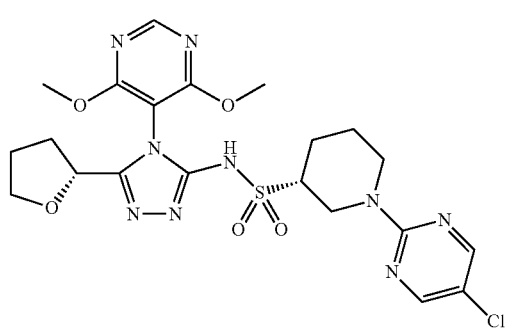 [SMILES: COc1ncnc(OC)c1-n1c(NS(=O)(=O)[C@H]2CCCN(c3ncc(Cl)cn3)C2)nnc1[C@H]1CCCO1]<br>AND<br>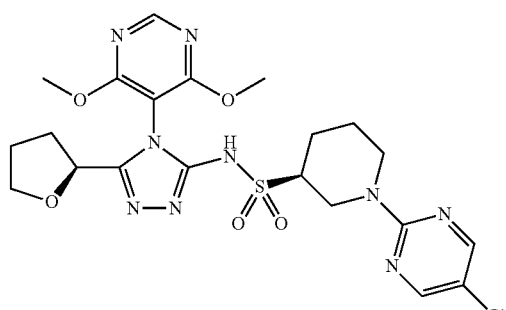<br>AND<br>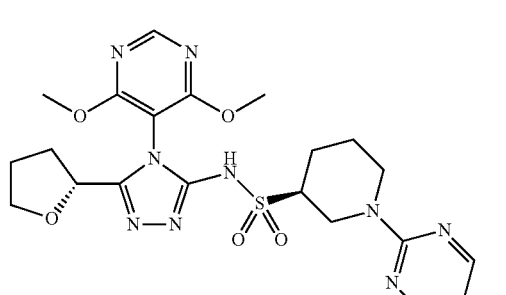<br>(S)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)piperidine-3-sulfonamide and (R)-1-(5-chloropyrimidin-2-yl)-N-(4-(4,6-dimethoxypyrimidin-5-yl)-5-((S)-tetrahydrofuran-2-yl)-4H-1,2,4-triazol-3-yl)piperidine-3-sulfonamide and (S)-1-(5-chloropyrimidin-2-yl)-N-(4-(4,6-dimethoxypyrimidin-5-yl)-5-((S)- |

US 9,988,369 B2

TABLE 15-continued

| Example | Reagents | Structure, Name and Data |
|---|---|---|
| | | tetrahydrofuran-2-yl)-4H-1,2,4-triazol-3-yl)piperidine-3-sulfonamide and (R)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)piperidine-3-sulfonamide. |
| 168.0 | Employing (S)-tert-butyl 3-sulfamoylpiperidine-1-carboxylate and (R)-tert-butyl 3-sulfamoylpiperidine-1-carboxylate (Example 227.0), (R)-tetrahydrofuran-2-cathohydrazide and (S)-tetrahydrofuran-2-carbohydrazide (commercially available from Enamine), 5-isothiocyanato-4,6-dimethoxypyrimidine (Example 10.1) under the conditions described would deliver the desired material; tert-butyl 3-(N-(4-(4,6-dimethoxypyrimidin-5-yl)-5-tetrahydrofuran-2-yl)-4H-1,2,4-triazol-3-yl)sulfamoyl)piperidine-1-carboxylate. Following the chemistry employed in Example 167.0 using 2-chloro-5-fluoro-pyrimidine would deliver the title compound. | 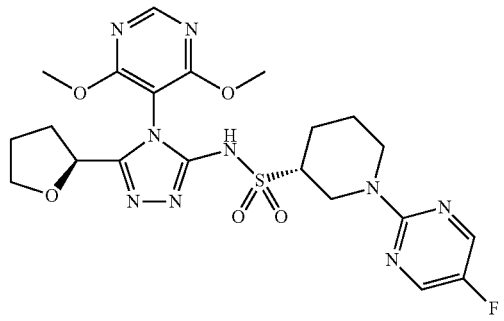<br><br>AND<br><br>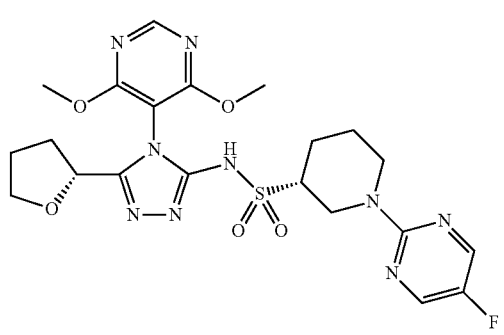<br><br>AND<br><br>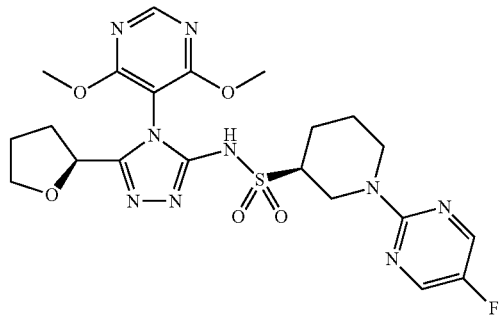 [SMILES: COc1ncnc(OC)c1-n1c(NS(=O)(=O)[C@H]2CCCN(c3ncc(F)cn3)C2)nnc1[C@H]1CCCO1]<br><br>AND<br><br>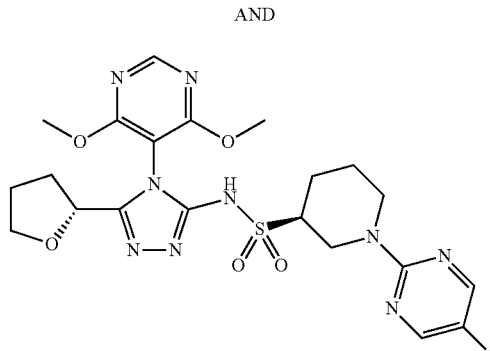<br><br>(S)-N-(4-(4,6-dimethoxypyrimidin-5-yl)-5-((R)-tetrahydrofuran-2-yl)-4H-1,2,4-triazol-3-yl)-1-(5- |

TABLE 15-continued

| Example | Reagents | Structure, Name and Data |
|---|---|---|
| | | fluoropyrimidin-2-yl)piperidine-3-sulfonamide and (S)-N-(4-(4,6-dimethoxypyrimidin-5-yl)-5-((S)-tetrahydrofuran-2-yl)-4H-1,2,4-triazol-3-yl)-1-(5-fluoropyrimidin-2-yl)piperidine-3-sulfonamide and (R)-N-(4-(4,6-dimethoxypyrimidin-5-yl)-5-((R)-tetrahydrofuran-2-yl)-4H-1,2,4-triazol-3-yl)-1-(5-fluoropyrimidin-2-yl)piperidine-3-sulfonamide and (R)-N-(4-(4,6-dimethoxypyrimidin-5-yl)-5-((S)-tetrahydrofuran-2-yl)-4H-1,2,4-triazol-3-yl)-1-(5-fluoropyrimidin-2-yl)piperidine-3-sulfonamide. |
| 169.0 | (3S,5S)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide, Example 228.0, (R)-tetrahydrofuran-2-cathohydrazide and (S)-tetrahydrofuran-2-carbohydrazide (commercially available from Enamine), 5-isothiocyanato-4,6-dimethoxypyrimidine (Example 10.1). | AND<br><br>AND<br><br>AND |

TABLE 15-continued
| Example | Reagents | Structure, Name and Data |
|---------|----------|--------------------------|
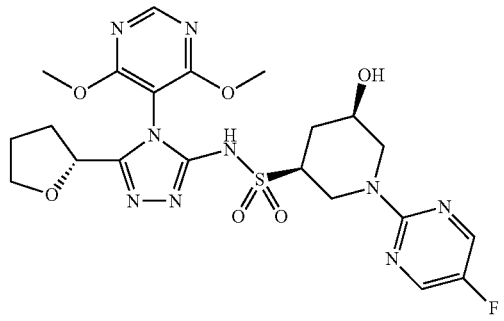
AND
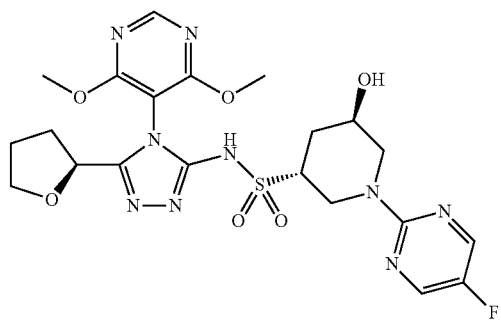
AND
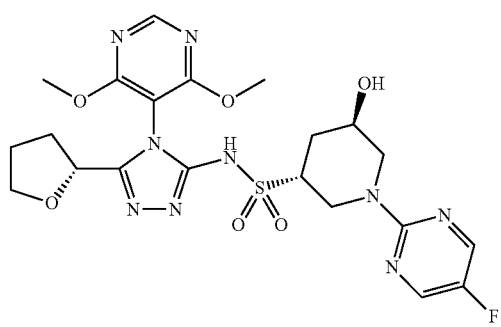
AND TABLE 15-continued

| Example | Reagents | Structure, Name and Data |
|---------|----------|--------------------------|

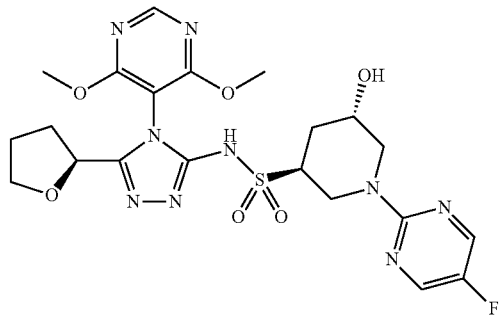

AND

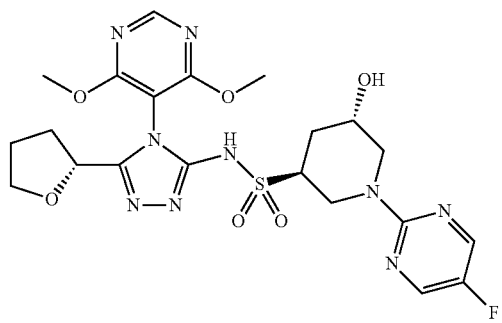 [SMILES: COc1ncnc(OC)c1-n1c(NS(=O)(=O)[C@H]2C[C@H](O)CN(c3ncc(F)cn3)C2)nnc1[C@H]1CCCO1]

(3R,5S)-N-(4-(4,6-dimethoxypyrimidin-5-yl)-5-
((S)-tetrahydrofuran-2-yl)-4H-1,2,4-triazol-3-yl)-
1-(5-fluoropyrimidin-2-yl)-5-hydroxypiperidine-
3-sulfonamide and (3R,5S)-N-(4-(4,6-
dimethoxypyrimidin-5-yl)-5-((R)-
tetrahydrofuran-2-yl)-4H-1,2,4-triazol-3-yl)-1-(5-
fluoropyrimidin-2-yl)-5-hydroxypiperidine-3-
sulfonamide and (3R,5R)-N-(4-(4,6-
dimethoxypyrimidin-5-yl)-5-((S)-tetrahydrofuran-
2-yl)-4H-1,2,4-triazol-3-yl)-1-(5-fluoropyrimidin-
2-yl)-5-hydroxypiperidine-3-sulfonamide and
(3R,5R)-N-(4-(4,6-dimethoxypyrimidin-5-yl)-5-
((R)-tetrahydrofuran-2-yl)-4H-1,2,4-triazol-3-yl)-
1-(5-fluoropyrimidin-2-yl)-5-hydroxypiperidine-
3-sulfonamide and (3S,5R)-N-(4-(4,6-
dimethoxypyrimidin-5-yl)-5-((S)-tetrahydrofuran-
2-yl)-4H-1,2,4-triazol-3-yl)-1-(5-fluoropyrimidin-
2-yl)-5-hydroxypiperidine-3-sulfonamide and
(3S,5R)-N-(4-(4,6-dimethoxypyrimidin-5-yl)-5-
((R)-tetrahydrofuran-2-yl)-4H-1,2,4-triazol-3-yl)-
1-(5-fluoropyrimidin-2-yl)-5-hydroxypiperidine-
3-sulfonamide and (3S,5S)-N-(4-(4,6-
dimethoxypyrimidin-5-yl)-5-((S)-tetrahydrofuran-
2-yl)-4H-1,2,4-triazol-3-yl)-1-(5-fluoropyrimidin-
2-yl)-5-hydroxypiperidine-3-sulfonamide and
(3S,5S)-N-(4-(4,6-dimethoxypyrimidin-5-yl)-5-((R)-
tetrahydrofuran-2-yl)-4H-1,2,4-triazol-3-yl)-1-(5-
fluoropyrimidin-2-yl)-5-hydroxypiperidine-3-sulfonamide.

TABLE 15-continued

| Example | Reagents | Structure, Name and Data |
|---|---|---|
| 170.0 | (3S,5R)-1-(5-fluoropyrimidin-2-yl)-5-methoxypiperidine-3-sulfonamide and (3R,5S)-1-(5-fluoropyrimidin-2-yl)-5-methoxypiperidine-3-sulfonamide, Example 229.3 and (3S,5S)-1-(5-fluoropyrimidin-2-yl)-5-methoxypiperidine-3-sulfonamide and (3R,5R)-1-(5-fluoropyrimidin-2-yl)-5-methoxypiperidine-3-sulfonamide, Example 229.4, (R)-tetrahydrofuran-2-catbohydrazide and (S)-tetrahydrofuran-2-carbohydrazide (commercially available from Enamine), 5-isothiocyanato-4,6-dimethoxypyrimidine (Example 10.1). | 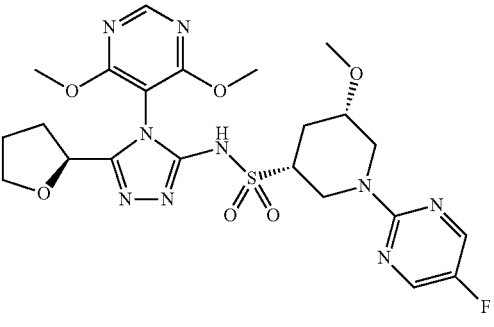<br>AND<br>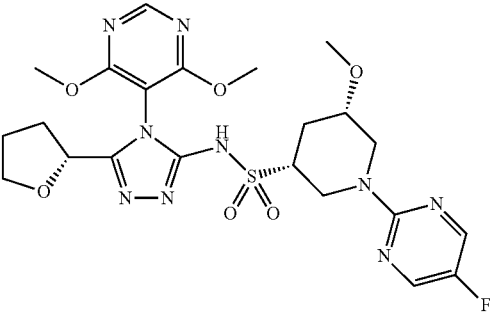<br>AND<br>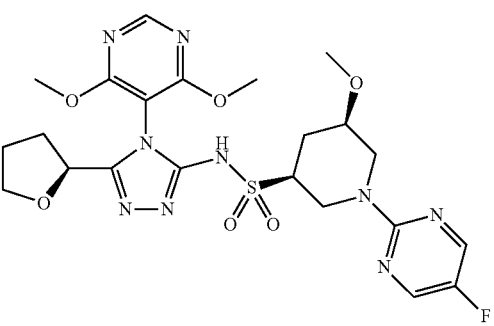<br>AND<br>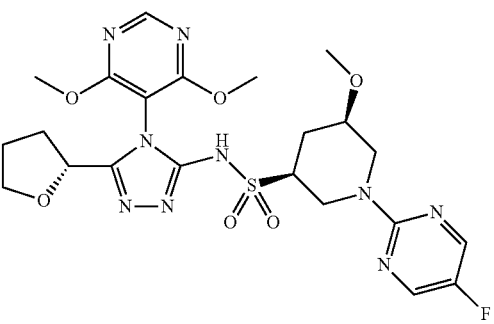<br>AND |

| Example | Reagents | Structure, Name and Data |
|---|---|---|
| | | 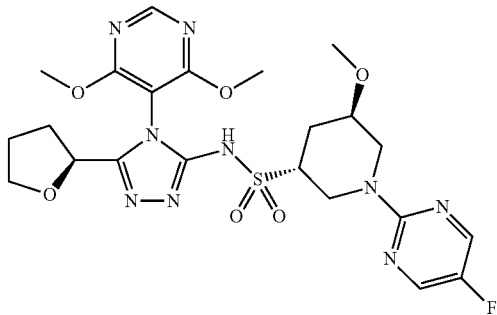 AND 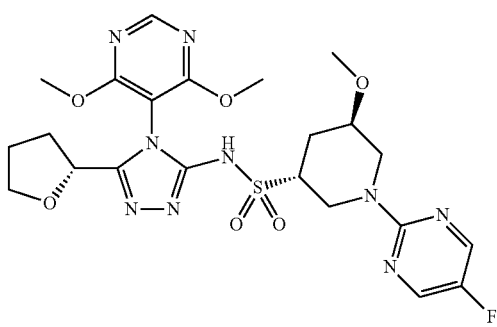 AND 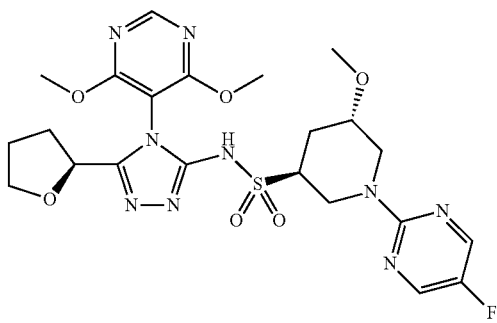 AND 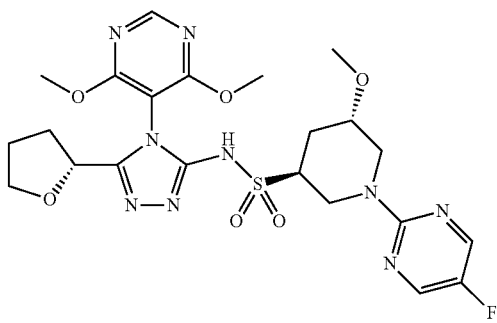 [SMILES: COc1ncnc(OC)c1-n1c(NS(=O)(=O)[C@H]2C[C@H](OC)CN(c3ncc(F)cn3)C2)nnc1[C@H]1CCCO1] (3R,5S)-N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide and (3R,5S)-N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide and (3R,5R)-N-(4-(4,6-dimethoxypyrimidin-5-yl)-5-((S)-tetrahydrofuran- |

TABLE 15-continued

| Example | Reagents | Structure, Name and Data |
|---|---|---|
| | | 2-yl)-4H-1,2,4-triazol-3-yl)-1-(5-fluoropyrimidin-2-yl)-5-methoxypiperidine-3-sulfonamide and (3R,5R)-N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide and (3S,5R)-N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide and (3S,5R)-N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide and (3S,5S)-N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide and (3S,5S)-N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide. |
| 171.0 | (3S,5S)-5-ethoxy-1-(5-fluoropyrimidin-2-yl)piperidine-3-sulfonamide and (3S,5R)-5-ethoxy-1-(5-fluoropyrimidin-2-yl)piperidine-3-sulfonamide and (3R,5S)-5-ethoxy-1-(5-fluoropyrimidin-2-yl)piperidine-3-sulfonamide and (3R,5R)-5-ethoxy-1-(5-fluoropyrimidin-2-yl)piperidine-3-sulfonamide will made in analogous manner to that described in Example 229.0 employing 5-ethoxypyridine-3-sulfonyl chloride, (R)-tetrahydrofuran-2-carbohydrazide and (S)-tetrahydrofuran-2-carbohydrazide (commercially available from Enamine), 5-isothiocyanato-4,6-dimethoxypyrimidine (Example 10.1). | 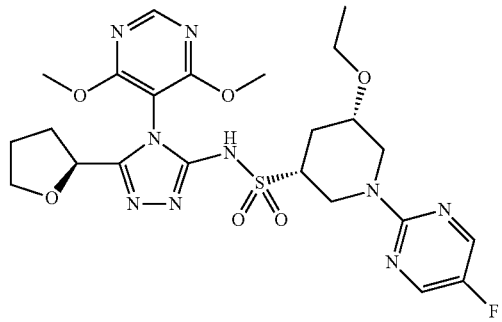\n\nAND\n\n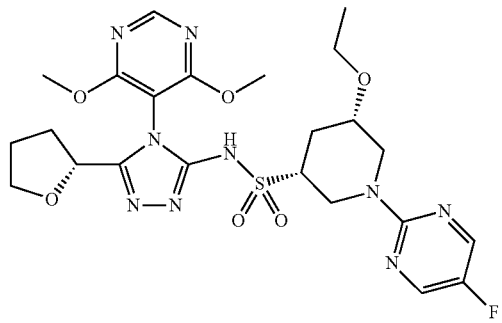\n\nAND\n\n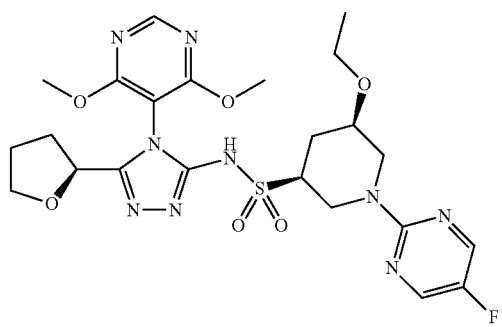\n\nAND |

TABLE 15-continued
| Example | Reagents | Structure, Name and Data |
|---------|----------|--------------------------|
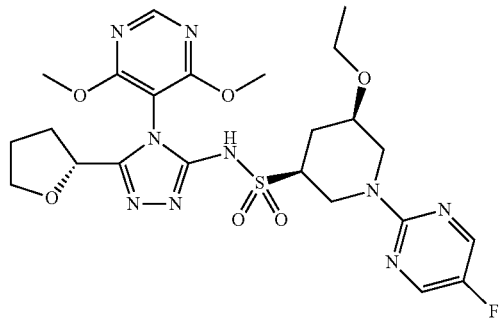
AND
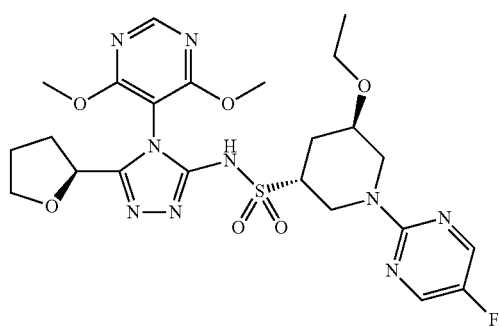
AND
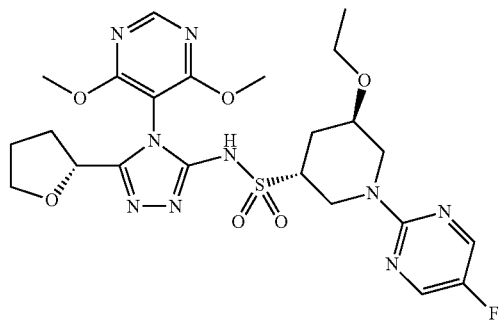
AND
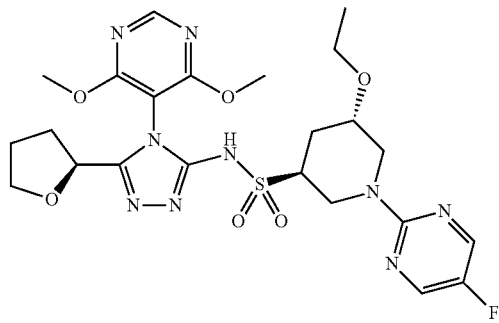
AND TABLE 15-continued

| Example | Reagents | Structure, Name and Data |
|---|---|---|
| | | 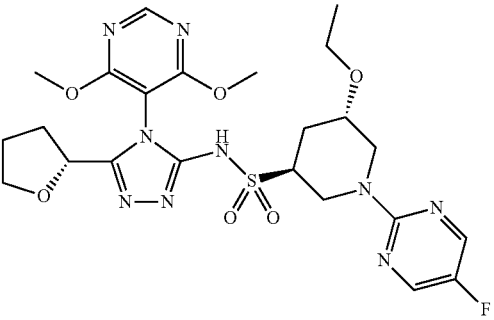 [SMILES: CCO[C@H]1C[C@H](S(=O)(=O)Nc2nnc([C@H]3CCCO3)n2-c2c(OC)ncnc2OC)CN(c2ncc(F)cn2)C1]<br>(3R,5S)-N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide and (3R,5S)-N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide and (3R,5R)-N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide and (3R,5R)-N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide and (3S,5R)-N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide and (3S,5R)-N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide and (3S,5S)-N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide and (3S,5S)-N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide. |

TABLE 15-continued

| Example | Reagents | Structure, Name and Data |
|---------|----------|--------------------------|
| 172.0 | (3S,5R)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide and (3R,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide, Example 179.4, (R)-tetrahydrofuran-2-carbohydrazide and (S)-tetrahydrofuran-2-carbohydrazide (commercially available from Enamine), 5-isothiocyanato-4,6-dimethoxypyrimidine (Example 10.1). | 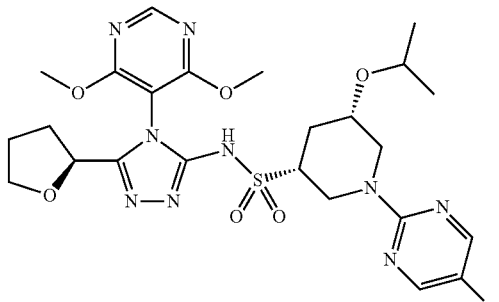

AND

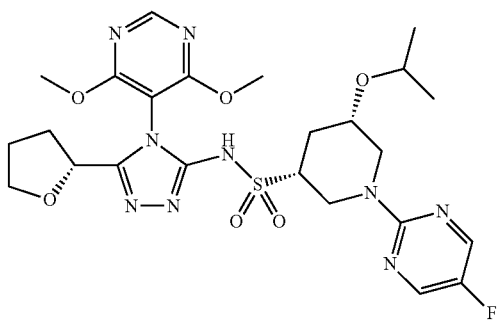

AND

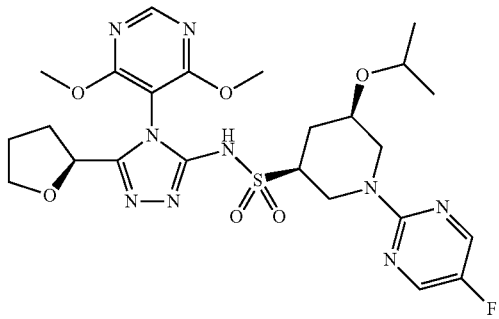

AND

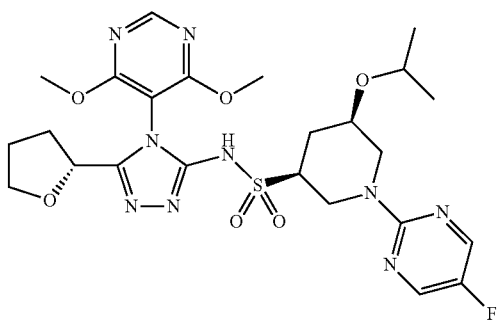

AND |

TABLE 15-continued

| Example | Reagents | Structure, Name and Data |
|---------|----------|--------------------------|

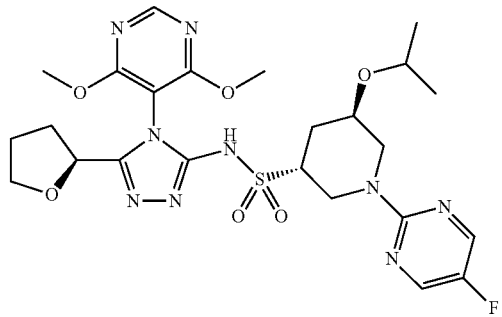

AND

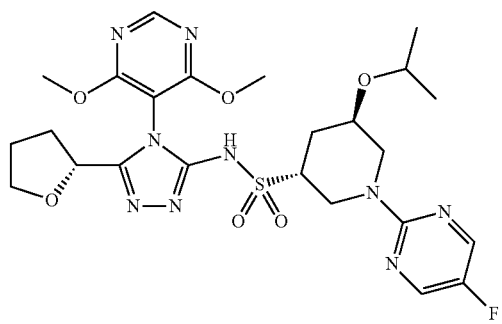

AND

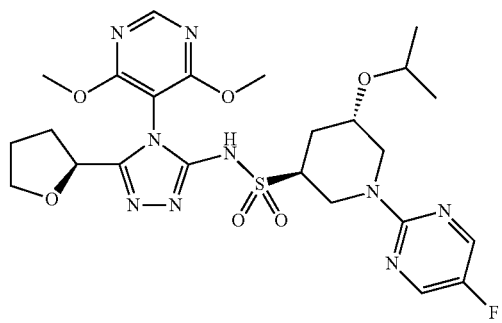

AND

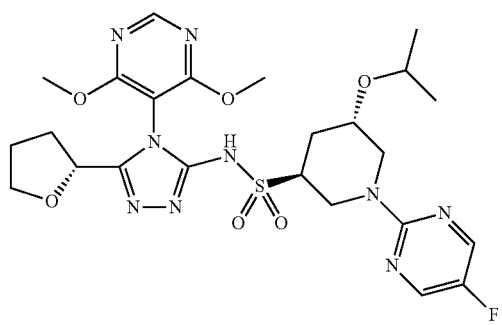 [SMILES: COc1ncnc(OC)c1-n1c(NS(=O)(=O)[C@H]2C[C@H](OC(C)C)CN(c3ncc(F)cn3)C2)nnc1[C@H]1CCCO1]

(3R,5S)-N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide and (3R,5S)-N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide and (3R,5R)-N-(4-(4,6-dimethoxypyrimidin-5-yl)-5-((S)-tetrahydrofuran-

TABLE 15-continued

| Example | Reagents | Structure, Name and Data |
|---|---|---|
| | | 2-yl)-4H-1,2,4-triazol-3-yl)-1-(5-fluoropyrimidin-2-yl)-5-isopropoxypiperidine-3-sulfonamide and (3R,5R)-N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide and (3S,5R)-N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide and (3S,5R)-N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide and (3S,5S)-N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide and (3S,5S)-N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide. |

The compounds set forth in the following table were synthesized following the procedure in Example 24.0 using the known starting material as described.

TABLE 16

| Example | Reagents | Structure, Name and Data |
|---|---|---|
| 173.0 | (2S,3R)-3-(5-chloropyrimidin-2-yl)-N-(4-(2,6-dimethoxyphenyl)-5-((R)-tetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-tetrahydrofuran-3-yl)-4H-1,2,4-triazol-3-yl)butane-2-sulfonamide (Example 60.0). | 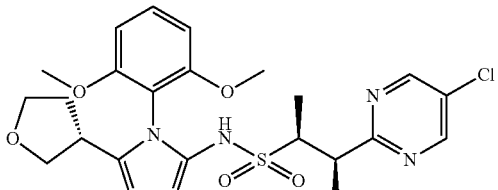<br>OR<br>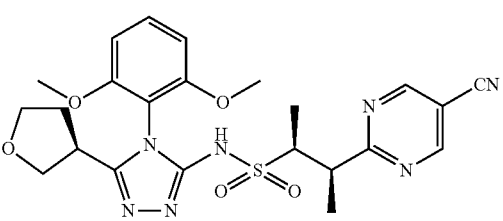 [SMILES: COc1cccc(OC)c1-n1c(NS(=O)(=O)[C@@H](C)[C@H](C)c2ncc(C#N)cn2)nnc1[C@@H]1CCOC1]<br>(2S,3R)-3-(5-cyano-2-pyrimidinyl)-N-(4-(2,6-dimethoxyphenyl)-5-((3R)-tetrahydro-3-furanyl)-4H-1,2,4-triazol-3-yl)-2-butanesulfonamide or (2S,3R)-3-(5-cyano-2-pyrimidinyl)-N-(4-(2,6-dimethoxyphenyl)-5-((3S)-tetrahydro-3-furanyl)-4H-1,2,4-triazol-3-yl)-2-butanesulfonamide. $^1$H NMR (500 MHz, CDCl$_3$) δ 10.68 (s, 1 H) 8.91 (s, 2 H) 7.43 (t, J = 8.56 Hz, 1 H) 3.84 (s, 1 H) 3.81 (s, 3 H) 3.80 (s, 3 H) 3.73-3.79 (m, 3 H) 2.88-3.10 (m, 2 H) 2.18-2.36 (m, 1 H) 1.97-2.10 (m, 1 H) 1.36 (d, J = 3.37 Hz, 3 H) 1.35 (d, J = 3.24 Hz, 3 H). LCMS-ESI (pos) m/z: 514.2 (M + H)$^+$. |

TABLE 16-continued

| Example | Reagents | Structure, Name and Data |
|---|---|---|
| 174.0 | (2S,3R)-3-(5-chloropyrimidin-2-yl)-N-4-(2,6-dimethoxyphenyl)-5-((R)-tetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-tetrahydrofuran-3-yl)-4H-1,2,4-triazol-3-yl)butane-2-sulfonamide (Example 61.0). | *[structure]*<br><br>OR<br><br>*[structure]*<br><br>(2S,3R)-3-(5-cyano-2-pyrimidinyl)-N-(2,6-dimethoxyphenyl)-5-((3R)-tetrahydro-3-furanyl)-4H-1,2,4-triazol-3-yl)-2-butanesulfonamide or (2S,3R)-3-(5-cyano-2-pyrimidinyl)-N-(4-(2,6-dimethoxyphenyl)-5-((3S)-tetrahydro-3-furanyl)-4H-1,2,4-triazol-3-yl)-2-butanesulfonamide. $^1$H NMR (500 MHz, CDCl$_3$) δ 10.65 (br s, 1 H) 8.91 (s, 2 H) 7.44 (t, J = 8.50 Hz, 1 H) 6.67 (dd, J = 8.50, 3.83 Hz, 2 H) 3.88-3.95 (m, 1 H) 3.82 (br s, 1 H) 3.81 (d, J = 0.91 Hz, 6 H) 3.72-3.80 (m, 3 H) 2.94-3.04 (m, 2 H) 2.21-2.31 (m, 1 H) 1.98-2.07 (m, 1 H) 1.36 (d, J = 4.28 Hz, 3 H) 1.35 (d, J = 4.15 Hz, 3 H). LCMS-ESI (pos) m/z: 514.2. (M + H)$^+$. |

Example 175.0. Preparation of (2S,3R)—N-(4-(2,6-dimethoxyphenyl)-5-((2R)-1,4-dioxan-2-yl)-4H-1,2,4-triazol-3-yl)-3-(5-methoxy-2-pyrimidinyl)-2-butanesulfonamide or (2S,3R)—N-(4-(2,6-dimethoxyphenyl)-5-((2S)-1,4-dioxan-2-yl)-4H-1,2,4-triazol-3-yl)-3-(5-methoxy-2-pyrimidinyl)-2-butanesulfonamide 175.1

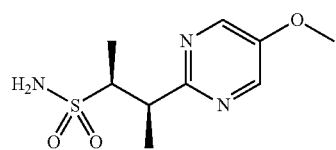

(2S,3R)-3-(5-Methoxypyrimidin-2-yl)butane-2-sulfonamide, Example 175.1

A round bottom flask was charged with (2S,3R)-3-(5-fluoropyrimidin-2-yl)butane-2-sulfonamide (575 mg, 2.47 mmol, Example 1.1), MeOH (7 mL), and potassium carbonate (679 mg, 4.91 mmol). The reaction was stirred at RT. After 48 h, the reaction was heated to 50° C. and the mixture was stirred for 24 h. The temperature was then raised to 65° C. and the mixture was stirred for 48 h. LCMS-ESI showed the reaction was 75% complete. The reaction was allowed to cool to RT and filtered. The solids were rinsed with MeOH (2×5 mL). The filtrate was concentrated in vacuo and the residue was adsorbed onto a plug of silica gel and chromatographed through a RediSep® pre-packed silica gel column, eluting with 0-40% EtOAc:EtOH (3:1) in heptanes. The chromatography solvents were contaminated with water. The organic layer from several fractions were concentrated in vacuo to give a mixture of starting material and the title compound (56 mg, 0.23 mmol, 9% yield) as an off-white solid. The fractions with a water layer were combined and the aqueous layer was saturated with NaCl and extracted with CHCl$_3$:IPA (9:1, 3×15 mL). The combined organic layers were dried over MgSO$_4$ and concentrated in vacuo to give more title compound (114 mg). The material was used without further purification. LCMS-ESI (pos) m/z: 246.1 (M+H)$^+$.

The compounds set forth in the following table were synthesized following the procedure in Example 140.0 using the known starting material as described.

TABLE 17

| Example | Reagents | Structure, Name and Data |
|---|---|---|
| 175.0 | (2S,3R)-3-(5-methoxypyrimidin-2-yl)butane-2-sulfonamide (Example 175.1), (R)-1,4-dioxane-2-carbohydrazide and (S)-1,4-dioxane-2-carbohydrazide (Frontier Scientific Services, Inc.), 2-isothiocyanato-1,3-dimethoxybenzene (Example 10.0). Example 175.0 was the first peak (earlier peak vs. its opposite dioxane epimer) on AD-H column. Peak assignment was determined by SFC: Chiralpak AD-H, 40% IPA/CO$_2$. | 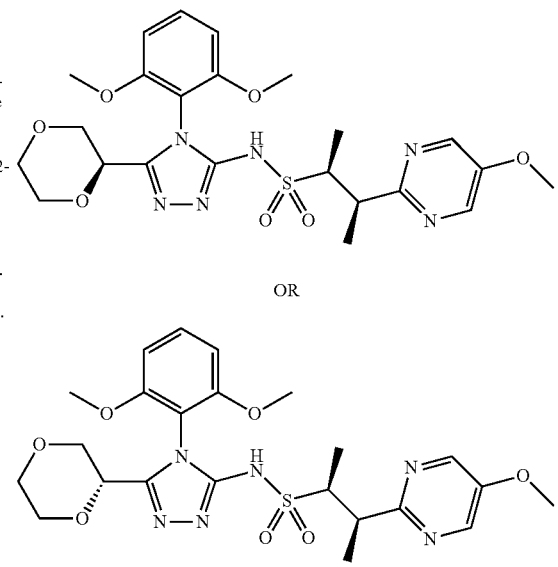<br>OR<br>(2S,3R)-N-(4-(2,6-diamethoxyphenyl)-5-((2R)-1,4-dioxan-2-yl)-4H-1,2,4-triazol-3-yl)-3-(5-methoxy-2-pyrimidinyl)-2-butanesulfonamide or (2S,3R)-N-(4-(2,6-dimethoxyphenyl)-5-((2S)-1,4-dioxan-2-yl)-4H-1,2,4-triazol-3-yl)-3-(5-methoxy-2-pyrimidinyl)-2-butanesulfonamide. $^1$H NMR (400 MHz, CDCl$_3$) δ 1.30 (d, J = 7.05 Hz, 3 H) 1.35 (d, J = 6.84 Hz, 3 H) 3.54-3.62 (m, 1 H) 3.68-3.89 (m, 13 H) 3.90 (s, 3 H) 4.29 (dd, J = 8.29, 3.32 Hz, 1 H) 6.65 (dd, J = 8.50, 3.32 Hz, 2 H) 7.41 (t, J = 8.50 Hz, 1 H) 8.36 (s, 2 H) 11.13 (br. s., 1 H). LCMS-ESI (pos) m/z: 535.2 (M + H)$^+$. |
| 176.0 | (2S,3R)-3-(5-methoxypyrimidin-2-yl)butane-2-sulfonamide (Example 175.1), (R)-1,4-dioxane-2-carbohydrazide and (S)-1,4-dioxane-2-carbohydrazide (Frontier Scientific Services, Inc.), 2-iosthiocyanato-1,3-dimethoxybenzene (Example 10.0). The title compound is the dioxane epimer of Example 175.0. The second peak (later peak vs. its dioxane epimer) on AD-H column. Peak assignment was determined by SFC: Chiralpak AD-H, 40% IPA/CO$_2$. | 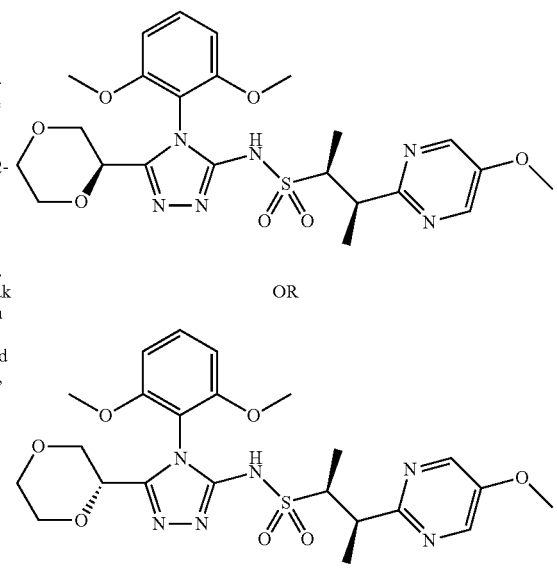<br>OR<br>(2S,3R)-N-(4-(2,6-dimethoxyphenyl)-5-((2R)-1,4-dioxan-2-yl)-4H-1,2,4-triazol-3-yl)-3-(5-methoxy-2-pyrimidinyl)-2-butanesulfonamide or (2S,3R)-N-(4-(2,6-dimethoxyphenyl)-5-((2S)-1,4-dioxan-2-yl)-4H-1,2,4-triazol-3-yl)-3-(5-methoxy-2-pyrimidinyl)-2-butanesulfonamide. $^1$H NMR (400 MHz, CDCl$_3$) δ 1.31 (d, J = 6.84 Hz, 3 H) 1.35 (d, J = 7.05 Hz, 3 H) 3.54-3.60 (m, 1 H) 3.67-3.88 (m, 13 H) 3.89 (s, 3 H) 4.28 (dd, J = 8.19, 3.42 Hz, 1 H) 6.63 (d, J = 8.50 Hz, 1 H) 6.66 (d, J = 8.50 Hz, 1 |

TABLE 17-continued

| Example | Reagents | Structure, Name and Data |
|---|---|---|
| | | H) 7.38 (s, 1 H) 7.40 (s, 1 H) 7.42 (s, 1 H) 8.35 (s, 2 H) 11.24 (br. s., 1 H). LCMS-ESI (pos) m/z: 535.2 (M + H)+. |
| 177.0 | (2S,3R)-3-(5-methoxypyrimidin-2-yl)butane-2-sulfonamide (Example 175.1), (R)-1,4-dioxane-2-carbohydrazide and (S)-1,4-dioxane-2-carbohydrazide (Frontier Scientific Services, Inc.), 5-isothiocyanato-4,6-dimethoxypyrimidine (Example 10.1). The title compound was the first peak (earlier peak vs. its opposite dioxane epimer) on AD-H column. Peak assignment was determined by SFC: Chiralpak AD-H, 35% IPA/CO$_2$. | 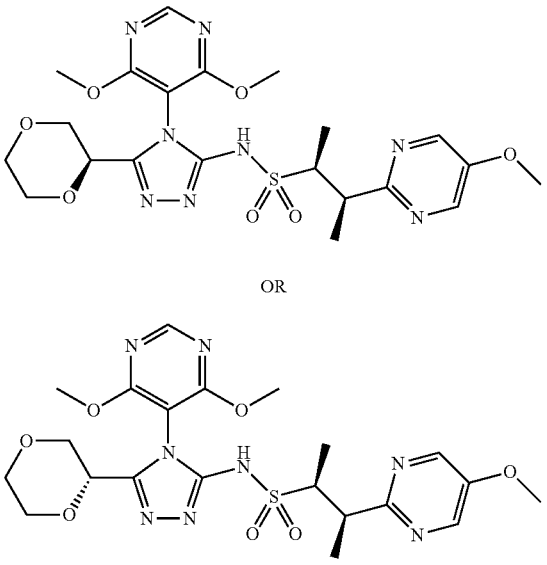<br>OR<br>(2S,3R)-N-(4-(4,6-dimethoxy-5-pyrimidinyl)-5-((2R)-1,4-dioxan-2-yl)-4H-1,2,4-triazol-3-yl)-3-(5-methoxy-2-pyrimidinyl)-2-butanesulfonamide or (2S,3R)-N-(4-(4,6-dimethoxy-5-pyrimidinyl)-5-((2S)-1,4-dioxan-2-yl)-4H-1,2,4-triazol-3-yl)-3-(5-methoxy-2-pyrimidinyl)-2-butanesulfonamide. $^1$H NMR (400 MHz, CDCl$_3$) δ 1.32 (d, J = 7.05 Hz, 3 H) 1.37 (d, J = 7.05 Hz, 3 H) 3.51-3.58 (m, 1 H) 3.62-3.77 (m, 4 H) 3.79-3.87 (m, 1 H) 3.90 (s, 3 H) 3.94 (d, J = 5.60 Hz, 2 H) 3.98 (s, 3 H) 4.00 (s, 3 H) 4.35 (t, J = 5.49 Hz, 1 H) 8.35 (s, 2 H) 8.50 (s, 1 H) 11.24 (s, 1 H). LCMS-ESI (pos) m/z: 537.2 (M + H)+. |
| 178.0 | (2S,3R)-3-(5-methoxypyrimidin-2-yl)butane-2-sulfonamide (Example 175.1), (R)-1,4-dioxane-2-carbohydrazide and (S)-1,4-dioxane-2-carbohydrazide (Frontier Scientific Services, Inc.), 5-isothiocyanato-4,6-dimethoxypyrimidine (Example 10.1). The title compound is the dioxane epimer of Example 177.0. The second peak (later peak vs. its dioxane epimer) on Chiralpak AD-H column. Peak assignment was determined by SFC: Chiralpak AD-H, 35% IPA/CO$_2$. | 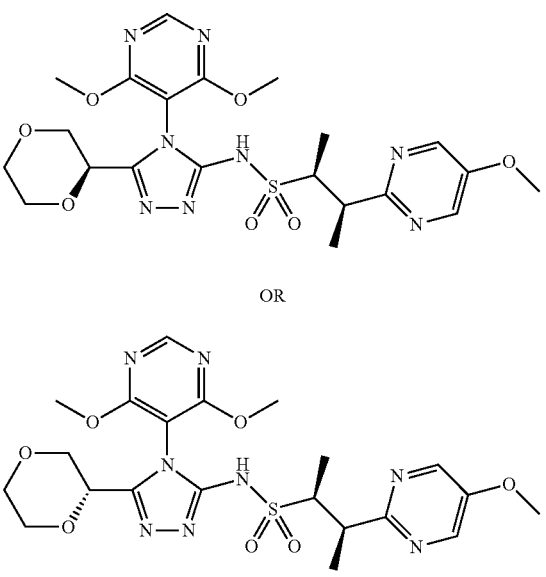<br>OR<br>(2S,3R)-N-(4-(4,6-dimethoxy-5-pyrimidinyl)-5-((2R)-1,4-dioxan-2-yl)-4H-1,2,4-triazol-3-yl)-3-(5-methoxy-2-pyrimidinyl)-2-butanesulfonamide or (2S,3R)-N-(4-(4,6-dimethoxy-5-pyrimidinyl)-5-((2S)-1,4-dioxan-2-yl)-4H-1,2,4-triazol-3-yl)-3-(5- | methoxy-2-pyrimidinyl)-2-butanesulfonamide. $^1$H NMR (400 MHz, CDCl$_3$) δ 1.34 (d, J = 6.84 Hz, 3 H) 1.37 (d, J = 7.05 Hz, 3 H) 3.51-3.58 (m, 1 H) 3.62-3.75 (m, 4 H) 3.78-3.85 (m, 1 H) 3.90 (s, 3 H) 3.94-3.97 (m, 2 H) 3.98 (s, 3 H) 4.00 (s, 3 H) 4.36 (dd, J = 6.32, 4.87 Hz, 1 H) 8.36 (s, 2 H) 8.50 (s, 1 H) 11.36 (s, 1 H). LCMS-ESI (pos) m/z: 537.2 (M + H)$^+$.

Example 179.0. Preparation of (3R,5S)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3R,5S)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide

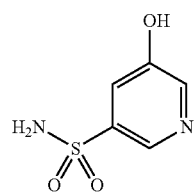

179.1

5-Hydroxypyridine-3-sulfonamide, Example 179.1

To a 100-mL round-bottomed flask was added 5-bromopyridine-3-sulfonamide (commercially available from Enamine, Kiev, Ukraine, 0.486 g, 2.05 mmol), 2-di-t-butyl-phosphino-3,4,5,6-tetramethyl-2',4',6'-tri-i-isopropylbiphenyl (commercially available from Strem Chemicals, Inc., MA, USA, 0.079 g, 0.16 mmol) and Pd$_2$(dba)$_3$ (Sigma-Aldrich Chemical Company, Inc., 0.038 g, 0.041 mmol). The flask was placed under vacuum and back-filled with potassium hydroxide (0.345 g, 6.15 mmol) solution in dioxane (5 mL) and water (5 mL). The reaction mixture was then stirred at 100° C. under N$_2$ for 17 h. LCMS analysis indicated that the reaction was complete. The reaction mixture was allowed to cool to RT. The reaction mixture was diluted with 1 N HCl and washed with Et$_2$O. The aqueous phase was concentrated in vacuo to afford the title compound 179.1 (0.387 g, 2.22 mmol, 100% yield) as a white solid, which was directly used in the next step without further purification. LCMS-ESI (pos), m/z: 175.1 (M+H)$^+$.

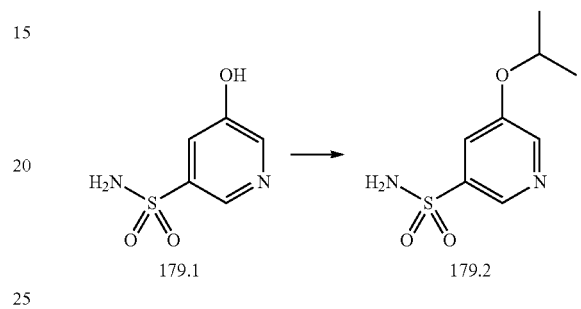

5-Isopropoxypyridine-3-sulfonamide, Example 179.2

To a suspension of 5-hydroxypyridine-3-sulfonamide, Example 179.1 (1.1 g, 6.32 mmol) in THF (16 mL) and IPA (16 mL) was added triphenylphosphine (1.99 g, 7.58 mmol). The mixture was bubbled with argon for 3 min before diisopropyl azodicarboxylate (1.49 mL, 7.58 mmol) was added dropwise at 0° C. under a stream of N$_2$. The reaction was then stirred at 0° C. to RT for 15 h. The reaction mixture was then concentrated in vacuo. The material thus obtained was absorbed onto a plug of silica gel and purified by chromatography through a RediSep-Sep pre-packed silica gel column (40 g), eluting with a gradient of 0% to 100% EtOAc in heptane, to provide the enriched product fractions, which were combined and extracted with 1N HCl. The desired product was enriched in acidic aqueous solution, which was then modified by saturated aqueous NaHCO$_3$ to pH>8. The basic aqueous solution was then extracted with DCM. The organic extract was washed with brine and dried over Na$_2$SO$_4$. The solution was filtered and concentrated in vacuo to give Example 179.2, 5-isopropoxypyridine-3-sulfonamide (0.95 g, 70% yield) as a white solid. LCMS-ESI (pos), m/z: 217.2 (M+H)$^+$.

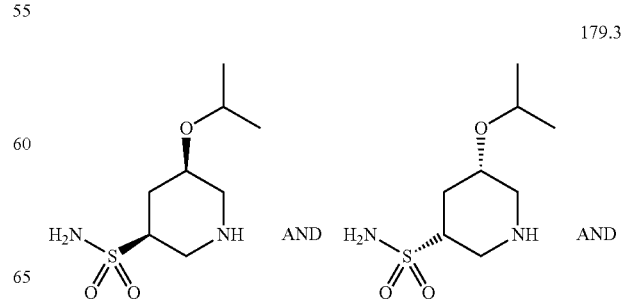

179.3

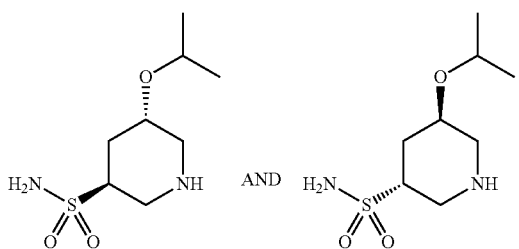

(3S,5R)-5-Isopropoxypiperidine-3-sulfonamide and (3R,5R)-5-isopropoxypiperidine-3-sulfonamide and (3S,5S)-5-isopropoxypiperidine-3-sulfonamide and (3R,5S)-5-isopropoxypiperidine-3-sulfonamide, Example 179.3

A solution of 5-isopropoxypyridine-3-sulfonamide, Example 179.2, (1.8 g, 8.32 mmol) in AcOH (41.6 mL) was bubbled with argon gas for 2 min before platinum (IV) oxide (1.89 g, 8.32 mmol) was added under a stream of argon. The reaction mixture was then stirred at 23° C. under 45 psi of hydrogen gas for 2 d. Next, Celite® brand filter agent (5 g) was added to the reaction mixture. The mixture was then stirred at RT for 10 min. The mixture was filtered and the solution was concentrated in vacuo to give the product mixture as a light yellow oil, which was used without further purification in the next step. LCMS-ESI (pos), m/z: 223.3 (M+H)+.

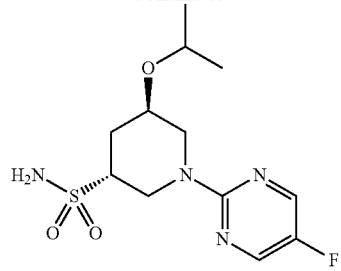

(3R,5R)-1-(5-Fluoropyrimidin-2-yl)-5-isopropoxypiperidine-3-sulfonamide and (3S,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide, Example 179.4

To a 40 mL vial (with pressure release septa) was added Example 179.3 (2.0 g, 4.96 mmol) and 2-chloro-5-fluoropyrimidine (3.29 g, 24.79 mmol). The reaction mixture was stirred at 90° C. for 21 h. LCMS indicated the reaction was complete. The reaction mixture was then concentrated in vacuo. The material thus obtained was absorbed onto a plug of silica gel and purified by chromatography through a RediSep-Sep pre-packed silica gel column (40 g), eluting with a gradient of 0% to 100% EtOAc in heptane, to provide Example 179.4, as a mixture of diastereomers (0.5 g, 1.6 mmol, 32% yield) as off-white solid. LCMS-ESI (pos), m/z: 319.2 (M+H)+.

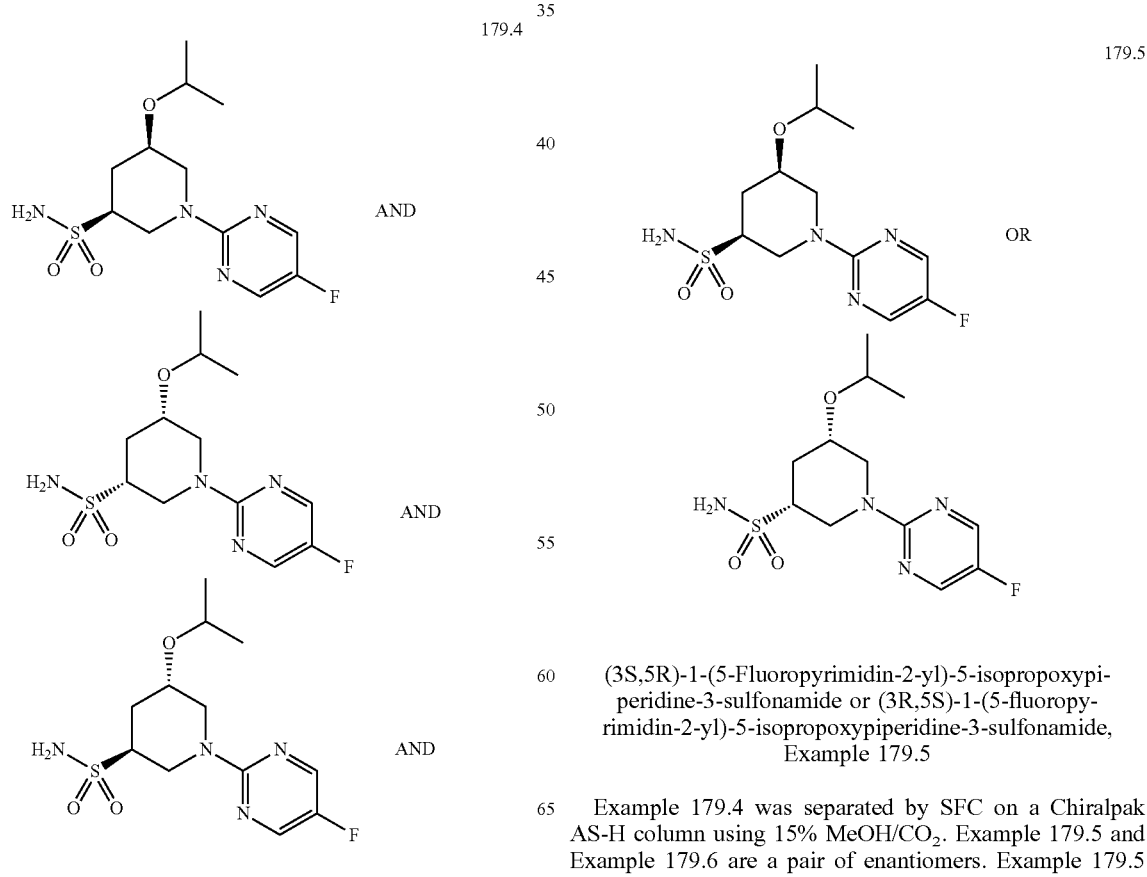

(3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 179.5

Example 179.4 was separated by SFC on a Chiralpak AS-H column using 15% MeOH/CO$_2$. Example 179.5 and Example 179.6 are a pair of enantiomers. Example 179.5 was the second peak among 4 isomers (earlier peak vs. its opposite enantiomer) on AS-H column ¹H NMR (400 MHz, CD₃OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos) m/z: 319.2 (M+H)⁺.

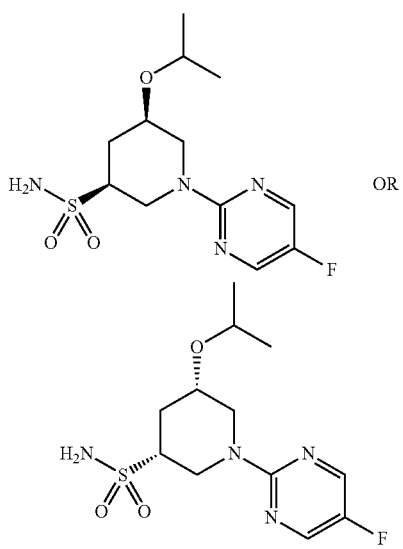

179.6

(3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 179.6

Further elution under the conditions described in Example 179.5 gave Example 179.6 as the third peak. ¹H NMR (400 MHz, CD₃OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos) m/z: 319.2 (M+H)⁺.

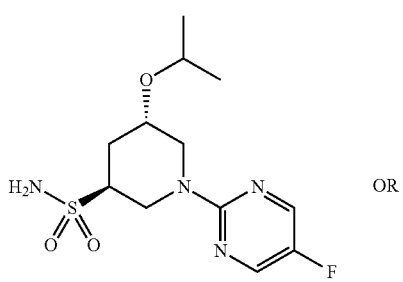

179.7

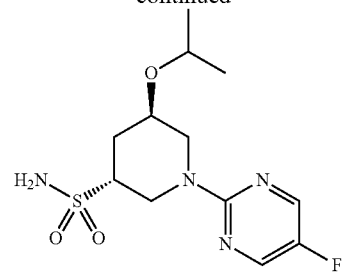

(3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 179.7

Examples 179.7 and 179.8 are a pair of enantiomers. Example 179.7 was the first peak to elute among 4 isomers (earlier peak vs. its opposite enantiomer) on an AS-H column under conditions described in Example 179.5. ¹H NMR (400 MHz, CD₃OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos) m/z: 319.2 (M+H)⁺.

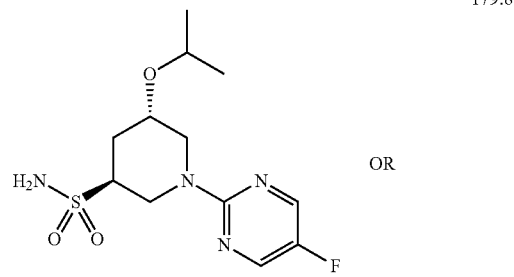

179.8

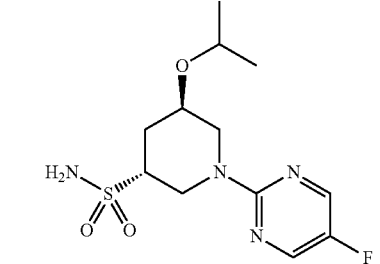

(3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 179.8

Further elution under the conditions described in Example 179.5 gave Example 179.8 as the fourth peak. ¹H NMR (400 MHz, CD₃OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos) m/z: 319.2 (M+H)⁺.

The compounds set forth in the following table were synthesized following the procedure in Example 140.0 using the known starting material as described.

TABLE 18

| Example | Reagents | Structure, Name and Data |
|---|---|---|
| 179.0 | (3S,5R)-1-(5-fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 179.5, (R)-1,4-dioxane-2-carbohydrazide and (S)-1,4-dioxane-2-carbohydrazide (Frontier Scientific Services, Inc.), 5-isothiocyanato-4,6-dimethoxypyrimidine (Example 10.1). The title compound is the dioxane epimer of Example 180.0. Example 179.0 was the first peak (earlier peak vs. its opposite dioxane epimer) on AD-H column. Peak assignment was determined by SFC: Chiralpak AD-H, 25% IPA/CO2, with 0.2% DEA. Note: DEA was used in the preparative purification. Poor separation was observed when it was absent. The order of elution was reversed when DEA is present. | 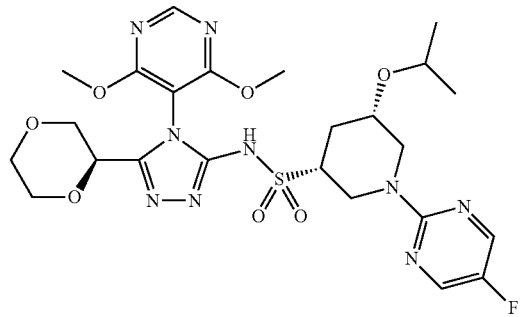 [SMILES: COc1ncnc(OC)c1-n1c(NS(=O)(=O)[C@@H]2C[C@H](OC(C)C)CN(c3ncc(F)cn3)C2)nnc1[C@@H]1COCCO1]<br>OR<br>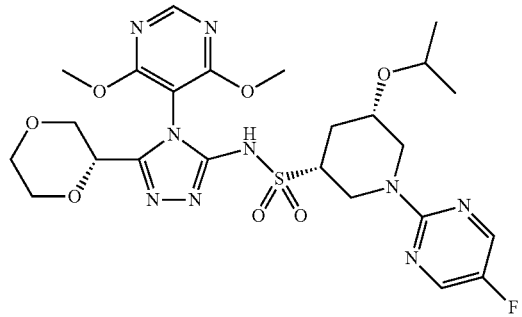 [SMILES: COc1ncnc(OC)c1-n1c(NS(=O)(=O)[C@@H]2C[C@H](OC(C)C)CN(c3ncc(F)cn3)C2)nnc1[C@H]1COCCO1]<br>OR<br>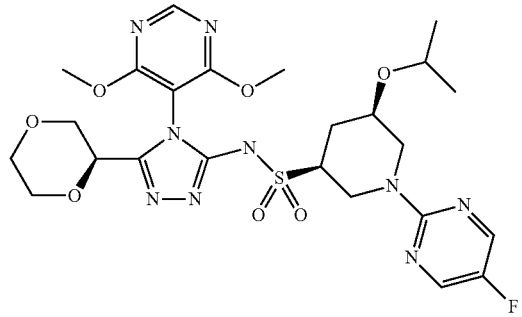 [SMILES: COc1ncnc(OC)c1-n1c(NS(=O)(=O)[C@H]2C[C@@H](OC(C)C)CN(c3ncc(F)cn3)C2)nnc1[C@@H]1COCCO1]<br>OR<br>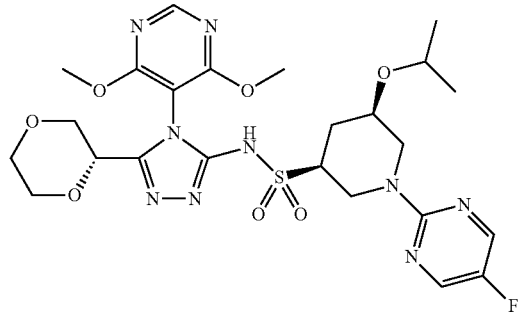 [SMILES: COc1ncnc(OC)c1-n1c(NS(=O)(=O)[C@H]2C[C@@H](OC(C)C)CN(c3ncc(F)cn3)C2)nnc1[C@H]1COCCO1]<br>(3R,5S)-N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-4-(1-methylethoxy)-3-piperidinesulfonamide or (3R,5S)-N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)-N-(4-(4,6- |

| Example | Reagents | Structure, Name and Data |
|---|---|---|
| | | dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)-N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide. $^1$H NMR (400 MHz, CD$_3$OD) δ 1.16 (d, J = 6.01 Hz, 3 H) 1.18 (d, J = 6.22 Hz, 3 H) 1.54-1.64 (m, 1 H) 2.43-2.53 (m, 2 H) 2.78-2.85 (m, 1 H) 3.07-3.15 (m, 1 H) 3.39-3.47 (m, 1 H) 3.50-3.61 (m, 2 H) 3.61-3.70 (m, 2 H) 3.82 (dt, J = 12.18, 6.04 Hz, 1 H) 3.89-3.98 (m, 2 H) 4.04 (s, 3 H) 4.06 (s, 3 H) 4.46 (dd, J = 7.26, 3.52 Hz, 1 H) 4.83-4.89 (m, 1 H) 5.03-5.09 (m, 1 H) 8.30 (s, 2 H) 8.58 (s, 1 H). LCMS-ESI (pos) m/z: 610.2 (M + H)$^+$. |
| 180.0 | (3S,5R)-1-(5-fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 179.5, (R)-1,4-dioxane-2-carbohydrazide and (S)-1,4-dioxane-2-carbohydrazide (Frontier Scientific Services, Inc.), 5-isothiocyanato-4,6-dimethoxypyrimidine (Example 10.1). The title compound is the dioxane epimer of Example 179.0. The second peak (later peak vs. its dioxane epimer) on AD-H column. Peak assignment was determined by SFC: Chiralpak AD-H, 25% IPA/CO$_2$, with 0.2% DEA. Note: DEA was used in the prep purification. Poor separation was observed when it was absent. The order of elution was reversed when DEA is present. | 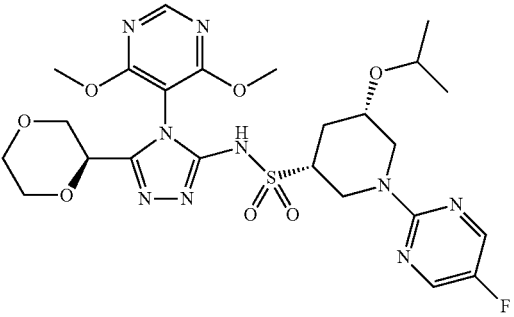 [SMILES: COc1ncnc(OC)c1-n1c(NS(=O)(=O)[C@@H]2C[C@H](OC(C)C)CN(c3ncc(F)cn3)C2)nnc1[C@@H]1COCCO1]

OR

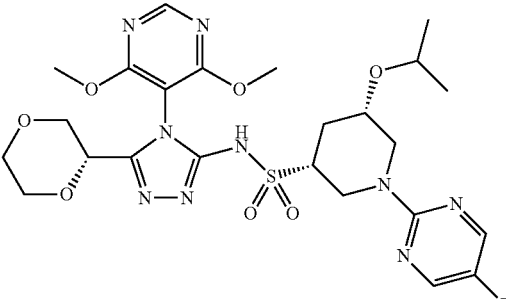

OR

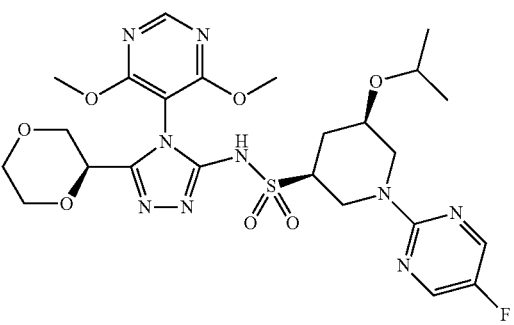 [SMILES: COc1ncnc(OC)c1-n1c(NS(=O)(=O)[C@H]2C[C@@H](OC(C)C)CN(c3ncc(F)cn3)C2)nnc1[C@@H]1COCCO1]

OR |

TABLE 18-continued

| Example | Reagents | Structure, Name and Data |
|---|---|---|
| | | 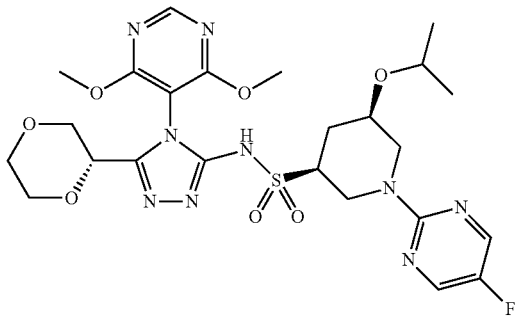 [SMILES: COc1ncnc(OC)c1-n1c(NS(=O)(=O)[C@H]2C[C@@H](OC(C)C)CN(c3ncc(F)cn3)C2)nnc1[C@H]1COCCO1]<br><br>(3R,5S)-N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3R,5S)-N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)-N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide (3S,5R)-N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide. $^1$H NMR (400 MHz, CD$_3$OD) δ 1.16 (d, J = 6.01 Hz, 3 H) 1.18 (d, J = 6.22 Hz, 3 H) 1.55-1.65 (m, 1 H) 2.44-2.53 (m, 2 H) 2.82 (dd, J = 12.85, 11.40 Hz, 1 H) 3.06-3.14 (m, 1 H) 3.40-3.48 (m, 1 H) 3.50-3.70 (m, 4 H) 3.80-3.99 (m, 3 H) 4.04 (s, 3H) 4.06 (s, 3 H) 4.46 (dd, J = 7.36, 3.42 Hz, 1 H) 4.84-4.91 (m, 1 H) 5.04-5.10 (m, 1 H) 8.30 (s, 2 H) 8.58 (s, 1 H). LCMS-ESI (pos) m/z: 610.2 (M + H)$^+$. |
| 181.0 | (3S,5R)-1-(5-fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 179.5, (R)-1,4-dioxane-2-carbohdrazide and (S)-1,4-dioxane-2-carbohydrazide (Frontier Scientific Services, Inc.), 2-isothiocyanato-1,3-dimethoxybenzene (Example 10.0). The title compound is the dioxane epimer of Example 182.0. Example 181.0 was the first peak (earlier peak vs. its opposite dioxane epimer) on AD-H column. Peak assignment was determined by SFC: Chiralpak AD-H, 35% IPA/CO$_2$, with 0.2% DEA. Note: DEA was used in the prep purification. Poor separation was observed when it was absent. | 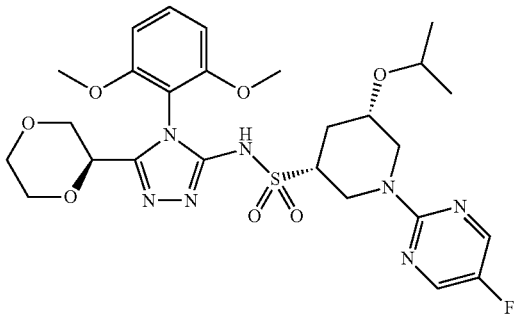 [SMILES: COc1cccc(OC)c1-n1c(NS(=O)(=O)[C@@H]2C[C@H](OC(C)C)CN(c3ncc(F)cn3)C2)nnc1[C@@H]1COCCO1]<br>OR<br>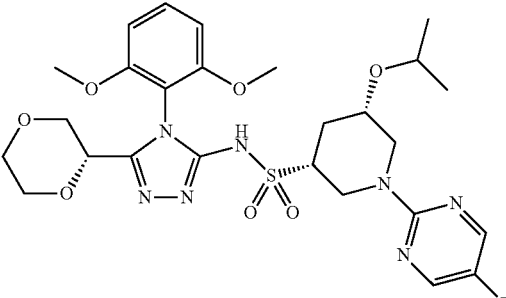<br>OR |

| Example | Reagents | Structure, Name and Data |
|---------|----------|--------------------------|

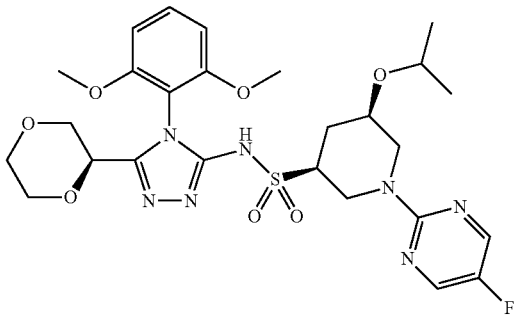 [SMILES: COc1cccc(OC)c1-n1c(NS(=O)(=O)[C@H]2C[C@@H](OC(C)C)CN(c3ncc(F)cn3)C2)nnc1[C@@H]1COCCO1]

OR

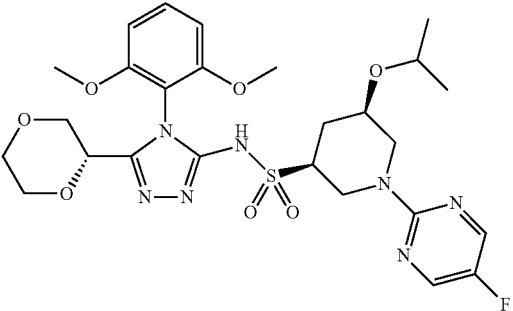 [SMILES: COc1cccc(OC)c1-n1c(NS(=O)(=O)[C@H]2C[C@@H](OC(C)C)CN(c3ncc(F)cn3)C2)nnc1[C@H]1COCCO1]

(3R,5S)-N-(4-(2,6-dimethoxyphenyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3R,5S)-N-(4-(2,6-dimethoxyphenyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)-N-(4-(2,6-dimethoxyphenyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)-N-(4-(2,6-dimethoxyphenyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide. $^1$H NMR (400 MHz, CD$_3$OD) δ 1.15 (d, J = 6.01 Hz, 3 H) 1.18 (d, J = 6.01 Hz, 3 H) 1.53-1.63 (m, 1 H) 2.42-2.50 (m, 2 H) 2.80 (dd, J = 12.85, 11.40 Hz, 1 H) 3.03-3.11 (m, 1 H) 3.37-3.52 (m, 2 H) 3.55-3.73 (m, 3 H) 3.77-3.91 (m, 9 H) 4.28 (dd, J = 7.26, 4.35 Hz, 1 H) 4.83-4.88 (m, 1 H) 5.02-5.08 (m, 1 H) 6.85 (d, J = 8.54 Hz, 2 H) 7.53 (t, J = 8.50 Hz, 1 H) 8.29 (s, 2 H). LCMS-ESI (pos) m/z: 608.2 (M + H)$^+$.

TABLE 18-continued

| Example | Reagents | Structure, Name and Data |
|---|---|---|
| 182.0 | (3S,5R)-1-(5-fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 179.5, (R)-1,4-dioxane-2-carbohydrazide and (S)-1,4-dioxane-2-carbohydrazide (Frontier Scientific Services, Inc.), 2-isothiocyanato-1,3-dimethoxybenzene (Example 10.0). The title compound is the dioxane epimer of Example 181.0. The second peak (later peak vs. its dioxane epimer) on AD-H column. Peak assignment was determined by SFC: Chiralpak AD-H, 35% IPA/CO$_2$. | 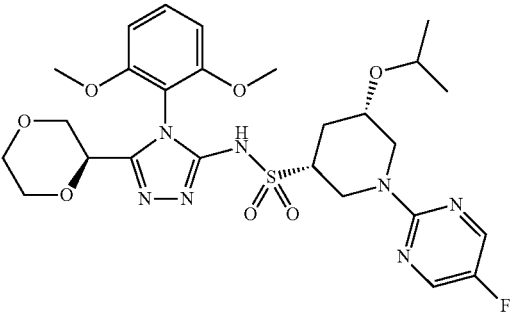 [SMILES: COc1cccc(OC)c1-n1c(NS(=O)(=O)[C@@H]2C[C@H](OC(C)C)CN(c3ncc(F)cn3)C2)nnc1[C@@H]1COCCO1]<br>OR<br>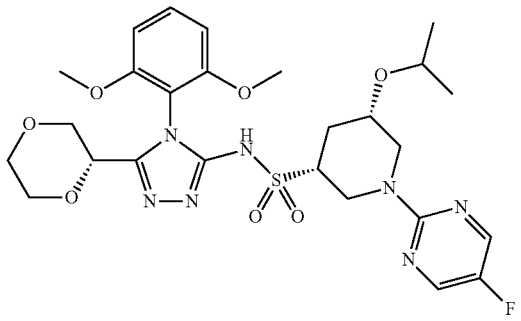 [SMILES: COc1cccc(OC)c1-n1c(NS(=O)(=O)[C@@H]2C[C@H](OC(C)C)CN(c3ncc(F)cn3)C2)nnc1[C@H]1COCCO1]<br>OR<br>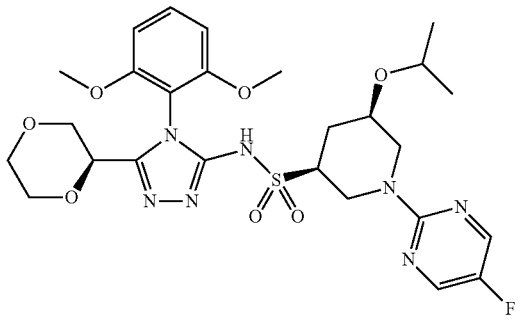 [SMILES: COc1cccc(OC)c1-n1c(NS(=O)(=O)[C@H]2C[C@@H](OC(C)C)CN(c3ncc(F)cn3)C2)nnc1[C@@H]1COCCO1]<br>OR<br>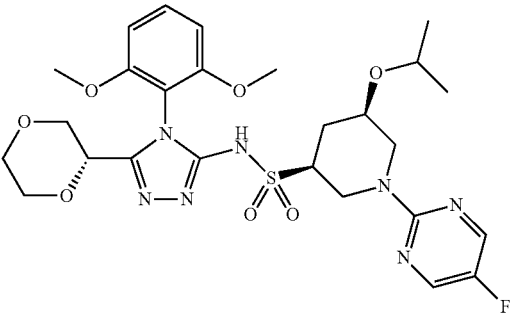<br>(3R,5S)-N-(4-(2,6-dimethoxyphenyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3R,5S)-N-(4-(2,6-dimethoxyphenyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)-N-(4-(2,6-dimethoxyphenyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)-N-(4-(2,6- |

TABLE 18-continued

| Example | Reagents | Structure, Name and Data |
|---|---|---|
| | | dimethoxyphenyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide. $^1$H NMR (400 MHz, CD$_3$OD) δ 1.16 (d, J = 6.22 Hz, 3 H) 1.18 (d, J = 6.01 Hz, 3 H) 1.58-1.65 (m, 1 H) 2.48 (dd, J = 12.85, 10.57 Hz, 2 H) 2.81 (dd, J = 12.85, 11.40 Hz, 1 H) 3.07 (tt, J = 12.00, 3.76 Hz, 1 H) 3.38-3.51 (m, 2 H) 3.55-3.62 (m, 1 H) 3.62-3.68 (m, 1 H) 3.68-3.73 (m, 1 H) 3.78-3.91 (m, 9 H) 4.28 (dd, J = 6.63, 4.77 Hz, 1 H) 4.82-4.91 (m, 1 H) 5.02-5.08 (m, 1 H) 6.85 (dd, J = 8.50, 3.94 Hz, 2 H) 7.53 (t, J = 8.50 Hz, 1 H) 8.29 (s, 2 H). LCMS-ESI (pos) m/z: 608.2 (M + H)$^+$. |
| 183.0 | (2S,3R)-3-(5-methylpyrimidin-2-yl)butane-2-sulfonamide (Example 1.0), (S)-tetrahydrothiophene-3-carbohydrazide 1,1-dioxide and (R)-tetrahydrothiophene-3-carbohydrazide 1,1-dioxide (commercially available from Enamine), 2-isothiocyanato-1,3-dimethoxybenzene (Example 10.0). The mixture was purified by preparative SFC using the following methodology: Column: AS-H (2 × 25 cm) Mobile Phase: 70:30 (A:B) A: Liquid CO$_2$, B: MeOH, Flow Rate: 80 mL/min, 220 nm, 100 bar inlet pressure to deliver peak 1. | 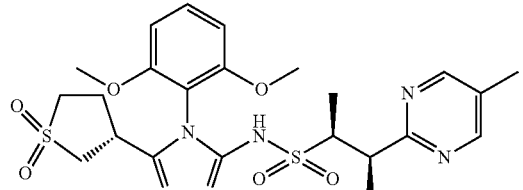<br><br>OR<br><br><br><br>(2S,3R)-N-(4-(2,6-dimethoxyphenyl)-5-((R)-1,1-dioxidotetrahydrothiophen-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-1,1-dioxidotetrahydrothiophen-3-yl)-4H-1,2,4-triazol-3-yl)-3-(5-methylpyrimidin-2-yl)butane-2-sulfonamide. $^1$H NMR (400 MHz, CD$_2$Cl$_2$) δ 11.21 (br. s., 1H), 8.50 (d, J = 0.6 Hz, 2H), 7.55-7.48 (m, 1H), 6.76-6.71 (m, 2H), 3.82 (s, 3H), 3.80 (s, 3H), 3.77-3.70 (m, 1H), 3.64-3.57 (m, 1H), 3.33-3.21 (m, 3H), 3.12-3.06 (m, 1H), 3.02-2.93 (m, 1H), 2.52-2.43 (m, 1H), 2.41-2.34 (m, 1H), 2.27 (s, 3H), 1.30 (d, J = 7.0 Hz, 3H), 1.25 (d, J = 7.0 Hz, 3H). LCMS (pos) m/z: 551.2 (M + H)$^+$. |

TABLE 18-continued

| Example | Reagents | Structure, Name and Data |
|---|---|---|
| 184.0 | (2S,3R)-3-(5-methylpyrimidin-2-yl)butane-2-sulfonamide (Exampe 1.0), (S)-tetrahydrothiophene-3-carbohydrazide 1,1-dioxide and (R)-tetrahydrothiophene-3-carbohydrazide 1,1-dioxide (commercially available from Enamine), 2-isothiocyanato-1,3-dimethoxybenzene (Example 10.0). The mixture was purified by preparative SFC using the following methodology: Column: AS-H (2 × 25 cm) Mobile Phase: 70:30 (A:B) A: Liquid $CO_2$, B: MeOH, Flow Rate: 80 mL/min, 220 nm, 100 bar inlet pressure to deliver peak 2. | 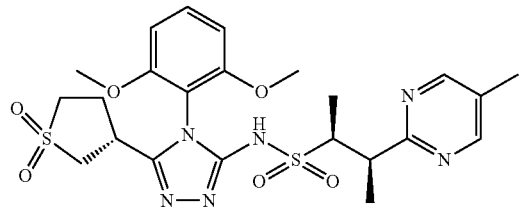 [SMILES: COc1cccc(OC)c1-n1c(NS(=O)(=O)[C@@H](C)[C@H](C)c2ncc(C)cn2)nnc1[C@H]1CCS(=O)(=O)C1]<br><br>OR<br><br>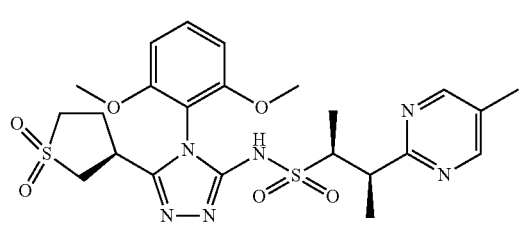 [SMILES: COc1cccc(OC)c1-n1c(NS(=O)(=O)[C@@H](C)[C@H](C)c2ncc(C)cn2)nnc1[C@@H]1CCS(=O)(=O)C1]<br><br>(2S,3R)-N-(4-(2,6-dimethoxyphenyl)-5-((R)-1,1-dioxidotetrahydrothiophen-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-1,1-dioxidotetrahydrothiophen-3-yl)-4H-1,2,4-triazol-3-yl)-3-(5-methylpyrimidin-2-yl)butane-2-sulfonamide. $^1$H NMR (400 MHz, $CD_2Cl_2$) δ 11.23 (br. s., 1H), 8.51 (s, 2H), 7.55-7.49 (m, 1H), 6.74 (dd, J = 2.0, 8.6 Hz, 2H), 3.82 (s, 3H), 3.81 (s, 3H), 3.76-3.70 (m, 1H), 3.64-3.57 (m, 1H), 3.34-3.21 (m, 3H), 3.14-3.06 (m, 1H), 2.97 (dddd, J = 0.8, 7.9, 9.2, 13.4 Hz, 1H), 2.50-2.42 (m, 1H), 2.42-2.34 (m, 1H), 2.27 (s, 3H), 1.31 (d, J = 7.0 Hz, 3H), 1.26 (d, J = 7.0 Hz, 3H). LCMS (pos) m/z: 551.2 (M + H)$^+$. |
| 185.0 | (1R,2S)-1-methoxy-1-(5-methylpyrazin-2-yl)propane-2-sulfonamide (Example 11.1), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: AD-H (2 × 25 cm) Mobile Phase: 75:25 (A:B) A: Liquid $CO_2$, B: IPA, Flow Rate: 80 mL/min, 215 nm, 100 bar inlet pressure to deliver peak 1. | 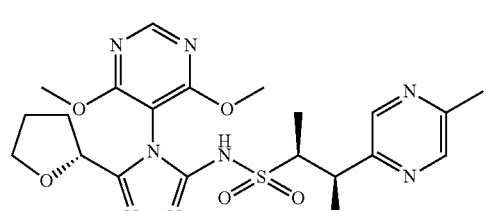<br><br>OR<br><br>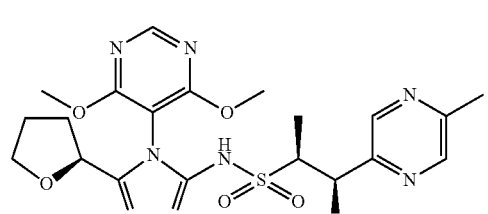<br><br>(1R,2S)-N-(4-(4,6-dimethoxypyrimidin-5-yl)-5-((S)-tetrahydrofuran-2-yl)-4H-1,2,4-triazol-3-yl)-1-methoxy-1-(5-methylpyrazin-2-yl)propane-2-sulfonamide or (1R,2S)-N-(4-(4,6-dimethoxypyrimidin-5-yl)-5-((R)-tetrahydrofuran-2-yl)-4H-1,2,4-triazol-3-yl)-1-methoxy-1-(5-methylpyrazin-2-yl)propane-2-sulfonamide. $^1$H NMR (400 MHz, $CD_2Cl_2$) δ 11.01 (br. s., 1H), 8.51 (s, 1H), 8.50 (d, J = 1.5 Hz, 1H), 8.41 (d, J = 1.0 Hz, 1H), 4.96 (d, J = 2.7 |

| Example | Reagents | Structure, Name and Data |
|---|---|---|
| | | Hz, 1H), 4.68 (dd, J = 5.0, 7.7 Hz, 1H), 4.00 (s, 3H), 3.99 (s, 3H), 3.74 (dt, J = 6.0, 7.9 Hz, 1H), 3.63 (td, J = 7.1, 8.1 Hz, 1H), 3.42-3.35 (m, 1H), 3.27 (s, 3H), 2.54 (s, 3H), 2.36 (dddd, J = 5.2, 6.4, 7.8, 12.8 Hz, 1H), 2.15-2.05 (m, 1H), 1.98-1.88 (m, 2H), 1.18-1.14 (m, 3H). LCMS (pos) m/z: 521.2 (M + H)$^+$. |
| 186.0 | (1R,2S)-1-methoxy-1-(5-methylpyrazin-2-yl)propane-2-sulfonamide (Example 11.1), (R)-tetrahydrofuran-2-carbohydrazide and (S)-tetrahydrofuran-2-carbohydrazide(commercially available from Enamine), 5-isothiocyanato-4,6-dimethoxypyrimidine (Example 10.1). The mixture was purified by preparative SFC using the following methodology: Column: AD-H (2 × 25 cm) Mobile Phase: 75:25 (A:B) A: Liquid $CO_2$, B: IPA, Flow Rate: 80 mL/min, 215 nm, 100 bar inlet pressure to deliver peak 2. | 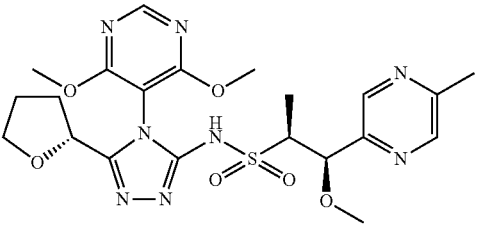 [SMILES: COc1ncnc(OC)c1-n1c(NS(=O)(=O)[C@@H](C)[C@H](OC)c2cnc(C)cn2)nnc1[C@H]1CCCO1]<br>OR<br>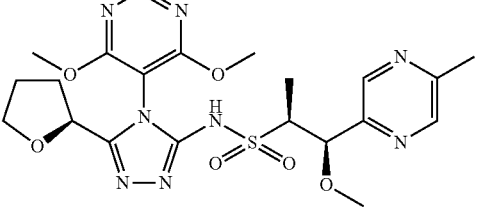<br>(1R,2S)-N-(4-(4,6-dimethoxypyrimidin-5-yl)-5-((S)-tetrahydrofuran-2-yl)-4H-1,2,4-triazol-3-yl)-1-methoxy-1-(5-methylpyrazin-2-yl)propane-2-sulfonamide or (1R,2S)-N-(4-(4,6-dimethoxypyrimidin-5-yl)-5-((R)-tetrahydrofuran-2-yl)-4H-1,2,4-triazol-3-yl)-1-methoxy-1-(5-methylpyrazin-2-yl)propane-2-sulfonamide. $^1$H NMR (400 MHz, $CD_2Cl_2$) δ 11.00 (br. s., 1H), 8.51 (s, 1H), 8.49 (d, J = 1.2 Hz, 1H), 8.40 (d, J = 1.0 Hz, 1H), 4.96 (d, J = 2.7 Hz, 1H), 4.67 (dd, J = 5.0, 7.7 Hz, 1H), 4.00-3.99 (m, 3H), 3.99 (s, 3H), 3.74 (dt, J = 6.0, 7.9 Hz, 1H), 3.66-3.59 (m, 1H), 3.42-3.34 (m, 1H), 3.28-3.24 (m, 3H), 2.53 (s, 3H), 2.35 (dddd, J = 5.2, 6.5, 7.9, 12.8 Hz, 1H), 2.15-2.05 (m, 1H), 1.99-1.87 (m, 2H), 1.17-1.14 (m, 3H). LCMS (pos) m/z: 521.2 (M + H)$^+$. |

US 9,988,369 B2

393                                                                                                                              394

TABLE 18-continued

| Example | Reagents | Structure, Name and Data |
|---|---|---|
| 187.0 | (1R,2S)-1-(5-chloropyrimidin-2-yl)-1-methoxypropane-2-sulfonamide (Example 11.3), (S)-tetrahydrothiophene-3-carbohydrazide 1,1-dioxide and (R)-tetrahydrothiophene-3-carbohydrazide 1,1-dioxide (commercially available from Enamine), 2-isothiocyanato-1,3-dimethoxybenzene (Example 10.0). The mixture was purified by preparative SFC using the following methodology: Column: AS-H (2 × 25 cm) Mobile Phase: 55:45 (A:B) A: Liquid $CO_2$, B: MeOH, Flow Rate: 80 mL/min, 215 nm, 100 bar inlet pressure to deliver peak 1. | 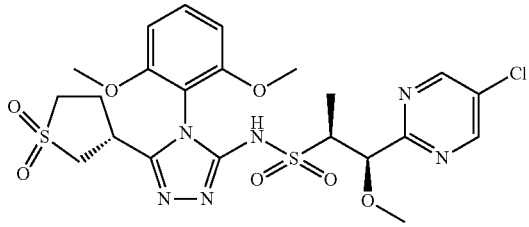 [SMILES: COc1cccc(OC)c1-n1c(NS(=O)(=O)[C@@H](C)[C@H](OC)c2ncc(Cl)cn2)nnc1[C@H]1CCS(=O)(=O)C1]<br>OR<br>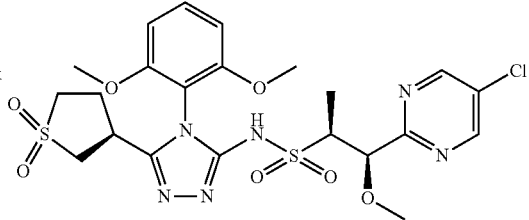<br><br>(1R,2S)-1-(5-chloropyrimidin-2-yl)-N-(4-(2,6-dimethoxyphenyl)-5-((R)-1,1-dioxidotetrahydrothiophen-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-1,1-dioxidotetrahydrothiophen-3-yl)-4H-1,2,4-triazol-3-yl)-1-methoxypropane-2-sulfonamide.<br>$^1$H NMR (400 MHz, $CD_2Cl_2$) δ 10.91 (br. s., 1H), 8.73-8.69 (m, 2H), 7.55-7.49 (m, 1H), 6.76 (s, 1H), 6.74 (s, 1H), 4.85 (d, J = 4.6 Hz, 1H), 3.83 (s, 3H), 3.82 (s, 3H), 3.57 (dq, J = 4.5, 7.0 Hz, 1H), 3.35-3.26 (m, 1H), 3.26-3.20 (m, 5H), 3.12-3.06 (m, 1H), 3.02-2.94 (m, 1H), 2.51-2.41 (m, 1H), 2.41-2.34 (m, 1H), 1.24 (d, J = 7.0 Hz, 3H). LCMS (pos) m/z: 587.0 (M + H)$^+$. |
| 188.0 | (1R,2S)-1-(5-chloropyrimidin-2-yl)-1-methoxypropane-2-sulfonamide (Example 11.3), (S)-tetrahydrothiophene-3-carbohydrazide 1,1-dioxide and (R)-tetrahydrothiophene-3-carbohydrazide 1,1-dioxide (commercially available from Enamine), 2-isothiocyanato-1,3-dimethoxybenzene (Example 10.0). The mixture was purified by preparative SFC using the following methodology: Column: AS-H (2 × 25 cm) Mobile Phase: 55:45 (A:B) A: Liquid $CO_2$, B: MeOH, Flow Rate: 80 mL/min, 215 nm, 100 bar inlet pressure to deliver peak 2. | 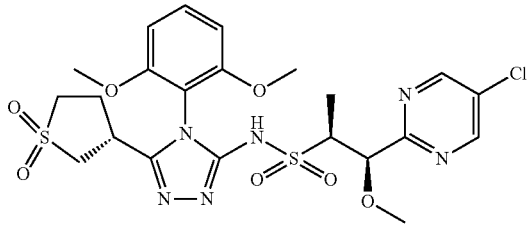 [SMILES: COc1cccc(OC)c1-n1c(NS(=O)(=O)[C@@H](C)[C@H](OC)c2ncc(Cl)cn2)nnc1[C@H]1CCS(=O)(=O)C1]<br>OR<br>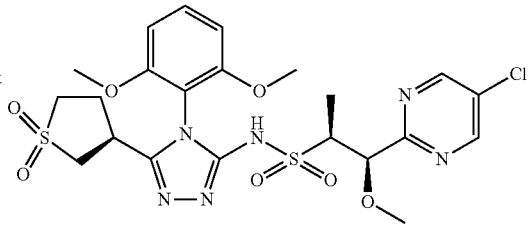<br><br>(1R,2S)-1-(5-chloropyrimidin-2-yl)-N-(4-(2,6-dimethoxyphenyl)-5-((R)-1,1-dioxidotetrahydrothiophen-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-1,1-dioxidotetrahydrothiophen-3-yl)-4H-1,2,4-triazol-3-yl)-1-methoxypropane-2-sulfonamide.<br>$^1$H NMR (400 MHz, $CD_2Cl_2$) δ 8.72-8.67 (m, |

TABLE 18-continued

| Example | Reagents | Structure, Name and Data |
|---|---|---|
| | | 2H), 7.56-7.48 (m, 1H), 6.76-6.73 (m, 2H), 4.86 (d, J = 4.6 Hz, 1H), 3.83 (s, 3H), 3.82 (s, 3H), 3.57 (dq, J = 4.6, 7.0 Hz, 1H), 3.35-3.27 (m, 1H), 3.27-3.19 (m, 5H), 3.13-3.06 (m, 1H), 2.98 (dddd, J = 0.8, 7.9, 9.2, 13.4 Hz, 1H), 2.51-2.42 (m, 1H), 2.41-2.34 (m, 1H), 1.24 (d, J = 7.0 Hz, 3H). LCMS (pos) m/z: 587.0 (M + H)$^+$. |
| 189.0 | (2S,3R)-3-(5-chloropyrimidin-2-yl)butane-2-sulfonamide (Example 1.4), (S)-tetrahydrothiophene-3-carbohydrazide 1,1-dioxide and (R)-tetrahydrothiophene-3-carbohydrazide 1,1-dioxide (commercially available from Enamine), 2-isothiocyanato-1,3-dimethoxybenzene (Example 10.0). The mixture was purified by preparative SFC using the following methodology: Column: AS-H (2 × 25 cm) Mobile Phase: 50:50 (A:B) A: Liquid CO$_2$, B: MeOH, Flow Rate: 80 mL/min, 215 nm, 100 bar inlet pressure to deliver peak 1. | 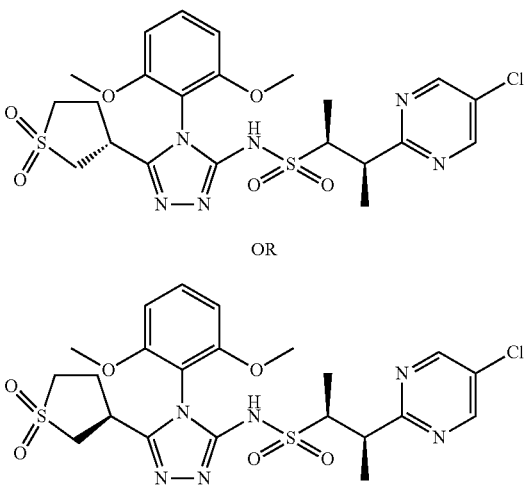<br><br>(2S,3R)-3-(5-chloropyrimidin-2-yl)-N-(4-(2,6-dimethoxyphenyl)-5-((R)-1,1-dioxidotetrahydrothiophen-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-1,1-dioxidotetrahydrothiophen-3-yl)-4H-1,2,4-triazol-3-yl)butane-2-sulfonamide. $^1$H NMR (400 MHz, CD$_2$Cl$_2$) δ 10.87 (br. s., 1H), 8.66-8.60 (m, 2H), 7.55-7.49 (m, 1H), 6.77-6.71 (m, 2H), 3.83 (s, 3H), 3.81 (s, 3H), 3.74-3.62 (m, 2H), 3.33-3.20 (m, 3H), 3.12-3.06 (m, 1H), 3.02-2.93 (m, 1H), 2.50-2.34 (m, 2H), 1.31 (d, J = 6.8 Hz, 3H), 1.26 (d, J = 6.8 Hz, 3H). LCMS (pos) m/z: 571.0 (M + H)$^+$. |
| 190.0 | (2S,3R)-3-(5-chloropyrimidin-2-yl)butane-2-sulfonamide (Example 1.4), (S)-tetrahydrothiophene-3-carbohydrazide 1,1-dioxide and (R)-tetrahydrothiophene-3-carbohydrazide 1,1-dioxide (commercially availabe from Enamine), 2-isothiocyanato-1,3-dimethoxybenzene (Example 10.0). The mixture was purified by preparative SFC using the following methodology: Column: AS-H (2 × 25 cm) Mobile Phase: 50:50 (A:B) A: Liquid CO$_2$, B: MeOH, Flow Rate: 80 mL/min, 215 nm, 100 bar inlet pressure to deliver peak 2. | 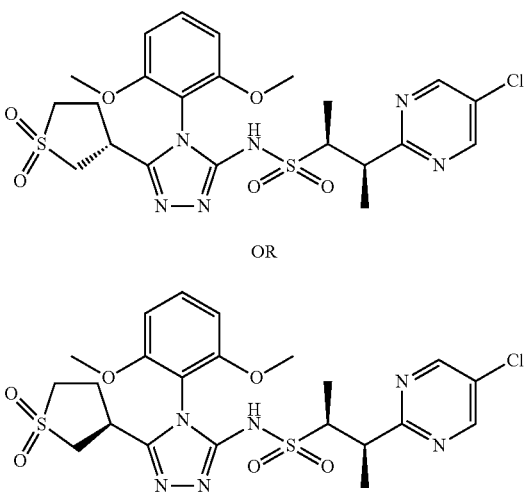<br><br>(2S,3R)-3-(5-chloropyrimidin-2-yl)-N-(4-(2,6-dimethoxyphenyl)-5-((R)-1,1-dioxidotetrahydrothiophen-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-1,1- |

| Example | Reagents | Structure, Name and Data |
|---|---|---|
| | | dioxidotetrahydrothiophen-3-yl)-4H-1,2,4-triazol-3-yl)butane-2-sulfonamide. $^1$H NMR (400 MHz, CD$_2$Cl$_2$) δ 10.91 (br. s., 1H), 8.66-8.59 (m, 2H), 7.56-7.49 (m, 1H), 6.77-6.71 (m, 2H), 3.82 (s, 3H), 3.81 (s, 3H), 3.75-3.63 (m, 2H), 3.34-3.21 (m, 3H), 3.12-3.06 (m, 1H), 2.97 (dddd, J = 0.9, 8.0, 9.2, 13.4 Hz, 1H), 2.50-2.42 (m, 1H), 2.42-2.35 (m, 1H), 1.31 (d, J = 7.0 Hz, 3H), 1.26 (d, J = 7.0 Hz, 3H). LCMS (pos) m/z: 571.0 (M + H)$^+$. |
| 191.0 | (2S,3R)-3-(5-chloropyrimidin-2-yl)butane-2-sulfonamide (Example 1.4), (R)-tetrahydro-2H-pyran-2-carbohydrazide and (S)-tetrahydro-2H-pyran-2-carbohydrazide (commercially available from Ukrorgsyntez), 5-isothiocyanato-4,6-dimethoxypyrimidine (Example 10.1). The mixture was purified by preparative SFC using the following methodology: Column: AS-H (2 × 25 cm) Mobile Phase: 65:35 (A:B) A: Liquid CO$_2$, B: IPA, Flow Rate: 60 mL/min, 215 nm, 100 bar inlet pressure to deliver peak 1. | 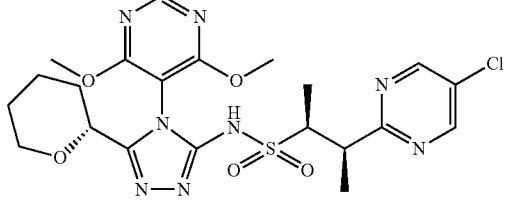<br>OR<br>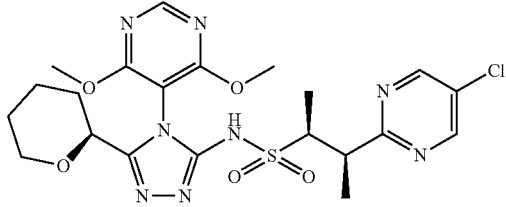 [SMILES: COc1ncnc(OC)c1-n1c(NS(=O)(=O)[C@@H](C)[C@H](C)c2ncc(Cl)cn2)nnc1[C@@H]1CCCCO1]<br>(2S,3R)-3-(5-chloropyrimidin-2-yl)-N-(4-(4,6-dimethoxypyrimidin-5-yl)-5-((S)-tetrahydro-2H-pyran-2-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((R)-tetrahydro-2H-pyran-2-yl)-4H-1,2,4-triazol-3-yl)butane-2-sulfonamide. $^1$H NMR (400 MHz, CD$_2$Cl$_2$) δ 10.82 (br. s., 1H), 8.64 (s, 2H), 8.51 (s, 1H), 4.19-4.15 (m, 1H), 3.99 (s, 3H), 3.99 (s, 3H), 3.73-3.63 (m, 3H), 3.29-3.23 (m, 1H), 1.96-1.86 (m, 4H), 1.55-1.50 (m, 2H), 1.33 (d, J = 7.0 Hz, 3H), 1.30-1.28 (m, 3H). LCMS (pos) m/z: 539.1 (M + H)$^+$. |
| 192.0 | (2S,3R)-3-(5-chloropyrimidin-2-yl)butane-2-sulfonamide (Example 1.4), (R)-tetrahydro-2H-pyran-2-carbohydrazide and (S)-tetrahydro-2H-pyran-2-carbohydrazide(commercially available from Ukrorgsyntez), 5-isothiocyanato-4,6-dimethoxypyrimidine (Example 10.1). The mixture was purified by preparative SFC using the following methodology: Column: AS-H (2 × 25 cm) Mobile Phase: 65:35 (A:B) A: Liquid CO$_2$, B: IPA, Flow Rate: 60 mL/min, 215 nm, 100 bar inlet pressure to deliver peak 2. | 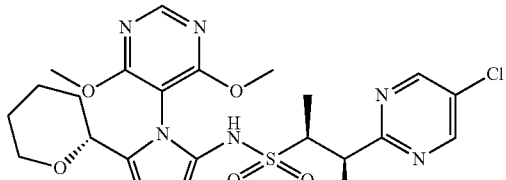<br>OR<br>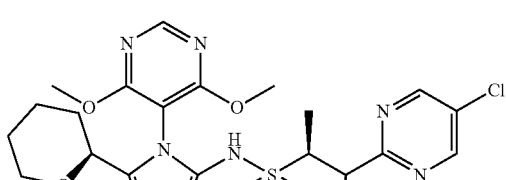<br>(2S,3R)-3-(5-chloropyrimidin-2-yl)-N-(4-(4,6-dimethoxypyrimidin-5-yl)-5-((S)-tetrahydro-2H-pyran-2-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((R)- |

| Example | Reagents | Structure, Name and Data |
|---|---|---|
| | | tetrrahydro-2H-pyran-2-yl)-4H-1,2,4-triazol-3-yl)butane-2-sulfonamide. $^1$H NMR (400 MHz, CD$_2$Cl$_2$) δ 10.85 (br. s., 1H), 8.65-8.62 (m, 2H), 8.53-8.50 (m, 1H), 4.21-4.15 (m, 1H), 4.00-3.98 (m, 3H), 3.98-3.96 (m, 3H), 3.76-3.63 (m, 3H), 3.30-3.22 (m, 1H), 1.96-1.84 (m, 3H), 1.59-1.48 (m, 3H), 1.32 (d, J = 7.0 Hz, 3H), 1.30-1.26 (m, 3H). LCMS (pos) m/z: 539.1 (M + H)$^+$. |
| 193.0 | (1R,2S)-1-((tert-butyldimethylsilyl)oxy)-1-(5-methylpyrimidin-2-yl)propane-2-sulfonamide, Example 28.0, (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The deprotected mixture was purified by preparative SFC using the following methodology: Column: AD-H (2 × 25 cm) Mobile Phase: 75:25 (A:B) A: Liquid CO$_2$, B: MeOH, Flow Rate: 70 mL/min, 215 nm, 100 bar inlet pressure to deliver peak 1. | 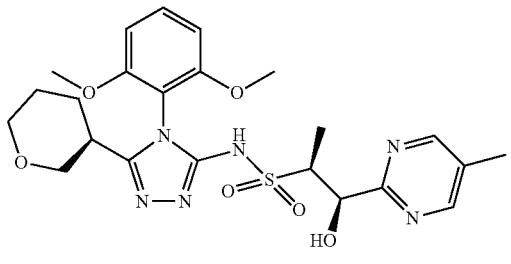 [SMILES: COc1cccc(OC)c1-n1c(NS(=O)(=O)[C@@H](C)[C@H](O)c2ncc(C)cn2)nnc1[C@@H]1CCCOC1]

OR

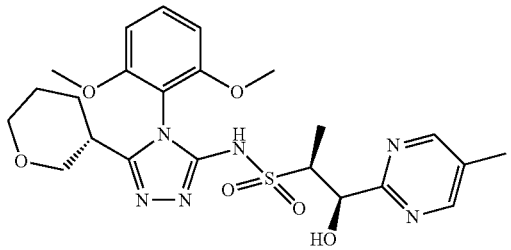 [SMILES: COc1cccc(OC)c1-n1c(NS(=O)(=O)[C@@H](C)[C@H](O)c2ncc(C)cn2)nnc1[C@H]1CCCOC1]

(1R,2S)-N-(4-(2,6-dimethoxyphenyl)-5-((S)-tetrahydro-2H-pyran-3-yl)-4H-1,2,4-triazol-3-yl)-1-hydroxy-1-(5-methylpyrimidin-2-yl)propane-2-sulfonamide or (1R,2S)-N-(4-(2,6-dimethoxyphenyl)-5-((R)-tetrahydro-2H-pyran-3-yl)-4H-1,2,4-triazol-3-yl)-1-hydroxy-1-(5-methylpyrimidin-2-yl)propane-2-sulfonamide. $^1$H NMR (500 MHz, DMSO-d$_6$) δ 12.83 (s, 1H), 8.62 (s, 2H), 7.52 (t, J = 8.4 Hz, 1H), 6.87 (d, J = 8.6 Hz, 2H), 5.13-5.07 (m, 1H), 5.03 (d, J = 5.2 Hz, 1H), 3.75 (s, 3H), 3.75 (s, 3H), 3.71 (br. s., 1H), 3.67 (dd, J = 2.9, 10.6 Hz, 1H), 3.50 (dq, J = 3.6, 6.9 Hz, 1H), 3.32-3.28 (m, 2H), 2.32 (tt, J = 4.0, 10.5 Hz, 1H), 2.26 (s, 3H), 1.84-1.77 (m, 1H), 1.74-1.65 (m, 1H), 1.62-1.55 (m, 1H), 1.46-1.35 (m, 1H), 1.06 (d, J = 7.0 Hz, 3H). LCMS (pos) m/z: 519.2 (M + H)$^+$. |

TABLE 18-continued

| Example | Reagents | Structure, Name and Data |
|---|---|---|
| 194.0 | (1R,2S)-1-((tert-butyldimethylsilyl)oxy)-1-(5-methylpyrimidin-2-yl)propane-2-sulfonamide, Example 28.0, (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The deprotected mixture was purified by preparative SFC using the following methodology: Column: AD-H (2 × 25 cm) Mobile Phase: 75:25 (A:B) A: Liquid $CO_2$, B: MeOH, Flow Rate: 70 mL/min, 215 nm, 100 bar inlet pressure to deliver peak 2. | 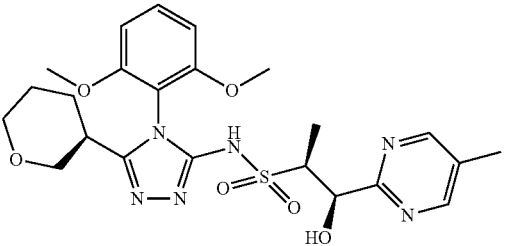 [SMILES: COc1cccc(OC)c1-n1c(NS(=O)(=O)[C@@H](C)[C@H](O)c2ncc(C)cn2)nnc1[C@@H]1CCCOC1]<br>OR<br>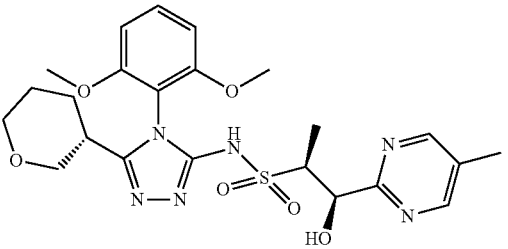 [SMILES: COc1cccc(OC)c1-n1c(NS(=O)(=O)[C@@H](C)[C@H](O)c2ncc(C)cn2)nnc1[C@H]1CCCOC1]<br>(1R,2S)-N-(4-(2,6-dimethoxyphenyl)-5-((S)-tetrahydro-2H-pyran-3-yl)-4H-1,2,4-triazol-3-yl)-1-hydroxy-1-(5-methylpyrimidin-2-yl)propane-2-sulfonamide or (1R,2S)-N-(4-(2,6-dimethoxyphenyl)-5-((R)-tetrahydro-2H-pyran-3-yl)-4H-1,2,4-triazol-3-yl)-1-hydroxy-1-(5-methylpyrimidin-2-yl)propane-2-sulfonamide. $^1$H NMR (500 MHz, DMSO-$d_6$) δ 12.83 (br. s., 1H), 8.63 (s, 2H), 7.52 (t, J = 8.6 Hz, 1H), 6.87 (dd, J = 2.9, 8.6 Hz, 2H), 5.09 (br. s., 1H), 5.03 (br. s., 1H), 3.75 (s, 3H), 3.74 (s, 3H), 3.73-3.69 (m, 1H), 3.65 (dd, J = 2.3, 11.2 Hz, 1H), 3.53-3.47 (m, 1H), 3.31-3.25 (m, 2H), 2.38-2.29 (m, 1H), 2.26 (s, 3H), 1.86-1.78 (m, 1H), 1.75-1.66 (m, 1H), 1.60 (d, J = 13.5 Hz, 1H), 1.48-1.35 (m, 1H), 1.06 (d, J = 7.0 Hz, 3H). LCMS (pos) m/z: 519.2 (M + H)$^+$. |
| 195.0 | (2S,3R)-3-(5-chloropyrimidin-2-yl)butane-2-sulfonamide (Example 1.4), (R)-1,4-dioxane-2-carbohydrazide and (S)-1,4-dioxane-2-carbohydrazide (commercially available from Enamine), 5-isothiocyanato-4,6-dimethoxypyrimidine (Example 10.1). The mixture was purified by preparative SFC using the following methodology: Column: AD-H (2 × 25 cm) Mobile Phase: 60:40 (A:B) A: Liquid $CO_2$, B: IPA, Flow Rate: 80 mL/min, 215 nm, 100 bar inlet pressure to deliver peak 1. | 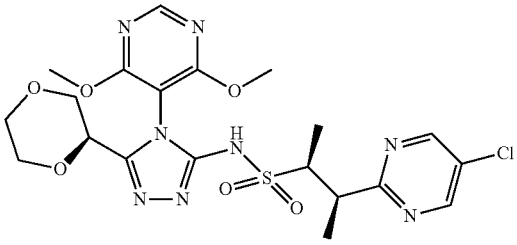 [SMILES: COc1ncnc(OC)c1-n1c(NS(=O)(=O)[C@@H](C)[C@H](C)c2ncc(Cl)cn2)nnc1[C@@H]1COCCO1]<br>OR<br>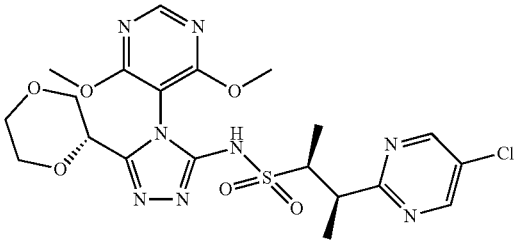 [SMILES: COc1ncnc(OC)c1-n1c(NS(=O)(=O)[C@@H](C)[C@H](C)c2ncc(Cl)cn2)nnc1[C@H]1COCCO1]<br>(2S,3R)-3-(5-chloropyrimidin-2-yl)-N-(4-(4,6-dimethoxypyrimidin-5-yl)-5-((R)-1,4-dioxan-2-yl)-4H-1,2,4-triazol-3-yl)butane-2-sulfonamide or (2S,3R)-3-(5-chloropyrimidin-2-yl)-N-(4-(4,6-dimethoxypyrimidin-4-yl)-5-((S)-1,4-dioxan-2- |

| Example | Reagents | Structure, Name and Data |
|---|---|---|
| | | yl)-4H-1,2,4-triazol-3-yl)butane-2-sulfonamide. ¹H NMR (500 MHz, DMSO-d₆) δ 13.27 (s, 1H), 8.91-8.81 (m, 2H), 8.66 (s, 1H), 4.44 (dd, J = 3.0, 7.1 Hz, 1H), 3.95 (s, 3H), 3.92 (s, 3H), 3.89-3.83 (m, 1H), 3.81-3.76 (m, 1H), 3.65-3.54 (m, 4H), 3.52-3.44 (m, 2H), 1.24 (d, J = 7.0 Hz, 3H), 1.12 (d, J = 7.0 Hz, 3H). LCMS (pos) m/z: 541.0 (M + H)⁺. |
| 196.0 | (2S,3R)-3-(5-chloropyrimidin-2-yl)butane-2-sulfonamide (Example 1.4), (R)-1,4-dioxane-2-carbohydrazide and (S)-1,4-dioxane-2-carbohydrazide (commercially available from Enamine), 5-isothiocyanato-4,6-dimethoxypyrimidine (Example 10.1). The mixture was purified by preparative SFC using the following methodology: Column: AD-H (2 × 25 cm) Mobile Phase: 60:40 (A:B) A: Liquid CO₂, B: IPA, Flow Rate: 80 mL/min, 215 nm, 100 bar inlet pressure to deliver peak 1. | OR<br><br>(2S,3R)-3-(5-chloropyrimidin-2-yl)-N-(4-(4,6-dimethoxypyrimidin-5-yl)-5-((R)-1,4-dioxan-2-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((S)-1,4-dioxan-2-yl)-4H-1,2,4-triazol-3-yl)butane-2-sulfonamide. ¹H NMR (500 MHz, DMSO-d₆) δ 13.26 (s, 1H), 8.86 (s, 2H), 8.69-8.63 (m, 1H), 4.44 (dd, J = 3.1, 7.3 Hz, 1H), 3.94 (s, 3H), 3.92 (s, 3H), 3.88-3.83 (m, 1H), 3.82-3.76 (m, 1H), 3.66-3.53 (m, 4H), 3.52-3.43 (m, 2H), 1.24 (d, J = 7.0 Hz, 3H), 1.11 (d, J = 7.0 Hz, 3H). LCMS (pos) m/z: 541.0 (M + H)⁺. |

| Example | Reagents | Structure, Name and Data |
|---|---|---|
| 197.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially avilable from Enamine), 2-isothiocyanato-1,3-dimethoxybenzene (Example 10.0). The mixture was purified by preparative SFC using the following methodology: Column: AD-H (2 × 25 cm) Mobile Phase: 65:35 (A:B) A: Liquid CO$_2$, B: IPA, Flow Rate: 80 mL/min, 215 nm, 100 bar inlet pressure to deliver peak 1. | 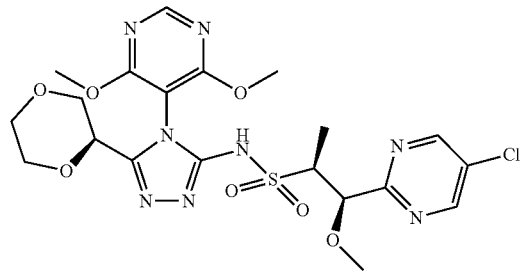 [SMILES: COc1ncnc(OC)c1-n1c(NS(=O)(=O)[C@@H](C)[C@H](OC)c2ncc(Cl)cn2)nnc1[C@@H]1COCCO1]<br>OR<br>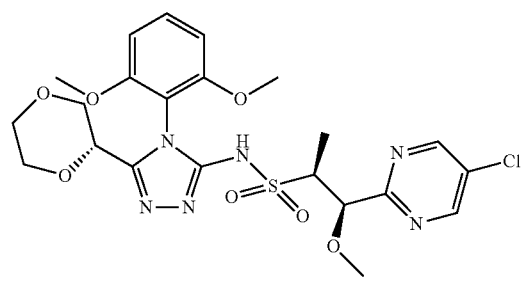 [SMILES: COc1cccc(OC)c1-n1c(NS(=O)(=O)[C@@H](C)[C@H](OC)c2ncc(Cl)cn2)nnc1[C@H]1COCCO1]<br>(1R,2S)-1-(5-chloropyrimidin-2-yl)-N-(4-(2,6-dimethoxyphenyl)-5-((R)-1,4-dioxan-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-1,4-dioxan-2-yl)-4H-1,2,4-triazol-3-yl)-1-methoxypropane-2-sulfonamide. $^1$H NMR (500 MHz, DMSO-d$_6$) δ 13.06 (s, 1H), 8.93 (s, 2H), 7.50 (t, J = 8.4 Hz, 1H), 6.85 (dd, J = 3.6, 8.6 Hz, 2H), 4.77 (d, J = 4.4 Hz, 1H), 4.21-4.13 (m, 1H), 3.77 (s, 3H), 3.76-3.71 (m, 5H), 3.63 (td, J = 2.5, 11.5 Hz, 1H), 3.58 (td, J = 2.6, 11.7 Hz, 1H), 3.51-3.45 (m, 1H), 3.44-3.36 (m, 2H), 3.14 (s, 3H), 1.13 (d, J = 7.0 Hz, 3H). LCMS (pos) m/z: 555.0 (M + H)$^+$. |

TABLE 18-continued

| Example | Reagents | Structure, Name and Data |
|---|---|---|
| 198.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), 2-isothiocyanato-1,3-dimethoxybenzene (Example 10.0). The mixture was purifed by preparative SFC using the following methodology: Column: AD-H (2 × 25 cm) Mobile Phase: 65:35 (A:B) A: Liquid CO₂, B: IPA, Flow Rate: 80 mL/min, 215 nm, 100 bar inlet pressure to deliver peak 2. | 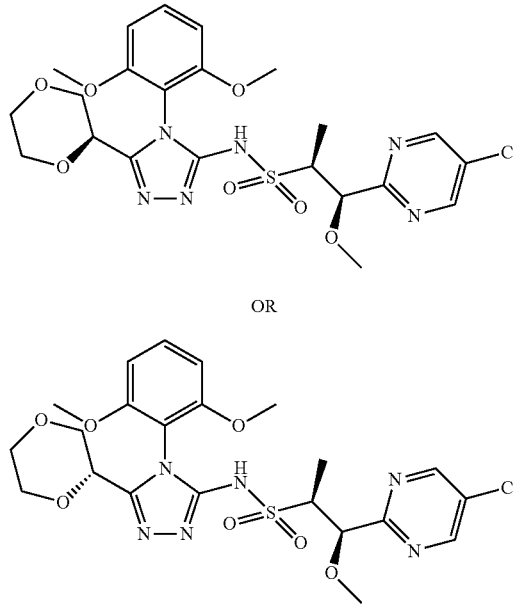<br>OR<br><br>(1R,2S)-1-(5-chloropyrimidin-2-yl)-N-(4-(2,6-dimethoxyphenyl)-5-((R)-1,4-dioxan-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-1,4-dioxan-2-yl)-4H-1,2,4-triazol-3-yl)-1-methoxypropane-2-sulfonamide. ¹H NMR (500 MHz, DMSO-d₆) δ 13.05 (s, 1H), 9.00-8.87 (m, 2H), 7.50 (t, J = 8.4 Hz, 1H), 6.85 (d, J = 8.6 Hz, 2H), 4.77 (d, J = 4.2 Hz, 1H), 4.21-4.13 (m, 1H), 3.75 (s, 3H), 3.75 (s, 3H), 3.74-3.71 (m, 2H), 3.67-3.62 (m, 1H), 3.61-3.56 (m, 1H), 3.52-3.46 (m, 1H), 3.43-3.36 (m, 2H), 3.14 (s, 3H), 1.14 (d, J = 6.7 Hz, 3H). LCMS (pos) m/z: 555.2 (M + H)⁺. |
| 199.0 | (1R,2S)-1-(5-chloropyrimidin-2-yl)-1-methoxypropane-2-sulfonamide (Example 11.3), (2S,5S)-5-methyltetrahydrofuran-2-carbohydrazide and (2R,5R)-5-methyltetrahydrofuran-2-carbohydrazide (commercially available from Ukrorgsyntez), 1-isothiocyanato-1-methylcyclopropane (commercially available from Enamine). The mixture was purified by preparative SFC using the following methodology: Column: AD-H (2 × 25 cm) Mobile Phase: 70:30 (A:B) A: Liquid CO₂, B: MeOH, Flow Rate: 80 mL/min, 220 nm, 100 bar inlet pressure to deliver peak 1. | 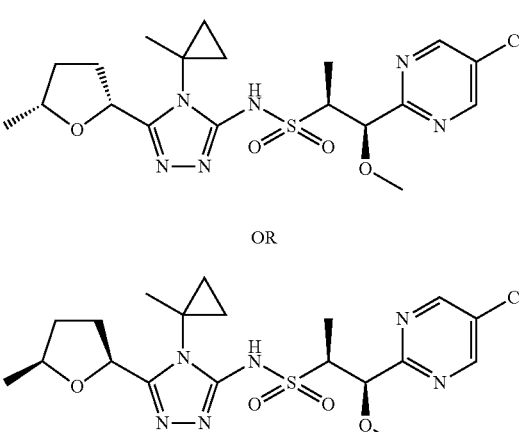<br>OR<br><br>(1R,2S)-1-(5-chloropyrimidin-2-yl)-1-methoxy-N-(4-(1-methylcyclopropyl)-5-((2S,5S)-5-methyltetrahydrofuran-2-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((2R,5R)-5-methyltetrahydrofuran-2-yl)-4H-1,2,4-triazol-3-yl)propane-2-sulfonamide. ¹H NMR (500 MHz, DMSO-d₆) δ 12.69 (s, 1H), 8.93 (s, 2H), 5.08 |

TABLE 18-continued

| Example | Reagents | Structure, Name and Data |
|---------|----------|--------------------------|
| | | (dd, J = 5.4, 7.5 Hz, 1H), 4.93 (d, J = 3.9 Hz, 1H), 4.17-4.08 (m, 1H), 3.48-3.42 (m, 1H), 3.07 (s, 3H), 2.48-2.40 (m, 1H), 2.20 (qd, J = 7.9, 12.5 Hz, 1H), 2.14-2.06 (m, 1H), 1.58 (qd, J = 8.3, 11.8 Hz, 1H), 1.43 (s, 3H), 1.28 (d, J = 7.0 Hz, 3H), 1.25-1.17 (m, 2H), 1.15 (d, J = 6.0 Hz, 3H), 0.97-0.89 (m, 2H). LCMS (pos) m/z: 471.0 (M + H)⁺. |
| 200.0 | (1R,2S)-1-(5-chloropyrimidin-2-yl)-1-methoxypropane-2-sulfonamide (Example 11.3), (2S,5S)-5-methyltetrahydrofuran-2-carbohydrazide and (2R,5R)-5-methyltetrahydrofuran-2-carbohydrazide (commercially available from Ukrorgsyntez), 1-isothiocyanato-1-methylcyclopropane (commercially available from Enamine). The mixture was purified by preparative SFC using the following methodology: Column: AD-H (2 × 25 cm) Mobile Phase: 70:30 (A:B) A: Liquid CO₂, B: MeOH, Flow Rate: 80 mL/min, 220 nm, 100 bar inlet pressure to deliver peak 2. | 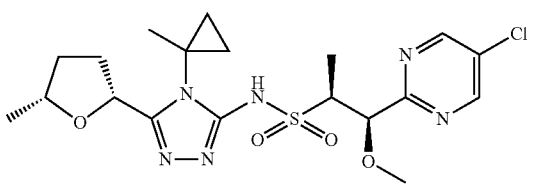 [SMILES: CO[C@H](c1ncc(Cl)cn1)[C@H](C)S(=O)(=O)Nc1nnc([C@H]2CC[C@@H](C)O2)n1C1(C)CC1]

OR

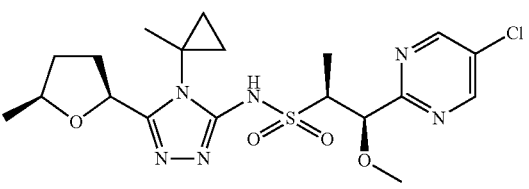 [SMILES: CO[C@H](c1ncc(Cl)cn1)[C@H](C)S(=O)(=O)Nc1nnc([C@@H]2CC[C@H](C)O2)n1C1(C)CC1]

(1R,2S)-1-(5-chloropyrimidin-2-yl)-1-methoxy-N-(4-(1-methylcyclopropyl)-5-((2S,5S)-5-methyltetrahydrofuran-2-yl)-4H-1,2,4-triazol-3-yl)propane-2-sulfonamide or (1R,2S)-1-(5-chloropyrimidin-2-yl)-1-methoxy-N-(4-(1-methylcyclopropyl)-5-((2R,5R)-5-methyltetrahydrofuran-2-yl)-4H-1,2,4-triazol-3-yl)propane-2-sulfonamide. ¹H NMR (500 MHz, DMSO-d₆) δ 12.69 (s, 1H), 8.95-8.90 (m, 2H), 5.07 (dd, J = 5.4, 7.8 Hz, 1H), 4.94 (d, J = 3.6 Hz, 1H), 4.17-4.09 (m, 1H), 3.43 (dq, J = 3.9, 7.0 Hz, 1H), 3.07 (s, 3H), 2.46 (dd, J = 8.2, 12.8 Hz, 1H), 2.20 (qd, J = 7.9, 12.5 Hz, 1H), 2.14-2.06 (m, 1H), 1.58 (qd, J = 8.1, 11.8 Hz, 1H), 1.43 (s, 3H), 1.27 (d, J = 7.0 Hz, 3H), 1.21 (br. s., 2H), 1.14 (d, J = 6.2 Hz, 3H), 0.96-0.86 (m, 2H). LCMS (pos) m/z: 471.0 (M + H)⁺. |

TABLE 18-continued

| Example | Reagents | Structure, Name and Data |
|---|---|---|
| 201.0 | (1R,2S)-1-methoxy-1-(5-methylpyrimidin-2-yl)propane-2-sulfonamide (Example 11.0), (R)-1,4-dioxane-2-carbohydrazide (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid $CO_2$, B: IPA, Flow Rate: 60 mL/min, 215 nm, 100 bar inlet pressure to deliver peak 1. | 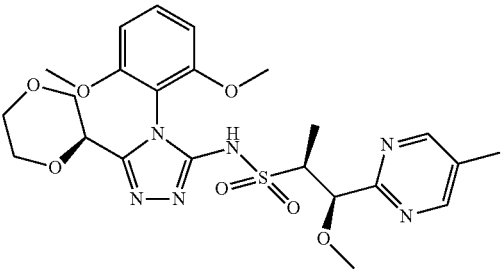 [SMILES: COc1cccc(OC)c1-n1c(NS(=O)(=O)[C@@H](C)[C@H](OC)c2ncc(C)cn2)nnc1[C@@H]1COCCO1]<br>OR<br>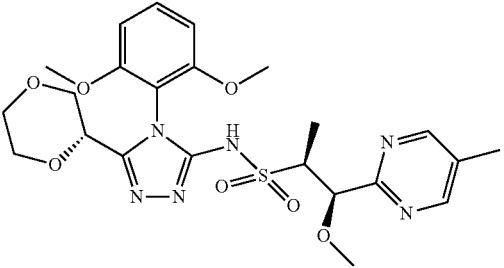 [SMILES: COc1cccc(OC)c1-n1c(NS(=O)(=O)[C@@H](C)[C@H](OC)c2ncc(C)cn2)nnc1[C@H]1COCCO1]<br>(1R,2S)-N-(4-(2,6-dimethoxyphenyl)-5-((R)-1,4-dioxan-2-yl)-4H-1,2,4-triazol-3-yl)-1-methoxy-1-(5-methylpyrimidin-2-yl)propane-2-sulfonamide or (1R,2S)-N-(4-(2,6-dimethoxyphenyl)-5-((S)-1,4-dioxan-2-yl)-4H-1,2,4-triazol-3-yl)-1-methoxy-1-(5-methylpyrimidin-2-yl)propane-2-sulfonamide.<br>$^1$H NMR (500 MHz, DMSO-$d_6$) δ 13.07 (s, 1H), 8.64 (s, 2H), 7.49 (t, J = 8.4 Hz, 1H), 6.84 (dd, J = 3.4, 8.6 Hz, 2H), 4.79 (d, J = 3.6 Hz, 1H), 4.21-4.12 (m, 1H), 3.76 (s, 3H), 3.75-3.70 (m, 5H), 3.66-3.61 (m, 1H), 3.60-3.55 (m, 1H), 3.51-3.45 (m, 1H), 3.42-3.35 (m, 2H), 3.13 (s, 3H), 2.26 (s, 3H), 1.10 (d, J = 7.0 Hz, 3H). LCMS (pos) m/z: 535.2 (M + H)$^+$. |

TABLE 18-continued

| Example | Reagents | Structure, Name and Data |
|---|---|---|
| 202.0 | (1R,2S)-1-methoxy-1-(5-methylpyrimidin-2-yl)propane-2-sulfonamide Example 11.0, (R)-1,4-dioxane-2-carbohydrazide (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid $CO_2$, B: IPA, Flow Rate: 60 mL/min, 215 nm, 100 bar inlet pressure to deliver peak 2. | 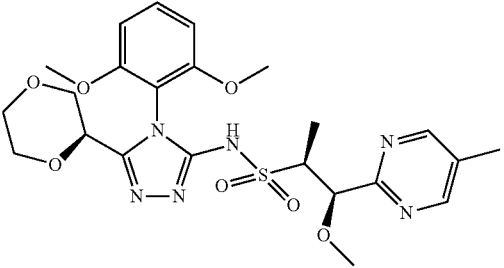 [SMILES: COc1cccc(OC)c1-n1c(NS(=O)(=O)[C@@H](C)[C@H](OC)c2ncc(C)cn2)nnc1[C@@H]1COCCO1]<br>OR<br>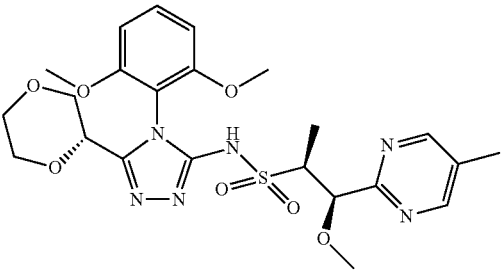 [SMILES: COc1cccc(OC)c1-n1c(NS(=O)(=O)[C@@H](C)[C@H](OC)c2ncc(C)cn2)nnc1[C@H]1COCCO1]<br>(1R,2S)-N-(4-(2,6-dimethoxyphenyl)-5-((R)-1,4-dioxan-2-yl)-4H-1,2,4-triazol-3-yl)-1-methoxy-1-(5-methylpyrimidin-2-yl)propane-2-sulfonamide or (1R,2S)-N-(4-(2,6-dimethoxyphenyl)-5-((S)-1,4-dioxan-2-yl)-4H-1,2,4-triazol-3-yl)-1-methoxy-1-(5-methylpyrimidin-2-yl)propane-2-sulfonamide.<br>$^1$H NMR (500 MHz, DMSO-$d_6$) δ 13.10-13.04 (m, 1H), 13.07 (s, 1H), 8.64 (s, 2H), 7.49 (t, J = 8.4 Hz, 1H), 6.84 (d, J = 8.6 Hz, 2H), 4.80 (d, J = 3.4 Hz, 1H), 4.20-4.13 (m, 1H), 3.74 (s, 3H), 3.74-3.69 (m, 5H), 3.66-3.61 (m, 1H), 3.58 (td, J = 2.7, 11.7 Hz, 1H), 3.51-3.45 (m, 1H), 3.42-3.35 (m, 2H), 3.13 (s, 3H), 2.26 (s, 3H), 1.11 (d, J = 7.0 Hz, 3H). LCMS (pos) m/z: 535.2 (M + H)$^+$. |

TABLE 18-continued

| Example | Reagents | Structure, Name and Data |
|---|---|---|
| 203.0 | (1R,2S)-1-ethoxy-1-(5-methylpyrimidin-2-yl)propane-2-sulfonamide (Example 29.0), (R)-1,4-dioxane-2-carbohydrazide and (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 65:35 (A:B) A: Liquid $CO_2$, B: IPA, Flow Rate: 80 mL/min, 215 nm, 100 bar inlet pressure to deliver peak 1. | 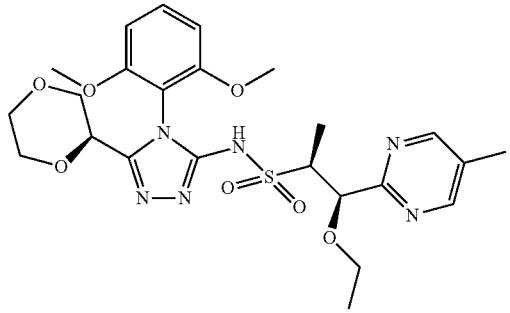 [SMILES: CCO[C@H](c1ncc(C)cn1)[C@H](C)S(=O)(=O)Nc1nnc([C@@H]2COCCO2)n1-c1c(OC)cccc1OC]<br>OR<br>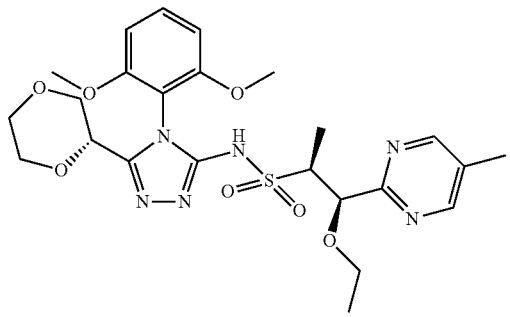 [SMILES: CCO[C@H](c1ncc(C)cn1)[C@H](C)S(=O)(=O)Nc1nnc([C@H]2COCCO2)n1-c1c(OC)cccc1OC]<br>(1R,2S)-N-(4-(2,6-dimethoxyphenyl)-5-((R)-1,4-dioxan-2-yl)-4H-1,2,4-triazol-3-yl)-1-ethoxy-1-(5-methylpyrimidin-2-yl)propane-2-sulfonamide or (1R,2S)-N-(4-(2,6-dimethoxyphenyl)-5-((S)-1,4-dioxan-2-yl)-4H-1,2,4-triazol-3-yl)-1-ethoxy-1-(5-methylpyrimidin-2-yl)propane-2-sulfonamide. $^1$H NMR (500 MHz, DMSO-$d_6$) δ 13.05 (br s, 1H), 8.63 (s, 2H), 7.49 (t, J = 8.4 Hz, 1H), 6.84 (dd, J = 3.4, 8.6 Hz, 2H), 4.89 (d, J = 4.2 Hz, 1H), 4.15 (dd, J = 4.9, 6.2 Hz, 1H), 3.76 (s, 3H), 3.73 (s, H), 3.72-3.68 m, 2H), 3.64 (td, J = 2.6, 11.6 Hz, 1H), 3.61-3.56 (m, 1H), 3.51-3.45 (m, 1H), 3.44-3.36 (m, 3H), 3.32-3.26 (m, 1H), 2.25 (s, 3H), 1.13 (d, J = 7.0 Hz, 3H), 0.97 (t, J = 7.0 Hz, 3H). LCMS (pos) m/z: 549.2 (M + H)$^+$. |

TABLE 18-continued

| Example | Reagents | Structure, Name and Data |
|---|---|---|
| 204.0 | (1R,2S)-1-ethoxy-1-(5-methylpyrimidin-2-yl)propane-2-sulfonamide (Example 29.0), (R)-1,4-dioxane-2-carbohydrazide and (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 65:35 (A:B) A: Liquid $CO_2$, B: IPA, Flow Rate: 80 mL/min, 215 nm, 100 bar inlet pressure to deliver peak 2. | 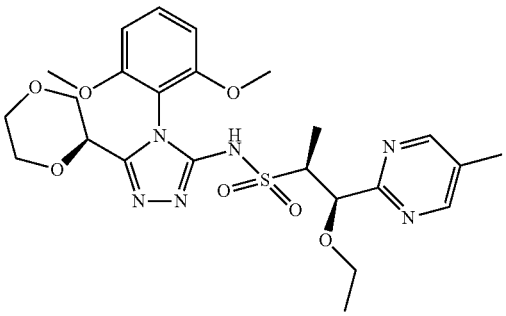 [SMILES: CCO[C@H](c1ncc(C)cn1)[C@H](C)S(=O)(=O)Nc1nnc([C@@H]2COCCO2)n1-c1c(OC)cccc1OC]    OR    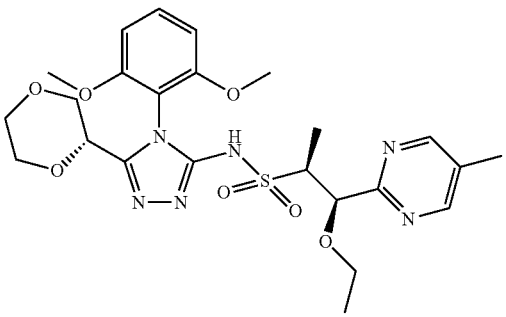 [SMILES: CCO[C@H](c1ncc(C)cn1)[C@H](C)S(=O)(=O)Nc1nnc([C@H]2COCCO2)n1-c1c(OC)cccc1OC]    (1R,2S)-N-(4-(2,6-dimethoxyphenyl)-5-((R)-1,4-dioxan-2-yl)-4H-1,2,4-triazol-3-yl)-1-ethoxy-1-(5-methylpyrimidin-2-yl)propane-2-sulfonamide or (1R,2S)-N-(4-(2,6-dimethoxyphenyl)-5-((S)-1,4-dioxan-2-yl)-4H-1,2,4-triazol-3-yl)-1-ethoxy-1-(5-methylpyrimidin-2-yl)propane-2-sulfonamide. $^1$H NMR (500 MHz, DMSO-$d_6$) δ 13.04 (s, 1H), 8.63 (s, 2H), 7.49 (t, J = 8.6 Hz, 1H), 6.84 (d, J = 8.6 Hz, 2H), 4.89 (d, J = 3.9 Hz, 1H), 4.16 (dd, J = 3.9, 7.3 Hz, 1H), 3.75 (s, 3H), 3.74-3.68 (m, 5H), 3.63 (td, J = 2.6, 11.7 Hz, 1H), 3.58 (td, J = 2.6, 11.7 Hz, 1H), 3.51-3.45 (m, 1H), 3.44-3.35 (m, 3H), 3.32-3.25 (m, 1H), 2.25 (s, 3H), 1.15 (d, J = 7.0 Hz, 3H), 0.98 (t, J = 7.0 Hz, 3H). LCMS (pos) m/z: 549.2 (M + H)$^+$. |

TABLE 18-continued

| Example | Reagents | Structure, Name and Data |
|---|---|---|
| 205.0 | (2S,3R)-3-(5-methylpyrimidin-2-yl)butane-2-sulfonamide (Example 1.0), (R)-1,4-dioxane-2-carbohydrazide and (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 65:35 (A:B) A: Liquid $CO_2$, B: IPA, Flow Rate: 80 mL/min, 215 nm, 100 bar inlet pressure to deliver peak 1. | 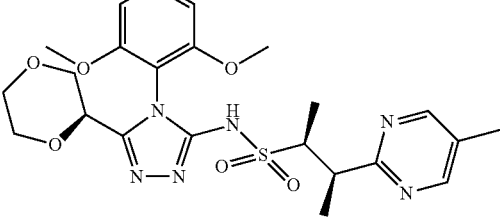<br>OR<br>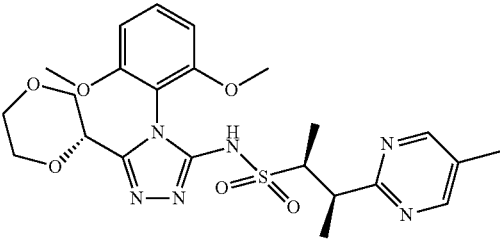 [SMILES: COc1cccc(OC)c1-n1c(NS(=O)(=O)[C@@H](C)[C@H](C)c2ncc(C)cn2)nnc1[C@H]1COCCO1]<br>(2S,3R)-N-(4-(2,6-dimethoxyphenyl)-5-((R)-1,4-dioxan-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-1,4-dioxan-2-yl)-4H-1,2,4-triazol-3-yl)-3-(5-methylpyrimidin-2-yl)butane-2-sulfonamide. $^1$H NMR (500 MHz, DMSO-$d_6$) δ 13.09 (s, 1H), 8.58 (s, 2H), 7.49 (t, J = 8.6 Hz, 1H), 6.83 (dd, J = 2.3, 8.6 Hz, 2H), 4.16 (dd, J = 4.2, 7.0 Hz, 1H), 3.77-3.73 (m, 4H), 3.72-3.68 (m, 4H), 3.67-3.61 (m, 2H), 3.60-3.53 (m, 2H), 3.50-3.45 (m, 1H), 3.38 (ddd, J = 2.6, 9.2, 11.5 Hz, 1H), 2.23 (s, 3H), 1.22 (d, J = 7.3 Hz, 3H), 1.07 (d, J = 7.0 Hz, 3H). LCMS (pos) m/z: 519.2 (M + H)$^+$. |
| 206.0 | (2S,3R)-3-(5-methylpyrimidin-2-yl)butane-2-sulfonamide (Example 1.0), (R)-1,4-dioxane-2-carbohydrazide and (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 65:35 (A:B) A: Liquid $CO_2$, B: IPA, Flow Rate: 80 mL/min, 215 nm, 100 bar inlet pressure to deliver peak 2. | 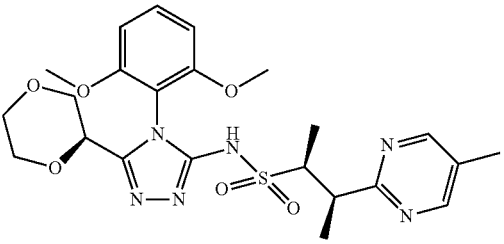 [SMILES: COc1cccc(OC)c1-n1c(NS(=O)(=O)[C@@H](C)[C@H](C)c2ncc(C)cn2)nnc1[C@@H]1COCCO1]<br>OR<br>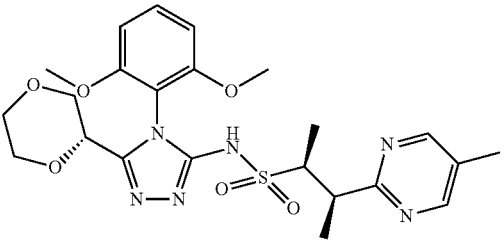 [SMILES: COc1cccc(OC)c1-n1c(NS(=O)(=O)[C@@H](C)[C@H](C)c2ncc(C)cn2)nnc1[C@H]1COCCO1]<br>((2S,3R)-N-(4-(2,6-dimethoxyphenyl)-5-((R)-1,4-dioxan-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-1,4-dioxan-2-yl)-4H-1,2,4-triazol-3-yl)-3-(5-methylpyrimidin-2-yl)butane-2-sulfonamide. $^1$H NMR (500 MHz, DMSO-$d_6$) δ 13.09 (s, 1H), |

| Example | Reagents | Structure, Name and Data |
|---|---|---|
| | | 8.58 (s, 2H), 7.49 (t, J = 8.6 Hz, 1H), 6.83 (dd, J = 1.8, 8.6 Hz, 2H), 4.16 (dd, J = 4.0, 7.1 Hz, 1H), 3.76-3.72 (m, 4H), 3.72-3.68 (m, 4H), 3.68-3.61 (m, 2H), 3.60-3.53 (m, 2H), 3.51-3.46 (m, 1H), 3.38 (ddd, J = 2.6, 9.1, 11.6 Hz, 1H), 2.23 (s, 3H), 1.22 (d, J = 7.0 Hz, 3H), 1.07 (d, J = 7.0 Hz, 3H). LCMS (pos) m/z: 519.2 (M + H)$^+$. |
| 207.0 | (2S,3R)-3-(5-methoxypyrazin-2-yl)butane-2-sulfonamide (Example 1.5), (R)-1,4-dioxane-2-carbohydrazide and (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 65:35 (A:B) A: Liquid CO$_2$, B: IPA, Flow Rate: 80 mL/min, 215 nm, 100 bar inlet pressure to deliver peak 1. | 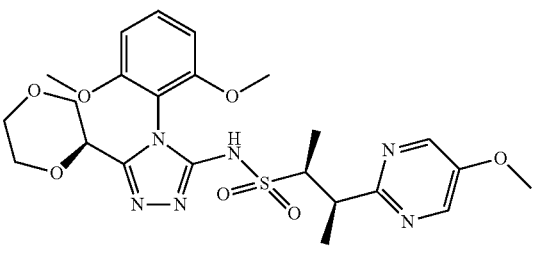 [SMILES: COc1cnc([C@@H](C)[C@H](C)S(=O)(=O)Nc2nnc([C@@H]3COCCO3)n2-c2c(OC)cccc2OC)nc1]<br>OR<br>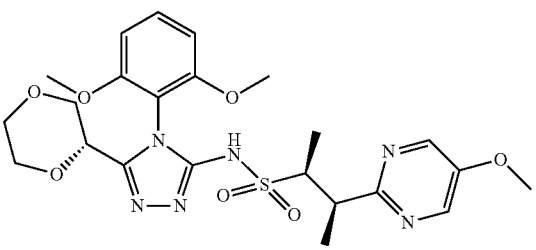 [SMILES: COc1cnc([C@@H](C)[C@H](C)S(=O)(=O)Nc2nnc([C@H]3COCCO3)n2-c2c(OC)cccc2OC)nc1]<br>(2S,3R)-N-(4-(2,6-dimethoxyphenyl)-5-((R)-1,4-dioxan-2-yl)-4H-1,2,4-triazol-3-yl)-3-(5-methoxypyrazin-2-yl)butane-2-sulfonamide or (2S,3R)-N-(4-(2,6-dimethoxyphenyl)-5-((S)-1,4-dioxan-2-yl)-4H-1,2,4-triazol-3-yl)-3-(5-methoxypyrazin-2-yl)butane-2-sulfonamide. $^1$H NMR (500 MHz, DMSO-d$_6$) δ 13.09 (s, 1H), 8.23 (s, 1H), 7.99 (s, 1H), 7.50 (t, J = 8.4 Hz, 1H), 6.84 (dd, J = 2.2, 8.4 Hz, 2H), 4.17 (dd, J = 4.0, 7.1 Hz, 1H), 3.87 (s, 3H), 3.76 (s, 3H), 3.75-3.69 (m, 5H), 3.65-3.60 (m, 1H), 3.60-3.52 (m, 2H), 3.51-3.45 (m, 1H), 3.42-3.36 (m, 1H), 3.29-3.22 (m, 1H), 1.21 (d, J = 7.3 Hz, 3H), 1.08 (d, J = 7.0 Hz, 3H). LCMS (pos) m/z: 535.2 (M + H)$^+$. |

TABLE 18-continued

| Example | Reagents | Structure, Name and Data |
|---|---|---|
| 208.0 | (2S,3R)-3-(5-methoxypyrazin-2-yl)butane-2-sulfonamide (Example 1.5), (R)-1,4-dioxane-2-carbohydrazide and (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 65:35 (A:B) A: Liquid CO$_2$, B: IPA, Flow Rate: 80 mL/min, 215 nm, 100 bar inlet pressure to deliver peak 2. | 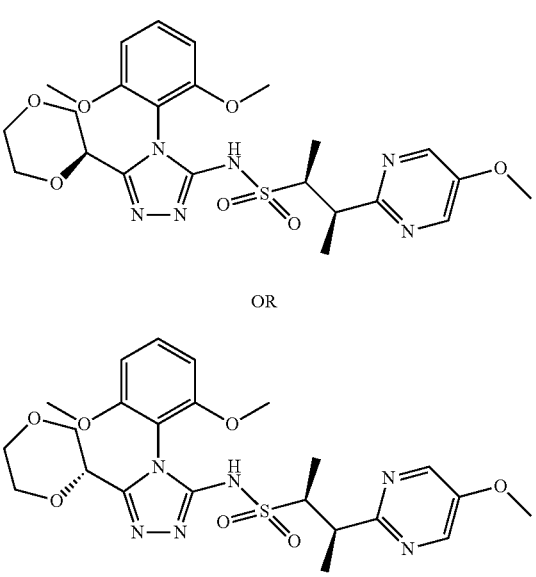<br>OR<br><br>(2S,3R)-N-(4-(2,6-dimethoxyphenyl)-5-((R)-1,4-dioxan-2-yl)-4H-1,2,4-triazol-3-yl)-3-(5-methoxypyrazin-2-yl)butane-2-sulfonamide or (2S,3R)-N-(4-(2,6-dimethoxyphenyl)-5-((S)-1,4-dioxan-2-yl)-4H-1,2,4-triazol-3-yl)-3-(5-methoxypyrazin-2-yl)butane-2-sulfonamide. $^1$H NMR (500 MHz, DMSO-d$_6$) δ 13.10 (br s, 1H), 8.23 (d, J = 0.8 Hz, 1H), 7.99 (s, 1H), 7.50 (t, J = 8.4 Hz, 1H), 6.84 (dd, J = 3.8, 8.4 Hz, 2H), 4.16 (dd, J = 4.4, 6.7 Hz, 1H), 3.91-3.85 (m, 3H), 3.75 (s, 3H), 3.74-3.66 (m, 5H), 3.66-3.61 (m, 1H), 3.61-3.52 (m, 2H), 3.51-3.46 (m, 1H), 3.42-3.36 (m, 1H), 3.29-3.23 (m, 1H), 1.21 (d, J = 7.3 Hz, 3H), 1.07 (d, J = 7.0 Hz, 3H). LCMS (pos) m/z: 535.2 (M + H)$^+$. |
| 209.0 | (1S,2S)-1-isopropoxy-1-(5-methylpyrimidin-2-yl)propane-2-sulfonamide (Example 13.5), (R)-5,5-dimethyltetrahydrofuran-2-carbohydrazide and (S)-5,5-dimethyltetrahydrofuran-2-carbohydrazide (Example 108.2), 2-isothiocyanato-1,3-dimethoxybenzene (Example 10.0). The mixture was purified by preparative SFC using the following methodology: Column: AD-H (2 × 25 cm) Mobile Phase: 80:20 (A:B) A: Liquid CO$_2$, B: IPA, Flow Rate: 80 mL/min, 215 nm, 100 bar inlet pressure to deliver peak 1. | 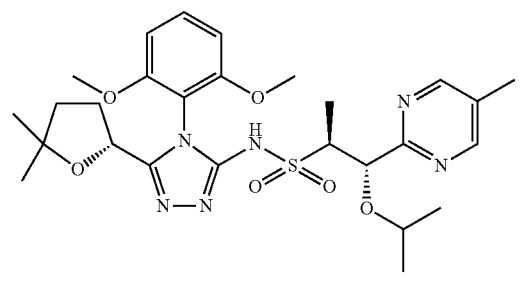<br>OR<br><br>(1S,2S)-N-(4-(2,6-dimethoxyphenyl)-5-((S)-5,5-dimethyltetrahydrofuran-2-yl)-4H-1,2,4-triazol-3-yl)-1-isopropoxy-1-(5-methylpyrimidin-2-yl)propane-2-sulfonamide or (1S,2S)-N-(4-(2,6- |

| Example | Reagents | Structure, Name and Data |
| --- | --- | --- |
| | | dimethoxyphenyl)-5-((R)-5,5-dimethyltetrahydrofuran-2-yl)-4H-1,2,4-triazol-3-yl)-1-isopropoxy-1-(5-methylpyrimidin-2-yl)propane-2-sulfonamide. $^1$H NMR (500 MHz, DMSO-$d_6$) δ 12.83 (s, 1H), 8.65 (s, 2H), 7.47 (t, J = 8.4 Hz, 1H), 6.82 (dd, J = 4.2, 8.6 Hz, 2H), 4.68 (d, J = 7.3 Hz, 1H), 4.62-4.56 (m, 1H), 3.79 (s, 3H), 3.76 (s, 3H), 3.42-3.35 (m, 2H), 2.26 (s, 3H), 2.21-2.08 (m, 2H), 1.69-1.62 (m, 1H), 1.52 (td, J = 8.1, 11.9 Hz, 1H), 1.04 (s, 3H), 1.02-0.96 (m, 6H), 0.90 (d, J = 7.3 Hz, 3H), 0.79 (d, J = 6.0 Hz, 3H). LCMS (pos) m/z: 575.2 (M + H)$^+$. |
| 210.0 | (1S,2S)-1-isopropoxy-1-(5-methylpyrimidin-2-yl)propane-2-sulfonamide (Example 13.5), (R)-5,5-dimethyltetrahydrofuran-2-carbohydrazide and (S)-5,5-dimethyltetrahydrofuran-2-carbohydrazide (Example 108.2), 2-isothiocyanato-1,3-dimethoxybenzene (Example 10.0). The mixture was purified by preparative SFC using the following methodology: Column: AD-H (2 × 25 cm) Mobile Phase: 80:20 (A:B) A: Liquid CO$_2$, B: IPA, Flow Rate: 80 mL/min, 215 nm, 100 bar inlet pressure to deliver peak 2. | 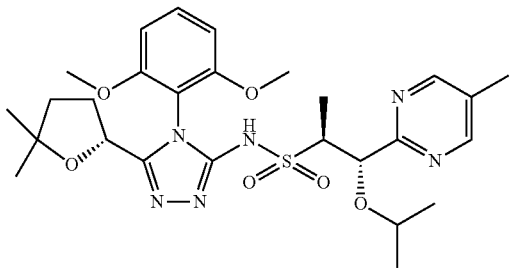<br>OR<br>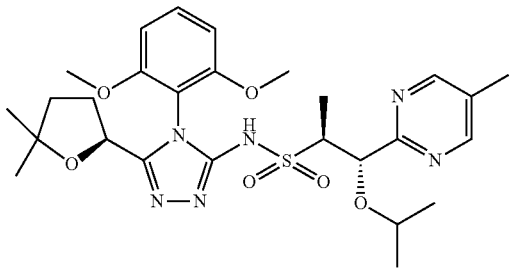<br>(1S,2S)-N-(4-(2,6-dimethoxyphenyl)-5-((S)-5,5-dimethyltetrahydrofuran-2-yl)-4H-1,2,4-triazol-3-yl)-1-isopropoxy-1-(5-methylpyrimidin-2-yl)propane-2-sulfonamide or (1S,2S)-N-(4-(2,6-dimethoxyphenyl)-5-((R)-5,5-dimethyltetrahydrofuran-2-yl)-4H-1,2,4-triazol-3-yl)-1-isopropoxy-1-(5-methylpyrimidin-2-yl)propane-2-sulfonamide. $^1$H NMR (500 MHz, DMSO-$d_6$) δ 12.84 (br s, 1H), 8.65 (s, 2H), 7.47 (t, J = 8.4 Hz, 1H), 6.82 (dd, J = 4.8, 8.4 Hz, 2H), 4.67 (d, J = 7.5 Hz, 1H), 4.58 (t, J = 6.7 Hz, 1H), 3.77 (s, 3H), 3.77 (s, 3H), 3.43-3.36 (m, 2H), 2.26 (s, 3H), 2.19-2.07 (m, 2H), 1.69-1.62 (m, 1H), 1.53 (td, J = 8.0, 12.0 Hz, 1H), 1.04 (s, 3H), 1.00 (s, 3H), 0.97 (d, J = 6.0 Hz, 3H), 0.88 (d, J = 7.3 Hz, 3H), 0.78 (d, J = 6.2 Hz, 3H). LCMS (pos) m/z: 575.2 (M + H)$^+$. Spectrum (pos) m/z: 575.2 (M + H)$^+$. |

TABLE 18-continued

| Example | Reagents | Structure, Name and Data |
|---|---|---|
| 211.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid $CO_2$, B: IPA, Flow Rate: 80 mL/min, 215 nm, 100 bar inlet pressure to deliver peak 1. | 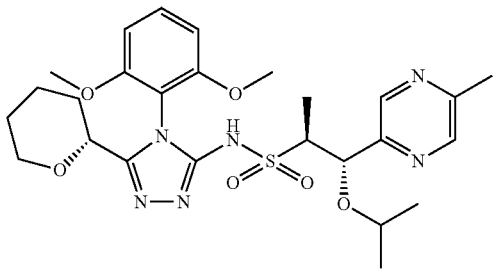 [SMILES: COc1cccc(OC)c1-n1c(NS(=O)(=O)[C@@H](C)[C@@H](OC(C)C)c2cnc(C)cn2)nnc1[C@H]1CCCCO1]<br>OR<br>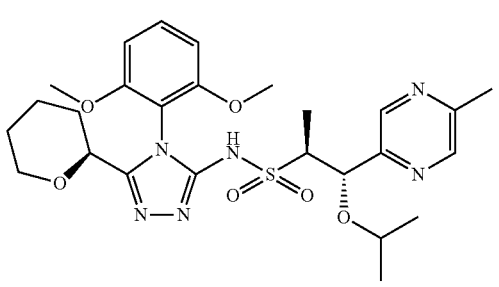 [SMILES: COc1cccc(OC)c1-n1c(NS(=O)(=O)[C@@H](C)[C@@H](OC(C)C)c2cnc(C)cn2)nnc1[C@@H]1CCCCO1]<br>OR<br>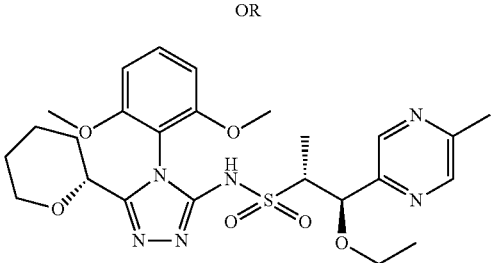<br>OR<br>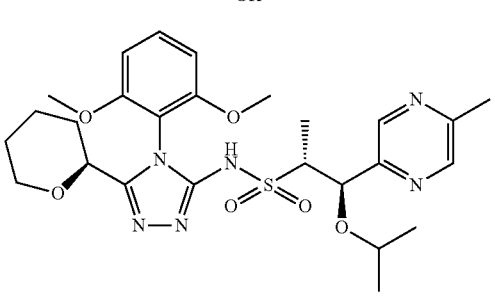<br>(1S,2S)-N-(4-(2,6-dimethoxyphenyl)-5-((S)-tetrahydro-2H-pyran-2-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-((R)-tetrahydro-2H-pyran-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((S)-tetrahydro-2H-pyran-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((R)-tetrahydro-2H-pyran-2-yl)-4H-1,2,4-triazol-3-yl)-1-isopropoxy-1-(5-methylpyrazin-2-yl)propane-2-sulfonamide.<br>$^1$H NMR (500 MHz, DMSO-$d_6$) δ 12.92 (s, 1H), 8.45 (s, 1H), 8.42 (s, 1H), 7.47 (t, J = 8.6 Hz, 1H), |

TABLE 18-continued

| Example | Reagents | Structure, Name and Data |
|---------|----------|--------------------------|
| | | 6.84 (dd, J = 1.4, 8.4 Hz, 2H), 4.76 (d, J = 5.7 Hz, 1H), 4.01 (dd, J = 3.2, 9.0 Hz, 1H), 3.76 (s, 3H), 3.75 (s, 3H), 3.65-3.59 (m, 1H), 3.44-3.36 (m, 2H), 3.16 (td, J = 6.1, 11.7 Hz, 1H), 2.46 (s, 3H), 1.84-1.77 (m, 1H), 1.77-1.70 (m, 1H), 1.70-1.65 (m, 1H), 1.51-1.42 (m, 1H), 1.42-1.35 (m, 2H), 1.02 (d, J = 6.0 Hz, 3H), 0.99 (d, J = 7.0 Hz, 3H), 0.87 (d, J = 6.0 Hz, 3H). LCMS (pos) m/z: 561.2 (M + H)$^+$. |
| 212.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydro-2H-pyran-2-carbohydrazide and (S)-tetrahydro-2H-pyran-2-carbohydrazide(commercially available from Ukrorgsyntez), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid CO$_2$, B: IPA, Flow Rate: 80 mL/min, 215 nm, 100 bar inlet pressure to deliver peak 2. | 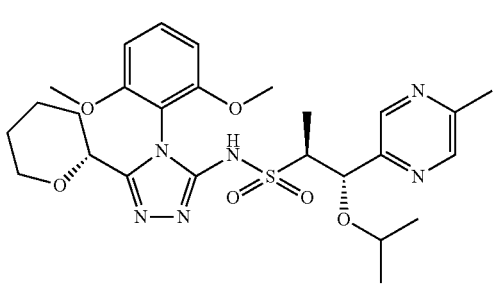 [SMILES: COc1cccc(OC)c1-n1c(NS(=O)(=O)[C@@H](C)[C@@H](OC(C)C)c2cnc(C)cn2)nnc1[C@H]1CCCCO1]

OR

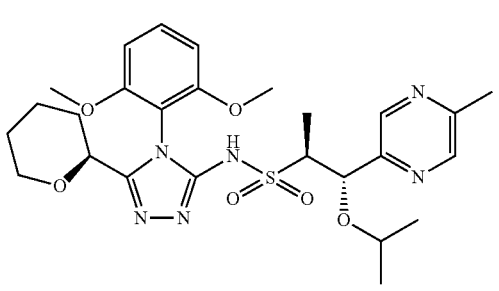 [SMILES: COc1cccc(OC)c1-n1c(NS(=O)(=O)[C@@H](C)[C@@H](OC(C)C)c2cnc(C)cn2)nnc1[C@@H]1CCCCO1]

OR

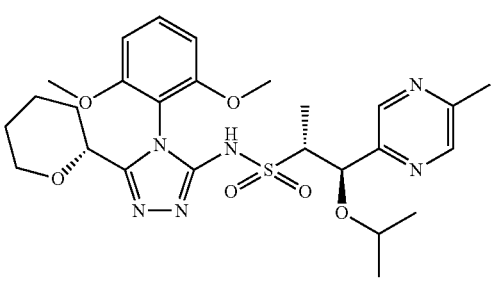 [SMILES: COc1cccc(OC)c1-n1c(NS(=O)(=O)[C@H](C)[C@H](OC(C)C)c2cnc(C)cn2)nnc1[C@H]1CCCCO1]

OR

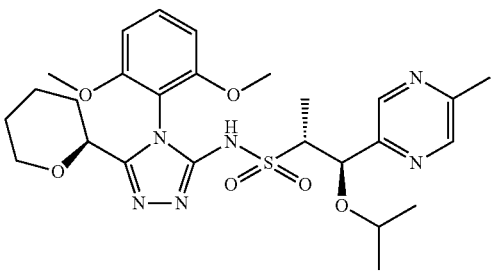 [SMILES: COc1cccc(OC)c1-n1c(NS(=O)(=O)[C@H](C)[C@H](OC(C)C)c2cnc(C)cn2)nnc1[C@@H]1CCCCO1]

(1S,2S)-N-(4-(2,6-dimethoxyphenyl)-5-((S)-tetrahydro-2H-pyran-2-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-((R)-tetrahydro-2H-pyran-2-yl)-4H-1,2,4-triazol-3-yl)-1-isopropoxy-1-(5-methylpyrazin-2-yl)propane-2-sulfonamide or |

TABLE 18-continued

| Example | Reagents | Structure, Name and Data |
|---|---|---|
| | | (1R,2R)-N-(4-(2,6-dimethoxyphenyl)-5-((S)-tetrahydro-2H-pyran-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((R)-tetrahydro-2H-pyran-2-yl)-4H-1,2,4-triazol-3-yl)-1-isopropoxy-1-(5-methylpyrazin-2-yl)propane-2-sulfonamide.<br>$^1$H NMR (500 MHz, DMSO-d$_6$) δ 12.93 (br s, 1H), 8.45 (s, 1H), 8.42 (s, 1H), 7.47 (t, J = 8.4 Hz, 1H), 6.83 (d, J = 8.6 Hz, 2H), 4.75 (d, J = 6.0 Hz, 1H), 4.01 (dd, J = 3.2, 9.0 Hz, 1H), 3.76 (s, 3H), 3.74 (s, 3H), 3.66-3.59 (m, 1H), 3.44-3.36 (m, 2H), 3.15 (td, J = 6.1, 11.7 Hz, 1H), 2.47 (s, 3H), 1.85-1.65 (m, 3H), 1.51-1.43 (m, 1H), 1.42-1.36 (m, 2H), 1.00 (d, J = 6.0 Hz, 3H), 0.98 (d, J = 7.3 Hz, 3H), 0.85 (d, J = 6.2 Hz, 3H). LCMS (pos) m/z: 561.2 (M + H)$^+$. |
| 213.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology:<br>Column: IC (2 × 15 cm) Mobile Phase: 45:55 (A:B) A: Liquid CO$_2$, B: MeOH, Flow Rate: 80 mL/min, 220 nm, 100 bar inlet pressure to deliver peak 1. | <br>OR<br><br>OR<br>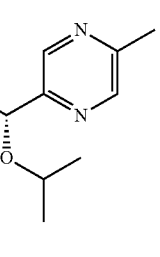<br>OR |

TABLE 18-continued

| Example | Reagents | Structure, Name and Data |
|---|---|---|
| | | 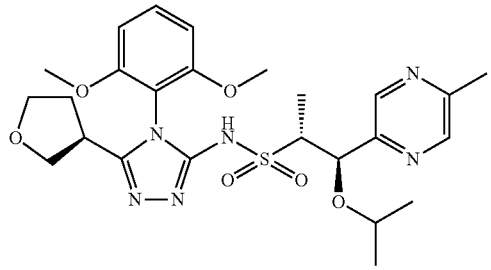 [SMILES: COc1cccc(OC)c1-n1c(NS(=O)(=O)[C@H](C)[C@H](OC(C)C)c2cnc(C)cn2)nnc1[C@@H]1CCOC1]<br><br>(1S,2S)-N-(4-(2,6-dimethoxyphenyl)-5-((R)-tetrahydrofuran-3-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-((S)-tetrahydrofuran-3-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((R)-tetrahydrofuran-3-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((S)-tetrahydrofuran-3-yl)-4H-1,2,4-triazol-3-yl)-1-isopropoxy-1-(5-methylpyrazin-2-yl)propane-2-sulfonamide.<br>$^1$H NMR (500 MHz, DMSO-$d_6$) δ 12.82 (s, 1H), 8.45 (s, 1H), 8.42 (d, J = 1.0 Hz, 1H), 7.53 (t, J = 8.6 Hz, 1H), 6.88 (dd, J = 3.9, 8.6 Hz, 2H), 4.74 (d, J = 6.2 Hz, 1H), 3.79 (s, 3H), 3.79 (s, 3H), 3.77-3.72 (m, 1H), 3.68-3.62 (m, 2H), 3.62-3.59 (m, 1H), 3.43-3.35 (m, 2H), 2.99-2.91 (m, 1H), 2.47 (s, 3H), 2.07-2.00 (m, 1H), 1.98-1.90 (m, 1H), 1.01 (d, J = 6.0 Hz, 3H), 0.98 (d, J = 7.0 Hz, 3H), 0.85 (d, J = 6.0 Hz, 3H). LCMS (pos) m/z: 547.2 (M + H)$^+$. |
| 214.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydrofuran-3-carbohydrazide and (S)-tetrahydrofuran-3-carbohydrazide (commercially available from Astatech Inc.), 2-isothiocyanato-1,3-dimethoxybenzene (Example 10.0). The mixture was purified by preparative SFC using the following methodology: Column: IC (2 × 15 cm) Mobile Phase: 45:55 (A:B) A: Liquid CO$_2$, B: MeOH, Flow Rate: 80 mL/min, 220 nm, 100 bar inlet pressure to deliver peak 2. | 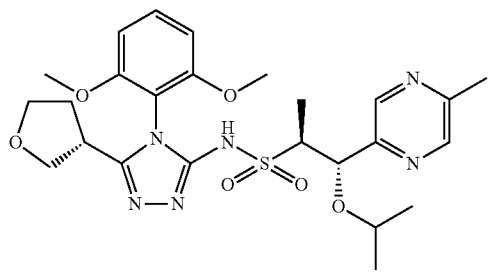<br>OR<br>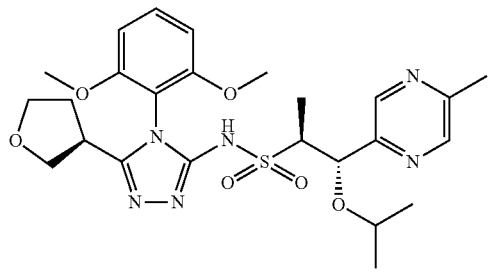<br>or |

TABLE 18-continued

| Example | Reagents | Structure, Name and Data |
|---------|----------|--------------------------|

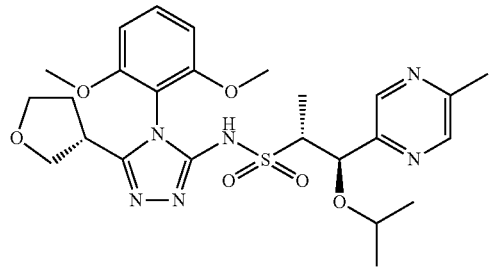 [SMILES: COc1cccc(OC)c1-n1c(NS(=O)(=O)[C@H](C)[C@H](OC(C)C)c2cnc(C)cn2)nnc1[C@H]1CCOC1]

OR

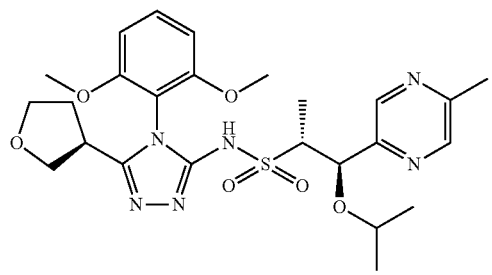 [SMILES: COc1cccc(OC)c1-n1c(NS(=O)(=O)[C@H](C)[C@H](OC(C)C)c2cnc(C)cn2)nnc1[C@@H]1CCOC1]

(1S,2S)-N-(4-(2,6-dimethoxyphenyl)-5-((R)-
tetrahydrofuran-3-yl)-4H-1,2,4-triazol-3-yl)-1-
isopropoxy-1-(5-methylpyrazin-2-yl)propane-2-
sulfonamide or (1S,2S)-N-(4-(2,6-
dimethoxyphenyl)-5-((S)-tetrahydrofuran-3-yl)-
4H-1,2,4-triazol-3-yl)-1-isopropoxy-1-(5-
methylpyrazin-2-yl)propane-2-sulfonamide or
(1R,2R)-N-(4-(2,6-dimethoxyphenyl)-5-((R)-
tetrahydrofuran-3-yl)-4H-1,2,4-triazol-3-yl)-1-
isopropoxy-1-(5-methylpyrazin-2-yl)propane-2-
sulfonamide or (1R,2R)-N-(4-(2,6-
dimethoxyphenyl)-5-((S)-tetrahydrofuran-3-yl)-
4H-1,2,4-triazol-3-yl)-1-isopropoxy-1-(5-
methylpyrazin-2-yl)propane-2-sulfonamide.
$^1$H NMR (500 MHz, DMSO-$d_6$) δ 12.82 (s, 1H),
8.45 (s, 1H), 8.42 (d, J = 1.0 Hz, 1H), 7.53 (t,
J = 8.4 Hz, 1H), 6.88 (d, J = 8.6 Hz, 2H), 4.74 (d,
J = 6.2 Hz, 1H), 3.79 (s, 3H), 3.79 (s, 3H), 3.74
(dt, J = 5.8, 8.0 Hz, 1H), 3.66-3.61 (m, 3H), 3.42-
3.35 (m, 2H), 2.98-2.91 (m, 1H), 2.47 (s, 3H),
2.07-1.99 (m, 1H), 1.97-1.89 (m, 1H), 1.01 (d,
J = 6.0 Hz, 3H), 0.98 (d, J = 7.3 Hz, 3H), 0.85 (d,
J = 6.0 Hz, 3H). LCMS (pos) m/z: 547.2
(M + H)$^+$.

TABLE 18-continued

| Example | Reagents | Structure, Name and Data |
|---|---|---|
| 215.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 25 cm) Mobile Phase: 60:40 (A:B) A: Liquid $CO_2$, B: IPA, Flow Rate: 80 mL/min, 220 nm, 100 bar inlet pressure to deliver peak 1. | 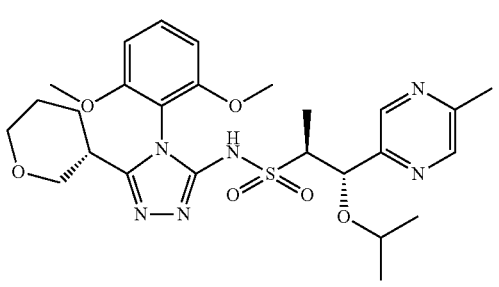 [SMILES: COc1cccc(OC)c1-n1c(NS(=O)(=O)[C@@H](C)[C@@H](OC(C)C)c2cnc(C)cn2)nnc1[C@H]1CCCOC1]<br><br>OR<br><br>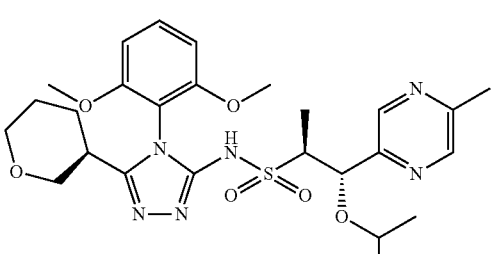<br><br>OR<br><br>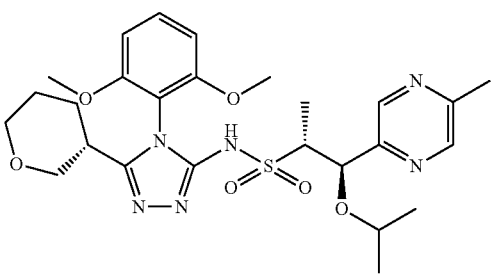 [SMILES: COc1cccc(OC)c1-n1c(NS(=O)(=O)[C@H](C)[C@H](OC(C)C)c2cnc(C)cn2)nnc1[C@H]1CCCOC1]<br><br>OR<br><br>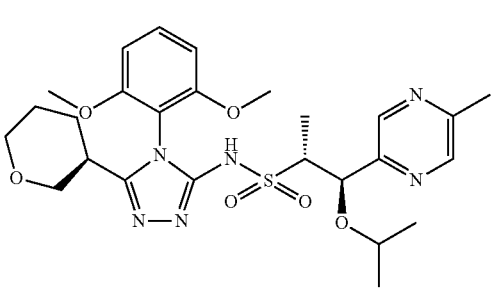 [SMILES: COc1cccc(OC)c1-n1c(NS(=O)(=O)[C@H](C)[C@H](OC(C)C)c2cnc(C)cn2)nnc1[C@@H]1CCCOC1]<br><br>(1S,2S)-N-(4-(2,6-dimethoxyphenyl)-5-((R)-tetrahydro-2H-pyran-3-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-((S)-tetrahydro-2H-pyran-3-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((R)-tetrahydro-2H-pyran-3-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((S)-tetrahydro-2H-pyran-3-yl)-4H-1,2,4-triazol-3-yl)-1-isopropoxy-1-(5-methylpyrazin-2-yl)propane-2-sulfonamide.<br>$^1$H NMR (500 MHz, DMSO-$d_6$) δ 12.85 (s, 1H), 8.45 (s, 1H), 8.42 (s, 1H), 7.53 (t, J = 8.6 Hz, 1H), |

TABLE 18-continued

| Example | Reagents | Structure, Name and Data |
|---|---|---|
| | | 6.89 (d, J = 8.6 Hz, 2H), 4.73 (d, J = 6.0 Hz, 1H), 3.79 (s, 3H), 3.79 (s, 3H), 3.76-3.71 (m, 1H), 3.69-3.63 (m, 1H), 3.44-3.35 (m, 2H), 3.33-3.26 (M, 2H), 2.47 (s, 3H), 2.32 (tt, J = 4.0, 10.6 Hz, 1H), 1.84-1.76 (m, 1H), 1.74-1.65 (m, 1H), 1.59 (br d, J = 13.5 Hz, 1H), 1.45-1.34 (m, 1H), 1.01 (d, J = 6.0 Hz, 3H), 0.97 (d, J = 7.0 Hz, 3H), 0.85 (d, J = 6.2 Hz, 3H). LCMS (pos) m/z: 561.2 (M + H)+. |
| 216.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydro-2H-pyran-3-carbohydrazide and (S)-tetrahydro-2H-pyran-3-carbohydrazide (commercially available from Synthonix), 2-isothiocyanato-1,3-dimethoxybenzene (Example 10.0). The mixture was purified by preparative SFC using the following methodology: Column: AD-H (2 × 25 cm) Mobile Phase: 60:40 (A:B) A: Liquid CO2, B: IPA, Flow Rate: 80 mL/min, 220 nm, 100 bar inlet pressure to deliver peak 2. | 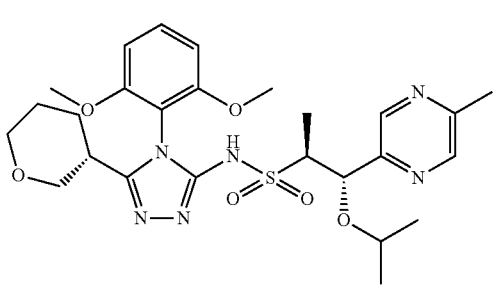<br>OR<br>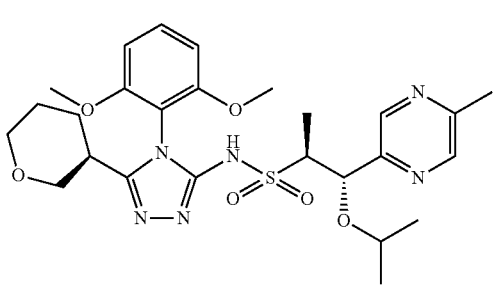 [SMILES: COc1cccc(OC)c1-n1c(NS(=O)(=O)[C@@H](C)[C@@H](OC(C)C)c2cnc(C)cn2)nnc1[C@@H]1CCCOC1]<br>OR<br>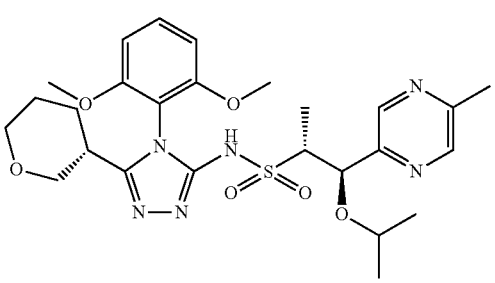<br>OR<br>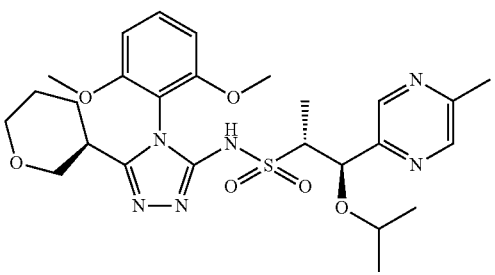 [SMILES: COc1cccc(OC)c1-n1c(NS(=O)(=O)[C@H](C)[C@H](OC(C)C)c2cnc(C)cn2)nnc1[C@@H]1CCCOC1]<br>(1S,2S)-N-(4-(2,6-dimethoxyphenyl)-5-((R)-tetrahydro-2H-pyran-3-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-((S)-tetrahydro-2H-pyran-3-yl)-4H-1,2,4-triazol-3-yl)-1-isopropoxy-1-(5-methylpyrazin-2-yl)propane-2-sulfonamide or |

TABLE 18-continued

| Example | Reagents | Structure, Name and Data |
|---|---|---|
| | | (1R,2R)-N-(4-(2,6-dimethoxyphenyl)-5-((R)-tetrahydro-2H-pyran-3-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((S)-tetrahydro-2H-pyran-3-yl)-4H-1,2,4-triazol-3-yl)-1-isopropoxy-1-(5-methylpyrazin-2-yl)propane-2-sulfonamide. <br> $^1$H NMR (500 MHz, DMSO-d$_6$) δ 12.82 (br s, 1H), 8.45 (s, 1H), 8.42 (s, 1H), 7.53 (t, J = 8.6 Hz, 1H), 6.89 (dd, J = 2.9, 8.6 Hz, 2H), 4.73 (d, J = 6.2 Hz, 1H), 3.79 (s, 3H), 3.79 (s, 3H), 3.73 (br d, J = 10.9 Hz, 1H), 3.65 (br dd, J = 2.3, 11.2 Hz, 1H), 3.38 (quin, J = 6.1 Hz, 2H), 3.34-3.26 (m, 2H), 2.47 (s, 3H), 2.36-2.29 (m, 1H), 1.88-1.76 (m, 1H), 1.75-1.65 (m, 1H), 1.59 (br d, J = 13.5 Hz, 1H), 1.47-1.35 (m, 1H), 1.01 (d, J = 6.0 Hz, 3H), 0.96 (d, J = 7.3 Hz, 3H), 0.85 (d, J = 6.2 Hz, 3H). LCMS (pos) m/z: 561.2 (M + H)$^+$. |
| 217.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-1,4-dioxane-2-carbohydrazide and (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid CO$_2$, B: MeOH, Flow Rate: 60 mL/min, 215 nm, 100 bar inlet pressure to deliver peak 1. | 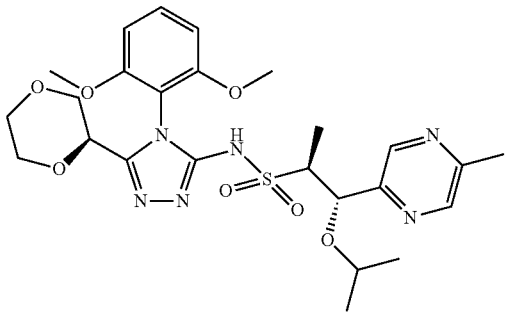 [SMILES: COc1cccc(OC)c1-n1c(NS(=O)(=O)[C@@H](C)[C@@H](OC(C)C)c2cnc(C)cn2)nnc1[C@@H]1COCCO1]<br>OR<br>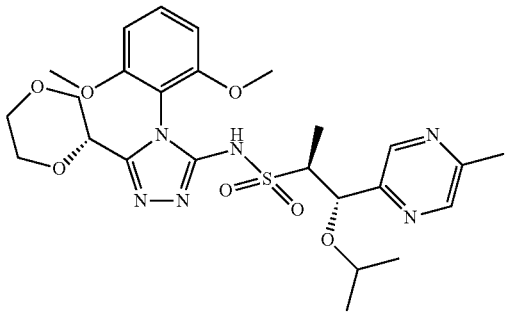 [SMILES: COc1cccc(OC)c1-n1c(NS(=O)(=O)[C@@H](C)[C@@H](OC(C)C)c2cnc(C)cn2)nnc1[C@H]1COCCO1]<br>or<br>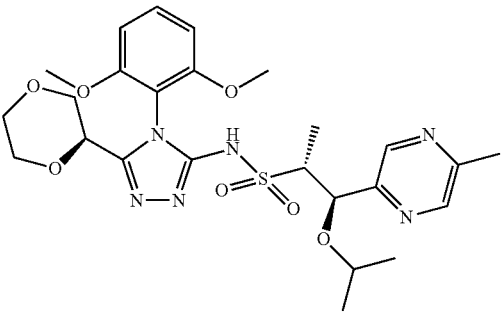 [SMILES: COc1cccc(OC)c1-n1c(NS(=O)(=O)[C@H](C)[C@H](OC(C)C)c2cnc(C)cn2)nnc1[C@@H]1COCCO1]<br>OR |

| Example | Reagents | Structure, Name and Data |
| --- | --- | --- |
| | | (1S,2S)-N-(4-(2,6-dimethoxyphenyl)-5-((R)-1,4-dioxan-2-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-((S)-1,4-dioxan-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-4-((R)-1,4-dioxan-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((S)-1,4-dioxan-2-yl)-4H-1,2,4-triazol-3-yl)-1-isopropoxy-1-(5-methylpyrazin-2-yl)propane-2-sulfonamide. $^1$H NMR (500 MHz, DMSO-$d_6$) δ 13.05 (br s, 1H), 8.45 (s, 1H), 8.42 (s, 1H), 7.50 (t, J = 8.4 Hz, 1H), 6.86 (dd, J = 5.7, 8.3 Hz, 2H), 4.75 (d, J = 6.0 Hz, 1H), 4.20-4.11 (m, 1H), 3.77 (s, 3H), 3.77 (s, 3H), 3.74-3.68 (m, 2H), 3.64 (d, J = 11.9 Hz, 1H), 3.61-3.56 (m, 1H), 3.51-3.45 (m, 1H), 3.42-3.35 (m, 3H), 2.47 (s, 3H), 1.02 (d, J = 6.0 Hz, 3H), 0.99 (d, J = 7.0 Hz, 3H), 0.86 (d, J = 6.0 Hz, 3H). LCMS (pos) m/z: 563.2 (M + H)$^+$. |
| 218.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-1,4-dioxane-2-carbohydrazide and (S)-1,4-dioxane-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid CO$_2$, B: MeOH, Flow Rate: 60 mL/min, 215 nm, 100 bar inlet pressure to deliver peak 2. | OR or |

TABLE 18-continued

| Example | Reagents | Structure, Name and Data |
| --- | --- | --- |
| | | 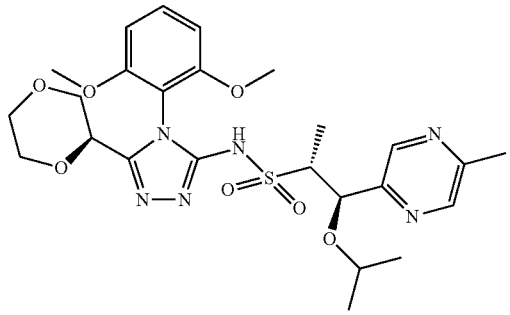 [SMILES: COc1cccc(OC)c1-n1c(NS(=O)(=O)[C@H](C)[C@H](OC(C)C)c2cnc(C)cn2)nnc1[C@@H]1COCCO1]<br>OR<br>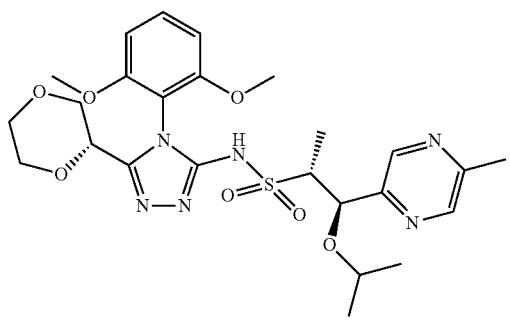 [SMILES: COc1cccc(OC)c1-n1c(NS(=O)(=O)[C@H](C)[C@H](OC(C)C)c2cnc(C)cn2)nnc1[C@H]1COCCO1]<br>(1S,2S)-N-(4-(2,6-dimethoxyphenyl)-5-((R)-1,4-dioxan-2-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-((S)-1,4-dioxan-2-yl)-4H-1,2,4-triazol-3-yl)-1-isopropoxy-1-(5-methylpyrazin-2-yl)propane-2-sulfonamide or sulfonamide or (1R,2R)-N-(4-(2,6-dimethoxyphenyl)-5-((R)-1,4-dioxan-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-((S)-1,4-dioxan-2-yl)-4H-1,2,4-triazol-3-yl)-1-isopropoxy-1-(5-methylpyrazin-2-yl)propane-2-sulfonamide.<br>$^1$H NMR (500 MHz, DMSO-$d_6$) δ 13.07 (s, 1H), 8.45 (s, 1H), 8.43 (s, 1H), 7.50 (t, J = 8.6 Hz, 1H), 6.93-6.82 (m, 2H), 4.74 (d, J = 6.2 Hz, 1H), 4.17 (dd, J = 4.2, 6.7 Hz, 1H), 3.78 (s, 3H), 3.77 (s, 3H), 3.75-3.69 (m, 2H), 3.66-3.61 (m, 1H), 3.60-3.56 (m, 1H), 3.52-3.45 (m, 1H), 3.43-3.35 (m, 3H), 2.47 (s, 3H), 1.00 (d, J = 6.0 Hz, 3H), 0.97 (d, J = 7.0 Hz, 3H), 0.85 (d, J = 6.2 Hz, 3H). LCMS (pos) m/z: 563.2 (M + H)$^+$. |

TABLE 18-continued

| Example | Reagents | Structure, Name and Data |
|---|---|---|
| 219.0 | (2R,3S)-3-(5-methylpyrimidin-2-yl)butane-2-sulfonamide (prepared in an analagous fashion to that of Example 1.0), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: AD-H (2 × 25 cm) Mobile Phase: 60:40 (A:B) A: Liquid $CO_2$, B: IPA, Flow Rate: 60 mL/min, 215 nm, 100 bar inlet pressure to deliver peak 1. | 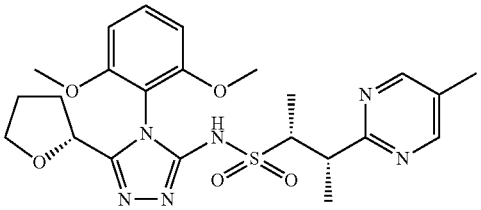 [SMILES: COc1cccc(OC)c1-n1c(NS(=O)(=O)[C@H](C)[C@@H](C)c2ncc(C)cn2)nnc1[C@H]1CCCO1]<br>OR<br>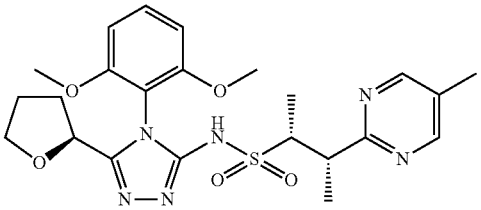<br>(2R,3S)-N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide or (2R,3S)-N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide.<br>$^1$H NMR (500 MHz, DMSO-$d_6$) δ 12.90 (br. s., 1H), 8.58 (s, 2H), 7.47 (t, J = 8.4 Hz, 1H), 6.82 (dd, J = 1.6, 8.6 Hz, 2H), 4.49 (dd, J = 5.6, 7.7 Hz, 1H), 3.73 (s, 3H), 3.71 (s, 3H), 3.68-3.61 (m, 2H), 3.59-3.53 (m, 1H), 3.51 (q, J = 7.3 Hz, 1H), 2.23 (s, 3H), 2.13-2.05 (m, 1H), 2.02-1.94 (m, 1H), 1.84-1.73 (m, 2H), 1.22 (d, J = 7.3 Hz, 3H), 1.06 (d, J = 7.0 Hz, 3H). LCMS (pos) m/z: 503.2 (M + H)$^+$. |
| 220.0 | (2R,3S)-3-(5-methylpyrimidin-2-yl)butane-2-sulfonamide (prepared in an analagous fashion to that of Example 1.0), (R)-tetrahydrofuran-2-carbohydrazide and (S)-tetrahydrofuran-2-carbohydrazide(commercially available from Enamine), 2-isothiocyanato-1,3-dimethoxybenzene (Example 10.0). The mixture was purified by preparative SFC using the following methodology: Column: AD-H (2 × 25 cm) Mobile Phase: 60:40 (A:B) A: Liquid $CO_2$, B: IPA, Flow Rate: 60 mL/min, 215 nm, 100 bar inlet pressure to deliver peak 2. | 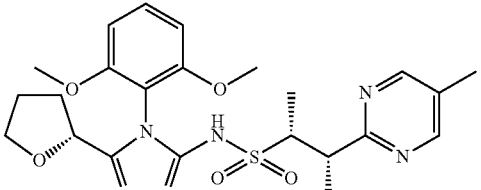<br>OR<br>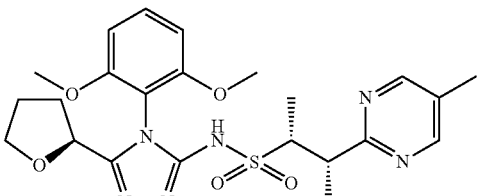<br>(2R,3S)-N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide or (2R,3S)-N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide.<br>$^1$H NMR (500 MHz, DMSO-$d_6$) δ 12.86 (br. s., 1H), 8.58 (s, 2H), 7.47 (t, J = 8.6 Hz, 1H), 6.82 (dd, J = 2.9, 8.6 Hz, 2H), 4.49 (dd, J = 5.6, 7.7 Hz, 1H), 3.73 (s, 3H), 3.71 (s, 3H), 3.68-3.61 (m, 2H), 3.56 (dq, J = 3.4, 6.9 Hz, 1H), 3.50 (q, J = 7.2 |

TABLE 18-continued

| Example | Reagents | Structure, Name and Data |
|---|---|---|
| | | Hz, 1H), 2.23 (s, 3H), 2.14-2.06 (m, 1H), 2.03-1.94 (m, 1H), 1.83-1.74 (m, 2H), 1.22 (d, J = 7.3 Hz, 3H), 1.07 (d, J = 7.0 Hz, 3H). LCMS (pos) m/z: 503.2 (M + H)$^+$. |
| 221.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide(Example 108.2), 4-isothiocyanatooxane (commercially available from Enamine.) The mixture was purified by preparative SFC using the following methodology: Column: AD-H (2 × 25 cm) Mobile Phase: 75:25 (A:B) A: Liquid CO$_2$, B: MeOH, Flow Rate: 80 mL/min, 220 nm, 100 bar inlet pressure to deliver peak 1. | 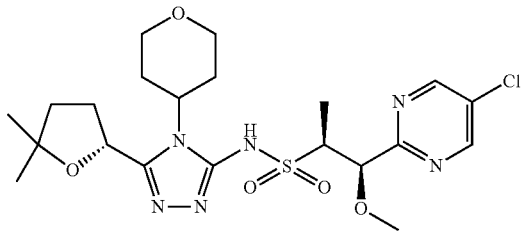 [SMILES: CO[C@H](c1ncc(Cl)cn1)[C@H](C)S(=O)(=O)Nc1nnc([C@H]2CCC(C)(C)O2)n1C1CCOCC1]<br>OR<br>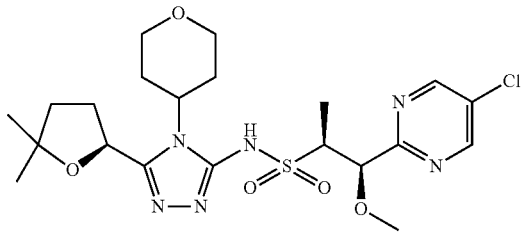 [SMILES: CO[C@H](c1ncc(Cl)cn1)[C@H](C)S(=O)(=O)Nc1nnc([C@@H]2CCC(C)(C)O2)n1C1CCOCC1]<br>(1R,2S)-1-(5-chloropyrimidin-2-yl)-N-(5-((S)-5,5-dimethyltetrahydrofuran-2-yl)-4-(tetrahydro-2H-pyran-4-yl)-4H-1,2,4-triazol-3-yl)-1-methoxypropane-2-sulfonamide or (1R,2S)-1-(5-chloropyrimidin-2-yl)-N-(5-((R)-5,5-dimethyltetrahydrofuran-2-yl)-4-(tetrahydro-2H-pyran-4-yl)-4H-1,2,4-triazol-3-yl)-1-methoxypropane-2-sulfonamide. $^1$H NMR (500 MHz, DMSO-d$_6$) δ 12.78 (s, 1H), 8.99-8.87 (m, 2H), 5.13 (t, J = 6.6 Hz, 1H), 4.90 (d, J = 3.9 Hz, 1H), 4.33 (tt, J = 4.0, 12.0 Hz, 1H), 3.97 (td, J = 5.5, 11.6 Hz, 2H), 3.51-3.44 (m, 1H), 3.38-3.27 (m, 2H), 3.16-3.10 (m, 3H), 2.72-2.52 (m, 2H), 2.52-2.44 (m, 1H), 2.32-2.23 (m, 1H), 1.90-1.80 (m, 2H), 1.62 (t, J = 9.9 Hz, 2H), 1.26 (d, J = 7.0 Hz, 3H), 1.24 (s, 3H), 1.13 (s, 3H). LCMS (pos) m/z: 515.2 (M + H)$^+$. |
| 222.0 | (1R,2S)-1-(5-chloropyrimidin-2-yl)-1-methoxypropane-2-sulfonamide (Example 11.3), (R)-5,5-dimethyltetrahydrofuran-2-carbohydrazide (S)-5,5-dimethyltetrahydrofuran-2-carbohydrazide (Example 108.2), 4-isothiocyanatooxane (commercially available from Enamine.) The mixture was purified by preparative SFC using the following methodology: Column: AD-H (2 × 25 cm) Mobile Phase: 75:25 (A:B) A: Liquid CO$_2$, B: MeOH, Flow Rate: 80 mL/min, 220 nm, 100 bar inlet pressure to deliver peak 2. | 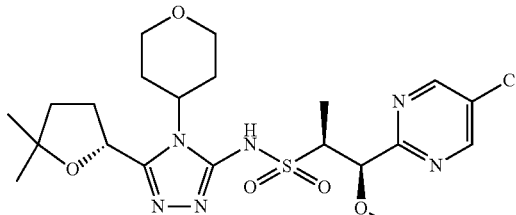<br>OR<br>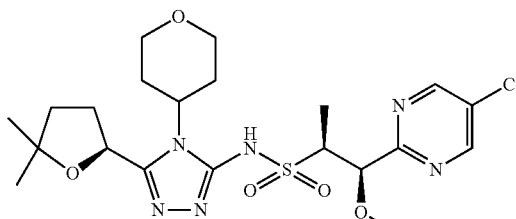<br>(1R,2S)-1-(5-chloropyrimidin-2-yl)-N-(5-((S)-5,5-dimethyltetrahydrofuran-2-yl)-4-(tetrahydro-2H-pyran-4-yl)-4H-1,2,4-triazol-3-yl)-1- |

| Example | Reagents | Structure, Name and Data |
|---|---|---|
| | | methoxypropane-2-sulfonamide or (1R,2S)-1-(5-chloropyrimidin-2-yl)-N-(5-((R)-5,5-dimethyltetrahydrofuran-2-yl)-4-(tetrahydro-2H-pyran-4-yl)-4H-1,2,4-triazol-3-yl)-1-methoxypropane-2-sulfonamide. $^1$H NMR (500 MHz, DMSO-$d_6$) δ 12.78 (br. s., 1H), 8.93 (s, 2H), 5.12 (t, J = 6.6 Hz, 1H), 4.93 (d, J = 3.6 Hz, 1H), 4.33 (tt, J = 4.0, 12.0 Hz, 1H), 4.02-3.91 (m, 2H), 3.46 (dq, J = 4.0, 6.9 Hz, 1H), 3.40-3.27 (m, 2H), 3.10 (s, 3H), 2.66 (dq, J = 4.7, 12.3 Hz, 1H), 2.60-2.47 (m, 2H), 2.31-2.23 (m, 1H), 1.84 (t, J = 7.4 Hz, 2H), 1.68-1.58 (m, 2H), 1.28-1.22 (m, 6H), 1.13 (s, 3H). LCMS (pos) m/z: 515.2 (M + H)$^+$. |
| 223.0 | (2S,3R)-3-(5-methylpyrimidin-2-yl)butane-2-sulfonamide (Example 1.0), (S)-tetrahydrothiophene-2-carbohydrazide and (R)-tetrahydrothiophene-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid CO$_2$, B: EtOH, Flow Rate: 60 mL/min, 215 nm, 100 bar inlet pressure to deliver peak 1. | 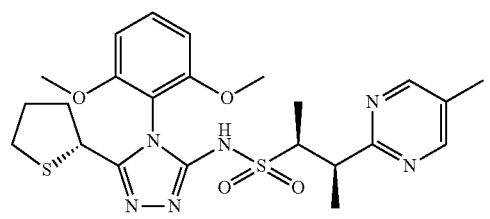 [SMILES: COc1cccc(OC)c1-n1c(NS(=O)(=O)[C@@H](C)[C@H](C)c2ncc(C)cn2)nnc1[C@H]1CCCS1]<br>OR<br>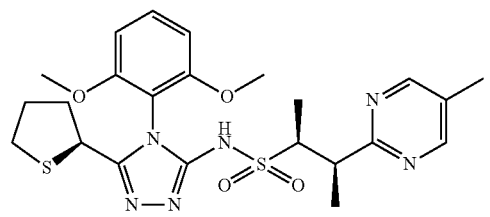 [SMILES: COc1cccc(OC)c1-n1c(NS(=O)(=O)[C@@H](C)[C@H](C)c2ncc(C)cn2)nnc1[C@@H]1CCCS1]<br>(2S,3R)-N-(4-(2,6-dimethoxyphenyl)-5-((S)-tetrahydrothiophen-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((R)-tetrahydrothiophen-2-yl)-4H-1,2,4-triazol-3-yl)-3-(5-methylpyrimidin-2-yl)butane-2-sulfonamide. $^1$H NMR (500 MHz, DMSO-$d_6$) δ 12.85 (br s, 1H), 8.58 (s, 2H), 7.49 (t, J = 8.6 Hz, 1H), 6.83 (dd, J = 0.9, 8.4 Hz, 2H), 3.91 (t, J = 6.4 Hz, 1H), 3.75 (s, 3H), 3.71 (s, 3H), 3.68-3.62 (m, 1H), 3.59-3.53 (m, 1H), 2.88-2.82 (m, 1H), 2.23 (s, 3H), 2.16-2.05 (m, 2H), 1.95-1.87 (m, 1H), 1.22 (d, J = 7.0 Hz, 3H), 1.07 (d, J = 7.0 Hz, 3H). LCMS (pos) m/z: 519.2 (M + H)$^+$. |

TABLE 18-continued

| Example | Reagents | Structure, Name and Data |
|---|---|---|
| 224.0 | (2S,3R)-3-(5-methylpyrimidin-2-yl)butane-2-sulfonamide (Example 1.0), (S)-tetrahydrothiophene-2-carbohydrazide and (R)-tetrahydrothiophene-2-carbohydrazide (commercially available from Enamine), 2-isothiocyanato-1,3-dimethoxybenzene (Example 10.0). The mixture was purified by preparative SFC using the following methodology: Column: AD-H (2 × 25 cm) Mobile Phase: 70:30 (A:B) A: Liquid $CO_2$, B: EtOH, Flow Rate: 60 mL/min, 215 nm, 100 bar inlet pressure to deliver peak 2. | (2S,3R)-N-(4-(2,6-dimethoxyphenyl)-5-((S)-tetrahydrothiophen-2-yl)-4H-1,2,4-triazol-3-yl)-3-(5-methylpyrimidin-2-yl)butane-2-sulfonamide or (2S,3R)-N-(4-(2,6-dimethoxyphenyl)-5-((R)-tetrahydrothiophen-2-yl)-4H-1,2,4-triazol-3-yl)-3-(5-methylpyrimidin-2-yl)butane-2-sulfonamide. $^1$H NMR (500 MHz, DMSO-$d_6$) δ 12.85 (br s, 1H), 8.58 (s, 2H), 7.49 (t, J = 8.4 Hz, 1H), 6.83 (dd, J = 2.9, 8.6 Hz, 2H), 3.91 (t, J = 6.4 Hz, 1H), 3.75 (s, 3H), 3.72 (s, 3H), 3.69-3.64 (m, 1H), 3.59-3.53 (m, 1H), 2.88-2.81 (m, 1H), 2.80-2.74 (m, 1H), 2.33-2.26 (m, 1H), 2.23 (s, 3H), 2.14-2.04 (m, 2H), 1.95-1.88 (m, 1H), 1.23 (d, J = 7.0 Hz, 3H), 1.07 (d, J = 7.0 Hz, 3H). LCMS (pos) m/z: 519.2 (M + H)$^+$. |
| 225.0 | (1R,2S)-1-(5-chloropyrimidin-2-yl)-1-methoxypropane-2-sulfonamide (Example 11.3), (2S,5S)-5-methyltetrahydrofuran-2-carbohydrazide and (2R,5R)-5-methyltetrahydrofuran-2-carbohydrazide (commercially available from Ukrorgsyntez), 4-isothiocyanatooxane (commercially available from Enamine.) The mixture was purified by preparative SFC using the following methodology: Column: AD-H (2 × 25 cm) Mobile Phase: 75:25 (A:B) A: Liquid $CO_2$, B: MeOH, Flow Rate: 80 mL/min, 220 nm, 100 bar inlet pressure to deliver peak 1. | (1R,2S)-1-(5-chloropyrimidin-2-yl)-1-methoxy-N-(5-((2S,5S)-5-methyltetrahydrofuran-2-yl)-4-(tetrahydro-2H-pyran-4-yl)-4H-1,2,4-triazol-3-yl)propane-2-sulfonamide or (1R,2S)-1-(5-chloropyrimidin-2-yl)-1-methoxy-N-(5-((2R,5R)-5-methyltetrahydrofuran-2-yl)-4-(tetrahydro-2H-pyran-4-yl)-4H-1,2,4-triazol-3-yl)propane-2-sulfonamide. $^1$H NMR (500 MHz, $CD_2Cl_2$) δ 8.82-8.69 (m, 2H), 5.03 (d, J = 3.9 Hz, 1H), 4.92 (dd, J = 5.6, 7.7 Hz, 1H), 4.48 (tt, J = 4.1, 12.2 Hz, 1H), 4.25-4.15 (m, 1H), 4.09 (br dd, |

| Example | Reagents | Structure, Name and Data |
|---|---|---|
| | | J = 4.3, 11.5 Hz, 2H), 3.63 (dq, J = 3.9, 6.9 Hz, 1H), 3.51-3.43 (m, 2H), 3.30 (s, 3H), 2.87 (dq, J = 4.7, 12.5 Hz, 1H), 2.76 (dq, J = 4.7, 12.3 Hz, 1H), 2.65-2.58 (m, 1H), 2.27 (qd, J = 8.0, 12.8 Hz, 1H), 2.21-2.13 (m, 1H), 1.80-1.63 (m, 3H), 1.36 (d, J = 7.0 Hz, 3H), 1.23 (d, J = 6.0 Hz, 3H). LCMS (pos) m/z: 501.2 (M + H)+. |
| 226.0 | (1R,2S)-1-(5-chloropyrimidin-2-yl)-1-methoxypropane-2-sulfonamide (Example 11.3), (2S,5S)-5-methyltetrahydrofuran-2-carbohydrazide and (2R,5R)-5-methyltetrahydrofuran-2-carbohydrazide (commercially available from Ukrorgsyntez), 4-isothiocyanatooxane (commercially available from Enamine.) The mixture was purified by preparative SFC using the following methodology: Column: AD-H (2 × 25 cm) Mobile Phase: 75:25 (A:B) A: Liquid $CO_2$, B: MeOH, Flow Rate: 80 mL/min, 220 nm, 100 bar inlet pressure to deliver peak 2. | 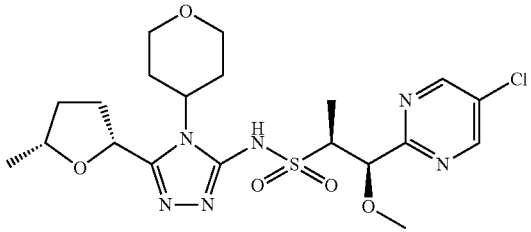 [SMILES: CO[C@H](c1ncc(Cl)cn1)[C@H](C)S(=O)(=O)Nc1nnc([C@H]2CC[C@@H](C)O2)n1C1CCOCC1]<br>OR<br>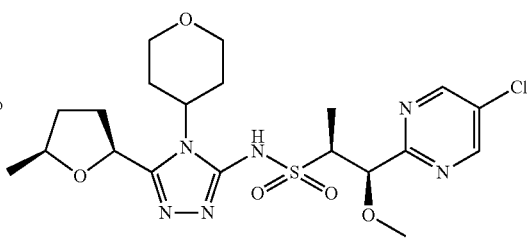<br>(1R,2S)-1-(5-chloropyrimidin-2-yl)-1-methoxy-N-(5-((2S,5S)-5-methyltetrahydrofuran-2-yl)-4-(tetrahydro-2H-pyran-4-yl)-4H-1,2,4-triazol-3-yl)propane-2-sulfonamide or (1R,2S)-1-(5-chloropyrimidin-2-yl)-1-methoxy-N-(5-((2R,5R)-5-methyltetrahydrofuran-2-yl)-4-(tetrahydro-2H-pyran-4-yl)-4H-1,2,4-triazol-3-yl)propane-2-sulfonamide. $^1$H NMR (500 MHz, $CD_2Cl_2$) δ 10.92 (br s, 1H), 8.80-8.66 (m, 2H), 5.02 (d, J = 3.4 Hz, 1H), 4.89 (dd, J = 5.7, 7.5 Hz, 1H), 4.46 (tt, J = 4.0, 12.1 Hz, 1H), 4.22-4.14 (m, 1H), 4.06 (br dd, J = 3.8, 11.5 Hz, 2H), 3.60-3.54 (m, 1H), 3.47-3.41 (m, 2H), 3.23 (s, 3H), 2.84 (dq, J = 4.9, 12.5 Hz, 1H), 2.72 (dq, J = 4.7, 12.2 Hz, 1H), 2.66-2.57 (m, 1H), 2.29-2.21 (m, 1H), 2.17-2.08 (m, 1H), 1.79-1.72 (m, 1H), 1.69-1.57 (m, 2H), 1.32 (d, J = 7.0 Hz, 3H), 1.19 (d, J = 6.0 Hz, 3H). LCMS (pos) m/z: 501.2 (M + H)+. |

Example 227.0. Preparation of (S)-tert-butyl 3-sulfamoylpiperidine-1-carboxylate and (R)-tert-butyl 3-sulfamoylpiperidine-1-carboxylate 227.1

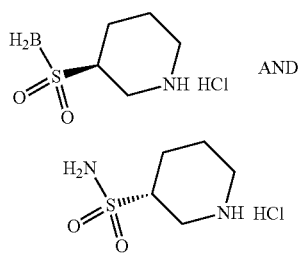

(S)-Piperidine-3-sulfonamide hydrochloride and (R)-piperidine-3-sulfonamide hydrochloride, Example 227.1

A solution of 4-chloropyridine-3-sulfonamide (5.0 g, 25.9 mmol) in AcOH (150 mL) was placed in a parr bottle. The solution was bubbled with nitrogen gas for 5 min. To this solution was added a suspension of platinum (IV) oxide (5.9 g, 25.9 mmol) in AcOH (30 mL). The reaction was stirred under hydrogen (50 psi) for 72 h. The reaction mixture was filtered through a Celite® brand filter agent pad and the pad was washed with MeOH (2×50 mL). The combined filtrate was concentrated under reduced pressure to provide Example 227.1 (6.0 g) as an oil which was used in the next step without further purification. LCMS-ESI (pos) m/z: 165 (M+H)+.

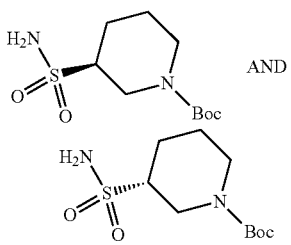

227.0

(S)-tert-Butyl 3-sulfamoylpiperidine-1-carboxylate and (R)-tert-butyl 3-sulfamoylpiperidine-1-carboxylate, Example 227.0

To a mixture of Example 227.1 (12.0 g, 59.8 mmol) and TEA (41.6 mL, 298.9 mmol) in DCM (215 mL) was added a solution of di-tert-butyl dicarbonate (15.7 mL, 71.8 mmol) in DCM (70 mL) at RT. The reaction mixture was stirred for 16 h at RT. The reaction mixture was washed with water (2×200 mL). The combined organic layer was washed with brine (100 mL), dried over sodium sulfate and evaporated under reduced pressure to obtain the product which was purified by column chromatography (silica: 100-200 mesh; elution: 0-30% EtOAc in DCM) to provide Example 227.0 (4.6 g, 34%, over two steps) as a white solid. $^1$H NMR (400 MHz, CD$_3$CN) δ 5.30 (s, 2H), 4.36 (d, J=11.8 Hz, 1H), 3.94 (d, J=13.3 Hz, 1H), 3.01-2.84 (m, 2H), 2.64-2.58 (s, 1H), 2.20 (d, J=13.3 Hz, 1H), 1.78 (d, J=13.5 Hz, 1H), 1.74-1.57 (m, 2H), 1.43 (s, 9H). LCMS-ESI (pos) m/z: 263 (M−H)$^+$.

Example 228.0: Preparation of (3S,5S)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide

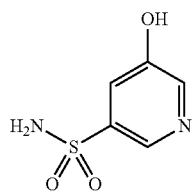

228.1

5-Hydroxypyridine-3-sulfonamide, Example 228.1

To a 100-mL round-bottomed flask was added 5-bromopyridine-3-sulfonamide (commercially available from Enamine, Kiev, Ukraine) (0.486 g, 2.05 mmol), 2-di-t-butylphosphino-3,4,5,6-tetramethyl-2',4',6'-tri-i-isopropyl-biphenyl (commercially available from Strem Chemicals, Inc., MA, USA, 0.079 g, 0.16 mmol) and Pd$_2$(dba)$_3$ (Sigma-Aldrich Chemical Company, Inc., 0.038 g, 0.041 mmol). The flask was placed under vacuum and back-filled with potassium hydroxide (0.345 g, 6.15 mmol) solution in dioxane (5 mL) and water (5 mL). The reaction mixture was then stirred at 100° C. under N$_2$ for 17 h. LCMS analysis indicated the reaction was complete. The reaction mixture was then allowed to cool to RT. The reaction mixture was diluted with 1.0 N HCl and washed with Et$_2$O. The aqueous phase was concentrated in vacuo to afford the title compound 228.1 (0.387 g, 2.22 mmol, 100% yield) as a white solid, which was directly used in the next step without further purification. LCMS-ESI (pos), m/z: 175.1 (M+H)$^+$.

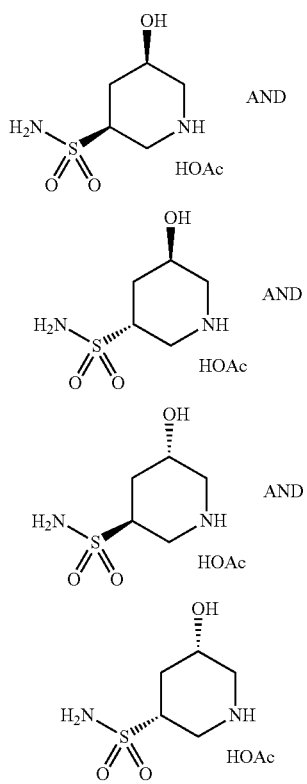

228.2

(3R,5R)-5-Hydroxypiperidine-3-sulfonamide acetate and (3S,5R)-5-hydroxypiperidine-3-sulfonamide acetate and (3R,5S)-5-hydroxypiperidine-3-sulfonamide acetate and (3S,5S)-5-hydroxypiperidine-3-sulfonamide acetate, Example 228.2

To a 1-L hydrogenation flask was added Example 228.1 (6.46 g, 37.1 mmol) and AcOH (250 mL, 4330 mmol). Water (20 mL) was added as a co-solvent. The mixture was bubbled with N$_2$ for 2 min before platinum (IV) oxide hydrate (8.42 g, 37.1 mmol) was added under N$_2$ flow. The flask was set up on a Parr shaker, vacuumed and back-filled with N$_2$ two times, and then placed under vacuum and filled with hydrogen gas (tank). The reaction mixture was stirred at RT under 50 psi of hydrogen gas for 24 h. LCMS analysis indicated that the reaction was complete. Celite® brand filter agent (20 g) was added to the mixture with stirring. The solid was removed by filtration after 10 min of stirring. The filter cake was rinsed with MeOH. The combined organics were concentrated in vacuo to afford Example 228.2 (8.91 g, 100% yield) as a light-yellow oil, which was directly used in the next step without purification. LCMS-ESI (pos), m/z: 181.1 (M+H)$^+$.

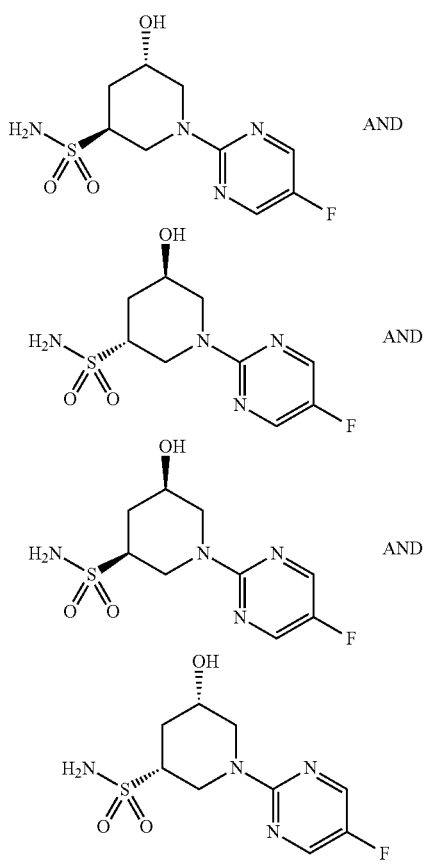

(3S,5S)-1-(5-Fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide, Example 228.0

To a 500-mL round-bottomed flask was added Example 228.2 (8.91 g, 37.1 mmol) and Hunig's base (32.3 mL, 185 mmol) in DMF (80 mL). 2-Chloro-5-fluoro-pyrimidine (18.32 mL, 148 mmol) was then added with stirring. The reaction mixture was stirred at 120° C. for 18 h. LCMS analysis indicated the reaction was complete. The reaction mixture was allowed to cool to RT and then was diluted with water and extracted with DCM. The organic layers were washed with brine and dried over Na₂SO₄. The solution was then filtered and concentrated in vacuo to give the initial material as an orange oil. The material thus obtained was purified by silica gel chromatography (a gradient of 0-100% EtOAc in DCM), to provide 228.0 (3.7 g, 10.93 mmol, 36% yield) as a light-yellow solid. LCMS-ESI (pos), m/z: 277.0 (M+H)$^+$.

Example 229.3. Preparation of (3S,5R)-1-(5-fluoropyrimidin-2-yl)-5-methoxypiperidine-3-sulfonamide and (3R,5S)-1-(5-fluoropyrimidin-2-yl)-5-methoxypiperidine-3-sulfonamide

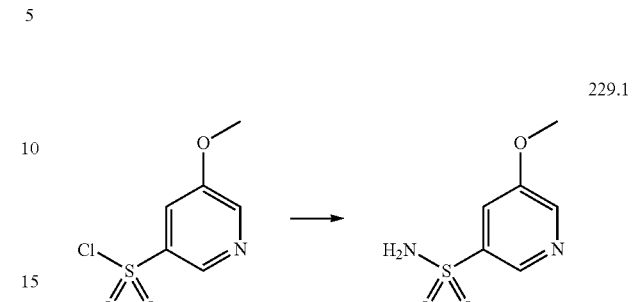

5-Methoxypyridine-3-sulfonamide, Example 229.1

The reaction mixture of 5-methoxypyridine-3-sulfonyl chloride (commercially available from Enamine, Kiev, Ukraine) (1.0 g, 4.82 mmol) and ammonia, (0.5 M solution in 1,4-dioxane, 96 mL, 48.2 mmol) was stirred at 0 to RT for 30 min. LCMS indicated that the reaction was complete. The reaction was then filtered and the cake was rinsed with dioxane. The combined solutions were concentrated in vacuo to give the title compound (0.91 g, 100% yield) as light yellow foam which was used in the next step without further purification. LCMS-ESI (pos) m/z: 189.2 (M+H)$^+$.

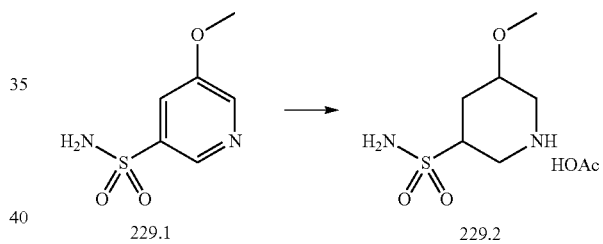

5-Methoxypiperidine-3-sulfonamide acetate, Example 229.2

A solution of 5-methoxypyridine-3-sulfonamide (0.9 g, 4.78 mmol) in AcOH (31.9 mL) was bubbled with argon gas for 2 min before platinum (IV) oxide (1.09 g, 4.78 mmol) was added under a stream of argon. The reaction mixture was then stirred at RT under 45 psi of hydrogen gas for 38 h. The mixture was filtered, and the filtrate was concentrated in vacuo to give the title compound (1.22 g, 100% yield) as light yellow foam which was used in the next step without further purification. LCMS-ESI (pos) m/z: 195.2 (M+H)$^+$.

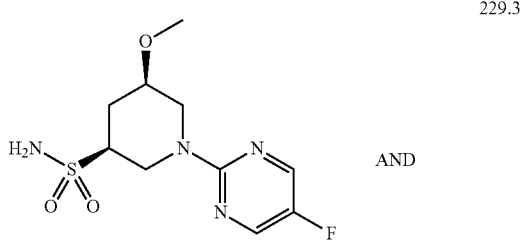

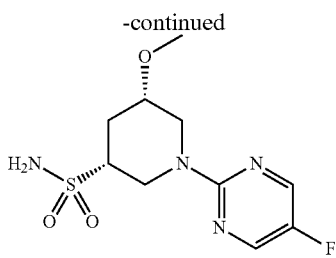

(3S,5R)-1-(5-Fluoropyrimidin-2-yl)-5-methoxypiperidine-3-sulfonamide and (3R,5S)-1-(5-fluoropyrimidin-2-yl)-5-methoxypiperidine-3-sulfonamide, Example 229.3

To a 40 mL vial (w/ pressure release septa) was added 5-methoxypiperidine-3-sulfonamide acetate, (229.2, 2.45 g, 9.62 mmol), N-ethyl-N-isopropylpropan-2-amine (16.75 mL, 96 mmol) and 2-chloro-5-fluoropyrimidine (6.37 g, 48.1 mmol) in DMSO (48 mL). The reaction mixture was stirred at 100° C. for 23 h. LCMS indicated formation of the desired product. The reaction mixture was then diluted with water and extracted with DCM. The organic extract was washed with saturated aqueous NaCl and dried over $Na_2SO_4$. The solution was then filtered and concentrated in vacuo to give the material as an orange oil. The material thus obtained was absorbed onto a plug of silica gel and purified by chromatography through a RediSep-Sep pre-packed silica gel column (40 g) eluting with a gradient of 0% to 100% 1/3 EtOH/EtOAc in heptane to provide the title compound 229.3 (0.51 g, 18% yield) as white solid, LCMS-ESI (pos) m/z: 291.0 $(M+H)^+$.

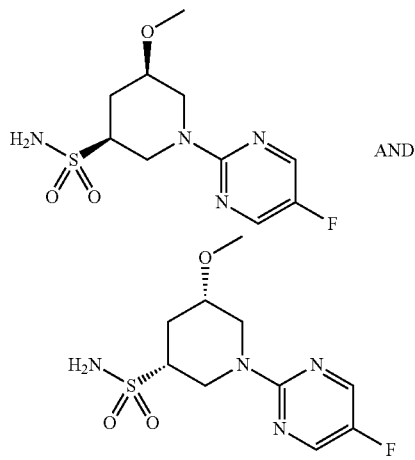

(3S,5R)-1-(5-Fluoropyrimidin-2-yl)-5-methoxypiperidine-3-sulfonamide or (3R,5S)-1-(5-fluoropyrimidin-2-yl)-5-methoxypiperidine-3-sulfonamide, Example 229.5

Example 229.5 was obtained by chiral separation of 229.3 on a SFC: Chiralpak AD-H column, 30% MeOH/$CO_2$, with 0.2% DEA. Example 229.5 was the earlier peak to elute on the Chiralpak AD-H column. $^1$H NMR (400 MHz, $CD_3OD$) δ 1.65 (td, J=12.28, 10.88 Hz, 1H) 2.57-2.72 (m, 2H) 2.98 (dd, J=13.06, 11.40 Hz, 1H) 3.14 (ddt, 1H) 3.27-3.36 (m, 1H) 3.45 (s, 3H) 4.97 (ddt, 1H) 5.17 (ddt, 1H) 8.32 (d, J=0.62 Hz, 2H). LCMS-ESI (pos) m/z: 291.0 $(M+H)^+$.

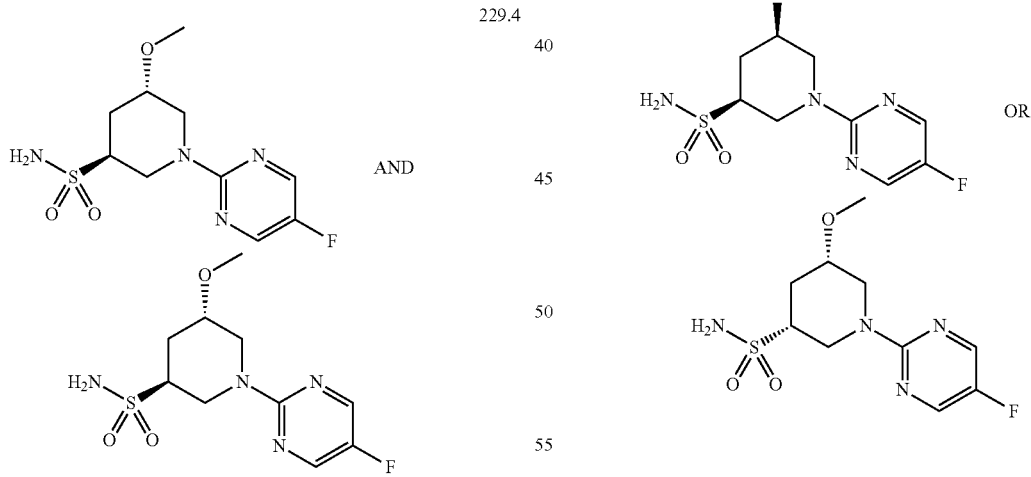

(3S,5S)-1-(5-Fluoropyrimidin-2-yl)-5-methoxypiperidine-3-sulfonamide and (3R,5R)-1-(5-fluoropyrimidin-2-yl)-5-methoxypiperidine-3-sulfonamide, Example 229.4

Further elution under the conditions described in Example 229.3 delivered 229.4 (0.24 g, 0.832 mmol, 8.65% yield) as light yellow solid. LCMS-ESI (pos) m/z: 291.0 $(M+H)^+$.

(3S,5R)-1-(5-Fluoropyrimidin-2-yl)-5-methoxypiperidine-3-sulfonamide or (3R,5S)-1-(5-fluoropyrimidin-2-yl)-5-methoxypiperidine-3-sulfonamide, Example 229.6

Further elution under the conditions described in Example 229.5 afforded Example 229.6. $^1$H NMR (400 MHz, $CD_3OD$) δ 1.65 (td, J=12.28, 10.88 Hz, 1H) 2.57-2.71 (m, 2H) 2.94-3.04 (m, 1H) 3.14 (ddt, 1H) 3.31-3.36 (m, 1H) 3.45 (s, 3H) 4.97 (ddt, 1H) 5.17 (ddt, 1H) 8.32 (s, 2H). LCMS-ESI (pos) m/z: 291.0 $(M+H)^+$.

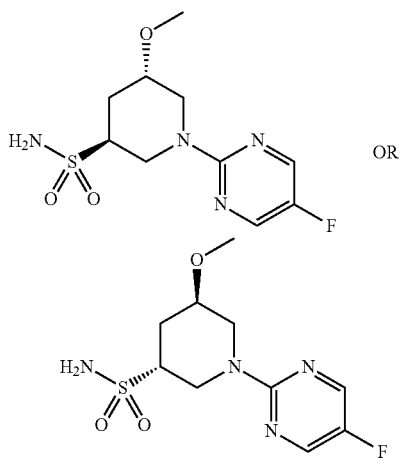

(3S,5S)-1-(5-Fluoropyrimidin-2-yl)-5-methoxypiperidine-3-sulfonamide or (3R,5R)-1-(5-fluoropyrimidin-2-yl)-5-methoxypiperidine-3-sulfonamide, Example 229.7

Example 229.7 was obtained by chiral separation of 229.3 on a SFC Chiralpak AD-H column, 25% MeOH/CO$_2$, with 0.2% DEA. Example 229.7 was the earlier peak to elute on Chiralpak AD-H column. $^1$H NMR (400 MHz, CD$_3$OD) δ 1.98 (ddd, J=13.42, 12.39, 3.01 Hz, 1H) 2.41-2.51 (m, 1H) 2.98 (dd, J=14.31, 1.66 Hz, 1H) 3.10 (dd, J=13.06, 11.20 Hz, 1H) 3.29-3.36 (m, 1H) 3.32 (s, 3H) 3.66-3.71 (m, 1H) 4.98 (dq, J=14.38, 2.19 Hz, 1H) 5.18 (ddt, 1H) 8.29 (d, J=0.83 Hz, 2H) LCMS-ESI (pos) m/z: 291.0 (M+H)$^+$.

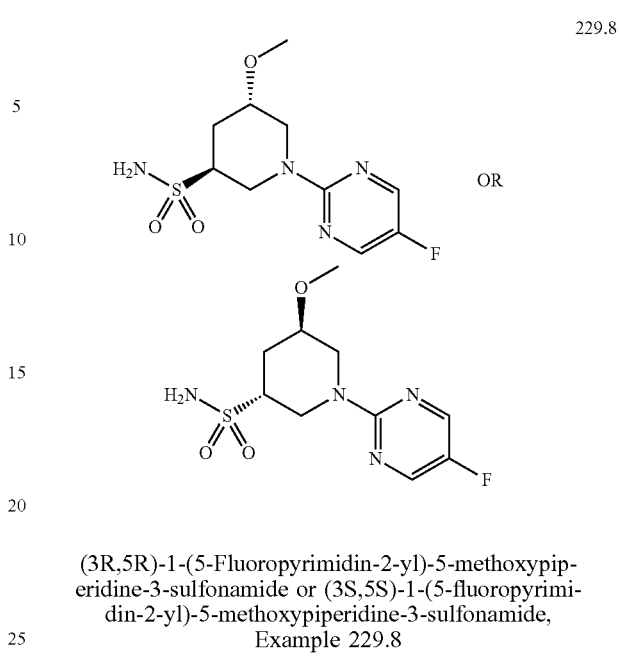

(3R,5R)-1-(5-Fluoropyrimidin-2-yl)-5-methoxypiperidine-3-sulfonamide or (3S,5S)-1-(5-fluoropyrimidin-2-yl)-5-methoxypiperidine-3-sulfonamide, Example 229.8

Further elution under the conditions described in Example 229.6 afforded Example 229.8. $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.32 (s, 3H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos) m/z: 291.0 (M+H)$^+$.

The compounds set forth in the following table were synthesized following the procedure in Example 140.0 using the known starting material as described.

TABLE 19

| | | |
|---|---|---|
| 230.0 | (2S,3R)-3-(5-methylpyrimidin-2-yl)butane-2-sulfonamide (Example 1.0), (R)-4-(methylsulfonyl)morpholine-2-carbohydrazide and (S)-4-(methylsulfonyl)morpholine-2-carbohydrazide (commercially available from Enamine), 2-isothiocyanato-1,3-dimethoxybenzene (Example 10.0). The mixture was purified by preparative SFC using the following methodolgy: Column: AY-H (2 × 25 cm) Mobile Phase: 50:50 (A:B) A: Liquid CO$_2$, B: EtOH, Flow Rate: 65 mL/min, 215 nm, 100 bar inlet pressure to deliver peak 1. | 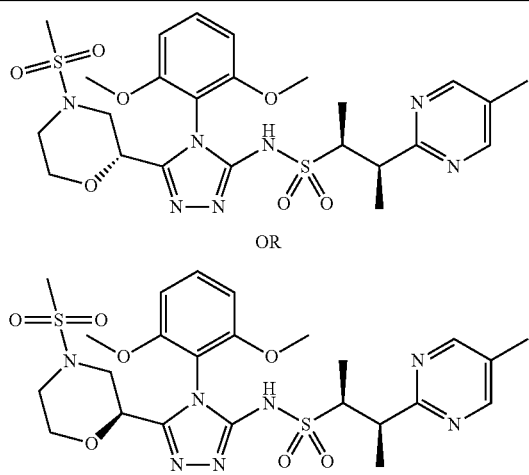<br><br>(2S,3R)-N-(4-(2,6-dimethoxyphenyl)-5-((R)-4-(methylsulfonyl)morpholin-2-yl)-4H-1,2,4-triazol-3-yl)-3-(5-methylpyrimidin-2-yl)butane-2-sulfonamide OR (2S,3R)-N-(4-(2,6-dimethoxyphenyl)-5-((S)-4-(methylsulfonyl)morpholin-2-yl)-4H-1,2,4-triazol-3-yl)-3-(5-methylpyrimidin-2-yl)butane-2-sulfonamide. $^1$H NMR (500 MHz, CD$_2$Cl$_2$) δ = 11.26 (br. s., 1H), 8.50 (s, 2H), 7.49 (t, J = 8.6 Hz, 1H), 6.72 (dd, J = 4.2, 8.6 Hz, 2H), 4.24 (dd, J = 2.6, |

| | | |
|---|---|---|
| | | 9.3 Hz, 1H), 3.92-3.87 (m, 1H), 3.82 (s, 3H), 3.78 (s, 3H), 3.77-3.70 (m, 2H), 3.62 (quin, J = 6.7 Hz, 1H), 3.51-3.40 (m, 2H), 3.22 (dd, J = 9.3, 11.9 Hz, 1H), 2.98-2.90 (m, 1H), 2.80 (s, 3H), 2.26 (s, 3H), 1.30 (d, J = 7.0 Hz, 3H), 1.29-1.22 (m, 3H). LCMS (pos) m/e: 596.2 (M + H)+. |
| 231.0 | (2S,3R)-3-(5-methylpyrimidin-2-yl)butane-2-sulfonamide (Example 1.0), (R)-4-(methylsulfonyl)morpholine-2-carbohydrazide and (S)-4-(methylsulfonyl)morpholine-2-carbohydrazide (commercially available from Enamine), 2-isothiocyanato-1,3-dimethoxybenzene (Example 10.0). The mixture was purified by preparative SFC using the following methodology: Column: AY-H (2 × 25 cm) Mobile Phase: 50:50 (A:B) A: Liquid CO2, B: EtOH, Flow Rate: 65 mL/min, 215 nm, 100 bar inlet pressure to deliver peak 2. | 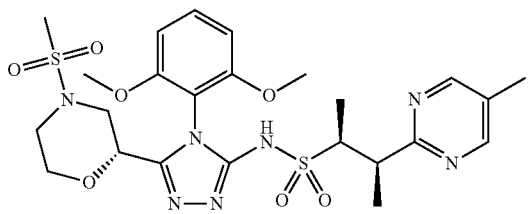<br>OR<br>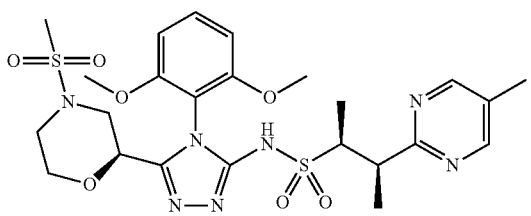<br>(2S,3R)-N-(4-(2,6-dimethoxyphenyl)-5-((R)-4-(methylsulfonyl)morpholin-2-yl)-4H-1,2,4-triazol-3-yl)-3-(5-methylpyrimidin-2-yl)butane-2-sulfonamide OR (2S,3R)-N-(4-(2,6-dimethoxyphenyl)-5-((S)-4-(methylsulfonyl)morpholin-2-yl)-4H-1,2,4-triazol-3-yl)-3-(5-methylpyrimidin-2-yl)butane-2-sulfonamide. 1H NMR (500 MHz, CD2Cl2) δ 11.34 (br. s., 1H), 8.51 (s, 2H), 7.49 (t, J = 8.6 Hz, 1H), 6.79-6.68 (m, 2H), 4.24 (dd, J = 2.3, 9.3 Hz, 1H), 3.89 (d, J = 11.4 Hz, 1H), 3.85-3.77 (m, 6H), 3.77-3.70 (m, 2H), 3.58 (quin, J = 6.8 Hz, 1H), 3.52-3.41 (m, 2H), 3.21 (dd, J = 9.6, 11.7 Hz, 1H), 2.98-2.90 (m, 1H), 2.80 (s, 3H), 2.27 (s, 3H), 1.31 (d, J = 7.0 Hz, 3H), 1.29-1.25 (m, 3H). LCMS (pos) m/e: 5 96.2 (M + H)+. |
| 232.0 | 2,3-dihydrobenzofuran-2-carbohydrazide (commercially available from Frontier Scientific Services Inc.), 5-isothiocyanato-4,6-dimethoxypyrimidine (Example 10.1), (1R,2S)-1-methoxy-1-(5-methylpyrimidin-2-yl)propane-2-sulfonamide (Example 11.0) The mixture was separated by SFC using the following methodology: Chiralpak AD-H, 20% MeOH. This was the first isomer to elute under these conditions. | <br>OR<br>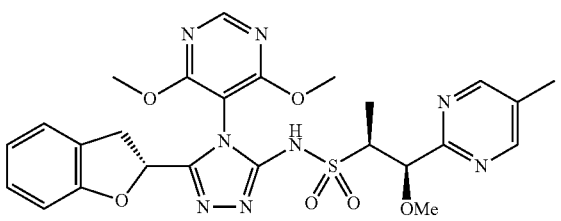<br>(1R,2S)-N-(5-((S)-2,3-dihydrobenzofuran-2-yl)-4-(4,6-dimethoxypyrimidin-5-yl)-4H-1,2,4-triazol-3-yl)-1-methoxy-1-(5-methylpyrimidin-2-yl)propane-2-sulfonamide or (1R,2S)-N-(5-((R)-2,3-dihydrobenzofuran-2-yl)-4-(4,6-dimethoxypyrimidin-5-yl)-4H-1,2,4-triazol-3-yl)-1-methoxy-1-(5-methylpyrimidin-2-yl)propane-2-sulfonamide. 1H NMR (500 MHz, CDC13) δ 11.10 (s, 1 H) 8.49-8.55 (m, 1 H) 8.42 (s, 1 H) 8.33-8.36 (m, 1 H) 7.28 (s, 1 H) 7.11 (d, J = 7.4 Hz, 1 H) |

TABLE 19-continued

| Example | Reagents | Structure, Name and Data |
|---|---|---|
| 233.0 | 2,3-dihydrobenzofuran-2-carbohydrazide (commercially available from Frontier Scientific Services Inc.), 5-isothiocyanato-4,6-dimethoxypyrimidine (Example 10.1), (1R,2S)-1-methoxy-1-(5-methylpyrimidin-2-yl)propane-2-sulfonamide, (Example 11.0) The mixture was separated by SFC using the following methodology: Chiralpak AD-H, 20% MeOH. This was the second isomer to elute under these conditions. | 7.00-7.06 (m, 1 H) 6.85 (t, J = 7.4 Hz, 1 H) 6.50 (d, J = 8.0 Hz, 1 H) 5.61 (dd, J = 10.3, 5.6 Hz, 1 H) 5.30 (s, 1 H) 5.02 (d, J = 2.7 Hz, 1 H) 4.00-4.03 (m, 3 H) 3.92 (s, 3 H) 3.62-3.68 (m, 1 H) 3.52-3.58 (m, 1 H) 3.49 (qd, J = 7.0, 2.9 Hz, 1 H) 3.30 (s, 3 H) 2.57 (s, 3H) 1.19-1.23 (m, 4H) 1.18-1.23 (m, 3 H). LCMS-ESI (pos) m/z: 569.2 (M + H)⁺.<br><br>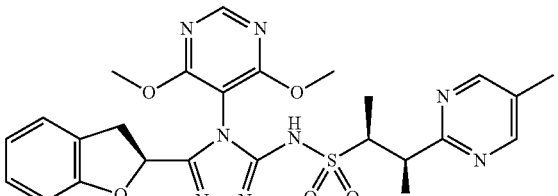<br>OR<br>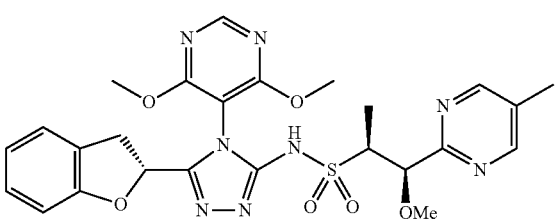<br><br>(1R,2S)-N-(5-((R)-2,3-dihydrobenzofuran-2-yl)-4-(4,6-dimethoxypyrimidin-5-yl)-4H-1,2,4-triazol-3-yl)-1-methoxy-1-(5-methylpyrimidin-2-yl)propane-2-sulfonamide or (1R,2S)-N-(5-((S)-2,3-dihydrobenzofuran-2-yl)-4-(4,6-dimethoxypyrimidin-5-yl)-4H-1,2,4-triazol-3-yl)-1-methoxy-1-(5-methylpyrimidin-2-yl)propane-2-sulfonamide. ¹H NMR (500 MHz, CDCl₃) δ 11.10 (s, 1 H) 8.49-8.55 (m, 1 H) 8.42 (s, 1 H) 8.33-8.36 (m, 1 H) 7.28 (s, 1 H) 7.11 (d, J = 7.4 Hz, 1 H) 7.00-7.06 (m, 1 H) 6.85 (t, J = 7.4 Hz, 1 H) 6.50 (d, J = 8.0 Hz, 1 H) 5.61 (dd, J = 10.3, 5.6 Hz, 1 H) 5.30 (s, 1 H) 5.02 (d, J = 2.7 Hz, 1 H) 4.00-4.03 (m, 3 H) 3.92 (s, 3 H) 3.62-3.68 (m, 1 H) 3.52-3.58 (m, 1 H) 3.49 (qd, J = 7.0, 2.9 Hz, 1 H) 3.30 (s, 3 H) 2.57 (s, 3 H) 1.19-1.23 (m, 4 H) 1.18-1.23 (m, 3 H). LCMS-ESI (pos) m/z: 569.2 (M + H)⁺. |

The compounds set forth in the following table were synthesized following the procedure in Example 108.0 using the known starting material as described.

TABLE 20

| Example | Reagents | Structure, Name and Data |
|---|---|---|
| 234.1 | 3-oxoisoindoline-1-carboxylic acid (commercially available from Accel Pharma Tech.). | (R)-3-oxoisoindoline-1-carbohydrazide and (S)-3-oxoisoindoline-1-carbohydrazide. LCMS-ESI (pos) m/z: 192.2 (M + H)⁺. |

TABLE 20-continued

| Example | Reagents | Structure, Name and Data |
|---|---|---|
| 238.1 | 2,3-dihydrobenzofuran-3-carboxylic acid (commercially available from Small Molecules, Inc.). | 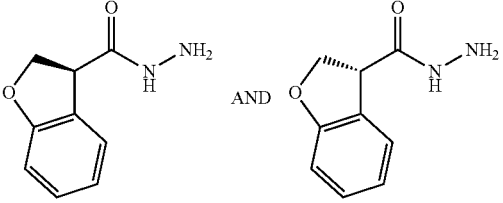<br>(R)-2,3-dihydrobenzofuran-3-carbohydrazide and (S)-2,3-dihydrobenzofuran-3-carbohydrazide. LCMS-ESI (pos) m/z: 179.2 (M + H)⁺. |

The compounds set forth in the following table were synthesized following the procedure described in Example 140.0 using the known starting material as described.

TABLE 21

| Example | Reagents | Structure, Name and Data |
|---|---|---|
| 234.0 | (R)-3-oxoisoindoline-1-carbohydrazide and (S)-3-oxoisoindoline-1-carbohydrazide (Example 234.1), 2-isothiocyanato-1,3-dimethoxybenzene (Example 10.0), and (2S,3R)-3-(5-chloropyrimidin-2-yl)butane-2-sulfonamide (Example 1.4). The mixture was separated by SFC Chiralpak AD-H, 50% IPA. This was the first isomer to elute under these conditions. | 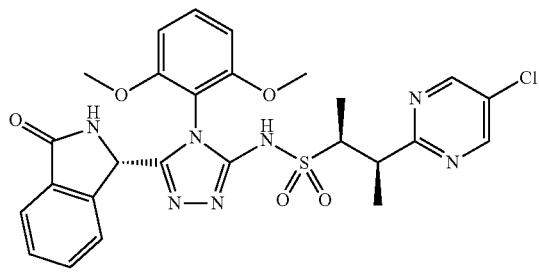<br>OR<br>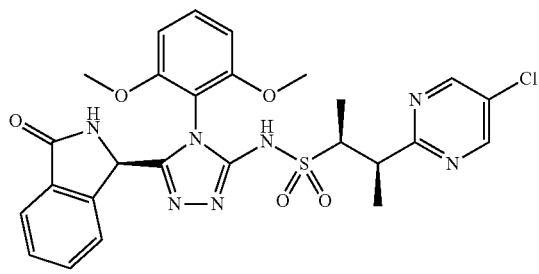<br>(2S,3R)-3-(5-chloropyrimidin-2-yl)-N-(4-(2,6-dimethoxyphenyl)-5-((S)-3-oxoisoindolin-1-yl)-4H-1,2,4-triazol-3-yl)butane-2-sulfonamide or (2S,3R)-3-(5-chloropyrimidin-2-yl)-N-(4-(2,6-dimethoxyphenyl)-5-((R)-3-oxoisoindolin-1-yl)-4H-1,2,4-triazol-3-yl)butane-2-sulfonamide. ¹H NMR (500 MHz, DMSO-$d_6$) δ 13.03-13.10 (m, 1 H) 8.88-8.94 (m, 1 H) 8.81-8.87 (m, 2 H) 7.50-7.58 (m, 1 H) 7.35-7.40 (m, 1 H) 7.30-7.34 (m, 1 H) 7.25-7.28 (m, 1 H) 7.12-7.18 (m, 1 H) 6.57-6.62 (m, 1 H) 6.08-6.13 (m, 1 H) 5.72-5.74 (m, 1 H) 3.75-3.80 (m, 3 H) 3.57-3.64 (m, 1 H) 3.45-3.51 (m, 1 H) 3.22-3.26 (m, 3 H) 1.15-1.19 (m, 3 H) 1.04-1.06 (m, 3 H). LCMS-ESI (pos) m/z: 584.2 (M + H)⁺. |

TABLE 21-continued

| Example | Reagents | Stucture, Name and Data |
|---|---|---|
| 235.0 | (R)-3-oxoisoindoline-1-carbohydrazide and (S)-3-oxoisoindoline-1-carbohydrazide (Example 234.1), 2-isothiocyanato-1,3-dimethoxybenzene (Example 10.0), and (2S,3R)-3-(5-chloropyrimidin-2-yl)butane-2-sulfonamide (Example 1.4). The mixture was separated by SFC Chiralpak AD-H, 50% IPA. This was the second isomer to elute under these conditions. | OR<br><br>(2S,3R)-3-(5-chloropyrimidin-2-yl)-N-(4-(2,6-dimethoxyphenyl)-5-((R)-3-oxoisoindolin-1-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-3-oxoisoindolin-1-yl)-4H-1,2,4-triazol-3-yl)butane-2-sulfonamide. $^1$H NMR (500 MHz, DMSO-$d_6$) δ 13.03-13.10 (m, 1 H) 8.88-8.94 (m, 1 H) 8.81-8.87 (m, 2 H) 7.50-7.58 (m, 1 H) 7.35-7.40 (m, 1 H) 7.30-7.34 (m, 1 H) 7.25-7.28 (m, 1 H) 7.12-7.18 (m, 1 H) 6.57-6.62 (m, 1 H) 6.08-6.13 (m, 1 H) 5.72-5.74 (m, 1 H) 3.75-3.80 (m, 3 H) 3.57-3.64 (m, 1 H) 3.45-3.51 (m, 1 H) 3.22-3.26 (m, 3 H) 1.15-1.19 (m, 3 H) 1.04-1.06 (m, 3 H). LCMS-ESI (pos) m/z: 584.2 (M + H)$^+$. |
| 236.0 | (R)-3-oxoisoindoline-1-carbohydrazide and (S)-3-oxoisoindoline-1-carbohydrazide (Example 234.1), 2-isothiocyanato-1,3-dimethoxybenzene (Example 10.0), and (1R,2S)-1-(5-methylpyrimidin-2-yl)-1-methoxypropane-2-sulfonamide (Example 11.0). The mixture was separated by SFC Chiralpak IC, 40% ACN/MeOH (50/50). This was the second eluting enantiomer under these conditions. | OR<br><br>(1R,2S)-N-(4-(2,6-dimethoxyphenyl)-5-((S)-3-oxoisoindolin-1-yl)-4H-1,2,4-triazol-3-yl)-1-methoxy-1-(5-methylpyrimidin-2-yl)propane-2-sulfonamide or (1R,2S)-N-(4-(2,6-dimethoxyphenyl)-5-((R)-3-oxoisoindolin-1-yl)- |

| Example | Reagents | Structure, Name and Data |
|---|---|---|
| | | 4H-1,2,4-triazol-3-yl)-1-methoxy-1-(5-methylpyrimidin-2-yl)propane-2-sulfonamide. $^1$H NMR (500 MHz, DMSO-d$_6$) δ 12.97-13.11 (m, 1 H) 8.83-8.95 (m, 1 H) 8.54-8.69 (m, 2 H) 7.49-7.56 (m, 1 H) 7.34-7.40 (m, 1 H) 7.24-7.32 (m, 2 H) 7.12-7.20 (m, 1 H) 6.55-6.64 (m, 1 H) 6.07-6.16 (m, 1 H) 5.70-5.74 (m, 1 H) 4.70-4.77 (m, 1 H) 3.75-3.82 (m, 3 H) 3.32-3.37 (m, 1 H) 3.17-3.24 (m, 3 H) 3.09-3.15 (m, 3 H) 2.21-2.28 (m, 3 H) 1.02-1.08 (m, 3 H). LCMS-ESI (pos) m/z: 580.2 (M + H)$^+$. |
| 237.0 | (R)-3-oxoisoindoline-1-carbohydrazide and (S)-3-oxoisoindoline-1-carbohydrazide (Example 234.1), 2-isothiocyanato-1,3-dimethoxybenzene (Example 10.0), and (1R,2S)-1-(5-methylpyrimidin-2-yl)-1-methoxypropane-2-sulfonamide (Example 11.0). The mixture was separated by SFC Chiralpak IC, 40% ACN/MeOH (50/50). This was the first eluting enantiomer under these conditions. | 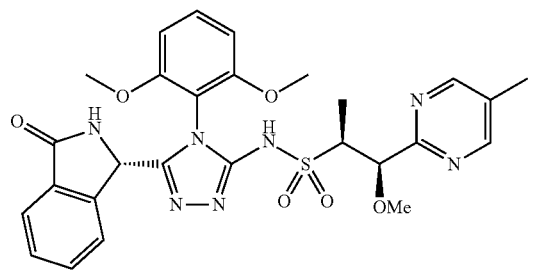<br>OR<br>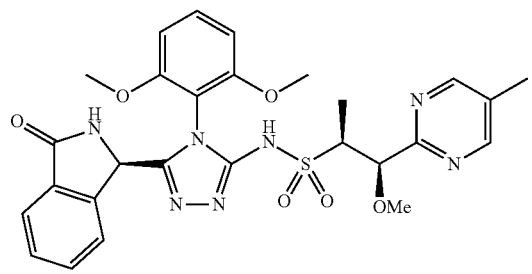<br>(1R,2S)-N-(4-(2,6-dimethoxyphenyl)-5-((S)-3-oxoisoindolin-1-yl)-4H-1,2,4-triazol-3-yl)-1-methoxy-1-(5-methylpyrimidin-2-yl)propane-2-sulfonamide or (1R,2S)-N-(4-(2,6-dimethoxphenyl)-5-((R)-3-oxoisoindolin-1-yl)-4H-1,2,4-triazol-3-yl)-1-methoxy-1-(5-methylpyrimidin-2-yl)propane-2-sulfonamide. $^1$H NMR (500 MHz, DMSO-d$_6$) δ 12.97-13.11 (m, 1 H) 8.83-8.95 (m, 1 H) 8.54-8.69 (m, 2 H) 7.49-7.56 (m, 1 H) 7.34-7.40 (m, 1 H) 7.24-7.32 (m, 2 H) 7.12-7.20 (m, 1 H) 6.55-6.64 (m, 1 H) 6.07-6.16 (m, 1 H) 5.70-5.74 (m, 1 H) 4.70-4.77 (m, 1 H) 3.75-3.82 (m, 3 H) 3.32-3.37 (m, 1 H) 3.17-3.24 (m, 3 H) 3.09-3.15 (m, 3 H) 2.21-2.28 (m, 3 H) 1.02-1.08 (m, 3 H). LCMS-ESI (pos) m/z: 580.2 (M + H)$^+$. |

TABLE 21-continued

| Example | Reagents | Structure, Name and Data |
|---|---|---|
| 238.0 | (R)-2,3-dihydrobenzofuran-3-carbohydrazide and (S)-2,3-dihydrobenzofuran-3-carbohydrazide (Example 238.1), 2-isothiocyanato-1,3-dimethoxybenzene (Example 10.0), and (1R,2S)-1-(5-methylpyrimidin-2-yl)-1-methoxypropane-2-sulfonamide (Example 11.0). The mixture was separated by SFC Chiralpak AD-H, 40% IPA. This was the first eluting enantiomer under these conditions | 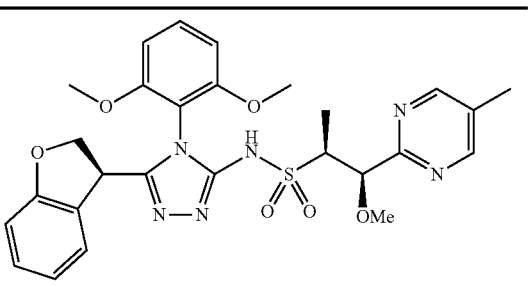<br>OR<br>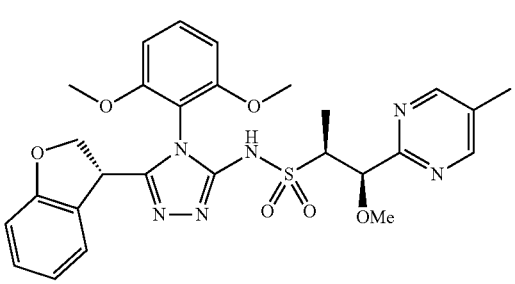<br><br>(1R,2S)-N-(5-((R)-2,3-dihydrobenzofuran-3-yl)-4-(2,6-dimethoxyphenyl)-4H-1,2,4-triazol-3-yl)-1-methoxy-1-(5-methylpyrimidin-2-yl)propane-2-sulfonamide or (1R,2S)-N-(5-((S)-2,3-dihydrobenzofuran-3-yl)-4-(2,6-dimethoxyphenyl)-4H-1,2,4-triazol-3-yl)-1-methoxy-1-(5-methylpyrimidin-2-yl)propane-2-sulfonamide. $^1$H NMR (500 MHz, DMSO-$d_6$) δ 12.90-13.02 (m, 1 H) 8.46-8.53 (m, 1 H) 8.36-8.43 (m, 1 H) 7.42-7.50 (m, 1 H) 7.05-7.14 (m, 1 H) 6.93-7.00 (m, 1 H) 6.80-6.89 (m, 2 H) 6.64-6.73 (m, 2 H) 4.79-4.86 (m, 1 H) 4.55-4.63 (m, 1 H) 4.45-4.53 (m, 2 H) 3.79-3.83 (m, 3 H) 3.64-3.69 (m, 3 H) 3.19-3.25 (m, 1 H) 3.14-3.18 (m, 3 H) 2.47-2.49 (m, 3 H) 1.01-1.04 (m, 3 H). LCMS-ESI (pos) m/z: 567.2 (M + H)$^+$. |
| 239.0 | (R)-2,3-dihyrdrobenzofuran-3-carbohydrazide and (S)-2,3-dihydrobenzofuran-3-carbohydrazide (Example 238.1), 5-isothiocyanato-4,6-dimethoxybenzene (Example 10.0), and (1R,2S)-1-(5-methylpyrimidin-2-yl)-1-methoxypropane-2-sulfonamide (Example 11.0). The mixture was separated by SFC Chiralpak AD-H, 40% IPA. This was the second eluting enantiomer under these conditions. | 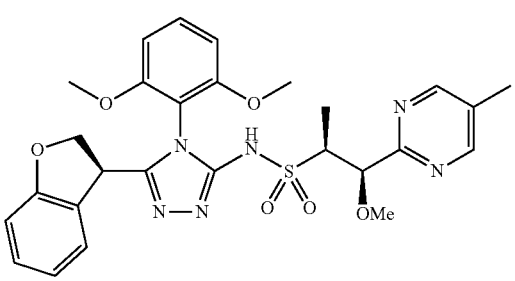<br>OR<br>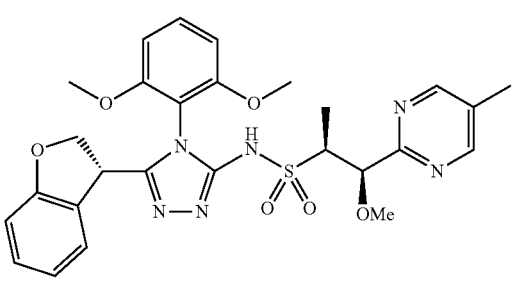<br><br>(1R,2S)-N-(5-((R)-2,3-dihydrobenzofuran-3-yl)-4-(2,6-dimethoxyphenyl)-4H-1,2,4-triazol-3-yl)-1-methoxy-1-(5-methylpyrimidin-2-yl)propane- |

TABLE 21-continued

| Example | Reagents | Structure, Name and Data |
|---|---|---|
| | | 2-sulfonamide or (1R,2S)-N-(5-((S)-2,3-dihydrobenzofuran-3-yl)-4-(2,6-dimethoxyphenyl)-4H-1,2,4-triazol-3-yl)-1-methoxy-1-(5-methylpyrimidin-2-yl)propane-2-sulfonamide. $^1$H NMR (500 MHz, DMSO-$d_6$) δ 12.90-13.02 (m, 1 H) 8.46-8.53 (m, 1 H) 8.36-8.43 (m, 1 H) 7.42-7.50 (m, 1 H) 7.05-7.14 (m, 1 H) 6.93-7.00 (m, 1 H) 6.80-6.89 (m, 2 H) 6.64-6.73 (m, 2 H) 4.79-4.86 (m, 1 H) 4.55-4.63 (m, 1 H) 4.45-4.53 (m, 2 H) 3.79-3.83 (m, 3 H) 3.64-3.69 (m, 3 H) 3.19-3.25 (m, 1 H) 3.14-3.18 (m, 3 H) 2.47-2.49 (m, 3 H) 1.01-1.04 (m, 3 H). LCMS-ESI (pos) m/z: 567.2 (M + H)$^+$. |
| 240.0 | (1R,2S)-1-(5-chloropyrimidin-2-yl)-1-methoxypropane-2-sulfonamide (Example 11.3), (S)-tetrahydrofuran-2-carbohydrazide (Enamine), and 2-methoxyphenyl isothiocyanate (Sigma Aldrich). | 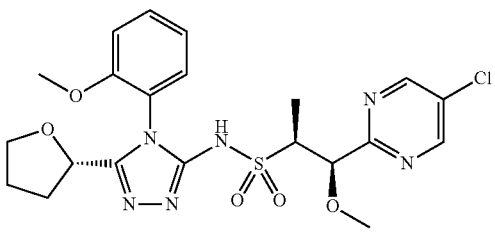 [SMILES: COc1ccccc1-n1c(NS(=O)(=O)[C@@H](C)[C@H](OC)c2ncc(Cl)cn2)nnc1[C@@H]1CCCO1]<br>(1R,2S)-1-(5-chloro-2-pyrimidinyl)-1-methoxy-N-(4-(2-methoxyphenyl)-5-((2S)-tetrahydro-2-furanyl)-4H-1,2,4-triazol-3-yl)-2-propanesulfonamide. 1H NMR (500 MHz, CDCl$_3$) δ 10.80 (br s, 2H), 8.72 (s, 2H), 8.70 (s, 2H), 7.43-7.53 (m, 2H), 7.34 (ddd, J = 1.62, 7.75, 13.59 Hz, 2H), 6.96-7.13 (m, 4H), 5.02 (d, J = 3.89 Hz, 1H), 4.95 (d, J = 4.67 Hz, 1H), 4.75 (t, J = 6.88 Hz, 1H), 4.60 (dd, J = 5.51, 7.33 Hz, 1H), 3.83 (s, 3H), 3.82 (s, 3H), 3.59-3.81 (m, 6H), 3.34 (s, 3H), 3.27 (s, 3H), 2.06-2.12 (m, 2H), 1.99-2.04 (m, 2H), 1.76-1.94 (m, 4H), 1.33-1.38 (m, 3H), 1.31 (d, J = 7.01 Hz, 3H). LCMS-ESI (pos) m/z: 509.0 (M + H)$^+$. |
| 241.0 | (1R,2S)-1-(5-chloropyrimidin-2-yl)-1-methoxypropane-2-sulfonamide (Example 11.3), (S)-tetrahydrofuran-2-carbohydrazide (Enamine), and 1-ethyl-2-isothiocyanatobenzene (Frontier Scientific Services. Inc.). | 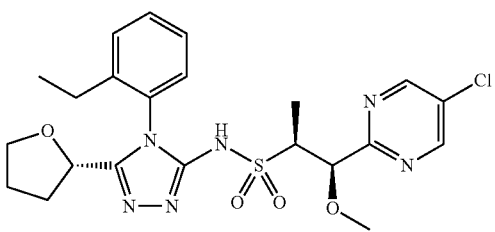<br>(1R,2S)-1-(5-chloro-2-pyrimidinyl)-N-(4-(2-ethylphenyl)-5-((2S)-tetrahydro-2-furanyl)-4H-1,2,4-triazol-3-yl)-1-methoxy-2-propanesulfonamide. $^1$H NMR (500 MHz, DMSO-$d_6$) δ 13.00-13.13 (br s, 1H), 8.86-8.98 (m, 1H), 7.42-7.60 (m, 2H), 7.38 (t, J = 6.75 Hz, 1H), 7.15-7.34 (m, 1H), 4.80 (d, J = 3.89 Hz, 1H), 4.50-4.62 (m, 1H), 3.51-3.70 (m, 2H), 3.34-3.49 (m, 2H), 3.06-3.15 (m, 3H), 2.40 (td, J = 7.83, 15.60 Hz, 2H), 2.15-2.32 (m, 1H), 2.06 (s, 1H), 1.72-1.91 (m, 2H), 1.05-1.19 (m, 6H). LCMS-ESI (pos) m/z: 507.20 (M + H)$^+$. |

TABLE 21-continued

| Example | Reagents | Structure, Name and Data |
|---|---|---|
| 242.0 | (1R,2S)-1-(5-chloropyrimidin-2-yl)-1-methoxypropane-2-sulfonamide (Example 11.3), (S)-tetrahydrofuran-2-carbohydrazide (Enamine), and 1-isothiocyanato-2-methylbenzene (Frontier Scientific Services, Inc.). | 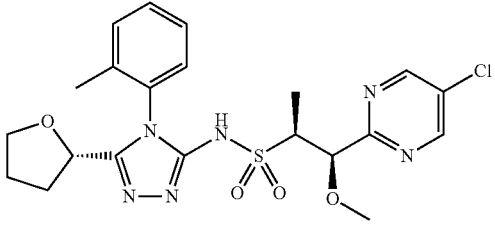 [SMILES: CO[C@H](c1ncc(Cl)cn1)[C@H](C)S(=O)(=O)Nc1nnc([C@@H]2CCCO2)n1-c1ccccc1C]<br>(1R,2S)-1-(5-chloro-2-pyrimidinyl)-1-methoxy-N-(4-(2-methylphenyl)-5-((2S)-tetrahydro-2-furanyl)-4H-1,2,4-triazol-3-yl)-2-propanesulfonamide. $^1$H NMR (500 MHz, DMSO-$d_6$) δ 8.87-8.97 (m, 1H), 7.28-7.48 (m, 4H), 4.80 (d, J = 3.76 Hz, 1H), 4.51-4.67 (m, 1H), 3.49-3.69 (m, 2H), 3.37-3.48 (m, 2H), 3.06-3.14 (m, 3H), 2.54 (s, 3H), 2.12-2.37 (m, 2H), 1.67-1.88 (m, 2H), 1.10 (d, J = 7.01 Hz, 3H). LCMS-ESI (pos) m/z: 493.20 (M + H)$^+$. |
| 243.0 | (1R,2S)-1-(5-chloropyrimidin-2-yl)-1-methoxypropane-2-sulfonamide (Example 11.3), (S)-tetrahydrofuran-2-carbohydrazide (Enamine), and 1-chloro-2-isothiocyanatobenzene (Frontier Scientific Services, Inc.). | 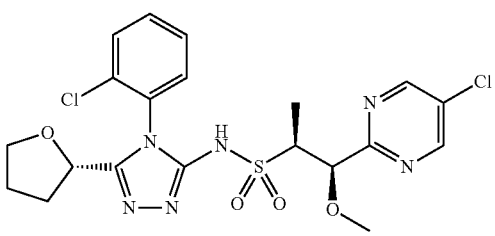 [SMILES: CO[C@H](c1ncc(Cl)cn1)[C@H](C)S(=O)(=O)Nc1nnc([C@@H]2CCCO2)n1-c1ccccc1Cl]<br>(1R,2S)-N-(4-(2-chlorophenyl)-5-((2S)-tetrahydro-2-furanyl)-4H-1,2,4-triazol-3-yl)-1-(5-chloro-2-pyrimidinyl)-1-methoxy-2-propanesulfonamide. $^1$H NMR (500 MHz, DMSO-$d_6$) δ 8.91 (d, J = 0.65 Hz, 2H), 7.69 (d, J = 7.40 Hz, 1H), 7.48-7.64 (m, 3H), 4.82 (dd, J = 4.02, 13.62 Hz, 1H), 3.58-3.78 (m, 1H), 3.39-3.57 (m, 3H), 2.54 (s, 3H), 2.15-2.33 (m, 1H), 1.94-2.13 (m, 1H), 1.68-1.88 (m, 2H), 1.14 (dd, J = 7.01, 10.64 Hz, 3H). LCMS-ESI (pos) m/z: 513.20 (M + H)$^+$. |
| 244.0 | (1R,2S)-1-(5-chloropyrimidin-2-yl)-1-methoxypropane-2-sulfonamide (Example 11.3), (S)-tetrahydrofuran-2-carbohydrazide (Enamine), and 1-fluoro-2-isothiocyanatobenzene (Frontier Scientific Services, Inc.). | 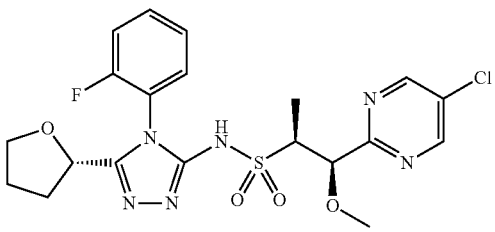<br>(1R,2S)-1-(5-chloro-2-pyrimidinyl)-N-(4-(2-fluorophenyl)-5-((2S)-tetrahydro-2-furanyl)-4H-1,2,4-triazol-3-yl)-1-methoxy-2-propanesulfonamide. $^1$H NMR (500 MHz, DMSO-$d_6$) δ 13.10 (br s, 1H), 8.91 (s, 2H), 7.53-7.68 (m, 2H), 7.48 (t, J = 9.02 Hz, 1H), 7.35-7.44 (m, 1H), 4.73-4.83 (m, 1H), 3.56-3.71 (m, 1H), 3.36-3.54 (m, 2H), 3.17 (s, 1H), 3.12 (d, J = 9.60 Hz, 3H), 2.15-2.30 (m, 1H), 2.02-2.15 (m, 1H), 1.71-1.89 (m, 2H), 1.13 (dd, J = 2.66, 6.81 Hz, 3H). LCMS-ESI (pos) m/z: 497.00 (M + H)$^+$. |

Example 289.1: Preparation of 1-isothiocyanato-1-(methoxymethyl)cyclopropane

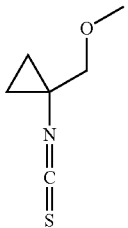

289.1

1-Isothiocyanato-1-(methoxymethyl)cyclopropane, Example 289.1

To a dry 200 mL round-bottomed flask was added 1-(methoxymethyl)cyclopropanamine hydrochloride (commercially available from J&W Pharm Lab, 2.06 g, 14.97 mmol) and di(2-pyridyl) thionocarbonate (3.65 g, 15.72 mmol) in DCM (49.9 ml). Hunig's base (2.86 ml, 16.47 mmol) in DCM (15 mL) was added dropwise via an addition funnel over 5 min at RT with stirring. The reaction mixture was stirred at RT for 3.5 h. The reaction mixture was then concentrated in vacuo. The initial material obtained was absorbed onto a plug of silica gel and purified by chromatography through a Redi-Sep pre-packed silica gel column (24 g), eluting with a gradient of 0% to 50% EtOAc in heptanes, to provide the title compound Example 289.1 (1.88 g, 13.13 mmol, 88% yield) as a colorless oil. $^1$H NMR (400 MHz, CDCl$_3$) δ 3.47 (s, 2H), 3.43 (s, 3H), 1.06-1.16 (m, 2H), 0.81-0.94 (m, 2H).

Example 250.1: Preparation of 2-isothiocyanato-1,3-dimethoxypropane

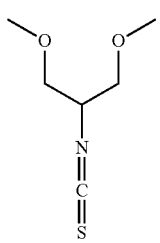

250.1

2Iisothiocyanato-1,3-dimethoxypropane, Example 250.1

To a dry 200 mL round-bottomed flask was added di(2-pyridyl) thionocarbonate (5.34 g, 23.00 mmol) in DCM (73.0 ml). 2-Amino-1,3-dimethoxypropane (commercially available from Combi-Blocks Inc., 2.61 g, 21.90 mmol) in DCM (15 mL) was then added dropwise via an addition funnel over 5 min at RT. The reaction mixture was stirred at RT for 3.5 h and then the reaction mixture was concentrated in vacuo. The initial material obtained was absorbed onto a plug of silica gel and purified by chromatography through a Redi-Sep pre-packed silica gel column (40 g), eluting with a gradient of 0% to 50% EtOAc in heptanes, to provide the title compound Example 250.1 (3.28 g, 20.34 mmol, 93% yield) as a colorless oil. $^1$H NMR (400 MHz, CDCl$_3$) δ 3.95 (quin, J=5.49 Hz, 1H) 3.50-3.60 (m, 4H) 3.41 (s, 6H). LCMS-ESI (pos) m/z: 162.2 (M+H)$^+$.

Example 325.1: Preparation of 1-isothiocyanato-1,1'-bi(cyclopropane)

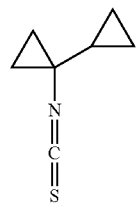

325.1

1-Isothiocyanato-1,1'-bi(cyclopropane), Example 325.1

The title compound was prepared using [1,1'-bi(cyclopropan)]-1-amine hydrochloride (commercially available from Enamine) following the procedure as described in Example 289.1. $^1$H NMR (400 MHz, CD$_3$CN) δ 0.77-1.06 (m, 4H) 1.22-1.40 (m, 4H) 3.21 (dd, J=6.63, 3.11 Hz, 1H). LCMS-ESI (pos) m/z: 148.0 (M+Na)$^+$.

The compounds set forth in the following table were synthesized following the procedure described in Example 140.0 using the known starting material as described.

TABLE 22

| Example | Reagents | Structure, Name and Data |
|---|---|---|
| 245.0 | 4-isothiocyanatooxane (Oakwood Products, Inc.), 1,4-dioxane-2-carbohydrazide (Enamine), and (2S,3R)-3-(5-chloropyrimidin-2-yl)butane-2-sulfonamide (Example 1.4).<br>The title compound was the first peak to elute on a Chiralpak AD-H column with 30% MeOH. | 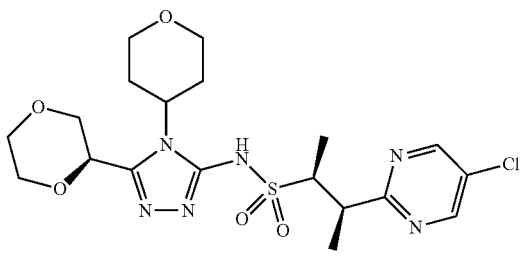<br>OR<br>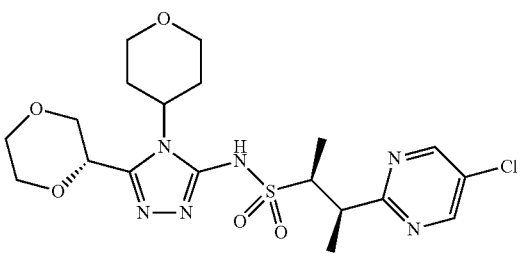<br>(2S,3R)-3-(5-chloro-2-pyrimidinyl)-N-(5-((2R)-1,4-dioxan-2-yl)-4-(tetrahydro-2H-pyran-4-yl)-4H-1,2,4-triazol-3-yl)-2-butanesulfonamide or (2S,3R)-3-(5-chloro-2-pyrimidinyl)-N-(5-((2S)-1,4-dioxan-2-yl)-4-(tetrahydro-2H-pyran-4-yl)-4H-1,2,4-triazol-3-yl)-2-butanesulfonamide. $^1$H NMR (400 MHz, CD$_3$OD) δ 8.71 (s, 2 H) 4.79 (dd, J = 8.91, 2.90 Hz, 1 H) 4.40 (tt, J = 12.13, 4.15 Hz, 1 H) 3.64-4.11 (m, 10 H) 3.49 (qd, J = 12.23, 1.45 Hz, 2 H) 2.56-2.81 (m, 2 H) 1.65-1.78 (m, 2 H) 1.43 (d, J = 2.49 Hz, 3 H) 1.41 (d, J = 2.49 Hz, 3 H). LCMS-ESI (pos) m/z: 487.2 (M + H)$^+$. |
| 246.0 | 4-isothiocyanotooxane (Oakwood Products, Inc.), 1,4-dioxane-2-carbohydrazide (Enamine), and (2S,3R)-3-(5-chloropyrimidin-2-yl)butane-2-sulfonamide (Example 1.4).<br>The title compound was the second peak to elute on a Chiralpak AD-H column with 30% MeOH. | 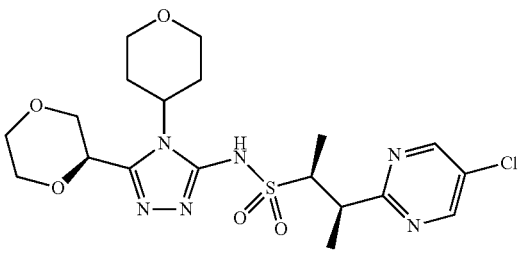<br>OR<br>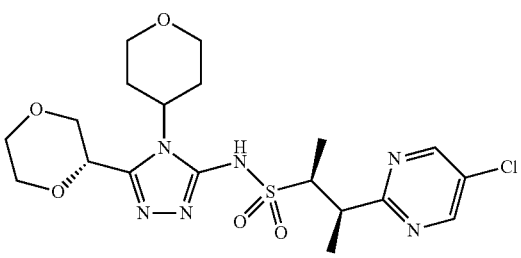<br>(2S,3R)-3-(5-chloro-2-pyrimidinyl)-N-(5-((2R)-1,4-dioxan-2-yl)-4-(tetrahydro-2H-pyran-4-yl)-4H-1,2,4-triazol-3-yl)-2-butanesulfonamide or (2S,3R)-3-(5-chloro-2-pyrimidinyl)-N-(5-((2S)-1,4-dioxan-2-yl)-4-(tetrahydro-2H-pyran-4-yl)-4H-1,2,4-triazol-3-yl)-2-butanesulfonamide. $^1$H NMR (400 MHz, CD$_3$OD) δ 8.71 (s, 2 H) 4.79 (dd, J = 8.91, 2.90 Hz, 1 H) 4.40 (tt, J = 12.13, 4.15 Hz, 1 H) 3.65-4.13 (m, 10 H) 3.49 (qd, |

TABLE 22-continued

| Example | Reagents | Structure, Name and Data |
|---|---|---|
| | | J = 11.96, 1.66 Hz, 2 H) 2.75 (qd, J = 12.44, 4.77 Hz, 1 H) 2.62 (qd, J = 12.34, 4.66 Hz, 1 H) 1.64-1.76 (m, 2 H) 1.43 (s, 3 H) 1.41 (s, 3 H). LCMS-ESI (pos) m/z: 487.2 (M + H)+. |
| 247.0 | 4-isothiocyanatooxane (Oakwood Products, Inc.), 1,4-dioxane-2-carbohydrazide (Enamine), and (1R,2S)-1-(5-chloropyrimidin-2-yl)-1-methoxypropane-2-sulfonamide (Example 11.3). The title compound was the first peak to elute on a Chiralpak AD-H column with 25% MeOH. | 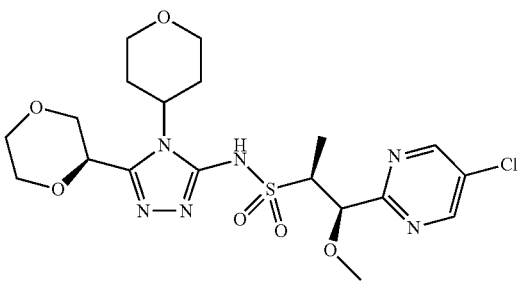<br>OR<br>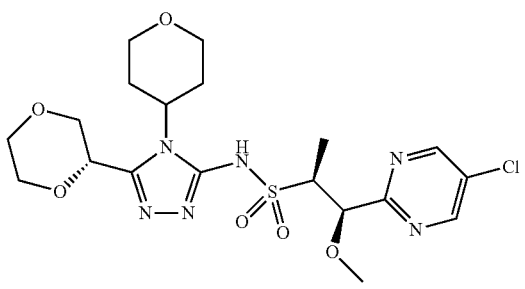<br>(1R,2S)-1-(5-chloro-2-pyrimidin-yl)-N-(5-((2R)-1,4-dioxan-2-yl)-4-(tetrahydro-2H-pyran-4-yl)-4H-1,2,4-triazol-3-yl)-1-methoxy-2-propanesulfonamide or (1R,2S)-1-(5-chloro-2-pyrimidinyl)-N-(5-((2S)-1,4-dioxan-2-yl)-4-(tetrahydro-2H-pyran-4-yl)-4H-1,2,4-triazol-3-yl)-1-methoxy-2-propanesulfonamide. $^1$H NMR (400 MHz, CDCl$_3$) δ 8.73 (s, 2 H) 5.10 (d, J = 3.52 Hz, 1 H) 4.65 (dd, J = 8.91, 2.90 Hz, 1 H) 4.38 (tt, J = 12.28, 3.99 Hz, 1 H) 4.05-4.18 (m, 3 H) 3.96-4.04 (m, 1 H) 3.80-3.93 (m, 3 H) 3.65-3.78 (m, 2 H) 3.40-3.51 (m, 2 H) 3.37 (s, 3 H) 2.61-2.82 (m, 2 H) 1.68-1.80 (m, 2 H) 1.39 (d, J = 7.05 Hz, 3 H). LCMS-ESI (pos) m/z: 503.2 (M + H)+. |

| Example | Reagents | Structure, Name and Data |
|---|---|---|
| 248.0 | 4-isothiocyanatooxane (Oakwood Products, Inc.), 1,4-dioxane-2-carbohydrazide (Enamine), and (1R,2S)-1-(5-chloropyrimidin-2-yl)-1-methoxypropane-2-sulfonamide (Example 11.3). The title compound was the second peak to elute on a Chiralpak AD-H column with 25% MeOH. | 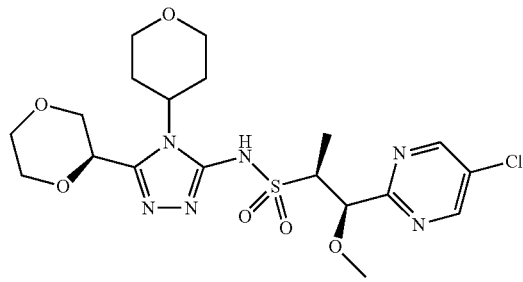<br>OR<br>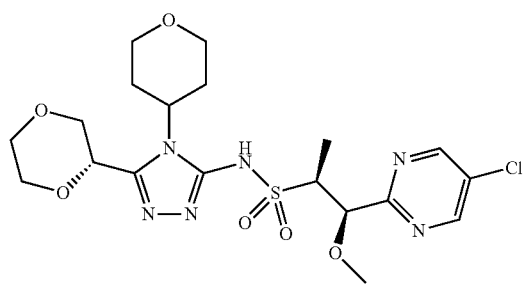<br>(1R,2S)-1-(5-chloro-2-pyrimidinyl)-N-(5-((2R)-1,4-dioxan-2-yl)-4-(tetrahydro-2H-pyran-4-yl)-4H-1,2,4-triazol-3-yl)-1-methoxy-2-propanesulfonamide or (1R,2S)-1-(5-chloro-2-pyrimidinyl)-N-(5-((2S)-1,4-dioxan-2-yl)-4-(tetrahydro-2H-pyran-4-yl)-4H-1,2,4-triazol-3-yl)-1-methoxy-2-propanesulfonamide. $^1$H NMR (400 MHz, CDCl$_3$) δ 8.73 (s, 2 H) 5.12 (d, J = 3.52 Hz, 1 H) 4.65 (dd, J = 8.91, 2.90 Hz, 1 H) 4.40 (tt, J = 12.23, 4.04 Hz, 1H), 4.10 (br dd, J = 12.02, 2.70 Hz, 3 H) 3.96-4.06 (m, 1 H) 3.80-3.93 (m, 3 H) 3.61-3.79 (m, 2 H) 3.41-3.50 (m, 2 H) 3.34 (s, 3 H) 2.55-2.85 (m, 2 H) 1.69-1.84 (m, 2 H) 1.39 (d, J = 7.05 Hz, 3 H). LCMS-ESI (pos) m/z: 503.2 (M + H)$^+$. |
| 249.0 | 2-isothiocyanato-1,3-dimethoxybenzene (Example 10.0), 5-methyltetrahydrofuran-2-carbohydrazide (Enamine), and (2S,3R)-3-(5-methoxypyrimidin-2-yl)butane-2-sulfonamide (Example 175.1). | 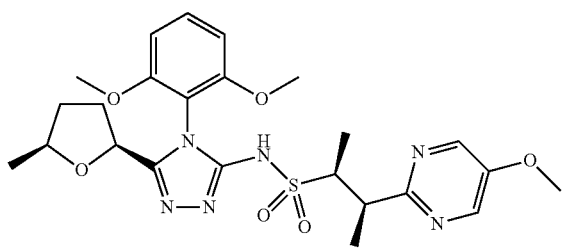<br>AND<br>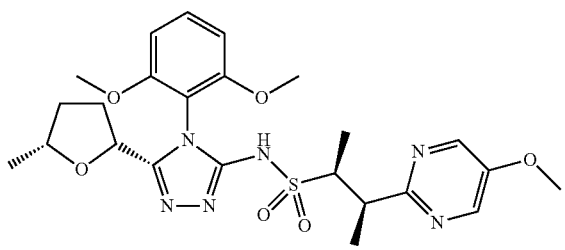<br>(2S,3R)-N-(4-(2,6-dimethoxyphenyl)-5-((2R,5R)-5-methyltetrahydro-2-furanyl)-4H-1,2,4-triazol-3-yl)-3-(5-methoxy-2-pyrimidinyl)-2-butanesulfonamide and (2S,3R)-N-(4-(2,6-dimethoxyphenyl)-5-((2S,5S)-5-methyltetrahydro-2-furanyl)-4H-1,2,4-triazol-3-yl)-3- |

TABLE 22-continued

| Example | Reagents | Structure, Name and Data |
|---|---|---|
| | | (5-methoxy-2-pyrimidinyl)-2-butanesulfonamide. $^1$H NMR (400 MHz, CDCl$_3$) δ 10.95 (br d, J = 3.11 Hz, 1 H) 8.35 (s, 2 H) 7.38 (t, J = 8.50 Hz, 1H) 6.56-6.67 (m, 2 H) 4.60 (dd, J = 7.67, 4.98 Hz, 1 H) 3.91-4.01 (m, 1 H) 3.89 (s, 3 H) 3.72-3.85 (m, 8 H) 2.16-2.32 (m, 1 H) 1.87-2.13 (m, 2 H) 1.39-1.53 (m, 1 H) 1.35 (d, J = 6.63 Hz, 3 H) 1.29 (d, J = 6.63 Hz, 3 H) 1.14 (d, J = 6.01 Hz, 3 H). LCMS-ESI (pos) m/z: 533.2 (M + H)$^+$. |
| 250.0 | 2-isothiocyanato-1,3-dimethoxypropane (Example 250.1), 1,4-dioxane-2-carbohydrazide (Enamine), and (1R,2S)-1-(5-chloropyrimidin-2-yl)-1-methoxypropane-2-sulfonamide (Example 11.3). The title compound was the first peak to elute on a Chiralpak IC column with 30% MeOH. | 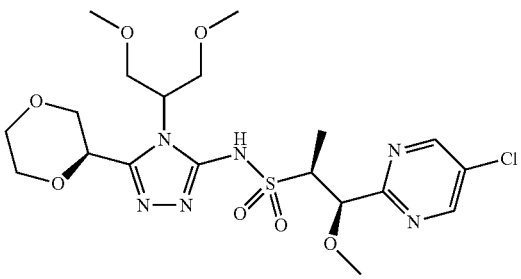<br>OR<br>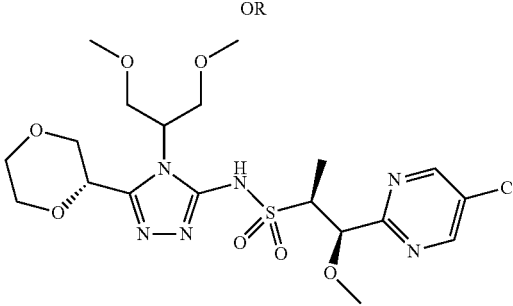<br>(1R,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1-methoxy-2-propanesulfonamide or (1R,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1-methoxy-2-propanesulfonamide. $^1$H NMR (400 MHz, CDCl$_3$) δ 10.91 (s, 1 H) 8.73 (s, 2 H) 5.02 (d, J = 4.35 Hz, 1 H) 4.76 (dd, J = 8.09, 3.52 Hz, 1 H) 4.63-4.73 (m, 1 H) 3.97-4.11 (m, 4 H) 3.67-3.93 (m, 6 H) 3.61 (dd, J = 9.74, 4.35 Hz, 1 H) 3.37 (s, 3 H) 3.35 (s, 3 H) 3.35 (s, 3 H) 1.41 (d, J = 7.05 Hz, 3 H). LCMS-ESI (pos) m/z: 521.2 (M + H)$^+$. |

TABLE 22-continued

| Example | Reagents | Structure, Name and Data |
|---|---|---|
| 251.0 | 2-isothiocyanato-1,3-dimethoxypropane (Example 250.1), 1,4-dioxane-2-carbohydrazide (Enamine), and (1R,2S)-1-(5-chloropyrimidin-2-yl)-1-methoxypropane-2-sulfonamide (Example 11.3). The title compound was the second peak to elute on a Chiralpak IC column with 25% MeOH. | 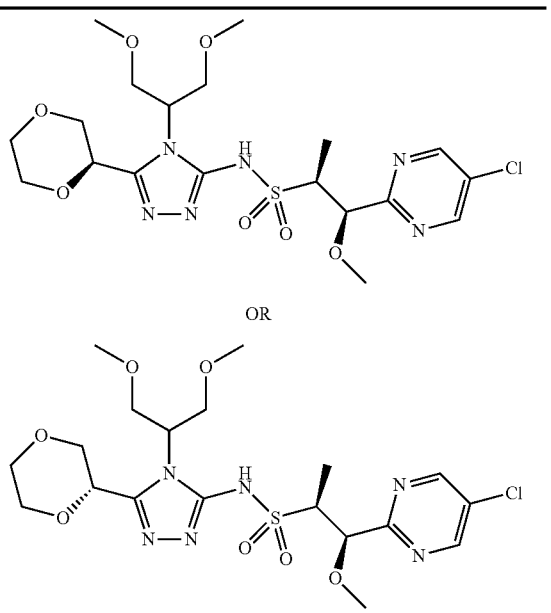<br>OR<br><br>(1R,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1-methoxy-2-propanesulfonamide or (1R,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1-methoxy-2-propanesulfonamide. $^1$H NMR (400 MHz, CDCl$_3$) δ 10.94 (s, 1 H) 8.74 (s, 2 H) 5.02 (d, J = 4.15 Hz, 1 H) 4.75 (dd, J = 8.40, 3.21 Hz, 1 H) 4.62-4.71 (m, 1 H) 3.96-4.11 (m, 4 H) 3.67-3.92 (m, 6 H) 3.61 (dd, J = 9.85, 4.25 Hz, 1 H) 3.37 (s, 3 H) 3.36 (s, 3 H) 3.32 (s, 3 H) 1.40 (d, J = 7.05 Hz, 3 H). LCMS-ESI (pos) m/z: 521.2 (M + H)$^+$. |
| 252.0 | 2-isothiocyanato-1,3-dimethoxypropane (Example 250.1), 5-methyltetrahydrofuran-2-carbohydrazide (Enamine), and (1R,2S)-1-(5-chloropyrimidin-2-yl)-1-methoxypropane-2-sulfonamide (Example 11.3). The title compound was the first peak to elute on Chiralpak AS-H column with 25% IPA. | 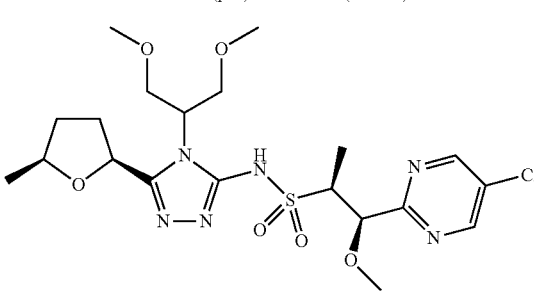<br>OR<br>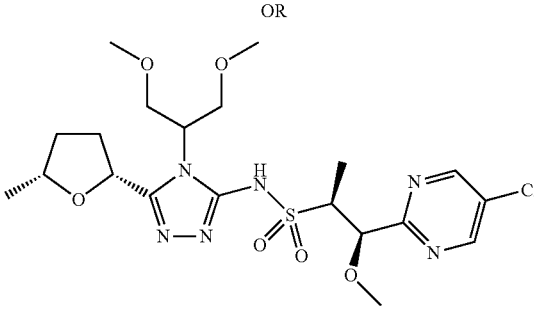<br>(1R,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide or (1R,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide. $^1$H |

TABLE 22-continued

| Example | Reagents | Structure, Name and Data |
|---|---|---|
| | | NMR (500 MHz, CDCl$_3$) δ 10.80 (br s, 1 H) 8.74 (s, 2 H) 5.05 (d, J = 3.89 Hz, 1 H) 4.93 (dd, J = 7.79, 5.45 Hz, 1 H) 4.66-4.85 (m, 1 H) 4.08-4.21 (m, 2 H) 3.95 (d, J = 6.75 Hz, 2 H) 3.70 (qd, J = 7.01, 4.15 Hz, 1 H) 3.65 (dd, J = 9.86, 4.41 Hz, 1 H) 3.38 (s, 3 H) 3.35 (s, 3 H) 3.31 (s, 3 H) 2.58-2.69 (m, 1 H) 2.23 (dq, J = 12.75, 8.12 Hz, 1 H) 2.12 (dddd, J = 12.23, 8.01, 6.10, 4.54 Hz, 1 H) 1.65 (dq, J = 12.10, 8.51 Hz, 1 H) 1.40 (d, J = 7.01 Hz, 3 H) 1.25 (d, J = 6.23 Hz, 3 H). LCMS-ESI (pos) m/z: 519.0 (M + H)$^+$. |
| 253.0 | 2-isothiocyanato-1,3-dimethoxypropane (Example 250.1), 5-methyltetrahydrofuran-2-carbohydrazide (Enamine), and (1R,2S)-1-(5-chloropyrimidin-2-yl)-1-methoxypropane-2-sulfonamide (Example 11.3). The title compound was the second peak to elute on a Chiralpak AS-H column with 25% IPA. | 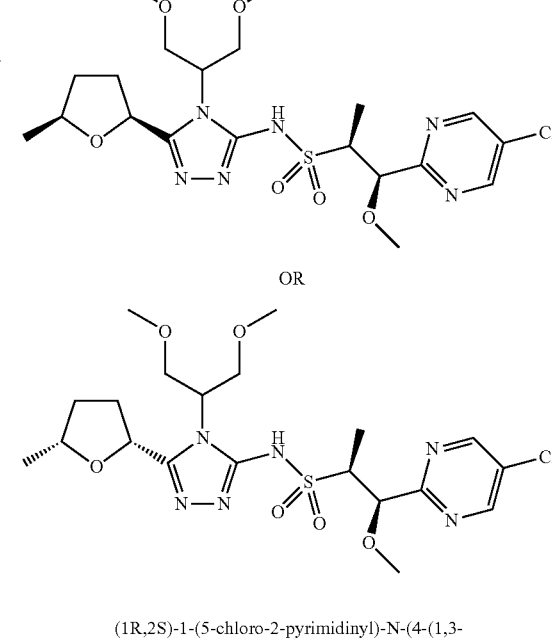<br>OR<br><br>(1R,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide or (1R,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide. $^1$H NMR (500 MHz, CDCl$_3$) δ 10.79 (br s, 1 H) 8.73 (s, 2 H) 5.03 (d, J = 4.41 Hz, 1 H) 4.93 (dd, J = 7.79, 5.45 Hz, 1 H) 4.74-4.82 (m, 1 H) 4.17 (dt, J = 8.04, 6.23 Hz, 1 H) 4.10 (t, J = 9.60 Hz, 1 H) 3.98 (dd, J = 10.12, 7.01 Hz, 1 H) 3.89 (dd, J = 10.12, 7.01 Hz, 1 H) 3.67-3.75 (m, 1 H) 3.64 (dd, J = 9.73, 4.54 Hz, 1 H) 3.36 (s, 3 H) 3.35 (s, 3 H) 3.33 (s, 3 H) 2.57-2.69 (m, 1 H) 2.23 (dq, J = 12.75, 8.12 Hz, 1 H) 2.12 (dddd, J = 12.23, 8.08, 6.03, 4.28 Hz, 1 H) 1.65 (dq, J = 12.10, 8.51 Hz, 1 H) 1.41 (d, J = 7.01 Hz, 3 H) 1.25 (d, J = 5.97 Hz, 3 H). LCMS-ESI (pos) m/z: 519.0 (M + H)$^+$ |

Example 254.0. Preparation of (2S,3R)-3-(5-chloro-pyrimidin-2-yl)-N-(4-(3,5-dibromo-2,6-dimethoxy-phenyl)-5-((R)-tetrahydrofuran-3-yl)-4H-1,2,4-triazol-3-yl)butane-2-sulfonamide or (2S,3R)-3-(5-chloropyrimidin-2-yl)-N-(4-(3,5-dibromo-2,6-dimethoxyphenyl)-5-((S)-tetrahydrofuran-3-yl)-4H-1,2,4-triazol-3-yl)butane-2-sulfonamide

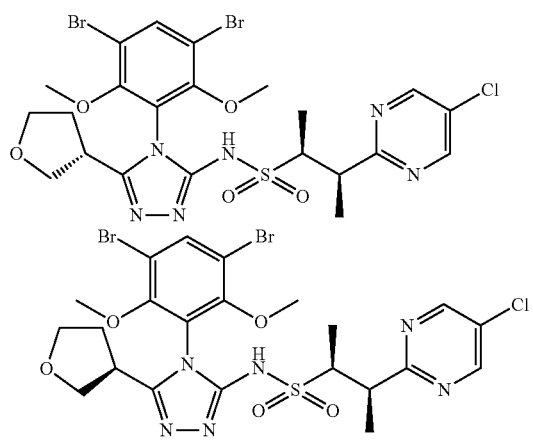

254.0

OR (2S,3R)-3-(5-Chloropyrimidin-2-yl)-N-(4-(3,5-dibromo-2,6-dimethoxyphenyl)-5-((R)-tetrahydrofuran-3-yl)-4H-1,2,4-triazol-3-yl)butane-2-sulfonamide or (2S,3R)-3-(5-chloropyrimidin-2-yl)-N-(4-(3,5-dibromo-2,6-dimethoxyphenyl)-5-((S)-tetrahydrofuran-3-yl)-4H-1,2,4-triazol-3-yl)butane-2-sulfonamide, Example 254.0

To a vial containing N-bromosuccinimide (1.02 g, 5.8 mmol) in DMF (2.6 mL) at <5° C. was added a homogeneous solution of Example 60.0 (376 mg, 0.72 mmol) in DMF (1 mL). Upon complete addition, the mixture was allowed to warm to RT and monitored with LC-MS. After 120 h, the mixture was diluted with EtOAc and washed with 1.0 N aqueous sodium thiosulfate solution and then with a saturated aqueous sodium chloride solution. The aqueous washes were combined and then extracted twice with EtOAc. The organic layers were combined, dried over anhydrous sodium sulfate, filtered, and then concentrated in vacuo. The residue was loaded onto a silica gel column (20-55% 3:1 EtOAc: EtOH in heptanes). Fractions containing pure product were combined and then concentrated in vacuo to afford Example 254.0 as a white foam. $^1$H NMR (400 MHz, DMSO-$d_6$) δ 13.21 (s, 1H), 8.84 (s, 2H), 8.30-8.27 (m, 1H), 3.83-3.77 (m, 1H), 3.75-3.73 (m, 3H), 3.73-3.72 (m, 3H), 3.72-3.66 (m, 3H), 3.65-3.63 (m, 1H), 3.63-3.58 (m, 1H), 3.06-2.98 (m, 1H), 2.06-1.97 (m, 2H), 1.25 (d, J=7.0 Hz, 3H), 1.16 (d, J=6.8 Hz, 3H).

Example 255.0. Preparation of (1S,2S)—N-(4-(2,6-dimethoxyphenyl)-5-((S)-1,4-dioxan-2-yl)-4H-1,2,4-triazol-3-yl)-1-isopropoxy-1-(5-methylpyrimidin-2-yl)propane-2-sulfonamide

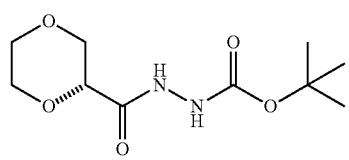

255.1

(R)-tert-Butyl 2-(1,4-dioxane-2-carbonyl)hydrazinecarboxylate, Example 255.1

A flask containing (R)-1,4-dioxane-2-carboxylic acid (commercially available from J&W Pharmlab LLC.) (948 mg, 7.2 mmol) in anhydrous DCM (14.5 mL) was cooled in an ice bath. After 20 min, 1-(3-dimethylaminopropyl)-3-ethylcarbodiimide hydrochloride (1.40 g, 7.3 mmol) and then tert-butyl carbazate (951 mg, 7.2 mmol) were carefully added in portions to the homogeneous solution. Upon complete addition of tert-butyl carbazate, the homogeneous solution was allowed to warm to RT. After 22 h, the reaction was carefully quenched with water and extracted three times with DCM. The organic layers were combined and then washed once with brine. The organic layer was dried over anhydrous magnesium sulfate, filtered, and concentrated in vacuo. The white solid was identified as Example 255.1 and was used without further purification. $^1$H NMR (500 MHz, DMSO-$d_6$) δ 9.60 (s, 1H), 8.72 (s, 1H), 4.08 (dd, J=2.9, 8.8 Hz, 1H), 3.81 (dd, J=2.9, 11.4 Hz, 2H), 3.68-3.59 (m, 2H), 3.53-3.43 (m, 2H), 1.44-1.32 (m, 9H).

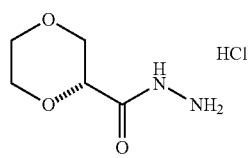

255.2

(R)-1,4-Dioxane-2-carbohydrazide hydrochloride, Example 255.2

A flask containing Example 255.1 (2.12 g, 8.6 mmol) in EtOH (8.5 mL) was cooled in an ice bath. After 20 min, hydrogen chloride, (1.25 M in EtOH, 28 mL, 35.0 mmol) was carefully added dropwise to the homogeneous solution. Upon addition, the homogeneous solution was allowed to warm to RT. After 22 h, the reaction was carefully filtered. The white solid was identified as Example 255.2 (907 mg, 4.1 mmol) and was used without purification. LCMS-ESI (pos) m/z: 219.2 (M+H)$^+$.

The compounds set forth in the following table were synthesized following the procedure described in Example 140.0 using the known starting material as described.

TABLE 23

| Example | Reagents | Structure, Name and Data |
|---|---|---|
| 255.0 | (1S,2S)-1-isopropoxy-1-(5-methylpyrimidin-2-yl)propane-2-sulfonamide (Example 13.5), (R)-1,4-dioxane-2-carbohydrazide hydrochloride (Example 255.2), and 2-isothiocyanato-1,3-dimethoxybenzene (Example 10.0). | 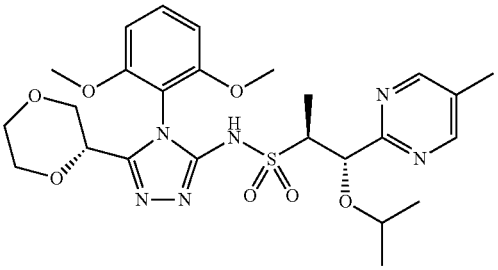 [SMILES: COc1cccc(OC)c1-n1c(NS(=O)(=O)[C@@H](C)[C@@H](OC(C)C)c2ncc(C)cn2)nnc1[C@H]1COCCO1]<br>(1S,2S)-N-(4-(2,6-dimethoxyphenyl)-5-((S)-1,4-dioxan-2-yl)-4H-1,2,4-triazol-3-yl)-1-isopropoxy-1-(5-methylpyrimidin-2-yl)propane-2-sulfonamide.<br>$^1$H NMR (500 MHz, DMSO-$d_6$) δ 13.09-13.01 (m, 1H), 8.69-8.61 (m, 2H), 7.53-7.47 (m, 1H), 6.89-6.83 (m, 2H), 4.73-4.67 (m, 1H), 4.20-4.14 (m, 1H), 3.82-3.78 (m, 3H), 3.78-3.76 (m, 3H), 3.74-3.69 (m, 2H), 3.68-3.63 (m, 1H), 3.61-3.56 (m, 1H), 3.52-3.45 (m, 1H), 3.43-3.34 (m, 3H), 2.30-2.24 (m, 3H), 1.01-0.96 (m, 3H), 0.94-0.89 (m, 3H), 0.81-0.76 (m, 3H). LCMS-ESI (pos) m/z: 563.2 (M + H)$^+$. |
| 256.0 | (1S,2S)-1-isopropoxy-1-(5-methylpyrimidin-2-yl)propane-2-sulfonamide (Example 13.5), (R)-1,4-dioxane-2-carbohydrazide and (S)-1,4-dioxane-2-carbohydrazide (Frontier Scientific Services, Inc.), and 2-isothiocyanato-1,3-dimethoxybenzene (Example 10.0). | 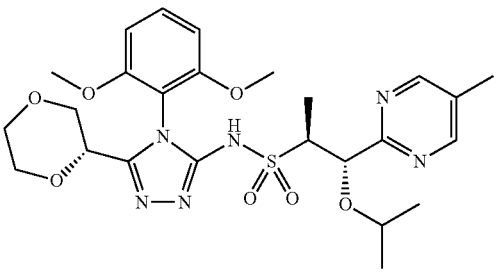<br>AND<br>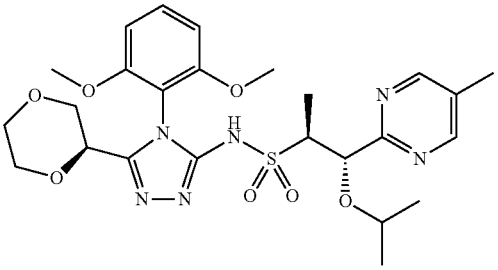<br>(1S,2S)-N-(4-(2,6-dimethoxyphenyl)-5-((2S)-1,4-dioxan-2-yl)-4H-1,2,4-triazol-3-yl)-1-isopropoxy-1-(5-methylpyrimidin-2-yl)propane-2-sulfonamide and (1S,2S)-N-(4-(2,6-dimethoxyphenyl)-5-((R)-1,4-dioxan-2-yl)-4H-1,2,4-triazol-3-yl)-1-isopropoxy-1-(5-methylpyrimidin-2-yl)propane-2-sulfonamide.<br>$^1$H NMR (500 MHz, DMSO-$d_6$) δ 13.04 (d, J = 2.9 Hz, 1H), 8.65 (s, 2H), 7.49 (t, J = 8.4 Hz, 1H), 6.85 (dd, J = 3.9, 8.6 Hz, 2H), 4.68 (t, J = 7.8 Hz, 1H), 4.19-4.14 (m, 1H), 3.79 (s, 3H), 3.78 (s, 3H), 3.73-3.69 (m, 2H), 3.65 (qd, J = 2.7, 11.6 Hz, 1H), 3.61-3.56 (m, 1H), 3.51-3.46 (m, 1H), 3.39 (td, J = 6.7, 13.3 Hz, 3H), 2.27 (s, 3H), 0.97 (dd, J = 6.2, 11.7 Hz, 3H), 0.90 (t, J = 7.0 Hz, 3H), 0.78 (dd, J = 6.1, 10.0 Hz, 3H). LCMS-ESI (pos) m/z: 563.2 (M + H)$^+$. |

TABLE 23-continued

| Example | Reagents | Structure, Name and Data |
|---|---|---|
| 257.0 | (2S,3R)-3-(5-methylpyrimidin-2-yl)butane-2-sulfonamide (Example 1.0), (3R,8aS)-hexahydro-1H-pyrrolo[2,1-c][1,4]oxazine-3-carbohydrazide and (3S,8aR)-hexahydro-1H-pyrrolo[2,1-c][1,4]oxazine-3-carbohydrazide and (3S,8aS)-hexahydro-1H-pyrrolo[2,1-c][1,4]oxazine-3-carbohydrazide and (3R,8aR)-hexahydro-1H-pyrrolo[2,1-c][1,4]oxazine-3-carbohydrazide (commercially available from Frontier Scientific Services, Inc), and 2-isothiocyanato-1,3-dimethoxybenzene (Example 10.0). | 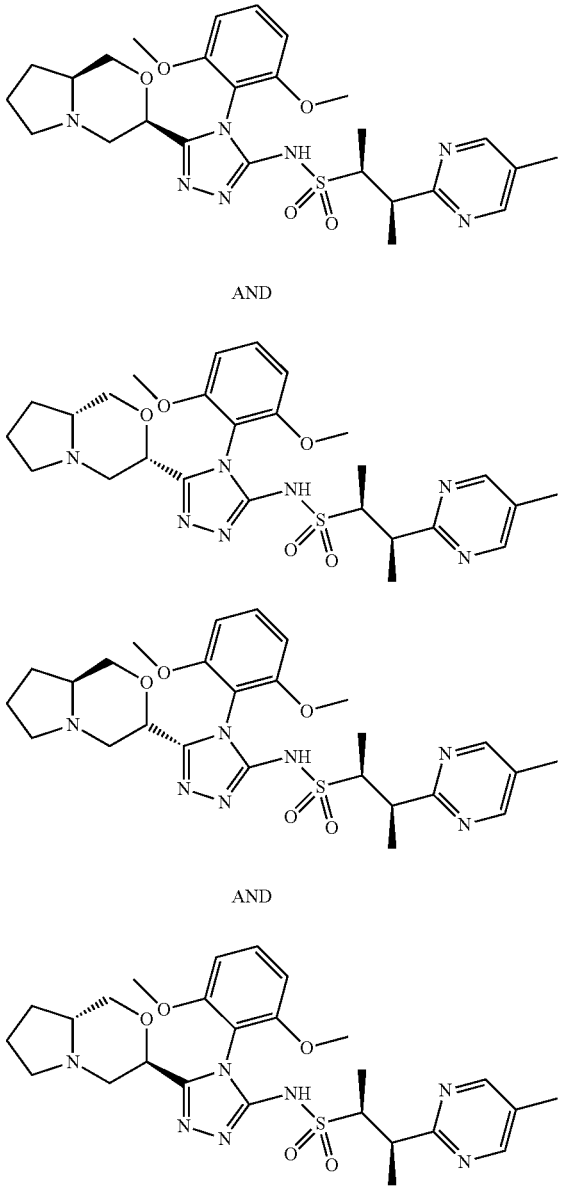<br>AND<br>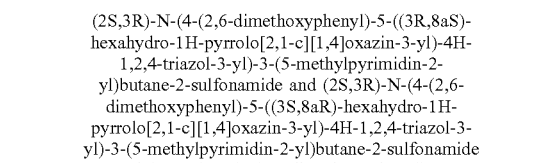<br>AND<br>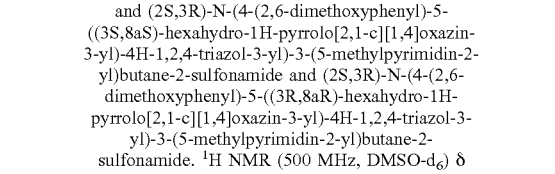<br><br>(2S,3R)-N-(4-(2,6-dimethoxyphenyl)-5-((3R,8aS)-hexahydro-1H-pyrrolo[2,1-c][1,4]oxazin-3-yl)-4H-1,2,4-triazol-3-yl)-3-(5-methylpyrimidin-2-yl)butane-2-sulfonamide and (2S,3R)-N-(4-(2,6-dimethoxyphenyl)-5-((3S,8aR)-hexahydro-1H-pyrrolo[2,1-c][1,4]oxazin-3-yl)-4H-1,2,4-triazol-3-yl)-3-(5-methylpyrimidin-2-yl)butane-2-sulfonamide and (2S,3R)-N-(4-(2,6-dimethoxyphenyl)-5-((3S,8aS)-hexahydro-1H-pyrrolo[2,1-c][1,4]oxazin-3-yl)-4H-1,2,4-triazol-3-yl)-3-(5-methylpyrimidin-2-yl)butane-2-sulfonamide and (2S,3R)-N-(4-(2,6-dimethoxyphenyl)-5-((3R,8aR)-hexahydro-1H-pyrrolo[2,1-c][1,4]oxazin-3-yl)-4H-1,2,4-triazol-3-yl)-3-(5-methylpyrimidin-2-yl)butane-2-sulfonamide. $^1$H NMR (500 MHz, DMSO-d$_6$) δ 13.00 (br s, 1H), 8.58 (s, 2H), 7.49 (t, J = 8.4 Hz, 1H), 6.83 (dd, J = 1.7, 8.7 Hz, 2H), 4.00 (dd, J = 2.6, 10.4 Hz, 1H), 3.78 (dd, J = 2.9, 10.6 Hz, 1H), 3.73 (s, 3H), 3.70 (s, 3H), 3.65 (dq, J = 3.5, 7.0 Hz, 1H), 3.57 (dq, J = 3.2, 6.9 Hz, 1H), 2.99 (dd, J = 2.3, 11.2 Hz, 1H), 2.97-2.91 (m, 2H), 2.37 (t, J = 10.8 Hz, 1H), 2.23 (s, |

TABLE 23-continued

| Example | Reagents | Structure, Name and Data |
|---|---|---|
| | | 3H), 2.06 (q, J = 8.4 Hz, 1H), 1.92-1.85 (m, 1H), 1.67-1.57 (m, 3H), 1.23 (d, J = 7.0 Hz, 3H), 1.15-1.09 (m, 1H), 1.07 (d, J = 7.0 Hz, 3H). LCMS-ESI (pos) m/z: 558.2 (M + H)⁺. |
| 258.0 | (1R,2S)-1-(5-chloropyrimidin-2-yl)-1-methoxypropane-2-sulfonamide (Example 11.3), (R)-2,3-dihydrobenzo[b][1,4]dioxine-2-carbohydrazide and (S)-2,3-dihydrobenzo[b][1,4]dioxine-2-carbohydrazide (commercially available from Enamine), and 2-isothiocyanato-1,3-dimethoxybenzene (Example 10.0). The racemic mixture was purified by preparative SFC using the following methodology: Column: IC (2 × 15 cm) Mobile Phase: 45:55 (A:B) A: Liquid CO$_2$, B: MeOH, Flow Rate: 80 mL/min, 220 nm, 100 bar inlet pressure to deliver peak 1. | OR<br><br>(1R,2S)-1-(5-chloropyrimidin-2-yl)-N-(5-((R)-2,3-dihydrobenzo[b][1,4]dioxin-2-yl)-4-(2,6-dimethoxyphenyl)-4H-1,2,4-triazol-3-yl)-1-methoxypropane-2-sulfonamide or (1R,2S)-1-(5-chloropyrimidin-2-yl)-N-(5-((S)-2,3-dihydrobenzo[b][1,4]dioxin-2-yl)-4-(2,6-dimethoxyphenyl)-4H-1,2,4-triazol-3-yl)-1-methoxypropane-2-sulfonamide. ¹H NMR (500 MHz, DMSO-d$_6$) δ 13.14 (s, 1H), 8.92 (s, 2H), 7.50 (t, J = 8.6 Hz, 1H), 6.88-6.78 (m, 5H), 6.61 (dd, J = 2.5, 6.6 Hz, 1H), 5.06 (t, J = 3.8 Hz, 1H), 4.77 (d, J = 4.2 Hz, 1H), 4.41-4.31 (m, 2H), 3.80 (s, 3H), 3.72 (s, 3H), 3.43-3.34 (m, 1H), 3.08 (s, 3H), 1.12 (d, J = 7.0 Hz, 3H). LCMS-ESI (pos) m/z: 603.1 (M + H)⁺. |
| 259.0 | (1R,2S)-1-(5-chloropyrimidin-2-yl)-1-methoxypropane-2-sulfonamide (Example 11.3), (R)-2,3-dihydrobenzo[b][1,4]dioxine-2-carbohydrazide and (S)-2,3-dihydrobenzo[b][1,4]dioxine-2-carbohydrazide (commercially available from Enamine), and 2-isothiocyanato-1,3-dimethoxybenzene (Example 10.0). The racemic mixture was purified by preparative SFC using the following methodology: Column: IC (2 × 15 cm) Mobile Phase: 45:55 (A:B) A: Liquid CO$_2$, B: MeOH, Flow Rate: 80 mL/min, 220 nm, 100 bar inlet prssure to deliver peak 2. | OR<br><br>(1R,2S)-1-(5-chloropyrimidin-2-yl)-N-(5-((R)-2,3-dihydrobenzo[b][1,4]dioxin-2-yl)-4-(2,6-dimethoxyphenyl)-4H-1,2,4-triazol-3-yl)-1-methoxypropane-2-sulfonamide or (1R,2S)-1-(5- |

TABLE 23-continued

| Example | Reagents | Structure, Name and Data |
|---|---|---|
| | | chloropyrimidin-2-yl)-N-(5-((S)-2,3-dihydrobenzo[b][1,4]dioxin-2-yl)-4-(2,6-dimethoxyphenyl)-4H-1,2,4-triazol-3-yl)-1-methoxypropane-2-sulfoanmide. $^1$H NMR (500 MHz, DMSO-$d_6$) δ 13.15 (s, 1H), 8.92 (s, 2H), 7.51 (t, J = 8.6 Hz, 1H), 6.88-6.78 (m, 5H), 6.64-6.57 (m, 1H), 5.09-5.03 (m, 1H), 4.76 (d, J = 4.2 Hz, 1H), 4.41-4.31 (m, 2H), 3.81 (s, 3H), 3.71 (s, 3H), 3.44-3.35 (m, 1H), 3.12 (s, 3H), 1.13 (d, J = 7.0 Hz, 3H). LCMS-ESI (pos) m/z: 603.2 (M + H)$^+$. |
| 260.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydrofuran-2-carbohydrazide and (S)-tetrahydrofuran-2-carbohydrazide (commercially available from Enamine), and 4-isothiocyanatooxane (commercially available from Enamine). The racemic mixture was purified by preparative SFC using the following methodology: Column: AS-H (2 × 25 cm) Mobile Phase: 80:20 (A:B) A: Liquid CO$_2$, B: MeOH, Flow Rate: 80 mL/min, 215 nm, 100 bar inlet pressure to deliver peak 1. | 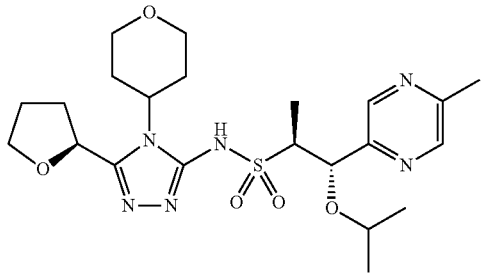<br>OR<br>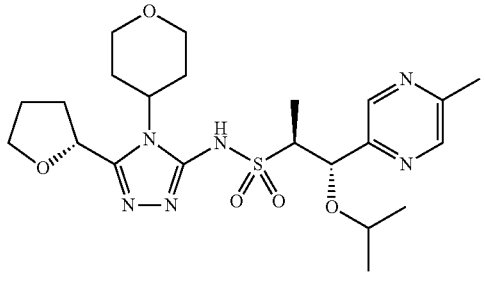<br>(1S,2S)-1-isopropoxy-1-(5-methylpyrazin-2-yl)-N-(4-(tetrahydro-2H-pyran-4-yl)-5-((R)-tetrahydrofuran-2-yl)-4H-1,2,4-triazol-3-yl)propane-2-sulfonamide or (1S,2S)-1-isopropoxy-1-(5-methylpyrazin-2-yl)-N-(4-(tetrahydro-2H-pyran-4-yl)-5-((S)-tetrahydrofuran-2-yl)-4H-1,2,4-triazol-3-yl)propane-2-sulfonamide. $^1$H NMR (500 MHz, DMSO-$d_6$) δ 12.67 (br s, 1H), 8.52 (s, 1H), 8.45 (s, 1H), 5.11 (dd, J = 6.1, 7.1 Hz, 1H), 4.87 (d, J = 5.7 Hz, 1H), 4.34 (tt, J = 4.0, 11.9 Hz, 1H), 3.95 (d, J = 8.0 Hz, 2H), 3.88-3.81 (m, 1H), 3.73 (q, J = 7.2 Hz, 1H), 3.54 (quin, J = 6.7 Hz, 1H), 3.44-3.32 (m, 3H), 2.67-2.58 (m, 1H), 2.56-2.51 (m, 1H), 2.48 (s, 3H), 2.45-2.38 (m, 1H), 2.19-2.08 (m, 1H), 2.02-1.89 (m, 2H), 1.64 (br d, J = 11.2 Hz, 1H), 1.60-1.53 (m, 1H), 1.14 (d, J = 7.0 Hz, 3H), 1.04 (d, J = 6.0 Hz, 3H), 0.84 (d, J = 6.2 Hz, 3H). LCMS-ESI (pos) m/z: 495.2 (M + H)$^+$. |

TABLE 23-continued

| Example | Reagents | Structure, Name and Data |
|---|---|---|
| 261.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (R)-tetrahydrofuran-2-carbohydrazide and (S)-tetrahydrofuran-2-carbohydrazide (commercially available from Enamine), and 4-isothiocyanatooxane (commercially available from Enamine). The racemic mixture was purified by preparative SFC using the following methodology: Column: AS-H (2 × 25 cm) Mobile Phase: 80:20 (A:B) A: Liquid CO$_2$, B: MeOH, Flow Rate: 80 mL/min, 215 nm, 100 bar inlet pressure to deliver peak 2. | 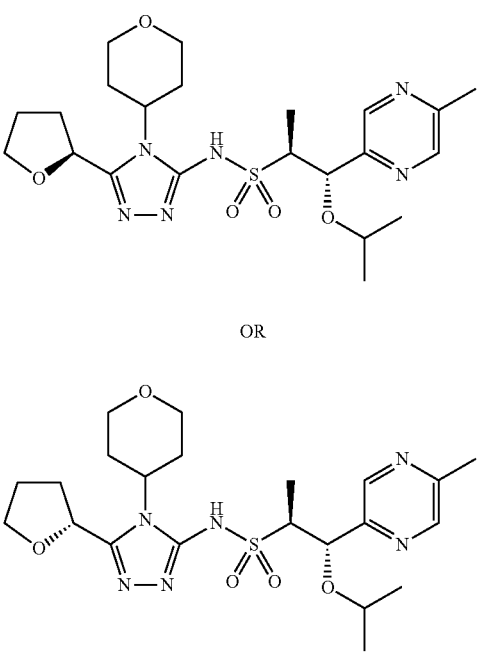 [SMILES: Cc1cnc([C@H](OC(C)C)[C@H](C)S(=O)(=O)Nc2nnc([C@@H]3CCCO3)n2C2CCOCC2)cn1 ; Cc1cnc([C@H](OC(C)C)[C@H](C)S(=O)(=O)Nc2nnc([C@H]3CCCO3)n2C2CCOCC2)cn1] OR  (1S,2S)-1-isopropoxy-1-(5-methylpyrazin-2-yl)-N-(4-(tetrahydro-2H-pyran-4-yl)-5-((R)-tetrahydrofuran-2-yl)-4H-1,2,4-triazol-3-yl)propane-2-sulfonamide or (1S,2S)-1-isopropoxy-1-(5-methylpryazin-2-yl)-N-(4-(tetrahydro-2H-pyran-4-yl)-5-((S)-tetrahydrofuran-2-yl)-4H-1,2,4-triazol-3-yl)propane-2-sulfonamide. $^1$H NMR (500 MHz, DMSO-d$_6$) δ 12.67 (br s, 1H), 8.53 (s, 1H), 8.50-8.45 (m, 1H), 5.12 (t, J = 6.5 Hz, 1H), 4.86 (d, J = 6.5 Hz, 1H), 4.34 (t, J = 11.8 Hz, 1H), 4.00-3.90 (m, 2H), 3.90-3.79 (m, 1H), 3.70 (q, J = 7.3 Hz, 1H), 3.55 (t, J = 6.7 Hz, 1H), 3.45-3.32 (m, 3H), 2.59 (d, J = 11.9 Hz, 2H), 2.48 (s, 3H), 2.45-2.39 (m, 1H), 2.19-2.08 (m, 1H), 2.02-1.88 (m, 2H), 1.62 (t, J = 13.0 Hz, 2H), 1.09 (d, J = 7.0 Hz, 3H), 1.06-1.00 (m, 3H), 0.81 (d, J = 6.0 Hz, 3H). LCMS-ESI (pos) m/z: 495.2 (M + H)$^+$. |

TABLE 23-continued

| Example | Reagents | Structure, Name and Data |
|---|---|---|
| 262.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (2S,5S)-5-methyltetrahydrofuran-2-carbohydrazide and (2R,5R)-5-methyltetrahydrofuran-2-carbohydrazide (commercially available from Ukrorgsyntez), and 4-isothiocyanatooxane (commercially available from Enamine).<br>The racemic mixture was purified by preparative SFC using the following methodology: Column: AS-H (2 × 25 cm) Mobile Phase: 75:25 (A:B) A: Liquid $CO_2$, B: MeOH, Flow Rate: 80 mL/min, 215 nm, 100 bar inlet pressure to deliver peak 1. | 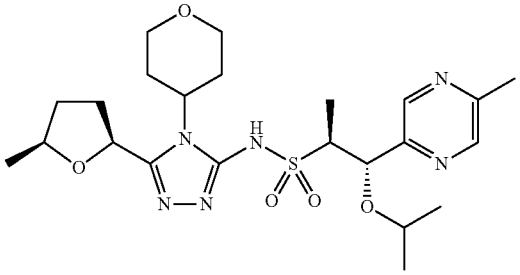<br>OR<br>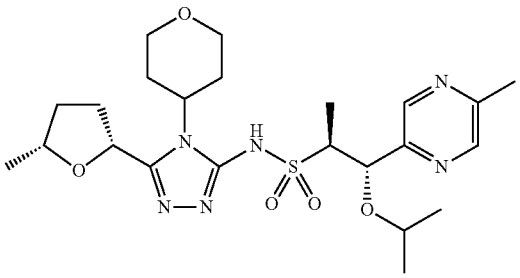<br>(1S,2S)-1-isopropoxy-1-(5-methylpyrazin-2-yl)-N-(5-((2S,5S)-5-methyltetrahydrofuran-2-yl)-4-(tetrahydro-2H-pyran-4-yl)-4H-1,2,4-triazol-3-yl)propane-2-sulfonamide or (1S,2S)-1-isopropoxy-1-(5-methylpyrazin-2-yl)-N-(5-((2R,5R)-5-methyltetrahydrofuran-2-yl)-4-(tetrahydro-2H-pyran-4-yl)-4H-1,2,4-triazol-3-yl)propane-2-sulfonamide. $^1$H NMR (500 MHz, DMSO-$d_6$) δ 12.66 (s, 1H), 8.55-8.51 (m, 1H), 8.46 (s, 1H), 5.03 (dd, J = 5.6, 7.7 Hz, 1H), 4.86 (d, J = 5.7 Hz, 1H), 4.35 (tt, J = 4.0, 11.9 Hz, 1H), 4.17-4.09 (m, 1H), 3.96 (dd, J = 4.0, 11.3 Hz, 2H), 3.54 (quin, J = 6.7 Hz, 1H), 3.45-3.32 (m, 3H), 2.72-2.60 (m, 1H), 2.58-2.51 (m, 1H), 2.48 (s, 3H), 2.45 (d, J = 4.9 Hz, 1H), 2.25-2.15 (m, 1H), 2.15-2.07 (m, 1H), 1.66-1.49 (m, 3H), 1.21-1.14 (m, 3H), 1.13 (d, J = 1.8 Hz, 3H), 1.03 (d, J = 6.0 Hz, 3H), 0.84 (d, J = 6.2 Hz, 3H). LCMS-ESI (pos) m/z: 509.2 (M + H)$^+$. |

TABLE 23-continued

| Example | Reagents | Structure, Name and Data |
|---|---|---|
| 263.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 27.0), (2S,5S)-5-methyltetrahydrofuran-2-carbohydrazide and (2R,5R)-5-methyltetrahydrofuran-2-carbohydrazide (commercially available from Ukrorgsyntez), and 4-isothiocyanatooxane (commercially available from Enamine). The racemic mixture was purified by preparative SFC using the following methodology: Column: AS-H (2 × 25 cm) Mobile Phase: 75:25 (A:B) A: Liquid CO$_2$, B: MeOH, Flow Rate: 80 mL/min, 215 nm, 100 bar inlet pressure to deliver peak 2. | 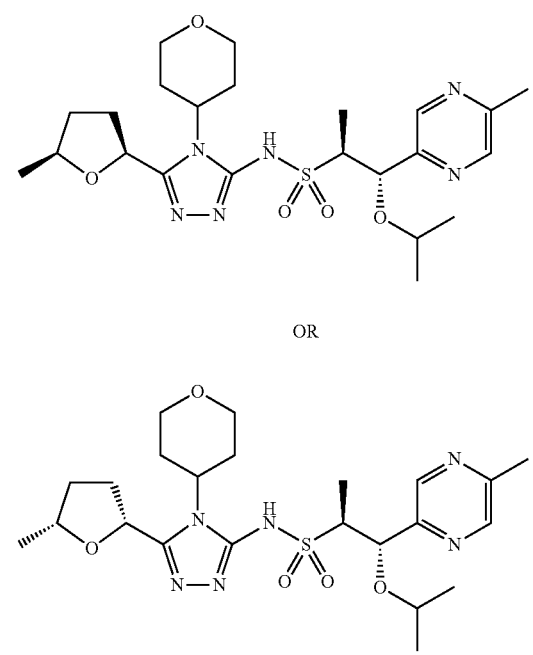<br>OR<br><br>(1S,2S)-1-isopropoxy-1-(5-methylpyrazin-2-yl)-N-(5-((2S,5S)-5-methyltetrahydrofuran-2-yl)-4-(tetrahydro-2H-pyran-4-yl)-4H-1,2,4-triazol-3-yl)propane-2-sulfonamide or (1S,2S)-1-isopropoxy-1-(5-methylpyrazin-2-yl)-N-(5-((2R,5R)-5-methyltetrahydrofuran-2-yl)-4-(tetrahydro-2H-pyran-4-yl)-4H-1,2,4-triazol-3-yl)propane-2-sulfonamide. $^1$H NMR (500 MHz, DMSO-d$_6$) δ 12.65 (br s, 1H), 8.53 (s, 1H), 8.47 (s, 1H), 5.03 (dd, J = 5.7, 7.5 Hz, 1H), 4.86 (d, J = 6.2 Hz, 1H), 4.35 (tt, J = 4.0, 11.9 Hz, 1H), 4.16-4.07 (m, 1H), 4.00-3.88 (m, 2H), 3.55 (quin, J = 6.8 Hz, 1H), 3.41-3.32 (m, 3H), 2.66-2.54 (m, 2H), 2.48 (s, 3H), 2.47-2.42 (m, 1H), 2.19 (qd, J = 7.9, 12.5 Hz, 1H), 2.13-2.06 (m, 1H), 1.62 (d, J = 9.3 Hz, 2H), 1.58-1.48 (m, 1H), 1.12 (d, J = 6.0 Hz, 3H), 1.09 (d, J = 7.0 Hz, 3H), 1.06-1.00 (m, 3H), 0.82 (d, J = 6.2 Hz, 3H). LCMS-ESI (pos) m/z: 509.2 (M + H)$^+$. |

TABLE 23-continued

| Example | Reagents | Structure, Name and Data |
|---|---|---|
| 264.0 | (1R,2S)-1-(5-chloropyridin-2-yl)-1-methoxypropane-2-sulfonamide (Example-11.9), (R)-1,4-dioxane-2-carbohydrazide and (S)-1,4-dioxane-2-carbohydrazide (commercially available from Enamine), and 2-isothiocyanato-1,3-dimethoxybenzene (Example 10.0).<br>The racemic mixture was purified by preparative SFC using the following methodology: Column: AD-H (2 × 15 cm) Mobile Phase: 65:35 (A:B) A: Liquid $CO_2$, B: IPA, Flow Rate: 80 mL/min, 225 nm, 100 bar inlet pressure to deliver peak 1. | 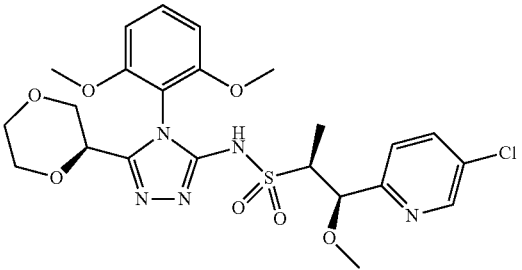<br>OR<br>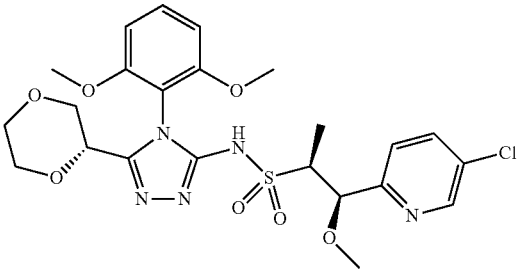<br>(1R,2S)-1-(5-chloropyridin-2-yl)-N-(4-(2,6-dimethoxyphenyl)-5-((R)-1,4-dioxan-2-yl)-4H-1,2,4-triazol-3-yl)-1-methoxyproapne-2-sulfonamide or (1R,2S)-1-(5-chloropyridin-2-yl)-N-(4-(2,6-dimethoxyphenyl)-5-((S)-1,4-dioxan-2-yl)-4H-1,2,4-triazol-3-yl)-1-methoxypropane-2-sulfonamide. $^1$H NMR (500 MHz, DMSO-$d_6$) δ 13.12 (s, 1H), 8.60 (d, J = 2.6 Hz, 1H), 7.94 (dd, J = 2.5, 8.4 Hz, 1H), 7.49 (t, J = 8.6 Hz, 1H), 7.37 (d, J = 8.6 Hz, 1H), 6.84 (dd, J = 2.3, 8.6 Hz, 2H), 4.85 (d, J = 2.1 Hz, 1H), 4.17 (dd, J = 4.2, 7.0 Hz, 1H), 3.75 (s, 3H), 3.74-3.72 (m, 1H), 3.71 (s, 3H), 3.67-3.62 (m, 1H), 3.61-3.56 (m, 1H), 3.51-3.46 (m, 1H), 3.42-3.37 (m, 1H), 3.21 (dq, J = 2.1, 7.0 Hz, 1H), 3.16 (s, 3H), 0.96 (d, J = 7.0 Hz, 3H). LCMS-ESI (pos) m/z: 554.0 (M + H)$^+$. |

TABLE 23-continued

| Example | Reagents | Structure, Name and Data |
|---|---|---|
| 265.0 | (1R,2S)-1-(5-chloropyridin-2-yl)-1-methoxypropane-2-sulfonamide (Example 11.9), (R)-1,4-dioxane-2-carbohydrazide and (S)-1,4-dioxane-2-carbohydrazide (commercially available from Enamine), and 2-isothiocyanato-1,3-dimethoxybenzene (Example 10.0). The racemic mixture was purified by preparative SFC using the following methodology: Column: AD-H (2 × 15 cm) Mobile Phase: 65:35 (A:B) A: Liquid $CO_2$, B: IPA, Flow Rate: 80 mL/min, 225 nm, 100 bar inlet pressure to deliver peak 2. | 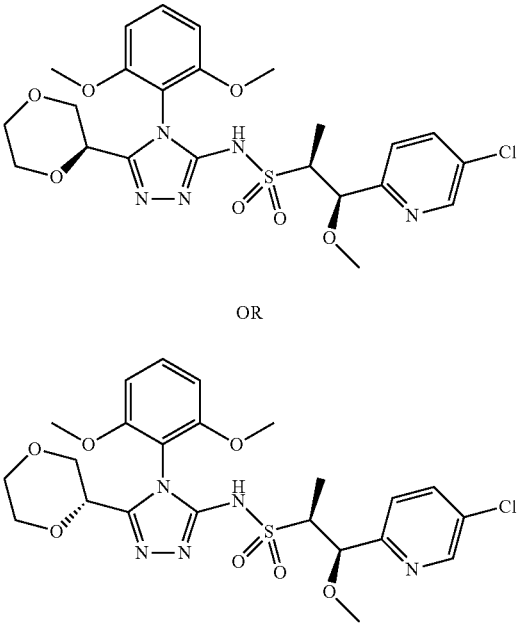 [SMILES: COc1cccc(OC)c1-n1c(NS(=O)(=O)[C@@H](C)[C@H](OC)c2ccc(Cl)cn2)nnc1[C@@H]1COCCO1 ; COc1cccc(OC)c1-n1c(NS(=O)(=O)[C@@H](C)[C@H](OC)c2ccc(Cl)cn2)nnc1[C@H]1COCCO1]<br>OR<br><br>(1R,2S)-1-(5-chloropyridin-2-yl)-N-(4-(2,6-dimethoxyphenyl)-5-((R)-1,4-dioxan-2-yl)-4H-1,2,4-triazol-3-yl)-1-methoxypropane-2-sulfonamide or (1R,2S)-1-(5-chloropyridin-2-yl)-N-(4-(2,6-dimethoxyphenyl)-5-((S)-1,4-dioxan-2-yl)-4H-1,2,4-triazol-3-yl)-1-methoxypropane-2-sulfonamide. $^1$H NMR (500 MHz, DMSO-$d_6$) δ 13.12 (s, 1H), 8.61 (d, J = 2.1 Hz, 1H), 7.95 (dd, J = 2.5, 8.4 Hz, 1H), 7.49 (t, J = 8.6 Hz, 1H), 7.38 (d, J = 8.3 Hz, 1H), 6.84 (dd, J = 3.6, 8.6 Hz, 2H), 4.86 (d, J = 2.3 Hz, 1H), 4.18 (dd, J = 4.4, 6.5 Hz, 1H), 3.76-3.71 (m, 8H), 3.64 (td, J = 2.6, 11.7 Hz, 1H), 3.61-3.56 (m, 1H), 3.52-3.46 (m, 1H), 3.42-3.37 (m, 1H), 3.22 (dq, J = 2.1, 7.0 Hz, 1H), 3.17 (s, 3H), 0.98 (d, J = 7.0 Hz, 3H). LCMS-ESI (pos) m/z: 554.1 (M + H)$^+$. |

The compounds set forth in the following table were synthesized following the procedure described in Example 11.0 using the known starting material as described.

TABLE 24

| Example | Reagents | Structure, Name and Data |
|---|---|---|
| 11.9 | 2,5-dichloropyridine (Oakwood). The chiral separation of 1-(5-chloropyridin-2-yl)-1-methoxypropane-2-sulfonamide (syn racemate) was done using the conditions [Column: CHIRAL PAK IC (250 × 4.6) mm 5u, Mobile Phase 'A': 0.1% DEA in hexanes: EtOH (80:20), Flow: 1.0 mL/min] to provide (1R,2S)-1-(5-chloropyridin-2-yl)-1-methoxypropane-2-sulfonamide (Isomer I) as and off white solid. | 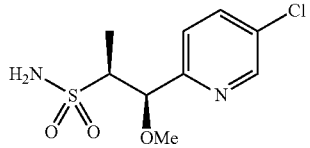<br>(1R,2S)-1-(5-chloropyridin-2-yl)-1-methoxypropane-2-sulfonamide. $^1$H NMR (400 MHz, DMSO-$d_6$) δ 8.64 (d, J = 2.5 Hz, 1H), 7.99 (dt, J = 8.4, 2.3 Hz, 1H), 7.44 (d, J = 8.4 Hz, 1H), 6.81 (s, 2H), 4.89 (d, J = 2.5 Hz, 1H), 3.33 (m, 4H), and 1.10 (dd, J = 7.0, 1.9 Hz, 3H). LCMS-ESI (pos) m/z: 265.9 (M + H)$^+$. |

Example 266.0: Preparation of (1R,2R)—N-(4-(2,6-dimethoxyphenyl)-5-((S)-1,4-dioxan-2-yl)-4H-1,2,4-triazol-3-yl)-1-(imidazo[1,2-a]pyridin-2-yl)-1-isopropoxypropane-2-sulfonamide or (1S,2S)—N-(4-(2,6-dimethoxyphenyl)-5-((S)-1,4-dioxan-2-yl)-4H-1,2,4-triazol-3-yl)-1-(imidazo[1,2-a]pyridin-2-yl)-1-isopropoxypropane-2-sulfonamide

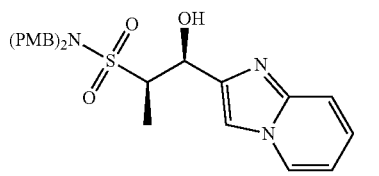
AND

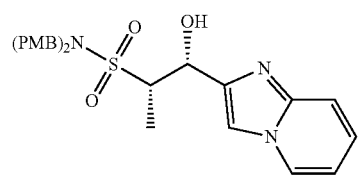

(1S,2R)-1-Hydroxy-1-(imidazo[1,2-a]pyridin-2-yl)-N,N-bis(4-methoxybenzyl)propane-2-sulfonamide and (1R,2S)-1-hydroxy-1-(imidazo[1,2-a]pyridin-2-yl)-N,N-bis(4-methoxybenzyl)propane-2-sulfonamide, Example 266.1

To a stirred solution of N,N-bis(4-methoxybenzyl)ethanesulfonamide Example 12.0 (1.0 g, 2.9 mmol) in THF (9.5 mL) at −78° C. was added n-butyllithium solution, (2.5 M in hexanes, 1.3 mL, 3.15 mmol) dropwise. After 5 min, a solution of imidazo[1,2-a]pyridine-2-carbaldehyde (460 mg, 3.15 mmol) in THF was added dropwise over 5 min. Upon complete addition, the reaction was maintained at −78° C. and monitored with LC-MS. After 3 h, the reaction was quenched with a saturated aqueous ammonium chloride solution. After extracting three times with EtOAc, the organic layers were pooled and then dried over anhydrous magnesium sulfate. After filtration and concentration in vacuo, the dark brown residue was purified on silica gel eluting with 0-60% of (3:1 EtOAc: EtOH) in heptanes to afford the following compounds Example 266.1 (0.5 g, 1.009 mmol, 35.3% yield).

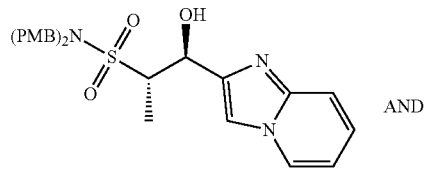
AND

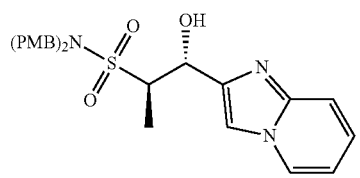

(1S,2S)-1-Hydroxy-1-(imidazo[1,2-a]pyridin-2-yl)-N,N-bis(4-methoxybenzyl)propane-2-sulfonamide and (1R,2R)-1-hydroxy-1-(imidazo[1,2-a]pyridin-2-yl)-N,N-bis(4-methoxybenzyl)propane-2-sulfonamide, Example 266.2

Further elution under the conditions described in Example 266.1 gave Example 266.2 (0.39 g, 0.787 mmol, 27.5% yield).

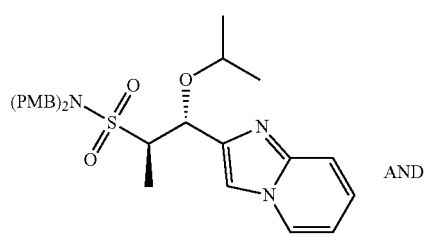
AND

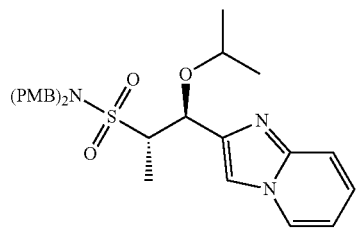

(1S,2S)-1-(Imidazo[1,2-a]pyridin-2-yl)-1-isopropoxy-N,N-bis(4-methoxybenzyl)propane-2-sulfonamide and (1R,2R)-1-(imidazo[1,2-a]pyridin-2-yl)-1-isopropoxy-N,N-bis(4-methoxybenzyl)propane-2-sulfonamide, Example 266.3

To a flask containing Example 266.2 (3.24 g, 6.5 mmol) and isopropyl iodide (9.2 mL, 92 mmol) in anhydrous toluene (26 mL) was added silver(I) oxide (3.12 g, 13.5 mmol) carefully in portions. Upon complete addition of silver oxide, the reaction was protected from light and heated to 75° C. and monitored with LC-MS. After 70 h, the mixture was cooled to RT and then filtered. The filtrate was concentrated in vacuo. The residue was loaded onto a silica gel column (15-75% EtOAc in heptanes). Fractions containing product were combined and then concentrated in vacuo to afford Example 266.3 (1.66 g, 3.12 mmol, 48% yield) as a light yellow oil that was used without further purification. $^1$H NMR (400 MHz, DMSO-$d_6$) δ 8.54 (td, J=1.2, 6.8 Hz, 1H), 7.98 (s, 1H), 7.55 (dd, J=0.7, 9.0 Hz, 1H), 7.23 (ddd, J=1.3, 6.7, 9.1 Hz, 1H), 7.20-7.15 (m, 4H), 6.92-6.84 (m, 5H), 4.87 (d, J=7.7 Hz, 1H), 4.41 (d, J=15.5 Hz, 2H), 4.12 (d, J=15.5 Hz, 2H), 3.79-3.71 (m, 7H), 3.44 (spt, J=6.1 Hz, 1H), 1.12 (d, J=6.0 Hz, 3H), 1.09 (d, J=7.3 Hz, 3H), 1.00 (d, J=6.2 Hz, 3H). LCMS-ESI (pos) m/z: 538.2 (M+H)$^+$.

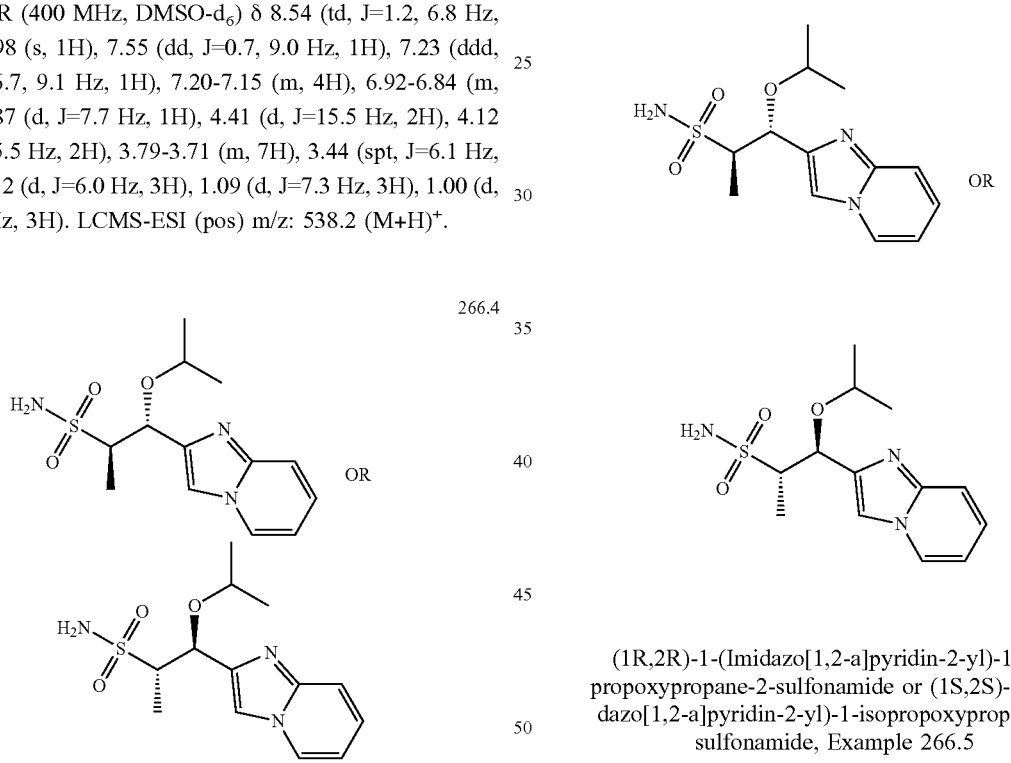

(1R,2R)-1-(Imidazo[1,2-a]pyridin-2-yl)-1-isopropoxypropane-2-sulfonamide or (1S,2S)-1-(imidazo[1,2-a]pyridin-2-yl)-1-isopropoxypropane-2-sulfonamide, Example 266.4

Anisole (1.4 mL, 12.8 mmol) was added to a flask containing Example 266.3 (1.68 g, 3.1 mmol) and DCM (7.8 mL). The homogeneous solution was cooled in an ice-water bath. After 15 min, TFA (8 mL, 104 mmol) was added dropwise to the reaction solution. Upon complete addition of TFA, the reaction was allowed to warm to RT. After 20 h, the brownish reaction solution was concentrated in vacuo. The residue was diluted with a 3:1 EtOAc: EtOH solution and then loaded onto a silica gel column (25-100% 3:1 EtOAc: EtOH in heptanes). Fractions containing pure product were concentrated in vacuo to afford an off-white solid that was purified by preparative SFC using the following conditions: Column: AD-H (2×25 cm) Mobile Phase: 75:25 (A:B) A: Liquid CO$_2$, B: IPA with 0.2% DEA, Flow Rate: 80 mL/min, 280 nm, 100 bar inlet pressure to deliver peak 1 as Example 266.4. $^1$H NMR (400 MHz, DMSO-$d_6$) δ 8.53 (td, J=1.2, 6.8 Hz, 1H), 7.97 (s, 1H), 7.54 (dd, J=0.7, 9.0 Hz, 1H), 7.24 (ddd, J=1.3, 6.8, 9.1 Hz, 1H), 6.90 (dt, J=1.2, 6.7 Hz, 1H), 6.52 (s, 2H), 4.85 (d, J=7.3 Hz, 1H), 3.57 (quin, J=6.1 Hz, 1H), 3.53-3.46 (m, 1H), 1.15 (d, J=6.0 Hz, 3H), 1.03 (d, J=7.0 Hz, 3H), 1.00 (d, J=6.2 Hz, 3H). LCMS-ESI (pos) m/z: 298.0 (M+H)$^+$.

(1R,2R)-1-(Imidazo[1,2-a]pyridin-2-yl)-1-isopropoxypropane-2-sulfonamide or (1S,2S)-1-(imidazo[1,2-a]pyridin-2-yl)-1-isopropoxypropane-2-sulfonamide, Example 266.5

Further elution under the conditions described in Example 266.4 delivered peak 2 as Example 266.5. $^1$H NMR (400 MHz, DMSO-$d_6$) δ 8.53 (td, J=1.1, 6.8 Hz, 1H), 7.97 (s, 1H), 7.54 (dd, J=0.8, 9.1 Hz, 1H), 7.24 (ddd, J=1.2, 6.7, 9.1 Hz, 1H), 6.90 (dt, J=1.0, 6.7 Hz, 1H), 6.52 (s, 2H), 4.86 (d, J=7.3 Hz, 1H), 3.62-3.54 (m, 1H), 3.53-3.46 (m, 1H), 1.15 (d, J=6.0 Hz, 3H), 1.04 (d, J=7.0 Hz, 3H), 1.00 (d, J=6.2 Hz, 3H). LCMS-ESI (pos) m/z: 298.0 (M+H)$^+$.

The compound set forth in the following table were synthesized following the procedure in Example 140.0 using the known starting material as described.

TABLE 25

| Example | Reagents | Structure, Name and Data |
|---|---|---|
| 266.0 | (1R,2R)-1-(imidazo[1,2-a]pyridin-2-yl)-1-isopropoxypropane-2-sulfonamide or (1S,2S)-1-(imidazo[1,2-a]pyridin-2-yl)-1-isopropoxypropane-2-sulfonamide (Example 266.4), (R)-1,4-dioxane-2-carbohydrazide hydrochloride (Example 255.2), and 2-isothiocyanato-1,3-dimethoxybenzene (Example 10.0). | 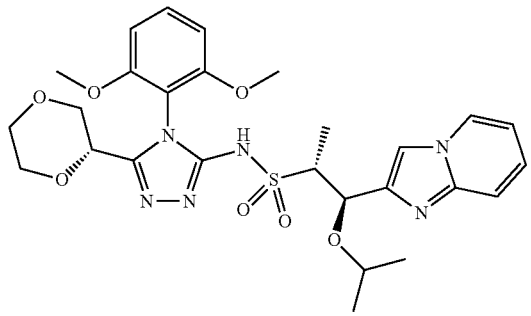<br>OR<br>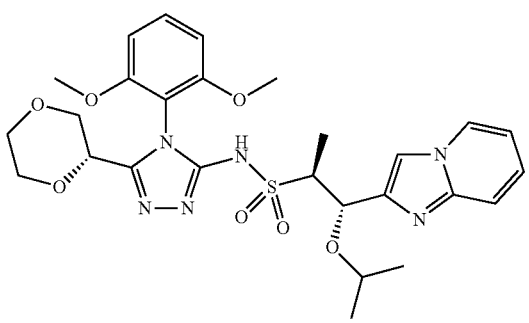<br>(1R,2R)-N-(4-(2,6-dimethoxyphenyl)-5-((S)-1,4-dioxan-2-yl)-4H-1,2,4-triazol-3-yl)-1-(imidazo[1,2-a]pyridin-2-yl)-1-isopropoxypropane-2-sulfonamide or (1S,2S)-N-(4-(2,6-dimethoxyphenyl)-5-((S)-1,4-dioxan-2-yl)-4H-1,2,4-triazol-3-yl)-1-(imidazo[1,2-a]pyridin-2-yl)-1-isopropoxypropane-2-sulfonamide. $^1$H NMR (500 MHz, DMSO-$d_6$) δ 13.48-12.93 (m, 1H), 8.49 (d, J = 6.7 Hz, 1H), 7.80 (s, 1H), 7.52-7.48 (m, 2H), 7.23-7.18 (m, 1H), 6.89-6.83 (m, 3H), 4.82 (d, J = 6.2 Hz, 1H), 4.16 (t, J = 5.6 Hz, 1H), 3.86-3.73 (m, 7H), 3.73-3.69 (m, 2H), 3.67-3.63 (m, 1H), 3.61-3.57 (m, 1H), 3.45 (br s, 1H), 3.41-3.37 (m, 1H), 3.36-3.32 (m, 1H), 1.05-1.03 (m, 3H), 1.01 (d, J = 6.2 Hz, 3H), 0.89 (d, J = 6.0 Hz, 3H). LCMS-ESI (pos) m/z: 587.2 (M + H)$^+$. |

TABLE 25-continued

| Example | Reagents | Structure, Name and Data |
|---|---|---|
| 267.0 | (2S,3R)-3-(5-chloropyridin-2-yl)butane-2-sulfonamide (Example 14.0), (R)-1,4-dioxane-2-carbohydrazide and (S)-1,4-dioxane-2-carbohydrazide (commercially available from Enamine), and 2-isothiocyanato-1,3-dimethoxybenzene (Example 10.0).<br>The racemic mixture was purified by preparative SFC using the following methodology: Column: AD-H (2 × 15 cm) Mobile Phase: 65:35 (A:B) A: Liquid CO$_2$, B: IPA, Flow Rate: 80 mL/min, 225 nm, 100 bar inlet pressure to deliver peak 1. | 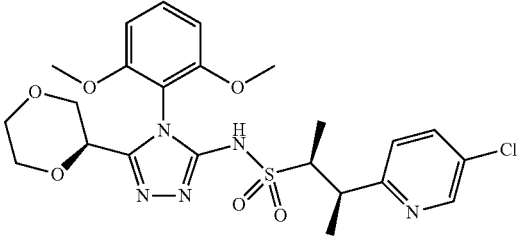<br>OR<br>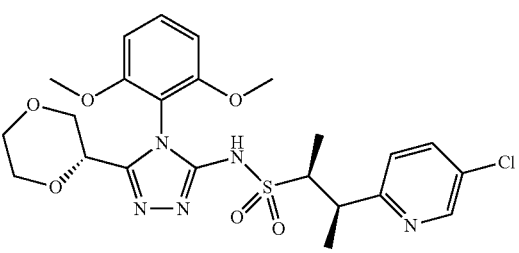<br>(2S,3R)-3-(5-chloropyridin-2-yl)-N-(4-(2,6-dimethoxyphenyl)-5-((R)-1,4-dioxan-2-yl)-4H-1,2,4-triazol-3-yl)butane-2-sulfonamide or (2S,3R)-3-(5-chloropyridin-3-yl)-N-(4-(2,6-dimethoxyphenyl)-5-((S)-1,4-dioxan-2-yl)-4H-1,2,4-triazol-3-yl)butane-2-sulfonamide. $^1$H NMR (500 MHz, DMSO-d$_6$) δ 13.09 (s, 1H), 8.53 (d, J = 2.6 Hz, 1H), 7.84 (dd, J = 2.6, 8.6 Hz, 1H), 7.49 (t, J = 8.4 Hz, 1H), 7.24 (d, J = 8.6 Hz, 1H), 6.84 (dd, J = 3.1, 8.6 Hz, 2H), 4.17 (dd, J = 4.3, 6.9 Hz, 1H), 3.74 (s, 3H), 3.74-3.69 (m, 5H), 3.64 (td, J = 2.7, 11.7 Hz, 1H), 3.60-3.55 (m, 2H), 3.52-3.46 (m, 1H), 3.42-3.36 (m, 1H), 3.35-3.29 (m, 1H), 1.20 (d, J = 7.0 Hz, 3H), 1.06 (d, J = 7.0 Hz, 3H). LCMS-ESI (pos) m/z: 538.2 (M + H)$^+$. |
| 268.0 | (2S,3R)-3-(5-chloropyridin-2-yl)butane-2-sulfonamide (Example 14.0), (R)-1,4-dioxane-2-carbohydrazide and (S)-1,4-dioxane-2-carbohydrazide (commercially available from Enamine), and 2-isothiocyanato-1,3-dimethoxybenzene (Example 10.0).<br>The racemic mixture was purified by preparative SFC using the following methodology: Column: AD-H (2 × 15 cm) Mobile Phase: 65:35 (A:B) A: Liquid CO$_2$, B: IPA, Flow Rate: 80 mL/min, 225 nm, 100 bar inlet pressure to deliver peak 2. | 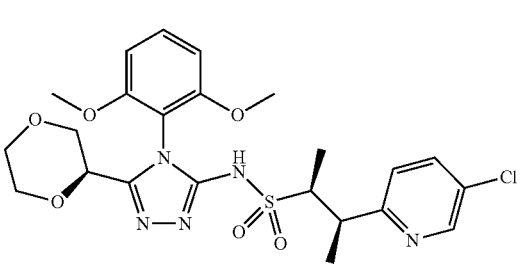<br>OR<br>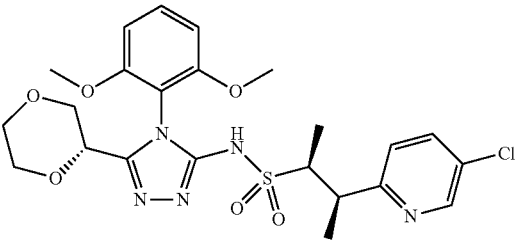<br>(2S,3R)-3-(5-chloropyridin-2-yl)-N-(4-(2,6-dimethoxyphenyl)-5-((R)-1,4-dioxan-2-yl)-4H-1,2,4-triazol-3-yl)butane-2-sulfonamide or |

TABLE 25-continued

| Example Reagents | Structure, Name and Data |
| --- | --- |
| | (2S,3R)-3-(5-chloropyridin-2-yl)-N-(4-(2,6-dimethoxyphenyl)-5-((S)-1,4-dioxan-2-yl)-4H-1,2,4-triazol-3-yl)butane-2-sulfonamide. $^1$H NMR (500 MHz, DMSO-$d_6$) δ 13.09 (s, 1H), 8.53 (d, J = 2.3 Hz, 1H), 7.84 (dd, J = 2.5, 8.4 Hz, 1H), 7.49 (t, J = 8.4 Hz, 1H), 7.25 (d, J = 8.3 Hz, 1H), 6.84 (dd, J = 2.2, 8.4 Hz, 2H), 4.17 (dd, J = 3.9, 7.3 Hz, 1H), 3.81-3.73 (m, 5H), 3.72 (s, 3H), 3.66-3.61 (m, 1H), 3.60-3.55 (m, 2H), 3.51-3.45 (m, 1H), 3.41-3.33 (m, 2H), 1.20 (d, J = 7.0 Hz, 3H), 1.06 (d, J = 7.0 Hz, 3H). LCMS-ESI (pos) m/z: 538.2 (M + H)$^+$. |
| 269.0 (2S,3R)-3-(5-methylpyrimidin-2-yl)butane-2-sulfonamide (Example 1.0), (R)-1-methylpiperidine-3-carbohydrazide and (S)-1-methylpiperidine-3-carbohydrazide (commercially available from Ochem Incorporation), and 2-isothiocyanato-1,3-dimethoxybenzene (Example 10.0). The racemic mixture was purified by preparative SFC using the following methodology: Column: AD-H (2 × 15 cm) Mobile Phase: 70:30 (A:B) A: Liquid CO$_2$, B: IPA, 0.2% Diethylamine, Flow Rate: 80 mL/min, 215 nm, 100 bar inlet pressure to deliver peak 1. | 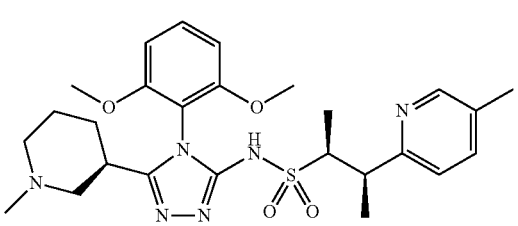<br>OR<br>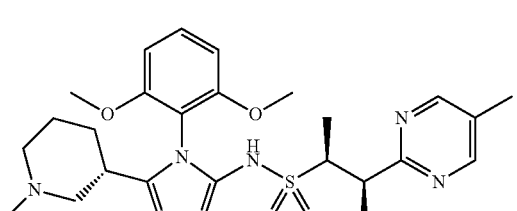<br>(2S,3R)-N-(4-(2,6-dimethoxyphenyl)-5-((R)-1-methylpiperidin-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-1-methylpiperidin-3-yl)-4H-1,2,4-triazol-3-yl)-3-(5-methylpyrimidin-2-yl)butane-2-sulfonamide. $^1$H NMR (400 MHz, CD$_2$Cl$_2$) δ 11.04-10.82 (m, 1H), 8.50 (s, 2H), 7.48 (t, J = 8.5 Hz, 1H), 6.71 (dd, J = 3.7, 8.7 Hz, 2H), 3.79 (s, 3H), 3.79-3.78 (m, 3H), 3.75-3.67 (m, 1H), 3.65-3.57 (m, 1H), 2.75 (d, J = 10.2 Hz, 1H), 2.71-2.64 (m, 1H), 2.50-2.41 (m, 1H), 2.27 (s, 3H), 2.16 (s, 3H), 2.04 (t, J = 10.9 Hz, 1H), 1.92-1.85 (m, 1H), 1.77 (dd, J = 3.6, 8.0 Hz, 1H), 1.67 (qd, J = 3.0, 9.2 Hz, 1H), 1.47-1.38 (m, 2H), 1.30 (d, J = 7.0 Hz, 3H), 1.24 (d, J = 7.0 Hz, 3H). LCMS-ESI (pos) m/z: 530.2 (M + H)$^+$. |

TABLE 25-continued

| Example | Reagents | Structure, Name and Data |
|---|---|---|
| 270.0 | (2S,3R)-3-(5-methylpyrimidin-2-yl)butane-2-sulfonamide (Example 1.0), (R)-1-methylpiperidine-3-carbohydrazide and (S)-1-methylpiperidine-3-carbohydrazide (commercially available from Ochem Incorporation), and 2-isothiocyanato-1,3-dimethoxybenzene (Example 10.0).<br>The racemic mixture was purified by preparative SFC using the following methodology: Column: AD-H (2 × 15 cm) Mobile Phase: 70:30 (A:B) A: Liquid $CO_2$, B: IPA, 0.2% Diethylamine, Flow Rate: 80 mL/min, 215 nm, 100 bar inlet pressure to deliver peak 1. | 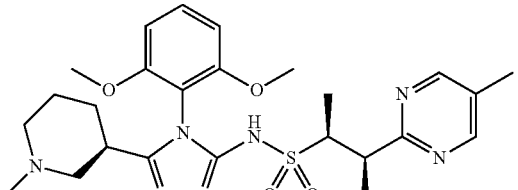<br>OR<br>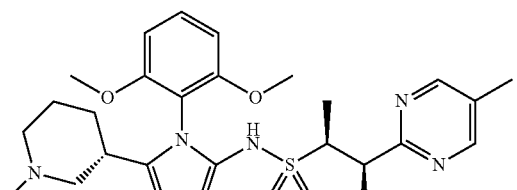<br>(2S,3R)-N-(4-(2,6-dimethoxyphenyl)-5-((R)-1-methylpiperidin-3-yl)-4H-1,2,4-triazol-3-yl)-3-(5-methylpyrimidin-2-yl)butane-2-sulfonamide or (2S,3R)-N-(4-(2,6-dimethoxyphenyl)-5-((S)-1-methylpiperidin-3-yl)-4H-1,2,4-triazol-3-yl)-3-(5-methylpyrimidin-2-yl)butane-2-sulfonamide. $^1$H NMR (500 MHz, $CD_2Cl_2$) δ 8.50 (s, 2H), 7.48 (t, J = 8.6 Hz, 1H), 6.71 (dd, J = 4.0, 8.4 Hz, 2H), 3.80 (s, 3H), 3.78 (s, 3H), 3.74-3.69 (m, 1H), 3.64-3.59 (m, 1H), 2.76 (d, J = 10.6 Hz, 1H), 2.68 (d, J = 10.9 Hz, 1H), 2.49-2.42 (m, 1H), 2.26 (s, 3H), 2.17 (s, 3H), 2.05 (t, J = 10.8 Hz, 1H), 1.94-1.84 (m, 1H), 1.80-1.74 (m, 1H), 1.70-1.63 (m, 1H), 1.50-1.39 (m, 2H), 1.30 (d, J = 7.0 Hz, 3H), 1.24 (d, J = 7.0 Hz, 3H). LCMS-ESI (pos) m/z: 530.2 (M + H)$^+$. |
| 271.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 1-isothiocyanato-1-methylcyclopropane (commercially available from Enamine).<br>The racemic mixture was purified by preparative SFC using the following methodology: Column: AD-H (2 × 15 cm) Mobile Phase: 75:25 (A:B) A: Liquid $CO_2$, B: MeOH, Flow Rate: 80 mL/min, 215 nm, 100 bar inlet pressure to deliver peak 1. | 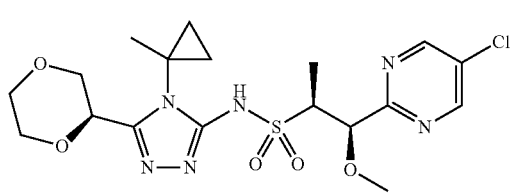<br>OR<br>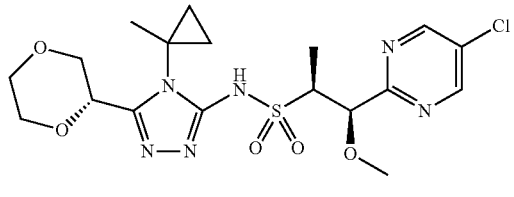<br>(1R,2S)-N-(5-((R)-1,4-dioxan-2-yl)-4-(1-methylcyclopropyl)-4H-1,2,4-triazol-3-yl)-1-(5-chloropyrimidin-2-yl)-1-methoxypropane-2-sulfonamide or (1R,2S)-N-(5-((S)-1,4-dioxan-2-yl)-4-(1-methylcyclopropyl)-4H-1,2,4-triazol-3-yl)-1-(5-chloropyrimidin-2-yl)-1-methoxypropane-2-sulfonamide. $^1$H NMR (500 MHz, DMSO-$d_6$) δ 12.84 (br s, 1H), 8.93 (s, 2H), 4.92 (d, J = 3.9 Hz, 1H), 4.81 (dd, J = 2.6, 9.3 Hz, 1H), 3.98 (dd, J = 2.3, 11.4 Hz, 1H), 3.86-3.72 (m, 4H), 3.63-3.57 (m, 1H), 3.45 (dd, |

| Example | Reagents | Structure, Name and Data |
|---|---|---|
| | | J = 3.9, 6.7 Hz, 1H), 3.07 (s, 3H), 1.40 (s, 3H), 1.27 (d, J = 7.0 Hz, 3H), 1.25-1.17 (m, 2H), 0.99-0.89 (m, 2H). LCMS-ESI (pos) m/z: 473.2 (M + H)+. |
| 272.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 1-isothiocyanato-1-methylcyclopropane (commercially available from Enamine).<br>The racemic mixture was purified by preparative SFC using the following methodology: Column: AD-H (2 × 15 cm) Mobile Phase: 75:25 (A:B) A: Liquid CO2, B: MeOH, Flow Rate: 80 mL/min, 215 nm, 100 bar inlet pressure to deliver peak 2. | 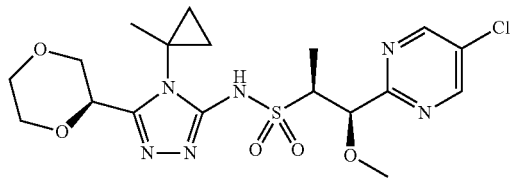<br><br>OR<br><br>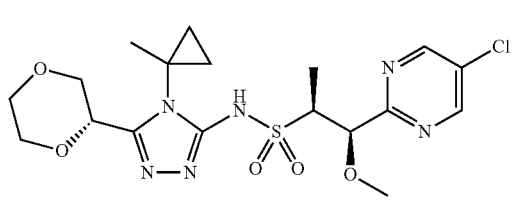<br><br>(1R,2S)-N-(5-((R)-1,4-dioxan-2-yl)-4-(1-methylcyclopropyl)-4H-1,2,4-triazol-3-yl)-1-(5-chloropyrimidin-2-yl)-1-methoxypropane-2-sulfonamide or (1R,2S)-N-(5-((S)-1,4-dioxan-2-yl)-4-(1-methylcyclopropyl)-4H-1,2,4-triazol-3-yl)-1-(5-chloropyrimidin-2-yl)-1-methoxypropane-2-sulfonamide. 1H NMR (500 MHz, DMSO-d6) δ 12.84 (br s, 1H), 8.93 (s, 2H), 4.92 (d, J = 3.9 Hz, 1H), 4.79 (dd, J = 2.6, 9.3 Hz, 1H), 3.98 (dd, J = 2.3, 11.4 Hz, 1H), 3.86-3.72 (m, 4H), 3.63-3.56 (m, 1H), 3.06 (s, 3H), 1.41 (s, 3H), 1.31-1.24 (m, 4H), 1.21-1.12 (m, 1H), 1.00-0.89 (m, 2H). LCMS-ESI (pos) m/z: 473.2 (M + H)+. |
| 273.0 | (2S,3R)-3-(5-fluoropyrimidin-2-yl)butane-2-sulfonamide (Example 1.1), (R)-tetrahydrofuran-3-carbohydrazide and (S)-tetrahydrofuran-3-carbohydrazide (commercially available from Astatech Inc.), and 2-isothiocyanato-1,3-dimethoxybenzene (Example 10.0).<br>The racemic mixture was purified by preparative SFC using the following methodology: Column: AS-H (2 × 25 cm) Mobile Phase: 75:25 (A:B) A: Liquid CO2, B: MeOH, Flow Rate: 80 mL/min, 215 nm, 100 bar inlet pressure to deliver peak 1. | 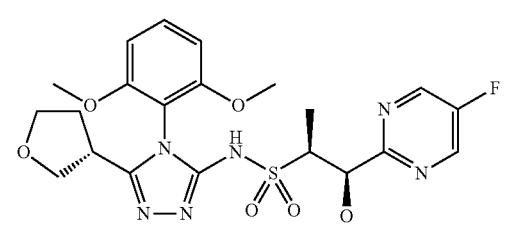<br><br>OR<br><br>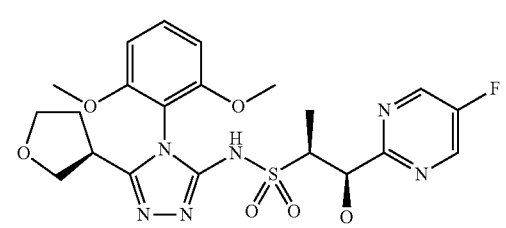<br><br>(2S,3R)-N-(4-(2,6-dimethoxyphenyl)-5-((R)-tetrahydrofuran-3-yl)-4H-1,2,4-triazol-3-yl)-3-(5-fluoropyrimidin-2-yl)butane-2-sulfonamide or (2S,3R)-N-(4-(2,6-dimethoxyphenyl)-5-((S)-tetrahydrofuran-3-yl)-4H-1,2,4-triazol-3-yl)-3-(5-fluoropyrimidin-2-yl)butane-2-sulfonamide. 1H NMR (400 MHz, DMSO-d6) δ 12.83 (br s, 1H), 8.83-8.81 (m, 2H), 7.52 (t, J = 8.5 Hz, 1H), 6.86 (dd, J = 3.7, 8.5 Hz, 2H), 3.79-3.72 (m, 7H), 3.72-3.66 (m, 1H), 3.65-3.58 (m, 3H), 3.52 (dq, |

| Example | Reagents | Structure, Name and Data |
|---|---|---|
| | | J = 4.0, 6.9 Hz, 1H), 2.95 (qd, J = 6.7, 8.9 Hz, 1H), 2.09-2.00 (m, 1H), 1.98-1.89 (m, 1H), 1.23 (d, J = 7.3 Hz, 3H), 1.08 (d, J = 7.0 Hz, 3H). LCMS-ESI (pos) m/z: 507.2 (M + H)+. |
| 274.0 | (2S,3R)-3-(5-fluoropyrimidin-2-yl)butane-2-sulfonamide (Example 1.1), (R)-tetrahydrofuran-3-carbohydrazide and (S)-tetrahydrofuran-3-carbohydrazide (commercially available from Astatech Inc.), and 2-isothiocyanato-1,3-dimethoxybenzene (Example 10.0). The racemic mixture was purified by preparative SFC using the following methodology: Column: AS-H (2 × 25 cm) Mobile Phase: 75:25 (A:B) A: Liquid CO$_2$, B: MeOH, Flow Rate: 80 mL/min, 215 nm, 100 bar inlet pressure to deliver peak 2. | 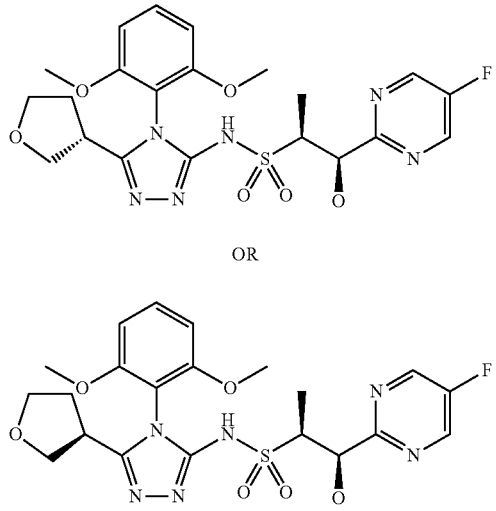 [SMILES: COc1cccc(OC)c1-n1c(NS(=O)(=O)[C@@H](C)[C@H](O)c2ncc(F)cn2)nnc1[C@H]1CCOC1 ; COc1cccc(OC)c1-n1c(NS(=O)(=O)[C@@H](C)[C@H](O)c2ncc(F)cn2)nnc1[C@@H]1CCOC1]<br>OR<br>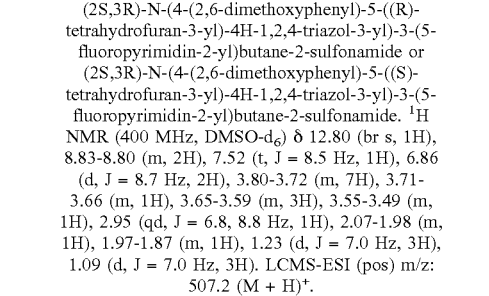<br>(2S,3R)-N-(4-(2,6-dimethoxyphenyl)-5-((R)-tetrahydrofuran-3-yl)-4H-1,2,4-triazol-3-yl)-3-(5-fluoropyrimidin-2-yl)butane-2-sulfonamide or (2S,3R)-N-(4-(2,6-dimethoxyphenyl)-5-((S)-tetrahydrofuran-3-yl)-4H-1,2,4-triazol-3-yl)-3-(5-fluoropyrimidin-2-yl)butane-2-sulfonamide. $^1$H NMR (400 MHz, DMSO-d$_6$) δ 12.80 (br s, 1H), 8.83-8.80 (m, 2H), 7.52 (t, J = 8.5 Hz, 1H), 6.86 (d, J = 8.7 Hz, 2H), 3.80-3.72 (m, 7H), 3.71-3.66 (m, 1H), 3.65-3.59 (m, 3H), 3.55-3.49 (m, 1H), 2.95 (qd, J = 6.8, 8.8 Hz, 1H), 2.07-1.98 (m, 1H), 1.97-1.87 (m, 1H), 1.23 (d, J = 7.0 Hz, 3H), 1.09 (d, J = 7.0 Hz, 3H). LCMS-ESI (pos) m/z: 507.2 (M + H)+. |
| 275.0 | (2S,3R)-3-(5-fluoropyrimidin-2-yl)butane-2-sulfonamide (Example 1.1), (R)-1,4-dioxane-2-carbohydrazide and (S)-1,4-dioxane-2-carbohydrazide (commercially available from Enamine), and 2-isothiocyanato-1,3-dimethoxybenzene (Example 10.0). The racemic mixture was purified by preparative SFC using the following methodology: Column: AD-H (2 × 25 cm) Mobile Phase: 60:40 (A:B) A: Liquid CO$_2$, B: IPA, Flow Rate: 80 mL/min, 220 nm, 100 bar inlet pressure to deliver peak 1. | 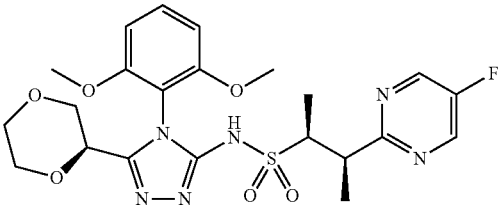<br>OR<br>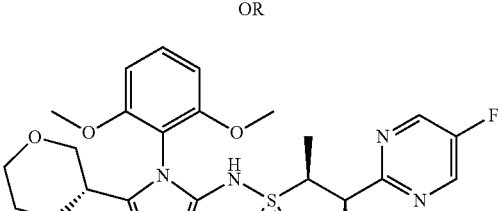<br>(2S,3R)-N-(4-(2,6-dimethoxyphenyl)-5-((R)-1,4-dioxan-2-yl)-4H-1,2,4-triazol-3-yl)-3-(5-fluoropyrimidin-2-yl)butane-2-sulfonamide or (2S,3R)-N-(4-(2,6-dimethoxyphenyl)-5-((S)-1,4-dioxan-2-yl)-4H-1,2,4-triazol-3-yl)-3-(5-fluoropyrimidin-2-yl)butane-2-sulfonamide. $^1$H NMR (400 MHz, DMSO-d$_6$) δ 13.08 (s, 1H), 8.83-8.80 (m, 2H), 7.49 (t, J = 8.5 Hz, 1H), 6.84 (dd, J = 1.1, 8.6 Hz, 2H), 4.17 (dd, J = 4.1, 7.0 Hz, 1H), |

TABLE 25-continued

| Example | Reagents | Structure, Name and Data |
|---|---|---|
| | | 3.76-3.70 (m, 8H), 3.69-3.65 (m, 1H), 3.65-3.45 (m, 4H), 3.41-3.35 (m, 1H), 1.24 (d, J = 7.3 Hz, 3H), 1.09 (d, J = 7.0 Hz, 3H). LCMS-ESI (pos) m/z: 523.2 (M + H)⁺. |
| 276.0 | (2S,3R)-3-(5-fluoropyrimidin-2-yl)butane-2-sulfonamide (Example 1.1), (R)-1,4-dioxane-2-carbohydrazide and (S)-1,4-dioxane-2-carbohydrazide (commercially available from Enamine), and 2-isothiocyanato-1,3-dimethoxybenzene (Example 10.0). The racemic mixture was purified by preparative SFC using the following methodology: Column: AD-H (2 × 25 cm) Mobile Phase: 60:40 (A:B) A: Liquid $CO_2$, B: IPA, Flow Rate: 80 mL/min, 220 nm, 100 bar inlet pressure to deliver peak 2. | 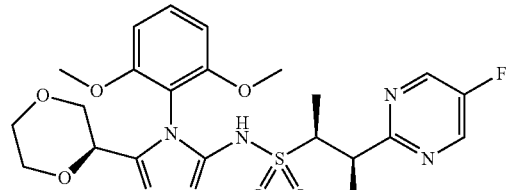<br><br>OR<br><br>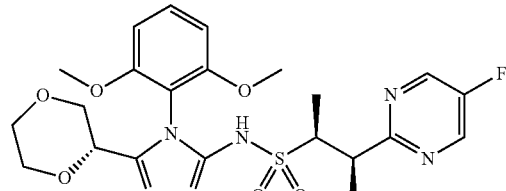<br><br>(2S,3R)-N-(4-(2,6-dimethoxyphenyl)-5-((R)-1,4-dioxan-2-yl)-4H-1,2,4-triazol-3-yl)-3-(5-fluoropyrimidin-2-yl)butane-2-sulfonamide or (2S,3R)-N-(4-(2,6-dimethoxyphenyl)-5-((S)-1,4-dioxan-2-yl)-4H-1,2,4-triazol-3-yl)-3-(5-fluoropyrimidin-2-yl)butane-2-sulfonamide. ¹H NMR (400 MHz, DMSO-d₆) δ 13.08 (s, 1H), 8.83-8.81 (m, 2H), 7.50 (t, J = 8.5 Hz, 1H), 6.84 (dd, J = 2.0, 8.6 Hz, 2H), 4.16 (dd, J = 4.3, 6.9 Hz, 1H), 3.77-3.71 (m, 8H), 3.71-3.66 (m, 1H), 3.65-3.45 (m, 4H), 3.43-3.35 (m, 1H), 1.24 (d, J = 7.0 Hz, 3H), 1.09 (d, J = 6.8 Hz, 3H). LCMS-ESI (pos) m/z: 523.2 (M + H)⁺. |
| 277.0 | (2S,3R)-3-(5-fluoropyrimidin-2-yl)butane-2-sulfonamide (Example 1.1), (R)-1,4-dioxane-2-carbohydrazide and (S)-1,4-dioxane-2-carbohydrazide (commercially available from Enamine), and 5-isothiocyanato-4,6-dimethoxypyrimidine (Example 10.1). The racemic mixture was purified by preparative SFC using the following methodology: Column: AD-H (2 × 25 cm) Mobile Phase: 65:35 (A:B) A: Liquid $CO_2$, B: IPA, Flow Rate: 80 mL/min, 220 nm, 100 bar inlet pressure to deliver peak 1. | 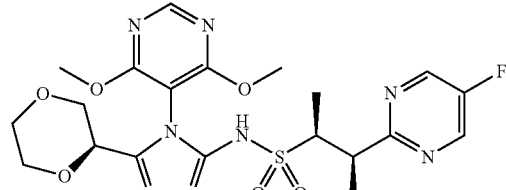<br><br>OR<br><br>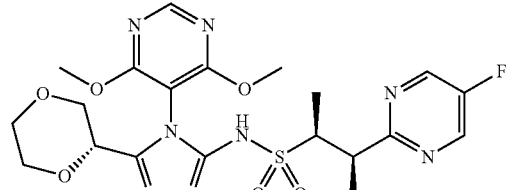<br><br>(2S,3R)-N-(4-(4,6-dimethoxypyrimidin-5-yl)-5-((R)-1,4-dioxan-2-yl)-4H-1,2,4-triazol-3-yl)-3-(5-fluoropyrimidin-2-yl)butane-2-sulfonamide or (2S,3R)-N-(4-(4,6-dimethoxypyrimidin-5-yl)-5-((S)-1,4-dioxan-2-yl)-4H-1,2,4-triazol-3-yl)-3-(5-fluoropyrimidin-2-yl)butane-2-sulfonamide. ¹H NMR (500 MHz, DMSO-d₆) δ 13.27 (s, 1H), 8.82 (s, 2H), 8.66 (s, 1H), 4.44 (dd, J = 3.1, 7.3 Hz, 1H), 3.94 (s, 3H), 3.93-3.91 (m, 3H), 3.88-3.83 (m, 1H), 3.82-3.76 (m, 1H), 3.69-3.64 (m, 1H), |

| Example | Reagents | Structure, Name and Data |
|---|---|---|
| | | 3.62-3.53 (m, 3H), 3.51-3.43 (m, 2H), 1.24 (d, J = 7.0 Hz, 3H), 1.11 (d, J = 7.0 Hz, 3H). LCMS-ESI (pos) m/z: 525.2 (M + H)+. |
| 278.0 | (2S,3R)-3-(5-fluoropyrimidin-2-yl)butane-2-sulfonamide (Example 1.1), (R)-1,4-dioxane-2-carbohydrazide and (S)-1,4-dioxane-2-carbohydrazide (commercially available from Enamin), and 5-isothiocyanato-4,6-dimethoxypyrimidine (Example 10.1). The racemic mixture was purified by preparative SFC using the following methodology: Column: AD-H (2 × 25 cm) Mobile Phase: 65:35 (A:B) A: Liquid CO2, B: IPA, Flow Rate: 80 mL/min, 220 nm, 100 bar inlet pressure to deliver peak 2. | 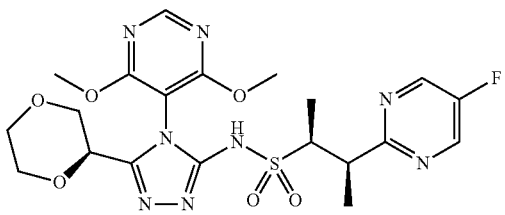<br>OR<br>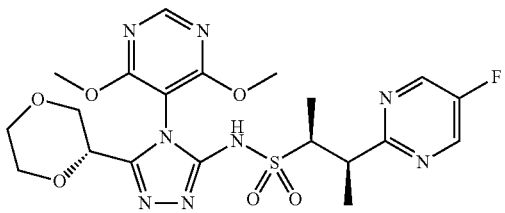<br>(2S,3R)-N-(4-(4,6-dimethoxypyrimidin-5-yl)-5-((R)-1,4-dioxan-2-yl)-4H-1,2,4-triazol-3-yl)-3-(5-fluoropyrimidin-2-yl)butane-2-sulfonamide or (2S,3R)-N-(4-(4,6-dimethoxypyrimidin-5-yl)-5-((S)-1,4-dioxan-2-yl)-4H-1,2,4-triaozl-3-yl)-3-(5-fluoropyrimidin-2-yl)butane-2-sulfonamide. 1H NMR (500 MHz, DMSO-d6) δ 13.27 (s, 1H), 8.82 (s, 2H), 8.66 (s, 1H), 4.43 (dd, J = 3.1, 7.3 Hz, 1H), 3.94 (s, 3H), 3.92-3.91 (m, 3H), 3.88-3.84 (m, 1H), 3.82-3.77 (m, 1H), 3.70-3.64 (m, 1H), 3.62-3.53 (m, 3H), 3.53-3.44 (m, 2H), 1.24 (d, J = 7.0 Hz, 3H), 1.11 (d, J = 7.0 Hz, 3H). LCMS-ESI (pos) m/z: 525.2 (M + H)+. |
| 279.0 | (1S,2S)-1-(5-chloropyrimidin-2-yl)-1-isopropoxypropane-2-sulfonamide (Example 13.6), (R)-5,5-dimethyltetrahydrofuran-2-carbohydrazide and (S)-5,5-dimethyltetrahydrofuran-2-carbohydrazide (Example 108.2), and 5-isothiocyanato-4,6-dimethoxypyrimidine (Example 10.1). The racemic mixture was purified by preparative SFC using the following methodology: Column: IC (3 × 25 cm ) Mobile Phase: 80:20 (A:B) A: Liquid CO2, B: MeOH, Flow Rate: 165 mL/min, 215 nm, 100 bar inlet pressure to deliver peak 1. | 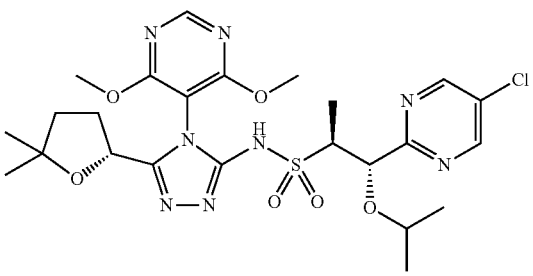<br>OR<br>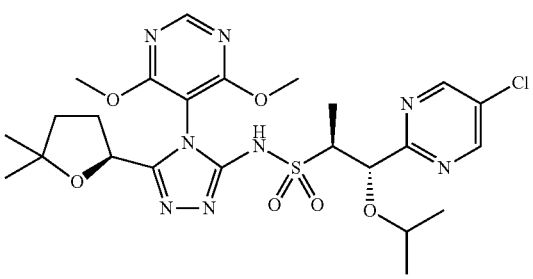<br>(1S,2S)-1-(5-chloropyrimidin-2-yl)-N-(4-(4,6-dimethoxypyrimidin-5-yl)-5-((R)-5,5-dimethyltetrahydrofuran-2-yl)-4H-1,2,4-triazol-3-yl)-1-isopropoxypropane-2-sulfonamide or (1S,2S)-1-(5-chloropyrimidin-2-yl)-N-(4-(4,6-dimethoxypyrimidin-5-yl)-5-((S)-5,5-dimethyltetrahydrofuran-2-yl)-4H-1,2,4-triazol-3- |

TABLE 25-continued

| Example | Reagents | Structure, Name and Data |
|---|---|---|
| | | yl)-1-isopropoxypropane-2-sulfonamide. $^1$H NMR (400 MHz, DMSO-$d_6$) δ 12.96 (br s, 1H), 8.92 (s, 2H), 8.66 (s, 1H), 4.77-4.71 (m, 2H), 3.97 (br s, 3H), 3.96-3.94 (m, 3H), 3.47-3.37 (m, 2H), 2.22 (q, J = 7.0 Hz, 2H), 1.74-1.67 (m, 1H), 1.53 (td, J = 7.9, 12.0 Hz, 1H), 1.04 (s, 3H), 1.03-0.94 (m, 6H), 0.92 (s, 3H), 0.81 (br d, J = 6.0 Hz, 3H). LCMS-ESI (pos) m/z: 597.2 (M + H)$^+$. |
| 280.0 | (1S,2S)-1-(5-chloropyrimidin-2-yl)-1-isopropoxypropane-2-sulfonamide (Example 13.6), (R)-5,5-dimethyltetrahydrofuran-2-carbohydrazide and (S)-5,5-dimethyltetrahydrofuran-2-carbohydrazide (Example 108.2), and 5-isothiocyanato-4,6-dimethoxypyrimidine (Example 10.1). The racemic mixture was purified by preparative SFC using the following methodology: Column: IC (3 × 25 cm) Mobile Phase: 80:20 (A:B) A: Liquid CO$_2$, B: MeOH, Flow Rate: 165 mL/min, 215 nm, 100 bar inlet pressure to deliver peak 2. | 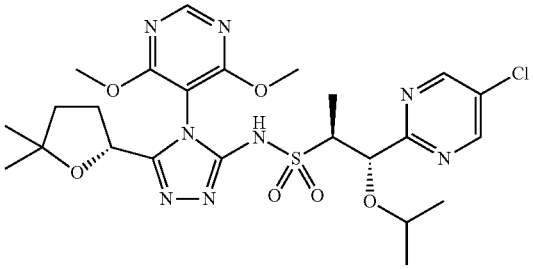<br><br>OR<br><br>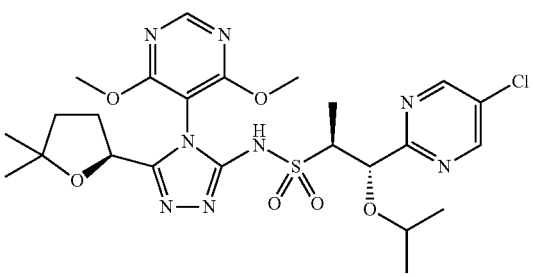<br><br>(1S,2S)-1-(5-chloropyrimidin-2-yl)-N-(4-(4,6-dimethoxypyrimidin-5-yl)-5-((R)-5,5-dimethyltetrahydrofuran-2-yl)-4H-1,2,4-triazol-3-yl)-1-isopropoxypropane-2-sulfonamide or (1S,2S)-1-5-chloropyrimidin-2-yl)-N-(4-(4,6-dimethoxypyrimidin-5-yl)-5-((S)-5,5-dimethyltetrahydrofuran-2-yl)-4H-1,2,4-triazol-3-yl)-1-isopropoxypropane-2-sulfonamide. $^1$H NMR (400 MHz, DMSO-$d_6$) δ 12.91 (s, 1H), 8.93 (s, 2H), 8.66 (s, 1H), 4.77-4.73 (m, 2H), 3.98 (s, 3H), 3.95 (s, 3H), 3.45-3.40 (m, 2H), 2.23 (q, J = 7.1 Hz, 2H), 1.75-1.68 (m, 1H), 1.57-1.50 (m, 1H), 1.05 (s, 3H), 1.00-0.98 (m, 6H), 0.93 (s, 3H), 0.83 (d, J = 6.2 Hz, 3H). LCMS-ESI (pos) m/z: 597.2 (M + H)$^+$. |

TABLE 25-continued

| Example | Reagents | Structure, Name and Data |
|---|---|---|
| 281.0 | (1S,2S)-1-(5-chloropyrimidin-2-yl)-1-isopropoxypropane-2-sulfonamide (Example 13.6), (R)-tetrahydrofuran-3-carbohydrazide and (S)-tetrahydrofuran-3-carbohydrazide (commercially available from Astatech Inc.), and 2-isothiocyanato-1,3-dimethoxybenzene (Example 10.0).<br>The racemic mixture was purified by preparative SFC using the following methodology: Column: AS-H (2 × 25 cm) + Column: AS-H (2 × 15 cm) Mobile Phase: 73:27 (A:B) A: Liquid $CO_2$, B: MeOH (20 mM $NH_3$), Flow Rate: 65 mL/min, 220 nm, 100 bar inlet pressure to deliver peak 1. | 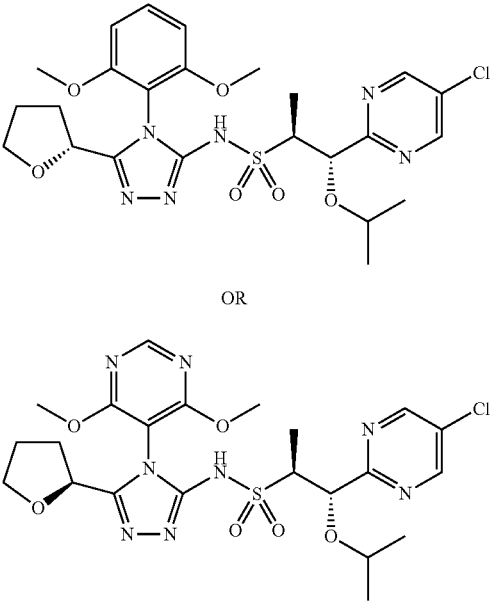 [SMILES: COc1cccc(OC)c1-n1c(NS(=O)(=O)[C@@H](C)[C@@H](OC(C)C)c2ncc(Cl)cn2)nnc1[C@H]1CCCO1 ; COc1ncnc(OC)c1-n1c(NS(=O)(=O)[C@@H](C)[C@@H](OC(C)C)c2ncc(Cl)cn2)nnc1[C@@H]1CCCO1]<br><br>(1S,2S)-1-(5-chloropyrimidin-2-yl)-N-(4-(2,6-dimethoxyphenyl)-5-((R)-tetrahydrofuran-3-yl)-4H-1,2,4-triazol-3-yl)-1-isopropoxypropane-2-sulfonamide or (1S,2S)-1-(5-chloropyrimidin-2-yl)-N-(4-(2,6-dimethoxyphenyl)-5-((S)-tetrahydrofuran-3-yl)-4H-1,2,4-triazol-3-yl)-1-isopropoxypropane-2-sulfonamide. $^1$H NMR (400 MHz, $CD_2Cl_2$) δ 11.60-11.42 (m, 1H), 8.74 (s, 1H), 7.49 (t, J = 8.5 Hz, 1H), 6.73 (t, J = 7.8 Hz, 2H), 4.84 (d, J = 4.6 Hz, 1H), 3.89-3.81 (m, 6H), 3.81-3.72 (m, 2H), 3.66-3.60 (m, 1H), 3.59-3.52 (m, 1H), 3.04-2.95 (m, 1H), 2.19-2.08 (m, 1H), 2.03-1.93 (m, 1H), 1.31 (d, J = 7.0 Hz, 3H), 1.09 (d, J = 6.0 Hz, 3H), 0.97 (d, J = 6.2 Hz, 3H). LCMS-ESI (pos) m/z: 567.2 (M + H)$^+$. |
| 282.0 | (1S,2S)-1-(5-chloropyrimidin-2-yl)-1-isopropoxypropane-2-sulfonamide (Example 13.6), (R)-tetrahydrofuran-3-carbohydrazide and (S)-tetrahydrofuran-3-carbohydrazide (commercially available from Astatech Inc.), and 2-isothiocyanato-1,3-dimethoxybenzene (Example 10.0).<br>The racemic mixture was purified by preparative SFC using the following methodology: Column: AS-H (2 × 25 cm) + Column: AS-H (2 × 15 cm) Mobile Phase: 73:27 (A:B) A: Liquid $CO_2$, B: MeOH (20 mM $NH_3$), Flow Rate: 65 mL/min, 220 nm, 100 bar inlet pressure to deliver peak 2. | 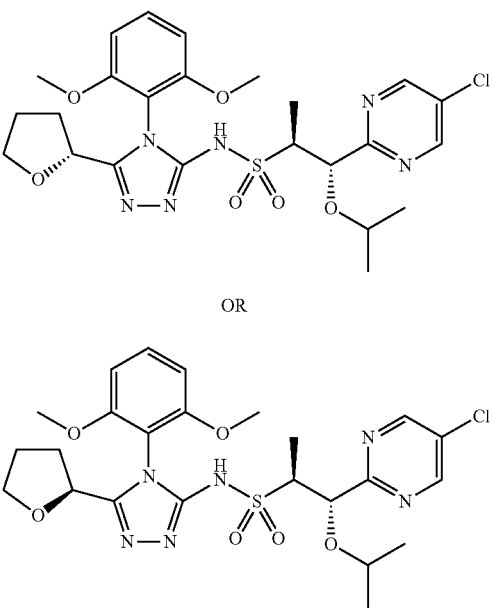 [SMILES: COc1cccc(OC)c1-n1c(NS(=O)(=O)[C@@H](C)[C@@H](OC(C)C)c2ncc(Cl)cn2)nnc1[C@H]1CCCO1 ; COc1cccc(OC)c1-n1c(NS(=O)(=O)[C@@H](C)[C@@H](OC(C)C)c2ncc(Cl)cn2)nnc1[C@@H]1CCCO1]<br><br>(1S,2S)-1-(5-chloropyrimidin-2-yl)-N-(4-(2,6-dimethoxyphenyl)-5-((R)-tetrahydrofuran-3-yl)-4H-1,2,4-triazol-3-yl)-1-isopropoxypropane-2- |

TABLE 25-continued

| Example | Reagents | Structure, Name and Data |
|---------|----------|--------------------------|
| | | sulfonamide or (1S,2)S-1-(5-chloropyrimidin-2-yl)-N-(4-(2,6-dimethoxyphenyl)-5-((S)-tetrahydrofuran-3-yl)-4H-1,2,4-triazol-3-yl)-1-isopropoxypropane-2-sulfonamide. $^1$H NMR (400 MHz, CD$_2$Cl$_2$) δ 11.81-11.31 (m, 1H), 8.75 (s, 2H), 7.49 (t, J = 8.4 Hz, 1H), 6.73 (dd, J = 4.7, 8.0 Hz, 2H), 4.84 (d, J = 4.1 Hz, 1H), 3.91-3.75 (m, 8H), 3.72 (d, J = 7.0 Hz, 2H), 3.67-3.60 (m, 1H), 3.58-3.52 (m, 1H), 3.00 (quin, J = 7.3 Hz, 1H), 2.33-2.20 (m, 1H), 2.08-1.98 (m, 1H), 1.32 (d, J = 7.0 Hz, 3H), 1.09 (d, J = 5.8 Hz, 3H), 0.97 (d, J = 6.0 Hz, 3H). LCMS-ESI (pos) m/z: 567.2 (M + H)$^+$. |
| 283.0 | (1S,2S)-1-(5-chloropyrimidin-2-yl)-1-isopropoxypropane-2-sulfonamide (Example 13.6), (R)-1,4-dioxane-2-carbohydrazide and (S)-1,4-dioxane-2-carbohydrazide (commercially available from Enamine), and 2-isothiocyanato-1,3-dimethoxybenzene (Example 10.0). The racemic mixture was purified by preparative SFC using the following methodology: Column: AD-H (2 × 25 cm), Mobile Phase: 78:22 (A:B) A: Liquid CO$_2$, B: IPA, Flow Rate: 90 mL/min, 226 nm, 100 bar inlet pressure to deliver peak 1. | 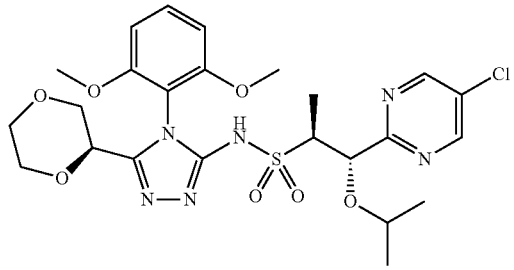<br><br>OR<br><br>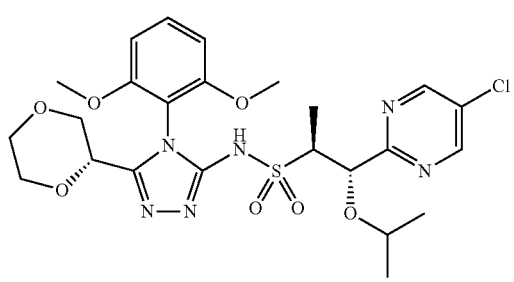<br><br>(1S,2S)-1-(5-chloropyrimidin-2-yl)-N-(4-(2,6-dimethoxyphenyl)-5-((R)-1,4-dioxan-2-yl)-4H-1,2,4-triazol-3-yl)-1-isopropoxypropane-2-sulfonamide or (1S,2S)-1-(5-chloropyrimidin-2-yl)-N-(4-(2,6-dimethoxyphenyl)-5-((S)-1,4-dioxan-2-yl)-4H-1,2,4-triazol-3-yl)-1-isopropoxypropane-2-sulfonamide. $^1$H NMR (400 MHz, DMSO-d$_6$) δ 12.97 (s, 1H), 8.92 (s, 2H), 7.49 (t, J = 8.5 Hz, 1H), 6.85 (dd, J = 1.7, 8.5 Hz, 2H), 4.76 (d, J = 7.0 Hz, 1H), 4.17 (dd, J = 4.5, 6.7 Hz, 1H), 3.82-3.78 (m, 3H), 3.78-3.75 (m, 3H), 3.73-3.67 (m, 2H), 3.66-3.56 (m, 2H), 3.52-3.36 (m, 4H), 1.03-0.90 (m, 6H), 0.81 (d, J = 6.0 Hz, 3H). LCMS-ESI (pos) m/z: 583.2 (M + H)$^+$. |

TABLE 25-continued

| Example | Reagents | Structure, Name and Data |
|---|---|---|
| 284.0 | (1S,2S)-1-(5-chloropyrimidin-2-yl)-1-isopropoxypropane-2-sulfonamide (Example 13.6), (R)-1,4-dioxane-2-carbohydrazide and (S)-1,4-dioxane-2-carbohydrazide (commercially available from Enamine), and 2-isothiocyanato-1,3-dimethoxybenzene (Example 10.0). The racemic mixture was purified by preparative SFC using the following methodology: Column: AD-H (2 × 25 cm), Mobile Phase: 78:22 (A:B) A: Liquid $CO_2$, B: IPA, Flow Rate: 90 mL/min, 226 nm, 100 bar inlet pressure to deliver peak 2. | 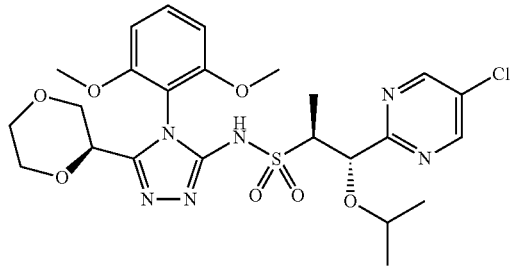<br>OR<br>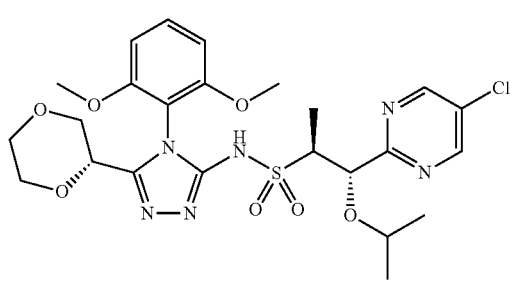<br>(1S,2S)-1-(5-chloropyrimidin-2-yl)-N-(4-(2,6-dimethoxyphenyl)-5-((R)-1,4-dioxan-2-yl)-4H-1,2,4-triazol-3-yl)-1-isopropoxypropane-2-sulfonamide or (1S,2S)-1-(5-chloropyrimidin-2-yl)-N-(4-(2,6-dimethoxyphenyl)-5-((S)-1,4-dioxan-2-yl)-4H-1,2,4-triazol-3-yl)-1-isopropoxypropane-2-sulfonamide. $^1$H NMR (400 MHz, DMSO-$d_6$) δ 12.95 (s, 1H), 8.92 (s, 2H), 7.50 (t, J = 8.5 Hz, 1H), 6.85 (dd, J = 2.9, 8.5 Hz, 2H), 4.77 (d, J = 6.8 Hz, 1H), 4.16 (t, J = 5.6 Hz, 1H), 3.84-3.78 (m, 3H), 3.78-3.68 (m, 5H), 3.67-3.62 (m, 1H), 3.61-3.55 (m, 1H), 3.51-3.35 (m, 4H), 1.02-0.95 (m, 6H), 0.83 (d, J = 6.2 Hz, 3H). LCMS-ESI (pos) m/z: 583.2 (M + H)$^+$. |
| 285.0 | (1R,2S)-1-(5-chloropyrimidin-2-yl)-1-methoxypropane-2-sulfonamide (Example 11.3), (2S,5S)-5-methyltetrahydrofuran-2-carbohydrazide and (2R,5R)-5-methyltetrahydrofuran-2-carbohydrazide (commercially available from Ukrorgsyntez), and 1-isothiocyanato-1-(methoxymethyl)cyclopropane (Example 289.1). The racemic mixture was purified by preparative SFC using the following methodology: Column: Regis Whelk-O (2 × 25 cm), Mobile Phase: 70:30 (A:B) A: Liquid $CO_2$, B: IPA, Flow Rate: 80 mL/min, 220 nm, 100 bar inlet pressure to deliver peak 1. | 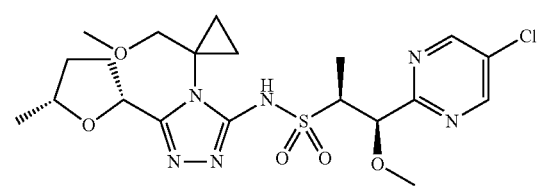<br>OR<br>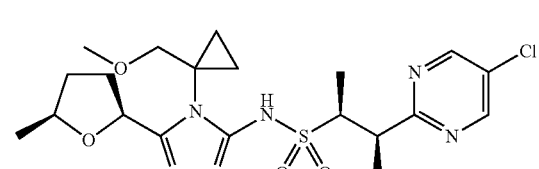<br>(1R,2S)-1-(5-chloropyrimidin-2-yl)-1-methoxy-N-(4-(1-(methoxymethyl)cyclopropyl)-5-((2S,5S)-5-methyltetrahydrofuran-2-yl)-4H-1,2,4-triazol-3-yl)propane-2-sulfonamide or (1R,2S)-1-(5-chloropyrimidin-2-yl)-1-methoxy-N-(4-(1-(methoxymethyl)cyclopropyl)-5-((2R,5R)-5-methyltetrahydrofuran-2-yl)-4H-1,2,4-triazol-3-yl)propane-2-sulfonamide. $^1$H NMR (400 MHz, DMSO-$d_6$) δ 12.76 (br s, 1H), 8.93 (s, 2H), 5.13 (t, J = 6.6 Hz, 1H), 4.92 (d, J = 3.7 Hz, 1H), 4.13-4.05 (m, 1H), 3.86-3.66 (m, 1H), 3.47-3.39 (m, 1H), 3.24-3.21 (m, 3H), 3.19-2.83 (m, 4H), |

US 9,988,369 B2

TABLE 25-continued

| Example | Reagents | Structure, Name and Data |
|---|---|---|
| | | 2.40-2.32 (m, 1H), 2.23-2.14 (m, 1H), 2.14-2.04 (m, 1H), 1.73-1.59 (m, 1H), 1.58-1.33 (m, 1H), 1.26 (d, J = 7.0 Hz, 3H), 1.20-1.06 (m, 6H). LCMS-ESI (pos) m/z: 501.2 (M + H)⁺. |
| 286.0 | (1R,2S)-1-(5-chloropyrimidin-2-yl)-1-methoxypropane-2-sulfonamide (Example 11.3), (2S,5S)-5-methyltetrahydrofuran-2-carbohydrazide and (2R,5R)-5-methyltetrahydrofuran-2-carbohydrazide (commercially available from Ukrorgsyntez), and 1-isothiocyanato-1-(methoxymethyl)cyclopropane (Example 289.1). The racemic mixture was purified by preparative SFC using the following methodology: Column: Regis Whelk-O s,s (2 × 25 cm), Mobile phase: 70:30 (A:B) A: Liquid CO₂, B: IPA, Flow Rate: 80 mL/min, 220 nm, 100 bar inlet pressure to deliver peak 2. | 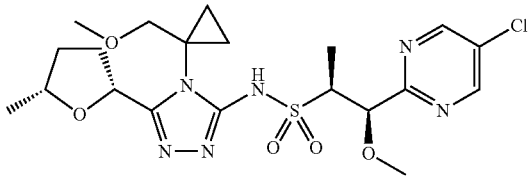<br><br>OR<br><br>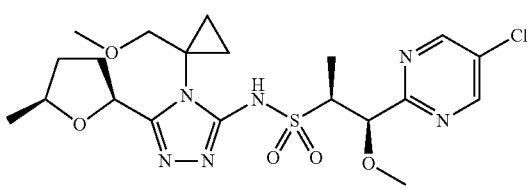<br><br>(1R,2S)-1-(5-chloropyrimidin-2-yl)-1-methoxy-N-(4-(1-(methoxymethyl)cyclopropyl)-5-((2S,5S)-5-methyltetrahydrofuran-2-yl)-4H-1,2,4-triazol-3-yl)propane-2-sulfonamide or (1R,2S)-1-(5-chloropyrimidin-2-yl)-1-methoxy-N-(4-(1-(methoxymethyl)cyclopropyl)-5-((2R,5R)-5-methyltetrahydrofuran-2-yl)-4H-1,2,4-triazol-3-yl)propane-2-sulfonamide. ¹H NMR (400 MHz, DMSO-d₆) δ 12.74 (br s, 1H), 8.94 (s, 2H), 5.12 (t, J = 6.6 Hz, 1H), 4.95 (d, J = 3.5 Hz, 1H), 4.14-4.04 (m, 1H), 3.96-3.70 (m, 1H), 3.48-3.42 (m, 1H), 3.24 (s, 3H), 3.15-2.92 (m, 4H), 2.39-2.29 (m, 1H), 2.22-2.05 (m, 2H), 1.65 (br d, J = 7.7 Hz, 1H), 1.53-1.37 (m, 1H), 1.26 (d, J = 7.0 Hz, 3H), 1.18-1.06 (m, 6H). LCMS-ESI (pos) m/z: 501.2 (M + H)⁺. |
| 287.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), and 2-methoxyethyl isothiocyanate (commercially available from Sigma Aldrich). The mixture was purified by preparative SFC using the following methodology: Column: AS-H (2 × 25 cm), Mobile Phase: 65:35 (A:B) A: Liquid CO₂, B: IPA, Flow Rate: 80 mL/min, 215 nm, 100 bar inlet pressure to deliver peak 1. | 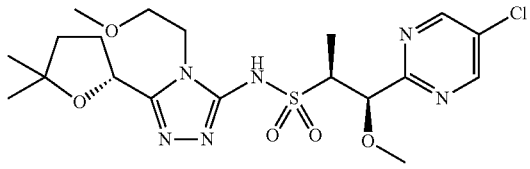<br><br>OR<br><br>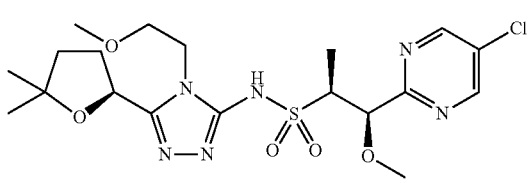<br><br>(1R,2S)-1-(5-chloropyrimidin-2-yl)-N-(5-((R)-5,5-dimethyltetrahydrofuran-2-yl)-4-(2-methoxyethyl)-4H-1,2,4-triazol-3-yl)-1-methoxypropane-2-sulfonamide or (1R,2S)-1-(5-chloropyrimidin-2-yl)-N-(5-((S)-5,5-dimethyltetrahydrofuran-2-yl)-4-(2-methoxyethyl)-4H-1,2,4-triazol-3-yl)-1-methoxypropane-2-sulfonamide. ¹H NMR (400 MHz, DMSO-d₆) δ 12.86 (s, 1H), 8.89 (s, 2H), 5.04 (t, J = 6.8 Hz, 1H), 4.82 (d, J = 4.6 Hz, 1H), 4.03-3.89 (m, 1H), 3.73 (td, J = 4.6, 14.3 Hz, 1H), 3.59-3.47 (m, 3H), 3.24 (s, 3H), 3.08 (s, 3H), 2.56-2.44 (m, 1H), 2.33-2.22 (m, 1H), |

TABLE 25-continued

| Example | Reagents | Structure, Name and Data |
|---|---|---|
| | | 1.84 (t, J = 7.4 Hz, 2H), 1.27 (d, J = 6.8 Hz, 3H), 1.25-1.23 (m, 3H), 1.16 (s, 3H). LCMS-ESI (pos) m/z: 489.2 (M + H)⁺. |
| 288.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), and 2-methoxyethyl isothiocyanate (commercially available from Sigma Aldrich). The mixture was purified by preparative SFC using the following methodology: Column: AS-H (2 × 25 cm), Mobile Phase: 65:35 (A:B) A: Liquid CO₂, B: IPA, Flow Rate: 80 mL/min, 215 nm, 100 bar inlet pressure to deliver peak 2. | 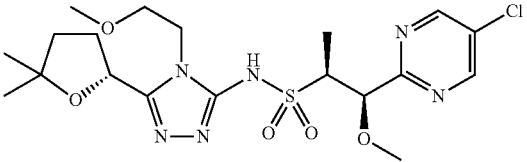<br>OR<br>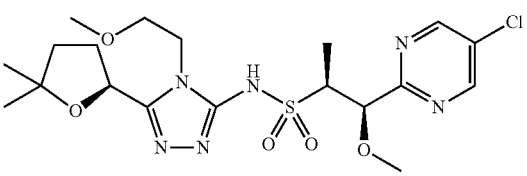<br>(1R,2S)-1-(5-chloropyrimidin-2-yl)-N-(5-((R)-5,5-dimethyltetrahydrofuran-2-yl)-4-(2-methoxyethyl)-4H-1,2,4-triazol-3-yl)-1-methoxypropane-2-sulfonamide or (1R,2S)-1-(5-chloropyrimidin-2-yl)-N-(5-((S)-5,5-dimethyltetrahydrofuran-2-yl)-4-(2-methoxyethyl)-4H-1,2,4-triazol-3-yl)-1-methoxypropane-2-sulfonamide. ¹H NMR (400 MHz, DMSO-d₆) δ 12.83 (s, 1H), 8.92 (s, 2H), 5.05 (t, J = 6.7 Hz, 1H), 4.88 (d, J = 4.1 Hz, 1H), 3.98 (ddd, J = 5.2, 8.6, 14.2 Hz, 1H), 3.91-3.79 (m, 1H), 3.64-3.44 (m, 3H), 3.25 (s, 3H), 3.08 (s, 3H), 2.55-2.44 (m, 1H), 2.34-2.21 (m, 1H), 1.83 (t, J = 7.5 Hz, 2H), 1.27-1.22 (m, 6H), 1.16 (s, 3H). LCMS-ESI (pos) m/z: 489.2 (M + H)⁺. |
| 289.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), and 1-isothiocyanato-1-(methoxymethyl)cyclopropane (Example 289.1). The mixture was purified by preparative SFC using the following methodology: Column: Regis Whelk-O s,s (2 × 15 cm), Mobile Phase: 75:25 (A:B) A: Liquid CO₂, B: IPA, Flow Rate: 80 mL/min, 220 nm, 100 bar inlet pressure to deliver peak 1. | 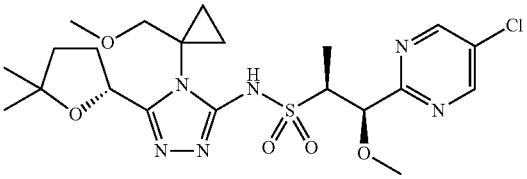<br>OR<br>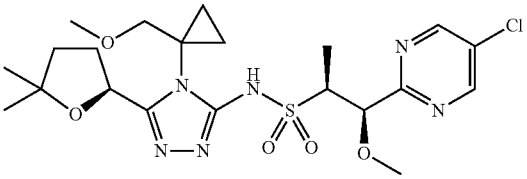<br>(1R,2S)-1-(5-chloropyrimidin-2-yl)-N-(5-((R)-5,5-dimethyltetrahydrofuran-2-yl)-4-(1-(methoxymethyl)cyclopropyl)-4H-1,2,4-triazol-3-yl)-1-methoxypropane-2-sulfonamide or (1R,2S)-1-(5-chloropyrimidin-2-yl)-N-(5-((S)-,5-5 dimethyltetrahydrofuran-2-yl)-4-(1-(methoxymethyl)cyclopropyl)-4H-1,2,4-triazol-3-yl)-1-methoxypropane-2-sulfonamide. ¹H NMR (400 MHz, DMSO-d₆) δ 12.76 (br s, 1H), 8.92 (s, 2H), 5.20 (t, J = 7.0 Hz, 1H), 4.92 (d, J = 3.5 Hz, 1H), 3.85-3.68 (m, 1H), 3.47-3.40 (m,1H), 3.22 (s, 3H), 3.18-2.88 (m, 4H), 2.49-2.39 (m, 1H), 2.33-2.19 (m, 1H), 1.98-1.89 (m, 1H), 1.87-1.78 (m, 1H), 1.64-1.32 (m, 1H), 1.26 (d, J = 6.8 Hz, 3H), 1.24-1.22 (m, 3H), 1.19-1.05 (m, 6H). LCMS-ESI (pos) m/z: 515.2 (M + H)⁺. |

TABLE 25-continued

| Example | Reagents | Structure, Name and Data |
|---|---|---|
| 290.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), and 1-isothiocyanato-1-(methoxymethyl)cyclopropane (Example 289.1).<br>The mixture was purified by preparative SFC using the following methodology: Column: Regis Whelk-O s,s (2 × 15 cm), Mobile Phase: 75:25 (A:B) A: Liquid $CO_2$, B: IPA, Flow Rate: 80 mL/min, 220 nm, 100 bar inlet pressure to deliver peak 2. | 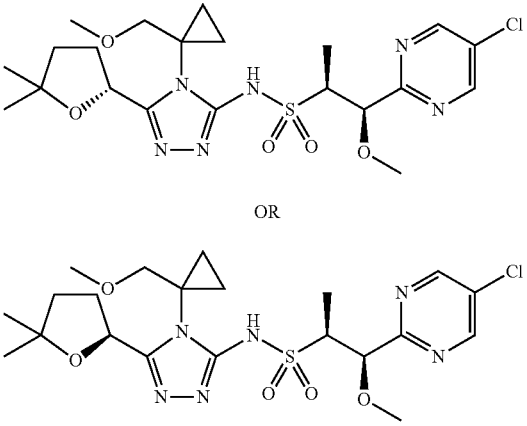 [SMILES: COCC1(n2c(NS(=O)(=O)[C@@H](C)[C@H](OC)c3ncc(Cl)cn3)nnc2[C@H]2CCC(C)(C)O2)CC1 ; COCC1(n2c(NS(=O)(=O)[C@@H](C)[C@H](OC)c3ncc(Cl)cn3)nnc2[C@@H]2CCC(C)(C)O2)CC1]<br>OR<br><br>(1R,2S)-1-(5-chloropyrimidin-2-yl)-N-(5-((R)-5,5-dimethyltetrahydrofuran-2-yl)-4-(1-(methoxymethyl)cyclopropyl)-4H-1,2,4-triazol-3-yl)-1-methoxypropane-2-sulfonamide or (1R,2S)-1-(5-chloropyrimidin-2-yl)-N-(5-((S)-5,5-dimethyltetrahydrofuran-2-yl)-4-(1-(methoxymethyl)cyclopropyl)-4H-1,2,4-triazol-3-yl)-1-methoxypropane-2-sulfonamide. $^1$H NMR (400 MHz, DMSO-$d_6$) δ 12.73 (br s, 1H), 8.94 (s, 2H), 5.20 (t, J = 7.0 Hz, 1H), 4.95 (d, J = 3.9 Hz, 1H), 3.86 (br s, 1H), 3.43 (dq, J = 3.7, 7.0 Hz, 1H), 3.24 (s, 3H), 3.19-2.90 (m, 4H), 2.47-2.35 (m, 1H), 2.35-2.17 (m, 1H), 1.98-1.89 (m, 1H), 1.87-1.78 (m, 1H), 1.58-1.35 (m, 1H), 1.30-1.24 (m, 3H), 1.23 (s, 3H), 1.19 (s, 3H), 1.15-1.03 (m, 3H). LCMS-ESI (pos) m/z: 515.2 (M + H)$^+$. |
| 291.0 | (1S,2S)-1-(5-chloropyrimidin-2-yl)-1-isopropoxypropane-2-sulfonamide (Example 13.6), (R)-tetrahydrofuran-3-carbohydrazide and (S)-tetrahydrofuran-3-carbohydrazide (commercially available from Astatech Inc.), and 5-isothiocyanato-4,6-dimethoxypyrimidine (Example 10.1).<br>The mixture was purified by preparative SFC using the following methodology: Column: AS-H (2 × 25 cm) + AS-H (2 × 25 cm), Mobile Phase: 70:30 (A:B) A: Liquid $CO_2$, B: IPA, Flow Rate: 70 mL/min, 215 nm, 100 bar inlet pressure to deliver peak 1. | 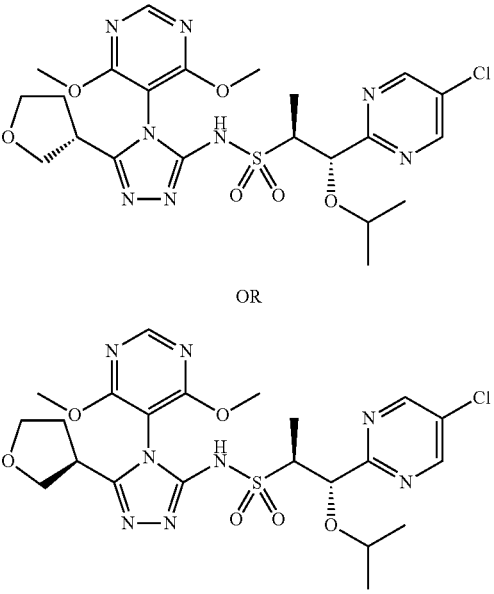 [SMILES: COc1ncnc(OC)c1-n1c(NS(=O)(=O)[C@@H](C)[C@@H](OC(C)C)c2ncc(Cl)cn2)nnc1[C@H]1CCOC1 ; COc1ncnc(OC)c1-n1c(NS(=O)(=O)[C@@H](C)[C@@H](OC(C)C)c2ncc(Cl)cn2)nnc1[C@@H]1CCOC1]<br>OR<br><br>(1S,2S)-1-(5-chloropyrimidin-2-yl)-N-(4-(4,6-dimethoxypyrimidin-5-yl)-5-((R)-tetrahydrofuran-3-yl)-4H-1,2,4-triazol-3-yl)-1-isopropoxypropane-2-sulfonamide or (1S,2S)-1-(5-chloropyrimidin-2-yl)-N-(4-(4,6-dimethoxypyrimidin-5-yl)-5-((S)-tetrahydrofuran-3-yl)-4H-1,2,4-triazol-3-yl)-1-isopropoxypropane-2-sulfonamide. $^1$H NMR (400 MHz, DMSO-$d_6$) δ 12.87 (br s, 1H), 8.93 (s, |

TABLE 25-continued

| Example | Reagents | Structure, Name and Data |
|---|---|---|
| | | 2H), 8.70 (s, 1H), 4.74 (d, J = 7.0 Hz, 1H), 4.00 (s, 3H), 3.99-3.98 (m, 3H), 3.81-3.71 (m, 2H), 3.71-3.63 (m, 2H), 3.46-3.36 (m, 2H), 3.21-3.12 (m, 1H), 2.09-1.95 (m, 2H), 0.98 (d, J = 6.4 Hz, 6H), 0.81 (d, J = 6.2 Hz, 3H). LCMS-ESI (pos) m/z: 569.2 (M + H)+. |
| 292.0 | (1S,2S)-1-(5-chloropyrimidin-2-yl)-1-isopropoxypropane-2-sulfonamide (Example 13.6), (R)-tetrahydrofuran-3-carbohydrazide and (S)-tetrahydrofuran-3-carbohydrazide (commercially available from Astatech Inc.), and 5-isothiocyanato-4,6-dimethoxypyrimidine (Example 10.1). The mixture was purified by preparative SFC using the following methodology: Column: AS-H (2 × 25 cm) + AS-H (2 × 25 cm), Mobile Phase: 70:30 (A:B) A: Liquid CO2, B: IPA, Flow Rate: 70 mL/min, 215 nm, 100 bar inlet pressure to deliver peak 2. | 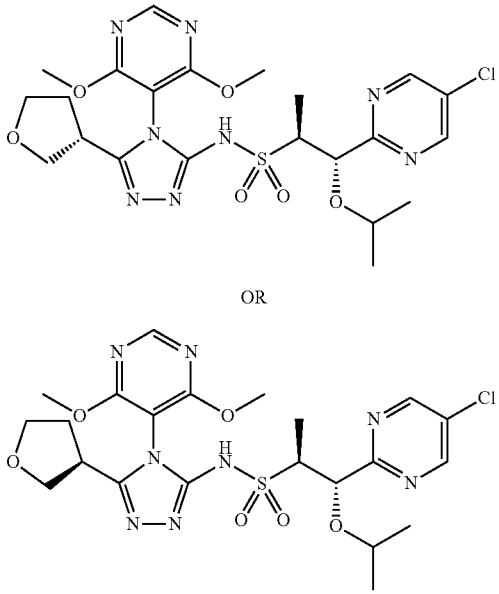 [SMILES: COc1ncnc(OC)c1-n1c(NS(=O)(=O)[C@@H](C)[C@@H](OC(C)C)c2ncc(Cl)cn2)nnc1[C@H]1CCOC1 ; COc1ncnc(OC)c1-n1c(NS(=O)(=O)[C@@H](C)[C@@H](OC(C)C)c2ncc(Cl)cn2)nnc1[C@@H]1CCOC1] (1S,2S)-1-(5-chloropyrimidin-2-yl)-N-(4-(4,6-dimethoxypyrimidin-5-yl)-5-((R)-tetrahydrofuran-3-yl)-4H-1,2,4-triazol-3-yl)-1-isopropoxypropane-2-sulfonamide or (1S,2S)-1-(5-chloropyrimidin-2-yl)-N-(4-(4,6-dimethoxypyrimidin-5-yl)-5-((S)-tetrahydrofuran-3-yl)-4H-1,2,4-triazol-3-yl)-1-isopropoxypropane-2-sulfonamide. 1H NMR (400 MHz, DMSO-d6) δ 12.87 (br s, 1H), 8.93 (s, 2H), 8.70 (s, 1H), 4.74 (d, J = 7.0 Hz, 1H), 4.04-3.99 (m, 3H), 3.99-3.96 (m, 3H), 3.80-3.73 (m, 2H), 3.71-3.63 (m, 2H), 3.46-3.38 (m, 2H), 3.20-3.12 (m, 1H), 2.05-1.95 (m, 2H), 0.98 (d, J = 6.2 Hz, 6H), 0.81 (d, J = 6.2 Hz, 3H). LCMS-ESI (pos) m/z: 569.2 (M + H)+. |

US 9,988,369 B2

TABLE 25-continued

| Example | Reagents | Structure, Name and Data |
|---|---|---|
| 293.0 | (1R,2S)-1-(5-chloropyrimidin-2-yl)-1-methoxypropane-2-sulfonamide (Example 11.3), (R)-1-methyl-5-oxopyrrolidine-3-carbohydrazide and (S)-1-methyl-5-oxopyrrolidine-3-carbohydrazide (commercially available from ChemBridge Corporation), and 2-isothiocyanato-1,3-dimethoxybenzene (Example 10.0).<br>The racemic mixture was purified by preparative SFC using the following methodology: Column: AD-H (2 × 15 cm) Mobile Phase: 60:40 (A:B) A: Liquid $CO_2$, B: IPA, Flow Rate: 80 mL/min, 220 nm, 100 bar inlet pressure to deliver peak 1. | 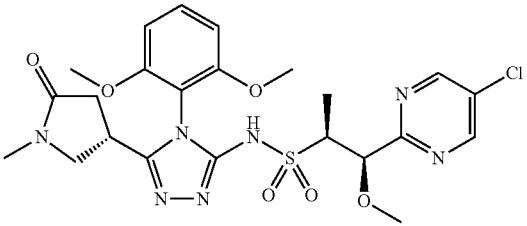<br>OR<br>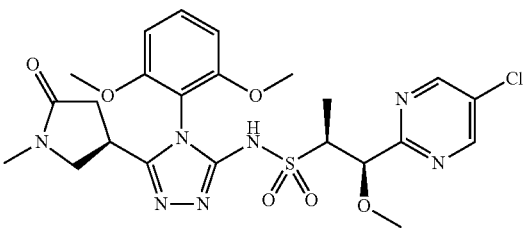<br>(1R,2S)-1-(5-chloropyrimidin-2-yl)-N-(4-(2,6-dimethoxyphenyl)-5-((R)-1-methyl-5-oxopyrrolidin-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-1-methyl-5-oxopyrrolidin-3-yl)-4H-1,2,4-triazol-3-yl)-1-methoxypropane-2-sulfonamide. $^1$H NMR (400 MHz, DMSO-$d_6$) δ 12.89 (s, 1H), 8.93 (s, 2H), 7.53 (t, J = 8.5 Hz, 1H), 6.88 (d, J = 8.5 Hz, 2H), 4.76 (d, J = 4.4 Hz, 1H), 3.79 (s, 3H), 3.77-3.75 (m, 3H), 3.44-3.37 (m, 3H), 3.24-3.17 (m, 1H), 3.14 (s, 3H), 2.64 (s, 3H), 2.42-2.29 (m, 2H), 1.13 (d, J = 7.0 Hz, 3H). LCMS-ESI (pos) m/z: 566.2 (M + H)$^+$. |
| 294.0 | (1R,2S)-1-(5-chloropyrimidin-2-yl)-1-methoxypropane-2-sulfonamide (Example 11.3), (R)-1-methyl-5-oxopyrrolidine-3-carbohydrazide and (S)-1-methyl-5-oxopyrrolidine-3-carbohydrazide (commercially available from ChemiBridge Corporation), and 2-isothiocyanato-1,3-dimethoxybenzene (Example 10.0).<br>The racemic mixture was purified by preparative SFC using the following methodology: Column: AD-H (2 × 15 cm) Mobile Phase: 60:40 (A:B) A: Liquid $CO_2$, B: IPA, Flow Rate: 80 mL/min, 220 nm, 100 bar inlet pressure to deliver peak 2. | 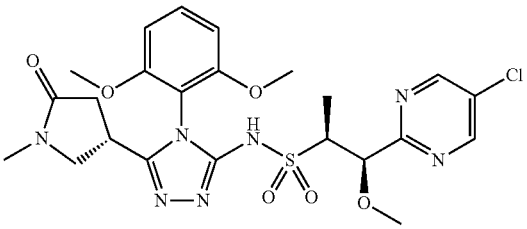<br>OR<br>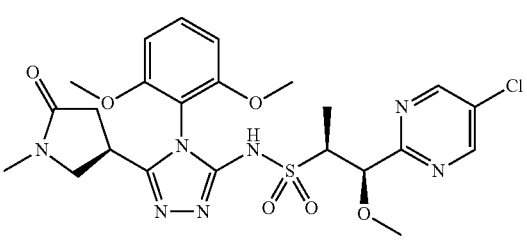<br>(1R,2S)-1-(5-chloropyrimidin-2-yl)-N-(4-(2,6-dimethoxyphenyl)-5-((R)-1-methyl-5-oxopyrrolidin-3-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-1-methyl-5-oxopyrrolidin-3-yl)-4H-1,2,4-triazol-3-yl)-1-methoxypropane-2-sulfonamide. $^1$H NMR (400 MHz, DMSO-$d_6$) δ 12.89 (s, 1H), 8.93 (s, |

TABLE 25-continued

| Example | Reagents | Structure, Name and Data |
|---|---|---|
| | | 2H), 7.53 (t, J = 8.5 Hz, 1H), 6.87 (dd, J = 1.6, 8.6 Hz, 2H), 4.76 (d, J = 4.4 Hz, 1H), 3.82-3.75 (m, 6H), 3.44-3.36 (m, 3H), 3.25-3.17 (m, 1H), 3.14 (s, 3H), 2.50 (td, J = 1.8, 3.6 Hz, 3H), 2.42-2.29 (m, 2H), 1.13 (d, J = 7.0 Hz, 3H). LCMS-ESI (pos) m/z: 566.2 (M + H)+. |

The compound set forth in the following table were synthesized following the procedure in Example 13.0 using the known starting material as described.

TABLE 26

| Example | Reagents | Structure, Name and Data |
|---|---|---|
| 13.6 | 2,5-dichloropyrimidine (Oakwood). | 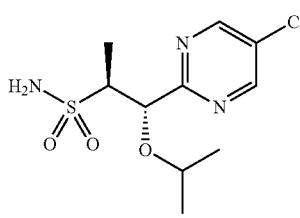 (1S,2S)-1-(5-chloropyrimidin-2-yl)-1-isopropoxypropane-2-sulfonamide. $^1$H NMR (400 MHz, DMSO-d$_6$) δ 9.01-8.96 (m, 2H), 6.51 (s, 2H), 4.82-4.76 (m, 1H), 3.60-3.53 (m, 2H), 1.16-1.11 (m, 3H), 1.03 (td, J = 7.0, 3.0 Hz, 3H), 0.94 (td, J = 6.1, 2.9 Hz, 3H). LCMS-ESI (pos) m/z: 294.2 (M + H)+. |

Example 295.0: Preparation of (1R,2S)—N-(5-((R)-1,4-dioxan-2-yl)-4-(1-(pyridin-3-yl)cyclopropyl)-4H-1,2,4-triazol-3-yl)-1-(5-chloropyrimidin-2-yl)-1-methoxypropane-2-sulfonamide or (1R,2S)—N-(5-((S)-1,4-dioxan-2-yl)-4-(1-(pyridin-3-yl)cyclopropyl)-4H-1,2,4-triazol-3-yl)-1-(5-chloropyrimidin-2-yl)-1-methoxypropane-2-sulfonamide

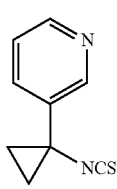

295.1

3-(1-Isothiocyanatocyclopropyl)pyridine, Example 295.1

To a flask containing 1-pyridin-3-yl-cyclopropylamine bis(4-nitrobenzoate) (commercially available from Chem-Ipex International Inc.) (2.09 g, 4.5 mmol) in anhydrous DCM (17.5 mL) was added N,N-diisopropylethylamine (1.7 mL, 9.7 mmol) dropwise at RT. After 15 min, 1,1"-thiocarbonyldi-2(1H)-pyridone (1.04 g, 4.5 mmol) was added carefully in portions to the reaction mixture and the reaction was monitored with TLC and LC-MS. After 1 h, the reaction was concentrated in vacuo and then loaded onto a silica gel column (15-65% EtOAc in heptanes). Fractions containing desired product were combined and then concentrated in vacuo to afford Example 295.1 (464 mg, 2.6 mmol, 59% yield) as a colorless liquid that was used without further purification. LCMS-ESI (pos) m/z: 177.0 (M+H)+.

The compound set forth in the following table were synthesized following the procedure in Example 140.0 using the known starting material as described.

TABLE 27

295.0 (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 3-(1-isothiocyanatocyclopropyl)pyridine (Example 295.1). The racemic mixture was purified by preparative SFC using the following methodology: Column: AD-H (2 × 25 cm) Mobile Phase: 65:35 (A:B) A: Liquid CO$_2$, B: MeOH, Flow Rate: 80 mL/min, 216 nm, 100 bar inlet pressure to deliver peak 1.

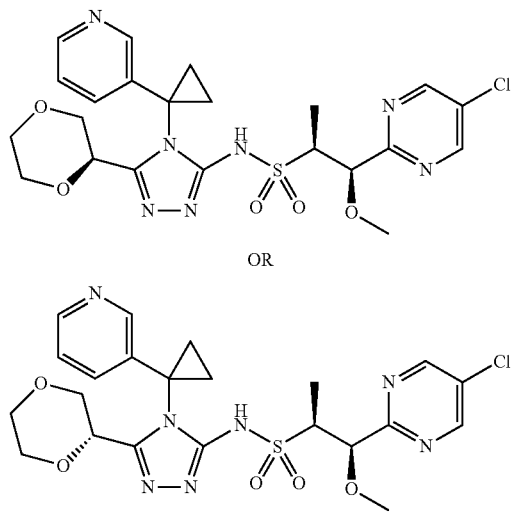 [SMILES: CO[C@H](c1ncc(Cl)cn1)[C@H](C)S(=O)(=O)Nc1nnc([C@@H]2COCCO2)n1C1(c2cccnc2)CC1 ; CO[C@H](c1ncc(Cl)cn1)[C@H](C)S(=O)(=O)Nc1nnc([C@H]2COCCO2)n1C1(c2cccnc2)CC1]

OR (1R,2S)-N-(5-((R)-1,4-dioxan-2-yl)-4-(1-(pyridin-3-yl)cyclopropyl)-4H-1,2,4-triazol-3-yl)-1-(5-chloropyrimidin-2-yl)-1-methoxypropane-2-sulfonamide or (1R,2S)-N-(5-((S)-1,4-dioxan-2-yl)-4-(1-(pyridin-3-yl)cyclopropyl)-4H-1,2,4-triazol-3-yl)-1-(5-chloropyrimidin-2-yl)-1-methoxypropane-2-sulfonamide. $^1$H NMR (400 MHz, CD$_2$Cl$_2$) δ 11.06 (br s, 1H), 8.71 (s, 2H), 8.49 (d, J = 4.1 Hz, 1H), 8.44 (br s, 1H), 7.59 (d, J = 7.9 Hz, 1H), 7.28 (dd, J = 4.8, 8.1 Hz, 1H), 4.93 (d, J = 4.1 Hz, 1H), 4.75 (dd, J = 3.2, 9.0 Hz, 1H), 4.01-3.93 (m, 1H), 3.93-3.85 (m, 1H), 3.80-3.75 (m, 2H), 3.74-3.64 (m, 2H), 3.63-3.56 (m, 1H), 3.21 (s, 3H), 2.03-1.96 (m, 1H), 1.80-1.60 (m, 3H), 1.29 (d, J = 7.0 Hz, 3H). LCMS-ESI (pos) m/z: 536.2 (M + H)$^+$.

296.0 (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 3-(1-isothiocyanatocyclopropyl)pyridine (Example 295.1). The racemic mixture was purified by preparative SFC using the following methodology: Column: AD-H (2 × 25 cm) Mobile Phase: 65:35 (A:B) A: Liquid CO$_2$, B: MeOH, Flow Rate: 80 mL/min, 216 nm, 100 bar inlet pressure to deliver peak 2.

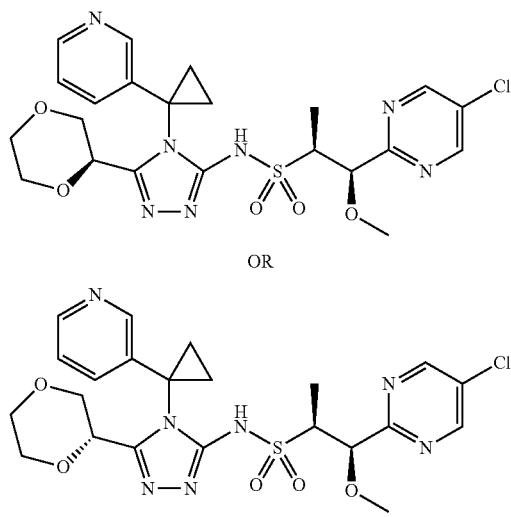 [SMILES: CO[C@H](c1ncc(Cl)cn1)[C@H](C)S(=O)(=O)Nc1nnc([C@@H]2COCCO2)n1C1(c2cccnc2)CC1 ; CO[C@H](c1ncc(Cl)cn1)[C@H](C)S(=O)(=O)Nc1nnc([C@H]2COCCO2)n1C1(c2cccnc2)CC1]

OR (1R,2S)-N-(5-((R)-1,4-dioxan-2-yl)-4-(1-(pyridin-3-yl)cyclopropyl)-4H-1,2,4-triazol-3-yl)-1-(5-chloropyrimidin-2-yl)-1-methoxypropane-2-sulfonamide or (1R,2S)-N-(5-((S)-1,4-dioxan-2-yl)-4-(1-(pyridin-3-yl)cyclopropyl)-4H-1,2,4-triazol-3-yl)-1-(5-chloropyrimidin-2-yl)-1-methoxypropane-2-sulfonamide. $^1$H NMR (400 MHz, CD$_2$Cl$_2$) δ 11.18 (br s, 1H), 8.72 (s, 2H), 8.53-8.46 (m, 1H), 8.42 (br s, 1H), 7.55 (d, J = 7.9 Hz, 1H), 7.28 (dd, J = 4.7, 8.0 Hz, 1H), 4.97 (d, J = 3.7 Hz, 1H), 4.74 (dd, J = 2.9, 9.3 Hz, 1H), 4.01-3.95 (m, 1H), 3.92-3.86 (m, 1H), 3.81-3.75 (m, 2H), 3.75-3.65 (m, 2H),

TABLE 27-continued 3.60-3.54 (m, 1H), 3.18 (s, 3H), 2.01-1.84 (m, 3H), 1.83-1.61 (m, 1H), 1.30 (d, J = 7.0 Hz, 3H). LCMS-ESI (pos) m/z: 536.2 (M + H)+.

297.0 tetrahydrofuran-3-carbohydrazide (commercially available from Astatech Inc.), 2-isothiocyanatopropane (comercially available from Sigma-Aldrich Inc.), and (1R,2S)-1-(5-methylpyrimidin-2-yl)-1-methoxypropane-2-sulfonamide (Example 11.3).
The mixture was separated by SFC Chiralpak IC using 50% MeOH. This was the first isomer to elute under these conditions.

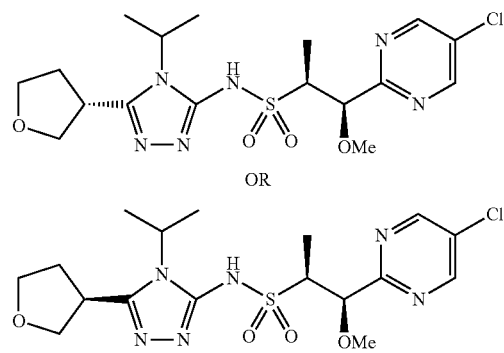 [SMILES: CO[C@H](c1ncc(Cl)cn1)[C@H](C)S(=O)(=O)Nc1nnc([C@H]2CCOC2)n1C(C)C ; CO[C@H](c1ncc(Cl)cn1)[C@H](C)S(=O)(=O)Nc1nnc([C@@H]2CCOC2)n1C(C)C]

(1R,2S)-1-(5-chloropyrimidin-2-yl)-N-(4-isopropyl-5-((R)-tetrahydrofuran-3-yl)-4H-1,2,4-triazol-3-yl)-1-methoxypropane-2-sulfonamide or (1R,2S)-1-(5-chloropyrimidin-2-yl)-N-(4-isopropyl-5-((S)-tetrahydrofuran-3-yl)-4H-1,2,4-triazol-3-yl)-1-methoxypropane-2-sulfonamide $^1$H NMR (500 MHz, DMSO-$d_6$) δ 12.45-12.72 (m, 1 H) 8.80-9.01 (m, 2 H) 4.83-4.91 (m, 1 H) 4.35-4.45 (m, 1 H) 3.98-4.06 (m, 1 H) 3.72-3.85 (m, 3 H) 3.55-3.65 (m, 1 H) 3.42-3.53 (m, 1 H) 3.08-3.14 (m, 3 H) 2.21-2.31 (m, 1 H) 2.02-2.14 (m, 1 H) 1.43-1.49 (m, 6 H) 1.24-1.29 (m, 3 H). LCMS-ESI (pos) m/z: 445.2 (M + H)+.

298.0 tetrahydrofuran-3-carbohydrazide (commercially available from Astatech Inc), 2-isothiocyanatopropane (comercially available from Sigma-Aldrich Inc.), and (1R,2S)-1-(5-methylpyrimidin-2-yl)-1-methoxypropane-2-sulfonamide (Example 11.3).
The mixture was separated by SFC Chiralpak IC using 50% MeOH. This was the second isomer to elute under these conditions.

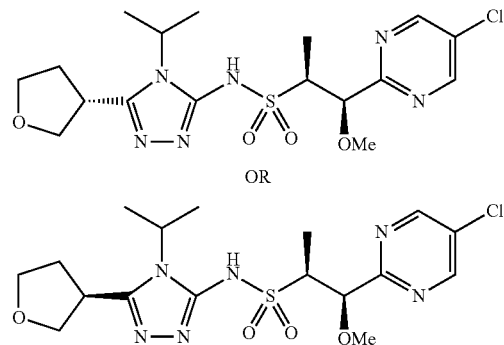 [SMILES: CO[C@H](c1ncc(Cl)cn1)[C@H](C)S(=O)(=O)Nc1nnc([C@H]2CCOC2)n1C(C)C ; CO[C@H](c1ncc(Cl)cn1)[C@H](C)S(=O)(=O)Nc1nnc([C@@H]2CCOC2)n1C(C)C]

(1R,2S)-1-(5-chloropyrimidin-2-yl)-N-(4-isopropyl-5-((R)-tetrahydrofuran-3-yl)-4H-1,2,4-triazol-3-yl)-1-methoxypropane-2-sulfonamide or (1R,2S)-1-(5-chloropyrimidin-2-yl)-N-(4-isopropyl-5-((S)-tetrahydrofuran-3-yl)-4H-1,2,4-triazol-3-yl)-1-methoxypropane-2-sulfonamide $^1$H NMR (500 MHz, DMSO-d6) δ 12.45-12.72 (m, 1 H) 8.80-9.01 (m, 2 H) 4.83-4.91 (m, 1 H) 4.35-4.45 (m, 1 H) 3.98-4.06 (m, 1 H) 3.72-3.85 (m, 3 H) 3.55-3.65 (m, 1 H) 3.42-3.53 (m, 1 H) 3.08-3.14 (m, 3 H) 2.21-2.31 (m, 1 H) 2.02-2.14 (m, 1 H) 1.43-1.49 (m, 6 H) 1.24-1.29 (m, 3 H). LCMS-ESI (pos) m/z: 445.2 (M + H)+.

TABLE 27-continued

| 299.0 | 5,5-dimethyltetrahydrofuran-2-carbohydrazide (Example 108.2), 2-isothiocyanatopropane (comercially available from Sigma-Aldrich Inc.), and (1R,2S)-1-(5-methylpyrimidin-2-yl)-1-methoxypropane-2-sulfonamide (Example 11.3). The mixture was separated by SFC Chiralpak AD using 25% MeOH. This was the first isomer to elute under these conditions. | 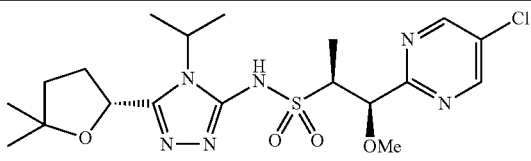<br>OR<br>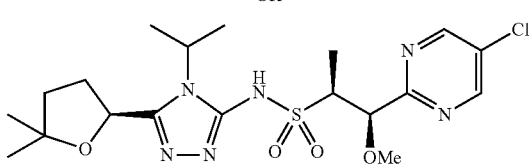<br><br>(1R,2S)-1-(5-chloropyrimidin-2-yl)-N-(5-((R)-5,5-dimethyltetrahydrofuran-2-yl)-4-isopropyl-4H-1,2,4-triazol-3-yl)-1-methoxypropane-2-sulfonamide or (1R,2S)-1-(5-chloropyrimidin-2-yl)-N-(5-((S)-5,5-dimethyltetrahydrofuran-2-yl)-4-isopropyl-4H-1,2,4-triazol-3-yl)-1-methoxypropane-2-sulfonamide $^1$H NMR (500 MHz, DMSO-d$_6$) δ 12.45-12.72 (m, 1 H) 8.80-9.01 (m, 2 H) 4.83-4.91 (m, 1 H) 4.35-4.45 (m, 1 H) 3.98-4.06 (m, 1 H) 3.72-3.85 (m, 3 H) 3.55-3.65 (m, 1 H) 3.42-3.53 (m, 1 H) 3.31-3.33 (m, 6 H) 2.52-2.55 (m, 3 H) 1.43-1.49 (m, 6 H) 1.24-1.29 (m, 3 H). LCMS-ESI (pos) m/z: 473.2 (M + H)$^+$. |
| --- | --- | --- |
| 300.0 | 5,5-dimethyltetrahydrofuran-2-carbohydrazide (Example 108.2), 2-isothiocyanatopropane (comercially available from Sigma-Aldrich Inc.), and (1R,2S)-1-(5-methylpyrimidin-2-yl)-1-methoxypropane-2-sulfonamide (Example 11.3). The mixture was separated by SFC Chiralpak AD using 25% MeOH. This was the second isomer to elute under these conditions. | 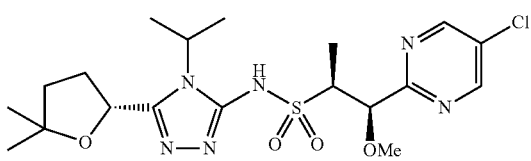<br>OR<br>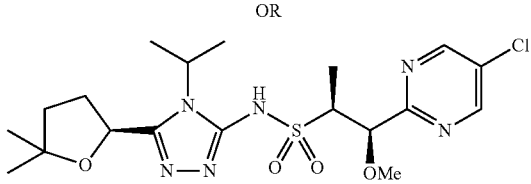<br><br>(1R,2S)-1-(5-chloropyrimidin-2-yl)-N-(5-((R)-5,5-dimethyltetrahydrofuran-2-yl)-4-isopropyl-4H-1,2,4-triazol-3-yl)-1-methoxypropane-2-sulfonamide or (1R,2S)-1-(5-chloropyrimidin-2-yl)-N-(5-((S)-5,5-dimethyltetrahydrofuran-2-yl)-4-isopropyl-4H-1,2,4-triazol-3-yl)-1-methoxypropane-2-sulfonamide $^1$H NMR (500 MHz, DMSO-d6) δ 12.45-12.72 (m, 1 H) 8.80-9.01 (m, 2 H) 4.83-4.91 (m, 1 H) 4.35-4.45 (m, 1 H) 3.98-4.06 (m, 1 H) 3.72-3.85 (m, 3 H) 3.55-3.65 (m, 1 H) 3.42-3.53 (m, 1 H) 3.31-3.33 (m, 6 H) 2.52-2.55 (m, 3 H) 1.43-1.49 (m, 6 H) 1.24-1.29 (m, 3 H). LCMS-ESI (pos) m/z: 473.2 (M + H)$^+$. |
| 301.0 | 1,4-dioxane-2-carbohydrazide (commercially available from Enamine), 2-isothiocyanatopropane (comercially available from Sigma-Aldrich Inc.), and (1R,2S)-1-(5-methylpyrimidin-2-yl)-1-methoxypropane-2-sulfonamide (Example 11.3). The mixture was separated by SFC Chiralpak AD-H, 25% IPA. This was the first eluting enantiomer under these conditions. | 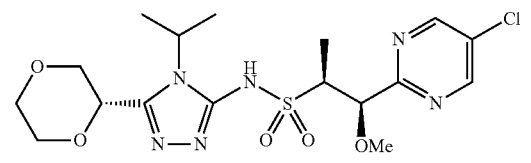<br>OR<br>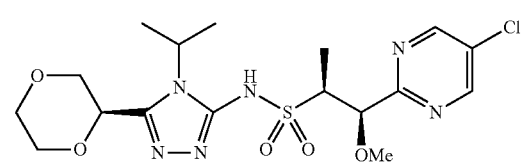<br><br>(1R,2S)-N-(5-((S)-1,4-dioxan-2-yl)-4-isopropyl-4H-1,2,4-triazol-3-yl)-1-(5-chloropyrimidin-2-yl)-1- |

TABLE 27-continued methoxypropane-2-sulfonamide or (1R,2S)-N-(5-((R)-1,4-dioxan-2-yl)-4-isopropyl-4H-1,2,4-triazol-3-yl)-1-(5-chloropyrimidin-2-yl)-1-methoxypropane-2-sulfonamide ¹H NMR (500 MHz, DMSO-d₆) δ 12.65-12.97 (m, 1 H) 8.75-9.05 (m, 2 H) 4.84-4.90 (m, 1 H) 4.74-4.81 (m, 1 H) 4.43-4.52 (m, 1 H) 3.95-4.01 (m, 1 H) 3.70-3.86 (m, 4 H) 3.55-3.62 (m, 1 H) 3.44-3.53 (m, 1 H) 3.11-3.15 (m, 3 H) 1.40-1.49 (m, 6H) 1.20-1.29 (m, 3 H). LCMS-ESI (pos) m/z: 461.2 (M + H)⁺.

302.0 1,4-dioxane-2-carbohydrazide (commercially available from Enamine), 2-isothiocyanatopropane (comercially available from Sigma-Aldrich Inc.), and (1R,2S)-1-(5-methylpyrimidin-2-yl)-1-methoxypropane-2-sulfonamide (Example 11.3).
The mixture was separated by SFC Chiralpak AD-H, 25% IPA. This was the second eluting enantiomer under these conditions.

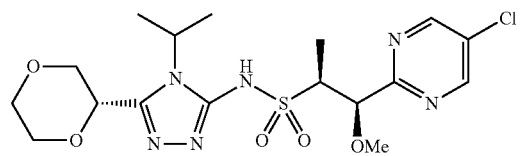

OR

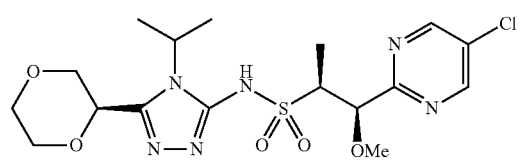

(1R,2S)-N-(5-((S)-1,4-dioxan-2-yl)-4-isopropyl-4H-1,2,4-triazol-3-yl)-1-(5-chloropyrimidin-2-yl)-1-methoxypropane-2-sulfonamide or (1R,2S)-N-(5-((R)-1,4-dioxan-2-yl)-4-isopropyl-4H-1,2,4-triazol-3-yl)-1-(5-chloropyrimidin-2-yl)-1-methoxypropane-2-sulfonamide ¹H NMR (500 MHz, DMSO-d₆) δ 12.65-12.97 (m, 1 H) 8.75-9.05 (m, 2 H) 4.84-4.90 (m, 1 H) 4.74-4.81 (m, 1 H) 4.43-4.52 (m, 1 H) 3.95-4.01 (m, 1 H) 3.70-3.86 (m, 4 H) 3.55-3.62 (m, 1 H) 3.44-3.53 (m, 1 H) 3.11-3.15 (m, 3 H) 1.40-1.49 (m, 6 H) 1.20-1.29 (m, 3 H). LCMS-ESI (pos) m/z: 461.2 (M + H)⁺.

303.0 (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (Enamine), and 1-isothiocyanato-1-(methoxymethyl)cyclopropane (Example 289.1).

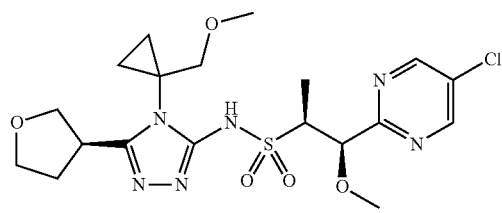

AND

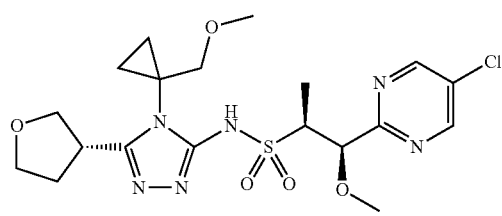

(1R,2S)-1-(5-chloro-2-pyrimidinyl)-1-methoxy-N-(4-(1-(methoxymethyl)cyclopropyl)-5-((3R)-tetrahydro-3-furanyl)-4H-1,2,4-triazol-3-yl)-2-propanesulfonamide and (1R,2S)-1-(5-chloro-2-pyrimidinyl)-1-methoxy-N-(4-(1-(methoxymethyl)cyclopropyl)-5-((3S)-tetrahydro-3-furanyl)-4H-1,2,4-triazol-3-yl)-2-propanesulfonamide. LCMS-ESI (pos) m/z: 487.0 (M + H)⁺.

TABLE 27-continued

| | | |
|---|---|---|
| 304.0 | (1R,2S)-1-(5-chloropyrimidin-2-yl)-1-methoxypropane-2-sulfonamide (Example 11.3), (S)-1,4-dioxane-2-carbohydrazide and (R)-1,4-dioxane-2-carbohydrazide (Enamine), and 1-isothiocyanato-1-(methoxymethyl)cyclopropane (Example 289.1). | 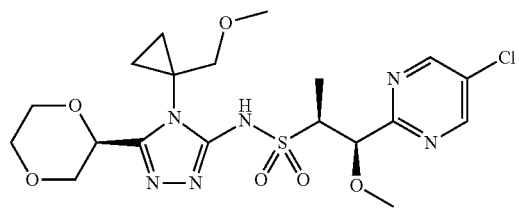<br>AND<br>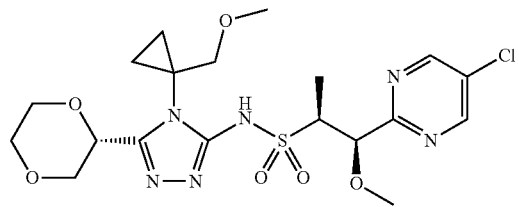<br>(1R,2S)-N-(5-((S)-1,4-dioxan-2-yl)-4-(1-(methoxymethyl)cyclopropyl)-4H-1,2,4-triazol-3-yl)-1-(5-chloropyrimidin-2-yl)-1-methoxypropane-2-sulfonamide and (1R,2S)-N-(5-((R)-1,4-dioxan-2-yl)-4-(1-(methoxymethyl)cyclopropyl)-4H-1,2,4-triazol-3-yl)-1-(5-chloropyrimidin-2-yl)-1-methoxypropane-2-sulfonamide. LCMS-ESI (pos) m/z: 503.2 (M + H)$^+$. |

The compound set forth in the following table were synthesized following the procedure in Example 140.0 using the known starting material as described.

TABLE 28

| Example | Reagents | Structure, Name and Data |
|---|---|---|
| 305.0 | (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.), and 2-isothiocyanato-1,3-dimethoxypropane (Example 250.1).<br>The title compound was the earlier isomer to elute on a SFC from Chiralpak AD-H column with 25% IPA. | (1R,2S)-1-(5-chloro-2-pyrimidinyl)-N-(4-(1,3-dimethoxy-2-propanyl)-5-((3S)-tetrahydro-3-furanyl)-4H-1,2,4-triazol-3-yl)-1-methoxy-2-propanesulfonamide or (1R,2S)-1-(5-chloro-2-pyrimidinyl)-N-(4-(1,3-dimethoxy-2-propanyl)-5-((3R)-tetrahydro-3-furanyl)-4H-1,2,4-triazol-3-yl)-1-methoxy-2-propanesulfonamide. $^1$H NMR (500 MHz, CDCl$_3$) δ 10.83 (br s, 1 H) 8.74 (s, 2 H) 5.04 (d, J = 4.41 Hz, 1 H) 4.34 (br d, J = 0.78 Hz, 1 H) 4.06-4.21 (m, 3 H) 3.95-4.05 (m, 2 H) 3.86-3.95 (m, 1 H) 3.71 (qd, J = 7.05, 4.28 Hz, 1 H) 3.63 (ddd, J = 16.02, 9.80, 4.54 Hz, 2 H) 3.41-3.51 (m, 1 H) 3.35 (s, 3 H) 3.35 (s, 3 H) 3.32 (s, 3 H) 2.24-2.41 (m, 2 H) 1.40 (d, J = 7.27 Hz, 3 H). LCMS-ESI (pos) m/z: 505.1 (M + H)$^+$. |

TABLE 28-continued

| Example | Reagents | Structure, Name and Data |
|---|---|---|
| 306.0 | (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.), and 2-isothiocyanato-1,3-dimethoxypropane (Example 250.1).<br>The title compound was the later isomer to elute on a SFC from Chiralpak AD-H column with 25% IPA. | 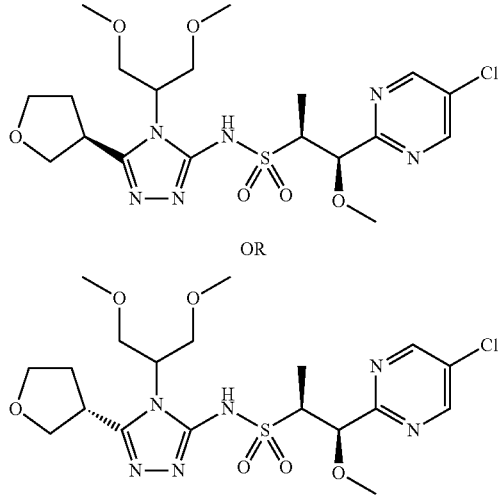 [SMILES: COCC(COC)n1c(NS(=O)(=O)[C@@H](C)[C@H](OC)c2ncc(Cl)cn2)nnc1[C@@H]1CCOC1 ; COCC(COC)n1c(NS(=O)(=O)[C@@H](C)[C@H](OC)c2ncc(Cl)cn2)nnc1[C@H]1CCOC1]<br>OR<br><br>(1R,2S)-1-(5-chloro-2-pyrimidinyl)-N-(4-(1,3-dimethoxy-2-propanyl)-5-((3S)-tetrahydro-3-furanyl)-4H-1,2,4-triazol-3-yl)-1-methoxy-2-propanesulfonamide or (1R,2S)-1-(5-chloro-2-pyrimidinyl)-N-(4-(1,3-dimethoxy-2-propanyl)-5-((3R)-tetrahydro-3-furanyl)-4H-1,2,4-triazol-3-yl)-1-methoxy-2-propanesulfonamide. $^1$H NMR (500 MHz, CDCl$_3$) δ 10.78 (br s, 1 H) 8.75 (s, 2 H) 5.04 (d, J = 4.41 Hz, 1 H) 4.27-4.40 (m, 1 H) 4.07-4.22 (m, 3 H) 3.96-4.05 (m, 2 H) 3.87-3.95 (m, 1 H) 3.72 (qd, J = 6.92, 4.41 Hz, 1 H) 3.64 (ddd, J = 9.86, 6.36, 4.54 Hz, 2 H) 3.42-3.53 (m, 1 H) 3.35 (s, 3 H) 3.35 (s, 3 H) 3.34 (s, 3 H) 2.25-2.43 (m, 2 H) 1.41 (d, J = 7.01 Hz, 3 H). LCMS-ESI (pos) m/z: 505.1 (M + H)$^+$. |
| 307.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), and 2-isothiocyanato-1,3-dimethoxypropane (Example 250.1).<br>The title compound was the later isomer to elute on an SFC from Chiralpak AS-H column with 10% MeOH. | 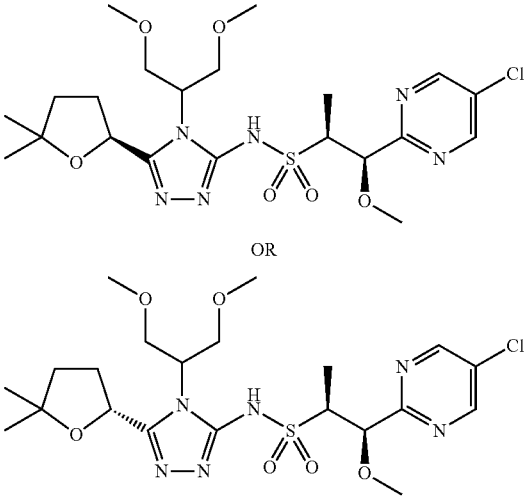 [SMILES: COCC(COC)n1c(NS(=O)(=O)[C@@H](C)[C@H](OC)c2ncc(Cl)cn2)nnc1[C@@H]1CCC(C)(C)O1 ; COCC(COC)n1c(NS(=O)(=O)[C@@H](C)[C@H](OC)c2ncc(Cl)cn2)nnc1[C@H]1CCC(C)(C)O1]<br>OR<br><br>(1R,2S)-1-(5-chloro-2-pyrimidinyl)-N-(4-(1,3-dimethoxy-2-propanyl)-5-((2R)-5,5-dimethyltetrahydro-2-furanyl)-4H-1,2,4-triazol-3-yl)-1-methoxy-2-propanesulfonamide or (1R,2S)-1-(5-chloro-2-pyrimidinyl)-N-(4-(1,3-dimethoxy-2-propanyl)-5-((2S)-5,5-dimethyltetrahydro-2-furanyl)-4H-1,2,4-triazol-3-yl)-1-methoxy-2-propanesulfonamide. $^1$H NMR (400 MHz, CDCl$_3$) δ 10.77 (br s, 1 H) 8.74 (s, 2 H) 4.99-5.06 (m, 2 H) 4.73-4.84 (m, 1 H) 4.10 (t, J = 9.64 Hz, 1 H) 3.88-4.00 (m, 2 H) 3.71 (qd, J = 7.05, 4.35 Hz, 1 H) 3.64 (dd, J = 9.85, 4.46 Hz, 1 H) 3.37 (s, 3 H) 3.36 (s, 3 H) 3.34 (s, 3 H) 2.67 (ddt, J = 12.75, 7.88, 6.27, 6.27 Hz, 1 H) 2.31 (dq, |

| Example | Reagents | Structure, Name and Data |
|---|---|---|
| | | J = 12.70, 7.58 Hz, 1 H) 1.81-1.99 (m, 2 H) 1.42 (d, J = 7.05 Hz, 3 H) 1.29 (s, 3 H) 1.24 (s, 3 H). LCMS-ESI (pos) m/z: 533.0 (M + H)+. |
| 308.0 | (1R,2S)-1-(5-chloropyrimidin-2-yl)-1-methoxypropane-2-sulfonamide (Example 11.3), (R)-5,5-dimethyltetrahydrofuran-2-carbohydrazide and (S)-5,5-dimethyltetrahydrofuran-2-carbohydrazide (Example 108.2), and 2-isothiocyanato-1,3-dimethoxypropane (Example 250.1). The title compound was the earlier isomer to elute on an SFC from Chiralpak AS-H column with 10% MeOH. | 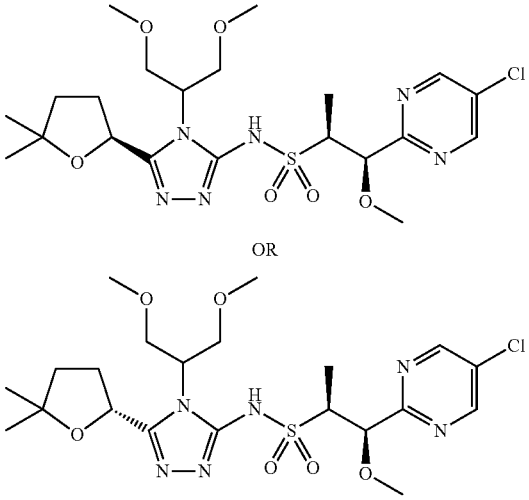 [SMILES: COCC(COC)n1c(NS(=O)(=O)[C@@H](C)[C@H](OC)c2ncc(Cl)cn2)nnc1[C@@H]1CCC(C)(C)O1 ; COCC(COC)n1c(NS(=O)(=O)[C@@H](C)[C@H](OC)c2ncc(Cl)cn2)nnc1[C@H]1CCC(C)(C)O1] OR (1R,2S)-1-(5-chloro-2-pyrimidinyl)-N-(4-(1,3-dimethoxy-2-propanyl)-5-((2R)-5,5-dimethyltetrahydro-2-furanyl)-4H-1,2,4-triazol-3-yl)-1-methoxy-2-propanesulfonamide or (1R,2S)-1-(5-chloro-2-pyrimidinyl)-N-(4-(1,3-dimethoxy-2-propanyl)-5-((2S)-5,5-dimethyltetrahydro-2-furanyl)-4H-1,2,4-triazol-3-yl)-1-methoxy-2-propanesulfonamide. $^1$H NMR (400 MHz, CDCl$_3$) δ 10.79 (br s, 1 H) 8.73 (s, 2 H) 5.05 (d, J = 4.04 Hz, 1 H) 5.02 (dd, J = 7.36, 5.91 Hz, 1 H) 4.72-4.83 (m, 1 H) 4.13 (t, J = 9.74 Hz, 1 H) 3.95 (qd, J = 10.12, 6.84 Hz, 2 H) 3.67-3.74 (m, 1 H) 3.64 (dd, J = 9.95, 4.46 Hz, 1 H) 3.38 (s, 3 H) 3.35 (s, 3 H) 3.31 (s, 3 H) 2.62-2.74 (m, 1 H) 2.31 (dq, J = 13.00, 7.42 Hz, 1 H) 1.81-1.98 (m, 2 H) 1.40 (d, J = 7.05 Hz, 3 H) 1.29 (s, 3 H) 1.23 (s, 3 H). LCMS-ESI (pos) m/z: 533.0 (M + H)+. |
| 309.0 | (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.), and 2-methoxyethyl isothiocyanate (commercially available from Sigma Aldrich. The racemic mixture was purified by preparative SFC using the following methodology: Column: IC (2 × 15 cm), Mobile Phase: 40:60 (A:B) A: Liquid CO$_2$, B: MeOH Flow Rate: 60 mL/min, 217 nm, 100 bar inlet pressure to deliver peak 2. | 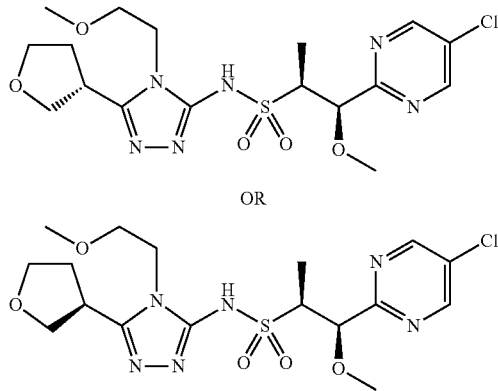 [SMILES: COCCn1c(NS(=O)(=O)[C@@H](C)[C@H](OC)c2ncc(Cl)cn2)nnc1[C@H]1CCOC1 ; COCCn1c(NS(=O)(=O)[C@@H](C)[C@H](OC)c2ncc(Cl)cn2)nnc1[C@@H]1CCOC1] OR (1R,2S)-1-(5-chloropyrimidin-2-yl)-1-methoxy-N-(4-(2-methoxyethyl)-5-((R)-tetrahydrofuran-3-yl)-4H-1,2,4-triazol-3-yl)propane-2-sulfonamide or (1R,2S)-1-(5-chloropyrimidin-2-yl)-1-methoxy-N-(4-(2-methoxyethyl)-5-((S)-tetrahydrofuran-3-yl)-4H-1,2,4-triazol-3-yl)propane-2-sulfonamide. $^1$H NMR (400 MHz, CD$_2$Cl$_2$) δ 8.71 (s, 2H), 4.95 (br s, 1H), 4.12-4.04 (m, 1H), 4.00-3.84 (m, 5H), 3.71-3.53 (m, 4H), 3.32 (s, 3H), 3.26-3.16 (m, 3H), 2.36-2.26 (m, 1H), 2.25-2.15 (m, 1H), 1.33 (d, J = 6.8 Hz, 3H). LCMS-ESI (pos) m/z: 461.0 (M + H)+. |

| Example | Reagents | Structure, Name and Data |
|---|---|---|
| 310.0 | (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.), and 2-methoxyethyl isothiocyanate (commercially available from Sigma Aldrich). The racemic mixture was purified by preparative SFC using the following methodology: Column: IC (2 × 15 cm), Mobile Phase: 40:60 (A:B) A: Liquid $CO_2$, B: MeOH Flow Rate: 60 mL/min, 217 nm, 100 bar inlet pressure to deliver peak 1. | 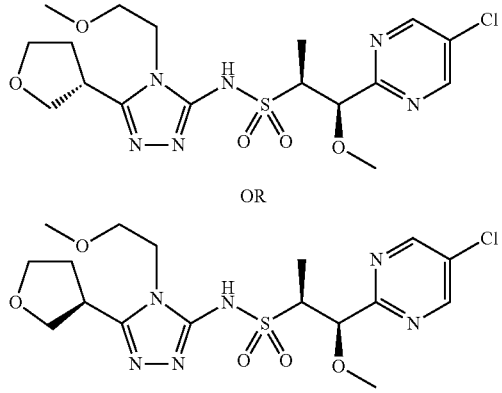 [SMILES: COCCn1c(NS(=O)(=O)[C@@H](C)[C@H](OC)c2ncc(Cl)cn2)nnc1[C@H]1CCOC1 ; COCCn1c(NS(=O)(=O)[C@@H](C)[C@H](OC)c2ncc(Cl)cn2)nnc1[C@@H]1CCOC1]<br>OR<br><br>(1R,2S)-1-(5-chloropyrimidin-2-yl)-1-methoxy-N-(4-(2-methoxyethyl)-5-((R)-tetrahydrofuran-3-yl)-4H-1,2,4-triazol-3-yl)propane-2-sulfonamide or (1R,2S)-1-(5-chloropyrimidin-2-yl)-1-methoxy-N-(4-(2-methoxyethyl)-5-((S)-tetrahydrofuran-3-yl)-4H-1,2,4-triazol-3-yl)propane-2-sulfonamide. $^1$H NMR (400 MHz, $CD_2Cl_2$) δ = 8.71 (s, 2H), 4.97 (d, J = 3.7 Hz, 1H), 4.08 (t, J = 8.0 Hz, 1H), 4.00-3.82 (m, 5H), 3.72-3.51 (m, 4H), 3.40-3.28 (m, 3H), 3.20 (s, 3H), 2.35-2.15 (m, 2H), 1.33 (d, J = 7.0 Hz, 3H). LCMS-ESI (pos) m/z: 461.0 $(M + H)^+$. |
| 311.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 2-methoxyethyl isothiocyanate (commercially available from Sigma Aldrich). The racemic mixture was purified by preparative SFC using the following methodology: Column: AS-H (2 × 25 cm) + AS-H (2 × 25 cm) + AS-H (2 × 15 cm), Mobile Phase: 85:15 (A:B) A: Liquid $CO_2$, B: MeOH Flow Rate: 70 mL/min, 217 nm, 100 bar inlet pressure to deliver peak 2. | 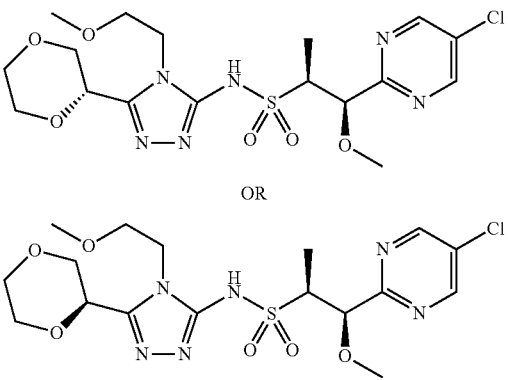 [SMILES: COCCn1c(NS(=O)(=O)[C@@H](C)[C@H](OC)c2ncc(Cl)cn2)nnc1[C@H]1COCCO1 ; COCCn1c(NS(=O)(=O)[C@@H](C)[C@H](OC)c2ncc(Cl)cn2)nnc1[C@@H]1COCCO1]<br>OR<br><br>(1R,2S)-N-(5-((R)-1,4-dioxan-2-yl)-4-(2-methoxyethyl)-4H-1,2,4-triazol-3-yl)-1-(5-chloropyrimidin-2-yl)-1-methoxypropane-2-sulfonamide or (1R,2S)-N-(5-((S)-1,4-dioxan-2-yl)-4-(2-methoxyethyl)-4H-1,2,4-triazol-3-yl)-1-(5-chloropyrimidin-2-yl)-1-methoxypropane-2-sulfonamide. $^1$H NMR (400 MHz, DMSO-$d_6$) δ 12.99 (s, 1H), 8.92 (s, 2H), 4.87 (d, J = 3.7 Hz, 1H), 4.77 (d, J = 8.7 Hz, 1H), 3.99-3.87 (m, 3H), 3.85-3.71 (m, 4H), 3.63-3.46 (m, 4H), 3.26 (s, 3H), 3.07 (s, 3H), 1.25 (d, J = 6.8 Hz, 3H). LCMS-ESI (pos) m/z: 477.0 $(M + H)^+$. |

TABLE 28-continued

| Example | Reagents | Structure, Name and Data |
|---|---|---|
| 312.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 2-methoxyethyl isothiocyanate (commercially available from Sigma Aldrich. The racemic mixture was purified by preparative SFC using the following methodology: Column: AS-H (2 × 25 cm) + AS-H (2 × 25 cm) + AS-H (2 × 15 cm), Mobile Phase: 85:15 (A:B) A: Liquid $CO_2$, B: MeOH Flow Rate: 70 mL/min, 217 nm, 100 bar inlet pressure to deliver peak 1. | 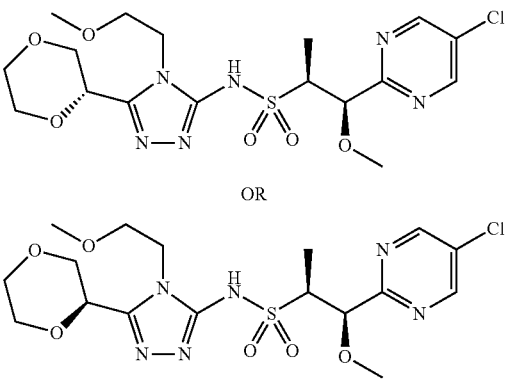 [SMILES: COCCn1c(NS(=O)(=O)[C@@H](C)[C@H](OC)c2ncc(Cl)cn2)nnc1[C@H]1COCCO1 ; COCCn1c(NS(=O)(=O)[C@@H](C)[C@H](OC)c2ncc(Cl)cn2)nnc1[C@@H]1COCCO1]<br><br>(1R,2S)-N-(5-((R)-1,4-dioxan-2-yl)-4-(2-methoxyethyl)-4H-1,2,4-triazol-3-yl)-1-(5-chloropyrimidin-2-yl)-1-methoxypropane-2-sulfonamide or (1R,2S)-N-(5-((S)-1,4-dioxan-2-yl)-4-(2-methoxyethyl)-4H-1,2,4-triazol-3-yl)-1-(5-chloropyrimidin-2-yl)-1-methoxypropane-2-sulfonamide. $^1$H NMR (400 MHz, DMSO-$d_6$) δ = 13.02 (s, 1H), 8.89 (s, 2H), 4.80 (d, J = 4.8 Hz, 1H), 4.75 (d, J = 7.3 Hz, 1H), 3.98-3.89 (m, 2H), 3.84-3.72 (m, 5H), 3.63-3.51 (m, 4H), 3.25 (s, 3H), 3.09 (s, 3H), 1.27 (d, J = 6.8 Hz, 3H). LCMS-ESI (pos) m/z: 477.0(M + H)$^+$. |

The compounds set forth in the following table were synthesized following the procedure in Example 255.0 using the known starting material as described.

TABLE 29

| Example | Reagents | Structure, Name and Data |
|---|---|---|
| 313.1 | 5,5-dimethyltetrahydrofuran-3-carboxylic acid (commercially available from Matrix Scientific.). | 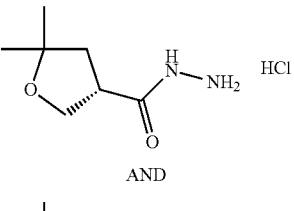<br><br>(R)-5,5-dimethyltetrahydrofuran-3-carbohydrazide hydrochloride and (S)-5,5-dimethyltetrahydrofuran-3-carbohydrazide hydrochloride. LCMS-ESI (pos) m/z: 159.2 (M + H)$^+$. |

The compounds set forth in the following table were synthesized following the procedure in Example 140.0 using the known starting material as described.

TABLE 30

| Example | Reagents | Structure, Name and Data |
|---|---|---|
| 313.0 | (1S,2S)-1-isopropoxy-1-(5-methylpyrimidin-2-yl)propane-2-sulfonamide (Example 13.5), (R)-5,5-dimethyltetrahydrofuran-3-carbohydrazide hydrochloride and (S)-5,5-dimethyltetrahydrofuran-3-carbohydrazide hydrochloride (Example 313.1), and 5-isothiocyanato-4,6-dimethoxypyrimidine (Example 10.1). The racemic mixture was purified by preparative SFC using the following methodology: Column: AD-H (2 × 25 cm) + AD-H (2 × 25 cm), Mobile Phase: 70:30 (A:B) A: Liquid CO$_2$, B: IPA, Flow Rate: 70 mL/min, 215 nm, 100 bar inlet pressure to deliver peak 1. | 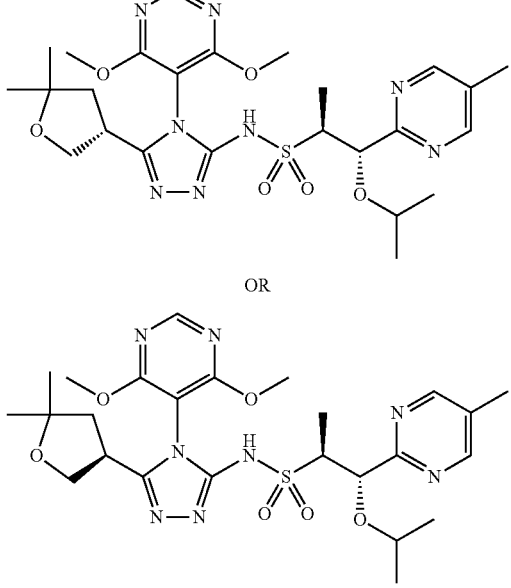<br>(1S,2S)-N-(4-(4,6-dimethoxypyrimidin-5-yl)-5-((R)-5,5-dimethyltetrahydrofuran-3-yl)-4H-1,2,4-triazol-3-yl)-1-isopropoxy-1-(5-methylpyrimidin-2-yl)propane-2-sulfonamide or (1S,2S)-N-(4-(4,6-dimethoxypyrimidin-5-yl)-5-((S)-5,5-dimethyltetrahydrofuran-3-yl)-4H-1,2,4-triazol-3-yl)-1-isopropoxy-1-(5-methylpyrimidin-2-yl)propane-2-sulfonamide.<br>$^1$H NMR (400 MHz, DMSO-d$_6$) δ 12.97 (s, 1H), 8.70 (s, 1H), 8.65 (s, 2H), 4.66 (d, J = 7.5 Hz, 1H), 4.02-3.99 (m, 3H), 3.99 (s, 3H), 3.85-3.80 (m, 1H), 3.76-3.71 (m, 1H), 3.45-3.34 (m, 2H), 3.29-3.23 (m, 1H), 2.27 (s, 3H), 1.90 (d, J = 8.7 Hz, 2H), 1.21 (s, 3H), 1.11 (s, 3H), 0.96 (d, J = 6.0 Hz, 3H), 0.91 (d, J = 7.0 Hz, 3H), 0.77 (d, J = 6.0 Hz, 3H). LCMS-ESI (pos) m/z: 577.2 (M + H)$^+$. |

… TABLE 30-continued

| Example | Reagents | Structure, Name and Data |
|---|---|---|
| 314.0 | (1S,2S)-1-isopropoxy-1-(5-methylpyrimidin-2-yl)propane-2-sulfonamide (Example 13.5), (R)-5,5-dimethyltetrahydrofuran-3-carbohydrazide hydrochloride and (S)-5,5-dimethyltetrahydrofuran-3-carbohydrazide hydrochloride (Example 313.1), and 5-isothiocyanato-4,6-dimethoxypyrimidine (Example 10.1).<br>The racemic mixture was purified by preparative SFC using the following methodology: Column: AD-H (2 × 25 cm) + AD-H (2 × 25 cm), Mobile Phase: 70:30 (A:B) A: Liquid CO$_2$, B: IPA, Flow Rate: 70 mL/min, 215 nm, 100 bar inlet pressure to deliver peak 2. | OR<br><br>(1S,2S)-N-(4-(4,6-dimethoxypyrimidin-5-yl)-5-((R)-5,5-dimethyltetrahydrofuran-3-yl)-4H-1,2,4-triazol-3-yl)-1-isopropoxy-1-(5-methylpyrimidin-2-yl)propane-2-sulfonamide or (1S,2S)-N-(4-(4,6-dimethoxypyrimidin-5-yl)-5-((S)-5,5-dimethyltetrahydrofuran-3-yl)-4H-1,2,4-triazol-3-yl)-1-isopropoxy-1-(5-methylpyrimidin-2-yl)propane-2-sulfonamide.<br>$^1$H NMR (400 MHz, DMSO-d$_6$) δ 12.97 (br s, 1H), 8.70 (s, 1H), 8.65 (s, 2H), 4.66 (d, J = 7.5 Hz, 1H), 4.04-4.00 (m, 3H), 3.99 (s, 3H), 3.85-3.79 (m, 1H), 3.76-3.71 (m, 1H), 3.44-3.34 (m, 2H), 3.29-3.23 (m, 1H), 2.27 (s, 3H), 1.91 (d, J = 8.5 Hz, 2H), 1.21 (s, 3H), 1.11 (s, 3H), 0.96 (d, J = 6.0 Hz, 3H), 0.91 (d, J = 7.0 Hz, 3H), 0.78 (d, J = 6.0 Hz, 3H). LCMS-ESI (pos) m/z: 577.2 (M + H)$^+$. |
| 315.0 | (1R,2S)-1-(5-chloropyrimidin-2-yl)-1-methoxypropane-2-sulfonamide (Example 11.3), (R)-5,5-dimethyltetrahydrofuran-3-carbohydrazide hydrochloride and (S)-5,5-dimethyltetrahydrofuran-3-carbohydrazide hydrochloride (Example 313.1), and 5-isothiocyanato-4,6-dimethoxypyrimidine (Example 10.1).<br>The racemic mixture was purified by preparative SFC using the following methodology: Column: AD-H (2 × 25 cm), Mobile Phase: 60:40 (A:B) A: Liquid CO$_2$, B: IPA, Flow Rate: 80 mL/min, 218 nm, 100 bar inlet pressure to deliver peak 1. | OR<br><br>(1R,2S)-1-(5-chloropyrimidin-2-yl)-N-(4-(4,6-dimethoxypyrimidin-5-yl)-5-((R)-5,5-dimethyltetrahydrofuran-3-yl)-4H-1,2,4-triazol-3-yl)-1-methoxypropane-2-sulfonamide |

TABLE 30-continued

| Example | Reagents | Structure, Name and Data |
|---------|----------|--------------------------|
| | | or (1R,2S)-1-(5-chloropyrimidin-2-yl)-N-(4-(4,6-dimethoxypyrimidin-5-yl)-5-((S)-5,5-dimethyltetrahydrofuran-3-yl)-4H-1,2,4-triazol-3-yl)-1-methoxypropane-2-sulfonamide. $^1$H NMR (400 MHz, DMSO-d$_6$) δ 13.01 (br s, 1H), 8.93 (s, 2H), 8.70 (s, 1H), 4.76 (d, J = 3.9 Hz, 1H), 3.99-3.96 (m, 3H), 3.96 (s, 3H), 3.86-3.79 (m, 1H), 3.76-3.70 (m, 1H), 3.46-3.38 (m, 1H), 3.29-3.23 (m, 1H), 3.12 (s, 3H), 1.91 (d, J = 8.5 Hz, 2H), 1.21 (s, 3H), 1.15-1.08 (m, 6H). LCMS-ESI (pos) m/z: 569.1 (M + H)$^+$. |
| 316.0 | (1R,2S)-1-(5-chloropyrimidin-2-yl)-1-methoxypropane-2-sulfonamide (Example 11.3), (R)-5,5-dimethyltetrahydrofuran-3-carbohydrazide hydrochloride and (S)-5,5-dimethyltetrahydrofuran-3-carbohydrazide hydrochloride (Example 313.1), and 5-isothiocyanato-4,6-dimethoxypyrimidine (Example 10.1).<br>The racemic mixture was purified by preparative SFC using the following methodology: Column: AD-H (2 × 25 cm), Mobile Phase: 60:40 (A:B) A: Liquid CO$_2$, B: IPA, Flow Rate: 80 mL/min, 218 nm, 100 bar inlet pressure to deliver peak 2. | (1R,2S)-1-(5-chloropyrimidin-2-yl)-N-(4-(4,6-dimethoxypyrimidin-5-yl)-5-((R)-5,5-dimethyltetrahydrofuran-3-yl)-4H-1,2,4-triazol-3-yl)-1-methoxypropane-2-sulfonamide or (1R,2S)-1-(5-chloropyrimidin-2-yl)-N-(4-(4,6-dimethoxypyrimidin-5-yl)-5-((S)-5,5-dimethyltetrahydrofuran-3-yl)-4H-1,2,4-triazol-3-yl)-1-methoxypropane-2-sulfonamide. $^1$H NMR (400 MHz, DMSO-d$_6$) δ 13.01 (s, 1H), 8.93 (s, 2H), 8.70 (s, 1H), 4.77 (d, J = 3.9 Hz, 1H), 3.97 (s, 3H), 3.97-3.94 (m, 3H), 3.85-3.79 (m, 1H), 3.76-3.71 (m, 1H), 3.42-3.37 (m, 1H), 3.29-3.23 (m, 1H), 3.13 (s, 3H), 1.91 (br d, J = 8.5 Hz, 2H), 1.21 (s, 3H), 1.14-1.09 (m, 6H). LCMS-ESI (pos) m/z: 569.0 (M + H)$^+$. |

| Example | Reagents | Structure, Name and Data |
|---|---|---|
| 317.0 | (2S,3R)-3-(5-chloropyrimidin-2-yl)butane-2-sulfonamide (Example 1.4), (R)-5,5-dimethyltetrahydrofuran-3-carbohydrazide hydrochloride and (S)-5,5-dimethyltetrahydrofuran-3-carbohydrazide hydrochloride (Example 313.1), and 5-isothiocyanato-4,6-dimethoxypyrimidine (Example 10.1)<br>The mixture was purified by preparative SFC using the following methodology: Column: AD-H (2 × 25 cm), Mobile Phase: 60:40 (A:B) A: Liquid $CO_2$, B: IPA, Flow Rate: 80 mL/min, 217 nm, 100 bar inlet pressure to deliver peak 1. | (2S,3R)-3-(5-chloropyrimidin-2-yl)-N-(4-(4,6-dimethoxypyrimidin-5-yl)-5-((R)-5,5-dimethyltetrahydrofuran-3-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((S)-5,5-dimethyltetrahydrofuran-3-yl)-4H-1,2,4-triazol-3-yl)butane-2-sulfonamide. $^1$H NMR (400 MHz, DMSO-$d_6$) δ 13.28-12.87 (m, 1H), 8.85 (s, 2H), 8.70 (s, 1H), 3.97-3.92 (m, 6H), 3.85-3.79 (m, 1H), 3.73 (dd, J = 6.9, 8.6 Hz, 1H), 3.65-3.59 (m, 1H), 3.57-3.52 (m, 1H), 3.31-3.25 (m, 1H), 1.90 (d, J = 8.7 Hz, 2H), 1.25-1.20 (m, 6H), 1.12-1.07 (m, 6H). LCMS-ESI (pos) m/z: 553.0 (M + H)$^+$. |
| 318.0 | (2S,3R)-3-(5-chloropyrimidin-2-yl)butane-2-sulfonamide (Example 1.4), (R)-5,5-dimethyltetrahydrofuran-3-carbohydrazide hydrochloride and (S)-5,5-dimethyltetrahydrofuran-3-carbohydrazide hydrochloride (Example 313.1), and 5-isothiocyanato-4,6-dimethoxypyrimidine (Example 10.1)<br>The mixture was purified by preparative SFC using the following methodology: Column: AD-H (2 × 25 cm), Mobile Phase: 60:40 (A:B) A: Liquid $CO_2$, B: IPA, Flow Rate: 80 mL/min, 217 nm, 100 bar inlet pressure to deliver peak 2. | (2S,3R)-3-(5-chloropyrimidin-2-yl)-N-(4-(4,6-dimethoxypyrimidin-5-yl)-5-((R)-5,5-dimethyltetrahydrofuran-3-yl)-4H-1,2,4-triazol-3-yl)butane-2-sulfonamide or (2S,3R)-3-(5-chloropyrimidin-2-yl)-N-(4-(4,6-dimethoxypyrimidin-5-yl)-5-((S)-5,5-dimethyltetrahydrofuran-3-yl)-4H-1,2,4-triazol-3-yl)butane-2-sulfonamide. $^1$H NMR (400 MHz, DMSO-$d_6$) δ 13.02 (s, 1H), 8.86 (s, 2H), 8.70 (s, 1H), 3.95 (s, 3H), 3.95 (s, 3H), 3.84-3.78 (m, 1H), 3.74-3.69 (m, 1H), 3.66-3.58 (m, 1H), 3.57-3.51 (m, 1H), 3.30-3.23 |

TABLE 30-continued

| Example | Reagents | Structure, Name and Data |
|---------|----------|--------------------------|
| | | (m, 1H), 1.91 (d, J = 8.5 Hz, 2H), 1.24-1.21 (m, 6H), 1.12-1.08 (m, 6H). LCMS-ESI (pos) m/z: 553.0 (M + H)⁺. |
| 319.0 | (1S,2S)-1-(5-chloropyrimidin-2-yl)-1-isopropoxypropane-2-sulfonamide (Example 13.6), (R)-tetrahydrofuran-3-carbohydrazide and (S)-tetrahydrofuran-3-carbohydrazide (commercially available from Astatech Inc.), and 1-isothiocyanato-1-(methoxymethyl)cyclopropane (Example 289.1). The racemic mixture was purified by preparative SFC using the following methodology: Column: AS-H (2 × 25 cm), Mobile Phase: 75:25 (A:B) A: Liquid CO₂, B: MeOH, Flow Rate: 80 mL/min, 219 nm, 100 bar inlet pressure to deliver peak 1. | 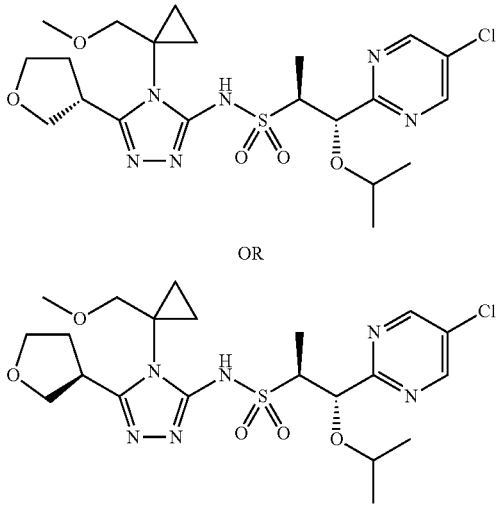 [SMILES: COCC1(n2c(NS(=O)(=O)[C@@H](C)[C@@H](OC(C)C)c3ncc(Cl)cn3)nnc2[C@H]2CCOC2)CC1 ; COCC1(n2c(NS(=O)(=O)[C@@H](C)[C@@H](OC(C)C)c3ncc(Cl)cn3)nnc2[C@@H]2CCOC2)CC1]<br><br>OR<br><br>(1S,2S)-1-(5-chloropyrimidin-2-yl)-1-isopropoxy-N-(4-(1-(methoxymethyl)cyclopropyl)-5-((R)-tetrahydrofuran-3-yl)-4H-1,2,4-triazol-3-yl)propane-2-sulfonamide or (1S,2S)-1-(5-chloropyrimidin-2-yl)-1-isopropoxy-N-(4-(1-(methoxymethyl)cyclopropyl)-5-((S)-tetrahydrofuran-3-yl)-4H-1,2,4-triazol-3-yl)propane-2-sulfonamide. ¹H NMR (400 MHz, DMSO-d₆) δ 12.43 (br s, 1H), 8.95 (s, 2H), 4.87 (br s, 1H), 4.03 (t, J = 7.8 Hz, 1H), 3.92-3.86 (m, 1H), 3.84-3.60 (m, 4H), 3.53 (quin, J = 7.0 Hz, 1H), 3.45-3.32 (m, 1H), 3.28-2.92 (m, 4H), 2.32-2.22 (m, 1H), 2.15-1.90 (m, 1H), 1.44-1.26 (m, 1H), 1.23-0.95 (m, 9H), 0.94-0.56 (m, 3H). LCMS-ESI (pos) m/z: 515.2 (M + H)⁺. |
| 320.0 | (1S,2S)-1-(5-chloropyrimidin-2-yl)-1-isopropoxypropane-2-sulfonamide (Example 13.6), (R)-tetrahydrofuran-3-carbohydrazide and (S)-tetrahydrofuran-3-carbohydrazide (commercially available from Astatech Inc.), and 1-isothiocyanato-1-(methoxymethyl)cyclopropane (Example 289.1). The racemic mixture was purified by preparative SFC using the following methodology: Column: AS-H (2 × 25 cm), Mobile Phase: 75:25 (A:B) A: Liquid CO₂, B: MeOH, Flow Rate: 80 mL/min, 219 nm, 100 bar inlet pressure to deliver peak 2. | 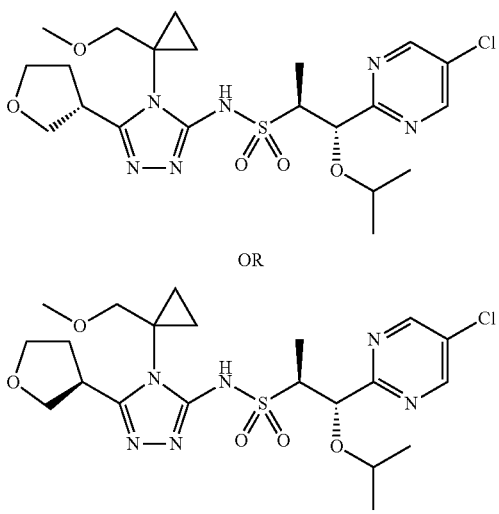 [SMILES: COCC1(n2c(NS(=O)(=O)[C@@H](C)[C@@H](OC(C)C)c3ncc(Cl)cn3)nnc2[C@H]2CCOC2)CC1 ; COCC1(n2c(NS(=O)(=O)[C@@H](C)[C@@H](OC(C)C)c3ncc(Cl)cn3)nnc2[C@@H]2CCOC2)CC1]<br><br>OR<br><br>(1S,2S)-1-(5-chloropyrimidin-2-yl)-1-isopropoxy-N-(4-(1-(methoxymethyl)cyclopropyl)-5-((R)-tetrahydrofuran-3-yl)-4H-1,2,4-triazol-3-yl)propane-2-sulfonamide or (1S,2S)-1-(5-chloropyrimidin-2-yl)-1- |

TABLE 30-continued

| Example | Reagents | Structure, Name and Data |
|---|---|---|
| | | isopropoxy-N-(4-(1-(methoxymethyl)cyclopropyl)-5-((S)-tetrahydrofuran-3-yl)-4H-1,2,4-triazol-3-yl)propane-2-sulfonamide. $^1$H NMR (400 MHz, DMSO-$d_6$) δ 12.38 (br s, 1H), 8.95 (br s, 2H), 4.88 (br s, 1H), 4.07-4.00 (m, 1H), 3.89 (br d, J = 5.6 Hz, 1H), 3.84-3.51 (m, 5H), 3.46-3.35 (m, 1H), 3.30-2.84 (m, 4H), 2.33-2.22 (m, 1H), 2.15-1.93 (m, 1H), 1.45-1.28 (m, 1H), 1.20-0.96 (m, 9H), 0.95-0.55 (m, 3H). LCMS-ESI (pos) m/z: 515.2 (M + H)$^+$. |
| 321.0 | (1S,2S)-1-(5-fluoropyrimidin-2-yl)-1-isopropoxypropane-2-sulfonamide (prepared in an analogous fashion to the procedure described in Example 13.0 employing 2-chloro-5-fluoropyrimidine), (R)-tetrahydrofuran-3-carbohydrazide and (S)-tetrahydrofuran-3-carbohydrazide (commercially available from Astatech Inc.), and 5-isothiocyanato-4,6-dimethoxypyrimidine (Example 10.1).<br>The racemic mixture was purified by preparative SFC using the following methodology: Column: Lux Cellulose-2 (2 × 15 cm) + Lux Cellulose-2 (2 × 15 cm) Mobile Phase: 70:30 (A:B) A: Liquid CO$_2$, B: MeOH Flow Rate: 80 mL/mM, 220 nm, 100 bar inlet pressure to deliver peak 1. | 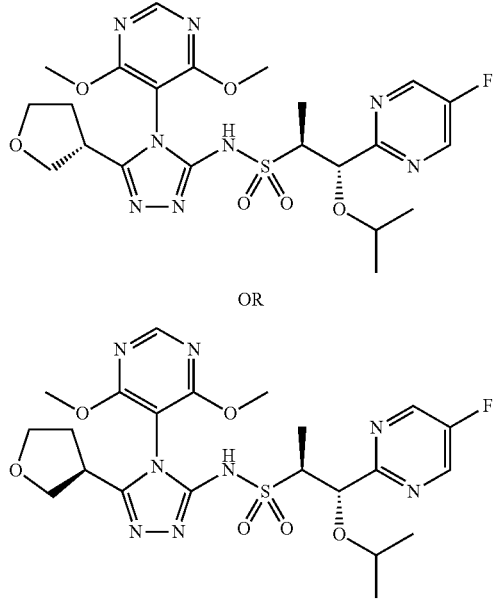 [SMILES: COc1ncnc(OC)c1-n1c(NS(=O)(=O)[C@@H](C)[C@@H](OC(C)C)c2ncc(F)cn2)nnc1[C@H]1CCOC1 ; COc1ncnc(OC)c1-n1c(NS(=O)(=O)[C@@H](C)[C@@H](OC(C)C)c2ncc(F)cn2)nnc1[C@@H]1CCOC1]<br><br>(1S,2S)-N-(4-(4,6-dimethoxypyrimidin-5-yl)-5-((R)-tetrahydrofuran-3-yl)-4H-1,2,4-triazol-3-yl)-1-(5-fluoropyrimidin-2-yl)-1-isopropoxypropane-2-sulfonamide or (1S,2S)-N-(4-(4,6-dimethoxypyrimidin-5-yl)-5-((S)-tetrahydrofuran-3-yl)-4H-1,2,4-triazol-3-yl)-1-(5-fluoropyrimidin-2-yl)-1-isopropoxypropane-2-sulfonamide. $^1$H NMR (400 MHz, DMSO-$d_6$) δ = 12.89 (s, 1H), 8.88 (s, 2H), 8.70 (s, 1H), 4.77 (d, J = 7.0 Hz, 1H), 3.99 (s, 3H), 3.99-3.97 (m, 3H), 3.81-3.70 (m, 2H), 3.70-3.63 (m, 2H), 3.48-3.37 (m, 2H), 3.16 (quin, J = 7.0 Hz, 1H), 2.06-1.97 (m, 2H), 1.00-0.96 (m, 3H), 0.96-0.91 (m, 3H), 0.80 (d, J = 6.0 Hz, 3H). LCMS-ESI (pos) m/z: 553.0 (M + H)$^+$. |

TABLE 30-continued

| Example | Reagents | Structure, Name and Data |
|---|---|---|
| 322.0 | (1S,2S)-1-(5-fluoropyrimidin-2-yl)-1-isopropoxypropane-2-sulfonamide (prepared in an analogous fashion to the procedure described in Example 13.0 employing 2-chloro-5-fluoropyrimidine), (R)-tetrahydrofuran-3-carbohydrazide and (S)-tetrahydrofuran-3-carbohydrazide (commercially available from Astatech Inc.), and 5-isothiocyanato-4,6-dimethoxypyrimidine (Example 10.1). The racemic mixture was purified by preparative SFC using the following methodology: Column: Lux Cellulose-2 (2 × 15 cm) + Lux Cellulose-2 (2 × 15 cm) Mobile Phase: 70:30 (A:B) A: Liquid $CO_2$, B: MeOH Flow Rate: 80 mL/mM, 220 nm, 100 bar inlet pressure to deliver peak 2. | 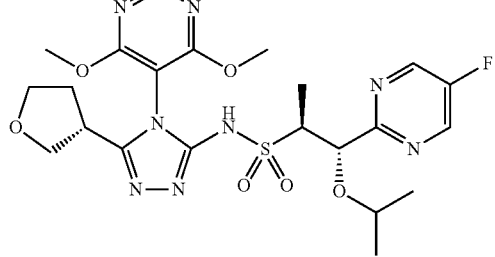<br>OR<br>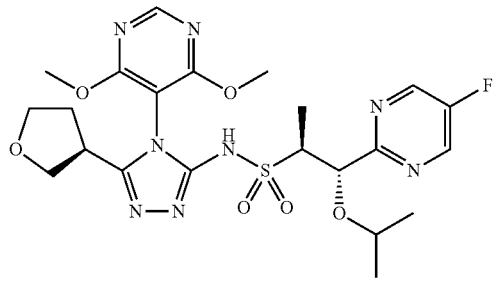<br>(1S,2S)-N-(4-(4,6-dimethoxypyrimidin-5-yl)-5-((R)-tetrahydrofuran-3-yl)-4H-1,2,4-triazol-3-yl)-1-(5-fluoropyrimidin-2-yl)-1-isopropoxypropane-2-sulfonamide or (1S,2S)-N-(4-(4,6-dimethoxypyrimidin-5-yl)-5-((S)-tetrahydrofuran-3-yl)-4H-1,2,4-triazol-3-yl)-1-(5-fluoropyrimidin-2-yl)-1-isopropoxypropane-2-sulfonamide. $^1$H NMR (400 MHz, DMSO-$d_6$) δ 12.89 (s, 1H), 8.88 (s, 2H), 8.70 (s, 1H), 4.77 (d, J = 7.0 Hz, 1H), 4.04-3.96 (m, 6H), 3.81-3.72 (m, 2H), 3.72-3.62 (m, 2H), 3.46-3.36 (m, 2H), 3.16 (quin, J = 7.1 Hz, 1H), 2.06-1.94 (m, 2H), 0.99-0.92 (m, 6H), 0.83-0.76 (m, 3H). LCMS-ESI (pos) m/z: 553.0 (M + H)$^+$. |
| 323.0 | (1S,2S)-1-isopropoxy-1-(5-methylpyridin-2-yl)propane-2-sulfonamide (prepared in an analogous fashion to the procedure described in Example 13.0 employing 2-chloro-4-methylpyridine), (R)-tetrahydrofuran-3-carbohydrazide and (S)-tetrahydrofuran-3-carbohydrazide (commercially available from Astatech Inc.), and 5-isothiocyanato-4,6-dimethoxypyrimidine (Example 10.1). The racemic mixture was purified by preparative SFC using the following methodology: Column: IC (2 × 25 cm) then IC (2 × 15 cm) (high pressure drop) Mobile Phase: 65:35 (A:B) A: Liquid $CO_2$, B: MeOH Flow Rate: 80 mL/min, 217 nm, 100 bar inlet pressure to deliver peak 1. | 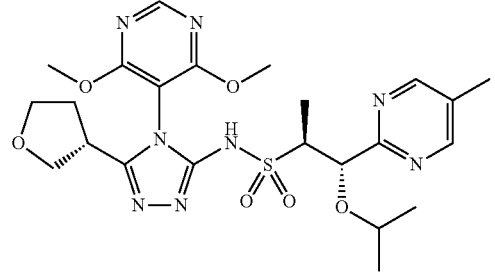<br>OR<br>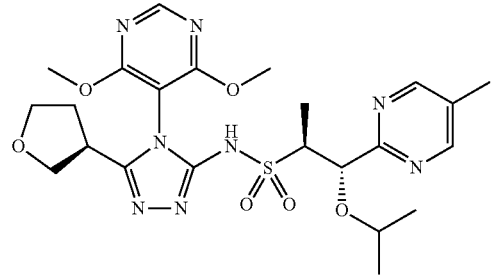<br>(1S,2S)-N-(4-(4,6-dimethoxypyrimidin-5-yl)-5-((R)-tetrahydrofuran-3-yl)-4H-1,2,4-triazol-3-yl)-1-isopropoxy-1-(5-methylpyridin-2-yl)propane-2-sulfonamide or (1S,2S)-N-(4- |

| Example | Reagents | Structure, Name and Data |
|---|---|---|
| | | (4,6-dimethoxypyrimidin-5-yl)-5-((S)-tetrahydrofuran-3-yl)-4H-1,2,4-triazol-3-yl)-1-isopropoxy-1-(5-methylpyridin-2-yl)propane-2-sulfonamide. $^1$H NMR (400 MHz, CD$_2$Cl$_2$) δ 8.55 (s, 1H), 8.41 (s, 1H), 7.56 (d, J = 7.7 Hz, 1H), 7.33 (d, J = 8.1 Hz, 1H), 4.79 (d, J = 4.6 Hz, 1H), 4.05 (s, 3H), 4.03-4.00 (m, 3H), 3.92-3.82 (m, 3H), 3.80-3.74 (m, 1H), 3.50-3.39 (m, 2H), 3.02 (quin, J = 7.2 Hz, 1H), 2.35 (s, 3H), 2.23-2.13 (m, 1H), 2.12-2.00 (m, 1H), 1.15 (d, J = 7.0 Hz, 3H), 1.08 (d, J = 5.8 Hz, 3H), 0.98 (d, J = 6.0 Hz, 3H). LCMS-ESI (pos) m/z: 548.0 (M + H)$^+$. |
| 324.0 | (1S,2S)-1-isopropoxy-1-(5-methylpyridin-2-yl)propane-2-sulfonamide (prepared in an analogous fashion to the procedure described in Example 13.0 employing 2-chloro-4-methylpyridine), (R)-tetrahydrofuran-3-carbohydrazide and (S)-tetrahydrofuran-3-carbohydrazide (commercially available from Astatech Inc.), and 5-isothiocyanato-4,6-dimethoxypyrimidine (Example 10.1).<br>The racemic mixture was purified by preparative SFC using the following methodology: Column: IC (2 × 25 cm) then IC (2 × 15 cm) (high pressure drop) Mobile Phase: 65:35 (A:B) A: Liquid CO$_2$, B: MeOH Flow Rate: 80 mL/min, 217 nm, 100 bar inlet pressure to deliver peak 2. | 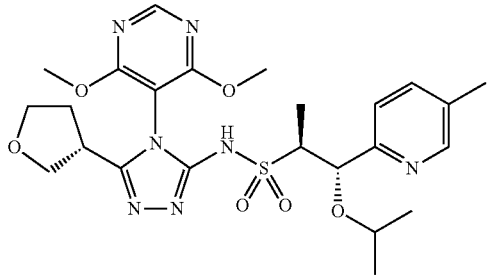<br><br>OR<br><br>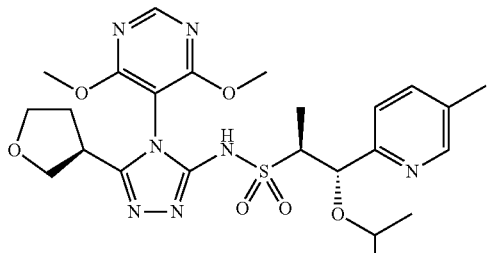<br><br>(1S,2S)-N-(4-(4,6-dimethoxypyrimidin-5-yl)-5-((R)-tetrahydrofuran-3-yl)-4H-1,2,4-triazol-3-yl)-1-isopropoxy-1-(5-methylpyridin-2-yl)propane-2-sulfonamide or (1S,2S)-N-(4-(4,6-dimethoxypyrimidin-5-yl)-5-((S)-tetrahydrofuran-3-yl)-4H-1,2,4-triazol-3-yl)-1-isopropoxy-1-(5-methylpyridin-2-yl)propane-2-sulfonamide. $^1$H NMR (400 MHz, CD$_2$Cl$_2$) δ 8.55 (s, 1H), 8.41 (s, 1H), 7.56 (d, J = 7.0 Hz, 1H), 7.36-7.31 (m, 1H), 5.19-5.01 (m, 1H), 4.87-4.74 (m, 1H), 4.10-4.04 (m, 3H), 4.03-3.98 (m, 3H), 3.92-3.86 (m, 1H), 3.84-3.73 (m, 3H), 3.45 (d, J = 5.4 Hz, 2H), 3.08-2.97 (m, 1H), 2.35 (s, 3H), 2.26-2.17 (m, 1H), 2.08 (d, J = 6.0 Hz, 1H), 1.15 (d, J = 6.4 Hz, 3H), 1.08 (d, J = 5.2 Hz, 3H), 0.97 (d, J = 5.2 Hz, 3H). LCMS-ESI (pos) m/z: 548.0 (M + H)$^+$. |

TABLE 30-continued

| Example | Reagents | Structure, Name and Data |
|---|---|---|
| 325.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 1-1-isothiocyanato-1,1'-bi(cyclopropane) (Example 325.1)<br>The title compound was the earlier isomer to elute on an SFC from Chiralpak IC column with 50% MeOH. | 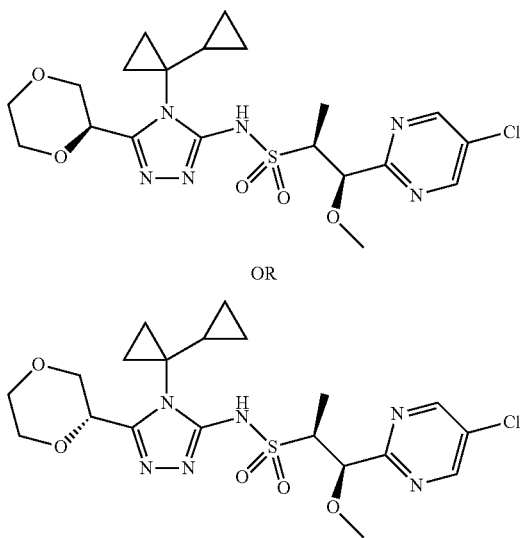 [SMILES: CO[C@H](c1ncc(Cl)cn1)[C@H](C)S(=O)(=O)Nc1nnc([C@@H]2COCCO2)n1C1(C2CC2)CC1 ; CO[C@H](c1ncc(Cl)cn1)[C@H](C)S(=O)(=O)Nc1nnc([C@H]2COCCO2)n1C1(C2CC2)CC1]<br>OR<br><br>(1R,2S)-N-(4-([1,1'-bi(cyclopropyl)]-1-yl)-5-((2S)-1,4-dioxan-2-yl)-4H-1,2,4-triazol-3-yl)-1-(5-chloro-2-pyrimidinyl)-1-methoxy-2-propanesulfonamide or (1R,2S)-N-(4-([1,1'-bi(cyclopropyl)]-1-yl)-5-((2R)-1,4-dioxan-2-yl)-4H-1,2,4-triazol-3-yl)-1-(5-chloro-2-pyrimidinyl)-1-methoxy-2-propanesulfonamide. $^1$H NMR (500 MHz, CDCl$_3$) δ 8.74 (d, J = 2.08 Hz, 2 H) 5.07 (d, J = 4.15 Hz, 1 H) 4.82 (br d, J = 9.60 Hz, 1 H) 4.02-4.10 (m, 1 H) 3.90-4.00 (m, 2 H) 3.78-3.90 (m, 3 H) 3.68-3.76 (m, 1 H) 3.50 (d, J = 3.76 Hz, 2 H) 3.37 (s, 3 H) 1.50-1.60 (m, 1 H) 1.43 (d, J = 7.01 Hz, 3 H) 1.29-1.36 (m, 1 H) 1.13 (br s, 1 H) 0.97-1.06 (m, 1 H) 0.87-0.95 (m, 1 H) 0.39-0.58 (m, 3 H) 0.33 (br d, J = 2.21 Hz, 1 H). LCMS-ESI (pos) m/z: 499.0 (M + H)$^+$. |
| 326.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 1-1-isothiocyanato-1,1'-bi(cyclopropane) (Example 325.1)<br>The title compound was the later isomer to elute on an SFC from Chiralpak IC column with 50% MeOH. | 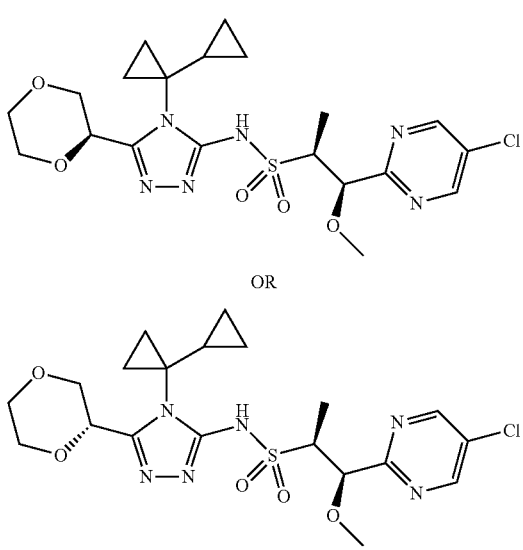 [SMILES: CO[C@H](c1ncc(Cl)cn1)[C@H](C)S(=O)(=O)Nc1nnc([C@@H]2COCCO2)n1C1(C2CC2)CC1 ; CO[C@H](c1ncc(Cl)cn1)[C@H](C)S(=O)(=O)Nc1nnc([C@H]2COCCO2)n1C1(C2CC2)CC1]<br>OR<br><br>(1R,2S)-N-(4-([1,1'-bi(cyclopropyl)]-1-yl)-5-((2S)-1,4-dioxan-2-yl)-4H-1,2,4-triazol-3-yl)-1-(5-chloro-2-pyrimidinyl)-1-methoxy-2-propanesulfonamide or (1R,2S)-N-(4-([1,1'-bi(cyclopropyl)]-1-yl)-5-((2R)-1,4-dioxan-2-yl)-4H-1,2,4-triazol-3-yl)-1-(5-chloro-2- |

| Example | Reagents | Structure, Name and Data |
|---|---|---|
| | | pyrimidinyl)-1-methoxy-2-propanesulfonamide. $^1$H NMR (600 MHz, DMSO-d$_6$) δ 8.95 (s, 2 H) 4.93 (d, J = 3.74 Hz, 1 H) 4.77 (br d, J = 8.25 Hz, 1 H) 3.96 (dd, J = 11.44, 1.79 Hz, 1 H) 3.71-3.89 (m, 4 H) 3.57-3.66 (m, 1 H) 3.46 (br dd, J = 5.92, 3.89 Hz, 1 H) 3.31-3.42 (m, 2 H) 3.17 (s, 1 H) 1.50 (br s, 1 H) 1.27 (d, J = 6.85 Hz, 3 H) 1.19 (br s, 1 H) 1.02-1.14 (m, 1 H) 0.82-0.97 (m, 2 H) 0.22-0.52 (m, 4 H). LCMS-ESI (pos) m/z: 499.0 (M + H)$^+$. |
| 328.0 | (1R,2S)-1-methoxy-1-(5-methylpyrazin-2-yl)propane-2-sulfonamide (Example 11.1), (R)-1,4-dioxane-2-carbohydrazide and (S)-1,4-dioxane-2-carbohydrazide (commercially available from Enamine), and 1-1-isothiocyanato-1,1'-bi(cyclopropane) (Example 325.1) The title compound was the earlier isomer to elute on an SFC from Chiralpak AD-H column with 30% MeOH. | 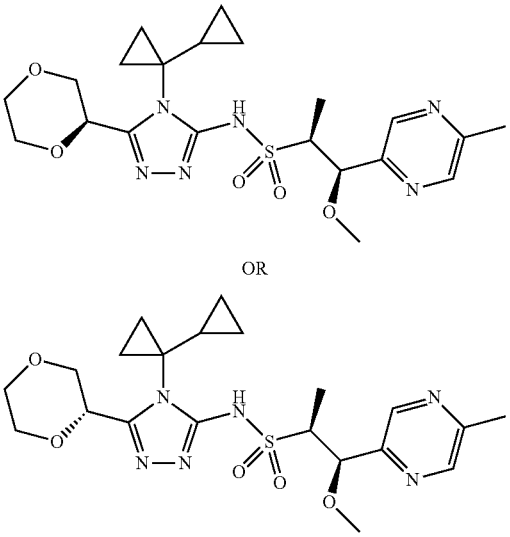 [SMILES: CO[C@H](c1cnc(C)cn1)[C@H](C)S(=O)(=O)Nc1nnc([C@@H]2COCCO2)n1C1(C2CC2)CC1 ; CO[C@H](c1cnc(C)cn1)[C@H](C)S(=O)(=O)Nc1nnc([C@H]2COCCO2)n1C1(C2CC2)CC1]<br>OR<br>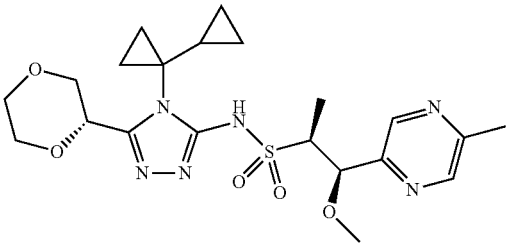<br>(1R,2S)-N-(4-([1,1'-bi(cyclopropyl)]-1-yl)-5-((2R)-1,4-dioxan-2-yl)-4H-1,2,4-triazol-3-yl)-1-methoxy-1-(5-methyl-2-pyrazinyl)-2-propanesulfonamide or (1R,2S)-N-(4-([1,1'-bi(cyclopropyl)]-1-yl)-5-((2S)-1,4-dioxan-2-yl)-4H-1,2,4-triazol-3-yl)-1-methoxy-1-(5-methyl-2-pyrazinyl)-2-propanesulfonamide. 1H NMR (500 MHz, CDCl$_3$) δ 10.98 (br s, 1 H) 8.57 (s, 1 H) 8.44 (s, 1 H) 5.10 (d, J = 2.72 Hz, 1 H) 4.81 (dd, J = 9.60, 2.72 Hz, 1 H) 4.01-4.10 (m, 1 H) 3.90-4.01 (m, 2 H) 3.75-3.90 (m, 3 H) 3.54 (qd, J = 7.03, 2.92 Hz, 1 H) 3.37 (s, 3 H) 2.58 (s, 3 H) 1.50-1.60 (m, 1 H) 1.27-1.38 (m, 4 H) 1.14 (br s, 1 H) 1.01 (dt, J = 9.80, 6.71 Hz, 1 H) 0.89 (dt, J = 9.76, 6.60 Hz, 1 H) 0.37-0.59 (m, 3 H) 0.28-0.37 (m, 1 H). LCMS-ESI (pos) m/z: 479.0 (M + H)$^+$. |

| Example | Reagents | Structure, Name and Data |
|---|---|---|
| 329.0 | (1R,2S)-1-methoxy-1-(5-methylpyrazin-2-yl)propane-2-sulfonamide (Example 11.1), (R)-1,4-dioxane-2-carbohydrazide and (S)-1,4-dioxane-2-carbohydrazide (commercially available from Enamine), and 1-1-isothiocyanato-1,1'-bi(cyclopropane) (Example 325.1)<br>The title compound was the later isomer to elute on an SFC from Chiralpak AD-H column with 30% MeOH. | 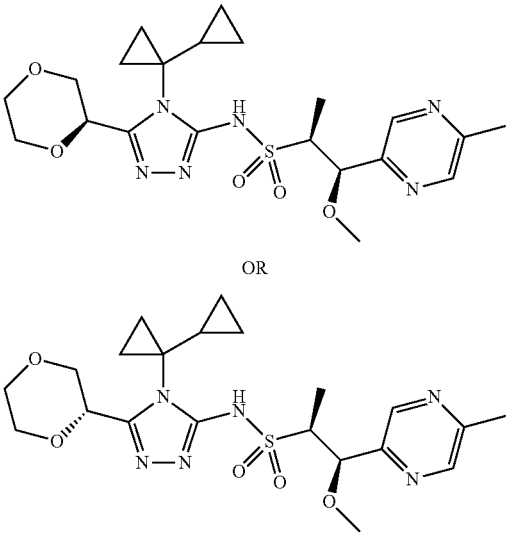 [SMILES: CO[C@H](c1cnc(C)cn1)[C@H](C)S(=O)(=O)Nc1nnc([C@@H]2COCCO2)n1C1(C2CC2)CC1 ; CO[C@H](c1cnc(C)cn1)[C@H](C)S(=O)(=O)Nc1nnc([C@H]2COCCO2)n1C1(C2CC2)CC1]<br>OR<br>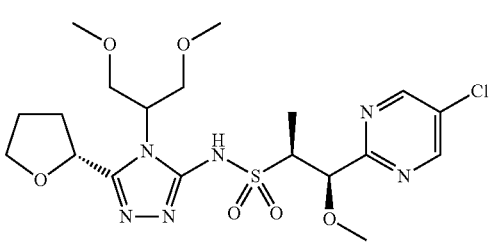<br>(1R,2S)-N-(4-([1,1'-bi(cyclopropyl)]-1-yl)-5-((2R)-1,4-dioxan-2-yl)-4H-1,2,4-triazol-3-yl)-1-methoxy-1-(5-methyl-2-pyrazinyl)-2-propanesulfonamide or (1R,2S)-N-(4-([1,1'-bi(cyclopropyl)]-1-yl)-5-((2S)-1,4-dioxan-2-yl)-4H-1,2,4-triazol-3-yl)-1-methoxy-1-(5-methyl-2-pyrazinyl)-2-propanesulfonamide. 1H NMR (500 MHz, CDCl$_3$) δ 10.97 (br s, 1 H) 8.56 (s, 1 H) 8.48 (s, 1 H) 5.13 (d, J = 2.59 Hz, 1 H) 4.81 (dd, J = 9.73, 2.72 Hz, 1 H) 4.03-4.10 (m, 1 H) 3.95-4.01 (m, 1 H) 3.75-3.95 (m, 4 H) 3.48-3.57 (m, 1 H) 3.34 (s, 3 H) 2.61 (s, 3 H) 1.51-1.60 (m, 1 H) 1.28-1.38 (m, 4 H) 1.14-1.28 (m, 1 H) 1.02 (dt, J = 9.70, 6.57 Hz, 1 H) 0.90 (dt, J = 9.83, 6.50 Hz, 1 H) 0.48-0.58 (m, 2 H) 0.28-0.45 (m, 2 H). LCMS-ESI (pos) m/z: 479.0 (M + H)$^+$. |
| 330.0 | (1R,2S)-1-(5-chloropyrimidin-2-yl)-1-methoxypropane-2-sulfonamide (Example 11.3), (R)-tetrahydrofuran-2-carbohydrazide (commercially available from Enamine), and 2-isothiocyanato-1,3-dimethoxypropane (Example 250.1). | (1R,2S)-1-(5-chloro-2-pyrimidinyl)-N-(4-(1,3-dimethoxy-2-propanyl)-5-((2R)-tetrahydro-2-furanyl)-4H-1,2,4-triazol-3-yl)-1-methoxy-2-propanesulfonamide. 1H NMR (600 MHz, DMSO-d$_6$) δ 12.88 (br s, 1 H) 8.96 (s, 2 H) 4.95 (dd, J = 7.08, 5.84 Hz, 1 H) 4.91 (d, J = 3.89 Hz, 1 H) 4.64-4.73 (m, 1 H) 3.97 (br d, J = 7.94 Hz, 1 H) 3.92 (dd, J = 9.89, 7.86 Hz, 1 H) 3.81-3.87 (m, 1 H) 3.76 (q, J = 7.16 Hz, 1 H) 3.72 (dd, J = 10.04, 6.31 Hz, 1 H) 3.58 (dd, J = 10.04, 4.75 Hz, 1 H) 3.44-3.51 (m, 1 H) 3.28 (s, 3 H) 3.24 (s, 3 H) 3.14 (s, 3 H) 2.55 (s, 1 H) 2.34-2.41 (m, 1 H) 2.12-2.20 (m, 1 H) 1.90- 1.98 (m, 2 H) 1.24 (d, J = 7.01 Hz, 3 H). LCMS-ESI (pos) m/z: 505.0 (M + H)$^+$. |

The compound set forth in the following table was synthesized following the procedure in Example 254.0 using the known starting material as described.

TABLE 31

| Example | Reagents | Structure, Name and Data |
|---|---|---|
| 331.0 | (2S,3R)-3-(5-chloro-2-pyrimidinyl)-N-(4-(2,6-dimethoxyphenyl)-5-((3R)-tetrahydro-3-furanyl)-4H-1,2,4-triazol-3-yl)-2-butanesulfonamide or (2S,3R)-3-(5-chloro-2-pyrimidinyl)-N-(4-(2,6-dimethoxyphenyl)-5-((3S)-tetrahydro-3-furanyl)-4H-1,2,4-triazol-3-yl)-2-butanesulfonamide (Example 61.0) | 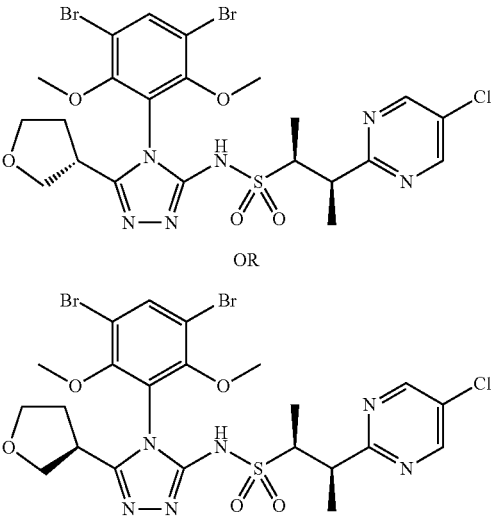 [SMILES: COc1c(Br)cc(Br)c(OC)c1-n1c(NS(=O)(=O)[C@@H](C)[C@H](C)c2ncc(Cl)cn2)nnc1[C@H]1CCOC1 ; COc1c(Br)cc(Br)c(OC)c1-n1c(NS(=O)(=O)[C@@H](C)[C@H](C)c2ncc(Cl)cn2)nnc1[C@@H]1CCOC1]<br>OR<br>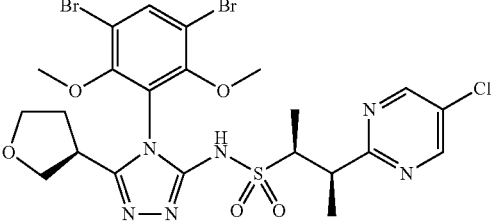<br><br>(2S,3R)-3-(5-chloropyrimidin-2-yl)-N-(4-(3,5-dibromo-2,6-dimethoxyphenyl)-5-((R)-tetrahydrofuran-3-yl)-4H-1,2,4-triazol-3-yl)butane-2-sulfonamide or (2S,3R)-3-(5-chloropyrimidin-2-yl)-N-(4-(3,5-dibromo-2,6-dimethoxyphenyl)-5-((S)-tetrahydrofuran-3-yl)-4H-1,2,4-triazol-3-yl)butane-2-sulfonamide.<br>$^1$H NMR (400 MHz, DMSO-$d_6$) δ = 13.21 (s, 1H), 8.84 (s, 2H), 8.29 (s, 1H), 3.83-3.76 (m, 1H), 3.75 (s, 3H), 3.71 (s, 3H), 3.70-3.57 (m, 4H), 3.31-3.27 (m, 1H), 3.02 (quin, J = 7.2 Hz, 1H), 2.05-1.94 (m, 2H), 1.25 (d, J = 6.8 Hz, 3H), 1.16 (d, J = 6.8 Hz, 3H). |

The compounds set forth in the following table were synthesized following the procedure in Example 140.0 using the known starting material as described.

TABLE 32

| Example | Reagents | Structure, Name and Data |
|---|---|---|
| 332.0 | (1R,2S)-1-(5-chloropyrimidin-2-yl)-1-methoxypropane-2-sulfonamide (Example 11.3), (S)-tetrahydrofuran-2-carbohydrazide (commercially available from Enamine), and 2-isothiocyanato-1,3-dimethoxypropane (Example 250.1). | 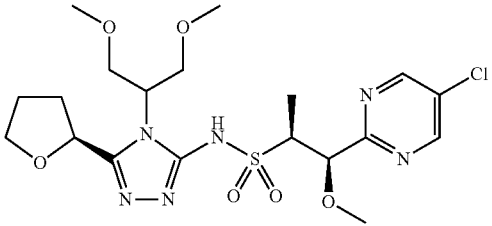 [SMILES: COCC(COC)n1c(NS(=O)(=O)[C@@H](C)[C@H](OC)c2ncc(Cl)cn2)nnc1[C@@H]1CCCO1]<br><br>(1R,2S)-1-(5-chloro-2-pyrimidinyl)-N-(4-(1,3-dimethoxy-2-propanyl)-5-((2S)-tetrahydro-2-furanyl)-4H-1,2,4-triazol-3-yl)-1-methoxy-2-propanesulfonamide. $^1$H NMR (600 MHz, DMSO-$d_6$) δ 12.76 (br s, 1H), 8.96 (s, 2 H) 4.95 (br t, J = 6.46 Hz, 1 H) 4.93 (d, J = 3.89 Hz, 1 H) 4.63-4.74 (m, 1 H) 3.90-4.03 (m, 2 H) 3.80-3.86 (m, 1 H) 3.77 (q, J = 7.32 Hz, 1 H) 3.69 (dd, J = 9.89, 6.31 Hz, 1 H) 3.57 (dd, J = 9.89, 4.44 Hz, 1 H) 3.43-3.50 (m, 1 H) 3.22-3.30 (m, 7 H) 3.13 (s, 3 H) 2.49-2.52 (m, 2 H) 2.33-2.42 (m, 1 H) 2.15 (td, J = 13.55, 7.63 Hz, 1 H) 1.89-2.00 (m, 2 H) 1.25 (d, J = 7.01 Hz, 3 H). LCMS-ESI (pos) m/z: 505.2 (M + H)$^+$. |
| 333.0 | (2S,3R)-3-(5-fluoropyrimidin-2-yl)butane-2-sulfonamide (Example 1.1), (R)-5,5-dimethyltetrahydrofuran-2-carbohydrazide and (S)-5,5-dimethyltetrahydrofuran-2-carbohydrazide (Example 108.2), and 2-isothiocyanato-1,3-dimethoxybenzene (Example 10.0). The racemic mixture was purified by preparative SFC using the following methodology: Column: AD-H (2 × 25 cm) + AD-H (2 × 25 cm) Mobile Phase: 75:25 (A:B) A: Liquid CO2, B: IPA Flow Rate: 60 mL/min, 215 nm, 100 bar inlet pressure to deliver peak 1. | 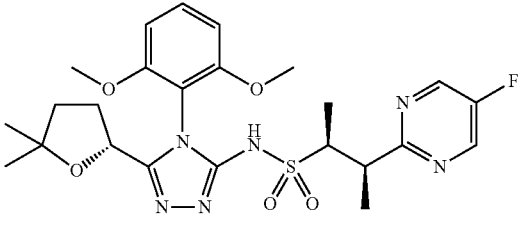<br><br>OR<br><br>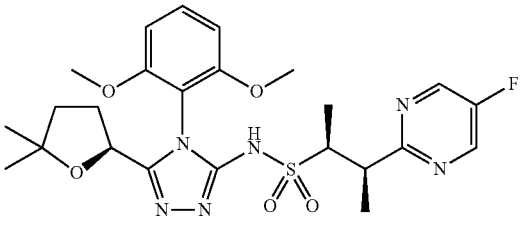<br><br>(2S,3R)-N-(4-(2,6-dimethoxyphenyl)-5-((R)-5,5-dimethyltetrahydrofuran-2-yl)-4H-1,2,4-triazol-3-yl)-3-(5-fluoropyrimidin-2-yl)butane-2-sulfonamide or (2S,3R)-N-(4-(2,6-dimethoxyphenyl)-5-((S)-5,5-dimethyltetrahydrofuran-2-yl)-4H-1,2,4-triazol-3-yl)-3-(5-fluoropyrimidin-2-yl)butane-2-sulfonamide. $^1$H NMR (400 MHz, DMSO-$d_6$) δ 12.84 (s, 1H), 8.81 (s, 2H), 7.47 (t, J = 8.5 Hz, 1H), 6.81 (dd, J = 5.0, 8.5 Hz, 2H), 4.57 (t, J = 6.7 Hz, 1H), 3.76-3.66 (m, 7H), 3.51 (br dd, J = 4.1, 6.6 Hz, 1H), 2.12 (q, J = 7.0 Hz, 2H), 1.69-1.61 (m, 1H), 1.55-1.47 (m, 1H), 1.22 (d, J = 7.3 Hz, 3H), 1.07 (d, J = 7.0 Hz, 3H), 1.04 (s, 3H), 0.99 (s, 3H). LCMS-ESI (pos) m/z: 535.0 (M + H)$^+$. |

TABLE 32-continued

| Example | Reagents | Structure, Name and Data |
|---|---|---|
| 334.0 | (2S,3R)-3-(5-fluoropyrimidin-2-yl)butane-2-sulfonamide (Example 1.1), (R)-5,5-dimethyltetrahydrofuran-2-carbohydrazide and (S)-5,5-dimethyltetrahydrofuran-2-carbohydrazide (Example 108.2), and 2-isothiocyanato-1,3-dimethoxybenzene (Example 10.0). The racemic mixture was purified by preparative SFC using the following methodology: Column: AD-H (2 × 25 cm) + AD-H (2 × 25 cm) Mobile Phase: 75:25 (A:B) A: Liquid $CO_2$, B: IPA Flow Rate: 60 mL/min, 215 nm, 100 bar inlet pressure to deliver peak 2. | 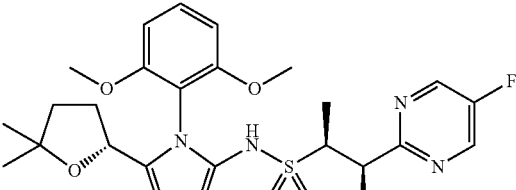<br>OR<br>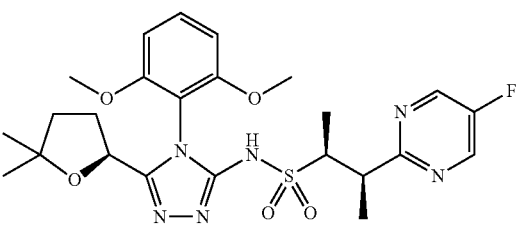<br>(2S,3R)-N-(4-(2,6-dimethoxyphenyl)-5-((R)-5,5-dimethyltetrahydrofuran-2-yl)-4H-1,2,4-triazol-3-yl)-3-(5-fluoropyrimidin-2-yl)butane-2-sulfonamide or (2S,3R)-N-(4-(2,6-dimethoxyphenyl)-5-((S)-5,5-dimethyltetrahydrofuran-2-yl)-4H-1,2,4-triazol-3-yl)-3-(5-fluoropyrimidin-2-yl)butane-2-sulfonamide. $^1$H NMR (400 MHz, DMSO-$d_6$) δ = 12.84 (s, 1H), 8.81 (s, 2H), 7.46 (t, J = 8.5 Hz, 1H), 6.81 (d, J = 8.5 Hz, 2H), 4.57 (t, J = 6.8 Hz, 1H), 3.75-3.66 (m, 7H), 3.56-3.47 (m, 1H), 2.18-2.08 (m, 2H), 1.69-1.60 (m, 1H), 1.51 (td, J = 8.0, 11.9 Hz, 1H), 1.23 (d, J = 7.0 Hz, 3H), 1.08 (d, J = 7.0 Hz, 3H), 1.03 (s, 3H), 0.98 (s, 3H). LCMS-ESI (pos) m/z: 535.0 (M + H)$^+$. |
| 335.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 3-isothiocyanatopentane (commercially available from Oakwood). The title compound was the earlier isomer to elute on an SFC from Chiralpak IC column with 35% MeOH. | 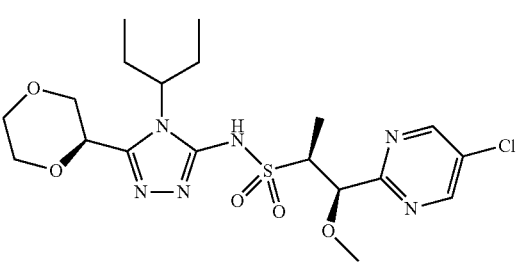<br>OR<br>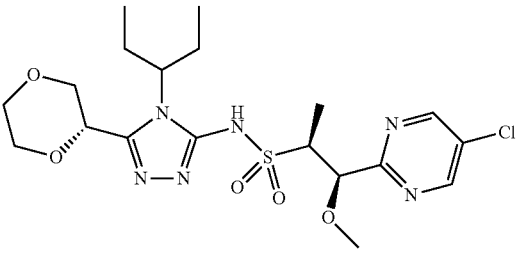<br>(1R,2S)-1-(5-chloro-2-pyrimidinyl)-N-(5-((2R)-1,4-dioxan-2-yl)-4-(3-pentanyl)-4H-1,2,4-triazol-3-yl)-1-methoxy-2-propanesulfonamide or (1R,2S)-1-(5-chloro-2-pyrimidinyl)-N-(5-((2S)-1,4-dioxan-2-yl)-4-(3-pentanyl)-4H-1,2,4-triazol-3-yl)-1-methoxy-2-propanesulfonamide. $^1$H NMR (500 MHz, CDCl$_3$) δ 10.91 (br s, 1H), 8.74 (s, 2 H) 5.02 (d, J = 4.41 Hz, 1 H) 4.58 (dd, J = 7.59, 3.96 Hz, 1 H) 4.00-4.10 (m, 3 H) 3.80-3.93 (m, 3 H) 3.68-3.80 (m, 2 H) 3.39 (s, 3 H) 2.18-2.39 (m, 2 H) 1.74-1.94 (m, 2 H) 1.41 (d, J = 7.14 Hz, 3 H) 0.89 (t, J = 7.40 Hz, 6 H). LCMS-ESI (pos) m/z: 489.0 (M + H)$^+$. |

TABLE 32-continued

| Example | Reagents | Structure, Name and Data |
|---|---|---|
| 336.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and 3-isothiocyanatopentane (commercially available from Oakwood). The title compound was the later isomer to elute on an SFC from Chiralpak IC column with 35% MeOH. | 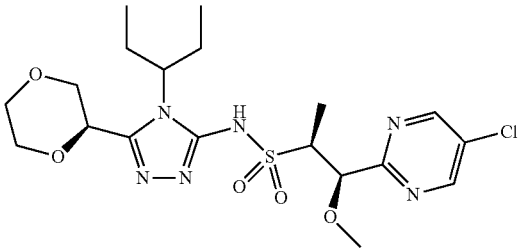 OR 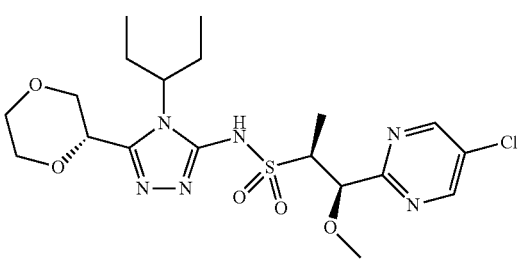 (1R,2S)-1-(5-chloro-2-pyrimidinyl)-N-(5-((2R)-1,4-dioxan-2-yl)-4-(3-pentanyl)-4H-1,2,4-triazol-3-yl)-1-methoxy-2-propanesulfonamide or (1R,2S)-1-(5-chloro-2-pyrimidinyl)-N-(5-((2S)-1,4-dioxan-2-yl)-4-(3-pentanyl)-4H-1,2,4-triazol-3-yl)-1-methoxy-2-propanesulfonamide. $^1$H NMR (600 MHz, DMSO-$d_6$) δ 12.93 (br s, 1 H) 8.96 (s, 2 H) 4.94 (d, J = 3.74 Hz, 1 H) 4.69 (br d, J = 7.32 Hz, 1 H) 4.04 (br s, 1 H) 3.99 (dd, J = 11.52, 2.34 Hz, 1 H) 3.81-3.89 (m, 2 H) 3.69-3.81 (m, 2 H) 3.54-3.63 (m, 1 H) 3.38-3.46 (m, 1 H) 3.13 (s, 3 H) 2.01-2.33 (m, 2 H) 1.71-1.73 (m, 2 H) 1.23 (d, J = 7.01 Hz, 3 H) 0.75-0.83 (m, 6 H). LCMS-ESI (pos) m/z: 489.2 (M + H)$^+$. |
| 337.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and isothiocyanato-methylene)dicyclopropane (commercially available from Enamine). The title compound was the earlier isomer to elute on an SFC from Chiralpak IC column with 40% MeOH. | 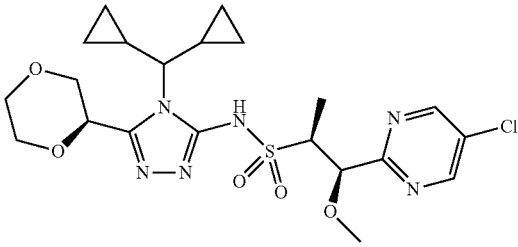 OR 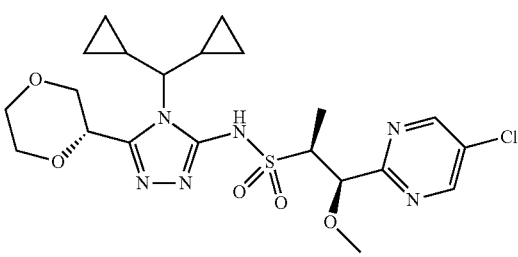 (1R,2S)-1-(5-chloro-2-pyrimidinyl)-N-(4-(dicyclopropylmethyl)-5-((2R)-1,4-dioxan-2-yl)-4H-1,2,4-triazol-3-yl)-1-methoxy-2-propanesulfonamide or (1R,2S)-1-(5-chloro-2-pyrimidinyl)-N-(4-(dicyclopropylmethyl)-5-((2S)-1,4-dioxan-2-yl)-4H-1,2,4-triazol-3-yl)-1-methoxy-2-propanesulfonamide. $^1$H NMR (500 MHz, CDCl$_3$) δ 11.07 (br s, 1 H) 8.72 (s, 2 H) 5.04 (br d, J = 0.91 Hz, 1 H) 4.84-4.96 (m, 1 H) 3.98-4.35 (m, 2 H) 3.56-3.96 (m, 5 H) 3.36 (br s, 3 H) 2.37-2.57 (m, 1 H) 1.97-2.31 (m, 1 H) 1.58-1.96 (m, 1 H) 1.25-1.55 (m, 4 H) 0.17-0.93 (m, 6 H). LCMS-ESI (pos) m/z: 513.0 (M + H)$^+$. |

TABLE 32-continued

| Example | Reagents | Structure, Name and Data |
|---|---|---|
| 338.0 | (1R,2S)-1-(5-chloropyrimidin-2-yl)-1-methoxypropane-2-sulfonamide (Example 11.3), (R)-1,4-dioxane-2-carbohydrazide and (S)-1,4-dioxane-2-carbohydrazide (commercially available from Enamine), and isothiocyanato-methylene)dicyclopropane (commercially available from Enamine). The title compound was the later isomer to elute on an SFC from Chiralpak IC column with 40% MeOH. | 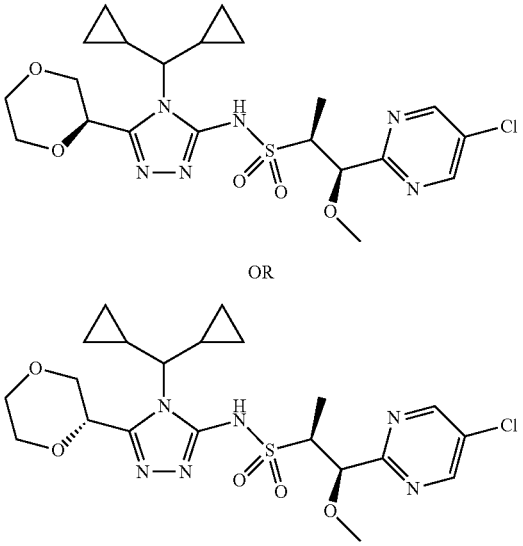 [SMILES: CO[C@H](c1ncc(Cl)cn1)[C@H](C)S(=O)(=O)Nc1nnc([C@@H]2COCCO2)n1C(C1CC1)C1CC1 ; CO[C@H](c1ncc(Cl)cn1)[C@H](C)S(=O)(=O)Nc1nnc([C@H]2COCCO2)n1C(C1CC1)C1CC1]<br>OR<br><br>(1R,2S)-1-(5-chloro-2-pyrimidinyl)-N-(4-(dicyclopropylmethyl)-5-((2R)-1,4-dioxan-2-yl)-4H-1,2,4-triazol-3-yl)-1-methoxy-2-propanesulfonamide or (1R,2S)-1-(5-chloro-2-pyrimidinyl)-N-(4-(dicyclopropylmethyl)-5-((2S)-1,4-dioxan-2-yl)-4H-1,2,4-triazol-3-yl)-1-methoxy-2-propanesulfonamide.<br>$^1$H NMR (500 MHz, DMSO-d$_6$) δ 11.04 (br s, 1H), 8.73 (s, 2 H) 4.97-5.12 (m, 1 H) 3.97-4.18 (m, 2 H) 3.62-3.96 (m, 6 H) 3.38 (s, 3 H) 2.35-2.55 (m, 1 H) 1.98-2.29 (m, 1 H) 1.29-1.45 (m, 3 H) 0.66-0.90 (m, 2 H) 0.17-0.62 (m, 6 H). LCMS-ESI (pos) m/z: 513.0 (M + H)$^+$. |
| 339.0 | Example 303.0 was purified by preparative SFC using the following methodology: Column: Chiralpak IC 2 × 15 cm, Mobile Phase: 50% MeOH, Flow Rate: 80 mL/min, 219 nm, Injection size: 1 mL of a 12.3 mg/mL solution in MeOH to deliver peak 1. | 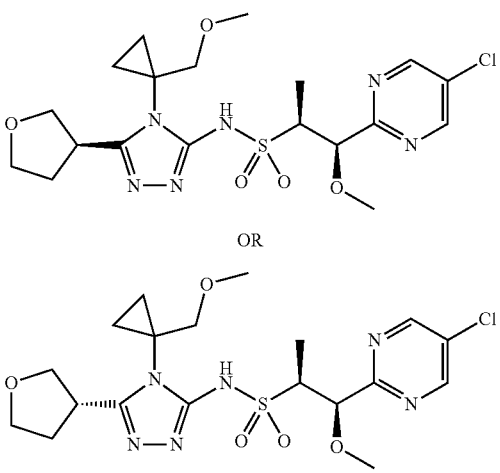<br>OR<br><br>(1R,2S)-1-(5-chloro-2-pyrimidinyl)-1-methoxy-N-(4-(1-(methoxymethyl)cyclopropyl)-5-((3R)-tetrahydro-3-furanyl)-4H-1,2,4-triazol-3-yl)-2-propanesulfonamide or (1R,2S)-1-(5-chloro-2-pyrimidinyl)-1-methoxy-N-(4-(1-(methoxymethyl)cyclopropyl)-5-((3S)-tetrahydro-3-furanyl)-4H-1,2,4-triazol-3-yl)-2-propanesulfonamide.<br>$^1$H NMR (500 MHz, CDCl$_3$) δ 8.70 (s, 2H), 5.08 (d, J = 3.50 Hz, 1H), 4.00-4.17 (m, 3H), 3.77-3.98 (m, 3H), 3.57-3.71 (m, 1H), 3.28 (s, 6H), 2.63-3.04 (m, 1H), 1.99-2.42 (m, 2H), 1.38 (d, J = 7.01 Hz, 3H), 0.59-1.29 (m, 4H). LCMS-ESI (pos) m/z: 487.0 (M + H)$^+$. |

TABLE 32-continued

| Example | Reagents | Structure, Name and Data |
|---|---|---|
| 340.0 | Example 303.0 was purified by preparative SFC using the following methodology: Column: Chiralpak IC 2 × 15 cm, Mobile Phase: 50% MeOH, Flow Rate: 80 mL/min, 219 nm, Injection size: 1 mL of a 12.3 mg/mL solution in MeOH to deliver peak 2. | 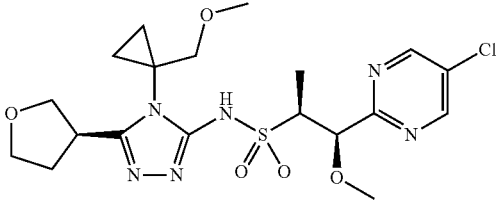<br>OR<br>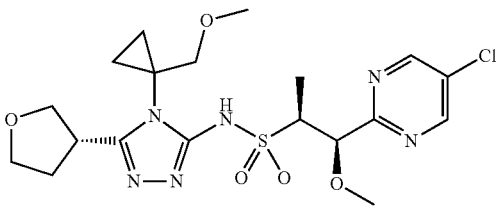<br><br>(1R,2S)-1-(5-chloro-2-pyrimidinyl)-1-methoxy-N-(4-(1-(methoxymethyl)cyclopropyl)-5-((3R)-tetrahydro-3-furanyl)-4H-1,2,4-triazol-3-yl)-2-propanesulfonamide or (1R,2S)-1-(5-chloro-2-pyrimidinyl)-1-methoxy-N-(4-(1-(methoxymethyl)cyclopropyl)-5-((3S)-tetrahydro-3-furanyl)-4H-1,2,4-triazol-3-yl)-2-propanesulfonamide.<br>$^1$H NMR (500 MHz, CDCl$_3$) δ 8.70 (s, 2H), 6.32 (br s, 1H), 5.07 (d, J = 3.50 Hz, 1H), 4.11 (br s, 1H), 4.03 (br d, J = 6.10 Hz, 1H), 3.92 (br d, J = 7.53 Hz, 1H), 3.84 (br s, 2H), 3.65 (br dd, J = 3.70, 6.94 Hz, 1H), 3.27 (br s, 6H), 2.64-2.99 (m, 1H), 1.90-2.40 (m, 2H), 1.39 (d, J = 7.01 Hz, 3H), 1.03-1.28 (m, 4H). LCMS-ESI (pos) m/z: 487.0 (M + H)$^+$. |
| 341.0 | Example 304.0 was purified by preparative SFC using the following methodology: Column: Regis Whelk-O s,s 2 × 15 cm, Mobile Phase: 25% MeOH, Flow Rate: 80 mL/min, 219 nm, Injection size: 0.5 mL of a 11.73 mg/mL solution in MeOH to deliver peak 1. | 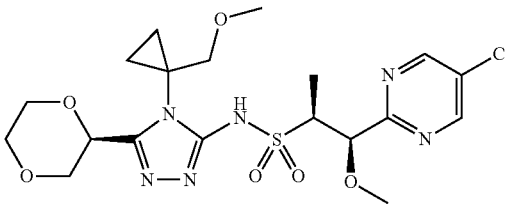<br>OR<br>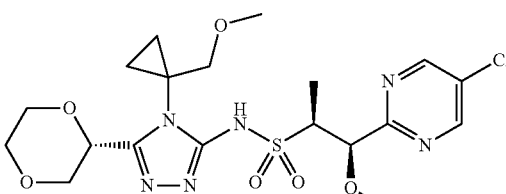<br><br>(1R,2S)-N-(5-((S)-1,4-dioxan-2-yl)-4-(1-(methoxymethyl)cyclopropyl)-4H-1,2,4-triazol-3-yl)-1-(5-chloropyrimidin-2-yl)-1-methoxypropane-2-sulfonamide or (1R,2S)-N-(5-((R)-1,4-dioxan-2-yl)-4-(1-(methoxymethyl)cyclopropyl)-4H-1,2,4-triazol-3-yl)-1-(5-chloropyrimidin-2-yl)-1-methoxypropane-2-sulfonamide. $^1$H NMR (500 MHz, CDCl$_3$) δ 8.71 (s, 2H), 6.04 (br s, 1H), 5.03-5.10 (m, 2H), 3.93-4.07 (m, 2H), 3.74-3.90 (m, 5H), 3.64 (dq, J = 3.57, 6.98 Hz, 1H), 3.24-3.32 (m, 3H), 3.21-3.24 (m, 3H), 2.78-2.99 (m, 1H), 1.43-1.50 (m, 1H), 1.39 (d, J = 7.01 Hz, 3H), 1.21 (t, J = 7.20 Hz, 1H), 1.13 (br d, J = 2.98 Hz, 2H). LCMS-ESI (pos) m/z: 503.2 (M + H)$^+$. |

TABLE 32-continued

| Example | Reagents | Structure, Name and Data |
|---|---|---|
| 342.0 | Example 304.0 was purified by preparative SFC using the following methodology: Column: Regis Whelk-O s,s 2 × 15 cm, Mobile Phase: 25% MeOH, Flow Rate: 80 mL/min, 219 nm, Injection size: 0.5 mL of a 11.73 mg/mL solution in MeOH to deliver peak 2. | 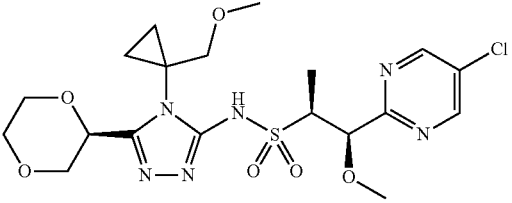<br>OR<br>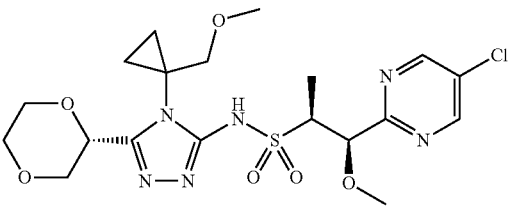<br>(1R,2S)-N-(5-((S)-1,4-dioxan-2-yl)-4-(1-(methoxymethyl)cyclopropyl)-4H-1,2,4-triazol-3-yl)-1-(5-chloropyrimidin-2-yl)-1-methoxypropane-2-sulfonamide or (1R,2S)-N-(5-((R)-1,4-dioxan-2-yl)-4-(1-(methoxymethyl)cyclopropyl)-4H-1,2,4-triazol-3-yl)-1-(5-chloropyrimidin-2-yl)-1-methoxypropane-2-sulfonamide. $^1$H NMR (500 MHz, CDCl$_3$) δ 8.70 (s, 2H), 5.93-6.08 (m, 1H), 5.01-5.08 (m, 2H), 3.92-4.08 (m, 2H), 3.73-3.88 (m, 5H), 3.66 (dq, J = 4.02, 6.96 Hz, 1H), 3.31 (s, 3H), 3.29 (s, 3H), 2.88-3.00 (m, 1H), 1.39 (d, J = 7.01 Hz, 3H), 1.18-1.31 (m, 2H), 1.07-1.17 (m, 2H). LCMS-ESI (pos) m/z: 503.2 (M + H)$^+$. |
| 343.0 | (2S,3R)-3-(5-chloropyrimidin-2-yl)butane-2-sulfonamide (Example 1.4), (R)-5-oxopyrrolidine-2-carbohydrazide and (S)-5-oxopyrrolidine-2-carbohydrazide (commercially available from Enamine), and 2-isothiocyanato-1,3-dimethoxybenzene (Example 10.0). The racemic mixture was purified by preparative SFC using the following methodology: Column: OJ-H (2 × 25 cm) + OJ-H (2 × 25 cM), Mobile Phase: 85: 15 (A:B) A: Liquid CO$_2$) B: IPA, Flow Rate: 80 mL/min, 220 nm, 100 bar inlet pressure to deliver peak 1. | 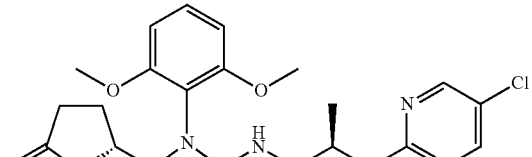<br>OR<br>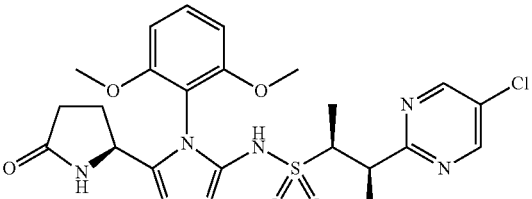<br>(2S,3R)-3-(5-chloropyrimidin-2-yl)-N-(4-(2,6-dimethoxyphenyl)-5-((R)-5-oxopyrrolidin-2-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-5-oxopyrrolidin-2-yl)-4H-1,2,4-triazol-3-yl)butane-2-sulfonamide. $^1$H NMR (400 MHz, DMSO-d$_6$) δ 13.19-12.49 (m, 1H), 8.86 (s, 2H), 8.03 (s, 1H), 7.51 (t, J = 8.5 Hz, 1H), 6.86-6.81 (m, 2H), 4.34 (dd, J = 3.3, 8.9 Hz, 1H), 3.78-3.75 (m, 3H), 3.75-3.74 (m, 3H), 3.68-3.60 (m, 1H), 3.57-3.50 (m, 1H), 2.17-2.05 (m, 1H), 2.04-1.92 (m, 1H), 1.85-1.72 (m, 2H), 1.22 (d, J = 7.3 Hz, 3H), 1.09 (d, J = 7.0 Hz, 3H). LCMS-ESI (pos) m/z: 536.0 (M + H)$^+$. |

TABLE 32-continued

| Example | Reagents | Structure, Name and Data |
|---|---|---|
| 344.0 | (2S,3R)-3-(5-chloropyrimidin-2-yl)butane-2-sulfonamide (Example 1.4), (R)-5-oxopyrrolidine-2-carbohydrazide and (S)-5-oxopyrrolidine-2-carbohydrazide (commercially available from Enamine), and 2-isothiocyanato-1,3-dimethoxybenzene (Example 10.0). The racemic mixture was purified by preparative SFC using the following methodology: Column: OJ-H (2 × 25 cm) + OJ-H (2 × 25 cM), Mobile Phase: 85: 15 (A:B) A: Liquid CO$_2$) B: IPA, Flow Rate: 80 mL/min, 220 nm, 100 bar inlet pressure to deliver peak 2. | 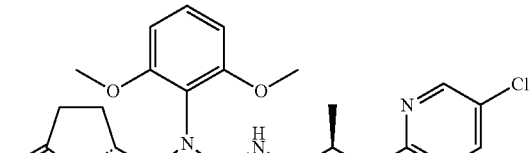<br>OR<br>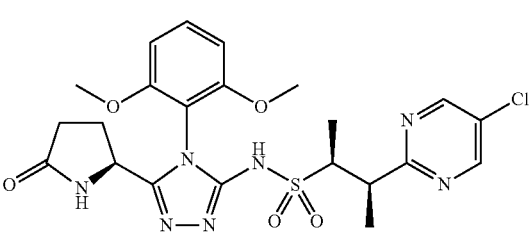<br>(2S,3R)-3-(5-chloropyrimidin-2-yl)-N-(4-(2,6-dimethoxyphenyl)-5-((R)-5-oxopyrrolidin-2-yl)-4H-1,2,4-triazol-3-yl)butane-2-sulfonamide or (2S,3R)-3-(5-chloropyrimidin-2-yl)-N-(4-(2,6-dimethoxyphenyl)-5-((S)-5-oxopyrrolidin-2-yl)-4H-1,2,4-triazol-3-yl)butane-2-sulfonamide. $^1$H NMR (400 MHz, DMSO-d$_6$) δ 12.91 (s, 1H), 8.86 (s, 2H), 8.05 (s, 1H), 7.51 (t, J = 8.5 Hz, 1H), 6.83 (br d, J = 8.7 Hz, 1H), 4.35 J = 3.0, 8.8 Hz, 1H), 3.78-3.75 (m, 3H), 3.75-3.71 (m, 3H), 3.67-3.59 (dd, (m, 1H), 3.56-3.48 (m, 1H), 2.16-2.06 (m, 1H), 2.05-1.95 (m, 1H), 1.84-1.72 (m, 2H), 1.23 (d, J = 7.0 Hz, 3H), 1.09 (d, J = 7.0 Hz, 3H). LCMS-ESI (pos) m/z: 536.0 (M + H)$^+$. |

Example 13.8. Preparation of (1R,2S)-1-hydroxy-N,N-bis(4-methoxybenzyl)-1-(5-methylpyrimidin-2-yl)propane-2-sulfonamide

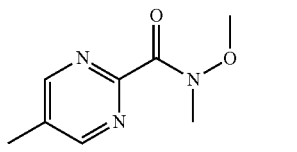

N-Methoxy-N,5-dimethylpyrimidine-2-carboxamide, Example 13.7

To a solution of 5-methylpyrimidine-2-carboxylic acid (1 g, 7.24 mmol) in DMF (72.4 ml) was added 5-methylpyrimidine-2-carboxylic acid (1 g, 7.24 mmol), and N,O-dimethyl hydroxylamine hydrochloride (0.777 g, 7.96 mmol). The mixture was cooled to 0° C. and 1-propanephosphonic acid cyclic anhydride, 50 wt. % solution in EtOAc (9.21 ml, 14.48 mmol) was added droppwise. The mixture was allowed to warm to RT overnight. LCMS indicated complete conversion to product. The mixture was diluted with water, extracted with CHCl$_3$:IPA (3:1) and washed with brine and NaHCO$_3$. The mixture was dried over Na$_2$SO$_4$, concentrated in vacuo and purified by silica gel chromatography (0-100% heptanes:EtOAc) to yield N-methoxy-N,5-dimethylpyrimidine-2-carboxamide (0.7 g, 3.86 mmol, 53.4% yield). $^1$H NMR (500 MHz, CDCl$_3$) δ 8.61-8.69 (m, 2H) 3.61-3.79 (m, 3H) 3.27-3.47 (m, 3H) 2.34-2.45 (m, 3H). LCMS-ESI (pos) m/z: 182.2 (M+H)$^+$.

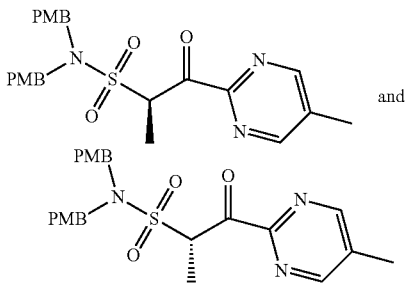

(R)—N,N-Bis(4-methoxybenzyl)-1-(5-methylpyrimidin-2-yl)-1-oxopropane-2-sulfonamide and (S)—N,N-bis(4-methoxybenzyl)-1-(5-methylpyrimidin-2-yl)-1-oxopropane-2-sulfonamide, Example 13.2

A solution of N,N-bis(4-methoxybenzyl)ethanesulfonamide (azeotroped three times with toluene before use) (Example 12.0, 0.771 g, 2.21 mmol) was dissolved in THF (3.68 ml) and then cooled to −78° C. using a dry ice acetone bath (internal reaction temperature/bath temperature not monitored). To this was added a solution of n-butyllithium (0.883 ml, 2.21 mmol, 2.5 M in hexanes). The reaction turned pink immediately and then slowly faded to yellow upon stirring at −78° C. for 30 mins. This solution was then added quickly to a solution of N-methoxy-N,5-dimethylpyrimidine-2-carboxamide (Example 13.7, 0.2 g, 1.104 mmol) in THF (0.5 mL) at RT. The reaction was stirred at RT for ~20 mins after which LCMS indicated complete consumption of Weinreb amide and conversion to product. The reaction was quenched by addition to separation funnel that contained 1M HCl (~15 mL). The mixture was extracted with DCM, dried over Na₂SO₄ and concentrated in vacuo. The mixture was purified by silica gel chromatography 0-100% EtOAc:heptanes to yield N,N-bis(4-methoxybenzyl)-1-(5-methylpyrimidin-2-yl)-1-oxopropane-2-sulfonamide (0.36 g, 0.767 mmol, 69.5% yield). ¹H NMR (500 MHz, DMSO-d₆) δ 8.86-8.93 (m, 2H) 7.06-7.15 (m, 4H) 6.79-6.87 (m, 4H) 5.87-5.95 (m, 1H) 4.20-4.34 (m, 4H) 3.67-3.73 (m, 6H) 2.38-2.42 (m, 3H) 1.46-1.55 (m, 3H). LCMS-ESI (pos) m/z: 470.0 (M+H)⁺.

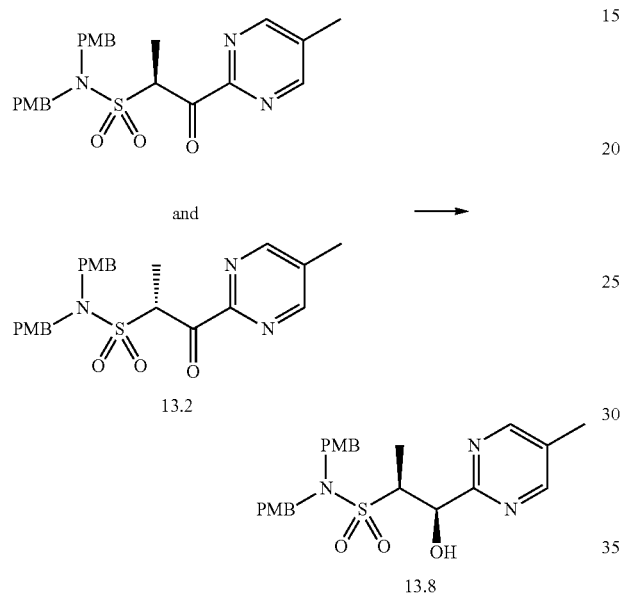

(1R,2S)-1-Hydroxy-N,N-bis(4-methoxybenzyl)-1-(5-methylpyrimidin-2-yl)propane-2-sulfonamide, Example 13.8

To a solution of Example 13.2 (1.0 g, 2.130 mmol) in DMF (22.18 ml) was added (N-((1S,2S)-1,2-diphenyl-2-((3-phenylpropyl)amino)ethyl)-4-methylphenylsulfonamido)ruthenium(II) chloride (9.91 mg, 0.016 mmol). The mixture was then degassed by placing under vacuum and backfilling with N₂ three times. To this was added a solution of HCOOH:Et₃N (5:2 v/v) (0.55 mL) and the reaction stirred at RT for 12 hrs after which LCMS indicated complete conversion to product and 7:1 d.r. (syn:anti). The mixture was then washed with 5% LiCl (aq), extracted with DCM and then with CHCl₃:IPA (3:1). The organic layer was dried over Na₂SO₄ and concentrated in vacuo. The mixture was loaded directly onto a silica gel column and purified using a gradient of 0-100% heptanes:EtOAc. DMF caused both syn and anti to co-elute. The factions were combined and concentrated in vacuo. The mixture was repurified using the same gradient to yield (1R,2S)-1-hydroxy-N,N-bis(4-methoxybenzyl)-1-(5-methylpyrimidin-2-yl)propane-2-sulfonamide (0.77 g, 1.63 mmol, 77% yield) as an off white solid. ¹H NMR (500 MHz, DMSO-d₆) δ 8.85-8.93 (m, 2H) 7.08-7.15 (m, 4H) 6.78-6.86 (m, 4H) 5.86-5.96 (m, 1H) 4.20-4.35 (m, 4H) 3.68-3.75 (m, 6H) 3.28-3.34 (m, 2H) 2.37-2.42 (m, 3H) 1.47-1.54 (m, 3H). LCMS-ESI (pos) m/z: 572.2 (M+H)⁺.

The compounds set forth in the following Table were synthesized following the procedure in Example 13.0 using the known starting material as described.

TABLE 33

| Example | Reagents | Structure, Name and Data |
|---|---|---|
| 360.1 | 2-chloro-5-fluoropyrimidine (commercially available from Aldrich). | (1S,2S)-1-(5-fluoropyrimidin-2-yl)-1-isopropoxypropane-2-sulfonamide. ¹H NMR (400 MHz, DMSO-d₆) δ 0.91 (br d, J = 5.70 Hz, 3 H) 0.98 (br d, J = 6.84 Hz, 3 H) 1.13 (br d, J = 5.39 Hz, 3 H) 3.50-3.55 (m, 2 H) 4.78 (br d, J = 8.09 Hz, 1 H) 6.47 (br s, 2 H) 8.94 (s, 2 H). LCMS-ESI (pos) m/z: 278.2 (M + H)⁺. |
| 362.1 | 2-chloro-5-methoxylpyrimidine (commercially available from Combi-Blocks). | (1S,2S)-1-(5-methoxylpyrimidin-2-yl)-1-isopropoxypropane-2-sulfonamide. ¹H NMR (400 MHz, DMSO-d6) δ 0.84-0.96 (m, 6 H) 1.13 (br d, J = 4.98 Hz, 3 H) 3.46-3.49 (m, 1 H) 3.50-3.68 (m, 1 H) 3.93 (br s, 3 H) 4.68 (br d, J = 8.71 Hz, 1 H) 6.41 (br s, 2 H) 8.58 (br s, 2 H). LCMS-ESI (pos) m/z: 290.2 (M + H)⁺. |
| 364.1 | 2-chloro-5-methylpyrazine (commercially available from Combi-Blocks). | (1S,2S)-1-(5-methylpyrazin-2-yl)-1-isopropoxypropane-2-sulfonamide. ¹H NMR (400 MHz, DMSO-d6) δ 0.96 (br d, J = 5.39 Hz, 3 H) 1.05 (br d, J = 6.74 Hz, 3 H) 1.15 (br d, J = 5.18 Hz, 3 H) 3.43-3.74 (m, 5 H) 4.78 (br d, J = 6.63 Hz, 1 H) 6.51 (br s, 2 H) 8.52 (s, 1 H) 8.60 (s, 1 H). LCMS-ESI (pos) m/z: 272.2 (M + H)+. |
| 366.1 | 2-chloro-5-methylpyridine (commercially available from Aldrich). | |

TABLE 33-continued

| Example | Reagents | Structure, Name and Data |
|---|---|---|
| | | (1S,2S)-1-(5-methylpyridin-2-yl)-1-isopropoxypropane-2-sulfonamide. $^1$H NMR (400 MHz, DMSO-d6) δ 0.93 (br d, J = 6.22 Hz, 6 H) 1.13 (br d, J = 5.29 Hz, 3 H) 2.30 (s, 3 H) 3.41-3.45 (m, 2 H) 4.65 (br d, J = 7.77 Hz, 1 H) 6.41 (br s, 2 H) 7.38 (br d, J = 7.77 Hz, 1 H) 7.64 (br d, J = 7.67 Hz, 1 H) 8.39 (br s, 1 H). LCMS-ESI (pos) m/z: 273.2 (M + H)+. |

The compounds set forth in the following Table were synthesized following the procedure in Example 11.0 using the known starting material as described.

TABLE 34

| Example | Reagents | Structure, Name and Data |
|---|---|---|
| 378.1 | 2-chloro-5-methoxypyrazine (commercially available from Combi-Blocks). | (1R,2S)-1-methoxy-1-(5-methoxypyrazin-2-yl)propane-2-sulfonamide. $^1$H NMR (400 MHz, DMSO-d6) δ 1.19 (br d, J = 6.74 Hz, 3 H) 3.29-3.32 (m, 3 H) 3.32-3.38 (m, 1 H) 3.92 (s, 3 H) 4.86 (br s, 1 H) 6.78 (br s, 2 H) 8.18 (s, 1 H) 8.32 (s, 1 H). LCMS-ESI (pos) m/z: 262.2 (M + H)$^+$. |

The compounds set forth in the following Table were synthesized following the procedure in Example 108.0 using the known starting material as described.

TABLE 35

| Example | Reagents | Structure, Name and Data |
|---|---|---|
| 346.1 | Hexahydro-2H-cyclopenta[b]furan-3a-carboxylic acid (commercially available from Enamine). | (3aS,6aR)-hexahydro-3aH-cyclopenta[b]furan-3a-carbohydrazide and (3aR,6aS)-hexahydro-3aH-cyclopenta[b]furan-3a-carbohydrazide. LCMS-ESI (pos) m/z: 171.2 (M + H)$^+$. |
| 405.1 | 1-methyl-5-oxopyrrolidine-2-carboxylic acid (commercially available from Enamine). | (R)-1-methyl-5-oxopyrrolidine-2-carbohydrazide hydrochloride and (S)-1-methyl-5-oxopyrrolidine-2-carbohydrazide hydrochloride. LCMS-ESI (pos) m/z: 158.2 (M + H)$^+$. |
| 345.1 | (3R)-oxolane-3-carboxylate (commercially available from Pharmablock Co. Ltd). | (R)-tetrahydrofuran-3-carbohydrazide (145.7 mg, 1.120 mmol, 21.74% yield). $^1$H NMR (400 MHz, CD$_2$Cl$_2$) δ 6.84 (br. s., 1H), 4.14-3.54 (m, 6H), 2.87-2.77 (m, 1H), 2.17-2.03 (m, 2H). |

The compounds set forth in the following Table were synthesized following the procedure in Example 140.0 using the known starting material as described except Example 383.0 was prepared using the procedure of Example 24.0.

TABLE 36

| Example | Reagents | Structure, Name and Data |
|---|---|---|
| 345.0 | 2-(2-cyano-4-fluorophenyl)ethanesulfonamide (Example 146.7), (R)-tetrahydrofuran-3-carbohydrazide, (Example 345.1), and isothiocyanato-1,3-dimethoxybenzene (Example 10.0). | 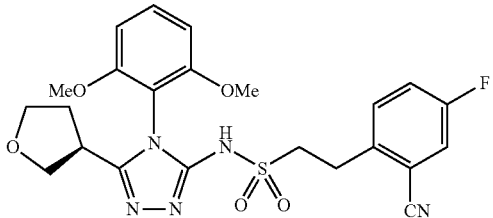 [SMILES: COc1cccc(OC)c1-n1c(NS(=O)(=O)CCc2ccc(F)cc2C#N)nnc1[C@@H]1CCOC1]<br>(S)-2-(2-cyano-4-fluorophenyl)-N-(4-(2,6-dimethoxyphenyl)-5-(tetrahydrofuran-3-yl)-4H-1,2,4-triazol-3-yl)ethanesulfonamide. $^1$H NMR (600 MHz, DMSO-$d_6$) δ 1.87-1.97 (m, 1 H) 2.03 (dq, J = 13.78, 6.41 Hz, 1 H) 2.95 (dq, J = 8.72, 6.75 Hz, 1 H) 3.04-3.10 (m, 2 H) 3.19-3.25 (m, 2 H) 3.59-3.66 (m, 3 H) 3.72-3.76 (m, 1 H) 3.77 (s, 3 H) 3.77 (s, 3 H) 6.87 (dd, J = 8.72, 2.18 Hz, 2 H) 7.46-7.50 (m, 1 H) 7.50-7.56 (m, 2 H) 7.80 (dd, J = 8.72, 2.80 Hz, 1 H) 13.03 (s, 1 H). LCMS-ESI (pos) m/z: 502.0 (M + H)$^+$. |
| 346.0 | Hexahydro-3aH-cyclopenta[b]furan-3a-carbohydrazide (Example 346.1), isothiocyanato-1,3-dimethoxybenzene (Example 10.0), and (1R,2S)-1-(5-chloropyrimidin-2-yl)-1-methoxypropane-2-sulfonamide (Example 11.3). The mixture was separated by SFC using the following conditions: Column: Chiralpak IC 2 × 15 cm + Chiralpak IC 2 × 25 cm, Mobile Phase: 50% MeOH, Flowrate: 60 mL/min, BPR: 100 bar, UV Detector Wavelength: 220 nm. This was the first peak to elute under these conditions. | 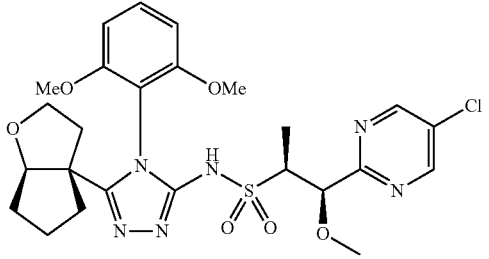<br>OR<br>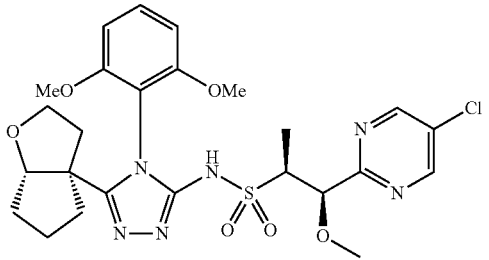<br>(1R,2S)-1-(5-chloropyrimidin-2-yl)-N-(4-(2,6-dimethoxyphenyl)-5-((3aR,6aR)-hexahydro-3aH-cyclopenta[b]furan-3a-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((3aS,6aS)-hexahydro-3aH-cyclopenta[b]furan-3a-yl)-4H-1,2,4-triazol-3-yl)-1-methoxypropane-2-sulfonamide. $^1$H NMR (500 MHz, DMSO-$d_6$) δ 12.66-12.85 (m, 1 H) 8.79-9.00 (m, 2 H) 7.45-7.59 (m, 1 H) 6.79-6.89 (m, 2 H) 5.60-5.78 (m, 1 H) 4.68-4.87 (m, 2 H) 3.79 (s, 3 H) 3.74 (s, 3 H) 3.71 (ddd, J = 8.6, 6.7, 4.9 Hz, 1 H) 3.34-3.38 (m, 1 H) 3.09-3.15 (m, 3 H) 2.21-2.28 (m, 1 H) 1.68-1.78 (m, 1 H) 1.59-1.67 (m, 1 H) 1.52-1.59 (m, 1 H) 1.42-1.51 (m, 2 H) 1.31-1.42 (m, 2 H) 1.10 (d, J = 6.9 Hz, 3 H). LCMS-ESI (pos) m/z: 579.2 (M + H)$^+$. |

TABLE 36-continued

| Example | Reagents | Structure, Name and Data |
|---|---|---|
| 347.0 | Hexahydro-3aH-cyclopenta[b]furan-3a-carbohydrazide (Example 346.1), isothiocyanato-1,3-dimethoxybenzene (Example 10.0), and (1R,2S)-1-(5-chloropyrimidin-2-yl)-1-methoxypropane-2-sulfonamide (Example 11.3). The mixture was separated by SFC using the following conditions: Column: Chiralpak IC 2 × 15 cm + Chiralpak IC 2 × 25 cm, Mobile Phase: 50% MeOH, Flowrate: 60 mL/min, BPR: 100 bar, UV Detector Wavelength: 220 nm. This was the second peak to elute under these conditions. | 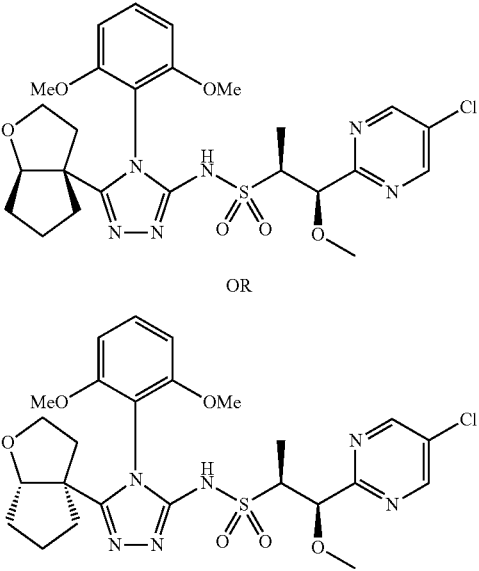 [SMILES: COc1cccc(OC)c1-n1c(NS(=O)(=O)[C@@H](C)[C@H](OC)c2ncc(Cl)cn2)nnc1[C@]12CCC[C@H]1OCC2 ; COc1cccc(OC)c1-n1c(NS(=O)(=O)[C@@H](C)[C@H](OC)c2ncc(Cl)cn2)nnc1[C@@]12CCC[C@@H]1OCC2]  (1R,2S)-1-(5-chloropyrimidin-2-yl)-N-(4-(2,6-dimethoxyphenyl)-5-((3aR,6aR)-hexahydro-3aH-cyclopenta[b]furan-3a-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((3aS,6aS)-hexahydro-3aH-cyclopenta[b]furan-3a-yl)-4H-1,2,4-triazol-3-yl)-1-methoxypropane-2-sulfonamide. $^1$H NMR (500 MHz, DMSO-$d_6$) δ 12.70-12.86 (m, 1 H) 8.85-8.98 (m, 2 H) 7.41-7.57 (m, 1 H) 6.79-6.90 (m, 2 H) 4.70-4.82 (m, 2 H) 3.68-3.80 (m, 7 H) 3.34-3.43 (m, 2 H) 3.13 (s, 3 H) 2.22-2.30 (m, 1 H) 1.66-1.78 (m, 1 H) 1.59-1.65 (m, 1 H) 1.53 (s, 1 H) 1.43-1.50 (m, 2 H) 1.30-1.41 (m, 2 H) 1.10 (d, J = 7.0 Hz, 3 H) LCMS-ESI (pos) m/z: 579.2 (M + H)$^+$. |
| 350.0 | Tetrahydrofuran-2-carbohydrazide (J & W PharmLab, LLC), isothiocyanato-1,3-dimethoxybenzene (Example 10.0), and 1-phenylethane-1-sulfonamide (Enamine). The mixture was separated by SFC: Column: Regis Whelk-O s,s 2 × 15 cm + Regis Whelk-O s,s 2 × 15 cm, Mobile Phase: 30% MeOH, Flowrate: 80 mL/min, BPR: 100 bar, UV Detector Wavelength: 225 nm. Under these conditions, this was the first peak to elute | 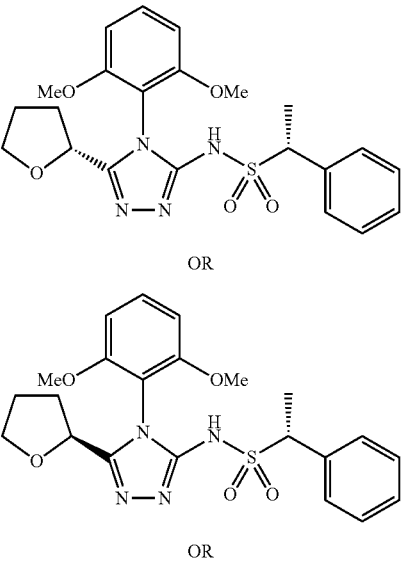 [SMILES: COc1cccc(OC)c1-n1c(NS(=O)(=O)[C@H](C)c2ccccc2)nnc1[C@H]1CCCO1 ; COc1cccc(OC)c1-n1c(NS(=O)(=O)[C@H](C)c2ccccc2)nnc1[C@@H]1CCCO1] |

| Example | Reagents | Structure, Name and Data |
|---|---|---|
| | | 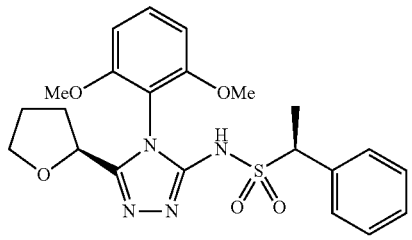
OR
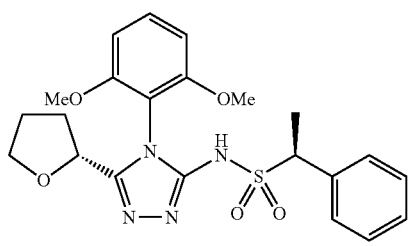
(S)-N-(4-(2,6-dimethoxyphenyl)-5-((S)-tetrahydrofuran-2-yl)-4H-1,2,4-triazol-3-yl)-1-phenylethane-1-sulfonamide or (R)-N-(4-(2,6-dimethoxyphenyl)-5-((S)-tetrahydrofuran-2-yl-4H-1,2,4-triazol-3-yl)-1-phenylethane-1-sulfonamide or (S)-N-(4-(2,6-dimethoxyphenyl)-5-((R)-tetrahydrofuran-2-yl)-4H-1,2,4-triazol-3-yl)-1-phenylethane-1-sulfonamide or (R)-N-(4-(2,6-dimethoxyphenyl)-5-((R)-tetrahydrofuran-2-yl)-4H-1,2,4-triazol-3-yl)-1-phenylethane-1-sulfonamide.
$^1$H NMR (500 MHz, DMSO-$d_6$) δ 12.69-12.83 (m, 1 H) 7.44-7.56 (m, 1 H) 7.12-7.37 (m, 5 H) 6.75-6.96 (m, 2 H) 4.39-4.53 (m, 1 H) 4.05-4.19 (m, 1 H) 3.76-3.82 (m, 6 H) 3.61-3.67 (m, 1 H) 3.47-3.53 (m, 1 H) 1.93-2.14 (m, 2 H) 1.75-1.83 (m, 2 H) 1.46-1.53 (m, 3 H) LCMS-ESI (pos) m/z: 459.2 (M + H)$^+$. |
| 351.0 | Tetrahydrofuran-2-carbohydrazide (J & W PharmLab, LLC), isothiocyanato-1,3-dimethoxybenzene (Example 10.0), and 1-phenylethane-1-sulfonamide (Enamine). The mixture was separated by SFC: Column: Regis Whelk-O s,s 2 × 15 cm + Regis Whelk-O s,s 2 × 15 cm, Mobile Phase: 30% MeOH, Flowrate: 80 mL/min, BPR: 100 bar, UV Detector Wavelength: 225 nm. Under these conditions, this was the second peak to elute | 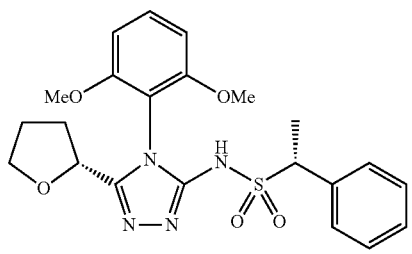
OR
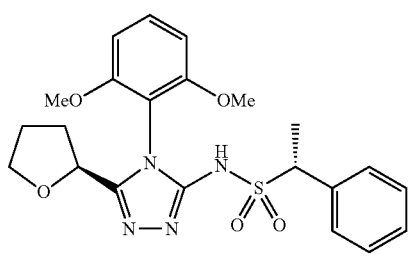
OR |

TABLE 36-continued

| Example | Reagents | Structure, Name and Data |
|---|---|---|
| | | 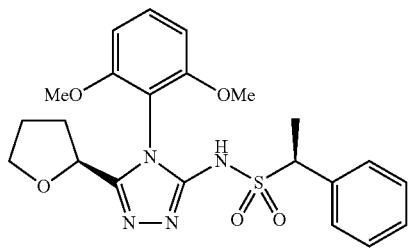<br>OR<br>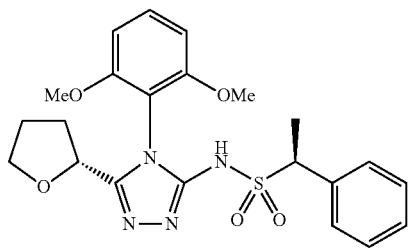<br>(S)-N-(4-(2,6-dimethoxyphenyl)-5-((S)-tetrahydrofuran-2-yl)-4H-1,2,4-triazol-3-yl)-1-phenylethane-1-sulfonamide or (R)-N-(4-(2,6-dimethoxyphenyl)-5-((S)-tetrahydrofuran-2-yl)-4H-1,2,4-triazol-3-yl)-1-phenylethane-1-sulfonamide or (S)-N-(4-(2,6-dimethoxyphenyl)-5-((R)-tetrahydrofuran-2-yl)-4H-1,2,4-triazol-3-yl)-1-phenylethane-1-sulfonamide or (R)-N-(4-(2,6-dimethoxyphenyl)-5-((R)-tetrahydrofuran-2-yl)-4H-1,2,4-triazol-3-yl)-1-phenylethane-1-sulfonamide.<br>$^1$H NMR (500 MHz, DMSO-$d_6$) δ 12.55-12.83 (m, 1 H) 7.45-7.55 (m, 1 H) 7.18-7.33 (m, 5 H) 6.82-6.91 (m, 2 H) 4.45-4.55 (m, 1 H) 4.13 (q, J = 7.0 Hz, 1 H) 3.75-3.85 (m, 6 H) 3.62-3.69 (m, 1 H) 3.48-3.56 (m, 1 H) 1.92-2.13 (m, 2 H) 1.72-1.83 (m, 2 H) 1.45-1.55 (m, 3 H) LCMS-ESI (pos) m/z: 459.2 (M + H)$^+$. |
| 352.0 | (1S,2S)-1-(5-chloropyrimidin-2-yl)-1-isopropoxypropane-2-sulfonamide (Example 13.6), (2S,5S)-5-methyltetrahydrofuran-2-carbohydrazide and (2R,5R)-5-methyltetrahydrofuran-2-carbohydrazide (commercially available from Ukrorgsyntez), and cyclopropyl isothiocyanate (commercially available from Sigma-Aldrich Corporation). The diastereomer mixture was purified by preparative SFC method: Column: Chiralpak AD-H (2 × 25 cm), Mobile Phase: 80:20 (A:B) A: Liquid $CO_2$, B: MeOH, Flow Rate: 80 mL/min, 219 nm, 100 bar inlet pressure to deliver peak 1. | 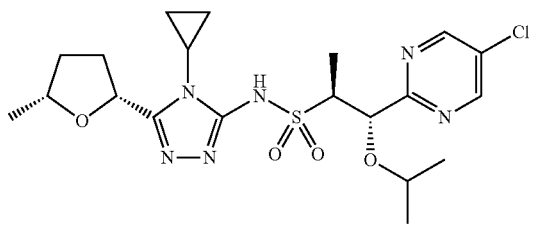<br>OR<br>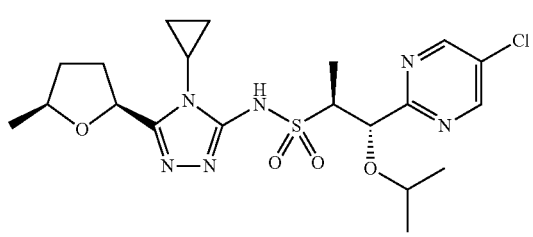<br>(1S,2S)-1-(5-chloro-2-pyrimidinyl)-N-(4-cyclopropyl-5-((2S,5S)-5-methyltetrahydro-2-furanyl)-4H-1,2,4-triazol-3-yl)-1-(2-propanyloxy)-2-propanesulfonamide or (1S,2S)-1-(5-chloro-2-pyrimidinyl)-N-(4-cyclopropyl-5-((2R,5R)-5-methyltetrahydro-2-furanyl)-4H-1,2,4-triazol-3-yl)-1-(2-propanyloxy)-2-propanesulfonamide.<br>$^1$H NMR (400 MHz, CDCl$_3$) δ 11.20 (s, 1 H) 8.70 (s, 2 H) 5.02 (dd, J = 7.72, 5.44 Hz, 1 H) 4.92 (d, J = 4.87 Hz, 1 H) 4.11-4.28 (m, 1 H) 3.80 (qd, J = 7.03, 5.03 Hz, 1 H) 3.49 (m, 1 H) 2.88 (tt, J = 7.22, 3.72 Hz, 1 H) 2.58 (ddt, J = 12.89, 8.31, 4.95, 4.95 Hz, 1 H) 2.18-2.31 (m, 1 H) 2.14 (dddd, J = 12.22, 7.81, 5.99, 4.66 Hz, 1 H) 1.72 (dq, J = |

US 9,988,369 B2

TABLE 36-continued

| Example | Reagents | Structure, Name and Data |
|---|---|---|
| | | 12.08, 8.24 Hz, 1 H) 1.39-1.52 (m, 4 H) 1.24 (d, J = 6.12 Hz, 3 H) 1.01-1.17 (m, 5 H) 0.88-0.98 (m, 1 H) 0.85 (d, J = 6.12 Hz, 3 H). LCMS-ESI (pos) m/z: 485.0 (M + H)+. |
| 353.0 | (1S,2S)-1-(5-chloropyrimidin-2-yl)-1-isopropoxypropane-2-sulfonamide (Example 13.6), (2S,5S)-5-methyltetrahydrofuran-2-carbohydrazide and (2R,5R)-5-methyltetrahydrofuran-2-carbohydrazide (commercially available from Ukrorgsyntez), and cyclopropyl isothiocyanate (commercially available from Sigma-Aldrich Corporation). The diastereomer mixture was purified by preparative SFC method: Column: Chiralpak AD-H (2 × 25 cm), Mobile Phase: 80:20 (A:B) A: Liquid CO2, B: MeOH, Flow Rate: 80 mL/min, 219 nm, 100 bar inlet pressure to deliver peak 2. | 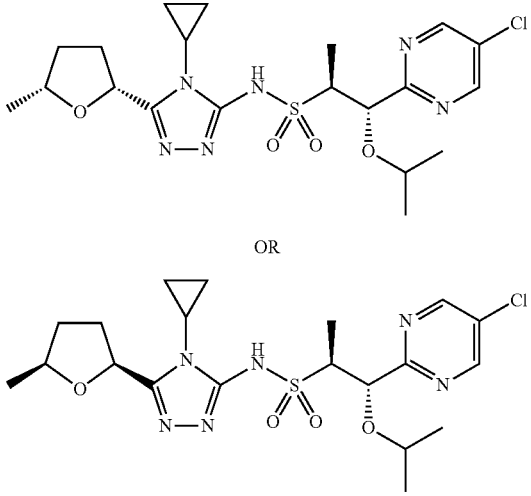 [SMILES: CC(C)O[C@@H](c1ncc(Cl)cn1)[C@H](C)S(=O)(=O)Nc1nnc([C@H]2CC[C@@H](C)O2)n1C1CC1 ; CC(C)O[C@@H](c1ncc(Cl)cn1)[C@H](C)S(=O)(=O)Nc1nnc([C@@H]2CC[C@H](C)O2)n1C1CC1]<br><br>(1S,2S)-1-(5-chloro-2-pyrimidinyl)-N-(4-cyclopropyl-5-((2S,5S)-5-methyltetrahydro-2-furanyl)-4H-1,2,4-triazol-3-yl)-1-(2-propanyloxy)-2-propanesulfonamide or (1S,2S)-1-(5-chloro-2-pyrimidinyl)-N-(4-cyclopropyl-5-((2R,5R)-5-methyltetrahydro-2-furanyl)-4H-1,2,4-triazol-3-yl)-1-(2-propanyloxy)-2-propanesulfonamide.<br>1H NMR (400 MHz, CDCl3) δ 11.15 (br s, 1 H) 8.71 (s, 2 H) 5.03 (dd, J = 7.72, 5.13 Hz, 1 H) 4.93 (d, J = 4.98 Hz, 1 H) 4.13-4.25 (m, 1 H) 3.83 (qd, J = 7.05, 5.08 Hz, 1 H) 3.44-3.56 (m, 1 H) 2.91 (tt, J = 7.20, 3.73 Hz, 1 H) 2.54-2.64 (m, 1 H) 2.20-2.31 (m, 1 H) 2.09-2.20 (m, 1 H) 1.72 (dq, J = 12.12, 8.30 Hz, 1 H) 1.46 (d, J = 7.15 Hz, 3 H) 1.29-1.41 (m, 1 H) 1.24 (d, J = 6.12 Hz, 3 H) 1.14 (dtd, J = 7.10, 3.55, 3.55, 1.35 Hz, 2 H) 1.07 (d, J = 6.01 Hz, 3 H) 0.97-1.04 (m, 1 H) 0.85 (d, J = 6.12 Hz, 3 H). LCMS-ESI (pos) m/z: 485.0 (M + H)+. |
| 354.0 | (1S,2S)-1-(5-chloropyrimidin-2-yl)-1-isopropoxypropane-2-sulfonamide (Example 13.6), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC method: Column: AS-H (2 × 25 cm), Mobile Phase: 85:15 (A:B) A: Liquid CO2, B: MeOH, Flow Rate: 80 mL/min, 219 nm, 100 bar inlet pressure to deliver peak 1. | 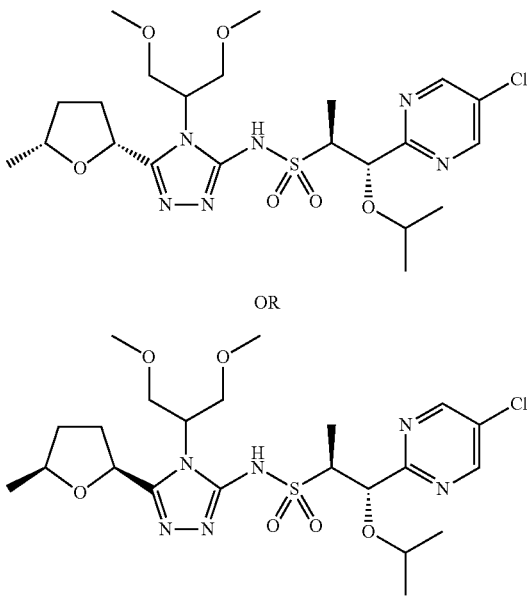 [SMILES: COCC(COC)n1c(NS(=O)(=O)[C@@H](C)[C@@H](OC(C)C)c2ncc(Cl)cn2)nnc1[C@H]1CC[C@@H](C)O1 ; COCC(COC)n1c(NS(=O)(=O)[C@@H](C)[C@@H](OC(C)C)c2ncc(Cl)cn2)nnc1[C@@H]1CC[C@H](C)O1]<br><br>(1S,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-(2-propanyloxy)-2-propanesulfonamide or (1S,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-(2-propanyloxy)-2-propanesulfonamide.<br>1H NMR (400 MHz, CDCl3) δ 11.51 (br s, 1 H) 8.73 (s, 2 H) 4.94 (dd, |

| Example | Reagents | Structure, Name and Data |
|---|---|---|
| | | J = 7.83, 5.34 Hz, 1 H) 4.89 (d, J = 3.84 Hz, 1 H) 4.70-4.81 (m, 1 H) 4.17 (m, 1 H) 4.07 (t, J = 9.54 Hz, 1 H) 4.00 (dd, J = 10.11, 6.69 Hz, 1 H) 3.87-3.94 (m, 1 H) 3.80 (qd, J = 7.05, 3.84 Hz, 1 H) 3.63 (dd, J = 9.90, 4.51 Hz, 1 H) 3.49-3.60 (m, 1 H) 3.39 (s, 3 H) 3.30 (s, 3 H) 2.63-2.74 (m, 1 H) 2.20-2.30 (m, 1 H) 2.12 (dddd, J = 12.22, 7.89, 5.96, 4.51 Hz, 1 H) 1.65 (dq, J = 12.12, 8.33 Hz, 1 H) 1.54 (d, J = 7.05 Hz, 3 H) 1.24 (d, J = 6.12 Hz, 3 H) 1.10 (d, J = 6.01 Hz, 3 H) 0.93 (d, J = 6.12 Hz, 3 H). LCMS-ESI (pos) m/z: 547.0 (M + H)$^+$. |
| 355.0 | (1S,2S)-1-(5-chloropyrimidin-2-yl)-1-isopropoxypropane-2-sulfonamide (Example 13.6), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC method: Column: AS-H (2 × 25 cm), Mobile Phase: 85:15 (A:B) A: Liquid CO$_2$, B: MeOH, Flow Rate: 80 mL/min, 219 nm, 100 bar inlet pressure to deliver peak 2. | 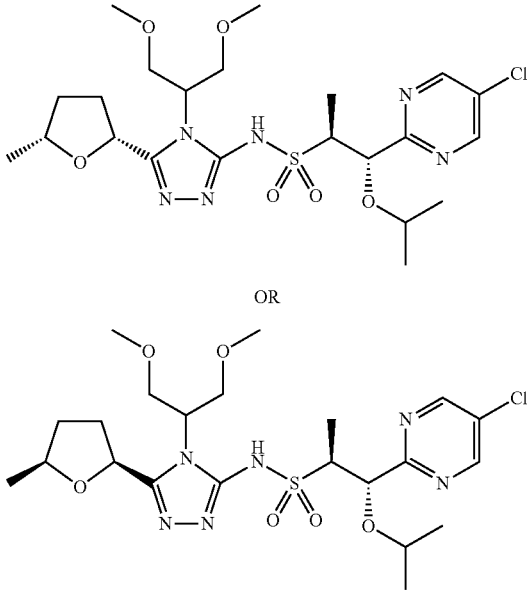 [SMILES: COCC(COC)n1c(NS(=O)(=O)[C@@H](C)[C@@H](OC(C)C)c2ncc(Cl)cn2)nnc1[C@H]1CC[C@@H](C)O1 ; COCC(COC)n1c(NS(=O)(=O)[C@@H](C)[C@@H](OC(C)C)c2ncc(Cl)cn2)nnc1[C@@H]1CC[C@H](C)O1]<br>OR<br>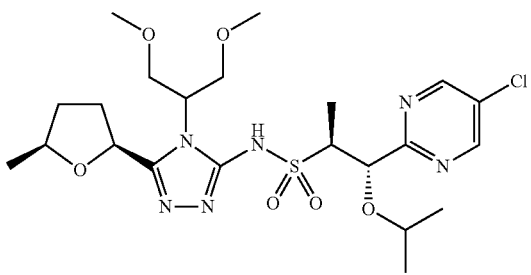<br>1S,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-(2-propanyloxy)-2-propanesulfonamide or (1S,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-(2-propanyloxy)-2-propanesulfonamide.<br>$^1$H NMR (400 MHz, CDCl$_3$) δ 11.58 (br s, 1 H) 8.73 (s, 2 H) 4.94 (dd, J = 7.77, 5.29 Hz, 1 H) 4.90 (d, J = 4.46 Hz, 1 H) 4.66-4.79 (m, 1 H) 4.08-4.22 (m, 2 H) 3.92 (qd, J = 10.31, 6.79 Hz, 2 H) 3.78 (qd, J = 7.05, 4.46 Hz, 1 H) 3.64 (dd, J = 9.80, 4.41 Hz, 1 H) 3.52 (quin, J = 6.06 Hz, 1 H) 3.35 (s, 3 H) 3.34 (s, 3 H) 2.59-2.70 (m, 1 H) 2.16-2.28 (m, 1 H) 2.11 (dddd, J = 12.17, 8.02, 6.04, 4.25 Hz, 1 H) 1.66 (dq, J = 12.10, 8.37 Hz, 1 H) 1.49 (d, J = 7.15 Hz, 3 H) 1.24 (d, J = 6.12 Hz, 3 H) 1.09 (d, J = 6.01 Hz, 3 H) 0.91 (d, J = 6.12 Hz, 3 H). LCMS-ESI (pos) m/z: 547.1 (M + H)$^+$. |

TABLE 36-continued

| Example | Reagents | Structure, Name and Data |
|---|---|---|
| 356.0 | (1S,2S)-1-(5-chloropyrimidin-2-yl)-1-isopropoxypropane-2-sulfonamide (Example 13.6), (R)-1,4-dioxane-2-carbohydrazide and (S)-1,4-dioxane-2-carbohydrazide (commercially available from Enamine), and 2-isothiocyanato-1,3-dimethoxypropane (Example 250.1). The diastereomer mixture was purified by preparative SFC method: Column: Chiralpak IC, Mobile Phase: 75:25 (A:B) A: Liquid CO₂, B: MeOH, Flow Rate: 80 mL/min, 219 nm, 100 bar inlet pressure to deliver peak 1. | 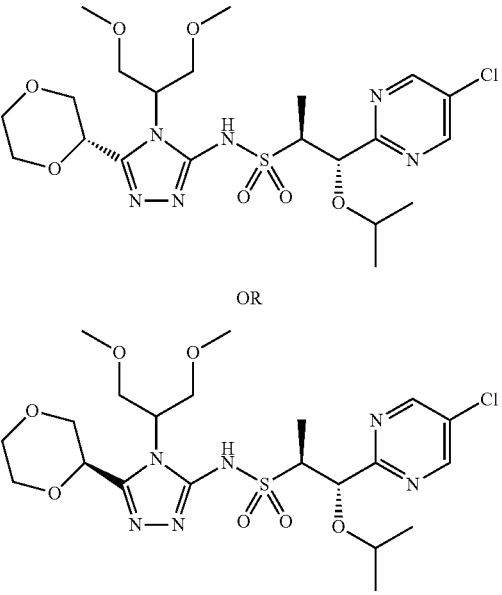 [SMILES: COCC(COC)n1c(NS(=O)(=O)[C@@H](C)[C@@H](OC(C)C)c2ncc(Cl)cn2)nnc1[C@H]1COCCO1 ; COCC(COC)n1c(NS(=O)(=O)[C@@H](C)[C@@H](OC(C)C)c2ncc(Cl)cn2)nnc1[C@@H]1COCCO1]<br><br>(1S,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1-(2-propanyloxy)-2-propanesulfonamide or (1S,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1-(2-propanyloxy)-2-propanesulfonamide.<br>¹H NMR (400 MHz, CDCl₃) δ 11.86 (br s, 1 H) 8.74 (s, 2 H) 4.88 (d, J = 3.84 Hz, 1 H) 4.76 (dd, J = 8.55, 3.16 Hz, 1 H) 4.56-4.67 (m, 1 H) 3.94-4.16 (m, 4 H) 3.72-3.94 (m, 6 H) 3.63 (dd, J = 9.69, 4.20 Hz, 1 H) 3.48-3.57 (m, 1 H) 3.36 (m, 6 H) 1.55 (d, J = 6.95 Hz, 3 H) 1.08 (d, J = 5.91 Hz, 3 H) 0.90 (d, J = 6.12 Hz, 3 H). LCMS-ESI (pos) m/z: 549.0 (M + H)⁺. |
| 357.0 | (1S,2S)-1-(5-chloropyrimidin-2-yl)-1-isopropoxypropane-2-sulfonamide (Example 13.6), (R)-1,4-dioxane-2-carbohydrazide and (S)-1,4-dioxane-2-carbohydrazide (commercially available from Enamine), and 2-isothiocyanato-1,3-dimethoxypropane (Example 250.1). The diastereomer mixture was purified by preparative SFC method: Column: Chiralpak IC, Mobile Phase: 75:25 (A:B) A: Liquid CO₂, B: MeOH, Flow Rate: 80 mL/min, 219 nm, 100 bar inlet pressure to deliver peak 2. | 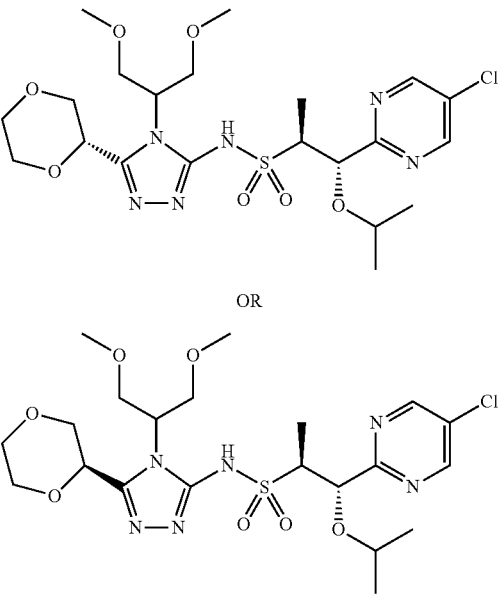 [SMILES: COCC(COC)n1c(NS(=O)(=O)[C@@H](C)[C@@H](OC(C)C)c2ncc(Cl)cn2)nnc1[C@H]1COCCO1 ; COCC(COC)n1c(NS(=O)(=O)[C@@H](C)[C@@H](OC(C)C)c2ncc(Cl)cn2)nnc1[C@@H]1COCCO1]<br><br>(1S,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1-(2-propanyloxy)-2-propanesulfonamide or (1S,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1-(2-propanyloxy)-2-propanesulfonamide. |

| Example | Reagents | Structure, Name and Data |
|---|---|---|
| | | $^1$H NMR (400 MHz, CDCl$_3$) δ 11.80 (br s, 1 H) 8.74 (s, 2 H) 4.89 (d, J = 3.84 Hz, 1 H) 4.76 (dd, J = 8.50, 3.21 Hz, 1 H) 4.61-4.71 (m, 1 H) 3.99-4.10 (m, 4 H) 3.71-3.95 (m, 6 H) 3.57-3.66 (m, 1 H) 3.51-3.57 (m, 1 H) 3.39 (s, 3 H) 3.31 (s, 3 H) 1.55 (m, 6 H) 1.10 (d, J = 6.01 Hz, 3 H) 0.94 (d, J = 6.12 Hz, 3 H). LCMS-ESI (pos) m/z: 549.0 (M + H)$^+$. |
| 358.0 | (1S,2S)-1-isopropoxy-1-(5-methylpyrimidin-2-yl)propane-2-sulfonamide (Example 13.5), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC method: Column: AS-H (2 × 25 cm), Mobile Phase: 90:10 (A:B) A: Liquid CO$_2$, B: MeOH, Flow Rate: 80 mL/min, 219 nm, 100 bar inlet pressure to deliver peak 1. | 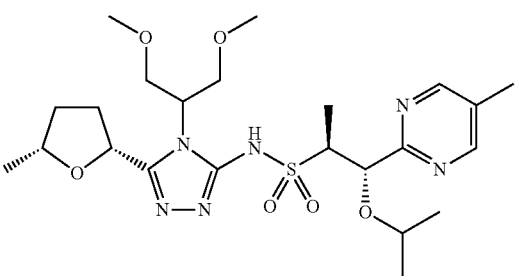

OR

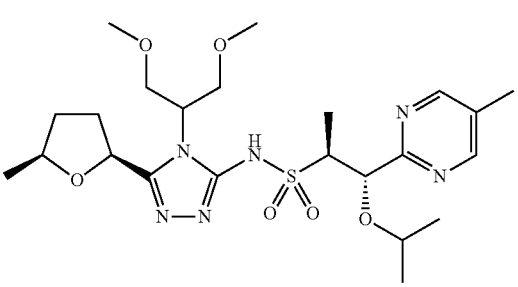

(1S,2S)-N-(4-(1,3-dimethoxy-2-propanyl)-5-((2R,5R)-5-methyltetrahydro-2-furanyl)-4H-1,2,4-triazol-3-yl)-1-(5-methyl-2-pyrimidinyl)-1-(2-propanyloxy)-2-propanesulfonamide or (1S,2S)-N-(4-(1,3-dimethoxy-2-propanyl)-5-((2S,5S)-5-methyltetrahydro-2-furanyl)-4H-1,2,4-triazol-3-yl)-1-(5-methyl-2-pyrimidinyl)-1-(2-propanyloxy)-2-propanesulfonamide.

$^1$H NMR (400 MHz, CDCl$_3$) δ 12.37 (s, 1 H) 8.60 (s, 2 H) 4.93 (dd, J = 7.78, 5.32 Hz, 1 H) 4.84 (d, J = 3.89 Hz, 1 H) 4.67-4.77 (m, 1 H) 4.11-4.21 (m, 1 H) 4.03-4.11 (m, 1 H) 3.94-4.00 (m, 1 H) 3.87-3.93 (m, 1 H) 3.73 (qd, J = 6.96, 3.89 Hz, 1 H) 3.62 (dd, J = 9.93, 4.48 Hz, 1 H) 3.51 (quin, J = 6.10 Hz, 1 H) 3.36 (s, 3 H) 3.27 (s, 3 H) 2.62-2.72 (m, 1 H) 2.31 (s, 3 H) 2.21 (dq, J = 12.78, 8.11 Hz, 1 H) 2.09 (dddd, J = 12.25, 7.83, 5.94, 4.61 Hz, 1 H) 1.63 (dq, J = 12.13, 8.37 Hz, 1 H) 1.51 (d, J = 7.01 Hz, 3 H) 1.21 (d, J = 6.10 Hz, 3 H) 1.05 (d, J = 5.97 Hz, 3 H) 0.88 (d, J = 6.10 Hz, 3 H). LCMS-ESI (pos) m/z: 527.2 (M + H)$^+$. |

TABLE 36-continued

| Example | Reagents | Structure, Name and Data |
|---|---|---|
| 359.0 | (1S,2S)-1-isopropoxy-1-(5-methylpyrimidin-2-yl)propane-2-sulfonamide (Example 13.5), (2S,5S)-5-methyltetrahydrofuran-2-carbohydrazide and (2R,5R)-5-methyltetrahydrofuran-2-carbohydrazide (commercially available from Ukrorgsyntez), 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid $CO_2$, B: MeOH, Flow Rate: 80 mL/min, 219 nm, 100 bar inlet pressure to deliver peak 2. | 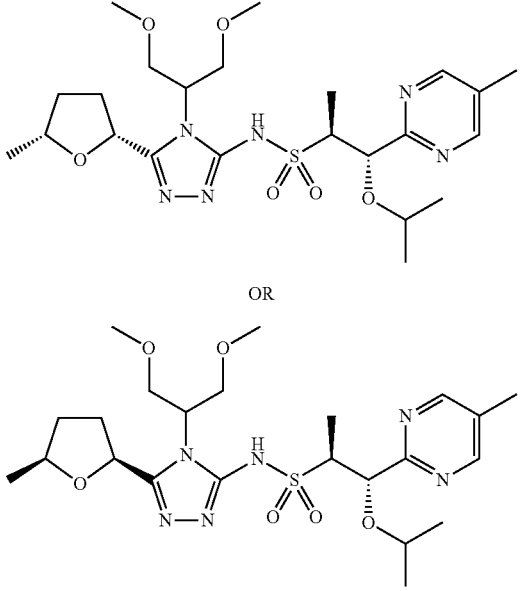<br><br>OR<br><br>(1S,2S)-N-(4-(1,3-dimethoxy-2-propanyl)-5-((2R,5R)-5-methyltetrahydro-2-furanyl)-4H-1,2,4-triazol-3-yl)-1-(5-methyl-2-pyrimidinyl)-1-(2-propanyloxy)-2-propanesulfonamide or (1S,2S)-N-(4-(1,3-dimethoxy-2-propanyl)-5-((2S,5S)-5-methyltetrahydro-2-furanyl)-4H-1,2,4-triazol-3-yl)-1-(5-methyl-2-pyrimidinyl)-1-(2-propanyloxy)-2-propanesulfonamide.<br>$^1$H NMR (400 MHz, CDCl$_3$) δ 12.39 (br d, J = 0.91 Hz, 1 H) 8.61 (s, 2 H) 4.94 (dd, J = 7.85, 5.26 Hz, 1 H) 4.86 (d, J = 4.28 Hz, 1 H) 4.66-4.76 (m, 1 H) 4.12-4.22 (m, 2 H) 3.86-4.00 (m, 2 H) 3.74 (qd, J = 7.01, 4.28 Hz, 1 H) 3.65 (dd, J = 9.80, 4.28 Hz, 1 H) 3.44-3.55 (m, 1 H) 3.35 (s, 3 H) 3.34 (s, 3 H) 2.61-2.70 (m, 1 H) 2.32 (s, 3 H) 2.21 (dq, J = 12.70, 8.09 Hz, 1 H) 2.11 (dddd, J = 12.21, 8.00, 6.07, 4.35 Hz, 1 H) 1.66 (dq, J = 12.20, 8.43 Hz, 1 H) 1.51 (d, J = 7.01 Hz, 3 H) 1.23 (d, J = 6.10 Hz, 3 H) 1.06 (d, J = 6.10 Hz, 3 H) 0.87 (d, J = 6.10 Hz, 3 H). LCMS-ESI (pos) m/z: 527.2 (M + H)$^+$. |
| 360.0 | (1S,2S)-1-(5-fluoropyrimidin-2-yl)-1-isopropoxypropane-2-sulfonamide (Example 360.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid $CO_2$, B: MeOH, Flow Rate: 80 mL/min, 219 nm, 100 bar inlet pressure to deliver peak 1. | 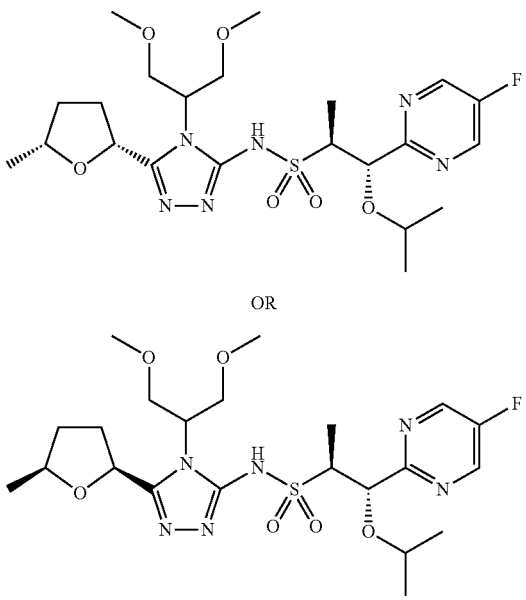 [SMILES: COCC(COC)n1c(NS(=O)(=O)[C@@H](C)[C@@H](OC(C)C)c2ncc(F)cn2)nnc1[C@H]1CC[C@@H](C)O1 ; COCC(COC)n1c(NS(=O)(=O)[C@@H](C)[C@@H](OC(C)C)c2ncc(F)cn2)nnc1[C@@H]1CC[C@H](C)O1]<br><br>OR<br><br>(1S,2S)-N-(4-(1,3-dimethoxy-2-propanyl)-5-((2R,5R)-5-methyltetrahydro-2-furanyl)-4H-1,2,4-triazol-3-yl)-1-(5-fluoro-2-pyrimidinyl)-1-(2-propanyloxy)-2-propanesulfonamide or (1S,2S)-N-(4-(1,3-dimethoxy-2-propanyl)-5-((2S,5S)-5-methyltetrahydro-2- |

| Example | Reagents | Structure, Name and Data |
|---|---|---|
| | | furanyl)-4H-1,2,4-triazol-3-yl)-1-(5-fluoro-2-pyrimidinyl)-1-(2-propanyloxy)-2-propanesulfonamide.<br>$^1$H NMR (400 MHz, CDCl$_3$) δ 11.54 (br s, 1 H) 8.63 (s, 2 H) 4.90-4.96 (m, 2 H) 4.75 (dtd, J = 9.12, 6.70, 6.70, 4.61 Hz, 1 H) 4.12-4.22 (m, 1 H) 4.07 (t, J = 9.54 Hz, 1 H) 3.99 (dd, J = 10.12, 6.75 Hz, 1 H) 3.87-3.93 (m, 1 H) 3.78 (qd, J = 7.03, 4.09 Hz, 1 H) 3.63 (dd, J = 9.86, 4.54 Hz, 1 H) 3.54 (quin, J = 6.10 Hz, 1 H) 3.38 (s, 3 H) 3.29 (s, 3 H) 2.67 (ddt, J = 13.07, 8.43, 4.88, 4.88 Hz, 1 H) 2.23 (dq, J = 12.76, 8.07 Hz, 1 H) 2.11 (dddd, J = 12.28, 7.93, 6.00, 4.54 Hz, 1 H) 1.64 (dq, J = 12.12, 8.37 Hz, 1 H) 1.51 (d, J = 7.01 Hz, 3 H) 1.23 (d, J = 6.10 Hz, 3 H) 1.09 (d, J = 5.97 Hz, 3 H) 0.92 (d, J = 6.10 Hz, 3 H). LCMS-ESI (pos) m/z: 531.2 (M + H)$^+$. |
| 361.0 | (1S,2S)-1-(5-fluoropyrimidin-2-yl)-1-isopropoxypropane-2-sulfonamide (Example 360.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid CO$_2$, B: MeOH, Flow Rate: 80 mL/min, 219 nm, 100 bar inlet pressure to deliver peak 2. | 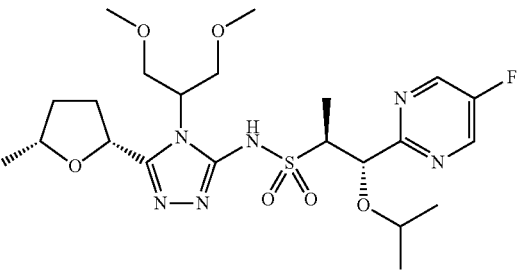<br>OR<br>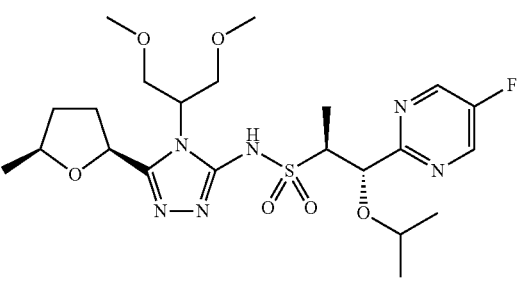<br><br>(1S,2S)-N-(4-(1,3-dimethoxy-2-propanyl)-5-((2R,5R)-5-methyltetrahydro-2-furanyl)-4H-1,2,4-triazol-3-yl)-1-(5-fluoro-2-pyrimidinyl)-1-(2-propanyloxy)-2-propanesulfonamide or (1S,2S)-N-(4-(1,3-dimethoxy-2-propanyl)-5-((2S,5S)-5-methyltetrahydro-2-furanyl)-4H-1,2,4-triazol-3-yl)-1-(5-fluoro-2-pyrimidinyl)-1-(2-propanyloxy)-2-propanesulfonamide.<br>$^1$H NMR (400 MHz, CDCl$_3$) δ 11.59 (br s, 1 H) 8.63 (s, 2 H) 4.90-4.97 (m, 2 H) 4.68-4.77 (m, 1 H) 4.10-4.22 (m, 2 H) 3.87-3.98 (m, 2 H) 3.77 (qd, J = 7.03, 4.61 Hz, 1 H) 3.64 (dd, J = 9.86, 4.41 Hz, 1 H) 3.51 (quin, J = 6.10 Hz, 1 H) 3.35 (s, 3 H) 3.34 (s, 3 H) 2.60-2.68 (m, 1 H) 2.22 (dq, J = 12.70, 8.09 Hz, 1 H) 2.11 (dddd, J = 12.28, 8.06, 6.07, 4.35 Hz, 1 H) 1.65 (dq, J = 12.18, 8.44 Hz, 1 H) 1.46 (d, J = 7.14 Hz, 3 H) 1.23 (d, J = 6.10 Hz, 3 H) 1.09 (d, J = 6.10 Hz, 3 H) 0.90 (d, J = 6.10 Hz, 3 H). LCMS-ESI (pos) m/z: 531.2 (M + H)$^+$. |

US 9,988,369 B2

TABLE 36-continued

| Example | Reagents | Structure, Name and Data |
|---|---|---|
| 362.0 | (1S,2S)-1-(5-methoxypyrimidin-2-yl)-1-isopropoxypropane-2-sulfonamide (Example 362.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid $CO_2$, B: MeOH, Flow Rate: 80 mL/min, 219 nm, 100 bar inlet pressure to deliver peak 1. | 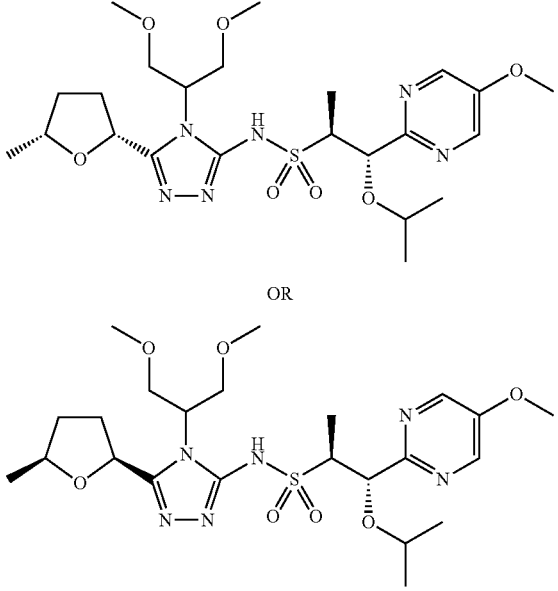<br><br>OR<br><br>(1S,2S)-N-(4-(1,3-dimethoxy-2-propanyl)-5-((2R,5R)-5-methyltetrahydro-2-furanyl)-4H-1,2,4-triazol-3-yl)-1-(5-methoxy-2-pyrimidinyl)-1-(2-propanyloxy)-2-propanesulfonamide or (1S,2S)-N-(4-(1,3-dimethoxy-2-propanyl)-5-((2S,5S)-5-methyltetrahydro-2-furanyl)-4H-1,2,4-triazol-3-yl)-1-(5-methoxy-2-pyrimidinyl)-1-(2-propanyloxy)-2-propanesulfonamide.<br>$^1$H NMR (400 MHz, CDCl$_3$) δ 12.13 (br s, 1 H) 8.45 (s, 2 H) 4.94 (dd, J = 7.85, 5.38 Hz, 1 H) 4.88 (d, J = 4.15 Hz, 1 H) 4.70-4.79 (m, 1 H) 4.13-4.22 (m, 1 H) 4.09 (t, J = 9.47 Hz, 1 H) 3.97-4.03 (m, 1 H) 3.88-3.95 (m, 4 H) 3.73 (qd, J = 7.01, 4.15 Hz, 1 H) 3.64 (dd, J = 9.86, 4.54 Hz, 1 H) 3.52 (quin, J = 6.10 Hz, 1 H) 3.38 (s, 3 H) 3.30 (s, 3 H) 2.64-2.72 (m, 1 H) 2.23 (dq, J = 12.73, 8.13 Hz. 1 H) 2.11 (dddd, J = 12.25, 7.87, 5.97, 4.54 Hz, 1 H) 1.65 (dq, J = 12.13, 8.37 Hz, 1 H) 1.51 (d, J = 7.14 Hz, 3 H) 1.23 (d, J = 6.10 Hz, 3 H) 1.08 (d, J = 5.97 Hz, 3 H) 0.90 (d, J = 6.10 Hz, 3 H). LCMS-ESI (pos) m/z: 543.2 (M + H)$^+$. |
| 363.0 | (1S,2S)-1-(5-methoxypyrimidin-2-yl)-1-isopropoxypropane-2-sulfonamide (Example 362.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid $CO_2$, B: MeOH, Flow Rate: 80 mL/min, 219 nm, 100 bar inlet pressure to deliver peak 2. | 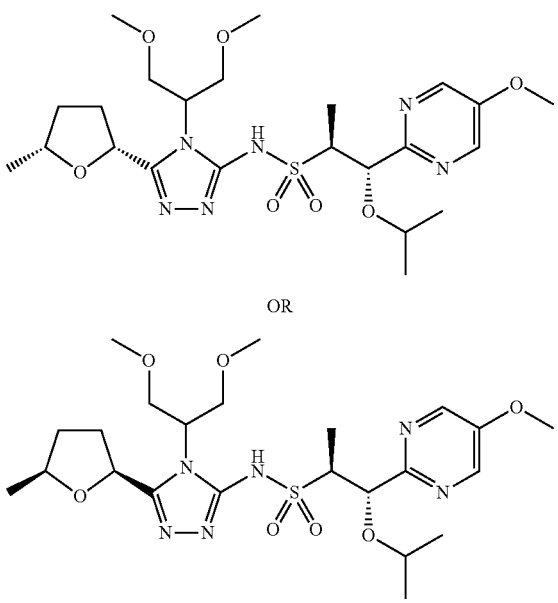<br><br>OR<br><br>(1S,2S)-N-(4-(1,3-dimethoxy-2-propanyl)-5-((2R,5R)-5-methyltetrahydro-2-furanyl)-4H-1,2,4-triazol-3-yl)-1-(5-methoxy-2- |

TABLE 36-continued

| Example | Reagents | Structure, Name and Data |
|---|---|---|
| | | pyrimidinyl)-1-(2-propanyloxy)-2-propanesulfonamide or (1S,2S)-N-(4-(1,3-dimethoxy-2-propanyl)-5-((2S,5S)-5-methyltetrahydro-2-furanyl)-4H-1,2,4-triazol-3-yl)-1-(5-methoxy-2-pyrimidinyl)-1-(2-propanyloxy)-2-propanesulfonamide.<br>¹H NMR (400 MHz, CDCl₃) δ 12.14 (br s, 1 H) 8.45 (s, 2 H) 4.94 (dd, J = 7.79, 5.32 Hz, 1 H) 4.89 (d, J = 4.54 Hz, 1 H) 4.68-4.77 (m, 1 H) 4.10-4.22 (m, 2 H) 3.88-4.00 (m, 5 H) 3.73 (qd, J = 7.01, 4.67 Hz, 1 H) 3.65 (dd, J = 9.80, 4.35 Hz, 1 H) 3.45-3.55 (m, 1 H) 3.35 (s, 3 H) 3.34 (s, 3 H) 2.61-2.70 (m, 1 H) 2.22 (dq, J = 12.70, 8.09 Hz, 1 H) 2.11 (dddd, J = 12.25, 8.00, 6.10, 4.41 Hz, 1 H) 1.66 (dq, J = 12.13, 8.46 Hz, 1 H) 1.48 (d, J = 7.14 Hz, 3 H) 1.24 (d, J = 6.10 Hz, 3 H) 1.07 (d, J = 5.97 Hz, 3 H) 0.88 (d, J = 6.10 Hz, 3 H). LCMS-ESI (pos) m/z: 543.2 (M + H)⁺. |
| 364.0 | (1S,2S)-1-(5-methylpyrazin-2-yl)-1-isopropoxypropane-2-sulfonamide (Example 364.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid CO₂, B: MeOH, Flow Rate: 80 mL/min, 219 nm, 100 bar inlet pressure to deliver peak 1. | 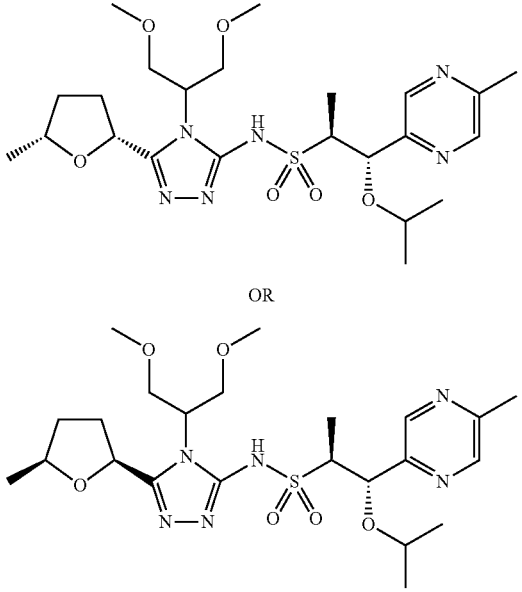<br>(1S,2S)-N-(4-(1,3-dimethoxy-2-propanyl)-5-((2R,5R)-5-methyltetrahydro-2-furanyl)-4H-1,2,4-triazol-3-yl)-1-(5-methyl-2-pyrazinyl)-1-(2-propanyloxy)-2-propanesulfonamide or (1S,2S)-N-(4-(1,3-dimethoxy-2-propanyl)-5-((2S,5S)-5-methyltetrahydro-2-furanyl)-4H-1,2,4-triazol-3-yl)-1-(5-methyl-2-pyrazinyl)-1-(2-propanyloxy)-2-propanesulfonamide.<br>¹H NMR (500 MHz, CDCl₃) δ 11.10 (br s, 1 H) 8.61 (s, 1 H) 8.41 (s, 1 H) 4.98 (d, J = 4.80 Hz, 1 H) 4.91 (dd, J = 7.66, 5.58 Hz, 1 H) 4.69-4.77 (m, 1 H) 4.12-4.21 (m, 1 H) 3.96 (t, J = 9.60 Hz, 1 H) 3.80-3.91 (m, 2 H) 3.63-3.71 (m, 1 H) 3.51-3.61 (m, 2 H) 3.36 (s, 3 H) 3.30 (s, 3 H) 2.61-2.69 (m, 1 H) 2.59 (s, 3 H) 2.22 (dq, J = 12.73, 8.08 Hz, 1 H) 2.07-2.16 (m, 1 H) 1.65 (dq, J = 12.15, 8.45 Hz, 1 H) 1.35 (d, J = 7.14 Hz, 3 H) 1.25 (d, J = 6.10 Hz, 3H) 1.17 (d, J = 6.10 Hz, 3 H) 1.01 (d, J = 6.10 Hz, 3 H). LCMS-ESI (pos) m/z: 527.2 (M + H)⁺. |

TABLE 36-continued

| Example | Reagents | Structure, Name and Data |
|---|---|---|
| 365.0 | (1S,2S)-1-(5-methylpyrazin-2-yl)-1-isopropoxypropane-2-sulfonamide (Example 364.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid CO$_2$, B: MeOH, Flow Rate: 80 mL/min, 219 nm, 100 bar inlet pressure to deliver peak 2. | 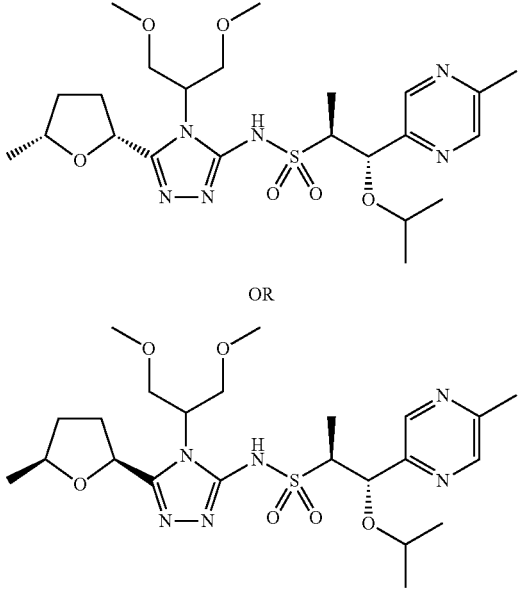<br>OR<br><br>(1S,2S)-N-(4-(1,3-dimethoxy-2-propanyl)-5-((2R,5R)-5-methyltetrahydro-2-furanyl)-4H-1,2,4-triazol-3-yl)-1-(5-methyl-2-pyrazinyl)-1-(2-propanyloxy)-2-propanesulfonamide or (1S,2S)-N-(4-(1,3-dimethoxy-2-propanyl)-5-((2S,5S)-5-methyltetrahydro-2-furanyl)-4H-1,2,4-triazol-3-yl)-1-(5-methyl-2-pyrazinyl)-1-(2-propanyloxy)-2-propanesulfonamide.<br>$^1$H NMR (500 MHz, CDCl$_3$) δ 11.09 (br s, 1 H) 8.60 (s, 1 H) 8.42 (s, 1 H) 4.96 (d, J = 5.71 Hz, 1 H) 4.92 (dd, J = 7.72, 5.38 Hz, 1 H) 4.68-4.77 (m, 1 H) 4.11-4.21 (m, 1 H) 4.04 (t, J = 9.54 Hz, 1 H) 3.87 (qd, J = 10.06, 6.94 Hz, 2 H) 3.57-3.68 (m, 2 H) 3.46-3.55 (m, 1 H) 3.36 (s, 3 H) 3.32 (s, 3 H) 2.62 (ddd, J = 13.01, 8.60, 4.61 Hz, 1 H) 2.58 (s, 3 H) 2.22 (dq, J = 12.76, 8.07 Hz, 1 H) 2.05-2.16 (m, 1 H) 1.64 (dq, J = 12.13, 8.46 Hz, 1 H) 1.29 (d, J = 7.14 Hz, 3 H) 1.23 (d, J = 6.10 Hz, 3 H) 1.15 (d, J = 5.97 Hz, 3 H) 0.97 (d, J = 6.10 Hz, 3 H). LCMS-ESI (pos) m/z: 527.2 (M + H)$^+$. |
| 366.0 | (1S,2S)-1-(5-methylpyrazin-2-yl)-1-isopropoxypropane-2-sulfonamide (Example 366.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid CO$_2$, B: MeOH, Flow Rate: 80 mL/min, 219 nm, 100 bar inlet pressure to deliver peak 1. | 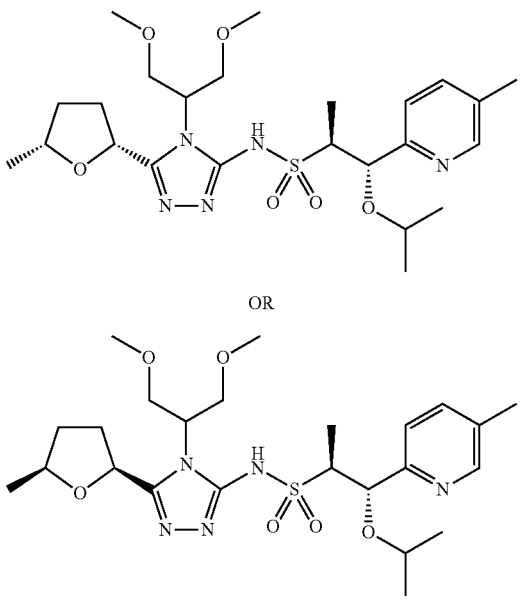<br>OR<br><br>(1S,2S)-N-(4-(1,3-dimethoxy-2-propanyl)-5-((2R,5R)-5-methyltetrahydro-2-furanyl)-4H-1,2,4-triazol-3-yl)-1-(5-methyl-2-pyridinyl)-1-(2-propanyloxy)-2-propanesulfonamide or (1S,2S)-N-(4-(1,3-dimethoxy-2-propanyl)-5-((2S,5S)-5-methyltetrahydro-2- |

| Example | Reagents | Structure, Name and Data |
|---|---|---|
| | | furanyl)-4H-1,2,4-triazol-3-yl)-1-(5-methyl-2-pyridinyl)-1-(2-propanyloxy)-2-propanesulfonamide.<br>$^1$H NMR (500 MHz, CDCl$_3$) δ 12.31 (br s, 1 H) 8.39 (s, 1 H) 7.53 (dd, J = 7.91, 1.30 Hz, 1 H) 7.35 (d, J = 8.04 Hz, 1 H) 4.92 (dd, J = 7.72, 5.51 Hz, 1 H) 4.89 (d, J = 4.93 Hz, 1 H) 4.69-4.77 (m, 1 H) 4.11-4.20 (m, 1 H) 4.01-4.10 (m, 1 H) 3.84-3.94 (m, 2 H) 3.57-3.64 (m, 2 H) 3.48 (m, 1 H) 3.36 (s, 3 H) 3.29 (s, 3 H) 2.62-2.70 (m, 1 H) 2.33 (s, 3 H) 2.21 (dq, J = 12.73, 8.08 Hz, 1 H) 2.06-2.15 (m, 1 H) 1.65 (dq, J = 12.13, 8.41 Hz, 1 H) 1.29 (d, J = 7.01 Hz, 3 H) 1.24 (d, J = 6.10 Hz, 3 H) 1.11 (d, J = 6.10 Hz, 3 H) 0.97 (d, J = 6.23 Hz, 3 H). LCMS-ESI (pos) m/z: 526.2 (M + H)$^+$. |
| 367.0 | (1S,2S)-1-(5-methylpyridin-2-yl)-1-isopropoxypropane-2-sulfonamide (Example 366.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid CO$_2$, B: MeOH, Flow Rate: 80 mL/min, 219 nm, 100 bar inlet pressure to deliver peak 1. | 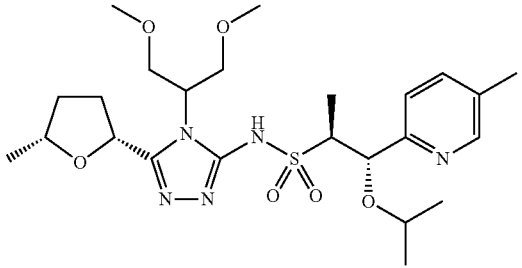<br><br>OR<br><br>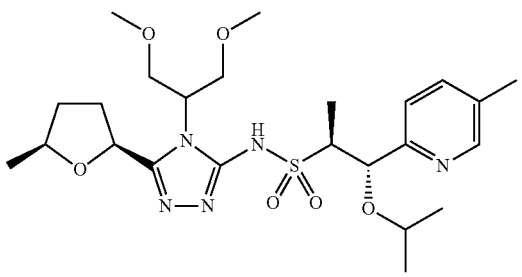<br><br>(1S,2S)-N-(4-(1,3-dimethoxy-2-propanyl)-5-((2R,5R)-5-methyltetrahydro-2-furanyl)-4H-1,2,4-triazol-3-yl)-1-(5-methyl-2-pyridinyl)-1-(2-propanyloxy)-2-propanesulfonamide or (1S,2S)-N-(4-(1,3-dimethoxy-2-propanyl)-5-((2S,5S)-5-methyltetrahydro-2-furanyl)-4H-1,2,4-triazol-3-yl)-1-(5-methyl-2-pyridinyl)-1-(2-propanyloxy)-2-propanesulfonamide.<br>$^1$H NMR (500 MHz, CDCl$_3$) δ 12.12 (br s, 1 H) 8.39 (s, 1 H) 7.51 (dd, J = 7.85, 1.23 Hz, 1 H) 7.33 (d, J = 7.92 Hz, 1 H) 4.92 (dd, J = 7.79, 5.45 Hz, 1 H) 4.85 (d, J = 5.97 Hz, 1 H) 4.67-4.76 (m, 1 H) 4.10-4.19 (m, 1 H) 4.07 (t, J = 9.54 Hz, 1 H) 3.86-3.97 (m, 2 H) 3.62 (dd, J = 9.86, 4.54 Hz, 1 H) 3.55 (quin, J = 6.81 Hz, 1 H) 3.40-3.46 (m, 1 H) 3.35 (s, 3 H) 3.30 (s, 3 H) 2.57-2.66 (m, 1 H) 2.32 (s, 3 H) 2.21 (dq, J = 12.78, 8.11 Hz, 1 H) 2.05-2.13 (m, 1 H) 1.63 (dq, J = 12.15, 8.49 Hz, 1 H) 1.23 m, 6 H) 1.08 (d, J = 5.97 Hz, 3 H) 0.92 (d, J = 6.23 Hz, 3 H). LCMS-ESI (pos) m/z: 526.2 (M + H)$^+$. |

| Example | Reagents | Structure, Name and Data |
|---|---|---|
| 368.0 | (2S,3R)-3-(5-fluoropyrimidin-2-yl)butane-2-sulfonamide (Example 1.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid $CO_2$, B: MeOH, Flow Rate: 80 mL/min, 219 nm, 100 bar inlet pressure to deliver peak 1. | 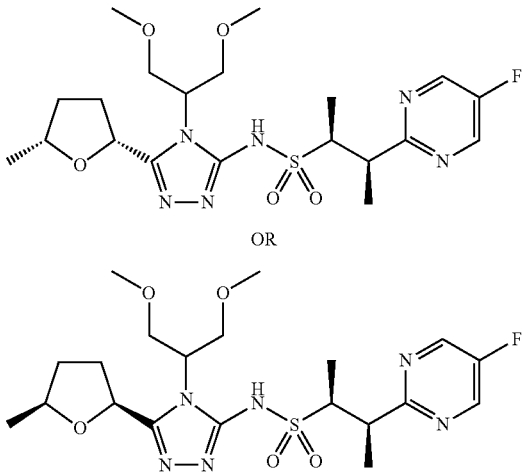 [SMILES: COCC(COC)n1c(NS(=O)(=O)[C@@H](C)[C@H](C)c2ncc(F)cn2)nnc1[C@H]1CC[C@@H](C)O1 ; COCC(COC)n1c(NS(=O)(=O)[C@@H](C)[C@H](C)c2ncc(F)cn2)nnc1[C@@H]1CC[C@H](C)O1] OR 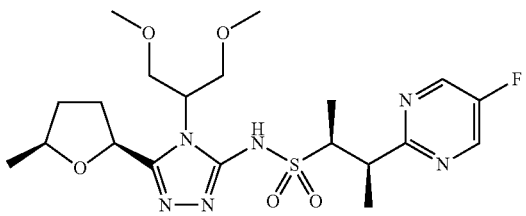<br>(2S,3R)-N-(4-(1,3-dimethoxy-2-propanyl)-5-((2R,5R)-5-methyltetrahydro-2-furanyl)-4H-1,2,4-triazol-3-yl)-3-(5-fluoro-2-pyrimidinyl)-2-butanesulfonamide or (2S,3R)-N-(4-(1,3-dimethoxy-2-propanyl)-5-((2S,5S)-5-methyltetrahydro-2-furanyl)-4H-1,2,4-triazol-3-yl)-3-(5-fluoro-2-pyrimidinyl)-2-butanesulfonamide.<br>$^1$H NMR (500 MHz, CDCl$_3$) δ 10.84 (br s, 1 H) 8.55 (s, 2 H) 4.91 (dd, J = 7.72, 5.51 Hz, 1 H) 4.73-4.82 (m, 1 H) 4.13-4.21 (m, 1 H) 4.07 (t, J = 9.60 Hz, 1 H) 3.97 (dd, J = 10.12, 6.88 Hz, 1 H) 3.80-3.90 (m, 3 H) 3.63 (dd, J = 9.86, 4.54 Hz, 1 H) 3.36 (s, 3 H) 3.30 (s, 3 H) 2.60-2.67 (m, 1 H) 2.23 (dq, J = 12.72, 8.04 Hz, 1 H) 2.09-2.16 (m, 1 H) 1.67 (dq, J = 12.18, 8.48 Hz, 1 H) 1.45 (d, J = 6.62 Hz, 3 H) 1.41 (d, J = 6.62 Hz, 3 H) 1.27 (d, J = 6.10 Hz, 3 H). LCMS-ESI (pos) m/z: 487.2 (M + H)$^+$. |
| 369.0 | (2S,3R)-3-(5-fluoropyrimidin-2-yl)butane-2-sulfonamide (Example 1.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid $CO_2$, B: MeOH, Flow Rate: 80 mL/min, 219 nm, 100 bar inlet pressure to deliver peak 2. | 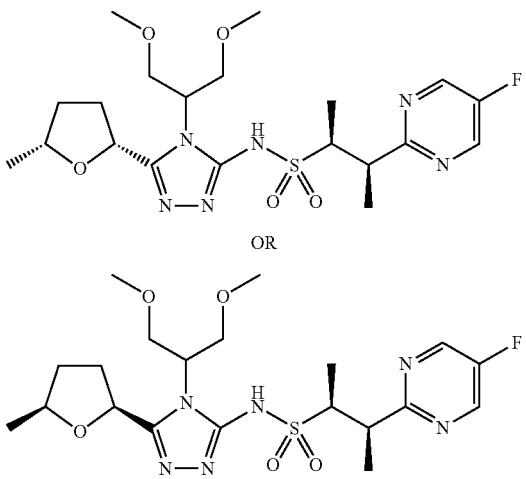 [SMILES: COCC(COC)n1c(NS(=O)(=O)[C@@H](C)[C@H](C)c2ncc(F)cn2)nnc1[C@H]1CC[C@@H](C)O1 ; COCC(COC)n1c(NS(=O)(=O)[C@@H](C)[C@H](C)c2ncc(F)cn2)nnc1[C@@H]1CC[C@H](C)O1] OR 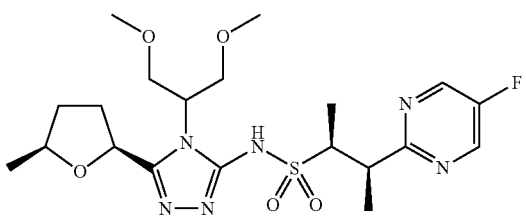<br>(2S,3R)-N-(4-(1,3-dimethoxy-2-propanyl)-5-((2R,5R)-5-methyltetrahydro-2-furanyl)-4H-1,2,4-triazol-3-yl)-3-(5-fluoro-2-pyrimidinyl)-2-butanesulfonamide or (2S,3R)-N-(4-(1,3-dimethoxy-2-propanyl)-5-((2S,5S)-5-methyltetrahydro-2-furanyl)-4H-1,2,4-triazol-3-yl)-3-(5-fluoro-2-pyrimidinyl)-2-butanesulfonamide.<br>$^1$H NMR (500 MHz, CDCl$_3$) δ 10.85 (br d, J = 1.69 Hz, 1 H) 8.55 (s, 2 H) 4.91 (dd, J = 7.72, 5.51 Hz, 1 H) 4.73-4.80 (m, 1 H) 4.13-4.21 (m, 1 H) 4.08 (t, J = 9.60 Hz, 1 H) 3.92-3.97 (m, 1 H) 3.80-3.90 (m, 3 H) 3.63 (dd, J = 9.86, 4.54 Hz, 1 H) 3.35 (s, 3 H) 3.31 (s, 3 H) 2.60-2.69 (m, 1 H) 2.22 (dq, J = 12.72, 8.09 Hz, 1 H) 2.07-2.16 (m, 1 H) 1.66 (dq, J = 12.13, 8.50 Hz, 1 H) 1.44 (d, J = 6.62 Hz, 3 H) 1.41 (d, J = 6.62 Hz, 3 H) 1.25 (d, J = 6.10 Hz, 3 H). LCMS-ESI (pos) m/z: 487.0 (M + H)$^+$. |

TABLE 36-continued

| Example | Reagents | Structure, Name and Data |
|---|---|---|
| 370.0 | (2S,3R)-3-(5-methoxypyrimidin-2-yl)butane-2-sulfonamide (Example 175.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid $CO_2$, B: MeOH, Flow Rate: 80 mL/min, 219 nm, 100 bar inlet pressure to deliver peak 1. | 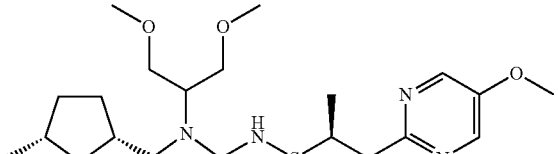<br>OR<br>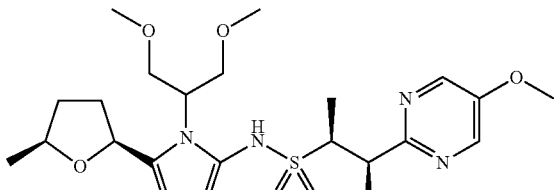<br><br>(2S,3R)-N-(4-(1,3-dimethoxy-2-propanyl)-5-((2R,5R)-5-methyltetrahydro-2-furanyl)-4H-1,2,4-triazol-3-yl)-3-(5-methoxy-2-pyrimidinyl)-2-butanesulfonamide or (2S,3R)-N-(4-(1,3-dimethoxy-2-propanyl)-5-((2S,5S)-5-methyltetrahydro-2-furanyl)-4H-1,2,4-triazol-3-yl)-3-(5-methoxy-2-pyrimidinyl)-2-butanesulfonamide.<br>$^1$H NMR (500 MHz, CDCl$_3$) δ 11.05 (br s, 1 H) 8.38 (s, 2 H) 4.92 (dd, J = 7.72, 5.51 Hz, 1 H) 4.72-4.81 (m, 1 H) 4.13-4.21 (m, 1 H) 4.09 (t, J = 9.60 Hz, 1 H) 3.98 (dd, J = 10.12, 6.88 Hz, 1 H) 3.74-3.93 (m, 6 H) 3.63 (dd, J = 9.86, 4.54 Hz, 1 H) 3.36 (s, 3 H) 3.30 (s, 3 H) 2.59-2.69 (m, 1 H) 2.23 (dq, J = 12.75, 8.03 Hz, 1 H) 2.12 (dddd, J = 12.28, 8.03, 6.10, 4.48 Hz, 1 H) 1.67 (dq, J = 12.20, 8.52 Hz, 1 H) 1.45 (d, J = 7.01 Hz, 3 H) 1.40 (d, J = 6.88 Hz, 3 H) 1.27 (d, J = 6.10 Hz, 3 H). LCMS-ESI (pos) m/z: 499.1 (M + H)$^+$. |
| 371.0 | (2S,3R)-3-(5-methoxypyrimidin-2-yl)butane-2-sulfonamide (Example 175.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid $CO_2$, B: MeOH, Flow Rate: 80 mL/min, 219 nm, 100 bar inlet pressure to deliver peak 2. | 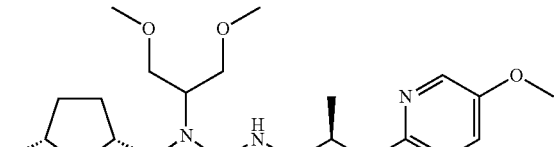<br>OR<br>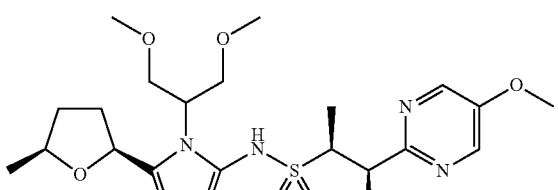<br><br>(2S,3R)-N-(4-(1,3-dimethoxy-2-propanyl)-5-((2R,5R)-5-methyltetrahydro-2-furanyl)-4H-1,2,4-triazol-3-yl)-3-(5-methoxy-2-pyrimidinyl)-2-butanesulfonamide or (2S,3R)-N-(4-(1,3-dimethoxy-2-propanyl)-5-((2S,5S)-5-methyltetrahydro-2-furanyl)-4H-1,2,4-triazol-3-yl)-3-(5-methoxy-2-pyrimidinyl)-2-butanesulfonamide.<br>$^1$H NMR (500 MHz, CDCl$_3$) δ 11.05 (br s, 1 H) 8.38 (s, 2 H) 4.92 (dd, J = 7.66, 5.45 Hz, 1 H) 4.72-4.80 (m, 1 H) 4.05-4.22 (m, 2 H) 3.74-4.00 (m, 7 H) 3.63 (dd, J = 9.80, 4.48 Hz, 1 H) 3.35 (s, 3 H) 3.31 (s, 3 H) 2.60-2.69 (m, 1 H) 2.22 (dq, J = 12.72, 8.09 Hz, 1 H) 2.12 (dddd, J = 12.23, 7.95, 6.10, 4.48 Hz, 1 H) 1.66 (dq, J = 12.13, 8.50 Hz, 1 H) 1.44 (d, J = 7.01 Hz, 3 H) 1.40 (d, J = 6.88 Hz, 3 H) 1.26 (d, J = 6.10 Hz, 3 H). LCMS-ESI (pos) m/z: 499.1 (M + H)$^+$. |

TABLE 36-continued

| Example | Reagents | Structure, Name and Data |
|---|---|---|
| 372.0 | (2S,3R)-3-(5-chloropyridin-2-yl)butane-2-sulfonamide (Example 14.0), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid CO$_2$, B: MeOH, Flow Rate: 80 mL/min, 219 nm, 100 bar inlet pressure to deliver peak 1. | (2S,3R)-3-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-2-butanesulfonamide or (2S,3R)-3-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-2-butanesulfonamide.<br>$^1$H NMR (500 MHz, CDCl$_3$) δ 10.85 (br s, 1 H) 8.51 (d, J = 2.34 Hz, 1 H) 7.63 (dd, J = 8.37, 2.40 Hz, 1 H) 7.22 (d, J = 8.43 Hz, 1 H) 4.92 (dd, J = 7.72, 5.38 Hz, 1 H) 4.73-4.81 (m, 1 H) 4.13-4.21 (m, 1 H) 4.05 (t, J = 9.60 Hz, 1 H) 3.95 (dd, J = 10.19, 6.94 Hz, 1 H) 3.84 (dd, J = 10.12, 7.01 Hz, 1 H) 3.74-3.80 (m, 1 H) 3.64-3.70 (m, 1 H) 3.61 (dd, J = 9.86, 4.54 Hz, 1 H) 3.35 (s, 3 H) 3.30 (s, 3 H) 2.60-2.68 (m, 1 H) 2.23 (dq, J = 12.76, 8.07 Hz, 1 H) 2.12 (dddd, J = 12.25, 8.00, 6.10, 4.41 Hz, 1 H) 1.67 (dq, J = 12.16, 8.49 Hz, 1 H) 1.44 (d, J = 7.14 Hz, 3 H) 1.36 (d, J = 7.01 Hz, 3 H) 1.26 (d, J = 6.10 Hz, 3 H). LCMS-ESI (pos) m/z: 502.0 (M + H)$^+$. |
| 373.0 | (2S,3R)-3-(5-chloropyridin-2-yl)butane-2-sulfonamide (Example 14.0), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid CO$_2$, B: MeOH, Flow Rate: 80 mL/min, 219 nm, 100 bar inlet pressure to deliver peak 2. | (2S,3R)-3-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-2-butanesulfonamide or (2S,3R)-3-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-2-butanesulfonamide.<br>$^1$H NMR (500 MHz, CDCl$_3$) δ 10.82 (br s, 1 H) 8.52 (d, J = 2.21 Hz, 1 H) 7.64 (dd, J = 8.30, 1.82 Hz, 1 H) 7.24 (d, J = 8.30 Hz, 1 H) 4.91 (dd, J = 7.72, 5.51 Hz, 1 H) 4.73-4.81 (m, 1 H) 4.13-4.22 (m, 1 H) 4.05 (t, J = 9.67 Hz, 1 H) 3.91-3.96 (m, 1 H) 3.83-3.89 (m, 1 H) 3.73-3.81 (m, 1 H) 3.66-3.73 (m, 1 H) 3.62 (dd, J = 9.80, 4.48 Hz, 1 H) 3.36 (s, 3 H) 3.30 (s, 3 H) 2.60-2.69 (m, 1 H) 2.23 (dq, J = 12.72, 8.09 Hz, 1 H) 2.08-2.17 (m, 1 H) 1.66 (dq, J = 12.13, 8.50 Hz, 1 H) 1.44 (d, J = 7.14 Hz, 3 H) 1.37 (d, J = 6.88 Hz, 3 H) 1.26 (d, J = 6.10 Hz, 3 H). LCMS-ESI (pos) m/z: 502.0 (M + H)$^+$. |

TABLE 36-continued

| Example | Reagents | Structure, Name and Data |
|---|---|---|
| 374.0 | (2S,3R)-3-(5-chloropyrimidin-2-yl)butane-2-sulfonamide (Example 1.4), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: Chiralpak AD-H (2 × 25 cm), Mobile Phase: 80:20 (A:B) A: Liquid CO$_2$, B: MeOH, Flow Rate: 80 mL/min, 219 nm, 100 bar inlet pressure to deliver peak 1. | 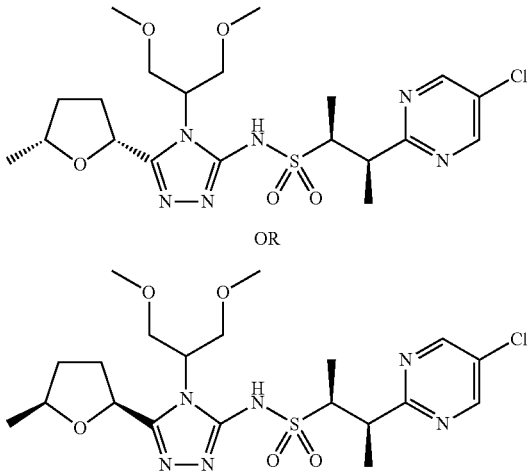 [SMILES: COCC(COC)n1c(NS(=O)(=O)[C@@H](C)[C@H](C)c2ncc(Cl)cn2)nnc1[C@H]1CC[C@@H](C)O1 ; COCC(COC)n1c(NS(=O)(=O)[C@@H](C)[C@H](C)c2ncc(Cl)cn2)nnc1[C@@H]1CC[C@H](C)O1]<br>OR<br><br>(2S,3R)-3-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-2-butanesulfonamide or (2S,3R)-3-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-2-butanesulfonamide.<br>$^1$H NMR (500 MHz, CDCl$_3$) δ 10.83 (br s, 1 H) 8.65 (s, 2 H) 4.91 (dd, J = 7.66, 5.45 Hz, 1 H) 4.72-4.82 (m, 1 H) 4.12-4.22 (m, 1 H) 4.08 (t, J = 9.60 Hz, 1 H) 3.91-3.97 (m, 1 H) 3.84-3.90 (m, 2 H) 3.79 (quin, J = 6.81 Hz, 1 H) 3.63 (dd, J = 9.86, 4.54 Hz, 1 H) 3.36 (s, 3 H) 3.31 (s, 3 H) 2.60-2.69 (m, 1 H) 2.23 (dq, J = 12.72, 8.09 Hz, 1 H) 2.07-2.16 (m, 1 H) 1.66 (dq, J = 12.13, 8.50 Hz, 1 H) 1.44 (d, J = 7.14 Hz, 3 H) 1.41 (d, J = 7.01 Hz, 3 H) 1.26 (d, J = 6.10 Hz, 3 H). LCMS-ESI (pos) m/z: 503.0 (M + H)$^+$. |
| 375.0 | (2S,3R)-3-(5-chloropyrimidin-2-yl)butane-2-sulfonamide (Example 1.4), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: Chiralpak AD-H (2 × 25 cm), Mobile Phase: 80:20 (A:B) A: Liquid CO$_2$, B: MeOH, Flow Rate: 80 mL/min, 219 nm, 100 bar inlet pressure to deliver peak 2. | 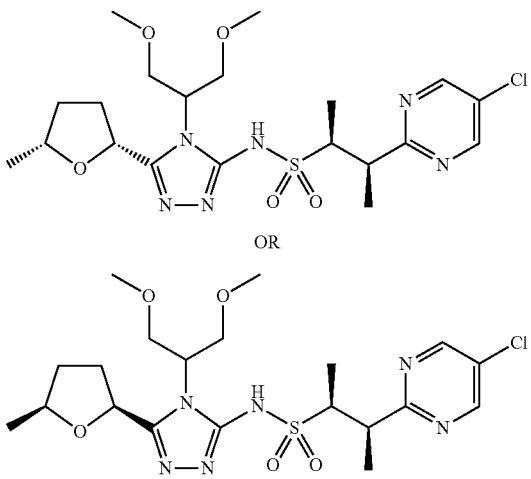 [SMILES: COCC(COC)n1c(NS(=O)(=O)[C@@H](C)[C@H](C)c2ncc(Cl)cn2)nnc1[C@H]1CC[C@@H](C)O1 ; COCC(COC)n1c(NS(=O)(=O)[C@@H](C)[C@H](C)c2ncc(Cl)cn2)nnc1[C@@H]1CC[C@H](C)O1]<br>OR<br><br>(2S,3R)-3-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-2-butanesulfonamide or (2S,3R)-3-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-2-butanesulfonamide.<br>$^1$H NMR (500 MHz, CDCl$_3$) δ 10.86 (br s, 1 H) 8.64 (s, 2 H) 4.91 (dd, J = 7.66, 5.58 Hz, 1 H) 4.73-4.81 (m, 1 H) 4.13-4.21 (m, 1 H) 4.07 (t, J = 9.60 Hz, 1 H) 3.97 (dd, J = 10.12, 6.88 Hz, 1 H) 3.75-3.90 (m, 3 H) 3.62 (dd, J = 9.86, 4.41 Hz, 1 H) 3.36 (s, 3 H) 3.30 (s, 3 H) 2.59-2.68 (m, 1 H) 2.22 (dq, J = 12.75, 8.03 Hz, 1 H) 2.12 (dddd, J = 12.28, 8.03, 6.10, 4.48 Hz, 1 H) 1.66 (dq, J = 12.13, 8.50 Hz, 1 H) 1.44 (d, J = 7.01 Hz, 3 H) 1.41 (d, J = 6.88 Hz, 3 H) 1.26 (d, J = 6.10 Hz, 3 H). LCMS-ESI (pos) m/z: 503.0 (M + H)$^+$. |

TABLE 36-continued

| Example | Reagents | Structure, Name and Data |
|---|---|---|
| 376.0 | (2S,3R)-3-(5-methoxypyrazin-2-yl)butane-2-sulfonamide (Example 1.5), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid $CO_2$, B: MeOH, Flow Rate: 80 mL/min, 219 nm, 100 bar inlet pressure to deliver peak 1. | 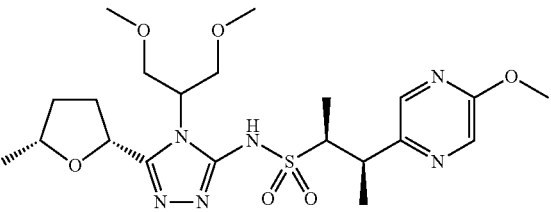<br>OR<br>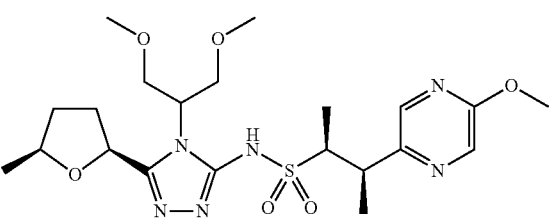<br><br>(2S,3R)-N-(4-(1,3-dimethoxy-2-propanyl)-5-((2R,5R)-5-methyltetrahydro-2-furanyl)-4H-1,2,4-triazol-3-yl)-3-(5-methoxy-2-pyrazinyl)-2-butanesulfonamide or (2S,3R)-N-(4-(1,3-dimethoxy-2-propanyl)-5-((2S,5S)-5-methyltetrahydro-2-furanyl)-4H-1,2,4-triazol-3-yl)-3-(5-methoxy-2-pyrazinyl)-2-butanesulfonamide.<br>$^1$H NMR (500 MHz, CDCl$_3$) δ 10.83 (br s, 1 H) 8.16 (s, 1 H) 8.03 (s, 1 H) 4.91 (dd, J = 7.66, 5.45 Hz, 1 H) 4.73-4.81 (m, 1 H) 4.12-4.21 (m, 1 H) 4.04 (t, J = 9.60 Hz, 1 H) 3.92-3.98 (m, 4 H) 3.74-3.86 (m, 2 H) 3.53-3.64 (m, 2 H) 3.34 (s, 3 H) 3.29 (s, 3 H) 2.59-2.68 (m, 1 H) 2.21 (dq, J = 12.78, 8.11 Hz, 1 H) 2.07-2.15 (m, 1 H) 1.65 (dq, J = 12.18, 8.48 Hz, 1 H) 1.45 (d, J = 7.14 Hz, 3 H) 1.36 (d, J = 7.01 Hz, 3 H) 1.25 (d, J = 6.10 Hz, 3 H). LCMS-ESI (pos) m/z: 499.0 (M + H)$^+$. |
| 377.0 | (2S,3R)-3-(5-methoxypyrazin-2-yl)butane-2-sulfonamide (Example 1.5), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid $CO_2$, B: MeOH, Flow Rate: 80 mL/min, 219 nm, 100 bar inlet pressure to deliver peak 2. | 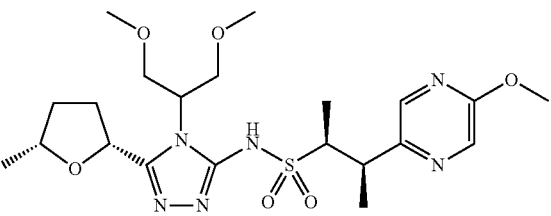<br>OR<br>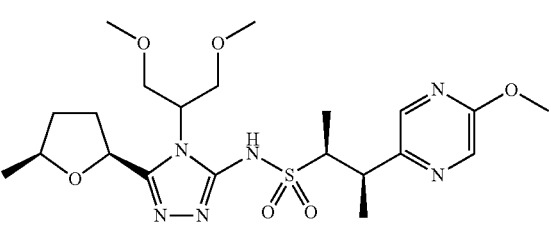<br><br>(2S,3R)-N-(4-(1,3-dimethoxy-2-propanyl)-5-((2R,5R)-5-methyltetrahydro-2-furanyl)-4H-1,2,4-triazol-3-yl)-3-(5-methoxy-2-pyrazinyl)-2-butanesulfonamide or (2S,3R)-N-(4-(1,3-dimethoxy-2-propanyl)-5-((2S,5S)-5-methyltetrahydro-2-furanyl)-4H-1,2,4-triazol-3-yl)-3-(5-methoxy-2-pyrazinyl)-2-butanesulfonamide.<br>$^1$H NMR (500 MHz, CDCl$_3$) δ 10.77 (br s, 1 H) 8.17 (s, 1 H) 8.02 (s, 1 H) 4.91 (dd, J = 7.66, 5.45 Hz, 1 H) 4.73-4.81 (m, 1 H) 4.13-4.21 (m, 1 H) 4.05 (t, J = 9.67 Hz, 1 H) 3.90-3.98 (m, 4 H) 3.83-3.88 (m, 1 H) 3.74-3.82 (m, 1 H) 3.55-3.64 (m, 2 H) 3.35 (s, 3 H) 3.30 (s, 3 H) 2.60-2.69 (m, 1 H) 2.22 (dq, J = 12.78, 8.11 Hz, 1 H) 2.06-2.16 (m, 1 H) 1.65 (dq, J = 12.13, 8.50 Hz, 1 H) 1.45 (d, J = 7.14 Hz, 3 H) 1.36 (d, J = 7.14 Hz, 3 H) 1.25 (d, J = 6.10 Hz, 3 H). LCMS-ESI (pos) m/z: 499.2 (M + H)$^+$. |

TABLE 36-continued

| Example | Reagents | Structure, Name and Data |
|---|---|---|
| 378.0 | (1R,2S)-1-methoxy-1-(5-methoxypyrazin-2-yl)propane-2-sulfonamide (Example 378.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid $CO_2$, B: MeOH, Flow Rate: 80 mL/min, 219 nm, 100 bar inlet pressure to deliver peak 1. | 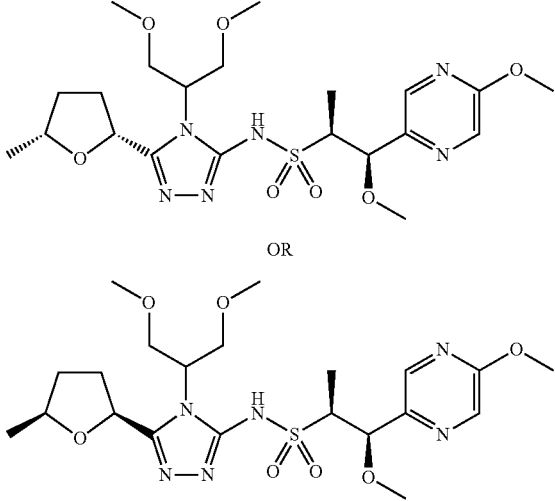<br>OR<br><br>(1R,2S)-N-(4-(1,3-dimethoxy-2-propanyl)-5-((2R,5R)-5-methyltetrahydro-2-furanyl)-4H-1,2,4-triazol-3-yl)-1-methoxy-1-(5-methoxy-2-pyrazinyl)-2-propanesulfonamide or (1R,2S)-N-(4-(1,3-dimethoxy-2-propanyl)-5-((2S,5S)-5-methyltetrahydro-2-furanyl)-4H-1,2,4-triazol-3-yl)-1-methoxy-1-(5-methoxy-2-pyrazinyl)-2-propanesulfonamide. $^1$H NMR (500 MHz, CDCl$_3$) δ 10.89 (br s, 1 H) 8.21 (d, J = 0.91 Hz, 1 H) 8.15 (s, 1 H) 5.06 (d, J = 2.72 Hz, 1 H) 4.93 (dd, J = 7.72, 5.38 Hz, 1 H) 4.72-4.81 (m, 1 H) 4.10-4.22 (m, 2 H) 3.88-4.01 (m, 5 H) 3.64 (dd, J = 9.86, 4.54 Hz, 1 H) 3.44-3.52 (m, 1 H) 3.37 (s, 3 H) 3.32 (s, 3 H) 3.31 (s, 3 H) 2.59-2.68 (m, 1 H) 2.23 (dq, J = 12.78, 8.11 Hz, 1 H) 2.12 (dddd, J = 12.25, 7.93, 6.10, 4.48 Hz, 1 H) 1.61-1.70 (m, 1 H) 1.32 (d, J = 7.14 Hz, 3 H) 1.25 (d, J = 6.10 Hz, 3 H). LCMS-ESI (pos) m/z: 515.2 (M + H)$^+$. |
| 379.0 | (1R,2S)-1-methoxy-1-(5-methoxypyrazin-2-yl)propane-2-sulfonamide (Example 378.1), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 90:10 (A:B) A: Liquid $CO_2$, B: MeOH, Flow Rate: 80 mL/min, 219 nm, 100 bar inlet pressure to deliver peak 2. | 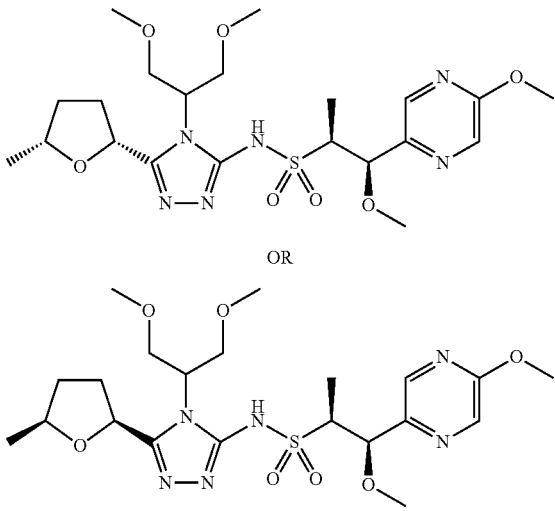<br>OR<br><br>(1R,2S)-N-(4-(1,3-dimethoxy-2-propanyl)-5-((2R,5R)-5-methyltetrahydro-2-furanyl)-4H-1,2,4-triazol-3-yl)-1-methoxy-1-(5-methoxy-2-pyrazinyl)-2-propanesulfonamide or (1R,2S)-N-(4-(1,3-dimethoxy-2-propanyl)-5-((2S,5S)-5-methyltetrahydro-2-furanyl)-4H-1,2,4-triazol-3-yl)-1-methoxy-1-(5-methoxy-2-pyrazinyl)-2-propanesulfonamide. $^1$H NMR (500 MHz, CDCl$_3$) δ 10.89 (br s, 1 H) 8.21 (s, 1 H) 8.14 (s, 1 H) 5.06 (d, J = 2.72 Hz, 1 H) 4.93 (dd, J = 7.72, 5.38 Hz, 1 H) 4.73-4.82 (m, 1 H) 4.06-4.22 (m, 2 H) 3.87-4.01 (m, 5 H) 3.63 (dd, J = 9.80, 4.35 Hz, 1 H) 3.45-3.52 (m, 1 H) 3.36 (s, 3 H) 3.33 (s, 3 H) 3.32 (s, 3 H) 2.59-2.68 (m, 1 H) 2.22 (dq, J = 12.76, 8.07 Hz, 1 H) 2.08-2.15 (m, 1 H) 1.65 (dq, J = 12.13, 8.50 Hz, 1 H) 1.32 (d, J = 7.01 Hz, 3 H) 1.24 (d, J = 6.10 Hz, 3 H). LCMS-ESI (pos) m/z: 515.2 (M + H)$^+$. |

TABLE 36-continued

| Example | Reagents | Structure, Name and Data |
|---|---|---|
| 380.0 | (1R,2S)-1-(5-chloropyridin-2-yl)-1-methoxypropane-2-sulfonamide (Example 11.9), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid $CO_2$, B: MeOH, Flow Rate: 80 mL/min, 219 nm, 100 bar inlet pressure to deliver peak 1. | (1R,2S)-1-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide or (1R,2S)-1-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide. $^1$H NMR (500 MHz, $CDCl_3$) δ 10.92 (br s, 1 H) 8.55 (d, J = 2.21 Hz, 1 H) 7.70 (dd, J = 8.37, 2.40 Hz, 1 H) 7.38 (d, J = 8.43 Hz, 1 H) 5.07 (d, J = 2.21 Hz, 1 H) 4.93 (dd, J = 7.72, 5.38 Hz, 1 H) 4.72-4.81 (m, 1 H) 4.11-4.23 (m, 2 H) 3.88-4.02 (m, 2 H) 3.64 (dd, J = 9.86, 4.54 Hz, 1 H) 3.47-3.55 (m, 1 H) 3.37 (s, 3 H) 3.32 (s, 3 H) 3.31 (s, 3 H) 2.59-2.69 (m, 1 H) 2.23 (dq, J = 12.78, 8.11 Hz, 1 H) 2.07-2.16 (m, 1 H) 1.65 (dq, J = 12.13, 8.46 Hz, 1 H) 1.26 (d, J = 3.63 Hz, 3 H) 1.24 (d, J = 2.60 Hz, 3 H). LCMS-ESI (pos) m/z: 518.0 (M + H)$^+$. |
| 381.0 | (1R,2S)-1-(5-chloropyridin-2-yl)-1-methoxypropane-2-sulfonamide (Example 11.9), (2S,5S)-5-methyltetrahydrofuran-2-carbohydrazide and (2R,5R)-5-methyltetrahydrofuran-2-carbohydrazide (commercially available from Ukrorgsyntez), and 2-isothiocyanato-1,3-dimethoxypropane (Example 250.1). The diastereomer mixture was purified by preparative SFC using the following conditions: Column: AS-H (2 × 25 cm), Mobile Phase: 85:15 (A:B) A: Liquid $CO_2$, B: MeOH, Flow Rate: 80 mL/min, 219 nm, 100 bar inlet pressure to deliver peak 2. | (1R,2S)-1-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide or (1R,2S)-1-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide. $^1$H NMR (500 MHz, $CDCl_3$) δ 10.92 (br s, 1 H) 8.54 (d, J = 2.34 Hz, 1 H) 7.69 (dd, J = 8.43, 2.34 Hz, 1 H) 7.37 (d, J = 8.43 Hz, 1 H) 5.07 (d, J = 2.34 Hz, 1 H) 4.93 (dd, J = 7.72, 5.38 Hz, 1 H) 4.73-4.82 (m, 1 H) 4.06-4.23 (m, 2 H) 3.98 (dd, J = 10.12, 6.75 Hz, 1 H) 3.87-3.93 (m, 1 H) 3.63 (dd, J = 9.80, 4.35 Hz, 1 H) 3.47-3.56 (m, 1 H) 3.36 (s, 3 H) 3.32 (s, 3 H) 3.32 (s, 3 H) 2.59-2.69 (m, 1 H) 2.22 (dq, J = 12.80, 8.15 Hz, 1 H) 2.07-2.16 (m, 1 H) 1.65 (dq, J = 12.18, 8.48 Hz, 1 H) 1.25 (d, J = 4.15 Hz, 3 H) 1.24 (d, J = 3.11 Hz, 3 H). LCMS-ESI (pos) m/z: 518.0 (M + H)$^+$. |

TABLE 36-continued

| Example | Reagents | Structure, Name and Data |
|---|---|---|
| 382.0 | The title compound was prepared following the procedure in Example 24.0 using (2S,3R)-3-(5-chloro-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide or (2S,3R)-3-(5-chloro-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide (Example 37.0). | 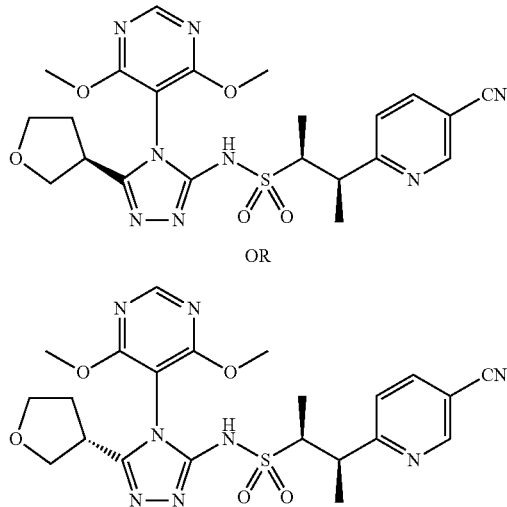 [SMILES: COc1ncnc(OC)c1-n1c(NS(=O)(=O)[C@@H](C)[C@H](C)c2ccc(C#N)cn2)nnc1[C@@H]1CCOC1 ; COc1ncnc(OC)c1-n1c(NS(=O)(=O)[C@@H](C)[C@H](C)c2ccc(C#N)cn2)nnc1[C@H]1CCOC1]<br>(2S,3R)-3-(5-cyano-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide or (2S,3R)-3-(5-cyano-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide.<br>$^1$H NMR (600 MHz, DMSO-$d_6$) δ 1.08 (d, J = 7.01 Hz, 3 H) 1.22 (d, J = 7.08 Hz, 3 H) 1.98-2.05 (m, 2 H) 3.13-3.20 (m, 1 H) 3.38-3.44 (m, 1 H) 3.57-3.69 (m, 3 H) 3.69-3.80 (m, 2 H) 3.94 (s, 3 H) 3.95 (s, 3 H) 7.47 (d, J = 8.10 Hz, 1 H) 8.24 (dd, J = 8.21, 2.22 Hz, 1 H) 8.71 (s, 1 H) 8.94 (s, 1 H) 13.08 (s, 1 H). LCMS-ESI (pos) m/z: 515.2 (M + H)$^+$. |
| 383.0 | The title compound was prepared following the procedure in Example 24.0 using (2S,3R)-3-(5-chloro-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide or (2S,3R)-3-(5-chloro-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide (Example 38.0). | 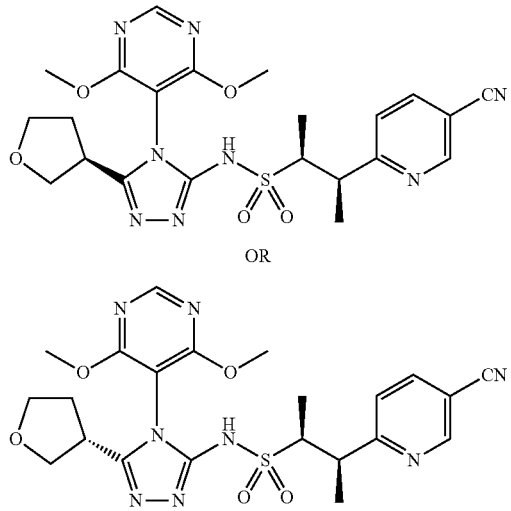 [SMILES: COc1ncnc(OC)c1-n1c(NS(=O)(=O)[C@@H](C)[C@H](C)c2ccc(C#N)cn2)nnc1[C@@H]1CCOC1 ; COc1ncnc(OC)c1-n1c(NS(=O)(=O)[C@@H](C)[C@H](C)c2ccc(C#N)cn2)nnc1[C@H]1CCOC1]<br>(2S,3R)-3-(5-cyano-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide or (2S,3R)-3-(5-cyano-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide.\|<br>$^1$H NMR (600 MHz, DMSO-$d_6$) δ 1.08 (d, J = 7.01 Hz, 3 H) 1.22 (d, J = 7.16 Hz, 3 H) 1.95-2.04 (m, 2 H) 3.13-3.20 (m, 1 H) 3.37-3.44 (m, 1 H) 3.57-3.71 (m, 3 H) 3.71-3.80 (m, 2 H) 3.94 (s, 3 H) 3.95 (s, 3 H) 7.47 (d, J = 8.10 Hz, 1 H) 8.24 (dd, J = 8.25, 2.18 Hz, 1 H) 8.71 (s, 1 H) 8.94 (dd, J = 2.10, 0.62 Hz, 1 H) 13.08 (s, 1 H). LCMS-ESI (pos) m/z: 515.2 (M + H)$^+$. |

TABLE 36-continued

| Example | Reagents | Structure, Name and Data |
|---|---|---|
| 386.0 | 2-(5-chloropyrimidin-2-yl)ethanesulfonamide (Example 386.1), (R)-tetrahydrofuran-3-carbohydrazide (commercially available from Enamine), and 2-isothiocyanato-1,3-dimethoxybenzene (Example 10.0). | 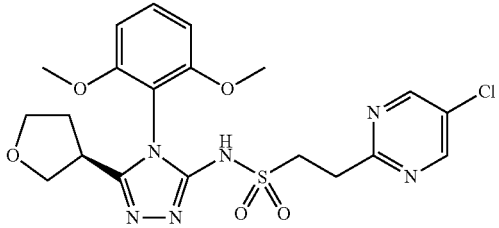 [SMILES: COc1cccc(OC)c1-n1c(NS(=O)(=O)CCc2ncc(Cl)cn2)nnc1[C@@H]1CCOC1]<br>2-(5-chloro-2-pyrimidinyl)-N-(4-(2,6-dimethoxyphenyl)-5-((3S)-tetrahydro-3-furanyl)-4H-1,2,4-triazol-3-yl)ethanesulfonamide.<br>$^1$H NMR (500 MHz, CDCl$_3$) δ 10.78 (br d, J = 3.50 Hz, 1 H) 8.63 (s, 2 H) 7.44 (t, J = 8.50 Hz, 1 H) 6.68 (d, J = 8.56 Hz, 2 H) 3.88-4.00 (m, 1 H) 3.75-3.86 (m, 9 H) 3.50-3.60 (m, 2 H) 3.39-3.48 (m, 2 H) 2.97-3.07 (m, 1 H) 2.23-2.33 (m, 1 H) 2.00-2.10 (m, 1 H). LCMS-ESI (pos) m/z: 495.0 (M + H)$^+$. |
| 387.0 | 2-(5-chloropyrimidin-2-yl)ethanesulfonamide (Example 386.1), (R)-1,4-dioxane-2-carbohydrazide and (S)-1,4-dioxane-2-carbohydrazide (commercially available from Enamine), and 2-isothiocyanato-1,3-dimethoxybenzene (Example 10.0). | 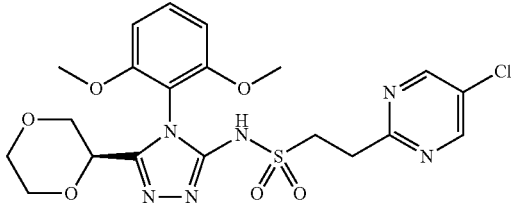<br>AND<br>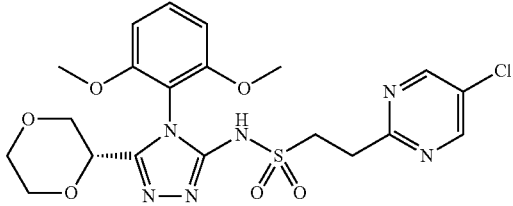<br>2-(5-chloro-2-pyrimidinyl)-N-(4-(2,6-dimethoxyphenyl)-5-((2R)-1,4-dioxan-2-yl)-4H-1,2,4-triazol-3-yl)ethanesulfonamide and 2-(5-chloro-2-pyrimidinyl)-N-(4-(2,6-dimethoxyphenyl)-5-((2S)-1,4-dioxan-2-yl)-4H-1,2,4-triazol-3-yl)ethanesulfonamide.<br>$^1$H NMR (600 MHz, DMSO-d$_6$) δ 13.25 (s, 1 H) 8.86 (s, 2 H) 7.50 (t, J = 8.52 Hz, 1 H) 6.85 (dd, J = 8.60, 0.90 Hz, 2 H) 4.17 (dd, J = 7.40, 3.74 Hz, 1 H) 3.76 (s, 3 H) 3.74 (s, 3 H) 3.67-3.74 (m, 3 H) 3.63 (dt, J = 11.76, 2.76 Hz, 1 H) 3.58 (dt, J = 11.74, 2.81 Hz, 1 H) 3.48 (ddd, J = 11.70, 9.17, 2.57 Hz, 1 H) 3.36 (br d, J = 2.41 Hz, 2 H) 3.14-3.22 (m, 2 H). LCMS-ESI (pos) m/z: 511.2 (M + H)$^+$. |
| 388.0 | 2-(5-chloropyrimidin-2-yl)ethanesulfonamide (Example 386.1), (S)-tetrahydrofuran-2-carbohydrazide (commercially available from Enamine), and 2-isothiocyanato-1,3-dimethoxybenzene (Example 10.0). | 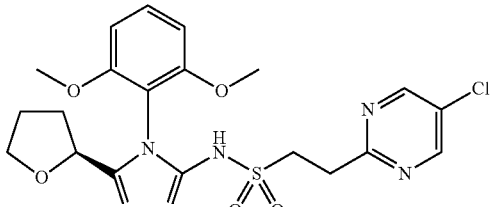<br>2-(5-chloro-2-pyrimidinyl)-N-(4-(2,6-dimethoxyphenyl)-5-((2S)-tetrahydro-2-furanyl)-4H-1,2,4-triazol-3-yl)ethanesulfonamide.<br>$^1$H NMR (600 MHz, DMSO-d$_6$) δ 1.75-1.84 (m, 2 H) 1.96-2.03 (m, 1 H) 2.05-2.13 (m, 1 H) 3.16-3.21 (m, 2 H) 3.34-3.37 (m, 2 H) 3.48-3.54 (m, 1 H) 3.62-3.70 (m, 1 H) 3.75 (s, 3 H) 3.75 (s, 3 H) 4.50 (dd, J = 7.71, 5.57 Hz, 1 H) 6.83 (d, J = 8.62 Hz, 2 H) 7.48 (t, J = 8.51 Hz, 1 H) 8.85 (s, 2 H) 13.04 (br s, 1 H). LCMS-ESI (pos) m/z: 495.2 (M + H)$^+$. |

TABLE 36-continued

| Example | Reagents | Structure, Name and Data |
|---|---|---|
| 389.0 | 2-(5-chloropyrimidin-2-yl)ethanesulfonamide (Example 386.1), (R)-tetrahydrofuran-2-carbohydrazide (commercially available from Enamine), and 2-isothiocyanato-1,3-dimethoxybenzene (Example 10.0). | 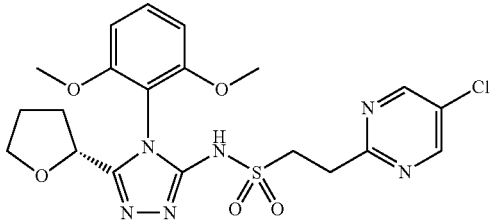 [SMILES: COc1cccc(OC)c1-n1c(NS(=O)(=O)CCc2ncc(Cl)cn2)nnc1[C@H]1CCCO1]<br>2-(5-chloro-2-pyrimidinyl)-N-(4-(2,6-dimethoxyphenyl)-5-((2R)-tetrahydro-2-furanyl)-4H-1,2,4-triazol-3-yl)ethanesulfonamide.<br>$^1$H NMR (600 MHz, DMSO-$d_6$) δ 1.75-1.84 (m, 2 H) 1.96-2.03 (m, 1 H) 2.06-2.12 (m, 1 H) 3.16-3.20 (m, 2 H) 3.34-3.37 (m, 2 H) 3.48-3.54 (m, 1 H) 3.61-3.70 (m, 1 H) 3.75 (s, 3 H) 3.75 (s, 3 H) 4.50 (dd, J = 7.74, 5.53 Hz, 1 H) 6.83 (d, J = 8.62 Hz, 2 H) 7.48 (t, J = 8.51 Hz, 1 H) 8.85 (s, 2 H) 13.04 (br s, 1 H). LCMS-ESI (pos) m/z: 495.2 (M + H)$^+$. |
| 390.0 | 2-(5-chloropyrimidin-2-yl)ethanesulfonamide (Example 386.1), (S)-tetrahydrofuran-3-carbohydrazide and (R)-tetrahydrofuran-3-carbohydrazide (commercially available from Enamine), and 2-isothiocyanato-1,3-dimethoxybenzene (Example 10.0). The racemic mixture was purified by preparative SFC using the following conditions: Column: AS-H (2 × 25 cm), Mobile Phase: 70:30 (A:B) A: Liquid CO$_2$, B: MeOH, Flow Rate: 80 mL/min, 219 nm, 100 bar inlet pressure to deliver peak 2. | 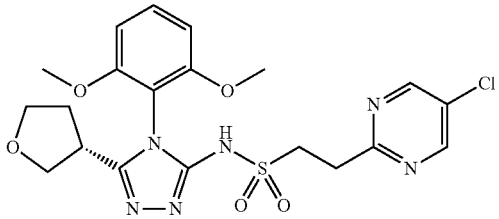 [SMILES: COc1cccc(OC)c1-n1c(NS(=O)(=O)CCc2ncc(Cl)cn2)nnc1[C@H]1CCOC1]<br>2-(5-chloro-2-pyrimidinyl)-N-(4-(2,6-dimethoxyphenyl)-5-((3R)-tetrahydro-3-furanyl)-4H-1,2,4-triazol-3-yl)ethanesulfonamide.<br>$^1$H NMR (500 MHz, CDCl$_3$) δ 10.83 (br s, 1 H) 8.62 (s, 2 H) 7.44 (t, J = 8.50 Hz, 1 H) 6.67 (d, J = 8.56 Hz, 2 H) 3.88-3.98 (m, 1 H) 3.75-3.87 (m, 9 H) 3.51-3.60 (m, 2 H) 3.40-3.46 (m, 2 H) 2.97-3.07 (m, 1 H) 2.23-2.32 (m, 1 H) 2.04 (td, J = 13.53, 7.98 Hz, 1 H). LCMS-ESI (pos) m/z: 495.0 (M + H)$^+$. |

Example 386.1: Preparation of 2-(5-chloropyrimidin-2-yl)ethanesulfonamide

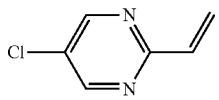

386.11

5-Chloro-2-vinylpyrimidine, Example 386.11

To a stirred solution of 2,5-dichloropyrimidine (Combi-block, 20.0 g, 134 mmol) in DMF (200 mL) was added tributyl(vinyl)stannane (42.6 g, 134 mmol) at RT. The reaction mixture was purged with N$_2$ for 5 minutes and tetrakis(triphenylphosphine)palladium(0) (4.65 g, 4.03 mmol) was added. The reaction mixture was further degassed with N$_2$ for 5 minutes and stirred at 100° C. for 16 h. After completion of the reaction (monitored by TLC), the reaction mixture was cooled to RT and quenched with water (40 mL). The aqueous layer was extracted with diethyl ether (2×200 mL) and the combined organic layers were washed with brine (200 mL), dried over anhydrous Na$_2$SO$_4$ and concentrated in vacuo to give desired product Example 386.11 (100 g) as a yellow liquid. The initial product was directly taken to the next step without further purification. LCMS-ESI (pos) m/z: 342.1 (M+H)$^+$.

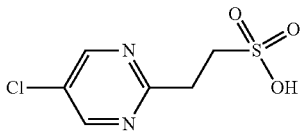

386.12

2-(5-Chloropyrimidin-2-yl)ethanesulfonic acid, Example 386.12

Example 386.11 (20 g, 142 mmol) was stirred in a saturated aqueous solution of sodium sulfite (80 mL, 142 mmol) at RT for 12 h. After completion of the reaction (monitored by TLC and UPLC), the reaction mixture was concentrated in vacuo and the residue was purified by reverse chromatography eluting with water to provide Example 386.12 (17.5 g, 79 mmol, 55% yield) as a white solid. LCMS-ESI (pos) m/z: 222.1 (M+H)$^+$.

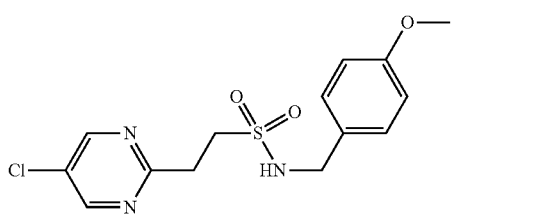

386.13

2-(5-Chloropyrimidin-2-yl)-N-(4-methoxybenzyl) ethanesulfonamide, Example 386.13

To a stirred solution of Example 386.12 (35 g, 157 mmol) in DCM (875 mL) was added oxalyl dichloride (59.9 g, 472 mmol) followed by DMF (2 mL) at 0° C. The reaction mixture was stirred at RT for 1 h and concentrated in vacuo. The reaction mixture was then azeotroped with cyclopentylmethylether. The reaction mixture was diluted with DCM (875 mL) and cooled to 0° C. (4-Methoxyphenyl)methanamine (64.7 g, 472 mmol) was added to the reaction mixture followed by TEA (80 g, 786 mmol). The reaction mixture was then stirred at RT for 12 h. The reaction was monitored by TLC. After completion of the reaction, the reaction mixture was quenched with water (600 mL). The aqueous layer was then extracted with DCM (2×800 mL). The organic layers were combined and washed with brine (600 mL), dried over anhydrous $Na_2SO_4$ and concentrated in vacuo to obtain the initial material. The initial material was absorbed onto a plug of silica gel and purified by chromatography through a Redi-Sep pre-packed silica gel column, eluting with a gradient of 55% to 60% EtOAc in hexanes, to provide Example 386.13 (16 g, 46.8 mmol, 30% yield) as an off-white solid. LCMS-ESI (pos) m/z: 342.1 $(M+H)^+$.

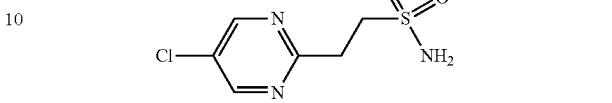

386.1

2-(5-Chloropyrimidin-2-yl)ethanesulfonamide, Example 386.1

To a stirred solution of Example 386.13 (16.0 g, 46.8 mmol) in DCM (300 mL) was added TFA (220 ml) at 0° C., and the mixture was stirred at RT for 16 h. The reaction was monitored by TLC which indicated completion of the reaction, and the resulting solution was concentrated in vacuo to afford the initial material. The initial material was absorbed onto a plug of silica gel and purified by chromatography through a Redi-Sep pre-packed silica gel column (120 g) eluting with a gradient of 55% to 70% EtOAc in hexanes to provide Example 386.1 (8 g, 36.1 mmol, 77% yield) as an off-white solid. LCMS-ESI (pos) m/z: 222.1 $(M+H)^+$.

The compounds set forth in the following Table were synthesized following the procedure in Example 140.0 using the known starting material as described.

TABLE 37

| | | |
|---|---|---|
| 391.0 | (2S,3R)-3-(5-chloropyrimidin-2-yl)butane-2-sulfonamide (Example 1.4), (R)-tetrahydrofuran-3-carbohydrazide and (S)-tetrahydrofuran-3-carbohydrazide (commercially available from Astatech Inc.), and 2-isothiocyanato-1,3-dimethoxybenzene (Example 446.0). The racemic mixture was purified by preparative SFC using the following conditions: Column: AS-H (2 × 25 cm) Mobile Phase: 70:30 (A:B) A: Liquid $CO_2$, B: MeOH, Flow Rate: 80 mL/min, 215 nm, 100 bar inlet pressure to deliver peak 1. | 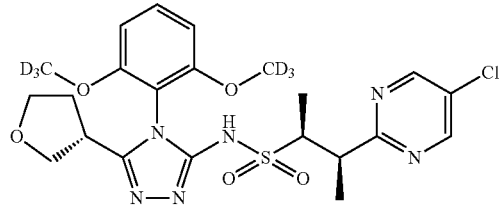 [SMILES: [2H]C([2H])([2H])Oc1cccc(OC([2H])([2H])[2H])c1-n1c(NS(=O)(=O)[C@@H](C)[C@H](C)c2ncc(Cl)cn2)nnc1[C@H]1CCOC1]<br>OR<br>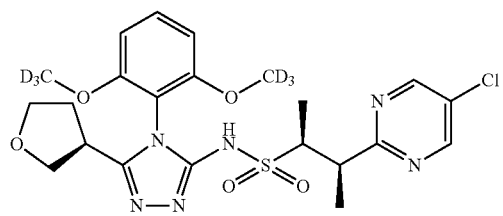 [SMILES: [2H]C([2H])([2H])Oc1cccc(OC([2H])([2H])[2H])c1-n1c(NS(=O)(=O)[C@@H](C)[C@H](C)c2ncc(Cl)cn2)nnc1[C@@H]1CCOC1]<br>(2S,3R)-N-(4-(2,6-bis((trideutero)methyloxy)phenyl)-5-((3R)-tetrahydro-3-furanyl)-4H-1,2,4-triazol-3-yl)-3-(5-chloro-2-pyrimidinyl)-2-butanesulfonamide or<br>(2S,3R)-N-(4-(2,6-bis((trideutero)methyloxy)phenyl)-5-((3S)-tetrahydro-3-furanyl)-4H-1,2,4-triazol-3-yl)-3-(5-chloro-2-pyrimidinyl)-2-butanesulfonamide.<br>$^1$H NMR (400 MHz, $CD_2Cl_2$) δ 10.75 (br s, 1H), 8.63 (s, 2H), 7.49 (t, J = 8.6 Hz, 1H), 6.74-6.69 (m, 2H), 3.86 (dt, J = 5.7, 8.2 Hz, 1H), 3.79-3.63 (m, 5H), 3.00 (qd, J = 7.0, 9.0 Hz, 1H), 2.26-2.17 (m, 1H), 2.00 (dddd, J = 5.8, 7.4, 9.0, 12.7 Hz, 1H), 1.31 (d, J = 6.8 Hz, 3H), 1.26 (d, J = 6.8 Hz, 3H). LCMS-ESI (pos) m/z: 529.0 $(M + H)^+$. |

| | | |
|---|---|---|
| 392.0 | (2S,3R)-3-(5-chloropyrimidin-2-yl)butane-2-sulfonamide (Example 1.4), (R)-tetrahydrofuran-3-carbohydrazide and (S)-tetrahydrofuran-3-carbohydrazide (commercially available) from Astatech Inc.), and 2-isothiocyanato-1,3-dimethoxybenzene (Example 446.0). The racemic mixture was purified by preparative SFC using the following conditions: Column: AS-H (2 × 25 cm) Mobile Phase: 70:30 (A:B) A: Liquid CO$_2$, B: MeOH, Flow Rate: 80 mL/min, 215 nm, 100 bar inlet pressure to deliver peak 2. | 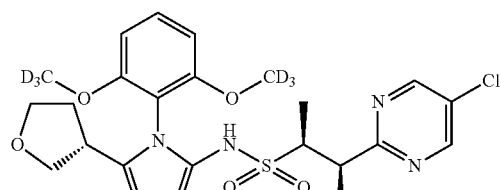<br>OR<br>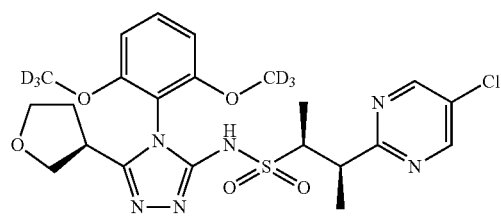 [SMILES: [2H]C([2H])([2H])Oc1cccc(OC([2H])([2H])[2H])c1-n1c(NS(=O)(=O)[C@@H](C)[C@H](C)c2ncc(Cl)cn2)nnc1[C@@H]1CCOC1]<br>(2S, 3R)-N-(4-(2,6-bis((tridutero)methyloxy)phenyl)-5-((3R)-tetrahydro-3-furanyl)-4H-1,2,4-triazol-3-yl)-3-(5-chloro-2-pyrimidinyl)-2-butanesulfonamide or (2S,3R)-N-(4-(2,6-bis((trideutero)methyloxy)phenyl)-5-((3S)-tetrahydro-3-furanyl)-4H-1,2,4-triazol-3-yl)-3-(5-chloro-2-pyrimidinyl)-2-butanesulfonamide.<br>$^1$H NMR (400 MHz, CD$_2$Cl$_2$) δ 10.81 (br s, 1H), 8.63 (s, 2H), 7.49 (t, J = 8.6 Hz, 1H), 6.71 (dd, J = 2.2, 8.6 Hz, 2H), 3.86 (dt, J = 5.8, 8.2 Hz, 1H), 3.81-3.64 (m, 5H), 3.04-2.96 (m, 1H), 2.26-2.16 (m, 1H), 2.00 (dddd, J = 5.8, 7.4, 8.9, 12.7 Hz, 1H), 1.31 (d, J = 6.8 Hz, 3H), 1.26 (d, J = 6.8 Hz, 3H). LCMS-ESI (pos) m/z: 529.0 (M + H)$^+$. |
| 393.0 | (2S,3R)-3-(5-chloropyrimidin-2-yl)butane-2-sulfonamide (Example 1.4), (R)-5,5-dimethyltetrahydrofuran-3-carbohydrazide hydrochloride and (S)-5,5-dimethyltetrahydrofuran-3-carbohydrazide (Example 313.1) and 2-isothiocyanato-1,3-dimethoxybenzene (Example 10.0). The racemic mixture was purified by preparative SFC using the following conditions: Column: AD-H (2 × 15 cm), Mobile Phase: 50:50 (A:B) A: Liquid CO$_2$, B: IPA, Flow Rate: 80 mL/min, 215 nm, 100 bar inlet pressure to deliver peak 1. | 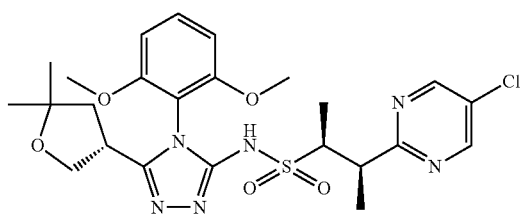 [SMILES: COc1cccc(OC)c1-n1c(NS(=O)(=O)[C@@H](C)[C@H](C)c2ncc(Cl)cn2)nnc1[C@@H]1COC(C)(C)C1]<br>OR<br>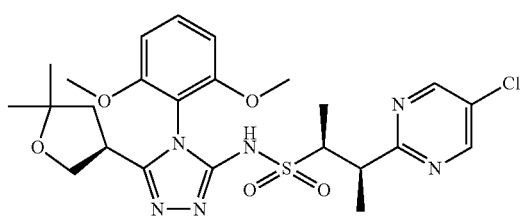 [SMILES: COc1cccc(OC)c1-n1c(NS(=O)(=O)[C@@H](C)[C@H](C)c2ncc(Cl)cn2)nnc1[C@H]1COC(C)(C)C1]<br>(2S, 3R)-3-(5-chloro-2-pyrimidinyl)-N-(4-(2,6-dimethoxyphenyl)-5-((3R)-5,5-dimethyltetrahydro-3-furanyl)-4H-1,2,4-triazol-3-yl)-2-butanesulfonamide or (2S,3R)-3-(5-chloro-2-pyrimidinyl)-N-(4-(2,6-dimethoxyphenyl)-5-((3S)-5,5-dimethyltetrahydro-3-furanyl)-4H-1,2,4-triazol-3-yl)-2-butanesulfonamide.<br>$^1$H NMR (400 MHz, CD$_2$Cl$_2$) δ 10.73 (br s, 1H), 8.63 (s, 2H), 7.49 (t, J = 8.5 Hz, 1H), 6.72 (d, J = 8.5 Hz, 2H), 3.84-3.77 (m, 8H), 3.72-3.62 (m, 2H), 3.14-3.05 (m, 1H), 2.09 (dd, J = 8.6, 12.5 Hz, 1H), 1.87 (dd, J = 9.0, 12.5 Hz, 1H), 1.31 (d, J = 7.0 Hz, 3H), 1.28-1.24 (m, 6H), 1.13 (s, 3H). LCMS-ESI (pos) m/z: 551.0 (M + H)$^+$. |

TABLE 37-continued

| 394.0 | (2S,3R)-3-(5-chloropyrimidin-2-yl)butane-2-sulfonamide (Example 1.4), (R)-5,5-dimethyltetrahydrofuran-3-carbohydrazide hydrochloride and (S)-5,5-dimethyltetrahydrofuran-3-carbohydrazide hydrochloride (Example 313.1), and 2-isothiocyanato-1,3-dimethoxybenzene (Example 10.0). The racemic mixture was purified by preparative SFC using the following conditions: Column: AD-H (2 × 15 cm), Mobile Phase: 50:50 (A:B) A: Liquid CO$_2$, B: IPA, Flow Rate: 80 mL/min, 215 nm, 100 bar inlet pressure to deliver peak 2. | 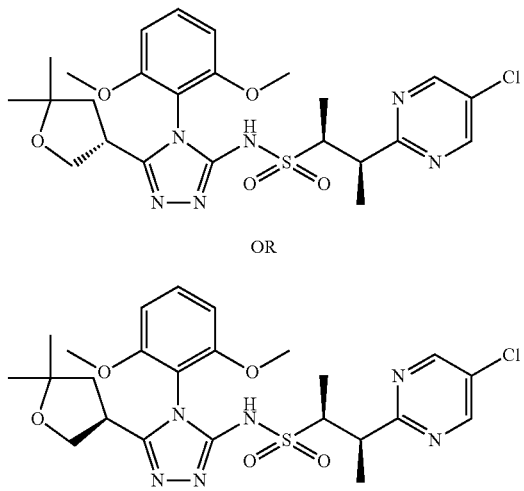<br>(2S,3R)-3-(5-chloro-2-pyrimidinyl)-N-(4-(2,6-dimethoxyphenyl)-5-((3R)-5,5-dimethyltetrahydro-3-furanyl)-4H-1,2,4-triazol-3-yl)-2-butanesulfonamide or (2S,3R)-3-(5-chloro-2-pyrimidinyl)-N-(4-(2,6-dimethoxyphenyl)-5-((3S)-5,5-dimethyltetrahydro-3-furanyl)-4H-1,2,4-triazol-3-yl)-2-butanesulfonamide.<br>$^1$H NMR (400 MHz, CD$_2$Cl$_2$) δ 10.71 (br s, 1H), 8.63 (s, 2H), 7.49 (t, J = 8.6 Hz, 1H), 6.72 (t, J = 7.5 Hz, 2H), 3.84-3.76 (m, 8H), 3.72-3.62 (m, 2H), 3.14-3.05 (m, 1H), 2.10 (dd, J = 8.5, 12.6 Hz, 1H), 1.88 (dd, J = 8.9, 12.6 Hz, 1H), 1.31 (d, J = 6.8 Hz, 3H), 1.28-1.24 (m, 6H), 1.13 (s, 3H). LCMS-ESI (pos) m/z: 551.0 (M + H)$^+$. |
| --- | --- | --- |
| 395.0 | (2S,3R)-3-(5-fluoropyrimidin-2-yl)butane-2-sulfonamide (Example 1.1), (R)-5,5-dimethyltetrahydrofuran-3-carbohydrazide hydrochloride and (S)-5,5-dimethyltetrahydrofuran-3-carbohydrazide hydrochloride (Example 313.1), and 2-isothiocyanato-1,3-dimethoxybenzene (Example 10.0). The racemic mixture was purified by preparative SFC using the following conditions: Column: AD-H (2 × 15 cm), Mobile Phase: 50:50 (A:B) A: Liquid CO$_2$, B: IPA, Flow Rate: 70 mL/min, 215 nm, 100 bar inlet pressure to deliver peak 1. | 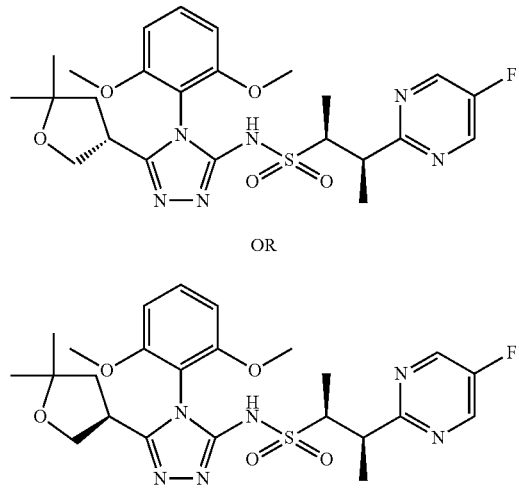<br>(2S,3R)-N-(4-(2,6-dimethoxyphenyl)-5-((3R)-5,5-dimethyltetrahydro-3-furanyl)-4H-1,2,4-triazol-3-yl)-3-(5-fluoro-2-pyrimidinyl)-2-butanesulfonamide or (2S,3R)-N-(4-(2,6-dimethoxyphenyl)-5-((3S)-5,5-dimethyltetrahydro-3-furanyl)-4H-1,2,4-triazol-3-yl)-3-(5-fluoro-2-pyrimidinyl)-2-butanesulfonamide.<br>$^1$H NMR (400 MHz, CD$_2$Cl$_2$) δ 10.76 (br s, 1H), 8.53 (s, 2H), 7.49 (t, J = 8.5 Hz, 1H), 6.72 (d, J = 8.5 Hz, 2H), 3.84-3.78 (m, 8H), 3.72-3.66 (m, 2H), 3.09 (t, J = 8.6 Hz, 1H), 2.09 (dd, J = 8.5, 12.6 Hz, 1H), 1.87 (dd, J = 9.1, 12.6 Hz, 1H), 1.33-1.29 (m, 3H), 1.28-1.24 (m, 6H), 1.13 (s, 3H). LCMS-ESI (pos) m/z: 535.0 (M + H)$^+$. |

TABLE 37-continued

| | | |
|---|---|---|
| 396.0 | (2S,3R)-3-(5-fluoropyrimidin-2-yl)butane-2-sulfonamide (Example 1.1), (R)-5,5-dimethyltetrahydrofuran-3-carbohydrazide hydrochloride and (S)-5,5-dimethyltetrahydrofuran-3-carbohydrazide hydrochloride (Example 313.1), and 2-isothiocyanato-1,3-dimethoxybenzene (Example 10.0). The racemic mixture was purified by preparative SFC using the following conditions: Column: AD-H (2 × 15 cm), Mobile Phase: 50:50 (A:B) A: Liquid $CO_2$, B: IPA, Flow Rate: 70 mL/min, 215 nm, 100 bar inlet pressure to deliver peak 2. | 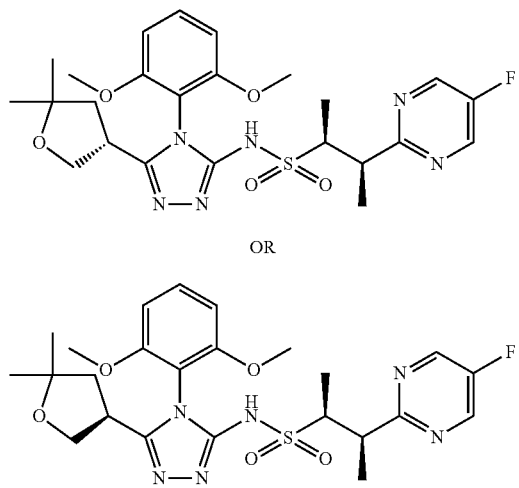<br><br>OR<br><br>(2S,3R)-N-(4-(2,6-dimethoxyphenyl)-5-((3R)-5,5-dimethyltetrahydro-3-furanyl)-4H-1,2,4-triazol-3-yl)-3-(5-fluoro-2-pyrimidinyl)-2-butanesulfonamide or (2S,3R)-N-(4-(2,6-dimethoxyphenyl)-5-((3S)-5,5-dimethyltetrahydro-3-furanyl)-4H-1,2,4-triazol-3-yl)-3-(5-fluoro-2-pyrimidinyl)-2-butanesulfonamide.<br>$^1$H NMR (400 MHz, $CD_2Cl_2$) δ 10.73 (br s, 1H), 8.55-8.51 (m, 2H), 7.49 (t, J = 8.5 Hz, 1H), 6.72 (dt, J = 0.7, 7.9 Hz, 2H), 3.83-3.77 (m, 8H), 3.73-3.65 (m, 2H), 3.13-3.05 (m, 1H), 2.10 (dd, J = 8.6, 12.5 Hz, 1H), 1.88 (dd, J = 9.1, 12.6 Hz, 1H), 1.33-1.29 (m, 3H), 1.28-1.24 (m, 6H), 1.13 (s, 3H). LCMS-ESI (pos) m/z: 535.0 (M + H)$^+$. |
| 397.0 | (1R,2S)-1-(5-chloropyrimidin-2-yl)-1-methoxypropane-2-sulfonamide (Example 11.3), (R)-5-oxopyrrolidine-2-carbohydrazide and (S)-5-oxopyrrolidine-2-carbohydrazide (commercially available from Enamine), and 2-isothiocyanato-1,3-dimethoxybenzene (Example 10.0). The racemic mixture was purified by preparative SFC using the following conditions: Column: AD-H (2 × 25 cm) + AD-H (2 × 15 cm), Mobile Phase: 60:40 (A:B) A: Liquid $CO_2$, B: IPA, Flow Rate: 50 mL/min, 215 nm, 100 bar inlet pressure to deliver peak 1. | 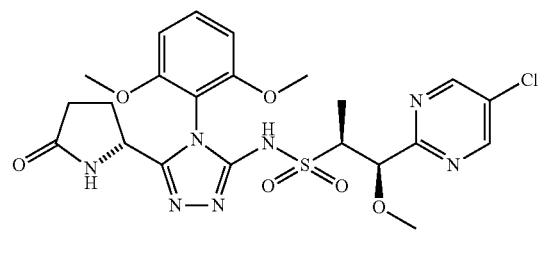<br><br>OR<br><br>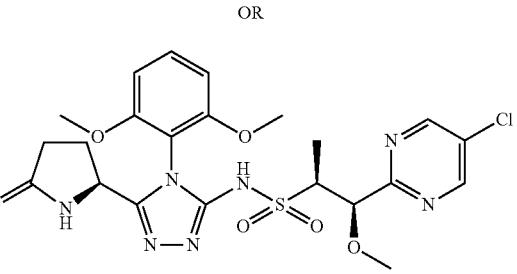<br><br>(1R,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1-methoxy-2-propanesulfonamide or (1R,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1-methoxy-2-propanesulfonamide.<br>$^1$H NMR (400 MHz, DMSO-$d_6$) δ = 12.92 (br s, 1H), 8.93 (s, 2H), 8.05 (s, 1H), 7.51 (t, J = 8.5 Hz, 1H), 6.85 (dd, J = 8.6, 10.9 Hz, 2H), 4.77 (d, J = 4.1 Hz, 1H), 4.35 (dd, J = 3.1, 8.7 Hz, 1H), 3.79-3.74 (m, 6H), 3.43-3.36 (m, 1H), 3.14 (s, 3H), 2.16-2.06 (m, 1H), 2.05-1.96 (m, 1H), 1.84-1.73 (m, 2H), 1.13 (d, J = 6.8 Hz, 3H). LCMS-ESI (pos) m/z: 552.2 (M + H)$^+$. |

TABLE 37-continued

| | | |
|---|---|---|
| 398.0 | (1R,2S)-1-(5-chloropyrimidin-2-yl)-1-methoxypropane-2-sulfonamide (Example 11.3), (R)-5-oxopyrrolidine-2-carbohydrazide and (S)-5-oxopyrrolidine-2-carbohydrazide (commercially available from Enamine), and 2-isothiocyanato-1,3-dimethoxybenzene (Example 10.0). The racemic mixture was purified by preparative SFC using the following conditions: Column: AD-H (2 × 25 cm) + AD-H (2 × 15 cm), Mobile Phase: 60:40 (A:B) A: Liquid CO$_2$, B: IPA, Flow Rate: 50 mL/min, 215 nm, 100 bar inlet pressure deliver peak 2. | 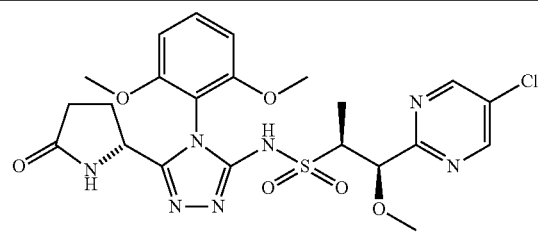<br>OR<br>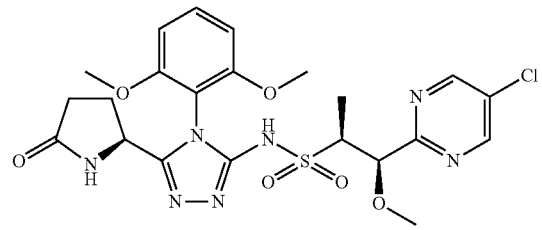<br>(1R,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1-methoxy-2-propanesulfonamide or (1R,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1-methoxy-2-propanesulfonamide.<br>$^1$H NMR (400 MHz, DMSO-d$_6$) δ = 12.91 (br s, 1H), 8.94-8.91 (m, 2H), 8.06 (s, 1H), 7.51 (t, J = 8.5 Hz, 1H), 6.85 (t, J = 7.7 Hz, 2H), 4.76 (d, J = 4.6 Hz, 1H), 4.38-4.33 (m, 1H), 3.78 (s, 3H), 3.77-3.74 (m, 3H), 3.43-3.36 (m, 1H), 3.14 (s, 3H), 2.18-2.07 (m, 1H), 2.06-1.95 (m, 1H), 1.85-1.72 (m, 2H), 1.13 (d, J = 7.0 Hz, 3H). LCMS-ESI (pos) m/z: 552.2 (M + H)$^+$. |
| 399.0 | (1S,2S)-1-(5-chloropyrimidin-2-yl)-1-isopropoxypropane-2-sulfonamide (Example 13.6), (R)-5-oxopyrrolidine-2-carbohydrazide and (S)-5-oxopyrrolidine-2-carbohydrazide (commercially available from Enamine), and 2-isothiocyanato-1,3-dimethoxybenzene (Example 10.0). The racemic mixture was purified by preparative SFC using the following conditions: Column: OJ-H (2 × 25 cm) + OJ-H (2 × 15 cm), Mobile Phase: 75:25 (A:B) A: Liquid CO$_2$, B: IPA, Flow Rate: 60 mL/min, 218 nm, 100 bar inlet pressure to deliver peak 1. | 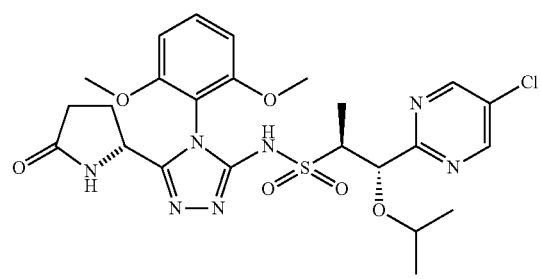<br>OR<br>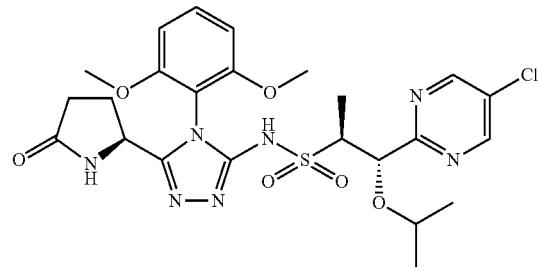 [SMILES: COc1cccc(OC)c1-n1c(NS(=O)(=O)[C@@H](C)[C@@H](OC(C)C)c2ncc(Cl)cn2)nnc1[C@@H]1CCC(=O)N1]<br>(1S,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1-(2-propanyloxy)-2-propanesulfonamide or (1S,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1-(2-propanyloxy)-2-propanesulfonamide.<br>$^1$H NMR (400 MHz, DMSO-d$_6$) δ 12.80 (br s, 1H), 8.94-8.91 (m, 2H), 8.05 (s, 1H), 7.51 (t, J = 8.4 Hz, 1H), 6.85 (t, J = 8.3 Hz, 2H), 4.76 (d, J = 6.8 Hz, 1H), 4.33 (br d, J = 5.8 Hz, 1H), 3.83-3.78 (m, 6H), 3.46-3.35 (m, |

| | | |
|---|---|---|
| | | 2H), 2.17-2.07 (m, 1H), 2.05-1.93 (m, 1H), 1.83-1.73 (m, 2H), 0.98 (m, 6H), 0.82 (d, J = 6.0 Hz, 3H). LCMS-ESI (pos) m/z: 580.0 (M + H)+. |
| 400.0 | (1S,2S)-1-(5-chloropyrimidin-2-yl)-1-isopropoxypropane-2-sulfonamide (Example 13.6), (R)-5-oxopyrrolidine-2-carbohydrazide and (S)-5-oxopyrrolidine-2-carbohydrazide (commercially available from Enamine), and 2-isothiocyanato-1,3-dimethoxybenzene (Example 10.0). The racemic mixture was purified by preparative SFC using the following conditions: Column: OJ-H (2 × 25 cm) + OJ-H (2 × 15 cm), Mobile Phase: 75:25 (A:B) A: Liquid CO₂, B: IPA, Flow Rate: 60 mL/min, 218 nm, 100 bar inlet pressure to deliver peak 2. | 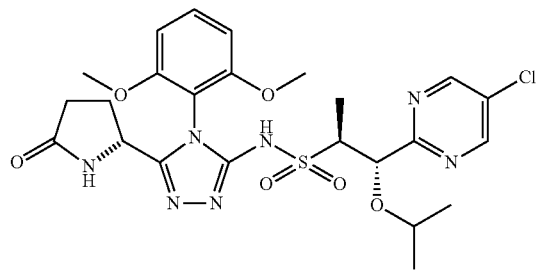<br>OR<br>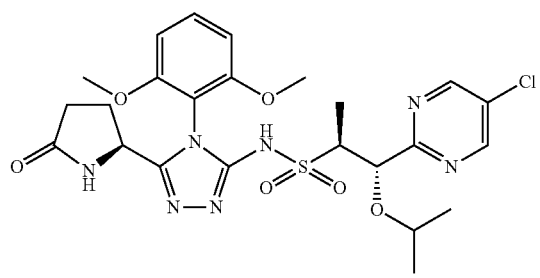 [SMILES: COc1cccc(OC)c1-n1c(NS(=O)(=O)[C@@H](C)[C@@H](OC(C)C)c2ncc(Cl)cn2)nnc1[C@@H]1CCC(=O)N1]<br>(1S,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1-(2-propanyloxy)-2-propanesulfonamide or (1S,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1-(2-propanyloxy)-2-propanesulfonamide.<br>¹H NMR (400 MHz, DMSO-d₆) δ 12.85 (s, 1H), 8.92 (s, 2H), 8.05 (s, 1H), 7.51 (t, J = 8.5 Hz, 1H), 6.85 (t, J = 8.2 Hz, 2H), 4.76 (d, J = 7.3 Hz, 1H), 4.38-4.33 (m, 1H), 3.83-3.80 (s, 3H), 3.80-3.78 (s, 3H), 3.46-3.34 (m, 2H), 2.17-2.04 (m, 1H), 2.03-1.93 (m, 1H), 1.84-1.73 (m, 2H), 0.99 (d, J = 6.0 Hz, 3H), 0.95 (d, J = 7.0 Hz, 3H), 0.81 (d, J = 6.0 Hz, 3H). LCMS-ESI (pos) m/z: 580.0 (M + H)+. |
| 401.0 | (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.), and 3-(isothiocyanatomethyl)-1,2-oxazole (commercially available from Enamine). The racemic mixture was purified by preparative SFC using the following conditions: Column: AD-H (2 × 25 cm), Mobile Phase: 55:45 (A:B) A: Liquid CO₂, B: MeOH, Flow Rate: 80 mL/min, 217 nm, 100 bar inlet pressure to deliver peak 1. | 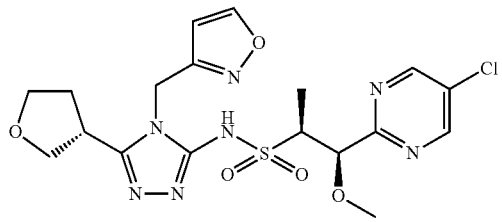 [SMILES: CO[C@H](c1ncc(Cl)cn1)[C@H](C)S(=O)(=O)Nc1nnc([C@H]2CCOC2)n1Cc1ccon1]<br>OR<br>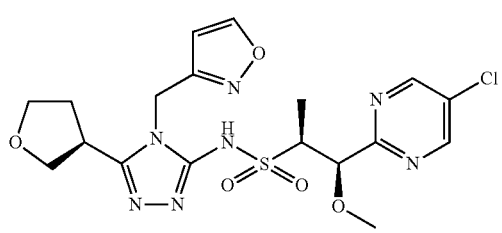 [SMILES: CO[C@H](c1ncc(Cl)cn1)[C@H](C)S(=O)(=O)Nc1nnc([C@@H]2CCOC2)n1Cc1ccon1]<br>(1R,2S)-1-(5-chloro-2-pyrimidinyl)-1-methoxy-N-(4-(1,2-oxazol-3-ylmethyl)-5-((3R)-tetrahydro-3-furanyl)-4H-1,2,4-triazol-3-yl)-2-propanesulfonamide or (1R,2S)-1-(5-chloro-2-pyrimidinyl)-1-methoxy-N-(4-(1,2-oxazol-3-ylmethyl)-5-((3S)-tetrahydro-3-furanyl)- |

TABLE 37-continued 4H-1,2,4-triazol-3-yl)-2-propanesulfonamide.
$^1$H NMR (400 MHz, CD$_2$Cl$_2$) δ 10.87 (br s, 1H), 8.72 (s, 2H), 8.47 (s, 1H), 6.62 (s, 1H), 5.15-5.05 (m, 2H), 4.95 (d, J = 3.9 Hz, 1H), 4.04-3.99 (m, 1H), 3.97-3.91 (m, 1H), 3.89-3.83 (m, 2H), 3.68-3.61 (m, 1H), 3.49-3.42 (m, 1H), 3.24 (s, 3H), 2.32-2.23 (m, 1H), 2.16-2.08 (m, 1H), 1.32 (d, J = 7.0 Hz, 3H). LCMS-ESI (pos) m/z: 484.0 (M + H)$^+$.

402.0 (1R,2S)-1-(5-chloropyrimidin-2-yl)-1-methoxypropane-2-sulfonamide (Example 11.3), (R)-tetrahydrofuran-3-carbohydrazide and (S)-tetrahydrofuran-3-carbohydrazide (commercially available from Astatech Inc.) , and 3-(isothiocyanatomethyl)-1,2-oxazole (commercially available from Enamine). The racemic mixture was purified by preparative SFC using the following conditions: Column: AD-H (2 × 25 cm), Mobile Phase: 55:45 (A:B) A: Liquid CO$_2$, B: MeOH, Flow Rate: 80 mL/min, 217 nm, 100 bar inlet pressure to deliver peak 2.

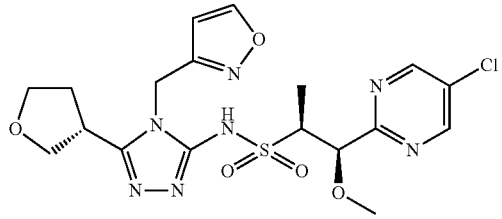 [SMILES: CO[C@H](c1ncc(Cl)cn1)[C@H](C)S(=O)(=O)Nc1nnc([C@H]2CCOC2)n1Cc1ccon1]

OR

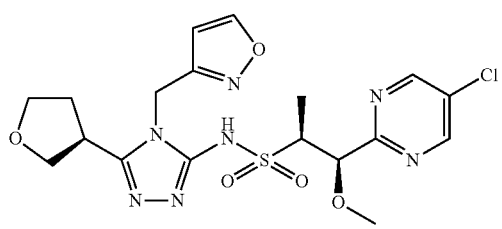 [SMILES: CO[C@H](c1ncc(Cl)cn1)[C@H](C)S(=O)(=O)Nc1nnc([C@@H]2CCOC2)n1Cc1ccon1]

(1R,2S)-1-(5-chloro-2-pyrimidinyl)-1-methoxy-N-(4-(1,2-oxazol-3-ylmethyl)-5-((3R)-tetrahydro-3-furanyl)-4H-1,2,4-triazol-3-yl)-2-propanesulfonamide or (1R,2S)-1-(5-chloro-2-pyrimidinyl)-1-methoxy-N-(4-(1,2-oxazol-3-ylmethyl)-5-((3S)-tetrahydro-3-furanyl)-4H-1,2,4-triazol-3-yl)-2-propanesulfonamide.
$^1$H NMR (400 MHz, CD$_2$Cl$_2$) δ 10.95 (br s, 1H), 8.72 (s, 2H), 8.47 (s, 1H), 6.62 (s, 1H), 5.15-5.05 (m, 2H), 4.96 (br d, J = 3.7 Hz, 1H), 4.02-3.92 (m, 2H), 3.88-3.80 (m, 2H), 3.67-3.61 (m, 1H), 3.50-3.42 (m, 1H), 3.22 (s, 3H), 2.34-2.26 (m, 1H), 2.20-2.13 (m, 1H), 1.32 (br d, J = 6.8 Hz, 3H). LCMS-ESI (pos) m/z: 484.0 (M + H)$^+$.

403.0 (1R,2S)-1-(5-chloropyrimidin-2-yl)-1-methoxypropane-2-sulfonamide (Example 11.3), (2S,5S)-5-methyltetrahydrofuran-2-carbohydrazide and (2R,5R)-5-methyltetrahydrofuran-2-carbohydrazide commercially available from Ukrorgsyntez), and 3-(isothiocyanatomethyl)-1,2-oxazole (commercially available from Enamine). The racemic mixture was purified by preparative SFC using the following conditions: Column: AS-H (2 × 25 cm), Mobile Phase: 65:35 (A:B) A: Liquid CO$_2$, B: IPA, Flow Rate: 80 mL/min, 217 nm, 100 bar inlet pressure to deliver peak 1.

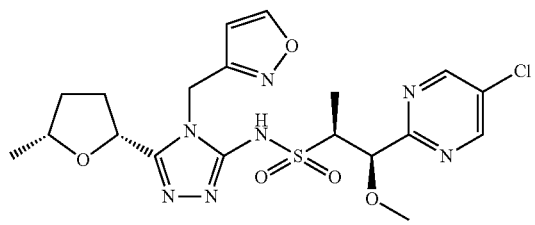 [SMILES: CO[C@H](c1ncc(Cl)cn1)[C@H](C)S(=O)(=O)Nc1nnc([C@H]2CC[C@@H](C)O2)n1Cc1ccon1]

OR

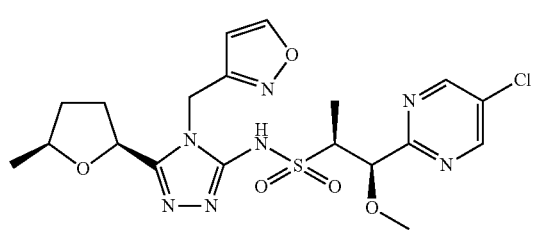 [SMILES: CO[C@H](c1ncc(Cl)cn1)[C@H](C)S(=O)(=O)Nc1nnc([C@@H]2CC[C@H](C)O2)n1Cc1ccon1]

(1R,2S)-1-(5-chloro-2-pyrimidinyl)-1-methoxy-N-(5-((2S,5S)-5-methyltetrahydro-2-furanyl)-4-(1,2-oxazol-3-ylmethyl)-4H-1,2,4-triazol-3-yl)-2-propanesulfonamide or (1R,2S)-1-(5-chloro-2-pyrimidinyl)-1-methoxy-N-(5-((2R,5R)-5-methyltetrahydro-2-furanyl)-4-(1,2-oxazol-3-

TABLE 37-continued ylmethyl)-4H-1,2,4-triazol-3-yl)-2-
propanesulfonamide.
¹H NMR (400 MHz, CD₂Cl₂) δ 10.91 (br s, 1H), 8.71
(s, 2H), 8.42 (s, 1H), 6.56 (s, 1H), 5.36-5.29 (m, 1H),
5.23-5.16 (m, 1H), 4.95-4.87 (m, 2H), 4.20-4.10
(m, 1H), 3.65-3.59 (m, 1H), 3.22 (s, 3H), 2.59-2.48
(m, 1H), 2.22 (qd, J = 8.0, 12.7 Hz, 1H), 2.15-2.07 (m,
1H), 1.65-1.54 (m, 1H), 1.31 (d, J = 7.0 Hz, 3H), 1.19
(d, J = 6.2 Hz, 3H). LCMS-ESI (pos) m/z: 498.0
(M + H)⁺.

404.0 (1R,2S)-1-(5-
chloropyrimidin-2-yl)-1-
methoxypropane-2-
sulfonamide (Example
11.3), (2S,5S)-5-
methyltetrahydrofuran-2-
carbohydrazide and
(2R,5R)-5-
methyltetrahydrofuran-2-
carbohydrazide
commercially available
from Ukrorgsyntez), and 3-
(isothiocyanatomethyl)-
1,2-oxazole (commercially
available from Enamine).
The racemic mixture was
purified by preparative
SFC using the following
conditions: Column: AS-
H (2 × 25 cm), Mobile
Phase: 65:35 (A:B) A:
Liquid CO₂, B: IPA, Flow
Rate: 80 mL/min, 217 nm,
100 bar inlet pressure to
deliver peak 2.

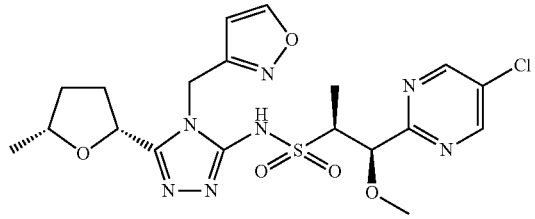 [SMILES: CO[C@H](c1ncc(Cl)cn1)[C@H](C)S(=O)(=O)Nc1nnc([C@H]2CC[C@@H](C)O2)n1Cc1ccon1]

OR

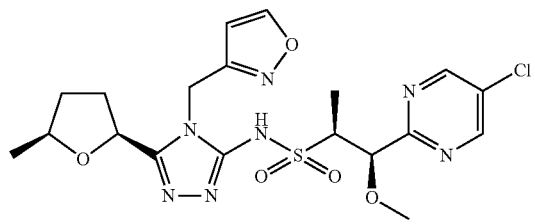 [SMILES: CO[C@H](c1ncc(Cl)cn1)[C@H](C)S(=O)(=O)Nc1nnc([C@@H]2CC[C@H](C)O2)n1Cc1ccon1]

(1R,2S)-1-(5-chloro-2-pyrimidinyl)-1-methoxy-N-(5-
((2S,5S)-5-methyltetrahydro-2-furanyl)-4-(1,2-oxazol-
3-ylmethyl)-4H-1,2,4-triazol-3-yl)-2-
propanesulfonamide or (1R,2S)-1-(5-chloro-2-
pyrimidinyl)-1-methoxy-N-(5-((2R,5R)-5-
methyltetrahydro-2-furanyl)-4-(1,2-oxazol-3-
ylmethyl)-4H-1,2,4-triazol-3-yl)-2-
propanesulfonamide.
¹H NMR (400 MHz, CD₂Cl₂) δ 10.88 (br s, 1H), 8.71
(s, 2H), 8.43 (s, 1H), 6.55 (s, 1H), 5.30-5.02 (m, 2H),
4.93-4.86 (m, 2H), 4.19-4.10 (m, 1H), 3.69-3.60
(m, 1H), 3.23 (s, 3H), 2.56-2.47 (m, 1H), 2.27-2.17
(m, 1H), 2.15-2.07 (m, 1H), 1.66-1.56 (m, 1H), 1.31
(d, J = 6.8 Hz, 3H), 1.23-1.17 (m, 3H). LCMS-ESI
(pos) m/z: 498.0 (M + H)⁺.

405.0 (1R,2S)-1-(5-chloropyrimidin-2-
yl)-1-methoxypropane-2-
sulfonamide (Example 11.3),
(R)-1-methyl-5-oxopyrrolidine-
2-carbohydrazide hydrochloride
and (S)-1-methyl-5-
oxopyrrolidine-2-
carbohydrazide hydrochloride
(Example 405.1), and 2-
isothiocyanato-1,3-
dimethoxybenzene (Example
10.0). The racemic mixture was
purified by preparative SFC
using the following conditions:
Column: AY-H (2 × 25 cm) +
OJ-H (2 × 15 cm), Mobile Phase:
65:35 (A:B) A: Liquid CO₂, B:
MeOH, Flow Rate: 80 mL/min,
220 nm, 100 bar inlet pressure
to deliver peak 1.

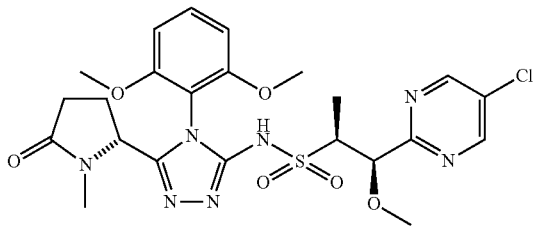

OR

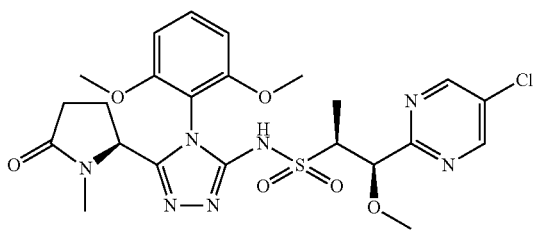 [SMILES: COc1cccc(OC)c1-n1c(NS(=O)(=O)[C@@H](C)[C@H](OC)c2ncc(Cl)cn2)nnc1[C@@H]1CCC(=O)N1C]

(1R,2S)-1-(5-chloropyrimidin-2-yl)-N-(4-(2,6-
dimethoxyphenyl)-5-((R)-1-methyl-5-oxopyrrolidin-2-

TABLE 37-continued yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-1-methyl-5-oxopyrrolidin-2-yl)-4H-1,2,4-triazol-3-yl)-1-methoxypropane-2-sulfonamide.

$^1$H NMR (400 MHz, CD$_2$Cl$_2$) δ 8.72 (s, 2H), 7.50 (t, J = 8.5 Hz, 1H), 6.72 (dd, J = 6.4, 8.3 Hz, 2H), 4.88 (d, J = 4.4 Hz, 1H), 4.40 (dd, J = 3.0, 9.2 Hz, 1H), 3.84-3.82 (s, 3H), 3.81-3.79 (s, 3H), 3.62-3.55 (m, 1H), 3.26 (s, 3H), 2.73 (s, 3H), 2.23-2.05 (m, 2H), 2.01-1.93 (m, 1H), 1.74-1.64 (m, 1H), 1.25 (d, J = 7.0 Hz, 3H). 1H), 1.84-1.73 (m, 2H), 1.13 (d, J = 6.8 Hz, 3H). LCMS-ESI (pos) m/z: 566.0 (M + H)$^+$.

406.0 (1R,2S)-1-(5-chloropyrimidin-2-yl)-1-methoxypropane-2-sulfonamide (Example 11.3), (R)-1-methyl-5-oxopyrrolidine-2-carbohydrazide hydrochloride and (S)-1-methyl-5-oxopyrrolidine-2-carbohydrazide hydrochloride (Example 405.1), and 2-isothiocyanato-1,3-dimethoxybenzene (Example 10.0). The racemic mixture was purified by preparative SFC using the following conditions:

Column: AY-H (2 × 25 cm) + OJ-H (2 × 15 cm), Mobile Phase: 65:35 (A:B) A: Liquid CO$_2$, B: MeOH, Flow Rate: 80 mL/min, 220 nm, 100 bar inlet pressure to deliver peak 2.

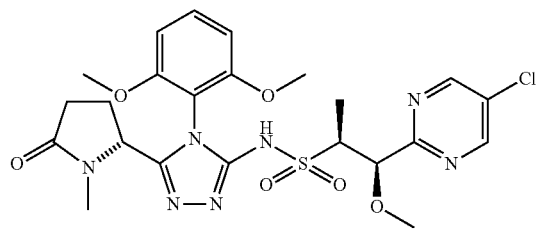

OR

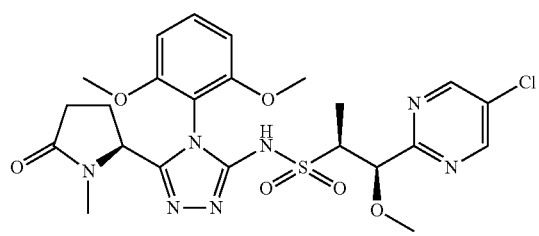 [SMILES: COc1cccc(OC)c1-n1c(NS(=O)(=O)[C@@H](C)[C@H](OC)c2ncc(Cl)cn2)nnc1[C@@H]1CCC(=O)N1C]

(1R,2S)-1-(5-chloropyrimidin-2-yl)-N-(4-(2,6-dimethoxyphenyl)-5-((R)-1-methyl-5-oxopyrrolidin-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-((S)-1-methyl-5-oxopyrrolidin-2-yl)-4H-1,2,4-triazol-3-yl)-1-methoxypropane-2-sulfonamide.

$^1$H NMR (400 MHz, CD$_2$Cl$_2$) δ 11.35-10.54 (m, 1H), 8.71 (s, 2H), 7.50 (t, J = 8.5 Hz, 1H), 6.73 (br d, J = 6.8 Hz, 2H), 4.86 (d, J = 4.4 Hz, 1H), 4.43-4.36 (m, 1H), 3.88-3.83 (m, 3H), 3.82-3.76 (m, 3H), 3.61-3.54 (m, 1H), 3.25 (s, 3H), 2.72 (s, 3H), 2.24-2.06 (m, 2H), 2.03-1.94 (m, 1H), 1.75-1.66 (m, 1H), 1.25 (d, J = 6.8 Hz, 3H). LCMS-ESI (pos) m/z: 566.0 (M + H)$^+$.

| | | |
|---|---|---|
| 407.0 | (1S,2S)-1-isopropoxy-1-(5-methylpyridin-2-yl)propane-2-sulfonamide (Example 366.1), (R)-tetrahydrofuran-3-carbohydrazide and (S)-tetrahydrofuran-3-carbohydrazide (commercially available from Astatech Inc.), and 2-isothiocyanato-1,3-dimethoxybenzene (Example 10.0). The racemic mixture was purified by preparative SFC using the following conditions: Column: IC (2 × 25 cm), Mobile Phase: 55:45 (A:B) A: Liquid CO$_2$, B: MeOH, Flow Rate: 80 mL/min, 222 nm, 100 bar inlet pressure to deliver peak 1. | 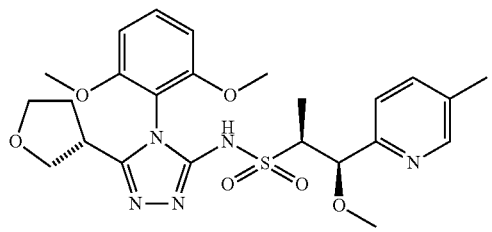<br>OR<br>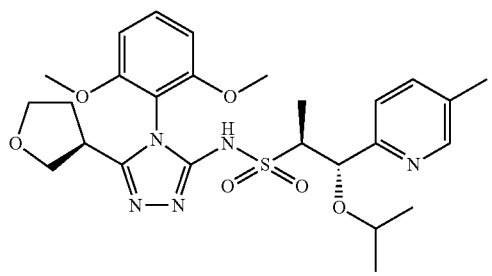 [SMILES: COc1cccc(OC)c1-n1c(NS(=O)(=O)[C@@H](C)[C@@H](OC(C)C)c2ccc(C)cn2)nnc1[C@@H]1CCOC1]<br>(1S,2S)-N-(4-(2,6-dimethoxyphenyl)-5-((3R)-tetrahydro-3-furanyl)-4H-1,2,4-triazol-3-yl)-1-(5-methyl-2-pyridinyl)-1-(2-propanyloxy)-2-propanesulfonamide or (1S,2S)-N-(4-(2,6-dimethoxyphenyl)-5-((3S)-tetrahydro-3-furanyl)-4H-1,2,4-triazol-3-yl)-1-(5-methyl-2-pyridinyl)-1-(2-propanyloxy)-2-propanesulfonamide.<br>$^1$H NMR (500 MHz, DMSO-d$_6$) δ = 12.86 (br s, 1H), 8.32 (s, 1H), 7.59-7.56 (m, 1H), 7.52 (t, J = 8.6 Hz, 1H), 7.26 (d, J = 8.0 Hz, 1H), 6.87 (d, J = 8.6 Hz, 2H), 4.62 (d, J = 7.3 Hz, 1H), 3.81-3.79 (m, 3H), 3.79-3.77 (m, 3H), 3.74 (dt, J = 6.1, 8.0 Hz, 1H), 3.66-3.59 (m, 3H), 3.38-3.31 (m, 1H), 3.30-3.24 (m, 1H), 2.98-2.92 (m, 1H), 2.27 (s, 3H), 2.09-2.02 (m, 1H), 1.98-1.91 (m, 1H), 0.98 (d, J = 6.0 Hz, 3H), 0.86-0.83 (m, 3H), 0.83-0.80 (m, 3H). LCMS-ESI (pos) m/z: 546.3 (M + H)$^+$. |
| 408.0 | (1S,2S)-1-isopropoxy-1-(5-methylpyridin-2-yl)propane-2-sulfonamide (Example 366.1), (R)-tetrahydrofuran-3-carbohydrazide and (S)-tetrahydrofuran-3-carbohydrazide (commercially available from Astatech Inc.), and 2-isothiocyanato-1,3-dimethoxybenzene (Example 10.0). The racemic mixture was purified by preparative SFC using the following conditions: Column: IC (2 × 25 cm), Mobile Phase: 55:45 (A:B) A: Liquid CO$_2$, B: MeOH, Flow Rate: 80 mL/min, 222 nm, 100 bar inlet pressure to deliver peak 2. | 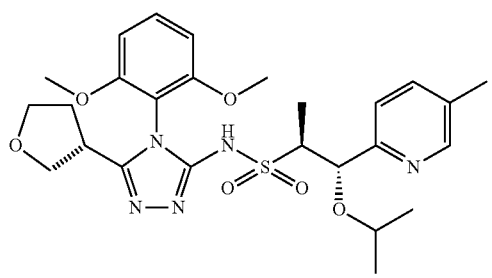<br>OR<br>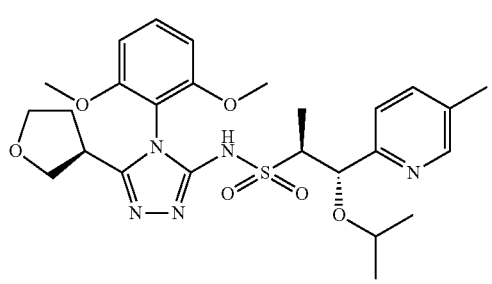 [SMILES: COc1cccc(OC)c1-n1c(NS(=O)(=O)[C@@H](C)[C@@H](OC(C)C)c2ccc(C)cn2)nnc1[C@@H]1CCOC1]<br>(1S,2S)-N-(4-(2,6-dimethoxyphenyl)-5-((3R)-tetrahydro-3-furanyl)-4H-1,2,4-triazol-3-yl)-1-(5-methyl-2-pyridinyl)-1-(2-propanyloxy)-2-propanesuflonamide or (1S,2S)-N-(4-(2,6-dimethoxyphenyl)-5-((3S)-tetrahydro-3-furanyl)-4H- |

TABLE 37-continued

| | | |
|---|---|---|
| | 1,2,4-triazol-3-yl)-1-(5-methyl-2-pyridinyl)-1-(2-propanyloxy)-2-propanesulfonamide.<br>¹H NMR (500 MHz, DMSO-d₆) δ = 12.85 (br s, 1H), 8.32 (s, 1H), 7.60-7.55 (m, 1H), 7.51 (t, J = 8.6 Hz, 1H), 7.26 (d, J = 8.0 Hz, 1H), 6.89-6.85 (m, 2H), 4.62 (d, J = 7.0 Hz, 1H), 3.82-3.77 (m, 6H), 3.76-3.71 (m, 1H), 3.66-3.61 (m, 3H), 3.33 (br d, J = 3.4 Hz, 2H), 2.97-2.91 (m, 1H), 2.27 (s, 3H), 2.06-1.98 (m, 1H), 1.96-1.88 (m, 1H), 1.00-0.97 (m, 3H), 0.86-0.83 (m, 3H), 0.83-0.80 (m, 3H). LCMS-ESI (pos) m/z: 546.3 (M + H)⁺. | |
| 409.0 | (2S,3R)-3-(5-chloropyridin-2-yl)butane-2-sulfonamide (Example 14.0), (R)-tetrahydrofuran-3-carbohydrazide and (S)-tetrahydrofuran-3-carbohydrazide (commercially available from Astatech Inc.), and 2-isothiocyanato-1,3-dimethoxybenzene (Example 10.0). The racemic mixture was purified by preparative SFC using the following conditions Column: AS-H (2 × 25 cm), Mobile Phase: 75:25 (A:B) A: Liquid CO₂, B: MeOH, Flow Rate: 80 mL/min, 218 nm, 100 bar inlet pressure to deliver peak 1. | 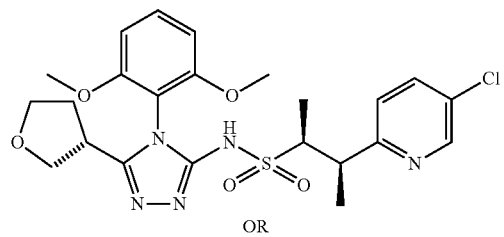<br>OR<br>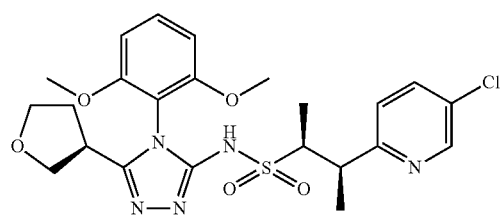 [SMILES: COc1cccc(OC)c1-n1c(NS(=O)(=O)[C@@H](C)[C@H](C)c2ccc(Cl)cn2)nnc1[C@@H]1CCOC1]<br>(1S,2S)-N-(4-(2,6-dimethoxyphenyl)-5-((3R)-tetrahydro-3-furanyl)-4H-1,2,4-triazol-3-yl)-1-(5-methyl-2-pyridinyl)-1-(2-propanyloxy)-2-propanesulfonamide or (1S,2S)-N-(4-(2,6-dimethoxyphenyl)-5-((3S)-tetrahydro-3-furanyl)-4H-1,2,4-triazol-3-yl)-1-(5-methyl-2-pyridinyl)-1-(2-propanyloxy)-2-propanesulfonamide.<br>¹H NMR (500 MHz, DMSO-d₆) δ 12.84 (br s, 1H), 8.53 (d, J = 2.3 Hz, 1H), 7.84 (dd, J = 2.6, 8.3 Hz, 1H), 7.52 (t, J = 8.6 Hz, 1H), 7.25 (d, J = 8.6 Hz, 1H), 6.88-6.84 (m, 2H), 3.78-3.75 (m, 4H), 3.75-3.74 (m, 3H), 3.64-3.61 (m, 2H), 3.59-3.55 (m, 1H), 3.36-3.30 (m, 2H), 3.00-2.92 (m, 1H), 2.09-2.02 (m, 1H), 1.98-1.90 (m, 1H), 1.24-1.19 (m, 3H), 1.07-1.03 (m, 3H). LCMS-ESI (pos) m/z: 522.2 (M + H)⁺. |
| 410.0 | (2S,3R)-3-(5-chloropyridin-2-yl)butane-2-sulfonamide (Example 14.0), (R)-tetrahydrofuran-3-carbohydrazide and (S)-tetrahydrofuran-3-carbohydrazide (commercially available from Astatech Inc.), and 2-isothiocyanato-1,3-dimethoxybenzene (Example 10.0). The racemic mixture was purified by preparative SFC using the following conditions Column: AS-H (2 × 25 cm), Mobile Phase: 75:25 (A:B) A: Liquid CO₂, B: MeOH, Flow Rate: 80 mL/min, 218 nm, 100 bar inlet pressure to deliver peak 2. | 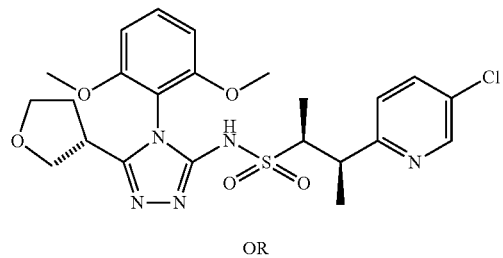<br>OR<br>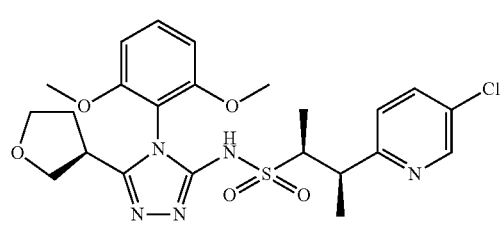 [SMILES: COc1cccc(OC)c1-n1c(NS(=O)(=O)[C@@H](C)[C@H](C)c2ccc(Cl)cn2)nnc1[C@@H]1CCOC1]<br>(1S,2S)-N-(4-(2,6-dimethoxyphenyl)-5-((3R)-tetrahydro-3-furanyl)-4H-1,2,4-triazol-3-yl)-1-(5-methyl-2-pyridinyl)-1-(2-propanyloxy)-2-propanesulfonamide or (1S,2S)-N-(4-(2,6-dimethoxyphenyl)-5-((3S)-tetrahydro-3-furanyl)-4H- |

TABLE 37-continued 1,2,4-triazol-3-yl)-1-(5-methyl-2-pyridinyl)-1-(2-propanyloxy)-2-propanesulfonamide.

$^1$H NMR (500 MHz, DMSO-d$_6$) δ 12.85 (s, 1H), 8.53 (d, J = 2.3 Hz, 1H), 7.84 (dd, J = 2.6, 8.6 Hz, 1H), 7.52 (t, J = 8.6 Hz, 1H), 7.25 (d, J = 8.6 Hz, 1H), 6.86 (d, J = 8.6 Hz, 2H), 3.81-3.73 (m, 7H), 3.65-3.62 (m, 2H), 3.60-3.54 (m, 1H), 3.33-3.28 (m, 2H), 2.99-2.92 (m, 1H), 2.07-1.99 (m, 1H), 1.97-1.89 (m, 1H), 1.20 (d, J = 7.0 Hz, 3H), 1.05 (d, J = 7.0 Hz, 3H). LCMS-ESI (pos) m/z: 522.2 (M + H)$^+$.

411.0 (1S,2S)-1-isopropoxy-1-(5-methylpyrimidin-2-yl)propane-2-sulfonamide (Example 13.5), (R)-5,5-dimethyltetrahydrofuran-3-carbohydrazide hydrochloride and (S)-5,5-dimethyltetrahydrofuran-3-carbohydrazide hydrochloride, (Example 313.1), and 2-isothiocyanato-1,3-dimethoxybenzene (Example 10.0). The racemic mixture was purified by preparative SFC using the following conditions Column: AD-H (2 × 25 cm), Mobile Phase: 60:40 (A:B) A: Liquid CO$_2$, B: IPA, Flow Rate: 50 mL/min, 215 nm, 100 bar inlet pressure to deliver peak 1.

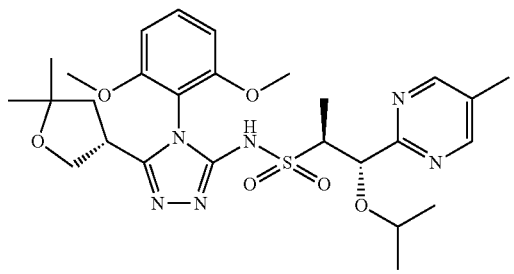

OR

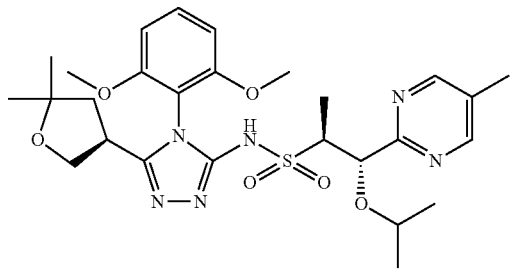

(1S,2S)-N-(4-(2,6-dimethoxyphenyl)-5-((3R)-5,5-dimethyltetrahydro-3-furanyl)-4H-1,2,4-triazol-3-yl)-1-(5-methyl-2-pyrimidinyl)-1-(2-propanyloxy)-2-propanesulfonamide or (1S,2S)-N-(4-(2,6-dimethoxyphenyl)-5-((3S)-5,5-dimethyltetrahydro-3-furanyl)-4H-1,2,4-triazol-3-yl)-1-(5-methyl-2-pyrimidinyl)-1-(2-propanyloxy)-2-propanesulfonamide.

$^1$H NMR (500 MHz, DMSO-d$_6$) δ 12.79 (s, 1H), 8.65 (s, 2H), 7.52 (t, J = 8.4 Hz, 1H), 6.87 (dd, J = 3.1, 8.6 Hz, 2H), 4.68 (d, J = 7.3 Hz, 1H), 3.80 (s, 3H), 3.80-3.79 (m, 3H), 3.73-3.67 (m, 2H), 3.42-3.35 (m, 2H), 3.09-3.01 (m, 1H), 2.27 (s, 3H), 1.94 (dd, J = 8.0, 12.5 Hz, 1H), 1.81 (dd, J = 9.1, 12.5 Hz, 1H), 1.19 (s, 3H), 1.07 (s, 3H), 0.97 (d, J = 6.0 Hz, 3H), 0.90 (d, J = 7.0 Hz, 3H), 0.78 (d, J = 6.2 Hz, 3H). LCMS-ESI (pos) m/z: 575.3 (M + H)$^+$.

| | | |
|---|---|---|
| 412.0 | (1S,2S)-1-isopropoxy-1-(5-methylpyrimidin-2-yl)propane-2-sulfonamide (Example 13.5), (R)-5,5-dimethyltetrahydrofuran-3-carbohydrazide hydrochloride and (S)-5,5-dimethyltetrahydrofuran-3-carbohydrazide hydrochloride (Example 313.1), and 2-isothiocyanato-1,3-dimethoxybenzene (Example 10.0). The racemic mixture was purified by preparative SFC using the following conditions Column: AD-H (2 × 25 cm), Mobile Phase: 60:40 (A:B) A: Liquid CO$_2$, B: IPA, Flow Rate: 50 mL/min, 215 nm, 100 bar inlet pressure to deliver peak 2. | 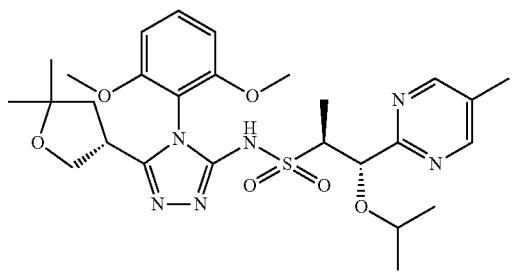<br>OR<br>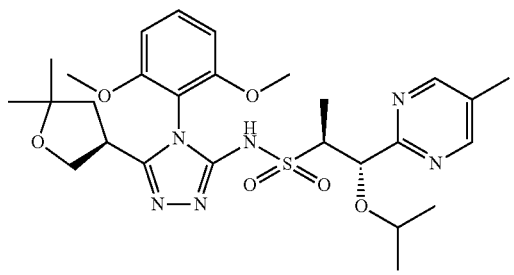<br>(1S,2S)-N-(4-(2,6-dimehoxyphenyl)-5-((3R)-5,5-dimethyltetrahydro-3-furanyl)-4H-1,2,4-triazol-3-yl)-1-(5-methyl-2-pyrimidinyl)-1-(2-propanyloxy)-2-propanesulfonamide or (1S,2S)-N-(4-(2,6-dimethoxyphenyl)-5-((3S)-5,5-dimethyltetrahydro-3-furanyl)-4H-1,2,4-triazol-3-yl)-1-(5-methyl-2-pyrimidinyl)-1-(2-propanyloxy)-2-propanesulfonamide. $^1$H NMR (500 MHz, DMSO-d$_6$) δ 12.80 (s, 1H), 8.65 (s, 2H), 7.52 (t, J = 8.6 Hz, 1H), 6.87 (dd, J = 2.1, 8.6 Hz, 2H), 4.68 (d, J = 7.3 Hz, 1H), 3.81 (s, 3H), 3.80-3.78 (m, 3H), 3.73-3.66 (m, 2H), 3.42-3.35 (m, 2H), 3.09-3.01 (m, 1H), 2.27 (s, 3H), 1.93 (dd, J = 8.0, 12.5 Hz, 1H), 1.85-1.78 (m, 1H), 1.19 (s, 3H), 1.07 (s, 3H), 0.97 (d, J = 6.0 Hz, 3H), 0.90 (d, J = 7.0 Hz, 3H), 0.78 (d, J = 6.2 Hz, 3H). LCMS-ESI (pos) m/z: 575.3 (M + H)$^+$. |
| 413.0 | (1S,2S)-1-(5-chloropyrimidin-2-yl)-1-isopropoxypropane-2-sulfonamide (Example 13.6), (R)-5,5-dimethyltetrahydrofuran-2-carbohydrazide and (S)-5,5-dimethyltetrahydrofuran-2-carbohydrazide (Example 108.2), and 2-isothiocyanato-1,3-dimethoxybenzene (Example 10.0). The racemic mixture was purified by preparative SFC using the following conditions: Column: AD-H (2 × 25 cm) + AD-H (2 × 25 cm) + AD-H (2 × 25 cm), Mobile Phase: 80:20 (A:B) A: Liquid CO$_2$, B: IPA, Flow Rate: 60 mL/min, 217 nm, 100 bar inlet pressure to deliver peak 1. | 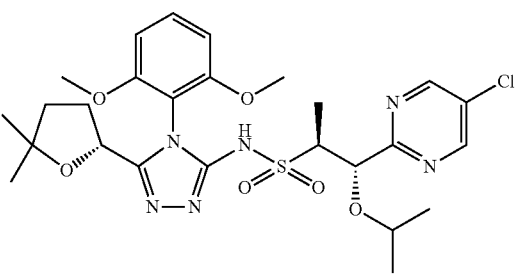 [SMILES: COc1cccc(OC)c1-n1c(NS(=O)(=O)[C@@H](C)[C@@H](OC(C)C)c2ncc(Cl)cn2)nnc1[C@H]1CCC(C)(C)O1]<br>OR<br>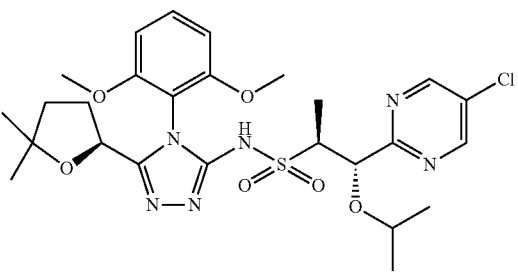 [SMILES: COc1cccc(OC)c1-n1c(NS(=O)(=O)[C@@H](C)[C@@H](OC(C)C)c2ncc(Cl)cn2)nnc1[C@@H]1CCC(C)(C)O1]<br>(1S,2S)-1-(5-chloro-2-pyrimidinyl)-N-(4-(2,6-dimethoxyphenyl)-5-((2R)-5,5-dimethyltetrahydro-2-furanyl)-4H-1,2,4-triazol-3-yl)-1-(2-propanyloxy)-2-propanesulfonamide or (1S,2S)-1-(5-chloro-2- |

TABLE 37-continued pyrimidinyl)-N-(4-(2,6-dimethoxyphenyl)-5-((2S)-5,5-dimethyltetrahydro-2-furanyl)-4H-1,2,4-triazol-3-yl)-1-(2-propanyloxy)-2-propanesulfonamide.

$^1$H NMR (500 MHz, DMSO-d$_6$) δ 12.73 (s, 1H), 8.92 (s, 2H), 7.47 (t, J = 8.6 Hz, 1H), 6.82 (dd, J = 4.8, 8.4 Hz, 2H), 4.76 (d, J = 6.7 Hz, 1H), 4.58 (dd, J = 6.0, 7.5 Hz, 1H), 3.78 (s, 3H), 3.75 (s, 3H), 3.46-3.40 (m, 1H), 3.40-3.34 (m, 1H), 2.19-2.08 (m, 2H), 1.69-1.61 (m, 1H), 1.52 (td, J = 8.0, 12.0 Hz, 1H), 1.05-1.03 (m, 3H), 1.01-0.95 (m, 9H), 0.83 (d, J = 6.2 Hz, 3H). LCMS-ESI (pos) m/z: 595.2 (M + H)$^+$.

414.0 (1S,2S)-1-(5-chloropyrimidin-2-yl)-1-isopropoxypropane-2-sulfonamide (Example 13.6), (R)-5,5-dimethyltetrahydrofuran-2-carbohydrazide and (S)-5,5-dimethyltetrahydrofuran-2-carbohydrazide (Example 108.2), and 2-isothiocyanato-1,3-dimethoxybenzene (Example 10.0). The racemic mixture was purified by preparative SFC using the following conditions: Column: AD-H (2 × 25 cm) + AD-H (2 × 25 cm) + AD-H (2 × 25 cm), Mobile Phase: 80:20 (A:B) A: Liquid CO$_2$, B: IPA, Flow Rate: 60 mL/min, 217 nm, 100 bar inlet pressure to deliver peak 2.

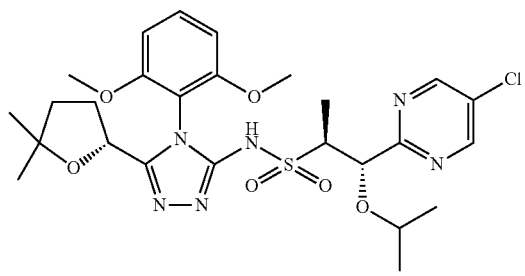 [SMILES: COc1cccc(OC)c1-n1c(NS(=O)(=O)[C@@H](C)[C@@H](OC(C)C)c2ncc(Cl)cn2)nnc1[C@H]1CCC(C)(C)O1]

OR

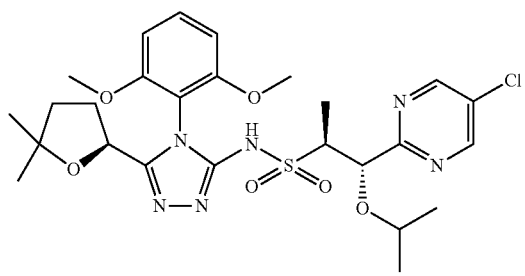 [SMILES: COc1cccc(OC)c1-n1c(NS(=O)(=O)[C@@H](C)[C@@H](OC(C)C)c2ncc(Cl)cn2)nnc1[C@@H]1CCC(C)(C)O1]

(1S,2S)-1-(5-chloro-2-pyrimidinyl)-N-(4-(2,6-dimethoxyphenyl)-5-((2R)-5,5-dimethyltetrahydro-2-furanyl)-4H-1,2,4-triazol-3-yl)-1-(2-propanyloxy)-2-propanesulfonamide or (1S,2S)-1-(5-chloro-2-pyrimidinyl)-N-(4-(2,6-dimethoxyphenyl)-5-((2S)-5,5-dimethyltetrahydro-2-furanyl)-4H-1,2,4-triazol-3-yl)-1-(2-propanyloxy)-2-propanesulfonamide.

$^1$H NMR (500 MHz, DMSO-d$_6$) δ 12.74 (br s, 1H), 8.92 (s, 2H), 7.47 (t, J = 8.4 Hz, 1H), 6.82 (dd, J = 3.1, 8.6 Hz, 2H), 4.76 (d, J = 7.0 Hz, 1H), 4.57 (t, J = 6.7 Hz, 1H), 3.79-3.74 (m, 6H), 3.46-3.37 (m, 2H), 2.19-2.08 (m, 2H), 1.68-1.62 (m, 1H), 1.52 (td, J = 7.9, 12.1 Hz, 1H), 1.04 (s, 3H), 1.01-0.97 (m, 6H), 0.95 (d, J = 7.0 Hz, 3H), 0.81 (d, J = 6.2 Hz, 3H). LCMS-ESI (pos) m/z: 595.3 (M + H)$^+$.

| | | |
|---|---|---|
| 415.0 | (2S,3R)-3-(5-chloropyrimidin-2-yl)butane-2-sulfonamide (Example 1.4), (R)-tetrahydrofuran-3-carbohydrazide (Example 345.1), and 3-(1-isothiocyanatoethyl)isoxazole (commercially available from Enamine). The racemic mixture was purified by preparative SFC using the following conditions: Column: AD-H (2 × 25 cm), Mobile Phase: 65:35 (A:B) A: Liquid $CO_2$, B: IPA, Flow Rate: 80 mL/min, 217 nm, 100 bar inlet pressure to deliver peak 1. | 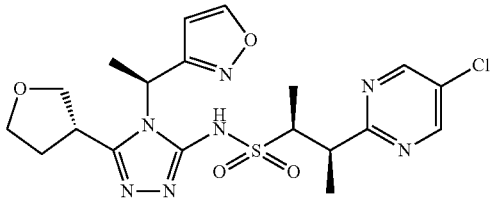 [SMILES: C[C@H](c1ncc(Cl)cn1)[C@H](C)S(=O)(=O)Nc1nnc([C@@H]2CCOC2)n1[C@@H](C)c1ccon1]<br>OR<br>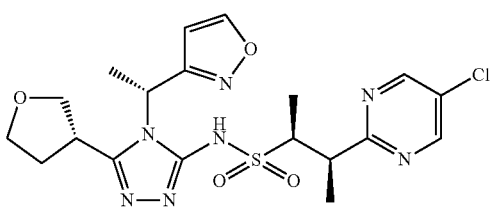 [SMILES: C[C@H](c1ncc(Cl)cn1)[C@H](C)S(=O)(=O)Nc1nnc([C@@H]2CCOC2)n1[C@H](C)c1ccon1]<br>(2S,3R)-3-(5-chloro-2-pyrimidinyl)-N-(4-((1R)-1-(1,2-oxazol-3-yl)ethyl)-5-((3S)-tetrahydro-3-furanyl)-4H-1,2,4-triazol-3-yl)-2-butanesulfonamide or (2S,3R)-3-(5-chloro-2-pyrimidinyl)-N-(4-((1S)-1-(1,2-oxazol-3-yl)ethyl)-5-((3S)-tetrahydro-3-furanyl)-4H-1,2,4-triazol-3-yl)-2-butanesulfonamide.<br>$^1$H NMR (500 MHz, $CD_2Cl_2$) δ 10.84 (br s, 1H), 8.63 (s, 2H), 8.45 (d, J = 1.8 Hz, 1H), 6.53 (d, J = 1.6 Hz, 1H), 5.68 (q, J = 7.3 Hz, 1H), 4.07 (t, J = 8.0 Hz, 1H), 3.97-3.89 (m, 2H), 3.84-3.79 (m, 1H), 3.74 (quin, J = 6.7 Hz, 1H), 3.65 (quin, J = 6.8 Hz, 1H), 3.40-3.34 (m, 1H), 2.16-2.09 (m, 2H), 1.94 (d, J = 7.3 Hz, 3H), 1.35 (d, J = 7.0 Hz, 3H), 1.30 (d, J = 7.0 Hz, 3H). LCMS-ESI (pos) m/z: 482.1 (M + H)$^+$. |
| 416.0 | (2S,3R)-3-(5-chloropyrimidin-2-yl)butane-2-sulfonamide (Example 1.4), (R)-tetrahydrofuran-3-carbohydrazide (Example 345.1), and 3-(1-isothiocyanatoethyl)isoxazole (commercially available from Enamine). The racemic mixture was purified by preparative SFC using the following conditions: Column: AD-H (2 × 25 cm), Mobile Phase: 65:35 (A:B) A: Liquid $CO_2$, B: IPA, Flow Rate: 80 mL/min, 217 nm, 100 bar inlet pressure to deliver peak 2. | 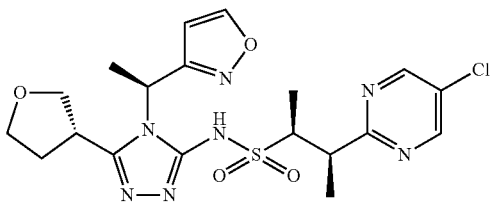 [SMILES: C[C@H](c1ncc(Cl)cn1)[C@H](C)S(=O)(=O)Nc1nnc([C@@H]2CCOC2)n1[C@@H](C)c1ccon1]<br>OR<br>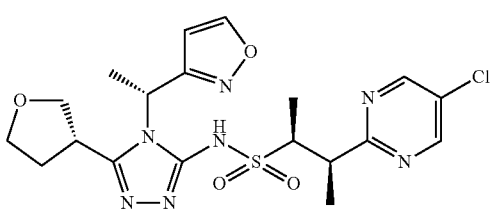 [SMILES: C[C@H](c1ncc(Cl)cn1)[C@H](C)S(=O)(=O)Nc1nnc([C@@H]2CCOC2)n1[C@H](C)c1ccon1]<br>(2S,3R)-3-(5-chloro-2-pyrimidinyl)-N-(4-((1R)-1-(1,2-oxazol-3-yl)ethyl)-5-((3S)-tetrahydro-3-furanyl)-4H-1,2,4-triazol-3-yl)-2-butanesulfonamide or (2S,3R)-3-(5-chloro-2-pyrimidinyl)-N-(4-((1S)-1-(1,2-oxazol-3-yl)ethyl)-5-((3S)-tetrahydro-3-furanyl)-4H-1,2,4-triazol-3-yl)-2-butanesulfonamide.<br>$^1$H NMR (500 MHz, $CD_2Cl_2$) δ 11.18-10.55 (m, 1H), 8.63 (s, 2H), 8.46 (d, J = 1.6 Hz, 1H), 6.53-6.49 (m, 1H), 5.68 (q, J = 7.3 Hz, 1H), 3.98-3.93 (m, 1H), 3.87-3.82 (m, 2H), 3.80-3.71 (m, 1H), 3.66-3.61 (m, 1H), 3.41-3.34 (m, 1H), 2.36-2.29 (m, 1H), 2.27-2.20 (m, 1H), 1.94 (d, J = 7.3 Hz, 3H), 1.35 (d, J = 7.0 Hz, 3H), 1.29 (d, J = 7.0 Hz, 3H). LCMS-ESI (pos) m/z: 482.1 (M + H)$^+$. |

TABLE 37-continued

| | | |
|---|---|---|
| 417.0 | (1S,2S)-1-(5-chloropyrimidin-2-yl)-1-isopropoxypropane-2-sulfonamide (Example 13.5), (R)-1-methyl-5-oxopyrrolidine-2-carbohydrazide hydrochloride and (S)-1-methyl-5-oxopyrrolidine-2-carbohydrazide hydrochloride (Example 405.1), and 2-isothiocyanato-1,3-dimethoxybenzene (Example 10.0). The racemic mixture was purified by preparative SFC using the following conditions: Column: AD-H (2 × 25 cm) + AD-H (2 × 15 cm), Mobile Phase: 70:30 (A:B) A: Liquid $CO_2$, B: IPA, Flow Rate: 60 mL/min, 215 nm, 100 bar inlet pressure to deliver peak 1. | 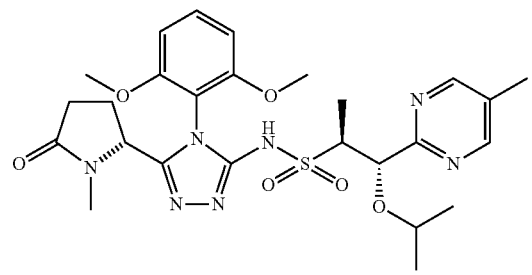<br>OR<br>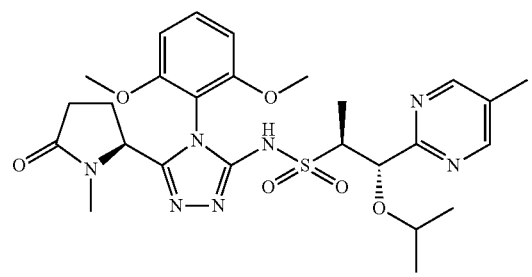 [SMILES: COc1cccc(OC)c1-n1c(NS(=O)(=O)[C@@H](C)[C@@H](OC(C)C)c2ncc(C)cn2)nnc1[C@@H]1CCC(=O)N1C]<br>(1S,2S)-N-(4-(2,6-dimethoxyphenyl)-5-((2R)-1-methyl-5-oxo-2-pyrrolidinyl)-4H-1,2,4-triazol-3-yl)-1-(5-methyl-2-pyrimidinyl)-1-(2-propanyloxy)-2-propanesulfonamide or (1S,2S)-N-(4-(2,6-dimethoxyphenyl)-5-((2S)-1-methyl-5-oxo-2-pyrrolidinyl)-4H-1,2,4-triazol-3-yl)-1-(5-methyl-2-pyrimidinyl)-1-(2-propanyloxy)-2-propanesulfonamide.<br>$^1$H NMR (500 MHz, $CD_2Cl_2$) δ 12.87 (br s, 1H), 8.64 (s, 2H), 7.50 (t, J = 8.6 Hz, 1H), 6.77-6.73 (m, 2H), 4.80 (d, J = 3.9 Hz, 1H), 4.35-4.30 (m, 1H), 3.87 (s, 3H), 3.84 (s, 3H0, 3.63-3.52 (m, 2H), 2.78 (s, 3H), 2.34 (s, 3H), 2.19-2.10 (m, 2H), 2.05-1.90 (m, 2H), 1.40 (d, J = 7.3 Hz, 3H), 1.09 (d, J = 6.0 Hz, 3H), 0.98 (d, J = 6.2 Hz, 3H). LCMS-ESI (pos) m/z: 574.3 (M + H)$^+$. |
| 418.0 | (1S,2S)-1-(5-chloropyrimidin-2-yl)-1-isopropoxypropane-2-sulfonamide (Example 13.5), (R)-1-methyl-5-oxopyrrolidine-2-carbohydrazide hydrochloride and (S)-1-methyl-5-oxopyrrolidine-2-carbohydrazide hydrochloride (Example 405.1), and 2-isothiocyanato-1,3-dimethoxybenzene (Example 10.0). The racemic mixture was purified by preparative SFC using the following conditions: Column: AD-H (2 × 25 cm) + AD-H (2 × 15 cm), Mobile Phase: 70:30 (A:B) A: Liquid $CO_2$, B: IPA, Flow Rate: 60 mL/min, 215 nm, 100 bar inlet pressure to deliver peak 2. | 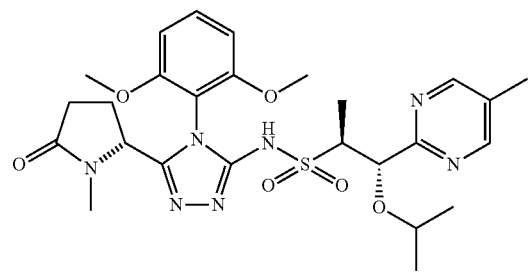<br>OR<br>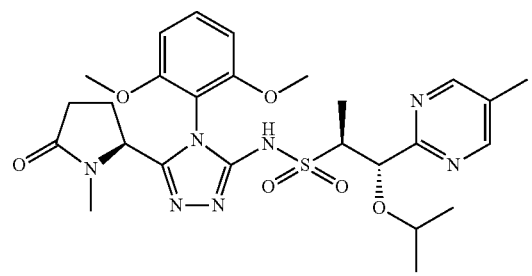 [SMILES: COc1cccc(OC)c1-n1c(NS(=O)(=O)[C@@H](C)[C@@H](OC(C)C)c2ncc(C)cn2)nnc1[C@@H]1CCC(=O)N1C]<br>(1S,2S)-N-(4-(2,6-dimethoxyphenyl)-5-((2R)-1-methyl-5-oxo-2-pyrrolidinyl)-4H-1,2,4-triazol-3-yl)-1-(5-methyl-2-pyrimidinyl)-1-(2-propanyloxy)-2-propanesulfonamide or (1S,2S)-N-(4-(2,6-dimethoxyphenyl)-5-((2S)-1-methyl-5-oxo-2-pyrrolidinyl)-4H-1,2,4-triazol-3-yl)-1-(5-methyl-2- |

| | | |
|---|---|---|
| | TABLE 37-continued | |
| | pyrimidinyl)-1-(2-propanyloxy)-2-propanesulfonamide.<br>¹H NMR (500 MHz, CD₂Cl₂) δ 13.17-12.59 (m, 1H),<br>8.64 (s, 2H), 7.50 (t, J = 8.6 Hz, 1H), 6.77-6.72 (m, 2H),<br>4.81 (d, J = 3.9 Hz, 1H), 4.35-4.31 (m, 1H), 3.90 (s,<br>3H), 3.80 (s, 3H), 3.63-3.58 (m, 1H), 3.58-3.52 (m,<br>1H), 2.73 (s, 3H), 2.34 (s, 3H), 2.21-2.10 (m, 2H), 2.06-<br>1.98 (m, 1H), 1.95-1.86 (m, 1H), 1.40 (d, J = 7.0 Hz,<br>3H), 1.10 (d, J = 6.0 Hz, 3H), 0.99 (d, J = 6.2 Hz, 3H).<br>LCMS-ESI (pos) m/z: 574.3 (M + H)⁺. | |
| 419.0 | (2S,3R)-3-(5-chloropyrimidin-2-yl)butane-2-sulfonamide (Example 1.4), (R)-1-methyl-5-oxopyrrolidine-2-carbohydrazide hydrochloride and (S)-1-methyl-5-oxopyrrolidine-2-carbohydrazide hydrochloride (Example 405.1), and 2-isothiocyanato-1,3-dimethoxybenzene (Example 10.0). The racemic mixture was purified by preparative SFC using the following conditions: Column: AS-H (2 × 25 cm), Mobile Phase: 65:35 (A:B) A: Liquid CO₂, B: MeOH, Flow Rate: 80 mL/min, 220 nm, 100 bar inlet pressure to deliver peak 1. | 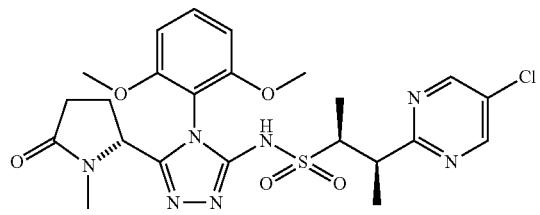<br>OR<br>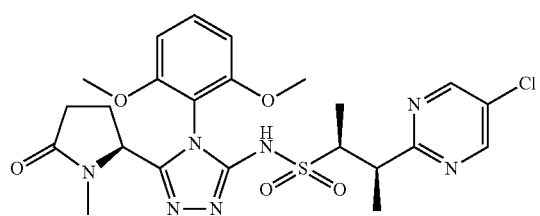 [SMILES: COc1cccc(OC)c1-n1c(NS(=O)(=O)[C@@H](C)[C@H](C)c2ncc(Cl)cn2)nnc1[C@@H]1CCC(=O)N1C]<br>(2S,3R)-3-(5-chloro-2-pyrimidinyl)-N-(4-(2,6-dimethoxyphenyl)-5-((2R)-1-methyl-5-oxo-2-pyrrolidinyl)-4H-1,2,4-triazol-3-yl)-2-butanesulfonamide or ((2S,3R)-3-(5-chloro-2-pyrimidinyl)-N-(4-(2,6-dimethoxyphenyl)-5-((2S)-1-methyl-5-oxo-2-pyrrolidinyl)-4H-1,2,4-triazol-3-yl)-2-butanesulfonamide.<br>¹H NMR (500 MHz, DMSO-d₆) δ 13.02 (s, 1H), 8.85 (s, 2H), 7.51 (t, J = 8.6 Hz, 1H), 6.86 (d, J = 8.3 Hz, 1H), 6.82 (d, J = 8.6 Hz, 1H), 4.42 (dd, J = 3.0, 9.7 Hz, 1H), 3.78 (s, 3H), 3.72 (s, 3H), 3.67-3.61 (m, 1H), 3.55-3.49 (m, 1H), 2.60 (s, 3H), 2.21-2.12 (m, 1H), 2.08-2.00 (m, 1H), 1.80-1.73 (m, 1H), 1.59-1.50 (m, 1H), 1.22 (d, J = 7.3 Hz, 3H), 1.09 (d, J = 7.0 Hz, 3H). LCMS-ESI (pos) m/z: 550.2 (M + H)⁺. |
| 424.0 | 2-(5-chloropyrimidin-2-yl)ethanesulfonamide (Example 386.1), (R)-1,4-dioxane-2-carbohydrazide and (S)-1,4-dioxane-2-carbohydrazide (commercially available from Enamine), and 2-isothiocyanato-1,3-dimethoxybenzene (Example 10.0). The racemic mixture was purified by preparative SFC using the following conditions: Column: Chiralpak AD-H (2 × 25 cm), Mobile Phase: 75:25 (A:B) A: Liquid CO₂, B: MeOH, Flow Rate: 80 mL/min, 219 nm, 100 bar inlet pressure to deliver peak 1. | 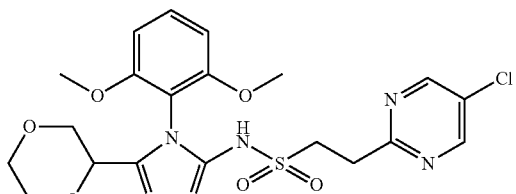<br>OR<br>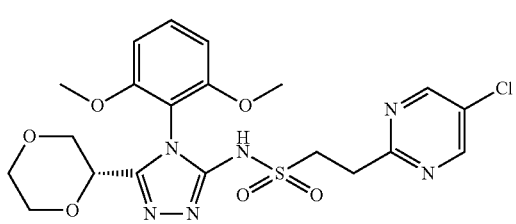 [SMILES: COc1cccc(OC)c1-n1c(NS(=O)(=O)CCc2ncc(Cl)cn2)nnc1C1COCCO1]<br>2-(5-chloro-2-pyrimidinyl)-N-(4-(2,6-dimethoxyphenyl)-5-((2R)-1,4-dioxan-2-yl)-4H-1,2,4-triazol-3-yl)ethanesulfonamide or 2-(5-chloro-2-pyrimidinyl)-N-(4-(2,6-dimethoxyphenyl)-5-((2S)-1,4-dioxan-2-yl)-4H-1,2,4-triazol-3-yl)ethanesulfonamide.<br>¹H NMR (500 MHz, CDCl₃) δ 11.04 (br s, 1 H) 8.62 (s, 2 |

TABLE 37-continued

H) 7.43 (t, J = 8.50 Hz, 1 H) 6.67 (t, J = 9.34 Hz, 2 H) 4.31 (dd, J = 8.37, 3.05 Hz, 1 H) 3.77-3.91 (m, 9 H) 3.66-3.72 (m, 2 H) 3.52-3.60 (m, 3 H) 3.39-3.45 (m, 2 H). LCMS-ESI (pos) m/z: 511.0 (M + H)+.

425.0 2-(5-chloropyrimidin-2-yl)ethanesulfonamide (Example 386.1), (R)-1,4-dioxane-2-carbohydrazide and (S)-1,4-dioxane-2-carbohydrazide (commercially available from Enamine), and 2-isothiocyanato-1,3-dimethoxybenzene (Example 10.0). The racemic mixture was purified by preparative SFC using the following conditions: Column: Chiralpak AD-H (2 × 25 cm), Mobile Phase: 75:25 (A:B) A: Liquid CO$_2$, B: MeOH, Flow Rate: 80 mL/min, 219 nm, 100 bar inlet pressure to deliver peak 2.

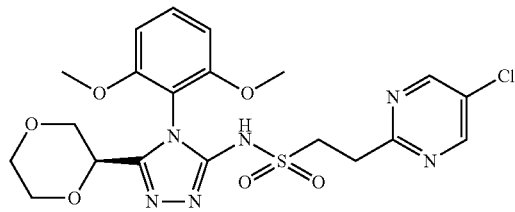 [SMILES: COc1cccc(OC)c1-n1c(NS(=O)(=O)CCc2ncc(Cl)cn2)nnc1[C@@H]1COCCO1]

OR

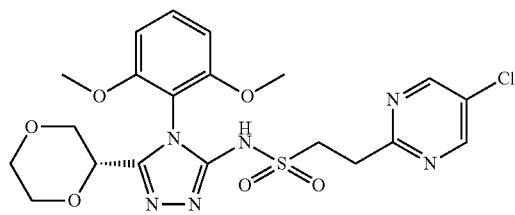 [SMILES: COc1cccc(OC)c1-n1c(NS(=O)(=O)CCc2ncc(Cl)cn2)nnc1[C@H]1COCCO1]

2-(5-chloro-2-pyrimidinyl)-N-(4-(2,6-dimethoxyphenyl)-5-((2R)-1,4-dioxan-2-yl)-4H-1,2,4-triazol-3-yl)ethanesulfonamide or 2-(5-chloro-2-pyrimidinyl)-N-(4-(2,6-dimethoxyphenyl)-5-((2S)-1,4-dioxan-2-yl)-4H-1,2,4-triazol-3-yl)ethanesulfonamide.

$^1$H NMR (500 MHz, CDCl$_3$) δ 11.01 (br s, 1 H) 8.62 (s, 2 H) 7.43 (t, J = 8.50 Hz, 1 H) 6.67 (t, J = 9.34 Hz, 2 H) 4.31 (dd, J = 8.30, 3.11 Hz, 1 H) 3.76-3.93 (m, 9 H) 3.66-3.73 (m, 2 H) 3.52-3.61 (m, 3 H) 3.38-3.46 (m, 2 H). LCMS-ESI (pos) m/z: 511.0 (M + H)+.

428.0 Tetrahydrofuran-2-carbohydrazide (J & W PharmLab, LLC), isothiocyanato-1,3-dimethoxybenzene (Example 10.0), and 1-(3-methoxyphenyl)ethane-1-sulfonamide (Enamine). The mixture was separated by SFC Regis Whelk-O s, s 2 × 15 cm + Regis Whelk-O s, s 2 × 15 cm Mobile Phase: 30% MeOH, Flow rate: 80 mL/min, BPR: 100 bar UV Detector Wavelength: 225 nm. Under these conditions, this was the first peak to elute.

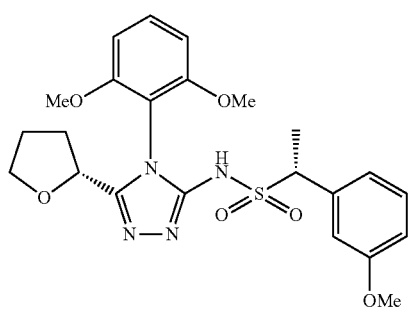 [SMILES: COc1cccc([C@@H](C)S(=O)(=O)Nc2nnc([C@H]3CCCO3)n2-c2c(OC)cccc2OC)c1]

OR

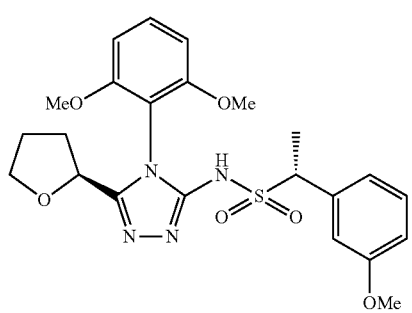 [SMILES: COc1cccc([C@@H](C)S(=O)(=O)Nc2nnc([C@@H]3CCCO3)n2-c2c(OC)cccc2OC)c1]

OR

TABLE 37-continued

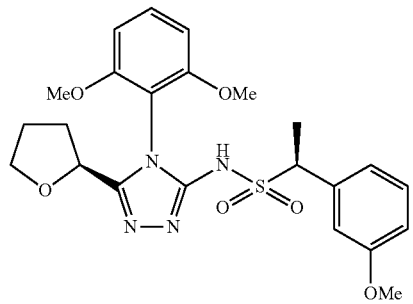 [SMILES: COc1cccc([C@H](C)S(=O)(=O)Nc2nnc([C@@H]3CCCO3)n2-c2c(OC)cccc2OC)c1]

OR

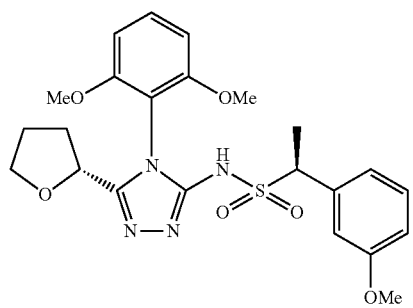 [SMILES: COc1cccc([C@H](C)S(=O)(=O)Nc2nnc([C@H]3CCCO3)n2-c2c(OC)cccc2OC)c1]

(1S)-N-(4-(2,6-dimethoxyphenyl)-5-((2S)-tetrahydro-2-furanyl)-4H-1,2,4-triazol-3-yl)-1-(3-methoxyphenyl)ethanesulfonamide or (1R)-N-(4-(2,6-dimethoxyphenyl)-5-((2R)-tetrahydro-2-furanyl)-4H-1,2,4-triazol-3-yl)-1-(3-methoxyphenyl)ethanesulfonamide or (1R)-N-(4-(2,6-dimethoxyphenyl)-5-((2S)-tetrahydro-2-furanyl)-4H-1,2,4-triazol-3-yl)-1-(3-methoxyphenyl)ethanesulfonamide or (1S)-N-(4-(2,6-dimethoxyphenyl)-5-((2R)-tetrahydro-2-furanyl)-4H-1,2,4-triazol-3-yl)-1-(3-methoxyphenyl)ethanesulfonamide.
$^1$H NMR (500 MHz, DMSO-$d_6$) δ 12.63-12.84 (m, 1 H) 7.41-7.55 (m, 1 H) 7.07-7.25 (m, 1 H) 6.69-6.94 (m, 5 H) 4.44-4.52 (m, 1 H) 4.06-4.14 (m, 1 H) 3.76-3.82 (m, 6 H) 3.68-3.72 (m, 3 H) 3.62-3.68 (m, 1 H) 3.47-3.54 (m, 1 H) 2.03-2.13 (m, 1 H) 1.93-2.03 (m, 1 H) 1.73-1.83 (m, 2 H) 1.44-1.51 (m, 3 H) LCMS-ESI (pos) m/z: 489.0 (M + H)$^+$.

| | | |
|---|---|---|
| 429.0 | Tetrahydrofuran-2-carbohydrazide (J & W PharmLab, LLC), isothiocyanato-1,3-dimethoxybenzene (Example 10.0), and 1-(3-methoxyphenyl)ethane-1-sulfonamide (Enamine). The mixture was separated by SFC Regis Whelk-O s, s 2 × 15 cm + Regis Whelk-O s, s 2 × 15 cm Mobile Phase: 30% MeOH, Flow rate: 80 mL/min, BPR: 100 bar UV Detector Wavelength: 225 nm. Under these conditions, this was the second peak to elute. | 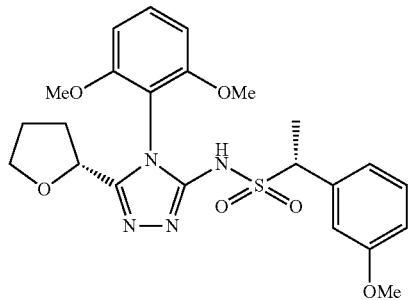 [SMILES: COc1cccc([C@@H](C)S(=O)(=O)Nc2nnc([C@H]3CCCO3)n2-c2c(OC)cccc2OC)c1]<br>OR<br>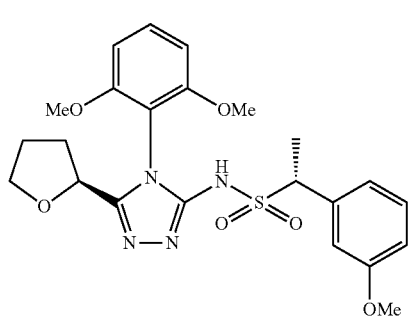<br>OR<br>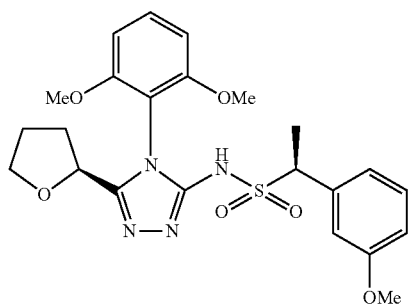 [SMILES: COc1cccc([C@H](C)S(=O)(=O)Nc2nnc([C@@H]3CCCO3)n2-c2c(OC)cccc2OC)c1]<br>OR<br>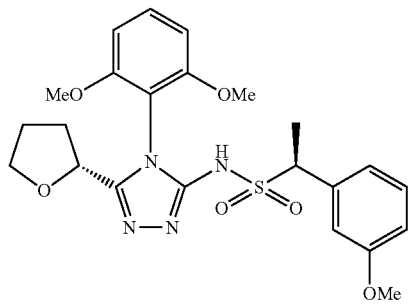 [SMILES: COc1cccc([C@H](C)S(=O)(=O)Nc2nnc([C@H]3CCCO3)n2-c2c(OC)cccc2OC)c1]<br>(1S)-N-(4-(2,6-dimethoxyphenyl)-5-((2S)-tetrahydro-2-furanyl)-4H-1,2,4-triazol-3-yl)-1-(3-methoxyphenyl)ethanesulfonamide or (1R)-N-(4-(2,6-dimethoxyphenyl)-5-((2R)-tetrahydro-2-furanyl)-4H-1,2,4-triazol-3-yl)-1-(3-methoxyphenyl)ethanesulfonamide or (1R)-N-(4-(2,6-dimethoxyphenyl)-5-((2S)-tetrahydro-2-furanyl)-4H-1,2,4-triazol-3-yl)-1-(3-methoxyphenyl)ethanesulfonamide or (1S)-N-(4-(2,6-dimethoxyphenyl)-5-((2R)-tetrahydro-2-furanyl)-4H-1,2,4-triazol-3-yl)-1-(3-methoxyphenyl)ethanesulfonamide.<br>$^1$H NMR (500 MHz, DMSO-$d_6$) δ 12.69-12.86 (m, 1 H) |

TABLE 37-continued 7.41-7.54 (m, 1 H) 7.10-7.21 (m, 1 H) 6.70-6.96 (m, 5 H) 4.39-4.52 (m, 1 H) 4.02-4.20 (m, 1 H) 3.75-3.82 (m, 6 H) 3.67-3.73 (m, 3 H) 3.61-3.67 (m, 1 H) 3.46-3.54 (m, 1 H) 2.05-2.14 (m, 1 H) 1.93-2.04 (m, 1 H) 1.75-1.84 (m, 2 H) 1.44-1.51 (m, 3 H) LCMS-ESI (pos) m/z: 489.0 (M + H)⁺.

430.0 Tetrahydrofuran-2-carbohydrazide (J & W PharmLab, LLC), isothiocyanato-1,3-dimethoxybenzene (Example 10.0), and 1-(3-methoxyphenyl)ethane-1-sulfonamide (Enamine). The mixture was separated by SFC Regis Whelk-O s, s 2 × 15 cm + Regis Whelk-O s, s 2 × 15 cm Mobile Phase: 30% MeOH Flowrate: 80 mL/min BPR: 100 bar, UV Detector Wavelength: 225 nm. Under these conditions, this was the third peak to elute.

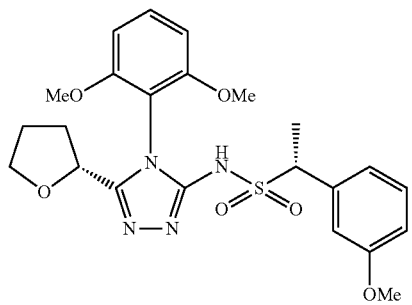 [SMILES: COc1cccc([C@@H](C)S(=O)(=O)Nc2nnc([C@H]3CCCO3)n2-c2c(OC)cccc2OC)c1]

OR

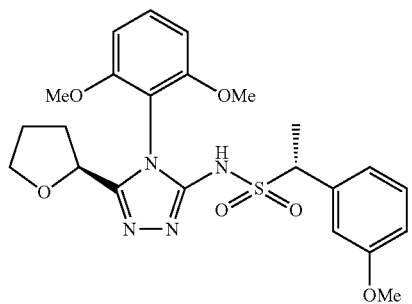 [SMILES: COc1cccc([C@@H](C)S(=O)(=O)Nc2nnc([C@@H]3CCCO3)n2-c2c(OC)cccc2OC)c1]

OR

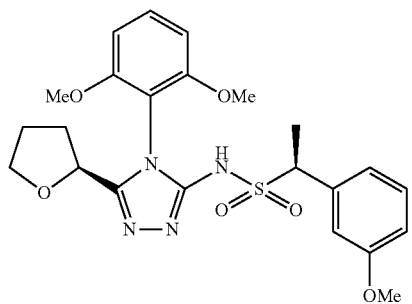 [SMILES: COc1cccc([C@H](C)S(=O)(=O)Nc2nnc([C@@H]3CCCO3)n2-c2c(OC)cccc2OC)c1]

OR

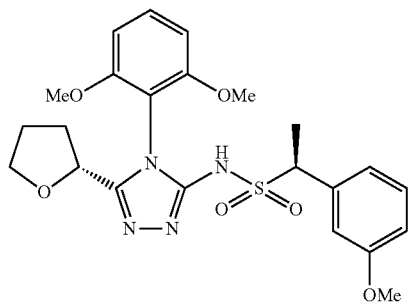 [SMILES: COc1cccc([C@H](C)S(=O)(=O)Nc2nnc([C@H]3CCCO3)n2-c2c(OC)cccc2OC)c1]

(1S)-N-(4-(2,6-dimethoxyphenyl)-5-((2S)-tetrahydro-2-furanyl)-4H-1,2,4-triazol-3-yl)-1-(3-methoxyphenyl)ethanesulfonamide or (1R)-N-(4-(2,6-dimethoxyphenyl)-5-((2R)-tetrahydro-2-furanyl)-4H-1,2,4-triazol-3-yl)-1-(3-methoxyphenyl)ethanesulfonamide or (1R)-N-(4-(2,6-dimethoxyphenyl)-5-((2S)-tetrahydro-2-furanyl)-4H-1,2,4-triazol-3-yl)-1-(3-

TABLE 37-continued methoxyphenyl)ethanesulfonamide or (1S)-N-(4-(2,6-dimethoxyphenyl)-5-((2R)-tetrahydro-2-furanyl)-4H-1,2,4-triazol-3-yl)-1-(3-methoxyphenyl)ethanesulfonamide.
$^1$H NMR (500 MHz, DMSO-d$_6$) δ 12.66-12.88 (m, 1 H) 7.41-7.54 (m, 1 H) 7.05-7.20 (m, 1 H) 6.70-6.99 (m, 5 H) 4.40-4.55 (m, 1 H) 4.08-4.11 (m, 1 H) 3.77-3.80 (m, 6 H) 3.68-3.71 (m, 3 H) 3.60-3.67 (m, 1 H) 3.45-3.55 (m, 1 H) 1.91-2.13 (m, 2 H) 1.73-1.84 (m, 2 H) 1.43-1.51 (m, 3 H) LCMS-ESI (pos) m/z: 489.0 (M + H)$^+$.

431.0 Tetrahydrofuran-2-carbohydrazide (J & W PharmLab, LLC), isothiocyanato-1,3-dimethoxybenzene (Example 10.0), and 1-(3-methoxyphenyl)ethane-1-sulfonamide (Enamine). The mixture was separated by SFC Regis Whelk-O s,s 2 × 15 cm + Regis Whelk-O s,s 2 × 15 cm Mobile Phase: 30% MeOH Flowrate: 80 mL/min BPR: 100 bar, UV Detector Wavelength: 225 nm. Under these conditions, this was teh fourth peak to elute,

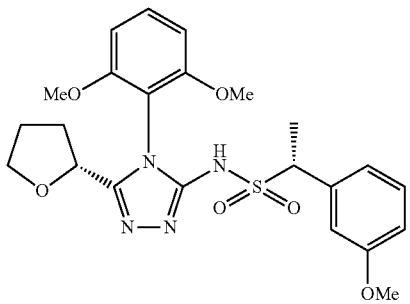 [SMILES: COc1cccc([C@@H](C)S(=O)(=O)Nc2nnc([C@H]3CCCO3)n2-c2c(OC)cccc2OC)c1]

OR

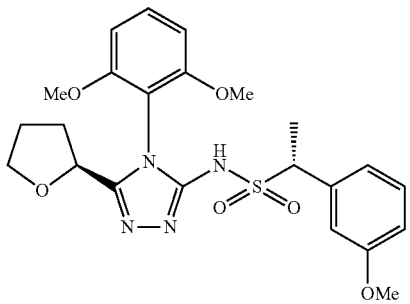 [SMILES: COc1cccc([C@@H](C)S(=O)(=O)Nc2nnc([C@@H]3CCCO3)n2-c2c(OC)cccc2OC)c1]

OR

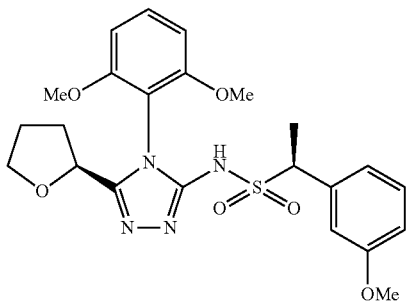 [SMILES: COc1cccc([C@H](C)S(=O)(=O)Nc2nnc([C@@H]3CCCO3)n2-c2c(OC)cccc2OC)c1]

OR

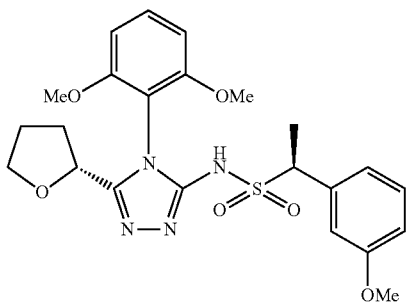 [SMILES: COc1cccc([C@H](C)S(=O)(=O)Nc2nnc([C@H]3CCCO3)n2-c2c(OC)cccc2OC)c1]

(1S)-N-(4-(2,6-dimethoxyphenyl)-5-((2S)-tetrahydro-2-furanyl)-4H-1,2,4-triazol-3-yl)-1-(3-methoxyphenyl)ethanesulfonamide or (1R)-N-(4-(2,6-

| | | |
|---|---|---|
| | | dimethoxyphenyl)-5-((2R)-tetrahydro-2-furanyl)-4H-1,2,4-triazol-3-yl)-1-(3-methoxyphenyl)ethanesulfonamide or (1R)-N-(4-(2,6-dimethoxyphenyl)-5-((2S)-tetrahydro-2-furanyl)-4H-1,2,4-triazol-3-yl)-1-(3-methoxyphenyl)ethanesulfonamide or (1S)-N-(4-(2,6-dimethoxyphenyl)-5-((2R)-tetrahydro-2-furanyl)-4H-1,2,4-triazol-3-yl)-1-(3-methoxyphenyl)ethanesulfonamide. $^1$H NMR (500 MHz, DMSO-$d_6$) δ 12.56-12.95 (m, 1 H) 7.41-7.60 (m, 1 H) 7.08-7.20 (m, 1 H) 6.71-6.92 (m, 5 H) 4.33-4.57 (m, 1 H) 4.05-4.16 (m, 1 H) 3.75-3.82 (m, 6 H) 3.61-3.68 (m, 1 H) 3.46-3.54 (m, 1 H) 1.92-2.16 (m, 2 H) 1.75-1.84 (m, 2 H) 1.45-1.51 (m, 3 H) LCMS-ESI (pos) m/z: 489.0 (M + H)$^+$. |
| 432.0 | Tetrahydrofuran-2-carbohydrazide (J & W PharmLab, LLC), isothiocyanato-1,3-dimethoxybenzene (Example 10.0), and 1-(2-fluorophenyl)ethane-1-sulfonamide (Enamine). The mixture was separated by SFC Chiralpak AS-H 2 × 25 cm + Chiralpak AS-H 2 × 25 cm Mobile Phase: 15% MeOH Flowrate: 50 mL/min BPR: 100 bar UV Detector Wavelength: 215 nm. Followed by separation using Chiralpak AD-H 2 × 25 cm + Chiralpak AD-H 2 × 25 cm Mobile Phase: 35% IPA, Flowrate: 50 mL/min BPR: 100 bar UV Detector Wavelength: 215 nm. Under these conditions, this was the first peak to elute. | 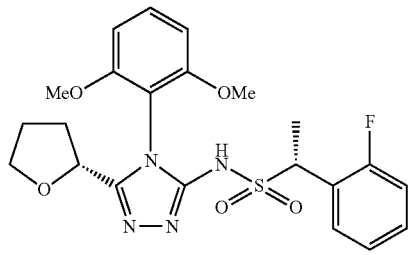 [SMILES: COc1cccc(OC)c1-n1c(NS(=O)(=O)[C@H](C)c2ccccc2F)nnc1[C@H]1CCCO1]<br>OR<br>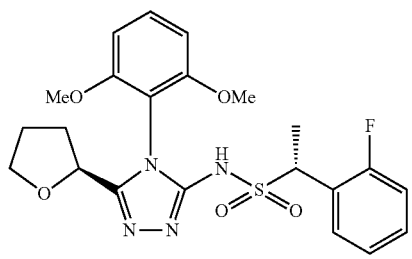 [SMILES: COc1cccc(OC)c1-n1c(NS(=O)(=O)[C@H](C)c2ccccc2F)nnc1[C@@H]1CCCO1]<br>OR<br>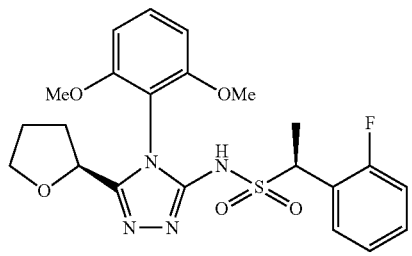 [SMILES: COc1cccc(OC)c1-n1c(NS(=O)(=O)[C@@H](C)c2ccccc2F)nnc1[C@@H]1CCCO1]<br>OR<br>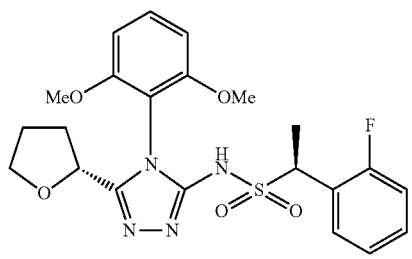 [SMILES: COc1cccc(OC)c1-n1c(NS(=O)(=O)[C@@H](C)c2ccccc2F)nnc1[C@H]1CCCO1]<br>(1S)-N-(4-(2,6-dimethoxyphenyl)-5-((2S)-tetrahydro-2-furanyl)-4H-1,2,4-triazol-3-yl)-1-(2-fluorophenyl)ethanesulfonamide or (1R)-N-(4-(2,6-dimethoxyphenyl)-4-((2R)-tetrahydro-2-furanyl)-4H-1,2,4-triazol-3-yl)-1-(2-fluorophenyl)ethanesulfonamide or (1R)-N-(4-(2,6-dimethoxyphenyl)-5-((2S)-tetrahydro-2-furanyl)-4H-1,2,4-triazol-3-yl)-1-(2-fluorophenyl)ethanesulfonamide or (1S)-N-(4-(2,6-dimethoxyphenyl)-5-((2R)-tetrahydro-2- |

| | |
|---|---|
| | furanyl)-4H-1,2,4-triazol-3-yl)-1-(2-fluorophenyl)ethanesulfonamide.<br>$^{1}$H NMR (500 MHz, DMSO-$d_6$) δ 12.75-12.94 (m, 1 H) 7.39-7.57 (m, 1 H) 7.22-7.37 (m, 2 H) 6.98-7.21 (m, 2 H) 6.76-6.94 (m, 2 H) 4.50 (dd, J = 7.8, 5.6 Hz, 1 H) 4.36-4.44 (m, 1 H) 3.78 (d, J = 10.9 Hz, 7 H) 3.46-3.69 (m, 2 H) 1.92-2.16 (m, 2 H) 1.74-1.85 (m, 2 H) 1.49 (d, J = 7.1 Hz, 3 H) LCMS-ESI (pos) m/z: 477.0 (M + H)$^{+}$. |
| 433.0 Tetrahydrofuran-2-carbohydrazide (J & W PharmLab, LLC), isothiocyanato-1,3-dimethoxybenzene (Example 10.0), and 1-(2-fluorophenyl)ethane-1-sulfonamide (Enamine). The mixture was separated by SFC Chiralpak AS-H 2 × 25 cm + Chiralpak AS-H 2 × 25 cm Mobile Phase: 15% MeOH Flowrate: 50 mL/min BPR: 100 bar UV Detector Wavelength: 215 nm. Followed by separation using Chiralpak AD-H 2 × 25 cm + Chiralpak AD-H 2 × 25 cm Mobile Phase: 35% IPA. Flow rate: 50 mL/min BPR: 100 bar UV Detector Wavelength: 215 nm. Under these conditions, this was the second peak to elute. | 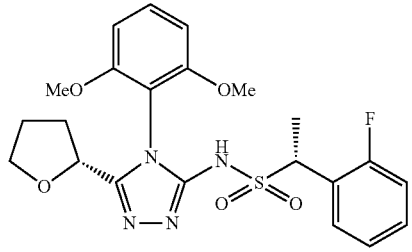 [SMILES: COc1cccc(OC)c1-n1c(NS(=O)(=O)[C@H](C)c2ccccc2F)nnc1[C@H]1CCCO1]<br>OR<br>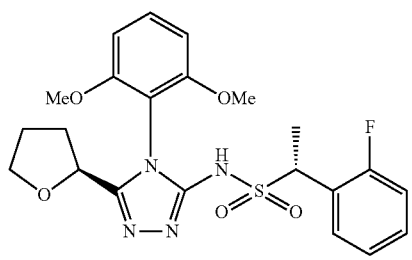 [SMILES: COc1cccc(OC)c1-n1c(NS(=O)(=O)[C@H](C)c2ccccc2F)nnc1[C@@H]1CCCO1]<br>OR<br>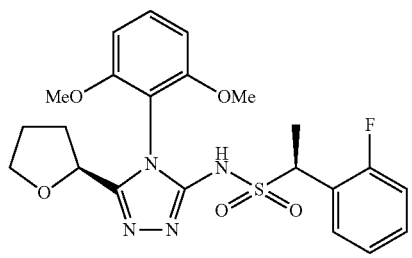 [SMILES: COc1cccc(OC)c1-n1c(NS(=O)(=O)[C@@H](C)c2ccccc2F)nnc1[C@@H]1CCCO1]<br>OR<br>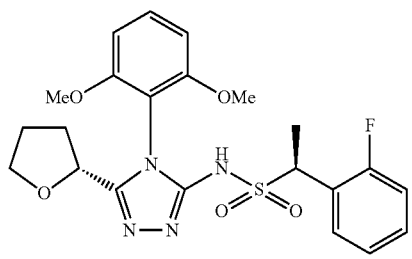 [SMILES: COc1cccc(OC)c1-n1c(NS(=O)(=O)[C@@H](C)c2ccccc2F)nnc1[C@H]1CCCO1]<br>(1S)-N-(4-(2,6-dimethoxyphenyl)-5-((2S)-tetrahydro-2-furanyl)-4H-1,2,4-triazol-3-yl)-1-(2-fluorophenyl)ethanesulfonamide or (1R)-N-(4-(2,6-dimethoxyphenyl)-5-((2R)-tetrahydro-2-furanyl)-4H-1,2,4-triazol-3-yl)-1-(2-fluorophenyl)ethanesulfonamide or (1R)-N-(4-(2,6-dimethoxyphenyl)-5-((2S)-tetrahydro-2-furanyl)-4H-1,2,4-triazol-3-yl)-1-(2-fluorophenyl)ethanesulfonamide or (1S)-N-(4-(2,6-dimethoxyphenyl)-5-((2R)-tetrahydro-2-furanyl)-4H-1,2,4-triazol-3-yl)-1-(2-fluorophenyl)ethanesulfonamide.<br>$^{1}$H NMR (500 MHz, DMSO-$d_6$) δ 12.81-12.97 (m, 1 H) 7.47-7.59 (m, 1 H) 7.25-7.38 (m, 2 H) 7.00-7.18 (m, 2 H) 6.79-6.97 (m, 2 H) 4.50 (dd, J = 7.8, 5.6 Hz, 1 H) 4.41 |

TABLE 37-continued (q, J = 7.0 Hz, 1 H) 3.78 (s, 3 H) 3.75 (s, 3 H) 3.61-3.69 (m, 1 H) 3.47-3.55 (m, 1 H) 1.94-2.14 (m, 2 H) 1.75-1.83 (m, 2 H) 1.47-1.53 (m, 3 H) LCMS-ESI (pos) m/z: 477.0 (M + H)⁺.

434.0 Tetrahydrofuran-2-carbohydrazide (J & W PharmLab, LLC), isothiocyanato-1,3-dimethoxybenzene (Example 10.0), and 1-(2-fluorophenyl)ethane-1-sulfonamide (Enamine). The mixture was separated by SFC Chiralpak AS-H 2 × 25 cm + Chiralpak AS-H 2 × 25 cm Mobile Phase: 15% MeOH. Flow rate: 50 mL/min BPR: 100 bar UV Detector Wavelength: 215 nm. Followed by separation using Chiralpak AD-H 2 × 25 cm + Chiralpak AD-H 2 × 25 cm Mobile Phase: 35% IPA. Flow rate: 50 mL/min BPR: 100 bar UV Detector Wavelength: 215 nm. Under these conditions, this was the third peak to elute.

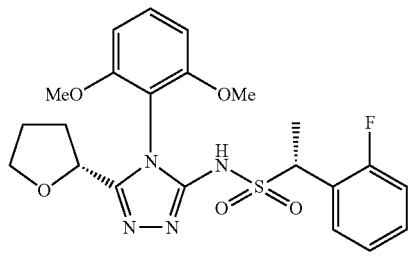 [SMILES: COc1cccc(OC)c1-n1c(NS(=O)(=O)[C@H](C)c2ccccc2F)nnc1[C@H]1CCCO1]

OR

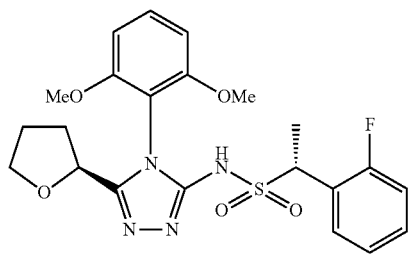 [SMILES: COc1cccc(OC)c1-n1c(NS(=O)(=O)[C@H](C)c2ccccc2F)nnc1[C@@H]1CCCO1]

OR

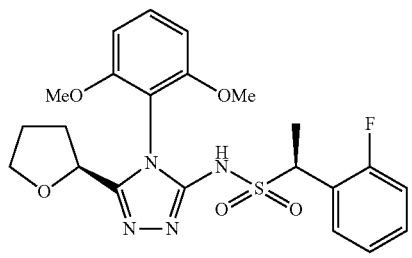 [SMILES: COc1cccc(OC)c1-n1c(NS(=O)(=O)[C@@H](C)c2ccccc2F)nnc1[C@@H]1CCCO1]

OR

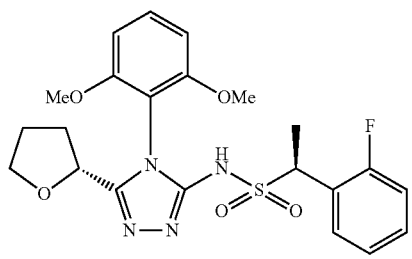 [SMILES: COc1cccc(OC)c1-n1c(NS(=O)(=O)[C@@H](C)c2ccccc2F)nnc1[C@H]1CCCO1]

(1S)-N-(4-(2,6-dimethoxyphenyl)-5-((2S)-tetrahydro-2-furanyl)-4H-1,2,4-triazol-3-yl)-1-(2-fluorophenyl)ethanesulfonamide or (1R)-N-(4-(2,6-dimethoxyphenyl)-5-((2R)-tetrahydro-2-furanyl)-4H-1,2,4-triazol-3-yl)-1-(2-fluorophenyl)ethanesulfonamide or (1R)-N-(4-(2,6-dimethoxyphenyl)-5-((2S)-tetrahydro-2-furanyl)-4H-1,2,4-triazol-3-yl)-1-(2-fluorophenyl)ethanesulfonamide or (1S)-N-(4-(2,6-dimethoxyphenyl)-5-((2R)-tetrahydro-2-furanyl)-4H-1,2,4-triazol-3-yl)-1-(2-fluorophenyl)ethanesulfonamide.
¹H NMR (500 MHz, DMSO-d₆) δ 12.81-12.99 (m, 1 H) 7.45-7.57 (m, 1 H) 7.23-7.39 (m, 2 H) 7.01-7.18 (m, 2 H) 6.76-6.92 (m, 2 H) 4.46-4.54 (m, 1 H) 4.36-4.46 (m, 1 H) 3.71-3.87 (m, 6 H) 3.59-3.73 (m, 1 H) 3.46-3.58 (m, 1 H) 1.92-2.18 (m, 2 H) 1.73-1.88 (m, 2 H) 1.42-1.55 (m, 3 H) LCMS-ESI (pos) m/z: 477.0 (M + H)⁺.

TABLE 37-continued

| | | |
|---|---|---|
| 435.0 | Tetrahydrofuran-2-carbohydrazide (J & W PharmLab, LLC), isothiocyanato-1,3-dimethoxybenzene (Example 10.0), and 1-(2-fluorophenyl)ethane-1-sulfonamide (Enamine). The mixture was separated by SFC Chiralpak AS-H 2 × 25 cm + Chiralpak AS-H 2 × 25 cm Mobile Phase: 15% MeOH Flow rate: 50 mL/min BPR: 100 bar UV Detector Wavelength: 215 nm. Followed by separation using Chiralpak AD-H 2 × 25 cm + Chiralpak AD-H 2 × 25 cm Mobile Phase: 35% IPA. Flow rate: 50 mL/min BPR: 100 bar UV Detector Wavelength: 215 nm. Under these conditions, this was the fourth peak to elute | 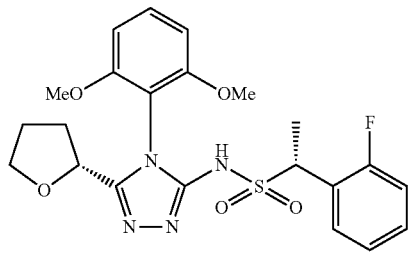 [SMILES: COc1cccc(OC)c1-n1c(NS(=O)(=O)[C@H](C)c2ccccc2F)nnc1[C@H]1CCCO1]<br>OR<br>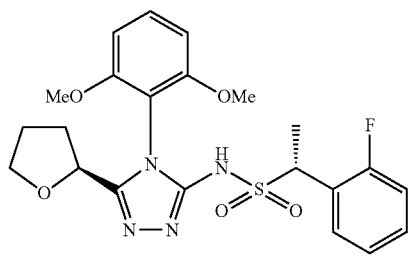 [SMILES: COc1cccc(OC)c1-n1c(NS(=O)(=O)[C@H](C)c2ccccc2F)nnc1[C@@H]1CCCO1]<br>OR<br>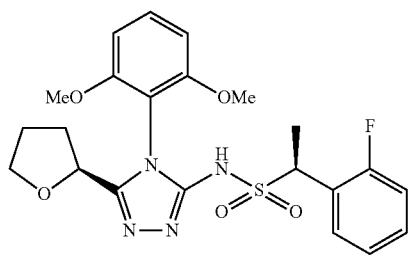 [SMILES: COc1cccc(OC)c1-n1c(NS(=O)(=O)[C@@H](C)c2ccccc2F)nnc1[C@@H]1CCCO1]<br>OR<br>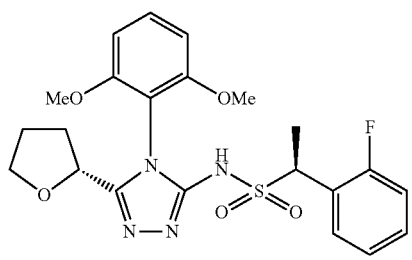 [SMILES: COc1cccc(OC)c1-n1c(NS(=O)(=O)[C@@H](C)c2ccccc2F)nnc1[C@H]1CCCO1]<br><br>(1S)-N-(4-(2,6-dimethoxyphenyl)-5-((2S)-tetrahydro-2-furanyl)-4H-1,2,4-triazol-3-yl)-1-(2-fluorophenyl)ethanesulfonamide or (1R)-N-(4-(2,6-dimethoxyphenyl)-5-((2R)-tetrahydro-2-furanyl)-4H-1,2,4-triazol-3-yl)-1-(2-fluorophenyl)ethanesulfonamide or (1R)-N-(4-(2,6-dimethoxyphenyl)-5-((2S)-tetrahydro-2-furanyl)-4H-1,2,4-triazol-3-yl)-1-(2-fluorophenyl)ethanesulfonamide or (1S)-N-(4-(2,6-dimethoxyphenyl)-5-((2R)-tetrahydro-2-furanyl)-4H-1,2,4-triazol-3-yl)-1-(2-fluorophenyl)ethanesulfonamide.<br>$^1$H NMR (500 MHz, DMSO-$d_6$) δ 12.77-12.98 (m, 1 H) 7.43-7.57 (m, 1 H) 7.24-7.39 (m, 2 H) 6.99-7.19 (m, 2 H) 6.78-6.95 (m, 2 H) 4.37-4.55 (m, 2 H) 3.75 (s, 3 H) 3.70 (s, 3 H) 3.60-3.68 (m, 1 H) 3.50 (d, J = 8.0 Hz, 1 H) 1.93-2.13 (m, 2 H) 1.74-1.83 (m, 2 H) 1.49 (d, J = 7.1 Hz, 3 H)LCMS-ESI (pos) m/z: 477.0 (M + H)$^+$. |

| | | |
|---|---|---|
| 436.0 | Tetrahydrofuran-2-carbohydrazide (J & W PharmLab, LLC), isothiocyanato-1,3-dimethoxybenzene (Example 10.0), and 1-phenylethane-1-sulfonamide (Enamine). The mixture was separated by SFC: Column: Regis Whelk-O s, s 2 × 25 cm + Regis Whelk-O s, s 2 × 25 cm Mobile Phase: 30% MeOH. Flow rate: 80 mL/min. BPR: 100 bar, UV Detector Wavelength: 225 nm. Under these conditions, this was the second peak to elute | 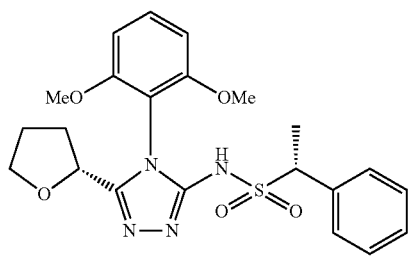 [SMILES: COc1cccc(OC)c1-n1c(NS(=O)(=O)[C@H](C)c2ccccc2)nnc1[C@H]1CCCO1]<br>OR<br>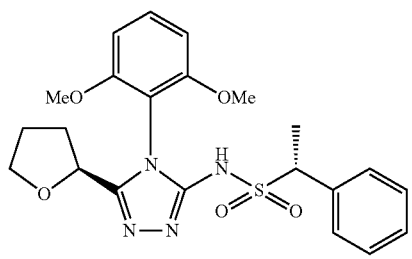 [SMILES: COc1cccc(OC)c1-n1c(NS(=O)(=O)[C@H](C)c2ccccc2)nnc1[C@@H]1CCCO1]<br>OR<br>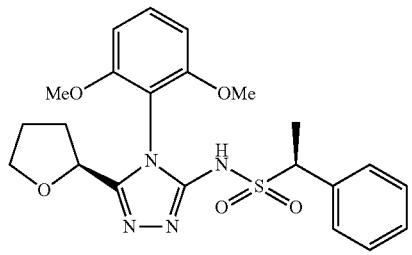 [SMILES: COc1cccc(OC)c1-n1c(NS(=O)(=O)[C@@H](C)c2ccccc2)nnc1[C@@H]1CCCO1]<br>OR<br>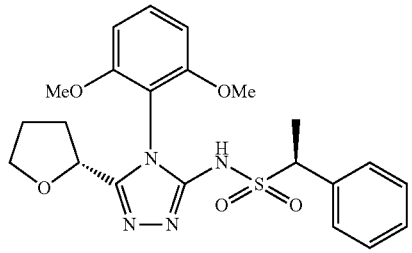 [SMILES: COc1cccc(OC)c1-n1c(NS(=O)(=O)[C@@H](C)c2ccccc2)nnc1[C@H]1CCCO1]<br>(S)-N-(4-(2,6-dimethoxyphenyl)-5-((S)-tetrahydrofuran-2-yl)-4H-1,2,4-triazol-3-yl)-1-phenylethane-1-sulfonamide or (R)-N-(4-(2,6-dimethoxyphenyl)-5-((S)-tetrahydrofuran-2-yl)-4H-1,2,4-triazol-3-yl)-1-phenylethane-1-sulfonamide or (S)-N-(4-(2,6-dimethoxyphenyl)-5-((R)-tetrahydrofuran-2-yl)-4H-1,2,4-triazol-3-yl)-1-phenylethane-1-sulfonamide or (R)-N-(4-(2,6-dimethoxyphenyl)-5-((R)-tetrahydrofuran-2-yl)-4H-1,2,4-triazol-3-yl)-1-phenylethane-1-sulfonamide.<br>$^1$H NMR (500 MHz, DMSO-$d_6$) δ 12.67-12.84 (m, 1 H) 7.51 (t, J = 8.5 Hz, 1 H) 7.15-7.34 (m, 5 H) 6.72-6.96 (m, 2 H) 4.43-4.60 (m, 1 H) 4.08-4.21 (m, 1 H) 3.77-3.84 (m, 6 H) 3.45-3.69 (m, 2 H) 1.94-2.16 (m, 2 H) 1.80 (quin, J = 7.1 Hz, 2 H) 1.51 (d, J = 7.0 Hz, 3 H) LCMS-ESI (pos) m/z: 459.2 (M + H)$^+$. |

| | | |
|---|---|---|
| 437.0 | Tetrahydrofuran-2-carbohydrazide (J & W PharmLab, LLC), isothiocyanato-1,3-dimethoxybenzene (Example 10.0), and 1-(3-chlorophenyl)ethane-1-sulfonamide (Enamine). The mixture was separated by SFC: Chiralpak AD-H 2 × 25 cm Mobile Phase: 35% IPA Flow rate: 60 mL/min BPR: 100 bar UV Detector Wavelength: 215 nm. Under these conditions, this was the first peak to elute | 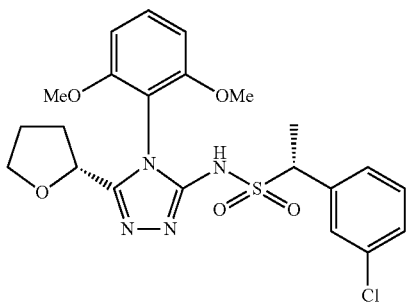 [SMILES: COc1cccc(OC)c1-n1c(NS(=O)(=O)[C@H](C)c2cccc(Cl)c2)nnc1[C@H]1CCCO1]<br>OR<br>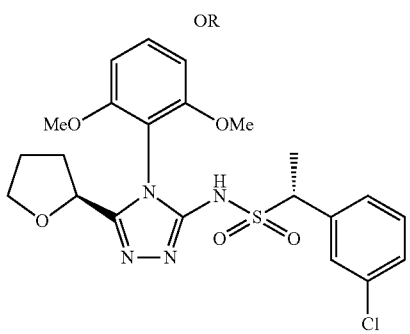<br>OR<br>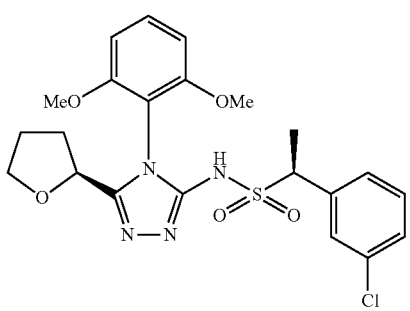 [SMILES: COc1cccc(OC)c1-n1c(NS(=O)(=O)[C@@H](C)c2cccc(Cl)c2)nnc1[C@@H]1CCCO1]<br>OR<br>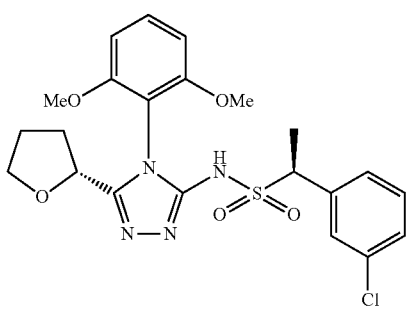 [SMILES: COc1cccc(OC)c1-n1c(NS(=O)(=O)[C@@H](C)c2cccc(Cl)c2)nnc1[C@H]1CCCO1]<br>(1S)-1-(3-chlorophenyl)-N-(4-(2,6-dimethoxyphenyl)-5-((2S)-tetrahydro-2-furanyl)-4H-1,2,4-triazol-3-yl)ethanesulfonamide or (1R)-1-(3-chlorophenyl)-N-(4-(2,6-dimethoxyphenyl)-5-((2R)-tetrahydro-2-furanyl)-4H-1,2,4-triazol-3-yl)ethanesulfonamide or (1R)-1-(3-chlorophenyl)-N-(4-(2,6-dimethoxyphenyl)-5-((2S)-tetrahydro-2-furanyl)-4H-1,2,4-triazol-3-yl)ethanesulfonamide or (1S)-1-(3-chlorophenyl)-N-(4-(2,6-dimethoxyphenyl)-5-((2R)-tetrahydro-2-furanyl)-4H-1,2,4-triazol-3-yl)ethanesulfonamide.<br>$^1$H NMR (500 MHz, DMSO-$d_6$) δ 12.69-12.93 (m, 1 H) 7.50 (t, J = 8.5 Hz, 1 H) 7.34-7.38 (m, 1 H) 7.17-7.34 (m, |

TABLE 37-continued

3 H) 6.87 (dd, J = 8.4, 5.8 Hz, 2 H) 4.46-4.57 (m, 1 H) 4.15-4.28 (m, 1 H) 3.76-3.85 (m, 6 H) 3.45-3.70 (m, 2 H) 1.92-2.13 (m, 2 H) 1.73-1.84 (m, 2 H) 1.44-1.54 (m, 3 H) LCMS-ESI (pos) m/z: 493.2 (M + H)+.

438.0 Tetrahydrofuran-2-carbohydrazide (J & W PharmLab, LLC), isothiocyanato-1,3-dimethoxybenzene (Example 10.0), and 1-(3-chlorophenyl)ethane-1-sulfonamide (Enamine). The mixture was separated by SFC: Chiralpak AD-H 2 × 25 cm Mobile Phase: 35% IPA Flow rate: 60 mL/min BPR: 100 bar UV Detector Wavelength: 215 nm. Under these conditions, this was the second peak to elute

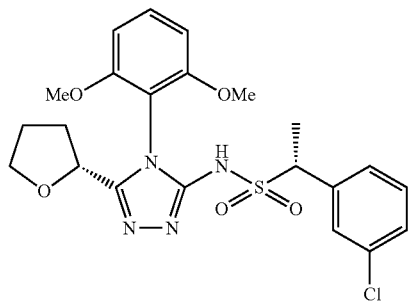 [SMILES: COc1cccc(OC)c1-n1c(NS(=O)(=O)[C@H](C)c2cccc(Cl)c2)nnc1[C@H]1CCCO1]

OR

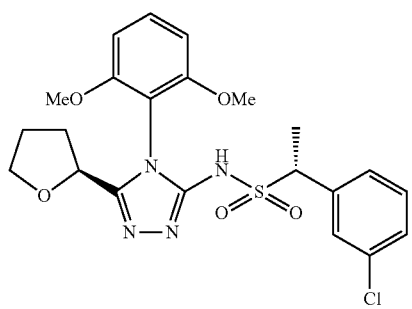 [SMILES: COc1cccc(OC)c1-n1c(NS(=O)(=O)[C@H](C)c2cccc(Cl)c2)nnc1[C@@H]1CCCO1]

OR

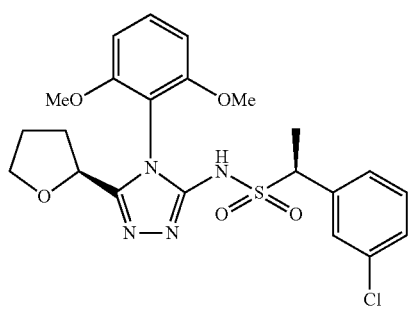 [SMILES: COc1cccc(OC)c1-n1c(NS(=O)(=O)[C@@H](C)c2cccc(Cl)c2)nnc1[C@@H]1CCCO1]

OR

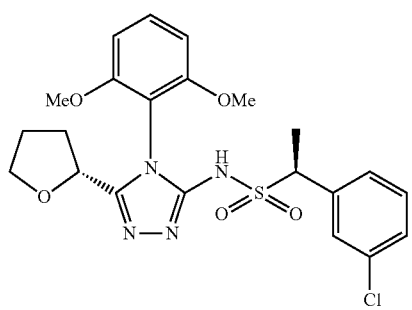 [SMILES: COc1cccc(OC)c1-n1c(NS(=O)(=O)[C@@H](C)c2cccc(Cl)c2)nnc1[C@H]1CCCO1]

(1S)-1-(3-chlorophenyl)-N-(4-(2,6-dimethoxyphenyl)-5-((2S)-tetrahydro-2-furanyl)-4H-1,2,4-triazol-3-yl)ethanesulfonamide or (1R)-1-(3-chlorophenyl)-N-(4-(2,6-dimethoxyphenyl)-5-((2R)-tetrahydro-2-furanyl)-4H-1,2,4-triazol-3-yl)ethanesulfonamide or (1R)-1-(3-chlorophenyl)-N-(4-(2,6-dimethoxyphenyl)-5-((2S)-tetrahydro-2-furanyl)-4H-1,2,4-triazol-3-yl)ethanesulfonamide or (1S)-1-(3-chlorophenyl)-N-(4-

TABLE 37-continued (2,6-dimethoxyphenyl)-5-((2R)-tetrahydro-2-furanyl)-4H-
1,2,4-triazol-3-yl)ethanesulfonamide.
¹H NMR (500 MHz, DMSO-d₆) δ 12.77-12.94 (m, 1 H)
7.44-7.57 (m, 1 H) 7.33-7.38 (m, 1 H) 7.21-7.33 (m, 3
H) 6.80-6.93 (m, 2 H) 4.42-4.53 (m, 1 H) 4.18-4.31 (m,
1 H) 3.75-3.82 (m, 6 H) 3.59-3.70 (m, 1 H) 3.47-3.56
(m, 1 H) 1.95-2.14 (m, 2 H) 1.74-1.86 (m, 2 H) 1.45-
1.51 (m, 3 H) LCMS-ESI (pos) m/z: 493.2 (M + H)⁺.

439.0 Tetrahydrofuran-2-
carbohydrazide (J & W
PharmLab, LLC),
isothiocyanato-1,3-
dimethoxybenzene (Example
10.0), and 1-(3-
chlorophenyl)ethane-1-
sulfonamide (Enamine). The
mixture was separated by SFC:
Chiralpak AD-H 2 × 25 cm
Mobile Phase: 35% IPA
Flow rate: 60 mL/min BPR: 100
bar UV Detector Wavelength:
215 nm. Under these conditions,
this was the third peak to elute

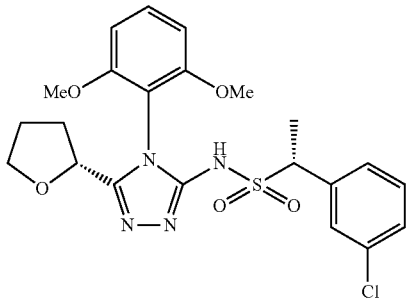 [SMILES: COc1cccc(OC)c1-n1c(NS(=O)(=O)[C@H](C)c2cccc(Cl)c2)nnc1[C@H]1CCCO1]

OR

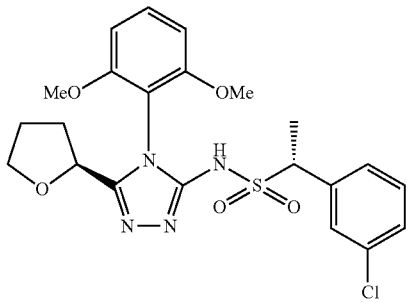

OR

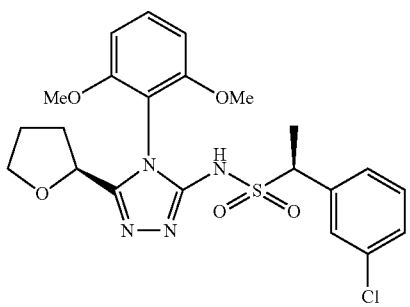 [SMILES: COc1cccc(OC)c1-n1c(NS(=O)(=O)[C@@H](C)c2cccc(Cl)c2)nnc1[C@@H]1CCCO1]

OR

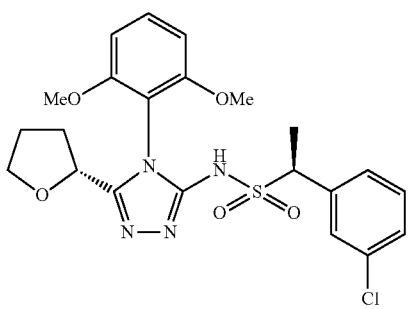 [SMILES: COc1cccc(OC)c1-n1c(NS(=O)(=O)[C@@H](C)c2cccc(Cl)c2)nnc1[C@H]1CCCO1]

(1S)-1-(3-chlorophenyl)-N-(4-(2,6-dimethoxyphenyl)-5-
((2S)-tetrahydro-2-furanyl)-4H-1,2,4-triazol-3-
yl)ethanesulfonamide or (1R)-1-(3-chlorophenyl)-N-(4-
(2,6-dimethoxyphenyl)-5-((2R)-tetrahydro-2-furanyl)-4H-
1,2,4-triazol-3-yl)ethanesulfonamide or (1R)-1-(3-

TABLE 37-continued chlorophenyl)-N-(4-(2,6-dimethoxyphenyl)-5-((2S)-tetrahydro-2-furanyl)-4H-1,2,4-triazol-3-yl)ethanesulfonamide or (1S)-1-(3-chlorophenyl)-N-(4-(2,6-dimethoxyphenyl)-5-((2R)-tetrahydro-furanyl)-4H-1,2,4-triazol-3-yl)ethanesulfonamide.

$^1$H NMR (500 MHz, DMSO-$d_6$) δ 12.74-12.91 (m, 1 H) 7.44-7.58 (m, 1 H) 7.17-7.40 (m, 4 H) 6.87 (dd, J = 8.2, 6.2 Hz, 2 H) 4.50 (dd, J = 7.7, 5.5 Hz, 1 H) 4.09-4.25 (m, 1 H) 3.78 (s, 3 H) 3.75 (s, 3 H) 3.59-3.70 (m, 1 H) 3.44-3.55 (m, 1 H) 1.91-2.13 (m, 2 H) 1.79 (d, J = 7.1 Hz, 2 H) 1.48 (d, J = 7.0 Hz, 3 H) LCMS-ESI (pos) m/z: 493.2 (M + H)$^+$.

440.0 Tetrahydrofuran-2-carbohydrazide (J & W PharmLab, LLC), isothiocyanato-1,3-dimethoxybenzene (Example 10.0), and 1-(3-chlorophenyl)ethane-1-sulfonamide (Enamine). The mixture was separated by SFC: Chiralpak AD-H 2 × 25 cm Mobile Phase: 35% IPA Flow rate: 60 mL/min BPR: 100 bar UV Detector Wavelength: 215 nm. Under these conditions, this was the fourth peak to elute

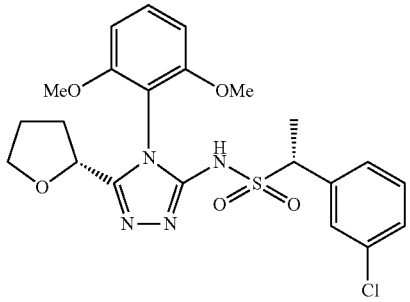 [SMILES: COc1cccc(OC)c1-n1c(NS(=O)(=O)[C@H](C)c2cccc(Cl)c2)nnc1[C@H]1CCCO1]

OR

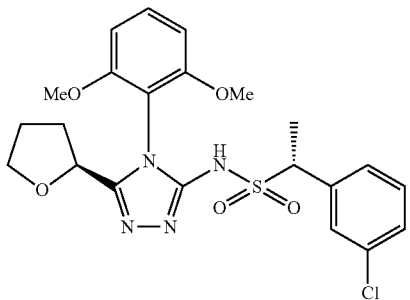 [SMILES: COc1cccc(OC)c1-n1c(NS(=O)(=O)[C@H](C)c2cccc(Cl)c2)nnc1[C@@H]1CCCO1]

OR

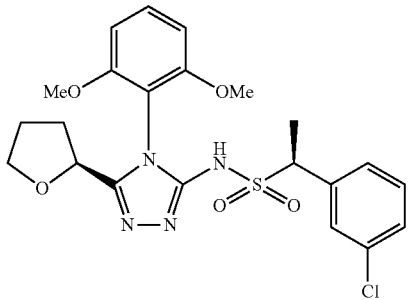 [SMILES: COc1cccc(OC)c1-n1c(NS(=O)(=O)[C@@H](C)c2cccc(Cl)c2)nnc1[C@@H]1CCCO1]

OR

TABLE 37-continued

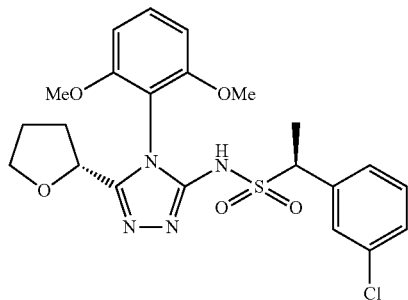 [SMILES: COc1cccc(OC)c1-n1c(NS(=O)(=O)[C@@H](C)c2cccc(Cl)c2)nnc1[C@H]1CCCO1]

(1S)-1-(3-chlorophenyl)-N-(4-(2,6-dimethoxyphenyl)-5-
((2S)-tetrahydro-2-furanyl)-4H-1,2,4-triazol-3-
yl)ethanesulfonamide or (1R)-1-(3-chlorophenyl)-N-(4-
(2,6-dimethoxyphenyl)-5-((2R)-tetrahydro-2-furanyl)-4H-
1,2,4-triazol-3-yl)ethanesulfonamide or (1R)-1-(3-
chlorophenyl)-N-(4-(2,6-dimethoxyphenyl)-5-((2S)-
tetrahydro-2-furanyl)-4H-1,2,4-triazol-3-
yl)ethanesulfonamide or (1S)-1-(3-chlorophenyl)-N-(4-
(2,6-dimethoxyphenyl)-5-((2R)-tetrahydro-2-furanyl)-4H-
1,2,4-triazol-3-yl)ethanesulfonamide.
$^1$H NMR (500 MHz, DMSO-$d_6$) δ 12.73-12.94 (m, 1 H)
7.44-7.56 (m, 1 H) 7.21-7.44 (m, 4 H) 6.81-6.94 (m, 2
H) 4.45-4.56 (m, 1 H) 4.13-4.27 (m, 1 H) 3.76-3.89 (m,
6 H) 3.60-3.71 (m, 1 H) 3.43-3.57 (m, 1 H) 1.96-2.17
(m, 2 H) 1.73-1.92 (m, 2 H) 1.42-1.56 (m, 3 H) LCMS-
ESI (pos) m/z: 493.2 (M + H)$^+$.

441.0 (2S,3R)-3-(5-chloropyrimidin-2-yl)butane-2-sulfonamide (Example 1.4), (3R, 5R)-5-methyltetrahydrofuran-3-carbohydrazide and (3S,5S)-5-methyltetrahydrofuran-3-carbohydrazide and (3R,5S)-5-methyltetrahydrofuran-3-carbohydrazide and (3S,5R)-5-methyltetrahydrofuran-3-carbohydrazide (commercially available from Enamine), and 2-isothiocyanato-1,3-dimethoxybenzene (Example 10.0). The racemic mixture was purified by preparative SFC using the following conditions: Column: AD-H (2 × 25 cm), Mobile Phase: 50:50 (A:B) A: Liquid CO$_2$, B: IPA, Flow Rate: 70 mL/min, 215 nm, 100 bar inlet pressure to deliver peak 1.

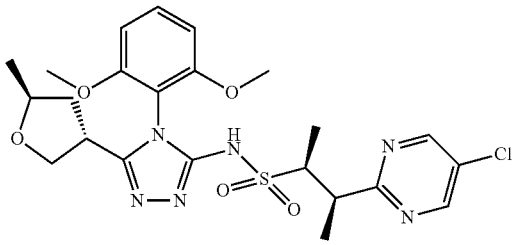

OR

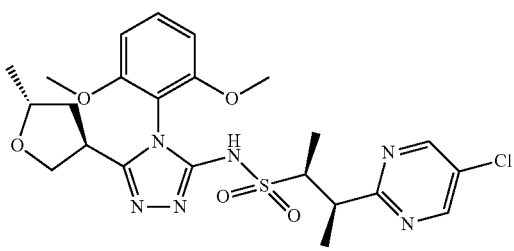 [SMILES: COc1cccc(OC)c1-n1c(NS(=O)(=O)[C@@H](C)[C@H](C)c2ncc(Cl)cn2)nnc1[C@H]1CO[C@H](C)C1]

OR

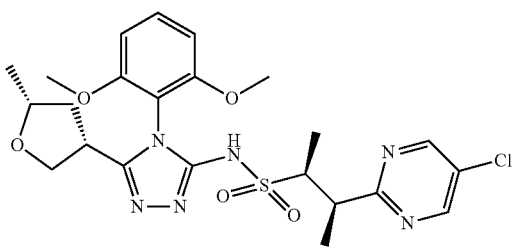 [SMILES: COc1cccc(OC)c1-n1c(NS(=O)(=O)[C@@H](C)[C@H](C)c2ncc(Cl)cn2)nnc1[C@@H]1CO[C@H](C)C1]

OR

TABLE 37-continued

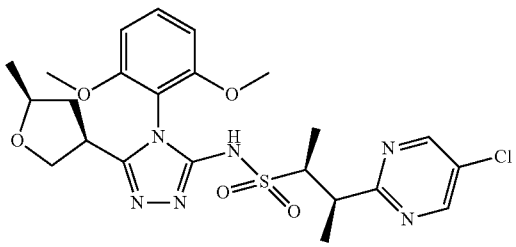

(2S,3R)-3-(5-chloropyrimidin-2-yl)-N-(4-(2,6-dimethoxyphenyl)-5-((3S,5S)-5-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((3R,5R)-5-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((3S,5R)-5-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((3R,5S)-5-methyltetrahydrofuran-3-yl)-4H-1,2,4-triazol-3-yl)butane-2-sulfonamide.
$^1$H NMR (500 MHz, CD$_2$Cl$_2$) δ = 10.74 (br s, 1H), 8.63 (s, 2H), 7.49 (t, J = 8.6 Hz, 1H), 6.72 (dd, J = 1.3, 8.6 Hz, 2H), 4.10-4.02 (m, 1H), 3.88-3.85 (m, 1H), 3.82-3.78 (m, 6H), 3.73-3.67 (m, 2H), 3.67-3.62 (m, 1H), 3.08-3.01 (m, 1H), 2.37-2.31 (m, 1H), 1.60-1.53 (m, 1H), 1.31 (d, J = 7.0 Hz, 3H), 1.26 (d, J = 7.0 Hz, 3H), 1.17 (d, J = 6.2 Hz, 3H). LCMS-ESI (pos) m/z: 537.2

442.0 (2S,3R)-3-(5-chloropyrimidin-2-yl)butane-2-sulfonamide (Example 1.4), (3R,5R)-5-methyltetrahydrofuran-3-carbohydrazide and (3S,5S)-5-methyltetrahydrofuran-3-carbohydrazide and (3R,5S)-5-methyltetrahydrofuran-3-carbohydrazide and (3S,5R)-5-methyltetrahydrofuran-3-carbohydrazide (commercially available from Enamine), and 2-isothiocyanato-1,3-dimethoxybenzene (Example 10.0). The racemic mixture was purified by preparative SFC using the following conditions: Column: AD-H (2 × 25 cm), Mobile Phase: 50:50 (A:B) A: Liquid CO$_2$, B: IPA, Flow Rate: 70 mL/min, 215 nm, 100 bar inlet pressure to deliver peak 2 that was further purified Column: AS-H 2 × 25 cm + Chiralpak AS-H 2 × 25 cm, Mobile Phase: 80:20 (A:B) A: Liquid CO$_2$, B: MeOH, Flow Rate: 70 mL/min, 215 nm, 100 bar inlet pressure to deliver peak 2.

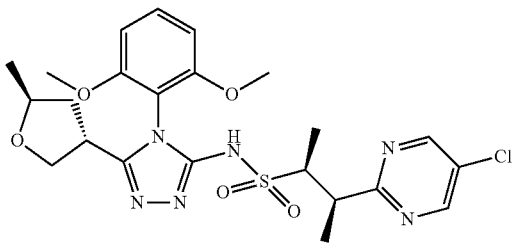 [SMILES: COc1cccc(OC)c1-n1c(NS(=O)(=O)[C@@H](C)[C@H](C)c2ncc(Cl)cn2)nnc1[C@@H]1CO[C@@H](C)C1]

OR

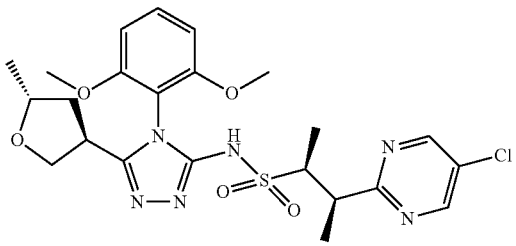 [SMILES: COc1cccc(OC)c1-n1c(NS(=O)(=O)[C@@H](C)[C@H](C)c2ncc(Cl)cn2)nnc1[C@H]1CO[C@H](C)C1]

OR

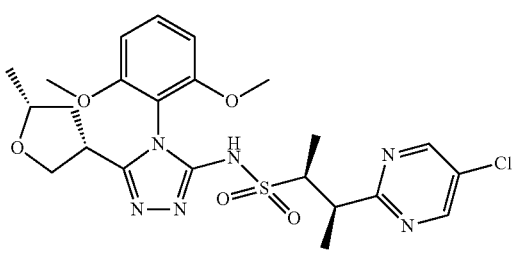 [SMILES: COc1cccc(OC)c1-n1c(NS(=O)(=O)[C@@H](C)[C@H](C)c2ncc(Cl)cn2)nnc1[C@@H]1CO[C@H](C)C1]

OR

TABLE 37-continued

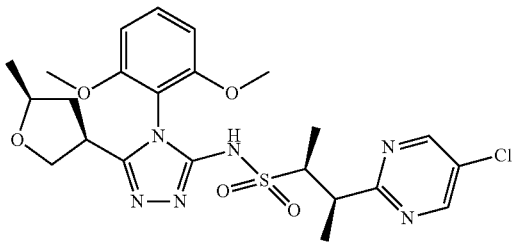 [SMILES: COc1cccc(OC)c1-n1c(NS(=O)(=O)[C@@H](C)[C@H](C)c2ncc(Cl)cn2)nnc1[C@H]1CO[C@@H](C)C1]

(2S,3R)-3-(5-chloropyrimidin-2-yl)-N-(4-(2,6-dimethoxyphenyl)-5-((3S,5S)-5-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((3R,5R)-5-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((3S,5R)-5-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((3R,5S)-5-methyltetrahydrofuran-3-yl)-4H-1,2,4-triazol-3-yl)butane-2-sulfonamide.

$^1$H NMR (500 MHz, CD$_2$Cl$_2$) δ = 10.76 (br s, 1H), 8.63 (s, 2H), 7.49 (t, J = 8.6 Hz, 1H), 6.72 (t, J = 8.3 Hz, 2H), 4.10-4.03 (m, 1H), 3.86 (t, J = 8.2 Hz, 1H), 3.81 (s, 3H), 3.80-3.78 (m, 3H), 3.73-3.64 (m, 3H), 3.04 (dtd, J = 5.4, 7.5, 9.8 Hz, 1H), 2.35 (ddd, J = 5.4, 6.7, 12.5 Hz, 1H), 1.57 (ddd, J = 7.8, 9.9, 12.5 Hz, 1H), 1.31 (d, J = 7.0 Hz, 3H), 1.26 (d, J = 7.0 Hz, 3H), 1.17 (d, J = 6.2 Hz, 3H). LCMS-ESI (pos) m/z: 537.2 (M + H)$^+$.

443.0 (2S,3R)-3-(5-chloropyrimidin-2-yl)butane-2-sulfonamide (Example 1.4), (3R,5R)-5-methyltetrahydrofuran-3-carbohydrazide and (3S,5S)-5-methyltetrahydrofuran-3-carbohydrazide and (3R,5S)-5-methyltetrahydrofuran-3-carbohydrazide and (3S,5R)-5-methyltetrahydrofuran-3-carbohydrazide (commercially available from Enamine), and 2-isothiocyanato-1,3-dimethoxybenzene (Example 10.0). The racemic mixture was purified by preparative SFC using the following conditions: Column: AD-H (2 × 25 cm), Mobile Phase: 50:50 (A:B) A: Liquid CO$_2$, B: IPA, Flow Rate: 70 mL/min, 215 nm, 100 bar inlet pressure to deliver peak 2 that was further purified Column: AS-H 2 × 25 cm + Chiralpak AS-H 2 × 15 cm, Mobile Phase: 80:20 (A:B) A: Liquid CO$_2$, B: MeOH, Flow Rate: 70 mL/min, 215 nm, 100 bar inlet pressure to deliver peak 3.

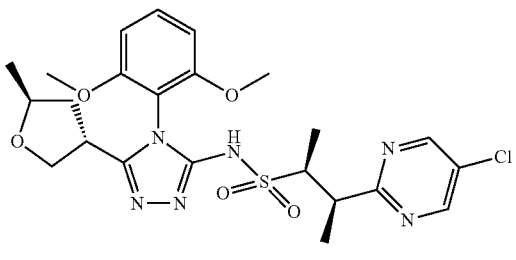 [SMILES: COc1cccc(OC)c1-n1c(NS(=O)(=O)[C@@H](C)[C@H](C)c2ncc(Cl)cn2)nnc1[C@@H]1CO[C@@H](C)C1]

OR

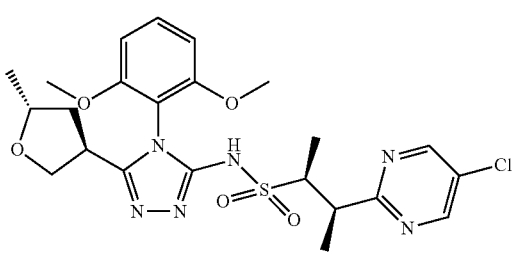

OR

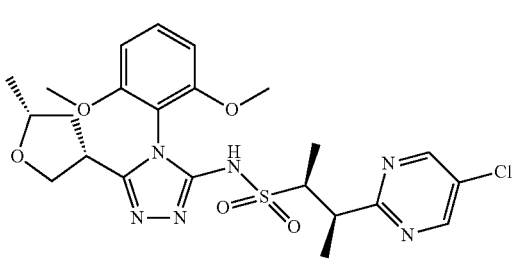 [SMILES: COc1cccc(OC)c1-n1c(NS(=O)(=O)[C@@H](C)[C@H](C)c2ncc(Cl)cn2)nnc1[C@@H]1CO[C@H](C)C1]

OR

TABLE 37-continued

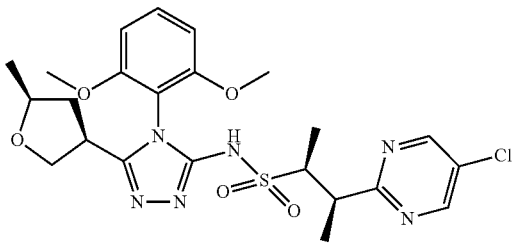 [SMILES: COc1cccc(OC)c1-n1c(NS(=O)(=O)[C@@H](C)[C@H](C)c2ncc(Cl)cn2)nnc1[C@H]1CO[C@@H](C)C1]

(2S,3R)-3-(5-chloropyrimidin-2-yl)-N-(4-(2,6-dimethoxyphenyl)-5-((3S,5S)-5-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((3R,5R)-5-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((3S,5R)-5-methyltetrahydrofuran-3-yl)-4H-1,2,4-triazol-3-yl)butane-2-sulfonamide or (2S,3R)-3-(5-chloropyrimidin-2-yl)-N-(4-(2,6-dimethoxyphenyl)-5-((3R,5S)-5-methyltetrahydrofuran-3-yl)-4H-1,2,4-triazol-3-yl)butane-2-sulfonamide.

$^1$H NMR (500 MHz, CD$_2$Cl$_2$) δ = 10.78 (br s, 1H), 8.63 (s, 2H), 7.49 (t, J = 8.6 Hz, 1H), 6.72 (dd, J = 2.1, 8.6 Hz, 2H), 3.93 (dd, J = 6.4, 8.7 Hz, 1H), 3.88 (td, J = 6.0, 9.3 Hz, 1H), 3.81-3.79 (m, 6H), 3.74-3.64 (m, 3H), 3.06 (dq, J = 6.2, 8.5 Hz, 1H), 2.11 (ddd, J = 5.7, 8.5, 12.5 Hz, 1H), 1.80 (td, J = 9.2, 12.5 Hz, 1H), 1.31 (d, J = 7.0 Hz, 3H), 1.28-1.25 (m, 3H), 1.25-1.23 (m, 3H). LCMS-ESI (pos) m/z: 537.2 (M + H)$^+$.

444.0 (2S,3R)-3-(5-chloropyrimidin-2-yl)butane-2-sulfonamide (Example 1.4), (3R,5R)-5-methyltetrahydrofuran-3-carbohydrazide and (3S,5S)-5-methyltetrahydrofuran-3-carbohydrazide and (3R,5S)-5-methyltetrahydrofuran-3-carbohydrazide and (3S,5R)-5-methyltetrahydrofuran-3-carbohydrazide (commercially available from Enamine), and 2-isothiocyanato-1,3-dimethoxybenzene (Example 10.0). The racemic mixture was purified by preparative SFC using the following conditions: Column: AD-H (2 × 25 cm), Mobile Phase: 50:50 (A:B) A: Liquid CO$_2$, B: IPA, Flow Rate: 70 mL/min, 215 nm, 100 bar inlet pressure to deliver peak 4.

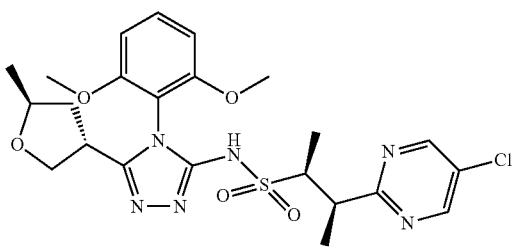 [SMILES: COc1cccc(OC)c1-n1c(NS(=O)(=O)[C@@H](C)[C@H](C)c2ncc(Cl)cn2)nnc1[C@@H]1CO[C@@H](C)C1]

OR

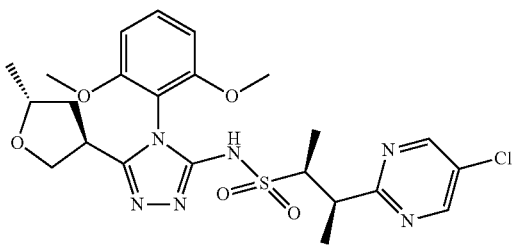 [SMILES: COc1cccc(OC)c1-n1c(NS(=O)(=O)[C@@H](C)[C@H](C)c2ncc(Cl)cn2)nnc1[C@H]1CO[C@H](C)C1]

OR

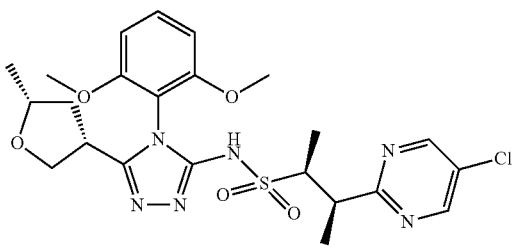 [SMILES: COc1cccc(OC)c1-n1c(NS(=O)(=O)[C@@H](C)[C@H](C)c2ncc(Cl)cn2)nnc1[C@@H]1CO[C@H](C)C1]

OR

TABLE 37-continued

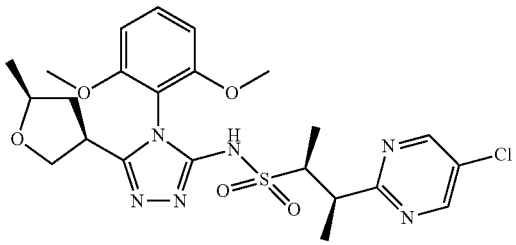 [SMILES: COc1cccc(OC)c1-n1c(NS(=O)(=O)[C@@H](C)[C@H](C)c2ncc(Cl)cn2)nnc1[C@H]1CO[C@@H](C)C1]

(2S,3R)-3-(5-chloropyrimidin-2-yl)-N-(4-(2,6-
dimethoxyphenyl)-5-((3S,5S)-5-methyltetrahydrofuran-3-
yl)-4H-1,2,4-triazol-3-yl)butane-2-sulfonamide or (2S,3R)-
3-(5-chloropyrimidin-2-yl)-N-(4-(2,6-dimethoxyphenyl)-5-
((3R,5R)-5-methyltetrahydrofuran-3-yl)-4H-1,2,4-triazol-3-
yl)butane-2-sulfonamide or (2S,3R)-3-(5-chloropyrimidin-
2-yl)-N-(4-(2,6-dimethoxyphenyl)-5-((3S,5R)-5-
methyltetrahydrofuran-3-yl)-4H-1,2,4-triazol-3-yl)butane-
2-sulfonamide or (2S,3R)-3-(5-chloropyrimidin-2-yl)-N-(4-
(2,6-dimethoxyphenyl)-5-((3R,5S)-5-
methyltetrahydrofuran-3-yl)-4H-1,2,4-triazol-3-yl)butane-
2-sulfonamide.
$^1$H NMR (500 MHz, CD$_2$Cl$_2$) δ = 10.79 (br s, 1H), 8.63 (s,
2H), 7.49 (t, J = 8.6 Hz, 1H), 6.72 (t, J = 8.0 Hz, 2H), 3.94-
3.91 (m, 1H), 3.90-3.85 (m, 1H), 3.82-3.80 (m, 3H), 3.80-
3.78 (m, 3H), 3.74-3.63 (m, 3H), 3.06 (dq, J = 6.4, 8.4 Hz,
1H), 2.12 (ddd, J = 5.7, 8.3, 12.5 Hz, 1H), 1.84-1.78 (m,
1H), 1.31 (d, J = 7.0 Hz, 3H), 1.27-1.25 (m, 3H), 1.25-
1.23 (m, 3H). LCMS-ESI (pos) m/z: 537.2 (M + H)$^+$.

445.0 (2S,3R)-3-(5-chloropyrimidin-2-
yl)butane-2-sulfonamide
(Example 1.4), (R)-Oxetane-2-
carbohydrazide and (S)-oxetane-
2-carbohydrazide (Example
142.2), and 2-isothiocyanato-
1,3-dimethoxybenzene
(Example 10.0). The racemic
mixture was purified by
preparative SFC using the
following conditions: Column:
AS-H (2 × 25 cm) + AS-H (2 ×
25 cm), Mobile Phase: 80:20
(A:B) A: Liquid CO$_2$, B: MeOH,
Flow Rate: 50 mL/min, 220 nm,
100 bar inlet pressure to deliver
peak 2.

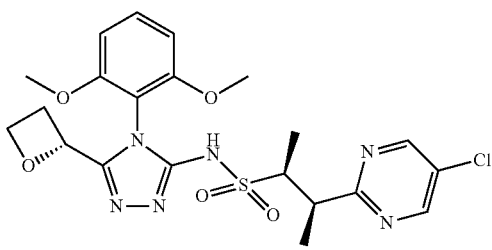 [SMILES: COc1cccc(OC)c1-n1c(NS(=O)(=O)[C@@H](C)[C@H](C)c2ncc(Cl)cn2)nnc1[C@H]1CCO1]

OR

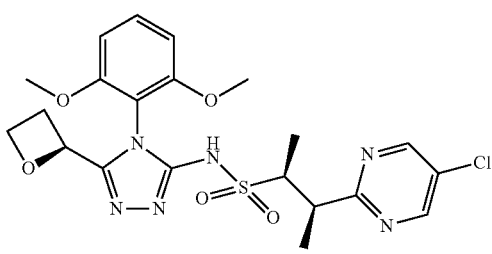 [SMILES: COc1cccc(OC)c1-n1c(NS(=O)(=O)[C@@H](C)[C@H](C)c2ncc(Cl)cn2)nnc1[C@@H]1CCO1]

(2S,3R)-3-(5-chloropyrimidin-2-yl)-N-(4-(2,6-
dimethoxyphenyl)-5-((R)-oxetan-2-yl)-4H-1,2,4-triazol-3-
yl)butane-2-sulfonamide or (2S,3R)-3-(5-chloropyrimidin-
2-yl)-N-(4-(2,6-dimethoxyphenyl)-5-((S)-oxetan-2-yl)-4H-
1,2,4-triazol-3-yl)butane-2-sulfonamide.
$^1$H NMR (400 MHz, CD$_2$Cl$_2$) δ = 10.91 (br s, 1H), 8.64 (s,
2H), 7.47 (t, J = 8.5 Hz, 1H), 6.73-6.67 (m, 2H), 5.36 (dd,
J = 6.6, 8.3 Hz, 1H), 4.57 (ddd, J = 5.7, 7.2, 8.5 Hz, 1H), 4.34
(td, J = 6.1, 8.9 Hz, 1H), 3.80 (s, 3H), 3.77 (s, 3H), 3.75-
3.62 (m, 2H), 2.99 (tdd, J = 7.0, 9.1, 11.5 Hz, 1H), 2.81 (dtd,
J = 6.3, 8.4, 11.5 Hz, 1H), 1.32 (d, J = 7.0 Hz, 3H), 1.28 (d,
J = 6.8 Hz, 3H). LCMS-ESI (pos) m/z: 509.2 (M + H)$^+$.

Example 446.0: Preparation of 2-isothiocyanato-1,3-di([²H₃]methoxy)benzene

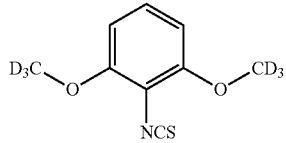

446.0

2-Isothiocyanato-1,3-di([²H₃]methoxy)benzene, Example 446.1

Step 1: 2-bromo-1,3-di([²H₃]methoxy)benzene

To a round-bottomed flask containing 2-bromoresorcinol (1.00 g, 5.29 mmol, Chem Impex International) was added DMF (10 mL), potassium carbonate (1.83 g, 13.23 mmol), and methyl iodide-d3 (0.988 mL, 15.87 mmol, IsoTec). The reaction was stirred at RT under $N_2$ for 20 h. The reaction was then diluted with water (50 mL) and extracted with EtOAc (3×40 mL). The organic layers were combined, dried over $MgSO_4$ and concentrated in vacuo. Purification by flash chromatography (40 g $SiO_2$ 0-20% EtOAc/hexanes) gave 2-bromo-1,3-di([²H₃]methoxy)benzene (1.06 g, 4.75 mmol, 90% yield) as a white solid.

Step 2: 2-amino-1,3-di([²H₃]methoxy)benzene, Example 446.2

To a 25 mL round bottomed flask containing 2-bromo-1,3-di([²H₃]methoxy)benzene (960 mg, 4.30 mmol), 2,2,2-trifluoroacetamide (973 mg, 8.61 mmol), potassium carbonate (2379 mg, 17.21 mmol), and copper (I) iodide (164 mg, 0.861 mmol) was added ACN (10 mL) and trans-N1,N2-dimethylcyclohexane-1,2-diamine (0.166 mL, 1.721 mmol). The bright blue suspension was sparged with Argon for 5 min and then the flask was fitted with an air cooled condenser and heated in a 80° C. oil bath and stirred for 16 h under $N_2$. The reaction was then cooled to RT and MeOH (5 mL) and $H_2O$ (5 mL) were added. The resulting mixture was then heated in a 65° C. oil bath for 7 h. The mixture was cooled to RT and EtOAc (25 mL) and water (25 mL) were added. The mixture was transferred to a separatory funnel and the layers were separated. The aqueous layer was extracted with EtOAc (50 mL). The combined organic layers were washed with water (50 mL), brine (100 mL), dried ($MgSO_4$), filtered and concentrated to give the amine as tan foam. Purification by flash chromatography (12 g $SiO_2$, 0-100% 3:1 EtOAc:EtOH/heptane) gave 2-amino-1,3-di([²H₃]methoxy)benzene (400 mg, 2.51 mmol, 58% yield) as a tan foam. LCMS-ESI pos.) m/z: 160.2 (M+H)⁺.

Step 3: 2-isothiocyanato-1,3-di([²H₃]methoxy)benzene, Example 446.0

To a 100 mL round bottomed flask with 2-amino-1,3-di([²H₃]methoxy)benzene (400 mg, 2.51 mmol) in DCM (20 mL) at RT was added 1,1''-thiocarbonyldi-2(1H)-pyridone (613 mg, 2.64 mmol). The reaction was stirred at RT under $N_2$ for 16 h. The reaction mixture was then concentrated to 10 mL and directly purified by flash chromatography (40 g $SiO_2$, 20-100% EtOAc/hexanes) to give the title compound (480 mg, 2.385 mmol, 95% yield) as a white solid. ¹H NMR (300 MHz, CDCl₃) δ 7.15 (t, J=8.4 Hz, 1H), 6.54 (d, J=8.5 Hz, 2H), LCMS-ESI (pos.) m/z: 202.2 (M+H)⁺.

Biological Activity

[³⁵S]GTPγS Binding

The human APJ receptor was cloned by polymerase chain reaction and the gene encoding the receptor was subcloned in pFLAG-CMV™-3 expression vector (Sigma, Saint Louis, Mo. USA) in-house at Amgen. A GTPγS binding assay was performed on membranes prepared from CHO cells stably expressing human APJ receptor. The optimum experimental conditions for the concentrations of GDP, $MgCl_2$, and NaCl in the assay buffer were initially determined. The assay was performed in assay buffer [20 mM HEPES, pH 7.5, 5 mM $MgCl_2$, and 0.1% (w/v) BSA with 200 mM NaCl, 3 μM GDP] and membranes expressing human APJ receptor/well along with WGA PS beads. The reaction was initiated by addition of 0.2 nM [35 S]GTPγS (Perkin Elmer Life and Analytical Sciences, Waltham USA) in the absence or presence of various ligands and incubated at RT for 90 min. Nonspecific binding was determined in the presence of 100 μM GTPγS and was always less than 0.2% of total binding. All the results presented are means of several independent experiments and analyzed by non-linear regression methods using commercially available program Prism (GraphPad, San Diego, Calif.) to obtain $EC_{50}$ detailed in Table 38.

Evidence for Load Independent Inotropic Effects with APJ Agonists Using Ex Vivo Assay (Isolated Perfused Rat Hearts)

Naive Sprague Dawley® SD rats (Harlan laboratories (Livermore, Calif. USA)) were anaesthetized and hearts were excised followed by cannulation in the Langendorff apparatus (Harvard apparatus, Holliston, Mass. USA) via aorta. The heart was perfused retrograde with modified oxygenated Krebs-Henseleit buffer (Skrzypiec-Spring M et al., (2007) J. Pharmacol Toxicol Methods 55: 113-126). The pressure of the solution causes the aortic valve to shut and the perfusate is then forced into the ostium and the coronary vessels. This allows the heart to beat for several h. A balloon was inserted into the left ventricle (LV) to measure $dP/dt_{max}$ (derivative of left ventricular pressure) as an index of cardiac contractility. The APJ agonist was perfused constantly in a dose dependent manner into the heart to examine cardiac contractility. Administration of APJ agonist showed a dose-dependent increase in inotropic and lusitropic effects at varying degrees (Table 39). APJ agonists of the present invention showed improvement in cardiac contractility and relaxation when perfused into the heart as described above.

Figure 1B:
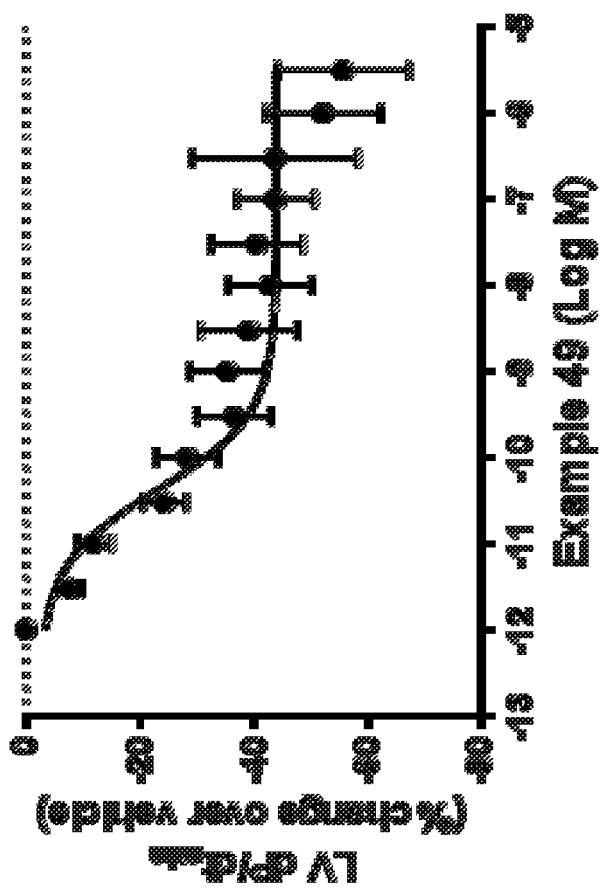
FIG. 1B is a graph of left ventricular dP/dt$_{min}$ as a function of concentration of Example 49.0 compared with vehicle in ex vivo naive Sprague Dawley rat hearts obtained using the Langendorff apparatus. This shows Example 49.0 increases load independent cardiac relaxation in isolated perfused rat hearts.
Figure 2A:
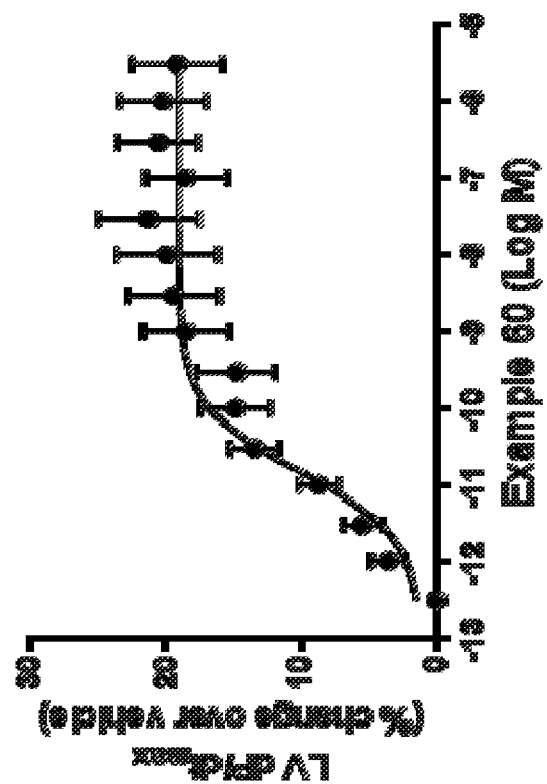
FIG. 2A is a graph of left ventricular dP/dt$_{max}$ as a function of concentration of Example 60.0 compared with vehicle in ex vivo naive Sprague Dawley rat hearts obtained using the Langendorff apparatus. This shows Example 60.0 increases load independent cardiac contractility in isolated perfused rat hearts.
Figure 2B:
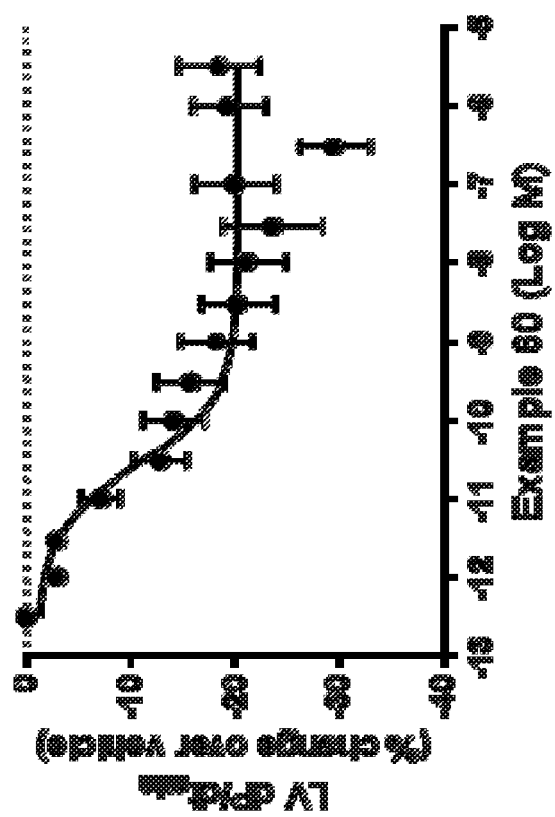
FIG. 2B is a graph of left ventricular dP/dt$_{min}$ as a function of concentration of Example 60.0 compared with vehicle in ex vivo naive Sprague Dawley rat hearts obtained using the Langendorff apparatus. This shows Example 60.0 increases load independent cardiac relaxation in isolated perfused rat hearts.

FIG. 1A shows the effect of Example 49.0 on load independent contractility in isolated perfused rat hearts. Example 49.0 was infused at different concentrations and load independent contractility was measured by index of LV $dP/dt_{max}$ and the results are expressed as a percent change over vehicle. FIG. 1B shows the effect of Example 49.0 on left ventricular relaxation in isolated perfused rat hearts. Example 49.0 was infused at different concentrations and load independent lusitropic effect (relaxation) was measured by index of LV $dP/dt_{min}$ where results are expressed as percent change over vehicle. FIG. 2A shows the effect of Example 60.0 on load independent contractility in isolated perfused rat hearts. Example 60.0 was infused at different concentrations and load independent contractility was measured by index of LV $dP/dt_{max}$ and the results are expressed as a percent change over vehicle. FIG. 2B shows the effect of Example 60.0 on left ventricular relaxation in isolated perfused rat hearts. Example 60.0 was infused at different concentrations and load independent lusitropic effect (relaxation) was measured by index of LV dP/dt$_{min}$ where results are expressed as percent change over vehicle.

Evidence for Improvement in Cardiac Contractility In Vivo in Heart Failure Rat Model Based on the ex vivo findings in isolated heart assay, APJ agonists were dosed in vivo to investigate the translation of cardiac contractility in in vivo settings. Male Lewis rats (Charles River, USA) at 2-3 months of age were used for the study. Heart failure was induced by permanent ligation of the left descending coronary artery which results in injury to the heart with an ejection fraction of <35%. APJ agonists were administered dose dependently acutely for a period of 30 min. Administration of Examples 49.0 and 60.0 lead to an increase in cardiac contractility as measured by dP/dt$_{max}$ (derivative of left ventricular pressure) (Table 39).

The following table includes biological activity data obtained using the procedures and assays set forth above for the Example compounds described herein.

TABLE 38

Biological Activity Information for Example Compounds.

| Example | Activity hAPJ SPA EC$_{50}$ IP (µM) |
|---|---|
| 2.0 | 0.24 |
| 3.0 | 1.2 |
| 4.0 | 0.89 |
| 5.0 | >4.2 |
| 6.0 | 0.40 |
| 7.0 | — |
| 8.0 | — |
| 9.0 | 0.21 |
| 15.0 | 0.47 |
| 16.0 | 0.38 |
| 17.0 | 0.81 |
| 18.0 | 0.12 |
| 19.0 | 0.060 |
| 20.0 | 0.16 |
| 21.0 | 0.11 |
| 22.0 | 0.26 |
| 23.0 | 0.11 |
| 24.0 | 0.0045 |
| 25.0 | 0.13 |
| 26.0 | 0.87 |
| 35.0 | 0.73 |
| 36.0 | 0.14 |
| 37.0 | 0.012 |
| 38.0 | 0.019 |
| 39.0 | 0.0053 |
| 40.0 | 0.014 |
| 41.0 | 0.82 |
| 42.0 | 0.21 |
| 43.0 | 1.19 |
| 44.0 | 0.43 |
| 45.0 | 0.51 |
| 47.0 | 0.00072 |
| 48.0 | 0.0039 |
| 49.0 | 0.0018 |
| 50.0 | 0.028 |
| 51.0 | 0.00059 |
| 52.0 | 0.020 |
| 53.0 | 0.013 |
| 54.0 | 0.037 |
| 55.0 | 0.066 |
| 56.0 | 0.019 |
| 57.0 | 0.021 |
| 58.0 | 0.12 |
| 59.0 | 0.016 |
| 60.0 | 0.0093 |
| 61.0 | 0.029 |
| 62.0 | 0.026 |
| 63.0 | 0.0015 |
| 64.0 | 0.029 |
| 65.0 | 0.0029 |
| 66.0 | 0.0069 |
| 67.0 | 0.18 |
| 68.0 | 0.014 |
| 69.0 | 0.082 |
| 70.0 | 0.015 |
| 71.0 | 0.45 |
| 72.0 | 0.0068 |
| 73.0 | 0.0014 |
| 74.0 | 0.12 |
| 75.0 | 0.21 |
| 76.0 | 0.0014 |
| 77.0 | 0.00014 |
| 78.0 | 0.0050 |
| 79.0 | 0.11 |
| 80.0 | 0.0091 |
| 81.0 | 0.082 |
| 82.0 | 0.0030 |
| 83.0 | 0.010 |
| 84.0 | 0.00080 |
| 85.0 | 0.0096 |
| 86.0 | 0.0021 |
| 87.0 | 0.0024 |
| 88.0 | 0.00042 |
| 89.0 | 0.023 |
| 90.0 | 0.37 |
| 91.0 | 0.29 |
| 92.0 | 0.042 |
| 93.0 | 0.17 |
| 94.0 | 0.19 |
| 95.0 | 0.015 |
| 96.0 | 0.19 |
| 97.0 | 0.015 |
| 98.0 | 0.00078 |
| 99.0 | 0.0025 |
| 100.0 | 0.024 |
| 101.0 | 0.26 |
| 102.0 | 0.0052 |
| 103.0 | 0.045 |
| 104.0 | 0.33 |
| 105.0 | 0.088 |
| 106.0 | 0.053 |
| 107.0 | 0.0051 |
| 108.0 | 0.025 |
| 109.0 | 0.00016 |
| 110.0 | 0.030 |
| 111.0 | 0.24 |
| 112.0 | 0.014 |
| 113.0 | 0.26 |
| 114.0 | 0.11 |
| 115.0 | 0.21 |
| 116.0 | 0.19 |
| 117.0 | 0.049 |
| 118.0 | 0.27 |
| 119.0 | 0.16 |
| 120.0 | 0.27 |
| 121.0 | 0.88 |
| 122.0 | 0.93 |
| 123.0 | 0.70 |
| 124.0 | 0.44 |
| 125.0 | 0.54 |
| 126.0 | 0.48 |
| 127.0 | 0.0077 |
| 128.0 | 0.79 |
| 129.0 | 2.1 |
| 130.0 | 1.8 |
| 131.0 | 0.55 |
| 132.0 | 0.14 |
| 133.0 | 0.32 |
| 134.0 | 0.40 |
| 135.0 | 0.035 |
| 136.0 | 0.13 |
| 137.0 | 0.0048 |
| 138.0 | 0.12 |
| 139.0 | 0.0048 |
| 140.0 | 0.090 |

TABLE 38-continued

Biological Activity Information for Example Compounds.

| Example | Activity hAPJ SPA EC$_{50}$ IP (µM) |
|---|---|
| 141.0 | 0.20 |
| 142.0 | 0.0019 |
| 143.0 | 0.12 |
| 144.0 | 0.080 |
| 145.0 | 0.83 |
| 146.0 | 0.45 |
| 147.0 | 0.037 |
| 148.0 | 0.68 |
| 173.0 | 0.13 |
| 174.0 | 0.21 |
| 175.0 | 0.0035 |
| 176.0 | 0.034 |
| 177.0 | 0.095 |
| 178.0 | 0.29 |
| 179.0 | 0.71 |
| 180.0 | 0.24 |
| 181.0 | 0.10 |
| 182.0 | 0.022 |
| 183.0 | 1.06 |
| 184.0 | 1.38 |
| 185.0 | 0.51 |
| 186.0 | 0.080 |
| 187.0 | 0.35 |
| 188.0 | 0.22 |
| 189.0 | 0.20 |
| 190.0 | 0.30 |
| 191.0 | 0.0041 |
| 192.0 | 0.0010 |
| 193.0 | 0.18 |
| 194.0 | 0.020 |
| 195.0 | 0.014 |
| 196.0 | 0.13 |
| 197.0 | 0.0010 |
| 198.0 | 0.0037 |
| 199.0 | 0.0027 |
| 200.0 | 0.29 |
| 201.0 | 0.031 |
| 202.0 | 0.12 |
| 203.0 | 0.033 |
| 204.0 | 0.10 |
| 205.0 | 0.019 |
| 206.0 | 0.035 |
| 207.0 | 0.0048 |
| 208.0 | 0.020 |
| 209.0 | 0.0092 |
| 210.0 | 0.00062 |
| 211.0 | 0.19 |
| 212.0 | 0.018 |
| 213.0 | 0.033 |
| 214.0 | 0.21 |
| 215.0 | 0.60 |
| 216.0 | 0.047 |
| 217.0 | 0.32 |
| 218.0 | 0.11 |
| 219.0 | 0.22 |
| 220.0 | 0.51 |
| 221.0 | 0.56 |
| 222.0 | 0.74 |
| 223.0 | 0.012 |
| 224.0 | 0.0015 |
| 225.0 | 0.070 |
| 226.0 | 1.4 |
| 230.0 | 0.45 |
| 231.0 | 0.88 |
| 232.0 | 0.22 |
| 233.0 | 1.27 |
| 234.0 | 0.23 |
| 235.0 | 0.83 |
| 236.0 | >4.2 |
| 237.0 | 0.59 |
| 238.0 | 0.81 |
| 239.0 | 0.033 |
| 240.0 | 0.0013 |
| 241.0 | 0.0014 |
| 242.0 | 0.0087 |
| 243.0 | 0.0056 |
| 244.0 | 0.021 |
| 245.0 | 0.62 |
| 246.0 | >4.2 |
| 247.0 | 0.24 |
| 248.0 | 0.00058 |
| 249.0 | 0.54 |
| 250.0 | 0.048 |
| 251.0 | 0.75 |
| 252.0 | 0.25 |
| 253.0 | 0.0063 |
| 254.0 | 0.31 |
| 255.0 | 0.016 |
| 256.0 | 0.015 |
| 257.0 | 1.2 |
| 258.0 | 0.033 |
| 259.0 | 0.088 |
| 260.0 | >4.2 |
| 261.0 | 0.15 |
| 262.0 | >4.2 |
| 263.0 | 0.46 |
| 264.0 | 0.0012 |
| 265.0 | 0.0035 |
| 266.0 | 0.15 |
| 267.0 | 0.0021 |
| 268.0 | 0.0019 |
| 269.0 | 0.42 |
| 270.0 | 0.41 |
| 271.0 | 0.14 |
| 272.0 | 1.01 |
| 273.0 | 0.029 |
| 274.0 | 0.078 |
| 275.0 | 0.020 |
| 276.0 | 0.033 |
| 277.0 | 0.023 |
| 278.0 | 0.51 |
| 279.0 | 0.00068 |
| 280.0 | 0.0075 |
| 281.0 | 0.00011 |
| 282.0 | 0.0016 |
| 283.0 | 0.00063 |
| 284.0 | 0.00063 |
| 285.0 | 0.064 |
| 286.0 | 0.0014 |
| 287.0 | 0.86 |
| 288.0 | 0.41 |
| 289.0 | 1.1 |
| 290.0 | 0.023 |
| 291.0 | 0.0052 |
| 292.0 | 0.018 |
| 293.0 | 0.10 |
| 294.0 | 0.27 |
| 295.0 | 0.016 |
| 296.0 | 0.17 |
| 297.0 | 1.47 |
| 298.0 | 1.89 |
| 299.0 | 0.94 |
| 300.0 | 1.4 |
| 301.0 | 2.9 |
| 302.0 | 0.71 |
| 303.0 | 0.34 |
| 304.0 | 0.21 |
| 305.0 | 0.74 |
| 306.0 | 0.90 |
| 307.0 | 0.014 |
| 308.0 | 0.41 |
| 309.0 | 2.6 |
| 310.0 | 0.54 |
| 311.0 | 1.7 |
| 312.0 | 1.9 |
| 313.0 | 0.53 |
| 314.0 | 0.071 |
| 315.0 | 0.085 |
| 316.0 | 0.026 |
| 317.0 | 0.052 |

TABLE 38-continued

Biological Activity Information for Example Compounds.

| Example | Activity hAPJ SPA EC$_{50}$ IP (µM) |
|---|---|
| 318.0 | 0.013 |
| 319.0 | 0.13 |
| 320.0 | 0.045 |
| 321.0 | 0.068 |
| 322.0 | 0.31 |
| 323.0 | 0.047 |
| 324.0 | 0.38 |
| 325.0 | 0.014 |
| 326.0 | 1.7 |
| 328.0 | 0.23 |
| 329.0 | 1.3 |
| 330.0 | 0.16 |
| 331.0 | 3.5 |
| 332.0 | 0.014 |
| 333.0 | 0.19 |
| 334.0 | 0.0025 |
| 335.0 | 0.038 |
| 336.0 | 1.4 |
| 337.0 | 0.0069 |
| 338.0 | 0.11 |
| 339.0 | 1.44 |
| 340.0 | 0.15 |
| 341.0 | 1.21 |
| 342.0 | 0.10 |
| 343.0 | 0.73 |
| 344.0 | 0.23 |
| 345.0 | 0.10 |
| 346.0 | 0.78 |
| 347.0 | 0.36 |
| 350.0 | 3.93 |
| 351.0 | 4.74 |
| 352.0 | 1.49 |
| 353.0 | 0.10 |
| 354.0 | 0.092 |
| 355.0 | 0.0012 |
| 356.0 | 0.026 |
| 357.0 | 0.28 |
| 358.0 | 0.43 |
| 359.0 | 0.011 |
| 360.0 | 0.31 |
| 361.0 | 0.010 |
| 362.0 | 0.39 |
| 363.0 | 0.028 |
| 364.0 | 0.069 |
| 365.0 | 0.072 |
| 366.0 | 0.68 |
| 367.0 | 0.012 |
| 368.0 | 0.10 |
| 369.0 | 0.021 |
| 370.0 | 0.62 |
| 371.0 | 0.015 |
| 372.0 | 0.24 |
| 373.0 | 0.0080 |
| 374.0 | 0.0056 |
| 375.0 | 0.092 |
| 376.0 | 0.12 |
| 377.0 | 0.024 |
| 378.0 | 0.17 |
| 379.0 | 0.021 |
| 380.0 | 0.060 |
| 381.0 | 0.0021 |
| 382.0 | 0.27 |
| 383.0 | 0.68 |
| 386.0 | 0.081 |
| 387.0 | 0.048 |
| 388.0 | 0.0098 |
| 389.0 | 0.096 |
| 390.0 | 0.33 |
| 391.0 | 0.015 |
| 392.0 | 0.025 |
| 393.0 | 0.018 |
| 394.0 | 0.020 |
| 395.0 | 0.067 |
| 396.0 | 0.058 |
| 397.0 | 0.16 |
| 398.0 | 0.56 |
| 399.0 | 0.47 |
| 400.0 | 0.33 |
| 401.0 | 0.10 |
| 402.0 | 0.41 |
| 403.0 | 0.28 |
| 404.0 | 0.081 |
| 405.0 | 1.72 |
| 406.0 | 1.08 |
| 407.0 | 0.010 |
| 408.0 | 0.064 |
| 409.0 | 0.011 |
| 410.0 | 0.019 |
| 411.0 | 0.086 |
| 412.0 | 0.040 |
| 413.0 | 0.0074 |
| 414.0 | 0.0012 |
| 415.0 | 0.23 |
| 416.0 | 0.19 |
| 417.0 | 0.19 |
| 418.0 | 0.35 |
| 419.0 | 3.43 |
| 424.0 | 0.052 |
| 425.0 | 0.13 |
| 428.0 | 0.15 |
| 429.0 | 0.59 |
| 430.0 | 0.45 |
| 431.0 | 0.39 |
| 432.0 | 0.13 |
| 433.0 | 0.26 |
| 434.0 | 0.39 |
| 435.0 | 0.24 |
| 436.0 | 2.65 |
| 437.0 | 2.60 |
| 438.0 | 0.91 |
| 439.0 | 2.99 |
| 440.0 | 1.73 |
| 441.0 | 0.0084 |
| 442.0 | 0.012 |
| 443.0 | 0.017 |
| 444.0 | 0.0019 |
| 445.0 | 0.030 |

The following table includes data obtained using the procedures and assays set forth above for the Example compounds described herein.

TABLE 39

Contractile Effects of Examples Observed in ex vivo (Isolated Heart Assay) and in vivo (MI Rat Model).

| Example(s) | Isolated Heart Assay | | MI Rat Model |
|---|---|---|---|
| | dP/dt$_{max}$ (%) | dP/dt$_{min}$ (%) | dP/dt$_{max}$ (%) |
| 40.0 | No effect | No effect | nd* |
| 47.0 | 6.5 | 1.0 | nd* |
| 49.0 | 20 | 55 | 20.0 |
| 50.0 | 2.0 | No effect | nd* |
| 51.0 | No effect | No effect | nd* |
| 53.0 | 14.0 | 12.4 | nd* |
| 56.0 | 6.8 | 7.1 | nd* |
| 57.0 | No effect | No effect | nd* |
| 60.0 | 19.1 | 18.3 | 20.0 |
| 61.0 | 3.0 | No effect | nd* |
| 63.0 | 14.0 | 11.0 | nd* |
| 65.0 | 6.0 | No effect | nd* |
| 72.0 | 5.9 | 2.5 | nd* |
| 73.0 | 2.0 | No effect | nd* |
| 74.0 | 5.8 | 2.1 | nd* |
| 77.0 | 5.0 | No effect | nd* |
| 78.0 | 7.09 | 8.61 | nd* |

TABLE 39-continued

Contractile Effects of Examples Observed in ex vivo
(Isolated Heart Assay) and in vivo (MI Rat Model).

| Example(s) | Isolated Heart Assay | | MI Rat Model |
|---|---|---|---|
| | dP/dt$_{max}$ (%) | dP/dt$_{min}$ (%) | dP/dt$_{max}$ (%) |
| 80.0 | No effect | No effect | nd* |
| 97.0 | 5.5 | 2.0 | nd* |
| 102.0 | 2.0 | 5.0 | nd* |
| 112.0 | No effect | No effect | nd* |
| 195.0 | 8.9 | 15.0 | nd* |
| 139.0 | 20.9 | 30.4 | nd* |
| 140.0 | 8.85 | 15.4 | nd* |
| 198.0 | −2.58 | 1.65 | nd* |
| 209.0 | 4.09 | 2.60 | nd* |
| 265.0 | 2.05 | 6.23 | nd* |
| 275.0 | 7.95 | 13.5 | nd* |

*nd is not determined.

APJ is a G-protein coupled receptor that is closely related to the Angiotensin II Type 1 receptor (AT1R) with 50% homology in the transmembrane domain. Apelin is a known endogenous ligand for APJ and recently another ligand named ELABELA has been identified as another potential ligand for the APJ receptor (Tatemoto, K. et al., Biochem. Biophys. Res. Commun., 251, pp. 471-476 (1998); Pauli, A. et al., Science, 343, pp. 1248636 (2014)). Since its discovery, there is accumulating evidence indicating the role of the apelin-APJ receptor in the pathophysiology of cardiovascular diseases. Pre-clinical and clinical studies have shown that acute infusion of apelin or APJ agonists improve cardiac function under heart failure settings (Berry, M. F., et al., Circulation, 110(11) pp. 11187-11193 (2004); Japp, A. G. et al., Circulation, 121, pp. 1818-1827 (2010)).

A key emerging aspect of the apelin-APJ system is its interaction with the renin-angiotensin system. Apelin is also known to counter-regulate the vasoconstriction actions of AngII. Apelin knockout mice show a strong increased vasopressor response to AngII indicating that the apelin/APJ system exerts the hypotensive effect in vivo against the pressor action of AngII. In addition, the apelin activated APJ pathway inhibited angiotensin-mediated formation of atherosclerosis through interaction with the AT1R (Chun, H. J., et al., J. Clin. Invest., 118, pp. 3343-3354 (2008), Siddiquee, K. et al., J. Hypertens., 29, pp. 724-731 (2011), Sun, X. et al., Hypertens. Res., 34, pp. 701-706 (2011)). This could be mediated by convergence of two independent intracellular signaling pathways or via direct physical interaction of APJ with AT1R to form a heterodimer. Siddiquee et al. showed that the AngII signaling is antagonized through apelin-dependent heterodimerization and APJ mediated negative allosteric modulation of AT1R function (Siddiquee, K. et al., Br. J. Pharmacol., 168, pp. 1104-1117 (2013).

We were interested to understand if the heterodimerization of APJ-AT1R upon activation by APJ agonists would have any beneficial outcome clinically in heart failure patients considering most of these patients are on standard of care drugs such as angiotensin blockers (angiotensin II receptor antagonists or angiotensin receptor blockers (ARBs)) and angiotensin converting enzyme (ACE) inhibitors. In order to explore the cross-talk between APJ and the AT1R receptor, we examined IP1 signaling mediated by AT1R upon activation with APJ agonists. Surprisingly and contrary to the findings by Siddique et al., activation of APJ pathway resulted in positive cooperativity of AngII by shifting its potency to the left and also increasing the efficacy of the IP response (see methods and results section below).

Conversely, blocking the AT1R receptor by an ARB such as losartan relieved the inhibition of the APJ receptor and up regulates its signaling which is observed as synergistic effects in both ex-vivo and in vivo studies. This work establishes a new paradigm for cross-talk interaction/heterodimerization between APJ & AT1R which might have implications for approaches to pharmacological interventions in heart failure populations.

The interaction between acetyl cholinesterase (ACE2) and Apelin biology is complicated. To investigate the interaction between the Apelin-APJ and ACE signaling pathways, we examined the improvement in cardiac function with APJ small molecule agonists in the presence of ACE inhibitor captopril in heart failure rats in vivo. Captopril alone, under acute settings, does not show a marked improvement in contractility or ejection fraction acutely. However, in the presence of an APJ agonist, there was a shift in potency to the left with marked improvement in contractility and ejection fraction without changes in heart rate. These findings provide a new reference for the understanding of the regulation of ACE2 for the renin angiotensin aldosterone system (RAAS), independent of AT1R signaling and offer new potential drug targets for the treatment of diseases such as hypertension and heart failure. This work clearly establishes that combination of an agonist of the APJ receptor with an ARB such as losartan and/or with an ACE inhibitor such as captopril which may play an important role in providing greater efficacy in treating heart failure patients, for example in improving contractility and ejection fraction without changing the heart rate.

Evidence for Allosteric Interaction Between APJ and AT1R Using IP Assay

Methods

Single and double stable recombinant cell lines were generated for human APJ and the AT1R receptor in CHO K1 cells tagged either with FLAG or hemagglutinin (HA) tag. Briefly, the CHO-K1 APJ/AT1R cells were seeded in culture medium of DMEM-F12 and 10% FBS at a density of 15 k/well in a 96 well plate overnight. The next day, the culture medium was replaced with medium containing no serum for 4 h. The compound AngII at a range of concentrations (1 pM-10 µM) with or without different concentrations of APJ agonists were diluted in stimulation buffer and added to the cell plate. The plate was sealed and incubated for 1 h. This was followed by addition of IP-d2 conjugate followed by europium cryptate antibody conjugate into the wells. The plate was sealed, followed with incubation for 2 h at room temperature. Time-resolved fluorescence resonance energy (TR-FRET) at 620 nm and 665 nm was measured after 2 h with an Envision reader. The signal ratios and delta F were calculated and the amount of IP1 produced was inversely proportional to the TR-FRET ratio, 665/620 nm.

Results

Figure 3:
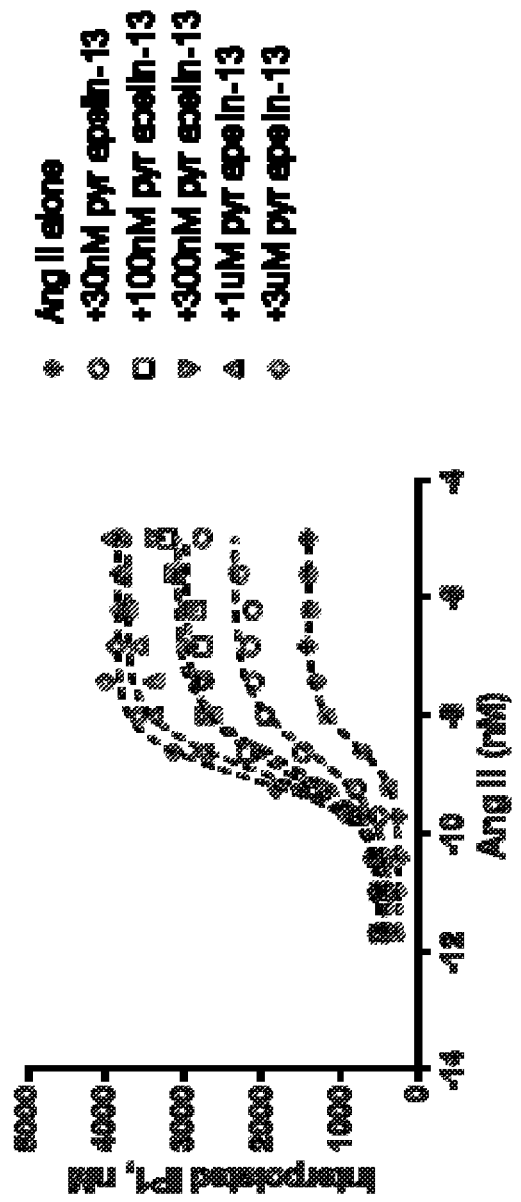
FIG. 3 is a graph plotting different concentrations of angiotensin (AngII) with fixed concentration of pyr apelin-13 added to the human APJ-AT1R (angiotensin Type 1) double stable CHO cell line. The function of the inositol phosphate accumulation (IP1) was measured by Time-resolved fluorescence resonance energy (TR-FRET) at 620 nm and 665 nm respectively. Addition of pyr apelin-13 induces the positive cooperativity on the AT1R upon activation by APJ receptor.
Figure 4:
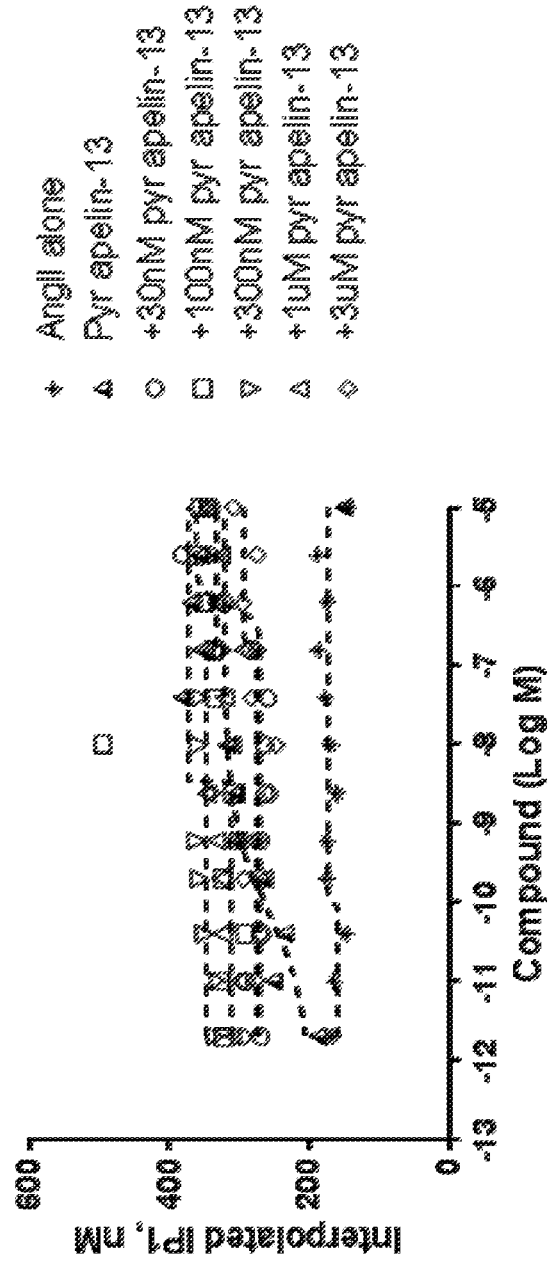
FIG. 4 is a graph plotting different concentrations of angiotensin (AngII) with fixed concentration of pyr apelin-13 added to the human APJ receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed upon treatment with pyr apelin-13 when the human APJ receptor is expressed alone.
Figure 5:
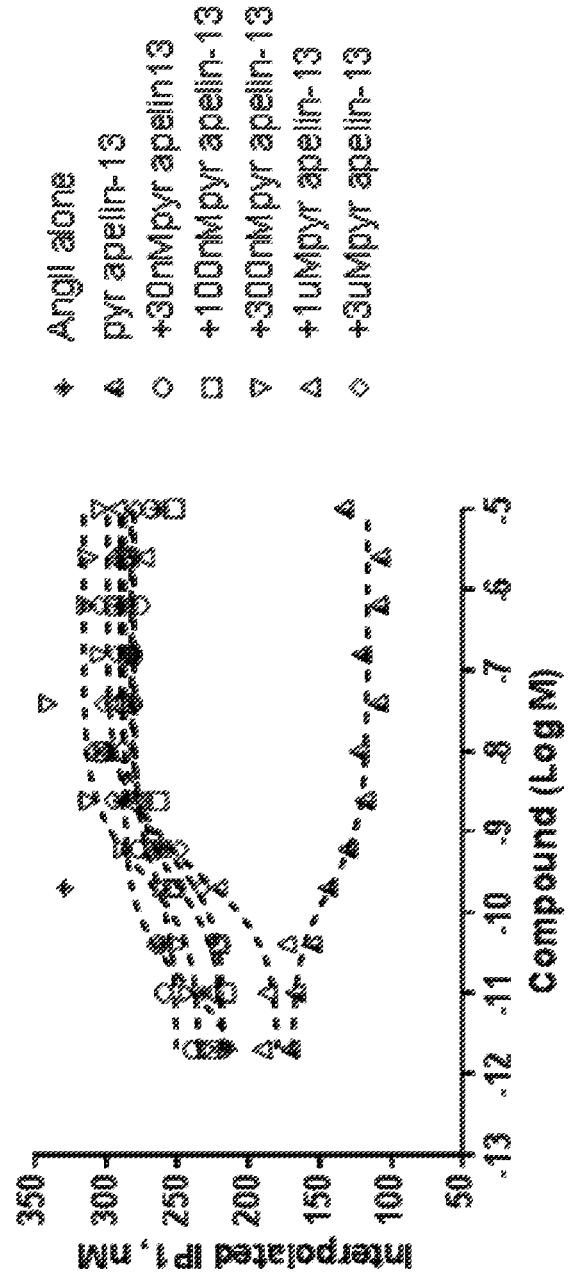
FIG. 5 is a graph plotting different concentrations of angiotensin (AngII) with fixed concentration of pyr apelin-13 added to the human AT1R receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed when the human AT1R receptor is expressed alone by pyr apelin-13 in the absence of APJ expression.

In cells expressing both APJ and the AT1R receptor, addition of APJ agonists at different concentrations increased the maximal response of AngII and also shifted the potency to the left. The increase in IP1 response reached a maximal effect both in potency and Emax indicating a ceiling effect which is a hallmark for allosteric cooperativity between the AT1R and APJ receptor (FIG. 3). However, this effect of cooperativity was not observed in either APJ or AT1R recombinant stable cell lines indicating that there is functional cross-talk between the two receptors through physical interaction or with downstream effectors (FIG. 4 and FIG. 5). Based on the above findings of cooperativity, we rationalized that if an APJ agonist can induce heterodimerization of APJ with AT1R, blocking the AT1R with losartan would enhance the activation of APJ upon addition of small molecule agonists. We observed that APJ small molecule agonists induced positive cooperativity in the presence of AngII and addition of losartan relieved this cooperativity and resulted in synergistic effects of enhancing the efficacy of the APJ receptor. This work clearly establishes that combination of an agonist of the APJ receptor with an ARB such as losartan or an ACE inhibitor such as captopril may play an important role in providing greater efficacy in treatment of heart failure patients.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound of Formula I or Formula II:

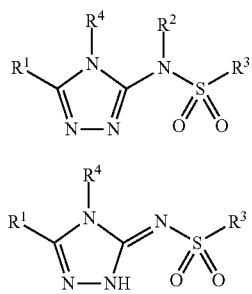

or a pharmaceutically acceptable salt thereof, a tautomer thereof, a pharmaceutically acceptable salt of the tautomer, a stereoisomer of any of the foregoing, or a mixture thereof, wherein:

$R^1$ is a 3-, 4-, 5-, 6-, 7-, or 8-membered saturated or partially saturated heterocyclic group that includes 1, 2, or 3 heteroatoms independently selected from N, O, or S that is unsubstituted or is substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —NHS(=O)$_2$—($C_1$-$C_6$ alkyl), or —S(=O)$_2$—($C_1$-$C_6$ alkyl), wherein $R^{1a}$ may also be oxo unless $R^1$ is a 6-membered heterocyclic group that includes one N atom and includes at least one double bond, and further wherein two $R^{1a}$ substituents on adjacent carbon atoms or on an adjacent carbon atom and an adjacent N atom of a 5- or 6-membered heterocyclic $R^1$ group may join to form a 6 membered ring that may be saturated, partially saturated, or aromatic and may include 0, 1, or 2 N atoms and may further optionally be substituted with 1 or 2 $R^{1a'}$ substituent and may include an oxo substituent if the ring is not an aromatic ring and further wherein two $R^{1a}$ substituents on adjacent carbon atoms or on an adjacent carbon atom and an adjacent N atom of a 5- or 6-membered heterocyclic $R^1$ group may join to form a 5 membered ring that may be saturated, partially saturated, or aromatic and may include 0, 1, or 2 heteroatoms selected from N, O, or S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —(CR$^{3b}$R$^{3c}$)-Q, a group of formula —(CR$^{3d}$R$^{3e}$)—(CR$^{3f}$R$^{3g}$)-Q, a group of formula —(CR$^{3d}$R$^{3e}$)—(CR$^{3f}$R$^{3g}$)—C(=O)-Q, a group of formula —(CR$^{3d}$R$^{3e}$)—(CR$^{3f}$R$^{3g}$)—CH(OH)-Q, a group of formula —(CR$^{3d}$R$^{3e}$)—(CR$^{3f}$R$^{3g}$)—(CR$^{3f}$R$^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —NH$_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-NH$_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, and the heterocyclyl $R^4$ group are unsubstituted or are substituted with 1, 2, 3, or 4 $R^{4a}$ substituents, and further wherein the cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S and is unsaturated or partially unsaturated and is optionally substituted with 1 or 2 oxo substituents, and further wherein the heterocyclyl of the $R^4$ group may be further substituted with 1 oxo substituent;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, heterocyclyl, a monocyclic 3-6 membered cycloalkyl group, or a 5 or 6 membered heteroaryl ring containing 1, 2, or 3 heteroatoms selected from N, O, or S, wherein the heterocyclyl of the —($C_1$-$C_6$ alkyl)-heterocyclyl and heterocyclyl $R^{4b}$ groups is a 3-6 membered ring comprising 1 or 2 heteroatoms independently selected from N, O, or S and is unsaturated or partially unsaturated and is optionally substituted with 1 or 2 oxo substituents, and further wherein the phenyl and heteroaryl $R^{4b}$ groups are unsubstituted or are substituted with 1 or 2 $R^{4aa}$ substituents;

$R^{4c}$ in each instance is independently selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a monocyclic 3-6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a monocyclic 3-6 membered cycloalkyl $R^{4c}$ group, the 3 to 6 membered heterocyclyl $R^{4c}$ group, the phenyl $R^{4c}$ group, or the a 5 or 6 membered heteroaryl $R^{4c}$ ring are unsubstituted or are substituted with 1 or 2 $R^{4aa}$ substituents; and further wherein the 3 to 6 membered cycloalkyl $R^{4c}$ group and the 3 to 6 membered heterocyclyl $R^{4c}$ group may optionally be additionally substituted with an oxo substituent; and $R^{4aa}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), or —S(=O)$_2$—($C_1$-$C_6$ alkyl).

2. The compound of claim 1 or the pharmaceutically acceptable salt thereof, the tautomer thereof, the pharmaceutically acceptable salt of the tautomer, the stereoisomer of any of the foregoing, or the mixture thereof, wherein one of the following is true:
1) two $R^{1a}$ substituents on adjacent carbon atoms or on an adjacent carbon atom and an adjacent N atom of a 5- or 6-membered heterocyclic $R^1$ group join to form a 6 membered ring that may be saturated, partially saturated, or aromatic and may include 0, 1, or 2 N atoms and may further optionally be substituted with 1 or 2 $R^{1a'}$ substituents and may include an oxo substituent if the ring is not an aromatic ring; or
2) two $R^{1a}$ substituents on adjacent carbon atoms or on an adjacent carbon atom and an adjacent N atom of a 5- or 6-membered heterocyclic $R^1$ group join to form a 5 membered ring that may be saturated, partially saturated, or aromatic and may include 0, 1, or 2 heteroatoms selected from N, O, or S and may further optionally be substituted with 1 or 2 $R^{1a'}$ substituent and may include an oxo substituent if the ring is not an aromatic ring.

3. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from

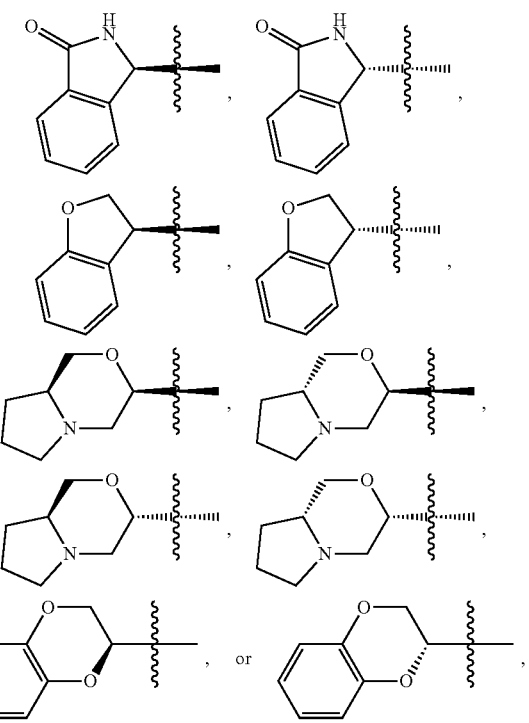

wherein the symbol ∿∿∿, when drawn across a bond, indicates the point of attachment to the rest of the molecule.

4. The compound of claim 1 or the pharmaceutically acceptable salt thereof, the stereoisomer of any of the foregoing, or the mixture thereof, wherein $R^4$ is selected from a straight or branched chain $C_1$-$C_6$ alkyl group that is unsubstituted or is substituted with 1, 2, or 3 $R^{4c}$ substituents.

5. The compound of claim 1 or the pharmaceutically acceptable salt thereof, the stereoisomer of any of the foregoing, or the mixture thereof, wherein $R^4$ is selected from

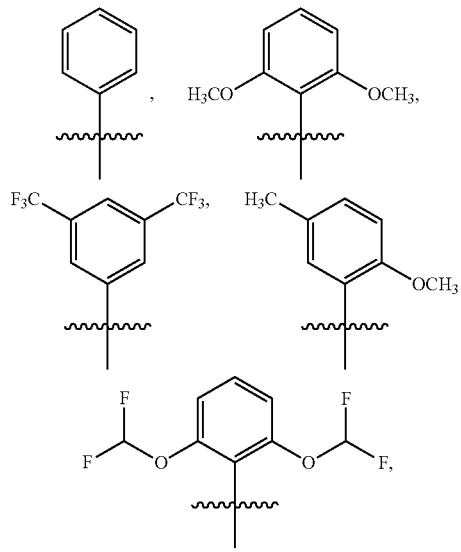

-continued
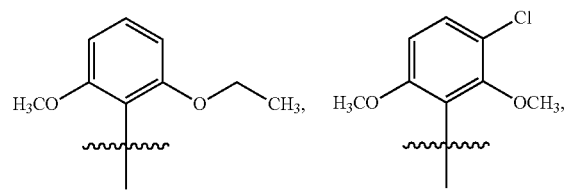
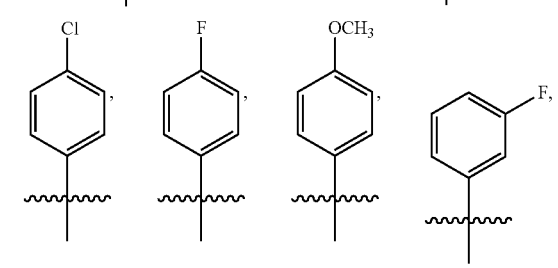
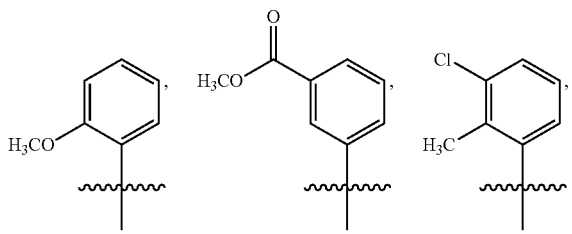
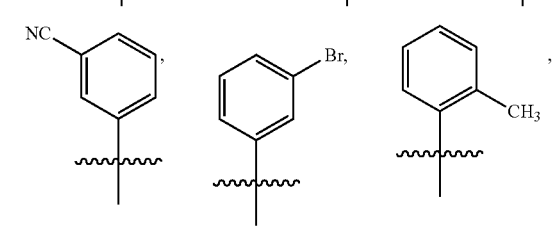
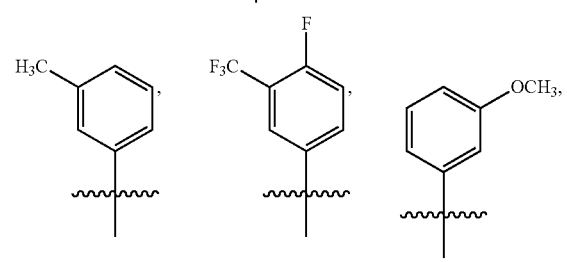
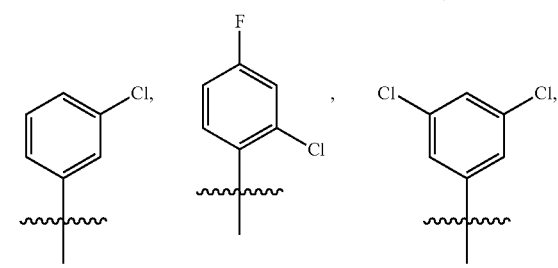
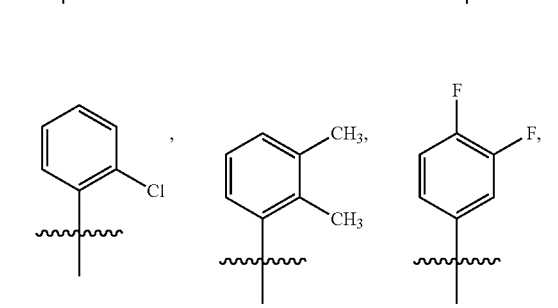
-continued
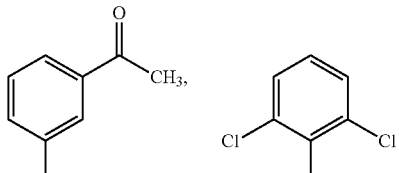
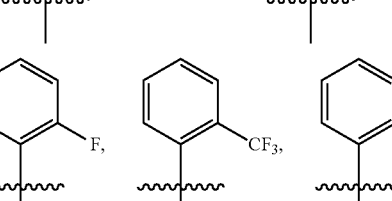
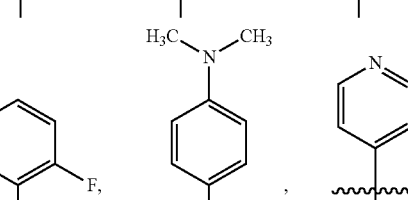
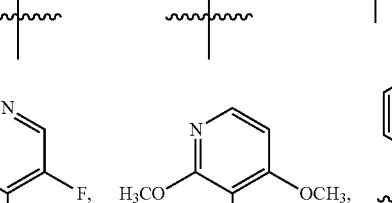
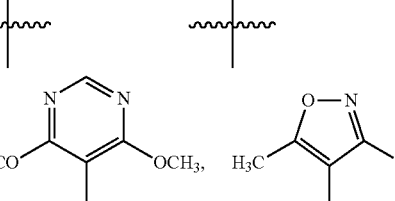
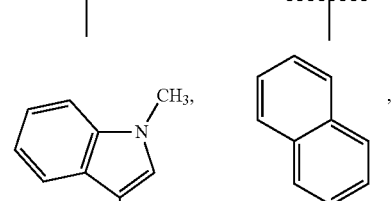
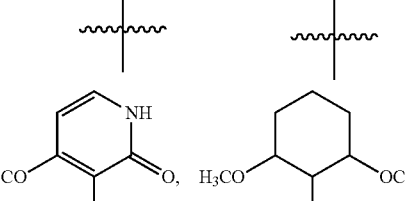
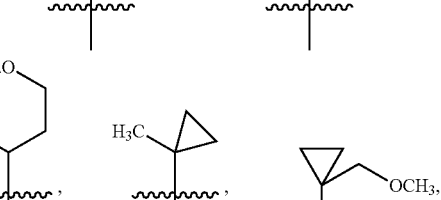

753

-continued

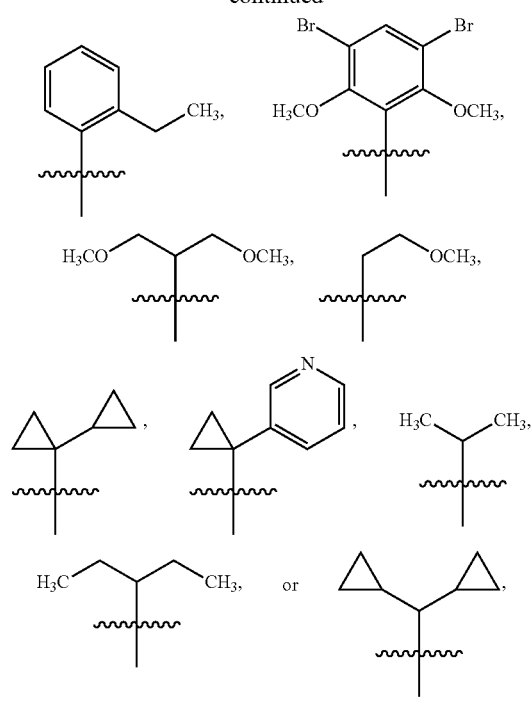

wherein the symbol ⌇⌇⌇, when drawn across a bond, indicates the point of attachment to the rest of the molecule.

6. The compound of claim 1 or the pharmaceutically acceptable salt thereof, the stereoisomer of any of the foregoing, or the mixture thereof, wherein $R^4$ is selected from

754

-continued

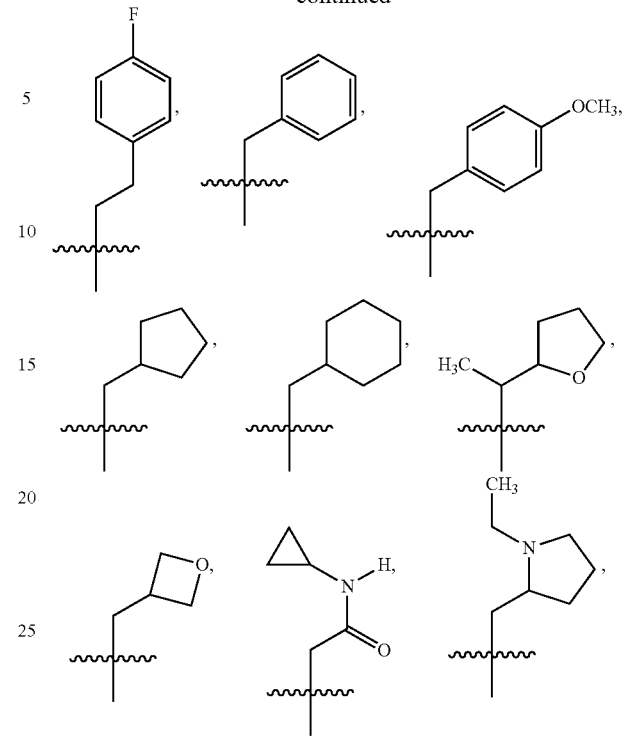

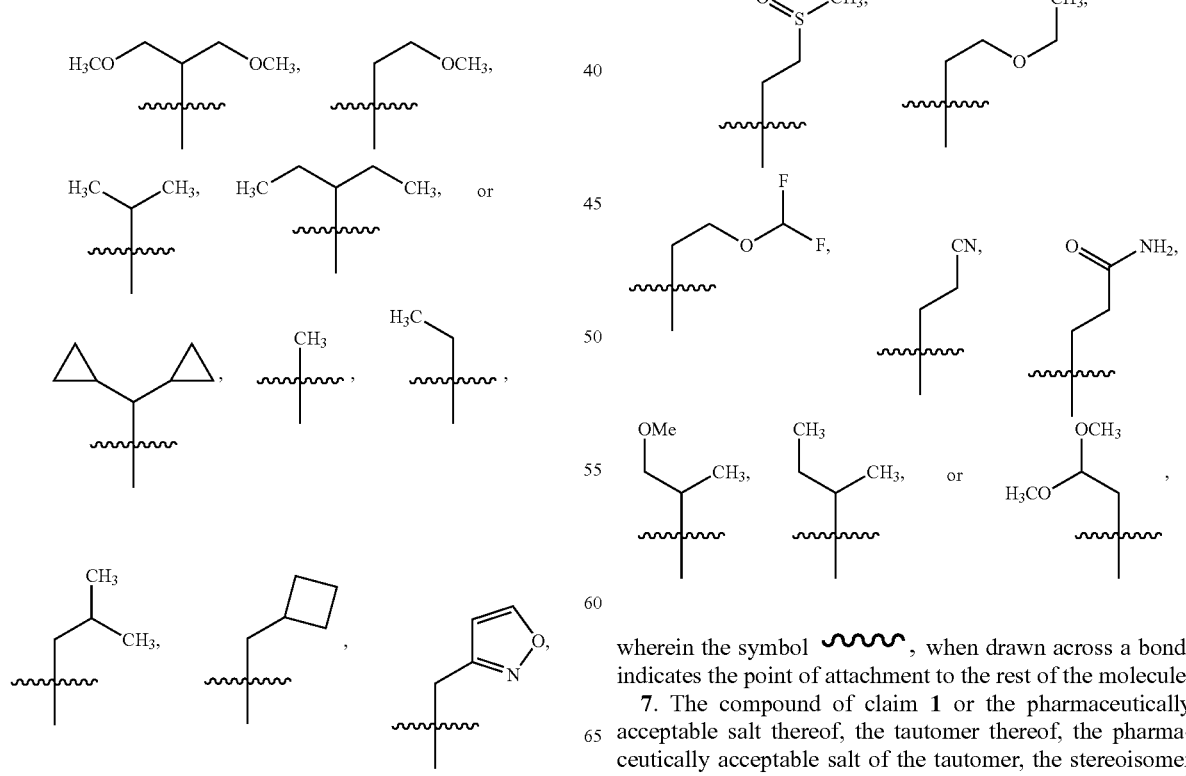

wherein the symbol ⌇⌇⌇, when drawn across a bond, indicates the point of attachment to the rest of the molecule.

7. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is a saturated 4-, 5-, or 6-membered heterocyclic group that includes 1 or 2 heteroatoms independently selected from N, O, or S and is unsubstituted or is substituted with 1, 2, or 3 $R^{1a}$ substituents.

8. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from tetrahydrofuranyl, tetrahydropyranyl, oxetanyl, dioxanyl, pyrrolidinyl, piperidinyl, dioxotetrahydrothiopyranyl, dioxotetrahydrothiophenyl, morpholinyl, dioxolanyl, or tetrahydrothiophenyl, any of which may unsubstituted or substituted with 1, 2, or 3 independently selected $R^{1a}$ substituents.

9. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from tetrahydrofuran-2-yl, tetrahydrofuran-3-yl, tetrahydropyran-2-yl, tetrahydropyran-3-yl, tetrahydropyran-4-yl, oxetan-2-yl, oxetan-3-yl, 1,4-dioxan-2-yl, pyrrolidin-2-yl, or pyrrolidin-3-yl any of which may unsubstituted or substituted with 1, 2, or 3 independently selected $R^{1a}$ substituents.

10. The compound of claim 8 or the pharmaceutically acceptable salt thereof, the tautomer thereof, the pharmaceutically acceptable salt of the tautomer, the stereoisomer of any of the foregoing, or the mixture thereof, wherein $R^1$ is unsubstituted or $R^1$ is substituted with 1, 2, or 3 $R^{1a}$ substituents independently selected from —$C_1$-$C_6$ alkyl, —C(=O)—O—($C_1$-$C_6$ alkyl), or oxo.

11. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from

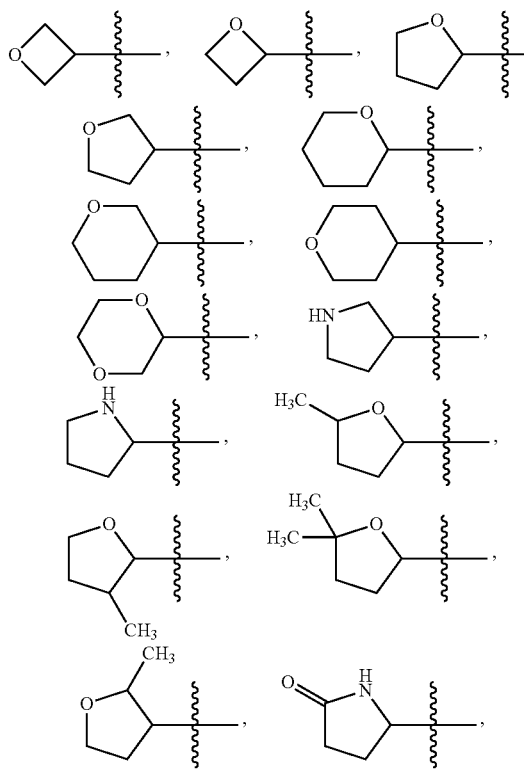

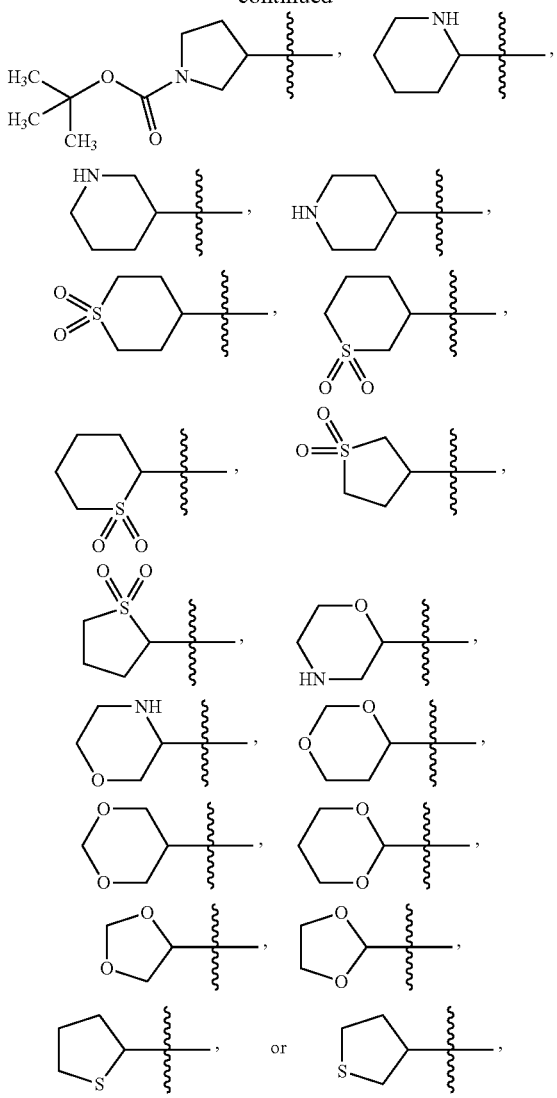

wherein the symbol ∼∼∼, when drawn across a bond, indicates the point of attachment to the rest of the molecule.

12. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from

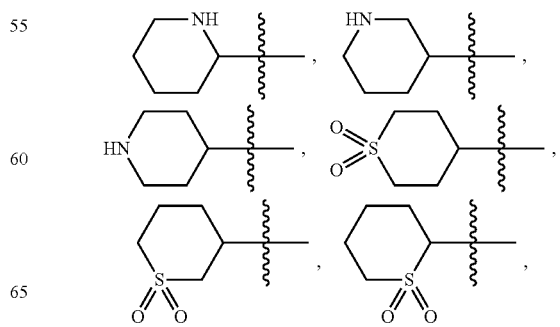

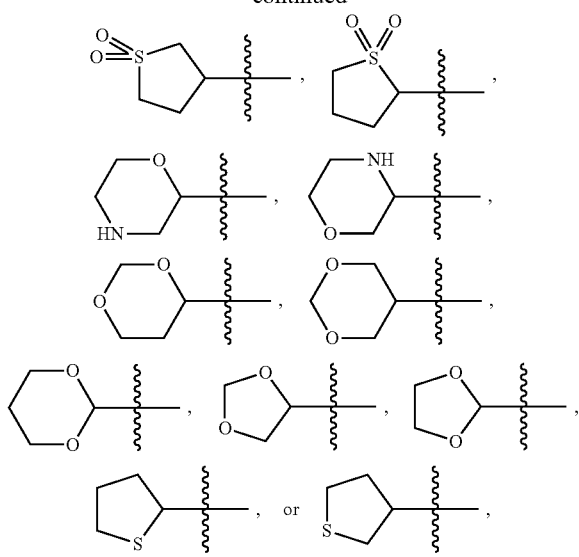

, or , wherein the symbol ⁓⁓⁓, when drawn across a bond, indicates the point of attachment to the rest of the molecule.

13. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, or pyrimidinyl, any of which may be unsubstituted or substituted with 1, 2, or 3 $R^{4a}$ substituents.

14. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a cyclopropyl, cyclobutyl, cyclopentyl, cyclohexyl, or tetrahydropyranyl, any of which may be unsubstituted or substituted with 1, 2, or 3 $R^{4a}$ substituents.

15. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —OH, —O—($C_1$-$C_6$ alkyl), —O—($C_1$-$C_6$ haloalkyl), —O—($C_1$-$C_6$ perhaloalkyl), —C(=O)OH, —C(=O)—O—($C_1$-$C_6$ alkyl), —$NH_2$, —NH($C_1$-$C_6$ alkyl), —N($C_1$-$C_6$ alkyl)$_2$, NH($C_1$-$C_6$ alkyl-OH), —C(=O)$NH_2$, —C(=O)NH($C_1$-$C_6$ alkyl), or —C(=O)N($C_1$-$C_6$ alkyl)$_2$.

16. The compound of claim 15 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —$CH_3$, —F, —Cl, —Br, —CN, —$CF_3$, —$OCH_3$, or —$OCHF_2$.

17. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is selected from

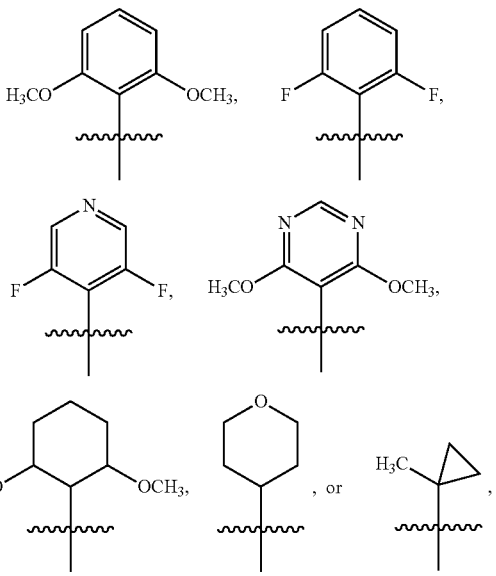

, or , wherein the symbol ⁓⁓⁓, when drawn across a bond, indicates the point of attachment to the rest of the molecule.

18. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is

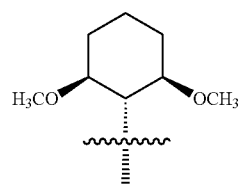

wherein the symbol ⁓⁓⁓, when drawn across a bond, indicates the point of attachment to the rest of the molecule.

19. The compound of claim 1 or the pharmaceutically acceptable salt thereof, the stereoisomer of any of the foregoing, or the mixture thereof, wherein $R^4$ is selected from

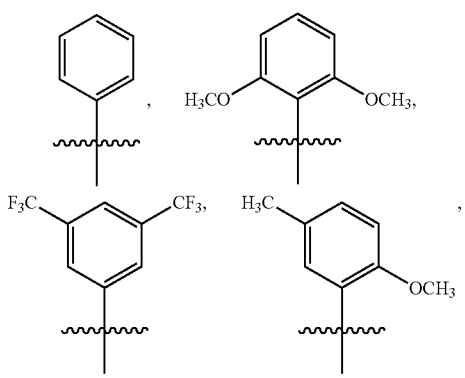

-continued
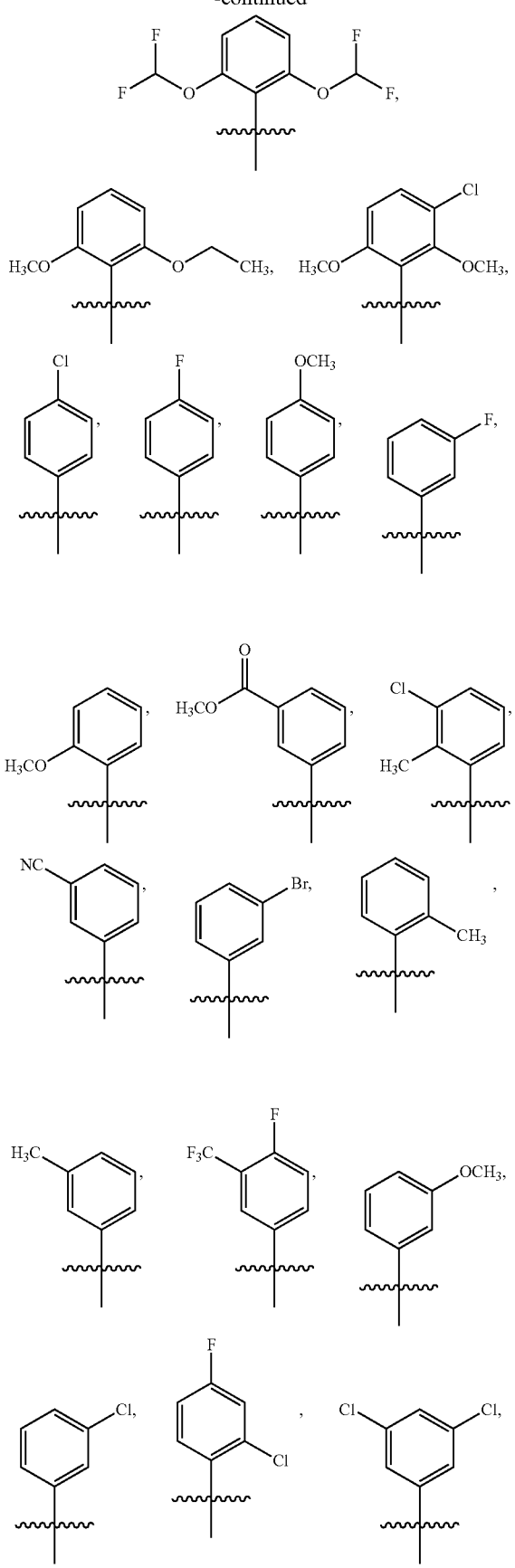
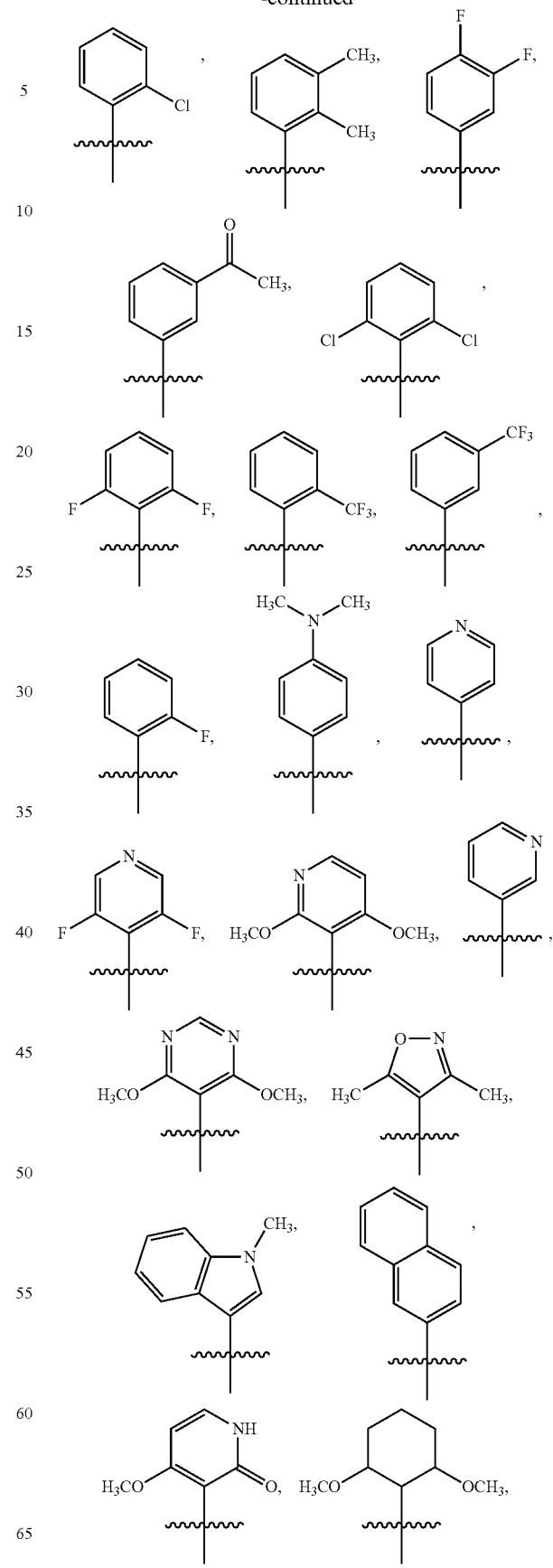

-continued

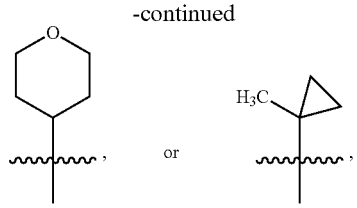

wherein the symbol ⌇⌇⌇, when drawn across a bond, indicates the point of attachment to the rest of the molecule.

20. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl substituted with 1 or 2 $R^{4a}$ substituents.

21. The compound of claim 20 or the pharmaceutically acceptable salt thereof, the tautomer thereof, the pharmaceutically acceptable salt of the tautomer, the stereoisomer of any of the foregoing, or the mixture thereof, wherein the $R^{4a}$ substituents are —O—($C_1$-$C_2$ alkyl) groups.

22. The compound of claim 20 or the pharmaceutically acceptable salt thereof, the tautomer thereof, the pharmaceutically acceptable salt of the tautomer, the stereoisomer of any of the foregoing, or the mixture thereof, wherein $R^4$ is

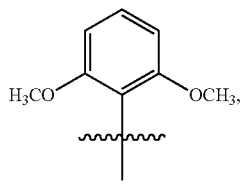 [SMILES: *c1c(OC)cccc1OC]

wherein the symbol ⌇⌇⌇, when drawn across a bond, indicates the point of attachment to the rest of the molecule.

23. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a pyrimidinyl substituted with 1 or 2 $R^{4a}$ substituents.

24. The compound of claim 23 or the pharmaceutically acceptable salt thereof, the tautomer thereof, the pharmaceutically acceptable salt of the tautomer, the stereoisomer of any of the foregoing, or the mixture thereof, wherein the $R^{4a}$ substituents are —O—($C_1$-$C_2$ alkyl) groups.

25. The compound of claim 23 or the pharmaceutically acceptable salt thereof, the tautomer thereof, the pharmaceutically acceptable salt of the tautomer, the stereoisomer of any of the foregoing, or the mixture thereof, wherein $R^4$ is

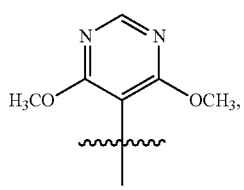

wherein the symbol ⌇⌇⌇, when drawn across a bond, indicates the point of attachment to the rest of the molecule.

26. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^2$ is —H or is absent in the compounds of Formula II.

27. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyrazine-1-oxide, pyridazinyl, pyridinyl, phenyl, oxazolyl, thiazolyl, imidazolyl, pyrazolyl, piperidinyl, piperidin-2-onyl, tetrahydropyrimidin-2(1H)-onyl, 1,3-oxazinan-2-onyl, pyrrolidin-2-onyl, pyrrolidinyl, cyclopentyl, cyclohexyl, benzimidazolyl, isoindolinonyl, 1H-imidazo[4,5-c]pyridinyl, pyrazolo[1,5-a]pyridinyl, imidazo[1,2-a]pyridinyl, imidazo[1,5-a]pyridinyl, 6,7-dihydro-5H-pyrazolo[5,1-b][1,3]oxazinyl, or 3,4-dihydro-2H-pyrano[3,2-b]pyridinyl, any of which may be unsubstituted or substituted with 1, 2, or 3 $R^Q$ substituents.

28. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyridinyl, or phenyl, any of which may be unsubstituted or substituted with 1, 2, or 3 $R^Q$ substituents.

29. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

30. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl group and Q is unsubstituted or is substituted with 1, 2, or 3 $R^Q$ substituents.

31. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), or —O—($C_1$-$C_6$ perhaloalkyl).

32. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, or —$CH_3$.

33. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from

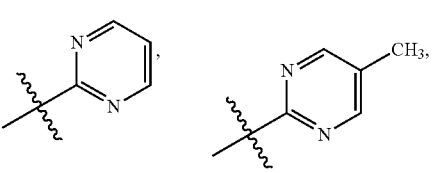

-continued
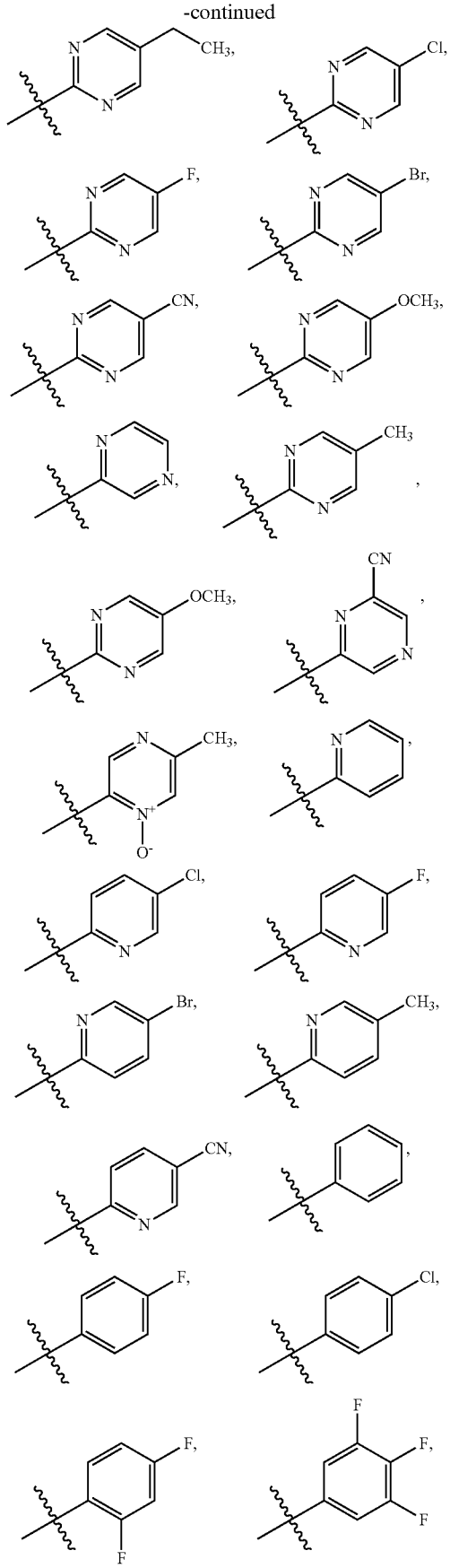
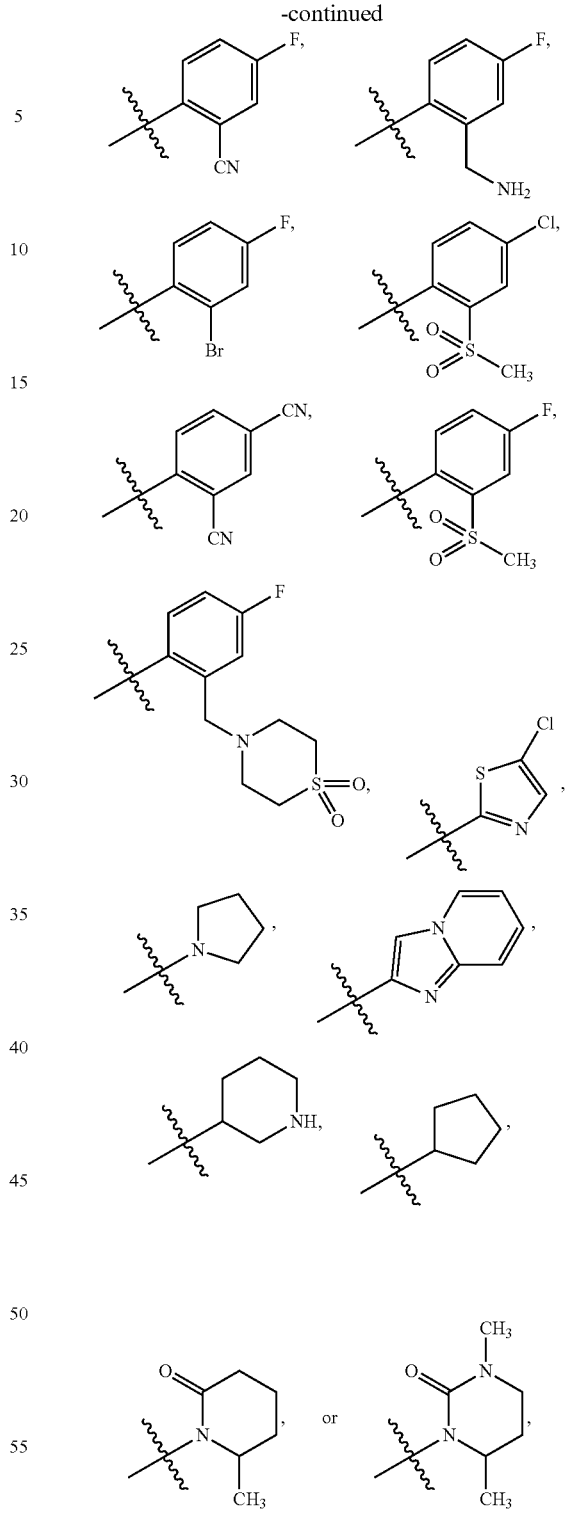
wherein the symbol ∼∼∼, when drawn across a bond, indicates the point of attachment to the rest of the molecule.
34. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from

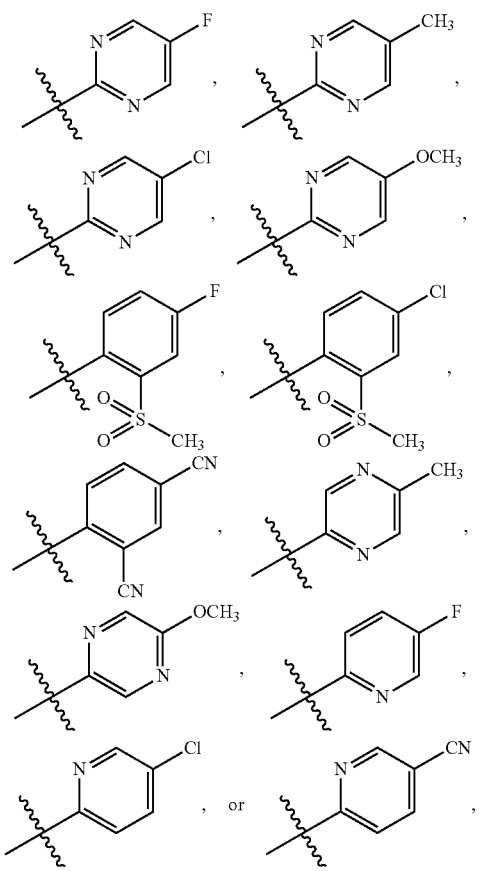

wherein the symbol 〜, when drawn across a bond, indicates the point of attachment to the rest of the molecule.

35. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from a group of formula —$(CR^{3d}R^{3e})$—$(CR^{3f}R^{3g})$-Q, or a group of formula -(heterocyclyl)-Q.

36. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q.

37. The compound of claim 36 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q and further wherein, $R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and $R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), or —O—($C_2$-$C_6$ alkenyl).

38. The compound of claim 36 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q and further wherein, $R^{3d}$ and $R^{3e}$ are independently selected from —H, or —$C_1$-$C_6$ alkyl; and $R^{3f}$ and $R^{3g}$ are independently selected from —H, —$C_1$-$C_6$ alkyl, —OH, or —O—($C_1$-$C_6$ alkyl).

39. The compound of claim 36 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, Or $R^{3g}$ is not —H.

40. The compound of any one of claim 36 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, r $R^{3g}$ is a —$C_1$-$C_6$ alkyl.

41. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula -(heterocyclyl)-Q.

42. The compound of claim 41 or the pharmaceutically acceptable salt thereof, the tautomer thereof, the pharmaceutically acceptable salt of the tautomer, the stereoisomer of any of the foregoing, or the mixture thereof, wherein the heterocyclyl of the -(heterocyclyl)-Q $R^3$ group is a piperidinyl that is unsubstituted or is substituted with 1 or 2 $R^{3h}$ substituent.

43. The compound of claim 42 or the pharmaceutically acceptable salt thereof, the tautomer thereof, the pharmaceutically acceptable salt of the tautomer, the stereoisomer of any of the foregoing, or the mixture thereof, wherein the heterocyclyl of the -(heterocyclyl)-Q $R^3$ group is a piperidinyl that is unsubstituted or is substituted with 1 or 2 $R^{3h}$ substituent independently selected from —OH, or —O—($C_1$-$C_6$ alkyl).

44. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from

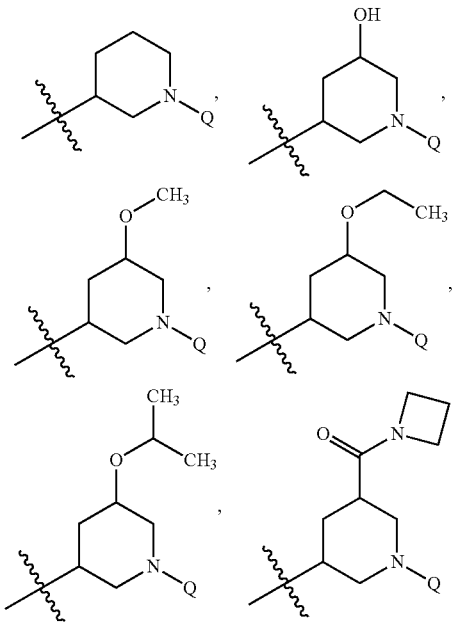

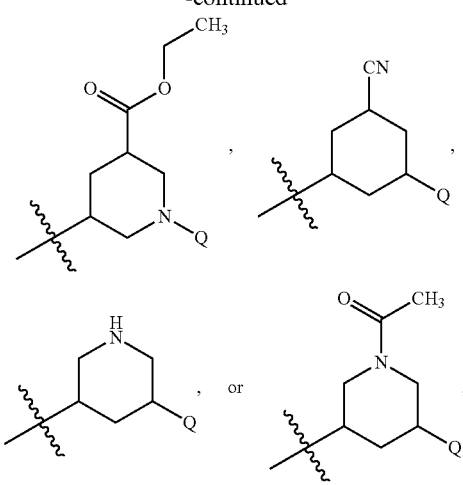
wherein the symbol ⌇⌇⌇, when drawn across a bond, indicates the point of attachment to the rest of the molecule.
45. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from
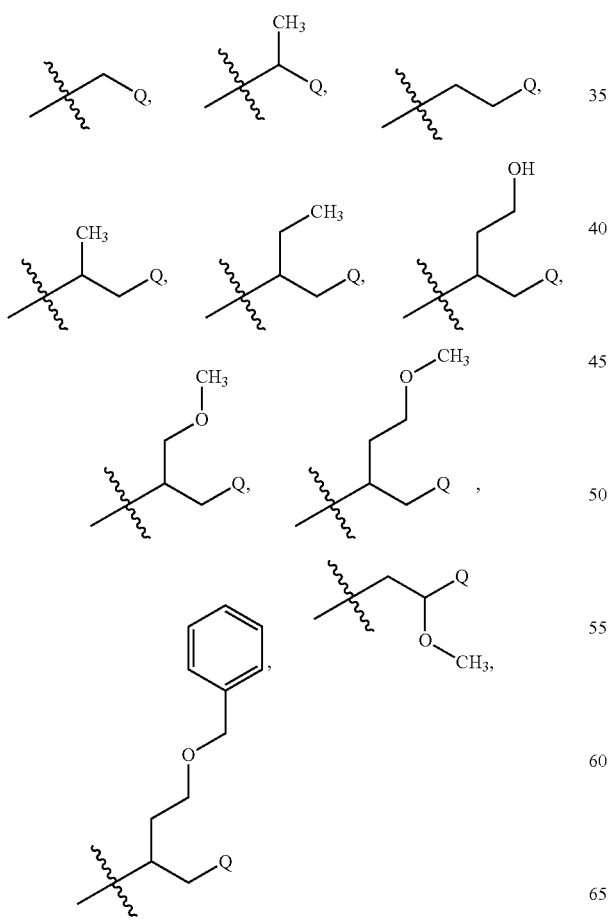
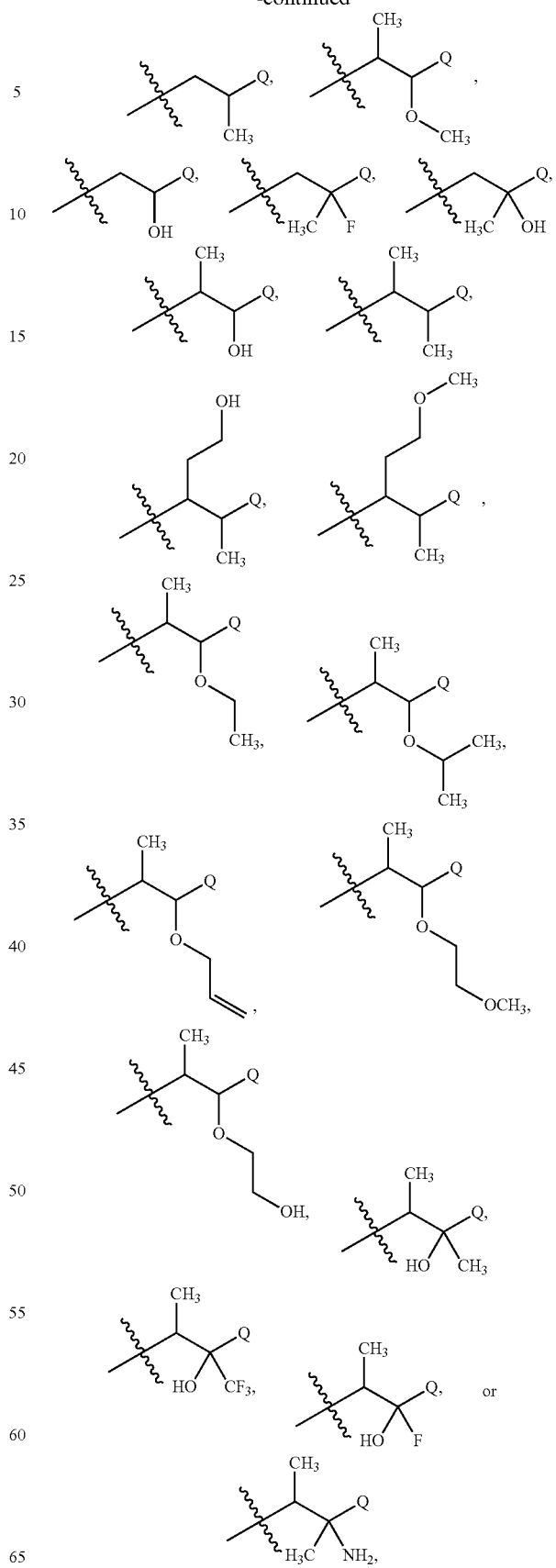

wherein the symbol ⁓, When drawn across a bond, indicates the point of attachment to the rest of the molecule.

46. The compound of claim 1 or the pharmaceutically acceptable salt thereof, the tautomer thereof, the pharmaceutically acceptable salt of the tautomer, the stereoisomer of any of the foregoing, or the mixture thereof, wherein R³ is selected from

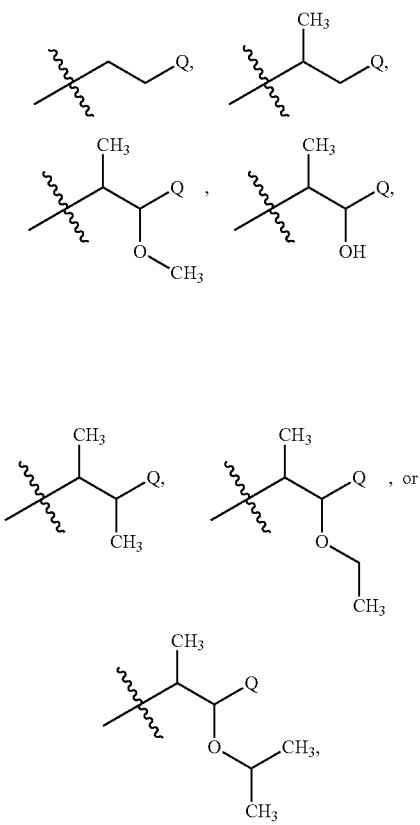

wherein the symbol ⁓, , when drawn across a bond, indicates the point of attachment to the rest of the molecule.

47. The compound of claim 1 or the pharmaceutically acceptable salt thereof, the tautomer thereof, the pharmaceutically acceptable salt of the tautomer, the stereoisomer of any of the foregoing, or the mixture thereof, wherein R³ is selected from

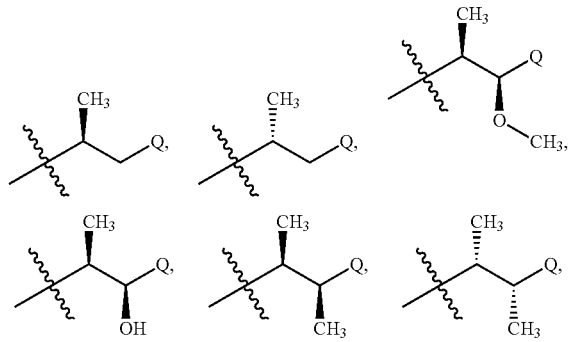

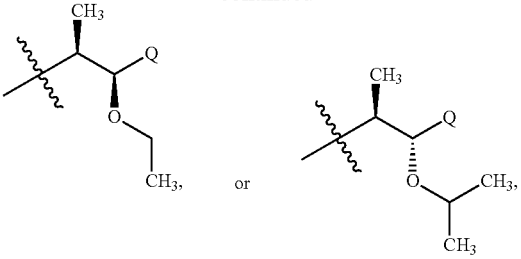

wherein the symbol ⁓, when drawn across a bond, indicates the point of attachment to the rest of the molecule.

48. The compound of claim 1, wherein the compound is selected from (2S,3R)—N-(4-((1r,2R,6S)-2,6-dimethoxycyclohexyl)-5-((2S)-tetrahydro-2-furanyl)-4H-1,2,4-triazol-3-yl)-3-(5-methyl-2-pyrimidinyl)-2-butanesulfonamide;

(2S,3R)—N-(4-((1r,2R,6S)-2,6-dimethoxycyclohexyl)-5-((2R)-tetrahydro-2-furanyl)-4H-1,2,4-triazol-3-yl)-3-(5-methyl-2-pyrimidinyl)-2-butanesulfonamide;

(2S,3R)—N-(4-((1r,2R,6S)-2,6-dimethoxycyclohexyl)-5-((3S)-tetrahydro-3-furanyl)-4H-1,2,4-triazol-3-yl)-3-(5-methyl-2-pyrimidinyl)-2-butanesulfonamide;

(2S,3R)—N-(4-((1r,2R,6S)-2,6-dimethoxycyclohexyl)-5-((3R)-tetrahydro-3-furanyl)-4H-1,2,4-triazol-3-yl)-3-(5-methyl-2-pyrimidinyl)-2-butanesulfonamide;

(R)—N-(4-(2,6-dimethoxyphenyl)-5-((R)-tetrahydrofuran-3-yl)-4H-1,2,4-triazol-3-yl)-1-(5-fluoropyrimidin-2-yl)propane-2-sulfonamide;

(R)—N-(4-(2,6-dimethoxyphenyl)-5-((S)-tetrahydrofuran-3-yl)-4H-1,2,4-triazol-3-yl)-1-(5-fluoropyrimidin-2-yl)propane-2-sulfonamide;

(S)—N-(4-(2,6-dimethoxyphenyl)-5-((R)-tetrahydrofuran-3-yl)-4H-1,2,4-triazol-3-yl)-1-(5-fluoropyrimidin-2-yl)propane-2-sulfonamide;

(S)—N-(4-(2,6-dimethoxyphenyl)-5-((S)-tetrahydrofuran-3-yl)-4H-1,2,4-triazol-3-yl)-1-(5-fluoropyrimidin-2-yl)propane-2-sulfonamide;

(R)-2-(4-chlorophenyl)-N-(4-(2,6-dimethoxyphenyl)-5-(tetrahydrofuran-3-yl)-4H-1,2,4-triazol-3-yl)ethanesulfonamide;

(S)-2-(4-chlorophenyl)-N-(4-(2,6-dimethoxyphenyl)-5-(tetrahydrofuran-3-yl)-4H-1,2,4-triazol-3-yl)ethanesulfonamide;

(2R)—N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide;

(2S)—N-(4-(2,6-dimethoxyphenyl)-5-(tetrahydro-2H-pyran-4-yl)-4H-1,2,4-triazol-3-yl)-1-(5-fluoro-2-pyrimidinyl)-2-propanesulfonamide;

(2S,3R)—N-(4-(2,6-difluorophenyl)-5-((2S)-tetrahydro-2-furanyl)-4H-1,2,4-triazol-3-yl)-3-(5-methyl-2-pyrimidinyl)-2-butanesulfonamide;

(2S,3R)—N-(4-(2,6-difluorophenyl)-5-((2R)-tetrahydro-2-furanyl)-4H-1,2,4-triazol-3-yl)-3-(5-methyl-2-pyrimidinyl)-2-butanesulfonamide;

(2S,3R)—N-(4-(2,6-difluorophenyl)-5-((3R)-tetrahydro-3-furanyl)-4H-1,2,4-triazol-3-yl)-3-(5-methyl-2-pyrimidinyl)-2-butanesulfonamide;

(2S,3R)—N-(4-(2,6-difluorophenyl)-5-((3S)-tetrahydro-3-furanyl)-4H-1,2,4-triazol-3-yl)-3-(5-methyl-2-pyrimidinyl)-2-butanesulfonamide;

(2S,3R)—N-(4-(2, 6-difluorophenyl)-5-((3S)-tetrahydro-2H-pyran-3-yl)-4H-1,2,4-triazol-3-yl)-3-(5-methyl-2-pyrimidinyl)-2-butanesulfonamide;

(2S,3R)—N-(4-(2,6-difluorophenyl)-5-((3R)-tetrahydro-2H-pyran-3-yl)-4H-1,2,4-triazol-3-yl)-3-(5-methyl-2-pyrimidinyl)-2-butanesulfonamide;

(2S,3R)-3-(5-cyano-2-pyrimidinyl)-N-(4-(2,6-dimethoxyphenyl)-5-((2S)-tetrahydro-2-furanyl)-4H-1,2,4-triazol-3-yl)-2-butanesulfonamide;

(2S,3R)-3-(5-cyano-2-pyrimidinyl)-N-(4-(2,6-dimethoxyphenyl)-5-((2R)-tetrahydro-2-furanyl)-4H-1,2,4-triazol-3-yl)-2-butanesulfonamide;

(2S,3R)—N-(4-(3,5-difluoro-4-pyridinyl)-5-((2S)-tetrahydro-2-furanyl)-4H-1,2,4-triazol-3-yl)-3-(5-methyl-2-pyrimidinyl)-2-butanesulfonamide;

(2S,3R)—N-(4-(3,5-difluoro-4-pyridinyl)-5-((2R)-tetrahydro-2-furanyl)-4H-1,2,4-triazol-3-yl)-3-(5-methyl-2-pyrimidinyl)-2-butanesulfonamide;

(2S,3R)-3-(5-chloro-2-pyrimidinyl)-N-(4-(4,6-dimethoxy-5-pyrimidinyl)-5-(3-oxetanyl)-4H-1,2,4-triazol-3-yl)-2-butanesulfonamide;

(2S,3R)-3-(5-chloro-2-pyrimidinyl)-N-(4-(2,6-dimethoxyphenyl)-5-(3-oxetanyl)-4H-1,2,4-triazol-3-yl)-2-butanesulfonamide;

(2S,3R)-3-(5-chloro-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide;

(2S,3R)-3-(5-chloro-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2R)-1,4-dioxan-2-yl)-4H-1,2,4-triazol-3-yl)-2-butanesulfonamide;

(2S,3R)-3-(5-chloro-2-pyrimidinyl)-N-(4-(2,6-dimethoxyphenyl)-5-((2S)-1,4-dioxan-2-yl)-4H-1,2,4-triazol-3-yl)-2-butanesulfonamide;

tert-butyl(3R)-3-(5-((((1S,2R)-2-(5-chloro-2-pyrimidinyl)-1-methylpropyl)sulfonyl)amino)-4-(2,6-dimethoxyphenyl)-4H-1,2,4-triazol-3-yl)-1-pyrrolidinecarboxylate;

1 tert-butyl(3S)-3-(5-((((1S,2R)-2-(5-chloro-2-pyrimidinyl)-1-methylpropyl)sulfonyl)amino)-4-(2,6-dimethoxyphenyl)-4H-1,2,4-triazol-3-yl)-1-pyrrolidinecarboxylate;

2-(2-cyano-4-fluorophenyl)-N-(4-(2,6-dimethoxyphenyl)-5-((2R)-5-oxo-2-pyrrolidinyl)-4H-1,2,4-triazol-3-yl)ethanesulfonamide;

2-(2-cyano-4-fluorophenyl)-N-(4-(2,6-dimethoxyphenyl)-5-((2S)-5-oxo-2-pyrrolidinyl)-4H-1,2,4-triazol-3-yl)ethanesulfonamide;

(1R,2S)—N-(4-(2,6-dimethoxyphenyl)-5-((R)-pyrrolidin-3-yl)-4H-1,2,4-triazol-3-yl)-1-methoxy-1-(5-methylpyrimidin-2-yl)propane-2-sulfonamide;

(1R,2S)—N-(4-(2,6-dimethoxyphenyl)-5-((S)-pyrrolidin-3-yl)-4H-1,2,4-triazol-3-yl)-1-methoxy-1-(5-methylpyrimidin-2-yl)propane-2-sulfonamide;

(2S,3R)-3-(5-chloro-2-pyrimidinyl)-N-(4-(2,6-dimethoxyphenyl)-5-((2S)-tetrahydro-2-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2R)-tetrahydro-2-furanyl)-4H-1,2,4-triazol-3-yl)-2-butanesulfonamide;

(2S,3R)—N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide;

(1R,2S)-1-(5-chloropyrimidin-2-yl)-N-(4-(2,6-dimethoxyphenyl)-5-((R)-tetrahydrofuran-2-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((S)-tetrahydrofuran-2-yl)-4H-1,2,4-triazol-3-yl)-1-methoxypropane-2-sulfonamide;

(2S,3R)—N-(4-(2,6-dimethoxyphenyl)-5-((R)-tetrahydrofuran-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-tetrahydrofuran-3-yl)-4H-1,2,4-triazol-3-yl)-3-(5-methylpyrimidin-2-yl)butane-2-sulfonamide;

(1R,2S)-1-(5-chloropyrimidin-2-yl)-N-(4-(2,6-dimethoxyphenyl)-5-((R)-tetrahydrofuran-3-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((S)-tetrahydrofuran-3-yl)-4H-1,2,4-triazol-3-yl)-1-methoxypropane-2-sulfonamide;

(2S,3R)—N-(4-(2,6-dimethoxyphenyl)-5-((R)-tetrahydro-2H-pyran-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-tetrahydro-2H-pyran-3-yl)-4H-1,2,4-triazol-3-yl)-3-(5-methylpyrimidin-2-yl)butane-2-sulfonamide;

(2S,3R)-3-(5-chloropyrimidin-2-yl)-N-(4-(2,6-dimethoxyphenyl)-5-((R)-tetrahydrofuran-3-yl)-4H-1,2,4-triazol-3-yl)butane-2-sulfonamide;

(2S,3R)-3-(5-chloropyrimidin-2-yl)-N-(4-(2,6-dimethoxyphenyl)-5-((S)-tetrahydrofuran-3-yl)-4H-1,2,4-triazol-3-yl)butane-2-sulfonamide;

(2S,3R)-3-(5-chloropyrimidin-2-yl)-N-(4-(2,6-dimethoxyphenyl)-5-((R)-tetrahydro-2H-pyran-3-yl)-4H-1,2,4-triazol-3-yl)butane-2-sulfonamide;

(2S,3R)-3-(5-chloropyrimidin-2-yl)-N-(4-(2,6-dimethoxyphenyl)-5-((S)-tetrahydro-2H-pyran-3-yl)-4H-1,2,4-triazol-3-yl)butane-2-sulfonamide;

(1R,2S)-1-(5-chloropyrimidin-2-yl)-N-(4-(2,6-dimethoxyphenyl)-5-((R)-tetrahydro-2H-pyran-3-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((S)-tetrahydro-2H-pyran-3-yl)-4H-1,2,4-triazol-3-yl)-1-methoxypropane-2-sulfonamide;

(1S,2S)—N-(4-(2,6-dimethoxyphenyl)-5-((S)-tetrahydrofuran-2-yl)-4H-1,2,4-triazol-3-yl)-1-isopropoxy-1-(5-methylpyrazin-2-yl)propane-2-sulfonamide;

(1S,2S)—N-(4-(2,6-dimethoxyphenyl)-5-((R)-tetrahydrofuran-2-yl)-4H-1,2,4-triazol-3-yl)-1-isopropoxy-1-(5-methylpyrazin-2-yl)propane-2-sulfonamide;

(2S,3R)-3-(5-chloropyrimidin-2-yl)-N-(4-(2,6-dimethoxyphenyl)-5-((2S,3R)-3-methyltetrahydrofuran-2-yl)-4H-1,2,4-triazol-3-yl)butane-2-sulfonamide;

(2S,3R)-3-(5-chloropyrimidin-2-yl)-N-(4-(2,6-dimethoxyphenyl)-5-((2R,3S)-3-methyltetrahydrofuran-2-yl)-4H-1,2,4-triazol-3-yl)butane-2-sulfonamide;

(2S,3R)—N-(4-(4,6-dimethoxypyrimidin-5-yl)-5-((S)-tetrahydrofuran-2-yl)-4H-1,2,4-triazol-3-yl)-3-(5-methylpyrimidin-2-yl)butane-2-sulfonamide;

(2S,3R)—N-(4-(4,6-dimethoxypyrimidin-5-yl)-5-((R)-tetrahydrofuran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((2R,3S)-3-methyltetrahydrofuran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((2S,3R)-3-methyltetrahydrofuran-2-yl)-4H-1,2,4-triazol-3-yl)-3-(5-methylpyrimidin-2-yl)butane-2-sulfonamide;
(1R,2S)-1-(5-chloropyrimidin-2-yl)-N-(4-(2,6-dimethoxyphenyl)-5-((2R,3S)-3-methyltetrahydrofuran-2-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((2S,3R)-3-methyltetrahydrofuran-2-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((2S,5S)-5-methyltetrahydrofuran-2-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((2R,5R)-5-methyltetrahydrofuran-2-yl)-4H-1,2,4-triazol-3-yl)-1-methoxypropane-2-sulfonamide;
(1R,2S)-1-(5-chloropyrimidin-2-yl)-N-(4-(4,6-dimethoxypyrimidin-5-yl)-5-((S)-tetrahydrofuran-2-yl)-4H-1,2,4-triazol-3-yl)-1-methoxypropane-2-sulfonamide;
(1R,2S)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)-1-methoxypropane-2-sulfonamide;
(2S,3R)-3-(5-chloropyrimidin-2-yl)-N-(4-(4,6-dimethoxypyrimidin-5-yl)-5-((S)-tetrahydrofuran-2-yl)-4H-1,2,4-triazol-3-yl)butane-2-sulfonamide;
(2S,3R)-3-(5-chloropyrimidin-2-yl)-N-(4-(4,6-dimethoxypyrimidin-5-yl)-5-((R)-tetrahydrofuran-2-yl)-4H-1,2,4-triazol-3-yl)butane-2-sulfonamide;
(1R,2S)-1-(5-chloropyrimidin-2-yl)-N-(4-(2,6-dimethoxyphenyl)-5-((S)-tetrahydro-2H-pyran-2-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((R)-tetrahydro-2H-pyran-2-yl)-4H-1,2,4-triazol-3-yl)-1-methoxypropane-2-sulfonamide;
(2S,3R)—N-(4-(2,6-dimethoxyphenyl)-5-((S)-tetrahydro-2H-pyran-2-yl)-4H-1,2,4-triazol-3-yl)-3-(5-methylpyrimidin-2-yl)butane-2-sulfonamide;
(2S,3R)—N-(4-(2,6-dimethoxyphenyl)-5-((R)-tetrahydro-2H-pyran-2-yl)-4H-1,2,4-triazol-3-yl)-3-(5-methylpyrimidin-2-yl)butane-2-sulfonamide;
(2S,3R)-3-(5-chloropyrimidin-2-yl)-N-(4-(2,6-dimethoxyphenyl)-5-((S)-tetrahydro-2H-pyran-2-yl)-4H-1,2,4-triazol-3-yl)butane-2-sulfonamide;
(2S,3R)—N-(4-(2,6-dimethoxyphenyl)-5-((S)-tetrahydrofuran-2-yl)-4H-1,2,4-triazol-3-yl)-3-(5-methylpyrazin-2-yl)butane-2-sulfonamide;
(2S,3R)—N-(4-(2,6-dimethoxyphenyl)-5-((R)-tetrahydrofuran-2-yl)-4H-1,2,4-triazol-3-yl)-3-(5-methylpyrazin-2-yl)butane-2-sulfonamide;
(1R,2S)-1-(5-chloropyrimidin-2-yl)-N-(4-(4,6-dimethoxypyrimidin-5-yl)-5-((S)-tetrahydro-2H-pyran-3-yl)-4H-1,2,4-triazol-3-yl)-1-methoxypropane-2-sulfonamide;
(1R,2S)-1-(5-chloropyrimidin-2-yl)-N-(4-(4,6-dimethoxypyrimidin-5-yl)-5-((R)-tetrahydro-2H-pyran-3-yl)-4H-1,2,4-triazol-3-yl)-1-methoxypropane-2-sulfonamide;
(2S,3R)-3-(5-chloropyrimidin-2-yl)-N-(4-(4,6-dimethoxypyrimidin-5-yl)-5-((R)-tetrahydrofuran-3-yl)-4H-1,2,4-triazol-3-yl)butane-2-sulfonamide;
(2S,3R)-3-(5-chloropyrimidin-2-yl)-N-(4-(4,6-dimethoxypyrimidin-5-yl)-5-((S)-tetrahydrofuran-3-yl)-4H-1,2,4-triazol-3-yl)butane-2-sulfonamide;
(1S,2S)—N-(4-(4,6-dimethoxypyrimidin-5-yl)-5-((S)-tetrahydrofuran-2-yl)-4H-1,2,4-triazol-3-yl)-1-isopropoxy-1-(5-methylpyrimidin-2-yl)propane-2-sulfonamide;
(1S,2S)—N-(4-(4,6-dimethoxypyrimidin-5-yl)-5-((R)-tetrahydrofuran-2-yl)-4H-1,2,4-triazol-3-yl)-1-isopropoxy-1-(5-methylpyrimidin-2-yl)propane-2-sulfonamide;
(1S,2S)—N-(4-(2,6-dimethoxyphenyl)-5-((S)-tetrahydrofuran-2-yl)-4H-1,2,4-triazol-3-yl)-1-isopropoxy-1-(5-methylpyrimidin-2-yl)propane-2-sulfonamide;
(1S,2S)—N-(4-(2,6-dimethoxyphenyl)-5-((R)-tetrahydrofuran-2-yl)-4H-1,2,4-triazol-3-yl)-1-isopropoxy-1-(5-methylpyrimidin-2-yl)propane-2-sulfonamide;
(1S,2S)—N-(4-(2,6-dimethoxyphenyl)-5-((R)-tetrahydrofuran-3-yl)-4H-1,2,4-triazol-3-yl)-1-isopropoxy-1-(5-methylpyrimidin-2-yl)propane-2-sulfonamide;
(1S,2S)—N-(4-(2,6-dimethoxyphenyl)-5-((S)-tetrahydrofuran-3-yl)-4H-1,2,4-triazol-3-yl)-1-isopropoxy-1-(5-methylpyrimidin-2-yl)propane-2-sulfonamide;
(2S,3R)-3-(5-chloropyrimidin-2-yl)-N-(4-(4,6-dimethoxypyrimidin-5-yl)-5-((S)-tetrahydro-2H-pyran-3-yl)-4H-1,2,4-triazol-3-yl)butane-2-sulfonamide;
(2S,3R)-3-(5-chloropyrimidin-2-yl)-N-(4-(4,6-dimethoxypyrimidin-5-yl)-5-((R)-tetrahydro-2H-pyran-3-yl)-4H-1,2,4-triazol-3-yl)butane-2-sulfonamide;
(1R,2S)-1-(5-chloropyrimidin-2-yl)-N-(4-(2,6-dimethoxyphenyl)-5-(tetrahydro-2H-pyran-4-yl)-4H-1,2,4-triazol-3-yl)-1-methoxypropane-2-sulfonamide;
(2S,3R)—N-(4-(4,6-dimethoxypyrimidin-5-yl)-5-((S)-tetrahydrofuran-2-yl)-4H-1,2,4-triazol-3-yl)-3-(5-methylpyrazin-2-yl)butane-2-sulfonamide;
(2S,3R)—N-(4-(4,6-dimethoxypyrimidin-5-yl)-5-((R)-tetrahydrofuran-2-yl)-4H-1,2,4-triazol-3-yl)-3-(5-methylpyrazin-2-yl)butane-2-sulfonamide;
(2S,3R)—N-(4-(2,6-dimethoxyphenyl)-5-((S)-tetrahydro-2H-pyran-2-yl)-4H-1,2,4-triazol-3-yl)-3-(5-methylpyrazin-2-yl)butane-2-sulfonamide;
(2S,3R)—N-(4-(2,6-dimethoxyphenyl)-5-((R)-tetrahydro-2H-pyran-2-yl)-4H-1,2,4-triazol-3-yl)-3-(5-methylpyrazin-2-yl)butane-2-sulfonamide;
(1R,2S)-1-(5-chloropyrimidin-2-yl)-N-(4-(2,6-dimethoxyphenyl)-5-((S)-5,5-dimethyltetrahydrofuran-2-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((R)-5,5-dimethyltetrahydrofuran-2-yl)-4H-1,2,4-triazol-3-yl)-1-methoxypropane-2-sulfonamide;
(1R,2S)-1-(5-chloropyrimidin-2-yl)-1-methoxy-N-(4-(1-methylcyclopropyl)-5-((S)-tetrahydrofuran-2-yl)-4H-1,2,4-triazol-3-yl)propane-2-sulfonamide;
(1R,2S)-1-(5-chloropyrimidin-2-yl)-1-methoxy-N-(4-(1-methylcyclopropyl)-5-((R)-tetrahydrofuran-2-yl)-4H-1,2,4-triazol-3-yl)propane-2-sulfonamide;
(1R,2S)-1-(5-chloropyrimidin-2-yl)-1-methoxy-N-(4-(1-methylcyclopropyl)-5-((S)-tetrahydro-2H-pyran-2-yl)-4H-1,2,4-triazol-3-yl)propane-2-sulfonamide;
(1R,2S)-1-(5-chloropyrimidin-2-yl)-1-methoxy-N-(4-(1-methylcyclopropyl)-5-((R)-tetrahydro-2H-pyran-2-yl)-4H-1,2,4-triazol-3-yl)propane-2-sulfonamide;
(1R,2S)-1-(5-chloropyrimidin-2-yl)-N-(4-(2,6-dimethoxyphenyl)-5-((2R,3R)-2-methyltetrahydrofuran-3-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((2S,3S)-2-methyltetrahydrofuran-3-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((2R,3S)-2-methyltetrahydrofuran-3-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((2S,3R)-2-methyltetrahydrofuran-3-yl)-4H-1,2,4-triazol-3-yl)-1-methoxypropane-2-sulfonamide;
(2S,3R)-3-(5-chloropyrimidin-2-yl)-N-(4-(2,6-dimethoxyphenyl)-5-((2R,3R)-2-methyltetrahydrofuran-3-yl)-4H-1,2,4-triazol-3-yl)butane-2-sulfonamide;
(2S,3R)-3-(5-chloropyrimidin-2-yl)-N-(4-(2,6-dimethoxyphenyl)-5-((2S,3S)-2-methyltetrahydrofuran-3-yl)-4H-1,2,4-triazol-3-yl)butane-2-sulfonamide;
(2S,3R)-3-(5-chloropyrimidin-2-yl)-N-(4-(2,6-dimethoxyphenyl)-5-((2R,3S)-2-methyltetrahydrofuran-3-yl)-4H-1,2,4-triazol-3-yl)butane-2-sulfonamide;
(2S,3R)-3-(5-chloropyrimidin-2-yl)-N-(4-(2,6-dimethoxyphenyl)-5-((2S,3R)-2-methyltetrahydrofuran-3-yl)-4H-1,2,4-triazol-3-yl)butane-2-sulfonamide;
(2S,3R)—N-(4-(2,6-dimethoxyphenyl)-5-((2S,3S)-2-methyltetrahydrofuran-3-yl)-4H-1,2,4-triazol-3-yl)-3-(5-methylpyrimidin-2-yl)butane-2-sulfonamide;
(2S,3R)—N-(4-(2,6-dimethoxyphenyl)-5-((2R,3R)-2-methyltetrahydrofuran-3-yl)-4H-1,2,4-triazol-3-yl)-3-(5-methylpyrimidin-2-yl)butane-2-sulfonamide;
(2S,3R)—N-(4-(2,6-dimethoxyphenyl)-5-((2R,3S)-2-methyltetrahydrofuran-3-yl)-4H-1,2,4-triazol-3-yl)-3-(5-methylpyrimidin-2-yl)butane-2-sulfonamide;
(2S,3R)—N-(4-(2,6-dimethoxyphenyl)-5-((2S,3R)-2-methyltetrahydrofuran-3-yl)-4H-1,2,4-triazol-3-yl)-3-(5-methylpyrimidin-2-yl)butane-2-sulfonamide;
(1R,2S)-1-(5-chloropyrimidin-2-yl)-1-methoxy-N-(4-(1-methylcyclopropyl)-5-((R)-tetrahydrofuran-3-yl)-4H-1,2,4-triazol-3-yl)propane-2-sulfonamide;
(1R,2S)-1-(5-chloropyrimidin-2-yl)-1-methoxy-N-(4-(1-methylcyclopropyl)-5-((S)-tetrahydrofuran-3-yl)-4H-1,2,4-triazol-3-yl)propane-2-sulfonamide;
(1R,2S)-1-(5-chloropyrimidin-2-yl)-1-methoxy-N-(4-(1-methylcyclopropyl)-5-((R)-tetrahydro-2H-pyran-3-yl)-4H-1,2,4-triazol-3-yl)propane-2-sulfonamide;
(1R,2S)-1-(5-chloropyrimidin-2-yl)-1-methoxy-N-(4-(1-methylcyclopropyl)-5-((S)-tetrahydro-2H-pyran-3-yl)-4H-1,2,4-triazol-3-yl)propane-2-sulfonamide;
(1R,2S)-1-methoxy-N-(4-(1-methylcyclopropyl)-5-((R)-tetrahydrofuran-3-yl)-4H-1,2,4-triazol-3-yl)-1-(5-methylpyrazin-2-yl)propane-2-sulfonamide;
(1R,2S)-1-methoxy-N-(4-(1-methylcyclopropyl)-5-((S)-tetrahydrofuran-3-yl)-4H-1,2,4-triazol-3-yl)-1-(5-methylpyrazin-2-yl)propane-2-sulfonamide;
(1R,2S)-1-methoxy-N-(4-(1-methylcyclopropyl)-5-((R)-tetrahydro-2H-pyran-3-yl)-4H-1,2,4-triazol-3-yl)-1-(5-methylpyrazin-2-yl)propane-2-sulfonamide;
(1R,2S)-1-methoxy-N-(4-(1-methylcyclopropyl)-5-((S)-tetrahydro-2H-pyran-3-yl)-4H-1,2,4-triazol-3-yl)-1-(5-methylpyrazin-2-yl)propane-2-sulfonamide;
(2S,3R)—N-(4-(2,6-dimethoxyphenyl)-5-((R)-tetrahydrofuran-3-yl)-4H-1,2,4-triazol-3-yl)-3-(5-methylpyrazin-2-yl)butane-2-sulfonamide;
(2S,3R)—N-(4-(2,6-dimethoxyphenyl)-5-((S)-tetrahydrofuran-3-yl)-4H-1,2,4-triazol-3-yl)-3-(5-methylpyrazin-2-yl)butane-2-sulfonamide;
(2S,3R)—N-(4-(2,6-dimethoxyphenyl)-5-((R)-tetrahydro-2H-pyran-3-yl)-4H-1,2,4-triazol-3-yl)-3-(5-methylpyrazin-2-yl)butane-2-sulfonamide;
(2S,3R)—N-(4-(2,6-dimethoxyphenyl)-5-((S)-tetrahydro-2H-pyran-3-yl)-4H-1,2,4-triazol-3-yl)-3-(5-methylpyrazin-2-yl)butane-2-sulfonamide;
(1S,2S)—N-(4-(2,6-dimethoxyphenyl)-5-((R)-tetrahydro-2H-pyran-3-yl)-4H-1,2,4-triazol-3-yl)-1-isopropoxy-1-(5-methylpyrimidin-2-yl)propane-2-sulfonamide;
(1S,2S)—N-(4-(2,6-dimethoxyphenyl)-5-((S)-tetrahydro-2H-pyran-3-yl)-4H-1,2,4-triazol-3-yl)-1-isopropoxy-1-(5-methylpyrimidin-2-yl)propane-2-sulfonamide;
(1R,2S)-1-(5-chloropyrimidin-2-yl)-N-(4-(4,6-dimethoxypyrimidin-5-yl)-5-((S)-5,5-dimethyltetrahydrofuran-2-yl)-4H-1,2,4-triazol-3-yl)-1-methoxypropane-2-sulfonamide;
(1R,2S)-1-(5-chloropyrimidin-2-yl)-N-(4-(4,6-dimethoxypyrimidin-5-yl)-5-((R)-5,5-dimethyltetrahydrofuran-2-yl)-4H-1,2,4-triazol-3-yl)-1-methoxypropane-2-sulfonamide;
(1R,2S)—N-(4-(2,6-dimethoxyphenyl)-5-((S)-tetrahydrofuran-3-yl)-4H-1,2,4-triazol-3-yl)-1-hydroxy-1-(5-methylpyrimidin-2-yl)propane-2-sulfonamide;
(1R,2S)—N-(4-(2,6-dimethoxyphenyl)-5-((R)-tetrahydrofuran-3-yl)-4H-1,2,4-triazol-3-yl)-1-hydroxy-1-(5-methylpyrimidin-2-yl)propane-2-sulfonamide;
(2S,3R)-3-(5-chloropyrimidin-2-yl)-N-(4-(2,6-dimethoxyphenyl)-5-((R)-oxetan-2-yl)-4H-1,2,4-triazol-3-yl)butane-2-sulfonamide;
(2S,3R)-3-(5-chloropyrimidin-2-yl)-N-(4-(2,6-dimethoxyphenyl)-5-((S)-oxetan-2-yl)-4H-1,2,4-triazol-3-yl)butane-2-sulfonamide;
(S)-2-(4-chlorophenyl)-N-(4-(2,6-dimethoxyphenyl)-5-(tetrahydrofuran-2-yl)-4H-1,2,4-triazol-3-yl)ethanesulfonamide;
(R)-2-(4-chlorophenyl)-N-(4-(2,6-dimethoxyphenyl)-5-(tetrahydrofuran-2-yl)-4H-1,2,4-triazol-3-yl)ethanesulfonamide;
(S)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide;
(R)-2-(2-cyano-4-fluorophenyl)-N-(4-(2,6-dimethoxyphenyl)-5-(tetrahydrofuran-2-yl)-4H-1,2,4-triazol-3-yl)ethane sulfonamide;
(2S,3R)-3-(5-cyano-2-pyrimidinyl)-N-(4-(2,6-dimethoxyphenyl)-5-((3R)-tetrahydro-3-furanyl)-4H-1,2,4-triazol-3-yl)-2-butanesulfonamide;
(2S,3R)-3-(5-cyano-2-pyrimidinyl)-N-(4-(2,6-dimethoxyphenyl)-5-((3S)-tetrahydro-3-furanyl)-4H-1,2,4-triazol-3-yl)-2-butanesulfonamide;
(2S,3R)—N-(4-(2,6-dimethoxyphenyl)-5-((2R)-1,4-dioxan-2-yl)-4H-1,2,4-triazol-3-yl)-3-(5-methoxy-2-pyrimidinyl)-2-butanesulfonamide;
(2S,3R)—N-(4-(2,6-dimethoxyphenyl)-5-((2S)-1,4-dioxan-2-yl)-4H-1,2,4-triazol-3-yl)-3-(5-methoxy-2-pyrimidinyl)-2-butanesulfonamide;
(2S,3R)—N-(4-(4,6-dimethoxy-5-pyrimidinyl)-5-((2R)-1,4-dioxan-2-yl)-4H-1,2,4-triazol-3-yl)-3-(5-methoxy-2-pyrimidinyl)-2-butanesulfonamide;
(2S,3R)—N-(4-(4,6-dimethoxy-5-pyrimidinyl)-5-((2S)-1,4-dioxan-2-yl)-4H-1,2,4-triazol-3-yl)-3-(5-methoxy-2-pyrimidinyl)-2-butanesulfonamide;
(3R,5S)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide;

(3R,5S)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide;

(3S,5R)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide;

(3S,5R)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide;

(3R,5S)—N-(4-(2,6-dimethoxyphenyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide;

(3R,5S)—N-(4-(2,6-dimethoxyphenyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide;

(3S,5R)—N-(4-(2,6-dimethoxyphenyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide;

(3S,5R)—N-(4-(2,6-dimethoxyphenyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide;

(2S,3R)—N-(4-(2,6-dimethoxyphenyl)-5-((R)-1-dioxidotetrahydrothiophen-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-1,1-dioxidotetrahydrothiophen-3-yl)-4H-1,2,4-triazol-3-yl)-3-(5-methylpyrimidin-2-yl)butane-2-sulfonamide;

(1R,2S)—N-(4-(4,6-dimethoxypyrimidin-5-yl)-5-((S)-tetrahydrofuran-2-yl)-4H-1,2,4-triazol-3-yl)-1-methoxy-1-(5-methylpyrazin-2-yl)propane-2-sulfonamide;

(1R,2S)—N-(4-(4,6-dimethoxypyrimidin-5-yl)-5-((R)-tetrahydrofuran-2-yl)-4H-1,2,4-triazol-3-yl)-1-methoxy-1-(5-methylpyrazin-2-yl)propane-2-sulfonamide;

(1R,2S)-1-(5-chloropyrimidin-2-yl)-N-(4-(2,6-dimethoxyphenyl)-5-((R)-1,1-dioxidotetrahydrothiophen-3-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((S)-1,1-dioxidotetrahydrothiophen-3-yl)-4H-1,2,4-triazol-3-yl)-1-methoxypropane-2-sulfonamide;

(2S,3R)-3-(5-chloropyrimidin-2-yl)-N-(4-(2,6-dimethoxyphenyl)-5-((R)-1,1-dioxidotetrahydrothiophen-3-yl)-4H-1,2,4-triazol-3-yl)butane-2-sulfonamide;

(2S,3R)-3-(5-chloropyrimidin-2-yl)-N-(4-(2,6-dimethoxyphenyl)-5-((S)-1,1-dioxidotetrahydrothiophen-3-yl)-4H-1,2,4-triazol-3-yl)butane-2-sulfonamide;

(2S,3R)-3-(5-chloropyrimidin-2-yl)-N-(4-(4,6-dimethoxypyrimidin-5-yl)-5-((S)-tetrahydro-2H-pyran-2-yl)-4H-1,2,4-triazol-3-yl)butane-2-sulfonamide;

(2S,3R)-3-(5-chloropyrimidin-2-yl)-N-(4-(4,6-dimethoxypyrimidin-5-yl)-5-((R)-tetrahydro-2H-pyran-2-yl)-4H-1,2,4-triazol-3-yl)butane-2-sulfonamide;

(1R,2S)—N-(4-(2,6-dimethoxyphenyl)-5-((S)-tetrahydro-2H-pyran-3-yl)-4H-1,2,4-triazol-3-yl)-1-hydroxy-1-(5-methylpyrimidin-2-yl)propane-2-sulfonamide;

(1R,2S)—N-(4-(2,6-dimethoxyphenyl)-5-((R)-tetrahydro-2H-pyran-3-yl)-4H-1,2,4-triazol-3-yl)-1-hydroxy-1-(5-methylpyrimidin-2-yl)propane-2-sulfonamide;

(2S,3R)-3-(5-chloropyrimidin-2-yl)-N-(4-(4,6-dimethoxypyrimidin-5-yl)-5-((R)-1,4-dioxan-2-yl)-4H-1,2,4-triazol-3-yl)butane-2-sulfonamide;

(2S,3R)-3-(5-chloropyrimidin-2-yl)-N-(4-(4,6-dimethoxypyrimidin-5-yl)-5-((S)-1,4-dioxan-2-yl)-4H-1,2,4-triazol-3-yl)butane-2-sulfonamide;

(1R,2S)-1-(5-chloropyrimidin-2-yl)-N-(4-(2,6-dimethoxyphenyl)-5-((R)-1,4-dioxan-2-yl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((S)-1,4-dioxan-2-yl)-4H-1,2,4-triazol-3-yl)-1-methoxypropane-2-sulfonamide;

(1R,2S)-1-(5-chloropyrimidin-2-yl)-1-methoxy-N-(4-(1-methylcyclopropyl)-5-((2S,5S)-5-methyltetrahydrofuran-2-yl)-4H-1,2,4-triazol-3-yl)propane-2-sulfonamide;

(1R,2S)-1-(5-chloropyrimidin-2-yl)-1-methoxy-N-(4-(1-methylcyclopropyl)-5-((2R,5R)-5-methyltetrahydrofuran-2-yl)-4H-1,2,4-triazol-3-yl)propane-2-sulfonamide;

(1R,2S)—N-(4-(2,6-dimethoxyphenyl)-5-((R)-1,4-dioxan-2-yl)-4H-1,2,4-triazol-3-yl)-1-methoxy-1-(5-methylpyrimidin-2-yl)propane-2-sulfonamide;

(1R,2S)—N-(4-(2,6-dimethoxyphenyl)-5-((S)-1,4-dioxan-2-yl)-4H-1,2,4-triazol-3-yl)-1-methoxy-1-(5-methylpyrimidin-2-yl)propane-2-sulfonamide;

(1R,2S)—N-(4-(2,6-dimethoxyphenyl)-5-((R)-1,4-dioxan-2-yl)-4H-1,2,4-triazol-3-yl)-1-ethoxy-1-(5-methylpyrimidin-2-yl)propane-2-sulfonamide;

(1R,2S)—N-(4-(2,6-dimethoxyphenyl)-5-((S)-1,4-dioxan-2-yl)-4H-1,2,4-triazol-3-yl)-1-ethoxy-1-(5-methylpyrimidin-2-yl)propane-2-sulfonamide;

(2S,3R)—N-(4-(2,6-dimethoxyphenyl)-5-((R)-1,4-dioxan-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-1,4-dioxan-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-1,4-dioxan-2-yl)-4H-1,2,4-triazol-3-yl)-3-(5-methoxypyrazin-2-yl)butane-2-sulfonamide;

(2S,3R)—N-(4-(2,6-dimethoxyphenyl)-5-((S)-1,4-dioxan-2-yl)-4H-1,2,4-triazol-3-yl)-3-(5-methoxypyrazin-2-yl)butane-2-sulfonamide;

(1S,2S)—N-(4-(2,6-dimethoxyphenyl)-5-((S)-5,5-dimethyltetrahydrofuran-2-yl)-4H-1,2,4-triazol-3-yl)-1-isopropoxy-1-(5-methylpyrimidin-2-yl)propane-2-sulfonamide;

(1S,2S)—N-(4-(2,6-dimethoxyphenyl)-5-((R)-5,5-dimethyltetrahydrofuran-2-yl)-4H-1,2,4-triazol-3-yl)-1-isopropoxy-1-(5-methylpyrimidin-2-yl)propane-2-sulfonamide;

(1S,2S)—N-(4-(2,6-dimethoxyphenyl)-5-((S)-tetrahydro-2H-pyran-2-yl)-4H-1,2,4-triazol-3-yl)-1-isopropoxy-1-(5-methylpyrazin-2-yl)propane-2-sulfonamide;

(1S,2S)—N-(4-(2,6-dimethoxyphenyl)-5-((R)-tetrahydro-2H-pyran-2-yl)-4H-1,2,4-triazol-3-yl)-1-isopropoxy-1-(5-methylpyrazin-2-yl)propane-2-sulfonamide;

(1S,2S)—N-(4-(2,6-dimethoxyphenyl)-5-((R)-tetrahydrofuran-3-yl)-4H-1,2,4-triazol-3-yl)-1-isopropoxy-1-(5-methylpyrazin-2-yl)propane-2-sulfonamide;

(1S,2S)—N-(4-(2,6-dimethoxyphenyl)-5-((S)-tetrahydrofuran-3-yl)-4H-1,2,4-triazol-3-yl)-1-isopropoxy-1-(5-methylpyrazin-2-yl)propane-2-sulfonamide;

(1S,2S)—N-(4-(2,6-dimethoxyphenyl)-5-((R)-tetra-hydro-2H-pyran-3-yl)-4H-1,2,4-triazol-3-yl)-1-isopropoxy-1-(5-methylpyrazin-2-yl)propane-2-sulfonamide;

(1S,2S)—N-(4-(2,6-dimethoxyphenyl)-5-((S)-tetrahydro-2H-pyran-3-yl)-4H-1,2,4-triazol-3-yl)-1-isopropoxy-1-(5-methylpyrazin-2-yl)propane-2-sulfonamide;

(1S,2S)—N-(4-(2,6-dimethoxyphenyl)-5-((R)-1,4-dioxan-2-yl)-4H-1,2,4-triazol-3-yl)-1-isopropoxy-1-(5-methylpyrazin-2-yl)propane-2-sulfonamide;

(1S,2S)—N-(4-(2,6-dimethoxyphenyl)-5-((S)-1,4-dioxan-2-yl)-4H-1,2,4-triazol-3-yl)-1-isopropoxy-1-(5-methylpyrazin-2-yl)propane-2-sulfonamide;

(2R,3S)—N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide;

(2R,3S)—N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide;

(1R,2S)-1-(5-chloropyrimidin-2-yl)-N-(5-((S)-5,5-dimethyltetrahydrofuran-2-yl)-4-(tetrahydro-2H-pyran-4-yl)-4H-1,2,4-triazol-3-yl)-1-methoxypropane-2-sulfonamide;

(1R,2S)-1-(5-chloropyrimidin-2-yl)-N-(5-((R)-5,5-dimethyltetrahydrofuran-2-yl)-4-(tetrahydro-2H-pyran-4-yl)-4H-1,2,4-triazol-3-yl)-1-methoxypropane-2-sulfonamide;

(2S,3R)—N-(4-(2,6-dimethoxyphenyl)-5-((S)-tetrahydrothiophen-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-tetrahydrothiophen-2-yl)-4H-1,2,4-triazol-3-yl)-3-(5-methylpyrimidin-2-yl)butane-2-sulfonamide;

(1R,2S)-1-(5-chloropyrimidin-2-yl)-1-methoxy-N-(5-((2S,5S)-5-methyltetrahydrofuran-2-yl)-4-(tetrahydro-2H-pyran-4-yl)-4H-1,2,4-triazol-3-yl)propane-2-sulfonamide;

(1R,2S)-1-(5-chloropyrimidin-2-yl)-1-methoxy-N-(5-((2R,5R)-5-methyltetrahydrofuran-2-yl)-4-(tetrahydro-2H-pyran-4-yl)-4H-1,2,4-triazol-3-yl)propane-2-sulfonamide;

(2S,3R)—N-(4-(2,6-dimethoxyphenyl)-5-((2R)-4-(methylsulfonyl)-2-morpholinyl)-4H-1,2,4-triazol-3-yl)-3-(5-methyl-2-pyrimidinyl)-2-butanesulfonamide;

(2S,3R)—N-(4-(2,6-dimethoxyphenyl)-5-((2S)-4-(methylsulfonyl)-2-morpholinyl)-4H-1,2,4-triazol-3-yl)-3-(5-methyl-2-pyrimidinyl)-2-butanesulfonamide;

(1R,2S)—N-(5-((S)-2,3-dihydrobenzofuran-2-yl)-4-(4,6-dimethoxypyrimidin-5-yl)-4H-1,2,4-triazol-3-yl)-1-methoxy-1-(5-methylpyrimidin-2-yl)propane-2-sulfonamide; or (1R,2S)—N-(5-((R)-2,3-dihydrobenzofuran-2-yl)-4-(4,6-dimethoxypyrimidin-5-yl)-4H-1,2,4-triazol-3-yl)-1-methoxy-1-(5-methylpyrimidin-2-yl)propane-2-sulfonamide; or the pharmaceutically acceptable salt thereof, or the mixture thereof.

49. The compound of claim 1, wherein the compound is selected from (2S,3R)—N-(4-(2,6-dimethoxyphenyl)-5-((S)-pyrrolidin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-pyrrolidin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-piperidin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-piperidin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-piperidin-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-piperidin-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-(piperidin-4-yl)-4H-1,2,4-triazol-3-yl)-3-(5-methylpyrimidin-2-yl)butane-2-sulfonamide;

(2S,3R)—N-(4-(2,6-dimethoxyphenyl)-5-(1,1-dioxido-tetrahydro-2H-thiopyran-4-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-1,1-dioxidotetrahydro-2H-thiopyran-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-1,1-dioxidotetrahydro-2H-thiopyran-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-1,1-dioxidotetrahydro-2H-thiopyran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-1,1-dioxidotetrahydro-2H-thiopyran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-1,1-dioxidotetrahydrothiophen-2-yl)-4H-1,2,4-triazol-2-yl)-3-(5-methylpyrimidin-2-yl)butane-2-sulfonamide;

(2S,3R)—N-(4-(2,6-dimethoxyphenyl)-5-((S)-1,1-dioxidotetrahydrothiophen-2-yl)-4H-1,2,4-triazol-2-yl)-3-(5-methylpyrimidin-2-yl)butane-2-sulfonamide;

((2S,3R)—N-(4-(2,6-dimethoxyphenyl)-5-((S)-morpholin-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-morpholin-3-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-morpholin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-morpholin-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-(1,3-dioxan-5-yl)-4H-1,2,4-triazol-3-yl)-3-(5-methylpyrimidin-2-yl)butane-2-sulfonamide;

(2S,3R)—N-(4-(2,6-dimethoxyphenyl)-5-((S)-1,3-dioxolan-4-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-1,3-dioxolan-4-yl)-4H-1,2,4-triazol-3-yl)-3-(5-methylpyrimidin-2-yl)butane-2-sulfonamide;

(2S,3R)—N-(4-(2,6-dimethoxyphenyl)-5-(1,3-dioxolan-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-(1,3-dioxan-2-yl)-4H-1,2,4-triazol-3-yl)-3-(5-methylpyrimidin-2-yl)butane-2-sulfonamide;

(3R,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3R,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3S,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide;
(3S,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide;
(3R,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide;
(3R,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide;
(3S,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-isopropoxypiperidine-3-sulfonamide;
(3S,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-isopropoxypiperidine-3-sulfonamide;
(2S,3R)—N-(4-(2,6-dimethoxyphenyl)-5-((S)-tetrahydrothiophen-3-yl)-4H-1,2,4-triazol-3-yl)-3-(5-methylpyrimidin-2-yl)butane-2-sulfonamide;
(2S,3R)—N-(4-(2,6-dimethoxyphenyl)-5-((R)-tetrahydrothiophen-3-yl)-4H-1,2,4-triazol-3-yl)-3-(5-methylpyrimidin-2-yl)butane-2-sulfonamide;
(S)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)piperidine-3-sulfonamide;
(R)-1-(5-chloropyrimidin-2-yl)-N-(4-(4,6-dimethoxypyrimidin-5-yl)-5-((S)-tetrahydrofuran-2-yl)-4H-1,2,4-triazol-3-yl)piperidine-3-sulfonamide;
(S)-1-(5-chloropyrimidin-2-yl)-N-(4-(4,6-dimethoxypyrimidin-5-yl)-5-((S)-tetrahydrofuran-2-yl)-4H-1,2,4-triazol-3-yl)piperidine-3-sulfonamide;
(R)-1-(5-chloropyrimidin-2-yl)-N-(4-(4,6-dimethoxypyrimidin-5-yl)-5-((R)-tetrahydrofuran-2-yl)-4H-1,2,4-triazol-3-yl)piperidine-3-sulfonamide;
(S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)piperidine-3-sulfonamide;
(S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)piperidine-3-sulfonamide;
(R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)piperidine-3-sulfonamide;
(R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)piperidine-3-sulfonamide;
(3R,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-hydroxypiperidine-3-sulfonamide;
(3R,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-hydroxypiperidine-3-sulfonamide;
(3R,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-hydroxypiperidine-3-sulfonamide;
(3R,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-hydroxypiperidine-3-sulfonamide;
(3S,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-hydroxypiperidine-3-sulfonamide;
(3S,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-hydroxypiperidine-3-sulfonamide;
(3S,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-hydroxypiperidine-3-sulfonamide;
(3S,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-hydroxypiperidine-3-sulfonamide;
(3R,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide;
(3R,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide;
(3R,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide;
(3R,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide;
(3S,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide;
(3S,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide;
(3S,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-methoxypiperidine-3-sulfonamide;
(3S,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-methoxypiperidine-3-sulfonamide;
(3R,5S)—N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide;
(3R,5S)—N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide;
(3R,5R)—N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide;
(3R,5R)—N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide;
(3S,5R)—N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide;
(3S,5R)—N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide;
(3S,5S)—N-(4-(4,6-dimethoxypyrimidin-5-yl)-5-((R)-tetrahydrofuran-2-yl)-4H-1,2,4-triazol-3-yl)-5-ethoxy-1-(5-fluoropyrimidin-2-yl)piperidine-3-sulfonamide;
(3S,5S)—N-(4-(4,6-dimethoxypyrimidin-5-yl)-5-((S)-tetrahydrofuran-2-yl)-4H-1,2,4-triazol-3-yl)-5-ethoxy-1-(5-fluoropyrimidin-2-yl)piperidine-3-sulfonamide;
(3R,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3R,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3R,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3R,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3S,5R)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3S,5R)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide;

(3S,5S)—N-(4-(4,6-dimethoxypyrimidin-5-yl)-5-((S)-tetrahydrofuran-2-yl)-4H-1,2,4-triazol-3-yl)-1-(5-fluoropyrimidin-2-yl)-5-isopropoxypiperidine-3-sulfonamide;

(3S,5S)—N-(4-(4,6-dimethoxypyrimidin-5-yl)-5-((R)-tetrahydrofuran-2-yl)-4H-1,2,4-triazol-3-yl)-1-(5-fluoropyrimidin-2-yl)-5-isopropoxypiperidine-3-sulfonamide;

(S)—N-(4-(2,6-dimethoxyphenyl)-5-((R)-tetrahydrofuran-2-yl)-4H-1,2,4-triazol-3-yl)-1-(5-fluoropyrimidin-2-yl)piperidine-3-sulfonamide;

(S)—N-(4-(2,6-dimethoxyphenyl)-5-((S)-tetrahydrofuran-2-yl)-4H-1,2,4-triazol-3-yl)-1-(5-fluoropyrimidin-2-yl)piperidine-3-sulfonamide;

(R)—N-(4-(2,6-dimethoxyphenyl)-5-((R)-tetrahydrofuran-2-yl)-4H-1,2,4-triazol-3-yl)-1-(5-fluoropyrimidin-2-yl)piperidine-3-sulfonamide;

(R)—N-(4-(2,6-dimethoxyphenyl)-5-((S)-tetrahydrofuran-2-yl)-4H-1,2,4-triazol-3-yl)-1-(5-fluoropyrimidin-2-yl)piperidine-3-sulfonamide;

(3R,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide;

(3R,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide;

(3R,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide;

(3R,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide;

(3S,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide;

(3S,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide;

(3S,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-hydroxypiperidine-3-sulfonamide;

(3S,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-hydroxypiperidine-3-sulfonamide;

(3R,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide;

(3R,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide;

(3R,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide;

(3R,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide;

(3S,5R)—N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide;

(3S,5R)—N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide;

(3S,5S)—N-(4-(2,6-dimethoxyphenyl)-5-((S)-tetrahydrofuran-2-yl)-4H-1,2,4-triazol-3-yl)-1-(5-fluoropyrimidin-2-yl)-5-methoxypiperidine-3-sulfonamide;

(3S,5S)—N-(4-(2,6-dimethoxyphenyl)-5-((R)-tetrahydrofuran-2-yl)-4H-1,2,4-triazol-3-yl)-1-(5-fluoropyrimidin-2-yl)-5-methoxypiperidine-3-sulfonamide;

(3R,5S)—N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide;

(3R,5S)—N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide;

(3R,5R)—N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide;

(3R,5R)—N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide;

(3S,5R)—N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide;

(3S,5R)—N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide;

(3S,5S)—N-(4-(2,6-dimethoxyphenyl)-5-((R)-tetrahydrofuran-2-yl)-4H-1,2,4-triazol-3-yl)-5-ethoxy-1-(5-fluoropyrimidin-2-yl)piperidine-3-sulfonamide; or (3S,5S)—N-(4-(2,6-dimethoxyphenyl)-5-((S)-tetrahydrofuran-2-yl)-4H-1,2,4-triazol-3-yl)-5-ethoxy-1-(5-fluoropyrimidin-2-yl)piperidine-3-sulfonamide; or the pharmaceutically acceptable salt thereof, or the mixture thereof.

50. The compound of claim 1, wherein the compound is selected from (2S,3R)-3-(5-chloropyrimidin-2-yl)-N-(4-(2,6-dimethoxyphenyl)-5-((R)-tetrahydrofuran-3-yl)-4H-1,2,4-triazol-3-yl)butane-2-sulfonamide;

(2S,3R)-3-(5-chloropyrimidin-2-yl)-N-(4-(2,6-dimethoxyphenyl)-5-((S)-tetrahydrofuran-3-yl)-4H-1,2,4-triazol-3-yl)butane-2-sulfonamide;

(2S,3R)—N-(4-(2,6-dimethoxyphenyl)-5-((S)-tetrahydrofuran-2-yl)-4H-1,2,4-triazol-3-yl)-3-(5-methylpyrimidin-2-yl)butane-2-sulfonamide;

(2S,3R)—N-(4-(2,6-dimethoxyphenyl)-5-((R)-tetrahydrofuran-2-yl)-4H-1,2,4-triazol-3-yl)-3-(5-methylpyrimidin-2-yl)butane-2-sulfonamide;

(2S,3R)-3-(5-chloro-2-pyrimidinyl)-N-(4-(2,6-dimethoxyphenyl)-5-((2R)-1,4-dioxan-2-yl)-4H-1,2,4-triazol-3-yl)-2-butanesulfonamide;

(2S,3R)-3-(5-chloro-2-pyrimidinyl)-N-(4-(2,6-dimethoxyphenyl)-5-((2S)-1,4-dioxan-2-yl)-4H-1,2,4-triazol-3-yl)-2-butanesulfonamide;

(2S,3R)-3-(5-chloropyrimidin-2-yl)-N-(4-(4,6-dimethoxypyrimidin-5-yl)-5-((R)-1,4-dioxan-2-yl)-4H-1,2,4-triazol-3-yl)butane-2-sulfonamide;
(2S,3R)-3-(5-chloropyrimidin-2-yl)-N-(4-(4,6-dimethoxypyrimidin-5-yl)-5-((S)-1,4-dioxan-2-yl)-4H-1,2,4-triazol-3-yl)butane-2-sulfonamide;
(1S,2S)—N-(4-(4,6-dimethoxypyrimidin-5-yl)-5-((S)-tetrahydrofuran-2-yl)-4H-1,2,4-triazol-3-yl)-1-isopropoxy-1-(5-methylpyrimidin-2-yl)propane-2-sulfonamide;
(1S,2S)—N-(4-(4,6-dimethoxypyrimidin-5-yl)-5-((R)-tetrahydrofuran-2-yl)-4H-1,2,4-triazol-3-yl)-1-isopropoxy-1-(5-methylpyrimidin-2-yl)propane-2-sulfonamide;
(1R,2S)-1-(5-chloropyrimidin-2-yl)-N-(4-(4,6-dimethoxypyrimidin-5-yl)-5-((S)-5,5-dimethyltetrahydrofuran-2-yl)-4H-1,2,4-triazol-3-yl)-1-methoxypropane-2-sulfonamide;
(1R,2S)-1-(5-chloropyrimidin-2-yl)-N-(4-(4,6-dimethoxypyrimidin-5-yl)-5-((R)-5,5-dimethyltetrahydrofuran-2-yl)-4H-1,2,4-triazol-3-yl)-1-methoxypropane-2-sulfonamide;
(1R,2S)-1-(5-chloropyrimidin-2-yl)-N-(4-(2,6-dimethoxyphenyl)-5-((R)-1,4-dioxan-2-yl)-4H-1,2,4-triazol-3-yl)-1-methoxypropane-2-sulfonamidep;
(1R,2S)-1-(5-chloropyrimidin-2-yl)-N-(4-(2,6-dimethoxyphenyl)-5-((S)-1,4-dioxan-2-yl)-4H-1,2,4-triazol-3-yl)-1-methoxypropane-2-sulfonamide;
(1S,2S)—N-(4-(2,6-dimethoxyphenyl)-5-((S)-5,5-dimethyltetrahydrofuran-2-yl)-4H-1,2,4-triazol-3-yl)-1-isopropoxy-1-(5-methylpyrimidin-2-yl)propane-2-sulfonamide;
(1S,2S)—N-(4-(2,6-dimethoxyphenyl)-5-((R)-5,5-dimethyltetrahydrofuran-2-yl)-4H-1,2,4-triazol-3-yl)-1-isopropoxy-1-(5-methylpyrimidin-2-yl)propane-2-sulfonamide;
(1R,2S)-1-(5-chloropyrimidin-2-yl)-N-(4-(2,6-dimethoxyphenyl)-5-((S)-tetrahydro-2H-pyran-2-yl)-4H-1,2,4-triazol-3-yl)-1-methoxypropane-2-sulfonamide; or
(1R,2S)-1-(5-chloropyrimidin-2-yl)-N-(4-(2,6-dimethoxyphenyl)-5-((R)-tetrahydro-2H-pyran-2-yl)-4H-1,2,4-triazol-3-yl)-1-methoxypropane-2-sulfonamide; or the pharmaceutically acceptable salt thereof, or the mixture thereof.

51. The compound of claim 1, wherein the compound is selected from
(2S,3R)-3-(5-chloro-2-pyrimidinyl)-N-(4-(2,6-dimethoxyphenyl)-5-((1S)-3-oxo-2,3-dihydro-1H-isoindol-1-yl)-4H-1,2,4-triazol-3-yl)-2-butanesulfonamide;
(2S,3R)-3-(5-chloro-2-pyrimidinyl)-N-(4-(2,6-dimethoxyphenyl)-5-((1R)-3-oxo-2,3-dihydro-1H-isoindol-1-yl)-4H-1,2,4-triazol-3-yl)-2-butanesulfonamide;
(1R,2S)—N-(4-(2,6-dimethoxyphenyl)-5-((1R)-3-oxo-2,3-dihydro-1H-isoindol-1-yl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-((1S)-3-oxo-2,3-dihydro-1H-isoindol-1-yl)-4H-1,2,4-triazol-3-yl)-1-methoxy-1-(5-methyl-2-pyrimidinyl)-2-propanesulfonamide;
(1R,2S)—N-(5-((3S)-2,3-dihydro-1-benzofuran-3-yl)-4-(2,6-dimethoxyphenyl)-4H-1,2,4-triazol-3-yl)-1-methoxy-1-(5-methyl-2-pyrimidinyl)-2-propanesulfonamide;
(1R,2S)—N-(5-((3R)-2,3-dihydro-1-benzofuran-3-yl)-4-(2,6-dimethoxyphenyl)-4H-1,2,4-triazol-3-yl)-1-methoxy-1-(5-methyl-2-pyrimidinyl)-2-propanesulfonamide;
(1R,2S)-1-(5-chloro-2-pyrimidinyl)-1-methoxy-N-(4-(2-methoxyphenyl)-5-((2S)-tetrahydro-2-furanyl)-4H-1,2,4-triazol-3-yl)-2-propanesulfonamide;
(1R,2S)-1-(5-chloro-2-pyrimidinyl)-N-(4-(2-ethylphenyl)-5-((2S)-tetrahydro-2-furanyl)-4H-1,2,4-triazol-3-yl)-1-methoxy-2-propanesulfonamide;
(1R,2S)-1-(5-chloro-2-pyrimidinyl)-1-methoxy-N-(4-(2-methylphenyl)-5-((2S)-tetrahydro-2-furanyl)-4H-1,2,4-triazol-3-yl)-2-propanesulfonamide;
(1R,2S)—N-(4-(2-chlorophenyl)-5-((2S)-tetrahydro-2-furanyl)-4H-1,2,4-triazol-3-yl)-1-(5-chloro-2-pyrimidinyl)-1-methoxy-2-propanesulfonamide;
(1R,2S)-1-(5-chloro-2-pyrimidinyl)-N-(4-(2-fluorophenyl)-5-((2S)-tetrahydro-2-furanyl)-4H-1,2,4-triazol-3-yl)-1-methoxy-2-propanesulfonamide;
(2S,3R)-3-(5-chloro-2-pyrimidinyl)-N-(5-((2R)-1,4-dioxan-2-yl)-4-(tetrahydro-2H-pyran-4-yl)-4H-1,2,4-triazol-3-yl)-2-butanesulfonamide;
(2S,3R)-3-(5-chloro-2-pyrimidinyl)-N-(5-((2S)-1,4-dioxan-2-yl)-4-(tetrahydro-2H-pyran-4-yl)-4H-1,2,4-triazol-3-yl)-2-butanesulfonamide;
(1R,2S)-1-(5-chloro-2-pyrimidinyl)-N-(5-((2R)-1,4-dioxan-2-yl)-4-(tetrahydro-2H-pyran-4-yl)-4H-1,2,4-triazol-3-yl)-1-methoxy-2-propanesulfonamide;
(1R,2S)-1-(5-chloro-2-pyrimidinyl)-N-(5-((2S)-1,4-dioxan-2-yl)-4-(tetrahydro-2H-pyran-4-yl)-4H-1,2,4-triazol-3-yl)-1l-methoxy-2-propanesulfonamide;
(2S,3R)—N-(4-(2,6-dimethoxyphenyl)-5-((2R,5R)-5-methyltetrahydro-2-furanyl)-4H-1,2,4-triazol-3-yl)-3-(5-methoxy-2-pyrimidinyl)-2-butanesulfonamide;
(2S,3R)—N-(4-(2,6-dimethoxyphenyl)-5-((2S,5S)-5-methyltetrahydro-2-furanyl)-4H-1,2,4-triazol-3-yl)-3-(5-methoxy-2-pyrimidinyl)-2-butanesulfonamide;
(1R,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1l-methoxy-2-propanesulfonamide;
(1R,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1l-methoxy-2-propanesulfonamide;
(1R,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide;
(1R,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide;
(2S,3R)-3-(5-chloro-2-pyrimidinyl)-N-(4-(3,5-dibromo-2,6-dimethoxyphenyl)-5-((3S)-tetrahydro-3-furanyl)-4H-1,2,4-triazol-3-yl)-2-butanesulfonamide;
(1S,2S)—N-(4-(2,6-dimethoxyphenyl)-5-((2S)-1,4-dioxan-2-yl)-4H-1,2,4-triazol-3-yl)-1-(1-methylethoxy)-1-(5-methyl-2-pyrimidinyl)-2-propanesulfonamide;
(1S,2S)—N-(4-(2,6-dimethoxyphenyl)-5-((2R)-1,4-dioxan-2-yl)-4H-1,2,4-triazol-3-yl)-1-(1-methylethoxy)-1-(5-methyl-2-pyrimidinyl)-2-propanesulfonamide;
(2S,3R)—N-(4-(2,6-dimethoxyphenyl)-5-((3R,8aR)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(2S,3R)—N-(4-(2,6-dimethoxyphenyl)-5-((3R,8aS)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(2S,3R)—N-(4-(2,6-dimethoxyphenyl)-5-((3S,8aR)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(2S,3R)—N-(4-(2,6-dimethoxyphenyl)-5-((3S,8aS)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(1R,2S)-1-(5-chloro-2-pyrimidinyl)-N-(5-((2R)-2,3-dihydro-1,4-benzodioxin-2-yl)-4-(2,6-dimethoxyphenyl)-4H-1,2,4-triazol-3-yl)-1l-methoxy-2-propanesulfonamide;

(1R,2S)-1-(5-chloro-2-pyrimidinyl)-N-(5-((2S)-2,3-dihydro-1,4-benzodioxin-2-yl)-4-(2,6-dimethoxyphenyl)-4H-1,2,4-triazol-3-yl)-1l-methoxy-2-propanesulfonamide;

(1S,2S)-1-(1-methylethoxy)-1-(5-methyl-2-pyrazinyl)-N-(5-((2S)-tetrahydro-2-furanyl)-4-(tetrahydro-2H-pyran-4-yl)-4H-1,2,4-triazol-3-yl)-2-propanesulfonamide;

(1S,2S)-1-(1-methylethoxy)-1-(5-methyl-2-pyrazinyl)-N-(5-((2R)-tetrahydro-2-furanyl)-4-(tetrahydro-2H-pyran-4-yl)-4H-1,2,4-triazol-3-yl)-2-propanesulfonamide;

(1S,2S)-1-(1-methylethoxy)-1-(5-methyl-2-pyrazinyl)-N-(5-((2S,5S)-5-methyltetrahydro-2-furanyl)-4-(tetrahydro-2H-pyran-4-yl)-4H-1,2,4-triazol-3-yl)-2-propanesulfonamide;

(1S,2S)-1-(1-methylethoxy)-1-(5-methyl-2-pyrazinyl)-N-(5-((2R,5R)-5-methyltetrahydro-2-furanyl)-4-(tetrahydro-2H-pyran-4-yl)-4H-1,2,4-triazol-3-yl)-2-propanesulfonamide;

(1R,2S)-1-(5-chloro-2-pyridinyl)-N-(4-(2,6-dimethoxyphenyl)-5-((2R)-1,4-dioxan-2-yl)-4H-1,2,4-triazol-3-yl)-1-methoxy-2-propanesulfonamide;

(1R,2S)-1-(5-chloro-2-pyridinyl)-N-(4-(2,6-dimethoxyphenyl)-5-((2S)-1,4-dioxan-2-yl)-4H-1,2,4-triazol-3-yl)-1-methoxy-2-propanesulfonamide;

(1R,2R)—N-(4-(2,6-dimethoxyphenyl)-5-((2S)-1,4-dioxan-2-yl)-4H-1,2,4-triazol-3-yl)-1-imidazo[1,2-a]pyridin-2-yl-1-(1-methylethoxy)-2-propanesulfonamide;

(2S,3R)-3-(5-chloro-2-pyridinyl)-N-(4-(2,6-dimethoxyphenyl)-5-((2R)-1,4-dioxan-2-yl)-4H-1,2,4-triazol-3-yl)-2-butanesulfonamide;

(2S,3R)-3-(5-chloro-2-pyridinyl)-N-(4-(2,6-dimethoxyphenyl)-5-((2S)-1,4-dioxan-2-yl)-4H-1,2,4-triazol-3-yl)-2-butanesulfonamide;

(2S,3R)—N-(4-(2,6-dimethoxyphenyl)-5-((3R)-1-methyl-3-piperidinyl)-4H-1,2,4-triazol-3-yl)-3-(5-methyl-2-pyrimidinyl)-2-butanesulfonamide;

(2S,3R)—N-(4-(2,6-dimethoxyphenyl)-5-((3S)-1-methyl-3-piperidinyl)-4H-1,2,4-triazol-3-yl)-3-(5-methyl-2-pyrimidinyl)-2-butanesulfonamide;

(1R,2S)-1-(5-chloro-2-pyrimidinyl)-N-(5-((2R)-1,4-dioxan-2-yl)-4-(1-methylcyclopropyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(1-methylcyclopropyl)-4H-1,2,4-triazol-3-yl)-1-methoxy-2-propanesulfonamide;

(2S,3R)—N-(4-(2,6-dimethoxyphenyl)-5-((3R)-tetrahydro-3-furanyl)-4H-1,2,4-triazol-3-yl)-3-(5-fluoro-2-pyrimidinyl)-2-butanesulfonamide;

(2S,3R)—N-(4-(2,6-dimethoxyphenyl)-5-((3S)-tetrahydro-3-furanyl)-4H-1,2,4-triazol-3-yl)-3-(5-fluoro-2-pyrimidinyl)-2-butanesulfonamide;

(2S,3R)—N-(4-(2,6-dimethoxyphenyl)-5-((2R)-1,4-dioxan-2-yl)-4H-1,2,4-triazol-3-yl)-3-(5-fluoro-2-pyrimidinyl)-2-butanesulfonamide;

(2S,3R)—N-(4-(2,6-dimethoxyphenyl)-5-((2S)-1,4-dioxan-2-yl)-4H-1,2,4-triazol-3-yl)-3-(5-fluoro-2-pyrimidinyl)-2-butanesulfonamide;

(2S,3R)—N-(4-(4,6-dimethoxy-5-pyrimidinyl)-5-((2R)-1,4-dioxan-2-yl)-4H-1,2,4-triazol-3-yl)-3-(5-fluoro-2-pyrimidinyl)-2-butanesulfonamide;

(2S,3R)—N-(4-(4,6-dimethoxy-5-pyrimidinyl)-5-((2S)-1,4-dioxan-2-yl)-4H-1,2,4-triazol-3-yl)-3-(5-fluoro-2-pyrimidinyl)-2-butanesulfonamide;

(1S,2S)-1-(5-chloro-2-pyrimidinyl)-N-(4-(4,6-dimethoxy-5-pyrimidinyl)-5-((2S)-5,5-dimethyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(4,6-dimethoxy-5-pyrimidinyl)-5-((2R)-5,5-dimethyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((3R)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((3S)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2R)-1,4-dioxan-2-yl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2S)-1,4-dioxan-2-yl)-4H-1,2,4-triazol-3-yl)-1-(2-propanyloxy)-2-propanesulfonamide;

(1R,2S)-1-(5-chloro-2-pyrimidinyl)-1-methoxy-N-(4-(1-(methoxymethyl)cyclopropyl)-5-((2S,5S)-5-methyltetrahydro-2-furanyl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-((2R,5R)-5-methyltetrahydro-2-furanyl)-4H-1,2,4-triazol-3-yl)-2-propanesulfonamide;

(1R,2S)-1-(5-chloro-2-pyrimidinyl)-N-(5-((2S)-5,5-dimethyltetrahydro-2-furanyl)-4-(2-methoxyethyl)-4H-1,2,4-triazol-3-yl)-1-methoxy-2-propanesulfonamide;

(1R,2S)-1-(5-chloro-2-pyrimidinyl)-N-(5-((2R)-5,5-dimethyltetrahydro-2-furanyl)-4-(2-methoxyethyl)-4H-1,2,4-triazol-3-yl)-1-methoxy-2-propanesulfonamide;

(1R,2S)-1-(5-chloro-2-pyrimidinyl)-N-(5-((2S)-5,5-dimethyltetrahydro-2-furanyl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(5-((2R)-5,5-dimethyltetrahydro-2-furanyl)-4-(1-(methoxymethyl)cyclopropyl)-4H-1,2,4-triazol-3-yl)-1-methoxy-2-propanesulfonamide;

(1S,2S)-1-(5-chloro-2-pyrimidinyl)-N-(4-(4,6-dimethoxy-5-pyrimidinyl)-5-((3S)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(4,6-dimethoxy-5-pyrimidinyl)-5-((3R)-tetrahydro-3-furanyl)-4H-1,2,4-triazol-3-yl)-1-(2-propanyloxy)-2-propanesulfonamide;

(1R,2S)-1-(5-chloro-2-pyrimidinyl)-N-(4-(2,6-dimethoxyphenyl)-5-((3R)-1-methyl-5-oxo-3-pyrrolidinyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((3S)-1-methyl-5-oxo-3-pyrrolidinyl)-4H-1,2,4-triazol-3-yl)-1-methoxy-2-propanesulfonamide;

(1R,2S)-1-(5-chloro-2-pyrimidinyl)-N-(5-((2R)-1,4-dioxan-2-yl)-4-(1-(3-pyridinyl)cyclopropyl)-4H-1,2,4-triazol-3-yl)-1l-methoxy-2-propanesulfonamide;

(1R,2S)-1-(5-chloro-2-pyrimidinyl)-N-(5-((2S)-1,4-dioxan-2-yl)-4-(1-(3-pyridinyl)cyclopropyl)-4H-1,2,4-triazol-3-yl)-1l-methoxy-2-propanesulfonamide;

(1R,2S)-1-(5-chloro-2-pyrimidinyl)-1-methoxy-N-(4-(2-propanyl)-5-((3R)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(2-propanyl)-5-((3S)-tetrahydro-3-furanyl)-4H-1,2,4-triazol-3-yl)-2-propanesulfonamide;

(1R,2S)-1-(5-chloro-2-pyrimidinyl)-N-(5-((2S)-5,5-dimethyltetrahydro-2-furanyl)-4-(2-propanyl)-4H-1,2,4-triazol-3-yl)-1-methoxy-2-propanesulfonamide;

(1R,2S)-1-(5-chloro-2-pyrimidinyl)-N-(5-((2R)-5,5-dimethyltetrahydro-2-furanyl)-4-(2-propanyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(2-propanyl)-4H-1,2,4-triazol-3-yl)-1-methoxy-2-propane sulfonamide;

(1R,2S)-1-(5-chloro-2-pyrimidinyl)-N-(5-((2R)-1,4-dioxan-2-yl)-4-(2-propanyl)-4H-1,2,4-triazol-3-yl)-1-methoxy-2-propane sulfonamide;

(1R,2S)-1-(5-chloro-2-pyrimidinyl)-1-methoxy-N-(4-(1-(methoxymethyl)cyclopropyl)-5-((3R)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-((3S)-tetrahydro-3-furanyl)-4H-1,2,4-triazol-3-yl)-2-propanesulfonamide;

(1R,2S)-1-(5-chloro-2-pyrimidinyl)-N-(5-((2R)-1,4-dioxan-2-yl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((3S)-tetrahydro-3-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((3R)-tetrahydro-3-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2R)-5,5-dimethyltetrahydro-2-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2S)-5,5-dimethyltetrahydro-2-furanyl)-4H-1,2,4-triazol-3-yl)-1-methoxy-2-propanesulfonamide;

(1R,2S)-1-(5-chloro-2-pyrimidinyl)-1-methoxy-N-(4-(2-methoxyethyl)-5-((3S)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(2-methoxyethyl)-5-((3R)-tetrahydro-3-furanyl)-4H-1,2,4-triazol-3-yl)-2-propanesulfonamide;

(1R,2S)-1-(5-chloro-2-pyrimidinyl)-N-(5-((2S)-1,4-dioxan-2-yl)-4-(2-methoxyethyl)-4H-1,2,4-triazol-3-yl)-1-methoxy-2-propanesulfonamide;

(1R,2S)-1-(5-chloro-2-pyrimidinyl)-N-(5-((2R)-1,4-dioxan-2-yl)-4-(2-methoxyethyl)-4H-1,2,4-triazol-3-yl)-1-methoxy-2-propanesulfonamide;

(1S,2S)—N-(4-(4,6-dimethoxy-5-pyrimidinyl)-5-((3R)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1S,2S)—N-(4-(4,6-dimethoxy-5-pyrimidinyl)-5-((3S)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1R,2S)-1-(5-chloro-2-pyrimidinyl)-N-(4-(4,6-dimethoxy-5-pyrimidinyl)-5-((3R)-5,5-dimethyltetrahydro-3-furanyl)-4H-1,2,4-triazol-3-yl)-1-methoxy-2-propane sulfonamide;

(1R,2S)-1-(5-chloro-2-pyrimidinyl)-N-(4-(4,6-dimethoxy-5-pyrimidinyl)-5-((3S)-5,5-dimethyltetrahydro-3-furanyl)-4H-1,2,4-triazol-3-yl)-1-methoxy-2-propane sulfonamide;

(2S,3R)-3-(5-chloro-2-pyrimidinyl)-N-(4-(4,6-dimethoxy-5-pyrimidinyl)-5-((3R)-5,5-dimethyltetrahydro-3-furanyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-((3S)-5,5-dimethyltetrahydro-3-furanyl)-4H-1,2,4-triazol-3-yl)-2-butanesulfonamide;

(1S,2S)-1-(5-chloro-2-pyrimidinyl)-N-(4-(1-(methoxymethyl)cyclopropyl)-5-((3R)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(1-(methoxymethyl)cyclopropyl)-5-((3S)-tetrahydro-3-furanyl)-4H-1,2,4-triazol-3-yl)-1-(2-propanyloxy)-2-propanesulfonamide;

(1S,2S)—N-(4-(4,6-dimethoxy-5-pyrimidinyl)-5-((3R)-tetrahydro-3-furanyl)-4H-1,2,4-triazol-3-yl)-1-(5-fluoro-2-pyrimidinyl)-1-(2-propanyloxy)-2-propanesulfonamide;

(1S,2S)—N-(4-(4,6-dimethoxy-5-pyrimidinyl)-5-((3S)-tetrahydro-3-furanyl)-4H-1,2,4-triazol-3-yl)-1-(5-fluoro-2-pyrimidinyl)-1-(2-propanyloxy)-2-propanesulfonamide;

(1S,2S)—N-(4-(4,6-dimethoxy-5-pyrimidinyl)-5-((3R)-tetrahydro-3-furanyl)-4H-1,2,4-triazol-3-yl)-1-(5-methyl-2-pyridinyl)-1-(2-propanyloxy)-2-propanesulfonamide;

(1S,2S)—N-(4-(4,6-dimethoxy-5-pyrimidinyl)-5-((3S)-tetrahydro-3-furanyl)-4H-1,2,4-triazol-3-yl)-1-(5-methyl-2-pyridinyl)-1-(2-propanyloxy)-2-propanesulfonamide;

(1R,2S)—N-(4-([1,1'-bi(cyclopropyl)]-1-yl)-5-((2R)-1,4-dioxan-2-yl)-4H-1,2,4-triazol-3-yl)-1-(5-chloro-2-pyrimidinyl)-1-methoxy-2-propanesulfonamide;

(1R,2S)—N-(4-([1,1'-bi(cyclopropyl)]-1-yl)-5-((2S)-1,4-dioxan-2-yl)-4H-1,2,4-triazol-3-yl)-1-(5-chloro-2-pyrimidinyl)-1-methoxy-2-propanesulfonamide;

(1R,2S)—N-(4-([1,1'-bi(cyclopropyl)]-1-yl)-5-((2R)-1,4-dioxan-2-yl)-4H-1,2,4-triazol-3-yl)-1-methoxy-1-(5-methyl-2-pyrazinyl)-2-propanesulfonamide;

(1R,2S)—N-(4-([1,1'-bi(cyclopropyl)]-1-yl)-5-((2S)-1,4-dioxan-2-yl)-4H-1,2,4-triazol-3-yl)-1-methoxy-1-(5-methyl-2-pyrazinyl)-2-propanesulfonamide;

(1R,2S)-1-(5-chloro-2-pyrimidinyl)-N-(4-(1,3-dimethoxy-2-propanyl)-5-((2R)-tetrahydro-2-furanyl)-4H-1,2,4-triazol-3-yl)-1-methoxy-2-propanesulfonamide;

(2S,3R)-3-(5-chloro-2-pyrimidinyl)-N-(4-(3,5-dibromo-2,6-dimethoxyphenyl)-5-((3R)-tetrahydro-3-furanyl)-4H-1,2,4-triazol-3-yl)-2-butanesulfonamide;

(1R,2S)-1-(5-chloro-2-pyrimidinyl)-N-(4-(1,3-dimethoxy-2-propanyl)-5-((2S)-tetrahydro-2-furanyl)-4H-1,2,4-triazol-3-yl)-1-methoxy-2-propanesulfonamide;

(2S,3R)—N-(4-(2,6-dimethoxyphenyl)-5-((2R)-5,5-dimethyltetrahydro-2-furanyl)-4H-1,2,4-triazol-3-yl)-3-(5-fluoro-2-pyrimidinyl)-2-butanesulfonamide;

(2S,3R)—N-(4-(2,6-dimethoxyphenyl)-5-((2S)-5,5-dimethyltetrahydro-2-furanyl)-4H-1,2,4-triazol-3-yl)-3-(5-fluoro-2-pyrimidinyl)-2-butanesulfonamide;

(1R,2S)-1-(5-chloro-2-pyrimidinyl)-N-(5-((2R)-1,4-dioxan-2-yl)-4-(3-pentanyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(3-pentanyl)-4H-1,2,4-triazol-3-yl)-1-methoxy-2-propanesulfonamide;

(1R,2S)-1-(5-chloro-2-pyrimidinyl)-N-(4-(dicyclopropylmethyl)-5-((2R)-1,4-dioxan-2-yl)-4H-1,2,4-triazol-3-yl)-1-methoxy-2-propanesulfonamide;

(1R,2S)-1-(5-chloro-2-pyrimidinyl)-N-(4-(dicyclopropylmethyl)-5-((2S)-1,4-dioxan-2-yl)-4H-1,2,4-triazol-3-yl)-1-methoxy-2-propanesulfonamide;

(2S,3R)-3-(5-chloro-2-pyrimidinyl)-N-(4-(2,6-dimethoxyphenyl)-5-((2R)-5-oxo-2-pyrrolidinyl)-4H-1,2,4-triazol-3-yl)-2-butanesulfonamide; or (2S,3R)-3-(5-chloro-2-pyrimidinyl)-N-(4-(2,6-dimethoxyphenyl)-5-((2S)-5-oxo-2-pyrrolidinyl)-4H-1,2,4-triazol-3-yl)-2-butanesulfonamide; or the pharmaceutically acceptable salt thereof, or the mixture thereof.

52. The compound of claim 1, wherein the compound has the Formula IA

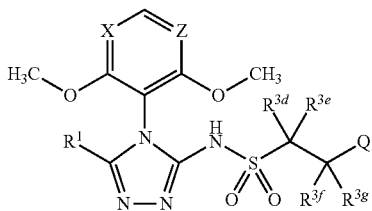

IA or is the pharmaceutically acceptable salt thereof, the tautomer thereof, the pharmaceutically acceptable salt of the tautomer, the stereoisomer of any of the foregoing, or the mixture thereof, wherein:

$R^1$ is as defined in claim 1;

X is selected from CH or N;

Z is selected from CH or N;

$R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and $R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), or —O—($C_2$-$C_5$ alkenyl)

Q is a phenyl group or a monocyclic heteroaryl group with 6 ring members containing 1 or 2 N heteroatoms, wherein the phenyl and the monocyclic heteroaryl Q groups are unsubstituted or are substituted with 1, 2, or 3 $R^Q$ substituent; and $R^Q$ is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), —($C_1$-$C_6$ alkyl)-$NH_2$ or —$S(=O)_2$—($C_1$-$C_6$ alkyl).

53. The compound of claim 52 or the pharmaceutically acceptable salt thereof, the tautomer thereof, the pharmaceutically acceptable salt of the tautomer, the stereoisomer of any of the foregoing, or the mixture thereof, wherein:

$R^{3d}$ and $R^{3e}$ are independently selected from —H, —$C_1$-$C_6$ alkyl, or —($C_1$-$C_6$ alkyl)-OH; and $R^{3f}$ and $R^{3g}$ are independently selected from —H, —$C_1$-$C_6$ alkyl, —OH, or —O—($C_1$-$C_6$ alkyl).

54. The compound of claim 52 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is not —H.

55. The compound of claim 52 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is —$CH_3$.

56. The compound of claim 52 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, or —$CH_3$.

57. The compound of claim 1, wherein the compound has the Formula IB

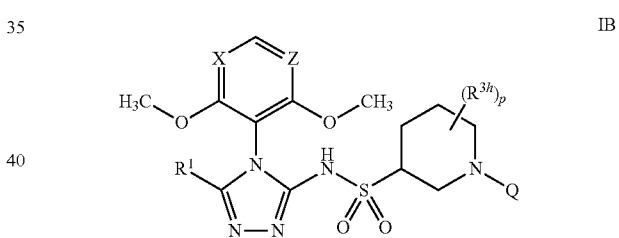

IB or is the pharmaceutically acceptable salt thereof, the tautomer thereof, the pharmaceutically acceptable salt of the tautomer, the stereoisomer of any of the foregoing, or the mixture thereof, wherein:

$R^1$ is as defined in claim 1;

X is selected from CH or N;

Z is selected from CH or N;

$R^{3h}$ is independently selected from —OH, or —O—($C_1$-$C_6$ alkyl);

the subscript p is selected from 0, 1, 2, or 3;

Q is a phenyl group or a monocyclic heteroaryl group with 6 ring members containing 1 or 2 N heteroatoms, wherein the phenyl and the monocyclic heteroaryl Q groups are unsubstituted or are substituted with 1, 2, or 3 $R^Q$ substituent; and $R^Q$ is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), —($C_1$-$C_6$ alkyl)-$NH_2$ or —$S(=O)_2$—($C_1$-$C_6$ alkyl).

58. The compound of claim 57 or the pharmaceutically acceptable salt thereof, the tautomer thereof, the pharmaceutically acceptable salt of the tautomer, the stereoisomer of any of the foregoing, or the mixture thereof, wherein p is 0 or 1 and $R^{3h}$ is selected from —OH, —OCH$_3$, —OCH$_2$CH$_3$, or —OCH(CH$_3$)$_2$.

59. The compound of claim 52 or the pharmaceutically acceptable salt thereof, the tautomer thereof, the pharmaceutically acceptable salt of the tautomer, the stereoisomer of any of the foregoing, or the mixture thereof, wherein:
X is CH;
Z is CH; and
Q is a phenyl, a pyrimidinyl, a pyridinyl, or a pyrazinyl any of which are unsubstituted or are substituted with 1, 2, or 3 $R^Q$ substituent.

60. The compound of claim 52 or the pharmaceutically acceptable salt thereof, the tautomer thereof, the pharmaceutically acceptable salt of the tautomer, the stereoisomer of any of the foregoing, or the mixture thereof, wherein:
X is N;
Z is N; and
Q is a phenyl, a pyrimidinyl, a pyridinyl, or a pyrazinyl any of which are unsubstituted or are substituted with 1, 2, or 3 $R^Q$ substituent.

61. The compound of claim 52 or the pharmaceutically acceptable salt thereof, the tautomer thereof, the pharmaceutically acceptable salt of the tautomer, the stereoisomer of any of the foregoing, or the mixture thereof, wherein $R^1$ is selected from tetrahydrofuranyl, tetrahydropyranyl, oxetanyl, dioxanyl, pyrrolidinyl, piperidinyl, dioxotetrahydrothiopyranyl, dioxotetrahydrothiophenyl, morpholinyl, dioxolanyl, or tetrahydrothiophenyl, any of which may unsubstituted or substituted with 1, 2, or 3 independently selected $R^{1a}$ substituents.

62. The compound of claim 1, wherein the compound is selected from
(S)-2-(2-cyano-4-fluorophenyl)-N-(4-(2,6-dimethoxyphenyl)-5-(tetrahydrofuran-3-yl)-4H-1,2,4-triazol-3-yl)ethanesulfonamide;
(1R,2S)-1-(5-chloro-2-pyrimidinyl)-N-(4-(2,6-dimethoxyphenyl)-5-((3aR,6aR)-hexahydro-3aH-cyclopenta[b]furan-3a-yl)-4H-1,2,4-triazol-3-yl)-1-methoxy-2-propane sulfonamide;
(1R,2S)-1-(5-chloro-2-pyrimidinyl)-N-(4-(2,6-dimethoxyphenyl)-5-((3aS,6aS)-hexahydro-3aH-cyclopenta[b]furan-3a-yl)-4H-1,2,4-triazol-3-yl)-1-methoxy-2-propanesulfonamide;
(1R)—N-(4-(2,6-dimethoxyphenyl)-5-((2S)-tetrahydro-2-furanyl)-4H-1,2,4-triazol-3-yl)-1-phenylethanesulfonamide;
(1S)—N-(4-(2,6-dimethoxyphenyl)-5-((2R)-tetrahydro-2-furanyl)-4H-1,2,4-triazol-3-yl)-1-phenylethanesulfonamide;
(1S,2S)-1-(5-chloro-2-pyrimidinyl)-N-(4-cyclopropyl-5-((2S,5S)-5-methyltetrahydro-2-furanyl)-4H-1,2,4-triazol-3-yl)-1-(2-propanyloxy)-2-propanesulfonamide;
(1S,2S)-1-(5-chloro-2-pyrimidinyl)-N-(4-cyclopropyl-5-((2R,5R)-5-methyltetrahydro-2-furanyl)-4H-1,2,4-triazol-3-yl)-1-(2-propanyloxy)-2-propanesulfonamide;
(1S,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-(2-propanyloxy)-2-propanesulfonamide;
(1S,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-(2-propanyloxy)-2-propanesulfonamide;
(1S,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1-(2-propanyloxy)-2-propanesulfonamide;
(1S,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1-(2-propanyloxy)-2-propanesulfonamide;
(1S,2S)—N-(4-(1,3-dimethoxy-2-propanyl)-5-((2S,5S)-5-methyltetrahydro-2-furanyl)-4H-1,2,4-triazol-3-yl)-1-(5-methyl-2-pyrimidinyl)-1-(2-propanyloxy)-2-propanesulfonamide;
(1S,2S)—N-(4-(1,3-dimethoxy-2-propanyl)-5-((2R,5R)-5-methyltetrahydro-2-furanyl)-4H-1,2,4-triazol-3-yl)-1-(5-methyl-2-pyrimidinyl)-1-(2-propanyloxy)-2-propanesulfonamide;
(1S,2S)—N-(4-(1,3-dimethoxy-2-propanyl)-5-((2S,5S)-5-methyltetrahydro-2-furanyl)-4H-2,4-triazol-3-yl)-1-(5-fluoro-2-pyrimidinyl)-1-(2-propanyloxy)-2-propanesulfonamide;
(1S,2S)—N-(4-(1,3-dimethoxy-2-propanyl)-5-((2R,5R)-5-methyltetrahydro-2-furanyl)-4H-1,2,4-triazol-3-yl)-1-(5-fluoro-2-pyrimidinyl)-1-(2-propanyloxy)-2-propanesulfonamide;
(1S,2S)—N-(4-(1,3-dimethoxy-2-propanyl)-5-((2S,5S)-5-methyltetrahydro-2-furanyl)-4H-2,4-triazol-3-yl)-1-(5-methoxy-2-pyrimidinyl)-1-(2-propanyloxy)-2-propanesulfonamide;
(1S,2S)—N-(4-(1,3-dimethoxy-2-propanyl)-5-((2R,5R)-5-methyltetrahydro-2-furanyl)-4H-1,2,4-triazol-3-yl)-1-(5-methoxy-2-pyrimidinyl)-1-(2-propanyloxy)-2-propanesulfonamide;
(1S,2S)—N-(4-(1,3-dimethoxy-2-propanyl)-5-((2S,5S)-5-methyltetrahydro-2-furanyl)-4H-1,2,4-triazol-3-yl)-1-(5-methyl-2-pyrazinyl)-1-(2-propanyloxy)-2-propane sulfonamide;
(1S,2S)—N-(4-(1,3-dimethoxy-2-propanyl)-5-((2R,5R)-5-methyltetrahydro-2-furanyl)-4H-1,2,4-triazol-3-yl)-1-(5-methyl-2-pyrazinyl)-1-(2-propanyloxy)-2-propane sulfonamide;
(1S,2S)—N-(4-(1,3-dimethoxy-2-propanyl)-5-((2S,5S)-5-methyltetrahydro-2-furanyl)-4H-1,2,4-triazol-3-yl)-1-(5-methyl-2-pyridinyl)-1-(2-propanyloxy)-2-propanesulfonamide;
(1S,2S)—N-(4-(1,3-dimethoxy-2-propanyl)-5-((2R,5R)-5-methyltetrahydro-2-furanyl)-4H-1,2,4-triazol-3-yl)-1-(5-methyl-2-pyridinyl)-1-(2-propanyloxy)-2-propanesulfonamide;
(2S,3R)—N-(4-(1,3-dimethoxy-2-propanyl)-5-((2S,5S)-5-methyltetrahydro-2-furanyl)-4H-1,2,4-triazol-3-yl)-3-(5-fluoro-2-pyrimidinyl)-2-butanesulfonamide;
(2S,3R)—N-(4-(1,3-dimethoxy-2-propanyl)-5-((2R,5R)-5-methyltetrahydro-2-furanyl)-4H-1,2,4-triazol-3-yl)-3-(5-fluoro-2-pyrimidinyl)-2-butanesulfonamide;
(2S,3R)—N-(4-(1,3-dimethoxy-2-propanyl)-5-((2S,5S)-5-methyltetrahydro-2-furanyl)-4H-1,2,4-triazol-3-yl)-3-(5-methoxy-2-pyrimidinyl)-2-butanesulfonamide;
(2S,3R)—N-(4-(1,3-dimethoxy-2-propanyl)-5-((2R,5R)-5-methyltetrahydro-2-furanyl)-4H-1,2,4-triazol-3-yl)-3-(5-methoxy-2-pyrimidinyl)-2-butanesulfonamide;
(2S,3R)-3-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-2-butanesulfonamide;
(2S,3R)-3-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-2-butanesulfonamide;

(2S,3R)-3-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-2-butanesulfonamide;

(2S,3R)-3-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-2-butanesulfonamide;

(2S,3R)—N-(4-(1,3-dimethoxy-2-propanyl)-5-((2S,5S)-5-methyltetrahydro-2-furanyl)-4H-1,2,4-triazol-3-yl)-3-(5-methoxy-2-pyrazinyl)-2-butanesulfonamide;

(2S,3R)—N-(4-(1,3-dimethoxy-2-propanyl)-5-((2R,5R)-5-methyltetrahydro-2-furanyl)-4H-1,2,4-triazol-3-yl)-3-(5-methoxy-2-pyrazinyl)-2-butanesulfonamide;

(1R,2S)—N-(4-(1,3-dimethoxy-2-propanyl)-5-((2S,5S)-5-methyltetrahydro-2-furanyl)-4H-1,2,4-triazol-3-yl)-1-methoxy-1-(5-methoxy-2-pyrazinyl)-2-propanesulfonamide;

(1R,2S)—N-(4-(1,3-dimethoxy-2-propanyl)-5-((2R,5R)-5-methyltetrahydro-2-furanyl)-4H-1,2,4-triazol-3-yl)-1-methoxy-1-(5-methoxy-2-pyrazinyl)-2-propanesulfonamide;

(1R,2S)-1-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide;

(1R,2S)-1-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide;

(2S,3R)-3-(5-cyano-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide;

(2S,3R)-3-(5-cyano-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide;

2-(5-chloro-2-pyrimidinyl)-N-(4-(2,6-dimethoxyphenyl)-5-((3S)-tetrahydro-2-furanyl)-4H-1,2,4-triazol-3-yl)ethane sulfonamide;

2-(5-chloro-2-pyrimidinyl)-N-(4-(2,6-dimethoxyphenyl)-5-((2S)-tetrahydro-2-furanyl)-4H-1,2,4-triazol-3-yl)ethane sulfonamide;

2-(5-chloro-2-pyrimidinyl)-N-(4-(2,6-dimethoxyphenyl)-5-((2R)-tetrahydro-2-furanyl)-4H-1,2,4-triazol-3-yl)ethane sulfonamide;

2-(5-chloro-2-pyrimidinyl)-N-(4-(2,6-dimethoxyphenyl)-5-((3R)-tetrahydro-3-furanyl)-4H-1,2,4-triazol-3-yl)ethane sulfonamide;

(2S,3R)-3-(5-chloro-2-pyrimidinyl)-N-(4-(2,6-dimethoxyphenyl)-5-((3R)-5,5-dimethyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3S)-5,5-dimethyltetrahydro-3-furanyl)-4H-1,2,4-triazol-3-yl)-2-butanesulfonamide;

(2S,3R)—N-(4-(2,6-dimethoxyphenyl)-5-((3R)-5,5-dimethyltetrahydro-3-furanyl)-4H-1,2,4-triazol-3-yl)-3-(5-fluoro-2-pyrimidinyl)-2-butanesulfonamide;

(2S,3R)—N-(4-(2,6-dimethoxyphenyl)-5-((3S)-5,5-dimethyltetrahydro-3-furanyl)-4H-1,2,4-triazol-3-yl)-3-(5-fluoro-2-pyrimidinyl)-2-butanesulfonamide;

(1R,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1l-methoxy-2-propanesulfonamide;

(1R,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1l-methoxy-2-propanesulfonamide;

(1S,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1-(2-propanyloxy)-2-propanesulfonamide;

(1R,2S)-1-(5-chloro-2-pyrimidinyl)-1-methoxy-N-(4-(1,2-oxazol-3-ylmethyl)-5-((3R)-tetrahydro-3-furanyl)-4H-1,2,4-triazol-3-yl)-2-propane sulfonamide;

(1R,2S)-1-(5-chloro-2-pyrimidinyl)-1-methoxy-N-(4-(1,2-oxazol-3-ylmethyl)-5-((3S)-tetrahydro-3-furanyl)-4H-1,2,4-triazol-3-yl)-2-propanesulfonamide;

(1R,2S)-1-(5-chloro-2-pyrimidinyl)-1-methoxy-N-(5-((2R,5R)-5-methyltetrahydro-2-furanyl)-4-(1,2-oxazol-3-ylmethyl)-4H-1,2,4-triazol-3-yl)-2-propanesulfonamide;

(1R,2S)-1-(5-chloro-2-pyrimidinyl)-1-methoxy-N-(5-((2S,5S)-5-methyltetrahydro-2-furanyl)-4-(1,2-oxazol-3-ylmethyl)-4H-1,2,4-triazol-3-yl)-2-propanesulfonamide;

(1R,2S)-1-(5-chloro-2-pyrimidinyl)-N-(4-(2,6-dimethoxyphenyl)-5-((2S)-1-methyl-5-oxo-2-pyrrolidinyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((2R)-1-methyl-5-oxo-2-pyrrolidinyl)-4H-1,2,4-triazol-3-yl)-1-methoxy-2-propanesulfonamide;

(1S,2S)—N-(4-(2,6-dimethoxyphenyl)-5-((3S)-tetrahydro-3-furanyl)-4H-1,2,4-triazol-3-yl)-1-(5-methyl-2-pyridinyl)-1-(2-propanyloxy)-2-propanesulfonamide;

(1S,2S)—N-(4-(2,6-dimethoxyphenyl)-5-((3R)-tetrahydro-3-furanyl)-4H-1,2,4-triazol-3-yl)-1-(5-methyl-2-pyridinyl)-1-(2-propanyloxy)-2-propanesulfonamide;

(2S,3R)-3-(5-chloro-2-pyridinyl)-N-(4-(2,6-dimethoxyphenyl)-5-((3S)-tetrahydro-3-furanyl)-4H-1,2,4-triazol-3-yl)-2-butanesulfonamide;

(2S,3R)-3-(5-chloro-2-pyridinyl)-N-(4-(2,6-dimethoxyphenyl)-5-((3R)-tetrahydro-3-furanyl)-4H-1,2,4-triazol-3-yl)-2-butanesulfonamide;

(1S,2S)—N-(4-(2,6-dimethoxyphenyl)-5-((3R)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1S,2S)—N-(4-(2,6-dimethoxyphenyl)-5-((3S)-5,5-dimethyltetrahydro-3-furanyl)-4H-1,2,4-triazol-3-yl)-1-(5-methyl-2-pyrimidinyl)-1-(2-propanyloxy)-2-propane sulfonamide;

(1S,2S)-1-(5-chloro-2-pyrimidinyl)-N-(4-(2,6-dimethoxyphenyl)-5-((2S)-5,5-dimethyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2R)-5,5-dimethyltetrahydro-2-furanyl)-4H-1,2,4-triazol-3-yl)-1-(2-propanyloxy)-2-propanesulfonamide;

(2S,3R)-3-(5-chloro-2-pyrimidinyl)-N-(4-((1R)-1-(1,2-oxazol-3-yl)ethyl)-5-((3S)-tetrahydro-3-furanyl)-4H-1,2,4-triazol-3-yl)-2-butanesulfonamide;

(2S,3R)-3-(5-chloro-2-pyrimidinyl)-N-(4-((1S)-1-(1,2-oxazol-3-yl)ethyl)-5-((3S)-tetrahydro-3-furanyl)-4H-1,2,4-triazol-3-yl)-2-butanesulfonamide;

(1S,2S)—N-(4-(2,6-dimethoxyphenyl)-5-((2S)-1-methyl-5-oxo-2-pyrrolidinyl)-4H-1,2,4-triazol-3-yl)-1-(5-methyl-2-pyrimidinyl)-1-(2-propanyloxy)-2-propanesulfonamide;

(1S,2S)—N-(4-(2,6-dimethoxyphenyl)-5-((2R)-1-methyl-5-oxo-2-pyrrolidinyl)-4H-1,2,4-triazol-3-yl)-1-(5-methyl-2-pyrimidinyl)-1-(2-propanyloxy)-2-propanesulfonamide;

(2S,3R)-3-(5-chloro-2-pyrimidinyl)-N-(4-(2,6-dimethoxyphenyl)-5-((2S)-1-methyl-5-oxo-2-pyrrolidinyl)-4H-1,2,4-triazol-3-yl)-2-butanesulfonamide;

2-(5-chloro-2-pyrimidinyl)-N-(4-(2,6-dimethoxyphenyl)-5-((2R)-1,4-dioxan-2-yl)-4H-1,2,4-triazol-3-yl)ethanesulfonamide;

2-(5-chloro-2-pyrimidinyl)-N-(4-(2,6-dimethoxyphenyl)-5-((2S)-1,4-dioxan-2-yl)-4H-1,2,4-triazol-3-yl)ethanesulfonamide;

(1S)—N-(4-(2,6-dimethoxyphenyl)-5-((2S)-tetrahydro-2-furanyl)-4H-1,2,4-triazol-3-yl)-1-(3-methoxyphenyl)ethanesulfonamide;

(1R)—N-(4-(2,6-dimethoxyphenyl)-5-((2R)-tetrahydro-2-furanyl)-4H-1,2,4-triazol-3-yl)-1-(3-methoxyphenyl)ethanesulfonamide;

(1R)—N-(4-(2,6-dimethoxyphenyl)-5-((2S)-tetrahydro-2-furanyl)-4H-1,2,4-triazol-3-yl)-1-(3-methoxyphenyl)ethanesulfonamide;

(1S)—N-(4-(2,6-dimethoxyphenyl)-5-((2R)-tetrahydro-2-furanyl)-4H-1,2,4-triazol-3-yl)-1-(3-methoxyphenyl)ethanesulfonamide;

(1S)—N-(4-(2,6-dimethoxyphenyl)-5-((2S)-tetrahydro-2-furanyl)-4H-1,2,4-triazol-3-yl)-1-(2-fluorophenyl)ethanesulfonamide;

(1R)—N-(4-(2,6-dimethoxyphenyl)-5-((2R)-tetrahydro-2-furanyl)-4H-1,2,4-triazol-3-yl)-1-(2-fluorophenyl)ethanesulfonamide;

(1R)—N-(4-(2,6-dimethoxyphenyl)-5-((2S)-tetrahydro-2-furanyl)-4H-1,2,4-triazol-3-yl)-1-(2-fluorophenyl)ethanesulfonamide;

(1S)—N-(4-(2,6-dimethoxyphenyl)-5-((2R)-tetrahydro-2-furanyl)-4H-1,2,4-triazol-3-yl)-1-(2-fluorophenyl)ethanesulfonamide;

(1R)—N-(4-(2,6-dimethoxyphenyl)-5-((2R)-tetrahydro-2-furanyl)-4H-1,2,4-triazol-3-yl)-1-phenylethanesulfonamide;

(1S)-1-(3-chlorophenyl)-N-(4-(2,6-dimethoxyphenyl)-5-((2S)-tetrahydro-2-furanyl)-4H-1,2,4-triazol-3-yl)ethanesulfonamide;

(1R)-1-(3-chlorophenyl)-N-(4-(2,6-dimethoxyphenyl)-5-((2R)-tetrahydro-2-furanyl)-4H-1,2,4-triazol-3-yl)ethanesulfonamide;

(1R)-1-(3-chlorophenyl)-N-(4-(2,6-dimethoxyphenyl)-5-((2S)-tetrahydro-2-furanyl)-4H-1,2,4-triazol-3-yl)ethanesulfonamide;

(1S)-1-(3-chlorophenyl)-N-(4-(2,6-dimethoxyphenyl)-5-((2R)-tetrahydro-2-furanyl)-4H-1,2,4-triazol-3-yl)ethanesulfonamide;

(2S,3R)-3-(5-chloro-2-pyrimidinyl)-N-(4-(2,6-dimethoxyphenyl)-5-((3S,5R)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3R,5R)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3S,5S)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3R,5S)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2S)-2-oxetanyl)-4H-1,2,4-triazol-3-yl)-2-butanesulfonamide;

(2S,3R)—N-(4-(2,6-bis((trideutero)methyloxy)phenyl)-5-((3S)-tetrahydro-3-furanyl)-4H-1,2,4-triazol-3-yl)-3-(5-chloro-2-pyrimidinyl)-2-butanesulfonamide; or (2S,3R)—N-(4-(2,6-bis((trideutero)methyloxy)phenyl)-5-((3R)-tetrahydro-3-furanyl)-4H-1,2,4-triazol-3-yl)-3-(5-chloro-2-pyrimidinyl)-2-butanesulfonamide; or the pharmaceutically acceptable salt thereof, or the mixture thereof.

63. A pharmaceutical composition, comprising the compound of claim 1 or the pharmaceutically acceptable salt thereof and at least one pharmaceutically acceptable excipient.

64. The pharmaceutical composition of claim 63, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

65. The pharmaceutical composition of claim 63, further comprising a therapeutic agent selected from an angiotensin converting enzyme (ACE) inhibitor or an angiotensin-receptor blocker (ARB).

66. A kit, the kit comprising: the compound of any claim 1 or the pharmaceutically acceptable salt thereof, the stereoisomer of any of the foregoing, or the mixture thereof.

67. The kit of claim 66, wherein the kit further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

* * * * *

UNITED STATES PATENT AND TRADEMARK OFFICE
CERTIFICATE OF CORRECTION

| | | |
|---|---|---|
| PATENT NO. | : 9,988,369 B2 | Page 1 of 11 |
| APPLICATION NO. | : 15/584109 | |
| DATED | : June 5, 2018 | |
| INVENTOR(S) | : Chen et al. | |

It is certified that error appears in the above-identified patent and that said Letters Patent is hereby corrected as shown below:

In the Claims

In Column 763 (Claim 33), the eighth and ninth structures in Column 763 (tenth and eleventh structures in Claim, replace the structures " 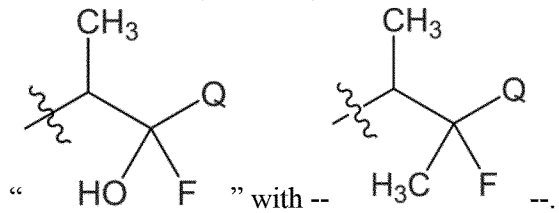 " with " 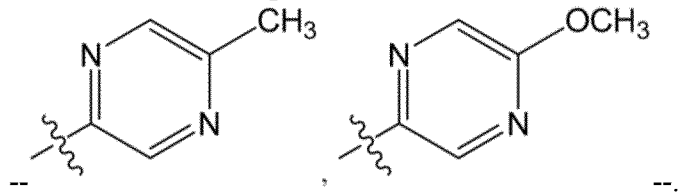 ".

In Claim 39, Column 766, Line 9, replace the phrase "$R^{3f}$, Or $R^{3g}$" with --$R^{3f}$, or $R^{3g}$--.

In Claim 40, Column 766, Line 10, replace the phrase "The compound of any one of claim 36" with --The compound of claim 36--.

In Claim 40, Column 766, Line 14, replace the phrase "$R^{3f}$, r $R^{3g}$" with --$R^{3f}$, or $R^{3g}$--.

In Column 768 (Claim 45), the second to last structure, replace the structure

"  " with --  --.

Signed and Sealed this
Twentieth Day of November, 2018

Andrei Iancu
*Director of the United States Patent and Trademark Office*

In Claim 48, Column 771, Lines 41-44, replace the phrase
"1 tert-butyl(3S)-3-(5-((((1S,2R)-2-(5-chloro-2-pyrimidinyl)-1-methylpropyl)sulfonyl)amino)-4-(2,6-dimethoxyphenyl)-4H-1,2,4-triazol-3-yl)-1-pyrrolidinecarboxylate" with
--tert-butyl(3S)-3-(5-((((1S,2R)-2-(5-chloro-2-pyrimidinyl)-1-methylpropyl)sulfonyl)amino)-4-(2,6-dimethoxyphenyl)-4H-1,2,4-triazol-3-yl)-1-pyrrolidinecarboxylate--.

In Claim 48, Column 776, Lines 43-45, replace the phrase
"(R)-2-(2-cyano-4-fluorophenyl)-N-(4-(2,6-dimethoxyphenyl)-5-(tetrahydrofuran-2-yl)-4H-1,2,4-triazol-3-yl)ethane sulfonamide" with
--(R)-2-(2-cyano-4-fluorophenyl)-N-(4-(2,6-dimethoxyphenyl)-5-(tetrahydrofuran-2-yl)-4H-1,2,4-triazol-3-yl)ethanesulfonamide--.

In Claim 52, Column 791, Lines 60-61, replace the phrase "or -O-($C_2$-$C_5$ alkenyl)" with
--or -O-($C_2$-$C_6$ alkenyl);--.

In Claim 51, Column 785, Line 47 through Column 791, Line 33, replace in its entirety with the following:
--51. The compound of claim 1, wherein the compound is selected from
(2S,3R)-3-(5-chloro-2-pyrimidinyl)-N-(4-(2,6-dimethoxyphenyl)-5-((1S)-3-oxo-2,3-dihydro-1H-isoindol-1-yl)-4H-1,2,4-triazol-3-yl)-2-butanesulfonamide;
(2S,3R)-3-(5-chloro-2-pyrimidinyl)-N-(4-(2,6-dimethoxyphenyl)-5-((1R)-3-oxo-2,3-dihydro-1H-isoindol-1-yl)-4H-1,2,4-triazol-3-yl)-2-butanesulfonamide;
(1R,2S)-N-(4-(2,6-dimethoxyphenyl)-5-((1R)-3-oxo-2,3-dihydro-1H-isoindol-1-yl)-4H-1,2,4-triazol-3-yl)-1-methoxy-1-(5-methyl-2-pyrimidinyl)-2-propanesulfonamide;
(1R,2S)-N-(4-(2,6-dimethoxyphenyl)-5-((1S)-3-oxo-2,3-dihydro-1H-isoindol-1-yl)-4H-1,2,4-triazol-3-yl)-1-methoxy-1-(5-methyl-2-pyrimidinyl)-2-propanesulfonamide;
(1R,2S)-N-(5-((3S)-2,3-dihydro-1-benzofuran-3-yl)-4-(2,6-dimethoxyphenyl)-4H-1,2,4-triazol-3-yl)-1-methoxy-1-(5-methyl-2-pyrimidinyl)-2-propanesulfonamide;
(1R,2S)-N-(5-((3R)-2,3-dihydro-1-benzofuran-3-yl)-4-(2,6-dimethoxyphenyl)-4H-1,2,4-triazol-3-yl)-1-methoxy-1-(5-methyl-2-pyrimidinyl)-2-propanesulfonamide;
(1R,2S)-1-(5-chloro-2-pyrimidinyl)-1-methoxy-N-(4-(2-methoxyphenyl)-5-((2S)-tetrahydro-2-furanyl)-4H-1,2,4-triazol-3-yl)-2-propanesulfonamide;
(1R,2S)-1-(5-chloro-2-pyrimidinyl)-N-(4-(2-ethylphenyl)-5-((2S)-tetrahydro-2-furanyl)-4H-1,2,4-triazol-3-yl)-1-methoxy-2-propanesulfonamide;
(1R,2S)-1-(5-chloro-2-pyrimidinyl)-1-methoxy-N-(4-(2-methylphenyl)-5-((2S)-tetrahydro-2-furanyl)-4H-1,2,4-triazol-3-yl)-2-propanesulfonamide;
(1R,2S)-N-(4-(2-chlorophenyl)-5-((2S)-tetrahydro-2-furanyl)-4H-1,2,4-triazol-3-yl)-1-(5-chloro-2-pyrimidinyl)-1-methoxy-2-propanesulfonamide;
(1R,2S)-1-(5-chloro-2-pyrimidinyl)-N-(4-(2-fluorophenyl)-5-((2S)-tetrahydro-2-furanyl)-4H-1,2,4-triazol-3-yl)-1-methoxy-2-propanesulfonamide;
(2S,3R)-3-(5-chloro-2-pyrimidinyl)-N-(5-((2R)-1,4-dioxan-2-yl)-4-(tetrahydro-2H-pyran-4-yl)-4H-1,2,4-triazol-3-yl)-2-butanesulfonamide;
(2S,3R)-3-(5-chloro-2-pyrimidinyl)-N-(5-((2S)-1,4-dioxan-2-yl)-4-(tetrahydro-2H-pyran-4-yl)-4H-1,2,4-triazol-3-yl)-2-butanesulfonamide;
(1R,2S)-1-(5-chloro-2-pyrimidinyl)-N-(5-((2R)-1,4-dioxan-2-yl)-4-(tetrahydro-2H-pyran-4-yl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(tetrahydro-2H-pyran-4-yl)-4H-1,2,4-triazol-3-yl)-1-methoxy-2-propanesulfonamide;

(2S,3R)-N-(4-(2,6-dimethoxyphenyl)-5-((2R,5R)-5-methyltetrahydro-2-furanyl)-4H-1,2,4-triazol-3-yl)-3-(5-methoxy-2-pyrimidinyl)-2-butanesulfonamide;

(2S,3R)-N-(4-(2,6-dimethoxyphenyl)-5-((2S,5S)-5-methyltetrahydro-2-furanyl)-4H-1,2,4-triazol-3-yl)-3-(5-methoxy-2-pyrimidinyl)-2-butanesulfonamide;

(1R,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide;

(2S,3R)-3-(5-chloro-2-pyrimidinyl)-N-(4-(3,5-dibromo-2,6-dimethoxyphenyl)-5-((3S)-tetrahydro-3-furanyl)-4H-1,2,4-triazol-3-yl)-2-butanesulfonamide;

(1S,2S)-N-(4-(2,6-dimethoxyphenyl)-5-((2S)-1,4-dioxan-2-yl)-4H-1,2,4-triazol-3-yl)-1-(1-methylethoxy)-1-(5-methyl-2-pyrimidinyl)-2-propanesulfonamide;

(1S,2S)-N-(4-(2,6-dimethoxyphenyl)-5-((2R)-1,4-dioxan-2-yl)-4H-1,2,4-triazol-3-yl)-1-(1-methylethoxy)-1-(5-methyl-2-pyrimidinyl)-2-propanesulfonamide;

(2S,3R)-N-(4-(2,6-dimethoxyphenyl)-5-((3R,8aR)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(2S,3R)-N-(4-(2,6-dimethoxyphenyl)-5-((3R,8aS)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(2S,3R)-N-(4-(2,6-dimethoxyphenyl)-5-((3S,8aR)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(2S,3R)-N-(4-(2,6-dimethoxyphenyl)-5-((3S,8aS)-hexahydro-1H-pyrrolo[2,1-c][1,4]oxazin-3-yl)-4H-1,2,4-triazol-3-yl)-3-(5-methyl-2-pyrimidinyl)-2-butanesulfonamide;

(1R,2S)-1-(5-chloro-2-pyrimidinyl)-N-(5-((2R)-2,3-dihydro-1,4-benzodioxin-2-yl)-4-(2,6-dimethoxyphenyl)-4H-1,2,4-triazol-3-yl)-1-methoxy-2-propanesulfonamide;

(1R,2S)-1-(5-chloro-2-pyrimidinyl)-N-(5-((2S)-2,3-dihydro-1,4-benzodioxin-2-yl)-4-(2,6-dimethoxyphenyl)-4H-1,2,4-triazol-3-yl)-1-methoxy-2-propanesulfonamide;

(1S,2S)-1-(1-methylethoxy)-1-(5-methyl-2-pyrazinyl)-N-(5-((2S)-tetrahydro-2-furanyl)-4-(tetrahydro-2H-pyran-4-yl)-4H-1,2,4-triazol-3-yl)-2-propanesulfonamide;

(1S,2S)-1-(1-methylethoxy)-1-(5-methyl-2-pyrazinyl)-N-(5-((2R)-tetrahydro-2-furanyl)-4-(tetrahydro-2H-pyran-4-yl)-4H-1,2,4-triazol-3-yl)-2-propanesulfonamide;

(1S,2S)-1-(1-methylethoxy)-1-(5-methyl-2-pyrazinyl)-N-(5-((2S,5S)-5-methyltetrahydro-2-furanyl)-4-(tetrahydro-2H-pyran-4-yl)-4H-1,2,4-triazol-3-yl)-2-propanesulfonamide;

(1S,2S)-1-(1-methylethoxy)-1-(5-methyl-2-pyrazinyl)-N-(5-((2R,5R)-5-methyltetrahydro-2-furanyl)-4-(tetrahydro-2H-pyran-4-yl)-4H-1,2,4-triazol-3-yl)-2-propanesulfonamide;

(1R,2S)-1-(5-chloro-2-pyridinyl)-N-(4-(2,6-dimethoxyphenyl)-5-((2R)-1,4-dioxan-2-yl)-4H-1,2,4-triazol-3-yl)-1-methoxy-2-propanesulfonamide;

(1R,2S)-1-(5-chloro-2-pyridinyl)-N-(4-(2,6-dimethoxyphenyl)-5-((2S)-1,4-dioxan-2-yl)-4H-1,2,4-triazol-3-yl)-1-methoxy-2-propanesulfonamide;

(1R,2R)-N-(4-(2,6-dimethoxyphenyl)-5-((2S)-1,4-dioxan-2-yl)-4H-1,2,4-triazol-3-yl)-1-imidazo[1,2-a]pyridin-2-yl-1-(1-methylethoxy)-2-propanesulfonamide;

(2S,3R)-3-(5-chloro-2-pyridinyl)-N-(4-(2,6-dimethoxyphenyl)-5-((2R)-1,4-dioxan-2-yl)-4H-1,2,4-triazol-3-yl)-2-butanesulfonamide;

(2S,3R)-3-(5-chloro-2-pyridinyl)-N-(4-(2,6-dimethoxyphenyl)-5-((2S)-1,4-dioxan-2-yl)-4H-1,2,4-triazol-3-yl)-2-butanesulfonamide;

(2S,3R)-N-(4-(2,6-dimethoxyphenyl)-5-((3R)-1-methyl-3-piperidinyl)-4H-1,2,4-triazol-3-yl)-3-(5-methyl-2-pyrimidinyl)-2-butanesulfonamide;

(2S,3R)-N-(4-(2,6-dimethoxyphenyl)-5-((3S)-1-methyl-3-piperidinyl)-4H-1,2,4-triazol-3-yl)-3-(5-methyl-2-pyrimidinyl)-2-butanesulfonamide;

(1R,2S)-1-(5-chloro-2-pyrimidinyl)-N-(5-((2R)-1,4-dioxan-2-yl)-4-(1-methylcyclopropyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(1-methylcyclopropyl)-4H-1,2,4-triazol-3-yl)-1-methoxy-2-propanesulfonamide;

(2S,3R)-N-(4-(2,6-dimethoxyphenyl)-5-((3R)-tetrahydro-3-furanyl)-4H-1,2,4-triazol-3-yl)-3-(5-fluoro-2-pyrimidinyl)-2-butanesulfonamide;

(2S,3R)-N-(4-(2,6-dimethoxyphenyl)-5-((3S)-tetrahydro-3-furanyl)-4H-1,2,4-triazol-3-yl)-3-(5-fluoro-2-pyrimidinyl)-2-butanesulfonamide;

(2S,3R)-N-(4-(2,6-dimethoxyphenyl)-5-((2R)-1,4-dioxan-2-yl)-4H-1,2,4-triazol-3-yl)-3-(5-fluoro-2-pyrimidinyl)-2-butanesulfonamide;

(2S,3R)-N-(4-(2,6-dimethoxyphenyl)-5-((2S)-1,4-dioxan-2-yl)-4H-1,2,4-triazol-3-yl)-3-(5-fluoro-2-pyrimidinyl)-2-butanesulfonamide;

(2S,3R)-N-(4-(4,6-dimethoxy-5-pyrimidinyl)-5-((2R)-1,4-dioxan-2-yl)-4H-1,2,4-triazol-3-yl)-3-(5-fluoro-2-pyrimidinyl)-2-butanesulfonamide;

(2S,3R)-N-(4-(4,6-dimethoxy-5-pyrimidinyl)-5-((2S)-1,4-dioxan-2-yl)-4H-1,2,4-triazol-3-yl)-3-(5-fluoro-2-pyrimidinyl)-2-butanesulfonamide;

(1S,2S)-1-(5-chloro-2-pyrimidinyl)-N-(4-(4,6-dimethoxy-5-pyrimidinyl)-5-((2S)-5,5-dimethyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(4,6-dimethoxy-5-pyrimidinyl)-5-((2R)-5,5-dimethyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((3R)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((3S)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2R)-1,4-dioxan-2-yl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2S)-1,4-dioxan-2-yl)-4H-1,2,4-triazol-3-yl)-1-(2-propanyloxy)-2-propanesulfonamide;

(1R,2S)-1-(5-chloro-2-pyrimidinyl)-1-methoxy-N-(4-(1-(methoxymethyl)cyclopropyl)-5-((2S,5S)-5-methyltetrahydro-2-furanyl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-((2R,5R)-5-methyltetrahydro-2-furanyl)-4H-1,2,4-triazol-3-yl)-2-propanesulfonamide;

(1R,2S)-1-(5-chloro-2-pyrimidinyl)-N-(5-((2S)-5,5-dimethyltetrahydro-2-furanyl)-4-(2-methoxyethyl)-4H-1,2,4-triazol-3-yl)-1-methoxy-2-propanesulfonamide;

(1R,2S)-1-(5-chloro-2-pyrimidinyl)-N-(5-((2R)-5,5-dimethyltetrahydro-2-furanyl)-4-(2-methoxyethyl)-4H-1,2,4-triazol-3-yl)-1-methoxy-2-propanesulfonamide;

(1R,2S)-1-(5-chloro-2-pyrimidinyl)-N-(5-((2S)-5,5-dimethyltetrahydro-2-furanyl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(5-((2R)-5,5-dimethyltetrahydro-2-furanyl)-4-(1-(methoxymethyl)cyclopropyl)-4H-1,2,4-triazol-3-yl)-1-methoxy-2-propanesulfonamide;

(1S,2S)-1-(5-chloro-2-pyrimidinyl)-N-(4-(4,6-dimethoxy-5-pyrimidinyl)-5-((3S)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(4,6-dimethoxy-5-pyrimidinyl)-5-((3R)-tetrahydro-3-furanyl)-4H-1,2,4-triazol-3-yl)-1-(2-propanyloxy)-2-propanesulfonamide;

(1R,2S)-1-(5-chloro-2-pyrimidinyl)-N-(4-(2,6-dimethoxyphenyl)-5-((3R)-1-methyl-5-oxo-3-pyrrolidinyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((3S)-1-methyl-5-oxo-3-pyrrolidinyl)-4H-1,2,4-triazol-3-yl)-1-methoxy-2-propanesulfonamide;

(1R,2S)-1-(5-chloro-2-pyrimidinyl)-N-(5-((2R)-1,4-dioxan-2-yl)-4-(1-(3-pyridinyl)cyclopropyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(1-(3-pyridinyl)cyclopropyl)-4H-1,2,4-triazol-3-yl)-1-methoxy-2-propanesulfonamide;

(1R,2S)-1-(5-chloro-2-pyrimidinyl)-1-methoxy-N-(4-(2-propanyl)-5-((3R)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(2-propanyl)-5-((3S)-tetrahydro-3-furanyl)-4H-1,2,4-triazol-3-yl)-2-propanesulfonamide;

(1R,2S)-1-(5-chloro-2-pyrimidinyl)-N-(5-((2S)-5,5-dimethyltetrahydro-2-furanyl)-4-(2-propanyl)-4H-1,2,4-triazol-3-yl)-1-methoxy-2-propanesulfonamide;

(1R,2S)-1-(5-chloro-2-pyrimidinyl)-N-(5-((2R)-5,5-dimethyltetrahydro-2-furanyl)-4-(2-propanyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(2-propanyl)-4H-1,2,4-triazol-3-yl)-1-methoxy-2-propanesulfonamide;

(1R,2S)-1-(5-chloro-2-pyrimidinyl)-N-(5-((2R)-1,4-dioxan-2-yl)-4-(2-propanyl)-4H-1,2,4-triazol-3-yl)-1-methoxy-2-propanesulfonamide;

(1R,2S)-1-(5-chloro-2-pyrimidinyl)-1-methoxy-N-(4-(1-(methoxymethyl)cyclopropyl)-5-((3R)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-((3S)-tetrahydro-3-furanyl)-4H-1,2,4-triazol-3-yl)-2-propanesulfonamide;

(1R,2S)-1-(5-chloro-2-pyrimidinyl)-N-(5-((2R)-1,4-dioxan-2-yl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((3S)-tetrahydro-3-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((3R)-tetrahydro-3-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2R)-5,5-dimethyltetrahydro-2-furanyl)-4H-1,2,4-triazol-3-yl)-1-methoxy-2-propanesulfonamide;

(1R,2S)-1-(5-chloro-2-pyrimidinyl)-N-(4-(1,3-dimethoxy-2-propanyl)-5-((2S)-5,5-dimethyltetrahydro-2-furanyl)-4H-1,2,4-triazol-3-yl)-1-methoxy-2-propanesulfonamide;

(1R,2S)-1-(5-chloro-2-pyrimidinyl)-1-methoxy-N-(4-(2-methoxyethyl)-5-((3S)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(2-methoxyethyl)-5-((3R)-tetrahydro-3-furanyl)-4H-1,2,4-triazol-3-yl)-2-propanesulfonamide;

(1R,2S)-1-(5-chloro-2-pyrimidinyl)-N-(5-((2S)-1,4-dioxan-2-yl)-4-(2-methoxyethyl)-4H-1,2,4-triazol-3-yl)-1-methoxy-2-propanesulfonamide;

(1R,2S)-1-(5-chloro-2-pyrimidinyl)-N-(5-((2R)-1,4-dioxan-2-yl)-4-(2-methoxyethyl)-4H-1,2,4-triazol-3-yl)-1-methoxy-2-propanesulfonamide;

(1S,2S)-N-(4-(4,6-dimethoxy-5-pyrimidinyl)-5-((3R)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1S,2S)-N-(4-(4,6-dimethoxy-5-pyrimidinyl)-5-((3S)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1R,2S)-1-(5-chloro-2-pyrimidinyl)-N-(4-(4,6-dimethoxy-5-pyrimidinyl)-5-((3R)-5,5-dimethyltetrahydro-3-furanyl)-4H-1,2,4-triazol-3-yl)-1-methoxy-2-propanesulfonamide;

(1R,2S)-1-(5-chloro-2-pyrimidinyl)-N-(4-(4,6-dimethoxy-5-pyrimidinyl)-5-((3S)-5,5-dimethyltetrahydro-3-furanyl)-4H-1,2,4-triazol-3-yl)-1-methoxy-2-propanesulfonamide;

(2S,3R)-3-(5-chloro-2-pyrimidinyl)-N-(4-(4,6-dimethoxy-5-pyrimidinyl)-5-((3R)-5,5-dimethyltetrahydro-3-furanyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-((3S)-5,5-dimethyltetrahydro-3-furanyl)-4H-1,2,4-triazol-3-yl)-2-butanesulfonamide;

(1S,2S)-1-(5-chloro-2-pyrimidinyl)-N-(4-(1-(methoxymethyl)cyclopropyl)-5-((3R)-tetrahydro-3-furanyl)-4H-1,2,4-triazol-3-yl)-1-(2-propanyloxy)-2-propanesulfonamide;

(1S,2S)-1-(5-chloro-2-pyrimidinyl)-N-(4-(1-(methoxymethyl)cyclopropyl)-5-((3S)-tetrahydro-3-furanyl)-4H-1,2,4-triazol-3-yl)-1-(2-propanyloxy)-2-propanesulfonamide;

(1S,2S)-N-(4-(4,6-dimethoxy-5-pyrimidinyl)-5-((3R)-tetrahydro-3-furanyl)-4H-1,2,4-triazol-3-yl)-1-(5-fluoro-2-pyrimidinyl)-1-(2-propanyloxy)-2-propanesulfonamide;

(1S,2S)-N-(4-(4,6-dimethoxy-5-pyrimidinyl)-5-((3S)-tetrahydro-3-furanyl)-4H-1,2,4-triazol-3-yl)-1-(5-fluoro-2-pyrimidinyl)-1-(2-propanyloxy)-2-propanesulfonamide;

(1S,2S)-N-(4-(4,6-dimethoxy-5-pyrimidinyl)-5-((3R)-tetrahydro-3-furanyl)-4H-1,2,4-triazol-3-yl)-1-(5-methyl-2-pyridinyl)-1-(2-propanyloxy)-2-propanesulfonamide;

(1S,2S)-N-(4-(4,6-dimethoxy-5-pyrimidinyl)-5-((3S)-tetrahydro-3-furanyl)-4H-1,2,4-triazol-3-yl)-1-(5-methyl-2-pyridinyl)-1-(2-propanyloxy)-2-propanesulfonamide;

(1R,2S)-N-(4-([1,1'-bi(cyclopropyl)]-1-yl)-5-((2R)-1,4-dioxan-2-yl)-4H-1,2,4-triazol-3-yl)-1-(5-chloro-2-pyrimidinyl)-1-methoxy-2-propanesulfonamide;

(1R,2S)-N-(4-([1,1'-bi(cyclopropyl)]-1-yl)-5-((2S)-1,4-dioxan-2-yl)-4H-1,2,4-triazol-3-yl)-1-(5-chloro-2-pyrimidinyl)-1-methoxy-2-propanesulfonamide;

(1R,2S)-N-(4-([1,1'-bi(cyclopropyl)]-1-yl)-5-((2R)-1,4-dioxan-2-yl)-4H-1,2,4-triazol-3-yl)-1-methoxy-1-(5-methyl-2-pyrazinyl)-2-propanesulfonamide;

(1R,2S)-N-(4-([1,1'-bi(cyclopropyl)]-1-yl)-5-((2S)-1,4-dioxan-2-yl)-4H-1,2,4-triazol-3-yl)-1-methoxy-1-(5-methyl-2-pyrazinyl)-2-propanesulfonamide;

(1R,2S)-1-(5-chloro-2-pyrimidinyl)-N-(4-(1,3-dimethoxy-2-propanyl)-5-((2R)-tetrahydro-2-furanyl)-4H-1,2,4-triazol-3-yl)-1-methoxy-2-propanesulfonamide;

(2S,3R)-3-(5-chloro-2-pyrimidinyl)-N-(4-(3,5-dibromo-2,6-dimethoxyphenyl)-5-((3R)-tetrahydro-3-furanyl)-4H-1,2,4-triazol-3-yl)-2-butanesulfonamide;

(1R,2S)-1-(5-chloro-2-pyrimidinyl)-N-(4-(1,3-dimethoxy-2-propanyl)-5-((2S)-tetrahydro-2-furanyl)-4H-1,2,4-triazol-3-yl)-1-methoxy-2-propanesulfonamide;

(2S,3R)-N-(4-(2,6-dimethoxyphenyl)-5-((2R)-5,5-dimethyltetrahydro-2-furanyl)-4H-1,2,4-triazol-3-yl)-3-(5-fluoro-2-pyrimidinyl)-2-butanesulfonamide;

(2S,3R)-N-(4-(2,6-dimethoxyphenyl)-5-((2S)-5,5-dimethyltetrahydro-2-furanyl)-4H-1,2,4-triazol-3-yl)-3-(5-fluoro-2-pyrimidinyl)-2-butanesulfonamide;

(1R,2S)-1-(5-chloro-2-pyrimidinyl)-N-(5-((2R)-1,4-dioxan-2-yl)-4-(3-pentanyl)-4H-1,2,4-triazol-3-yl)-1-methoxy-2-propanesulfonamide;

(1R,2S)-1-(5-chloro-2-pyrimidinyl)-N-(5-((2S)-1,4-dioxan-2-yl)-4-(3-pentanyl)-4H-1,2,4-triazol-3-yl)-1-methoxy-2-propanesulfonamide;

(1R,2S)-1-(5-chloro-2-pyrimidinyl)-N-(4-(dicyclopropylmethyl)-5-((2R)-1,4-dioxan-2-yl)-4H-1,2,4-triazol-3-yl)-1-methoxy-2-propanesulfonamide;

(1R,2S)-1-(5-chloro-2-pyrimidinyl)-N-(4-(dicyclopropylmethyl)-5-((2S)-1,4-dioxan-2-yl)-4H-1,2,4-triazol-3-yl)-1-methoxy-2-propanesulfonamide;

(2S,3R)-3-(5-chloro-2-pyrimidinyl)-N-(4-(2,6-dimethoxyphenyl)-5-((2R)-5-oxo-2-pyrrolidinyl)-4H-1,2,4-triazol-3-yl)-2-butanesulfonamide; or (2S,3R)-3-(5-chloro-2-pyrimidinyl)-N-(4-(2,6-dimethoxyphenyl)-5-((2S)-5-oxo-2-pyrrolidinyl)-4H-1,2,4-triazol-3-yl)-2-butanesulfonamide; or
the pharmaceutically acceptable salt thereof, or the mixture thereof--.

In Claim 62, Column 793, Line 32 through Column 798, Line 26, replace in its entirety with the following:
--62. The compound of claim 1, wherein the compound is selected from (S)-2-(2-cyano-4-fluorophenyl)-N-(4-(2,6-dimethoxyphenyl)-5-(tetrahydrofuran-3-yl)-4H-1,2,4-triazol-3-yl)ethanesulfonamide;

(1R,2S)-1-(5-chloro-2-pyrimidinyl)-N-(4-(2,6-dimethoxyphenyl)-5-((3aR,6aR)-hexahydro-3aH-cyclopenta[b]furan-3a-yl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((3aS,6aS)-hexahydro-3aH-cyclopenta[b]furan-3a-yl)-4H-1,2,4-triazol-3-yl)-1-methoxy-2-propanesulfonamide;

(1R)-N-(4-(2,6-dimethoxyphenyl)-5-((2S)-tetrahydro-2-furanyl)-4H-1,2,4-triazol-3-yl)-1-phenylethanesulfonamide;

(1S)-N-(4-(2,6-dimethoxyphenyl)-5-((2R)-tetrahydro-2-furanyl)-4H-1,2,4-triazol-3-yl)-1-phenylethanesulfonamide;

(1S,2S)-1-(5-chloro-2-pyrimidinyl)-N-(4-cyclopropyl-5-((2S,5S)-5-methyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-cyclopropyl-5-((2R,5R)-5-methyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(1,3-dimethoxy-2-propanyl)-5-((2R)-1,4-dioxan-2-yl)-4H-1,2,4-triazol-3-yl)-1-(2-propanyloxy)-2-propanesulfonamide;

(1S,2S)-1-(5-chloro-2-pyrimidinyl)-N-(4-(1,3-dimethoxy-2-propanyl)-5-((2S)-1,4-dioxan-2-yl)-4H-1,2,4-triazol-3-yl)-1-(2-propanyloxy)-2-propanesulfonamide;

(1S,2S)-N-(4-(1,3-dimethoxy-2-propanyl)-5-((2S,5S)-5-methyltetrahydro-2-furanyl)-4H-1,2,4-triazol-3-yl)-1-(5-methyl-2-pyrimidinyl)-1-(2-propanyloxy)-2-propanesulfonamide;

(1S,2S)-N-(4-(1,3-dimethoxy-2-propanyl)-5-((2R,5R)-5-methyltetrahydro-2-furanyl)-4H-1,2,4-triazol-3-yl)-1-(5-methyl-2-pyrimidinyl)-1-(2-propanyloxy)-2-propanesulfonamide;

(1S,2S)-N-(4-(1,3-dimethoxy-2-propanyl)-5-((2S,5S)-5-methyltetrahydro-2-furanyl)-4H-1,2,4-triazol-3-yl)-1-(5-fluoro-2-pyrimidinyl)-1-(2-propanyloxy)-2-propanesulfonamide;

(1S,2S)-N-(4-(1,3-dimethoxy-2-propanyl)-5-((2R,5R)-5-methyltetrahydro-2-furanyl)-4H-1,2,4-triazol-3-yl)-1-(5-fluoro-2-pyrimidinyl)-1-(2-propanyloxy)-2-propanesulfonamide;

(1S,2S)-N-(4-(1,3-dimethoxy-2-propanyl)-5-((2S,5S)-5-methyltetrahydro-2-furanyl)-4H-1,2,4-triazol-3-yl)-1-(5-methoxy-2-pyrimidinyl)-1-(2-propanyloxy)-2-propanesulfonamide;

(1S,2S)-N-(4-(1,3-dimethoxy-2-propanyl)-5-((2R,5R)-5-methyltetrahydro-2-furanyl)-4H-1,2,4-triazol-3-yl)-1-(5-methoxy-2-pyrimidinyl)-1-(2-propanyloxy)-2-propanesulfonamide;

(1S,2S)-N-(4-(1,3-dimethoxy-2-propanyl)-5-((2S,5S)-5-methyltetrahydro-2-furanyl)-4H-1,2,4-triazol-3-yl)-1-(5-methyl-2-pyrazinyl)-1-(2-propanyloxy)-2-propanesulfonamide;

(1S,2S)-N-(4-(1,3-dimethoxy-2-propanyl)-5-((2R,5R)-5-methyltetrahydro-2-furanyl)-4H-1,2,4-triazol-3-yl)-1-(5-methyl-2-pyrazinyl)-1-(2-propanyloxy)-2-propanesulfonamide;

(1S,2S)-N-(4-(1,3-dimethoxy-2-propanyl)-5-((2S,5S)-5-methyltetrahydro-2-furanyl)-4H-1,2,4-triazol-3-yl)-1-(5-methyl-2-pyridinyl)-1-(2-propanyloxy)-2-propanesulfonamide;

(1S,2S)-N-(4-(1,3-dimethoxy-2-propanyl)-5-((2R,5R)-5-methyltetrahydro-2-furanyl)-4H-1,2,4-triazol-3-yl)-1-(5-methyl-2-pyridinyl)-1-(2-propanyloxy)-2-propanesulfonamide;

(2S,3R)-N-(4-(1,3-dimethoxy-2-propanyl)-5-((2S,5S)-5-methyltetrahydro-2-furanyl)-4H-1,2,4-triazol-3-yl)-3-(5-fluoro-2-pyrimidinyl)-2-butanesulfonamide;

(2S,3R)-N-(4-(1,3-dimethoxy-2-propanyl)-5-((2R,5R)-5-methyltetrahydro-2-furanyl)-4H-1,2,4-triazol-3-yl)-3-(5-fluoro-2-pyrimidinyl)-2-butanesulfonamide;

(2S,3R)-N-(4-(1,3-dimethoxy-2-propanyl)-5-((2S,5S)-5-methyltetrahydro-2-furanyl)-4H-1,2,4-triazol-3-yl)-3-(5-methoxy-2-pyrimidinyl)-2-butanesulfonamide;

(2S,3R)-N-(4-(1,3-dimethoxy-2-propanyl)-5-((2R,5R)-5-methyltetrahydro-2-furanyl)-4H-1,2,4-triazol-3-yl)-3-(5-methoxy-2-pyrimidinyl)-2-butanesulfonamide;

(2S,3R)-3-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-2-butanesulfonamide;

(2S,3R)-3-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-2-butanesulfonamide;

(2S,3R)-3-(5-chloro-2-pyrimidinyl)-N-(4-(1,3-dimethoxy-2-propanyl)-5-((2S,5S)-5-methyltetrahydro-2-furanyl)-4H-1,2,4-triazol-3-yl)-2-butanesulfonamide;

(2S,3R)-3-(5-chloro-2-pyrimidinyl)-N-(4-(1,3-dimethoxy-2-propanyl)-5-((2R,5R)-5-methyltetrahydro-2-furanyl)-4H-1,2,4-triazol-3-yl)-2-butanesulfonamide;

(2S,3R)-N-(4-(1,3-dimethoxy-2-propanyl)-5-((2S,5S)-5-methyltetrahydro-2-furanyl)-4H-1,2,4-triazol-3-yl)-3-(5-methoxy-2-pyrazinyl)-2-butanesulfonamide;

(2S,3R)-N-(4-(1,3-dimethoxy-2-propanyl)-5-((2R,5R)-5-methyltetrahydro-2-furanyl)-4H-1,2,4-triazol-3-yl)-3-(5-methoxy-2-pyrazinyl)-2-butanesulfonamide;

(1R,2S)-N-(4-(1,3-dimethoxy-2-propanyl)-5-((2S,5S)-5-methyltetrahydro-2-furanyl)-4H-1,2,4-triazol-3-yl)-1-methoxy-1-(5-methoxy-2-pyrazinyl)-2-propanesulfonamide;

(1R,2S)-N-(4-(1,3-dimethoxy-2-propanyl)-5-((2R,5R)-5-methyltetrahydro-2-furanyl)-4H-1,2,4-triazol-3-yl)-1-methoxy-1-(5-methoxy-2-pyrazinyl)-2-propanesulfonamide;

(1R,2S)-1-(5-chloro-2-pyridinyl)-N-(4-(1,3-dimethoxy-2-propanyl)-5-((2S,5S)-5-methyltetrahydro-2-furanyl)-4H-1,2,4-triazol-3-yl)-1-methoxy-2-propanesulfonamide;

(1R,2S)-1-(5-chloro-2-pyridinyl)-N-(4-(1,3-dimethoxy-2-propanyl)-5-((2R,5R)-5-methyltetrahydro-2-furanyl)-4H-1,2,4-triazol-3-yl)-1-methoxy-2-propanesulfonamide;

(2S,3R)-3-(5-cyano-2-pyridinyl)-N-(4-(4,6-dimethoxy-5-pyrimidinyl)-5-((3S)-tetrahydro-3-furanyl)-4H-1,2,4-triazol-3-yl)-2-butanesulfonamide;

(2S,3R)-3-(5-cyano-2-pyridinyl)-N-(4-(4,6-dimethoxy-5-pyrimidinyl)-5-((3R)-tetrahydro-3-furanyl)-4H-1,2,4-triazol-3-yl)-2-butanesulfonamide;

2-(5-chloro-2-pyrimidinyl)-N-(4-(2,6-dimethoxyphenyl)-5-((3S)-tetrahydro-3-furanyl)-4H-1,2,4-triazol-3-yl)ethanesulfonamide;

2-(5-chloro-2-pyrimidinyl)-N-(4-(2,6-dimethoxyphenyl)-5-((2S)-tetrahydro-2-furanyl)-4H-1,2,4-triazol-3-yl)ethanesulfonamide;

2-(5-chloro-2-pyrimidinyl)-N-(4-(2,6-dimethoxyphenyl)-5-((2R)-tetrahydro-2-furanyl)-4H-1,2,4-triazol-3-yl)ethanesulfonamide;

2-(5-chloro-2-pyrimidinyl)-N-(4-(2,6-dimethoxyphenyl)-5-((3R)-tetrahydro-3-furanyl)-4H-1,2,4-triazol-3-yl)ethanesulfonamide;

(2S,3R)-3-(5-chloro-2-pyrimidinyl)-N-(4-(2,6-dimethoxyphenyl)-5-((3R)-5,5-dimethyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3S)-5,5-dimethyltetrahydro-3-furanyl)-4H-1,2,4-triazol-3-yl)-2-butanesulfonamide;

(2S,3R)-N-(4-(2,6-dimethoxyphenyl)-5-((3R)-5,5-dimethyltetrahydro-3-furanyl)-4H-1,2,4-triazol-3-yl)-3-(5-fluoro-2-pyrimidinyl)-2-butanesulfonamide;

(2S,3R)-N-(4-(2,6-dimethoxyphenyl)-5-((3S)-5,5-dimethyltetrahydro-3-furanyl)-4H-1,2,4-triazol-3-yl)-3-(5-fluoro-2-pyrimidinyl)-2-butanesulfonamide;

(1R,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1-methoxy-2-propanesulfonamide;

(1S,2S)-1-(5-chloro-2-pyrimidinyl)-N-(4-(2,6-dimethoxyphenyl)-5-((2R)-5-oxo-2-pyrrolidinyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2S)-5-oxo-2-pyrrolidinyl)-4H-1,2,4-triazol-3-yl)-1-(2-propanyloxy)-2-propanesulfonamide;

(1R,2S)-1-(5-chloro-2-pyrimidinyl)-1-methoxy-N-(4-(1,2-oxazol-3-ylmethyl)-5-((3R)-tetrahydro-3-furanyl)-4H-1,2,4-triazol-3-yl)-2-propanesulfonamide;

(1R,2S)-1-(5-chloro-2-pyrimidinyl)-1-methoxy-N-(4-(1,2-oxazol-3-ylmethyl)-5-((3S)-tetrahydro-3-furanyl)-4H-1,2,4-triazol-3-yl)-2-propanesulfonamide;

(1R,2S)-1-(5-chloro-2-pyrimidinyl)-1-methoxy-N-(5-((2R,5R)-5-methyltetrahydro-2-furanyl)-4-(1,2-oxazol-3-ylmethyl)-4H-1,2,4-triazol-3-yl)-2-propanesulfonamide;

(1R,2S)-1-(5-chloro-2-pyrimidinyl)-1-methoxy-N-(5-((2S,5S)-5-methyltetrahydro-2-furanyl)-4-(1,2-oxazol-3-ylmethyl)-4H-1,2,4-triazol-3-yl)-2-propanesulfonamide;

(1R,2S)-1-(5-chloro-2-pyrimidinyl)-N-(4-(2,6-dimethoxyphenyl)-5-((2S)-1-methyl-5-oxo-2-pyrrolidinyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-((2R)-1-methyl-5-oxo-2-pyrrolidinyl)-4H-1,2,4-triazol-3-yl)-1-methoxy-2-propanesulfonamide;

(1S,2S)-N-(4-(2,6-dimethoxyphenyl)-5-((3S)-tetrahydro-3-furanyl)-4H-1,2,4-triazol-3-yl)-1-(5-methyl-2-pyridinyl)-1-(2-propanyloxy)-2-propanesulfonamide;

(1S,2S)-N-(4-(2,6-dimethoxyphenyl)-5-((3R)-tetrahydro-3-furanyl)-4H-1,2,4-triazol-3-yl)-1-(5-methyl-2-pyridinyl)-1-(2-propanyloxy)-2-propanesulfonamide;

(2S,3R)-3-(5-chloro-2-pyridinyl)-N-(4-(2,6-dimethoxyphenyl)-5-((3S)-tetrahydro-3-furanyl)-4H-1,2,4-triazol-3-yl)-2-butanesulfonamide;

(2S,3R)-3-(5-chloro-2-pyridinyl)-N-(4-(2,6-dimethoxyphenyl)-5-((3R)-tetrahydro-3-furanyl)-4H-1,2,4-triazol-3-yl)-2-butanesulfonamide;

(1S,2S)-N-(4-(2,6-dimethoxyphenyl)-5-((3R)-5,5-dimethyltetrahydro-3-furanyl)-4H-1,2,4-triazol-3-yl)-1-(5-methyl-2-pyridinyl)-1-(2-propanyloxy)-2-propanesulfonamide;

(1S,2S)-N-(4-(2,6-dimethoxyphenyl)-5-((3S)-5,5-dimethyltetrahydro-3-furanyl)-4H-1,2,4-triazol-3-yl)-1-(5-methyl-2-pyrimidinyl)-1-(2-propanyloxy)-2-propanesulfonamide;

(1S,2S)-1-(5-chloro-2-pyrimidinyl)-N-(4-(2,6-dimethoxyphenyl)-5-((2S)-5,5-dimethyltetrahydro-2-furanyl)-4H-1,2,4-triazol-3-yl)-1-(2-propanyloxy)-2-propanesulfonamide;

(1S,2S)-1-(5-chloro-2-pyrimidinyl)-N-(4-(2,6-dimethoxyphenyl)-5-((2R)-5,5-dimethyltetrahydro-2-furanyl)-4H-1,2,4-triazol-3-yl)-1-(2-propanyloxy)-2-propanesulfonamide;

(2S,3R)-3-(5-chloro-2-pyrimidinyl)-N-(4-((1R)-1-(1,2-oxazol-3-yl)ethyl)-5-((3S)-tetrahydro-3-furanyl)-4H-1,2,4-triazol-3-yl)-2-butanesulfonamide;

(2S,3R)-3-(5-chloro-2-pyrimidinyl)-N-(4-((1S)-1-(1,2-oxazol-3-yl)ethyl)-5-((3S)-tetrahydro-3-furanyl)-4H-1,2,4-triazol-3-yl)-2-butanesulfonamide;

(1S,2S)-N-(4-(2,6-dimethoxyphenyl)-5-((2S)-1-methyl-5-oxo-2-pyrrolidinyl)-4H-1,2,4-triazol-3-yl)-1-(5-methyl-2-pyrimidinyl)-1-(2-propanyloxy)-2-propanesulfonamide;

(1S,2S)-N-(4-(2,6-dimethoxyphenyl)-5-((2R)-1-methyl-5-oxo-2-pyrrolidinyl)-4H-1,2,4-triazol-3-yl)-1-(5-methyl-2-pyrimidinyl)-1-(2-propanyloxy)-2-propanesulfonamide;

(2S,3R)-3-(5-chloro-2-pyrimidinyl)-N-(4-(2,6-dimethoxyphenyl)-5-((2S)-1-methyl-5-oxo-2-pyrrolidinyl)-4H-1,2,4-triazol-3-yl)-2-butanesulfonamide;

2-(5-chloro-2-pyrimidinyl)-N-(4-(2,6-dimethoxyphenyl)-5-((2R)-1,4-dioxan-2-yl)-4H-1,2,4-triazol-3-yl)ethanesulfonamide;

2-(5-chloro-2-pyrimidinyl)-N-(4-(2,6-dimethoxyphenyl)-5-((2S)-1,4-dioxan-2-yl)-4H-1,2,4-triazol-3-yl)ethanesulfonamide;

(1S)-N-(4-(2,6-dimethoxyphenyl)-5-((2S)-tetrahydro-2-furanyl)-4H-1,2,4-triazol-3-yl)-1-(3-methoxyphenyl)ethanesulfonamide;

(1R)-N-(4-(2,6-dimethoxyphenyl)-5-((2R)-tetrahydro-2-furanyl)-4H-1,2,4-triazol-3-yl)-1-(3-methoxyphenyl)ethanesulfonamide;

(1R)-N-(4-(2,6-dimethoxyphenyl)-5-((2S)-tetrahydro-2-furanyl)-4H-1,2,4-triazol-3-yl)-1-(3-methoxyphenyl)ethanesulfonamide;

(1S)-N-(4-(2,6-dimethoxyphenyl)-5-((2R)-tetrahydro-2-furanyl)-4H-1,2,4-triazol-3-yl)-1-(3-methoxyphenyl)ethanesulfonamide;

(1S)-N-(4-(2,6-dimethoxyphenyl)-5-((2S)-tetrahydro-2-furanyl)-4H-1,2,4-triazol-3-yl)-1-(2-fluorophenyl)ethanesulfonamide;

(1R)-N-(4-(2,6-dimethoxyphenyl)-5-((2R)-tetrahydro-2-furanyl)-4H-1,2,4-triazol-3-yl)-1-(2-fluorophenyl)ethanesulfonamide;

(1R)-N-(4-(2,6-dimethoxyphenyl)-5-((2S)-tetrahydro-2-furanyl)-4H-1,2,4-triazol-3-yl)-1-(2-fluorophenyl)ethanesulfonamide;

(1S)-N-(4-(2,6-dimethoxyphenyl)-5-((2R)-tetrahydro-2-furanyl)-4H-1,2,4-triazol-3-yl)-1-(2-fluorophenyl)ethanesulfonamide;

(1R)-N-(4-(2,6-dimethoxyphenyl)-5-((2R)-tetrahydro-2-furanyl)-4H-1,2,4-triazol-3-yl)-1-phenylethanesulfonamide;

(1S)-1-(3-chlorophenyl)-N-(4-(2,6-dimethoxyphenyl)-5-((2S)-tetrahydro-2-furanyl)-4H-1,2,4-triazol-3-yl)ethanesulfonamide;

(1R)-1-(3-chlorophenyl)-N-(4-(2,6-dimethoxyphenyl)-5-((2R)-tetrahydro-2-furanyl)-4H-1,2,4-triazol-3-yl)ethanesulfonamide;

(1R)-1-(3-chlorophenyl)-N-(4-(2,6-dimethoxyphenyl)-5-((2S)-tetrahydro-2-furanyl)-4H-1,2,4-triazol-3-yl)ethanesulfonamide;

(1S)-1-(3-chlorophenyl)-N-(4-(2,6-dimethoxyphenyl)-5-((2R)-tetrahydro-2-furanyl)-4H-1,2,4-triazol-3-yl)ethanesulfonamide;

(2S,3R)-3-(5-chloro-2-pyrimidinyl)-N-(4-(2,6-dimethoxyphenyl)-5-((3S,5R)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3R,5R)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3S,5S)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((3R,5S)-5-methyltetrahydro-3-furanyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2S)-2-oxetanyl)-4H-1,2,4-triazol-3-yl)-2-butanesulfonamide;

(2S,3R)-N-(4-(2,6-bis((trideutero)methyloxy)phenyl)-5-((3S)-tetrahydro-3-furanyl)-4H-1,2,4-triazol-3-yl)-3-(5-chloro-2-pyrimidinyl)-2-butanesulfonamide; or (2S,3R)-N-(4-(2,6-bis((trideutero)methyloxy)phenyl)-5-((3R)-tetrahydro-3-furanyl)-4H-1,2,4-triazol-3-yl)-3-(5-chloro-2-pyrimidinyl)-2-butanesulfonamide; or
the pharmaceutically acceptable salt thereof, or the mixture thereof.--.

In Claim 66, Column 798, Line 42, replace the phrase "the compound of any claim" with --the compound of claim--.